US012799098B2

(12) United States Patent
Sapienza et al.

(10) Patent No.: US 12,799,098 B2
(45) Date of Patent: Nov. 17, 2026

(54) WEE1 DEGRADING COMPOUNDS AND USES THEREOF

(71) Applicant: Bristol-Myers Squibb Company, Princeton, NJ (US)

(72) Inventors: John Sapienza, Chula Vista, CA (US); Jennifer R. Riggs, Cardiff, CA (US); Jacob T. Edwards, San Francisco, CA (US); Daniel K. Cashion, San Diego, CA (US); Meekyum Olivia Pierce, Winchester, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 458 days.

(21) Appl. No.: 18/343,898

(22) Filed: Jun. 29, 2023

(65) Prior Publication Data

US 2024/0067632 A1 Feb. 29, 2024

Related U.S. Application Data

(60) Provisional application No. 63/357,866, filed on Jul. 1, 2022, provisional application No. 63/357,449, filed on Jun. 30, 2022.

(51) Int. Cl.

| | |
|---|---|
| ***C07D 401/14*** | (2006.01) |
| ***A61P 35/00*** | (2006.01) |
| ***C07D 405/14*** | (2006.01) |
| ***C07D 413/14*** | (2006.01) |
| ***C07D 471/04*** | (2006.01) |
| ***C07D 491/052*** | (2006.01) |
| ***C07D 491/107*** | (2006.01) |
| ***C07D 498/04*** | (2006.01) |
| ***C07D 498/08*** | (2006.01) |

(52) U.S. Cl.

CPC ............ *C07D 401/14* (2013.01); *A61P 35/00* (2018.01); *C07D 405/14* (2013.01); *C07D 413/14* (2013.01); *C07D 471/04* (2013.01); *C07D 491/052* (2013.01); *C07D 491/107* (2013.01); *C07D 498/04* (2013.01); *C07D 498/08* (2013.01)

(58) Field of Classification Search

CPC ..... A61P 35/00; C07D 401/14; C07D 405/14; C07D 413/14; C07D 417/14; C07D 471/04; C07D 491/048; C07D 491/052; C07D 491/08; C07D 491/107; C07D 498/04; C07D 498/08

See application file for complete search history.

(56) References Cited

U.S. PATENT DOCUMENTS

2022/0047709 A1 2/2022 Gray et al.

FOREIGN PATENT DOCUMENTS

| | | | |
|---|---|---|---|
| CN | 113292536 | A | 8/2021 |
| EP | 4186904 | A1 | 5/2023 |
| WO | 2018071606 | A1 | 4/2018 |
| WO | 2018102725 | A1 | 6/2018 |
| WO | 2021077010 | A1 | 4/2021 |
| WO | 2021127443 | A1 | 6/2021 |
| WO | 2021231174 | A1 | 11/2021 |
| WO | 2022019597 | A1 | 1/2022 |
| WO | 2022056368 | A1 | 3/2022 |
| WO | 2022125969 | A1 | 6/2022 |

OTHER PUBLICATIONS

Vakili-Samiana et al., "Cell cycle involvement in cancer therapy; WEE1 kinase, a potential target as therapeutic strategy", Mutation Research—Fundamental and Molecular Mechanisms of Mutagenesis (Year: 2022).*

International Search Report and Written Opinion in PCT/US2023/069331 dated Sep. 25, 2023, Applicant: Bristol-Myers Squibb Company, 15 pages.

Machine translation of CN113292536, dated Aug. 24, 2021, Zhang et al., 76 pages.

Vakili-Samiani et al., "Cell cycle involvement in cancer therapy; WEE1 kinase, a potential target as therapeutic strategy," Mutation Research, 2022, 824: 111776 (12 pages).

Yin et al., "Chimera induced protein degradation: PROTACs and beyond," Euro J Med Chem, 2020, 206:112494 (17 pages).

* cited by examiner

*Primary Examiner* — Jeffrey H Murray
*Assistant Examiner* — Daniel John Burkett
(74) *Attorney, Agent, or Firm* — McNeill PLLC

(57) ABSTRACT

Provided herein are compounds and compositions thereof that reduce WEE1 kinase protein levels. In some embodiments, the compounds and compositions are provided for treatment of WEE1 associated diseases such as cancer. In some embodiments, the compound is a compound according to Formula (I)

(I)

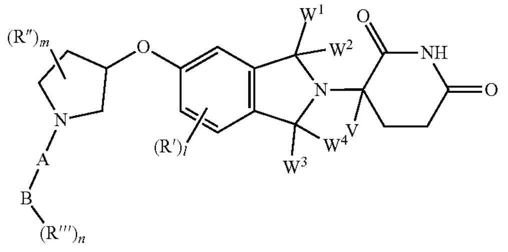

or a pharmaceutically acceptable salt, tautomer, isotopologue, or stereoisomer thereof.

6 Claims, No Drawings

WEE1 DEGRADING COMPOUNDS AND USES THEREOF

This application claims the benefit of priority of U.S. Provisional Application No. 63/357,449, filed Jun. 30, 2022, and U.S. Provisional Application No. 63/357,866, filed Jul. 1, 2022, each of which is incorporated herein by reference in its entirety for any purpose.

FIELD

The present disclosure relates generally to compounds, compositions, and methods for their preparation and use of the compounds and compositions for treating diseases and conditions associated with the WEE1 protein.

BACKGROUND

Targeted protein degradation is a therapeutic modality whereby small molecules induce novel protein-protein interactions and enable destruction of target proteins that drive disease. CRBN E3 ligase modulator (CELMoD) small molecules are a class of targeted protein therapeutics that co-opts the CRL4-Cereblon E3 ubiquitin ligase complex, generating a new molecular "glue" interface on the surface of Cereblon that recruits and polyubiquitinates target proteins that are not normally ubiquitinated by Cereblon. The ubiquitin tagged proteins are then trafficked to and subsequently degraded by the 26S proteasome. The selection of target proteins recruited by Cereblon is determined by the specific molecular structure of the CELMoD compound.

WEE1 is a tyrosine kinase that phosphorylates the CDK1 and CDK2 cyclin-dependent kinases at their tyrosine-15 residue consequently inhibiting kinase activity and halting the cell cycle at the intra-S and G2/M cell cycle checkpoints. While halted at these checkpoints, cells repair stalled replication forks and DNA damage before entering mitosis; if the DNA damage cannot be repaired or rises above acceptable thresholds, cells undergo programmed apoptosis or mitotic catastrophe. Cancer cells frequently exhibit excessive replication stress, mutagenesis, and genomic instability prompting a reliance on cell cycle checkpoints to maintain DNA damage below apoptotic thresholds. Compared to normal cells, cancer cells frequently rely solely upon the intra-S and G2/M checkpoints because their G1 cell cycle checkpoint is disabled by a various mechanisms, for instance, by restricting p53 and pRB activation, or, by hyper-activating replication-promoting factors such as Cyclin D and Cyclin E. Tumors that rely heavily upon the WEE1-mediated intra-S and G2/M checkpoints are hypothesized to be exceptionally sensitive to WEE1 loss and therapeutics that target WEE1 are expected to exhibit antitumor activity with a favorable therapeutic window.

Certain cancer therapeutics function by inducing replication stress and DNA damage, including, for example, carboplatin, cisplatin, gemcitabine, pemetrexed, topotecan, doxorubicin, decitabine, and methotrexate. By inducing DNA damage and replication stress, these agents enhance the reliance of dividing tumor cells upon the WEE1-mediated cell cycle checkpoints. Therefore, CELMoD compounds that degrade WEE1 are proposed synergistically combine with DNA damaging agents.

Accordingly, in one aspect, provided herein are CELMoD compounds that induce the Cereblon-mediated ubiquitination and degradation of WEE1 to elicit broad antitumor activity as a single agent or in combination with sensitizing therapeutics.

SUMMARY

Described herein, in certain embodiments, are compounds and compositions thereof that degrade WEE1. In various embodiments, the compounds and compositions thereof may be used for treatment of diseases associated with WEE1, for example, cancer.

The present embodiments can be understood more fully by reference to the detailed description and examples, which are intended to exemplify non-limiting embodiments.

In some embodiments, provided herein are compounds of Formula (I)

(I)

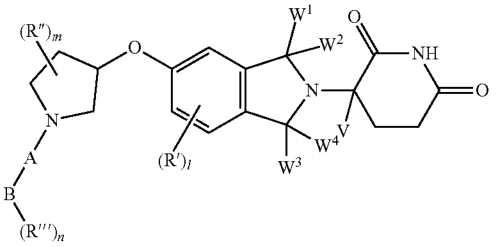

or a pharmaceutically acceptable salt, tautomer, isotopologue, or stereoisomer thereof, wherein

- A is a direct bond or an optionally substituted $C_{1-5}$ alkyl;
- B is selected from optionally substituted $C_{3-10}$ cycloalkyl, optionally substituted 3-14 membered heterocyclyl, optionally substituted $C_{6-14}$ aryl, and optionally substituted 5-14 membered heteroaryl;
- $W^1$ and $W^2$ are each independently selected from H and $CH_3$, or taken together to form an oxo group;
- $W^3$ and $W^4$ are each H or are taken together to form an oxo group;
- V is selected from H and $CH_3$;
- R' is a halogen atom;
- R" is selected from halogen atom, optionally substituted $C_{1-5}$ alkyl, and optionally substituted $C_{1-5}$ alkoxy or two R" can combine to form an oxo group with the carbon to which they are attached;
- R''' is selected from halogen atom, —CN, —OH, optionally substituted amino, optionally substituted amido, optionally substituted $C_{1-5}$ alkyl, optionally substituted $C_{1-5}$ alkoxy, optionally substituted $C_{3-6}$ cycloalkyl-oxy, optionally substituted 5-10 membered heterocyclyl-oxy, optionally substituted 5-10 membered heteroaryl-oxy, optionally substituted $C_{3-6}$ cycloalkyl, optionally substituted 3-10 membered heterocyclyl, optionally substituted 5-10 membered aryl, and optionally substituted 5-10 membered heteroaryl;
- l is an integer from 0 to 3;
- m is an integer from 0 to 3;
- n is an integer from 0 to 7; and wherein at least one of $W^1$ and $W^2$ or $W^3$ and $W^4$ are taken together form an oxo group.

In some embodiments, provided herein are methods for reducing WEE1 kinase protein levels, the method comprising contacting a cell with an effective amount of a compound of Formula (I) or a pharmaceutically acceptable salt, tautomer, isotopologue, or stereoisomer thereof. In some embodiments, provided herein are uses of a compound of Formula (I) or a pharmaceutically acceptable salt, tautomer, isotopologue, or stereoisomer thereof, in the manufacture of a medicament for reducing WEE1 kinase protein levels.

In some embodiments, provided herein are methods of preventing or treating cancer in a subject comprising administering to a subject in need thereof an effective amount of a compound of Formula (I) or a pharmaceutically acceptable salt, tautomer, isotopologue, or stereoisomer thereof. In some embodiments, provided herein are uses of a compound of Formula (I) or a pharmaceutically acceptable salt, tautomer, isotopologue, or stereoisomer thereof, in the manufacture of a medicament for the prevention or treatment of cancer.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the terms "about" and "approximately" mean±20%, ±10%, ±5%, or ±1% of the indicated range, value, or structure, unless otherwise indicated.

An "alkyl" group is a saturated, partially saturated, or unsaturated straight chain or branched non-cyclic hydrocarbon having from 1 to 10 carbon atoms ($C_1$-$C_{10}$ alkyl), typically from 1 to 8 carbons ($C_1$-$C_8$ alkyl) or, in some embodiments, from 1 to 6 ($C_1$-$C_6$ alkyl), 1 to 4 ($C_1$-$C_4$ alkyl), 1 to 3 ($C_1$-$C_3$ alkyl), or 2 to 6 ($C_2$-$C_6$ alkyl) carbon atoms. In some embodiments, the alkyl group is a saturated alkyl group. Representative saturated alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. In some embodiments, an alkyl group is an unsaturated alkyl group, also termed an alkenyl or alkynyl group. An "alkenyl" group is an alkyl group that contains one or more carbon-carbon double bonds. An "alkynyl" group is an alkyl group that contains one or more carbon-carbon triple bonds. Examples of unsaturated alkyl groups include, but are not limited to, vinyl, allyl, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, $-C{\equiv}CH$, $-C{\equiv}C(CH_3)$, $-C{\equiv}C(CH_2CH_3)$, $-CH_2C{\equiv}CH$, $-CH_2CC(CH_3)$ and $-CH_2CC(CH_2CH_3)$, among others. An alkyl group can be substituted or unsubstituted. When the alkyl groups described herein are said to be "substituted," they may be substituted with any substituent or substituents as those found in the exemplary compounds and embodiments disclosed herein, as well as halogen; hydroxy; alkoxy; cycloalkyloxy, aryloxy, heterocyclyloxy, heteroaryloxy, cycloalkylalkyloxy, arylalkyloxy, heterocyclylalkyloxy, heteroarylalkyloxy; oxo (=O); amino, alkylamino, cycloalkylamino, arylamino, heterocyclylamino, heteroarylamino, cycloalkylalkylamino, arylalkylamino, heterocyclylalkylamino, heteroarylalkylamino; imino; imido; amidino; guanidino; enamino; acylamino; sulfonylamino; urea, nitrourea; oxime; hydroxylamino; alkoxyamino; aralkoxyamino; hydrazino; hydrazido; hydrazono; azido; nitro; thio (—SH), alkylthio; =S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or $-B(OH)_2$. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; $B(OH)_2$, or —O(alkyl)aminocarbonyl.

A "cycloalkyl" group is a saturated, or partially saturated cyclic alkyl group of from 3 to 10 carbon atoms ($C_3$-$C_{10}$ cycloalkyl) having a single cyclic ring or multiple condensed or bridged rings that can be optionally substituted. In some embodiments, the cycloalkyl group has 3 to 8 ring carbon atoms ($C_3$-$C_8$ cycloalkyl), whereas in other embodiments the number of ring carbon atoms ranges from 3 to 5 ($C_3$-$C_5$ cycloalkyl), 3 to 6 ($C_3$-$C_6$ cycloalkyl), or 3 to 7 ($C_3$-$C_7$ cycloalkyl). In some embodiments, the cycloalkyl groups are saturated cycloalkyl groups. Such saturated cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. In other embodiments, the cycloalkyl groups are unsaturated cycloalkyl groups. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

A "heterocyclyl" is a non-aromatic cycloalkyl in which one to four of the ring carbon atoms are independently replaced with a heteroatom selected from O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass saturated and partially saturated ring systems. Further, the term heterocyclyl is intended to encompass any non-aromatic ring containing at least one heteroatom, which ring may be fused to an aryl or heteroaryl ring, regardless of the attachment to the remainder of the molecule. The phrase also includes bridged polycyclic ring systems containing a heteroatom. Representative examples of a heterocyclyl group include, but are not limited to, aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

An "aryl" group is an aromatic carbocyclic group of from 6 to 14 carbon atoms ($C_6$-$C_{14}$ aryl) having a single ring (e.g., phenyl) or multiple condensed rings (e.g., naphthyl or anthryl). In some embodiments, aryl groups contain 6-14 carbons ($C_6$-$C_{14}$ aryl), and in others from 6 to 12 ($C_6$-$C_{12}$ aryl) or even 6 to 10 carbon atoms ($C_6$-$C_{10}$ aryl) in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups. A heteroaryl group can be substituted or unsubstituted.

A "halogen" or "halo" is fluorine, chlorine, bromine or iodine.

An "alkoxy" group is —O-(alkyl), wherein alkyl is defined above.

An "oxo" group is a "=O" group bonded to a carbon.

An "amino" group is $—NH_2$, wherein one or both of the hydrogen atoms may be substituted with alkyl, cycloalkyl, heterocyclyl, aryl, or heteroaryl.

An "amido" group is an amide group with the formula —NHC(O)—, wherein the hydrogen atom may be substituted with alkyl, cycloalkyl, heterocyclyl, aryl, or heteroaryl.

A "heteroaryl-oxy" group is —O-(heteroaryl), wherein the heteroaryl is defined above. A "heterocyclyl-oxy" group is —O-(heterocyclyl), wherein the heterocyclyl is defined above. A "cycloalkyl-oxy" group is —O-(cycloalkyl), wherein the cycloalkyl is defined above When the groups described herein, with the exception of alkyl group, amino group, and amido group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxo (=O); $B(OH)_2$, —O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl); cycloalkyloxy, aryloxy, heterocyclyloxy, heteroaryloxy, cycloalkylalkyloxy, arylalkyloxy, heterocyclylalkyloxy, and heteroarylalkyloxy.

Embodiments of the disclosure are meant to encompass pharmaceutically acceptable salts, tautomers, isotopologues, and stereoisomers of the compounds provided herein, such as the compounds of Formula (I).

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of Formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride, formic, and mesylate salts. Others are well-known in the art, see for example, *Remington's Pharmaceutical Sciences,* $18^{th}$ eds., Mack Publishing, Easton PA (1990) or *Remington: The Science and Practice of Pharmacy,* $19^{th}$ eds., Mack Publishing, Easton PA (1995).

As used herein and unless otherwise indicated, the term "stereoisomer" or "stereoisomerically pure" means one stereoisomer of a particular compound that is substantially free of other stereoisomers of that compound. For example, a stereoisomerically pure compound having one chiral center will be substantially free of the opposite enantiomer of the compound. A stereoisomerically pure compound having two chiral centers will be substantially free of other diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds disclosed herein can have chiral centers and can occur as racemates, individual enantiomers or diastereomers, and mixtures thereof. All such isomeric forms are included within the embodiments disclosed herein, including mixtures thereof.

The use of stereoisomerically pure forms of the compounds disclosed herein, as well as the use of mixtures of those forms, are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); Wilen, S. H., *Tables of Resolving Agents and Optical Resolutions* p. 268 (E. L. Eliel, Ed., Univ. of Notre Dame Press, Notre Dame, IN, 1972); Todd, M., *Separation Of Enantiomers: Synthetic Methods* (Wiley-VCH Verlag GmbH & Co. KgaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuj a, S., *Chiral Separation Methods for Pharmaceutical and Biotechnological Products* (John Wiley & Sons, 2011).

"Tautomers" refers to isomeric forms of a compound that are in equilibrium based on proton transfers. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

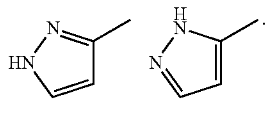

As readily understood by one skilled in the art, a wide variety of functional groups and other structures may exhibit tautomerism and all tautomers of compounds of Formula (I) are within the scope of the present disclosure.

It should also be noted the compounds disclosed herein can contain unnatural proportions of atomic isotopes at one or more of the atoms. For example, the compounds may be radiolabeled with radioactive isotopes, such as for example tritium ($^3H$), iodine-125 ($^{125}I$), sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds disclosed herein, for example, the isotopologues are deuterium, carbon-13, and/or nitrogen-15 enriched compounds. As used herein, "deuterated", means a compound wherein at least one hydrogen (H) has been replaced by deuterium (indicated by D or $^2H$), that is, the compound is enriched in deuterium in at least one position.

It is understood that, independently of stereoisomerical or isotopic composition, each compound disclosed herein can be provided in the form of any of the pharmaceutically acceptable salts discussed herein. Equally, it is understood that the isotopic composition may vary independently from the stereoisomerical composition of each compound referred to herein. Further, the isotopic composition, while being restricted to those elements present in the respective compound or salt thereof disclosed herein, may otherwise vary independently from the selection of the pharmaceutically acceptable salt of the respective compound.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a neurodegenerative disease, as described herein, or a symptom thereof.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a neurodegenerative disease, as described herein, or symptoms thereof.

The term "effective amount" in connection with a compound disclosed herein means an amount capable of treating or preventing a disorder, disease or condition, or symptoms thereof, disclosed herein.

The term "subject" or "patient" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having an WEE1 mediated disease, or a symptom thereof.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Compounds

In one aspect, provided herein is a compound of Formula (I)

(I)

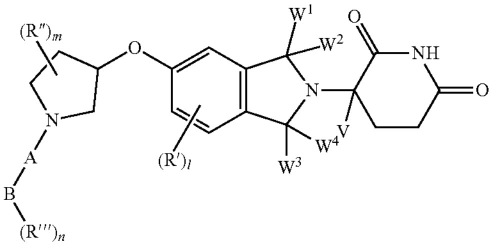

or a pharmaceutically acceptable salt, tautomer, isotopologue, or stereoisomer thereof, wherein A is a direct bond or an optionally substituted $C_{1-5}$ alkyl;

B is selected from optionally substituted $C_{3-10}$ cycloalkyl, optionally substituted 3-14 membered heterocyclyl, optionally substituted $C_{6-14}$ aryl, and optionally substituted 5-14 membered heteroaryl;

$W^1$ and $W^2$ are each independently selected from H and $CH_3$, or taken together to form an oxo group;

$W^3$ and $W^4$ are each H or are taken together to form an oxo group;

V is selected from H and $CH_3$;

R' is a halogen atom;

R" is selected from halogen atom, optionally substituted $C_{1-5}$ alkyl, and optionally substituted $C_{1-5}$ alkoxy or two R" can combine to form an oxo group with the carbon to which they are attached;

R''' is selected from halogen atom, —CN, —OH, optionally substituted amino, optionally substituted amido, optionally substituted $C_{1-5}$ alkyl, optionally substituted $C_{1-5}$ alkoxy, optionally substituted $C_{3-6}$ cycloalkyl-oxy, optionally substituted 5-10 membered heterocyclyl-oxy, optionally substituted 5-10 membered heteroaryl-oxy, optionally substituted $C_{3-6}$ cycloalkyl, optionally substituted 3-10 membered heterocyclyl, optionally substituted 5-10 membered aryl, and optionally substituted 5-10 membered heteroaryl;

l is an integer from 0 to 3;

m is an integer from 0 to 3;

n is an integer from 0 to 7; and wherein at least one of $W^1$ and $W^2$ or $W^3$ and $W^4$ are taken together form an oxo group.

In some embodiments, the compound of Formula (I) is a compound of Formula (Ia)

(Ia)

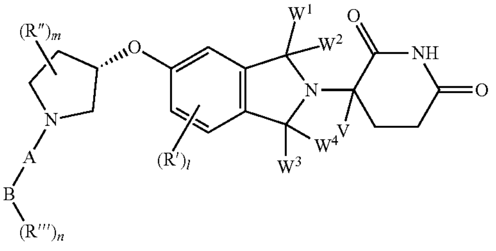

In some embodiments, $W^3$ and $W^4$ are taken together form an oxo group. In some embodiments, A is a direct bond. In some embodiments, A is an optionally substituted $C_{1-3}$ alkyl. In some embodiments, A is —$CH_2$—.

In some embodiments, B is monocyclic. In some embodiments, B is bicyclic. In some embodiments, B is selected from optionally substituted $C_{6-14}$ aryl and optionally substituted 5-14 membered heteroaryl. In some embodiments, B is selected from optionally substituted $C_{3-10}$ cycloalkyl and optionally substituted 3-14 membered heterocyclyl.

In some embodiments, $W^1$ and $W^2$ are both H. In some embodiments, $W^1$ and $W^2$ are taken together to form an oxo group. In some embodiments, $W^1$ is H and $W^2$ is $CH_3$. In some embodiments, V is H. In some embodiments, V is $CH_3$.

In some embodiments, R' is selected from F and Cl. In some embodiments, R' is F. In some embodiments, R" is selected from F, Cl, optionally substituted $C_{1-3}$ alkyl, and optionally substituted $C_{1-3}$ alkoxy. In some embodiments, R" is selected from F, Cl, $C_{1-3}$ alkyl, and $C_{1-3}$ alkoxy. In some embodiments, R" is selected from F and —$CH_3$.

In some embodiments, R' is selected from halogen atom, —CN, —OH, optionally substituted amino, optionally substituted amido, optionally substituted $C_{1-5}$ alkyl, optionally substituted $C_{1-5}$ alkoxy, optionally substituted $C_{3-6}$ cycloalkyl-oxy, optionally substituted 5-10 membered heterocyclyl-oxy, optionally substituted 5-10 membered heteroaryl-oxy, optionally substituted $C_{3-6}$ cycloalkyl, optionally substituted 3-10 membered heterocyclyl, optionally substituted 5-10 membered aryl, and optionally substituted 5-10 membered heteroaryl. In some embodiments, R' is selected from F, $C_1$, —CN, —OH, optionally substituted amino, optionally substituted $C_{1-3}$ alkyl, optionally substituted $C_{1-3}$ alkoxy, optionally substituted $C_{3-6}$ cycloalkyl, optionally substituted 3-10 membered heterocyclyl, and optionally substituted 5-10 membered heteroaryl.

In some embodiments, R''' is selected from —$NH_2$, —NH($CH_3$), —$N(CH_3)_2$, and —$OCH_3$. In some embodiments, R''' is a $C_{1-3}$ alkyl optionally substituted with 1 to 3 groups selected from F atoms, —O—($C_{1-3}$ alkyl), —O—$C_{4-6}$ heterocyclyl, and OH. In some embodiments, R' is a $C_{3-6}$ cycloalkyl optionally substituted with 1 to 2 groups selected from —OH, —$C_{1-3}$ alkoxy, and —$CH_2OCH_3$. In some embodiments, R''' is a 3-10 membered heterocyclyl optionally substituted with 1 to 3 groups selected from F, OH, $C_{1-3}$ alkyl optionally substituted with 1-3 F atoms or —$NH_2$, $C_{1-3}$ alkoxy optionally substituted with 1-3 F atoms, —C(O)$CH_3$, —$CH_2OCH_3$, —$NH_2$, —NH($CH_3$), and —$N(CH_3)_2$. In some embodiments, R' is a 5-10 membered heteroaryl optionally substituted with 1 to 3 groups selected from F, $C_1$, CN, OH, $C_{1-3}$ alkyl optionally substituted with 1-3 F atoms or —$NH_2$, $C_{1-3}$ alkoxy optionally substituted with 1-3 F atoms, —C(O)$CH_3$, —$CH_2OCH_3$, —$NH_2$, —NH($CH_3$), —N$(CH_3)_2$, and $C_{4-6}$ heterocycle.

In some embodiments, 1 is 0 or 1. In some embodiments, 1 is 0. In some embodiments, m is 0 or 1. In some embodiments, m is 0. In some embodiments, n is 0 or 1.

In some embodiments, the compound is a compound according to Formula (II)

(II)

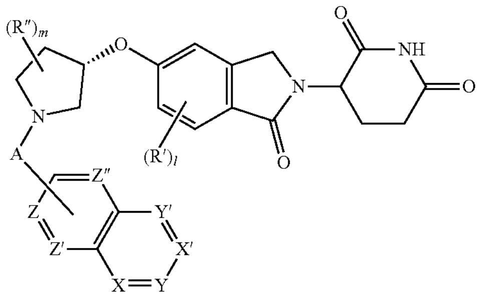

wherein

A is a direct bond or an optionally substituted $C_{1-5}$ alkyl;

R' is a halogen atom;

R" is selected from halogen atom, optionally substituted $C_{1-5}$ alkyl, and optionally substituted $C_{1-5}$ alkoxy or two R" can combine to form an oxo group with the carbon to which they are attached;

Z, Z', and Z" are each independently selected from N and $CR^1$;

X, Y, X', and Y' are each independently selected from N and $CR^2$;

each $R^1$ is independently selected from H, halogen atom, —CN, optionally substituted $C_{1-5}$ alkyl, optionally substituted $C_{1-5}$ alkoxy, optionally substituted 5-10 membered heteroaryl-oxy, optionally substituted $C_{3-6}$ cycloalkyl, and optionally substituted 3-6 membered heterocyclyl;

each $R^2$ is independently selected from H, halogen atom, —CN, —OH, optionally substituted amino, optionally substituted amido, optionally substituted $C_{1-5}$ alkyl, optionally substituted $C_{3-6}$ cycloalkyl, optionally substituted 3-10 membered heterocyclyl, and optionally substituted 5-10 membered heteroaryl;

l is an integer from 0 to 2; and m is an integer from 0 to 2.

In some embodiments, A is a direct bond. In some embodiments, A is an optionally substituted $C_{1-3}$ alkyl. In some embodiments, A is —$CH_2$—.

In some embodiments, R' is selected from F and Cl. In some embodiments, R" is selected from F, Cl, optionally substituted $C_{1-3}$ alkyl, and optionally substituted $C_{1-3}$ alkoxy.

In some embodiments, Z, Z', and Z" are all $CR^1$. In some embodiments, Z is N and Z' and Z" are both $CR^1$.

In some embodiments, X is N and Y, X', and Y' are $CR^2$. In some embodiments, X and X' are both N and Y and Y' are both $CR^2$. In some embodiments, X, Y, X', and Y' are all $CR^2$.

In some embodiments, each $R^1$ is independently selected from H, F $C_1$, —CN, optionally substituted $C_{1-3}$ alkyl, optionally substituted $C_{1-3}$ alkoxy, optionally substituted $C_{3-6}$ cycloalkyl, and optionally substituted 3-6 membered heterocyclyl.

In some embodiments, each $R^2$ is independently selected from H, F, $C_1$, —CN, —OH, optionally substituted amino, optionally substituted amido, optionally substituted $C_{1-3}$ alkyl, optionally substituted $C_{3-6}$ cycloalkyl, and optionally substituted 4-8 membered heterocyclyl.

In some embodiments, the $C_{1-3}$ alkyl of $R^1$ or $R^2$ is substituted with 1-3 groups selected from halogen, OH and $C_{1-3}$ alkoxy. In some embodiments, the $C_{3-6}$ cycloalkyl of $R^1$ or $R^2$ is substituted with 1-3 groups selected from halogen, —OH, $C_{1-3}$ alkyl, $C_{1-3}$ alkoxy, and —$CH_2OCH_3$. In some embodiments, the 3-6 membered heterocyclyl of $R^1$ or 4-8 membered heterocyclyl $R^2$ is substituted with 1-3 groups selected from halogen, —OH, $C_{1-3}$ alkyl, $C_{1-3}$ alkoxy, —$NH_2$, —NH($CH_3$), —N$(CH_3)_2$, and —C(O)$CH_3$.

In some embodiments, 1 is 0 or 1. In some embodiments, 1 is 0. In some embodiments, m is 0 or 1. In some embodiments, m is 0.

In some embodiments, the compound is a compound according to Formula (IIa)

(IIa)

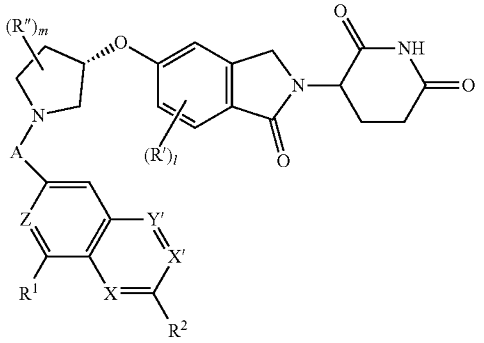

wherein

A is a direct bond or an optionally substituted $C_{1-5}$ alkyl;

R' is a halogen atom;

R" is selected from halogen atom, optionally substituted $C_{1-5}$ alkyl, and optionally substituted $C_{1-5}$ alkoxy or two R" can combine to form an oxo group with the carbon to which they are attached;

Z is selected from N and $CR^3$;

X, X', and Y' are each independently selected from N and $CR^4$;

$R^1$ and $R^3$ are each independently selected from H, halogen atom, —CN, optionally substituted $C_{1-5}$ alkyl, optionally substituted $C_{1-5}$ alkoxy, optionally substituted 5-10 membered heteroaryl-oxy, optionally substituted $C_{3-6}$ cycloalkyl, and optionally substituted 3-6 membered heterocyclyl;

$R^2$ and $R^4$ are each independently selected from H, halogen atom, —CN, —OH, oxo, optionally substituted amino, optionally substituted amido, optionally substituted $C_{1-5}$ alkyl, optionally substituted $C_{3-6}$ cycloalkyl, optionally substituted 3-10 membered heterocyclyl, and optionally substituted 5-10 membered heteroaryl;

l is an integer from 0 to 1; and m is an integer from 0 to 1.

In some embodiments, A is a direct bond. In some embodiments, A is an optionally substituted $C_{1-3}$ alkyl. In some embodiments, A is —$CH_2$—.

In some embodiments, R' is selected from F and Cl. In some embodiments, R" is selected from F, Cl, optionally substituted $C_{1-3}$ alkyl, and optionally substituted $C_{1-3}$ alkoxy.

In some embodiments, Z is N. In some embodiments, Z is $CR^1$. In some embodiments, X is N and X' and Y' are both $CR^2$. In some embodiments, X and X' are both N and Y' is $CR^2$. In some embodiments, X, X', and Y' are all $CR^2$.

In some embodiments, $R^1$ and $R^3$ are each independently selected from H, F $C_1$, —CN, optionally substituted $C_{1-3}$ alkyl, optionally substituted $C_{1-3}$ alkoxy, optionally substituted $C_{3-6}$ cycloalkyl, and optionally substituted 3-6 membered heterocyclyl. In some embodiments, $R^1$ is independently selected from H and F. In some embodiments, $R^3$ is H.

In some embodiments, $R^2$ and $R^4$ are each independently selected from H, F, $C_1$, —CN, —OH, oxo, optionally substituted amino, optionally substituted amido, optionally substituted $C_{1-3}$ alkyl, optionally substituted $C_{3-6}$ cycloalkyl, optionally substituted 3-10 membered heterocyclyl, and optionally substituted 5-10 membered heteroaryl. In some embodiments, $R^2$ is independently selected from optionally substituted $C_{1-3}$ alkyl and optionally substituted 3-10 membered heterocyclyl. In some embodiments, $R^4$ is H.

In some embodiments,

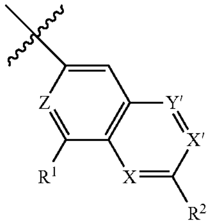

is

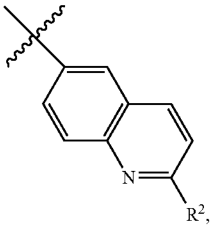

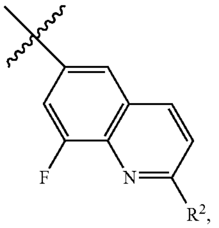

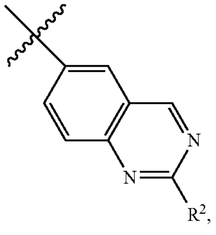

or

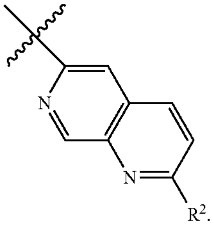

In some embodiments, $R^2$ is

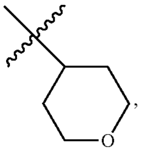

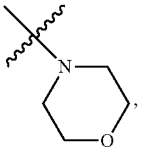

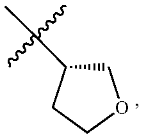

-continued

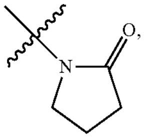

or

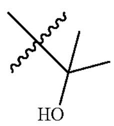

In some embodiments, 1 is 0. In some embodiments, m is 0.

In some embodiments, the compound is a compound according to Formula (III):

(III)

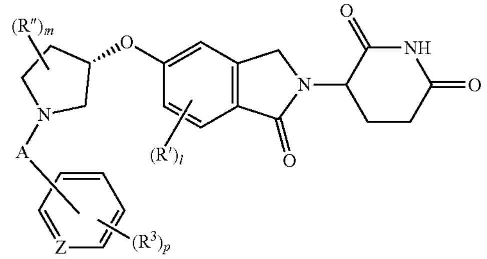

wherein

A is a direct bond or an optionally substituted $C_{1-5}$ alkyl;

R' is a halogen atom;

R" is selected from halogen atom, optionally substituted $C_{1-5}$ alkyl, and optionally substituted $C_{1-5}$ alkoxy or two R" can combine to form an oxo group with the carbon to which they are attached;

Z is selected from N, CH, and $CR^3$;

each $R^3$ is independently selected from —CN, optionally substituted $C_{1-5}$ alkyl, optionally substituted $C_{3-6}$ membered cycloalkyl, optionally substituted 3-6 membered heterocyclyl, optionally substituted 5-10 membered aryl, and optionally substituted 5-10 membered heteroaryl;

1 is an integer from 0 to 2;

m is an integer from 0 to 2; and p is an integer from 0 to 3.

In some embodiments, A is a direct bond. In some embodiments, A is an optionally substituted $C_{1-3}$ alkyl. In some embodiments, A is $—CH_2—$.

In some embodiments, R' is selected from F and Cl. In some embodiments, R" is selected from F, Cl, optionally substituted $C_{1-3}$ alkyl, and optionally substituted $C_{1-3}$ alkoxy.

In some embodiments, Z is N. In some embodiments, Z is CH.

In some embodiments, each $R^3$ is independently selected from —CN, optionally substituted $C_{1-3}$ alkyl, optionally substituted 3-6 membered heterocyclyl, and optionally substituted 5-10 membered heteroaryl.

In some embodiments, 1 is 0 or 1. In some embodiments, 1 is 0. In some embodiments, m is 0 or 1. In some embodiments, m is 0. In some embodiments, p is an integer from 0 to 2. In some embodiments, p is 0 or 1.

In some embodiments, the compound is a compound according to Formula (IIIa) or (IIIb):

(IIIa)

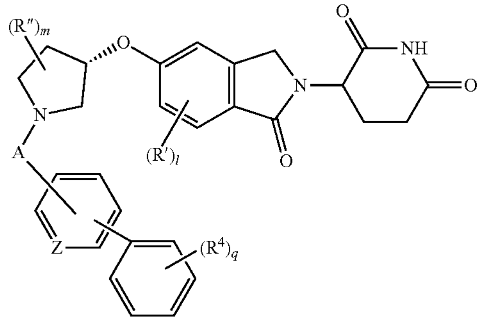

(IIIb)

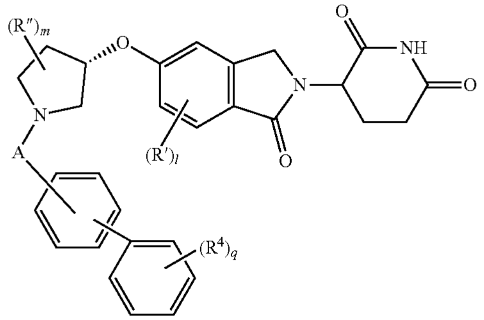

wherein

A is a direct bond or an optionally substituted $C_{1-5}$ alkyl;

R' is a halogen atom;

R" is selected from halogen atom, optionally substituted $C_{1-5}$ alkyl, and optionally substituted $C_{1-5}$ alkoxy or two R" can combine to form an oxo group with the carbon to which they are attached;

$R^4$ is an optionally substituted 3-6 membered heterocyclyl;

l is 0 or 1;

m is 0 or 1; and q is 0 or 2.

In some embodiments, A is a direct bond. In some embodiments, A is an optionally substituted $C_{1-3}$ alkyl. In some embodiments, A is —$CH_2$—.

In some embodiments, R' is selected from F and Cl. In some embodiments, R" is selected from F, Cl, optionally substituted $C_{1-3}$ alkyl, and optionally substituted $C_{1-3}$ alkoxy. In some embodiments, $R^4$ is an optionally substituted 6 membered heterocyclyl.

In some embodiments, l is 0. In some embodiments, m is 0. In some embodiments, q is 0 or 1.

In some embodiments, the compound is a compound from Table 1. In some embodiments, the compound is a compound from Table 2.

In the descriptions herein, it is understood that every description, variation, embodiment, or aspect of a moiety may be combined with every description, variation, embodiment, or aspect of other moieties the same as if each and every combination of descriptions is specifically and individually listed. For example, every description, variation, embodiment, or aspect provided herein with respect to the "B" group of Formula (I) may be combined with every description, variation, embodiment, or aspect of A, $W^1$, $W^2$, V, R', R", R''', l, m and n, the same as if each and every combination were specifically and individually listed. It is also understood that all descriptions, variations, embodiments, or aspects of Formula (I), where applicable, apply equally to other formulae detailed herein, and are equally described, the same as if each and every description, variation, embodiment, or aspect were separately and individually listed for all formulae. For example, all descriptions, variations, embodiments, or aspects of Formula (I), where applicable, apply equally to any of the formulae as detailed herein, such as Formulae (II), (Ha), (III), (Ma) and (IIIb), are equally described, the same as if each and every description, variation, embodiment, or aspect were separately and individually listed for all formulae.

In some embodiments, provided is a compound selected from the compounds in Tables 1 or 2 or a pharmaceutically acceptable salt thereof. Although certain compounds described in the present disclosure, including in Tables 1 and 2, may be presented as specific stereoisomers and/or in a non-stereochemical form, it is understood that any or all stereochemical forms, including any enantiomeric or diastereomeric forms, and any tautomers or other forms of the compounds of the present disclosure, including in Tables 1 and 2, are herein described.

TABLE 1

| Compound No. | Structure | Name |
|---|---|---|
| 1 | 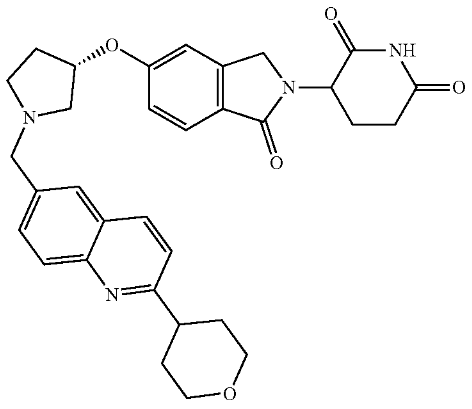 | 3-(1-oxo-5-(((S)-1-((2-(tetrahydro-2H-pyran-4-yl)quinolin-6-yl)methyl)pyrrolidin-3-yl)oxy)isoindolin-2-yl)piperidine-2,6-dione |

TABLE 1-continued
| Compound No. | Structure | Name |
|---|---|---|
| 2 | 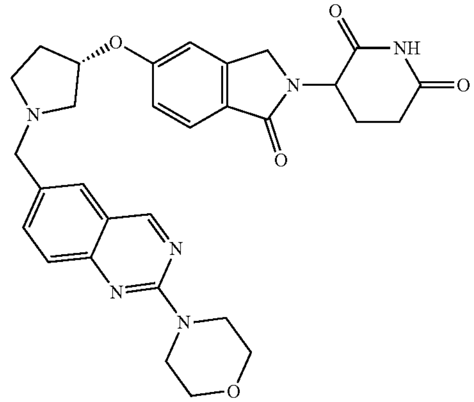 | 3-(5-(((S)-1-((2-morpholinoquinazolin-6-yl)methyl)pyrrolidin-3-yl)oxy)-1-oxoisoindolin-2-yl)piperidine-2,6-dione |
| 3 | 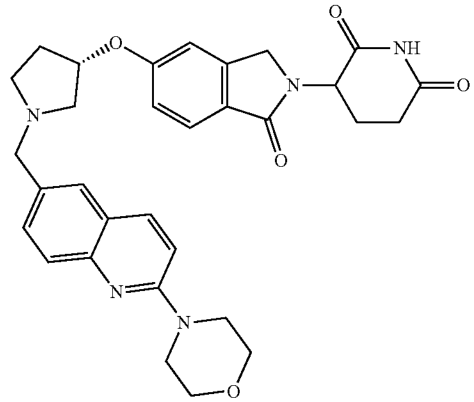 | 3-(5-(((S)-1-((2-morpholinoquinolin-6-yl)methyl)pyrrolidin-3-yl)oxy)-1-oxoisoindolin-2-yl)piperidine-2,6-dione |
| 4 | 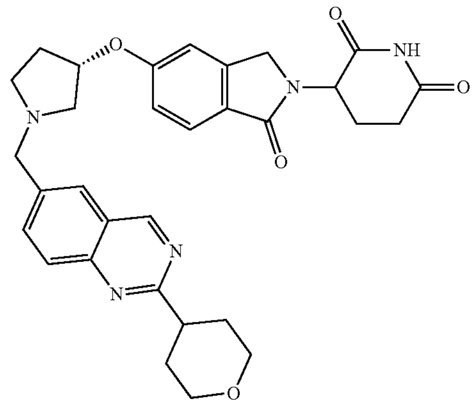 | 3-(1-oxo-5-(((S)-1-((2-(tetrahydro-2H-pyran-4-yl)quinazolin-6-yl)methyl)pyrrolidin-3-yl)oxy)isoindolin-2-yl)piperidine-2,6-dione |

TABLE 1-continued

| Compound No. | Structure | Name |
| --- | --- | --- |
| 5 | 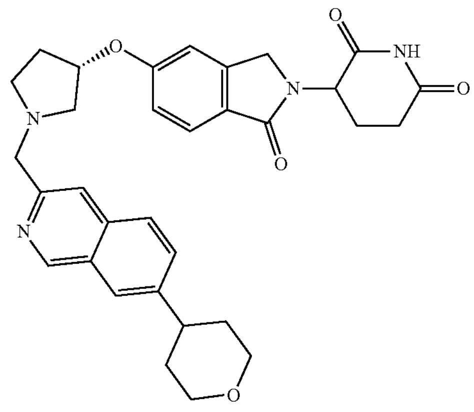 | 3-(1-oxo-5-(((S)-1-((7-(tetrahydro-2H-pyran-4-yl)isoquinolin-3-yl)methyl)pyrrolidin-3-yl)oxy)isoindolin-2-yl)piperidine-2,6-dione |
| 6 | 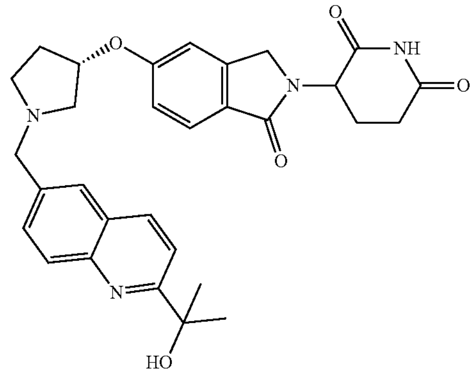 | 3-(5-(((S)-1-((2-(2-hydroxypropan-2-yl)quinolin-6-yl)methyl)pyrrolidin-3-yl)oxy)-1-oxoisoindolin-2-yl)piperidine-2,6-dione |
| 7 | 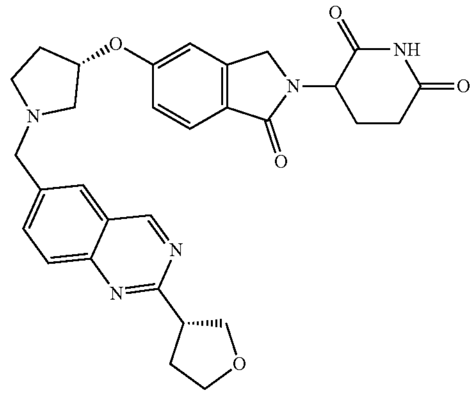 [SMILES: O=C1CCC(N2Cc3cc(O[C@H]4CCN(Cc5ccc6nc([C@H]7CCOC7)ncc6c5)C4)ccc3C2=O)C(=O)N1] | 3-(1-oxo-5-(((S)-1-((2-((R)-tetrahydrofuran-3-yl)quinazolin-6-yl)methyl)pyrrolidin-3-yl)oxy)isoindolin-2-yl)piperidine-2,6-dione |
| 8 | 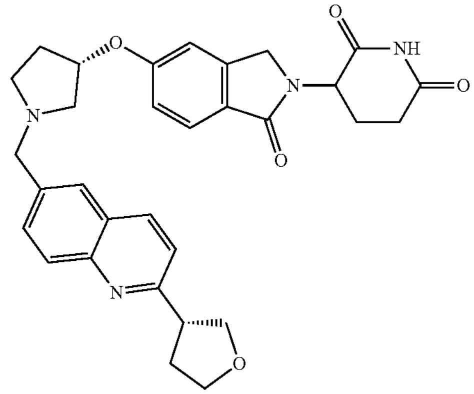 [SMILES: O=C1CCC(N2Cc3cc(O[C@H]4CCN(Cc5ccc6nc([C@H]7CCOC7)ccc6c5)C4)ccc3C2=O)C(=O)N1] | 3-(1-oxo-5-(((S)-1-((2-((R)-tetrahydrofuran-3-yl)quinolin-6-yl)methyl)pyrrolidin-3-yl)oxy)isoindolin-2-yl)piperidine-2,6-dione |

TABLE 1-continued
| Compound No. | Structure | Name |
|---|---|---|
| 9 | 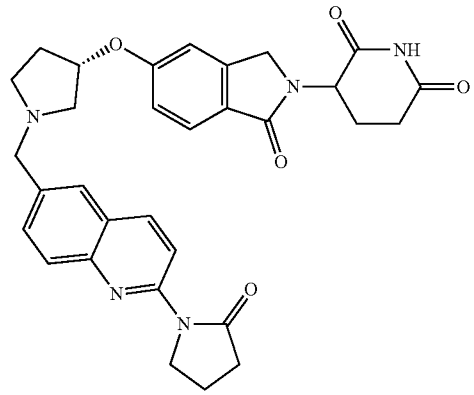 [SMILES: O=C1CCC(N2Cc3cc(O[C@H]4CCN(Cc5ccc6nc(N7CCCC7=O)ccc6c5)C4)ccc3C2=O)C(=O)N1] | 3-(1-oxo-5-(((S)-1-((2-(2-oxopyrrolidin-1-yl)quinolin-6-yl)methyl)pyrrolidin-3-yl)oxy)isoindolin-2-yl)piperidine-2,6-dione |
| 10 | 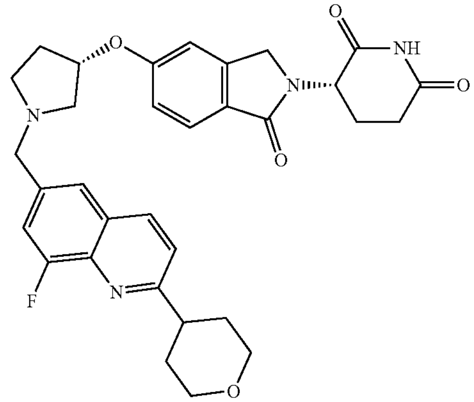 [SMILES: O=C1CC[C@H](N2Cc3cc(O[C@H]4CCN(Cc5cc(F)c6nc(C7CCOCC7)ccc6c5)C4)ccc3C2=O)C(=O)N1] | (S)-3-(5-(((S)-1-((8-fluoro-2-(tetrahydro-2H-pyran-4-yl)quinolin-6-yl)methyl)pyrrolidin-3-yl)oxy)-1-oxoisoindolin-2-yl)piperidine-2,6-dione |
| 11 | 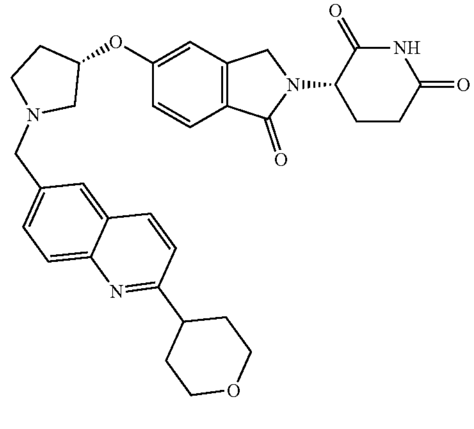 | (S)-3-(1-oxo-5-(((S)-1-((2-(tetrahydro-2H-pyran-4-yl)quinolin-6-yl)methyl)pyrrolidin-3-yl)oxy)isoindolin-2-yl)piperidine-2,6-dione |

TABLE 1-continued
| Compound No. | Structure | Name |
| --- | --- | --- |
| 12 | 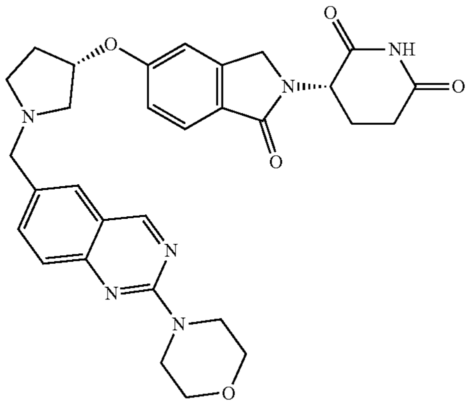 | (S)-3-(5-(((S)-1-((2-morpholinoquinazolin-6-yl)methyl)pyrrolidin-3-yl)oxy)-1-oxoisoindolin-2-yl)piperidine-2,6-dione |
| 13 | 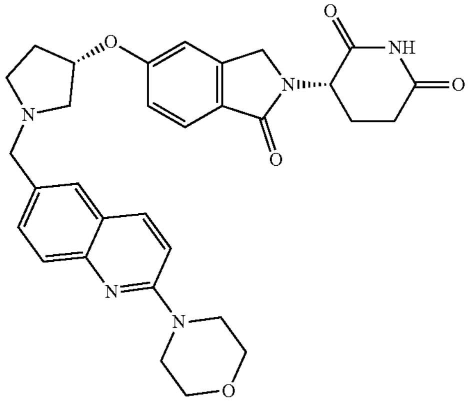 | (S)-3-(5-(((S)-1-((2-morpholinoquinolin-6-yl)methyl)pyrrolidin-3-yl)oxy)-1-oxoisoindolin-2-yl)piperidine-2,6-dione |
| 14 | 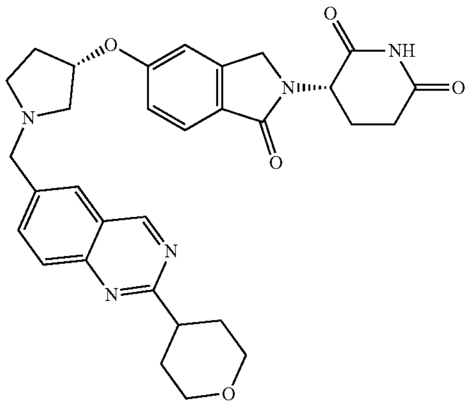 [SMILES: O=C1CC[C@H](N2Cc3cc(O[C@H]4CCN(Cc5ccc6nc(C7CCOCC7)ncc6c5)C4)ccc3C2=O)C(=O)N1] | (S)-3-(1-oxo-5-(((S)-1-((2-(tetrahydro-2H-pyran-4-yl)quinazolin-6-yl)methyl)pyrrolidin-3-yl)oxy)isoindolin-2-yl)piperidine-2,6-dione |

TABLE 1-continued

| Compound No. | Structure | Name |
|---|---|---|
| 15 | 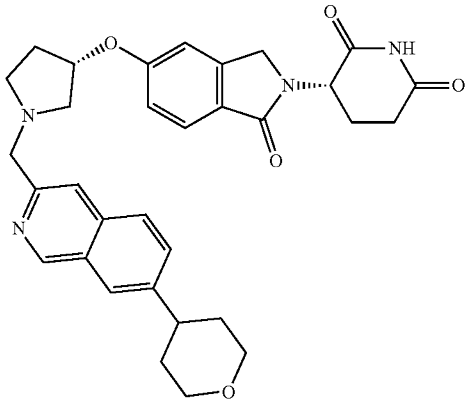 | (S)-3-(1-oxo-5-(((S)-1-((7-(tetrahydro-2H-pyran-4-yl)isoquinolin-3-yl)methyl)pyrrolidin-3-yl)oxy)isoindolin-2-yl)piperidine-2,6-dione |
| 16 | 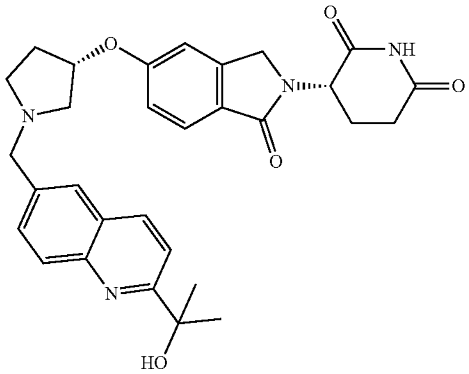 [SMILES: CC(C)(O)c1ccc2cc(CN3CC[C@H](Oc4ccc5c(c4)CN([C@H]4CCC(=O)NC4=O)C5=O)C3)ccc2n1] | (S)-3-(5-(((S)-1-((2-(2-hydroxypropan-2-yl)quinolin-6-yl)methyl)pyrrolidin-3-yl)oxy)-1-oxoisoindolin-2-yl)piperidine-2,6-dione |

or a pharmaceutically acceptable salt thereof.

It is understood that in the present description, combinations of substituents and/or variables of the depicted formulae are permissible only if such contributions result in stable compounds.

Furthermore, all compounds of Formula (I) that exist in free base or acid form can be converted to their pharmaceutically acceptable salts by treatment with the appropriate inorganic or organic base or acid by methods known to one skilled in the art. Salts of the compounds of Formula (I) can be converted to their free base or acid form by standard techniques.

Methods of Synthesis

The compounds described herein can be made using conventional organic syntheses and commercially available starting materials, or the methods provided herein. By way of example and not limitation, compounds of Formula (I) can be prepared as outlined in Schemes 1-3 and i1-i8, as well as in the examples set forth herein. It should be noted that one skilled in the art would know how to modify the procedures set forth in the illustrative schemes and examples to arrive at the desired products, including, for example, selecting starting materials having different stereochemistry (or racemic starting materials) to arrive at desired products having different stereochemistry.

In general, the compounds of Formula (I) can be obtained by reacting an aldehyde of interest to the amine in the pyrrolidine group of Formula (I). In some embodiments, the reaction of the aldehyde is the last step in the reaction sequence. See, e.g., Schemes 1 and 2 below. In some embodiments, the reaction of the aldehyde to the amine in the pyrrolidine group is performed in the middle of the reaction sequence. See, e.g., Scheme 3 below. Preparation of the aldehyde intermediates can be accomplished by, for example, synthetic routes shown in Schemes i1-i8. All reactions in the schemes below are at room temperature unless noted otherwise.

Scheme 1

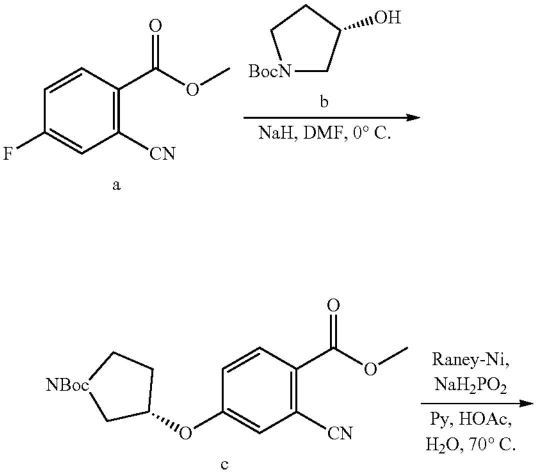

-continued

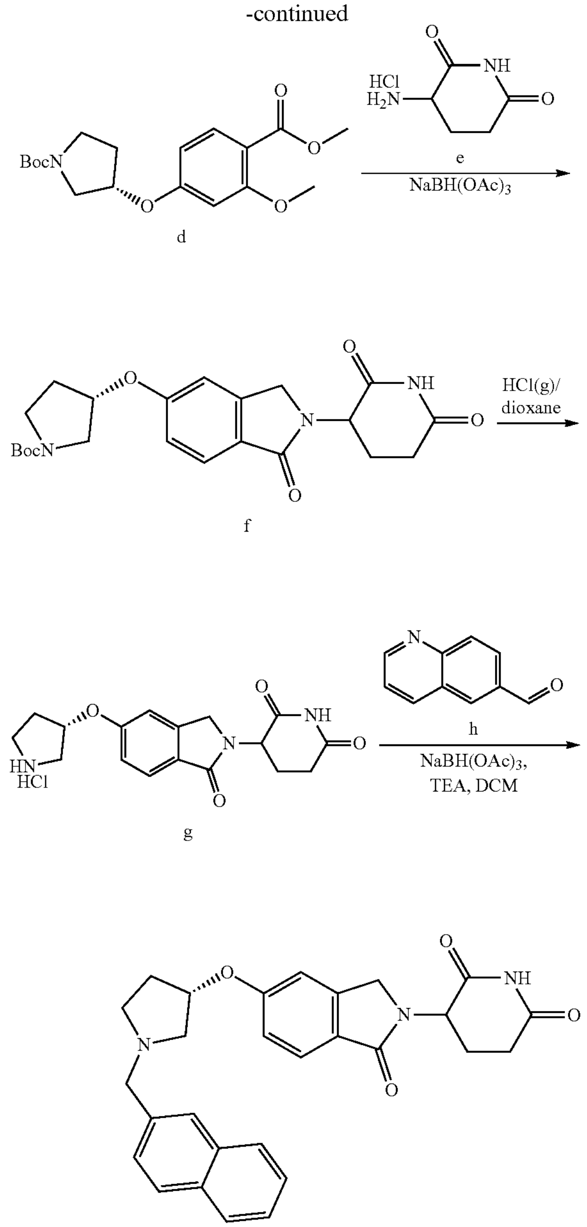

A

Scheme 2

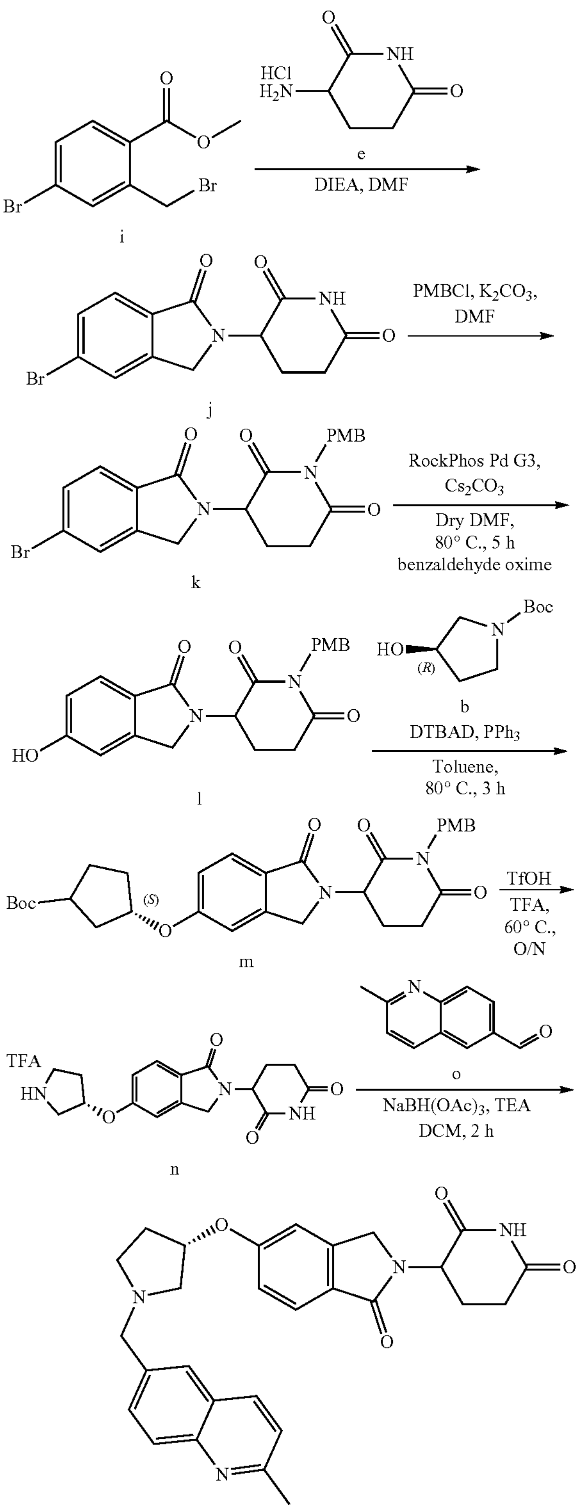

B

As outlined in Scheme 1, Compound A can be synthesized from condensation of starting material a and starting material b under basic conditions to generate intermediate c. The nitrile group of intermediate c can be reduced to an aldehyde, for example, with a Raney nickel catalyst, to form intermediate d, which can then be condensed with a glutarimide intermediate e in the presence of a reducing agent such as sodium triacetoxyborohydride to form intermediate f. Deprotection of the pyrrolidine in acidic conditions provides intermediate g, which can then be reductively alkylated with aldehyde h to yield Compound A. As noted above, one skilled in the art would know how to modify these procedures to arrive at the desired products beyond Compound A, including, for example, selecting starting materials having different stereochemistry (or racemic starting materials) to arrive at desired products having different stereochemistry from Compound A.

As outlined in Scheme 2, Compound B can be synthesized by coupling the glutarimide starting material e to starting material i to form intermediate j, which can then be protected to form intermediate k. Subsequent Pd-catalyzed substitution under basic conditions can provide intermediate 1, which via a Mitsunobu reaction with intermediate b can form intermediate m. Intermediate m can then be deprotected to form intermediate n and coupled with aldehyde o to yield Compound B. As noted above, one skilled in the art would know how to modify these procedures to arrive at the desired products beyond Compound B, including, for example, selecting starting materials having different stereochemistry (or racemic starting materials) to arrive at desired products having different stereochemistry from Compound B.

Scheme 3

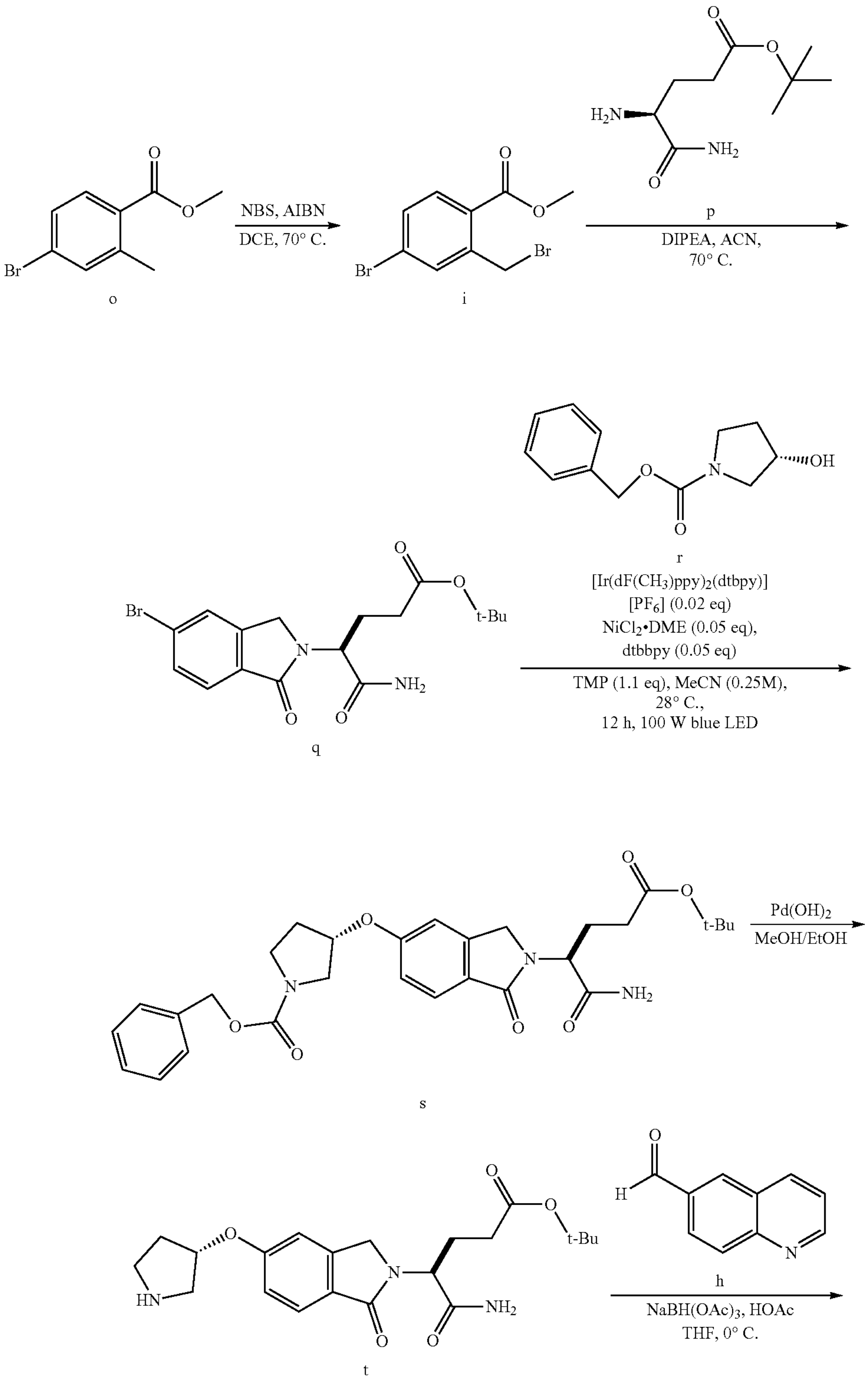

-continued

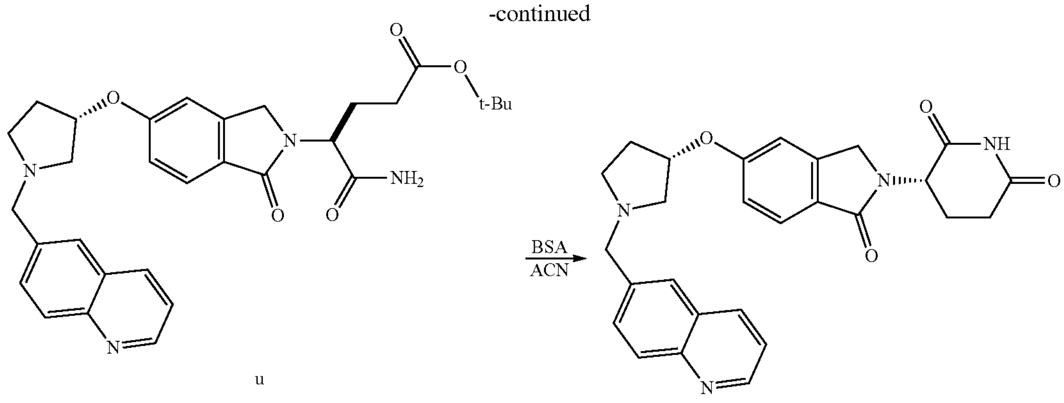

u

C

As outlined in Scheme 3, Compound C can be synthesized by brominating starting material i to form intermediate o, which can then be coupled with amide p to form intermediate q. Intermediate q can be coupled with intermediate r to form intermediate s, which can undergo a Pd-catalyzed hydrogenolysis to form intermediate t. Coupling of aldehyde h to intermediate t can form intermediate u, which can subsequently undergo a cyclization reaction to yield Compound C. As noted above, one skilled in the art would know how to modify these procedures to arrive at the desired products beyond Compound C, including, for example, selecting starting materials having different stereochemistry (or racemic starting materials) to arrive at desired products having different stereochemistry from Compound C. Indeed, Compound C is a single stereoisomer of Compound A in Scheme 1.

Aldehyde intermediates that can be used in synthesizing the compounds of Formula (I) can be prepared as outlined in Schemes i1-i8, as well as in the examples set forth herein. It should be noted that one skilled in the art would know how to modify the procedures set forth in the illustrative schemes and examples to arrive at the desired products.

Scheme i1

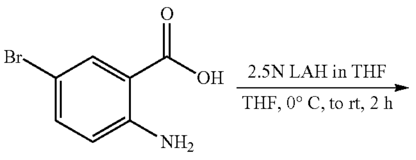

ia

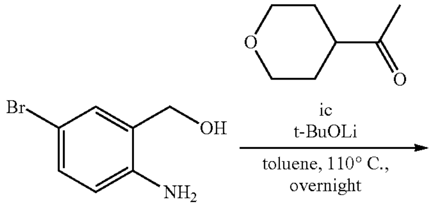

ib

-continued

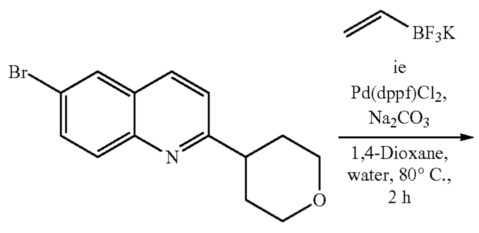

id

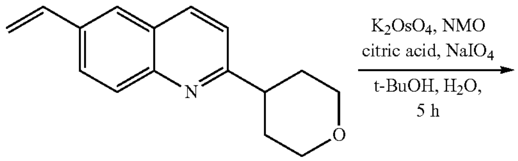

if

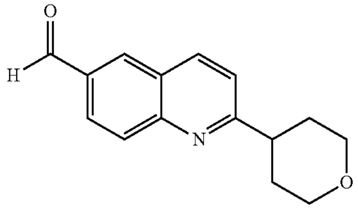

iA

As outlined in Scheme il, Aldehydes such as Aldehyde iA can be synthesized by reducing starting material is to form intermediate ib, which can be condensed with intermediate is under basic conditions to form intermediate id that contains a fused conjugated ring system. Pd-catalyzed Suzuki coupling of intermediate id with intermediate ie can form intermediate if, in which the alkene of intermediate if can undergo oxidation to form Aldehyde iA.

Scheme i2

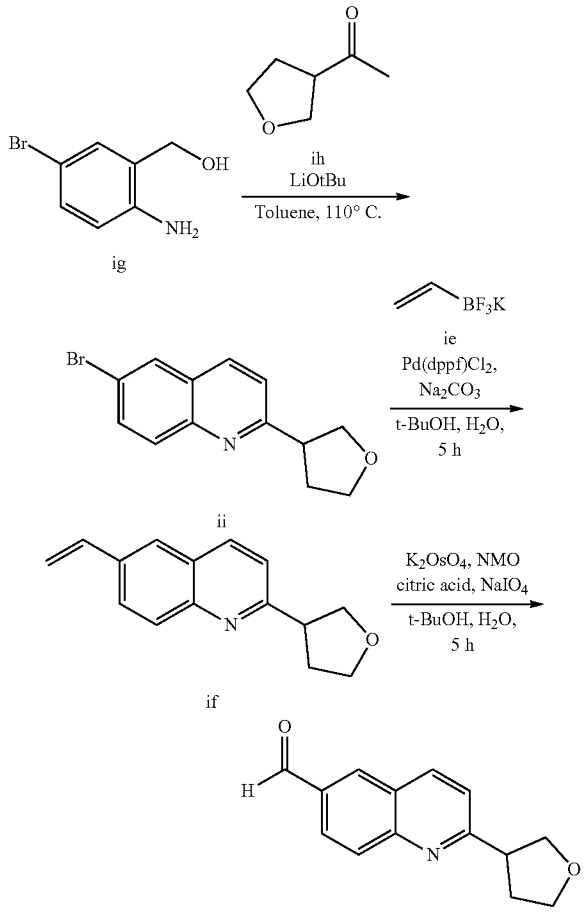

iB

As outlined in Scheme i2, Aldehyde iB can be synthesized by coupling starting material ig with starting material ih under basic conditions to form intermediate ii, which can subsequently undergo Pd-catalyzed Suzuki coupling with intermediate ie to form intermediate if. Oxidation of the alkene of intermediate if can provide Aldehyde iB.

Scheme i3

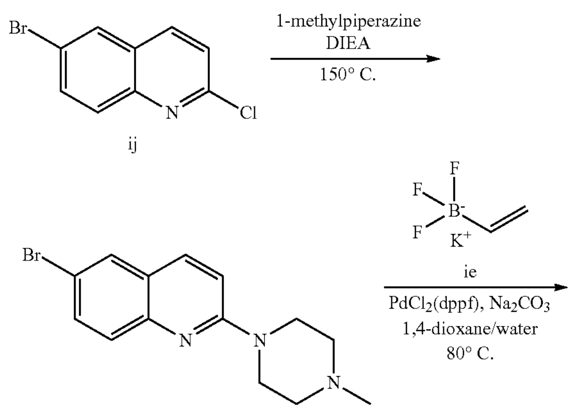

ik

-continued

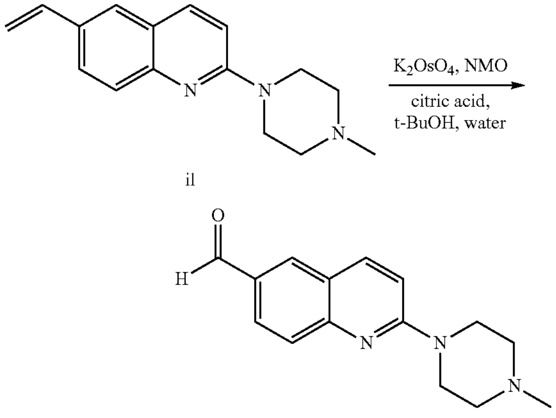

iC

As outlined in Scheme i3, Aldehyde iC can be synthesized by conjugating starting material ij with amine such as 1-methylpiperazine to form intermediate ik, followed by Pd-catalyzed Suzuki coupling with intermediate ie to form intermediate il, which can then undergo oxidation to form Aldehyde iC. The quinazoline equivalent to Aldehyde iC can be prepared following Scheme i3, but starting with a quinazoline equivalent to starting material ij.

Scheme i4

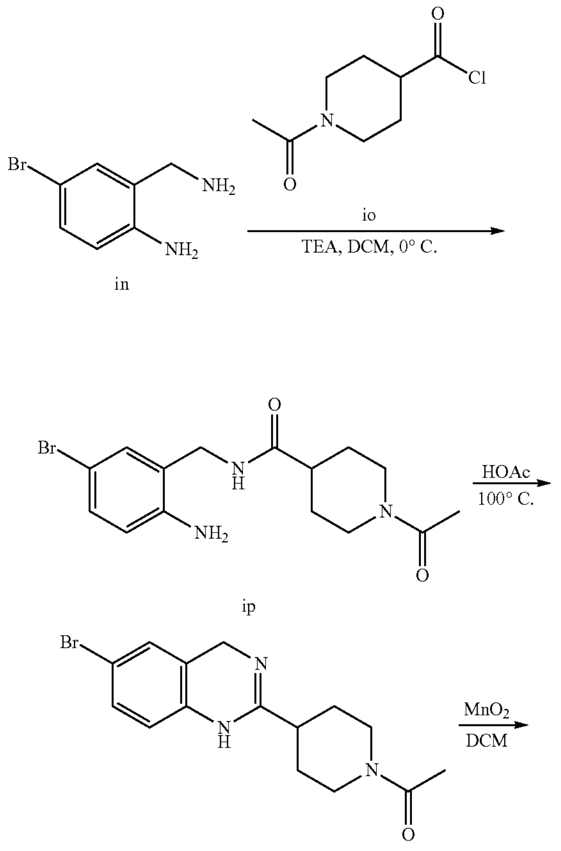

iq

-continued

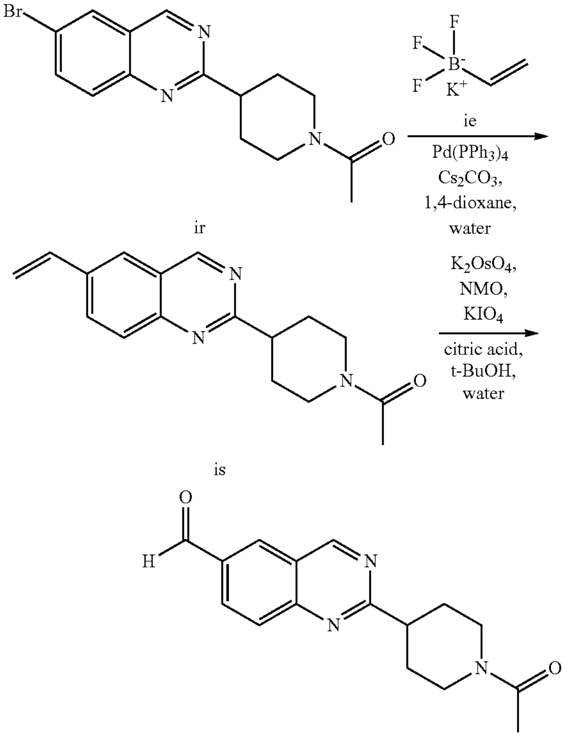

ir is iD

As outlined in Scheme i4, Aldehyde iD can be synthesized by coupling starting material in and starting material io to form intermediate ip, which can then undergo an intramolecular condensation to form intermediate iq. Oxidation of intermediate iq can form intermediate ir, which can then be coupled with alkene intermediate ie to form intermediate is. Oxidation of the alkene provides Aldehyde iD.

Scheme i5

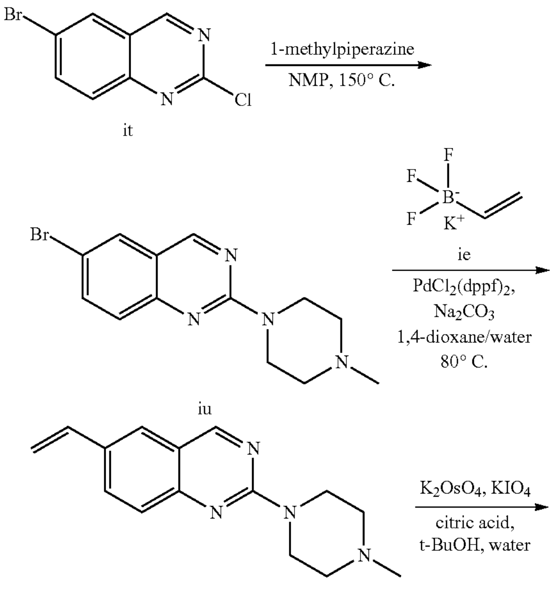

it iu iv

-continued

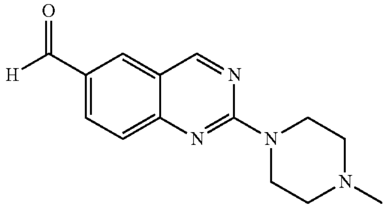

iE

As outlined in Scheme i5, Aldehyde iE can be synthesized by conjugating starting material it with amines such as 1-methylpiperazine to form intermediate iu, followed by Pd-catalyzed Suzuki coupling with intermediate ie to form intermediate iv, which can then be oxidized to yield Aldehyde iE.

Scheme i6

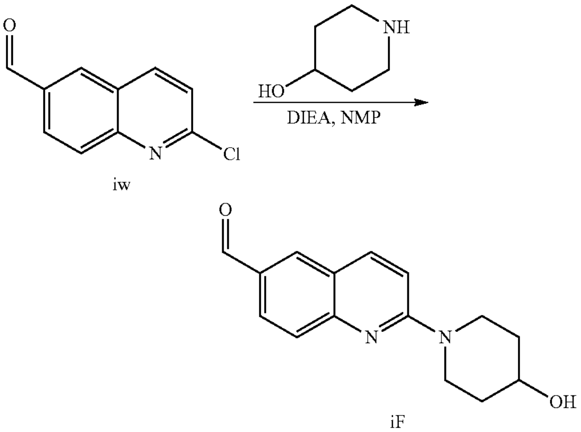

iw iF

As outlined in Scheme i6, Aldehyde iF can be synthesized by conjugating intermediate iw with amines such as piperidin-4-ol to yield Aldehyde iF.

Scheme i7

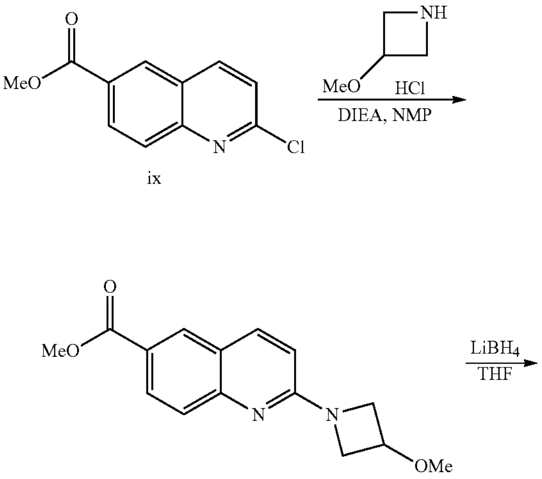

ix iy

-continued

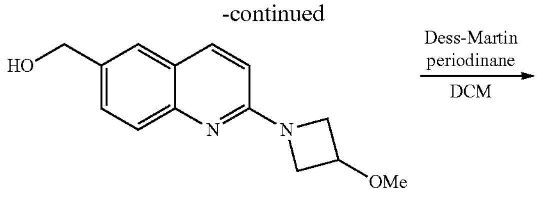

iz

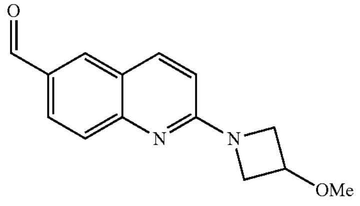

iG

As outlined in Scheme i7, Aldehyde iG can be synthesized by conjugating starting material ix with amines such as 3-methoxyazetidine to yield intermediate iy. Intermediate iy can then be reduced using lithium borohydride, for example, to afford intermediate iz, which can then be subjected to a Dess-Martin oxidation to provide Aldehyde iG.

Scheme i8

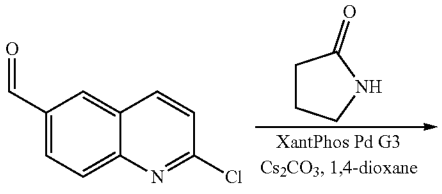

ia'

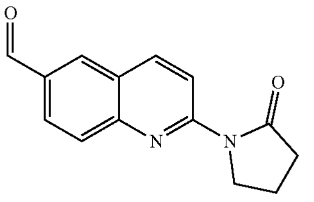

iH

As outlined in Scheme i8, Aldehyde iG can be synthesized by coupling starting material ia' with pyrrolidine-2-one to yield Intermediate iH.

Methods of Use

Embodiments of the present disclosure provide a method for degrading WEE1, a method for reducing WEE1 proteins levels, and a method of preventing or treating diseases such as cancer in a subject in need thereof.

In one aspect, provided herein is a method for degrading WEE1 in a subject in need thereof, the method comprising contacting a cell with an effective amount of a compound of Formula (I). Degradation of WEE1 can be assessed and demonstrated by a wide variety of methods known in the art. Kits and commercially available assays, including cell-based assays, can be utilized for determining whether and to what degree WEE1 has been degraded. In some embodiments, the compound of Formula (I) partially degrades WEE1. In some embodiments, the compound of Formula (I) fully degrades WEE1.

In some embodiments, a compound of Formula (I) degrades WEE1 by about 1%, 5%, 10%, 15%, 20%, 25%, 30%, 35%, 40%, 45%, 50%, 55%, 60%, 65%, 70%, 75%, 80%, 85%, 90%, 95%, or 100%. In some embodiments, a compound of Formula (I) degrades WEE1 by about 1-100%, 5-100%, 10-100%, 15-100%, 20-100%, 25-100%, 30-100%, 35-100%, 40-100%, 45-100%, 50-100%, 55-100%, 60-100%, 65-100%, 70-100%, 75-100%, 80-100%, 85-100%, 90-100%, 95-100%, 5-95%, 5-90%, 5-85%, 5-80%, 5-75%, 5-70%, 5-65%, 5-60%, 5-55%, 5-50%, 5-45%, 5-40%, 5-35%, 5-30%, 5-25%, 5-20%, 5-15%, 5-10%, 10-90%, 20-80%, or 40-60%.

In some embodiments, provided herein is a method for reducing WEE1 kinase protein levels, the method comprising contacting a cell with an effective amount of a compound of Formula (I). Reduction of WEE1 kinase protein levels can be assessed and demonstrated by a wide variety of methods known in the art. Kits and commercially available assays, including cell-based assays, can be utilized for determining whether and to what degree kinase protein levels have been reduced.

In some embodiments, a compound of Formula (I) reduces WEE1 kinase protein levels by about 1%, 5%, 10%, 15%, 20%, 25%, 30%, 35%, 40%, 45%, 50%, 55%, 60%, 65%, 70%, 75%, 80%, 85%, 90%, 95%, or 100%. In some embodiments, a compound of Formula (I) reduces WEE1 kinase protein levels by about 1-100%, 5-100%, 10-100%, 15-100%, 20-100%, 30-100%, 35-100%, 40-100%, 45-100%, 50-100%, 55-100%, 60-100%, 65-100%, 75-100%, 80-100%, 85-100%, 90-100%, 95-100%, 5-95%, 5-90%, 5-85%, 5-80%, 5-75%, 5-70%, 5-65%, 5-60%, 5-55%, 5-50%, 5-45%, 5-40%, 5-35%, 5-30%, 5-25%, 5-20%, 5-15%, 5-10%, 10-90%, 20-80%, 30-70%, or 40-60%.

In some embodiments, a compound of Formula (I) has an $EC_{50}$ value as measured in a WEE1 degradation assay of from about 0.0003 μM to about 1 μM or from about 0.0003 μM to about 0.2 μM or from about 0.0003 μM to about 0.05 μM. In some embodiments, a compound of Formula (I) has an $EC_{50}$ of from about 0.05 μM to about 0.2 μM. In some embodiments, a compound of Formula (I) has an $EC_{50}$ of from about 0.2 μM to about 1 μM. In some embodiments, a compound of Formula (I) has an EC50 of less than about 1 μM. In some embodiments, a compound of Formula (I) has an EC50 value of less than 0.2 μM, less than 0.05 μM, less than 0.001 μM, or less than about 0.0003 μM.

In another aspect, provided herein is a method for treating cancer in a subject in need thereof, comprising administering to the subject an effective amount of a compound of Formula (I). In some embodiments, provided herein is a method for preventing cancer in a subject in need thereof, comprising administering to the subject an effective amount of a compound of Formula (I). In some embodiments, the cancer is selected from a brain cancer, a cervicocerebral cancer, an esophageal cancer, a thyroid cancer, small cell cancer, a non-small cell cancer, a breast cancer, a lung cancer, a stomach cancer, gallbladder/bile duct cancer, a liver cancer, a pancreatic cancer, a colon cancer, a rectal cancer, an ovarian cancer, a choriocarcinoma, an uterus body cancer, an uterocervical cancer, a renal pelvis/ureter cancer, a bladder cancer, a prostate cancer, a penis cancer, a testicular cancer, a fetal cancer, Wilms' cancer, a skin cancer, malignant melanoma, a neuroblastoma, an osteosarcoma, an Ewing's tumor, a soft part sarcoma, an acute leukemia, a chronic lymphatic leukemia, a chronic myelocytic leukemia, polycythemia vera, a malignant lymphoma, multiple myeloma, a Hodgkin's lymphoma, and a non-Hodgkin's lymphoma.

In some embodiments, the cancer is selected from gastric, lung, pancreatic, ovarian, breast, skin, colon, neuroblastoma, osteosarcoma, uterine, rectal, and kidney cancer. In some embodiments, the cancer is selected from pancreatic ductal adenocarcinoma (PDAC), small cell lung cancer, non-small cell lung cancer (NSCLC), high grade serous ovarian cancer, triple negative breast cancer, uterine serous carcinoma, Ewing's sarcoma, melanoma, colon, and clear cell renal cell carcinoma (ccRCC).

In some embodiments, administering a compound of Formula (I) to a subject that is predisposed to cancer prevents the subject from developing any symptoms of the cancer (such as tumor growth or metastasis). In some embodiments, administering a compound of Formula (I) to a subject that does not yet display symptoms of cancer prevents the subject from developing any symptoms of the cancer. In some embodiments, administering a compound of Formula (I) to a subject in need thereof diminishes the extent of the cancer in the subject. In some embodiments, administering a compound of Formula (I) to a subject in need thereof stabilizes the cancer (prevents or delays the worsening of the cancer). In some embodiments, administering a compound of Formula (I) to a subject in need thereof delays the occurrence or recurrence of the cancer. In some embodiments, administering a compound of Formula (I) to a subject in need thereof slows the progression of the cancer. In some embodiments, administering a compound of Formula (I) to a subject in need thereof provides a partial remission of the cancer. In some embodiments, administering a compound of Formula (I) to a subject in need thereof provides a total remission of the cancer. In some embodiments, administering a compound of Formula (I) to a subject in need thereof decreases the dose of one or more other medications required to treat the cancer. In some embodiments, administering a compound of Formula (I) to a subject in need thereof enhances the effect of another medication used to treat the cancer. In some embodiments, administering a compound of Formula (I) to a subject in need thereof delays the progression of the cancer. In some embodiments, administering a compound of Formula (I) to a subject in need thereof increases the quality of life of the subject having cancer. In some embodiments, administering a compound of Formula (I) to a subject in need thereof prolongs survival of a subject having cancer.

In one aspect, provided herein is method of preventing a subject that is predisposed to cancer from developing cancer, the method comprising administering a compound of Formula (I) to the subject.

In some aspects, provided herein is a method of diminishing the extent of cancer in a subject, the method comprising administering a compound of Formula (I) to the subject. In some embodiments, provided herein is a method of stabilizing cancer in a subject, the method comprising administering a compound of Formula (I) to the subject. In some embodiments, the method prevents the worsening of the cancer.

In another aspect, provided herein is a method of delaying the occurrence or recurrence of cancer in a subject, the method comprising administering a compound of Formula (I) to the subject.

In some embodiments, provided herein is a method of slowing the progression of cancer in a subject, the method comprising administering a compound of Formula (I) to the subject. In some embodiments, the method provides a partial remission of the cancer. In some embodiments, the method provides a total remission of the cancer.

In further aspects, provided herein is a method of decreasing the dose of one or more other medications required to treat cancer in a subject, the method comprising administering a compound of Formula (I) to the subject. In some embodiments, provided herein is a method of enhancing the effect of another medication used to treat cancer in a subject, the method comprising administering a compound of Formula (I) to the subject.

Also provided here is a method of delaying the progression of cancer in a subject, the method comprising administering a compound of Formula (I) to the subject. In some embodiments, the method increases the quality of life of the subject having cancer. In some embodiments, the method prolongs survival of the subject having cancer.

In some embodiments, compounds of Formula (I) are useful in the manufacture of a medicament for reducing WEE1 kinase protein levels. In some embodiments, compounds of Formula (I) are useful in the manufacture of a medicament for the prevention or treatment of a disease associates with WEE1. In some embodiments, compounds of Formula (I) are useful in the manufacture of a medicament for the prevention or treatment of cancer. In some embodiments, the cancer is selected from gastric, lung, pancreatic, ovarian, breast, skin, colon, neuroblastoma, osteosarcoma, uterine, rectal, and kidney cancer. In some embodiments, the cancer is selected from pancreatic ductal adenocarcinoma (PDAC), small cell lung cancer, non-small cell lung cancer (NSCLC), high grade serous ovarian cancer, triple negative breast cancer, uterine serous carcinoma, Ewing's sarcoma, melanoma, colon, and clear cell renal cell carcinoma (ccRCC).

The methods and uses of the present disclosure may include a compound of Formula (I) used alone or in combination with one or more additional therapies (e.g., non-drug treatments or therapeutic agents).

A compound of Formula (I) may be administered before, after, or concurrently with one or more of such additional therapies. When combined, dosages of the compound of Formula (I) and dosages of the one or more additional therapies (e.g., non-drug treatment or therapeutic agent) may provide a therapeutic effect (e.g., synergistic or additive therapeutic effect). A compound of Formula (I) and an additional therapy, such as an anti-cancer agent, may be administered together, such as in a unitary pharmaceutical composition, or separately and, when administered separately, this may occur simultaneously or sequentially. Such sequential administration may be close or remote in time.

In some embodiments, the additional therapy is the administration of side-effect limiting agents (e.g., agents intended to lessen the occurrence or severity of side effects of treatment). For example, in some embodiments, the compounds of Formula (I) can be used in combination with a therapeutic agent that treats nausea. Examples of agents that can be used to treat nausea include, but are not limited to, dronabinol, granisetron, metoclopramide, ondansetron, prochlorperazine, and pharmaceutically acceptable salts thereof.

In some embodiments, one or more additional therapies includes a non-drug treatment (e.g., surgery or radiation therapy). In some embodiments, one or more additional therapies includes a therapeutic agent (e.g., a compound or biologic that is an antiproliferative agent). In some embodiments, one or more additional therapies includes a non-drug treatment and a therapeutic agent. In other embodiments, one or more additional therapies includes two therapeutic agents. In still other embodiments, one or more additional therapies includes three therapeutic agents. In some embodiments, one or more additional therapies includes four or more therapeutic agents.

Pharmaceutical Compositions and Routes of Administration

The compounds provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions.

The compounds disclosed herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfate, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the compounds of Formula (I) in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a compound of Formula (I) to be administered to a subject is rather widely variable and can be subject to the judgment of a health-care practitioner. In general, the compounds disclosed herein can be administered one to four times a day in a dose of about 0.001 mg/kg of a subject's body weight to about 10 mg/kg of a subject's body weight, but the above dosage may be properly varied depending on the age, body weight and medical condition of the subject and the type of administration. In one embodiment, the dose is about 0.001 mg/kg of a subject's body weight to about 5 mg/kg of a subject's body weight, about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the compound of Formula (I) administered will depend on such factors as the solubility of the active component, the formulation used, and the route of administration.

In some embodiments, a compound of Formula (I) is administered to a subject at a dose of about 0.01 mg/day to about 750 mg/day, about 0.1 mg/day to about 375 mg/day, about 0.1 mg/day to about 150 mg/day, about 0.1 mg/day to about 75 mg/day, about 0.1 mg/day to about 50 mg/day, about 0.1 mg/day to about 25 mg/day, or about 0.1 mg/day to about 10 mg/day.

In another embodiment, provided herein are unit dosage formulations that comprise between about 0.1 mg and 500 mg, about 1 mg and 250 mg, about 1 mg and about 100 mg, about 1 mg and about 50 mg, about 1 mg and about 25 mg, or between about 1 mg and about 10 mg of a compound of Formula (I).

In a particular embodiment, provided herein are unit dosage formulations comprising about 0.1 mg or 100 mg of a compound of Formula (I).

In another embodiment, provided herein are unit dosage formulations that comprise 0.5 mg, 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg, or 1400 mg of a compound of Formula (I).

A compound of Formula (I) can be administered once, twice, three, four or more times daily. As a nonlimiting example, doses of 100 mg or less are administered as a once daily dose and doses of more than 100 mg are administered twice daily in an amount equal to one half of the total daily dose.

A compound of Formula (I) can be administered orally for reasons of convenience. In one embodiment, when administered orally, a compound of Formula (I) is administered with a meal and water. In another embodiment, the compound of Formula (I) is dispersed in water or juice (e.g., apple juice or orange juice) or any other liquid and administered orally as a solution or a suspension.

The compounds disclosed herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a compound of Formula (I) without an additional carrier, excipient or vehicle.

In another embodiment, provided herein are compositions comprising an effective amount of a compound of Formula (I) and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories, spray dried dispersions, and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a compound of Formula (I) with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants, and disintegrators as well as the compound. Typical diluents include, for example, various types of starch, lactose, mannitol, kaolin, calcium phosphate or sulfate, inorganic salts such as sodium chloride, and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose, and waxes can also serve as binders.

A lubricant might be necessary in a tablet formulation to prevent the tablet and punches from sticking in the dye. The lubricant can be selected from such slippery solids as talc, magnesium and calcium stearate, stearic acid, and hydrogenated vegetable oils. Tablet disintegrators are substances that swell when wetted to break up the tablet and release the compound. They include starches, clays, celluloses, algins, and gums. More particularly, corn and potato starches, methylcellulose, agar, bentonite, wood cellulose, powdered natural sponge, cation-exchange resins, alginic acid, guar gum, citrus pulp, and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a compound of Formula (I) as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the compound of Formula (I) can be delayed or prolonged by proper formulation. For example, a slowly soluble pellet of the compound of Formula (I) can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound of Formula (I) in oily or emulsified vehicles that allow it to disperse slowly in the serum.

EXAMPLES

The following Examples are presented by way of illustration, not limitation. One skilled in the art can modify the procedures set forth in the illustrative examples to arrive at the desired products.

Salts of the compounds described herein can be prepared by standard methods, such as inclusion of an acid (for example TFA, formic acid, or HCl) in the mobile phases during chromatography purification, or stirring of the products after chromatography purification, with a solution of an acid (for example, aqueous HCl).

All reactions are at room temperature unless noted otherwise.

The following abbreviations may be relevant for the application.

Abbreviations

| | |
|---|---|
| Boc | tert-butyloxycarbonyl |
| AIBN | azobisisobutyronitrile |
| ACN | acetonitrile |
| BSA | bis(trimethylsilyl)acetamide |
| DCE | 1,2-dichloroethane |
| DCM | dichloromethane |
| DIEA | N,N-diisopropylethylamine |
| DIPEA | N,N-diisopropylethylamine |
| DME | dimethyl ether |
| DMF | dimethyl formamide |
| DMSO | dimethyl sulfoxide |
| DTBAD | di-tert-butyl azodicarboxylate |
| Dtbbpy | 4,4'-di-tert-butyl-2,2'-bipyridine |
| equiv | equivalent |
| ESI | electrospray ionization |
| EtOH | ethanol |
| FA | formic acid |
| h | hour |
| HATU | O-(7-azabenzotriazol-1-yl)-N,N,N',N'-tetramethyluronium hexafluorophosphate |
| HCl | hydrochloric acid |
| HOAc | Acetic acid |
| HPLC | high performance liquid chromatography |
| LAH | lithium aluminum hydride |
| LED | light-emitting diode |
| LiOtBu | lithium tert-butoxide |
| MeCN | acetonitrile |
| MeOH | methanol |
| min | minute |
| MS | mass spectrometry |
| NBS | N-bromo succinimide |
| NMO | 4-methylmorpholine 4-oxide |
| NMP | N-methyl-2-pyrrolidone |
| NMR | nuclear magnetic resonance |
| PivOH | pivalic acid |
| PMBCl | 4-methoxybenzyl chloride |
| Py | pyridine |
| rt | room temperature |
| RT | retention time |
| sat. | saturated |
| t-BuOH | tert-butyl alcohol |
| t-BuOLi | lithium tert-butoxide |
| TEA | triethylamine |
| TFA | trifluoroacetic acid |
| TfOH | triflic acid |
| THF | tetrahydrofuran |
| TLC | thin layer chromatography |
| TMP | 2,2,6,6-tetramethylpiperidine |

SYNTHETIC EXAMPLES

As will be apparent to one skilled in the art, the compounds disclosed below and in Tables 1 and 2 can exist in various stereochemical forms. Where stereochemistry is shown for the ether linkage between the pyrrolidine and isoindolinone as well as stereochemistry shown between the piperidine-dione to the isoindolinone in the compounds in the Examples and Tables 1 and 2, the stereochemistry is absolute. Other stereocenters in which stereochemistry is shown and indicated as R or S, for example, in the B and R''' groups in Formula (I), may be relative stereochemistry.

Example S1. 3-(5-(((S)-1-((2-Methylquinazolin-6-yl)methyl)pyrrolidin-3-yl)oxy)-1-oxoisoindolin-2-yl)piperidine-2,6-dione

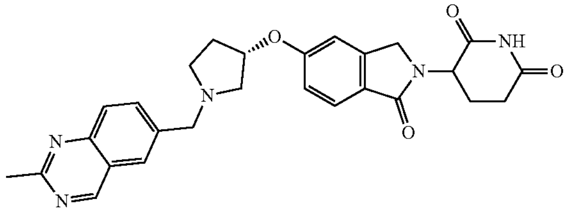 [SMILES: Cc1ncc2cc(CN3CC[C@H](Oc4ccc5c(c4)CN(C4CCC(=O)NC4=O)C5=O)C3)ccc2n1]

N-(4-bromo-2-formylphenyl)acetamide. To a solution of 2-amino-5-bromobenzaldehyde (1.5 g, 7.50 mmol) in acetic anhydride (30 mL) was stirred at 50° C. for 2 h under nitrogen. The precipitated solids were collected by filtration and washed with ethyl acetate (3×50 mL) to afford the title compound (1.7 g, 7.02 mmol, 94% yield) as a light yellow solid. MS (ESI) m/z 242.1 $[M+1]^+$.

6-Bromo-2-methylquinazoline. To a solution of N-(4-bromo-2-formyl-pheny-1)acetamide (1.7 g, 7.03 mmol) in ethanol (20 mL) was added ammonia (7 M in ethanol, 2 mL, 14 mmol) and the mixture was stirred for 12 h at 140° C. under nitrogen. The mixture was concentrated, and the crude product was recrystallized from 90% hexane in ethyl acetate to afford the title compound (1.5 g, 6.72 mmol, 96% yield) as a yellow solid. MS (ESI) m/z 223.1$[M+1]^+$.

2-Methyl-6-vinylquinazoline. To a solution of the compound 6-bromo-2-methylquinazoline (1.0 g, 4.48 mmol), tributyl(vinyl)stannane (1.7 g, 5.38 mmol) in 1,4-dioxane (10 mL) was added bis(triphenylphosphine)palladium(II) chloride (629 mg, 0.90 mmol) and cesium fluoride (2.0 g, 13.17 mmol) and the mixture was stirred for 3 h at 100° C. under nitrogen. The resulting mixture was added water and extracted with ethyl acetate. The extracts were washed with brine, dried over anhydrous sodium sulfate, filtered and concentrated. The residue was purified by silica gel chromatography (0 to 30% ethyl acetate in petroleum ether) to afford the title compound (450 mg, 2.64 mmol, 59% yield) as a light-yellow solid. MS (ESI) m/z 171.1 $[M+1]^+$.

2-Methylquinazoline-6-carbaldehyde. To a solution of 2-methyl-6-vinyl-quinazoline (450 mg, 2.64 mmol), 4-methylmorpholine N-oxide (619 mg, 5.29 mmol) and citric acid (1.0 g, 5.29 mmol) in tert-butanol (5 mL) and water (5 mL) was added potassium osmate (97 mg, 0.26 mmol) and the mixture was stirred for 5 h at room temperature. The mixture was added sodium periodate (1.7 g, 7.93 mmol) and stirred for another 1 h. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (220 mg, 1.28 mmol, 48% yield) as a light yellow solid. MS (ESI) m/z 173.1$[M+1]^+$.

3-(5-(((S)-1-((2-Methylquinazolin-6-yl)methyl)pyrrolidin-3-yl)oxy)-1-oxoiso-indol-in-2-yl)piperidine-2,6-dione. To a solution of 3-[1-oxo-5-[(3S)-pyrrolidin-3-yl]oxy-isoindolin-2-yl]piperidine-2,6-dione; hydrochloride (120 mg, 0.33 mmol), 2-methylquinazoline-6-carbaldehyde (79 mg, 0.46 mmol) and triethylamine (50 mg, 0.49 mmol) in dichloromethane (10 mL) was added sodium triacetoxyborohydride (278 mg, 1.31 mmol) and the mixture was stirred for 12 h at room temperature. The resulting solution was concentrated and the residue was purified by silica gel chromatography (0-10% methanol in dichloromethane) and recrystallized from n-hexane/dichloromethane to afford the title compound (66.5 mg, 0.14 mmol, 41% yield) as an off-white solid. $^1H$ NMR (400 MHz, DMSO-$d_6$) δ 10.97 (s, 1H), 9.49 (s, 1H), 8.02 (s, 1H), 7.95 (d, J=8.8 Hz, 1H), 7.88 (d, J=8.7 Hz, 1H), 7.61 (d, J=8.4 Hz, 1H), 7.12 (s, 1H), 7.01 (d, J=8.5 Hz, 1H), 5.07 (m, 2H), 4.37 (d, J=17.2 Hz, 1H), 4.25 (d, J=17.2 Hz, 1H), 3.85 (s, 2H), 2.99-2.90 (m, 2H), 2.76 (m, 5H), 2.59 (m, 2H), 2.37 (m, 2H), 1.98-1.80 (m, 3H); MS (ESI) m/z 486.2 $[M+1]^+$.

Example S2. 3-(5-(((3S,4S)-4-Methyl-1-((2-methylquinolin-6-yl)methyl)pyrrolidin-3-yl)oxy)-1-oxoisoindolin-2-yl)piperidine-2,6-dione

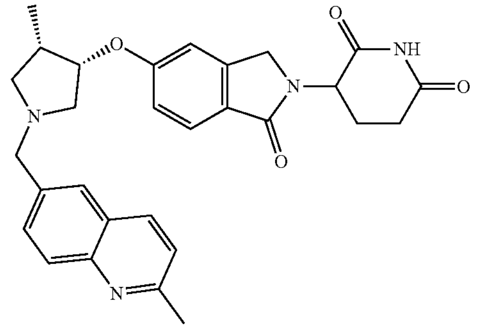 [SMILES: Cc1ccc2cc(CN3C[C@H](C)[C@H](Oc4ccc5c(c4)CN(C4CCC(=O)NC4=O)C5=O)C3)ccc2n1]

Tert-butyl (3S,4S)-34(2-(1-(4-methoxybenzyl)-2,6-dioxopiperidin-3-yl)-1-oxoisoindolin-5-yl)oxy)-4-methylpyrrolidine-1-carboxylate. To a vacuum purged solution of 3-(5-bromo-1-oxoisoindolin-2-yl)-1-(4-methoxybenzyl)piperidine-2,6-dione (200 mg, 0.45 mmol), tert-butyl (3S,4S)-3-hydroxy-4-methylpyrrolidine-1-carboxylate (182 mg, 0.90 mmol), (4,4'-di-t-butyl-2,2'-bipyridine)bis[3,5-difluoro-2-[5-trifluoromethyl-2-pyridinyl-kN)-phenyl-kC] iridium(III) hexafluorophosphate (5 mg, 0.005 mmol), quinuclidine (13 mg, 0.11 mmol), potassium carbonate (91 mg, 0.90 mmol), nickel(II) chloride, dimethoxyethane adduct (5 mg, mmol) and 4,4'-di-tert-butyl-2,2'-bipyridine (6 mg, 0.02 mmol) in 1,2-dimethoxyethane (2 mL) was evacuated and flushed three times with nitrogen before being irradiated with three 34 W blue LEDs. The reaction was stirred for 12 h at room temperature under nitrogen. The resulting mixture was added water and extracted with ethyl acetate. The extracts were washed with brine, dried over anhydrous sodium sulfate, filtered and concentrated. The residue was purified by silica gel chromatography (0-10% methanol in dichloromethane) to afford the title compound (70 mg, 0.12 mmol, 24% yield) as a light-yellow oil. MS (ESI) m/z 586.4 [M+23]+.

3-(5-(((3S,4S)-4-Methylpyrrolidin-3-yl)oxy)-1-oxoisoindolin-2-yl)piperidine-2,6-dione; 2,2,2-trifluoroacetic acid. To a stirred solution of tert-butyl (3S, 4S)-3-[2-[1-[(4-methoxyphenyl)methyl]-2,6-dioxo-3-piperidyl]-1-oxo-isoindolin-5-yl]oxy-4-methyl-pyrrolidine-1-carboxylate (70 mg, 0.12 mmol) in TFA (1.5 mL) was added trifluoromethanesulfonic acid (0.1 mL). The solution was stirred for 12 h at 50° C. under nitrogen. The mixture was concentrated. The pH of the residue was adjusted with sodium bicarbonate to pH~5, filtered and the filtrate was purified by reverse flash (10-40% acetonitrile+0.05% TFA in water, over min) to afford the title compound (40 mg, 0.087 mmol, 73% yield) as a light-yellow oil. MS (ESI) m/z 344.2 $[M+1]^+$.

3-(5-(((3S,4S)-4-Methyl-1-((2-methylquinolin-6-yl)methyl)pyrrolidin-3-yl)-oxy)-1-oxoisoindolin-2-yl)piperidine-2,6-dione. To a solution of 3-[5-[(3S,4S)-4-methylpyrrolidin-3-yl]oxy-1-oxo-isoindolin-2-yl]piperidine-2,6-dione; 2,2,2-trifluoroacetic acid (40 mg, 0.087 mmol), 2-methylquinoline-6-carbaldehyde (25 mg, 0.15 mmol) and triethylamine (22 mg, 0.22 mmol) in dichloromethane (3 mL) was added sodium triacetoxyborohydride (93 mg, 0.44 mmol) at room temperature. The mixture was stirred for 3 h at room temperature. The resulting solution was concentrated and the residue was purified by silica gel chromatography (10% methanol in dichloromethane) and preparative HPLC with the following conditions: SunFire Prep C18 OBD Column, 19×150 mm 5 μm 10 nm; Mobile Phase A: water (0.1% formic acid), Mobile Phase B: acetonitrile; Flow rate: 60 mL/min; Gradient: 5 B to 25 B in 7 min; 254/210 nm; $RT_1$: 6.67. The fractions containing desired product were collected and evaporated under reduced pressure to afford the title compound (13 mg, 0.026 mmol, 30% yield) as a light yellow solid. $^1H$ NMR (400 MHz, Methanol-$d_4$) δ 8.35 (s, 1H), 8.22 (s, 1H), 8.04-7.94 (m, 2H), 7.83 (d, J=8.7 Hz, 1H), 7.69 (m, 1H), 7.54-7.46 (m, 1H), 7.12-7.06 (m, 2H), 5.17-5.06 (m, 2H), 4.91-4.86 (m, 4H), 3.81 (m, 1H), 3.62 (m, 1H), 3.48 (m, 1H), 3.25 (m, 1H), 2.92 (m, 1H), 2.81-2.75 (m, 5H), 2.53-2.41 (m, 1H), 2.19 (m, 1H), 1.22 (m, 3H); MS (ESI) m/z 499.1 $[M+1]^+$.

Example S3. 2-(2,6-Dioxopiperidin-3-yl)-5-(((R)-1-(quinolin-3-ylmethyl)pyrrolidin-3-yl)oxy)isoindoline-1,3-dione

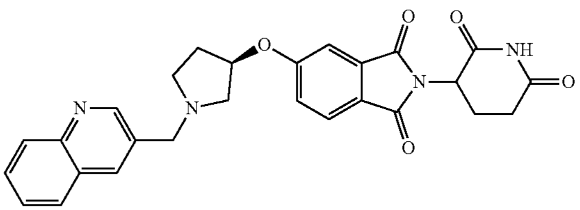 [SMILES: O=C1CCC(N2C(=O)c3ccc(O[C@@H]4CCN(Cc5cnc6ccccc6c5)C4)cc3C2=O)C(=O)N1]

Dimethyl (R)-4-((1-(tert-butoxycarbonyl)pyrrolidin-3-yl)oxy)phthalate. To a solution of dimethyl 4-hydroxybenzene-1,2-dicarboxylate (840 mg, 4 mmol), tert-butyl (3S)-3-hydroxypyrrolidine-1-carboxylate (1 g, 5.34 mmol), and triphenylphosphine (2 g, 7.61 mmol) in THF (20 mL) was added diisopropyl azodicarboxylate (2 g, 9.89 mmol) at 0° C. The mixture was stirred for 2 h at room temperature under nitrogen. The resulting mixture was concentrated, and the residue was stirred diethyl ether. The solids were filtered and the filtrate was concentrated. The crude product was purified by silica gel column chromatography (0-10% hexanes in ethyl acetate) to afford the title compound (1 g, 2.63 mmol, 66% yield) as a light-yellow oil. MS (ESI) m/z 380.2 $[M+1]^+$.

(R)-4-((1-(tert-butoxycarbonyl)pyrrolidin-3-yl)oxy)phthalic acid. To a stirred solution of dimethyl 4-[(3R)-1-tert-butoxycarbonylpyrrolidin-3-yl]oxybenzene-1,2-dicarboxylate (1 g, 2.63 mmol) in methanol (30 mL) and water (3 mL) was added sodium hydroxide (624 mg, 15.60 mmol) and the mixture was stirred for 12 h at 50° C. under nitrogen. The mixture was concentrated and the residue was added in hydrochloric acid (1 M in water) dropwise until pH~3. The solids were collected and washed with acetone (3 mL) to afford the title compound (870 mg, 2.47 mmol, 94% yield) as a light-yellow solid. MS (ESI) m/z 352.1 $[M+1]^+$.

Tert-butyl (3R)-3-((2-(2,6-dioxopiperidin-3-yl)-1,3-dioxoisoindolin-5-yl)oxy)-pyrrolidine-1-carboxylate. A stirred solution of 4-[(3R)-1-tert-butoxycarbonylpyrolidin-3-yl]oxyphthalic acid (300 mg, 0.85 mmol) and 3-aminopiperidine-2,6-dione; hydrochloride (281 mg, 1.71 mmol) in pyridine (2 mL) was stirred for 3 h at 150° C. under nitrogen. The reaction mixture was diluted with ether (30 mL) and the solids were collected to afford the title compound (300 mg, 0.68 mmol, 80% yield) as a grey solid. MS (ESI) m/z 444.1 $[M+1]^+$.

2-(2,6-dioxopiperidin-3-yl)-5-(((R)-pyrrolidin-3-yl)oxy)isoindoline-1,3-dione; hydrochloride. A solution of tert-butyl (3R)-3-[2-(2,6-dioxo-3-piperidyl)-1,3-dioxo-isoindolin-5-yl]oxypyrrolidine-1-carboxylate (300 mg, 0.68 mmol) in hydrochloric acid (4 M in dioxane, 1.70 mL, 6.81 mmol) was stirred 2 h at room temperature under nitrogen. The solids were collected, washed with ether (3 mL) and acetone to afford the title compound (200 mg, 0.52 mmol, 76% yield) as a light-yellow solid. MS (ESI) m/z 344.1 $[M+1]^+$.

2-(2,6-dioxopiperidin-3-yl)-5-(((R)-1-(quinolin-3-ylmethyl)pyrrolidin-3-yl)-oxy)isoindoline-1,3-dione. To a solution of the compound 2-(2,6-dioxo-3-piperidyl)-5-[(3R)-pyrrolidin-3-yl]oxy-isoindoline-1,3-dione; hydrochloride (120 mg, 0.32 mmol), quinoline-3-carbaldehyde (74 mg, 0.47 mmol) and triethylamine (48 mg, 0.47 mmol) in dichloromethane (3 mL) was added sodium triacetoxyborohydride (268 mg, 1.26 mmol) and the mixture was stirred for 2 h at room temperature under nitrogen. The resulting mixture was concentrated. The residue was purified by silica gel chromatography (10% methanol in dichloromethane) and preparative HPLC with the following conditions: Sunfire prep C18 column, 30*150 mm, 5 um; Mobile Phase A: water (0.05% formic acid), Mobile Phase B: acetonitrile; Flow rate: 60 mL/min; Gradient: 5 B to 21 B in 7 min; 254/210 nm; RT1:7.00; The fractions containing desired product were collected and evaporated under reduced pressure to afford the title compound (43 mg, 0.09 mmol, 28% yield) as an off-white solid. $^1H$ NMR (400 MHz, Methanol-$d_4$) δ 8.92 (s, 1H), 8.37 (d, J=2.7 Hz, 1H), 8.05 (d, J=8.5 Hz, 1H), 7.97 (d, J=8.4 Hz, 1H), 7.79 (m, 2H), 7.65 (m, 1H), 7.39-7.33 (m, 1H), 7.28 (m, J=8.5, 4.5, 2.3 Hz, 1H), 5.16-5.11 (m, 2H), 4.06 (m, 2H), 3.21-3.12 (m, 1H), 3.06 (m, 2H), 2.95-2.65 (m, 4H), 2.51 (m, 1H), 2.18-2.03 (m, 2H); MS (ESI) m/z 485.2 $[M+1]^+$.

Example S4. 2-(2,6-Dioxopiperidin-3-yl)-5-(((R)-1-(quinolin-6-ylmethyl)pyrrolidin-3-yl)oxy)isoindoline-1,3-dione

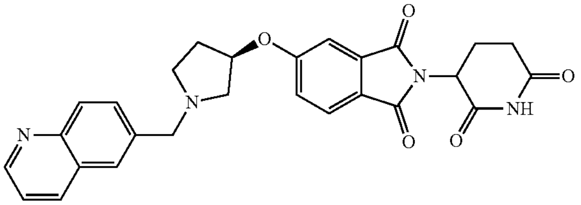 [SMILES: O=C1CCC(N2C(=O)c3ccc(O[C@@H]4CCN(Cc5ccc6ncccc6c5)C4)cc3C2=O)C(=O)N1]

2-(2,6-Dioxopiperidin-3-yl)-5-(((R)-1-(quinolin-6-ylmethyl)pyrrolidin-3-yl)oxy)isoindoline-1,3-dione. To a solution of 2-(2,6-dioxo-3-piperidyl)-5-[(3R)-pyrrolidin-3-yl]oxy-isoindoline-1,3-dione; hydrochloride (120 mg, 0.32 mmol), quinoline-6-carbaldehyde (74 mg, 0.47 mmol) and triethylamine (48 mg, 0.47 mmol) in dichloromethane (10 mL) was added sodium triacetoxyborohydride (268 mg, 1.26 mmol) and the mixture was stirred for 2 h at room temperature under nitrogen. The resulting mixture was concentrated. The residue was purified by silica gel chromatography (10% methanol in dichloromethane) and preparative HPLC with the following conditions: Sunfire prep C18 column, 30*150 mm, 5 um; Mobile Phase A: water (0.05% formic acid), Mobile Phase B: acetonitrile; Flow rate: 60 mL/min; Gradient: 5 B to 21 B in 7 min; 254/210 nm; RT1:7.00. The fractions containing desired product were collected and evaporated under reduced pressure to afford the title compound (59 mg, 0.12 mmol, 38% yield) as an off-white solid. $^1$H NMR (400 MHz, Methanol-$d_4$) δ 8.85 (m, J=4.3, 1.7 Hz, 1H), 8.46 (m, J=8.3, 1.5 Hz, 1H), 8.04 (d, J=8.7 Hz, 1H), 7.97 (d, J=1.9 Hz, 1H), 7.86 (m, 1H), 7.78 (d, J=8.3 Hz, 1H), 7.55 (m, 1H), 7.35 (m, 1H), 7.27 (m, 1H), 5.19-5.15 (m, 1H), 5.09 (m, 1H), 4.17-4.04 (m, 2H), 3.22 (m, 1H), 3.19-3.08 (m, 2H), 2.93-2.79 (m, 2H), 2.79-2.63 (m, 2H), 2.50 (m, 1H), 2.16-2.06 (m, 2H); MS (ESI) m/z 485.2 [M+1]$^+$.

Example S5. 2-(2,6-Dioxopiperidin-3-yl)-5-(((S)-1-(quinolin-5-ylmethyl)pyrrolidin-3-yl)oxy)isoindoline-1,3-dione

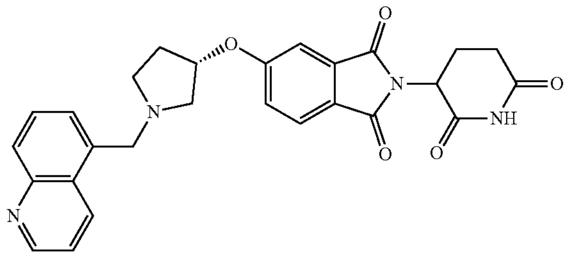 [SMILES: O=C1CCC(N2C(=O)c3ccc(O[C@H]4CCN(Cc5cccc6ncccc56)C4)cc3C2=O)C(=O)N1]

2-(2,6-Dioxopiperidin-3-yl)-5-(((S)-1-(quinolin-5-ylmethyl)pyrrolidin-3-yl)oxy)isoindoline-1,3-dione. To a solution of 2-(2,6-dioxo-3-piperidyl)-5-[(3R)-pyrrolidin-3-yl]oxy-isoindoline-1,3-dione; hydrochloride (120 mg, 0.32 mmol), quinoline-5-carbaldehyde (74 mg, 0.47 mmol) and triethylamine (47 mg, 0.47 mmol) in dichloromethane (10 mL) was added sodium triacetoxyborohydride (268 mg, 1.26 mmol) and the mixture was stirred for 2 h at room temperature under nitrogen. The resulting mixture was concentrated and purified by silica gel chromatography (10% methanol in dichloromethane) and preparative HPLC with the following conditions: Sunfire prep C18 column, 30*150 mm, 5 um; Mobile Phase A: Water (0.05% formic acid), Mobile Phase B: acetonitrile; Flow rate: 60 mL/min; Gradient: 5 B to 21 B in 7 min; 254/210 nm; RT1:7.00. The fractions containing desired product were collected and evaporated under reduced pressure to afford the title compound (35 mg, 0.072 mmol, 24% yield) as an off-white solid. $^1$H NMR (400 MHz, Methanol-$d_4$) δ 8.90-8.81 (m, 2H), 8.01 (d, J=8.5 Hz, 1H), 7.81-7.70 (m, 2H), 7.68-7.62 (m, 2H), 7.33 (d, J=2.3 Hz, 1H), 7.25 (m, 1H), 5.16-5.12 (m, 2H), 4.29 (s, 2H), 3.17 (m, 1H), 3.06-2.95 (m, 2H), 2.81-2.71 (m, 4H), 2.44 (m, 1H), 2.16-1.96 (m, 2H); MS (ESI) m/z 485.0 [M+1]$^+$.

Example S6. 3-(5-(((S)-14(2-Methylquinolin-6-yl)methyl)pyrrolidin-3-yl)amino)-1-oxoisoindolin-2-yl)piperidine-2,6-dione

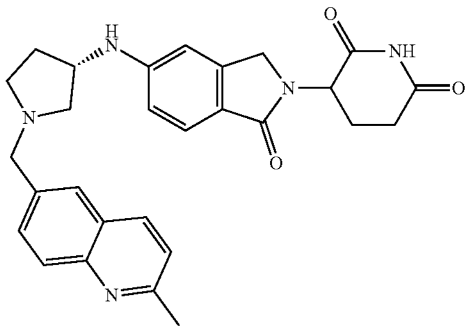 [SMILES: Cc1ccc2cc(CN3CC[C@H](Nc4ccc5c(c4)CN(C4CCC(=O)NC4=O)C5=O)C3)ccc2n1]

3-(5-(((S)-1-((2-Methylquinolin-6-yl)methyl)pyrrolidin-3-yl)amino)-1-oxoiso-indolin-2-yl)piperidine-2,6-dione. To a solution of the 3-(1-oxo-5-(((S)-pyrrolidin-3-yl)amino)isoindolin-2-yl)piperidine-2,6-dione hydrochloride (80 mg, 0.22 mmol), 2-methylquinoline-6-carbaldehyde (56 mg, 0.33 mmol) and triethylamine (33 mg, 0.33 mmol) in dichloromethane (10 mL) was added sodium triacetoxyborohydride (186 mg, 0.87 mmol) and the resulting mixture was stirred for 12 h at room temperature under nitrogen. The reaction mixture was concentrated and the residue was purified by preparative HPLC with following condition: Column: Sunfire prep C18 column, 30*150 mm, 5 um; mobile phase A: water (0.05% formic acid), mobile phase B: acetonitrile; flow rate: 60 mL/min; gradient: 5 B to 21 B in 7 min; 254/210 nm; $RT_1$: 7.00. The fractions containing desired product were collected and evaporated under reduced pressure to afford the title compound (14 mg, 0.029 mmol, 9% yield) as a light-yellow solid. $^1$H NMR (400 MHz, Methanol-$d_4$) δ 8.35 (s, H), 8.26 (d, J=8.5 Hz, 1H), 8.04-7.95 (m, 2H), 7.83 (dd, J=8.7, 2.0 Hz, 1H), 7.58-7.46 (m, 2H), 6.76-6.67 (m, 2H), 5.09 (dd, J=13.3, 5.1 Hz, 1H), 4.36-4.21 (m, 5H), 3.45 (m, 1H), 3.30 (m, 1H), 3.15 (m, 1H), 3.00 (m, 1H), 2.85 (m, 1H), 2.75 (m, 1H), 2.49 (m, 2H), 2.15 (m, 1H), 1.90 (m, 1H); MS (ESI) m/z 484.3 [M+1]$^+$.

Example S7. 3-(1-Oxo-5-(((R)-1-(quinolin-3-ylmethyl)pyrrolidin-3-yl)methyl)isoindolin-2-yl)-piperidine-2,6-dione

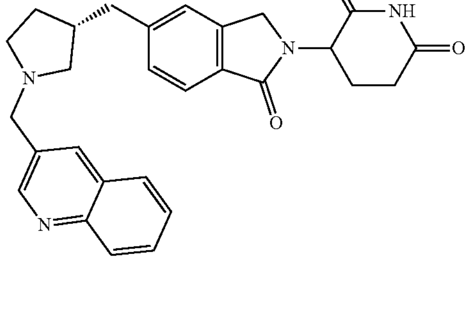

Tert-butyl (3S)-34(2-(2,6-dioxopiperidin-3-yl)-1-oxoisoindolin-5-yl)methyl)-pyrrolidine-1-carboxylate. To a solution of 3-(5-bromo-1-oxoisoindolin-2-yl)-piperidine-2,6-dione (300 mg, 0.93 mmol) in acetonitrile (20 mL) was added tert-butyl (S)-3-(bromomethyl)pyrrolidine-1-carboxylate (737 mg, 2.79 mmol), quinuclidine (10 mg, 0.093 mmol), 4,4'-di-tert-butyl-2,2'-bipyridine (12 mg, 0.046 mmol), (4,4'-di-t-butyl-2,2'-bipyridine)bis[3,5-difluoro-2-[5-trifluoromethyl-2-pyridinyl-kN)phenyl-kC]iridium(III) hexafluorophosphate (10 mg, 0.0093 mmol), nickel(II) chloride ethylene glycol dimethyl ether complex (10 mg, 0.046 mmol), potassium carbonate (128 mg, 0.93 mmol). The mixture was stirred for 16 h at room temperature with 34 W blue LED under nitrogen. The resulting mixture was added water and extracted with ethyl acetate. The extracts were washed with brine, dried over anhydrous sodium sulfate, filtered and concentrated. The residue was purified by silica gel chromatography (0-10% methanol in dichloromethane) to afford the title compound (285 mg, 0.66 mmol, 71% yield) as a yellow solid. MS (ESI) m/z 428.2 $[M+1]^+$.

3-(1-Oxo-5-(((S)-pyrrolidin-3-yl)methyl)isoindolin-2-yl) piperidine-2,6-dione hydrochloride. To a solution of the tert-butyl (3S)-3-((2-(2,6-dioxopiperidin-3-yl)-1-oxoisoindolin-5-yl)methyl)pyrrolidine-1-carboxylate (285 mg, 0.66 mmol) in 1,4-dioxane (4 mL) was added hydrogen chloride (1M in dioxane, 20 mL, 20 mmol). The mixture was stirred for 12 h at room temperature under nitrogen. The solid were collected to afford the title compound (180 mg, 0.55 mmol, 83% yield) as an off-white solid. MS (ESI) m/z 328.0 $[M+1]^+$.

3-(1-Oxo-5-(((S)-1-(quinolin-3-ylmethyl) pyrrolidin-3-yl)methyl)isoindolin-2-yl)piperidine-2,6-dione. To a solution of quinoline-3-carbaldehyde (90 mg, 0.58 mmol) in dichloromethane (10 mL) were added 3-(1-oxo-5-(((S)-pyrrolidin-3-yl)-methyl)isoindolin-2-yl)piperidine-2,6-dione hydrochloride (160 mg, 0.44 mmol), sodium triacetoxyborohydride (380 mg, 1.80 mmol) and triethylamine (70 mg, 0.70 mmol). The mixture was stirred for 12 h at room temperature under nitrogen. The resulting mixture was added water and extracted with ethyl acetate. The extracts were washed with brine, dried over anhydrous sodium sulfate, filtered and concentrated. The residue was purified by preparative HPLC using the following gradient conditions: Column: Sunfire prep C18 column, 30*150 mm, 5 um; Mobile Phase A: water (0.05% formic acid), Mobile Phase B: ACETONITRILE; Flow rate: 60 mL/min; Gradient: 5 B to 18 B in 7 min; 254/210 nm; RT1:6.45. The fractions containing desired product were collected and evaporated under reduced pressure to afford the title compound (26.6 mg, mmol, 10% yield) as an off-white solid. $^1$H NMR (400 MHz, Methanol-$d_4$) δ 9.01 (d, J=2.2 Hz, 1H), 8.62 (d, J=2.2 Hz, 1H), 8.14 (d, J=8.5 Hz, 1H), 8.07 (d, J=8.2 Hz, 1H), 7.93 (t, J=8.5, 6.9, 1.4 Hz, 1H), 7.76 (m, 2H), 7.49-7.43 (m, 2H), 5.17 (dd, J=13.3, 5.1 Hz, 1H), 4.69 (s, 2H), 4.56-4.41 (m, 2H), 3.59 (m, 2H), 2.98-2.86 (m, 4H), 2.85-2.75 (m, 2H), 2.51 (m, 1H), 2.20 (m, 1H), 2.00 (m, 1H); MS (ESI) m/z 469.1 $[M+1]^+$.

Example S8. 3-(1-Oxo-5-(((S)-1-(quinolin-5-ylmethyl)pyrrolidin-3-yl)oxy)isoindolin-2-yl)piperidine-2,6-dione

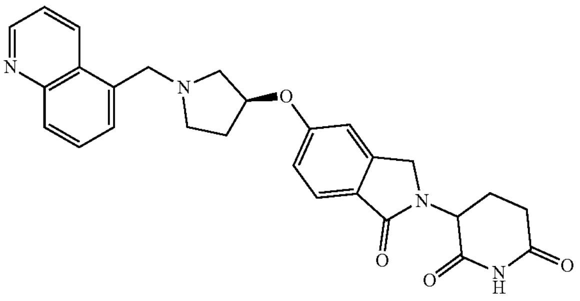 [SMILES: O=C1CCC(N2Cc3cc(O[C@H]4CCN(Cc5cccc6ncccc56)C4)ccc3C2=O)C(=O)N1]

3-(1-Oxo-5-(((S)-1-(quinolin-5-ylmethyl)pyrrolidin-3-yl) oxy)isoindolin-2-yl)-piperidine-2,6-dione. To a solution of quinoline-5-carbaldehyde (62 mg, 0.39 mmol) in dichloromethane (10 mL) was added 3-[1-oxo-5-[(3S)-pyrrolidin-3-yl]oxy-isoindolin-2-yl]piperidine-2,6-dione; hydrochloride (100 mg, 0.27 mmol), sodium triacetoxyborohydride (256 mg, 1.21 mmol) and triethylamine (45 mg, 0.45 mmol). The mixture was flushed three times with nitrogen and was stirred for 12 h under nitrogen. The mixture was added water and extracted with ethyl acetate. The extracts were washed with brine, dried over anhydrous sodium sulfate, filtered and concentrated. The residue was purified by preparative HPLC using the following conditions: Column: Sunfire prep C18 column, 30*150 mm, 5 um; Mobile Phase A: water (0.05% hydrogen chloride), Mobile Phase B: acetonitrile; Flow rate: 60 mL/min; Gradient: 2 B to 2 B in 2 min; 254/210 nm; RT1:7.07. The fractions containing desired product were collected and evaporated under reduced pressure to afford the title compound (47.7 mg, mmol, 26%) as an off-white solid. $^1$H NMR (400 MHz, Methanol-$d_4$) δ 9.82-9.65 (m, 1H), 9.37 (d, J=4.0 Hz, 1H), 8.44 (d, J=8.0 Hz, 1H), 8.40-8.25 (m, 3H), 7.75 (m, 1H), 7.22-7.12 (m, 2H), 5.41 (m, 1H), 5.27 (m, 2H), 5.14 (m, 1H), 4.56-4.39 (m, 2H), 4.21-3.60 (m, 4H), 2.99-2.72 (m, 2H), 2.56-2.44 (m, 2H), 2.39-2.13 (m, 2H); MS (ESI) m/z 471.2 $[M+1]^+$.

Example S9. 3-(5-(((S)-1-((1,8-Naphthyridin-4-yl) methyl)pyrrolidin-3-yl)oxy)-1-oxoisoindolin-2-yl) piperidine-2,6-dione

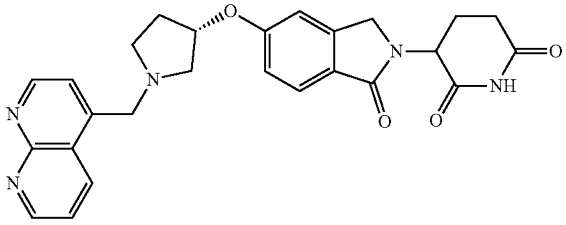 [SMILES: O=C1CCC(N2Cc3cc(O[C@H]4CCN(Cc5ccnc6ncccc56)C4)ccc3C2=O)C(=O)N1]

1,8-Naphthyridine-4-carbaldehyde. To a solution of the 4-methyl-1,8-naphthyridine (370 mg, 2.57 mmol) in 1,4-dioxane (16 mL) and water (2 mL) was added selenium dioxide (569 mg, 5.13 mmol). The mixture was stirred for 1 h at 80° C. under nitrogen. The mixture was filtered and the filtrate was concentrated. The residue was purified by silica gel chromatography (0 to 50% ethyl acetate in petroleum ether) to afford the title compound (296 mg, 1.86 mmol, 73% yield) as an orange oil. MS (ESI) m/z 159.0 $[M+1]^+$.

3-(5-(((S)-1-((1,8-Naphthyridin-4-yl)methyl)pyrrolidin-3-yl)oxy)-1-oxoisoin-dolin-2-yl)piperidine-2,6-dione. To a solution of 1,8-naphthyridine-4-carbaldehyde (45 mg, 0.28 mmol) in dichloromethane (10 mL) were added 3-[1-oxo-5-[(3S)-pyrrolidin-3-yl]oxy-isoindolin-2-yl]piperidine-2,6-dione; hydrochloride (80 mg, 0.22 mmol), sodium triacetoxyborohydride (185 mg, 0.87 mmol) and triethylamine (33 mg, 0.33 mmol). The mixture was stirred for 12 h at room temperature under nitrogen. The mixture was concentrated and the residue was purified by preparative HPLC using the following conditions: Column: XSelect CSH Prep C18 OBD Column, 5 um, 19*150 mm; Mobile Phase A: water (0.05% TFA), Mobile Phase B: acetonitrile; Flow rate: 25 mL/min; Gradient: 2 B to 2 B in 2 min; 254/210 nm; RT1:7.50. The fractions containing desired product were collected and evaporated under reduced pressure to afford the title compound (29.3 mg, 0.062 mmol, 21% yield) as an off-white solid. $^1$H NMR (400 MHz, Methanol-$d_4$) δ 9.26-9.19 (m, 2H), 9.02-8.95 (m, 1H), 7.99 (d, J=4.0 Hz, 1H), 7.90-7.84 (m, 1H), 7.74 (dd, J=8.0 Hz, J=4.0 Hz, 1H), 7.18-7.06 (m, 2H), 5.38 (m, 1H), 5.23-5.08 (m, 3H), 4.54-4.36 (m, 2H), 3.95 (m, 1H), 3.91-3.79 (m, 2H), 3.76-3.65 (m, 1H), 2.98-2.85 (m, 1H), 2.84-2.74 (m, 1H), 2.73-2.63 (m, 1H), 2.57-2.37 (m, 2H), 2.23-2.12 (m, 1H); MS (ESI) m/z 472.2 $[M+1]^+$.

Example S10. 3-(1-Oxo-6-(((S)-1-(quinolin-3-ylmethyl)pyrrolidin-3-yl)oxy)isoindolin-2-yl)piperidine-2,6-dione

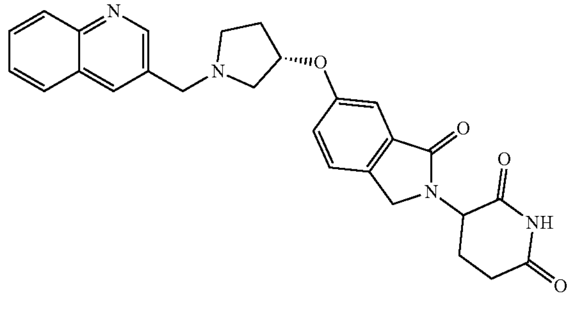 [SMILES: O=C1CCC(N2Cc3ccc(O[C@H]4CCN(Cc5cnc6ccccc6c5)C4)cc3C2=O)C(=O)N1]

3-(1-Oxo-6-(((S)-1-(quinolin-3-ylmethyl) pyrrolidin-3-yl) oxy) isoindolin-2-yl) piperidine-2,6-dione. To a solution of quinoline-3-carbaldehyde (65 mg, 0.41 mmol) in dichloromethane (10 mL) was added 3-[1-oxo-5-[(3S)-pyrrolidin-3-yl] oxy-isoindolin-2-yl]piperidine-2,6-dione; hydrochloride (100 mg, 0.27 mmol), sodium triacetoxyborohydride (256 mg, 1.21 mmol) and triethylamine (45 mg, 0.45 mmol). The mixture was stirred for 12 h at room temperature under nitrogen. The resulting mixture was added water and extracted with ethyl acetate. The extracts were washed with brine, dried over anhydrous sodium sulfate, filtered and concentrated. The residue was purified by preparative HPLC using the following gradient conditions: Column: XBridge Prep C18 OBD Column, 19×150 mm 5 um; Mobile Phase A: water (0.1% formic acid), Mobile Phase B: acetonitrile; Flow rate: 25 mL/min; Gradient: 2 B to 16 B in 8 min; 254, 210 nm; RT1:7.63. The fractions containing desired product were collected and evaporated under reduced pressure to afford the title compound (41.7 mg, 0.088 mmol, 21%) as an off-white solid. $^1$H NMR (400 MHz, Methanol-$d_4$) δ 8.93 (d, J=4.0 Hz, 1H), 8.06 (d, J=8.0 Hz, 1H), 7.97 (d, J=8.0 Hz, 1H), 7.84-7.76 (m, 1H), 7.71 (d, J=8.0 Hz, 1H), 7.69-7.61 (m, 1H), 7.11-7.01 (m, 2H), 5.17-5.05 (m, 2H), 4.50-4.36 (m, 2H), 4.07 (s, 2H), 3.22-3.12 (m, 1H), 3.11-3.00 (m, 2H), 2.98-2.74 (m, 3H), 2.55-2.41 (m, 2H), 2.21-2.04 (m, 2H); MS (ESI) m/z 471.2 $[M+1]^+$.

Example S11. 3-(1-Oxo-5-(((S)-1-(quinolin-4-ylmethyl)pyrrolidin-3-yl)oxy)isoindolin-2-yl)piperidine-2,6-dione

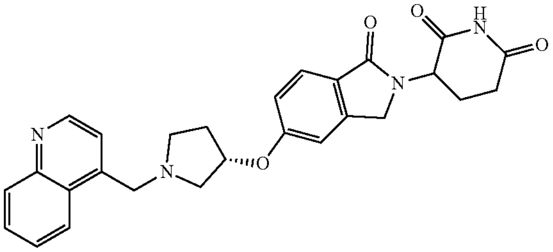 [SMILES: O=C1CCC(N2Cc3cc(O[C@H]4CCN(Cc5ccnc6ccccc56)C4)ccc3C2=O)C(=O)N1]

3-(1-Oxo-5-(((S)-1-(quinolin-4-ylmethyl) pyrrolidin-3-yl) oxy) isoindolin-2-yl) piperidine-2,6-dione. To a solution of quinoline-4-carbaldehyde (84 mg, 0.53 mmol) in dichloromethane (10 mL) was added 3-[1-oxo-5-[(3S)-pyrrolidin-3-yl] oxy-isoindolin-2-yl]piperidine-2,6-dione; hydrochloride (150 mg, 0.41 mmol), sodium triacetoxyborohydride (261 mg, 1.23 mmol) and triethylamine (62 mg, 0.62 mmol). The mixture was stirred for 12 h under nitrogen. The resulting mixture was concentrated. The residue was purified by preparative HPLC using the following gradient conditions: Column: Sunfire prep C18 column, 30*150 mm, 5 um; Mobile Phase A: water (0.05% formic acid), Mobile Phase B: acetonitrile; Flow rate: 60 mL/min; Gradient: 2 B to 2 B in 2 min; 254/210 nm; RT1:8.92. The fractions containing desired product were collected and evaporated under reduced pressure to afford the title compound (58 mg, 0.12 mmol, 23% yield) as an off-white solid. $^1$H NMR (400 MHz, Methanol-$d_4$) δ 8.81 (d, J=4.0 Hz, 1H), 8.40-8.31 (m, 1H), 8.06 (d, J=8.0 Hz, 1H), 7.84-7.76 (m, 1H), 7.74-7.58 (m, 3H), 7.08-6.98 (m, 2H), 5.16-5.09 (m, 1H), 5.02 (m, 1H), 4.44-4.39 (m, 2H), 4.23 (d, J=8.0 Hz, 2H), 3.16-3.07 (m, 1H), 2.99-2.84 (m, 3H), 2.83-2.68 (m, 2H), 2.49-2.37 (m, 2H), 2.16 (m, 1H), 2.06-1.96 (m, 1H); MS (ESI) m/z 471.2 $[M+1]^+$.

Example S12. 3-(1-Oxo-6-(((R)-1-(quinolin-3-ylmethyl)pyrrolidin-3-yl)oxy)isoindolin-2-yl)piperidine-2,6-dione

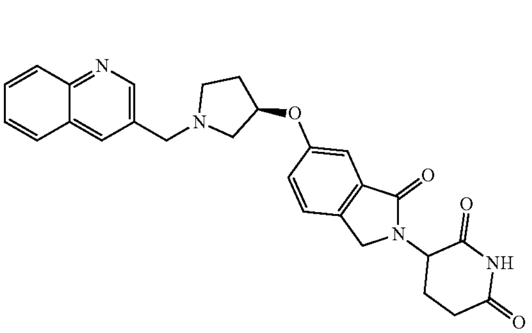 [SMILES: O=C1CCC(N2Cc3ccc(O[C@@H]4CCN(Cc5cnc6ccccc6c5)C4)cc3C2=O)C(=O)N1]

Tert-butyl (3R)-3-((2-(2,6-dioxopiperidin-3-yl)-1-oxoisoindolin-5-yl) oxy) pyrrolidine-1-carboxylate. A solution of 3-(5-bromo-1-oxo-isoindolin-2-yl) piperidine-2,6-dione (300 mg, 0.93 mmol) in acetonitrile (20 mL) was added tert-butyl (R)-3-hydroxypyrrolidine-1-carboxylate (736 mg, 3.93 mmol), quinuclidine (10 mg, 0.09 mmol), 4,4'-Di-tert-butyl-2,2'-bipyridine (12 mg, 0.045 mmol), (4,4'-Di-t-butyl-2,2'-bipyridine)bis[3,5-difluoro-2-[5-trifluoromethyl-2-pyridinyl-kN)phenyl-kC]iridium(III) hexafluorophosphate (10 mg, 0.01 mmol), Nickel(II) chloride, dimethoxyethane adduct (10 mg, 0.0455 mmol), potassium carbonate (128 mg, 0.93 mmol). The reaction was evacuated and flushed three times with nitrogen before being irradiated with three 80 W blue LEDs for 16 h at room temperature under nitrogen. The resulting mixture was added water and extracted with ethyl acetate. The extracts were washed with brine, dried over anhydrous sodium sulfate, filtered and concentrated. The residue was purified by silica gel chromatography (20 to 70% ethyl acetate in petroleum ether) to afford the title compound (250 mg, 0.58 mmol, 62% yield) as a yellow solid. MS (ESI) m/z 430.2 $[M+1]^+$.

3-(1-Oxo-5-(((R)-pyrrolidin-3-yl) oxy) isoindolin-2-yl) piperidine-2,6-dione hydrochloride. To a solution of tert-butyl (3R)-3-((2-(2,6-dioxopiperidin-3-yl)-1-oxoisoindolin-oxy) pyrrolidine-1-carboxylate (250 mg, 0.58 mmol) in 1,4-dioxane (4 mL) was added HCl (1M in dioxane, 20 mL, 20 mmol). The mixture was stirred for 12 h at room temperature under nitrogen. The solid was filtered and re-crystallized from diethyl ether to afford the title compound (75 mg, 0.20 mmol, 34% yield) as an off-white solid. MS (ESI) m/z 330.0 $[M+1]^+$.

3-(1-Oxo-6-(((R)-1-(quinolin-3-ylmethyl) pyrrolidin-3-yl)oxy) isoindolin-2-yl) piperidine-2,6-dione. To a solution of the compound quinoline-3-carbaldehyde (41 mg, 0.27 mmol) in dichloromethane (10 mL) were added 3-[1-oxo-5-[(3R)-pyrrolidin-3-yl]oxy-isoindolin-2-yl]piperidine-2,6-dione hydrochloride (75 mg, 0.20 mmol), sodium triacetoxyborohydride (130 mg, 0.62 mmol) and triethylamine (31 mg, 0.31 mmol). The mixture was stirred for 12 h at room temperature under nitrogen. The resulting mixture was concentrated. The residue was purified by preparative HPLC using the following gradient conditions: Column: XSelect CSH Prep C18 OBD Column, 5 um, 19*150 mm; Mobile Phase A: water (0.05% formic acid), Mobile Phase B: acetonitrile; Flow rate: 25 mL/min; Gradient: 2 B to B in 7 min; 254/210 nm; RT1:5.60. The fractions containing desired product were collected and evaporated under reduced pressure to afford the title compound (50.2 mg, 0.11 mmol, 55% yield) as an off-white solid. $^1$H NMR (400 MHz, Methanol-$d_4$) δ 8.95 (d, J=4.0 Hz, 1H), 8.41 (s, 1H), 8.07 (d, J=8.0 Hz, 1H), 7.99 (d, J=12.0 Hz, 1H), 7.86-7.78 (m, 1H), 7.75-7.63 (m, 2H), 7.12-7.03 (m, 2H), 5.17-5.08 (m, 2H), 4.51-4.36 (m, 2H), 4.02 (s, 2H), 3.28 (m, 1H), 3.24-3.14 (m, 2H), 3.01-2.85 (m, 2H), 2.80-2.75 (m, 1H), 2.58-2.41 (m, 2H), 2.19-2.10 (m, 2H); MS (ESI) m/z 471.2 $[M+1]^+$.

Example S13. 3-(1-Oxo-5-(((R)-1-(quinolin-3-ylmethyl)pyrrolidin-3-yl)methyl)isoindolin-2-yl)-piperidine-2,6-dione

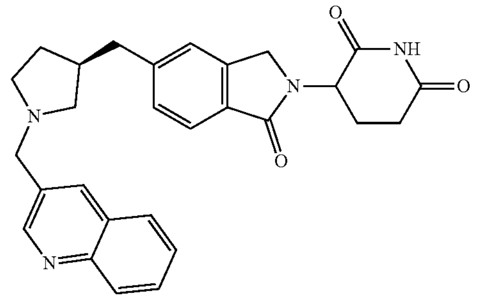 [SMILES: O=C1CCC(N2Cc3cc(C[C@@H]4CCN(Cc5cnc6ccccc6c5)C4)ccc3C2=O)C(=O)N1]

Tert-butyl (3R)-34(2-(2,6-dioxopiperidin-3-yl)-1-oxoisoindolin-5-yl)methyl)-pyrrolidine-1-carboxylate. To a solution of 3-(5-bromo-1-oxoisoindolin-2-yl)piperidine-2,6-dione (323 mg, 1.00 mmol) in acetonitrile (20 mL) was added tert-butyl (R)-3-(bromomethyl)pyrrolidine-1-carboxylate (792 mg, 3.00 mmol), quinuclidine (11 mg, 0.10 mmol), 4,4'-di-tert-butyl-2,2'-bipyridine (13 mg, 0.05 mmol), (4,4'-di-t-butyl-2,2'-bipyridine)bis[3,5-difluoro-2-[5-trifluoromethyl-2-pyridinyl-kN)phenyl-kC]iridium(III) hexafluorophosphate (11 mg, 0.01 mmol), nickel(II) chloride ethylene glycol dimethyl ether complex (11 mg, 0.05 mmol), potassium carbonate (138 mg, 1.00 mmol). The mixture was stirred for 16 h at room temperature with 34 W blue LED under nitrogen. The resulting mixture was added water and extracted with ethyl acetate. The extracts were washed with brine, dried over anhydrous sodium sulfate, filtered and concentrated. The residue was purified by silica gel chromatography (0-10% methanol in dichloromethane) to afford the title compound (264 mg, mmol, 62% yield) as a yellow solid. MS (ESI) m/z 428.2 $[M+1]^+$.

3-(1-Oxo-5-(((R)-pyrrolidin-3-yl)methyl)isoindolin-2-yl) piperidine-2,6-dione hydrochloride. To a solution of the compound tert-butyl (3R)-3-((2-(2,6-dioxopipe-ridin-3-yl)-1-oxoisoindolin-5-yl) methyl) pyrrolidine-1-carboxylate (264 mg, 0.62 mmol) in 1,4-dioxane (4 mL) was added hydrogen chloride (1M in dioxane, 20 mL, 20 mmol). The mixture was stirred for 12 h at room temperature under nitrogen. The solid were collected to afford the title compound (174 mg, 0.48 mmol, 77% yield) as an off-white solid. MS (ESI) m/z 328.0 $[M+1]^+$.

3-(1-Oxo-5-(((R)-1-(quinolin-3-ylmethyl) pyrrolidin-3-yl)methyl)isoindolin-2-yl)piperidine-2,6-dione. To a solution of quinoline-3-carbaldehyde (45 mg, 0.29 mmol) in dichloromethane (10 mL) were added 3-(1-oxo-5-(((R)-pyrrolidin-3-yl) methyl)isoindolin-2-yl)piperidine-2,6-dione hydrochloride (80 mg, 0.22 mmol), sodium triacetoxyborohydride (190 mg, 0.90 mmol) and triethylamine (33 mg, 0.33 mmol). The mixture was stirred for 12 h at room temperature under nitrogen. The resulting mixture was concentrated and the residue was purified by preparative HPLC using the following gradient conditions: Column: Sunfire prep C18 column, 30*150 mm, 5 um; Mobile Phase A: water (0.05% formic acid), Mobile Phase B: ACETONITRILE; Flow rate: 60 mL/min; Gradient: 5 B to 18 B in 7 min; 254/210 nm; RT1:6.45. The fractions containing desired product were collected and evaporated under reduced pressure to afford the title compound (30.2 mg, 0.064 mmol, 29% yield) as an off-white solid. $^1$H NMR (400 MHz, Methanol-$d_4$) δ 8.95 (d, J=4.0 Hz, 1H), 8.70 (d, J=4.0 Hz, 1H), 8.08 (d, J=8.0 Hz, 1H), 8.00 (dd, J=8.0 Hz, J=4.0 Hz, 1H), 7.85 (t, J=8.0 Hz, 1H), 7.76-7.65 (m, 2H), 7.45 (s, 1H), 7.40 (d, J=8.0 Hz, 1H), 5.15 (dd, J=12.0 Hz, J=4.0 Hz, 1H), 4.54-4.31 (m, 4H), 3.32-3.14 (m, 3H), 2.99-2.85 (m, 4H), 2.84-2.69 (m, 2H), 2.57-2.41 (m, 1H), 2.22-2.03 (m, 2H), 1.86-1.72 (m, 1H); MS (ESI) m/z 469.2 $[M+1]^+$.

Example S14. 2-(2,6-Dioxopiperidin-3-yl)-5-(((S)-1-(quinolin-3-ylmethyl)pyrrolidin-3-yl)oxy)isoindoline-1,3-dione

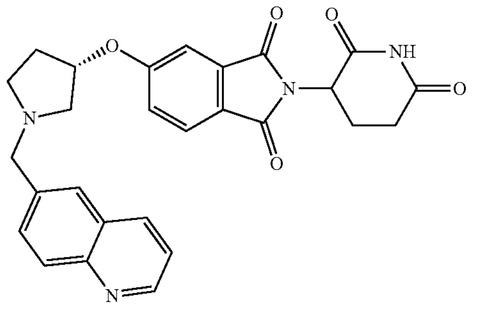 [SMILES: O=C1CCC(N2C(=O)c3ccc(O[C@H]4CCN(Cc5ccc6ncccc6c5)C4)cc3C2=O)C(=O)N1]

Dimethyl (S)-4-((1-(tert-butoxycarbonyl)pyrrolidin-3-yl)oxy)phthalate. To a solution of dimethyl 4-hydroxybenzene-1,2-dicarboxylate (1000 mg, 4.76 mmol), tert-butyl (3R)-3-hydroxypyrrolidine-1-carboxylate (1.19 g, 6.35 mmol), and triphenylphosphine (2.38 g, 9.06 mmol) in THF (20 mL) was added diisopropyl azodicarboxylate (2.38 g, 11.77 mmol) and the mixture was stirred for 2 h at room temperature under nitrogen. The resulting mixture was concentrated, and the residue was stirred diethyl ether. The solids were filtered and the filtrate was concentrated. The crude product was purified by silica gel column chromatography (0-10% hexanes in ethyl acetate) to afford the title compound (1.5 g, 3.95 mmol, 83% yield) as a light-yellow oil. MS (ESI) m/z 380.2 $[M+1]^+$.

(S)-4-((1-(Tert-butoxycarbonyl)pyrrolidin-3-yl)oxy) phthalic acid. To a stirred solution of dimethyl 4-[(3S)-1-tert-butoxycarbonylpyrrolidin-3-yl]oxybenzene-1,2-dicarboxylate (1 g, 2.63 mmol) in methanol (30 mL) and water (3 mL) was added sodium hydroxide (600 mg, mmol) and the mixture was stirred for 12 h at 50° C. under nitrogen. The mixture was concentrated and the residue was added in hydrochloric acid (1 M in water) dropwise until pH 3. The solids were collected and washed with acetone (3 mL) to afford the title compound (720 mg, 2.04 mmol, 78% yield) as a light-yellow solid. MS (ESI) m/z 352.1 $[M+1]^+$.

Tert-butyl (3S)-3-((2-(2,6-dioxopiperidin-3-yl)-1,3-dioxoisoindolin-5-yl)oxy)-pyrrolidine-1-carboxylate. A stirred solution of 4-[(3S)-1-tert-butoxycarbonylpyrrolidin-3-yl]oxyphthalic acid (300 mg, 0.85 mmol) and 3-aminopiperidine-2,6-dione; hydrochloride (281 mg, 1.71 mmol) in pyridine (3 mL) was stirred for 3 h at 150° C. under nitrogen. The reaction mixture was diluted with ether (30 mL) and the solids were collected to afford the title compound (350 mg, 0.68 mmol, 79% yield) as a grey solid. MS (ESI) m/z 444.1 $[M+1]^+$.

2-(2,6-Dioxopiperidin-3-yl)-5-(((S)-pyrrolidin-3-yl)oxy) isoindoline-1,3-dione hydrochloride. A solution of tert-butyl (3 S)-3-[2-(2,6-dioxo-3-piperidyl)-1,3-dioxisoindolin-5-yl] oxypyrrolidine-1-carboxylate (300 mg, 0.68 mmol) in hydrochloric acid (4 M in 1,4-dioxane, 3 mL, 12 mmol) was stirred 2 h at room temperature under nitrogen. The solids were collected, washed with diethyl ether (3 mL) and acetone to afford the title compound (250 mg, 0.65 mmol, 96% yield) as a light-yellow solid. MS (ESI) m/z 344.1 $[M+1]^+$.

2-(2,6-Dioxopiperidin-3-yl)-5-(((S)-1-(quinolin-3-ylmethyl)pyrrolidin-3-yl)-oxy)isoindoline-1,3-dione. To a solution of the compound 2-(2,6-dioxopiperidin-3-yl)-5-(((S)-pyrrolidin-3-yl)oxy)isoindoline-1,3-dione hydrochloride (120 mg, 0.32 mmol), quinoline-3-carbaldehyde (74 mg, 0.47 mmol) and triethylamine (48 mg, 0.47 mmol) in dichloromethane (3 mL) was added sodium triacetoxyborohydride (268 mg, 1.26 mmol) and the mixture was stirred for 2 h at room temperature under nitrogen. The resulting mixture was concentrated. The residue was purified by silica gel chromatography (10% methanol in dichloromethane) and preparative HPLC with the following conditions: Sunfire prep C18 column, 30*150 mm, 5 um; Mobile Phase A: water (0.05% formic acid), Mobile Phase B: acetonitrile; Flow rate: 60 mL/min; Gradient: 5 B to 21 B in 7 min; 254/210 nm; RT1:7.00; The fractions containing desired product were collected and evaporated under reduced pressure to afford the title compound (43 mg, 0.09 mmol, 28% yield) as an off-white solid. $^1H$ NMR (400 MHz, Methanol-$d_4$) δ 8.92 (s, 1H), 8.37 (d, J=2.7 Hz, 1H), 8.05 (d, J=8.5 Hz, 1H), 7.97 (d, J=8.4 Hz, 1H), 7.79 (m, 2H), 7.65 (m, 1H), 7.39-7.33 (m, 1H), 7.28 (m, J=8.5, 4.5, 2.3 Hz, 1H), 5.16-5.11 (m, 2H), 4.06 (m, 2H), 3.21-3.12 (m, 1H), 3.06 (m, 2H), 2.95-2.65 (m, 4H), 2.51 (m, 1H), 2.18-2.03 (m, 2H); MS (ESI) m/z 485.2 $[M+1]^+$.

Example S15. 3-(5-(((S)-1-((5-Fluoroquinolin-3-yl)methyl)pyrrolidin-3-yl)oxy)-1-oxoisoindolin-2-yl)piperidine-2,6-dione

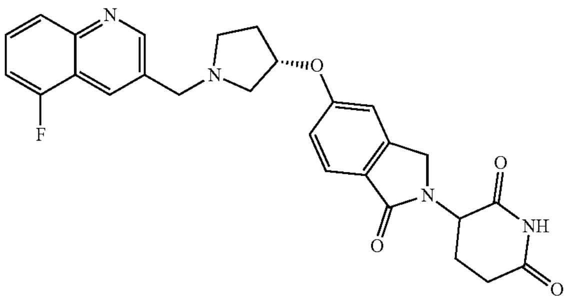 [SMILES: O=C1CCC(N2Cc3cc(O[C@H]4CCN(Cc5cnc6cccc(F)c6c5)C4)ccc3C2=O)C(=O)N1]

5-Fluoroquinoline-3-carbaldehyde. To a solution of 3-bromo-5-fluoroquinoline (200 mg, 0.88 mmol) in DMSO (3 mL) was added 2-isocyano-2-methyl-propane (88 mg, 1.06 mmol), palladium (II) acetate (10 mg, 0.04 mmol), 1,2-bis(diphenylphosphino)ethane (23 mg, mmol) and sodium formate (120 mg, 1.77 mmol). The mixture was stirred for 3 h at 120° C. under nitrogen. The mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (145 mg, 0.82 mmol, 93% yield) as a brown solid. MS (ESI) m/z 176.0 $[M+1]^+$.

3-(5-(((S)-1-((5-Fluoroquinolin-3-yl)methyl)pyrrolidin-3-yl)oxy)-1-oxoisoin-dolin-2-yl)piperidine-2,6-dione. To a solution of 3-[1-oxo-5-[(3S)-pyrrolidin-3-yl] oxy-isoindolin-2-yl] piperidine-2,6-dione; hydrochloride (209 mg, 0.57 mmol) in dichloromethane (10 mL) was added 5-fluoroquinoline-3-carbaldehyde (129 mg, 0.74 mmol), sodium triacetoxyborohydride (363 mg, 1.71 mmol) and triethylamine (86 mg, 0.85 mmol). The mixture was stirred for 12 h at room temperature under nitrogen. The mixture was added water and extracted with ethyl acetate. The extracts were washed with brine, dried over anhydrous sodium sulfate, filtered and concentrated. The residue was purified by preparative HPLC using the following gradient conditions: Column: XSelect CSH Prep C18 OBD Column, 5 um, 19*150 mm; Mobile Phase A: water (0.05% formic acid), Mobile Phase B: acetonitrile; Flow rate: 25 mL/min; Gradient: 5 B to 20 B in 7 min; 254/210 nm; RT1:6.37. The fractions containing desired product were collected and evaporated under reduced pressure to afford the title compound (17.3 mg, 0.035 mmol, 6% yield) as an off-white solid. $^1$H NMR (400 MHz, Methanol-$d_4$) δ 9.00 (d, J=4.0 Hz, 1H), 8.59 (s, 1H), 7.91 (d, J=8.0 Hz, 1H), 7.83-7.69 (m, 2H), 7.38-7.34 (m, 1H), 7.12-7.02 (m, 2H), 5.17-5.08 (m, 2H), 4.44 (m, 2H), 4.14 (m, 2H), 3.26-3.06 (m, 3H), 2.98-2.73 (m, 3H), 2.56-2.40 (m, 2H), 2.22-2.04 (m, 2H); MS (ESI) m/z 489.2 $[M+1]^+$.

Example S16. 3-(5-(((S)-1-((1-Methylisoquinolin-3-yl)methyl)pyrrolidin-3-yl)oxy)-1-oxoisoindolin-2-yl) piperidine-2,6-dione

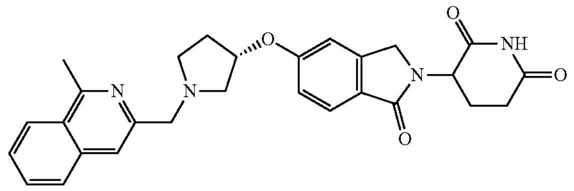 [SMILES: Cc1nc(CN2CC[C@H](Oc3ccc4c(c3)CN(C3CCC(=O)NC3=O)C4=O)C2)cc2ccccc12]

(Z)-1-phenylethan-1-one oxime. To a solution of 1-phenylethanone (500 mg, 4.16 mmol) in ethanol (20 mL) was added hydroxylamine hydrochloride (431 mg, 6.24 mmol) and triethylamine (1.74 mL, 12.48 mmol). The mixture was stirred for 3 h at 85° C. under nitrogen. The resulting mixture was added water and extracted with ethyl acetate. The extracts were washed with brine, dried over anhydrous sodium sulfate, filtered and concentrated. The residue was purified by silica gel chromatography (0 to 30% ethyl acetate in petroleum ether) to afford the title compound (430 mg, 3.15 mmol, 76% yield) as a light-yellow solid. MS (ESI) m/z 136.1 $[M+1]^+$.

Methylisoquinoline-3-carbaldehyde. To a solution of 1-phenylethanone oxime (250 mg, 1.85 mmol) in acetonitrile (20 mL) was added prop-2-enal (275 mg, 4.910 mmol), pivalic acid (370 mg, 0.53 mmol), Bis[(pentamethylcyclopentadienyl)dichloro-rhodium] (10 mg, 0.10 mmol) and Silver(I) carbonate (1000 mg, 5.26 mmol). The mixture was stirred for 12 h under nitrogen atmosphere. The resulting mixture was added water and extracted with ethyl acetate. The extracts were washed with brine, dried over anhydrous sodium sulfate, filtered and concentrated. The residue was purified by silica gel chromatography (0 to 20% ethyl acetate in petroleum ether) to afford the title compound (155 mg, 92% yield) as an off-white solid. MS (ESI) m/z 172.1 $[M+1]^+$.

3-(5-(((S)-1-((1-methylisoquinolin-3-yl)methyl)pyrrolidin-3-yl)oxy)-1-oxoiso-indolin-2-yl)piperidine-2,6-dione.

To a solution of 1-methylisoquinoline-3-carbaldehyde (70 mg, 0.41 mmol) in dichloromethane (10 mL) were added 3-[1-oxo-5-[(3S)-pyrrolidin-3-yl]oxy-isoindolin-2-yl] piperidine-2,6-dione; hydrochloride (100 mg, 0.27 mmol), sodium triacetoxyborohydride (240 mg, 1.13 mmol) and triethylamine (50 mg, 0.49 mmol). The mixture was stirred for 12 h under nitrogen. The resulting mixture was concentrated. The residue was purified by preparative HPLC using the following gradient conditions: Column: Column: Sunfire prep C18 column, 30*150, 5 um; Mobile Phase A: water (0.1% formic acid), Mobile Phase B: acetonitrile; Flow rate: 60 mL/min; Gradient: 6 B to 30 B in 7 min; 254/210 nm; RT1:6.38. The fractions containing desired product were collected and evaporated under reduced pressure to afford the title compound (51.9 mg, 0.10 mmol, 26% yield) as an off-white solid. $^1$H NMR (400 MHz, Methanol-$d_4$) δ 8.31 (d, J=8.0 Hz, 1H), 7.79 (d, J=8.0 Hz, 1H), 7.90-7.73 (m, 4H), 7.21-7.09 (m, 2H), 5.37 (m, 1H), 5.14 (dd, J=16.0 Hz, J=8.0 Hz, 1H), 4.79-4.66 (m, 2H), 4.54-4.39 (m, 2H), 3.93-3.76 (m, 3H), 3.76-3.65 (m, 1H), 3.00 (s, 3H), 2.98-2.75 (m, 2H), 2.70-2.57 (m, 1H), 2.56-2.42 (m, 2H), 2.21-2.14 (m, 1H); MS (ESI) m/z 485.2 $[M+1]^+$.

Example S17. 3-(5-(((S)-1-((7-Fluoroisoquinolin-3-yl)methyl)pyrrolidin-3-yl)oxy)-1-oxoisoindolin-2-yl) piperidine-2,6-dione

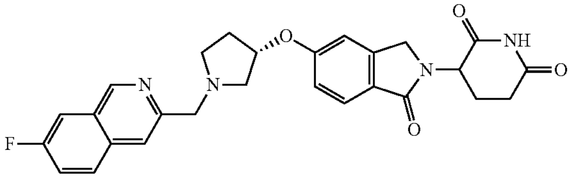 [SMILES: O=C1CCC(N2Cc3cc(O[C@H]4CCN(Cc5cc6ccc(F)cc6cn5)C4)ccc3C2=O)C(=O)N1]

2-(3,3-Diethoxyprop-1-yn-1-yl)-5-fluorobenzaldehyde. To a solution of 2-bromo-5-fluoro-benzaldehyde (1.0 g, 4.93 mmol) in THF (20 mL) was added 3,3-diethoxyprop-1-yne (0.8 g, 6.24 mmol), palladium (II) acetate (0.2 g, 0.89 mmol), triethylamine (1.5 g, 14.78 mmol) and 2-dicyclohexylphosphino-2',4',6'-tri-i-propyl-1,1'-biphenyl (0.90 g, 1.89 mmol). The mixture was stirred for 12 h at 60° C. under nitrogen. The resulting mixture was added water and extracted with ethyl acetate. The extracts were washed with brine, dried over anhydrous sodium sulfate, filtered and concentrated. The residue was purified by silica gel chromatography (10 to 30% ethyl acetate in petroleum ether) to afford the title compound (250 mg, 0.99 mmol, 20% yield) as a yellow solid. MS (ESI) m/z 251.1 $[M+1]^+$.

3-(Diethoxymethyl)-7-fluoroisoquinoline. A solution of 2-(3,3-diethoxyprop-1-yn-1-yl)-5-fluorobenzaldehyde (250 mg, 0.99 mmol) in ammonia (7 M in methanol, 15 mL) was heated with microwave irradiation in a microwave reactor at 100° C. for 20 min under nitrogen. The solution was concentrated to afford the crude title compound which was used for the next step directly without further purification. MS (ESI) m/z 250.1 $[M+1]^+$.

7-Fluoroisoquinoline-3-carbaldehyde. A solution of 3-(diethoxymethyl)-7-fluoroisoquinoline (335 mg, 1.34 mmol) in water (1 mL) was added hydrochloric acid (6 M in water, 10 mL). The mixture was stirred for 12 h under nitrogen. The mixture was concentrated and the residue was basified with saturated sodium bicarbonate to pH~7 and extracted with ethyl acetate. The extracts were washed with brine, dried over anhydrous sodium sulfate, filtered and concentrated.

The residue was purified by silica gel chromatography (0 to 25% ethyl acetate in petroleum ether) to afford the title compound (70 mg, 0.40 mmol, 30% yield) as a yellow solid. MS (ESI) m/z 176.0 $[M+1]^+$.

3-(5-(((S)-1-((7-Fluoroisoquinolin-3-yl)methyl)pyrrolidin-3-yl)oxy)-1-oxois-oindolin-2-yl)piperidine-2,6-dione. To a solution of 3-[1-oxo-5-[(3S)-pyrrolidin-3-yl]oxy-isoindolin-2-yl] piperidine-2,6-dione; hydrochloride (100 mg, 0.27 mmol) in dichloromethane (10 mL) were added 7-fluoroisoquinoline-3-carbaldehyde (62 mg, 0.35 mmol), sodium triacetoxyborohydride (200 mg, 0.81 mmol) and triethylamine (83 mg, 0.82 mmol). The mixture was flushed three times with nitrogen and was stirred for 12 h under nitrogen. The resulting mixture was added water and extracted with ethyl acetate. The extracts were washed with brine, dried over anhydrous sodium sulfate, filtered and concentrated. The residue was purified by preparative HPLC using the following gradient conditions: Column: Sunfire prep C18 column, 30*150 mm, 5 um; Mobile Phase A: water (0.1% formic acid), Mobile Phase B: acetonitrile; Flow rate: 60 mL/min; Gradient: 6 B to 30 B in 7 min; 254/210 nm; RT1:6.38. The fractions containing desired product were collected and evaporated under reduced pressure to afford the title compound (29.3 mg, 0.060 mmol, 21% yield) as an off-white solid. $^1$H NMR (400 MHz, Methanol-$d_4$) δ 9.27 (s, 1H), 8.03 (dd, J=8.0 Hz, J=4.0 Hz, 1H), 7.94 (s, 1H), 7.82 (dd, J=8.0 Hz, J=4.0 Hz, 1H), 7.72 (d, J=8.0 Hz, 1H), 7.69-7.61 (m, 1H), 7.11 (s, 1H), 7.09-7.03 (m, 1H), 5.21-5.08 (m, 2H), 4.53-4.41 (m, 2H), 4.40-4.26 (m, 2H), 3.47-3.38 (m, 1H), 3.38-3.27 (m, 2H), 3.18-3.08 (m, 1H), 2.98-2.85 (m, 1H), 2.83-2.75 (m, 1H), 2.58-2.41 (m, 2H), 2.25-2.10 (m, 2H); MS (ESI) m/z 489.2 $[M+1]^+$.

Example S18. 3-(6-(((S)-1-((2-Methylquinolin-3-yl) methyl)pyrrolidin-3-yl)oxy)-1-oxoisoindolin-2-yl) piperidine-2,6-dione

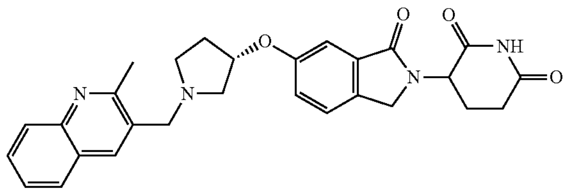 [SMILES: Cc1nc2ccccc2cc1CN1CC[C@H](Oc2ccc3c(c2)C(=O)N(C2CCC(=O)NC2=O)C3)C1]

2-Methylquinoline-3-carbaldehyde. To a solution of 2-chloroquinoline-3-carbaldehyde (750 mg, 3.91 mmol) in 1,4-dioxane (15 mL) were added 2,4,6-trimethyl-1,3,5,2,4,6-trioxatriborinane (1012 mg, 8.06 mmol), potassium carbonate (1612 mg, 11.74 mmol) and [1,1'-Bis(diphenylphosphino)ferrocene]dichloropalladium(II) (340 mg, 0.39 mmol). The mixture was stirred for 12 h at 100° C. under nitrogen. The resulting mixture was added water and extracted with ethyl acetate. The extracts were washed with brine, dried over anhydrous sodium sulfate, filtered and concentrated. The residue was purified by silica gel chromatography (0 to 90% ethyl acetate in petroleum ether) to afford the title compound (350 mg, 2.03 mmol, 52% yield) as a brown solid. MS (ESI) m/z 172.1 $[M+1]^+$.

3-(5-(((S)-1-((5-Fluoroquinolin-3-yl)methyl)pyrrolidin-3-yl)oxy)-1-oxoisoin-dolin-2-yl)piperidine-2,6-dione. To a solution of 3-[1-oxo-6-[(3S)-pyrrolidin-3-yl] oxy-isoindolin-2-yl] piperidine-2,6-dione; hydrochloride (100 mg, 0.27 mmol) in dichloromethane (10 mL) were added 2-methylquinoline-3-carbaldehyde (70 mg, 0.41 mmol), sodium triacetoxyborohydride (250 mg, 1.18 mmol) and triethylamine (55 mg, 0.55 mmol). The mixture was stirred for 12 h under nitrogen. The mixture was concentrated and the residue was purified by preparative HPLC using the following gradient conditions: Column: XSelect CSH Prep C18 OBD Column, 5 um, 19*150 mm; Mobile Phase A: water (0.05% formic acid), Mobile Phase B: acetonitrile; Flow rate: 25 mL/min; Gradient: 5 B to 15 B in 7 min; 254/210 nm; RT1:6.28. The fractions containing desired product were collected and evaporated under reduced pressure to afford the title compound (27.1 mg, 0.056 mmol, 20% yield) as an off-white solid. $^1$H NMR (400 MHz, Methanol-$d_4$) δ 8.27 (s, 1H), 7.97 (d, J=8.0 Hz, 1H), 7.91 (d, J=8.0 Hz, 1H), 7.74 (t, J=8.0 Hz, 1H), 7.57 (m, 1H), 7.48 (m, 1H), 7.31-7.17 (m, 2H), 5.14 (dd, J=12.0 Hz, J=4.0 Hz, 1H), 5.05 (s, 1H), 4.50-4.34 (m, 2H), 4.03 (s, 2H), 3.21 (m, 1H), 3.11-2.99 (m, 2H), 2.97-2.74 (m, 6H), 2.56-2.39 (m, 2H), 2.21-2.03 (m, 2H); MS (ESI) m/z 485.2 $[M+1]^+$.

Example S19. 3-(1-Oxo-5-(((S)-1-(quinazolin-2-ylmethyl)pyrrolidin-3-yl)oxy)isoindolin-2-yl)piperidine-2,6-dione

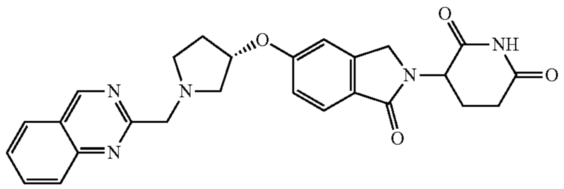

3-(1-Oxo-5-(((S)-1-(quinazolin-2-ylmethyl) pyrrolidin-3-yl) oxy) isoindolin-2-yl) piperidine-2,6-dione. To a solution of 3-[1-oxo-5-[(3S)-pyrrolidin-3-yl] oxy-isoindolin-2-yl]piperidine-2,6-dione; hydrochloride (100 mg, 0.27 mmol) in DMF (3 mL) was added 2-(chloromethyl)quinazoline (60 mg, 0.34 mmol) and triethylamine (140 mg, 1.38 mmol). The mixture was stirred for 12 h at room temperature under nitrogen. The resulting mixture was concentrated and the residue was purified by preparative HPLC using the following gradient conditions: Column: XSelect CSH Prep C18 OBD Column, 5 um, 19*150 mm; Mobile Phase A: water (0.05% formic acid), Mobile Phase B: acetonitrile; Flow rate: 25 mL/min; Gradient: 5 B to 17 B in 7 min; 254/210 nm; RT1:5.85. The fractions containing desired product were collected and evaporated under reduced pressure to afford the title compound (59.8 mg, 0.13 mmol, 48%) as an off-white solid. $^1$H NMR (400 MHz, Methanol-$d_4$) δ 9.57 (s, 1H), 8.15 (d, J=8.0 Hz, 1H), 8.11-8.00 (m, 2H), 7.83-7.70 (m, 2H), 7.16-7.06 (m, 2H), 5.26-5.09 (m, 2H), 4.56-4.38 (m, 4H), 3.54 (m, 1H), 3.50-3.38 (m, 2H), 3.26 (m, 1H), 2.99-2.85 (m, 1H), 2.85-2.74 (m, 1H), 2.61-2.42 (m, 2H), 2.27-2.14 (m, 2H); MS (ESI) m/z 472.2 $[M+1]^+$.

Example S20. 3-(5-(((S)-1-((2-Chloroquinolin-6-yl)methyl)pyrrolidin-3-yl)oxy)-1-oxoisoindolin-2-yl)piperidine-2,6-dione

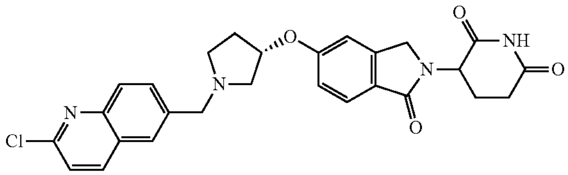 [SMILES: O=C1CCC(N2Cc3cc(O[C@H]4CCN(Cc5ccc6nc(Cl)ccc6c5)C4)ccc3C2=O)C(=O)N1]

3-(5-(((S)-1-((2-Chloroquinolin-6-yl)methyl)pyrrolidin-3-yl)oxy)-1-oxoisoindolin-2-yl)piperidine-2,6-dione. To a solution of 3-[1-oxo-5-[(3S)-pyrrolidin-3-yl]oxy-isoindolin-2-yl] piperidine-2,6-dione; hydrochloride (100 mg, 0.27 mmol) and triethylamine (0.07 mL, 0.50 mmol) in dichloromethane (10 mL) were added 2-chloroquinoline-6-carbaldehyde (65 mg, 0.34 mmol) and sodium triacetoxyborohydride (235 mg, 1.11 mmol). The mixture was stirred for 12 h at room temperature under nitrogen. The resulting mixture was concentrated and the residue was purified by preparative HPLC using the following gradient conditions: Column: XSelect CSH Prep C18 OBD Column, 5 um, 19*150 mm; Mobile Phase A: water (0.1% formic acid), Mobile Phase B: acetonitrile; Flow rate: 25 mL/min; Gradient: 2 B to 8 B in 7 min; 254/210 nm; RT: 7.20 min. The fractions containing desired product were collected and evaporated under reduced pressure to afford the title compound (59.2 mg, 0.12 mmol, 43% yield) as a light-yellow solid. $^1$H NMR (400 MHz, Methanol-$d_4$) δ 8.33 (d, J=8.0 Hz, 2H), 8.04-7.93 (m, 2H), 7.90 (d, J=8.0 Hz, 1H), 7.70 (d, J=8.0 Hz, 1H), 7.54 (d, J=8.0 Hz, 1H), 7.11-7.01 (m, 2H), 5.18-5.07 (m, 2H), 4.50-4.35 (m, 2H), 4.28-4.17 (m, 2H), 3.40-3.32 (m, 1H), 3.30-3.18 (m, 2H), 3.09-2.99 (m, 1H), 2.93-2.84 (m, 1H), 2.83-2.73 (m, 1H), 2.58-2.39 (m, 2H), 2.21-2.11 (m, 2H); MS (ESI) m/z 505.2 $[M+1]^+$.

Example S21. 3-(5-(((2S,3S)-2-Methyl-1-((2-methylquinolin-6-yl)methyl)pyrrolidin-3-yl)oxy)-1-oxoisoindolin-2-yl) piperidine-2,6-dione

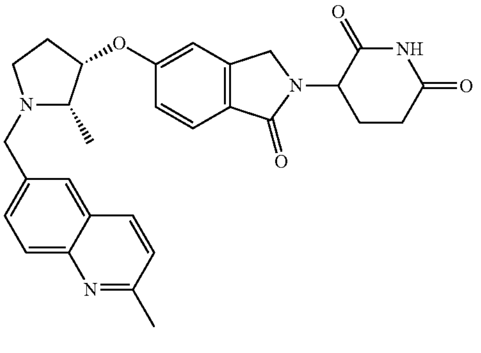 [SMILES: Cc1ccc2cc(CN3CC[C@H](Oc4ccc5c(c4)CN(C4CCC(=O)NC4=O)C5=O)[C@@H]3C)ccc2n1]

Tert-butyl (2S,3S)-3-((2-(1-(4-methoxybenzyl)-2,6-dioxopiperidin-3-yl)-1-oxoisoindolin-5-yl)oxy)-2-methylpyrrolidine-1-carboxylate. To a solution of 3-(5-bromo-1-oxoisoindolin-2-yl)-1-(4-methoxybenzyl)piperidine-2,6-dione (200 mg, 0.45 mmol), tert-butyl (2S,3S)-3-hydroxy-2-methylpyrrolidine-1-carboxylate (272 mg, 1.35 mmol), (4,4'-di-t-butyl-2,2'-bipyridine)bis[3,5-difluoro-2-[5-trifluoromethyl-2-pyridinyl-kN)phenyl-kC]iridium(III) hexafluorophosphate (5 mg, 0.005 mmol), quinuclidine (12 mg, 0.11 mmol), potassium carbonate (62 mg, 0.45 mmol) in dry acetonitrile (4 mL) was added the solution of Nickel (II) chloride, dimethoxyethane adduct (5 mg, 0.023 mmol) and 4,4'-Di-tert-butyl-2,2'-bipyridine (6 mg, 0.022 mmol) in dry acetonitrile (2 mL). The reaction was evacuated and flushed three times with nitrogen before being irradiated with three 34 W blue LEDs. The reaction was stirred for 12 h at room temperature under nitrogen. The resulting reaction mixture was filtered and the filtrate was concentrated under reduced pressure. The residue was purified by silica gel chromatography (0 to 70% ethyl acetate in petroleum ether) to afford the title compound (65 mg, 0.12 mmol, 25% yield) as a light-yellow solid. MS (ESI) m/z 564.3 $[M+1]^+$.

3-(5-(((2S,3S)-2-Methylpyrrolidin-3-yl)oxy)-1-oxoisoindolin-2-yl)piperidine-2,6-dione; 2,2,2-trifluoroacetic acid. To a solution of tert-butyl (2S,3S)-3-((2-(1-(4-methoxybenzyl)-2,6-dioxopiperidin-3-yl)-1-oxoisoindolin-5-yl)oxy)-2-methylpyrrolidine-1-carboxylate (70 mg, 0.12 mmol) in TFA (3 mL) was added trifluoromethanesulfonic acid (0.2 mL, 2.27 mmol). The mixture was stirred for 12 h at 60° C. under nitrogen. The resulting solution was concentrated under reduced pressure. The residue was diluted with water and adjusted to pH 6-7 with saturated sodium bicarbonate. The crude product was purified by reverse phase flash (10-30% acetonitrile+0.05% TFA in water, over 20 min) to give the title compound (40 mg, 0.087 mmol, 73% yield) as a light-yellow oil. MS (ESI) m/z 344.1 $[M+1]^+$.

3-(5-(((2S,3S)-2-Methyl-1-((2-methylquinolin-6-yl)methyl)pyrrolidin-3-yl) oxy)-1-oxoisoindolin-2-yl)piperidine-2,6-dione. To a solution of 3-(5-(((2S,3S)-2-methylpyrrolidin-3-yl)oxy)-1-oxoisoindolin-2-yl)piperidine-2,6-dione; 2,2,2-trifluoroacetic acid (40 mg, 0.087 mmol), 2-methylquinoline-6-carbaldehyde (20 mg, 0.12 mmol) and triethylamine (0.03 mL, 0.23 mmol) in dichloromethane (4 mL) was added sodium triacetoxyborohydride (99 mg, 0.47 mmol). The flask was evacuated and flushed five times with nitrogen. The mixture was stirred at room temperature for 2 h under nitrogen. The resulting solution was concentrated at 25° C. under reduced pressure. The crude was purified by silica gel column chromatography (0-10% methanol in dichloromethane) and further purified by reverse-phased preparative HPLC with the following conditions: Column: Sun Fire Prep C18 OBD Column, 19×150 mm 5 um 10 nm; Mobile Phase A: water (0.1% formic acid), Mobile Phase B: acetonitrile; Flow rate: 60 mL/min; Gradient: 5 B to 18 B in 7 min; 254/210 nm; $RT_1$: 6.42. The fractions containing desired product were collected and evaporated under reduced pressure to afford the title compound (11.4 mg, 0.022 mmol, 25% yield) as an off-white solid. $^1$H NMR (400 MHz, Methanol-$d_4$) δ 8.35-8.27 (m, 2H), 8.10-8.01 (m, 2H), 7.89 (dd, J=8.7, 2.0 Hz, 1H), 7.76 (d, J=8.5 Hz, 1H), 7.52 (d, J=8.5 Hz, 1H), 7.20-7.15 (m, 2H), 5.14-5.10 (m, 2H), 4.64 (d, J=13.0 Hz, 1H), 4.54-4.39 (m, 2H), 4.12 (d, J=13.0 Hz, 1H), 3.52 (m, 1H), 3.34 (m, 1H), 3.10-3.01 (m, 1H), 2.92-2.87 (m, 1H), 2.84-2.73 (m, 1H), 2.77 (s, 3H), 2.62-2.41 (m, 2H), 2.21-2.13 (m, 1H), 2.11-2.01 (m, 1H), 1.51 (d, J=6.6 Hz, 3H). MS (ESI) m/z 499.1 $[M+1]^+$.

Example S22. 3-(5-(((2S,3S)-2-Methyl-1-((2-methylquinolin-6-yl)methyl)pyrrolidin-3-yl)oxy)-1-oxoisoindolin-2-yl)piperidine-2,6-dione

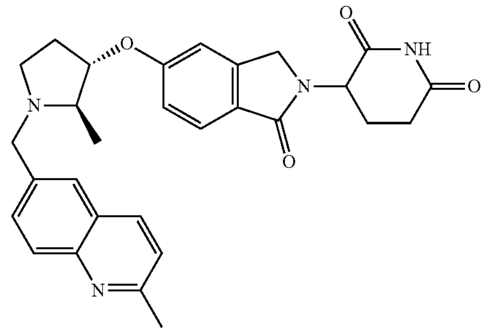 [SMILES: Cc1ccc2cc(CN3CC[C@H](Oc4ccc5c(c4)CN(C4CCC(=O)NC4=O)C5=O)[C@H]3C)ccc2n1]

Tert-butyl (2R,3R)-3-(benzoyloxy)-2-methylpyrrolidine-1-carboxylate. To a stirred solution of tert-butyl (2R,3S)-3-hydroxy-2-methylpyrrolidine-1-carboxylate (500 mg, 2.48 mmol), benzoic acid (303 mg, 2.48 mmol) and triphenylphosphine (980 mg, 3.73 mmol) in toluene (10 mL) was added di-tert-butyl azodicarboxylate (857 mg, 3.73 mmol). Then the reaction mixture was stirred at 80° C. for 3 h under nitrogen. The resulting solution was concentrated under reduced pressure. The crude was purified by reverse phase flash (0-80% acetonitrile+0.05% TFA in water, over 20 min) to afford the title compound (200 mg, 0.65 mmol, 26% yield) as a light yellow oil. MS (ESI) m/z 250.0 $[M-55]^+$.

Tert-butyl (2R,3R)-3-hydroxy-2-methylpyrrolidine-1-carboxylate. To a stirred solution of tert-butyl (2R,3R)-3-(benzoyloxy)-2-methylpyrrolidine-1-carboxylate (200 mg, 0.65 mmol) in methanol (6 mL) and water (3 mL) was added lithium hydroxide monohydrate (55 mg, 1.31 mmol) at room temperature and then stirred at 50° C. for 1 h under nitrogen. The reaction mixture was diluted with water and extracted with ethyl acetate. The organic phase was washed with brine, dried over anhydrous sodium sulfate, concentrated under reduced pressure to afford the title compound (130 mg, 0.64 mmol, 98% yield) which was used in the next step directly without further purification. $^1H$ NMR (400 MHz, Chloroform-d) δ 4.34-4.29 (m, 1H), 3.86 (t, J=6.6 Hz, 1H), 3.48-3.31 (m, 2H), 2.08-2.01 (m, 1H), 1.87-1.82 (m, 1H), 1.75-1.60 (m, 1H), 1.46 (s, 9H), 1.19 (d, J=6.5 Hz, 3H).

3-(5-Hydroxy-1-oxoisoindolin-2-yl)-1-(4-methoxybenzyl)piperidine-2,6-dione. To a solution of 3-(5-bromo-1-oxoisoindolin-2-yl)-1-(4-methoxybenzyl) piperidine-2,6-dione (120 mg, 0.27 mmol) in DMF (3 mL) was added methanesulfonato(2-(di-t-butylphosphino)-3-methoxy-6-methyl-2',4',6'-tri-i-propyl-1,1'-biphenyl)(2'-amino-1,1'-biphenyl-2-yl)palladium(II) (6.8 mg, 0.0081 mmol), (E)-benzaldehyde oxime (39 mg, 0.32 mmol) and cesium carbonate (176 mg, 0.54 mmol) at room temperature. Then the reaction mixture was stirred for 12 h at 80° C. under nitrogen. The resulting mixture was filtered and purified by reverse phase flash (0-80% acetonitrile+0.05% TFA in water, over 20 min) to afford the title compound (75 mg, 0.19 mmol, 70% yield) as a light-yellow solid. MS (ESI) m/z 403.1 $[M+1]^+$.

Tert-butyl (2R,3S)-3-((2-(1-(4-methoxybenzyl)-2,6-dioxopiperidin-3-yl)-1-oxoisoindolin-5-yl)oxy)-2-methylpyrrolidine-1-carboxylate. To a stirred solution of 3-(5-hydroxy-1-oxoisoindolin-2-yl)-1-(4-methoxybenzyl) piperidine-2,6-dione (200 mg, 0.53 mmol), tert-butyl (2R,3R)-3-hydroxy-2-methylpyrrolidine-1-carboxylate (158 mg, 0.79 mmol) and triphenylphosphine (207 mg, 0.79 mmol) in toluene (10 mL) was added di-tert-butyl azodicarboxylate (181 mg, 0.79 mmol). Then the reaction mixture was stirred at 80° C. for 3 h under nitrogen. The resulting reaction mixture was concentrated in vacuum. The crude was purified by reverse phase flash (0-80% acetonitrile+0.05% TFA in water, over 20 min) to afford the title compound (130 mg, 0.23 mmol, 44% yield) as a light-yellow solid. MS (ESI) m/z 586.3 $[M+23]^+$.

3-(5-(((2R,3S)-2-Methylpyrrolidin-3-yl)oxy)-1-oxoisoindolin-2-yl)piperidine-2,6-dione. To a solution of tert-butyl (2R,3S)-3-((2-(1-(4-methoxybenzyl)-2,6-dioxopiperidin-3-yl)-1-oxoisoindolin-5-yl)oxy)-2-methylpyrrolidine-1-carboxylate (120 mg, 0.21 mmol) in TFA (3 mL) was added trifluoromethanesulfonic acid (0.3 mL). The mixture was stirred for 12 h at 60° C. under nitrogen. The resulting solution was concentrated under reduced pressure. The residue was diluted with water and adjusted to pH 6-7 with saturated sodium bicarbonate. The crude product was purified by reverse phase flash (10-30% acetonitrile+0.05% TFA in water, over 20 min) to give the title compound (70 mg, 0.20 mmol, 95% yield) as a light-yellow oil. MS (ESI) m/z 344.1 $[M+1]^+$.

3-(5-(((2R,3S)-2-Methyl-1-((2-methylquinolin-6-yl) methyl)pyrrolidin-3-yl) oxy)-1-oxoisoindolin-2-yl)piperidine-2,6-dione. To a solution of 3-(5-(((2R,3S)-2-methylpyrrolidin-3-yl)oxy)-1-oxoisoindolin-2-yl)piperidine-2,6-dione (70 mg, 0.20 mmol), 2-methylquinoline-6-carbaldehyde (42 mg, 0.24 mmol) and triethylamine (0.06 mL, 0.41 mmol) in dichloromethane (4 mL) was added sodium triacetoxyborohydride (172 mg, 0.82 mmol). The flask was evacuated and flushed five times with nitrogen. The mixture was stirred at room temperature for 2 h under nitrogen. The resulting solution was concentrated at room temperature under reduced pressure. The crude was purified by silica gel column chromatography (0-10% methanol in dichloromethane) and further purified by reverse-phased preparative HPLC with the following conditions: Column: X select CSH OBD Column 30*150 mm, 5 um; Mobile Phase A: water (0.05% TFA), Mobile Phase B: acetonitrile; Flow rate: 60 mL/min; Gradient: 2 B to 20 B in 7 min; 210/254 nm; $RT_1$: 5.2. The fractions containing desired product were collected and evaporated under reduced pressure to afford the title compound (38.6 mg, 0.077 mmol, 37% yield) as a white solid. $^1H$ NMR (400 MHz, Methanol-$d_4$) δ 8.82 (dd, J=8.6, 3.2 Hz, 1H), 8.40 (t, J=2.6 Hz, 1H), 8.27-8.17 (m, 2H), 7.91 (dd, J=8.6, 2.9 Hz, 1H), 7.74 (dd, J=14.7, 8.5 Hz, 1H), 7.17-7.09 (m, 2H), 5.21-5.10 (m, 1H), 5.04 (m, 1H), 4.98 (m, 1H), 4.73 (d, J=13.2 Hz, 1H), 4.56-4.41 (m, 2H), 4.08 (m, 1H), 3.78-3.63 (m, 2H), 2.99-2.81 (m, 5H), 2.50-2.39 (m, 3H), 2.21-2.19 (m, 1H), 1.59 (dd, J=7.1, 1.7 Hz, 3H); MS (ESI) m/z 499.1 $[M+1]^+$.

Example S23. 3-(5-(((S)-1-((2,3-Dihydrofuro[2,3-c]pyridin-5-yl)methyl)pyrrolidin-3-yl)oxy)-1-oxoisoindolin-2-yl) piperidine-2,6-dione

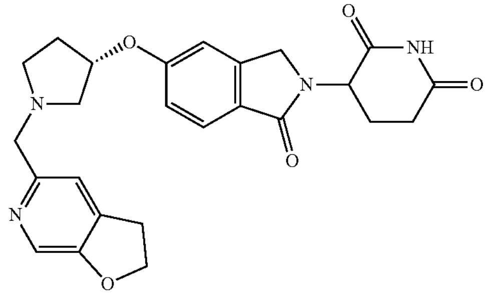 [SMILES: O=C1CCC(N2Cc3cc(O[C@H]4CCN(Cc5cc6c(cn5)OCC6)C4)ccc3C2=O)C(=O)N1]

(2,3-Dihydrofuro[2,3-c]pyridin-5-yl)methanol. To a solution of furo[2,3-c]pyridine-5-carbaldehyde (100 mg, 0.68 mmol) in methanol (6 mL) was added palladium 10% on carbon (100 mg, wetted with ca. 55% water) and the mixture was stirred for 12 h at room temperature under hydrogen (~2 bar). The resulting mixture was filtered and concentrated to afford the title compound (70 mg, 0.46 mmol, 68% yield) as an off-white solid. MS (ESI) m/z 152.0 $[M+1]^+$.

2,3-Dihydrofuro[2,3-c]pyridine-5-carbaldehyde. To a stirred solution of 2,3-dihydrofuro[2,3-c]pyridin-5-ylmethanol (65 mg, 0.43 mmol) in dichloromethane (4 mL) was added manganese dioxide (299 mg, 3.44 mmol) at room temperature. Then the reaction mixture was stirred for 3 h at 60° C. under nitrogen. The resulting reaction mixture was diluted with dichloromethane, filtered and concentrated to afford the title compound (60 mg, 0.40 mmol, 93% yield) as a light-yellow solid. MS (ESI) m/z 150.0 $[M+1]^+$.

3-(5-(((S)-1-((2,3-Dihydrofuro[2,3-c]pyridin-5-yl)methyl)pyrrolidin-3-yl)oxy)-1-oxoisoindolin-2-yl)piperidine-2,6-dione. To a stirred solution of 2,3-dihydrofuro[2,3-c]pyridine-5-carbaldehyde (45 mg, 0.30 mmol) and 3-(1-oxo-5-(((S)-pyrrolidin-3-yl)oxy)isoindolin-2-yl)piperidine-2,6-dione (100 mg, 0.30 mmol) in dichloromethane (6 mL) were added triethylamine (0.08 mL, 0.60 mmol) and sodium triacetoxyborohydride (257 mg, 1.21 mmol) at 0° C. The mixture was stirred for 2 h at room temperature under nitrogen. The resulting solution was concentrated at 25° C. The residue was purified by silica gel column chromatography (0-10% methanol in dichloromethane) and further purified by reverse phase preparative HPLC with the following conditions: Column: Sun Fire Prep C18 OBD Column, 19×150 mm 5 um 10 nm; Mobile Phase A: water (0.1% formic acid), Mobile Phase B: acetonitrile; Flow rate: 60 mL/min; Gradient: 5 B to 30 B in 7 min; 254/210 nm; RT1: 4.65. The fractions containing desired product were collected and evaporated under reduced pressure to afford the title compound (12.1 mg, 0.026 mmol, 9% yield) as an off-white solid. $^1H$ NMR (400 MHz, Methanol-$d_4$) δ 8.35 (s, 1H), 8.06 (s, 1H), 7.75 (d, J=8.4 Hz, 1H), 7.42 (s, 1H), 7.15-7.10 (m, 2H), 5.23 (s, 1H), 5.14 (dd, J=13.3, 5.2 Hz, 1H), 4.67 (t, J=8.9 Hz, 2H), 4.54-4.39 (m, 2H), 4.33-4.20 (m, 2H), 3.53-3.38 (m, 3H), 3.33-3.22 (m, 3H), 2.97-2.88 (m, 1H), 2.83-2.76 (m, 1H), 2.60-2.41 (m, 2H), 2.28-2.23 (m, 1H), 2.21-2.15 (m, 1H). MS (ESI) m/z 463.1 $[M+1]^+$.

Example S24. 3-(1-Oxo-5-(((S)-1-((2-(prop-1-yn-1-yl)quinolin-6-yl)methyl)pyrrolidin-3-yl)oxy)isoindolin-2-yl)piperidine-2,6-dione

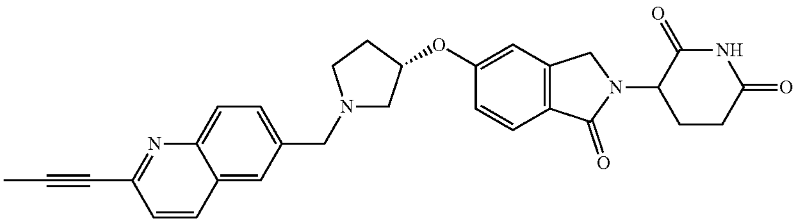 [SMILES: CC#Cc1ccc2cc(CN3CC[C@H](Oc4ccc5c(c4)CN(C4CCC(=O)NC4=O)C5=O)C3)ccc2n1]

2-(Prop-1-yn-1-yl)quinoline-6-carbaldehyde. To a stirred solution of 2-chloroquinoline-6-carbaldehyde (150 mg, 0.78 mmol), prop-1-yne (63 mg, 1.57 mmol) in acetonitrile (6 mL) was added dichlorobis(triphenylphosphine)palladium (II) dichloromethane adduct (64 mg, 0.08 mmol), triethylamine (0.42 mL, 3.06 mmol), copper(I) iodide (30 mg, 0.16 mmol) at room temperature. Then the reaction mixture was stirred at 60° C. for 2 h under nitrogen. The resulting mixture was filtered and the filtrate was concentrated. The crude product was purified by reverse phase flash (10-40% acetonitrile+0.05% ammonium bicarbonate in water, over 20 min) to give the title compound (55 mg, 0.28 mmol, 36% yield) as a yellow solid. MS (ESI) m/z 196.1 $[M+1]^+$.

3-(1-Oxo-5-(((S)-1-((2-(prop-1-yn-1-yl)quinolin-6-yl)methyl)pyrrolidin-3-yl) oxy)isoindolin-2-yl)piperidine-2,6-dione. To a stirred solution of 2-(prop-1-yn-1-yl)quinoline-6-carbaldehyde (50 mg, 0.26 mmol), 3-[1-oxo-5-[(3S)-pyrrolidin-3-yl]oxy-isoindolin-2-yl]piperidine-2,6-dione; 2,2-2-trifluoroacetic acid (115 mg, 0.26 mmol), triethylamine (0.07 mL, 0.52 mmol) in dichloromethane (5 mL) pre-stirred for 15 min was added sodium triacetoxyborohydride (220 mg, 1.0 mmol) at 0° C. and the solution was stirred at room temperature for 4 h under nitrogen. The resulting solution was purified by silica gel chromatography (0 to 10% methanol in dichloromethane). The pure fractions were evaporated and purified further by preparative HPLC with the following conditions: Column: Sun fire Prep C18 OBD Column, 19*250 mm, 10 μm; Mobile Phase A: water (0.1% formic acid), Mobile Phase B: acetonitrile; Flow rate: 60 mL/min; Gradient: 2% B to 18% B in 10 min, 18% B to 18% B in 11 min, 18% B; Wave Length: 254/210 nm; RT1 (min): 10.38; Number Of Runs: 0. The fractions containing desired product were collected and evaporated under reduced pressure to afford the title compound (28.8 mg, 0.056 mmol, 22% yield) as a white solid. $^1H$ NMR (400 MHz, DMSO-$d_6$) δ 10.97 (s, 1H), 8.32 (m, 1H), 8.14 (s, 1H), 7.90 (d, J=8.6 Hz, 2H), 7.76 (m, 1H), 7.61 (d, J=8.5 Hz, 1H), 7.52 (d, J=8.4 Hz, 1H), 7.11 (t, J=1.8 Hz, 1H), 7.01 (m, 1H), 5.04 (m, 2H), 4.37 (d, J=17.2 Hz, 1H), 4.24 (m, 1H), 3.85 (s, 2H), 3.07-2.70 (m, 4H), 2.59 (d, J=17.3 Hz, 2H), 2.40-2.32 (m, 2H), 2.14 (s, 3H), 1.97 (m, 1H), 1.87 (m, 1H); MS (ESI) m/z 509.1 $[M+1]^+$.

Example S25. 3-(5-(Methyl((S)-1-(quinolin-3-ylmethyl)pyrrolidin-3-yl)amino)-1-oxoisoindolin-2-yl) piperidine-2,6-dione

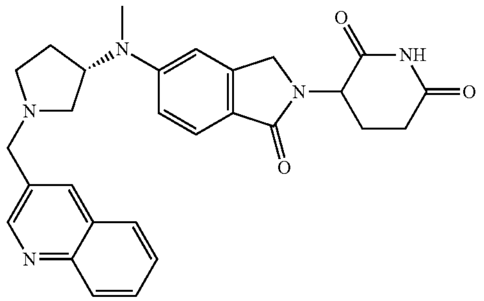 [SMILES: CN(c1ccc2c(c1)CN(C1CCC(=O)NC1=O)C2=O)[C@H]1CCN(Cc2cnc3ccccc3c2)C1]

Tert-butyl (3S)-3-((2-(1-(3,4-dimethoxybenzyl)-2,6-dioxopiperidin-3-yl)-1-oxoisoindolin-5-yl)(methyl)amino) pyrrolidine-1-carboxylate. To a solution of 3-(5-bromo-1-oxoisoindolin-2-yl)-1-(3,4-dimethoxybenzyl)piperidine-2,6-dione (450 mg, 0.95 mmol), tert-butyl (S)-3-(methylamino)pyrrolidine-1-carboxylate (228 mg, 1.14 mmol) and cesium carbonate (929 mg, 2.85 mmol) in 1,4-dioxane (10.0 mL) was added methanesulfonato(2-dicyclohexylphosphino-2',6'-di-i-propoxy-1,1'-biphenyl)-(2'-amino-1,1'-biphenyl-2-yl)palladium(II) (79 mg, 0.094 mmol). The flask was evacuated and flushed five times with nitrogen. The mixture was stirred at 100° C. for 3 h under nitrogen. The mixture was diluted with ethyl acetate and filtered. The resulting solution was concentrated and purified by silica gel chromatography (0 to 90% ethyl acetate in petroleum ether) to afford the title compound (250 mg, 0.42 mmol, 44% yield) as a light-yellow oil. MS (ESI) m/z 537.0 $[M+1-56]^+$.

3-(5-(Methyl((S)-pyrrolidin-3-yl)amino)-1-oxoisoindolin-2-yl)piperidine-2,6-dione; 2,2,2-trifluoroacetic acid. To a solution of tert-butyl (3S)-3-((2-(1-(3,4-dimethoxybenzyl)-2,6-dioxopiperidin-3-yl)-1-oxoisoindolin-5-yl) (methyl) amino)pyrrolidine-1-carboxylate (250 mg, 0.42 mmol) in TFA (2.5 mL) was added trifluoromethanesulfonic acid (0.5 mL) dropwise 0° C. The mixture was stirred at 50° C. for 12 h under nitrogen. The resulting solution was concentrated and the residue was added saturated ammonium bicarbonate to pH 5~6 and purified by reverse phase flash (10-40% acetonitrile+0.05% TFA in water, over 25 min) to afford the title compound (75 mg, 0.16 mmol, 38% yield) as an oil. MS (ESI) m/z 343.0 $[M+1]^+$.

3-(5-(Methyl((S)-1-(quinolin-3-ylmethyl)pyrrolidin-3-yl) amino)-1-oxoisoindolin-2-yl)piperidine-2,6-dione. To a solution of 3-(5-(methyl((S)-pyrrolidin-3-yl)-amino)-1-oxoisoindolin-2-yl)piperidine-2,6-dione; 2,2,2-trifluoroacetic acid (75 mg, 0.17 mmol), quinoline-3-carbaldehyde (52 mg, 0.33 mmol) and triethylamine (27 mg, 0.26 mmol) in dichloromethane (10 mL) was added sodium triacetoxyborohydride (186 mg, 0.88 mmol). The flask was evacuated and flushed five times with nitrogen. The mixture was stirred for 2 h at room temperature under nitrogen. The resulting mixture was concentrated and the residue was purified by preparative HPLC using the following conditions: Column: Xselect CSH OBD Column 30*150 mm 5 um; Mobile Phase A: water (0.05% TFA), Mobile Phase B: acetonitrile; Flow rate: 60 mL/min; Gradient: 5 B to 5 B in 2 min; 254/210 nm; RT1:8.48 min. The fractions containing desired product were collected and evaporated under reduced pressure to afford the title compound (25.5 mg, 0.053 mmol, 31% yield) as a yellow solid. $^1H$ NMR (400 MHz, Methanol-$d_4$) δ 9.09 (d, J=2.2 Hz, 1H), 8.72 (d, J=2.2 Hz, 1H), 8.16 (d, J=8.5 Hz, 1H), 8.11 (d, J=8.2 Hz, 1H), 7.96 (m, 1H), 7.79 (m, 1H), 7.65 (d, J=9.3 Hz, 1H), 7.04 (m, 2H), 5.11 (m, 1H), 4.99 (m, 1H), 4.80 (d, J=13.2 Hz, 1H), 4.75 (d, J=13.3 Hz, 1H), 4.49-4.34 (m, 2H), 3.86-3.76 (m, 1H), 3.71-3.52 (m, 3H), 3.01 (s, 3H), 2.91 (m, 1H), 2.84-2.74 (m, 1H), 2.55-2.41 (m, 2H), 2.34 (m, 1H), 2.16 (m, 1H); MS (ESI) m/z 484.1 $[M+1]^+$.

Example S26. 3-(5-(((S)-1-(Isoquinolin-3-ylmethyl) pyrrolidin-3-yl)oxy)-1-oxoisoindolin-2-yl)piperidine-2,6-dione

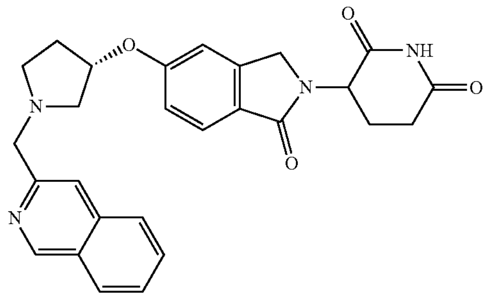 [SMILES: O=C1CCC(N2Cc3cc(O[C@H]4CCN(Cc5cc6ccccc6cn5)C4)ccc3C2=O)C(=O)N1]

3-(5-(((S)-1-(Isoquinolin-3-ylmethyl)pyrrolidin-3-yl) oxy)-1-oxoisoindolin-2-yl)piperidine-2,6-dione. To a solution of 3-(1-oxo-5-(((S)-pyrrolidin-3-yl)oxy)isoindolin-2-yl)piperidine-2,6-dione hydrochloride (100 mg, 0.27 mmol), isoquinoline-3-carbaldehyde (65 mg, 0.41 mmol) and triethylamine (33 mg, 0.33 mmol) in dichloromethane (10.0 mL) was added sodium triacetoxyborohydride (232 mg, 1.09 mmol). The solution was stirred for 2 h at room temperature under nitrogen. The resulting mixture was concentrated and the residue was purified by silica gel chromatography (0 to 5% methanol in dichloromethane) and further purified by preparative HPLC with following condition: Column: XSelect CSH Prep C18 OBD Column, 5 um, 19*150 mm; Mobile Phase A: water (0.05% formic acid), Mobile Phase B: acetonitrile; Flow rate: 25 mL/min; Gradient: 5 B to 20 B in 7 min; 254/210 nm; RT: 6.67 min. The pure fractions were concentrated to afford title compound (26.0 mg, 0.05 mmol, 35% yield) as an off-white solid. $^1H$ NMR (300 MHz, Methanol-$d_4$) δ 9.29 (s, 1H), 8.13 (d, J=8.2 Hz, 1H), 8.00-7.89 (m, 2H), 7.88-7.77 (m, 1H), 7.83-7.67 (m, 2H), 7.15-7.03 (m, 2H), 5.19-5.13 (m, 1H), 4.45 (m, 2H), 4.35 (m, 2H), 3.43 (m, 1H), 3.32 (m, 2H), 3.17 (m, 1H), 3.01-2.70 (m, 2H), 2.62-2.39 (m, 2H), 2.24-2.05 (m, 2H); MS (ESI) m/z 471.1 $[M+1]^+$.

Example S27. 3-(5-(((S)-1-((2,3-Dimethylpyridin-4-yl)methyl)pyrrolidin-3-yl)oxy)-1-oxoisoindolin-2-yl) piperidine-2,6-dione

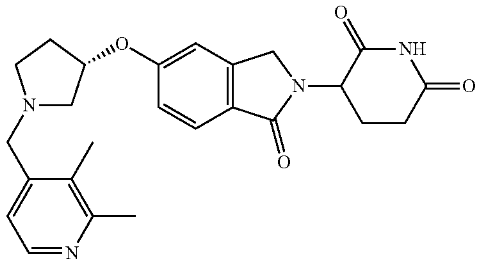 [SMILES: Cc1nccc(CN2CC[C@H](Oc3ccc4c(c3)CN(C3CCC(=O)NC3=O)C4=O)C2)c1C]

2,3-Dimethylisonicotinaldehyde. To a solution of 4-bromo-2,3-dimethylpyridine (200 mg, 1.07 mmol), 2-isocyano-2-methyl-propane (107 mg, 1.29 mmol), 1,2-bis(diphenylphosphino)ethane (86 mg, 0.21 mmol) and sodium formate (146 mg, 2.15 mmol) in DMSO (5.0 mL) was added Palladium (II) acetate (24 mg, 0.11 mmol). The mixture was stirred at 120° C. for 3 h under nitrogen. The resulting solution was diluted with water and extracted with ethyl acetate. The combined organic layers were washed with brine, dried and concentrated under reduced pressure. The residue was purified by silica gel chromatography (30% to 100% ethyl acetate in petroleum ether) to give title compound (80 mg, 0.59 mmol, 55% yield) as a yellow oil. MS (ESI) m/z 136.0 $[M+1]^+$.

6-Bromo-5-fluoro-2-(tetrahydro-2H-pyran-4-yl)quinoline. To a solution of 2,3-dimethylisonicotinaldehyde (44 mg, 0.33 mmol), 3-(1-oxo-5-(((S)-pyrrolidin-3-yl)oxy) isoindolin-2-yl)piperidine-2,6-dione hydrochloride (100 mg, 0.27 mmol) and triethylamine (33 mg, 0.33 mmol) in dichloromethane (10.0 mL) was added sodium triacetoxyborohydride (232 mg, 1.09 mmol). The mixture was stirred for 2 h at room temperature under nitrogen. The resulting mixture was concentrated under reduced pressure. The residue was purified by preparative HPLC with following condition: Column: Sunfire prep C18 column, 30*150 mm, 5 um; Mobile Phase A: water (0.05% formic acid), Mobile Phase B: acetonitrile; Flow rate: 60 mL/min; Gradient: 2 B to 2 B in 2 min; 254/210 nm; RT1:7.53. The fractions containing desired product were collected and evaporated under reduced pressure to afford the title compound (18.5 mg, 0.041 mmol, 15% yield) as an off-white solid. $^1$H NMR (400 MHz, Methanol-$d_4$) δ 8.29-8.20 (m, 2H), 7.73 (d, J=8.4 Hz, 1H), 7.44 (d, J=5.5 Hz, 1H), 7.10 (d, J=2.2 Hz, 1H), 7.06 (dd, J=8.5, 2.2 Hz, 1H), 5.13 (dd, J=13.3, 5.2 Hz, 1H), 5.08 (m, 1H), 4.53-4.38 (m, 2H), 3.92-3.87 (m, 2H), 3.13 (m, 1H), 3.01-2.85 (m, 2H), 2.85-2.72 (m, 2H), 2.68 (m, 1H), 2.58 (s, 3H), 2.49 (m, 2H), 2.38 (s, 3H), 2.22-2.13 (m, 1H), 2.10-2.02 (m, 1H; MS (ESI) m/z 449.1 $[M+1]^+$.

Example S28. 3-(5-(((S)-1-((3,4-dihydro-2H-pyrano [2,3-c]pyridin-5-yl)methyl)pyrrolidin-3-yl)oxy)-1-oxoisoindolin-2-yl)piperidine-2,6-dione

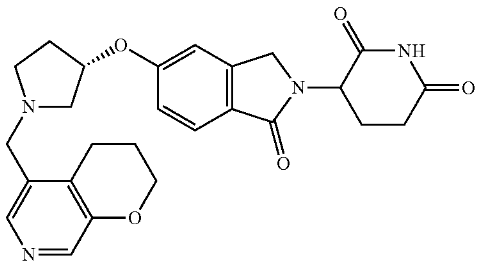 [SMILES: O=C1CCC(N2Cc3cc(O[C@H]4CCN(Cc5cncc6c5CCCO6)C4)ccc3C2=O)C(=O)N1]

Ethyl (E)-3-(3,5-dibromopyridin-4-yl)acrylate. To a solution of 3,5-dibromoisonicotinaldehyde (1.0 g, 3.78 mmol) in toluene (5.0 mL) was added ethyl 2-(triphenyl-λ^5-phosphanylidene)acetate (1.5 g, 4.15 mmol). The flask was evacuated and flushed three times with nitrogen. The mixture was stirred for 12 h at 80° C. under nitrogen. The resulting solution was concentrated under reduced pressure. The residue was purified by silica gel chromatography (0 to 25% ethyl acetate in petroleum ether) to afford title compound (1.2 g, 3.58 mmol, 95% yield) as a light-yellow solid. MS (ESI) m/z 334.0 $[M+1]^+$.

3-(3,5-Dibromopyridin-4-yl)propan-1-ol. To a solution of ethyl (E)-3-(3,5-dibromopyridin-4-yl)acrylate (600 mg, 1.79 mmol) in methanol (10.0 mL) was added sodium borohydride (135 mg, 3.58 mmol). The mixture was stirred at room temperature for 1.5 h. Then the mixture was added lithium borohydride (35 mg, 1.59 mmol) and stirred for 12 h at 50° C. under nitrogen. After cooling to room temperature, glacial acetic acid is added and the mixture was concentrated under reduced pressure. The residue was dissolved in ethyl acetate, and washed with aqueous hydrogen chloride (1M), saturated sodium bicarbonate, and saturated sodium chloride. The organic layer was dried with anhydrous sodium sulfate, filtered, and concentrated under reduced pressure. The crude product is purified by silica gel chromatography (0 to 25% ethyl acetate in petroleum ether) to give title compound (400 mg, 1.35 mmol, 76% yield) as an off-white solid. MS (ESI) m/z 294.0$[M+1]^+$.

5-Bromo-3,4-dihydro-2H-pyrano[2,3-c]pyridine. To a solution of 3-(3,5-dibromopyridin-4-yl)propan-1-ol (400 mg, 1.36 mmol), pyridin-2-amine (13 mg, 0.14 mmol) and copper(I) chloride (13 mg, 0.14 mmol) in was added sodium methanolate (30% in methanol, 366 mg, 2.03 mmol). The sealed tube was filled with nitrogen. The mixture was heated, with microwave irradiation, in a microwave reactor at 135° C. for 6 h. Then saturated sodium bicarbonate solution is added, and the mixture is extracted with ethyl acetate. The organic layer is dried with anhydrous sodium sulfate, filtered, and the filtrate was concentrated under reduced pressure. The residue was purified by silica gel chromatography (0 to 25% ethyl acetate in petroleum ether) to give title compound (280 mg, 1.30 mmol, 96% yield) as a yellow oil. MS (ESI) m/z 214.0 $[M+1]^+$.

5-Vinyl-3,4-dihydro-2H-pyrano[2,3-c]pyridine. To a solution of 5-bromo-3,4-dihydro-2H-pyrano[2,3-c]pyridine (280 mg, 1.31 mmol), tributyl(vinyl)stannane (498 mg, 1.57 mmol) and cesium fluoride (298 mg, 1.96 mmol) in 1,4-dioxane (5.0 mL) was added dichlorobis(triphenylphosphine)palladium(II) dichloromethane adduct (184 mg, 0.26 mmol). The flask was evacuated and flushed five times with nitrogen. The mixture was stirred at 80° C. for 3 h under nitrogen. The resulting solution was diluted with water and extracted with ethyl acetate. The organic layers were combined, washed with brine, dried and concentrated under reduced pressure. The residue was purified by silica gel chromatography (20% to 100% ethyl acetate in petroleum ether) to give title compound (120 mg, 0.75 mmol, 57% yield) as a colorless oil. MS (ESI) m/z 162.0 $[M+1]^+$.

3,4-Dihydro-2H-pyrano[2,3-c]pyridine-5-carbaldehyde To a solution of 5-vinyl-3,4-dihydro-2H-pyrano[2,3-c]pyridine (120 mg, 0.74 mmol), potassium osmate (27 mg, 0.07 mmol), 4-methylmorpholine N-oxide (174 mg, 1.49 mmol) in tert-butanol (3.0 mL) and water (3.0 mL) was added citric acid (285 mg, 1.49 mmol). The mixture was stirred at room temperature for 6 h under nitrogen, then sodium periodate (478 mg, 2.23 mmol) was added and the mixture was stirred at room temperature for another 3 h. The resulting solution was diluted with water, and then extracted with ethyl acetate. The organic layers were combined, washed with brine, dried and concentrated to afford title compound (80 mg, 0.49 mmol, 66% yield) as a brown oil. MS (ESI) m/z 164.0 $[M+1]^+$.

3-(5-(((S)-1-((3,4-Dihydro-2H-pyrano[2,3-c]pyridin-5-yl)methyl)pyrrolidin-3-yl)oxy)-1-oxoisoindolin-2-yl)piperidine-2,6-dione. To a solution of 3,4-dihydro-2H-pyrano[2,3-c]pyridine-5-carbaldehyde (80 mg, 0.49 mmol), 3-(1-oxo-5-(((S)-pyrrolidin-3-yl)oxy)isoindolin-2-yl)piperidine-2,6-dione hydrochloride (100 mg, 0.27 mmol) and triethylamine (33 mg, 0.33 mmol) in dichloromethane was added sodium triacetoxyborohydride (232 mg, 1.09 mmol). The flask was evacuated and flushed five times with nitrogen. The mixture was stirred for 2 h at room temperature under nitrogen atmosphere. The resulting solution was concentrated under reduced pressure. The residue was purified by preparative HPLC with following condition: Column: XSelect CSH Prep C18 OBD Column, 5 um, 19*150 mm; Mobile Phase A: water (0.05% formic acid), Mobile Phase B: acetonitrile; Flow rate: 25 mL/min; Gradient: 2 B to 14 B in 7 min; 254/210 nm; RT1:6.30. The pure fractions were concentrated to afford title compound (13.7 mg, 0.03 mmol, 10%) as an off-white solid. $^1H$ NMR (400 MHz, Methanol-$d_4$) δ 8.02 (d, J=12.0 Hz, 2H), 7.73 (d, J=8.5 Hz, 1H), 7.13-7.03 (m, 2H), 5.13 (m, 2H), 4.53-4.38 (m, 2H), 4.28-4.21 (m, 2H), 3.91 (s, 2H), 3.29-3.11 (m, 1H), 3.08 (m, 2H), 2.99-2.76 (m, 5H), 2.49 (m, 2H), 2.26-2.10 (m, 1H), 2.13-2.04 (m, 3H); MS (ESI) m/z 477.1 $[M+1]^+$.

Example S29. 3-(5-(((S)-1-((8-Fluoroisoquinolin-3-yl)methyl)pyrrolidin-3-yl)oxy)-1-oxoisoindolin-2-yl) piperidine-2,6-dione

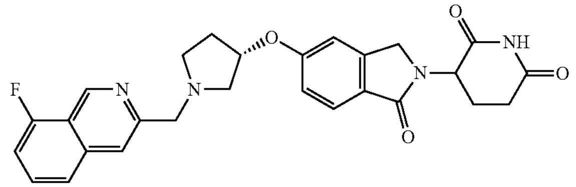 [SMILES: O=C1CCC(N2Cc3cc(O[C@H]4CCN(Cc5cc6cccc(F)c6cn5)C4)ccc3C2=O)C(=O)N1]

2-(3,3-Diethoxyprop-1-yn-1-yl)-6-fluorobenzaldehyde. To a solution of 2-bromo-6-fluorobenzaldehyde (1.0 g, 4.93 mmol) and 3,3-diethoxyprop-1-yne (631 mg, 4.93 mmol) in triethylamine (30 mL) was added dichlorobis(triphenylphosphine)-palladium(II) dichloromethane adduct (346 mg, 0.49 mmol) and cuprous iodide (47 mg, 0.25 mmol). The flask was evacuated and flushed three times with nitrogen. The mixture was stirred at 60° C. for 12 h under nitrogen. The mixture was diluted with water and extracted with ethyl acetate. The organic layers were combined, washed with brine, dried and concentrated under reduced pressure. The residue was purified by silica gel chromatography (0 to 25% ethyl acetate in petroleum ether) to give title compound (500 mg, 1.99 mmol, 41% yield) as a brown oil. MS (ESI) m/z 251.0 $[M+1]^+$.

3-(Diethoxymethyl)-8-fluoroisoquinoline. 2-(3,3-diethoxyprop-1-yn-1-yl)-6-fluorobenzaldehyde (500 mg, 1.99 mmol) was added in ammonia (7 M in MeOH, 10 mL) and the reaction were heated with microwave irradiation, in a microwave reactor at 100° C. for 20 min under nitrogen. The resulting solution was concentrated to give a crude title compound. MS (ESI) m/z 250.0 $[M+1]^+$.

8-Fluoroisoquinoline-3-carbaldehyde. To a solution of 3-(diethoxymethyl)-8-fluoroisoquinoline (1.0 g crude, ~4.01 mmol) in THF (10.0 mL) was added HCl (6 M, 10.0 mL). The flask was evacuated and flushed three times with nitrogen. The mixture was stirred at 40° C. for 12 h under nitrogen. The resulting solution was concentrated under reduced pressure. The residue was purified by silica gel chromatography (30% to 100% ethyl acetate in petroleum ether) to give title compound (75 mg, 0.42 mmol, 11% yield) as an off-white solid. MS (ESI) m/z 176.0 $[M+1]^+$.

3-(5-(((S)-1-((8-Fluoroisoquinolin-3-yl)methyl)pyrrolidin-3-yl)oxy)-1-oxoisoindolin-2-yl)piperidine-2,6-dione. To a solution of 8-fluoroisoquinoline-3-carbaldehyde (80 mg, 0.46 mmol), 3-(1-oxo-5-(((S)-pyrrolidin-3-yl)oxy)isoindolin-2-yl)piperidine-2,6-dione hydrochloride (100 mg, 0.27 mmol) and triethylamine (33 mg, 0.33 mmol) in dichloromethane (10.0 mL) was added sodium triacetoxyborohydride (232 mg, 1.09 mmol). The flask was evacuated and flushed five times with nitrogen. The mixture was stirred for 2 h at room temperature under nitrogen. The resulting mixture was concentrated under reduced pressure. The residue was purified by preparative HPLC with following condition: Column: XSelect CSH Prep C18 OBD Column, 5 um, 19*150 mm; Mobile Phase A: water (0.05% formic acid), Mobile Phase B: acetonitrile; Flow rate: 25 mL/min; Gradient: 8 B to 20 B in 7 min; 254/210 nm; RT1:5.92. The pure fractions were concentrated to afford title compound (20.7 mg, 0.04 mmol, 15% yield) as a colorless solid. $^1H$ NMR (400 MHz, Methanol-$d_4$) δ 9.51 (s, 1H), 8.34 (s, 1H), 7.97 (s, 1H), 7.86-7.77 (m, 2H), 7.74 (d, J=8.4 Hz, 1H), 7.46-7.37 (m, 1H), 7.16-7.06 (m, 2H), 5.21 (m, 1H), 5.14 (dd, J=13.3, 5.2 Hz, 1H), 4.46 (d, J=6.8 Hz, 2H), 4.41 (m, 2H), 3.48 (m, 1H), 3.41-3.32 (m, 2H), 3.21-3.15 (m, 1H), 2.92 (m, 1H), 2.79 (m, 1H), 2.59-2.45 (m, 2H), 2.29-2.11 (m, 2H); MS (ESI) m/z 489.2 $[M+1]^+$.

Example S30. 3-(1-Oxo-5-(((S)-1-(quinoxalin-2-ylmethyl)pyrrolidin-3-yl)oxy)isoindolin-2-yl)piperidine-2,6-dione

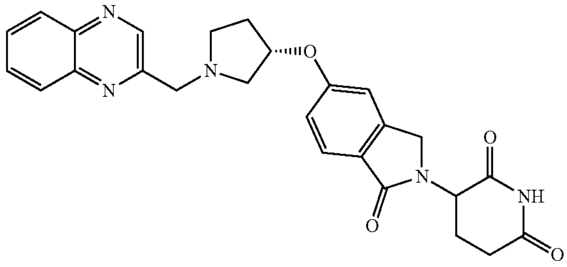 [SMILES: O=C1CCC(N2Cc3cc(O[C@H]4CCN(Cc5cnc6ccccc6n5)C4)ccc3C2=O)C(=O)N1]

3-(1-Oxo-5-(((S)-1-(quinoxalin-2-ylmethyl)pyrrolidin-3-yl)oxy)isoindolin-2-yl)piperidine-2,6-dione. To a solution of 3-[1-oxo-5-[(3S)-pyrrolidin-3-yl]oxoisoindolin-2-yl]piperidine-2,6-dione; hydrochloride (120 mg, 0.33 mmol), quinoxaline-2-carbaldehyde (78 mg, 0.49 mmol) and triethylamine (49 mg, 0.49 mmol) in dichloromethane (5 mL) was added sodium triacetoxyborohydride (278 mg, 1.31 mmol) and the mixture was stirred 2 h at room temperature. The mixture was concentrated and the residue was purified by silica gel chromatography (10% methanol in dichloromethane) and preparative HPLC with the following conditions: XSelect CSH Prep C18 OBD Column, 5 um, 19*150 mm; Mobile Phase A: water (0.05% formic acid), Mobile Phase B: acetonitrile; Flow rate: 25 mL/min; Gradient: 5 B to 23 B in 7 min; 254/210 nm; RT1:5.33. The fractions containing desired product were collected and evaporated under reduced pressure to afford the title (45.4 mg, 0.096 mmol, 29% yield) as an off-white solid. $^1$H NMR (400 MHz, Methanol-$d_4$) δ 9.01 (d, J=1.8 Hz, 1H), 8.16-8.06 (m, 2H), 7.92-7.82 (m, 2H), 7.72 (d, J=8.5 Hz, 1H), 7.14-7.03 (m, 2H), 5.14 (m, 2H), 4.42 (m, 4H), 3.39 (m, 1H), 3.20 (m, 2H), 3.03-2.85 (m, 2H), 2.83-2.74 (m, 1H), 2.57-2.42 (m, 2H), 2.17 (m, 2H); MS (ESI) m/z 472.2 $[M+1]^+$.

Example S31. 3-(5-(Methyl((R)-1-(quinolin-3-ylmethyl)pyrrolidin-3-yl)amino)-1-oxoisoindolin-2-yl)piperidine-2,6-dione

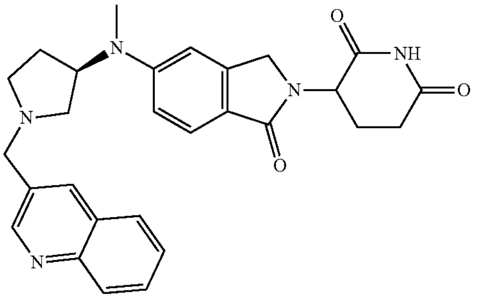 [SMILES: CN(c1ccc2c(c1)CN(C1CCC(=O)NC1=O)C2=O)[C@@H]1CCN(Cc2cnc3ccccc3c2)C1]

Tert-butyl (3R)-3-((2-(1-(3,4-dimethoxybenzyl)-2,6-dioxopiperidin-3-yl)-1-oxoisoindolin-5-yl)(methyl)amino)pyrrolidine-1-carboxylate. To a stirred solution of 3-(5-bromo-1-oxoisoindolin-2-yl)-1-(2,4-dimethoxybenzyl)piperidine-2,6-dione (500 mg, 1.06 mmol), tert-butyl (R)-3-(methylamino)pyrrolidine-1-carboxylate (254 mg, 1.27 mmol) and cesium carbonate (1.0 g, 3.07 mmol) in DMF (5.0 mL) was added methanesulfonato(2-dicyclohexylphosphino-2',6'-di-i-propoxy-1,1'-biphenyl) (2'-amino-1,1'-biphenyl-2-yl)palladium(II) (90 mg, 0.11 mmol) and the mixture was stirred for 12 h at 120° C. under nitrogen. The resulting mixture was diluted with water and extracted with ethyl acetate. The extracts were washed with brine, dried over anhydrous sodium sulfate, filtered and concentrated. The residue was purified by silica gel chromatography (0-10% methanol in dichloromethane) to give the title compound (238 mg, 0.40 mmol, 45% yield) as a light yellow solid. MS (ESI) m/z 537.0 $[M+1-56]^+$.

3-(5-(Methyl((R)-pyrrolidin-3-yl)amino)-1-oxoisoindolin-2-yl)piperidine-2,6-dione; 2,2,2-trifluoroacetic acid. To a solution of tert-butyl (3R)-3-((2-(1-(3,4-dimethoxybenzyl)-2,6-dioxopiperidin-3-yl)-1-oxoisoindolin-5-yl)(methyl)amino)pyrrolidine-1-carboxylate (200 mg, 0.34 mmol) in TFA (5.0 mL) was added trifluoromethanesulfonic acid (0.2 mL) at room temperature and the resulting mixture was stirred 4 h at 50° C. under nitrogen. The resulting solution was concentrated and the residue was added saturated ammonium bicarbonate to pH 5-6, filtered and the filtrate was purified by reverse phase flash (10-40% acetonitrile+0.05% TFA in water, over 25 min) to afford the title compound (90 mg, 0.20 mmol, 59% yield) as a light yellow oil. MS (ESI) m/z 343.0 $[M+1]^+$.

3-(5-(Methyl((R)-1-(quinolin-3-ylmethyl)pyrrolidin-3-yl)amino)-1-oxoisoindolin-2-yl)piperidine-2,6-dione. To a solution of the compound 3-(5-(methyl((R)-pyrrolidin-3-yl)amino)-1-oxoisoindolin-2-yl)piperidine-2,6-dione; 2,2,2-trifluoroacetic acid (95 mg, 0.25 mmol), quinoline-3-carbaldehyde (59 mg, 0.37 mmol) and triethylamine (38 mg, 0.38 mmol) in dichloromethane (5.0 mL) was added sodium triacetoxyborohydride (213 mg, 1.00 mmol) and the mixture was stirred 2 h at room temperature under nitrogen. The mixture was concentrated and the crude product was purified by preparative HPLC with following condition: Column: XSelect CSH Prep C18 OBD Column, 5 um, 19*150 mm; Mobile Phase A: water (0.05% formic acid), Mobile Phase B: acetonitrile; Flow rate: 25 mL/min; Gradient: 5 B to 20 B in 7 min; 254/210 nm; RT1:6.22. The fractions containing desired product were collected and evaporated under reduced pressure to afford the title compound (9.5 mg, 0.020 mmol, 8% yield) as a light yellow solid. $^1$H NMR (400 MHz, DMSO-$d_6$) δ 10.94 (s, 1H), 8.92 (d, J=2.1 Hz, 1H), 8.28 (s, 1H), 8.06-7.95 (m, 2H), 7.75 (m, 1H), 7.62 (m, 1H), 7.47 (d, J=8.4 Hz, 1H), 6.94-6.86 (m, 2H), 5.03 (dd, J=13.3, 5.1 Hz, 1H), 4.63 (m, 1H), 4.29 (d, J=16.7 Hz, 1H), 4.17 (d, J=16.7 Hz, 1H), 3.89 (m, 2H), 2.95 (s, 3H), 2.92-2.83 (m, 2H), 2.74-2.58 (m, 3H), 2.38-2.20 (m, 3H), 1.94 (m, 1H), 1.77 (m, 1H); MS (ESI) m/z 484.3 $[M+1]^+$.

Example S32. 3-(5-(((S)-1-((3-Methylquinolin-6-yl)methyl)pyrrolidin-3-yl)oxy)-1-oxoisoindolin-2-yl)piperidine-2,6-dione

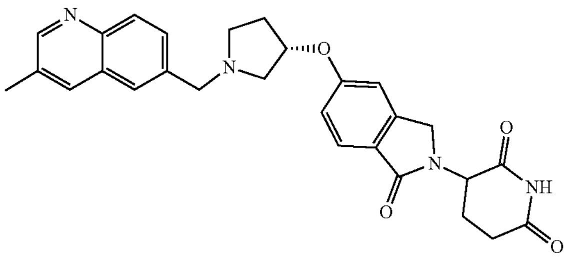 [SMILES: Cc1cnc2ccc(CN3CC[C@H](Oc4ccc5c(c4)CN(C4CCC(=O)NC4=O)C5=O)C3)cc2c1]

3-Methylquinoline-6-carbaldehyde. To a solution of 6-bromo-3-methyl-quinoline (450 mg, 2.03 mmol), 2-isocyano-2-methyl-propane (202 mg, 4.10 mmol), palladium acetate (23 mg, 0.10 mmol) and potassium formate (341 mg, 4.05 mmol) in DMSO (2 mL) was added 1,2-bis(diphenylphosphino)ethane (52 mg, 0.13 mmol) and the resulting mixture was stirred for 3 h at 120° C. under nitrogen. The mixture was diluted with water and extracted with ethyl acetate. The extracts were washed with brine, dried over anhydrous sodium sulfate, filtered and concentrated. The residue was purified by silica gel chromatography (10% hexane in ethyl acetate) to afford the title compound (183 mg, 1.06 mmol, 53% yield) as a yellow solid. MS (ESI) m/z 172.1 $[M+1]^+$.

3-(5-(((S)-1-((3-Methylquinolin-6-yl)methyl)pyrrolidin-3-yl)oxy)-1-oxoisoindolin-2-yl)piperidine-2,6-dione. To a solution of 3-[1-oxo-5-[(3S)-pyrrolidin-3-yl]oxy-isoindolin-2-yl]piperidine-2,6-dione; hydrochloride (128 mg, 0.35 mmol), 3-methylquinoline-6-carbaldehyde (90 mg, 0.53 mmol) and triethylamine (53 mg, 0.53 mmol) in dichloromethane (5 mL) was added sodium triacetoxyborohydride (297 mg, 1.40 mmol) and the resulting mixture was stirred for 2 h at room temperature. The resulting mixture was concentrated and purified by silica gel chromatography (10% methanol in dichloromethane) and preparative HPLC with the following conditions: XSelect CSH Prep C18 OBD Column, 5 um, 19*150 mm; Mobile Phase A: water (0.1% formic acid), Mobile Phase B: acetonitrile; Flow rate: 25 mL/min; Gradient: 5 B to 35 B in 7 min; 254/210 nm; RT1:3.77; The fractions containing desired product were collected and evaporated under reduced pressure to afford the title compound (11.8 mg, 0.02 mmol, 7% yield) as an off-white solid. $^1H$ NMR (400 MHz, DMSO-$d_6$) δ 10.97 (s, 1H), 8.75 (d, J=2.2 Hz, 1H), 8.10 (m, 1H), 7.96 (d, J=8.6 Hz, 1H), 7.84 (m, 1H), 7.69 (d, J=8.7 Hz, 1H), 7.62 (d, J=8.4 Hz, 1H), 7.13 (m, 1H), 7.02 (m, 1H), 5.06 (m, 2H), 4.38 (d, J=17.2 Hz, 1H), 4.25 (m, 1H), 3.92 (m, 2H), 2.90 (m, 4H), 2.59 (m, 2H), 2.48 (s, 3H), 2.38 (m, 2H), 1.98-1.80 (m, 2H); MS (ESI) m/z 485.1 $[M+1]^+$.

Example S33. 3-(5-(((S)-1-((5,6-difluoroquinolin-3-yl)methyl)pyrrolidin-3-yl)oxy)-1-oxoisoindolin-2-yl)piperidine-2,6-dione

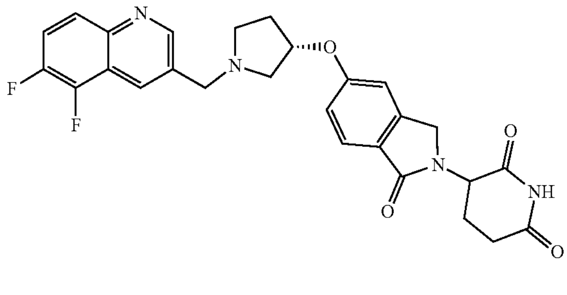 [SMILES: O=C1CCC(N2Cc3cc(O[C@H]4CCN(Cc5cnc6ccc(F)c(F)c6c5)C4)ccc3C2=O)C(=O)N1]

1,2-Difluoro-3-nitro-4-vinylbenzene. To a solution of 1-bromo-3,4-difluoro-2-nitro-benzene (1.0 g, 4.20 mmol), tributyl(vinyl)stannane (1.6 g, 5.04 mmol) and potassium carbonate (1.7 g, 12.61 mmol) in 1,4-dioxane (20 mL) and water (2 mL) was added [1'1-Bis(diphenylphosphino)ferrocene] dichloro palladiuM(II) (615 mg, 0.84 mmol) and the mixture was stirred for 12 h under nitrogen at 100° C. The resulting mixture was added water and extracted with ethyl acetate. The extracts were washed with brine, dried over anhydrous sodium sulfate, filtered and concentrated. The residue was purified by silica gel chromatography (0 to 20% ethyl acetate in petroleum ether) to afford the title compound (410 mg, 2.20 mmol, 53% yield) as a yellow solid. MS (ESI) m/z 186.1 $[M+1]^+$.

3,4-Difluoro-2-nitrobenzaldehyde. To a solution of the compound 1,2-difluoro-3-nitro-4-vinyl-benzene (410 mg, 2.22 mmol), potassium osmate (163 mg, 0.44 mmol), 4-methylmorpholine N-oxide (519 mg, 4.43 mmol) in tert-butanol (5 mL) and water (5 mL) was added citric acid (851 mg, 4.43 mmol) under an air atmosphere. The resulting mixture was stirred 5 h at room temperature. Then the mixture was added sodium periodate (1.4 g, 6.64 mmol) under an air atmosphere. The resulting mixture was stirred 1 h at room temperature. The resulting mixture was added water and extracted with ethyl acetate. The extracts were washed with brine, dried over anhydrous sodium sulfate, filtered and concentrated. The residue was purified by silica gel chromatography (0 to 20% ethyl acetate in petroleum ether) to afford the title compound (330 mg, 1.76 mmol, 78% yield) as a yellow oil. MS (ESI) m/z 188.1 $[M+1]^+$.

Methyl 5,6-difluoroquinoline-3-carboxylate. To a solution of the compound 4,5-difluoro-6-nitro-cyclohexa-2,4-diene-1-carbaldehyde (300 mg, 1.59 mmol), methyl 3,3-dimethoxypropionate (588 mg, 3.97 mmol) in ethanol (5 mL) was added tin chloride (1.4 g, 6.35 mmol) under a nitrogen atmosphere. The resulting mixture was stirred 3 h at 90° C. The resulting mixture was added water and extracted with ethyl acetate. The extracts were washed with brine, dried over anhydrous sodium sulfate, filtered and concentrated. The residue was purified by silica gel chromatography (0 to 10% ethyl acetate in petroleum ether) to afford the title compound (190 mg, 0.85 mmol, 54% yield) as a yellow solid. MS (ESI) m/z 224.2 $[M+1]^+$.

5,6-Difluoroquinoline-3-carbaldehyde. To a solution of methyl 5,6-difluoroquinoline-3-carboxylate in THF (10 mL) was added lithium aluminium hydride (2.5 M in THF, 0.36 mL, 0.89 mmol) under a nitrogen atmosphere at 0° C. The resulting mixture was stirred 1 h at room temperature. The mixture was quenched with water, and the value of pH=5 was adjusted with 15% sodium hydroxide. The solids were filtered out and washed with ethyl acetate. Filtrate was concentrated and purified by pre-TLC (5% methanol in dichloromethane) to afford the title compound (118 mg, 0.66 mmol, 71% yield) as a light yellow solid. Then the (5,6-difluoro-3-quinolyl)methanol (118 mg, 0.614 mmol, 1 equiv) in chloroform (3 mL) was added manganese dioxide (530 mg, 6.15 mmol) under an air atmosphere. The resulting mixture was stirred for 12 h at room temperature. The solids were filtered out and filtrate was concentrated to afford the title compound (90 mg, 0.51 mmol, 76% yield) as a light yellow solid. MS (ESI) m/z 178.2 $[M+1]^+$.

3-(5-(((S)-1-((5,6-difluoroquinolin-3-yl)methyl)pyrrolidin-3-yl)oxy)-1-oxoisoindolin-2-yl)piperidine-2,6-dione. To a solution of the compound 3-[1-oxo-5-[(3S)-pyrrolidin-3-yl]oxy-isoindolin-2-yl]piperidine-2,6-dione; hydrochloride (113 mg, 0.31 mmol), 5,6-difluoroquinoline-3-carbaldehyde (90 mg, 0.46 mmol) and triethylamine (47 mg, 0.46 mmol) in dichloromethane (5 mL) was added sodium triacetoxyborohydride (262 mg, 1.24 mmol) under a nitrogen atmosphere. The resulting mixture was stirred 2 h at room temperature. The resulting mixture was stirred 3 h at room temperature. The resulting solution concentrated and the residue was purified by prep-TLC (10% methanol in dichloromethane) and preparative HPLC with the following conditions: XSelect CSH Prep C18 OBD Column, 5 um, 19*150 mm; Mobile Phase A: Water (0.05% formic acid), Mobile Phase B: acetonitrile; Flow rate: 25 mL/min; Gradient: 5 B to 25 B in 7 min; 254/210 nm; RT1:6.12; The fractions containing desired product were collected and evaporated under reduced pressure to afford the title (32.5 mg, 0.06 mmol, 20% yield) as an off-white solid. $^1$H NMR (400 MHz, DMSO-$d_6$) δ 10.98 (s, 1H), 8.96 (d, J=2.1 Hz, 1H), 8.41 (d, J=2.1 Hz, 1H), 7.95 (m, J=9.5, 4.7 Hz, 1H), 7.87 (m, J=10.6, 8.8 Hz, 1H), 7.61 (d, J=8.4 Hz, 1H), 7.12 (d, J=2.0 Hz, 1H), 7.02 (m, J=8.4, 2.2 Hz, 1H), 5.12-4.99 (m, 2H), 4.38 (d, J=17.2 Hz, 1H), 4.25 (d, J=16.8 Hz, 1H), 3.92 (s, 2H), 2.99 (s, 1H), 2.91 (m, J=18.2, 13.5, 5.4 Hz, 1H), 2.82 (s, 1H), 2.75 (m, J=8.2 Hz, 1H), 2.64-2.55 (m, 2H), 2.45-2.33 (m, 2H), 1.91-1.83 (m, 2H); MS (ESI) m/z 507.2 $[M+1]^+$.

Example S34. 3-(5-(((S)-1-((5,6-Dimethylpyridin-3-yl)methyl)pyrrolidin-3-yl)oxy)-1-oxoisoindolin-2-yl) piperidine-2,6-dione

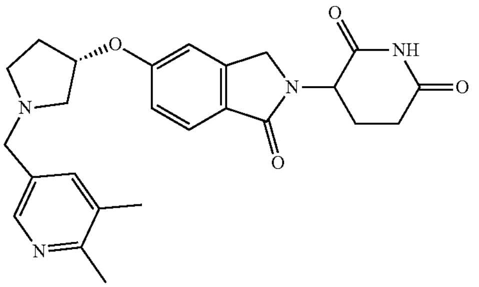 [SMILES: Cc1cc(CN2CC[C@H](Oc3ccc4c(c3)CN(C3CCC(=O)NC3=O)C4=O)C2)cnc1C]

5,6-Dimethylnicotinaldehyde. To a solution of 5-bromo-2,3-dimethylpyridine (200 mg, 1.08 mmol), 2-isocyano-2-methyl-propane (107 mg, 1.29 mmol) and sodium formate (146 mg, 2.15 mmol) in DMSO (3 mL) were added palladium acetate (12 mg, 0.05 mmol), 1,2-bis(diphenylphosphino)ethane (104 mg, 0.26 mmol) and the mixture was stirred 3 h at 120° C. under nitrogen. The mixture was diluted with water and extracted with ethyl acetate. The extracts were washed with brine, dried over sodium sulfate, filtered and concentrated. The residue was purified silica gel chromatography (0-50% petroleum ether in ethyl acetate) to afford the title compound (86 mg, 0.63 mmol, 59% yield) as a yellow oil. MS (ESI) m/z 136.1 $[M+1]^+$.

3-(5-(((S)-1-((5,6-Dimethylpyridin-3-yl)methyl)pyrrolidin-3-yl)oxy)-1-oxoisoindolin-2-yl)piperidine-2,6-dione. To a solution of 3-[1-oxo-5-[(3S)-pyrrolidin-3-yl]oxy-isoindolin-2-yl]piperidine-2,6-dione; hydrochloride (100 mg, 0.27 mmol), 5,6-dimethylpyridine-3-carbaldehyde (55 mg, 0.40 mmol) and triethylamine (41 mg, 0.41 mmol) in dichloromethane (5 mL) was added sodium triacetoxyborohydride (232 mg, 1.09 mmol) and the mixture was stirred for 12 h at room temperature under nitrogen. The resulting mixture was concentrated. The residue was purified by silica gel chromatography (10% methanol in dichloromethane) and preparative HPLC with the following conditions: Sunfire prep C18 column, 30*150 mm, 5 um; Mobile Phase A: Water (0.05% formic acid), Mobile Phase B: acetonitrile; Flow rate: 60 mL/min; Gradient: 2 B to 2 B in 2 min; 254/210 nm; RT1:7.75. The fractions containing desired product were collected and evaporated under reduced pressure to afford the title compound (37.7 mg, 0.075 mmol, 28% yield) as an off-white solid. $^1$H NMR (400 MHz, DMSO-$d_6$) δ 10.98 (s, 1H), 8.17 (m, J=9.7, 1.9 Hz, 2H), 7.61 (d, J=8.4 Hz, 1H), 7.45 (d, J=2.1 Hz, 1H), 7.11 (s, 1H), 7.00 (m, 1H), 5.08 (m, 1H), 5.00 (m, 1H), 4.39 (d, J=17.2 Hz, 1H), 4.25 (m, J=17.4, 2.9 Hz, 1H), 3.58 (s, 2H), 2.98-2.87 (m, 2H), 2.80-2.60 (m, 3H), 2.50-2.30 (m, 6H), 2.24 (s, 3H), 1.98 (m, 1H), 1.82 (m, 1H); MS (ESI) m/z 449.2 $[M+1]^+$.

Example S35. 3-(1-oxo-5-(((S)-1-((5-(Trifluoromethyl)pyridin-3-yl)methyl)pyrrolidin-3-yl)oxy)isoindolin-2-yl)piperidine-2,6-dione

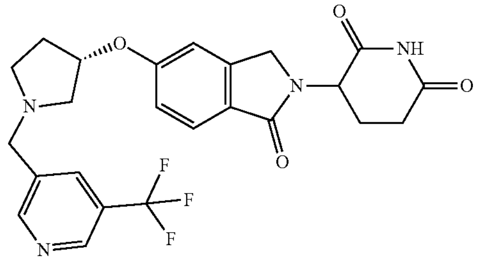 [SMILES: O=C1CCC(N2Cc3cc(O[C@H]4CCN(Cc5cncc(C(F)(F)F)c5)C4)ccc3C2=O)C(=O)N1]

5-(Trifluoromethyl)nicotinaldehyde. To a solution of (5-(trifluoromethyl)-pyridin-3-yl)methanol (100 mg, 0.57 mmol) in dichloromethane (5 mL) was added manganese dioxide (492 mg, 5.65 mmol) and the resulting mixture was stirred for 12 h at room temperature under nitrogen. The mixture was diluted with dichloromethane, filtered and the filtrate was concentrated to afford the title compound (95 mg, 0.54 mmol, 96% yield) as a yellow oil. MS (ESI) m/z 176.1 $[M+1]^+$.

3-(1-oxo-5-(((S)-1-((5-(trifluoromethyl)pyridin-3-yl)methyl)pyrrolidin-3-yl)-oxy)isoindolin-2-yl)piperidine-2,6-dione. To a solution of 3-[1-oxo-5-[(3S)-pyrrolidin-3-yl]oxy-isoindolin-2-yl]piperidine-2,6-dione; hydrochloride (100 mg, 0.27 mmol), 5-(trifluoromethyl)pyridine-3-carbaldehyde (57 mg, 0.33 mmol) and triethylamine (41 mg, 0.41 mmol) in dichloromethane (5 mL) was added sodium triacetoxyborohydride (232 mg, 1.09 mmol) and the mixture was stirred 2 h at room temperature under nitrogen. The resulting mixture was concentrated. The residue was purified by ilica gel chromatography column (10% methanol in dichloromethane) and preparative HPLC with the following conditions: XSelect CSH Prep C18 OBD Column, 5 um, 19*150 mm; Mobile Phase A: water (0.05% formic acid), Mobile Phase B: acetonitrile; Flow rate: 25 mL/min; Gradient: 2 B to 2 B in 1 min; 254/210 nm; RT1:7.95. The fractions containing desired product were collected and evaporated under reduced pressure to afford the title (35.8 mg, 0.07 mmol, 26% yield) as an off-white solid. $^1$H NMR (400 MHz, DMSO-$d_6$) δ 10.98 (s, 1H), 8.91-8.83 (m, 2H), 8.18-8.10 (m, 1H), 7.62 (d, J=8.4 Hz, 1H), 7.12 (d, J=2.2 Hz, 1H), 7.01 (m, 1H), 5.12-5.01 (m, 1H), 5.01 (d, J=6.9 Hz, 1H), 4.39 (d, J=17.2 Hz, 1H), 4.26 (d, J=17.1 Hz, 1H), 3.85-3.73 (m, 2H), 3.00-2.92 (m, 2H), 2.85-2.75 (m, 2H), 2.69-2.57 (m, 2H), 2.46-2.31 (m, 2H), 1.98-1.87 (m, 2H); MS (ESI) m/z 489.1 [M+1]+.

Example S36. 3-(1-Oxo-6-(((S)-1-(quinolin-6-ylmethyl)pyrrolidin-3-yl)oxy)isoindolin-2-yl)piperidine-2,6-dione

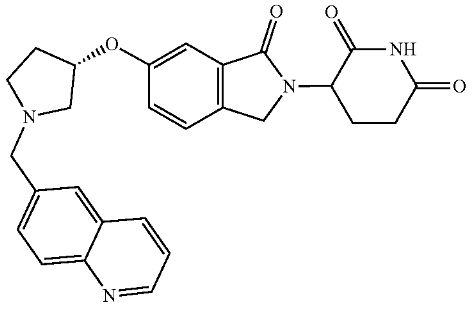 [SMILES: O=C1CCC(N2Cc3ccc(O[C@H]4CCN(Cc5ccc6ncccc6c5)C4)cc3C2=O)C(=O)N1]

3-(1-Oxo-6-(((S)-1-(quinolin-6-ylmethyl)pyrrolidin-3-yl)oxy)isoindolin-2-yl)-piperidine-2,6-dione. To a solution of 3-(1-oxo-6-(((S)-pyrrolidin-3-yl)oxy)isoind-olin-2-yl)piperidine-2,6-dione hydrochloride (150 mg, 0.41 mmol) in dichloromethane (10.0 mL) were added quinoline-6-carbaldehyde (84 mg, 0.53 mmol), triethylamine (0.17 mL, 1.23 mmol) and sodium triacetoxyborohydride (348 mg, 1.64 mmol). The mixture was stirred for 2 h at room temperature. The crude product was purified by preparative HPLC with following gradient conditions: Column: Sunfire prep C18 column, 5 um; 30*150 mm; Mobile Phase A: water (0.05% formic acid), Mobile Phase B: acetonitrile; Flow rate: 60 m/min; Gradient: 5 B to 13 B in 7 min; 254/210 nm; RT: 6.32 min. The fractions containing desired product were collected and evaporated under reduced pressure to afford the title compound (74.1 mg, 0.16 mmol, 39% yield) as an off-white solid. $^1$H NMR (400 MHz, Methanol-$d_4$) δ 8.90 (d, J=4.3 Hz, 1H), 8.41 (d, J=8.3 Hz, 1H), 8.13-8.04 (m, 2H), 7.91 (d, J=8.6 Hz, 1H), 7.60 (dd, J=8.3, 4.3 Hz, 1H), 7.50 (d, J=8.3 Hz, 1H), 7.30 (d, J=2.3 Hz, 1H), 7.22 (d, J=8.4 Hz, 1H), 5.15 (m, 2H), 4.51-4.28 (m, 4H), 3.44 (m, 1H), 3.35 (m, 2H), 3.16 (m, 1H), 2.92-2.74 (m, 2H), 2.51 (m, 2H), 2.10 (m, 2H); MS (ESI) m/z 471.1[M+1]$^+$.

Example S37. 3-(6-(((S)-1-(Isoquinolin-3-ylmethyl)pyrrolidin-3-yl)oxy)-1-oxoisoindolin-2-yl)-piperidine-2,6-dione

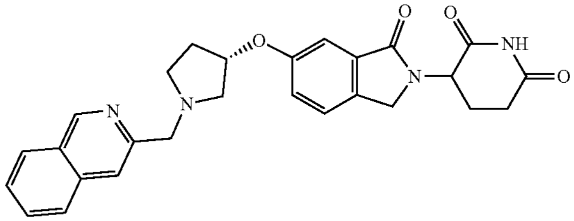 [SMILES: O=C1CCC(N2Cc3ccc(O[C@H]4CCN(Cc5cc6ccccc6cn5)C4)cc3C2=O)C(=O)N1]

3-(6-(((S)-1-(Isoquinolin-3-ylmethyl)pyrrolidin-3-yl)oxy)-1-oxoisoindolin-2-yl)piperidine-2,6-dione. To a solution of isoquinoline-3-carbaldehyde (65 mg, 0.41 mmol), 3-(1-oxo-6-(((S)-pyrrolidin-3-yl)oxy)isoindolin-2-yl)piperidine-2,6-dione hydrochloride (100 mg, 0.27 mmol) and triethylamine (33 mg, 0.330 mmol) in dichloromethane (10 mL) was added sodium triacetoxyborohydride (232 mg, 1.09 mmol). The mixture was stirred for 2 h at room temperature under nitrogen. The resulting solution was concentrated under reduced pressure. The residue was purified by preparative HPLC with following condition: Column: Sunfire prep C18 column, 30*150 mm, 5 um; Mobile Phase A: water (0.05% formic acid), Mobile Phase B: acetonitrile; Flow rate: 60 mL/min; Gradient: 7 B to 20 B in 7 min; 254/210 nm; RT1:6.60. The fractions containing desired product were collected and evaporated under reduced pressure to afford the title compound (29.3 mg, 0.06 mmol, 22% yield) as a light-yellow solid. $^1$H NMR (400 MHz, Methanol-$d_4$) δ 9.32 (s, 1H), 8.14 (d, J=8.2 Hz, 1H), 8.00-7.92 (m, 2H), 7.84 (t, J=7.6 Hz, 1H), 7.74 (t, J=7.5 Hz, 1H), 7.52 (d, J=8.3 Hz, 1H), 7.33 (d, J=2.3 Hz, 1H), 7.25 (d, J=8.3 Hz, 1H), 5.21 (m, 1H), 5.15 (dd, J=13.3, 5.1 Hz, 1H), 4.50 (m, 2H), 4.44 (d, J=8.4 Hz, 2H), 3.68-3.53 (m, 3H), 3.39-3.31 (m, 1H), 2.92 (m, 1H), 2.80 (m, 1H), 2.50 (m, 2H), 2.29 (m, 1H), 2.18 (m, 1H); MS (ESI) m/z 471.1 [M+1]$^+$.

Example S38. 3-(6-(((S)-1-(Isoquinolin-6-ylmethyl)pyrrolidin-3-yl)oxy)-1-oxoisoindolin-2-yl)piperidine-2,6-dione

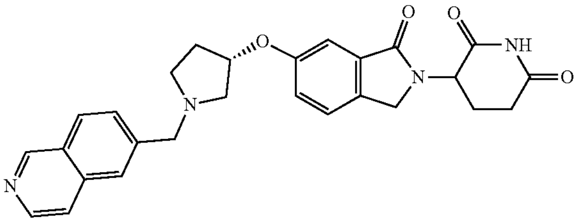 [SMILES: O=C1CCC(N2Cc3ccc(O[C@H]4CCN(Cc5ccc6cnccc6c5)C4)cc3C2=O)C(=O)N1]

3-(6-(((S)-1-(Isoquinolin-6-ylmethyl)pyrrolidin-3-yl)oxy)-1-oxoisoindolin-2-yl)piperidine-2,6-dione. To a solution of isoquinoline-6-carbaldehyde (65 mg, 0.41 mmol), 3-(1-oxo-6-(((S)-pyrrolidin-3-yl)oxy)isoindolin-2-yl)piperidine-2,6-dione hydrochloride (100 mg, 0.27 mmol) and triethylamine (33 mg, 0.33 mmol) in dichloromethane (10.0 mL) was added sodium triacetoxyborohydride (232 mg, 1.09 mmol). The mixture was stirred for 2 h at room temperature under nitrogen. The resulting solution was concentrated under reduced pressure. The residue was purified by preparative HPLC with following condition: Column: XSelect CSH Prep C18 OBD Column, 5 um, 19*150 mm; Mobile Phase A: water (0.05% formic acid), Mobile Phase B: acetonitrile; Flow rate: 25 mL/min; Gradient: 2 B to 12 B in 7 min; 254/210 nm; RT1:5.78. The pure fractions were concentrated to afford title compound (21.8 mg, 0.046 mmol, 17% yield) as an off-white solid. $^1$H NMR (400 MHz, Methanol-$d_4$) δ 9.28 (s, 1H), 8.49 (d, J=5.8 Hz, 1H), 8.18 (d, J=8.5 Hz, 1H), 8.04 (s, 1H), 7.86 (d, J=5.9 Hz, 1H), 7.82 (dd, J=8.5, 1.6 Hz, 1H), 7.51 (d, J=8.4 Hz, 1H), 7.30 (m, 1H), 7.22 (m, 1H), 5.19-5.10 (m, 2H), 4.47 (d, J=16.8 Hz, 1H), 4.40 (d, J=16.9 Hz, 1H), 4.31 (m, 2H), 3.39 (m, 1H), 3.31 (m, 2H), 3.11 (m, 1H), 2.92 (m, 1H), 2.85-2.75 (m, 1H), 2.61-2.42 (m, 2H), 2.20 (m, 2H); MS (ESI) m/z 471.2 [M+1]$^+$.

Example S39. 3-(5-(((S)-1-((4-Chloro-2-methylquinolin-6-yl)methyl)pyrrolidin-3-yl)oxy)-1-oxoisoindolin-2-yl)piperidine-2,6-dione

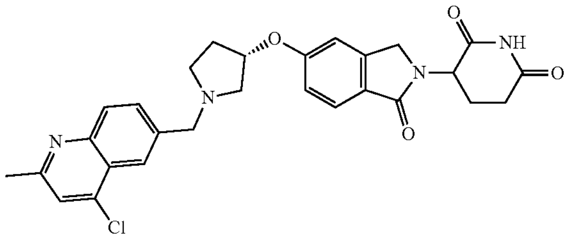 [SMILES: Cc1cc(Cl)c2cc(CN3CC[C@H](Oc4ccc5c(c4)CN(C4CCC(=O)NC4=O)C5=O)C3)ccc2n1]

4-Chloro-2-methylquinoline-6-carbaldehyde. To a solution of 6-bromo-4-chloro-2-methylquinoline (200 mg, 0.78 mmol), tert-butyl isocyanide (97 mg, 1.17 mmol), 1,2-bis(diphenylphosphino)ethane (124 mg, 0.31 mmol) and sodium formate (106 mg, 1.56 mmol) in DMSO (2.5 mL) in a sealed tube was added palladium (II) acetate (35 mg, 0.16 mmol). The sealed tube was filled with nitrogen. The mixture was stirred at 120° C. for 3 h under nitrogen. The resulting solution was quenched with water and extracted with ethyl acetate. The organic layer was washed with brine, dried and concentrated under reduced pressure. The residue was purified by silica gel chromatography (0 to 25% ethyl acetate in petroleum ether) to give title compound (80 mg, 0.39 mmol, 50% yield) as an off-white solid. MS (ESI) m/z 206.0 $[M+1]^+$.

3-(5-(((S)-1-((4-Chloro-2-methylquinolin-6-yl)methyl)pyrrolidin-3-yl)oxy)-1-oxoisoindolin-2-yl)piperidine-2,6-dione. To a solution of 4-chloro-2-methylquinoline-6-carbaldehyde (84 mg, 0.41 mmol), 3-(1-oxo-5-(((S)-pyrrolidin-3-yl)oxy)isoindolin-2-yl)piperidine-2,6-dione hydrochloride (100 mg, 0.27 mmol) and triethylamine (33 mg, 0.33 mmol) in dichloromethane (10.0 mL) was added sodium triacetoxyborohydride (232 mg, 1.09 mmol). The flask was evacuated and flushed five times with nitrogen. The mixture was stirred for 2 h at room temperature under nitrogen. The resulting solution was concentrated under reduced pressure. The residue was purified by silica gel chromatography (0 to 5% methanol in dichloromethane) and preparative HPLC with following condition: Column: Xselect CSH OBD Column 30*150 mm, 5 um; Mobile Phase A: water (0.1% formic acid), Mobile Phase B: acetonitrile; Flow rate: 60 mL/min; Gradient: 3 B to 25 B in 9 min; 210/254 nm; RT1:8.13. The fractions containing desired product were collected and evaporated under reduced pressure to afford the title compound (27.7 mg, 0.05 mmol, 19% yield) as an off-white solid. $^1H$ NMR (400 MHz, DMSO-$d_6$) δ 10.96 (s, 1H), 8.05 (s, 1H), 7.96 (d, J=8.6 Hz, 1H), 7.80 (dd, J=8.7, 1.9 Hz, 1H), 7.67 (s, 1H), 7.61 (d, J=8.3 Hz, 1H), 7.11 (d, J=2.0 Hz, 1H), 7.01 (dd, J=8.5, 2.2 Hz, 1H), 5.12-4.98 (m, 2H), 4.38 (d, J=17.1 Hz, 1H), 4.25 (dd, J=17.2, 3.3 Hz, 1H), 3.91-3.82 (m, 2H), 2.93 (m, 2H), 2.83-2.71 (m, 2H), 2.65 (s, 3H), 2.62 (m, 1H), 2.56 (m, 1H), 2.38 (m, 2H), 1.98 (m, 1H), 1.87 (m, 1H); MS (ESI) m/z 519.0 $[M+1]^+$.

Example S40. 3-Methyl-3-(5-(((S)-1-((2-methylquinolin-6-yl)methyl)pyrrolidin-3-yl)oxy)-1-oxoisoindolin-2-yl)piperidine-2,6-dione

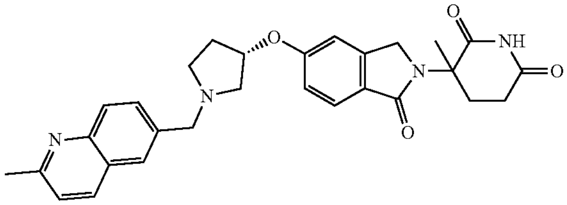 [SMILES: Cc1ccc2cc(CN3CC[C@H](Oc4ccc5c(c4)CN(C4(C)CCC(=O)NC4=O)C5=O)C3)ccc2n1]

3-Methyl-3-(5-(((S)-1-((2-methylquinolin-6-yl) methyl) pyrrolidin-3-yl) oxy)-1-oxoisoindolin-2-yl) piperidine-2,6-dione. To a solution of 3-methyl-3-[1-oxo-5-[(3S)-pyrrolidin-3-yl] oxy-isoindolin-2-yl] piperidine-2,6-dione; hydrochloride (70 mg, 0.18 mmol), 2-methylquinoline-6-carbaldehyde (41 mg, 0.24 mmol) and triethylamine (0.05 mL, 0.37 mmol) in dichloromethane (10 mL) was added sodium triacetoxyborohydride (117 mg, 0.55 mmol) at room temperature. The mixture was stirred for 12 h under nitrogen. The mixture was added water and extracted with ethyl acetate. The extracts were washed with brine, dried over anhydrous sodium sulfate, filtered and concentrated. The residue was purified by preparative HPLC using the following gradient conditions: Column: SunFire Prep C18 OBD Column, 19×150 mm 5 um 10 nm; Mobile Phase A: water (0.1% formic acid), Mobile Phase B: acetonitrile; Flow rate: 60 mL/min; Gradient: 8 B to 20 B in 10 min; 210/254 nm; RT1:8.45. The fractions containing desired product were collected and evaporated under reduced pressure to afford the title compound (25.7 mg, 0.051 mmol, 28% yield) as an off-white solid. $^1H$ NMR (400 MHz, Methanol-$d_4$) δ 8.35 (s, 1H), 8.26 (d, J=8.0 Hz, 1H), 8.03-7.85 (m, 2H), 7.74 (d, J=8.0 Hz, 1H), 7.53 (d, J=8.0 Hz, 1H), 735 (d, J=8.0 Hz, 1H), 7.01 (s, 1H), 6.94 (d, J=8.0 Hz, 1H), 5.18 (m, 1H), 4.60-4.48 (m, 2H), 4.31-4.22 (m, 2H), 3.29 (m, 1H), 3.21-3.13 (m, 2H), 3.01 (m, 1H), 2.80-2.62 (m, 5H), 2.61-2.11 (m, 1H), 2.50-2.36 (m, 1H), 2.15-2.03 (m, 1H), 1.97-1.83 (m, 1H), 1.67 (s, 3H); MS (ESI) m/z 499.1 $[M+1]^+$.

Example S41. 3-(((3S)-3-((2-(2,6-Dioxopiperidin-3-yl)-1-oxoisoindolin-5-yl)oxy)pyrrolidin-1-yl)methyl)quinoline-2-carbonitrile

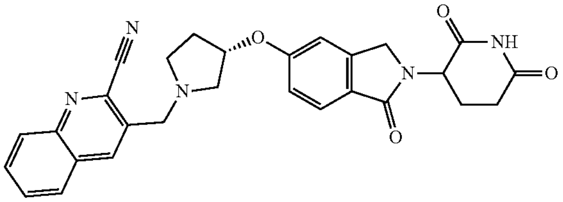 [SMILES: N#Cc1nc2ccccc2cc1CN1CC[C@H](Oc2ccc3c(c2)CN(C2CCC(=O)NC2=O)C3=O)C1]

2-Iodoquinoline-3-carbaldehyde. To a solution of 2-chloroquinoline-3-carbaldehyde (800 mg, 4.18 mmol) and sodium iodide (4.4 g, 29.23 mmol) in acetonitrile (20.0 mL) was added hydrochloric acid (12 M, 0.1 mL). The flask was flushed and evacuated five times with nitrogen. The mixture was stirred at 90° C. for 3 h under nitrogen. The resulting mixture was concentrated. The residue was diluted with water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford title compound 2-iodoquinoline-3-carbaldehyde (400 mg, 1.41 mmol, 34% yield) as an orange solid. MS (ESI) m/z 284.0 $[M+1]^+$.

3-Formylquinoline-2-carbonitrile. To a solution of 2-iodoquinoline-3-carbaldehyde (400 mg, 1.41 mmol) in acetonitrile (5.0 mL) was added copper(I) cyanide (152 mg, 1.70 mmol). The flask was flushed and evacuated five times with nitrogen. The mixture was stirred at 90° C. for 5 h under nitrogen. The resulting mixture was filtered and the filter cake was washed with acetonitrile. The filtrate was concentrated and the residue was purified by silica gel chromatography (0 to 10% ethyl acetate in petroleum ether) to afford title compound (200 mg, 1.09 mmol, 78% yield) as a brown solid. MS (ESI) m/z 183.0 $[M+1]^+$.

3-(((3S)-3-((2-(2,6-Dioxopiperidin-3-yl)-1-oxoisoindolin-5-yl)oxy)pyrrolidinyl)methyl)quinoline-2-carbonitrile. To a solution of 3-formylquinoline-2-carbonitrile (90 mg, 0.49 mmol), 3-(1-oxo-5-(((S)-pyrrolidin-3-yl)oxy)isoindolin-2-yl)piperidine-2,6-dione hydrochloride (150 mg, 0.41 mmol) and triethylamine (50 mg, 0.49 mmol) in dichloromethane (15.0 mL) was added sodium triacetoxyborohydride (261 mg, 1.23 mmol). The flask was evacuated and flushed five times with nitrogen. The mixture was stirred for 2 h at room temperature under nitrogen. The resulting mixture was concentrated under reduced pressure. The residue was purified by silica gel chromatography (0 to 5% methanol in dichloromethane) and preparative HPLC with following condition: Column: SunFire Prep C18 OBD Column, 19×150 mm 5 um 10 nm; Mobile Phase A: water (0.1% formic acid), Mobile Phase B: acetonitrile; Flow rate: 60 mL/min; Gradient: 5 B to 23 B in 10 min; 210/254 nm; RT1:9.73. The fractions containing desired product were collected and evaporated under reduced pressure to afford the title compound (6.6 mg, 0.01 mmol, 3% yield) as an off-white solid. $^1H$ NMR (400 MHz, DMSO-$d_6$) δ 10.97 (s, 1H), 8.62 (s, 1H), 8.14 (d, J=8.4 Hz, 2H), 7.91 (m, 1H), 7.85-7.77 (m, 1H), 7.61 (d, J=8.4 Hz, 1H), 7.13 (d, J=2.2 Hz, 1H), 7.02 (dd, J=8.4, 2.2 Hz, 1H), 5.06 (m, 2H), 4.38 (d, J=17.2 Hz, 1H), 4.25 (d, J=17.2 Hz, 1H), 4.04 (d, J=13.9 Hz, 1H), 3.98 (d, J=13.8 Hz, 1H), 3.11 (m, 1H), 2.97-2.81 (m, 2H), 2.78 (m, 1H), 2.68-2.54 (m, 2H), 2.37 (m, 2H), 1.97 (m, 1H), 1.89 (m, 1H); MS (ESI) m/z 496.1 $[M+1]^+$.

Example S42. 3-(5-(((3S,5R)-5-Methyl-1-((2-methylquinolin-6-yl)methyl)pyrrolidin-3-yl) oxy)-1-oxoisoindolin-2-yl)piperidine-2,6-dione

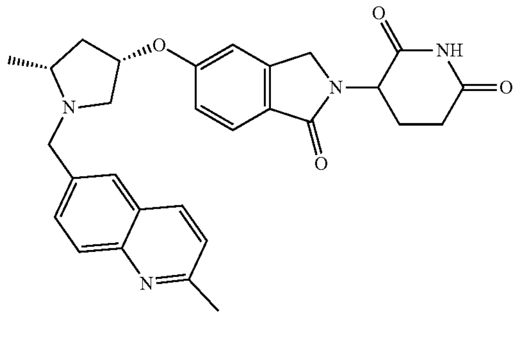 [SMILES: Cc1ccc2cc(CN3C[C@@H](Oc4ccc5c(c4)CN(C4CCC(=O)NC4=O)C5=O)C[C@H]3C)ccc2n1]

Tert-butyl (2R,4S)-4-((2-(1-(4-methoxybenzyl)-2,6-dioxopiperidin-3-yl)-1-oxoisoindolin-5-yl)oxy)-2-methylpyrrolidine-1-carboxylate. To a solution of 3-(5-bromo-1-oxoisoindolin-2-yl)-1-(4-methoxybenzyl)piperidine-2,6-dione (200 mg, 0.45 mmol), tert-butyl (2R,4S)-4-hydroxy-2-methylpyrrolidine-1-carboxylate (272 mg, 1.35 mmol), (4,4'-Di-t-butyl-2,2'-bipyridine)bis[3,5-difluoro-2-[5-trifluoromethyl-2-pyridinyl-kN)phenyl-kC]iridium(III) hexafluorophosphate (5 mg, 0.005 mmol), quinuclidine (13 mg, 0.12 mmol), potassium carbonate (62 mg, 0.45 mmol) in dry acetonitrile (4 mL) was added the solution of Nickel (II) chloride, dimethoxyethane adduct (5 mg, 0.023 mmol) and 4,4'-Di-tert-butyl-2,2'-bipyridine (6 mg, 0.022 mmol) in dry acetonitrile (2 mL). The reaction was evacuated and flushed three times with nitrogen before being irradiated with three 34 W blue LEDs. The reaction was stirred for 12 h at room temperature under nitrogen. The resulting mixture was filtered and the filtrate was concentrated under reduced pressure. The residue was purified by silica gel chromatography (0 to 70% ethyl acetate in petroleum ether) to afford the title compound (140 mg, 0.25 mmol, 55% yield) as a light-yellow solid. MS (ESI) m/z 564.5 $[M+1]^+$.

3-(5-(((3S,5R)-5-Methylpyrrolidin-3-yl)oxy)-1-oxoisoindolin-2-yl)piperidine-2,6-dione. To a solution of tert-butyl (2R,4S)-4-((2-(1-(4-methoxybenzyl)-2,6-dioxopiperidin-3-yl)-1-oxoisoindolin-5-yl)oxy)-2-methylpyrrolidine-1-carboxylate (140 mg, 0.25 mmol) in TFA (3 mL) was added trifluoromethanesulfonic acid (0.1 mL). The mixture was stirred for 12 h at 60° C. under nitrogen. The resulting solution was concentrated under reduced pressure. The residue was diluted with water, then adjusted to pH 6-7 with saturated sodium bicarbonate and filtered. The crude product was purified by reverse phase flash (10-30% acetonitrile+0.05% TFA in water, over 20 min) to give the title compound (40 mg, 0.12 mmol, 40% yield) as a light-yellow oil. MS (ESI) m/z 344.1 $[M+1]^+$.

3-(5-(((3S,5R)-5-Methyl-1-((2-methylquinolin-6-yl)methyl)pyrrolidin-3-yl) oxy)-1-oxoisoindolin-2-yl)piperidine-2,6-dione. To a solution of 3-(5-(((3S,5R)-5-methylpyrrolidin-3-yl)oxy)-1-oxoisoindolin-2-yl)piperidine-2,6-dione; 2,2,2-trifluoroacetic acid (140 mg, 0.30 mmol), 2-methylquinoline-6-carbaldehyde (60 mg, 0.35 mmol) and triethylamine (0.08 mL, 0.60 mmol) in dichloromethane (3 mL) was added sodium triacetoxyborohydride (197 mg, 0.93 mmol). The flask was evacuated and flushed three times with nitrogen. The reaction mixture was stirred at room temperature for 2 h under nitrogen. The resulting solution was concentrated at room temperature under reduced pressure. The crude product was purified by silica gel column chromatography (0-10% methanol in dichloromethane) and reverse-phased preparative HPLC with the following conditions: Column: X select CSH OBD Column 30*150 mm, 5 um; Mobile Phase A: water (0.05% TFA), Mobile Phase B: acetonitrile; Flow rate: 60 mL/min; Gradient: 3 B to 18 B in 7 min; 210/254 nm; RT1:7.85. The fractions containing desired product were collected and evaporated under reduced pressure to afford the title compound (36.1 mg, 0.072 mmol, 24% yield) as an off-white solid. $^1H$ NMR (400 MHz, Methanol-$d_4$) δ 8.96 (d, J=8.7 Hz, 1H), 8.48 (s, 1H), 8.26 (d, J=3.7 Hz, 2H), 7.98 (d, J=9.2 Hz, 1H), 7.73 (d, J=8.4 Hz, 1H), 7.13-7.07 (m, 2H), 5.30 (m, 1H), 5.14-5.12 (m, 1H), 4.97 (m, 1H), 4.61 (m, 1H), 4.52-4.36 (m, 2H), 3.94 (m, 1H), 3.81-3.76 (m, 1H), 3.70 (m, 1H), 3.11-2.94 (m, 4H), 2.91-2.79 (m, 1H), 2.76-2.67 (m, 1H), 2.49-2.45 (m, 1H), 2.21-2.03 (m, 2H), 1.60 (d, J=6.6 Hz, 3H). MS (ESI) m/z 499.2 $[M+1]^+$.

Example S43. 3-(5-(((3S,5S)-5-Methyl-1-((2-methylquinolin-6-yl)methyl)pyrrolidin-3-yl)oxy)-1-oxoisoindolin-2-yl)piperidine-2,6-dione

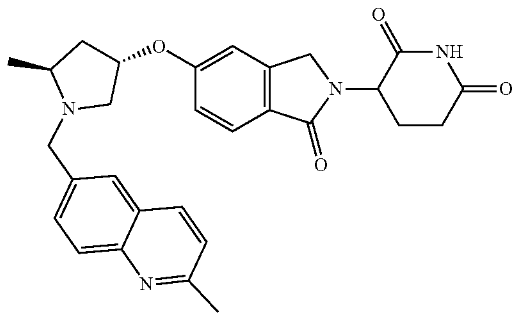 [SMILES: Cc1ccc2cc(CN3C[C@@H](Oc4ccc5c(c4)CN(C4CCC(=O)NC4=O)C5=O)C[C@@H]3C)ccc2n1]

Tert-butyl (2S,4S)-4-((2-(1-(4-methoxybenzyl)-2,6-dioxopiperidin-3-yl)-1-oxoisoindolin-5-yl)oxy)-2-methylpyrrolidine-1-carboxylate. To a solution of 3-(5-bromo-1-oxoisoindolin-2-yl)-1-(4-methoxybenzyl)piperidine-2,6-dione (100 mg, 0.23 mmol), tert-butyl (2S,4S)-4-hydroxy-2-methylpyrrolidine-1-carboxylate (136 mg, 0.68 mmol), (4,4'-Di-t-butyl-2,2'-bipyridine)bis[3,5-difluoro-2-[5-trifluoromethyl-2-pyridinyl-kN)phenyl-kC]iridium(III) hexafluorophosphate (3 mg, 0.003 mmol), quinuclidine (6 mg, 0.06 mmol), potassium carbonate (31 mg, 0.23 mmol) in dry acetonitrile (2 mL) was added the solution of nickel (II) chloride, dimethoxyethane adduct (3 mg, 0.014 mmol) and 4,4'-di-tert-butyl-2,2'-bipyridine (3 mg, 0.01 mmol) in dry acetonitrile (2 mL). The reaction was evacuated and flushed three times with nitrogen before being irradiated with three 34 W blue LEDs. The reaction was stirred for 12 h at room temperature under nitrogen. The resulting reaction mixture was filtered and the filtrate was concentrated under reduced pressure. The residue was purified by silica gel chromatography (0 to 70% ethyl acetate in petroleum ether) to afford the title compound (70 mg, 0.12 mmol, 55% yield) as a light-yellow solid. MS (ESI) m/z 564.5 $[M+1]^+$.

3-(5-(((3S,5S)-5-Methylpyrrolidin-3-yl)oxy)-1-oxoisoindolin-2-yl)piperidine-2,6-dione. To a solution of tert-butyl (2S,4S)-4-((2-(1-(4-methoxybenzyl)-2,6-dioxopiperidin-3-yl)-1-oxoisoindolin-5-yl)oxy)-2-methylpyrrolidine-1-carboxylate (70 mg, 0.12 mmol) in TFA (3 mL, 0.12 mmol) was added trifluoromethanesulfonic acid (0.05 mL, 0.62 mmol). The mixture was stirred for 12 h at 60° C. under nitrogen. The resulting solution was concentrated under reduced pressure. The residue was diluted with water, adjusted to pH 6-7 with saturated sodium bicarbonate and filtered. The crude product was purified by reverse phase flash (10-30% acetonitrile+0.05% TFA in water, over 20 min) to give the title compound (40 mg, 0.12 mmol, 97% yield) as a light-yellow oil. MS (ESI) m/z 344.1 $[M+1]^+$.

3-(5-(((3S,5S)-5-Methyl-1-((2-methylquinolin-6-yl) methyl)pyrrolidin-3-yl) oxy)-1-oxoisoindolin-2-yl)piperidine-2,6-dione. To a solution of 3-(5-(((3S,5S)-5-methylpyrrolidin-3-yl)oxy)-1-oxoisoindolin-2-yl)piperidine-2,6-dione (40 mg, 0.12 mmol), 2-methylquinoline-6-carbaldehyde (30 mg, 0.17 mmol) and triethylamine (0.02 mL, 0.14 mmol) in dichloromethane (3 mL) was added sodium triacetoxyborohydride (99 mg, 0.47 mmol). The flask was evacuated and flushed three times with nitrogen. The reaction mixture was stirred at room temperature for 2 h under nitrogen. The resulting solution was concentrated at 25° C. under reduced pressure. The crude was purified by silica gel column chromatography (0-10% methanol in dichloromethane) and further purified by reverse-phased preparative HPLC with the following conditions: Column: X select CSH OBD Column 30*150 mm, 5 um; Mobile Phase A: water (0.05% TFA), Mobile Phase B: acetonitrile; Flow rate: 60 mL/min; Gradient: 3 B to 23 B in 7 min; 210/254 nm; RT1:7.47. The fractions containing desired product were collected and evaporated under reduced pressure to afford the title compound (22.4 mg, 0.045 mmol, 38% yield) as an off-white solid. $^1H$ NMR (400 MHz, Methanol-$d_4$) δ 8.78 (t, 1H), 8.35 (d, 1H), 8.25-8.15 (m, 2H), 7.92-7.88 (m, 1H), 7.70-7.59 (m, 1H), 7.09 (m, 1H), 7.01-6.92 (m, 1H), 5.27-5.12 (m, 2H), 4.88 (m, 1H), 4.68 (m, 1H), 4.53-4.37 (m, 2H), 4.15 (m, 1H), 4.06-3.96 (m, 1H), 3.70 (t, J=12.4 Hz, 2H), 3.00 (s, 3H), 2.99-2.92 (m, 1H), 2.86-2.82 (m, 1H), 2.66-2.62 (m, 1H), 2.51-2.40 (m, 1H), 2.27-2.20 (m, 1H), 2.20-2.17 (m, 1H), 1.61 (t, 3H); MS (ESI) m/z 499.2 $[M+1]^+$.

Example S44. 3-(5-(((S)-1-((2-(Difluoromethyl) quinolin-6-yl)methyl)pyrrolidin-3-yl)oxy)-1-oxoisoindolin-2-yl)piperidine-2,6-dione

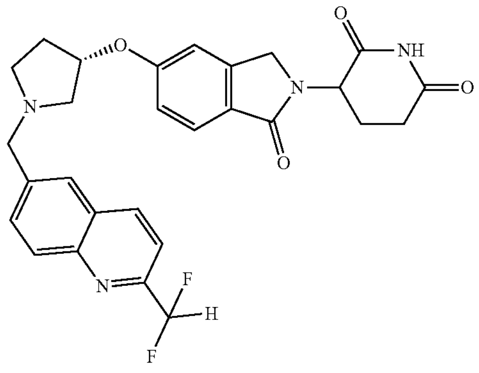 [SMILES: O=C1CCC(N2Cc3cc(O[C@H]4CCN(Cc5ccc6nc(C(F)F)ccc6c5)C4)ccc3C2=O)C(=O)N1]

6-Bromo-2-(difluoromethyl)quinolone. To a stirred solution of 6-bromoquinoline-2-carbaldehyde (400 mg, 1.69 mmol) in dichloromethane (15 mL) was added the solution of bis(2-methoxyethyl)aminosulfur trifluoride (749 mg, 3.39 mmol) in dichloromethane and ethanol (0.02 mL) at 0° C. The mixture was stirred for 12 h at room temperature. The resulting mixture was diluted with dichloromethane, washed with saturated sodium bicarbonate, brine, dried over anhydrous sodium sulfate, filtered and concentrated. The residue was purified by silica gel chromatography (0 to 50% ethyl acetate in petroleum ether) to afford the title compound (300 mg, 1.16 mmol, 68% yield) as a light-yellow solid. MS (ESI) m/z 258.0 $[M+1]^+$.

2-(Difluoromethyl)quinoline-6-carbaldehyde. To a solution of 6-bromo-2-(difluoromethyl)quinoline (290 mg, 1.12 mmol), tert-butyl isocyanide (93 m, 1.12 mmol), 1,2-bis (diphenylphosphino)ethane (90 mg, 0.22 mmol) and sodium formate (153 mg, 2.25 mmol) in DMSO (6 mL) was added palladium (II) acetate (25 mg, 0.11 mmol). The mixture was stirred for 3 h at 120° C. under nitrogen. The resulting solution was diluted with water, and extracted with ethyl acetate. The organic layers were combined, washed with brine, dried over sodium sulfate, filtered and concentrated under reduced pressure. The crude was purified by silica gel chromatography (0 to 50% ethyl acetate in petroleum ether) to afford the title compound (70 mg, 0.33 mmol, 30% yield) as a light-yellow solid. MS (ESI) m/z 208.1 $[M+1]^+$.

3-(5-(((S)-1-((2-(Difluoromethyl)quinolin-6-yl)methyl)pyrrolidin-3-yl)oxy)-1-oxoisoindolin-2-yl)piperidine-2,6-dione. To a solution of 3-(1-oxo-5-(((S)-pyrrolidin-3-yl)oxy)isoindolin-2-yl)piperidine-2,6-dione (95 mg, 0.29 mmol), 2-(difluoromethyl)quinoline-6-carbaldehyde (60 mg, 0.29 mmol) and triethylamine (0.08 mL, 0.58 mmol) in dichloromethane (4 mL) was added sodium triacetoxyborohydride (245 mg, 1.16 mmol). The flask was evacuated and flushed five times with nitrogen. The mixture was stirred at room temperature for 2 h under nitrogen. The resulting solution was concentrated at 25° C. under reduced pressure. The crude was purified by silica gel column chromatography (0-10% methanol in dichloromethane) and further purified by preparative HPLC with the following conditions: Column: Sun Fire Prep C18 OBD Column, 19×150 mm 5 um 10 nm; Mobile Phase A: water (0.1% formic acid), Mobile Phase B: acetonitrile; Flow rate: 60 mL/min; Gradient: 5 B to 18 B in 10 min; 254/210 nm; $RT_1$: 10.33. The fractions containing desired product were collected and evaporated under reduced pressure to afford the title compound (36.8 mg, 0.07 mmol, 24% yield) as a white solid. $^1$H NMR (400 MHz, Methanol-$d_4$) δ 8.52 (dd, J=8.5, 1.9 Hz, 1H), 8.13 (d, J=8.7 Hz, 1H), 8.02 (s, 1H), 7.93 (dd, J=8.7, 1.9 Hz, 1H), 7.80 (d, J=8.5 Hz, 1H), 7.71 (d, J=8.4 Hz, 1H), 7.11-6.98 (m, 2H), 6.87-6.72 (m, 1H), 5.14-5.07 (m, 2H)), 4.51-4.36 (m, 2H), 4.12-4.00 (m, 2H), 3.16-3.13 (m, 1H), 3.11-2.99 (m, 2H), 2.91-2.73 (m, 3H), 2.55-2.39 (m, 2H), 2.21-2.03 (m, 2H); MS (ESI) m/z 521.1 $[M+1]^+$.

Example S45. 3-(5-(((S)-1-((2-Cyclopropylquinolin-6-yl)methyl)pyrrolidin-3-yl)oxy)-1-oxoisoindolin-2-yl)piperidine-2,6-dione

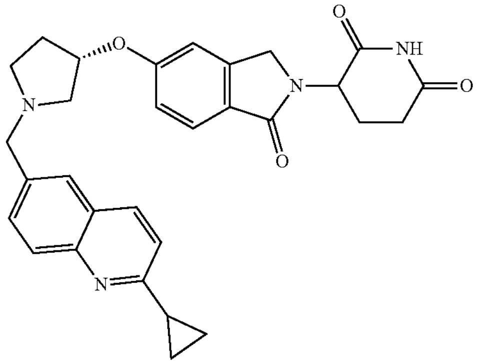 [SMILES: O=C1CCC(N2Cc3cc(O[C@H]4CCN(Cc5ccc6nc(C7CC7)ccc6c5)C4)ccc3C2=O)C(=O)N1]

6-Bromo-2-cyclopropylquinoline. To a stirred solution of (2-amino-5-bromophenyl)methanol (700 mg, 3.46 mmol) in toluene (10 mL) was added 1-cyclopropylethanone (583 mg, 6.93 mmol) and lithium tert-butoxide (554 mg, 6.93 mmol). The reaction mixture was stirred at 110° C. for 2 days. Then the resulting mixture was diluted with water and extracted with ethyl acetate. The extracts were washed with brine, dried over sodium sulfate, filtered and concentrated. The residue was purified by silica gel chromatography (0 to 50% ethyl acetate in petroleum ether) to afford the title compound (300 mg, 1.21 mmol, 35% yield) as a yellow oil. MS (ESI) m/z 248.0 $[M+1]^+$.

2-Cyclopropylquinoline-6-carbaldehyde. To a stirred solution of 6-bromo-2-cyclopropylquinoline (290 mg, 1.17 mmol) in DMSO (5 mL) was added sodium formate (0.16 g, 2.34 mmol), 1,2-bis(diphenylphosphino)ethane (47 mg, 0.12 mmol), palladium acetate (53 mg, 0.23 mmol) and tert-butyl isocyanide (1.5 mL, 1.32 mmol). The resulting mixture was stirred at 120° C. for 3 h under nitrogen. The reaction solution was added water and extracted with ethyl acetate. The extracts were washed with brine, dried over anhydrous sodium sulfate, filtered and concentrated. The residue was purified by reverse phase flash to afford the title compound (130 mg, 0.65 mmol, 56% yield) as a yellow solid. MS (ESI) m/z 198.2 $[M+1]^+$.

3-(5-(((S)-1-((2-Cyclopropylquinolin-6-yl)methyl)pyrrolidin-3-yl)oxy)-1-oxoisoindolin-2-yl)piperidine-2,6-dione. To a stirred solution of 3-(1-oxo-5-(((S)-pyrrolidin-3-yl)oxy)isoindolin-2-yl)piperidine-2,6-dione (100 mg, 0.30 mmol) in dichloromethane (3 mL) was added 2-cyclopropylquinoline-6-carbaldehyde (72 mg, 0.37 mmol), sodium triacetoxyborohydride (258 mg, 1.22 mmol) and triethylamine (0.05 mL, 0.37 mmol). The reaction mixture was stirred at room temperature for 1.5 h under nitrogen. The reaction mixture was filtered and the filtrates were concentrated. The residue was dissolved with DMF and purified by preparative HPLC with the following conditions: SunFire Prep C18 OBD Column, 19×150 mm 5 um 10 nm; Mobile Phase A: water (0.1% formic acid), Mobile Phase B: acetonitrile; Flow rate: 60 mL/min; Gradient: 3 B to 20 B in 7 min; 254/210 nm; RT1:5.96; RT2. The fractions containing desired product were collected and evaporated under reduced pressure to afford the title compound (37.2 mg, 0.073 mmol, 24% yield) as a white solid. $^1$H NMR (300 MHz, Methanol-$d_4$) δ 88.18 (d, J=8.6 Hz, 1H), 7.96 (d, J=8.7 Hz, 1H), 7.90 (d, J=1.7 Hz, 1H), 7.83-7.68 (m, 2H), 7.30 (d, J=8.6 Hz, 1H), 7.13-7.02 (m, 2H), 5.13 (m, 2H), 4.44 (m, 2H), 4.22 (d, J=2.3 Hz, 2H), 3.42 (m, 1H), 3.25 (m, 2H), 3.07 (m, 1H), 2.92-2.73 (m, 2H), 2.53-2.40 (m, 2H), 2.31 (m, 1H), 2.20-2.10 (m, 2H), 1.16 (m, 4H); MS (ESI) m/z 511.0 $[M+1]^+$.

Example S46. 3-(5-(((S)-1-((2-Cyclopropylquinolin-6-yl)methyl)pyrrolidin-3-yl)oxy)-1-oxoisoindolin-2-yl)piperidine-2,6-dione

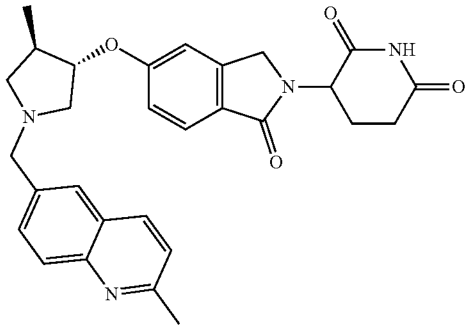 [SMILES: Cc1ccc2cc(CN3C[C@@H](C)[C@H](Oc4ccc5c(c4)CN(C4CCC(=O)NC4=O)C5=O)C3)ccc2n1]

Tert-butyl (3R,4S)-3-(bromomethyl)-4-hydroxypyrrolidine-1-carboxylate. To a solution of tert-butyl (3S,4S)-3-hydroxy-4-(hydroxymethyl)pyrrolidine-1-carboxylate (300 mg, 1.38 mmol), 2,6-dimethylpyridine (600 mg, 5.60 mmol) in acetone (15 mL) was added methanesulfonyl chloride (0.12 mL, 1.53 mmol) dropwise at 0° C. and the resulting solution was stirred at room temperature for 3 h under nitrogen. Then the reaction mixture was filtered. The filtrate was added sodium bromide (600 mg, 5.83 mmol) and the mixture was stirred for 3 h at 75° C. under nitrogen. The resulting mixture was added water and extracted with ethyl acetate. The extracts were dried over anhydrous sodium sulfate, filtered and concentrated. The residue was purified by silica gel chromatography (0 to 50% ethyl acetate in petroleum ether) to afford the title compound (350 mg, 1.25 mmol, 90% yield) as a colorless oil. $^1$H NMR (400 MHz, Chloroform-d) δ 4.31 (m, 1H), 3.70 (m, 2H), 3.42 (m, 2H), 3.27 (m, 2H), 2.52 (m, 1H), 1.48 (s, 9H).

Tert-butyl (3S,4R)-3-hydroxy-4-methylpyrrolidine-1-carboxylate. To a solution of tert-butyl (3R,4S)-3-(bromomethyl)-4-hydroxypyrrolidine-1-carboxylate (600 mg, 2.14 mmol) in DMSO (8 mL) was added sodium borohydride (600 mg, 15.86 mmol) at 0° C. in several portions and the resulting solution was stirred at 80° C. for 2 h under nitrogen. The resulting mixture was added water and extracted with ethyl acetate. The extracts were dried over anhydrous sodium sulfate, filtered and concentrated. The residue was purified by silica gel chromatography (0 to 50% ethyl acetate in petroleum ether) to afford the title compound (350 mg, 1.74 mmol, 81% yield) as a colorless oil. $^1$H NMR (400 MHz, Chloroform-d) δ 3.86 (m, 1H), 3.66-3.49 (m, 2H), 3.25-3.11 (m, 1H), 2.96 (m, 1H), 2.09 (m, 1H), 1.42 (s, 9H), 1.03-0.91 (d, 3H).

Tert-butyl (3S,4R)-3-((2-(1-(4-methoxybenzyl)-2,6-dioxopiperidin-3-yl)-1-oxoisoindolin-5-yl)oxy)-4-methylpyrrolidine-1-carboxylate. A mixture of 3-(5-bromo-1-oxoisoindolin-2-yl)-1-(4-methoxybenzyl)piperidine-2,6-dione (350 mg, 0.79 mmol), tert-butyl (3S,4R)-3-hydroxy-4-methylpyrrolidine-1-carboxylate (500 mg, 2.48 mmol), potassium carbonate (110 mg, 0.80 mmol), 4,4'-Di-tert-butyl-2,2'-bipyridine (11 mg, 0.04 mmol), quinuclidine (24 mg, 0.22 mmol) and (4,4'-Di-t-butyl-2,2'-bipyridine)bis[3,5-difluoro-2-[5-trifluoromethyl-2-pyridinyl-kN)phenyl-kC]iridium(III) hexafluorophosphate (10 mg, 0.01 mmol) in acetonitrile (0.50 mL)/N,N-Dimethylacetamide (1.5 mL) was stirred at room temperature for 12 h with 90 W blue LED irradiation under nitrogen. The resulting mixture was added water and extracted with ethyl acetate. The extracts were dried over anhydrous sodium sulfate, filtered and concentrated. The residue was purified by silica gel chromatography (0 to 50% ethyl acetate in petroleum ether) to afford the title compound (150 mg, 0.27 mmol, 34% yield) as a light-yellow semi-solid. MS (ESI) m/z 586.1 [M+23]$^+$.

3-(5-(((3S,4R)-4-Methylpyrrolidin-3-yl)oxy)-1-oxoisoindolin-2-yl)piperidine-2,6-dione; 2,2,2-trifluoroacetic acid. To a solution of tert-butyl (3S,4R)-3-((2-(1-(4-methoxybenzyl)-2,6-dioxopiperidin-3-yl)-1-oxoisoindolin-5-yl)oxy)-4-methylpyrrolidine-1-carboxylate (200 mg, 0.35 mmol) in TFA (5 mL) was added trifluoromethanesulfonic acid (0.2 mL) at 0° C. and the solution was stirred at 60° C. for 2 h under nitrogen. The solution was concentrated and the residue was added sodium bicarbonate to pH~5 and filtered. The filtrate was purified by reverse phase flash (0-40% acetonitrile+0.05% TFA in water, over 25 min) to afford the title compound (120 mg, 0.26 mmol, 74% yield) as an off-white semi-solid. MS (ESI) m/z 344.0 [M+1]$^+$.

3-(5-(((3S,4R)-4-Methyl-1-((2-methylquinolin-6-yl)methyl)pyrrolidin-3-yl)-oxy)-1-oxoisoindolin-2-yl)piperidine-2,6-dione. To a solution of 3-(5-(((3S,4R)-4-methylpyrrolidin-3-yl)oxy)-1-oxoisoindolin-2-yl)piperidine-2,6-dione; 2,2,2-trifluoroacetic acid (120 mg, 0.26 mmol) and 2-methylquinoline-6-carbaldehyde (50 mg, 0.29 mmol) in dichloromethane (5 mL) was added triethylamine (0.08 mL, 0.59 mmol) and sodium triacetoxyborohydride (110 mg, 0.52 mmol) at 0° C. The resulting mixture was stirred at room temperature for 2 h. Most solution was removed and the residue was purified by silica gel column chromatography (0-10% methanol in dichloromethane) and further purified by preparative HPLC with the following conditions: SunFire Prep C18 OBD Column, 19×150 mm 5 um 10 nm; Mobile Phase A: water (0.1% formic acid), Mobile Phase B: acetonitrile; Flow rate: 60 mL/min; Gradient: 2 B to 20 B in 7 min; 254/220 nm; RT1:6.53; RT2. The fractions containing desired product were collected and evaporated under reduced pressure to afford the title compound (23.4 mg, 0.047 mmol, 19% yield) as an off-white solid. $^1$H NMR (400 MHz, Methanol-$d_4$) δ 8.25 (m, 1H), 8.02-7.92 (m, 2H), 7.83 (dd, J=8.7, 2.0 Hz, 1H), 7.72 (dd, J=8.4, 1.9 Hz, 1H), 7.48 (d, J=8.5 Hz, 1H), 7.11-7.01 (m, 2H), 5.13 (dd, J=13.4, 5.1 Hz, 1H), 4.75 (m, 1H), 4.61-4.35 (m, 2H), 4.20 (m, 2H), 3.42 (m, 2H), 3.33-3.21 (m, 1H), 2.98-2.85 (m, 1H), 2.84-2.74 (m, 4H), 2.71-2.56 (m, 2H), 2.48 (m, 1H), 2.16 (m, 1H), 1.26 (d, J=6.7 Hz, 3H); MS (ESI) m/z 499.1 [M+1]$^+$.

Example S47. 3-(1-Oxo-5-(((S)-1-((1,2,3,4-tetrahydroquinolin-6-yl)methyl)pyrrolidin-3-yl)oxy)isoindolin-2-yl)piperidine-2,6-dione

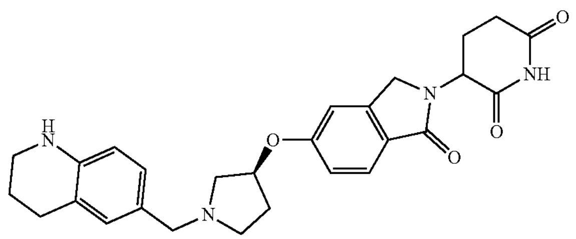 [SMILES: O=C1CCC(N2Cc3cc(O[C@H]4CCN(Cc5ccc6c(c5)CCCN6)C4)ccc3C2=O)C(=O)N1]

1-(2,4-Dimethoxybenzyl)-1,2,3,4-tetrahydroquinoline. To a solution of 1,2,3,4-tetrahydroquinoline (1 g, 7.51 mmol) and 2,4-dimethoxybenzaldehyde (1.5 g, 9.01 mmol) in methanol (15 mL) was added acetic acid (0.1 mL) at room temperature. After stirring for 0.5 hour at 0° C., sodium cyanoborohydride (1.44 g, 22.92 mmol) was added to the reaction in several portions at 0° C. under nitrogen. The reaction mixture was stirred for 12 h at room temperature. The resulting mixture was quenched with water and extracted with ethyl acetate. The extracts were washed with brine, dried over anhydrous sodium sulfate, filtered and concentrated. The crude was purified by silica gel column chromatography (0 to 50% ethyl acetate in petroleum ether) to give the title compound (1.2 g, 4.22 mmol, 56% yield) as a light-yellow oil. MS (ESI) m/z 284.1 [M+1]$^+$.

1-(2,4-Dimethoxybenzyl)-1,2,3,4-tetrahydroquinoline-6-carbaldehyde. Phosphorus oxychloride (1.08 g, 7.05 mmol) was added dropwise to anhydrous DMF (773 mg, 10.59 mmol) at 0° C., then the mixture was stirred for 30 min at this temperature. The reaction mixture was added dropwise a solution of 1-(2,4-dimethoxybenzyl)-1,2,3,4-tetrahydroquinoline (1 g, 3.53 mmol) in DMF (2 mL). The resulting mixture was stirred for 12 h at room temperature. The reaction mixture was quenched with water and extracted with ethyl acetate. The extracts were washed with brine, dried over anhydrous sodium sulfate and concentrated. The crude was purified by silica gel column chromatography (0 to 50% ethyl acetate in petroleum ether) to afford the title compound (450 mg, 1.44 mmol, 40% yield) as a light-yellow oil. MS (ESI) m/z 312.1 [M+1]$^+$.

3-(5-(((S)-1-((1-(2,4-Dimethoxybenzyl)-1,2,3,4-tetrahydroquinolin-6-yl)meth yl)pyrrolidin-3-yl)oxy)-1-oxoisoindolin-2-yl)piperidine-2,6-dione. To a stirred solution of 3-(1-oxo-5-(((S)-pyrrolidin-3-yl)oxy)isoindolin-2-yl)piperidine-2,6-dione (150 mg, 0.46 mmol), 1-(2,4-dimethoxybenzyl)-1,2,3,4-tetrahydroquinoline-6-carbaldehyde (142 mg, 0.45 mmol) and triethylamine (92 mg, 0.91 mmol) in dichloromethane (8 mL) was added sodium triacetoxyborohydride (386 mg, 1.82 mmol) at 0° C. Then the reaction mixture was stirred for 3 h at room temperature under nitrogen. The resulting mixture was concentrated and purified by silica gel column chromatography (0 to 100% ethyl acetate in petroleum ether) to afford the title compound (200 mg, 0.32 mmol, 71% yield) as a light-yellow oil. MS (ESI) m/z 625.3 $[M+1]^+$.

3-(1-Oxo-5-(((S)-1-((1,2,3,4-tetrahydroquinolin-6-yl) methyl)pyrrolidin-3-yl) oxy)isoindolin-2-yl)piperidine-2,6-dione. To a stirred solution of 3-(5-(((S)-1-((1-(2,4-dimethoxybenzyl)-1,2,3,4-tetrahydroquinolin-6-yl)methyl) pyrrolidin-3-yl)oxy)-1-oxoisoindolin-2-yl)piperidine-2,6-dione (180 mg, 0.29 mmol) in dichloromethane (4 mL) was added TFA (1 mL) at 0° C. The mixture was stirred for 1 h at room temperature under nitrogen. The resulting solution was concentrated at room temperature under reduced pressure. The crude was purified by silica gel column chromatography (0-10% methanol in dichloromethane) and further purified by preparative HPLC with the following conditions: Column: Sun Fire Prep C18 OBD Column, 19×150 mm 5 um 10 nm; Mobile Phase A: water (0.1% formic acid), Mobile Phase B: acetonitrile; Flow rate: 60 mL/min; Gradient: 2 B to 18 B in 7 min; 254/210 nm; $RT_1$: 5.26. The fractions containing desired product were collected and evaporated under reduced pressure to afford the title compound (33.6 mg, 0.070 mmol, 23% yield) as an off-white solid. $^1H$ NMR (400 MHz, Methanol-$d_4$) δ 8.50 (s, 1H), 7.74 (d, J=8.4 Hz, 1H), 7.13 (d, J=2.2 Hz, 1H), 7.07 (dd, J=8.4, 2.2 Hz, 1H), 7.00-6.92 (m, 2H), 6.52-6.45 (m, 1H), 5.22 (s, 1H), 5.12 (dd, J=13.3, 5.2 Hz, 1H), 4.48-4.44 (m, 2H), 4.16-4.04 (m, 2H), 3.50-3.42 (m, 3H), 3.30-3.21 (m, 3H), 2.95-2.85 (m, 1H), 2.83-2.76 (m, 1H), 2.73-2.68 (m, 2H), 2.59-2.39 (m, 2H), 2.31-2.20 (m, 1H), 2.19-2.12 (m, 1H), 1.93-1.82 (m, 2H); MS (ESI) m/z 473.3 $[M-1]^-$.

Example S48. 3-(5-(((S)-1-((5,8-Dihydro-6H-pyrano[3,4-b]pyridin-3-yl)methyl)pyrrolidin-3-yl)oxy)-1-oxoisoindolin-2-yl)piperidine-2,6-dione

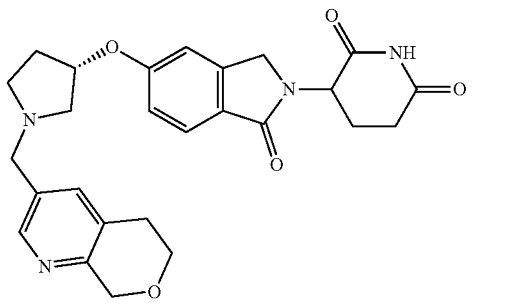 [SMILES: O=C1CCC(N2Cc3cc(O[C@H]4CCN(Cc5cnc6c(c5)CCOC6)C4)ccc3C2=O)C(=O)N1]

(5, 8-Dihydro-6H-pyrano[3,4-b]pyridin-3-yl)methanol. To a stirred solution of 6,8-dihydro-5H-pyrano[3,4-b]pyridine-3-carboxylic acid (150 mg, 0.84 mmol) in THF (8 mL) was added lithium aluminum hydride (2.5 N in THF, 0.5 mL, 1.25 mmol) at 0° C. under nitrogen. Then the reaction mixture was stirred for 1 h at this temperature. The mixture was quenched with water, filtered, concentrated and the crude product was purified by reverse phase flash (10-70% acetonitrile+0.05% ammonium bicarbonate in water, over 20 min) to afford the title compound (50 mg, 0.30 mmol, 36% yield) as a light-yellow oil. MS (ESI) m/z 166.1 $[M+1]^+$.

5, 8-Dihydro-6H-pyrano[3,4-b]pyridine-3-carbaldehyde. To a stirred solution of (5, 8-dihydro-6H-pyrano[3,4-b] pyridin-3-yl)methanol (50 mg, 0.30 mmol) in dichloromethane (5 mL) was added manganese dioxide (395 mg, 4.54 mmol) at room temperature and stirred for 12 h at 60° C. under nitrogen. The reaction mixture was filtered and the filtrate was concentrated to afford the title compound (40 mg, 0.24 mmol, 81% yield). MS (ESI) m/z 164.1 $[M+1]^+$.

3-(5-(((S)-1-((5,8-Dihydro-6H-pyrano[3,4-b]pyridin-3-yl)methyl)pyrrolidin-3-yl)oxy)-1-oxoisoindolin-2-yl)piperidine-2,6-dione. To a stirred solution of 3-(1-oxo-5-(((S)-pyrrolidin-3-yl)oxy)isoindolin-2-yl)piperidine-2,6-dione (60 mg, 0.18 mmol) and 5, 8-dihydro-6H-pyrano[3,4-b] pyridine-3-carbaldehyde (30 mg, 0.18 mmol) in dichloromethane (6 mL) were added triethylamine (0.05 mL, 0.37 mmol) and sodium triacetoxyborohydride (154 mg, 0.73 mmol) at 0° C. and the mixture was stirred for 2 h at room temperature under nitrogen. The resulting solution was concentrated at 25° C. under reduced pressure. The crude was purified by silica gel column chromatography (0-10% methanol in dichloromethane) and further purified by preparative HPLC with the following conditions: Column: X select CSH OBD Column 30*150 mm, 5 um; Mobile Phase A: water (0.05% TFA), Mobile Phase B: acetonitrile; Flow rate: 60 mL/min; Gradient: 3 B to 17 B in 10 min; 254/210 nm; $RT_1$: 7.98. The fractions containing desired product were collected and evaporated under reduced pressure to afford the title compound (20 mg, 0.042 mmol, 23% yield) as a light-yellow semi-solid. $^1H$ NMR (400 MHz, Methanol-$d_4$) δ 8.53 (s, 1H), 7.83-7.77 (m, 2H), 7.18 (s, 1H), 7.13 (d, J=8.3 Hz, 1H), 5.36 (s, 1H), 5.15 (dd, J=13.3, 5.2 Hz, 1H), 4.79 (s, 2H), 4.56 (s, 2H), 4.51-4.40 (m, 2H), 4.01 (t, J=5.6 Hz, 2H), 3.75 (m, 3H), 3.58 (m, 1H), 3.00-2.86 (m, 3H), 2.80-2.75 (m, 1H), 2.65 (m, 1H), 2.49-2.31 (m, 2H), 2.20-2.16 (m, 1H). MS (ESI) m/z 477.1 $[M+1]^+$.

Example S49. 6-(((3S)-3-((2-(2,6-dioxopiperidin-3-yl)-1-oxoisoindolin-5-yl)oxy)pyrrolidin-1-yl)methyl) quinazoline-2-carbonitrile

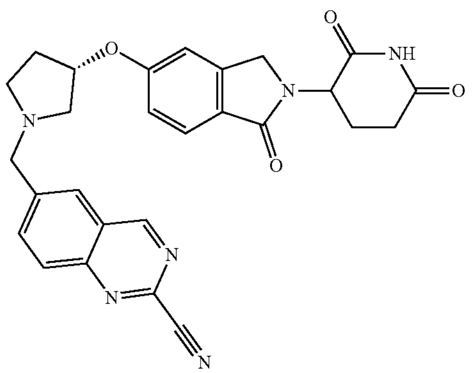 [SMILES: N#Cc1ncc2cc(CN3CC[C@H](Oc4ccc5c(c4)CN(C4CCC(=O)NC4=O)C5=O)C3)ccc2n1]

6-Methylquinazoline-2-carbonitrile. To a stirred solution of 2-chloro-6-methylquinazoline (160 mg, 0.90 mmol) in NMP (5 mL) were added zinccyanide (126 mg, 1.07 mmol) and tris(dibenzylideneacetone)dipalladium (65 mg, 0.070 mmol). The above mixture was stirred at 90° C. for 12 h under nitrogen. The reaction mixture was diluted with water and extracted with ethyl acetate. The extracts were dried over sodium sulfate, filtered and concentrated. The residue was purified by silica gel chromatography (0 to 35% ethyl acetate in petroleum ether) to afford the title compound (120 mg, 0.71 mmol, 79% yield) as a yellow solid. MS (ESI) m/z 170.2 $[M+1]^+$.

6-(Bromomethyl)quinazoline-2-carbonitrile. To a solution of 6-methylquinazoline-2-carbonitrile (100 mg, 0.59 mmol) in carbon tetrachloride (3 mL) was added NBS (125 mg, 0.70 mmol) and benzoyl peroxide (15 mg, 0.06 mmol). The above mixture was stirred at 80° C. for 12 h under nitrogen. The reaction mixture was diluted with water and extracted with ethyl acetate. The extracts were dried over sodium sulfate, filtered and concentrated. The residue was purified by silica gel chromatography (0 to 35% ethyl acetate in petroleum ether) to afford the title compound (60 mg, 0.24 mmol, 41% yield) as a yellow solid. MS (ESI) m/z 248.1 $[M+1]^+$.

6-(((3S)-3-((2-(2,6-Dioxopiperidin-3-yl)-1-oxoisoindolin-5-yl)oxy)pyrrolidin-1-yl)methyl)quinazoline-2-carbonitrile. To a solution of 6-(bromomethyl)quinazoline-2-carbonitrile (60 mg, 0.24 mmol) and 3-[1-oxo-5-[(3S)-pyrrolidin-3-yl]oxy-isoindolin-2-yl]piperidine-2,6-dione (80 mg, 0.24 mmol) in acetonitrile (3 mL) was added potassium carbonate (100 mg, 0.72 mmol). The flask was evacuated and flushed five times with nitrogen. The mixture was stirred 5 h at room temperature under nitrogen. The resulting mixture was filtered and the filtrate was concentrated. The residue was purified by reverse phase flash (10-100% acetonitrile+0.05% TFA in water, over 25 min) and preparative—HPLC (Column: SunFire Prep C18 OBD Column, 19×150 mm 5 um 10 nm; Mobile Phase A: water (0.1% formic acid), Mobile Phase B: acetonitrile; Flow rate: 60 mL/min; Gradient: 5 B to 30 B in 7 min; 254/210 nm; $RT_1$: 4.97. The fractions containing desired product were collected and evaporated under reduced pressure to afford the title compound (16 mg, 0.032 mmol, 13% yield) as a white solid. $^1H$ NMR (300 MHz, Methanol-$d_4$) δ 9.60 (d, J=0.9 Hz, 1H), 8.22 (d, J=9.9 Hz, 2H), 8.12 (d, J=8.6 Hz, 1H), 7.70 (d, J=8.4 Hz, 1H), 7.09-7.00 (m, 2H), 5.11-5.07 (m, 2H), 4.42 (d, J=3.9 Hz, 2H), 4.04 (s, 2H), 3.09-2.74 (m, 6H), 2.49-2.45 (m, 2H), 2.20-2.02 (m, 2H). MS (ESI) m/z 497.2 $[M+1]^+$.

Example S50. 3-(1-Oxo-5-(((S)-1-((2-(trifluoromethyl)quinazolin-6-yl)methyl)pyrrolidin-3-yl)oxy)isoindolin-2-yl)piperidine-2,6-dione

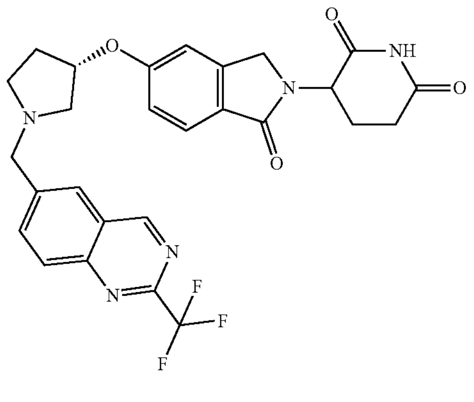 [SMILES: O=C1CCC(N2Cc3cc(O[C@H]4CCN(Cc5ccc6nc(C(F)(F)F)ncc6c5)C4)ccc3C2=O)C(=O)N1]

6-Methyl-2-(trifluoromethyl)-4H-benzo[d][1,3]oxazin-4-one. To a solution of 2-amino-5-methylbenzoic acid (2 g, 13.23 mmol) in dichloromethane (30 mL) was added slowly with stirring trifluoroacetic anhydride (3.5 mL). The reaction mixture was stirred for 12 h at room temperature under nitrogen. The resulting mixture was evaporated under reduced pressure. The residue was poured into ice and filtered to afford the title compound (500 mg, 2.18 mmol, 16% yield) as a light-yellow solid.

6-Methyl-2-(trifluoromethyl)quinazolin-4(1H)-one. A solution of 6-methyl-2-(trifluoromethyl)-4H-benzo[d][1,3]oxazin-4-one (500 mg, 2.18 mmol) in DMF (10 mL) was stirred at 0° C. firstly and then warmed to room temperature overnight under ammonia (~2 bar). The crude product was purified by reverse phase flash (10-40% acetonitrile+0.05% ammonium bicarbonate in water, over 25 min) to afford the title compound (350 mg, 1.53 mmol, 70% yield) as a light-yellow solid. MS (ESI) m/z 229.0 $[M+1]^+$.

4-Chloro-6-methyl-2-(trifluoromethyl)quinazoline. The solution of 6-methyl-2-(trifluoromethyl)quinazolin-4(1H)-one (330 mg, 1.31 mmol) in phosphorus oxychloride (10 mL) was stirred at 100° C. for 3 h under nitrogen. The reaction mixture was cooled and evaporated under reduced pressure. The residue was diluted with ethyl acetate, washed with saturated sodium bicarbonate and brine. The organic phase was dried over anhydrous sodium sulfate, filtered and concentrated. The crude product was purified by silica gel column chromatography (0 to 50% ethyl acetate in petroleum ether) to afford the title compound (220 mg, 0.89 mmol, 68% yield) as an off-white solid. MS (ESI) m/z 246.9 $[M+1]^+$.

6-Methyl-2-(trifluoromethyl)quinazoline. To a solution of 4-chloro-6-methyl-2-(trifluoromethyl)quinazoline (200 mg, 0.81 mmol) in ethyl acetate (10 mL) were added cesium carbonate (790 mg, 2.43 mmol) and 10% palladium on carbon (100 mg, wetted with ca. 50% water) under nitrogen. Then the reaction mixture was stirred for 1 h at room temperature under hydrogen (~2 bar). The resulting mixture was diluted with ethyl acetate, filtered and concentrated to afford the title compound (160 mg, 0.75 mmol, 93% yield). MS (ESI) m/z 213.1 $[M+1]^+$.

6-(Bromomethyl)-2-(trifluoromethyl)quinazoline. To a stirred solution of 6-methyl-2-(trifluoromethyl)quinazoline (150 mg, 0.70 mmol) in carbon tetrachloride (10 mL) were added NBS (151 mg, 0.85 mmol) and benzoyl peroxide (17 mg, 0.07 mmol) at room temperature. Then the reaction mixture was stirred for 12 h at 60° C. under nitrogen. The resulting mixture was concentrated and the residue was diluted with water, extracted with ethyl acetate. The extracts were washed with brine, dried over anhydrous sodium sulfate, filtered and concentrated. The crude product was purified by silica gel chromatography (0 to 50% ethyl acetate in petroleum ether) to afford the title compound (150 mg, 0.52 mmol, 74% yield) as a white solid. MS (ESI) m/z 290.9 $[M+1]^+$.

3-(1-Oxo-5-(((S)-1-((2-(trifluoromethyl)quinazolin-6-yl)methyl)pyrrolidin-3-yl)oxy)isoindolin-2-yl)piperidine-2,6-dione. To a stirred solution of 6-(bromomethyl)-2-(trifluoromethyl)quinazoline (62 mg, 0.21 mmol) in acetonitrile (3 mL) were added potassium carbonate (88 mg, 0.64 mmol) and 3-(1-oxo-5-(((S)-pyrrolidin-3-yl)oxy)isoindolin-2-yl)piperidine-2,6-dione (70 mg, 0.21 mmol) at room temperature. Then the reaction mixture was stirred for 1 h at room temperature. The resulting reaction mixture was filtered and concentrated at room temperature under reduced pressure. The crude product was purified by silica gel chromatography (0-10% methanol in dichloromethane) and further purified by preparative HPLC with the following conditions: Column: Sun Fire Prep C18 OBD Column, 19×150 mm 5 um 10 nm; Mobile Phase A: water (0.1% formic acid), Mobile Phase B: acetonitrile; Flow rate: 60 mL/min; Gradient: 5 B to 35 B in 7 min, 254/210 nm; $RT_1$: 6.32. The fractions containing desired product were collected and evaporated under reduced pressure to afford the title compound (34.3 mg, 0.06 mmol, 29% yield) as a white solid. $^1$H NMR (400 MHz, Methanol-$d_4$) δ 9.68 (s, 1H), 8.24-8.18 (m, 3H), 7.71 (dd, J=8.6, 1.8 Hz, 1H), 7.11-7.01 (m, 2H), 5.12-5.08 (m, 2H), 4.51-4.36 (m, 2H), 4.07 (s, 2H), 3.18-3.09 (m, 1H), 3.08-2.91 (m, 3H), 2.84-2.72 (m, 2H), 2.55-2.43 (m, 2H), 2.22-2.02 (m, 2H). MS (ESI) m/z 540.1 [M+1]$^+$.

Example S51. 3-(5-(((S)-1-((3-(Methoxymethyl)quinolin-6-yl)methyl)pyrrolidin-3-yl)oxy)-1-oxoisoindolin-2-yl)piperidine-2,6-dione

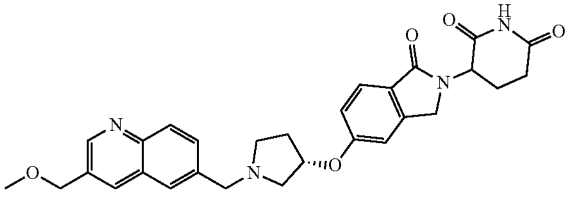 [SMILES: COCc1cnc2ccc(CN3CC[C@H](Oc4ccc5c(c4)CN(C4CCC(=O)NC4=O)C5=O)C3)cc2c1]

(6-Bromoquinolin-3-yl)methanol. To a stirred solution of methyl 6-bromoquinoline-3-carboxylate (500 mg, 1.88 mmol) in THF (20 mL) was added lithium aluminum hydride (2.5 M in THF, 0.75 mL, 1.88 mmol) at 0° C. under nitrogen. Then the reaction mixture was stirred for 0.5 h at 0° C. under nitrogen. The resulting mixture was quenched with water, added anhydrous sodium sulfate, filtered and concentrated to afford the title compound (380 mg, 1.60 mmol, 88% yield) as an orange solid. MS (ESI) m/z 238.0 [M+1]$^+$.

6-Bromo-3-(methoxymethyl)quinoline. To a stirred solution of (6-bromoquinolin-3-yl)methanol (380 mg, 1.60 mmol) in THF (15 mL) was added sodium hydride (60% dispersion in mineral oil, 65 mg, 1.63 mmol) at 0° C. and the resulting mixture was stirred for 30 min at room temperature, and then iodomethane (339 mg, 2.39 mmol) was added. The reaction mixture was stirred for 12 h at room temperature. The resulting mixture was quenched with water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (260 mg, 1.03 mmol, 64% yield) as a yellow solid. MS (ESI) m/z 252.0 [M+1]$^+$.

3-(Methoxymethyl)quinoline-6-carbaldehyde. To a solution of 6-bromo-3-(methoxymethyl)quinoline (240 mg, 0.95 mmol), sodium formate (129 mg, 1.90 mmol), palladium (II) acetate (21 mg, 0.0094 mmol) and 1,2-bis(diphenylphosphino)ethane (76 mg, 0.19 mmol) in DMSO (10 mL) was added tert-butylisocyanide (118 mg, 1.43 mmol). The mixture was stirred at 120° C. for 4 h under nitrogen. The resulting solution was diluted with water and extracted with ethyl acetate. The extracts were washed with brine, dried over sodium sulfate, filtered and concentrated. The crude was purified by silica gel chromatography (0 to 50% ethyl acetate in petroleum ether) to afford the title compound (80 mg, 0.39 mmol, 41% yield) as a yellow solid. MS (ESI) m/z 202.2 [M+1]$^+$.

3-(5-(((S)-1-((3-(Methoxymethyl)quinolin-6-yl)methyl)pyrrolidin-3-yl)oxy)-1-oxoisoindolin-2-yl)piperidine-2,6-dione. To a stirred solution of 3-(methoxymethyl)quinoline-6-carbaldehyde (70 mg, 0.35 mmol), 3-(1-oxo-5-(((S)-pyrrolidin-3-yl)oxy)isoindolin-2-yl)piperidine-2,6-dione (115 mg, 0.35 mmol) and triethylamine (0.10 mL, 0.69 mmol) in dichloromethane (3 mL) was added sodium triacetoxyborohydride (295 mg, 1.39 mmol). The mixture was stirred at room temperature for 2 h under nitrogen. The resulting reaction mixture was filtered and concentrated at 25° C. under reduced pressure. The crude product was purified by silica gel chromatography (0-10% methanol in dichloromethane) and further purified by preparative HPLC with the following conditions: Column: Sun Fire Prep C18 OBD Column, 19×150 mm 5 um 10 nm; Mobile Phase A: water (0.1% formic acid), Mobile Phase B: acetonitrile; Flow rate: 60 mL/min; Gradient: 5 B to 30 B in 7 min, 254/210 nm; $RT_1$: 4.52. The fractions containing desired product were collected and evaporated under reduced pressure to afford the title compound (35.1 mg, 0.068 mmol, 19% yield) as an off-white solid. $^1$H NMR (400 MHz, Methanol-$d_4$) δ 8.87 (d, J=2.1 Hz, 1H), 8.31 (m, 2H), 8.08 (d, J=8.7 Hz, 1H), 8.01 (s, 1H), 7.87 (dd, J=8.8, 2.0 Hz, 1H), 7.72 (d, J=8.4 Hz, 1H), 7.13-7.03 (m, 2H), 5.18-5.08 (m, 2H), 4.71 (s, 2H), 4.51-4.36 (m, 2H), 4.24 (m, 2H), 3.50 (s, 3H), 3.40-3.34 (m, 1H), 3.24 (m, 2H), 3.05 (m, 1H), 2.91-2.84 (m, 1H), 2.83-2.74 (m, 1H), 2.59-2.41 (m, 2H), 2.17-2.11 (m, 2H); MS (ESI) m/z 515.2 [M+1]$^+$.

Example S52. 3-(((3S)-3-((2-(2,6-Dioxopiperidin-3-yl)-1-oxoisoindolin-5-yl)oxy)pyrrolidin-1-yl)methyl)-N-methylisoquinoline-7-carboxamide

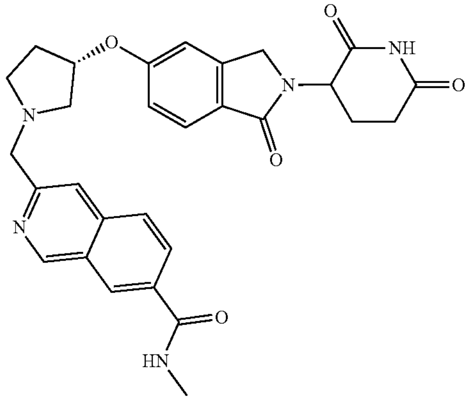 [SMILES: CNC(=O)c1ccc2cc(CN3CC[C@H](Oc4ccc5c(c4)CN(C4CCC(=O)NC4=O)C5=O)C3)ncc2c1]

(7-Bromoisoquinolin-3-yl)methanol. To a stirred solution of methyl 7-bromoisoquinoline-3-carboxylate (500 mg, 1.88 mmol) in THF (4 mL) and ethanol (0.40 mL) was added sodium borohydride (142 mg, 3.76 mmol) at room temperature. Then the reaction mixture was stirred for 12 h at room temperature under nitrogen. The resulting mixture was diluted with water and extracted with ethyl acetate. The extracts were washed with brine, dried over anhydrous sodium sulfate, filtered and concentrated to afford the title compound (350 mg, 1.47 mmol, 78% yield) as a light-yellow oil which was used in the next step directly without further purification. MS (ESI) m/z 238.1 [M+1]$^+$.

7-Bromo-3-(((tert-butyldiphenylsilyl)oxy)methyl)isoquinoline. To a stirred solution of (7-bromo-3-isoquinolyl)methanol (350 mg, 1.47 mmol) in THF (15 mL) were added sodium hydride (60% dispersion in mineral oil, 70 mg, 1.75 mmol) and tert-butylchlorodiphenylsilane (808 mg, 2.94 mmol) sequently at 0° C. under nitrogen. Then the reaction mixture was stirred for 12 h at room temperature. The resulting mixture was added water and extracted with ethyl acetate. The extracts were washed with brine, dried over anhydrous sodium sulfate, filtered and concentrated. The residue was purified by silica gel chromatography (0 to 10% ethyl acetate in petroleum ether) to afford the title compound (450 mg, 0.94 mmol, 64% yield) as a light-yellow oil. MS (ESI) m/z 476.1 $[M+1]^+$.

Methyl 3-(((tert-butyldiphenylsilyl)oxy)methyl)isoquinoline-7-carboxylate. To a solution of (7-bromo-3-isoquinolyl) methoxy-tert-butyl-diphenyl-silane (450 mg, 0.94 mmol) in methanol (15 mL) was added 1,1'-Bis(diphenylphosphino) ferrocene-palladium(II)dichloride dichloromethane complex (77 mg, 0.09 mmol) and triethylamine (0.39 mL, 2.83 mmol). Then the reaction mixture was stirred for 12 h at 120° C. under 50 bar carbon monoxide. The resulting mixture was filtered and concentrated. The crude product was purified by silica gel column chromatography (0 to 20% ethyl acetate in petroleum ether) to afford the title compound (380 mg, 0.83 mmol, 88% yield) as a light-yellow oil. MS (ESI) m/z 456.1 $[M+1]^+$.

3-(((Tert-butyldiphenylsilyl)oxy)methyl)-N-methylisoquinoline-7-carbox amide. A solution of methyl 3-(((tert-butyldiphenylsilyl)oxy)methyl)isoquinoline-7-carboxylate (380 mg, 0.83 mmol) in 30% methylamine in ethanol (4 mL) was stirred for 12 h at 50° C. under nitrogen. The resulting mixture was concentrated and the crude product was purified by silica gel column chromatography (0 to 35% ethyl acetate in petroleum ether) to afford the title compound (360 mg, 0.79 mmol, 94% yield) as a light-yellow oil. MS (ESI) m/z 455.3 $[M+1]^+$.

3-(Hydroxymethyl)-N-methylisoquinoline-7-carboxamide. To a stirred solution of 3-(((tert-butyldiphenylsilyl)oxy) methyl)-N-methylisoquinoline-7-carboxamide (320 mg, 0.70 mmol) in THF (7 mL) was added triethylamine trihydrofluoride (2.3 g, 14.26 mmol) at room temperature and stirred for 5 h at this temperature. The reaction mixture was concentrated to afford the title compound (150 mg, 0.69 mmol, 98% yield) as a light-yellow oil which was used in the next step directly without further purification. MS (ESI) m/z 217.2 $[M+1]^+$.

3-Formyl-N-methylisoquinoline-7-carboxamide. To a stirred solution of 3-(hydroxymethyl)-N-methylisoquinoline-7-carboxamide (140 mg, 0.65 mmol) in dichloromethane (4 mL) was added manganese dioxide (563 mg, 6.47 mmol) at room temperature and stirred for 3 h at 60° C. under nitrogen. The reaction mixture filtered and concentrated. The crude product was purified by silica gel column chromatography (0 to 40% ethyl acetate in petroleum ether) to afford the title compound (35 mg, 0.16 mmol, 25% yield) as a white solid. MS (ESI) m/z 215.2 $[M+1]^+$.

3-(((3S)-3-((2-(2,6-Dioxopiperidin-3-yl)-1-oxoisoindolin-5-yl)oxy)pyrrolidin-1-yl)methyl)-N-methylisoquinoline-7-carboxamide. To a stirred solution of 3-formyl-N-methylisoquinoline-7-carboxamide (30 mg, 0.14 mmol), 3-(1-oxo-5-(((S)-pyrrolidin-3-yl)oxy)isoindolin-2-yl)piperidine-2,6-dione (46 mg, 0.14 mmol) and triethylamine (0.04 mL, 0.28 mmol) in dichloromethane (3 mL) was added sodium triacetoxyborohydride (119 mg, 0.56 mmol). The mixture was stirred at room temperature for 2 h under nitrogen. The resulting mixture was filtered and concentrated at room temperature. The crude product was purified by silica gel chromatography (0-10% methanol in dichloromethane) and further purified by preparative HPLC with the following conditions: Column: Column: Sun fire prep C18 column, 30*150, 5 um; Mobile Phase A: water (0.1% formic acid), Mobile Phase B: acetonitrile; Flow rate: 60 mL/min; Gradient: 2 B to 25 B in 8 min; 254/220 nm; $RT_1$: 7. The fractions containing desired product were collected and evaporated under reduced pressure to afford the title compound (14.6 mg, 0.028 mmol, 20% yield) as a white solid. $^1H$ NMR (400 MHz, Methanol-$d_4$) δ 9.25 (s, 1H), 8.46 (d, J=1.7 Hz, 1H), 8.08-8.06 (m, 1H), 7.92-7.84 (m, 2H), 7.61 (dd, J=8.4, 1.9 Hz, 1H), 6.99-6.94 (m, 2H), 5.07-4.98 (m, 2H), 4.37-4.24 (m, 4H), 3.46 (m, 1H), 3.42-3.35 (m, 2H), 3.22-3.14 (m, 1H), 2.89 (s, 3H), 2.79-2.65 (m, 2H), 2.41-2.33 (m, 2H), 2.11-2.03 (m, 2H); MS (ESI) m/z 528.2 $[M+1]^+$.

Example S53. 3-(6-Fluoro-5-(((S)-1-(isoquinolin-3-ylmethyl)pyrrolidin-3-yl)oxy)-1-oxoisoindolin-2-yl) piperidine-2,6-dione

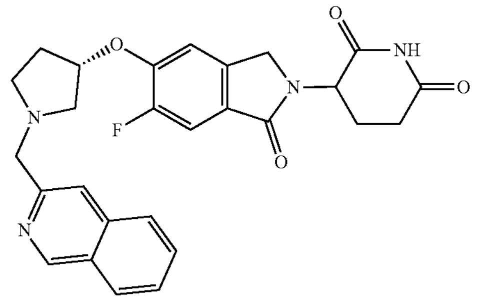 [SMILES: O=C1CCC(N2Cc3cc(O[C@H]4CCN(Cc5cc6ccccc6cn5)C4)c(F)cc3C2=O)C(=O)N1]

Methyl 4-bromo-2-(bromomethyl)-5-fluorobenzoate. To a stirred solution of methyl 4-bromo-5-fluoro-2-methylbenzoate (1.8 g, 7.29 mmol) in carbon tetrachloride (25 mL) was added NBS (930 mg, 8.74 mmol) and 2,2'-azobis(2-methylpropionitrile) (179 mg, 1.09 mmol) at room temperature. Then the reaction mixture was stirred for 12 h at 80° C. under nitrogen. The resulting reaction mixture was concentrated. The residue was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (2.4 g, 7.36 mmol, 101% yield) containing starting material as a light yellow oil.

Methyl 2-(((2,6-bis(benzyloxy)pyridin-3-yl)amino) methyl)-4-bromo-5-fluorobenzoate. To a stirred solution of methyl 4-bromo-2-(bromomethyl)-5-fluorobenzoate (2.4 g, 7.36 mmol) and 2,6-bis(benzyloxy)pyridin-3-amine (2.48 g, 8.1 mmol) in DMF (50 mL) was added N,N-Diisopropylethylamine (1.13 mL, 14.73 mmol) at room temperature. Then the reaction mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (2.6 g, 4.71 mmol, 64% yield) as an orange oil. MS (ESI) m/z 551.1 $[M+1]^+$.

2-(2,6-Bis(benzyloxy)pyridin-3-yl)-5-bromo-6-fluoroisoindolin-1-one. A solution of methyl 2-(((2,6-bis(benzyloxy)pyridin-3-yl)amino)methyl)-4-bromo-5-fluorobenzoate (2.59 g, 4.7 mmol) in acetic acid (3 mL) was stirred at 100° C. for 0.5 h under nitrogen. The resulting mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (1.4 g, 2.69 mmol, 57% yield) as a light-yellow solid. MS (ESI) m/z 518.9 $[M+1]^+$.

2-(2,6-Bis(benzyloxy)pyridin-3-yl)-6-fluoro-5-hydroxyisoindolin-1-one. To a solution of 2-(2,6-bis(benzyloxy)pyridin-3-yl)-5-bromo-6-fluoroisoindolin-1-one (1.38 g, 2.66 mmol) in dry DMF (20 mL) was added methanesulfonato (2-(di-t-butylphosphino)-3-methoxy-6-methyl-2',4',6'-tri-i-propyl-1,1'-biphenyl)(2'-amino-1,1'-biphenyl-2-yl)palladium(II) (67 mg, 0.08 mmol), (E)-benzaldehyde oxime (385 mg, 3.19 mmol) and cesium carbonate (1.73 g, 5.31 mmol) at room temperature. Then the reaction mixture was stirred for 3 h at 80° C. under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (1.02 g, 2.23 mmol, 84% yield) as a light-orange solid. MS (ESI) m/z 457.1 $[M+1]^+$.

Tert-butyl (S)-3-((2-(2,6-bis(benzyloxy)pyridin-3-yl)-6-fluoro-1-oxoiso indolin-5-yl)oxy)pyrrolidine-1-carboxylate. To a stirred solution of 2-(2,6-bis(benzyloxy)pyridin-3-yl)-6-fluoro-5-hydroxyisoindolin-1-one (1 g, 2.19 mmol), tert-butyl (R)-3-hydroxypyrrolidine-1-carboxylate (410 mg, 2.19 mmol) and triphenylphosphine (862 mg, 3.29 mmol) in toluene (20 mL) was added di-tert-butyl azodicarboxylate (756 mg, 3.29 mmol). Then the reaction mixture was stirred at 80° C. for 2 h under nitrogen. The resulting mixture was concentrated under reduced pressure. The crude was purified by silica gel column chromatography (0 to 50% ethyl acetate in petroleum ether) to afford the title compound (1.25 g, 1.99 mmol, 91% yield) as an off-white solid. MS (ESI) m/z 626.3 $[M+1]^+$.

Tert-butyl (3S)-3-((2-(2,6-dioxopiperidin-3-yl)-6-fluoro-1-oxoisoindolin-5-yl)oxy)pyrrolidine-1-carboxylate. To a solution of tert-butyl (S)-3-((2-(2,6-bis(benzyloxy)pyridin-3-yl)-6-fluoro-1-oxoisoindolin-5-yl)oxy)pyrrolidine-1-carboxylate (1.24 g, 1.98 mmol) in ethanol (100 mL) was added $Pd(OH)_2/C$ (1.2 g, 11.28 mmol) under nitrogen. Then the reaction mixture was stirred for 2 h at room temperature under hydrogen (~2 bar). The resulting mixture was filtered and the filtrate was concentrated to afford the title compound (500 mg, 1.11 mmol, 56% yield) as a light-yellow solid. MS (ESI) m/z 446.2 $[M-1]^-$.

3-(6-Fluoro-1-oxo-5-(((S)-pyrrolidin-3-yl)oxy)isoindolin-2-yl)piperidine-2,6-dione. To a stirred solution of tert-butyl (3S)-3-((2-(2,6-dioxopiperidin-3-yl)-6-fluoro-1-oxoisoindolin-5-yl)oxy)pyrrolidine-1-carboxylate (470 mg, 1.05 mmol) in dichloromethane (3 mL) was added TFA (1 mL, 1.05 mmol) at room temperature and stirred for 1 h at this temperature. The mixture was concentrated to afford the title compound (300 mg, 0.86 mmol, 82% yield) which was used directly in the next step without further purification. MS (ESI) m/z 348.2 $[M+1]^+$.

3-(6-Fluoro-5-(((S)-1-(isoquinolin-3-ylmethyl)pyrrolidin-3-yl)oxy)-1-oxoiso indolin-2-yl)piperidine-2,6-dione. To a stirred solution of 3-(6-fluoro-1-oxo-5-(((S)-pyrrolidin-3-yl)oxy)isoindolin-2-yl)piperidine-2,6-dione (150 mg, 0.43 mmol), isoquinoline-3-carbaldehyde (68 mg, 0.43 mmol) and triethylamine (0.15 mL, 0.87 mmol) in dichloromethane (5 mL) was added sodium triacetoxyborohydride (366 mg, 1.73 mmol). The mixture was stirred at room temperature for 2 h under nitrogen. The resulting mixture was concentrated at 25° C. under reduced pressure. The crude was purified by silica gel column chromatography (0-10% methanol in dichloromethane) and further purified by preparative HPLC with the following conditions: Column: Sun fire prep C18 column, 30*150, 5 um; Mobile Phase A: water (0.1% formic acid), Mobile Phase B: acetonitrile; Flow rate: 60 mL/min; Gradient: 5 B to 20 B in 10 min; $RT_1$: 9.67. The fractions containing desired product were collected and evaporated under reduced pressure to afford the title compound (76.6 mg, 0.15 mmol, 36% yield) as a white solid. $^1H$ NMR (400 MHz, Methanol-$d_4$) δ 9.30 (s, 1H), 8.38 (s, 1H), 8.13 (d, J=8.2 Hz, 1H), 7.99-7.91 (m, 2H), 7.83-7.81 (m, 1H), 7.73-7.71 (m, 1H), 7.50 (dd, J=9.8, 3.1 Hz, 1H), 7.30 (d, J=7.0 Hz, 1H), 5.25 (m, 1H), 5.15-5.10 (m, 1H), 4.51-4.35 (m, 4H), 3.68-3.57 (m, 1H), 3.51-3.47 (m, 2H), 3.31-3.25 (m, 1H), 2.90-2.84 (m, 1H), 2.83-2.74 (m, 1H), 2.62-2.39 (m, 2H), 2.34-2.26 (m, 1H), 2.17-2.11 (m, 1H). MS (ESI) m/z 489.1 $[M+1]^+$.

Example S54. 3-(5-(((S)-1-((2-Ethynylquinolin-6-yl)methyl)pyrrolidin-3-yl)oxy)-1-oxoisoindolin-2-yl) piperidine-2,6-dione

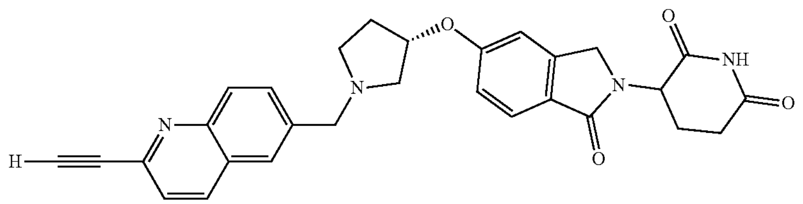 [SMILES: C#Cc1ccc2cc(CN3CC[C@H](Oc4ccc5c(c4)CN(C4CCC(=O)NC4=O)C5=O)C3)ccc2n1]

(2-Chloroquinolin-6-yl)methanol. To a stirred solution of methyl 2-chloroquinoline-6-carboxylate (410 mg, 1.85 mmol) in THF (10 mL) was added lithium aluminum hydride (2.5 M in THF, 1.6 mL, 4 mmol) dropwised at 0° C. under nitrogen. Then the reaction mixture was warmed and stirred for 2 h at room temperature. The resulting mixture was quenched with sodium hydroxide (2 M in water, 5 mL, 10 mmol) at 0° C., then stirred for 30 min at this temperature and filtered. The filter cake was washed with 20 mL THF and 10 mL methanol. The filtrates combined were concentrated to afford the title compound (350 mg, 1.80 mmol, 97% yield) as a yellow solid. MS (ESI) m/z 194.0 $[M+1]^+$.

2-Chloroquinoline-6-carbaldehyde. To a stirred solution of (2-chloro-6-quinolyl)methanol (380 mg, 1.96 mmol) in dichloromethane (2 mL) was added manganese(IV) oxide (341 mg, 3.90 mmol) at room temperature. Then the reaction mixture was stirred for 12 h at room temperature under nitrogen. The mixture was filtered and the filtrate was concentrated to afford the title compound (300 mg, 1.56 mmol, 79% yield) as a yellow solid. MS (ESI) m/z 192.1 $[M+1]^+$.

2-((Trimethylsilyl)ethynyl)quinoline-6-carbaldehyde. To a stirred solution of 2-chloroquinoline-6-carbaldehyde (150 mg, 0.78 mmol), ethynyl(trimethyl)silane (153 mg, 1.6 mmol) in acetonitrile (6 mL) were added dichlorobis(triphenylphosphine)palladium(II) (64 mg, 0.092 mmol), triethylamine (0.54 mL, 3.9 mmol), copper(I) iodide (30 mg, 0.16 mmol) at room temperature. Then the reaction mixture was stirred at 60° C. for 2 h under nitrogen. The resulting mixture was filtered and the filtrate was concentrated. The crude product was purified by reverse phase flash (10-40% acetonitrile+0.05% ammonium bicarbonate in water, over 20 min) to give the title compound (85 mg, 0.33 mmol, 42% yield) as a yellow solid. MS (ESI) m/z 254.1 $[M+1]^+$.

3-[1-Oxo-5-[(3S)-1-[[2-(2-trimethylsilylethynyl)-6-quinolyl]methyl]pyrrolidin-3-yl]oxy-isoindolin-2-yl]piperidine-2,6-dione. To a stirred solution of 2-(2-trimethylsilylethynyl)quinoline-6-carbaldehyde (45.6 mg, 0.18 mmol), 3-[1-oxo-5-[(3S)-pyrrolidin-3-yl]oxy-isoindolin-2-yl] piperidine-2,6-dione (118 mg, 0.36 mmol), triethylamine (0.05 mL, 0.37 mmol) in dichloromethane (5 mL) pre-stirred for 15 min was added sodium triacetoxyborohydride (154 mg, 0.73 mmol) at 0° C. and the solution was stirred at room temperature for 12 h under nitrogen. The resulting solution was purified directly by reverse phase flash (10-40% acetonitrile+0.05% TFA in water, over 25 min) to afford the title compound (70 mg, 0.12 mmol, 68% yield) as a yellow oil. MS (ESI) m/z 567.2 $[M+1]^+$.

3-(5-(((S)-1-((2-Ethynylquinolin-6-yl)methyl)pyrrolidin-3-yl)oxy)-1-oxoisoindolin-2-yl)piperidine-2,6-dione. To a stirred solution of 3-[1-oxo-5-[(3S)-1-[[2-(2-trimethylsilylethynyl)-6-quinolyl]methyl]pyrrolidin-3-yl]oxy-isoindolin-2-yl]piperidine-2,6-dione (80 mg, 0.14 mmol) in THF (5 mL) was added tetrabutylammonium fluoride (46 mg, 0.18 mmol) at 0° C. Then the reaction mixture was stirred at room temperature for 2 h under nitrogen. The resulting solution was purified silica gel chromatography (0 to 5% methanol in dichloromethane). The pure fractions were evaporated and purified further by reverse-phased semi-preparative HPLC (10-30% acetonitrile+0.05% TFA in water, over 30 min) to afford the title compound (3.7 mg, 0.007 mmol, 5% yield) as a light orange solid. $^1$H NMR (400 MHz, DMSO-$d_6$) δ 8.38 (d, J=8.5 Hz, 1H), 8.00-7.86 (m, 2H), 7.79 (m, 1H), 7.61 (t, J=8.2 Hz, 2H), 7.11 (s, 1H), 7.01 (m, 1H), 5.13-4.95 (m, 2H), 4.46 (s, 1H), 4.37 (d, J=17.2 Hz, 1H), 4.24 (d, J=17.1 Hz, 1H), 3.90-3.76 (m, 2H), 3.02-2.84 (m, 2H), 2.84-2.68 (m, 2H), 2.65-2.52 (m, 2H), 2.35 (m, 2H), 1.98 (s, 1H), 1.85 (d, J=7.6 Hz, 1H); MS (ESI) m/z 495.2 $[M+1]^+$.

Example S55. 3-(1-Oxo-5-(((S)-1-((2-(prop-1-yn-1-yl)quinazolin-6-yl)methyl)pyrrolidin-3-yl)oxy)isoindolin-2-yl)piperidine-2,6-dione

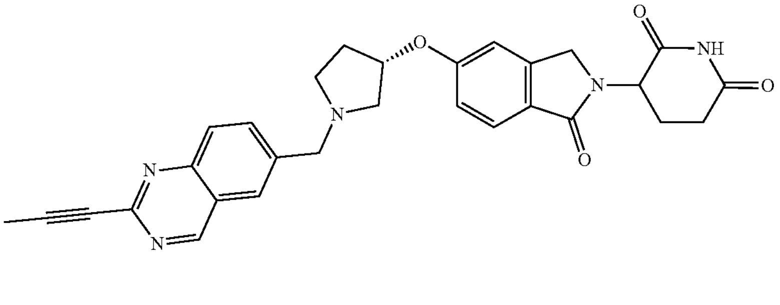 [SMILES: CC#Cc1ncc2cc(CN3CC[C@H](Oc4ccc5c(c4)CN(C4CCC(=O)NC4=O)C5=O)C3)ccc2n1]

2-(Prop-1-yn-1-yl)quinazoline-6-carbaldehyde. A mixture of 2-chloroquina zoline-6-carbaldehyde (90 mg, 0.47 mmol), prop-1-yne (187 mg, 4.67 mmol), copper(I) iodide (18 mg, 0.095 mmol) and [1,1'-bis(diphenylphosphino)ferrocene] dichloropalladium(II) (34 mg, 0.05 mmol) in THF (1 mL) was added triethylamine (0.41 mL, 2.34 mmol) and the mixture was heated, with microwave irradiation, in a microwave reactor at 130° C. for 1 h. The resulting mixture was added water and extracted with ethyl acetate. The extracts were washed with brine, dried over anhydrous sodium sulfate, filtered and concentrated. The residue was purified by silica gel chromatography (0 to 30% ethyl acetate in petroleum ether) to afford the title compound (20 mg, 0.10 mmol, 22% yield) as a light-yellow oil. MS (ESI) m/z 197.1 $[M+1]^+$.

3-(1-Oxo-5-(((S)-1-((2-(prop-1-yn-1-yl)quinazolin-6-yl)methyl)pyrrolidin-3-yl)oxy)isoindolin-2-yl)piperidine-2,6-dione. To a solution of 2-(prop-1-yn-1-yl) quinazoline-6-carbaldehyde (20 mg, 0.10 mmol), 3-(1-oxo-5-(((S)-pyrrolidin-3-yl)oxy)isoindolin-2-yl)piperidine-2,6-dione (70 mg, 0.21 mmol) and triethylamine (40 mg, 0.40 mmol) in dichloromethane (4 mL) was added sodium triacetoxyborohydride (95 mg, 0.45 mmol). The mixture was stirred for 3 h at room temperature under nitrogen. The resulting mixture was concentrated. The residue was purified by preparative HPLC with the following conditions: column: Xselect CSH OBD column 30*150 mm 5 μm; mobile phase A: water (0.05% TFA), mobile phase B: acetonitrile; flow rate: 60 mL/min; gradient: 6 B to 26 B in 7 min; $RT_1$: 5.75. The fractions containing desired product were collected and evaporated under reduced pressure to afford the title compound (10.5 mg, 0.02 mmol, 20% yield) as a light-yellow solid. $^1$H NMR (300 MHz, DMSO-$d_6$) δ 9.59 (s, 1H), 8.30 (s, 1H), 8.19-8.11 (m, 1H), 8.04 (d, J=8.7 Hz, 1H), 7.68 (d, J=8.3 Hz, 1H), 7.18 (s, 1H), 7.08 (d, J=8.4 Hz, 1H), 5.28 (m, 1H), 5.10-4.99 (m, 1H), 4.68 (m, 2H), 4.43-4.24 (m, 2H), 3.50 (m, 4H), 2.87 (m, 1H), 2.64 (m, 2H), 2.37 (m, 2H), 2.15 (s, 3H), 2.06-1.94 (m, 1H); MS (ESI) m/z 510.3 $[M+1]^+$.

Example S56. 3-(5-(((S)-1-((2-(4-Methyltetrahydro-2H-pyran-4-yl)quinolin-6-yl)methyl)pyrrolidin-3-yl)oxy)-1-oxoisoindolin-2-yl)piperidine-2,6-dione

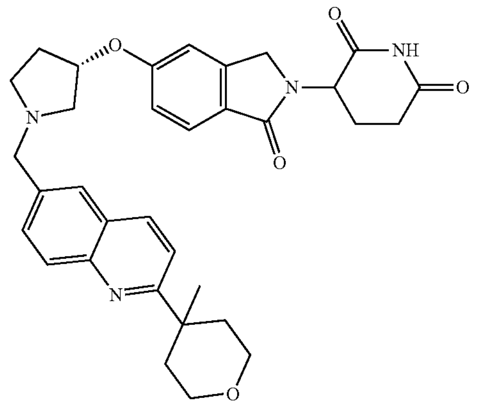 [SMILES: CC1(c2ccc3cc(CN4CC[C@H](Oc5ccc6c(c5)CN(C5CCC(=O)NC5=O)C6=O)C4)ccc3n2)CCOCC1]

6-Bromo-2-(4-methyltetrahydro-2H-pyran-4-yl)quinoline. To a stirred solution of 1-(4-methyltetrahydro-2H-pyran-4-yl)ethan-1-one (1126 mg, 7.92 mmol) and (2-amino-5-bromophenyl)methanol (800 mg, 3.96 mmol) in toluene (25 mL) was added lithium tert-butoxide (640 mg, 7.92 mmol) at room temperature. Then the mixture was stirred at 110° C. for 12 h under nitrogen. The resulting mixture was filtered and concentrated. The crude product was purified by reverse phase flash (40-80% acetonitrile+0.05% ammonium bicarbonate in water, over 20 min) to give the title compound (490 mg, 1.60 mmol, 40% yield) as a yellow solid. MS (ESI) m/z 306.1 $[M+1]^+$.

2-(4-Methyltetrahydro-2H-pyran-4-yl)-6-vinylquinoline. To a solution of 6-bromo-2-(4-methyltetrahydro-2H-pyran-4-yl)quinoline (470 mg, 1.53 mmol) in 1,4-dioxane (12.5 mL) and water (2.5 mL) were added potassium trifluoro(vinyl)borate (308 mg, 2.30 mmol), 1,1'-bis(diphenylphosphino)ferrocene-palladium(II)dichloride dichloromethane complex (125 mg, 0.15 mmol) and sodium carbonate (488 mg, 4.60 mmol) at room temperature. Then the reaction mixture was stirred at 80° C. for 2 h under nitrogen. The resulting mixture was filtered and the filter cake was washed with ethyl acetate. The filtrate was concentrated and purified by silica gel column chromatography (0 to 40% ethyl acetate in petroleum ether) to afford the title compound (290 mg, 1.14 mmol, 74% yield) as yellow oil. MS (ESI) m/z 254.2 $[M+1]^+$.

2-(4-Methyltetrahydro-2H-pyran-4-yl)quinoline-6-carbaldehyde. To a stirred solution of 2-(4-methyltetrahydro-2H-pyran-4-yl)-6-vinylquinoline (280 mg, 1.11 mmol), 4-methylmorpholine N-oxide (259 mg, 2.21 mmol) and citric acid (464 mg, 2.21 mmol) in tert-butanol (4 mL) and water (4 mL) were added potassium osmate (41 mg, 0.11 mmol) under nitrogen. The reaction mixture was stirred for 3 h at room temperature under nitrogen. Then the reaction mixture was added sodium periodate (591 mg, 2.76 mmol) and stirred for 1 h. The resulting reaction mixture was adjusted to pH~7 with saturated aqueous sodium bicarbonate solution and extracted with ethyl acetate. The organic layers were washed with brine, dried over anhydrous sodium sulfate and filtered. The filtrate was concentrated to afford the title compound (200 mg, 0.78 mmol, 70% yield) as a light-yellow oil. MS (ESI) m/z 256.1 $[M+1]^+$.

3-(5-(((S)-1-((2-(4-Methyltetrahydro-2H-pyran-4-yl)quinolin-6-yl)methyl) pyrrolidin-3-yl)oxy)-1-oxoisoindolin-2-yl)piperidine-2,6-dione. To a stirred solution of 2-(4-methyltetrahydro-2H-pyran-4-yl)quinoline-6-carbaldehyde (100 mg, 0.39 mmol), 3-(1-oxo-5-(((S)-pyrrolidin-3-yl)oxy)isoindolin-2-yl)piperidine-2,6-dione (129 mg, 0.39 mmol) and triethylamine (0.11 mL, 0.78 mmol) in dichloromethane (4 mL) was added sodium triacetoxyborohydride (332 mg, 1.57 mmol). The mixture was stirred at room temperature for 2 h under nitrogen. The resulting mixture was concentrated at room temperature under reduced pressure. The crude was purified by silica gel column chromatography (0-10% methanol in dichloromethane) and further purified by preparative HPLC with the following conditions: Column: Sun fire prep C18 column, 30*150 mm, 5 um; Mobile Phase A: water (0.1% formic acid), Mobile Phase B: acetonitrile; Flow rate: 60 mL/min; Gradient: 5 B to 20 B in 11 min, 254/220 nm; $RT_1$: 10.38. The fractions containing desired product were collected and evaporated under reduced pressure to afford the title compound (38.6 mg, 0.068 mmol, 17% yield) as a white solid. $^1H$ NMR (400 MHz, Methanol-$d_4$) δ 8.28-8.21 (m, 1H), 8.02 (d, J=8.7 Hz, 1H), 7.89 (s, 1H), 7.82-7.75 (m, 1H), 7.71 (d, J=8.4 Hz, 1H), 7.63 (d, J=8.7 Hz, 1H), 7.12-7.01 (m, 2H), 5.16-5.07 (m, 2H), 4.51-4.36 (m, 2H), 4.16-4.04 (m, 2H), 3.84-3.81 (m, 2H), 3.66-3.59 (m, 2H), 3.25-3.18 (m, 1H), 3.13 (m, 2H), 2.97-2.88 (m, 2H), 2.83-2.73 (m, 1H), 2.53-2.41 (m, 4H), 2.21-2.08 (m, 2H), 1.92-1.81 (m, 2H), 1.38 (s, 3H); MS (ESI) m/z 569.2 $[M+1]^+$.

Example S57. (3-(5-(((S)-1-((2-(((1S,4R)-4-Methoxycyclohexyl)oxy)quinolin-6-yl)methyl)pyrrolidin-3-yl)oxy)-1-oxoisoindolin-2-yl)piperidine-2,6-dione

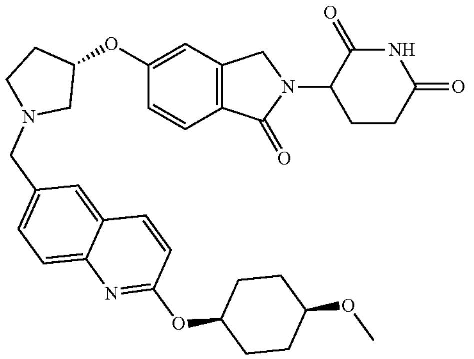 [SMILES: CO[C@H]1CC[C@@H](Oc2ccc3cc(CN4CC[C@H](Oc5ccc6c(c5)CN(C5CCC(=O)NC5=O)C6=O)C4)ccc3n2)CC1]

6-Bromoquinolin-2-ol. To a stirred solution of 6-bromo-2-chloro-quinoline (1 g, 4.12 mmol) in 4-methoxycyclohexanol (6 mL) was added potassium 2-methylpropan-2-olate (2.3 g, 20.5 mmol). The above mixture was stirred at 120° C. for 12 h under nitrogen. The reaction mixture was concentrated. The residue was purified by reverse phase flash (10-100% acetonitrile+0.05% ammonium bicarbonate in water, over 25 min) to afford the title compound (600 mg, 2.68 mmol, 65% yield) as an off-white solid. MS (ESI) m/z 223.8 $[M+1]^+$.

6-Bromo-2-((4-methoxycyclohexyl)oxy)quinoline. A solution of 6-bromoquinolin-2-ol (600 mg, 2.68 mmol), 4-methoxycyclohexanol (348 mg, 2.68 mmol), triphenylphosphine (1053 mg, 4.02 mmol) and diisopropyl azodicarboxylate (813 mg, 4.02 mmol) in toluene (10 mL)

was stirred at 100° C. for 12 h under nitrogen. Then the solution was concentrated. The residue was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (400 mg, 1.19 mmol, 44% yield) as a light-yellow oil. MS (ESI) m/z 336.1 $[M+1]^+$.

2-(((1S,4S)-4-Methoxycyclohexyl)oxy)-6-vinylquinoline. To a stirred solution of 6-bromo-2-((4-methoxycyclohexyl)oxy)quinoline (300 mg, 0.89 mmol) and potassium trifluoro(vinyl)borate (143 mg, 1.07 mmol) in 1,4-dioxane (6 mL) and water (0.5 ml) were added tetrakis(triphenylphosphine)palladium (75 mg, 0.064 mmol) and cesium carbonate (580 mg, 1.78 mmol). The above mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 25% ethyl acetate in petroleum ether). Then the residue was further purified by Anal-SFC with the following conditions: Column: CHIRALPAK AD-H SFC, 5*25 cm, 5 μm; Mobile Phase A: carbon dioxide, Mobile Phase B: ethanol: hexane=1:1 (2M ammonia in methanol); Flow rate: 150 mL/min; Gradient: 30% B; 220 nm; $RT_1$: 3.3; RT2:3.89; Injection Volume: 3 ml; Number of Runs: 10 to afford the title compound (40 mg, 0.14 mmol, 16% yield) as a light-yellow oil. MS (ESI) m/z 284.2 $[M+1]^+$.

2-(((1S,4S)-4-Methoxycyclohexyl)oxy)quinoline-6-carbaldehyde. To a stirred solution of 2-((4-methoxycyclohexyl)oxy)-6-vinylquinoline (40 mg, 0.14 mmol) in tert-butanol (4 mL) and water (4 mL) were added 4-methyl-morpholin4-oxide (33 mg, 0.28 mmol), potassium osmate (6 mg, 0.016 mmol) and citric acid (54 mg, 0.28 mmol). The above mixture was stirred at room temperature for 3 h under nitrogen. Then the mixture was added sodium periodate (90 mg, 0.42 mmol) and stirred for another 1 h. The mixture was added saturated sodium bicarbonate solution to pH~7 and extracted with ethyl acetate. The extracts were washed with brine, dried over sodium sulfate, filtered and concentrated. The residue was purified by silica gel chromatography (0 to 25% ethyl acetate in petroleum ether) to afford the title compound (30 mg, 0.10 mmol, 71% yield) as a light-yellow oil. MS (ESI) m/z 286.1 $[M+1]^+$.

(3-(5-(((S)-1-((2-(((1S,4R)-4-Methoxycyclohexyl)oxy)quinolin-6-yl)methyl)pyrrolidin-3-yl)oxy)-1-oxoisoindolin-2-yl)piperidine-2,6-dione. To a solution of 2-(((1S,4S)-4-methoxycyclohexyl)oxy)quinoline-6-carbaldehyde (30 mg, 0.10 mmol), 3-(1-oxo-5-(((S)-pyrrolidin-3-yl)oxy)isoindolin-2-yl)piperidine-2,6-dione (53 mg, 0.16 mmol) and triethylamine (35 mg, 0.35 mmol) in dichloromethane (4 mL) was added sodium triacetoxyborohydride (90 mg, 0.42 mmol). The mixture was stirred for 48 h at room temperature under nitrogen. The resulting mixture was concentrated. The residue was purified by silica gel chromatography (0 to 10% methanol in dichloromethane) and preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 5% B in 2 min, 5% B to 25% B in 10 min, 25% B; Wave Length: 254/220 nm; $RT_1$ (min): 10.38. The fractions containing desired product were collected and evaporated under reduced pressure to afford the title compound (12.2 mg, 0.02 mmol, 20% yield) as a white solid. $^1H$ NMR (400 MHz, DMSO-$d_6$) δ 10.96 (s, 1H), 8.18-8.16 (m, 1H), 7.79-7.67 (m, 2H), 7.64-7.55 (m, 2H), 7.15-6.88 (m, 3H), 5.21-5.18 (m, 1H), 5.10-4.96 (m, 2H), 4.37 (d, J=17.2 Hz, 1H), 4.24-4.20 (m, 1H), 3.81-3.70 (m, 2H), 3.30 (m, 4H), 2.99-2.85 (m, 2H), 2.75 (m, 1H), 2.71-2.67 (m, 1H), 2.63-2.55 (m, 2H), 2.42-2.29 (m, 2H), 2.15-2.05 (m, 2H), 2.04-1.91 (m, 3H), 1.90-1.77 (m, 1H), 1.61-1.47 (m, 2H), 1.40-1.37 (m, 2H); MS (ESI) m/z 599.3 [M+1]+.

Example S58. 3-(5-(((S)-1-((2-(((1R,4S)-4-Methoxycyclohexyl)oxy)quinolin-6-yl)methyl)pyrrolidin-3-yl)oxy)-1-oxoisoindolin-2-yl)piperidine-2,6-dione

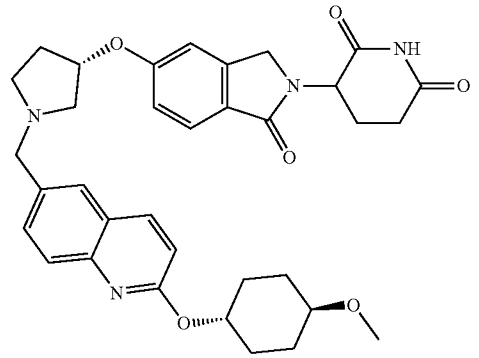 [SMILES: CO[C@H]1CC[C@H](Oc2ccc3cc(CN4CC[C@H](Oc5ccc6c(c5)CN(C5CCC(=O)NC5=O)C6=O)C4)ccc3n2)CC1]

2-(((1R,4R)-4-Methoxycyclohexyl)oxy)-6-vinylquinoline. The crude compound (200 mg) was purified by Anal-SFC with the following conditions: Column: CHIRALPAK AD-H SFC, 5*25 cm, 5 μm; Mobile Phase A: carbon dioxide, Mobile Phase B: ethanol:hexane=1:1 (2 M ammonia in methanol); Flow rate: 150 mL/min; Gradient: 30% B; 220 nm; $RT_1$: 3.3; RT2:3.89; Injection Volume: 3 ml; Number of Runs: 10. The fractions containing desired product were collected and evaporated under reduced pressure to afford the title compound (55 mg, 0.19 mmol, 27% yield) as a light-yellow oil. MS (ESI) m/z 284.2 $[M+1]^+$.

2-(((1R,4R)-4-Methoxycyclohexyl)oxy)quinoline-6-carbaldehyde. To a stirred solution of 2-(((1R,4R)-4-methoxycyclohexyl)oxy)-6-vinylquinoline (55 mg, 0.19 mmol) in tert-butanol (4 mL) and water (4 mL) were added potassium osmate (8 mg, 0.02 mmol), 4-methyl-morpholin4-oxide (45 mg, 0.39 mmol) and citric acid (83 mg, 0.39 mmol). The above mixture was stirred at room temperature for 3 h under nitrogen. Then the mixture was added sodium periodate (124 mg, 0.58 mmol) and stirred for another 1 h. The mixture was added saturated sodium bicarbonate solution to pH~7 and extracted with ethyl acetate. The extracts were washed with brine, dried over sodium sulfate, filtered and concentrated. The residue was purified by silica gel chromatography (0 to 25% ethyl acetate in petroleum ether) to afford the title compound (50 mg, 0.17 mmol, 89% yield) as a light-yellow oil. MS (ESI) m/z 286.1 $[M+1]^+$.

3-(5-(((S)-1-((2-(((1R,4S)-4-Methoxycyclohexyl)oxy)quinolin-6-yl)methyl)pyrolidin-3-yl)oxy)-1-oxoisoindolin-2-yl)piperidine-2,6-dione. To a solution of 2-(((1R,4R)-4-methoxycyclohexyl)oxy)quinoline-6-carbaldehyde (50 mg, 0.17 mmol), 3-(1-oxo-5-(((S)-pyrrolidin-3-yl)oxy)isoindolin-2-yl)piperidine-2,6-dione (60 mg, 0.18 mmol) and triethylamine (40 mg, 0.4 mmol) in dichloromethane (4 mL) was added triacetoxyborohydride (140 mg, 0.66 mmol). The mixture was stirred for 48 h at room temperature under nitrogen. The resulting mixture was concentrated. The residue was purified by silica gel chromatography (0 to 10% methanol in dichloromethane) and preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 10% B in 2 min, 10% B to 30% B in 10 min, 30% B; Wave Length: 254/220 nm; $RT_1$ (min): 9.67. The fractions containing desired product were collected and evaporated under reduced pressure to afford the title compound (24.2 mg, 0.04 mmol, 23% yield) as a white solid. $^1H$ NMR (400 MHz, DMSO-$d_6$) δ 10.96 (s, 1H), 8.22-8.15 (m, 1H), 7.77 (s, 1H), 7.72-7.58 (m, 3H), 7.10 (t, J=2.2 Hz, 1H), 7.03-6.92 (m, 2H), 5.28 (m, 1H), 5.06-5.01 (m, 2H), 4.37 (d, J=17.2 Hz, 1H), 4.24-4.20 (m, 1H), 3.82-3.70 (m, 2H), 3.30 (m, 1H), 3.25 (s, 3H), 2.98-2.85 (m, 2H), 2.80-2.66 (m, 2H), 2.61 (m, 2H), 2.36 (m, 2H), 1.97-1.95 (m, 1H), 1.91-1.64 (m, 9H); MS (ESI) m/z 599.3 $[M+1]^+$.

Example S59. 3-(5-(((S)-1-((2-(3,3-Dimethylmorpholino)quinazolin-6-yl)methyl)pyrrolidin-3-yl)oxy)-1-oxoisoindolin-2-yl)piperidine-2,6-dione

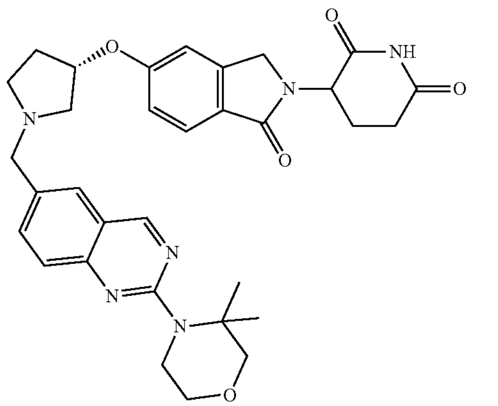 [SMILES: CC1(C)COCCN1c1ncc2cc(CN3CC[C@H](Oc4ccc5c(c4)CN(C4CCC(=O)NC4=O)C5=O)C3)ccc2n1]

4-(6-Bromoquinazolin-2-yl)-3,3-dimethylmorpholine. To a stirred solution of 6-bromo-2-chloroquinazoline (300 mg, 1.23 mmol) in NMP (12 mL) were added 3,3-dimethylmorpholine (420 mg, 3.65 mmol) and N,N-diisopropylethylamine (0.42 mL, 2.48 mmol). The above mixture was stirred at 80° C. for 12 h under nitrogen. The reaction mixture was filtered and the filtrate was purified by reverse phase flash (10-100% acetonitrile+0.05% ammonium bicarbonate in water, over 25 min) to afford the title compound (120 mg, 0.37 mmol, 30% yield) as a light-yellow oil. MS (ESI) m/z 321.9 $[M+1]^+$.

3,3-Dimethyl-4-(6-vinylquinazolin-2-yl)morpholine. To a stirred solution of 4-(6-bromoquinazolin-2-yl)-3,3-dimethyl-morpholine (120 mg, 0.37 mmol) and potassium trifluoro(vinyl)borate (60 mg, 0.45 mmol) in 1,4-dioxane (5 mL) were added tetrakis(triphenylphosphine)palladium (32 mg, 0.03 mmol) and cesium carbonate (242 mg, 0.74 mmol). The above mixture was stirred at 80° C. for 3 h under nitrogen. Then the mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (80 mg, 0.30 mmol, 81% yield) as a light-yellow oil. MS (ESI) m/z 270.1 $[M+1]^+$.

2-(3,3-Dimethylmorpholino)quinazoline-6-carbaldehyde. To a stirred solution of 3,3-dimethyl-4-(6-vinylquinazolin-2-yl)morpholine (80 mg, 0.30 mmol) in tert-butanol (4 mL) and water (4 mL) were added potassium osmate (11 mg, 0.03 mmol), 4-Methylmorpholine N-oxide (70 mg, 0.59 mmol) and citric acid (127 mg, 0.59 mmol). The above mixture was stirred at room temperature for 3 h under nitrogen. Then the mixture was added sodium periodate (190 mg, 0.89 mmol) and stirred for another 1 h. The mixture was added saturated sodium bicarbonate solution to pH~7 and extracted with ethyl acetate. The extracts were washed with brine, dried over sodium sulfate, filtered and concentrated. The residue was purified by silica gel chromatography (0 to 40% ethyl acetate in petroleum ether) to afford the title compound (40 mg, 0.15 mmol, 50% yield) as a light-yellow oil. MS (ESI) m/z 272.2 $[M+1]^+$.

3-(5-(((S)-1-((2-(3,3-Dimethylmorpholino)quinazolin-6-yl)methyl)pyrrolidin-3-yl)oxy)-1-oxoisoindolin-2-yl)piperidine-2,6-dione. To a solution of 2-(3,3-dimethylmorpholino)quinazoline-6-carbaldehyde (40 mg, 0.15 mmol), 3-(1-oxo-5-(((S)-pyrrolidin-3-yl)oxy)isoindolin-2-yl)piperidine-2,6-dione (80 mg, 0.24 mmol) and triethylamine (50 mg, 0.50 mmol) in dichloromethane (4 mL) was added sodium triacetoxyborohydride (130 mg, 0.61 mmol). The mixture was stirred for 12 h at room temperature under nitrogen. The resulting mixture was concentrated. The residue was purified by silica gel chromatography (0 to 10% methanol in dichloromethane) and preparative HPLC with the following conditions: Column: Sunfire prep C18 column, 30*150, 5 μm; Mobile Phase A: water (0.1% formic acid), Mobile Phase B: acetonitrile; Flow rate: 60 mL/min; Gradient: 5 B to 35 B in 7 min, 254/220 nm; $RT_1$: 6.32. The fractions containing desired product were collected and evaporated under reduced pressure to afford the title compound (25.4 mg, 0.043 mmol, 29% yield) as an off-white solid. $^1H$ NMR (300 MHz, Methanol-$d_4$) δ 9.12 (t, J=0.8 Hz, 1H), 7.85-7.78 (m, 2H), 7.72 (d, J=8.4 Hz, 1H), 7.63 (d, J=9.2 Hz, 1H), 7.12-7.03 (m, 2H), 5.12-5.09 (m, 2H), 4.44 (d, J=3.5 Hz, 2H), 4.09-3.90 (m, 6H), 3.53 (s, 2H), 3.24-3.22 (m, 1H), 3.14 (m, 2H), 2.97-2.85 (m, 2H), 2.83-2.74 (m, 1H), 2.48-2.44 (m, 2H), 2.13-2.10 (m, 2H), 1.61 (s, 6H); MS (ESI) m/z 585.4 $[M+1]^+$.

Example S60. 3-(5-(((S)-1-((2-(3,3-Dimethylmorpholino)quinolin-6-yl)methyl)pyrrolidin-3-yl)oxy)-1-oxoisoindolin-2-yl)piperidine-2,6-dione

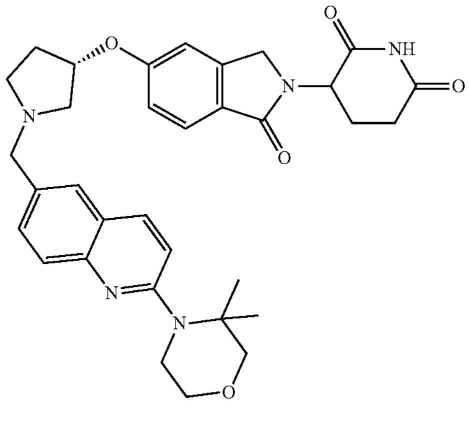 [SMILES: CC1(C)COCCN1c1ccc2cc(CN3CC[C@H](Oc4ccc5c(c4)CN(C4CCC(=O)NC4=O)C5=O)C3)ccc2n1]

Methyl 2-(3,3-dimethylmorpholino)quinoline-6-carboxylate. To a stirred solution of methyl 2-chloroquinoline-6-carboxylate (100 mg, 0.45 mmol) in toluene (5 mL) were added 3,3-dimethylmorpholine (80 mg, 0.69 mmol), bis(di-tert-butyl)-4-dimethylaminophenylphosphine (11 mg, 0.04 mmol), methanesulfonato{[4-(N,N-dimethylamino)phenyl] di-t-butylphosphino}(2'-Amino-1,1'-biphenyl-2-yl)palladium(II) (43 mg, 0.067 mmol) and cesium carbonate (440 mg, 1.35 mmol) at room temperature. Then the reaction mixture was stirred 12 h at 100° C. under nitrogen. The resulting mixture was filtered and the filtrate was concentrated. The crude product was purified by silica gel chromatography (0 to 50% ethyl acetate in petroleum ether) to give the title compound (99 mg, 0.33 mmol, 73% yield) as a yellow oil. MS (ESI) m/z 301.0 $[M+1]^+$.

(2-(3,3-Dimethylmorpholino)quinolin-6-yl)methanol. To a stirred solution of methyl 2-(3,3-dimethylmorpholin-4-yl) quinoline-6-carboxylate (90 mg, 0.30 mmol) in THF (5 mL) was added lithium aluminum hydride (2.5 M in THF, 0.24 mL, 0.47 mmol) dropwise at 0° C. under nitrogen. Then the reaction mixture was warmed and stirred for 2 h at room temperature. The resulting mixture was quenched with sodium hydroxide (2 M in water, 1 mL, 2 mmol) at 0° C., then stirred for 30 min at this temperature and filtered. The filter cake was washed with 10 mL THF and 5 mL methanol. The filtrate combined were concentrated to afford the title compound (80 mg, 0.29 mmol, 97% yield) as a yellow solid. MS (ESI) m/z 273.2 $[M+1]^+$.

2-(3,3-Dimethylmorpholino)quinoline-6-carbaldehyde. To a stirred solution of [2-(3,3-dimethylmorpholin-4-yl)-6-quinolyl]methanol (80 mg, 0.29 mmol) in dichloromethane (5 mL) was added Dess-Martin periodinane (160 mg, 0.38 mmol) at 0° C. Then the reaction mixture was stirred for 2 h at room temperature under nitrogen. The resulting solution was purified by silica gel chromatography (0 to 40% ethyl acetate in petroleum ether). The pure fractions were evaporated to afford the title compound (55 mg, 0.20 mmol, 69% yield) as a yellow oil. MS (ESI) m/z 271.1 $[M+1]^+$.

3-(5-(((S)-1-((2-(3,3-Dimethylmorpholino)quinolin-6-yl) methyl)pyrrolidin-3-yl)oxy)-1-oxoisoindolin-2-yl)piperidine-2,6-dione. To a stirred solution of 2-(3,3-dimethylmorpholin-4-yl)quinoline-6-carbaldehyde (50 mg, 0.18 mmol), 3-[1-oxo-5-[(3S)-pyrrolidin-3-yl]oxy-isoindolin-2-yl]piperidine-2,6-dione; 2,2,2-triflu-oroacetic acid (70 mg, 0.16 mmol), triethylamine (0.05 mL, 0.33 mmol) in dichloromethane (5 mL) pre-stirred for 15 min was added sodium triacetoxyborohydride (154 mg, 0.73 mmol) at 0° C. and the solution was stirred at room temperature for 4 h under nitrogen. The resulting solution was purified silica gel chromatography (0 to 15% methanol in dichloromethane). The pure fractions were evaporated and purified further by preparative HPLC with the following conditions: Column: Sunfire prep C18 column, 30*150, 5 μm; mobile phase A: water (0.1% formic acid), mobile phase B: acetonitrile; flow rate: 60 mL/min; gradient: 5 B to 35 B in 7 min, 254/220 nm; $rt_1$:4.82. The fractions containing desired product were collected and evaporated under reduced pressure to afford the title compound (70 mg, 0.12 mmol, 67% yield) as a yellow oil. $^1H$ NMR (300 MHz, DMSO-$d_6$) δ 10.96 (s, 1H), 8.03 (dd, J=9.1, 1.1 Hz, 1H), 7.70-7.51 (m, 4H), 7.26 (d, J=9.1 Hz, 1H), 7.11 (t, J=1.9 Hz, 1H), 7.01 (m, 1H), 5.12-4.94 (m, 2H), 4.38 (d, J=17.2 Hz, 1H), 4.25 (m, 1H), 3.86-3.67 (m, 4H), 3.50 (t, J=5.0 Hz, 2H), 3.40 (s, 2H), 2.91 (m, 2H), 2.69 (m, 1H), 2.50 (m, 1H), 2.35-2.27 (m, 2H), 2.04-1.92 (m, 1H), 1.84 (m, 1H), 1.48 (s, 6H). MS (ESI) m/z 584.3 $[M+1]^+$.

Example S61. 3-(5-(((S)-1-((2-((S)-3,3-Dimethyltetrahydro-2H-pyran-4-yl)quinolin-6-yl)methyl)pyrrolidin-3-yl)oxy)-1-oxoisoindolin-2-yl)piperidine-2,6-dione

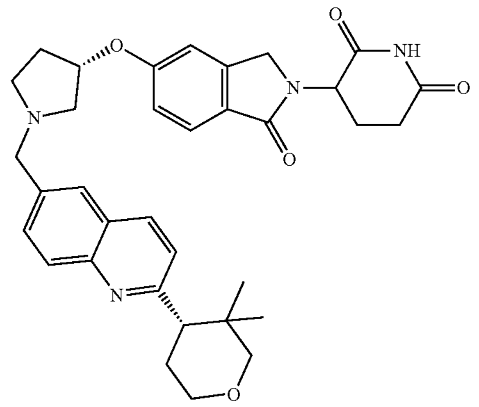 [SMILES: CC1(C)COCC[C@@H]1c1ccc2cc(CN3CC[C@H](Oc4ccc5c(c4)CN(C4CCC(=O)NC4=O)C5=O)C3)ccc2n1]

N-methoxy-N,3,3-trimethyltetrahydro-2H-pyran-4-carboxamide. To a stirred solution of 3,3-dimethyltetrahydropyran-4-carboxylic acid (1.0 g, 6.32 mmol) in dichloromethane (20 mL) were added N-methoxymethanamine; hydrochloride (1.1 g, 11.3 mmol) and CDI (1.1 g, 6.78 mmol) at room temperature. Then the mixture was stirred for 12 h at room temperature under nitrogen. The resulting mixture was added water and extracted with dichloromethane. The extracts were dried over anhydrous sodium sulfate, filtered and concentrated. The residue was purified with reverse phase flash (20-70% acetonitrile+0.05% ammonium bicarbonate in water, over 25 min) to give the title compound (350 mg, 1.73 mmol, 27% yield) as a yellow solid. MS (ESI) m/z 202.2 $[M+1]^+$.

1-(3,3-Dimethyltetrahydro-2H-pyran-4-yl)ethan-1-one. To a stirred solution of N-methoxy-N,3,3-trimethyl-tetrahydropyran-4-carboxamide (600 mg, 2.96 mmol) in THF (20 mL) was added methylmagnesium bromide (1.5 M in diethyl ether, 2 mL, 3 mmol) dropwise at 0° C. and the mixture was stirred at room temperature for 2 h under nitrogen. The reaction mixture was added saturated ammonium chloride and extracted with ethyl acetate. The extracts were dried over anhydrous sodium sulfate, filtered and concentrated to give the title compound (400 mg, 2.55 mmol, 86% yield) as a yellow oil. MS (ESI) m/z 157.1 $[M+1]^+$.

6-Bromo-2-(3,3-dimethyltetrahydro-2H-pyran-4-yl)quinoline. To a stirred solution of 1-(3,3-dimethyltetrahydropyran-4-yl)ethanone (400 mg, 2.55 mmol) in toluene (10 mL) was added (2-amino-5-bromo-phenyl)methanol (773 mg, 3.83 mmol), lithium tert-butoxide (616 mg, 7.7 mmol) at room temperature. Then the reaction mixture was stirred for 12 h at 100° C. under nitrogen. The mixture was filtered and the filtrate was concentrated. The residue was purified with reverse phase flash (30-80% acetonitrile+0.05% ammonium bicarbonate in water, over 20 min) to afford the title compound (200 mg, 0.62 mmol, 24% yield) as a yellow oil. MS (ESI) m/z 320.1 $[M+1]^+$.

2-(3,3-Dimethyltetrahydro-2H-pyran-4-yl)-6-vinylquinoline. To a solution of 6-bromo-2-(3,3-dimethyltetrahydropyran-4-yl)quinoline (353 mg, 1.10 mmol) in 1,4-dioxane (10 mL) and water (2 mL) were added potassium trifluoro(vinyl) borate (300 mg, 2.24 mmol), dichlorobis(triphenylphosphine) palladium(II) dichloromethane adduct (182 mg, 0.24 mmol) and sodium carbonate (116.9 mg, 1.13 mmol) at room temperature. Then the reaction mixture was stirred at 80° C. for 4 h under nitrogen. The resulting mixture was diluted with water and extracted with ethyl acetate. The extracts were washed with brine, dried over anhydrous sodium sulfate, filtered and concentrated. The residue was purified by silica gel chromatography (0 to 30% ethyl acetate in petroleum ether) to give the title compound (160 mg, 0.60 mmol, 54% yield) as light-yellow oil. MS (ESI) m/z 268.1 $[M+1]^+$.

(S)-2-(3,3-Dimethyltetrahydro-2H-pyran-4-yl)-6-vinylquinoline. The 2-(3,3-dimethyltetrahydro-2H-pyran-4-yl)-6-vinylquinoline (160 mg, 0.60 mmol) was purified by preparative SFC with the following conditions: Column: CHIRALPAK IH, 2*25 cm, 5 μm; mobile phase A: hexane (0.5% 2M ammonia-methanol)-HPLC, mobile phase B: ethanol—HPLC; flow rate: 20 mL/min; gradient: 3% B to 3% B in 7.5 min; wave length: 220/254 nm; room temperature$_1$(min): 4.76; room temperature$_2$(min): 5.80; sample solvent: ethanol—HPLC; injection volume: 0.5 mL; number of runs: 13. The fractions containing desired product were collected and evaporated under reduced pressure to afford the title compound (31 mg, 0.12 mmol, 20% yield). MS (ESI) m/z 268.1 $[M+1]^+$.

(S)-2-(3,3-Dimethyltetrahydro-2H-pyran-4-yl)quinoline-6-carbaldehyde. To a stirred solution of 2-[(4S)-3,3-dimethyltetrahydropyran-4-yl]-6-vinyl-quinoline (31 mg, 0.12 mmol), 4-methylmorpholine N-oxide (26.3 mg, 0.22 mmol) and citric acid (43 mg, 0.22 mmol) in water (2 mL) and tert-butanol (2 mL) was added potassium osmate (4 mg, 0.010 mmol). The reaction mixture was stirred at room temperature for 3 h under nitrogen. Then sodium periodate (75 mg, 0.35 mmol) was added into the above mixture. The resulting mixture was stirred for 1 h at room temperature under nitrogen. The mixture was added saturated sodium bicarbonate to pH~7 and extracted with ethyl acetate. The extracts were dried over anhydrous sodium sulfate, filtered and concentrated. The residue was purified by silica gel chromatography (0 to 50% ethyl acetate in petroleum ether) to give the title compound (30 mg, 0.11 mmol, 92% yield) as a yellow oil. MS (ESI) m/z 270.2 $[M+1]^+$.

3-(5-(((S)-1-((2-((S)-3,3-Dimethyltetrahydro-2H-pyran-4-yl)quinolin-6-yl) methyl)pyrrolidin-3-yl)oxy)-1-oxoisoindolin-2-yl)piperidine-2,6-dione. To a stirred solution of 2-[(4S)-3,3-dimethyltetrahydropyran-4-yl]quinoline-6-carbaldehyde (25 mg, 0.092 mmol), 3-[1-oxo-5-[(3S)-pyrrolidin-3-yl]oxy-isoindolin-2-yl] piperidine-2,6-dione; 2,2,2-trifluoroacetic acid (56 mg 0.13 mmol), triethylamine (0.03 mL, 0.22 mmol) in dichloromethane (5 mL) pre-stirred for 15 min was added sodium triacetoxyborohydride (94 mg, 0.44 mmol) at 0° C. and the solution was stirred at room temperature for 4 h under nitrogen. The resulting solution was purified silica gel chromatography (0 to 5% methanol in dichloromethane). The pure fractions were evaporated and purified further by preparative HPLC with the following conditions: column: Sunfire prep C18 column, 30*150 mm, 5 μm; mobile phase A: water (0.1% TFA), mobile phase B: acetonitrile; flow rate: 60 mL/min; gradient: 2% B to 27% B in 7 min, 27% B; wave length: 254/220 nm; room temperature$_1$(min): 6.98. The fractions containing desired product were collected and evaporated under reduced pressure to afford the title compound (45.3 mg, 0.078 mmol, 85% yield) as a white solid. $^1$H NMR (400 MHz, DMSO-$d_6$) δ 8.44 (d, J=8.6 Hz, 1H), 8.21-8.07 (m, 2H), 7.93 (m, 1H), 7.64 (m, 2H), 7.18 (s, 1H), 7.08 (d, J=8.4 Hz, 1H), 5.28 (s, 1H), 5.04 (m, 1H), 4.65 (s, 2H), 4.40 (m, 1H), 4.27 (d, J=17.4 Hz, 1H), 4.05 (m, 1H), 3.60-3.40 (m, 7H), 3.25 (m, 1H), 3.08 (m, 1H), 2.95-2.82 (m, 1H), 2.66-2.57 (m, 1H), 2.39 (m, 2H), 2.16 (m, 1H), 2.03-1.95 (m, 1H), 1.57-1.49 (m, 1H), 0.90 (s, 3H), 0.74 (s, 3H); MS (ESI) m/z 583.2 $[M+1]^+$.

Example S62. 3-(5-(((S)-1-((2-Methoxyquinazolin-6-yl)methyl)pyrrolidin-3-yl)oxy)-1-oxoisoindolin-2-yl)piperidine-2,6-dione

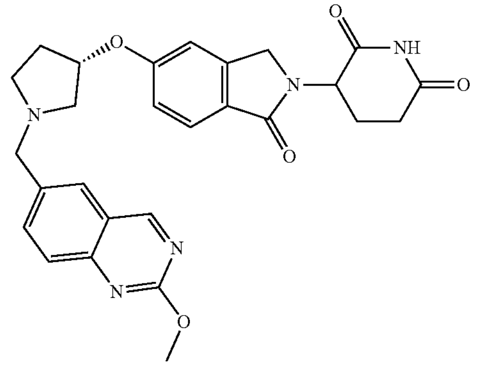 [SMILES: COc1ncc2cc(CN3CC[C@H](Oc4ccc5c(c4)CN(C4CCC(=O)NC4=O)C5=O)C3)ccc2n1]

6-Bromo-2-methoxyquinazoline. To a stirred solution of 6-bromo-2-chloroquinazoline (500 mg, 2.05 mmol) in methanol (6 mL) was added sodium methoxide (30% in methanol, 2 mL). The above mixture was stirred at 70° C. for 12 h under nitrogen. The resulting mixture was added water and extracted with ethyl acetate. The extracts were washed with brine, dried over anhydrous sodium sulfate, filtered and concentrated to afford the title compound (400 mg, 1.67 mmol, 81% yield) as a light-yellow solid. MS (ESI) m/z 238.9 $[M+1]^+$.

2-Methoxy-6-vinylquinazoline. To a stirred solution of 6-bromo-2-methoxyquinazoline (400 mg, 1.67 mmol) and potassium trifluoro(vinyl)borate (269 mg, 2.01 mmol) in 1,4-dioxane (5 mL) and water (0.5 mL) were added tetrakis (triphenylphosphine)palladium (141 mg, 0.12 mmol) and cesium carbonate (1087 mg, 3.35 mmol). The above mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (180 mg, 0.96 mmol, 57% yield) as a light-yellow oil. MS (ESI) m/z 187.0 $[M+1]^+$.

2-Methoxyquinazoline-6-carbaldehyde. To a stirred solution of 2-methoxy-6-vinyl-quinazoline (100 mg, 0.54 mmol)

in tert-butanol (4 mL) and water (4 mL) were added potassium osmate (20 mg, 0.05 mmol), 4-methylmorpholine N-oxide (126 mg, 1.07 mmol) and citric acid (230 mg, 1.20 mmol). The above mixture was stirred at room temperature for 3 h under nitrogen. Then the mixture was added sodium periodate (345 mg, 1.61 mmol) and stirred for another 1 h. The reaction mixture was concentrated and the residue was purified by reverse phase flash (10-100% acetonitrile+0.05% ammonium bicarbonate in water, over 25 min) to afford the title compound (50 mg, 0.26 mmol, 48% yield) as an off-white solid. MS (ESI) m/z 189.2 $[M+1]^+$.

3-(5-(((S)-1-((2-Methoxyquinazolin-6-yl)methyl)pyrrolidin-3-yl)oxy)-1-oxoisoindolin-2-yl)piperidine-2,6-dione. To a solution of 2-methoxyquinazoline-6-carbaldehyde (50 mg, 0.26 mmol), 3-(1-oxo-5-(((S)-pyrrolidin-3-yl)oxy)isoindolin-2-yl)piperidine-2,6-dione (183 mg, 0.56 mmol) and triethylamine (104 mg, 1.03 mmol) in dichloromethane (4 mL) was added triacetoxyborohydride (248 mg, 1.17 mmol). The mixture was stirred for 12 h at room temperature under nitrogen. The resulting mixture was concentrated. The residue was purified by silica gel chromatography (0 to 10% methanol in dichloromethane) and preparative HPLC with the following conditions: Column: Sunfire prep C18 column, 30*150 mm, 5 um; Mobile Phase A: water (0.1% formic acid), Mobile Phase B: acetonitrile; Flow rate: 60 mL/min; Gradient: 5 B to 35 B in 7 min; $RT_1$: 6.32. The fractions containing desired product were collected and evaporated under reduced pressure to afford the title compound (30.5 mg, 0.061 mmol, 22% yield) as a white solid. $^1H$ NMR (400 MHz, Methanol-$d_4$) δ 9.33 (d, J=0.7 Hz, 1H), 8.06-7.97 (m, 2H), 7.84 (d, J=8.6 Hz, 1H), 7.71 (d, J=8.4 Hz, 1H), 7.10-7.03 (m, 2H), 5.16-5.08 (m, 2H), 4.49-4.38 (m, 2H), 4.11 (m, 5H), 3.23-3.20 (m, 1H), 3.18-3.08 (m, 2H), 2.90-2.88 (m, 2H), 2.79-2.75 (m, 1H), 2.56-2.41 (m, 2H), 2.21-2.07 (m, 2H); MS (ESI) m/z 502.2 $[M+1]^+$.

Example S63. 3-(5-(((S)-1-((2-((R)-3,3-Dimethyltetrahydro-2H-pyran-4-yl)quinolin-6-yl)methyl)pyrrolidin-3-yl)oxy)-1-oxoisoindolin-2-yl)piperidine-2,6-dione

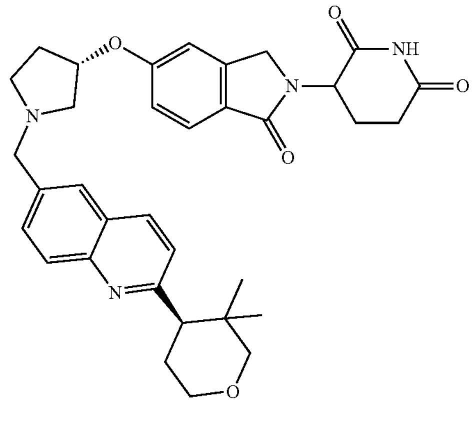 [SMILES: CC1(C)COCC[C@H]1c1ccc2cc(CN3CC[C@H](Oc4ccc5c(c4)CN(C4CCC(=O)NC4=O)C5=O)C3)ccc2n1]

(R)-2-(3,3-Dimethyltetrahydro-2H-pyran-4-yl)-6-vinylquinoline. The 2-(3,3-dimethyltetrahydro-2H-pyran-4-yl)-6-vinylquinoline (160 mg, 0.60 mmol) was purified by preparative SFC with the following conditions: Column: CHIRALPAK IH, 2*25 cm, 5 μm; mobile phase A: hexane (0.5% 2M ammonia-methanol)-HPLC, mobile phase B: ethanol—HPLC; flow rate: 20 mL/min; gradient: 3% B to 3% B in 7.5 min; wave length: 220/254 nm; room temperature$_1$ (min): 4.76; room temperature$_2$ (min): 5.80; sample solvent: ethanol-HPLC; injection volume: 0.5 mL; number of runs: 13. The fractions containing desired product were collected and evaporated under reduced pressure to afford the title compound (30 mg, 0.11 mmol, 19% yield). MS (ESI) m/z 268.1 $[M+1]^+$.

(R)-2-(3,3-Dimethyltetrahydro-2H-pyran-4-yl)quinoline-6-carbaldehyde. To a stirred solution of (R)-2-(3,3-dimethyltetrahydro-2H-pyran-4-yl)-6-vinyl quinoline (30 mg, 0.11 mmol), 4-methylmorpholine N-oxide (26.3 mg, 0.22 mmol) and citric acid (43 mg, 0.22 mmol) in water (2 mL) and tert-butanol (2 mL) was added potassium osmate (4 mg, 0.01 mmol). The reaction mixture was stirred at room temperature for 3 h under nitrogen. Then sodium periodate (75 mg, 0.35 mmol) was added into the above mixture. The resulting mixture was stirred for 1 h at room temperature under nitrogen. The mixture was added saturated sodium bicarbonate to pH~7 and extracted with ethyl acetate. The extracts were dried over anhydrous sodium sulfate, filtered and concentrated. The residue was purified by silica gel chromatography (0 to 50% ethyl acetate in petroleum ether) to give the title compound (28 mg, 0.10 mmol, 93% yield) as a yellow oil. MS (ESI) m/z 270.2 $[M+1]^+$.

3-(5-(((S)-1-((2-((R)-3,3-Dimethyltetrahydro-2H-pyran-4-yl)quinolin-6-yl) methyl)pyrrolidin-3-yl)oxy)-1-oxoisoindolin-2-yl)piperidine-2,6-dione. To a stirred solution of (R)-2-(3,3-dimethyltetrahydro-2H-pyran-4-yl)quinoline-6-carbaldehyde (25 mg, 0.090 mmol), 3-[1-oxo-5-[(3S)-pyrrolidin-3-yl]oxy-isoindolin-2-yl] piperidine-2,6-dione; 2,2,2-trifluoroacetic acid (56 mg, 0.13 mmol), triethylamine (20 mg, 0.2 mmol) in dichloromethane (5 mL) pre-stirred for 15 min was added sodium triacetoxyborohydride (94 mg, 0.44 mmol) at 0° C. and the solution was stirred at room temperature for 4 h under nitrogen. The resulting solution was purified silica gel chromatography (0 to 5% methanol in dichloromethane). The pure fractions were evaporated and purified further by preparative HPLC with the following conditions: column: sun fire prep C18 column, 30*150 mm, 5 μm; mobile phase A: water (0.1% TFA), mobile phase B: acetonitrile; flow rate: 60 mL/min; gradient: 2% B to 27% B in 7 min, wave length: 254/220 nm; room temperature$_1$ (min): 6.98. The fractions containing desired product were collected and evaporated under reduced pressure to afford the title compound (34.9 mg, 0.060 mmol, 67% yield) as a white solid. $^1H$ NMR (400 MHz, DMSO-$d_6$) δ 8.42 (d, J=8.5 Hz, 1H), 8.188.07 (m, 2H), 7.92 (m, 1H), 7.67 (d, J=8.4 Hz, 1H), 7.59 (d, J=8.6 Hz, 1H), 7.19 (s, 1H), 7.08 (d, J=8.2 Hz, 1H), 5.28 (s, 1H), 5.04 (m, 1H), 4.65 (s, 2H), 4.40 (m, 1H), 4.28 (d, J=17.4 Hz, 1H), 4.08-4.01 (m, 1H), 3.60-3.40 (m, 7H), 3.25 (d, J=11.1 Hz, 1H), 3.07 (m, 1H), 2.88 (m, 1H), 2.61 (m, 1H), 2.40 (m, 2H), 2.16 (m, 1H), 2.04-1.94 (m, 1H), 1.55-1.50 (m, 1H), 0.90 (s, 3H), 0.74 (s, 3H); MS (ESI) m/z 583.3 [M+1]+.

Example S64. 3-(5-(((S)-1-((2-((1R,3R)-3-Methoxy-cyclopentyl)quinolin-6-yl)methyl)pyrrolidin-3-yl)oxy)-1-oxoisoindolin-2-yl)piperidine-2,6-dione

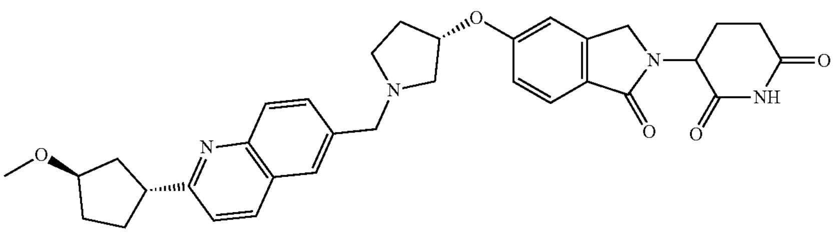 [SMILES: CO[C@@H]1CC[C@@H](c2ccc3cc(CN4CC[C@H](Oc5ccc6c(c5)CN(C5CCC(=O)NC5=O)C6=O)C4)ccc3n2)C1]

(2-((1R,3R)-3-Methoxycyclopentyl)quinolin-6-yl)methanol. The product of (2-(3-methoxycyclopentyl)quinolin-6-yl)methanol (460 mg, 1.89 mmol) was separated by preparative Chiral-HPLC (Column: CHIRALPAK IH, 2*25 cm, 5 μm; Mobile Phase A: Hex (0.5% 2M ammonia-methanol)—HPLC, Mobile Phase B: EtOH—HPLC; Flow rate: 20 mL/min; Gradient: 20% B to 20% B in 14 min; Wave Length: 220/254 nm; RT1 (min): 5.921; RT2 (min): 10.26; Sample Solvent: EtOH—HPLC; Injection Volume: 0.5 mL; Number of Runs: 5) to afford the title compound (the 3 rd peak, 60 mg, 0.23 mmol, 13% yield). MS (ESI) m/z 258.2 $[M+1]^+$.

2-((1R,3R)-3-Methoxycyclopentyl)quinoline-6-carbaldehyde. To a stirred solution of (2-((1R,3R)-3-methoxycyclopentyl)quinolin-6-yl)methanol (60 mg, 0.23 mmol) in dichloromethane (3 mL) was added manganese dioxide (203 mg, 2.33 mmol) at room temperature. Then the reaction mixture was stirred for 12 h at 50° C. under nitrogen. The resulting mixture was filtered and concentrated under reduced pressure to afford the title compound (60 mg, 0.23 mmol, 100% yield) as a light-yellow oil. MS (ESI) m/z 256.1 $[M+1]^+$.

3-(5-(((S)-1-((2-((1R,3S)-3-Methoxycyclopentyl)quinolin-6-yl)methyl)pyrolidin-3-yl)oxy)-1-oxoisoindolin-2-yl)piperidine-2,6-dione. To a stirred solution of 2-((1R,3R)-3-methoxycyclopentyl)quinoline-6-carbaldehyde (60 mg, 0.23 mmol), 3-(1-oxo-5-(((S)-pyrrolidin-3-yl)oxy)isoindolin-2-yl)piperidine-2,6-dione; 2,2,2-trif-luoroacetic acid (100 mg, 0.23 mmol) and triethylamine (47 mg, 0.47 mmol) in dichloromethane (4 mL) was added sodium triacetoxyborohydride (192 mg, 0.91 mmol). The mixture was stirred at room temperature for 2 h under nitrogen. The resulting solution was concentrated. The residue was purified by silica gel column chromatography (0-10% methanol in dichloromethane) and further by preparative HPLC with the following conditions: Column: Sun fire prep C18 column, 30*150 mm, 5 μm; Mobile Phase A: water (0.1% formic acid), Mobile Phase B: acetonitrile; Flow rate: 60 mL/min; Gradient: 5% B to 30% B in 7 min, 30% B; Wave Length: 254/220 nm; $RT_1$ (min): 5.5. The fractions containing desired product were collected and evaporated under reduced pressure to afford the title compound (32.6 mg, 0.057 mmol, 25% yield) as a white solid. $^1H$ NMR (400 MHz, Methanol-$d_4$) δ 8.34-8.22 (m, 1H), 8.03 (d, J=8.7 Hz, 1H), 7.93 (s, 1H), 7.82 (dd, J=8.6, 1.9 Hz, 1H), 7.72 (dd, J=8.4, 1.2 Hz, 1H), 7.52 (d, J=8.5 Hz, 1H), 7.13-7.02 (m, 2H), 5.13 (dd, J=13.6, 5.4 Hz, 2H), 4.52-4.37 (m, 2H), 4.21-4.15 (m, 2H), 4.02 (m, 1H), 3.63-3.45 (m, 1H), 3.36 (s, 3H), 3.31-3.30 (m, 1H), 3.22 (m, 2H), 3.12-3.01 (m, 1H), 2.99-2.88 (m, 1H), 2.83-2.72 (m, 1H), 2.58-2.41 (m, 3H), 2.26-2.13 (m, 3H), 2.06-1.88 (m, 4H); MS (ESI) m/z 569.2 $[M+1]^+$.

Example S65. 3-(5-(((S)-1-((2-((1S,3S)-3-Methoxy-cyclopentyl)quinolin-6-yl)methyl)pyrrolidin-3-yl)oxy)-1-oxoisoindolin-2-yl)piperidine-2,6-dione

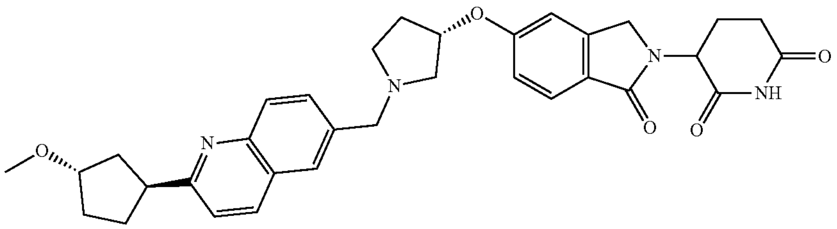 [SMILES: CO[C@H]1CC[C@H](c2ccc3cc(CN4CC[C@H](Oc5ccc6c(c5)CN(C5CCC(=O)NC5=O)C6=O)C4)ccc3n2)C1]

(2-((1S,3S)-3-Methoxycyclopentyl)quinolin-6-yl)methanol. The product of (2-(3-methoxycyclopentyl)quinolin-6-yl)methanol (460 mg, 1.79 mmol) was separated by Preparative Chiral-HPLC (Column: CHIRALPAK IH, 2*25 cm, 5 μm; Mobile Phase A: Hex (0.5% 2M ammonia-methanol)-HPLC, Mobile Phase B: EtOH—HPLC; Flow rate: 20 mL/min; Gradient: 20% B to 20% B in 14 min; Wave Length: 220/254 nm; RT1 (min): 5.921; RT2 (min): 10.26; Sample Solvent: EtOH—HPLC; Injection Volume: 0.5 mL; Number Of Runs: 5) to obtain the title compound (the 4 th peak, 40 mg, 0.15 mmol, 8% yield). MS (ESI) m/z 258.2 $[M+1]^+$.

2-((1S,3S)-3-Methoxycyclopentyl)quinoline-6-carbaldehyde. To a stirred solution of (2-((1S,3S)-3-methoxycyclopentyl)quinolin-6-yl)methanol (40 mg, 0.15 mmol) in dichloromethane (3 mL) was added manganese dioxide (135 mg, 1.55 mmol) at room temperature. Then the reaction mixture was stirred for 12 h at 50° C. under nitrogen. The resulting mixture was diluted with dichloromethane, filtered and concentrated under reduced pressure to afford the title compound (40 mg, 0.15 mmol, 100% yield) as a light-yellow oil. MS (ESI) m/z 256.1 $[M+1]^+$.

3-(5-(((S)-1-((2-((1R,3S)-3-Methoxycyclopentyl)quinolin-6-yl)methyl)pyrolidin-3-yl)oxy)-1-oxoisoindolin-2-yl) piperidine-2,6-dione. To a stirred solution of 2-((1S,3S)-3-methoxycyclopentyl)quinoline-6-carbaldehyde (40 mg, 0.15 mmol), 3-(1-oxo-5-(((S)-pyrrolidin-3-yl)oxy)isoindolin-2-yl)piperidine-2,6-dione; 2,2,2-trifluoroacetic acid (70 mg, 0.16 mmol) and triethylamine (32 mg, 0.32 mmol) in dichloromethane (4 mL) was added sodium triacetoxyborohydride (134 mg, 0.63 mmol). The mixture was stirred at room temperature for 2 h under nitrogen. The resulting solution was concentrated. The residue was purified by silica gel column chromatography (0-10% methanol in dichloromethane) and further by preparative HPLC with the following conditions: Column: Sun fire prep C18 column, 30*150 mm, 5 μm; Mobile Phase A: water (0.1% formic acid), Mobile Phase B: acetonitrile; Flow rate: 60 mL/min; Gradient: 5% B to 30% B in 7 min, 30% B; Wave Length: 254/220 nm; RT1 (min): 5.5. The fractions containing desired product were collected and evaporated under reduced pressure to afford the title compound (29.1 mg, 0.05 mmol, 32% yield) as a white solid. $^1H$ NMR (400 MHz, Methanol-$d_4$) δ 8.34-8.22 (m, 1H), 8.03 (d, J=8.7 Hz, 1H), 7.93 (s, 1H), 7.82 (dd, J=8.6, 1.9 Hz, 1H), 7.72 (dd, J=8.4, 1.2 Hz, 1H), 7.62 (d, J=8.5 Hz, 1H), 7.13-7.02 (m, 2H), 5.21-5.13 (m, 2H), 4.52-4.39 (m, 2H), 4.23-4.17 (m, 2H), 4.04 (m, 1H), 3.51-3.42 (m, 1H), 3.36 (s, 3H), 3.31-3.30 (m, 1H), 3.22 (m, 2H), 3.12-3.01 (m, 1H), 2.99-2.88 (m, 1H), 2.83-2.75 (m, 1H), 2.58-2.41 (m, 3H), 2.26-2.13 (m, 3H), 2.06-1.82 (m, 4H); MS (ESI) m/z 569.2$[M+1]^+$.

Example S66. 3-(5-(((S)-1-((2-((1s,4R)-4-Hydroxycyclohexyl) quinolin-6-yl) methyl)pyrrolidin-3-yl) oxy)-1-oxoisoindolin-2-yl) piperidine-2,6-dione 4.6*50 mm, 3 μm; Mobile phase B: methanol; Flow rate: 2 mL/min; Gradient: isocratic 10% B; Wave Length: 220 nm. The fractions containing desired product were collected and evaporated under reduced pressure to afford the title compound (500 mg, 1.94 mmol, 52% yield) as a white solid. MS (ESI) m/z 258.2 $[M+1]^+$.

2-((1s,4s)-4-Hydroxycyclohexyl)quinoline-6-carbaldehyde. To a stirred solution of (130 mg, 0.51 mmol) in dichloromethane (10 mL) was added manganese dioxide (421 mg, 4.84 mmol) and the mixture was stirred at 50° C. for 5 h under nitrogen. The resulting mixture was filtered and the filtrate was concentrated to afford the title compound (100 mg, 0.39 mmol, 76% yield) as a white solid. MS (ESI) m/z 256.0 $[M+1]^+$.

3-(5-(((S)-1-((2-((1s,4R)-4-Hydroxycyclohexyl)quinolin-6-yl)methyl)pyrrolidin-3-yl)oxy)-1-oxoisoindolin-2-yl)piperidine-2,6-dione. To a stirred mixture of 2-((1s,4s)-4-hydroxycyclohexyl)quinoline-6-carbaldehyde (50 mg, 0.20 mmol), 3-[1-oxo-5-[(3S)-pyrrolidin-3-yl]oxy-isoindolin-2-yl]piperidine-2,6-dione; hydrochloride (70 mg, 0.2 mmol) and triethylamine (0.06 mL, 0.4 mmol) in dichloromethane (5 mL) was added sodium triacetoxyborohydride (160 mg, 0.75 mmol) in several portions and the mixture was stirred at room temperature for 2 h under nitrogen. The resulting mixture was concentrated. The residue was purified by silica gel chromatography (0-10% methanol in dichloromethane) and purified further by preparative HPLC with the following conditions: Column: sunfire prep C18 column, 30*150 mm, 5 μm; Mobile phase A: water (0.1% formic acid), Mobile phase B: acetonitrile; Flow rate: 60 mL/min; Gradient: 5% B to 20% B in 7 min, 20% B; Wave Length: 254/210 nm; RT1 (min): 4.92; The fractions containing desired product were collected and evaporated under reduced pressure to afford the title compound (32 mg, 0.056 mmol, 28% yield) as a white solid. $^1H$ NMR (400 MHz, Methanol-$d_4$) δ 8.26 (m, 1H), 8.01-8.03 (d, J=8.6 Hz, 1H), 7.89 (s, 1H), 7.80 (m, 1H), 7.71 (d, J=8.4 Hz, 1H), 7.50 (d, J=8.6 Hz, 1H), 7.11-7.02 (m, 2H), 5.14-5.12 (m, 2H), 4.51-4.36 (m, 2H),

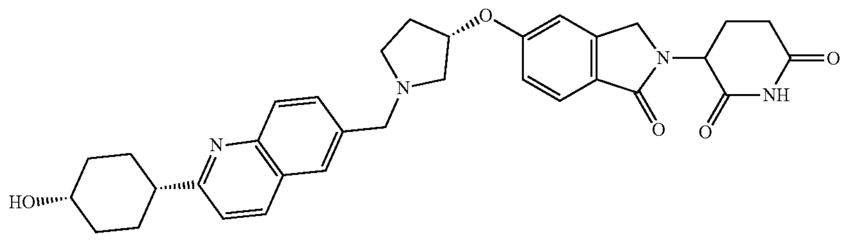 [SMILES: O=C1CCC(N2Cc3cc(O[C@H]4CCN(Cc5ccc6nc([C@H]7CC[C@@H](O)CC7)ccc6c5)C4)ccc3C2=O)C(=O)N1]

(1s,4s)-4-(6-(Hydroxymethyl)quinolin-2-yl)cyclohexan-1-ol. The 4-(6-(hydroxymethyl)quinolin-2-yl)cyclohexan-1-ol (1 g, 3.70 mmol) was purified by preparative Chiral SFC with the following conditions: Column: daicel dcpak p4vp, 4.09-3.97 (m, 2H), 3.69-3.67 (m, 1H), 3.16-3.00 (m, 3H), 2.98-2.74 (m, 4H), 2.47 (m, 2H), 2.13 (m, 3H), 2.04 (m, 3H), 1.88-1.74 (m, 2H), 1.51-1.47 (m, 2H); MS (ESI) m/z 569.4 $[M+1]^+$.

Example S67. 3-(5-(((S)-1-((2-((1r,4S)-4-Hydroxy-cyclohexyl)quinolin-6-yl)methyl)pyrrolidin-3-yl)oxy)-1-oxoisoindolin-2-yl)piperidine-2,6-dione

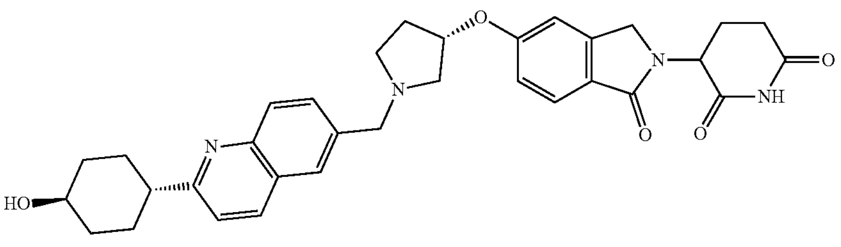 [SMILES: O=C1CCC(N2Cc3cc(O[C@H]4CCN(Cc5ccc6nc([C@H]7CC[C@H](O)CC7)ccc6c5)C4)ccc3C2=O)C(=O)N1]

Methyl 2-(1,4-dioxaspiro[4.5]dec-7-en-8-yl)quinoline-6-carboxylate. To a stirred mixture of methyl 2-chloroquinoline-6-carboxylate (2 g, 9.03 mmol), 4,4,5,5-tetramethyl-2-(1,4-dioxaspiro[4.5]dec-7-en-8-yl)-1,3,2-dioxaborolane (1.5 g, 5.64 mmol) and [1,1'-bis(diphenylphosphino)ferrocene] dichloropalladium(II) (800 mg, 1.09 mmol) in 1,4-dioxane (200 mL) and water (20 mL) was added sodium carbonate (2 g, 18.87 mmol) and the resulting mixture was stirred at 90° C. for 3 h under nitrogen. The mixture was concentrated and the residue was purified by reverse-phase flash (10-70% acetonitrile+0.05% ammonium bicarbonate in water, over 20 min) to afford the title compound (1.8 g, 5.52 mmol, 61% yield) as a yellow solid. MS (ESI) m/z 326.2 $[M+1]^+$.

Methyl 2-(1,4-dioxaspiro[4.5]decan-8-yl)quinoline-6-carboxylate. To a stirred solution of methyl 2-(1,4-dioxaspiro[4.5]dec-7-en-8-yl)quinoline-6-carboxylate (1.8 g, 5.53 mmol) in methanol (30 mL) was added palladium 10% on carbon (360 mg, wetted with ca. 55% water) at room temperature and the resulting mixture was stirred at room temperature for 2 h under hydrogen (~2 bar). The resulting mixture was filtered and the filtrate was concentrated to afford the title compound (1.7 g, 5.19 mmol, 94% yield) as a white solid. MS (ESI) m/z 328.0 $[M+1]^+$.

Methyl 2-(4-oxocyclohexyl)quinoline-6-carboxylate. To a stirred solution of methyl 2-(1,4-dioxaspiro[4.5]decan-8-yl)quinoline-6-carboxylate (1.7 g, 5.19 mmol) in dichloromethane (12 mL) was added TFA (12 mL, 156.7 mmol) at 0° C. The solution was stirred at room temperature for 3 h under nitrogen. The mixture was concentrated. The residue was added saturated sodium bicarbonate to pH~7 and extracted with ethyl acetate. The extracts were washed with brine, dried over anhydrous sodium sulfate, filtered and concentrated. The residue was purified by silica gel chromatography (0-30% ethyl acetate in petroleum ether) to afford the title compound (1.1 g, 3.87 mmol, 75% yield) as a yellow solid. MS (ESI) m/z 284.2 $[M+1]^+$.

4-(6-(Hydroxymethyl)quinolin-2-yl)cyclohexan-1-ol. To a stirred solution of methyl 2-(4-oxocyclohexyl)quinoline-6-carboxylate (1.1 g, 3.87 mmol) in THF (15 mL) was added lithium aluminum hydride (1 N in THF, 4 mL, 4 mmol) at 0° C. and the resulting solution was stirred at this temperature for 0.5 h under nitrogen. The mixture was diluted with THF, added sodium sulfate decahydrate, filtered and concentrated to afford the title compound (550 mg, 2.13 mmol, 55% yield) as a yellow solid. MS (ESI) m/z 258.2 $[M+1]^+$.

(1R,4r)-4-(6-(Hydroxymethyl)quinolin-2-yl)cyclohexan-1-ol. The 4-(6-(hyd-roxymethyl)quinolin-2-yl)cyclohexan-1-ol (1 g, 3.87 mmol) was purified by preparative Chiral SFC with the following conditions: Column: daicel dcpak p4vp, 4.6*50 mm, 3 um; Mobile phase B: methanol; Flow rate: 2 mL/min; Gradient: isocratic 10% B; Wave Length: 220 nm. The fractions containing desired product were collected and evaporated under reduced pressure to afford the title compound (500 mg, 1.94 mmol, 50% yield) as a white solid. MS (ESI) m/z 258.2 $[M+1]^+$.

2-((1R,4r)-4-Hydroxycyclohexyl)quinoline-6-carbaldehyde. To a stirred solution of (1r,4r)-4-(6-(hydroxymethyl)quinolin-2-yl)cyclohexan-1-ol (130 mg, 0.51 mmol) in dichloromethane (10 mL) was added manganese dioxide (439 mg, 5.1 mmol) and the mixture was stirred at 50° C. for 5 h under nitrogen. The mixture was filtered and the filtrate was concentrated to afford the title compound (100 mg, 0.39 mmol, 76% yield) as a white solid. MS (ESI) m/z 256.0 $[M+1]^+$.

3-(5-(((S)-1-((2-((1r,4S)-4-hydroxycyclohexyl)quinolin-6-yl)methyl)pyrrolidin-3-yl)oxy)-1-oxoisoindolin-2-yl)piperidine-2,6-dione. To a stirred mixture of 2-((1r,4r)-4-hydroxycyclohexyl)quinoline-6-carbaldehyde (50 mg, 0.20 mmol), 3-[1-oxo-5-[(3S)-pyrrolidin-3-yl]oxy-isoindolin-2-yl]piperidine-2,6-dione; hydrochloride (70 mg, 0.2 mmol) and triethylamine (0.06 mL, 0.4 mmol) in dichloromethane (5 mL) was added sodium triacetoxyborohydride (160 mg, 0.75 mmol) in several portions and stirred at room temperature for 2 h under nitrogen. The resulting mixture was concentrated. The residue was purified by silica gel chromatography (0-10% methanol in dichloromethane) and purified further by preparative HPLC with the following conditions: Column: Sunfire prep C18 column, 30*150 mm, 5 μm; Mobile phase A: water (0.1% formic acid), Mobile phase B: acetonitrile; Flow rate: 60 mL/min; Gradient: 2% B to 17% B in 9 min, 17% B; Wave Length: 254/210 nm; RT1 (min): 8.72] to afford the title compound (35 mg, 0.061 mmol, 31% yield) as a white solid. $^1H$ NMR (400 MHz, Methanol-$d_4$) δ 8.26 (m, 1H), 8.01-8.03 (d, J=8.6 Hz, 1H), 7.89 (s, 1H), 7.80-7.82 (m, 1H), 7.71 (d, J=8.4 Hz, 1H), 7.50 (d, J=8.6 Hz, 1H), 7.11-7.02 (m, 2H), 5.12-5.14 (m, 2H), 4.51-4.36 (m, 2H), 4.15-4.05 (m, 2H), 3.29-3.20 (m, 1H), 3.08-3.00 (m, 3H), 2.98-2.74 (m, 4H), 2.55 (m, 3H), 2.10 (m, 4H), 2.00-1.90 (m, 2H), 1.80-1.70 (m, 4H); MS (ESI) m/z 569.1 $[M+1]^+$.

Example S68. 3-(5-(((S)-1-((7-(2-Methoxypropan-2-yl)isoquinolin-3-yl)methyl)pyrrolidin-3-yl)oxy)-1-oxoisoindolin-2-yl)piperidine-2,6-dione

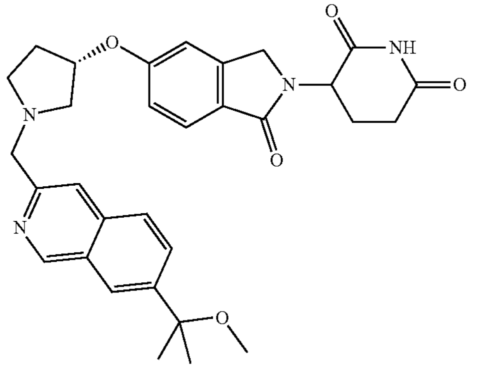 [SMILES: COC(C)(C)c1ccc2cc(CN3CC[C@H](Oc4ccc5c(c4)CN(C4CCC(=O)NC4=O)C5=O)C3)ncc2c1]

3-Chloro-7-(2-methoxypropan-2-yl)isoquinoline. To a solution of 2-(3-chloroisoquinolin-7-yl)propan-2-ol (210 mg, 0.95 mmol) in THF (5 mL) was added sodium hydride (60% dispersion in mineral oil, 45 mg, 1.12 mmol) at 0° C. and the suspension was stirred for 30 min. Then iodomethane (267 mg, 1.88 mmol) was added and the mixture was stirred for 1 h at 0° C. The resulting mixture was diluted with water and extracted with ethyl acetate. The extracts were washed with brine, dried over anhydrous sodium sulfate, filtered and concentrated. The residue was purified by reverse phase flash (10-70% acetonitrile+0.05% ammonium bicarbonate in water, over 20 min) to afford the title compound (200 mg, 0.85 mmol, 89% yield) as a white solid. MS (ESI) m/z 236.2 $[M+1]^+$.

7-(2-Methoxypropan-2-yl)-3-vinylisoquinoline. To a solution of 3-chloro-7-(2-methoxypropan-2-yl)isoquinoline (200 mg, 0.85 mmol), potassium vinyltrifluoroborate (300 mg, 2.22 mmol) in 1,4-dioxane (5 mL) and water (0.50 mL) were added tetrakis(triphenylphosphine)palladium (71 mg, 0.06 mmol) and cesium carbonate (827 mg, 2.55 mmol). The mixture was stirred at 100° C. for 5 h under nitrogen. The resulting mixture was diluted with water and extracted with ethyl acetate. The extracts were washed with brine, dried over anhydrous sodium sulfate, filtered and concentrated. The residue was purified by reverse phase flash (10-70% acetonitrile+0.05% ammonium bicarbonate in water, over 20 min) to afford the title compound (110 mg, 0.48 mmol, 57% yield) as a white solid. MS (ESI) m/z 228.0 $[M+1]^+$.

7-(2-Methoxypropan-2-yl)isoquinoline-3-carbaldehyde. To a solution of 7-(2-methoxypropan-2-yl)-3-vinylisoquinoline (110 mg, 0.48 mmol), potassium osmate (40 mg, 0.11 mmol) and 4-methylmorpholine N-oxide (110 mg, 0.94 mmol) in 1-butanol (5 mL) and water (5 mL) was added citric acid (380 mg, 1.04 mmol) and the resulting mixture was stirred at room temperature for 4 h under nitrogen. Then sodium periodate (310 mg, 1.45 mmol) was added in several portions into the above mixture at 0° C. and the resulting mixture was stirred at room temperature for 1 h. The mixture was added saturated sodium bicarbonate solution to pH~7 and extracted with ethyl acetate. The extracts were washed with brine, dried over sodium sulfate, filtered and concentrated to afford the crude title compound (35 mg, 0.15 mmol, 31% yield) as a yellow solid. MS (ESI) m/z 230.2 $[M+1]^+$.

3-(5-(((S)-1-((7-(2-methoxypropan-2-yl) isoquinolin-3-yl) methyl)pyrrolidin-3-yl)oxy)-1-oxoisoindolin-2-yl)piperidine-2,6-dione. To a stirred mixture of 7-(2-methoxypropan-2-yl)isoquinoline-3-carbaldehyde (35 mg, 0.15 mmol), 3-[1-oxo-5-[(3S)-pyrrolidin-3-yl]oxy-isoindolin-2-yl]piperidine-2,6-dione (60 mg, 0.18 mmol) and triethylamine (0.05 mL, 0.35 mmol) in dichloromethane (5 mL) was added sodium triacetoxyborohydride (140 mg, 0.66 mmol) in several portions and was stirred at room temperature for 3 h under nitrogen. The mixture was concentrated and the residue was purified by silica gel chromatography (0-10% methanol in dichloromethane) firstly and further by silica gel column: xselect csh obd Column 30*150 mm, 5 μm; Mobile phase A: water (0.05% TFA), Mobile phase B: acetonitrile; Flow rate: 60 mL/min; Gradient: 10% B to 28% B in 10 min, 28% B; Wave Length: 254/220 nm; RT1 (min): 8.45. The fractions containing desired product were collected and evaporated under reduced pressure to afford the title compound (15.6 mg, 0.03 mmol, 18% yield) as a white solid. $^1H$ NMR (400 MHz, Methanol-$d_4$) δ 9.37 (s, 1H), 8.16 (s, 1H), 7.99 (s, 2H), 7.94 (s, 1H), 7.76 (d, J=8.4 Hz, 1H), 7.20 (m, 1H), 7.14 (d, J=8.2 Hz, 1H), 5.37 (m, 1H), 5.14-5.12 (m, 1H), 4.84-4.72 (m, 2H), 4.56-4.40 (m, 2H), 3.83-3.76 (m, 3H), 3.75-3.68 (m, 1H), 3.14 (m, 3H), 2.92-2.90 (m, 1H), 2.79 (m, 1H), 2.70-2.60 (m, 1H), 2.60-2.50 (m, 2H), 2.20-2.14 (m, 1H), 1.71-1.63 (m, 6H); MS (ESI) m/z 543.2 $[M+1]^+$.

Example S69. 3-(5-(((S)-1-((7-(2-Hydroxypropan-2-yl)isoquinolin-3-yl) methyl) pyrrolidin-3-yl) oxy)-1-oxoisoindolin-2-yl) piperidine-2,6-dione

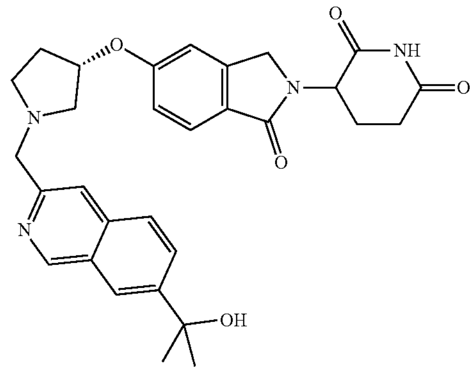 [SMILES: CC(C)(O)c1ccc2cc(CN3CC[C@H](Oc4ccc5c(c4)CN(C4CCC(=O)NC4=O)C5=O)C3)ncc2c1]

1-(3-Chloroisoquinolin-7-yl)ethan-1-one. A solution of 7-bromo-3-chloroisoquinoline (1.5 g, 6.19 mmol), tributyl (1-ethoxyvinyl)stannane (4.4 g, 12.18 mmol) and tetrakis (triphenylphosphine)palladium (523 mg, 0.45 mmol) in toluene (8 mL) was stirred at 100° C. for 6 h under nitrogen. Then hydrochloric acid (2 N in water, 8 mL) was added to the above mixture and the mixture was stirred at room temperature for 3 h. The resulting mixture was filtered and the filtrate was concentrated. The residue was purified by reverse phase flash (10-70% acetonitrile+0.05% ammonium bicarbonate in water, over 20 min) to afford the title compound (350 mg, 1.70 mmol, 28% yield) as a yellow solid. MS (ESI) m/z 206.1 $[M+1]^+$.

2-(3-Chloroisoquinolin-7-yl)propan-2-ol. To a solution of 1-(3-chloroisoquinolin-7-yl)ethan-1-one (1.24 g, 6.03 mmol) in THF (20 mL) was added methylmagne-sium bromide (1N in THF, 18 mL, 18 mmol) dropwise at 0° C. The mixture was stirred for 3 h at room temperature under nitrogen. The resulting mixture was added water and extracted with ethyl acetate. The extracts were washed with sodium carbonate, brine, dried over anhydrous sodium sulfate, filtered and concentrated to afford the title compound (600 mg, 2.71 mmol, 45% yield) as a yellow oil. MS (ESI) m/z 222.1 $[M+1]^+$.

2-(3-Vinylisoquinolin-7-yl)propan-2-ol. To a solution of 2-(3-chloroisoquinolin-7-yl)propan-2-ol (600 mg, 2.71 mmol), potassium vinyltrifluoroborate (1.1 g, 8.15 mmol) in 1,4-dioxane (5 mL) and water (5 mL) was added tetrakis (triphenylphosphine)palladium (270 mg, 0.23 mmol) and cesium carbonate (2.64 g, 8.12 mmol). The mixture was stirred at 100° C. for 5 h under nitrogen. The resulting mixture was added water and extracted with ethyl acetate. The extracts were washed with brine, dried over anhydrous sodium sulfate, filtered and concentrated. The residue was purified by silica gel chromatography (0 to 30% ethyl acetate in petroleum ether) to afford the title compound (310 mg, 1.45 mmol, 54% yield) as a white solid. MS (ESI) m/z 214.0 $[M+1]^+$.

7-(2-Hydroxypropan-2-yl)isoquinoline-3-carbaldehyde. To a solution of 2-(3-vinylisoquinolin-7-yl)propan-2-ol (310 mg, 1.45 mmol), potassium osmate (40 mg, 0.11 mmol) and 4-methylmorpholine N-oxide (330 mg, 2.82 mmol) in 1-butanol (5 mL) and water (5 mL) was added citric acid (550 mg, 2.86 mmol) at room temperature and the resulting mixture was stirred at room temperature for 4 h under nitrogen. Then sodium periodate (930 mg, 4.31 mmol) was added in several portions into the above mixture at 0° C. and the resulting mixture was stirred at room temperature for 3 h under nitrogen. The resulting mixture was added water and extracted with ethyl acetate. The extracts were washed with brine, dried over anhydrous sodium sulfate, filtered and concentrated. The residue was purified by silica gel chromatography (0-50% ethyl acetate in petroleum ether) to give the title compound (50 mg, 0.23 mmol, 16% yield) as a yellow solid. MS (ESI) m/z 216.2 $[M+1]^+$.

3-(5-(((S)-1-((7-(2-hydroxypropan-2-yl) isoquinolin-3-yl) methyl)pyrrolidin-3-yl)oxy)-1-oxoisoindolin-2-yl) piperidine-2,6-dione. To a stirred mixture of 7-(2-hydroxypropan-2-yl)isoquinoline-3-carbaldehyde (50 mg, 0.23 mmol), 3-[1-oxo-5-[(3S)-pyrrolidin-3-yl]oxy-isoindolin-2-yl]piperidine-2,6-dione; 2,2,2-trifluoroacetic acid (108 mg, 0.24 mmol) and triethylamine (0.06 mL, 0.47 mmol) in dichloromethane (5 mL) was added sodium triacetoxyborohydride (200 mg, 0.94 mmol) in several portions and the mixture was stirred for 2 h at room temperature under nitrogen. The mixture was concentrated and the residue was purified by silica gel chromatography (0-10% methanol in dichloromethane) firstly and further by preparative HPLC with the following conditions: Sunfire prep C18 column, 30*150 mm, 5 μm; Mobile phase A: water (0.1% formic acid), Mobile phase B: acetonitrile; Flow rate: 60 mL/min; Gradient: 5% B to 30% B in 7 min, 30% B; Wave Length: 254/220 nm; RT1 (min): 5.08; The fractions containing desired product were collected and evaporated under reduced pressure to afford the title compound (15.6 mg, 0.03 mmol, 0.13% yield) as a white solid. $^1$H NMR (300 MHz, Methanol-$d_4$) δ 9.28 (s, 1H), 8.21 (d, J=1.8 Hz, 1H), 8.00-7.98 (m, 1H), 7.96-7.86 (m, 2H), 7.73 (d, J=8.4 Hz, 1H), 7.16-7.04 (m, 2H), 5.22 (m, 1H), 5.13-5.11 (m, 1H), 4.54-4.33 (m, 4H), 3.58-3.35 (m, 3H), 3.26 (m, 1H), 2.92-2.87 (m, 1H), 2.84-2.72 (m, 1H), 2.63-2.38 (m, 2H), 2.30-2.12 (m, 2H), 1.66 (s, 6H); MS (ESI) m/z 529.1 $[M+1]^+$.

Example S70. 3-(5-(((S)-1-((2-(1-Hydroxycyclobutyl)quinolin-6-yl)methyl)pyrrolidin-3-yl)oxy)-1-oxoisoindolin-2-yl)piperidine-2,6-dione

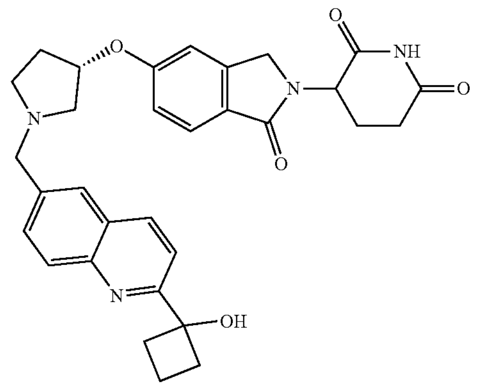 [SMILES: O=C1CCC(N2Cc3cc(O[C@H]4CCN(Cc5ccc6nc(C7(O)CCC7)ccc6c5)C4)ccc3C2=O)C(=O)N1]

1-(6-Methylquinolin-2-yl)cyclobutan-1-ol. A solution of 2-bromo-6-methyl-quinoline (450 mg, 2.03 mmol) in THF (10 mL) was cooled to −78° C. under nitrogen before addition of lithium-butyl (3 M in THF, 3.0 mL, 9.00 mmol) dropwise over 10 min. The reaction mixture was stirred for 30 min at this temperature and then a solution of cyclobutanone (800 mg, 11.26 mmol) in THF (0.5 mL) was added over 5 min. The reaction mixture was stirred for 1 h at −78° C. under nitrogen. The mixture was quenched with water and extracted with ethyl acetate. The extracts were washed with brine, dried over anhydrous sodium sulfate, filtered and concentrated. The residue was purified by silica gel chromatography (0 to 20% ethyl acetate in petroleum ether) to afford the title compound (320 mg, 1.50 mmol, 74% yield) as a light yellow oil. MS (ESI) m/z 214.2 $[M+1]^+$.

1-(6-(Bromomethyl)quinolin-2-yl)cyclobutan-1-ol. To a solution of 1-(6-methyl-2-quinolyl)cyclobutanol (100 mg, 0.47 mmol) in carbon tetrachloride (5 mL) were added NBS (75 mg, 0.42 mmol) and 2,2'-dimethyl-2,2'-azodipropionitrile (23 mg, 0.14 mmol) under nitrogen. The resulting mixture was stirred at 70° C. for 2 h under nitrogen. The mixture was filtered, and the filtrate was concentrated. The residue was purified by silica gel chromatography (0 to 50% ethyl acetate in petroleum ether) to afford the title compound (80 mg, 0.27 mmol, 57% yield) as a yellow oil. MS (ESI) m/z 292.1 $[M+1]^+$.

3-(5-(((S)-1-((2-(1-Hydroxycyclobutyl)quinolin-6-yl) methyl)pyrrolidin-3-yl)-oxy)-1-oxoisoindolin-2-yl)piperidine-2,6-dione. A solution of 3-[1-oxo-5-[(3S)-pyrrolidin-3-yl]oxy-isoindolin-2-yl]piperidine-2,6-dione; hydrochloride (80 mg, 0.22 mmol) and 1-[6-(bromomethyl)-2-quinolyl] cyclobutanol (70 mg, 0.24 mmol) in acetonitrile (5 mL) was added potassium carbonate (91 mg, 0.66 mmol) at room temperature. The mixture was stirred for 12 h at room temperature. The resulting mixture was concentrated and the residue was purified by silica gel chromatography (0-10% methanol in dichloromethane) and preparative HPLC with the with the following conditions: Sunfire prep C18 column, 30*150 mm, 5 μm; Mobile Phase A: water (0.1% formic acid), Mobile Phase B: acetonitrile; Flow rate: 60 mL/min; Gradient: 5% B to 14% B in 10 min, 14% B; Wave Length: 254/220 nm; $RT_1$ (min): 9.67. The fractions containing desired product were collected and evaporated under reduced pressure to afford the title compound (16.7 mg, 0.031 mmol, 14% yield) as a light yellow solid. $^1$H NMR (400 MHz, Methanol-$d_4$) δ 8.32 (d, J=8.6 Hz, 1H), 8.14 (d, J=8.5 Hz, 1H), 8.01 (s, 1H), 7.84 (m, 2H), 7.71 (m, J=8.4, 2.9 Hz, 1H), 7.11 (s, 1H), 7.06 (m, 1H), 5.23 (d, J=6.1 Hz, 1H), 5.12 (m, 1H), 4.51-4.36 (m, 4H), 3.56 (d, J=12.6 Hz, 1H), 3.45 (m, 2H), 3.29 (d, J=7.5 Hz, 1H), 2.90 (m, 1H), 2.79 (m, 3H), 2.56 (m, 1H), 2.45 (m, 3H), 2.30-2.22 (m, 1H), 2.15 (m, 1H), 2.05 (m, 1H), 2.01-1.87 (m, 1H); MS (ESI) m/z 541.2 $[M+1]^+$.

Example S71. 3-(5-(((S)-1-((2-(1-Methoxycyclobutyl)quinolin-6-yl)methyl)pyrrolidin-3-yl)oxy)-1-oxoisoindolin-2-yl)piperidine-2,6-dione

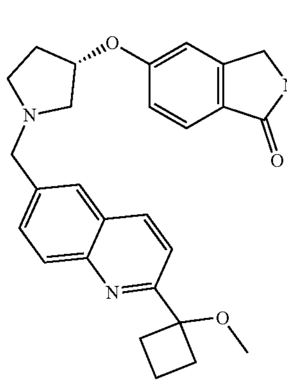

2-(1-Methoxycyclobutyl)-6-methylquinoline. To a solution of 1-(6-methylquinolin-2-yl)cyclobutan-1-ol (100 mg, 0.47 mmol) in THF (10 mL) was added sodium hydride (60% dispersion in mineral oil, 34 mg, 0.85 mmol) at 0° C. under nitrogen and the suspension was stirred for 30 min. Then iodomethane (70 mg, 0.52 mmol) was added to the above mixture at 0° C. and the mixture was stirred for 1 h at room temperature under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound. (100 mg, 0.44 mmol, 94% yield) as a light yellow oil. MS (ESI) m/z 228.1 $[M+1]^+$.

6-(Bromomethyl)-2-(1-methoxycyclobutyl)quinolone. To a solution of 2-(1-methoxycyclobutyl)-6-methyl-quinoline (90 mg, 0.40 mmol) in carbon tetrachloride (5 mL) was added NBS (63 mg, 0.36 mmol) and 2,2'-dimethyl-2,2'-azodipropionitrile (20 mg, 0.12 mmol). The mixture was stirred at 70° C. for 2 h under nitrogen. The mixture was filtered, and the filtrate was concentrated. The residue was purified by silica gel chromatography (0 to 50% ethyl acetate in petroleum ether) to afford the title compound (80 mg, 0.26 mmol, 66% yield) as a yellow oil. MS (ESI) m/z 306.0 $[M+1]^+$.

3-(5-(((S)-1-((2-(1-Methoxycyclobutyl)quinolin-6-yl)methyl)pyrrolidin-3-yl)oxy)-1-oxoisoindolin-2-yl)piperidine-2,6-dione. To a solution of 3-[1-oxo-5-[(3S)-pyrrolidin-3-yl]oxy-isoindolin-2-yl]piperidine-2,6-dione; hydrochloride (80 mg, 0.22 mmol), 6-(bromomethyl)-2-(1-methoxycyclobutyl)quinoline (73 mg, 0.24 mmol) in acetonitrile (5 mL) was added potassium carbonate (91 mg, 0.66 mmol) at room temperature. The mixture was stirred for 12 h at room temperature under nitrogen. The resulting mixture was concentrated and the residue was purified by silica gel chromatography (0 to 50% ethyl acetate in petroleum ether) and preparative HPLC with the following conditions: Sunfire prep C18 column, 30*150 mm, 5 μm; Mobile Phase A: water (0.1% formic acid), Mobile Phase B: acetonitrile; Flow rate: 60 mL/min; Gradient: 10% B to 30% B in 10 min, 30% B; Wave Length: 254/220 nm; $RT_1$ (min): 9.67. The fractions containing desired product were collected and evaporated under reduced pressure to afford the title compound (44.6 mg, 0.08 mmol, 36% yield) as an off-white solid. $^1H$ NMR (300 MHz, Methanol-$d_4$) δ 8.31 (d, J=8.6 Hz, 1H), 8.12 (d, J=8.7 Hz, 1H), 7.94 (s, 1H), 7.88-7.79 (m, 1H), 7.72 (d, J=8.4 Hz, 1H), 7.66 (d, J=8.6 Hz, 1H), 7.13-7.01 (m, 2H), 5.12 (m, J=13.3, 5.2 Hz, 2H), 4.44 (d, J=3.7 Hz, 2H), 4.16 (d, J=2.7 Hz, 2H), 3.27 (s, 1H), 3.16 (d, J=8.8 Hz, 2H), 3.03 (s, 3H), 3.03-2.87 (m, 2H), 2.90-2.67 (m, 3H), 2.53 (m, J=14.2, 7.0 Hz, 1H), 2.50-2.34 (m, 3H), 2.16 (m, 2H), 1.96 (m, 1H), 1.87-1.72 (m, 1H); MS (ESI) m/z 555.3 $[M+1]^+$.

Example S72. 3-(5-(((S)-1-((2-(3-(Methylamino)oxetan-3-yl)quinolin-6-yl)methyl)pyrrolidin-3-yl)oxy)-1-oxoisoindolin-2-yl)piperidine-2,6-dione

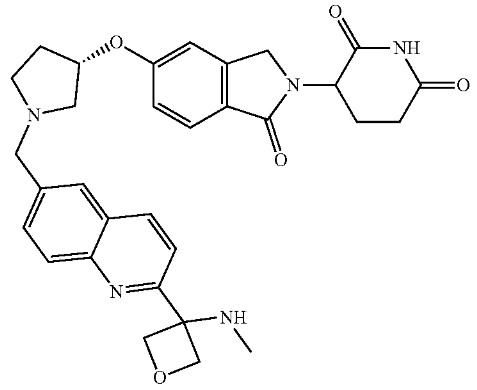 [SMILES: CNC1(c2ccc3cc(CN4CC[C@H](Oc5ccc6c(c5)CN(C5CCC(=O)NC5=O)C6=O)C4)ccc3n2)COC1]

6-(Methoxycarbonyl)quinoline 1-oxide. To a stirred solution of methyl quinoline-6-carboxylate (5.0 g, 26.7 mmol) in dichloromethane (50 mL) was added meta-chloroperoxybenzoic acid (12.5 g, 72.4 mmol) at room temperature. Then the reaction mixture was stirred for 12 h at room temperature under nitrogen. The reaction mixture was added saturated sodium bicarbonate solution to PH~7 and extracted with dichloromethane. The extracts were dried over anhydrous sodium sulfate, filtered and concentrated to give the title compound (4.0 g, 19.7 mmol, 74% yield) as a yellow solid. MS (ESI) m/z 204.1 $[M+1]^+$.

Methyl 2-hydroxyquinoline-6-carboxylate. To a stirred solution of 1-oxoquinoline-6-carboxylate (4.0 g, 19.7 mmol) in water (50 mL) was added methanesulfonyl chloride (4.8 g, 41.9 mmol) dropwise at 0° C. and the mixture was stirred at room temperature for 1 h under nitrogen. The reaction mixture was filtered and the filtrate was concentrated to give the title compound (4.0 g, 19.6 mmol, 99% yield) as a yellow solid. MS (ESI) m/z 204.2 $[M+1]^+$.

Methyl 2-bromoquinoline-6-carboxylate. To a stirred solution of methyl 2-hydroxyquinoline-6-carboxylate (4.0 g, 19.7 mmol) in chloroform (30 mL) was added phosphorus oxybromide (14.0 g, 48.8 mmol) at room temperature. Then the reaction mixture was stirred for 12 h at 65° C. under nitrogen. The reaction mixture was added saturated sodium bicarbonate solution to pH~7 and extracted with dichloromethane. The extracts were dried over anhydrous sodium sulfate, filtered and concentrated to afford the title compound (4.5 g, 16.9 mmol, 86% yield) as a yellow solid. MS (ESI) m/z 266.0 $[M+1]^+$.

(2-Bromoquinolin-6-yl)methanol. To a solution of calcium chloride (2.53 g, 22.76 mmol) and sodium borohydride (1.6 g, 41.7 mmol) in THF (20 mL) and ethanol (20 mL) pre-stirred 20 min at 0° C. under nitrogen was added methyl 2-bromoquinoline-6-carboxylate (2.0 g, 7.5 mmol) at 0° C. Then the reaction mixture was stirred at 0° C. for 5 h under nitrogen. The resulting mixture was diluted with water and extracted with dichloromethane. The extracts were washed with brine, dried over anhydrous sodium sulfate, filtered and concentrated to give the title compound (1.7 g, 7.1 mmol, 95% yield) as a yellow solid. MS (ESI) m/z 238.1 $[M+1]^+$.

2-Bromo-6-(((tert-butyldimethylsilyl)oxy)methyl)quinoline. To a solution of (2-bromoquinolin-6-yl)methanol (1.8 g, 7.60 mmol) in DMF (10 mL) was added imidazole (1.0 g, 14.8 mmol), t-butylchlorodimethylsilane (1.4 g, 9.1 mmol) at room temperature. Then the reaction mixture was stirred 12 h at room temperature under nitrogen. The resulting mixture was added water and extracted with dichloromethane. The extracts were washed with brine, dried over anhydrous sodium sulfate, filtered and concentrated. The crude product was purified by reverse phase flash (40-100% acetonitrile+0.05% ammonium bicarbonate in water, over 15 min) to give the title compound (1.3 g, 3.70 mmol, 49% yield) as a yellow solid. MS (ESI) m/z 352.2 $[M+1]^+$.

N-(3-(6-(((Tert-butyldimethylsilyl)oxy)methyl)quinolin-2-yl)oxetan-3-yl)-2-methylpropane-2-sulfinamide. To a stirred solution of 2-bromo-6-(((tert-butyldim-ethylsilyl)oxy)methyl)quinoline (800 mg, 2.3 mmol) in THF (20 mL) was added n-butyllithium (2.5 M in diethyl ether, 4.5 mL, 11.3 mmol) dropwise at −78° C. and the mixture was stirred at −78° C. for 0.5 h under nitrogen. The reaction mixture was added 2-methyl-N-(oxetan-3-ylidene)propane-2-sulfinamide (2.0 g, 11.5 mmol) at −78° C. and stirred at room temperature for 3 h under nitrogen. The reaction mixture was added saturated ammonium chloride and extracted with ethyl acetate. The extracts were dried over anhydrous sodium sulfate, filtered and concentrated. The residue was purified with reverse phase flash (30-70% acetonitrile+0.05% ammonium bicarbonate in water, over 20 min) to give the title compound (300 mg, 0.67 mmol, 29% yield) as a yellow oil. MS (ESI) m/z 449.3 $[M+1]^+$.

N-(3-(6-(((Tert-butyldimethylsilyl)oxy)methyl)quinolin-2-yl)oxetan-3-yl)-N,2-dimethylpropane-2-sulfinamide. To a stirred solution of N-[3-[6-[[tert-butyl (dimethyl)silyl] oxymethyl]-2-quinolyl]oxetan-3-yl]-2-methyl-propane-2-sulfinamide (150 mg, 0.33 mmol) in DMF (5 mL) was added sodium hydride (60% dispersion in mineral oil, 16 mg, 0.40 mmol) at 0° C. and stirred for 1 h under nitrogen. Then the solution was added iodomethane (57 mg, 0.4 mmol) at 0° C. under nitrogen and stirred for 2 h under nitrogen. The reaction mixture was added water and extracted with ethyl acetate. The extracts were dried over anhydrous sodium sulfate, filtered and concentrated. The residue was purified with reverse phase flash (20-70% acetonitrile+0.05% ammonium bicarbonate in water, over 20 min) to give the title compound (110 mg, 0.23 mmol, 70% yield) as a yellow solid. MS (ESI) m/z 463.2 $[M+1]^+$.

N-(3-(6-(Hydroxymethyl)quinolin-2-yl)oxetan-3-yl)-N,2-dimethylpropane-2-sulfinamide. To a stirred solution of N-[3-[6-[[tert-butyl(dimethyl)silyl]oxymethyl]-2-quinolyl] oxetan-3-yl]-N,2-dimethyl-propane-2-sulfinamide (110 mg, 0.23 mmol) in THF (5 mL) was added tetrabutylammonium fluoride (70 mg, 0.26 mmol) at 0° C. The resulting solution was stirred at 0° C. for 1 h under nitrogen. The reaction mixture was added water and extracted with ethyl acetate. The extracts were dried over anhydrous sodium sulfate, filtered and concentrated to give the title compound (80 mg, 0.23 mmol, 99% yield) as a yellow oil. MS (ESI) m/z 349.1 $[M+1]^+$.

N-(3-(6-Formylquinolin-2-yl)oxetan-3-yl)-N,2-dimethylpropane-2-sulfinamide. To a stirred solution of N-[3-[6-(hydroxymethyl)-2-quinolyl]oxetan-3-yl]-N,2-dimethylpropane-2-sulfinamide (80 mg, 0.23 mmol) in dichloromethane (10 mL) was added manganese dioxide (200 mg, 2.30 mmol) at room temperature. Then the reaction mixture was stirred at room temperature for 12 h under nitrogen. The reaction mixture was filtered and concentrated to give the title compound (78 mg, 0.22 mmol, 96% yield) as a yellow solid. MS (ESI) m/z 347.2 $[M+1]^+$.

N-(3-(6-(((3S)-3-((2-(2,6-Dioxopiperidin-3-yl)-1-oxoisoindolin-5-yl)oxy)pyrrolidin-1-yl)methyl)quinolin-2-yl) oxetan-3-yl)-N,2-dimethylpropane-2-sulfinamide. To a stirred solution of N-[3-(6-formyl-2-quinolyl)oxetan-3-yl]-N,2-dimethyl-propane-2-sulfinamide (78 mg, 0.22 mmol), 3-(1-oxo-5-(((S)-pyrrolidin-3-yl)oxy)isoindolin-2-yl)piperidine-2,6-dione; 2,2,2-trifluoroacetic acid (111 mg, 0.25 mmol) and triethylamine (0.07 mL, 0.49 mmol) in dichloromethane (5 mL) pre-stirred for 15 min was added sodium triacetoxyborohydride (200 mg, 0.94 mmol) at 0° C. and the solution was stirred at room temperature for 4 h under nitrogen. The resulting solution was purified by silica gel chromatography (0 to 10% methanol in dichloromethane). The pure fractions were evaporated to afford the title compound (140 mg, 0.21 mmol, 94% yield) as a yellow oil. MS (ESI) m/z 660.3 $[M+1]^+$.

3-(5-(((S)-1-((2-(3-(Methylamino)oxetan-3-yl)quinolin-6-yl)methyl)pyrrolidin-3-yl)oxy)-1-oxoisoindolin-2-yl)piperidine-2,6-dione. A solution of N-[3-[6-[[(3S)-3-[2-(2,6-dioxo-3-piperidyl)-1-oxo-isoindolin-5-yl]oxypyrrolidin-1-yl]methyl]-2-quinolyl]oxetan-3-yl]-N,2-dimethyl-propane-2-sulfinamide (100 mg, 0.15 mmol) and TFA (1.0 mL, 13.1 mmol) in dichloromethane (15 mL) was stirred at 0° C. for 2 h under nitrogen. The resulting mixture was concentrated. The crude product was purified directly by preparative HPLC with the following conditions: Column: sunfire prep C18 column, 30*150 mm, 5 μm; mobile phase A: water (0.1% TFA), mobile phase B: acetonitrile; flow rate: 60 mL/min; gradient: 4% B to 20% B in 10 min, 20% B; wave length: 254/220 nm; $RT_1$ (min): 8.6. The fractions containing desired product were collected and evaporated under reduced pressure to afford the title compound (19.3 mg, 0.03 mmol, 23% yield) as a white solid. $^1H$ NMR (400 MHz, DMSO-$d_6$) δ 8.66 (d, J=8.7 Hz, 1H), 8.24 (d, J=2.0 Hz, 1H), 8.12 (dd, J=18.6, 8.7 Hz, 2H), 7.99 (dd, J=8.8, 2.0 Hz, 1H), 7.66 (dd, J=8.4, 2.5 Hz, 1H), 7.19 (d, J=2.3 Hz, 1H), 7.06 (m, 1H), 5.28 (s, 1H), 5.11 (d, J=8.3 Hz, 2H), 5.04 (dd, J=8.3, 3.0 Hz, 3H), 4.67 (s, 2H), 4.40 (dd, J=17.6, 2.9 Hz, 1H), 4.28 (dd, J=17.5, 2.8 Hz, 1H), 3.41-3.53 (m, 4H), 2.95-2.83 (m, 1H), 2.68 (s, 3H), 2.61 (m, 1H), 2.39 (m, J=13.2, 4.5 Hz, 2H), 2.18 (m, 1H), 2.05-1.92 (m, 1H); MS (ESI) m/z 556.2 $[M+1]^+$.

Example S73. 3-(1-Oxo-5-(((S)-1-((6-(tetrahydro-2H-pyran-4-yl)isoquinolin-3-yl)methyl)pyrrolidin-3-yl)oxy)isoindolin-2-yl)piperidine-2,6-dione

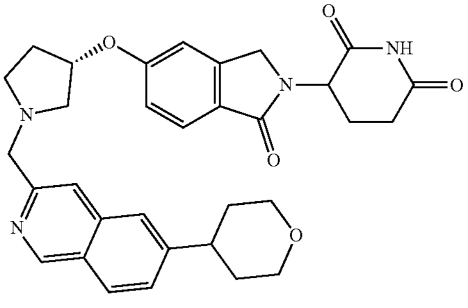 [SMILES: O=C1CCC(N2Cc3cc(O[C@H]4CCN(Cc5cc6cc(C7CCOCC7)ccc6cn5)C4)ccc3C2=O)C(=O)N1]

Ethyl 6-(3,6-dihydro-2H-pyran-4-yl)isoquinoline-3-carboxylate. To a solution of ethyl 6-bromoisoquinoline-3-carboxylate (100 mg, 0.36 mmol), 2-(3,6-dihydro-2H-pyran-4-yl)-4,4,5,5-tetramethyl-1,3,2-dioxaborolane (75 mg, 0.36 mmol) and sodium carbonate (76 mg, 0.71 mmol) in 1,4-dioxane (10 mL) and water (1 mL) was added [1'1-bis(diphenylphosphino)ferrocene] dichloro palladiuM (II) (26 mg, 0.035 mmol). The resulting mixture was stirred at 90° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (80 mg, 0.28 mmol, 77% yield) as a light yellow solid. MS (ESI) m/z 284.1 $[M+1]^+$.

Ethyl 6-(tetrahydro-2H-pyran-4-yl)isoquinoline-3-carboxylate. To a solution of ethyl 6-(3,6-dihydro-2H-pyran-4-yl)isoquinoline-3-carboxylate (80 mg, 0.28 mmol) in methanol (10 mL) was added palladium 10% on carbon (40 mg, wetted with ca. 50% water). The mixture was stirred for 2 h at room temperature under hydrogen (~2 bar). The resulting mixture was filtered and the filter cake was washed with dichloromethane (3×10 mL). The filtrate was concentrated under reduced pressure to afford the title compound (80 mg, 0.28 mmol, 99% yield) as a light-yellow solid. MS (ESI) m/z 286.2 $[M+1]^+$.

(6-(Tetrahydro-2H-pyran-4-yl)-1,2-dihydroisoquinolin-3-yl)methanol. To a solution of ethyl 6-tetrahydropyran-4-ylisoquinoline-3-carboxylate (45 mg, 0.16 mmol) in THF (5 mL) was added lithium aluminum hydride (2.5 M in THF, 0.08 mL, 0.20 mmol) at 0° C. The resulting mixture was stirred at this temperature for 30 min. The mixture was quenched with water, and the pH of the solution was adjusted with 15% sodium hydroxide solution to pH~8 and extracted with ethyl acetate. The extracts were washed with brine, dried over anhydrous sodium sulfate, filtered and concentrated. The residue was purified by silica gel chromatography (0-10% methanol in dichloromethane) to afford the title compound (38 mg, 0.15 mmol, 94% yield) as a light yellow solid. MS (ESI) m/z 246.2 $[M+1]^+$.

6-(Tetrahydro-2H-pyran-4-yl)isoquinoline-3-carbaldehyde. To a solution of (6-tetrahydropyran-4-yl-1,2-dihydroisoquinolin-3-yl)methanol (38 mg, 0.15 mmol) in dichloromethane (5 mL) was added manganese dioxide (270 mg, 3.10 mmol). The mixture was stirred for 12 h at room temperature under nitrogen. The resulting mixture was filtered and the filter cake was washed with dichloromethane (3×10 mL). The filtrate was concentrated under reduced pressure to afford the title compound (35 mg, 0.14 mmol, 93% yield) as a black solid. MS (ESI) m/z 242.1 $[M+1]^+$.

3-(1-Oxo-5-(((S)-1-((6-(tetrahydro-2H-pyran-4-yl)isoquinolin-3-yl)methyl)pyrrolidin-3-yl)oxy)isoindolin-2-yl)piperidine-2,6-dione. To a solution of 3-[1-oxo-5-[(3S)-pyrrolidin-3-yl]oxy-isoindolin-2-yl]piperidine-2,6-dione (40 mg, 0.12 mmol), 6-tetrahydropyran-4-ylisoquinoline-3-carbaldehyde (35 mg, 0.14 mmol) and triethylamine (19 mg, 0.19 mmol) in dichloromethane (2 mL) was added sodium triacetoxyborohydride (77 mg, 0.36 mmol) at room temperature. The mixture was stirred for 2 h at room temperature. The resulting mixture was concentrated and the residue was purified by silica gel chromatography (0-5% methanol in dichloromethane) and preparative HPLC with the following conditions: Xselect CSH OBD Column 30*150 mm 5 μm, n; Mobile Phase A: water (0.05% TFA), Mobile Phase B: acetonitrile; Flow rate: 60 mL/min; Gradient: 7 B to 37 B in 7 min; 254/210 nm; $RT_1$: 5.66. The fractions containing desired product were collected and evaporated under reduced pressure to afford the title compound (4 mg, 0.007 mmol, 6% yield) as an off-white solid. $^1H$ NMR (400 MHz, Methanol-$d_4$) δ 9.31 (d, J=2.3 Hz, 1H), 8.12 (d, J=8.5 Hz, 1H), 7.93 (m, 1H), 7.82 (m, 1H), 7.79-7.70 (m, 2H), 7.18 (d, J=3.7 Hz, 1H), 7.11 (m, 1H), 5.36 (m, 1H), 5.13 (d, J=13.1 Hz, 1H), 4.76 (m, 2H), 4.46 (m, 2H), 4.15-4.06 (m, 2H), 3.87 (m, 3H), 3.65 (m, 3H), 3.13-3.05 (m, 1H), 2.89 (m, 1H), 2.79 (m, 1H), 2.65-2.41 (m, 2H), 2.19 (m, 1H), 1.90 (m, 4H); MS (ESI) m/z 555.2 $[M+1]^+$.

Example S74. 3-(1-Oxo-5-(((S)-1-((7-((S)-tetrahydrofuran-3-yl)isoquinolin-3-yl)methyl)pyrrolidin-3-yl)oxy)isoindolin-2-yl)piperidine-2,6-dione

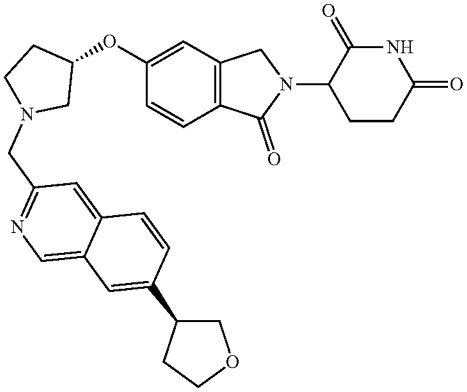 [SMILES: O=C1CCC(N2Cc3cc(O[C@H]4CCN(Cc5cc6ccc([C@@H]7CCOC7)cc6cn5)C4)ccc3C2=O)C(=O)N1]

(S)-(7-(Tetrahydrofuran-3-yl)isoquinolin-3-yl)methanol. The (7-(tetrahydrofuran-3-yl)isoquinolin-3-yl) methanol (200 mg, 0.87 mmol) was purified by preparative SFC with the following conditions: Column: CHIRALPAK AD-H, 2*25 cm, 5 μm; Mobile Phase A: Carbon dioxide, Mobile Phase B: Methanol (0.1% 2M ammonia-methanol); Flow rate: 50 mL/min; Gradient: 40% B; Column Temperature: 35° C.; Back Pressure: 100 bar; 220 nm; RT1:4.93; $RT_2$: 7.72; Injection Volume: 4.8 ml; Number of Runs: 4. The fractions containing desired product were collected and evaporated under reduced pressure to afford the title compound (65 mg, 0.28 mmol, 32% yield). MS (ESI) m/z 230.1 $[M+1]^+$.

(S)-7-(Tetrahydrofuran-3-yl)isoquinoline-3-carbaldehyde. To a stirred solution of (S)-(7-(tetrahydrofuran-3-yl)

isoquinolin-3-yl)methanol (65 mg, 0.28 mmol) in dichloromethane (5 mL) was added Dess-Martin periodinane (156 mg, 0.37 mmol) at 0° C. Then the reaction mixture was stirred for 2 h at room temperature under nitrogen. The resulting mixture was concentrated and the residue was purified by silica gel chromatography (0 to 30% ethyl acetate in petroleum ether). The pure fractions were evaporated to afford the title compound (35 mg, 0.15 mmol, 54% yield) as a yellow oil. MS (ESI) m/z 228.2 $[M+1]^+$.

3-(1-Oxo-5-(((S)-1-((7-((S)-tetrahydrofuran-3-yl)isoquinolin-3-yl)methyl) pyrrolidin-3-yl)oxy)isoindolin-2-yl)piperidine-2,6-dione. To a stirred solution of (S)-7-(tetrahydrofuran-3-yl)isoquinoline-3-carbaldehyde (35 mg, 0.15 mmol), 3-[1-oxo-5-[(3S)-pyrrolidin-3-yl]oxy-isoindolin-2-yl]piperidine-2,6-dione (61 mg, 0.19 mmol), triethylamine (0.04 mL, 0.30 mmol) in dichloromethane (5 mL) pre-stirred for 15 min was added sodium triacetoxyborohydride (130 mg, 0.61 mmol) at 0° C. and the mixture was stirred at room temperature for 12 h under nitrogen. The resulting mixture was purified by silica gel chromatography (0 to 15% methanol in dichloromethane). The pure fractions were evaporated and purified further by preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 5 B to 30 B in 7 min; 254/220 nm; RT1:5.51; RT2. The fractions containing desired product were collected and evaporated under reduced pressure to afford the title compound (41.7 mg, 0.077 mmol, 51% yield) as a white solid. $^1$H NMR (400 MHz, DMSO-$d_6$) δ 10.96 (s, 1H), 9.20 (s, 1H), 8.15 (d, J=1.9 Hz, 2H), 8.01-7.82 (m, 2H), 7.80-7.56 (m, 3H), 7.12 (s, 1H), 7.01 (dd, J=8.4, 2.2 Hz, 1H), 5.11-4.97 (m, 2H), 4.37 (d, J=17.2 Hz, 1H), 4.30-4.20 (m, 1H), 4.11 (t, J=7.6 Hz, 1H), 4.01 (m, 1H), 3.97-3.79 (m, 3H), 3.64 (m, 2H), 3.08-2.97 (m, 1H), 2.95-2.75 (m, 3H), 2.58 (m, 2H), 2.39 (m, 3H), 2.08-1.92 (m, 2H), 1.86 (m, 1H); MS (ESI) m/z 541.2 $[M+1]^+$.

Example S75. 3-(5-(((S)-1-((2-((R)-2,2-Dimethyltetrahydro-2H-pyran-4-yl)quinazolin-6-yl)methyl)pyrrolidin-3-yl)oxy)-1-oxoisoindolin-2-yl)piperidine-2,6-dione

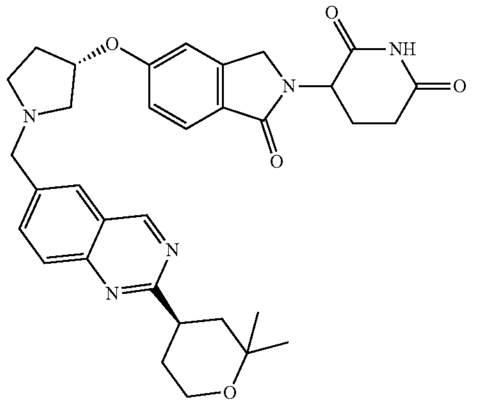 [SMILES: CC1(C)C[C@H](c2ncc3cc(CN4CC[C@H](Oc5ccc6c(c5)CN(C5CCC(=O)NC5=O)C6=O)C4)ccc3n2)CCO1]

6-Bromo-2-(2,2-dimethyltetrahydro-2H-pyran-4-yl)-1,2,3,4-tetrahydroquinazolin-2-ol. A stirred solution of 2,2-dimethyltetrahydro-2H-pyran-4-carboxylic acid (1 g, 6.32 mmol) in thionyl chloride (12 mL) was stirred at 80° C. for 2 h under nitrogen. The mixture was concentrated to afford 2,2-dimethyltetrahydro-2H-pyran-4-carbonyl chloride. To a stirred solution of 2-(aminomethyl)-4-bromoaniline (1.5 g, 7.46 mmol) and triethylamine (7.85 mL, 56.3 mmol) in dichloromethane (30 mL) was added 2,2-dimethyltetrahydro-2H-pyran-4-carbonyl chloride (1 g, 5.66 mmol) dropwise at 0° C. and the above mixture was stirred at room temperature for 2 h under nitrogen. The mixture was concentrated to afford the crude title compound. MS (ESI) m/z 341.1 $[M+1]^+$.

6-Bromo-2-(2,2-dimethyltetrahydro-2H-pyran-4-yl)-1,4-dihydroquinazoline. A solution of 6-bromo-2-(2,2-dimethyltetrahydro-2H-pyran-4-yl)-1,2,3,4-tetrahydro quinazolin-2-ol (800 mg, 2.34 mmol) in phosphorus oxychloride (10 mL) was stirred at 80° C. for 2 h under nitrogen. The mixture was concentrated and the residue was basified to pH~8 with sodium carbonate carefully and extracted with ethyl acetate. The extracts were washed with brine, dried over anhydrous sodium sulfate, filtered and concentrated. The mixture was concentrated to afford the crude title compound. MS (ESI) m/z 323.0 $[M+1]^+$.

6-Bromo-2-(2,2-dimethyltetrahydro-2H-pyran-4-yl)quinazoline. To a stirred solution of 6-bromo-2-(2,2-dimethyltetrahydro-2H-pyran-4-yl)-1,4-dihydro quinazoline (500 mg, 1.55 mmol) in dichloromethane (10 mL) was added manganese dioxide (2.69 g, 30.94 mmol). The above mixture was stirred at room temperature for 48 h under nitrogen. The mixture was filtered and the filtrate was concentrated. The residue was purified by silica gel chromatography (0 to 20% ethyl acetate in petroleum ether) to afford the title compound (400 mg, 1.25 mmol, 80% yield) as a light-yellow oil. MS (ESI) m/z 321.0 $[M+1]^+$.

(R)-2-(2,2-Dimethyltetrahydro-2H-pyran-4-yl)-6-vinylquinazoline. To a stirred solution of 6-bromo-2-(2,2-dimethyltetrahydro-2H-pyran-4-yl)quinazoline (400 mg, 1.25 mmol) and potassium trifluoro(vinyl)borate (240 mg, 1.79 mmol) in 1,4-dioxane (6 mL) and water (0.6 ml) were added tetrakis(triphenylphosphine)palladium (172 mg, 0.15 mmol) and cesium carbonate (1.2 g, 3.68 mmol). The above mixture was stirred at 80° C. for 3 h under nitrogen. Then the mixture was added water and extracted with ethyl acetate. The extracts were washed with brine, dried over anhydrous sodium sulfate, filtered and concentrated. The residue was purified by silica gel chromatography (0 to 25% ethyl acetate in petroleum ether) to afford the racemate version of title compound (450 mg) which was further purified by Anal-SFC with the following conditions: Column: CHIRALPAK ID-3, 4.6*50 mm 3 um; Mobile Phase A: hexane (0.1% diethylamine): ethanol=95:5; Flow rate: 1 mL/min; Gradient: 0% B to 0% B; Injection Volume: 5 μl. Pure fractions were evaporated to afford the title compound (70 mg, 0.26 mmol, 21% yield) as a light-yellow oil. MS (ESI) m/z 269.1 $[M+1]^+$.

(R)-2-(2,2-Dimethyltetrahydro-2H-pyran-4-yl)quinazoline-6-carbaldehyde. To a stirred solution of (R)-2-(2,2-dimethyltetrahydro-2H-pyran-4-yl)-6-vinyl quinazoline (70 mg, 0.26 mmol) in tert-butanol (4 mL) and water (4 mL) were added potassium osmate (10 mg, 0.03 mmol), 4-methyl-morpholin4-oxide (61 mg, 0.52 mmol) and citric acid (111 mg, 0.52 mmol). The above mixture was stirred at room temperature for 3 h under nitrogen. Then the mixture was added sodium periodate (167 mg, 0.78 mmol) and the mixture was stirred for another 1 h. The reaction mixture was added saturated sodium bicarbonate to PH~7 and extracted with ethyl acetate. The extracts were dried over sodium sulfate, filtered and concentrated. The residue was purified by silica gel chromatography (0 to 25% ethyl acetate in petroleum ether) to afford the title compound (40 mg, 0.15 mmol, 57% yield) as a light-yellow oil. MS (ESI) m/z 271.2 $[M+1]^+$.

3-(5-(((S)-1-((2-((R)-2,2-Dimethyltetrahydro-2H-pyran-4-yl)quinazolin-6-yl)methyl)pyrrolidin-3-yl)oxy)-1-oxoisoindolin-2-yl)piperidine-2,6-dione. To a solution of (R)-2-(2,2-dimethyltetrahydro-2H-pyran-4-yl)quinazoline-6-carbaldehyde (40 mg, 0.15 mmol), 3-(1-oxo-5-(((S)-pyrrolidin-3-yl)oxy)isoindolin-2-yl)piperidine-2,6-dione; 2,2,2-trifluoroacetic acid (80 mg, 0.18 mmol) and triethylamine (50 mg, 0.50 mmol) in dichloromethane (4 mL) was added sodium triacetoxyborohydride (130 mg, 0.61 mmol). The mixture was stirred for 48 h at room temperature under nitrogen. The resulting mixture was concentrated. The residue was purified by silica gel chromatography (0 to 10% methanol in dichloromethane) and preparative HPLC further with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 5% B to 25% B in 7 min, 25% B; Wave Length: 254/220 nm; $RT_1$ (min): 6.32. The fractions containing desired product were collected and evaporated under reduced pressure to afford the title compound (28.7 mg, 0.05 mmol, 32% yield) as a white solid. $^1H$ NMR (400 MHz, Methanol-$d_4$) δ 9.48 (s, 1H), 8.28 (s, 1H), 8.08-8.04 (m, 2H), 8.01 (d, J=8.6 Hz, 1H), 7.72 (d, J=8.4 Hz, 1H), 7.12-7.02 (m, 2H), 5.16-5.07 (m, 2H), 4.44 (d, J=6.5 Hz, 2H), 4.14 (m, 2H), 3.99-3.84 (m, 2H), 3.50-3.47 (m, 1H), 3.25-3.23 (m, 1H), 3.18-3.08 (m, 2H), 2.96-2.87 (m, 2H), 2.82-2.75 (m, 1H), 2.55-2.45 (m, 2H), 2.16 (m, 2H), 2.03-1.84 (m, 4H), 1.41 (s, 3H), 1.30 (s, 3H); MS (ESI) m/z 584.4 $[M+1]^+$.

Example S76. 3-(5-(((S)-1-((2-((S)-2,2-Dimethyltetrahydro-2H-pyran-4-yl)quinazolin-6-yl)methyl)pyrrolidin-3-yl)oxy)-1-oxoisoindolin-2-yl)piperidine-2,6-dione

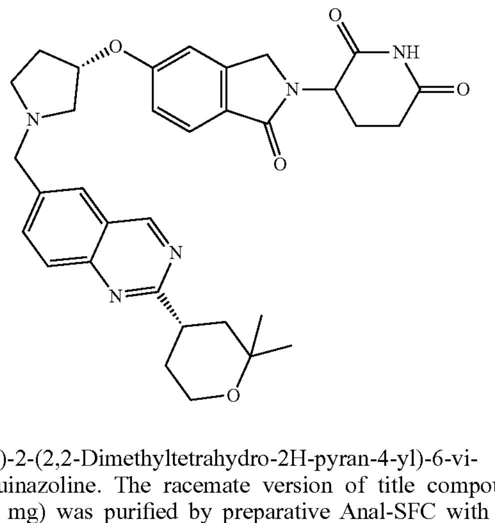

(S)-2-(2,2-Dimethyltetrahydro-2H-pyran-4-yl)-6-vinylquinazoline. The racemate version of title compound (450 mg) was purified by preparative Anal-SFC with the following conditions: Column: CHIRALPAK ID-3, 4.6*50 mm, 3 um; Mobile Phase A: hexane (0.1% diethylamine): ethanol=95:5; Flow rate: 1 mL/min; Gradient: 0% B to 0% B; Injection Volume: 5 μL to afford the title compound (60 mg, 0.22 mmol, 12% yield) as a light-yellow oil. MS (ESI) m/z 269.1 $[M+1]^+$.

(S)-2-(2,2-Dimethyltetrahydro-2H-pyran-4-yl)quinazoline-6-carbaldehyde. To a stirred solution of (S)-2-(2,2-dimethyltetrahydro-2H-pyran-4-yl)-6-vinyl quinazoline (60 mg, 0.22 mmol) in tert-butanol (4 mL) and water (4 mL) were added potassium osmate (9 mg, 0.02 mmol), 4-methylmorpholin4-oxide (52 mg, 0.45 mmol) and citric acid (95 mg, 0.45 mmol). The above mixture was stirred at room temperature for 3 h under nitrogen. Then to the above mixture was added sodium periodate (143 mg, 0.67 mmol) and the mixture was stirred for another 1 h. The reaction mixture was added saturated sodium bicarbonate to pH~7 and extracted with ethyl acetate. The extracts were washed with brine, dried over anhydrous sodium sulfate, filtered and concentrated. The residue was purified by silica gel chromatography (0 to 25% ethyl acetate in petroleum ether) to afford the title compound (40 mg, 0.15 mmol, 66% yield) as a light-yellow oil. MS (ESI) m/z 271.2 $[M+1]^+$.

3-(5-(((S)-1-((2-((S)-2,2-Dimethyltetrahydro-2H-pyran-4-yl)quinazolin-6-yl)methyl)pyrrolidin-3-yl)oxy)-1-oxoisoindolin-2-yl)piperidine-2,6-dione. To a solution of (S)-2-(2,2-dimethyltetrahydro-2H-pyran-4-yl)quinazoline-6-carbaldehyde (40 mg, 0.15 mmol), 3-(1-oxo-5-(((S)-pyrrolidin-3-yl)oxy)isoindolin-2-yl)piperidine-2,6-dione; 2,2,2-trifluoroacetic acid (80 mg, 0.18 mmol) and triethylamine (50 mg, 0.50 mmol) in dichloromethane (4 mL) was added sodium triacetoxyborohydride (130 mg, 0.61 mmol). The mixture was stirred for 48 h at room temperature under nitrogen. The resulting mixture was concentrated. The residue was purified by silica gel chromatography (0 to 10% methanol in dichloromethane) and preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 5% B to 25% B in 7 min, 25% B; Wave Length: 254/220 nm; $RT_1$ (min): 6.32. The fractions containing desired product were collected and evaporated under reduced pressure to afford the title compound (30.3 mg, 0.05 mmol, 34% yield) as a white solid. $^1H$ NMR (400 MHz, Methanol-$d_4$) δ 9.48 (s, 1H), 8.13-8.05 (m, 2H), 8.02 (d, J=8.6 Hz, 1H), 7.72 (d, J=8.4 Hz, 1H), 7.13-7.03 (m, 2H), 5.12-5.07 (m, 2H), 4.50-4.40 (m, 2H), 4.19 (d, J=2.1 Hz, 2H), 3.98-3.83 (m, 2H), 3.50-3.47 (m, 1H), 3.31-3.24 (m, 1H), 3.23-3.12 (m, 2H), 3.01-2.85 (m, 2H), 2.83-2.75 (m, 1H), 2.56-2.41 (m, 2H), 2.17 (m, 2H), 2.06-1.83 (m, 4H), 1.41 (s, 3H), 1.30 (s, 3H); MS (ESI) m/z 584.4 $[M+1]^+$.

Example S77. 3-(5-(((S)-1-((5-Fluoro-2-(tetrahydro-2H-pyran-4-yl)quinolin-6-yl)methyl)pyrrolidin-3-yl)oxy)-1-oxoisoindolin-2-yl)piperidine-2,6-dione

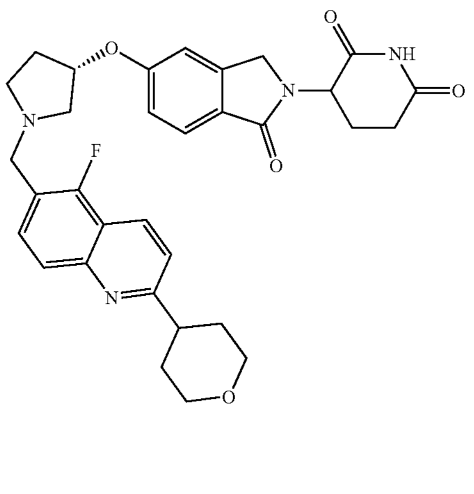 [SMILES: O=C1CCC(N2Cc3cc(O[C@H]4CCN(Cc5ccc6nc(C7CCOCC7)ccc6c5F)C4)ccc3C2=O)C(=O)N1]

(6-Amino-3-bromo-2-fluorophenyl)methanol. To a stirred solution of 6-amino-3-bromo-2-fluorobenzoic acid (900 mg, 3.85 mmol) in THF (15 mL) was added lithium aluminum hydride (2.5 M in THF, 3 mL, 7.50 mmol) dropwise at 0° C. under nitrogen. The mixture was warmed to room temperature and stirred for 1 h. The resulting mixture was quenched with sodium hydroxide (2 M in water, 5 mL, 10 mmol) at 0° C., then stirred for 30 min at this temperature and filtered. The filter cake was washed with 60 mL THF. The filtrate combined were concentrated to afford the title compound (750 mg, 3.40 mmol, 88% yield) as a yellow solid. MS (ESI) m/z 219.9 $[M+1]^+$.

6-Bromo-5-fluoro-2-(tetrahydro-2H-pyran-4-yl)quinoline. To a stirred solution of (6-amino-3-bromo-2-fluorophenyl)methanol (730 mg, 3.40 mmol) and 1-tetrahydropyran-4-ylethanone (850 mg, 6.64 mmol) in toluene (15 mL) was added lithium tert-butoxide (530 mg, 6.64 mmol) at room temperature. Then the reaction mixture was stirred at 110° C. for 12 h under nitrogen. The mixture was filtered and the filtrate was concentrated. The crude product was purified by reverse phase flash (10-40% acetonitrile+0.05% ammonium bicarbonate in water, over 25 min) to give the title compound (375 mg, 1.20 mmol, 36% yield) as a yellow solid. MS (ESI) m/z 310.0 $[M+1]^+$.

5-Fluoro-2-(tetrahydro-2H-pyran-4-yl)-6-vinylquinoline. To a solution of 6-bromo-5-fluoro-2-(tetrahydro-2H-pyran-4-yl)quinoline (360 mg, 1.16 mmol) in 1,4-dioxane (10 mL) and water (2 mL) were added potassium trifluoro(vinyl) borate (310 mg, 2.32 mmol), dichlorobis(triphenylphosphine)palladium(II) dichloromethane adduct (169 mg, 0.23 mmol) and sodium carbonate (369 mg, 3.48 mmol) at room temperature under nitrogen. Then the reaction mixture was stirred at 80° C. for 2 h under nitrogen. The resulting mixture was diluted with water and extracted with ethyl acetate. The extracts were washed with brine, dried over anhydrous sodium sulfate, filtered and concentrated. The residue was purified by silica gel chromatography (0 to 50% ethyl acetate in petroleum ether) to give the title compound (230 mg, 0.89 mmol, 76% yield) as a yellow solid. MS (ESI) m/z 258.1 $[M+1]^+$.

5-Fluoro-2-(tetrahydro-2H-pyran-4-yl)quinoline-6-carbaldehyde. To a stirred solution of 5-fluoro-2-(tetrahydro-2H-pyran-4-yl)-6-vinylquinoline (120 mg, 0.47 mmol), 4-methylmorpholine N-oxide (109 mg, 0.93 mmol) and citric acid (179 mg, 0.93 mmol) in water (5 mL) and tert-butanol (5 mL) was added potassium osmate (15 mg, 0.04 mmol). The reaction mixture was stirred at room temperature for 3 h under nitrogen. Then sodium periodate (299 mg, 1.40 mmol) was added into the above mixture. The resulting mixture was stirred for 1 h at room temperature under nitrogen. The mixture was added saturated sodium bicarbonate to pH~7 and extracted with ethyl acetate. The extracts were dried over anhydrous sodium sulfate, filtered and concentrated. The residue was purified by silica gel chromatography (0 to 50% ethyl acetate in petroleum ether) to afford the title compound (100 mg, 0.38 mmol, 81% yield) as an off-white solid. MS (ESI) m/z 260.0 $[M+1]^+$.

3-(5-(((S)-1-((5-fluoro-2-(tetrahydro-2H-pyran-4-yl)quinolin-6-yl)methyl)pyrolidin-3-yl)oxy)-1-oxoisoindolin-2-yl)piperidine-2,6-dione. To a stirred solution of 5-fluoro-2-(tetrahydro-2H-pyran-4-yl)quinoline-6-carbaldehyde (100 mg, 0.38 mmol) in dichloromethane (5 mL) was added (S)-3-(1-oxo-5-(((S)-pyrrolidin-3-yl) oxy)isoindolin-2-yl) piperidine-2,6-dione; 2,2-2-trifluoroacetic acid (480 mg, 1.08 mmol) and triethylamine (56 mg, 0.56 mmol), triethylamine (0.20 mL, 1.48 mmol) and sodium triacetoxyborohydride (200 mg, 0.94 mmol). The reaction mixture was stirred at 30° C. for 1 h under nitrogen. Most of the solvent was removed under reduced pressure and the residue was purified by normal phase flash (0-10% methanol in dichloromethane) and further purified by preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 30% B in 7 min, 30% B; Wave Length: 254/210 nm; $RT_1$ (min): 6.82. The fractions containing desired product were collected and evaporated under reduced pressure to give the desired product (42.9 mg, 0.075 mmol, 19% yield) as a white solid. $^1$H NMR (400 MHz, Methanol-$d_4$) δ 8.50 (d, J=8.7 Hz, 1H), 7.89-7.80 (m, 2H), 7.72-7.69 (m, 1H), 7.60 (d, J=8.7 Hz, 1H), 7.08-7.02 (m, 2H), 5.15-5.07 (m, 2H), 4.49-4.39 (m, 2H), 4.14-4.10 (m, 4H), 3.68-3.62 (m, 2H), 3.25-3.19 (m, 2H), 3.10-3.07 (m, 2H), 2.95-2.76 (m, 3H), 2.53-2.42 (m, 2H), 2.18-2.00 (m, 4H), 1.95-1.91 (m, 2H); MS (ESI) m/z 573.1 $[M+1]^+$.

Example S78. (S)-3-(5-(((S)-1-((2-Morpholinoquinazolin-6-yl)methyl)pyrrolidin-3-yl)oxy)-1-oxoisoindolin-2-yl)piperidine-2,6-dione

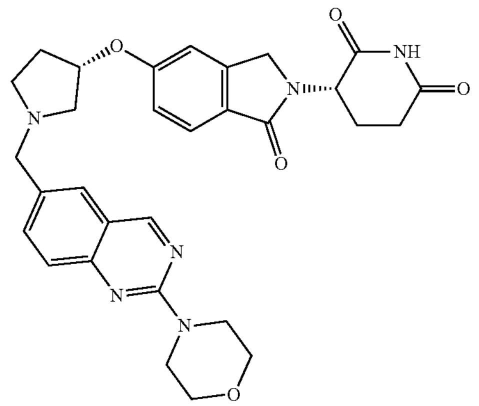 [SMILES: O=C1CC[C@H](N2Cc3cc(O[C@H]4CCN(Cc5ccc6nc(N7CCOCC7)ncc6c5)C4)ccc3C2=O)C(=O)N1]

Tert-butyl (S)-5-amino-4-(5-bromo-1-oxoisoindolin-2-yl)-5-oxopentanoate. To a stirred solution of methyl 4-bromo-2-(bromomethyl)benzoate (5 g, 16.23 mmol) in acetonitrile (20 mL) was added N,N-diisopropylethylamine (8.6 mL, 49.2 mmol), tert-butyl (4S)-4,5-diamino-5-oxopentanoate (3.3 g, 16.20 mmol) at room temperature. Then the reaction mixture was stirred at 50° C. for 18 h under nitrogen. The resulting mixture was concentrated. The crude product was stirred with tert-butyl methyl ether (50 ml) at room temperature for 1 h. The solids collected was stirred with water (50 ml) at room temperature for 1 h. The solids were collected to give the title compound (4.7 g, 11.84 mmol, 73% yield) as an off-white solid. MS (ESI) m/z 397.0 [M+1]+.

Benzyl (S)-3-((2-((S)-1-amino-5-(tert-butoxy)-1,5-dioxopentan-2-yl)-1-oxoiso indolin-5-yl)oxy)pyrrolidine-1-carboxylate. The reaction was performed in a 250 mL round-bottomed flask and irradiated with dish blue-LED (450 nm) equipped photoreactor with fan cooling (to maintain <30 deg celsius temp.). To a stirred solution of 2,2,6,6-tetramethylpiperidine (3.2 g, 22.7 mmol), (4,4'-Di-tert-butyl-2,2'-bipyridine)bis[2-(2',4'-difluorophenyl)-5-methylpyridine]iridium (III) Hexafluorophosphate (410 mg, 0.40 mmol) in acetonitrile (100 mL) was added (S)-1-benzylpyrrolidin-3-ol (6.7 g, 37.81 mmol), tert-butyl (4S)-5-amino-4-(5-bromo-1-oxo-isoindolin-2-yl)-5-oxo-pentanoate (8.0 g, 20.1 mmol), 4,4'-di-tert-butyl-2,2'-bipyridine (271 mg, 1.0 mmol), nickel (II) chloride ethylene glycol dimethyl ether complex (222 mg, 1.0 mmol) under nitrogen. Then the reaction mixture was stirred at room temperature for 18 h under nitrogen. The resulting mixture was filtered and concentrated. The residue was purified by silica gel chromatography (50% to 100% ethyl acetate in petroleum ether) to give the title compound (5 g, 9.30 mmol, 46% yield) as a yellow solid. MS (ESI) m/z 538.4 $[M+1]^+$.

Tert-butyl (S)-5-amino-5-oxo-4-(1-oxo-5-(((S)-pyrrolidin-3-yl)oxy)isoindolin-2-yl)pentanoate. To a stirred solution of (3S)-3-[2-[(1S)-4-tert-butoxy-1-carbamoyl-4-oxo-butyl]-1-oxo-isoindolin-5-yl]oxypyrrolidine-1-carboxylate (1.0 g, 1.9 mmol) in ethanol (20 mL) was added palladium 10% on carbon (150 mg, wetted with ca. 55% water), acetic acid (134 mg) at room temperature and the reaction mixture was stirred at room temperature for 12 h under hydrogen. The resulting mixture was filtered and the filtrate was concentrated to give the title compound (700 mg, 1.74 mmol, 91% yield) as a yellow solid. MS (ESI) m/z 404.3 $[M+1]^+$.

Tert-butyl (S)-5-amino-4-(5-(((S)-1-((2-morpholinoquinazolin-6-yl)methyl) pyrrolidin-3-yl)oxy)-1-oxoisoindolin-2-yl)-5-oxopentanoate. To a stirred solution of tert-butyl (S)-5-amino-5-oxo-4-(1-oxo-5-(((S)-pyrrolidin-3-yl)oxy) isoindolin-2-yl) pentanoate (200 mg, 0.49 mmol), 2-morpholinoquinazoline-6-carbaldehyde (105 mg, 0.43 mmol), acetic acid (25 µL) in THF (5 mL) pre-stirred for 30 min was added sodium triacetoxyborohydride (229 mg, 1.10 mmol) at 0° C. and the solution was stirred at room temperature for 12 h under nitrogen. The resulting solution was concentrated and the residue was purified silica gel chromatography (0 to 5% methanol in dichloromethane) to afford the title compound (200 mg, 0.32 mmol, 74% yield) as a yellow solid. MS (ESI) m/z 631.5 $[M+1]^+$.

(S)-3-(5-(((S)-1-((2-Morpholinoquinazolin-6-yl)methyl) pyrrolidin-3-yl)oxy)-1-oxoisoindolin-2-yl)piperidine-2,6-dione. A solution of tert-butyl (S)-5-amino-4-(5-(((S)-1-((2-morpholinoquinazolin-6-yl)methyl)pyrrolidin-3-yl)oxy)-1-oxoisoindolin-2-yl)-5-oxopentanoate (100 mg, 0.16 mmol) and benzenesulfonic acid (75 mg, 0.48 mmol) in acetonitrile (10 mL) was stirred at 60° C. for 12 h under nitrogen. The resulting solution was added saturated sodium bicarbonate to pH~7 and extracted with dichloromethane. The extracts were washed with brine, dried over anhydrous sodium sulfate, filtered and concentrated. The residue was purified by preparative SFC with the following conditions: Column: exsil chieal-NR, 3*25 cm, 8 µm; mobile phase A: carbon dioxide, mobile phase B: isopropyl alcohol:acetonitrile: dichloromethane=2:1:1; flow rate: 80 mL/min; gradient: isocratic 50% B; column temperature (° C.): 35; back pressure (bar): 100; wave length: 220 nm; $RT_1$ (min): 13.23; sample solvent: dichloromethane:acetonitrile=1:1; injection volume: 4.8 mL; number of runs: 12. The fractions containing desired product were collected and evaporated under reduced pressure to afford the title compound (38.4 mg, 0.069 mmol, 43% yield) as a yellow solid. $^1$H NMR (300 MHz, DMSO-$d_6$) δ 9.21 (s, 1H), 7.82-7.67 (m, 2H), 7.62 (d, J=8.4 Hz, 1H), 7.50 (d, J=8.6 Hz, 1H), 7.11 (d, J=2.1 Hz, 1H), 7.01 (dd, J=8.4, 2.2 Hz, 1H), 5.05 (m, 2H), 4.38 (d, J=17.3 Hz, 1H), 4.25 (d, J=17.3 Hz, 1H), 3.82 (m, 4H), 3.70 (m, 6H), 3.00-2.59 (m, 4H), 2.57 (m, 2H), 2.37 (m, 2H), 2.05-1.92 (m, 1H), 1.90-1.76 (m, 1H); MS (ESI) m/z 557.3 $[M+1]^+$.

Example S79. 3-(5-(((S)-1-((2-((1s,4R)-4-Methoxy-cyclohexyl) quinolin-6-yl) methyl)pyrrolidin-3-yl) oxy)-1-oxoisoindolin-2-yl)piperidine-2,6-dione

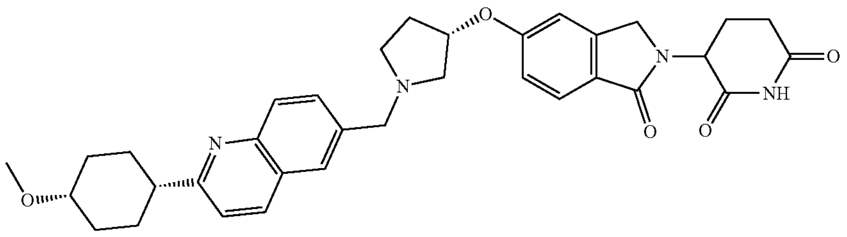 [SMILES: CO[C@H]1CC[C@@H](c2ccc3cc(CN4CC[C@H](Oc5ccc6c(c5)CN(C5CCC(=O)NC5=O)C6=O)C4)ccc3n2)CC1]

(2-((1s,4s)-4-Methoxycyclohexyl)quinolin-6-yl)methanol. The (2-(4-methoxycyclohexyl)quinolin-6-yl)methanol (260 mg, 0.96 mmol) was purified by preparative Chiral SFC with the following conditions: Column: Lux 3 µCellulose-3, 4.6*100 mm, 3 um; Mobile phase B: methanol (1%-2M-ammonia-methanol); Flow rate: 2 mL/min; Gradient: isocratic 10% B; Wave Length: 220 nm. The fractions containing desired product were collected and evaporated under reduced pressure to afford the title compound (80 mg, 0.29 mmol, 31% yield) as a white solid. MS (ESI) m/z 272.0 $[M+1]^+$.

2-((1s,4s)-4-Methoxycyclohexyl)quinoline-6-carbaldehyde. A solution of (2-((1s,4s)-4-methoxycyclohexyl)quinolin-6-yl)methanol (80 mg, 0.29 mmol) and manganese dioxide (256 mg, 2.95 mmol) in dichloromethane (5 mL) was stirred at 50° C. for 5 h under nitrogen. The mixture was diluted with dichloromethane, filtered and the filtrate was concentrated to afford the title compound (65 mg, 0.24 mmol, 81% yield) as a white solid. MS (ESI) m/z 272.2 $[M+1]^+$.

3-(5-(((S)-1-((2-((1s,4R)-4-Methoxycyclohexyl)quinolin-6-yl)methyl)pyrrole-din-3-yl)oxy)-1-oxoisoindolin-2-yl) piperidine-2,6-dione. To a stirred mixture of 2-((1s,4s)-4-Methoxycyclohexyl)quinoline-6-carbaldehyde (45 mg, 0.17 mmol), 3-[1-oxo-5-[(3S)-pyrrolidin-3-yl]oxy-isoindolin-2-yl]piperidine-2,6-dione; hydrochloride (70 mg, 0.19 mmol) and triethylamine (0.06 mL, 0.40 mmol) in dichloromethane (5 mL) was added sodium triacetoxyborohydride (160 mg, 0.75 mmol) in several portions and the mixture was stirred at room temperature for 2 h under nitrogen. The resulting mixture was concentrated and the residue was purified by silica gel chromatography (0-10% methanol in dichloromethane) and purified further by preparative thin layer chromatography with the following conditions: Column: sunfire prep C18 column, 30*150 mm, 5 um; Mobile phase A: water (0.1% formic acid), Mobile phase B: acetonitrile; Flow rate: 60 mL/min; Gradient: 2% B to 17% B in 9 min, 17% B; Wave Length: 254/220 nm; RT1 (min): 10.38. to afford the title compound (56 mg, 0.09 mmol, 53% yield) as a white solid. $^1$H NMR (400 MHz, Methanol-$d_4$) δ 8.21 (m, 1H), 8.01 (d, J=8.7 Hz, 1H), 7.87 (s, 1H), 7.79-7.77 (m, 1H), 7.71 (d, J=8.4 Hz, 1H), 7.58 (m, 1H), 7.10-7.00 (m, 2H), 5.12-5.10 (m, 2H), 4.50-4.36 (m, 2H), 4.01-3.92 (m, 2H), 3.50 (s, 3H), 3.41 (m, 1H), 3.11-3.09 (m, 1H), 3.00 (m, 4H), 2.80-2.74 (m, 2H), 2.50-2.40 (m, 2H), 2.30-2.20 (m, 2H), 2.16-2.00 (m, 4H), 1.80-1.61 (m, 2H), 1.40 (m, 2H); MS (ESI) m/z 583.3 [M+1]+.

Example S80. 3-(5-(((S)-1-((2-((1S,3R)-3-Hydroxycyclohexyl)quinolin-6-yl)methyl)pyrrolidin-3-yl)oxy)-1-oxoisoindolin-2-yl)piperidine-2,6-dione

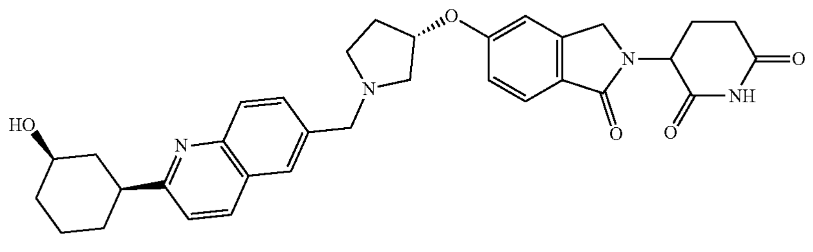 [SMILES: O=C1CCC(N2Cc3cc(O[C@H]4CCN(Cc5ccc6nc([C@H]7CCC[C@@H](O)C7)ccc6c5)C4)ccc3C2=O)C(=O)N1]

2-((1S,3R)-3-Hydroxycyclohexyl)quinoline-6-carbaldehyde. To a solution of (1R,3S)-3-[6-(hydroxymethyl)-2-quinolyl]cyclohexanol (170 mg, 0.66 mmol) in dichloromethane (10 mL) was added manganese dioxide (1.2 g, 13.80 mmol) under nitrogen atmosphere. The mixture was stirred for 12 h at room temperature under nitrogen. The resulting mixture was filtered and the filter cake was washed with dichloromethane (3×10 mL). The filtrate was concentrated under reduced pressure to afford the title compound (170 mg, 0.66 mmol, 100% yield) as a black solid. MS (ESI) m/z 256.1 $[M+1]^+$.

3-(5-(((S)-1-((2-((1S,3R)-3-Hydroxycyclohexyl)quinolin-6-yl)methyl)pyrrolidin-3-yl)oxy)-1-oxoisoindolin-2-yl)piperidine-2,6-dione. To a solution of 3-[1-oxo-5-[(3S)-pyrrolidin-3-yl]oxy-isoindolin-2-yl]piperidine-2,6-dione (60 mg, 0.18 mmol), 2-(oxetan-3-yl)quinazoline-6-carbaldehyde (40 mg, 0.16 mmol) and triethylamine (28 mg, 0.28 mmol) in dichloromethane (5 mL) was added sodium triacetoxyborohydride (116 mg, 0.55 mmol) at room temperature. The solution was stirred for 2 h at room temperature. The resulting solution was concentrated and the residue was purified by silica gel chromatography (0-10% methanol in dichloromethane) and preparative HPLC with the following conditions: Sunfire prep C18 column, 30*150 mm, 5 μm; Mobile Phase A: water (0.1% formic acid), Mobile Phase B: acetonitrile; Flow rate: 60 mL/min; Gradient: 2% B to 16% B in 10 min, 16% B; Wave Length: 254/210 nm; $RT_1$ (min): 10.33. The fractions containing desired product were collected and evaporated under reduced pressure to afford the title compound (11.6 mg, 0.02 mmol, 12% yield) as an off-white solid. $^1H$ NMR (400 MHz, Methanol-$d_4$) δ 8.29 (d, J=8.6 Hz, 1H), 8.05 (d, J=8.7 Hz, 1H), 7.97 (s, 1H), 7.84 (d, J=8.7 Hz, 1H), 7.72 (m, J=8.5, 2.3 Hz, 1H), 7.54 (d, J=8.6 Hz, 1H), 7.13-7.03 (m, 2H), 5.18 (s, 1H), 5.12 (m, 1H), 4.52-4.37 (m, 2H), 4.31 (m, 2H), 3.77 (m, 1H), 3.32 (m, 2H), 3.20 (m, 1H), 3.09-2.85 (m, 2H), 2.79 (m, 2H), 2.50 (m, 2H), 2.19 (m, 4H), 1.95 (m, 2H), 1.74-1.52 (m, 3H), 1.37 (m, 1H); MS (ESI) m/z 569.2 $[M+1]^+$.

Example S81. 3-(5-(((S)-1-((2-((1R,3R)-3-Hydroxycyclohexyl)quinolin-6-yl)methyl)pyrrolidin-3-yl)oxy)-1-oxoisoindolin-2-yl)piperidine-2,6-dione

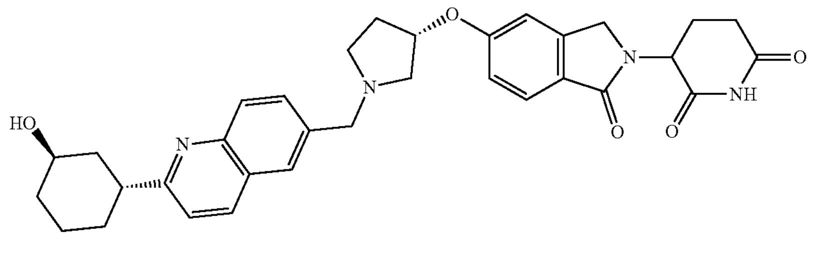 [SMILES: O=C1CCC(N2Cc3cc(O[C@H]4CCN(Cc5ccc6nc([C@@H]7CCC[C@@H](O)C7)ccc6c5)C4)ccc3C2=O)C(=O)N1]

Methyl 2-(3-oxocyclohex-1-en-1-yl)quinoline-6-carboxylate. To a solution of methyl 2-chloroquinoline-6-carboxylate (2.0 g, 9.02 mmol), 3-(4,4,5,5-tetramethyl-1,3,2-dioxaborolan-2-yl)cyclohex-2-en-1-one (2.0 g, 9.02 mmol), sodium carbonate (1.9 g, 18.05 mmol) in 1,4-dioxane (20 mL) and water (2 mL) was added [1,1'-bis(diphenylphosphino)ferrocene]dichloropalladium(II) (661 mg, 0.91 mmol). The mixture was stirred for 12 h at 90° C. under nitrogen. The resulting mixture was added water and extracted with ethyl acetate. The extracts were washed with brine, dried over anhydrous sodium sulfate, filtered and concentrated. The residue was purified by silica gel chromatography (0 to 5% ethyl acetate in petroleum ether) to afford the title compound (2.3 g, 8.18 mmol, 91% yield) as a light yellow oil. MS (ESI) m/z 282.1 $[M+1]^+$.

Methyl 2-(3-oxocyclohexyl)quinoline-6-carboxylate. To a solution of methyl 2-(3-oxocyclohexen-1-yl)quinoline-6-carboxylate (2.3 g, 8.18 mmol) in methanol (25 mL) was added 10% palladium on carbon (1.2 g, wetted with ca. 50% water). The mixture was stirred for 2 h at room temperature under hydrogen (~2 bar). The resulting mixture was filtered and the filter cake was washed with dichloromethane (3×10 mL). The filtrate was concentrated under reduced pressure to afford the title compound (2.3 g, 8.180 mmol, 99% yield) as a light-yellow solid. MS (ESI) m/z 284.1 $[M+1]^+$.

3-(6-(Hydroxymethyl)quinolin-2-yl)cyclohexan-1-ol. To a solution of methyl 2-(3-oxocyclohexyl)quinoline-6-carboxylate (1.5 g, 5.29 mmol) in THF (15 mL) was added lithium aluminum hydride (2.5 M in THF, 2.1 mL, 5.25 mmol) at 0° C. under nitrogen. The resulting mixture was stirred at this temperature for 30 min. The mixture was quenched with water, and the pH of the solution was adjusted with 15% sodium hydroxide solution to pH~8 and extracted with ethyl acetate. The extracts were washed with brine, dried over anhydrous sodium sulfate, filtered and concentrated. The residue was purified by silica gel chromatography (0-10% methanol in dichloromethane) to afford the title compound (510 mg, 1.98 mmol, 37% yield) as a yellow solid. MS (ESI) m/z 258.1 $[M+1]^+$.

(1R,3R)-3-(6-(Hydroxymethyl)quinolin-2-yl)cyclohexan-1-ol and (1R,3S)-3-(6-(hydroxymethyl)quinolin-2-yl)cyclohexan-1-ol. The racemate (510 mg) was separated by preparative SFC with the following conditions: Column: CHIRALPAK IH, 3*25 cm, 5 μm; Mobile Phase A: carbon dioxide, Mobile Phase B: methanol (0.1% 2M ammonia-methanol); Flow rate: 100 mL/min; Gradient: 50% B; Column Temperature: 35° C.; Back Pressure: 100 bar; 220 nm; $RT_1$: 2; $RT_2$: 4.25; Injection Volume: 4.8 ml; Number Of Runs: 8. Pure fractions were evaporated to afford the title compound (RR isomer, RT1:2, 180 mg, 0.70 mmol) as a light yellow solid and the RS isomer (RT2:4.25, 170 mg, 0.661 mmol) as a light yellow solid. MS (ESI) m/z 258.1 $[M+1]^+$.

2-((1R,3R)-3-Hydroxycyclohexyl)quinoline-6-carbaldehyde. To a solution of (1R,3R)-3-[6-(hydroxymethyl)-2-quinolyl]cyclohexanol (80 mg, 0.31 mmol) in dichloromethane (10 mL) was added manganese dioxide (540 mg, 6.22 mmol). The mixture was stirred for 12 h at room temperature under nitrogen. The resulting mixture was filtered and the filter cake was washed with dichloromethane (3×10 mL). The filtrate was concentrated under reduced pressure to afford the title compound (80 mg, 0.31 mmol, 100% yield) as a black solid. MS (ESI) m/z 256.1 $[M+1]^+$.

3-(5-(((S)-1-((2-(Oxetan-3-yl)quinazolin-6-yl)methyl)pyrrolidin-3-yl)oxy)-1-oxoisoindolin-2-yl)piperidine-2,6-dione. To a solution of 3-[1-oxo-5-[(3S)-pyrrolidin-3-yl]oxy-isoindolin-2-yl]piperidine-2,6-dione (60 mg, 0.18 mmol), 2-(oxetan-3-yl)quinazoline-6-carbaldehyde (40 mg, 0.19 mmol) and triethylamine (28 mg, 0.28 mmol) in dichloromethane (5 mL) was added sodium triacetoxyborohydride (116 mg, 0.55 mmol) and the solution was stirred for 2 h at room temperature under nitrogen. The resulting solution was concentrated and the residue was purified by silica gel chromatography (0-5% methanol in dichloromethane) and preparative HPLC with the following conditions: Xselect CSH OBD Column 30*150 mm, 5 μm; Mobile Phase A: water (0.05% TFA), Mobile Phase B: acetonitrile; Flow rate: 60 mL/min; Gradient: 3% B to 25% B in 7 min, 25% B; Wave Length: 254/210 nm; $RT_1$ (min): 6.3. The fractions containing desired product were collected and evaporated under reduced pressure to afford the title compound (11.6 mg, 0.02 mmol, 12% yield) as an off-white solid. $^1H$ NMR (300 MHz, Methanol-$d_4$) δ 8.83 (d, 1H), 8.35 (s, 1H), 8.27 (d, J=8.8 Hz, 1H), 8.15 (d, J=8.9 Hz, 1H), 7.97 (d, J=9.5 Hz, 1H), 7.73 (m, 1H), 7.17 (s, 1H), 7.10 (m, 1H), 5.36 (m, 1H), 5.20-5.07 (m, 1H), 4.75 (m, 2H), 4.45 (m, 2H), 3.87-3.60 (m, 5H), 3.26 (m, 1H), 2.92 (m, 2H), 2.80-2.53 (m, 3H), 2.40 (m, 1H), 2.25-2.00 (m, 4H), 1.83-1.51 (m, 3H), 1.42 (m, 1H); MS (ESI) m/z 569.2 $[M+1]^+$.

Example S82. (S)-3-(5-(((S)-1-((2-(2-Hydroxypropan-2-yl)quinolin-6-yl)methyl)pyrrolidin-3-yl)oxy)-1-oxoisoindolin-2-yl)piperidine-2,6-dione

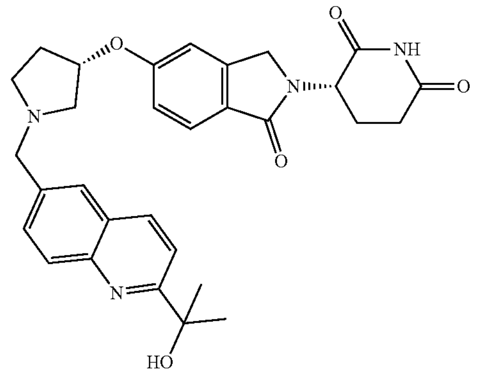 [SMILES: CC(C)(O)c1ccc2cc(CN3CC[C@H](Oc4ccc5c(c4)CN([C@H]4CCC(=O)NC4=O)C5=O)C3)ccc2n1]

Methyl 6-bromoquinoline-2-carboxylate. To a stirred solution of 6-bromoquinoline-2-carboxylic acid (5.00 g, 19.84 mmol) in methanol (50 mL) was added concentrated sulfuric acid (5 mL) dropwise under 0° C. The resulting solution was stirred at 70° C. for 12 h under nitrogen. The light-yellow solution was concentrated and the residue was added saturated sodium bicarbonate carefully to PH~7, then extracted with ethyl acetate. The extracts were dried over anhydrous sodium sulfate, filtered and concentrated to afford the title compound (4.20 g, 15.78 mmol, 79% yield) as a yellow solid. MS (ESI) m/z 266.1 $[M+1]^+$.

2-(6-Bromoquinolin-2-yl)propan-2-ol. To a stirred solution of methyl 6-bromoquinoline-2-carboxylate (4.20 g, 15.78 mmol) in THF (50 mL) was added methylmagnesium bromide (3 M in diethyl ether, 10.5 mL, 31.50 mmol) dropwise at 0° C. and the mixture was stirred at room temperature for 12 h under nitrogen. The reaction mixture was added saturated ammonium chloride and extracted with ethyl acetate. The extracts were dried over anhydrous sodium sulfate, filtered and concentrated. The residue was purified with reverse phase flash (10-40% acetonitrile+0.05% ammonium bicarbonate in water, over 25 min) to give the title compound (2.20 g, 8.30 mmol, 52% yield) as a yellow oil. MS (ESI) m/z 266.1 $[M+1]^+$.

2-(6-Vinylquinolin-2-yl)propan-2-ol. To a stirred mixture of 2-(6-bromoquinolin-2-yl)propan-2-ol (2.1 g, 7.89 mmol) in 1,4-dioxane (20 mL) and water (2 mL) was added potassium trifluoro(vinyl)boranuide (2.73 g, 20.38 mmol), cesium carbonate (7.72 g, 23.67 mmol) and tetrakis(triphenylphosphine)palladium (0.88 g, 0.79 mmol). The reaction mixture was stirred at 100° C. for 12 h under nitrogen. The resulting mixture was added water and extracted with ethyl acetate. The organic layers were washed with brine, dried over anhydrous sodium sulfated, filtered, concentrated and the residue was purified by silica gel chromatography (0-10% methanol in dichloromethane) to give the title compound (1.90 g, 8.87 mmol, 113% yield) as a yellow semi-solid. MS (ESI) m/z 214.2 $[M+1]^+$.

2-(2-Hydroxypropan-2-yl)quinoline-6-carbaldehyde. To a stirred solution of 2-(6-vinylquinolin-2-yl)propan-2-ol (1.40 g, 6.56 mmol), 4-methylmorpholine N-oxide (1.54 g, 13.13 mmol) and citric acid (2.76 g, 13.13 mmol) in water (10 mL) and tert-butanol (10 mL) was added potassium osmate (0.24 g, 0.66 mmol). The reaction mixture was stirred at room temperature for 3 h under nitrogen. Then sodium periodate (4.21 g, 19.49 mmol) was added into the above mixture. The resulting mixture was stirred for 1 h at room temperature under nitrogen. The mixture was added saturated sodium bicarbonate to pH~7 and extracted with ethyl acetate. The extracts were dried over anhydrous sodium sulfate, filtered and concentrated. The residue was purified by silica gel chromatography (0 to 50% ethyl acetate in petroleum ether) to give the title compound (970 mg, 4.49 mmol, 69% yield) as an off-white semi-solid. MS (ESI) m/z 216.0 $[M+1]^+$.

Tert-butyl (S)-5-amino-4-(5-(((S)-1-((2-(2-hydroxypropan-2-yl)quinolin-6-yl)methyl)pyrrolidin-3-yl)oxy)-1-oxoisoindolin-2-yl)-5-oxopentanoate; 2,2,2-trifluoroacetic acid. To a stirred solution of tert-butyl (S)-5-amino-5-oxo-4-(1-oxo-5-(((S)-pyrrolidin-3-yl)oxy)isoind-olin-2-yl)pentanoate (700 mg, 1.62 mmol) in THF (20 mL) was added 2-(2-hydroxypropan-2-yl)quinoline-6-carbaldehyde (410 mg, 1.91 mmol), acetic acid (0.1 mL) and sodium triacetoxyborohydride (919 mg, 4.34 mmol). The reaction mixture was stirred at room temperature for 12 h under nitrogen. Most of the solvent was removed under reduced pressure and the residue was purified by reverse phase flash (10-30% acetonitrile+0.05% TFA in water, over 20 min) to afford the title compound (1.40 g, 1.95 mmol, 102% yield) as an off-white semi-solid. MS (ESI) m/z 603.3 $[M+1]^+$.

(S)-3-(5-(((S)-1-((2-(2-Hydroxypropan-2-yl)quinolin-6-yl)methyl)pyrrolidin-3-yl)oxy)-1-oxoisoindolin-2-yl)piperidine-2,6-dione. A solution of tert-butyl (S)-5-amino-4-(5-(((S)-1-((2-(2-hydroxypropan-2-yl)quinolin-6-yl)methyl) pyrrolidin-3-yl)oxy)-1-oxoisoindolin-2-yl)-5-oxopentanoate; 2,2,2-trifluoroacetic acid (1200 mg, 1.67 mmol) and benzenesulfonic acid (800 mg, 5.03 mmol) in acetonitrile (30 mL) was stirred at 60° C. for 12 h under nitrogen. The resulting solution was added saturated sodium bicarbonate to pH~6 and purified by reverse phase flash (10-40% acetonitrile+0.05% TFA in water, over 25 min). The pure fractions were evaporated and purified again by reverse phase flash (10-20% acetonitrile+0.1% formic acid in water, over 25 min). The pure fractions were evaporated and purified further by preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 18% B in 9 min, 18% B; Wave Length: 254/210 nm; RT1 (min): 7.77. The fractions containing desired product were collected and evaporated under reduced pressure to afford the title compound (331.7 mg, 0.63 mmol, 38% yield) as a white solid. $^1$H NMR (400 MHz, Methanol-$d_4$) δ 8.30 (m, 1H), 8.08 (m, 1H), 7.94 (d, J=2.0 Hz, 2H), 7.87-7.80 (m, 2H), 7.72 (d, J=8.4 Hz, 1H), 7.11-7.02 (m, 2H), 5.15-5.05 (m, 2H), 4.46-4.40 (m, 2H), 4.10-4.03 (m, 2H), 3.20-3.03 (m, 3H), 3.00-2.75 (m, 3H), 2.49 (m, 2H), 2.20-2.15 (m, 2H), 1.65 (s, 6H); MS (ESI) m/z 529.2 $[M+1]^+$.

Example S83. 3-(5-(((S)-1-((2-((1R,5S)-3-Oxa-8-azabicyclo[3.2.1]octan-8-yl)quinolin-6-yl)methyl) pyrrolidin-3-yl)oxy)-1-oxoisoindolin-2-yl)piperidine-2,6-dione

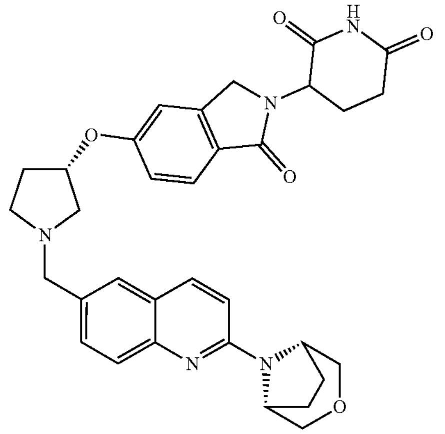 [SMILES: O=C1CCC(N2Cc3cc(O[C@H]4CCN(Cc5ccc6nc(N7[C@@H]8CC[C@H]7COC8)ccc6c5)C4)ccc3C2=O)C(=O)N1]

Methyl 2-((1R,5S)-3-oxa-8-azabicyclo[3.2.1]octan-8-yl) quinoline-6-carboxy late. To a stirred solution of methyl 2-chloroquinoline-6-carboxylate (300 mg, 1.35 mmol) in NMP (2 mL) were added (1R,5S)-3-oxa-8-azabicyclo [3.2.1]octane; hydrochloride (612 mg, 4.1 mmol), N-ethyl-N-isopropylpropan-2-amine (1.0 mL, 5.74 mmol) at room temperature. Then the reaction mixture was stirred for 2 h at 140° C. under nitrogen. The resulting mixture was purified by reverse phase flash (20-80% acetonitrile+0.05% ammonium bicarbonate in water, over 20 min) to give the title compound (350 mg, 1.17 mmol, 87% yield) as a yellow solid. MS (ESI) m/z 299.2 $[M+1]^+$.

(2-((1R,5S)-3-Oxa-8-azabicyclo[3.2.1]octan-8-yl)quinolin-6-yl)methanol. To a stirred solution of methyl 2-[(1R, 5S)-3-oxa-8-azabicyclo[3.2.1]octan-8-yl] quinoline-6-carboxylate (200 mg, 0.67 mmol) in THF (10 mL) was added lithium aluminum hydride (2.5 M in THF, 0.33 mL, 0.81 mmol) dropwised at 0° C. under nitrogen. Then the reaction mixture was warmed and stirred for 1 h at room temperature. The resulting mixture was quenched with sodium hydroxide (2 M in water, 1 mL, 2 mmol) at 0° C., then stirred for 10 min at this temperature and filtered. The filter cake was washed with 10 mL THF and 10 mL methanol. The filtrate combined were concentrated to afford the title compound (160 mg, 0.59 mmol, 88% yield) as a yellow solid. MS (ESI) m/z 271.2 $[M+1]^+$.

2-((1R,5S)-3-Oxa-8-azabicyclo[3.2.1]octan-8-yl)quinoline-6-carbaldehyde. To a stirred solution of [2-[(1R,5S)-3-oxa-8-azabicyclo[3.2.1]octan-8-yl]-6-quinolyl] methanol (150 mg, 0.55 mmol) in dichloromethane (10 mL) was added manganese oxide (1.0 g, 11.49 mmol) at room temperature. Then the reaction mixture was stirred for 12 h at room temperature under nitrogen. The mixture was filtered and the filtrate was concentrated to afford the title compound (110 mg, 0.41 mmol, 74% yield) as a yellow solid. MS (ESI) m/z 269.2 $[M+1]^+$.

3-(5-(((S)-1-((2-((1R,5S)-3-Oxa-8-azabicyclo[3.2.1]octan-8-yl)quinolin-6-yl) methyl)pyrrolidin-3-yl)oxy)-1-oxoisoindolin-2-yl)piperidine-2,6-dione. To a stirred solution of 2-[(1R,5S)-3-oxa-8-azabicyclo[3.2.1]octan-8-yl]quinoline-6-carbaldehyde (60 mg, 0.22 mmol), 3-[1-oxo-5-[(3S)-pyrrolidin-3-yl] oxy-isoindolin-2-yl]piperidine-2,6-dione; 2,2, 2-trifluoroacetic acid (110 mg, 0.25 mmol), triethylamine (0.06 mL, 0.43 mmol) in dichloromethane (5 mL) pre-stirred for 10 min was added sodium triacetoxyborohydride (190 mg, 0.90 mmol) at 0° C. and the solution was stirred at room temperature for 4 h under nitrogen. The resulting solution was purified by silica gel chromatography (0 to 10% methanol in dichloromethane) and purified further by preparative HPLC with the following conditions: Column: Sunfire prep C18 column, 30*150 mm, 5 μm; mobile phase A: water (0.1% formic acid), mobile phase B: acetonitrile; flow rate: 60 mL/min; gradient: 2% B to 18% B in 7 min, 18% B; wave length: 254/220 nm; $rt_1$ (min): 6.98. The fractions containing desired product were collected and evaporated under reduced pressure to afford the title compound (38.3 mg, 0.07 mmol, 29% yield) as a white solid. $^1H$ NMR (300 MHz, DMSO-$d_6$) δ 10.97 (s, 1H), 8.16 (d, J=2.0 Hz, 1H), 8.03 (d, J=9.1 Hz, 1H), 7.61 (d, J=8.0 Hz, 2H), 7.51 (m, 2H), 7.19-7.08 (m, 2H), 7.01 (dd, J=8.4, 2.2 Hz, 1H), 5.04 (m, 2H), 4.66 (s, 2H), 4.38 (d, J=17.2 Hz, 1H), 4.25 (d, J=17.2 Hz, 1H), 3.69 (m, 4H), 3.58 (m, 2H), 2.99-2.84 (m, 2H), 2.81-2.53 (m, 4H), 2.42-2.26 (m, 2H), 1.93 (m, 6H); MS (ESI) m/z 582.1 $[M+1]^+$.

Example S84. 3-(5-(((S)-1-((2-((1R,5S)-6-Oxa-3-azabicyclo[3.1.1]heptan-3-yl)quinolin-6-yl)methyl)pyrrolidin-3-yl)oxy)-1-oxoisoindolin-2-yl)piperidine-2,6-dione

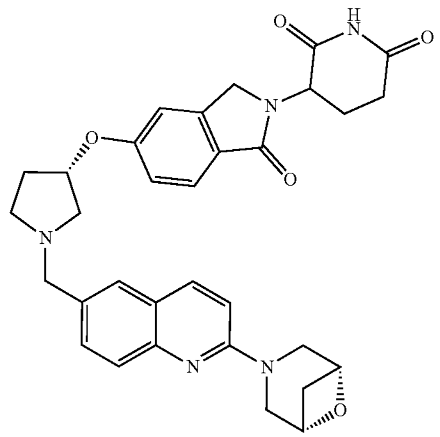 [SMILES: O=C1CCC(N2Cc3cc(O[C@H]4CCN(Cc5ccc6nc(N7C[C@H]8C[C@@H](C7)O8)ccc6c5)C4)ccc3C2=O)C(=O)N1]

Methyl 2-((1R,5S)-6-oxa-3-azabicyclo[3.1.1]heptan-3-yl)quinoline-6-carboxylate. To a solution of methyl 2-chloroquinoline-6-carboxylate (250 mg, 1.13 mmol), (1S,5R)-6-oxa-3-azabicyclo[3.1.1]heptane; hydrochloride (765 mg, 5.64 mmol) in ethanol (5 mL) was added N,N-Diisopropylethylamine (1.5 g, 11.28 mmol) under nitrogen. The mixture was stirred for 12 h at 80° C. under nitrogen. The resulting mixture was added water and extracted with ethyl acetate. The extracts were dried over anhydrous sodium sulfate, filtered and concentrated. The residue was purified by silica gel chromatography (0 to 50% ethyl acetate in petroleum ether) to afford the title compound (300 mg, 1.06 mmol, 94% yield) as a light yellow oil. MS (ESI) m/z 285.1 $[M+1]^+$.

(2-((1R,5S)-6-Oxa-3-azabicyclo[3.1.1]heptan-3-yl)quinolin-6-yl)methanol. To a solution of methyl 2-[(1S,5R)-6-oxa-3-azabicyclo[3.1.1]heptan-3-yl]quinoline-6-carboxylate (290 mg, 1.02 mmol) in THF (5 mL) was added lithium aluminium hydride (2.5 M in THF, 0.40 mL, 1.00 mmol) dropwise at 0° C. and stirred at this temperature for 30 min under nitrogen. The solution was quenched with water, and the pH of the resulting solution was adjusted with 15% sodium hydroxide to pH~8 and extracted with dichloromethane. The extracts were washed with brine, dried over anhydrous sodium sulfate, filtered and concentrated. The residue was purified by silica gel chromatography (0 to 50% ethyl acetate in petroleum ether) to afford the title compound (250 mg, 0.98 mmol, 96% yield) as a light yellow solid. MS (ESI) m/z 257.1 $[M+1]^+$.

2-((1R,5S)-6-Oxa-3-azabicyclo[3.1.1]heptan-3-yl)quinoline-6-carbaldehyde. To a solution of [2-[(1S,5R)-6-oxa-3-azabicyclo[3.1.1]heptan-3-yl]-6-quinolyl]methanol (250 mg, 0.98 mmol) in dichloromethane (15 mL) was added manganese dioxide (1.7 g, 19.51 mmol) and the mixture was stirred for 12 h at room temperature. The mixture was filtered and the filter cake was washed with dichloromethane (3×10 mL). The filtrate was concentrated under reduced pressure to afford the title compound (230 mg, 0.91 mmol, 93% yield) as a black solid. MS (ESI) m/z 255.1 $[M+1]^+$.

3-(5-(((S)-1-((2-((1R,5S)-6-Oxa-3-azabicyclo[3.1.1]heptan-3-yl)quinolin-6-yl)methyl)pyrrolidin-3-yl)oxy)-1-oxoisoindolin-2-yl)piperidine-2,6-dione. To a solution of 3-[1-oxo-5-[(3S)-pyrrolidin-3-yl]oxy-isoindolin-2-yl]piperidine-2,6-dione; 2,2,2-trifluoroacetic acid (108 mg, 0.24 mmol), 2-((1R,5S)-6-oxa-3-azabicyclo[3.1.1]heptan-3-yl)quinoline-6-carbaldehyde (61 mg, 0.24 mmol) in dichloromethane (5 mL) were added triethylamine (37 mg, 0.37 mmol) and triacetoxyborohydride (153 mg, 0.72 mmol) at room temperature. The mixture was stirred for 2 h at 35° C. under nitrogen. The resulting mixture was concentrated. The residue was by silica gel chromatography (0-5% methanol in dichloromethane) and preparative HPLC with the following conditions: Sunfire prep C18 column, 30*150 mm, 5 μm; Mobile Phase A: water (0.1% formic acid), Mobile Phase B: acetonitrile; Flow rate: 60 mL/min; Gradient: 2% B to 18% B in 7 min, 18% B; Wave Length: 254/220 nm; RT1 (min): 6.58. The fractions containing desired product were collected and evaporated under reduced pressure to afford the title compound (37.8 mg, 0.07 mmol, 27% yield) as an off-white solid. $^1H$ NMR (400 MHz, Methanol-$d_4$) δ 8.07 (d, J=9.2 Hz, 1H), 7.85-7.76 (m, 2H), 7.73 (m, J=8.4, 3.2 Hz, 1H), 7.68 (m, J=8.7, 1.8 Hz, 1H), 7.19-7.04 (m, 3H), 5.27 (m, 1H), 5.13 (m, 1H), 4.84 (m, 2H), 4.53-4.38 (m, 4H), 4.00 (d, J=12.5 Hz, 2H), 3.86 (d, J=12.4 Hz, 2H), 3.65 (m, J=12.8, 5.1 Hz, 3H), 3.61-3.50 (m, 1H), 3.48-3.37 (m, 1H), 2.92 (m, 1H), 2.79 (m, 1H), 2.52 (m, 2H), 2.36-2.28 (m, 1H), 2.17 (m, 1H), 2.06-1.98 (m, 1H); MS (ESI) m/z 568.2 $[M+1]^+$.

Example S85. 3-(5-(((S)-1-((2-((1R,5S)-3-Oxa-6-azabicyclo[3.1.1]heptan-6-yl)quinolin-6-yl)methyl)pyrrolidin-3-yl)oxy)-1-oxoisoindolin-2-yl)piperidine-2,6-dione

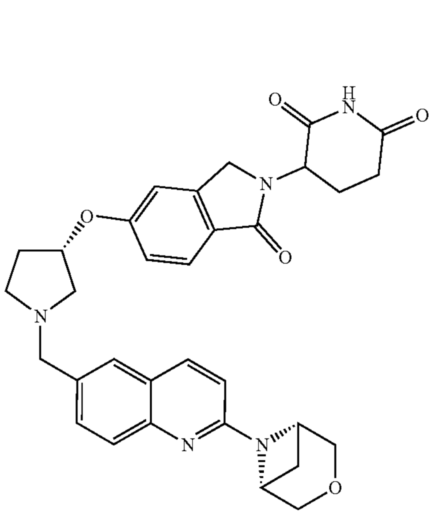 [SMILES: O=C1CCC(N2Cc3cc(O[C@H]4CCN(Cc5ccc6nc(N7[C@@H]8COC[C@H]7C8)ccc6c5)C4)ccc3C2=O)C(=O)N1]

Methyl 2-((1R,5S)-3-Oxa-6-azabicyclo[3.1.1]heptan-6-yl)quinoline-6-carboxylate. To a solution of methyl 2-chloroquinoline-6-carboxylate (250 mg, 1.13 mmol), (1R,5S)-3-oxa-6-azabicyclo[3.1.1]heptane hydrogen chloride (362 mg, 2.67 mmol) in 1,4-dioxane (5 mL) were added methanesulfonato{[4-(N,N-dimethylamino)phenyl]di-t-butylphosphino}(2'-amino-1,1'-biphenyl-2-yl)palladium(II) (204 mg, 0.32 mmol), bis(di-tert-butyl)-4-dimethylaminophenylphosphine (127 mg, 0.48 mmol), cesium carbonate (1.3 g, 4.01 mmol) under nitrogen. The mixture was stirred for 12 h at 100° C. under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (180 mg, 0.63 mmol, 47% yield) as a light yellow solid. MS (ESI) m/z 285.0 $[M+1]^+$.

(2-((1R,5S)-3-Oxa-6-azabicyclo[3.1.1]heptan-6-yl)quinolin-6-yl)methanol. To a solution of methyl 2-((1R,5S)-3-oxa-6-azabicyclo[3.1.1]heptan-6-yl)quinoline-6-carboxylate (165 mg, 0.58 mmol) in THF (5 mL) was added lithium aluminium hydride (2.5 M in THF, 0.23 mL, 0.58 mmol) at 0° C. and the mixture was stirred at this temperature for 30 min. The mixture was quenched with water, and the pH of the resulting solution was adjusted with 15% sodium hydroxide to pH~8. The aqueous was added water and extracted with dichloromethane. The extracts were washed with brine, dried over anhydrous sodium sulfate, filtered and concentrated. The residue was purified by silica gel chromatography (0 to 50% ethyl acetate in petroleum ether) to afford the title compound (140 mg, 0.55 mmol, 94% yield) as a light yellow solid. MS (ESI) m/z 257.1 $[M+1]^+$.

2-((1R,5S)-3-Oxa-6-azabicyclo[3.1.1]heptan-6-yl)quinoline-6-carbaldehyde. To a solution of [2-[(1R,5S)-3-oxa-6-azabicyclo[3.1.1]heptan-6-yl]-6-quinolyl]methanol (140 mg, 0.55 mmol) in dichloromethane (15 mL) was added manganese dioxide (950 mg, 10.93 mmol) and the mixture was stirred for 12 h at room temperature under nitrogen. The resulting mixture was filtered and the filter cake was washed with dichloromethane (3×10 mL). The filtrate was concentrated under reduced pressure to afford the title compound (130 mg, 0.51 mmol, 94% yield) as a black solid. MS (ESI) m/z 255.1 $[M+1]^+$.

3-(5-(((S)-1-((2-((1R,5S)-3-oxa-6-azabicyclo[3.1.1]heptan-6-yl)quinolin-6-yl)-methyl)pyrrolidin-3-yl)oxy)-1-oxoisoindolin-2-yl)piperidine-2,6-dione. To a solution of 3-(1-oxo-5-(((S)-pyrrolidin-3-yl)oxy)isoindolin-2-yl)piperidine-2,6-dione; 2,2,2-trifluoroacetic acid (108 mg, 0.24 mmol), 2-[(1R,5S)-3-oxa-6-azabicyclo[3.1.1]heptan-6-yl]quinoline-6-carbaldehyde (60 mg, 0.24 mmol) in dichloromethane (5 mL) was added triethylamine (37 mg, 0.37 mmol) and sodium triacetoxyborohydride (153 mg, 0.72 mmol) at room temperature. The mixture was stirred for 2 h at room temperature under nitrogen. The resulting mixture was concentrated and purified by silica gel chromatography (6% methanol in dichloromethane) and preparative HPLC with the following conditions: Sunfire prep C18 column, 30*150 mm, 5 μm; Mobile Phase A: water (0.1% formic acid), Mobile Phase B: acetonitrile; Flow rate: 60 mL/min; Gradient: 2% B to 17% B in 7 min, 17% B; Wave Length: 254/220 nm; RT1 (min): 6.67. The fractions containing desired product were collected and evaporated under reduced pressure to afford the title compound (38.9 mg, 0.068 mmol, 28% yield) as an off-white solid. $^1H$ NMR (400 MHz, Methanol-$d_4$) δ 8.04 (d, J=8.9 Hz, 1H), 7.78 (d, J=1.9 Hz, 1H), 7.72 (d, J=8.6 Hz, 2H), 7.67 (m, 3H), 7.12-7.01 (m, 2H), 6.89 (d, J=8.9 Hz, 1H), 5.19-5.12 (m, 2H), 4.59 (d, J=6.1 Hz, 2H), 4.43 (d, J=6.6 Hz, 2H), 4.40-4.32 (m, 2H), 4.30-4.18 (m, 2H), 3.85 (d, J=10.6 Hz, 2H), 3.47-3.35 (m, 2H), 3.30 (m, 1H), 3.21-3.10 (m, 1H), 2.97-2.78 (m, 3H), 2.59-2.40 (m, 2H), 2.26-2.11 (m, 2H), 2.00 (m, 1H); MS (ESI) m/z 568.3 $[M+1]^+$.

Example S86. 3-(5-(((S)-1-((2-((1S,4S)-2-Oxa-5-azabicyclo[2.2.1]heptan-5-yl)quinolin-6-yl)methyl)pyrrolidin-3-yl)oxy)-1-oxoisoindolin-2-yl)piperidine-2,6-dione

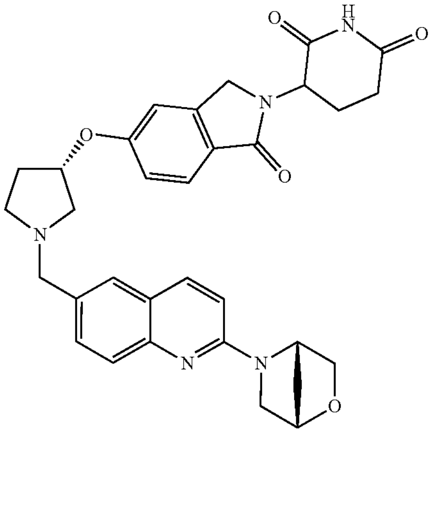 [SMILES: O=C1CCC(N2Cc3cc(O[C@H]4CCN(Cc5ccc6nc(N7C[C@@H]8C[C@H]7CO8)ccc6c5)C4)ccc3C2=O)C(=O)N1]

Methyl 2-((1S,4S)-2-oxa-5-azabicyclo[2.2.1]heptan-5-yl) quinoline-6-carboxylate. To a mixture of methyl 2-chloroquinoline-6-carboxylate (764 mg, 3.45 mmol), (1S,4S)-2-oxa-5-azabicyclo[2.2.1]heptane (400 mg, 4.04 mmol) and N,N-diisopropylethylamine (729 mg, 5.64 mmol) in ethanol (3 mL) was stirred at 80° C. for 12 h under nitrogen. The resulting mixture was diluted with water and extracted with ethyl acetate. The extracts were washed with brine, dried over anhydrous sodium sulfate, filtered and concentrated. The residue was purified by reverse phase flash (10-70% acetonitrile+0.05% ammonium bicarbonate in water, over 20 min) to afford the title compound (210 mg, 0.74 mmol, 21% yield) as a yellow solid. MS (ESI) m/z 285.0 $[M+1]^+$.

(2-((1S,4S)-2-Oxa-5-azabicyclo[2.2.1]heptan-5-yl)quinolin-6-yl)methanol. To a stirred solution of methyl 2-((1S,4S)-2-oxa-5-azabicyclo[2.2.1]heptan-5-yl)quinoline-6-carboxylate (210 mg, 0.74 mmol) in THF (3 mL) was added lithium aluminum hydride (2.5 M in THF, 0.26 mL, 0.65 mmol) at 0° C. dropwise and the solution was stirred at this temperature for 3 h under nitrogen. The resulting mixture was diluted with THF, added sodium sulfate decahydrate, filtered and concentrated to afford the title compound (190 mg, 0.74 mmol, 100% yield) as a yellow solid. MS (ESI) m/z 257.2 $[M+1]^+$.

2-((1S,4S)-2-Oxa-5-azabicyclo[2.2.1]heptan-5-yl)quinoline-6-carbaldehyde. To a stirred solution of (2-((1S,4S)-2-oxa-5-azabicyclo[2.2.1]heptan-5-yl)quinolin-6-yl)methanol (190 mg, 0.74 mmol) in dichloromethane (10 mL) was added manganese dioxide (1.29 g, 14.83 mmol) and the mixture was stirred at 50° C. for 3 h under nitrogen. The mixture was filtered and the filtrate was concentrated. to obtain afford the title compound (180 mg, 0.71 mmol, 95% yield) as a white solid. MS (ESI) m/z 255.2 $[M+1]^+$.

3-(5-(((S)-1-((2-((1S,4S)-2-Oxa-5-azabicyclo[2.2.1]heptan-5-yl)quinolin-6-yl)methyl)pyrrolidin-3-yl)oxy)-1-oxoisoindolin-2-yl)piperidine-2,6-dione. To a stirred mixture of 2-((1S,4S)-2-oxa-5-azabicyclo[2.2.1]heptan-5-yl)quinolone-6-carb-aldehyde (60 mg, 0.24 mmol), 3-[1-oxo-5-[(3S)-pyrrolidin-3-yl]oxy-isoindolin-2-yl]-piperidine-2,6-dione; 2,2,2-trifluoroacetic acid (100 mg, 0.23 mmol) and triethylamine (48 mg, 0.47 mmol) in dichloromethane (5 mL) was added sodium triacetoxyborohydride (200 mg, 0.94 mmol) in several portions and the mixture was stirred at room temperature for 2 h under nitrogen. The mixture was concentrated and the residue was purified by silica gel chromatography (0-10% methanol in dichloromethane) firstly and further by preparative HPLC with the following conditions: Column: sunfire prep C18 column, 30*150 mm, 5 μm; Mobile phase A: water (0.1% formic acid), Mobile phase B: acetonitrile; Flow rate: 60 mL/min; Gradient: 2% B to 18% B in 7 min, 18% B; Wave Length: 254/220 nm; RT1 (min): 6.17; The fractions containing desired product were collected and evaporated under reduced pressure to afford the title compound (37.6 mg, 0.07 mmol, 29% yield) as a white solid. $^1H$ NMR (400 MHz, Methanol-$d_4$) δ 8.02 (d, J=9.1 Hz, 1H), 7.79-7.69 (m, 3H), 7.66-7.61 (m, 1H), 7.13 (d, J=2.2 Hz, 1H), 7.08-7.06 (m, 1H), 6.99 (d, J=9.1 Hz, 1H), 5.23 (m, 1H), 5.13-5.09 (m, 2H), 4.79 (s, 1H), 4.48 (d, J=17.1 Hz, 1H), 4.42 (d, J=17.1 Hz, 1H), 4.38-4.27 (m, 2H), 3.96-3.94 (m, 1H), 3.89 (d, J=7.5 Hz, 1H), 3.71-3.69 (m, 1H), 3.60-3.44 (m, 4H), 3.27-3.25 (m, 1H), 2.92-2.90 (m, 1H), 2.79-2.77 (m, 1H), 2.52-2.47 (m, 2H), 2.32-2.11 (m, 2H), 2.07 (s, 2H); MS (ESI) m/z 568.2 $[M+1]^+$.

Example S87. 3-(5-(((S)-1-((2-(1,1-Dioxidothiomorpholino)quinolin-6-yl)methyl)pyrrolidin-3-yl)oxy)-1-oxoisoindolin-2-yl)piperidine-2,6-dione

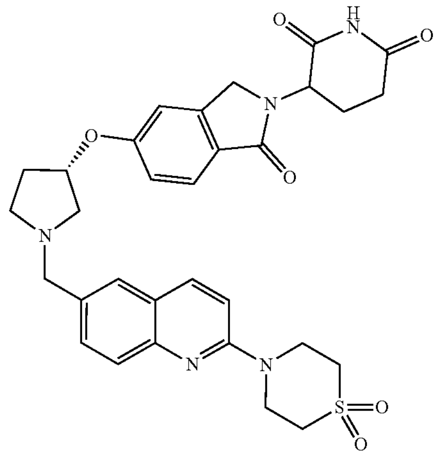 [SMILES: O=C1CCC(N2Cc3cc(O[C@H]4CCN(Cc5ccc6nc(N7CCS(=O)(=O)CC7)ccc6c5)C4)ccc3C2=O)C(=O)N1]

Methyl 2-(1,1-dioxidothiomorpholino)quinoline-6-carboxylate. To a stirred solution of methyl 2-chloroquinoline-6-carboxylate (300 mg, 1.35 mmol) in NMP (5 mL) were added thiomorpholine 1,1-dioxide (914 mg, 6.77 mmol) and N,N-diisopropylethylamine (0.71 mL, 4.06 mmol) at 0° C. The reaction solution was stirred for 12 h at 140° C. under nitrogen. The resulting solution was purified by reverse phase flash (10-40% acetonitrile+0.05% ammonium bicarbonate in water, over 30 min) to give the title compound (356 mg, 1.10 mmol, 81% yield) as a yellow solid. MS (ESI) m/z 321.1 $[M+1]^+$.

4-(6-(Hydroxymethyl)quinolin-2-yl)thiomorpholine 1,1-dioxide. To a stirred solution of methyl 2-(1,1-dioxidothiomorpholino)quinoline-6-carboxylate (330 mg, 1.03 mmol) in THF (5 mL) was added lithium aluminum hydride (2.5 M in THF, 0.4 mL, 1.00 mmol) dropwise at 0° C. and the mixture was stirred for 1 h at 0° C. The reaction mixture was quenched with sodium hydroxide (2 M in water, 5 mL, 10 mmol) at 0° C. and then stirred for 30 min at this temperature and filtered. The filter cake was washed with 30 mL THF. The filtrate combined were concentrated to afford the title compound (300 mg, 1.02 mmol, 99% yield) as a yellow solid. MS (ESI) m/z 293.2 $[M+1]^+$.

2-(1,1-Dioxidothiomorpholino)quinoline-6-carbaldehyde. To a stirred mixture of 4-(6-(hydroxymethyl)quinolin-2-yl)thiomorpholine 1,1-dioxide (300 mg, 1.02 mmol) in dichloromethane (15 mL) was added manganese oxide (1.30 g, 14.95 mmol). The reaction mixture was stirred for 12 h at 60° C. under nitrogen. The resulting mixture was filtered and the filter cake was washed with dichloromethane (30 mL). The filtrate was concentrated under reduced pressure to afford title compound (200 mg, 0.68 mmol, 66% yield) as a yellow solid. MS (ESI) m/z 291.0 $[M+1]^+$.

3-(5-(((S)-1-((2-(1,1-Dioxidothiomorpholino)quinolin-6-yl)methyl)pyrroliin-3-yl)oxy)-1-oxoisoindolin-2-yl)piperidine-2,6-dione. To a stirred solution of 2-(1,1-dioxidothiomorpholino)quinoline-6-carbaldehyde (80 mg, 0.28 mmol), 3-(1-oxo-5-(((S)-pyrrolidin-3-yl)oxy)isoindolin-2-yl)piperidine-2,6-dione; 2,2,2-trifluoroacetic acid (120 mg, 0.27 mmol) and triethylamine (66 mg, 0.66 mmol) in dichloromethane (5 mL) was added sodium triacetoxyborohydride (170 mg, 0.80 mmol) under nitrogen. The reaction mixture was stirred for 1 h at 30° C. under nitrogen. Most of the solvent was removed under reduced pressure and the residue was purified by normal phase flash (0-10% methanol in dichloromethane) and further purified by preparative HPLC with the following conditions: Column: Sunfire prep C18 column, 30×150 mm, 5 μm; Mobile Phase A: water (0.1% formic acid), Mobile Phase B: acetonitrile; Flow rate: 60 mL/min; Gradient: 2% B to 25% B in 7 min, 25% B; Wave Length: 254/220 nm; RT1 (min): 7.7. The fractions containing desired product were collected and evaporated under reduced pressure to give the desired product (28.5 mg, 0.047 mmol, 17% yield) as an off-white solid. $^1$H NMR (400 MHz, Methanol-$d_4$) δ 8.08 (d, J=9.1 Hz, 1H), 7.77-7.65 (m, 4H), 7.33 (d, J=9.1 Hz, 1H), 7.09-7.04 (m, 2H), 5.17-5.10 (m, 2H), 4.48-4.34 (m, 6H), 4.25-4.17 (m, 2H), 3.40-3.30 (m, 5H), 3.17-3.13 (m, 5H), 2.95-2.86 (m, 1H), 2.80-2.76 (m, 1H), 2.55-2.43 (m, 2H), 2.22-2.14 (m, 2H); MS (ESI) m/z 604.1 $[M+1]^+$.

Example S88. (S)-3-(1-Oxo-5-(((S)-1-((2-((R)-tetrahydrofuran-3-yl)quinazolin-6-yl)methyl)pyrrolidin-3-yl)oxy)isoindolin-2-yl)piperidine-2,6-dione

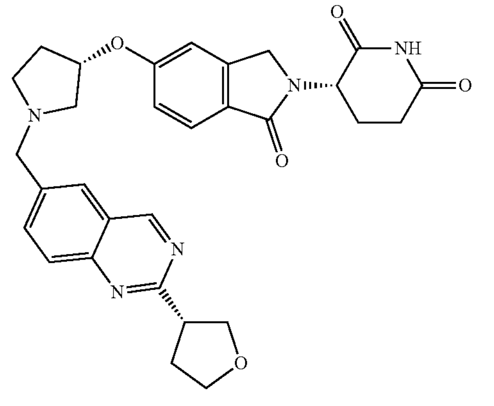

N-(2-amino-5-bromobenzyl)oxetane-3-carboxamide. A solution of tetrahydrofuran-3-carboxylic acid (6.5 g, 56.00 mmol) in thionyl chloride (33 mL) was heated at 80° C. and stirred for 2 h under nitrogen. The reaction mixture was concentrated to give crude tetrahydrofuran-3-carbonyl chloride. To a solution of 2-(aminomethyl)-4-bromo-aniline; dihydrochloride (20.0 g, 73.00 mmol) in dichloromethane (30 mL) was added triethylamine (100 mL, 730 mmol) under nitrogen atmosphere. The mixture was stirred at room temperature for 15 min, then to the above mixture was added tetrahydrofuran-3-carbonyl chloride (7.9 g, 58.40 mmol) and the mixture was stirred for 2 h at room temperature under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (10.2 g, 35.79 mmol, 49% yield) as a yellow oil. MS (ESI) m/z 285.0 $[M+1]^+$.

6-Bromo-2-(tetrahydrofuran-3-yl)-1,4-dihydroquinazoline. A solution of N-[(2-amino-5-bromo-phenyl)methyl]oxetane-3-carboxamide (10.0 g, 35.07 mmol) in phosphorus oxychloride (20 mL) was stirred at 100° C. for 30 min under nitrogen. Then the mixture was diluted with water, and the pH of the resulting solution was adjusted with sodium carbonate to pH~8. The organic layer was separated and the aqueous phase was extracted with ethyl acetate two times, and the extracts were dried over anhydrous sodium sulfate, filtered and concentrated to afford the title compound (8.0 g, 28.46 mmol, 81% yield) as a light yellow oil. MS (ESI) m/z 280.9 $[M+1]^+$.

6-Bromo-2-(tetrahydrofuran-3-yl)quinazoline. To a solution of 6-bromo-2-tetrahydrofuran-3-yl-1,4-dihydroquinazoline (8.0 g, 28.46 mmol) in dichloromethane (80 mL) was added manganese dioxide (25.0 g, 284.55 mmol) and the mixture was stirred for 12 h at room temperature under nitrogen. The resulting mixture was filtered and the filter cake was washed with dichloromethane (3×100 mL). The filtrate was concentrated under reduced pressure to afforded the title compound (3.0 g, 10.75 mmol, 38% yield) as a black solid. MS (ESI) m/z 279.2 $[M+1]^+$.

2-(Tetrahydrofuran-3-yl)-6-vinylquinazoline. To a solution of 6-bromo-2-tetrahydrofuran-3-yl-quinazoline (3.0 g, 10.75 mmol), potassium vinyltrifluoroborate (2.9 g, 21.51 mmol) in 1,4-dioxane (30 mL) were added [1'1-bis(diphenylphosphino)ferrocene]dichloro palladium(II) (877 mg, 0.11 mmol) and sodium carbonate (3.4 g, 32.26 mmol) and the mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (1.5 g, 6.63 mmol, 63% yield) as a light yellow oil. MS (ESI) m/z 227.1 $[M+1]^+$.

(R)-2-(Tetrahydrofuran-3-yl)-6-vinylquinazoline and (S)-2-(tetrahydrofuran-3-yl)-6-vinylquinazoline. The 2-(tetrahydrofuran-3-yl)-6-vinylquinazoline (1.5 g, 6.63 mmol) was separated by preparative SFC with the following conditions: Column: CHIRALPAK IH, 3*25 cm, 5 μm; Mobile Phase A: carbon dioxide, Mobile Phase B: methanol:acetonitrile=3:2 (0.1% 2M ammonia-methanol); Flow rate: 70 mL/min; Gradient: isocratic 50% B; Column Temperature (° C.): 35; Back Pressure (bar): 100; Wave Length: 220 nm; $RT_1$ (min): 2.8; RT2 (min): 8.92; Sample Solvent: methanol-Preparative; Injection Volume: 4.8 mL; Number of Runs: 3 to afford the title compound ($RT_1$ (min): 2.8, 500 mg, 2.21 mmol, 33% yield) and the S isomer compound (RT2 (min): 8.92, 500 mg, 2.21 mmol, 33% yield) as a light yellow oil. MS (ESI) m/z 227.1 $[M+1]^+$.

(R)-2-(Tetrahydrofuran-3-yl)quinazoline-6-carbaldehyde. To a solution of (R)-2-(Tetrahydrofuran-3-yl)-6-vinylquinazoline (500 mg, 2.21 mmol), 4-methylmorpholine N-oxide (95 mg, 0.81 mmol) and citric acid (156 mg, 0.81 mmol) in tert-butanol (5 mL) and Water (5 mL) were added potassium osmate (15 mg, 0.04 mmol) and the mixture was stirred for 5 h at room temperature under nitrogen. The mixture was added sodium periodate (261 mg, 1.22 mmol) and the mixture was stirred for 1 h at room temperature. The mixture was added saturated sodium bicarbonate to pH~7 and extracted with ethyl acetate. The extracts were dried over anhydrous sodium sulfate, filtered and concentrated. The residue was purified by silica gel chromatography (0 to 50% ethyl acetate in petroleum ether) to afford the title compound (500 mg, 2.18 mmol, 99% yield) as a white solid. MS (ESI) m/z 229.1 $[M+1]^+$.

(S)-3-(1-Oxo-5-(((S)-1-((2-((R)-tetrahydrofuran-3-yl)quinazolin-6-yl)methyl)-pyrrolidin-3-yl)oxy)isoindolin-2-yl)piperidine-2,6-dione. To a solution of rac-(3S)-3-[1-oxo-5-[rac-(3S)-pyrrolidin-3-yl]oxy-isoindolin-2-yl]piperidine-2,6-dione (acetic acid salt, 307 mg, 0.79 mmol), (R)-2-(tetrahydrofuran-3-yl)quinazoline-6-carbaldehyde (198 mg, 0.87 mmol) in dichloromethane (10 mL) was added triethylamine (153 mg, 1.53 mmol) and sodium triacetoxyborohydride (501 mg, 2.36 mmol) at room temperature. The mixture was stirred for 2 h at room temperature under nitrogen. The resulting mixture was concentrated and purified by silica gel chromatography (5% methanol in dichloromethane) and preparative HPLC with the following conditions: Xselect CSH OBD Column 30*150 mm 5 μm; Mobile Phase A: water (0.05% TFA), Mobile Phase B: acetonitrile; Flow rate: 60 mL/min; Gradient: 5% B to 35% B in 7 min, 35% B; Wave Length: 254/220 nm; $RT_1$ (min): 6.55, and further by preparative Chiral-SFC with the following conditions: Column: CHIRALPAK IF, 2*25 cm, 5 μm; Mobile Phase A: tert-butyl methyl ether (0.1% formic acid)-HPLC, Mobile Phase B: ethanol:dichloromethane=1:1; Flow rate: 20 mL/min; Gradient: 60% B to 60% B in 15 min; Wave Length: 220/254 nm; $RT_1$ (min): 8.4; $RT_2$ (min): 13; Sample Solvent: EtOH—HPLC; Injection Volume: 0.8 mL; Number of Runs: 11. The fractions containing desired product were collected and evaporated under reduced pressure to afford the title compound (97.2 mg, 0.18 mmol, 22% yield) as an off-white solid. $^1H$ NMR (400 MHz, Methanol-$d_4$) δ 9.54 (d, J=1.6 Hz, 1H), 8.25 (d, J=2.0 Hz, 1H), 8.10 (m, J=8.7, 2.0 Hz, 2H), 7.74 (m, J=8.4, 3.7 Hz, 1H), 7.16 (s, 1H), 7.10 (m, J=8.7, 2.7 Hz, 1H), 5.31 (m, 1H), 5.18-5.09 (m, 1H), 4.61 (s, 2H), 4.49 (d, J=17.0 Hz, 1H), 4.43 (d, J=17.1 Hz, 1H), 4.28 (m, J=8.1 Hz, 1H), 4.20-4.06 (m, 2H), 4.04-3.89 (m, 2H), 3.70-3.46 (m, 4H), 2.99-2.80 (m, 2H), 2.62 (m, 1H), 2.50 (m, 3H), 2.38-2.31 (m, 1H), 2.17 (m, 1H); MS (ESI) m/z 542.2 $[M+1]^+$.

Example S89. (S)-3-(1-Oxo-5-(((S)-1-((7-(tetrahydro-2H-pyran-4-yl)isoquinolin-3-yl)methyl)pyrrolidin-3-yl)oxy)isoindolin-2-yl)piperidine-2,6-dione

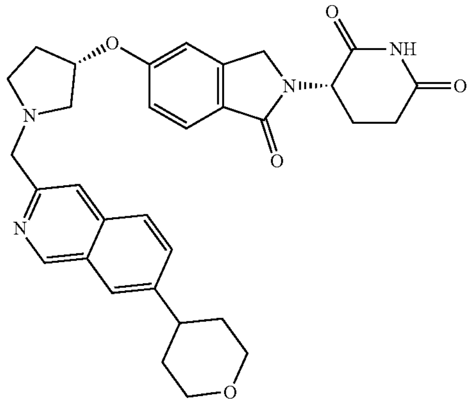 [SMILES: O=C1CC[C@H](N2Cc3cc(O[C@H]4CCN(Cc5cc6ccc(C7CCOCC7)cc6cn5)C4)ccc3C2=O)C(=O)N1]

Methyl 7-bromoisoquinoline-3-carboxylate. To a stirred solution of 7-bromoisoquinoline-3-carboxylic acid (2 g, 7.93 mmol) in methanol (30 mL) was added concentrated sulfuric acid (2 mL) dropwise at 0° C. and the resulting solution was stirred at 75° C. for 12 h under nitrogen. The yellow solution was concentrated. The residue was added sodium bicarbonate to pH~7 and extracted with chloroform. The extracts were washed with brine, dried over anhydrous sodium sulfate, filtered and concentrated to give the title compound (1.8 g, 6.76 mmol, 84% yield) as an off-white solid. MS (ESI) m/z 266.1 $[M+1]^+$.

Methyl 7-(3,6-dihydro-2H-pyran-4-yl)isoquinoline-3-carboxylate. To a stirred solution of methyl 7-bromoisoquinoline-3-carboxylate (1.8 g, 6.76 mmol), 2-(3,6-dihydro-2H-pyran-4-yl)-4,4,5,5-tetramethyl-1,3,2-dioxaborolane (2.5 g, 11.9 mmol) and [1,1'-Bis(diphenylphosphino)ferrocene]dichloropalladium(II) (540 mg, 0.74 mmol) in 1,4-dioxane (30 mL) was added a solution of sodium carbonate (1.8 g, 16.98 mmol) in water (3 mL) at room temperature and the resulting mixture was stirred at 85° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (1.5 g, 5.55 mmol, 82% yield) as an off-white solid. MS (ESI) m/z 270.2 $[M+1]^+$.

Methyl 7-(tetrahydro-2H-pyran-4-yl)isoquinoline-3-carboxylate. To a stirred solution of methyl 7-(3,6-dihydro-2H-pyran-4-yl)isoquinoline-3-carboxylate (1.48 g, 5.50 mmol) and 10% palladium on carbon (300 mg, wetted with ca. 50% water) in methanol (40 mL) was stirred at room temperature for 5 h under hydrogen (~2 bar). The resulting mixture was filtered and the filtrate cake was washed with methanol. The filtrate was concentrated to give the title compound (1.4 g, 5.15 mmol, 92% yield) as an off-white solid. MS (ESI) m/z 272.1 $[M+1]^+$.

(7-(Tetrahydro-2H-pyran-4-yl)isoquinolin-3-yl)methanol. To a mixture of methyl 7-(tetrahydro-2H-pyran-4-yl)isoquinoline-3-carboxylate (1 g, 3.69 mmol) and calcium chloride (800 mg, 7.21 mmol) in ethanol (15 mL) was added sodium borohydride (280 mg, 7.40 mmol) in several portions at 0° C. and the resulting mixture was stirred for 12 h under nitrogen. The resulting mixture was diluted with DMF and filtered. The filtrate was purified by reverse phase flash (10-40% acetonitrile+0.05% ammonium bicarbonate in water, over 25 min) to afford the title compound (600 mg, 2.47 mmol, 67% yield) as a light-yellow solid. MS (ESI) m/z 244.2 $[M+1]^+$.

7-(Tetrahydro-2H-pyran-4-yl)isoquinoline-3-carbaldehyde. A mixture of (7-(tetrahydro-2H-pyran-4-yl)isoquinolin-3-yl)methanol (740 mg, 3.04 mmol) and manganese dioxide (2.1 g, 24.14 mmol) in dichloromethane (25 mL) was stirred at 50° C. for 12 h under nitrogen. The resulting mixture was filtered and the filtrate cake was washed with dichloromethane. The combined filtrates were concentrated to afford the title compound (450 mg, 1.87 mmol, 61% yield) as a light-yellow solid. MS (ESI) m/z 242.2 $[M+1]^+$.

Tert-butyl (S)-5-amino-5-oxo-4-(1-oxo-5-(((S)-1-((7-(tetrahydro-2H-pyran-4-yl)isoquinolin-3-yl)methyl)pyrrolidin-3-yl)oxy)isoindolin-2-yl)pentanoate; 2,2,2-trifluoroacetic acid. To a solution of 7-tetrahydropyran-4-ylisoquinoline-3-carbaldehyde (450 mg, 1.86 mmol), tert-butyl (S)-5-amino-5-oxo-4-(1-oxo-5-(((S)-pyrrolidin-3-yl)oxy)isoindolin-2-yl)-pentanoate (acetic acid salt, 860 mg, 1.86 mmol) and acetic acid (0.15 mL, 1.93 mmol) in THF (10 mL) pre-stirred for 1 h at room temperature was added sodium triacetoxyborohydride (988 mg, 4.66 mmol) in several portions at 0° C. The reaction mixture was stirred for 12 h at room temperature under nitrogen. The resulting mixture added little methanol and purified by reverse phase flash (10-40% acetonitrile+0.05% TFA in water, over 25 min to afford the title compound (1200 mg, 1.62 mmol, 87% yield) as a light-yellow oil. MS (ESI) m/z 629.3 $[M+1]^+$.

(S)-3-(1-Oxo-5-(((S)-1-((7-(tetrahydro-2H-pyran-4-yl)isoquinolin-3-yl)methyl)pyrrolidin-3-yl)oxy)isoindolin-2-yl)piperidine-2,6-dione. A solution of tert-butyl (S)-5-amino-5-oxo-4-(1-oxo-5-(((S)-1-((7-(tetrahydro-2H-pyran-4-yl)isoquinolin-3-yl)methyl)pyrrolidin-3-yl)oxy)isoindolin-2-yl)pentanoate; 2,2,2-trifluoroacetic acid (1200 mg, 1.62 mmol) and benzenesulfonic acid (781 mg, 4.91 mmol) in acetonitrile (20 mL) was stirred at 60° C. for 12 h under nitrogen. The resulting solution was added saturated sodium bicarbonate to pH~7, filtered and the resulting solution was purified directly by reverse phase flash (10-40% acetonitrile+0.05% TFA in water, over 25 min). The pure fractions combined were evaporated and purified further by preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 5% B to 21% B in 10 min, 21% B; Wave Length: 254/210 nm; RT1 (min): 10.23. The fractions containing desired product were collected and evaporated under reduced pressure to afford the title compound (140.3 mg, 0.25 mmol, 15.4% yield) as a white solid. $^1$H NMR (400 MHz, Methanol-$d_4$) δ 9.26 (s, 1H), 8.39 (s, 1H), 7.98 (d, J=1.7 Hz, 1H), 7.95-7.86 (m, 2H), 7.79 (dd, J=8.6, 1.8 Hz, 1H), 7.72 (m, 2H), 7.13 (d, J=2.1 Hz, 1H), 7.07 (dd, J=8.5, 2.2 Hz, 1H), 5.21-5.13 (m, 3H), 4.45 (m, 2H), 4.15-4.07 (m, 4H), 3.72-3.57 (m, 2H), 3.25 (m, 1H), 3.07 (m, 3H), 2.91 (m, 1H), 2.79 (m, 2H), 2.60-2.46 (m, 2H), 2.20-2.00 (m, 2H), 1.93-1.85 (m, 3H); MS (ESI) m/z 555.3 [M+1]$^+$.

Example S90. (S)-3-(1-Oxo-5-(((S)-1-((2-(tetrahydro-2H-pyran-4-yl)quinazolin-6-yl)methyl)pyrrolidin-3-yl)oxy)isoindolin-2-yl)piperidine-2,6-dione

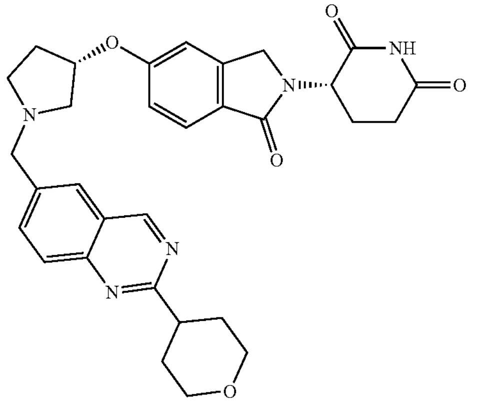

N-(2-Amino-5-bromobenzyl)tetrahydro-2H-pyran-4-carboxamide. To a stirred solution of 2-(aminomethyl)-4-bromo-aniline; dihydrochloride (8.42 g, 30.74 mmol), tetrahydropyran-4-carboxylic acid (4 g, 30.74 mmol) and HATU (17.54 g, 46.10 mmol) in DMF (30 mL) was added N,N-diisopropylethyl-amine (20 mL, 112.34 mmol) dropwise at 0° C. under nitrogen over 30 min. The resulting solution was stirred at 0° C. for 2 h under nitrogen. The reaction mixture was diluted with water and extracted with ethyl acetate. The extracts were dried over anhydrous sodium sulfate, filtered and concentrated. The residue was purified by reverse phase flash (10-40% acetonitrile+0.05% ammonium bicarbonate in water, over 35 min) to afford the title compound (6.4 g, 20.45 mmol, 66% yield) as an off-white solid. MS (ESI) m/z 313.0 [M+1]$^+$.

6-Bromo-2-(tetrahydro-2H-pyran-4-yl)-1,4-dihydroquinazoline. The solution of N-(2-amino-5-bromobenzyl)tetrahydro-2H-pyran-4-carboxamide (6.4 g, 20.45 mmol) in acetic acid (20 mL) was stirred at 100° C. for 2 h under nitrogen. The resulting mixture was concentrated. The residue was added saturated sodium bicarbonate to pH~7 and extracted with ethyl acetate. The extracts were dried over anhydrous sodium sulfate, filtered and concentrated to give the title compound (3.5 g, 11.86 mmol, 58% yield) as an off-white solid. MS (ESI) m/z 295.0 [M+1]$^+$.

6-Bromo-2-(tetrahydro-2H-pyran-4-yl)quinazoline. To the solution of 6-bromo-2-(tetrahydro-2H-pyran-4-yl)-1,4-dihydroquinazoline (3.5 g, 11.86 mmol) in chloroform (40 mL) was added manganese oxide (10.3 g, 118.58 mmol). The resulting mixture was stirred at 50° C. for 2 h under nitrogen. The resulting mixture was filtered and the filter cake was washed with dichloromethane (30 mL). The filtrate was concentrated under reduced pressure to afford the title compound (2.5 g, 8.53 mmol, 72% yield) as an off-white solid. MS (ESI) m/z 293.0 [M+1]$^+$.

2-(Tetrahydro-2H-pyran-4-yl)-6-vinylquinazoline. To a solution of 6-bromo-2-(tetrahydro-2H-pyran-4-yl)quinazoline (2.5 g, 8.53 mmol) and potassium trifluoro(vinyl)borate (2.3 g, 17.06 mmol) in 1,4-dioxane (20 mL) and water (4 mL) was added sodium carbonate (2.71 g, 25.58 mmol) and dichlorobis(triphenylphosphine)palladium(II) dichloromethane adduct (597 mg, 0.85 mmol) under nitrogen. The resulting mixture was stirred at 80° C. for 2 h under nitrogen. The mixture was diluted with water and extracted with ethyl acetate. The combined organic layers were dried over anhydrous sodium sulfate, filtered and concentrated. The residue was purified by silica gel chromatography (0 to 50% ethyl acetate in petroleum ether) to give the title compound (1.4 g, 5.81 mmol, 68% yield) as a yellow solid. MS (ESI) m/z 241.1 [M+1]$^+$.

2-(Tetrahydro-2H-pyran-4-yl)quinazoline-6-carbaldehyde. To a solution of 2-(tetrahydro-2H-pyran-4-yl)-6-vinylquinazoline (1.4 g, 5.81 mmol), 4-methylmorpholine N-oxide (1.56 g, 13.32 mmol) and critic acid (2.56 g, 13.32 mmol) in tert-butanol (10 mL) and water (10 mL) was added potassium osmate (221 mg, 0.60 mmol) at room temperature. The mixture was stirred for 3 h at room temperature. The resulting mixture was added sodium periodate (4.27 g, 19.98 mmol) at 0° C. and stirred for 1 h at room temperature. The mixture was added saturated sodium bicarbonate solution to pH~7 and extracted with ethyl acetate. The extracts were washed with brine, dried over anhydrous sodium sulfate, filtered and concentrated. The residue was purified by silica gel column chromatography (0 to 50% ethyl acetate in petroleum ether) to give the title compound (800 mg, 3.29 mmol, 56% yield) as an off-white solid. MS (ESI) m/z 243.1 [M+1]$^+$.

(S)-3-(1-Oxo-5-(((S)-1-((2-(tetrahydro-2H-pyran-4-yl)quinazolin-6-yl)methyl)pyrrolidin-3-yl)oxy)isoindolin-2-yl)piperidine-2,6-dione. A solution of 2-(tetrahydro-2H-pyran-4-yl)quinazoline-6-carbaldehyde (300 mg, 1.24 mmol), (S)-3-(1-oxo-5-(((S)-pyrrolidin-3-yl)oxy)isoindolin-2-yl)piperidine-2,6-dione; 2,2-2-trifluoroacetic acid (480 mg, 1.23 mmol) and triethylamine (0.51 mL, 3.66 mmol) in dichloromethane (5 mL) was added sodium triacetoxyborohydride (780 mg, 3.68 mmol) under nitrogen. The resulting mixture was stirred for 2 h at room temperature. Most solution was removed and was purified by silica gel chromatography (0 to 10% methanol in dichloromethane). Then the fractions were concentrated and further purified by preparative HPLC with the following conditions: Column: Xselect CSH C18 OBD Column 30*150 mm 5 μm; Mobile Phase A: water (0.05% TFA), Mobile Phase B; Flow rate: 60 mL/min; Gradient: 3% B to 24% B in 7 min, 24% B; Wave Length: 254/210 nm; $RT_1$ (min): 5.17. The pure fractions were concentrated and further purified by preparative chiral HPLC with the following conditions: Column: CHIRALPAK IA, 2*25 cm, 20 μm; Mobile Phase A: methyl tert-butyl ether (0.1% formic acid)-HPLC, Mobile Phase B: methanol: dichloromethane=1:1; Flow rate: 20 mL/min; Gradient: 50% B to 50% B in 20 min; Wave Length: 254/220 nm; $RT_1$ (min): 12.2; $RT_2$ (min): 16.2; Sample Solvent: ethanol—HPLC; Injection Volume: 1.2 mL. The pure fractions were collected and evaporated under reduced pressure to afford the title compound (90.2 mg, 0.16 mmol, 13% yield) as a brown solid. $^1$H NMR (400 MHz, DMSO-$d_6$) δ 9.52 (s, 1H), 8.13-7.93 (m, 3H), 7.62 (d, J=8.3 Hz, 1H), 7.10-7.00 (m, 2H), 5.04-4.99 (m, 2H), 4.40-4.22 (m, 2H), 3.98-3.89 (m, 4H), 3.53-3.47 (m, 2H), 3.24-3.19 (m, 1H), 3.04-2.99 (m, 1H), 2.91-2.74 (m, 3H), 2.62-2.58 (m, 2H), 2.40-2.34 (m, 2H), 2.00-1.86 (m, 6H); MS (ESI) m/z 556.3 $[M+1]^+$.

Example S91. 3-(5-(((S)-1-((2-((Oxetan-3-yloxy)methyl)quinolin-6-yl)methyl)pyrrolidin-3-yl)oxy)-1-oxoisoindolin-2-yl)piperidine-2,6-dione 2-((Oxetan-3-yloxy)methyl)quinoline-6-carbaldehyde. To a solution of 2-(oxetan-3-yloxymethyl)-6-vinyl-quinoline (150 mg, 0.62 mmol), potassium osmate (23 mg, 0.06 mmol), 4-methylmorpholine N-oxide (146 mg, 1.24 mmol) in tert-butanol (5 mL) and water (5 mL) was added citric acid (239 mg, 1.24 mmol) and the mixture was stirred for 12 h at room temperature under nitrogen. Then the above mixture was added sodium periodate (399 mg, 1.87 mmol) and stirred for 1 h under nitrogen. The mixture was basified to pH~7 with saturated sodium bicarbonate and extracted with ethyl acetate. The combined organic layers were washed with brine, dried over anhydrous sodium sulfate, filtered and concentrated afford the title compound (100 mg, 0.41 mmol, 66% yield) as a light yellow solid. MS (ESI) m/z 244.1 $[M+1]^+$.

3-(5-(((S)-1-((2-((Oxetan-3-yloxy)methyl)quinolin-6-yl)methyl)pyrrolidin-3-yl)oxy)-1-oxoisoindolin-2-yl)piperidine-2,6-dione. To a solution of 3-[1-oxo-5-[(3S)-pyrrolidin-3-yl]oxy-isoindolin-2-yl]piperidine-2,6-dione; 2,2,2-trifluoroacetic acid (60 mg, 0.14 mmol), 2-(oxetan-3-yloxymethyl)quinoline-6-carbaldehyde (40 mg, 0.16 mmol) in dichloromethane (2 mL) were added triethylamine (26 mg, 0.20 mmol) and sodium triacetoxyborohydride (86 mg, 0.41 mmol) and the mixture was stirred for 12 h at room temperature under nitrogen. The resulting mixture was concentrated and purified by silica gel chromatography (10% methanol in dichloromethane) and preparative Achiral SFC with the following conditions: DAICEL DCpak P4VP, 2*25 cm, 5 μm; Mobile Phase A: carbon dioxide, Mobile Phase B: methanol:acetonitrile=2:8 (0.1% ammonia); Flow rate: 50 mL/min; Gradient: isocratic 40% B; Column Temperature(° C.): 35; Back Pressure(bar): 100; Wave Length: 254 nm; $RT_1$ (min): 3.97; Sample Solvent: Ethanol-HPLC; Injection Volume: 1 mL; Number of Runs: 4. The fractions containing desired product were collected and evaporated under reduced pressure to afford the title compound (4.6 mg, 0.008 mmol, 6% yield) as a yellow solid. $^1$H NMR (400 MHz, DMSO-$d_6$) δ 10.97 (s, 1H), 8.37 (d, J=8.5 Hz, 1H), 7.98-7.88 (m, 2H), 7.75 (d, J=8.7 Hz, 1H), 7.61 (d, J=8.5 Hz, 2H), 7.12 (s, 1H), 7.05-6.98 (m, 1H), 5.11-5.02 (m, 2H), 4.78-4.65 (m, 5H), 4.53-4.46 (m, 2H), 4.37 (d, J=17.1 Hz, 1H), 4.25 (d, J=17.1 Hz, 1H), 3.84 (m, 2H), 2.99 (m, 2H), 2.93-2.79 (m, 1H), 2.55 (m, 3H), 2.36 (m, 2H), 1.98 (m, 1H), 1.86 (m, 1H); MS (ESI) m/z 557.2 $[M+1]^+$.

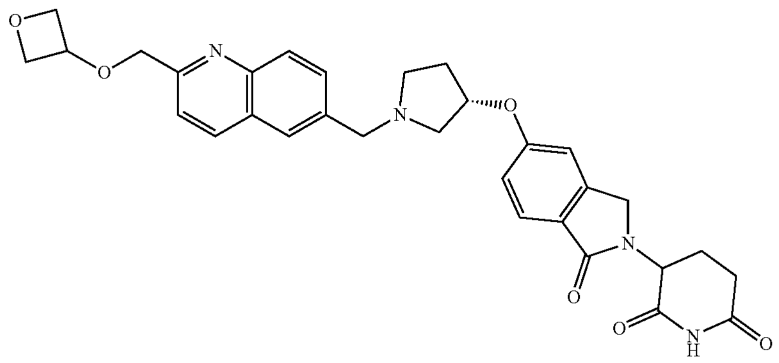 [SMILES: O=C1CCC(N2Cc3cc(O[C@H]4CCN(Cc5ccc6nc(COC7COC7)ccc6c5)C4)ccc3C2=O)C(=O)N1]

6-Bromo-2-((oxetan-3-yloxy)methyl)quinolone. To a solution of 6-bromo-2-(bromomethyl)quinoline (300 mg, 1.00 mmol), oxetan-3-ol (148 mg, 1.99 mmol) in THF (5 mL) was added potassium tert-butoxide (335 mg, 2.99 mmol) under nitrogen. The resulting mixture was stirred at 60° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (150 mg, 0.51 mmol, 51% yield) as a brown solid. MS (ESI) m/z 293.9 $[M+1]^+$.

2-((Oxetan-3-yloxy)methyl)-6-vinylquinoline. To a solution of 6-bromo-2-(oxetan-3-yloxymethyl)quinoline (270 mg, 0.92 mmol) and potassium vinyltrifluoroborate (248 mg, 1.84 mmol) in 1,4-dioxane (10 mL) and water (1 mL) were added [1'1-Bis(diphenylphosphino)ferrocene] dichloro palladiuM(II) (75 mg, 0.09 mmol) and sodium carbonate (292 mg, 2.75 mmol). The mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (150 mg, 0.62 mmol, 68% yield) as a light yellow solid. MS (ESI) m/z 242.2 $[M+1]^+$.

Example S92. 3-(5-(((S)-1-((2-(Isopropoxymethyl)quinolin-6-yl)methyl)pyrrolidin-3-yl)oxy)-1-oxoisoindolin-2-yl)piperidine-2,6-dione

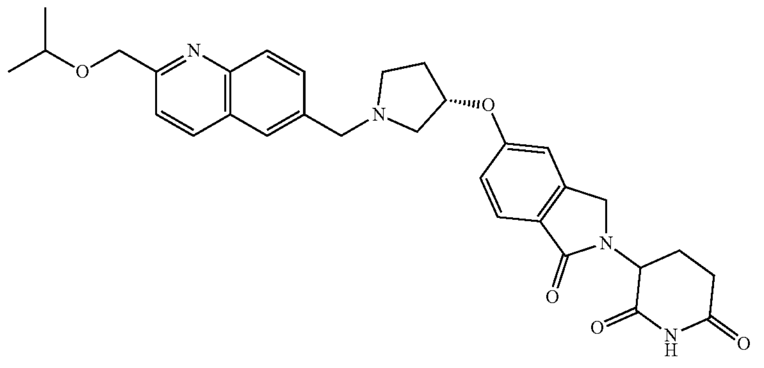 [SMILES: CC(C)OCc1ccc2cc(CN3CC[C@H](Oc4ccc5c(c4)CN(C4CCC(=O)NC4=O)C5=O)C3)ccc2n1]

6-Bromo-2-(bromomethyl)quinoline. A solution of 6-bromo-2-methyl quinoline (5 g, 22.51 mmol), NBS (4.81 g, 27.02 mmol) and 2,2'-azobisisobutyronitrile (0.37 g, 2.25 mmol) in 1,2-dichloroethane (30 mL) was stirred for 16 h at 80° C. under nitrogen. The mixture was concentrated. The residue was purified by reverse phase flash (10-100% acetonitrile+0.05% ammonium bicarbonate in water, over 25 min) to afford the title compound (3 g, 9.97 mmol, 44% yield) as a brown solid. MS (ESI) m/z 301.8 $[M+1]^+$.

6-Bromo-2-(isopropoxymethyl)quinoline. A solution of 6-bromo-2-(bromomethyl)quinoline (300 mg, 0.99 mmol) and potassium tert-butoxide (223 mg, 1.98 mmol) in propan-2-ol (4 mL) was stirred for 4 h at 80° C. under nitrogen. The mixture was concentrated and the residue was purified by reverse phase flash (10-100% acetonitrile+0.05% TFA in water, over 25 min) to afford the title compound (150 mg, 0.54 mmol, 54% yield) as a brown solid. MS (ESI) m/z 280.0 $[M+1]^+$.

2-(Isopropoxymethyl)-6-vinylquinoline. To a stirred solution of 6-bromo-2-(isopropoxymethyl)quinoline (150 mg, 0.54 mmol) and potassium trifluoro(vinyl)boranuide (86 mg, 0.64 mmol) in 1,4-dioxane (3 mL) and water (0.3 ml) were added tetrakis(triphenylphosphine)palladium (45 mg, 0.039 mmol) and cesium carbonate (348 mg, 1.07 mmol). The above mixture was stirred at 80° C. for 3 h under nitrogen. The mixture was diluted with water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (100 mg, 0.44 mmol, 82% yield) as a light-yellow oil. MS (ESI) m/z 228.2 $[M+1]^+$.

2-(Isopropoxymethyl)quinoline-6-carbaldehyde. To a stirred solution of 2-(isopropoxymethyl)-6-vinylquinoline (80 mg, 0.35 mmol) in tert-butanol (4 mL) and water (4 mL) were added potassium osmate (13 mg, 0.035 mmol), 4-methyl-morpholin-4-oxide (82 mg, 0.70 mmol) and citric acid (150 mg, 0.78 mmol). The above mixture was stirred at room temperature for 3 h under nitrogen. Then the mixture was added sodium periodate (225 mg, 1.06 mmol) and stirred for another 1 h. The mixture was added saturated sodium bicarbonate solution to pH~7 and extracted with ethyl acetate. The extracts were washed with brine, dried over sodium sulfate, filtered and concentrated. The residue was purified by silica gel chromatography (0 to 25% ethyl acetate in petroleum ether) to afford the title compound (30 mg, 0.13 mmol, 37% yield) as a light-yellow oil. MS (ESI) m/z 230.0 $[M+1]^+$.

3-(5-(((S)-1-((2-(Isopropoxymethyl)quinolin-6-yl)methyl)pyrrolidin-3-yl)oxy)-1-oxoisoindolin-2-yl)piperidine-2,6-dione. To a solution of 2-(isopropoxymethyl) quinoline-6-carbaldehyde (30 mg, 0.13 mmol), 3-(1-oxo-5-(((S)-pyrrolidin-3-yl)oxy) isoindolin-2-yl)piperidine-2,6-dione; 2,2,2-trifluoroacetic acid (70 mg, 0.16 mmol) and triethylamine (40 mg, 0.40 mmol) in dichloromethane (4 mL) was added sodium triacetoxyborohydride (110 mg, 0.52 mmol). The mixture was stirred for 12 h at room temperature under nitrogen. The resulting mixture was concentrated and the residue was purified by silica gel chromatography (0 to 10% methanol in dichloromethane) and preparative HPLC with the following conditions: Column: Sunfire prep Cis column, 30*150 mm, 5 μm; Mobile Phase A: water (0.1% formic acid), Mobile Phase B: acetonitrile; Flow rate: 60 mL/min; Gradient: 5% B to 30% B in 7 min, 30% B; Wave Length: 254/220 nm; $RT_1$ (min): 5.5. The fractions containing desired product were collected and evaporated under reduced pressure to afford the title compound (19.9 mg, 0.037 mmol, 28% yield) as a white solid. $^1H$ NMR (300 MHz, Methanol-$d_4$) δ 8.35 (d, J=8.5 Hz, 1H), 8.01 (d, J=8.7 Hz, 1H), 7.92 (s, 1H), 7.84 (d, J=8.3 Hz, 1H), 7.71 (d, J=8.4 Hz, 2H), 7.12-7.02 (m, 2H), 5.17-5.01 (m, 2H), 4.79 (s, 2H), 4.43 (d, J=3.9 Hz, 2H), 3.98 (d, J=4.2 Hz, 2H), 3.82 (m, 1H), 3.16-2.72 (m, 6H), 2.46-2.42 (m, 2H), 2.23-2.00 (m, 2H), 1.28-1.21 (m, 6H); MS (ESI) m/z 543.3 $[M+1]^+$.

Example S93. 3-(1-Oxo-5-(((S)-1-((2-((((S)-tetrahydrofuran-3-yl)oxy)methyl)quinolin-6-yl)methyl) pyrrolidin-3-yl)oxy)isoindolin-2-yl)piperidine-2,6-dione

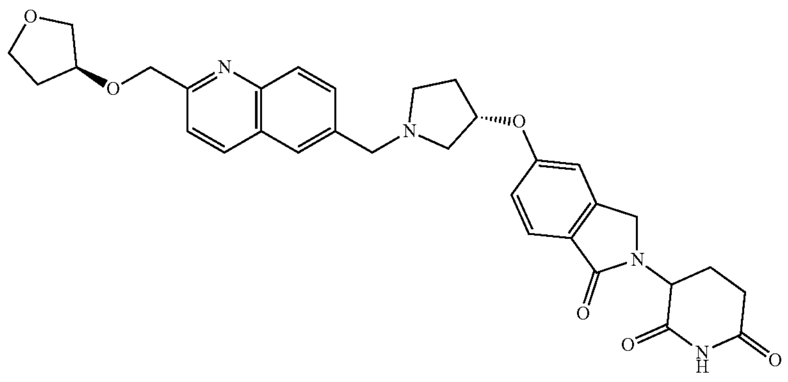 [SMILES: O=C1CCC(N2Cc3cc(O[C@H]4CCN(Cc5ccc6nc(CO[C@H]7CCOC7)ccc6c5)C4)ccc3C2=O)C(=O)N1]

(S)-6-Bromo-2-(((tetrahydrofuran-3-yl)oxy)methyl)quinoline. To a solution of 6-bromo-2-(bromomethyl)quinoline (300 mg, 1.00 mmol), (S)-tetrahydrofuran-3-ol (440 mg, 4.99 mmol) and potassium tert-butoxide (341 mg, 3.04 mmol) in DMF (5 mL). The mixture was stirred 4 h at 80° C. under nitrogen. The resulting mixture was filtered and the filtrate was purified by reverse phase flash (10-100% acetonitrile+0.05% TFA in water, over 25 min) to afford the title compound (200 mg, 0.65 mmol, 65% yield) as a brown solid. MS (ESI) m/z 308.0 $[M+1]^+$.

(S)-2-(((Tetrahydrofuran-3-yl)oxy)methyl)-6-vinylquinoline. To a stirred solution of (S)-6-bromo-2-(((tetrahydrofuran-3-yl)oxy)methyl)quinoline (170 mg, 0.55 mmol) and potassium trifluoro(vinyl)borate (89 mg, 0.66 mmol) in 1,4-dioxane (3 mL) and water (0.6 mL) were added tetrakis (triphenylphosphine) palladium (47 mg, 0.041 mmol) and cesium carbonate (358 mg, 1.10 mmol). The above mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (80 mg, 0.31 mmol, 57% yield) as a light-yellow oil. MS (ESI) m/z 256.2 $[M+1]^+$.

(S)-2-(((Tetrahydrofuran-3-yl)oxy)methyl)quinoline-6-carbaldehyde. To a stirred solution of (S)-2-(((tetrahydrofuran-3-yl)oxy)methyl)-6-vinylquinoline (80 mg, 0.31 mmol) in tert-butanol (4 mL) and water (4 mL) were added potassium osmate (12 mg, 0.03 mmol), 4-methyl-morpholin4-oxide (73 mg, 0.63 mmol) and citric acid (134 mg, 0.70 mmol). The above mixture was stirred at room temperature for 3 h under nitrogen. Then the mixture was added sodium periodate (201 mg, 0.94 mmol) and stirred for another 1 h. The mixture was added saturated sodium bicarbonate solution to pH~7 and extracted with ethyl acetate. The extracts were washed with brine, dried over sodium sulfate, filtered and concentrated. The residue was purified by silica gel chromatography (0 to 25% ethyl acetate in petroleum ether) to afford the title compound (40 mg, 0.16 mmol, 50% yield) as a light-yellow oil. MS (ESI) m/z 258.2 $[M+1]^+$.

3-(1-Oxo-5-(((S)-1-((2-((((S)-tetrahydrofuran-3-yl)oxy) methyl)quinolin-6-yl) methyl)pyrrolidin-3-yl)oxy)isoindolin-2-yl)piperidine-2,6-dione. To a solution of (S)-2-(((tetrahydrofuran-3-yl)oxy)methyl)quinoline-6-carbaldehyde (40 mg, 0.16 mmol), 3-(1-oxo-5-(((S)-pyrrolidin-3-yl)oxy) isoindolin-2-yl)piperidine-2,6-dione; 2,2,2-trifluoroacetic acid (83 mg, 0.19 mmol) and triethylamine (45 mg, 0.45 mmol) in dichloromethane (4 mL) was added sodium triacetoxyborohydride (130 mg, 0.61 mmol). The mixture was stirred for 12 h at room temperature under nitrogen. The resulting mixture was concentrated and the residue was purified by silica gel chromatography (0 to 10% methanol in dichloromethane) and preparative HPLC further with the following conditions: Column: Sunfire prep Cis column, 30*150 mm, 5 μm; Mobile Phase A: water (0.1% formic acid), Mobile Phase B: acetonitrile; Flow rate: 60 mL/min; Gradient: 2% B to 25% B in 7 min, 25% B; Wave Length: 254/220 nm; $RT_1$ (min): 6.3. The fractions containing desired product were collected and evaporated under reduced pressure to afford the title compound (17.9 mg, 0.03 mmol, 20% yield) as a white solid. $^1H$ NMR (400 MHz, Methanol-$d_4$) δ 8.37 (m, 2H), 8.03 (d, J=8.7 Hz, 1H), 7.96 (s, 1H), 7.85-7.83 (m, 1H), 7.71-7.66 (m, 2H), 7.11-7.02 (m, 2H), 5.16-5.06 (m, 2H), 4.80 (d, J=4.5 Hz, 2H), 4.49-4.37 (m, 3H), 4.17-4.05 (m, 2H), 4.02-3.81 (m, 4H), 3.25-3.04 (m, 3H), 2.96-2.74 (m, 3H), 2.55-2.43 (m, 2H), 2.13-2.09 (m, 4H); MS (ESI) m/z 571.3 $[M+1]^+$.

Example S94. 3-(1-Oxo-5-(((S)-1-((2-((((R)-tetrahydrofuran-3-yl)oxy)methyl)quinolin-6-yl)methyl)pyrrolidin-3-yl)oxy)isoindolin-2-yl)piperidine-2,6-dione

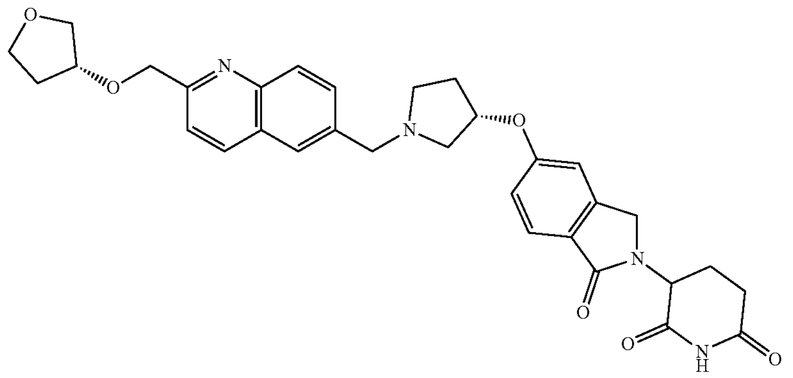 [SMILES: O=C1CCC(N2Cc3cc(O[C@H]4CCN(Cc5ccc6nc(CO[C@@H]7CCOC7)ccc6c5)C4)ccc3C2=O)C(=O)N1]

(R)-6-Bromo-2-(((tetrahydrofuran-3-yl)oxy)methyl)quinoline. To a solution of 6-bromo-2-(bromomethyl)quinoline (300 mg, 1.00 mmol), (R)-tetrahydrofuran-3-ol (440 mg, 4.99 mmol) and potassium tert-butoxide (340 mg, 3.04 mmol) in DMF (5 mL) was stirred for 4 h at 80° C. under nitrogen. The resulting mixture was filtered and the filtrate was purified by reverse phase flash (10-100% acetonitrile+0.05% TFA in water, over 25 min) to afford the title compound (170 mg, 0.55 mmol, 55% yield) as a brown solid. MS (ESI) m/z 307.9 $[M+1]^+$.

(R)-2-(((Tetrahydrofuran-3-yl)oxy)methyl)-6-vinylquinoline. To a stirred solution of (R)-6-bromo-2-(((tetrahydrofuran-3-yl)oxy)methyl)quinoline (150 mg, 0.49 mmol) and potassium trifluoro(vinyl)borate (78 mg, 0.58 mmol) in 1,4-dioxane (3 mL) and water (0.3 mL) were added tetrakis (triphenyl phosphine)palladium (41 mg, 0.035 mmol) and cesium carbonate (316 mg, 0.97 mmol). The above mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (60 mg, 0.23 mmol, 48% yield) as a light-yellow oil. MS (ESI) m/z 256.2 $[M+1]^+$.

(R)-2-(((Tetrahydrofuran-3-yl)oxy)methyl)quinoline-6-carbaldehyde. To a stirred solution of (R)-2-(((tetrahydrofuran-3-yl)oxy)methyl)-6-vinylquinoline (60 mg, 0.23 mmol) in tert-butanol (4 mL) and water (4 mL) were added potassium osmate (9 mg, 0.02 mmol), 4-methyl-morpholin-4-oxide (55 mg, 0.47 mmol) and citric acid (100 mg, 0.47 mmol). The above mixture was stirred at room temperature for 3 h under nitrogen. Then the mixture was added sodium periodate (150 mg, 0.71 mmol) and stirred for another 1 h. The mixture was added saturated sodium bicarbonate solution to pH~7 and extracted with ethyl acetate. The extracts were washed with brine, dried over sodium sulfate, filtered and concentrated. The residue was purified by silica gel chromatography (0 to 25% ethyl acetate in petroleum ether) to afford the title compound (30 mg, 0.12 mmol, 50% yield) as a light-yellow oil. MS (ESI) m/z 258.2 $[M+1]^+$.

3-(1-Oxo-5-(((S)-1-((2-((((R)-tetrahydrofuran-3-yl)oxy)methyl)quinolin-6-yl)methyl)pyrrolidin-3-yl)oxy)isoindolin-2-yl)piperidine-2,6-dione. To a solution of (R)-2-(((tetrahydrofuran-3-yl)oxy)methyl)quinoline-6-carbaldehyde (30 mg, 0.12 mmol), 3-(1-oxo-5-(((S)-pyrrolidin-3-yl)oxy)isoindolin-2-yl)piperidine-2,6-dione; 2,2,2-trifluoroacetic acid (70 mg, 0.16 mmol) and triethylamine (34 mg, 0.34 mmol) in dichloromethane (4 mL) was added sodium triacetoxyborohydride (98 mg, 0.46 mmol). The mixture was stirred for 12 h at room temperature under nitrogen. The resulting mixture was concentrated. The residue was purified by silica gel chromatography (0 to 10% methanol in dichloromethane) and preparative HPLC further with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 25% B in 7 min, 25% B; Wave Length: 254/220 nm; $RT_1$ (min): 5.6. The fractions containing desired product were collected and evaporated under reduced pressure to afford the title compound (22.6 mg, 0.04 mmol, 34% yield) as a white solid. $^1$H NMR (400 MHz, Methanol-$d_4$) δ 8.36 (d, J=8.5 Hz, 2H), 8.03 (d, J=8.7 Hz, 1H), 7.97 (s, 1H), 7.86-7.84 (m, 1H), 7.71-7.67 (m, 2H), 7.12-7.01 (m, 2H), 5.18-5.07 (m, 2H), 4.85-4.75 (m, 2H), 4.50-4.35 (m, 3H), 4.20-4.09 (m, 2H), 4.00-3.81 (m, 4H), 3.27-3.09 (m, 3H), 2.97-2.75 (m, 3H), 2.56-2.40 (m, 2H), 2.13-2.08 (m, 4H); MS (ESI) m/z 571.3 $[M+1]^+$.

Example S95. 3-(5-(((S)-1-((2-(2,2-Dimethylmorpholino)quinolin-6-yl)methyl)pyrrolidin-3-yl)oxy)-1-oxoisoindolin-2-yl)piperidine-2,6-dione

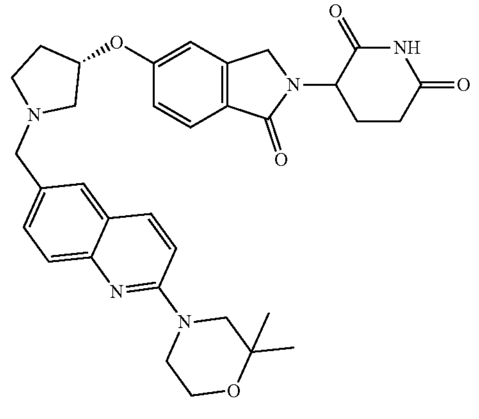 [SMILES: CC1(C)CN(c2ccc3cc(CN4CC[C@H](Oc5ccc6c(c5)CN(C5CCC(=O)NC5=O)C6=O)C4)ccc3n2)CCO1]

Methyl 2-(2,2-dimethylmorpholino)quinoline-6-carboxylate. A mixture of methyl 2-chloroquinoline-6-carboxylate (300 mg, 1.35 mmol) and 2,2-dimethylmorpholine (623 mg, 5.41 mmol) in ethanol (6 mL) was stirred at 80° C. for 12 h under nitrogen. The resulting mixture was concentrated. The residue was purified by silica gel chromatography (0 to 40% ethyl acetate in petroleum ether) to afford the title compound (350 mg, 1.16 mmol, 86% yield) as a yellow solid. MS (ESI) m/z 300.4 $[M+1]^+$.

(2-(2,2-Dimethylmorpholino)quinolin-6-yl)methanol. To a solution of methyl 2-(2,2-dimethylmorpholino)quinoline-6-carboxylate (300 mg, 1 mmol) in THF (8 mL) at 0° C. was added lithium aluminum hydride (2.5 M in THF, 0.6 mL, 1.5 mmol) under nitrogen. The resulting mixture was stirred at 0° C. for 2 h under nitrogen. The reaction mixture was quenched with sodium sulfate decahydrate and stirred for 5 min. The mixture was diluted with THF, filtered and the filtrate was concentrated. The residue was purified by reverse phase flash (10-30% acetonitrile+0.05% ammonium bicarbonate in water, over 20 min) to give the title compound (250 mg, 0.92 mmol, 92% yield) as a light-yellow solid. MS (ESI) m/z 273.2 $[M+1]^+$.

2-(2,2-Dimethylmorpholino)quinoline-6-carbaldehyde. To a stirred solution of (2-(2,2-dimethylmorpholino)quinolin-6-yl)methanol (250 mg, 0.92 mmol) in dichloromethane (6 mL) was added manganese dioxide (1.6 g, 18.36 mmol) and the mixture was stirred at room temperature for 12 h under nitrogen. The mixture was filtered and the filtrate cake was washed with dichloromethane. The filtrate was concentrated and the residue was purified by silica gel chromatography (0 to 40% ethyl acetate in petroleum ether) to afford the title compound (200 mg, 0.74 mmol, 80% yield) as a light-yellow solid. MS (ESI) m/z 271.0 $[M+1]^+$.

3-(5-(((S)-1-((2-(2,2-Dimethylmorpholino)quinolin-6-yl)methyl)pyrrolidin-3-yl)oxy)-1-oxoisoindolin-2-yl)piperidine-2,6-dione. To a solution of 2-(2,2-dimethylmorpholino)quinoline-6-carbaldehyde (50 mg, 0.18 mmol), 3-(1-oxo-5-(((S)-pyrrolidin-3-yl)oxy)isoindolin-2-yl)piperidine-2,6-dione; 2,2,2-trifluoroacetic acid (100 mg, 0.23 mmol) and triethylamine (50 mg, 0.5 mmol) in dichloromethane (4 mL) was added sodium triacetoxyborohydride (150 mg, 0.71 mmol). The mixture was stirred for 12 h at room temperature under nitrogen. The resulting mixture was concentrated. The residue was purified by silica gel chromatography (0 to 10% methanol in dichloromethane) and preparative-HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 25% B in 7 min, 25% B; Wave Length: 254/220 nm; $RT_1$ (min): 7.23. The fractions containing desired product were collected and evaporated under reduced pressure to afford the title compound (32 mg, 0.05 mmol, 30% yield) as an off-white solid. $^1H$ NMR (400 MHz, Methanol-$d_4$) δ 8.00-7.98 (m, 1H), 7.75-7.71 (m, 2H), 7.68 (d, J=8.6 Hz, 1H), 7.65-7.60 (m, 1H), 7.20 (d, J=9.3 Hz, 1H), 7.11 (t, J=2.2 Hz, 1H), 7.06-7.03 (m, 1H), 5.19 (m, 1H), 5.12-5.09 (m, 1H), 4.50-4.38 (m, 2H), 4.32-4.21 (m, 2H), 3.87-3.83 (m, 2H), 3.75-3.71 (m, 2H), 3.61 (s, 2H), 3.50-3.41 (m, 1H), 3.38-3.33 (m, 2H), 3.23-3.15 (m, 1H), 2.91-2.88 (m, 1H), 2.78-2.75 (m, 1H), 2.58-2.42 (m, 2H), 2.28-2.12 (m, 2H), 1.30 (s, 6H); MS (ESI) m/z 584.3 $[M+1]^+$.

Example S96. 3-(5-(((S)-1-((2-(2,2-Dimethylmorpholino)quinazolin-6-yl)methyl)pyrrolidin-3-yl)oxy)-1-oxoisoindolin-2-yl)piperidine-2,6-dione

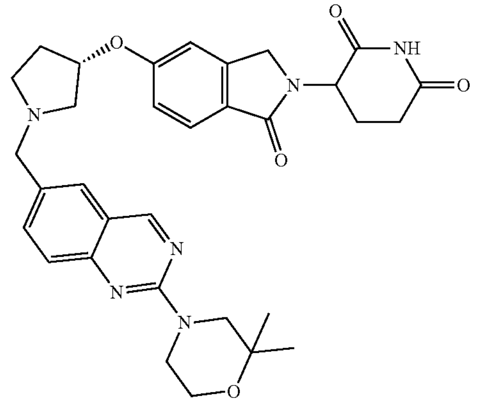 [SMILES: CC1(C)CN(c2ncc3cc(CN4CC[C@H](Oc5ccc6c(c5)CN(C5CCC(=O)NC5=O)C6=O)C4)ccc3n2)CCO1]

4-(6-Bromoquinazolin-2-yl)-2,2-dimethylmorpholine. To a stirred solution of 6-bromo-2-chloro-quinazoline (300 mg, 1.23 mmol) in acetonitrile (6 mL) was added 2,2-dimethylmorpholine (420 mg, 3.65 mmol) and potassium carbonate (500 mg, 3.62 mmol). The above mixture was stirred at 80° C. for 12 h under nitrogen. The reaction mixture was filtered and the filtrate was concentrated. The residue was purified by silica gel chromatography (0 to 40% ethyl acetate in petroleum ether) to afford the title compound (250 mg, 0.77 mmol, 63% yield) as a light-yellow oil. MS (ESI) m/z 321.9 $[M+1]^+$.

2,2-Dimethyl-4-(6-vinylquinazolin-2-yl)morpholine. To a stirred solution of 4-(6-bromoquinazolin-2-yl)-2,2-dimethylmorpholine (250 mg, 0.77 mmol) and potassium trifluoro(vinyl)borate (124 mg, 0.93 mmol) in 1,4-dioxane (3 mL) were added tetrakis(triphenylphosphine)palladium (65 mg, 0.056 mmol) and cesium carbonate (504 mg, 1.55 mmol). The above mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (150 mg, 0.56 mmol, 72% yield) as a light-yellow oil. MS (ESI) m/z 270.0 $[M+1]^+$.

2-(2,2-Dimethylmorpholino)quinazoline-6-carbaldehyde. To a stirred solution of 2,2-dimethyl-4-(6-vinylquinazolin-2-yl)morpholine (150 mg, 0.56 mmol) in tert-butanol (3 mL) and water (3 mL) were added potassium osmate (20 mg, 0.06 mmol), 4-methyl-morpholin4-oxide (130 mg, 1.11 mmol) and citric acid (238 mg, 1.11 mmol). The above mixture was stirred at room temperature for 3 h under nitrogen. Then the mixture was added sodium periodate (357 mg, 1.67 mmol) and stirred for another 1 h. The mixture was added saturated sodium bicarbonate to pH~7 and extracted with ethyl acetate. The extracts were dried over anhydrous sodium sulfate, filtered and concentrated. The residue was purified by silica gel chromatography (0 to 40% ethyl acetate in petroleum ether) to give the title compound (100 mg, 0.36 mmol, 66% yield) as a light-yellow oil. MS (ESI) m/z 272.1 $[M+1]^+$.

3-(5-(((S)-1-((2-(2,2-Dimethylmorpholino)quinazolin-6-yl)methyl)pyrrolidin-3-yl)oxy)-1-oxoisoindolin-2-yl)piperidine-2,6-dione. To a solution of 2-(2,2-dimethylmorpholino)

quinazoline-6-carbaldehyde (50 mg, 0.18 mmol), 3-(1-oxo-5-(((S)-pyrrolidin-3-yl)oxy)isoindolin-2-yl)piperidine-2,6-dione; 2,2,2-trifluoroacetic acid (100 mg, 0.23 mmol) and triethylamine (50 mg, 0.5 mmol) in dichloromethane (4 mL) was added sodium triacetoxyborohydride (150 mg, 0.71 mmol). The mixture was stirred for 12 h at room temperature under nitrogen. The resulting mixture was concentrated. The residue was purified by silica gel chromatography (0 to 10% methanol in dichloromethane) and preparative-HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 30% B in 7 min, 30% B; Wave Length: 254/210 nm; $RT_1$ (min): 6.38. The fractions containing desired product were collected and evaporated under reduced pressure to afford the title compound (32.9 mg, 0.05 mmol, 29% yield) as a light-yellow solid. $^1$H NMR (400 MHz, Methanol-$d_4$) δ 9.09 (s, 1H), 7.79-7.75 (m, 2H), 7.72 (d, J=8.4 Hz, 1H), 7.61-7.55 (m, 1H), 7.10 (t, J=2.1 Hz, 1H), 7.06-7.04 (m, 1H), 5.17-5.09 (m, 2H), 4.50-4.38 (m, 2H), 4.10-3.99 (m, 2H), 3.94-3.90 (m, 2H), 3.90-3.79 (m, 4H), 3.30-3.24 (m, 1H), 3.19-3.10 (m, 2H), 3.01-2.85 (m, 2H), 2.79-2.77 (m, 1H), 2.56-2.43 (m, 2H), 2.21-2.07 (m, 2H), 1.27 (s, 6H); MS (ESI) m/z 585.4 $[M+1]^+$.

Example S97. 3-(5-(((S)-1-((2-(2-Oxa-6-azaspiro[3.3]heptan-6-yl)quinolin-6-yl)methyl)pyrroled-in-3-yl)oxy)-1-oxoisoindolin-2-yl)piperidine-2,6-dione

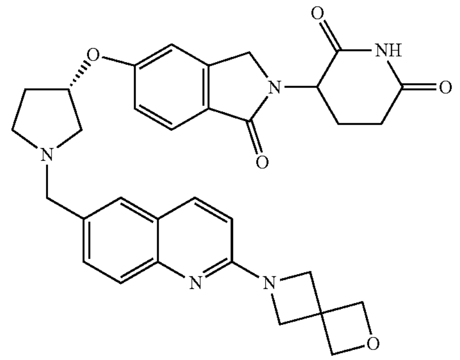 [SMILES: O=C1CCC(N2Cc3cc(O[C@H]4CCN(Cc5ccc6nc(N7CC8(COC8)C7)ccc6c5)C4)ccc3C2=O)C(=O)N1]

Methyl 2-(2-oxa-6-azaspiro[3.3]heptan-6-yl)quinoline-6-carboxylate. A mixture of methyl 2-chloroquinoline-6-carboxylate (150 mg, 0.70 mmol), 2-oxa-6-azaspiro[3.3]heptane (100 mg, 1.00 mmol), palladium G3-(4-(N,N-Dimethylamino)phenyl)di-tert-butylphosphine (40 mg, 0.10 mmol), bis(di-tert-butyl)-4-dimethylaminophenylphosphine (40 mg, 0.063 mmol) and cesium carbonate (670 mg, 2.06 mmol) in toluene (10. mL) was stirred at 100° C. for 12 h under nitrogen. Then the mixture was diluted with water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (151 mg, 0.53 mmol, 76% yield) as a light yellow oil. MS (ESI) m/z 285.2 $[M+1]^+$.

(2-(2-Oxa-6-azaspiro[3.3]heptan-6-yl)quinolin-6-yl)methanol. A mixture of methyl 2-(2-oxa-6-azaspiro[3.3]heptan-6-yl)quinoline-6-carboxylate (150 mg, 0.58 mmol) in THF (20 mL) was added lithium aluminum hydride (2.5 M in THF, 0.5 mL, 1.25 mmol) and the resulting solution was stirred at 0° C. for 2 h under nitrogen. The resulting mixture was diluted with THF, added sodium sulfate decahydrate and filtered. The filtrate was concentrated and the residue was purified by silica gel chromatography (0 to 50% ethyl acetate in petroleum ether) to afford the title compound (140 mg, 0.54 mmol, 93% yield) as a light yellow solid. MS (ESI) m/z 257.0 $[M+1]^+$.

2-(2-Oxa-6-azaspiro[3.3]heptan-6-yl)quinoline-6-carbaldehyde. A mixture of (2-(2-oxa-6-azaspiro[3.3]heptan-6-yl)quinolin-6-yl)methanol (140 mg, 0.54 mmol), and manganese dioxide (200 mg, 2.30 mmol) in dichloromethane (15 mL) was stirred at room temperature for 3 h under nitrogen. The resulting mixture was filtered to afford the title compound (42 mg, 0.16 mmol, 30% yield) as a light red solid. MS (ESI) m/z 255.1 $[M+1]^+$.

3-(5-(((S)-1-((2-(2-oxa-6-azaspiro[3.3]heptan-6-yl)quinolin-6-yl)methyl)pyrrolidin-3-yl)oxy)-1-oxoisoindolin-2-yl)piperidine-2,6-dione. To a solution of 2-(2-oxa-6-azaspiro[3.3]heptan-6-yl)quinoline-6-carbaldehyde (42 mg, 0.16 mmol), 3-(1-oxo-5-(((S)-pyrrolidin-3-yl)oxy)isoindolin-2-yl)piperidine-2,6-dione; hydrochloriide (60 mg, 0.16 mmol) and triethylamine (0.06 mL, 0.46 mmol) in dichloromethane (5 mL) was added sodium triacetoxyborohydride (150 mg, 0.71 mmol) in several portions at 0° C. and the resulting mixture was stirred at room temperature for 2 h. The mixture was concentrated and purified by preparative HPLC with the following conditions: Sunfire prep C18 column, 30*150 mm, 5 μm; Mobile Phase A: water (0.1% formic acid), Mobile Phase B: acetonitrile; Flow rate: 60 mL/min; Gradient: 2% B to 20% B in 7 min, 20% B; Wave Length: 254/220 nm; $RT_1$ (min): 6.3. The fractions containing desired product were collected and evaporated under reduced pressure to afford the title compound (26.2 mg, 0.043 mmol, 27% yield) as a light-yellow solid. $^1$H NMR (400 MHz, Methanol-$d_4$) δ 9.11 (s, 1H), 7.87-7.79 (m, 2H), 7.72-7.60 (m, 4H), 7.12-7.02 (m, 2H), 6.75 (m, 1H), 5.12 (m, 2H), 4.85 (m, 4H), 4.50-4.37 (m, 6H), 4.20-4.10 (m, 2H), 3.71 (m, 1H), 3.30-3.20 (m, 2H), 3.10-3.00 (m, 2H), 2.92-2.76 (m, 2H), 2.55-2.40 (m, 2H), 2.21-2.06 (m, 2H); MS (ESI) m/z 568.2 $[M+1]^+$.

Example S98. 3-(5-(((S)-1-((2-(2-Oxa-6-azaspiro[3.3]heptan-6-yl)quinazolin-6-yl)methyl)pyrrolidin-3-yl)oxy)-1-oxoisoindolin-2-yl)piperidine-2,6-dione

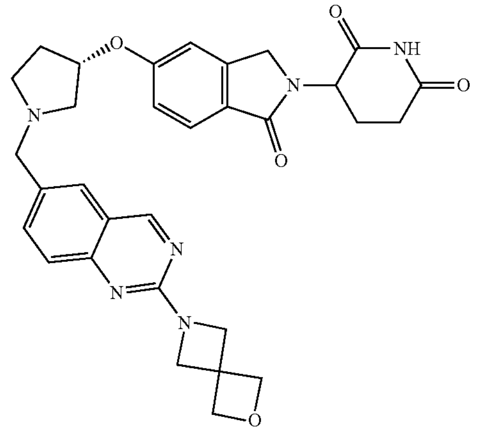 [SMILES: O=C1CCC(N2Cc3cc(O[C@H]4CCN(Cc5ccc6nc(N7CC8(COC8)C7)ncc6c5)C4)ccc3C2=O)C(=O)N1]

6-(6-Bromoquinazolin-2-yl)-2-oxa-6-azaspiro[3.3]heptane. To a solution of 6-bromo-2-chloro-quinazoline (200 mg, 0.82 mmol), 2-oxa-6-azaspiro[3.3]heptane (407 mg, 4.11 mmol) in ethanol (5 mL) was added N,N-diisopropylethylamine (1.1 g, 8.21 mmol) under nitrogen. The mixture was stirred for 12 h at 80° C. under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (200 mg, 0.65 mmol, 80% yield) as a light yellow oil. MS (ESI) m/z 306.0 $[M+1]^+$.

6-(6-Vinylquinazolin-2-yl)-2-oxa-6-azaspiro[3.3]heptane. To a solution of 6-(6-bromoquinazolin-2-yl)-2-oxa-6-azaspiro[3.3]heptane (160 mg, 0.52 mmol), potassium vinyltrifluoroborate (141 mg, 1.05 mmol) in 1,4-dioxane (10 mL) and water (0.1 mL) were added [1'1-Bis(diphenylphosphino)ferrocene]dichloro palladiuM(II) (43 mg, 0.059 mmol) and sodium carbonate (166 mg, 1.57 mmol). The mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (100 mg, 0.40 mmol, 76% yield) as a light yellow solid. MS (ESI) m/z 254.2 $[M+1]^+$.

2-(2-Oxa-6-azaspiro[3.3]heptan-6-yl)quinazoline-6-carbaldehyde. To a solution of 6-(6-vinylquinazolin-2-yl)-2-oxa-6-azaspiro[3.3]heptane (90 mg, 0.36 mmol) in THF (5 mL) and water (5 mL) was added ad-mix-β (1.4 g, 1.78 mmol). The mixture was stirred for 12 h at room temperature under nitrogen. Then the mixture was added sodium periodate (228 mg, 1.07 mmol) and the mixture was stirred at room temperature for 6 h under nitrogen. The resulting mixture was added saturated sodium bicarbonate solution to pH~7 and extracted with ethyl acetate. The extracts were washed with brine, dried over sodium sulfate, filtered and concentrated to afford the title compound (70 mg, 0.27 mmol, 75% yield) as a light yellow solid. MS (ESI) m/z 256.0 $[M+1]^+$.

3-(5-(((S)-1-((2-(2-oxa-6-azaspiro[3.3]heptan-6-yl)quinazolin-6-yl)methyl)pyrrolidin-3-yl)oxy)-1-oxoisoindolin-2-yl)piperidine-2,6-dione. To a solution of 3-[1-oxo-5-[(3S)-pyrrolidin-3-yl]oxy-isoindolin-2-yl]piperidine-2,6-dione; 2,2,2-trifluoroacetic acid (100 mg, 0.23 mmol), 2-(2-oxa-6-azaspiro[3.3]heptan-6-yl)quinazolin-e-6-carbaldehyde (58 mg, 0.23 mmol) in dichloromethane (5 mL) were added triethylamine (43 mg, 0.43 mmol) and sodium triacetoxyborohydride (141 mg, 0.67 mmol) at room temperature. The mixture was stirred 2 h at 35° C. under nitrogen. The resulting mixture was concentrated. The residue was purified by silica gel chromatography (0 to 10% methanol in dichloromethane) and further purified by preparative chiral HPLC with following condition: Sunfire prep C18 column, 30*150 mm, 5 μm; Mobile Phase A: water (0.1% formic acid), Mobile Phase B: acetonitrile; Flow rate: 60 mL/min; Gradient: 2% B to 25% B in 7 min, 25% B; Wave Length: 254/220 nm; $RT_1$ (min): 5.25. The fractions containing desired product were collected and evaporated under reduced pressure to afford the title compound (52 mg, 0.091 mmol, 40% yield) as an off-white solid. $^1H$ NMR (400 MHz, Deuterium Oxide) δ 8.66 (d, J=8.9 Hz, 1H), 7.72-7.64 (m, 2H), 7.41-7.27 (m, 2H), 6.75-6.64 (m, 2H), 5.07 (m, 2H), 4.94-4.81 (m, 4H), 4.47 (d, J=13.3 Hz, 1H), 4.35 (m, 1H), 4.22-4.13 (m, 6H), 3.65-3.58 (m, 4H), 2.85-2.68 (m, 2H), 2.33-2.23 (m, 3H), 2.07 (m, 1H); MS (ESI) m/z 569.3 $[M+1]^+$.

Example S99. 3-(5-(((S)-1-((2-(7-Oxa-2-azaspiro[3.5]nonan-2-yl)quinolin-6-yl)methyl)pyrrolidin-3-yl)oxy)-1-oxoisoindolin-2-yl)piperidine-2,6-dione

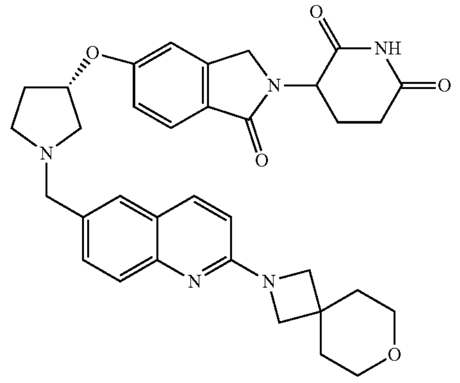 [SMILES: O=C1CCC(N2Cc3cc(O[C@H]4CCN(Cc5ccc6nc(N7CC8(CCOCC8)C7)ccc6c5)C4)ccc3C2=O)C(=O)N1]

Methyl 2-(7-oxa-2-azaspiro[3.5]nonan-2-yl)quinoline-6-carboxylate. A mixture of methyl 2-chloroquinoline-6-carboxylate (150 mg, 0.68 mmol), 7-oxa-2-azaspiro[3.5]nonane (100 mg, 0.79 mmol), palladium G3-(4-(N,N-Dimethylamino)phenyl)di-tert-butylphosphine (40 mg, 0.063 mmol), bis(di-tert-butyl)-4-dimethylaminophenylphosphine (40 mg, 0.081 mmol) and cesium carbonate (670 mg, 2.06 mmol) in toluene (10 mL) was stirred at 100° C. for 12 h under nitrogen. Then the resulting mixture was diluted with water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (151 mg, 0.48 mmol, 74% yield) as a light yellow oil. MS (ESI) m/z 313.0 $[M+1]^+$.

(2-(7-Oxa-2-azaspiro[3.5]nonan-2-yl)quinolin-6-yl)methanol. To a solution of methyl 2-(7-oxa-2-azaspiro[3.5]nonan-2-yl)quinoline-6-carboxylate (350 mg, 1.12 mmol) in THF (10 mL) was added lithium aluminum hydride (2.5 M in THF, 0.6 mL, 1.5 mmol) dropwise at 0° C. and the reaction solution was stirred at this temperature for 30 min. The resulting solution was quenched with sodium hydroxide (2 M in water) and filtered. The filtrate was concentrated to afford title compound (300 mg, 1.05 mmol, 94% yield) as a light-yellow solid. MS (ESI) m/z 285.0 $[M+1]^+$.

2-(7-Oxa-2-azaspiro[3.5]nonan-2-yl)quinoline-6-carbaldehyde. A mixture of (2-(7-oxa-2-azaspiro[3.5]nonan-2-yl)quinolin-6-yl)methanol (120 mg, 0.42 mmol) and manganese dioxide (380 mg, 4.37 mmol) in dichloromethane (10 mL) was stirred at 60° C. for 12 h under nitrogen. The resulting mixture was filtered and the filtrate was concentrated to afford the title compound (60 mg, 0.21 mmol, 50% yield) as a light-yellow semi-solid. MS (ESI) m/z 283.0 $[M+1]^+$.

3-(5-(((S)-1-((2-(7-Oxa-2-azaspiro[3.5]nonan-2-yl)quinolin-6-yl)methyl)pyrrolidin-3-yl)oxy)-1-oxoisoindolin-2-yl)piperidine-2,6-dione. To a solution of 2-(7-oxa-2-azaspiro[3.5]nonan-2-yl)quinoline-6-carbaldehyde (60 mg, 0.21 mmol), 3-(1-oxo-5-(((S)-pyrrolidin-3-yl)oxy)isoindolin-2-yl)piperidine-2,6-dione; hydrochloride (80 mg, 0.22 mmol) and triethylamine (0.09 mL, 0.62 mmol) in dichloromethane (8 mL) was added sodium triacetoxyborohydride (150 mg, 0.71 mmol) in several portions at 0° C. and the reaction mixture was stirred at room temperature for 2 h. The resulting mixture was added little methanol to become a clean solution and purified by preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 22% B in 7 min, 22% B; Wave Length: 254/220 nm; $RT_1$ (min): 5.2. The fractions containing desired product were collected and evaporated under reduced pressure to afford the title compound (34.7 mg, 0.057 mmol, 27% yield) as a white solid. $^1$H NMR (400 MHz, DMSO-$d_6$) δ 10.97 (s, 1H), 7.99 (dd, J=9.0, 1.7 Hz, 1H), 7.63-7.57 (m, 2H), 7.55-7.45 (m, 2H), 7.10 (t, J=2.2 Hz, 1H), 7.00 (dd, J=8.4, 2.2 Hz, 1H), 6.71 (d, J=8.9 Hz, 1H), 5.06 (dd, J=13.3, 5.0 Hz, 1H), 4.99 (t, J=6.9 Hz, 1H), 4.37 (d, J=17.2 Hz, 1H), 4.24 (dd, J=17.3, 3.2 Hz, 1H), 3.84 (s, 4H), 3.75-3.64 (m, 2H), 3.65 (m, 4H), 2.97-2.84 (m, 2H), 2.79-2.53 (m, 4H), 2.40-2.30 (m, 2H), 1.97 (m, 1H), 1.85 (s, 1H), 1.86-1.72 (m, 5H); MS (ESI) m/z 596.2 $[M+1]^+$.

Example S100. 3-(5-(((S)-1-((2-((1R,5S)-8-Oxa-3-azabicyclo[3.2.1]octan-3-yl)quinazolin-6-yl)methyl) pyrrolidin-3-yl)oxy)-1-oxoisoindolin-2-yl)piperidine-2,6-dione

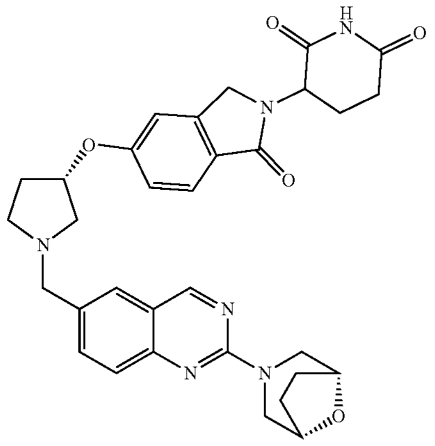 [SMILES: O=C1CCC(N2Cc3cc(O[C@H]4CCN(Cc5ccc6nc(N7C[C@H]8CC[C@@H](C7)O8)ncc6c5)C4)ccc3C2=O)C(=O)N1]

(1R,5S)-3-(6-Bromoquinazolin-2-yl)-8-oxa-3-azabicyclo [3.2.1]octane. A solution of 6-bromo-2-chloroquinazoline (300 mg, 1.23 mmol) and (1R,5S)-3-oxa-8-azabicyclo [3.2.1]octane (697 mg, 6.16 mmol) in NMP (5 mL) was added N,N-diisopropylethylamine (2.14 mL, 12.32 mmol) at room temperature. The solution was stirred at 120° C. for 12 h. The solution was purified by reverse phase flash (10-40% acetonitrile+0.05% ammonium bicarbonate in water, over 30 min) to afford title compound (380 mg, 1.17 mmol, 95% yield) as a yellow solid. MS (ESI) m/z 320.0 $[M+1]^+$.

(1R,5S)-3-(6-Vinylquinazolin-2-yl)-8-oxa-3-azabicyclo [3.2.1]octane. To a stirred solution of (1R,5S)-3-(6-bromoquinazolin-2-yl)-8-oxa-3-azabicyclo[3.2.1] octane (200 mg, 0.62 mmol), potassium trifluoro(vinyl)borate (168 mg, 1.25 mmol) and sodium carbonate (198 mg, 1.87 mmol) in 1,4-dioxane (5 mL) and water (1 mL) was added dichlorobis (triphenylphosphine)palladium(II) dichloromethane adduct (51 mg, 0.06 mmol) and the mixture was stirred at 90° C. for 2 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (90 mg, 0.32 mmol, 52% yield) as a yellow solid. MS (ESI) m/z 268.0 $[M+1]^+$.

2-((1R,5S)-8-Oxa-3-azabicyclo[3.2.1]octan-3-yl)quinazoline-6-carbaldehyde. To a stirred solution of (1R,5S)-3-(6-vinylquinazolin-2-yl)-8-oxa-3-azabicyclo[3.2.1] octane (90 mg, 0.34 mmol) in tert-butanol (5 mL) and water (5 mL) was added potassium osmate (11 mg, 0.03 mmol), 4-methylmorpholine N-oxide (78 mg, 0.67 mmol) and critic acid (129 mg, 0.67 mmol). The reaction mixture was stirred at room temperature for 3 h under nitrogen. The sodium periodate (216 mg, 1.01 mmol) was added into the above mixture at 0° C. The reaction mixture was stirred for 1 h under nitrogen. The mixture was added saturated sodium bicarbonate to pH~7 and extracted with ethyl acetate. The organic layers were washed with brine, dried over anhydrous sodium sulfated, filtered and concentrated. The residue was purified by silica gel chromatography (0 to 50% ethyl acetate in petroleum ether) to give the title product (50 mg, 0.17 mmol, 50% yield) as a yellow solid. MS (ESI) m/z 270.0 $[M+1]^+$.

3-(5-(((S)-1-((2-((1R,5S)-8-Oxa-3-azabicyclo[3.2.1]octan-3-yl)quinazolin-6-yl) methyl)pyrrolidin-3-yl)oxy)-1-oxoisoindolin-2-yl)piperidine-2,6-dione. To a stirred mixture of 2-((1R,5S)-8-oxa-3-azabicyclo[3.2.1]octan-3-yl) quinazoline-6-carb aldehyde (50 mg, 0.17 mmol), (3S)-3-(1-oxo-5-((3S)-pyrrolidin-3-yl)oxy-isoindolin-2-yl) piperidine-2,6-dione; 2,2,2-trifluoroacetic acid (82 mg, 0.18 mmol) and triethylamine (0.08 mL, 0.56 mmol) in dichloromethane (3 mL) was added sodium triacetoxyborohydride (118 mg, 0.56 mmol) in several portions under nitrogen. The mixture was stirred for 12 h at room temperature under nitrogen. The resulting mixture was concentrated and the residue was firstly purified by silica gel chromatography (0 to 10% methanol in dichloromethane) and purified further by preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 25% B in 7 min, 25% B; Wave Length: 254/220 nm; $RT_1$ (min): 6.3. The fractions were concentrated to afford title compound (32.9 mg, 0.056 mmol, 33% yield) as a yellow solid. $^1$H NMR (400 MHz, Methanol-$d_4$) δ 9.10 (s, 1H), 7.79-7.71 (m, 3H), 7.58 (d, J=9.3 Hz, 1H), 7.13-6.95 (m, 2H), 5.15-5.12 (m, 2H), 4.51-4.39 (m, 6H), 4.05-3.97 (m, 2H), 3.26-3.19 (m, 3H), 3.15-3.08 (m, 2H), 2.96-2.85 (m, 2H), 2.82-2.76 (m, 1H), 2.52-2.40 (m, 2H), 2.18-2.00 (m, 2H), 1.97-1.80 (m, 4H); MS (ESI) m/z 583.2 $[M+1]^+$.

Example S101. 3-(5-(((S)-1-((2-((1R,5S)-3-Oxa-8-azabicyclo[3.2.1]octan-8-yl)quinazolin-6-yl)methyl)pyrrolidin-3-yl)oxy)-1-oxoisoindolin-2-yl)piperidine-2,6-dione

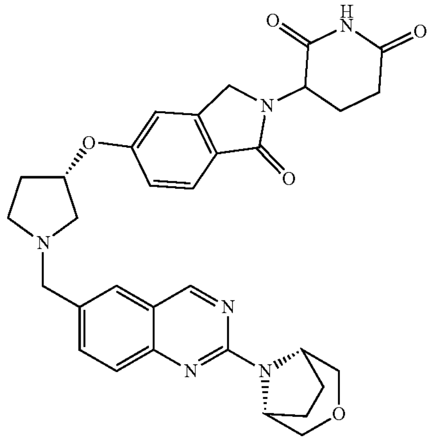 [SMILES: O=C1CCC(N2Cc3cc(O[C@H]4CCN(Cc5ccc6nc(N7[C@@H]8CC[C@H]7COC8)ncc6c5)C4)ccc3C2=O)C(=O)N1]

(1R,5S)-8-(6-Bromoquinazolin-2-yl)-3-oxa-8-azabicyclo[3.2.1]octane. To a stirred solution of 6-bromo-2-chloroquinazoline (250 mg, 1.03 mmol) in NMP (4 mL) were added (1R,5S)-3-oxa-8-azabicyclo[3.2.1]octane (464 mg, 4.11 mmol) and N,N-diisopropylethylamine (0.79 mL, 4.53 mmol). The above mixture was stirred at 120° C. for 12 h under nitrogen. The reaction solution was purified by reverse phase flash (40-100% acetonitrile+0.05% ammonium bicarbonate in water, over 25 min) to afford the title compound (220 mg, 0.68 mmol, 67% yield) as a light-yellow solid. MS (ESI) m/z 320.1 $[M+1]^+$.

(1R,5S)-8-(6-Vinylquinazolin-2-yl)-3-oxa-8-azabicyclo[3.2.1]octane. To a stirred solution of ((1R,5S)-8-(6-bromoquinazolin-2-yl)-3-oxa-8-azabicyclo[3.2.1]oct ane (200 mg, 0.62 mmol) and potassium trifluoro(vinyl)borate (100 mg, 0.75 mmol) in 1,4-dioxane (5 mL) and water (0.5 mL) were added tetrakis(triphenylphosphine)palladium (52 mg, 0.045 mmol) and cesium carbonate (406 mg, 1.25 mmol). The above mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (120 mg, 0.45 mmol, 72% yield) as a light-yellow oil. MS (ESI) m/z 268.0 $[M+1]^+$.

2-((1R,5S)-3-Oxa-8-azabicyclo[3.2.1]octan-8-yl)quinazoline-6-carbaldehyde. To a stirred solution of (1R,5S)-8-(6-vinylquinazolin-2-yl)-3-oxa-8-azabicyclo[3.2.1]octane (120 mg, 0.45 mmol) in tert-butanol (3 mL) and water (3 mL) were added 4-methyl-morpholin4-oxide (105 mg, 0.90 mmol), potassium osmate (330 mg, 0.9 mmol) and citric acid (172 mg, 0.9 mmol). The above mixture was stirred at room temperature for 3 h under nitrogen. Then the mixture was added sodium periodate (288 mg, 1.35 mmol) and stirred for another 1 h. The reaction mixture was concentrated. The reaction mixture was added saturated sodium bicarbonate to pH~7 and extracted with ethyl acetate. The extracts were washed with brine, dried over sodium sulfate, filtered and concentrated. The residue was purified by silica gel chromatography (0 to 40% ethyl acetate in petroleum ether) to afford the title compound (60 mg, 0.22 mmol, 50% yield) as a light-yellow oil. MS (ESI) m/z 270.0 $[M+23]^+$.

3-(5-(((S)-1-((2-((1R,5S)-3-Oxa-8-azabicyclo[3.2.1]octan-8-yl)quinazolin-6-yl) methyl)pyrrolidin-3-yl)oxy)-1-oxoisoindolin-2-yl)piperidine-2,6-dione. To a solution of 2-((1R,5S)-3-oxa-8-azabicyclo[3.2.1]octan-8-yl)quinazoline-6-carbaldehyde (60 mg, 0.22 mmol), 3-(1-oxo-5-(((S)-pyrrolidin-3-yl)oxy)isoindolin-2-yl)piperidine-2,6-dione; 2,2,2-trifluoroacetic acid (100 mg, 0.23 mmol) and triethylamine (46 mg, 0.46 mmol) in dichloromethane (5 mL) was added sodium triacetoxyborohydride (160 mg, 0.75 mmol). The mixture was stirred for 12 h at room temperature under nitrogen. The resulting mixture was concentrated. The residue was purified by silica gel chromatography (0 to 10% methanol in dichloromethane) and preparative-HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 22% B in 10 min, 22% B; Wave Length: 254/220 nm; $RT_1$ (min): 10.42. The fractions containing desired product were collected and evaporated under reduced pressure to afford the title compound (33.1 mg, 0.057 mmol, 25% yield) as a light-yellow solid. $^1H$ NMR (400 MHz, Methanol-$d_4$) δ 9.13 (s, 1H), 7.89-7.79 (m, 2H), 7.73 (d, J=8.4 Hz, 1H), 7.60 (d, J=8.6 Hz, 1H), 7.13-7.03 (m, 2H), 5.24-5.08 (m, 2H), 4.91-4.81 (m, 1H), 4.51-4.37 (m, 2H), 4.21-4.10 (m, 2H), 3.81 (m, 2H), 3.69 (m, 2H), 3.36 (m, 1H), 3.24 (m, 2H), 3.07-2.99 (m, 1H), 2.96-2.75 (m, 2H), 2.50-2.46 (m, 2H), 2.22-2.02 (m, 6H); MS (ESI) m/z 583.2 $[M+1]^+$.

Example S102. 3-(5-(((S)-1-((2-((1R,5S)-6-Oxa-3-azabicyclo[3.1.1]heptan-3-yl)quinazolin-6-yl)methyl)pyrrolidin-3-yl)oxy)-1-oxoisoindolin-2-yl)piperidine-2,6-dione

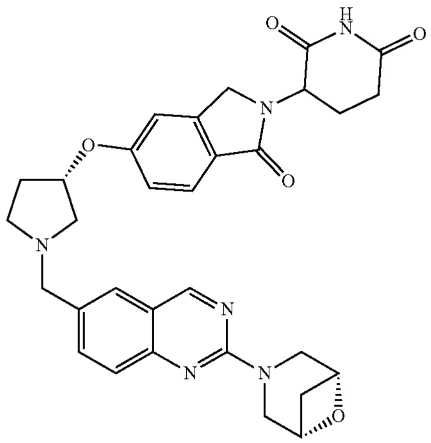 [SMILES: O=C1CCC(N2Cc3cc(O[C@H]4CCN(Cc5ccc6nc(N7C[C@H]8C[C@@H](C7)O8)ncc6c5)C4)ccc3C2=O)C(=O)N1]

(1R,5S)-3-(6-Bromoquinazolin-2-yl)-6-oxa-3-azabicyclo[3.1.1]heptane. To a stirred solution of 6-bromo-2-chloroquinazoline (200 mg, 0.82 mmol) in NMP (6 mL) were added (1R,5S)-6-oxa-3-azabicyclo[3.1.1]heptane (244 mg, 2.46 mmol) and N,N-diisopropylethylamine (0.72 mL, 4.13 mmol). The above mixture was stirred at 120° C. for 12 h under nitrogen. The reaction mixture was filtered and the filtrate was purified by reverse phase flash (10-100% acetonitrile+0.05% ammonium bicarbonate in water, over 25 min) to afford the title compound (180 mg, 0.59 mmol, 71% yield) as a light-yellow solid. MS (ESI) m/z 306.2 $[M+1]^+$.

(1R,5S)-3-(6-Vinylquinazolin-2-yl)-6-oxa-3-azabicyclo [3.1.1]heptane. To a stirred solution of (1R,5S)-3-(6-bromo-quinazolin-2-yl)-6-oxa-3-azabicyclo[3.1.1] heptane (180 mg, 0.59 mmol) and potassium trifluoro(vinyl)borate (94 mg, 0.71 mmol) in 1,4-dioxane (5 mL) and water (0.5 mL) were added tetrakis(triphenylphosphine)palladium (49 mg, 0.04 mmol) and cesium carbonate (382 mg, 1.18 mmol) at room temperature. The above mixture was stirred at 80° C. for 3 h under nitrogen. Then the mixture diluted with water and extracted with ethyl acetate. The extracts were washed with brine, dried over anhydrous sodium sulfate, filtered and concentrated. The residue was purified by silica gel chromatography (0 to 60% ethyl acetate in petroleum ether) to afford the title compound (90 mg, 0.35 mmol, 60% yield) as a light-yellow oil. MS (ESI) m/z 253.3 $[M+1]^+$.

2-((1R,5S)-6-Oxa-3-azabicyclo[3.1.1]heptan-3-yl)quinazoline-6-carbaldehyde. To a stirred solution of (1R,5S)-3-(6-vinylquinazolin-2-yl)-6-oxa-3-azabicyclo[3.1.1]heptane (100 mg, 0.39 mmol) in tert-butanol (3 mL) and water (3 mL) were added 4-methyl-morpholin4-oxide (46 mg, 0.39 mmol), potassium osmate (145 mg, 0.39 mmol) and citric acid (75 mg, 0.39 mmol). The above mixture was stirred at room temperature for 3 h under nitrogen. Then to the reaction mixture was added sodium periodate (84 mg, 0.39 mmol) and stirred for another 1 h. The resulting mixture was added saturated sodium bicarbonate to pH~7 and extracted with ethyl acetate. The extracts were washed with brine, dried over sodium sulfate, filtered and concentrated. The residue was purified by silica gel chromatography (0 to 40% ethyl acetate in petroleum ether) to afford the title compound (50 mg, 0.2 mmol, 50% yield) as a light-yellow oil. MS (ESI) m/z 256.0 $[M+1]^+$.

3-(5-(((S)-1-((2-((1R,5S)-6-Oxa-3-azabicyclo[3.1.1]heptan-3-yl)quinazolin-6-yl)methyl)pyrrolidin-3-yl)oxy)-1-oxoisoindolin-2-yl)piperidine-2,6-dione. To a solution of 2-((1R,5S)-6-oxa-3-azabicyclo[3.1.1]heptan-3-yl)quinazoline-6-carbalde hyde (40 mg, 0.16 mmol), 3-(1-oxo-5-(((S)-pyrrolidin-3-yl)oxy)isoindolin-2-yl) piperidine-2,6-dione; 2,2,2-trifluoroacetic acid (60 mg, 0.14 mmol) and triethylamine (31 mg, 0.31 mmol) in dichloromethane (5 mL) was added sodium triacetoxyborohydride (130 mg, 0.61 mmol). The mixture was stirred for 12 h at room temperature under nitrogen. The resulting mixture was concentrated. The residue was purified by silica gel chromatography (0 to 10% methanol in dichloromethane) and preparative-HPLC further with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 22% B in 7 min, 22% B; Wave Length: 254/220 nm; $RT_1$ (min): 7.25. The fractions containing desired product were collected and evaporated under reduced pressure to afford the title compound (12.8 mg, 0.022 mmol, 14% yield) as an off-white solid. $^1H$ NMR (300 MHz, DMSO-$d_6$) δ 10.98 (s, 1H), 9.25 (s, 1H), 7.86-7.69 (m, 2H), 7.57-7.53 (m, 2H), 7.11 (m, 1H), 7.01-6.98 (m, 1H), 5.14-4.95 (m, 2H), 4.73 (d, J=6.4 Hz, 2H), 4.43-4.22 (m, 2H), 3.98 (m, 2H), 3.81-3.68 (m, 4H), 3.15 (m, 2H), 2.99-2.86 (m, 2H), 2.82-2.67 (m, 2H), 2.59 (m, 1H), 2.37 (m, 2H), 2.06-1.79 (m, 3H); MS (ESI) m/z 569.2 $[M+1]^+$.

Example S103. 3-(5-(((S)-1-((2-((1R,5S)-3-Oxa-6-azabicyclo[3.1.1]heptan-6-yl)quinazolin-6-yl)methyl)pyrrolidin-3-yl)oxy)-1-oxoisoindolin-2-yl)piperidine-2,6-dione

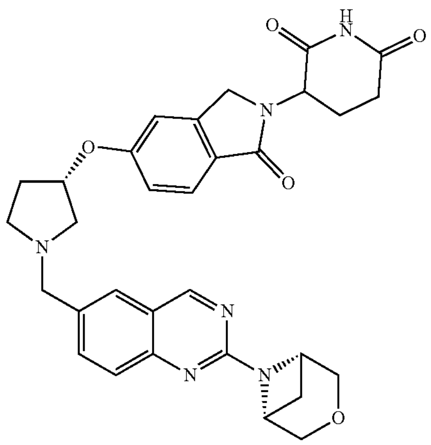 [SMILES: O=C1CCC(N2Cc3cc(O[C@H]4CCN(Cc5ccc6nc(N7[C@@H]8COC[C@H]7C8)ncc6c5)C4)ccc3C2=O)C(=O)N1]

(1R,5S)-6-(6-Bromoquinazolin-2-yl)-3-oxa-6-azabicyclo [3.1.1]heptane. To a stirred solution of 6-bromo-2-chloroquinazoline (250 mg, 1.03 mmol), N,N-diisopropylethylamine (0.89 mL, 5.10 mmol) in NMP (5 mL) were added (1R,5S)-3-oxa-6-azabicyclo[3.1.1]heptane (254 mg, 2.57 mmol) and the solution was stirred at 120° C. for 3 h under nitrogen. The resulting solution was purified by reverse phase flash (10-80% acetonitrile+0.05% ammonium bicarbonate in water, over 30 min) to give the title compound (240 mg, 0.78 mmol, 76% yield) as a yellow solid. MS (ESI) m/z 305.9 $[M+1]^+$.

(1R,5S)-6-(6-Vinylquinazolin-2-yl)-3-oxa-6-azabicyclo [3.1.1]heptane. To a solution of (1R,5S)-6-(6-bromoquinazolin-2-yl)-3-oxa-6-azabicyclo[3.1.1]heptane (240 mg, 0.78 mmol) in 1,4-dioxane (10 mL) and water (2 mL) were added [1,1'-bis(diphenylphosphino)ferrocene]dichloropalladium(II) (20 mg, 0.028 mmol) and sodium carbonate (249 mg, 2.35 mmol) at room temperature. The mixture was heated to 90° C. and stirred for 3 h under nitrogen. The resulting mixture was diluted with water and extracted with ethyl acetate. The extracts were washed with brine, dried over anhydrous sodium sulfate, filtered and concentrated. The residue was purified by reverse phase flash (10-70% acetonitrile+0.05% ammonium bicarbonate in water, over 20 min) to give the title compound (200 mg, 0.78 mmol, 100% yield) as a yellow solid. MS (ESI) m/z 254.2 $[M+1]^+$.

2-((1R,5S)-3-Oxa-6-azabicyclo[3.1.1]heptan-6-yl)quinazoline-6-carbaldehyde. To a solution of (1R,5S)-6-(6-vinylquinazolin-2-yl)-3-oxa-6-azabicyclo[3.1.1]-heptane (200 mg, 0.78 mmol), potassium osmate (16 mg, 0.04 mmol) and 4-methylmorpholine N-oxide (185 mg, 1.58 mmol) in 1-butanol (5 mL) and water (5 mL) was added citric acid (304 mg, 1.58 mmol) at room temperature and the resulting mixture was stirred at room temperature for 4 h under nitrogen. Then sodium periodate (506 mg, 2.37 mmol) was added in several portions to the above mixture at 0° C. and the resulting mixture was stirred at room temperature for 1 h. The mixture was added saturated sodium bicarbonate solution to pH~7 and extracted with ethyl acetate. The extracts were washed with brine, dried over sodium sulfate, filtered and concentrated to afford the title compound (100 mg, 0.39 mmol, 50% yield) as a yellow solid. MS (ESI) m/z 256.1 $[M+1]^+$.

3-(5-(((S)-1-((2-((1R,5S)-3-oxa-6-azabicyclo[3.1.1] heptan-6-yl)quinazolin-6-yl)methyl)pyrrolidin-3-yl)oxy)-1-oxoisoindolin-2-yl)piperidine-2,6-dione. To a stirred mixture of 2-((1R,5S)-3-oxa-6-azabicyclo[3.1.1]heptan-6-yl) quinazoline-6-carbaldehyde (50 mg, 0.20 mmol), 3-[1-oxo-5-[(3S)-pyrrolidin-3-yl]oxy-isoindolin-2-yl]piperidine-2,6-dione; 2,2,2-trifluoroacetic acid (85 mg, 0.19 mmol) and triethylamine (39 mg, 0.39 mmol) in dichloromethane (10 mL) was added sodium triacetoxyborohydride (165 mg, 0.78 mmol) in several portions and was stirred at room temperature for 2 h under nitrogen. The mixture was concentrated and the residue was purified by silica gel chromatography (0-10% methanol in dichloromethane) firstly and further by preparative silica gel chromatography Column: Sunfire prep C18 column, 30*150 mm, 5 μm; Mobile phase A: water (0.1% formic acid), Mobile phase B: acetonitrile; Flow rate: 60 mL/min; Gradient: 2% B to 25% B in 7 min, 25% B; Wave Length: 254/220 nm; $RT_1$ (min): 6.3; The fractions containing desired product were collected and evaporated under reduced pressure to afford the title compound (33 mg, 0.054 mmol, 27% yield) as a white solid. $^1H$ NMR (300 MHz, Methanol-$d_4$) δ 9.19 (s, 1H), 8.35 (s, 1H), 7.95-7.83 (m, 2H), 7.73 (d, J=8.4 Hz, 1H), 7.65 (d, J=8.7 Hz, 1H), 7.15-7.02 (m, 2H), 5.23-5.07 (m, 2H), 4.56 (d, J=6.2 Hz, 2H), 4.44 (d, J=4.2 Hz, 2H), 4.36 (d, J=11.1 Hz, 2H), 4.20 (m, 2H), 3.44-3.34 (m, 1H), 3.29 (m, 2H), 3.26 (m, 4H), 3.08 (m, 1H), 3.07-2.86 (m, 1H), 2.85-2.72 (m, 1H), 2.62-2.40 (m, 2H), 2.24-2.11 (m, 2H); MS (ESI) m/z 605.1 $[M+1]^+$.

Example S104. 3-(5-(((S)-1-((2-(1,1-Dioxidothiomorpholino)quinazolin-6-yl)methyl)pyrrolidin-3-yl)oxy)-1-oxoisoindolin-2-yl)piperidine-2,6-dione

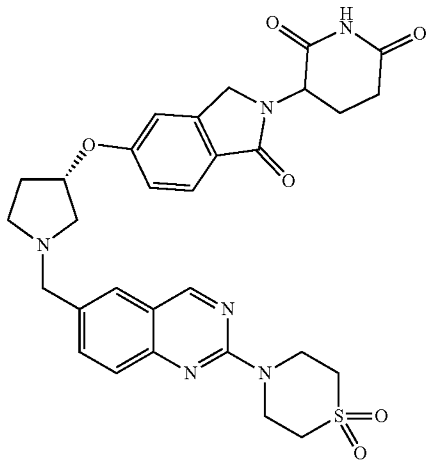 [SMILES: O=C1CCC(N2Cc3cc(O[C@H]4CCN(Cc5ccc6nc(N7CCS(=O)(=O)CC7)ncc6c5)C4)ccc3C2=O)C(=O)N1]

4-(6-Bromoquinazolin-2-yl)thiomorpholine 1,1-dioxide. To a stirred solution of 6-bromo-2-chloroquinazoline (300 mg, 1.23 mmol) in ethanol (8 mL) was added thiomorpholine 1,1-dioxide (499 mg, 3.7 mmol) and the solution was stirred at 80° C. for 3 h under nitrogen. The solution was concentrated to afford the title compound (240 mg, 0.70 mmol, 57% yield) as a yellow solid. MS (ESI) m/z 341.9 $[M+1]^+$.

4-(6-Vinylquinazolin-2-yl)thiomorpholine 1,1-dioxide. To a solution of 4-(6-bromoquinazolin-2-yl)thiomorpholine 1,1-dioxide (240 mg, 0.70 mmol) and potassium trifluoro(vinyl)borate (150 mg, 1.12 mmol) in 1,4-dioxane (10 mL) and water (2 mL) were added [1,1'-bis(diphenylphosphino)ferrocene]dichloropalladium(II) (120 mg, 0.16 mmol) and sodium carbonate (223 mg, 2.10 mmol) at room temperature. The reaction was heated to 90° C. and stirred for 5 h under nitrogen. The resulting mixture was diluted with water and extracted with ethyl acetate. The extracts were washed with brine, dried over anhydrous sodium sulfate, filtered and concentrated. The residue was purified by reverse phase flash (10-70% acetonitrile+0.05% ammonium bicarbonate in water, over 20 min) to give the title compound (140 mg, 0.48 mmol, 68% yield) as a yellow solid. MS (ESI) m/z 290.0 $[M+1]^+$.

4-(6-Vinylquinazolin-2-yl)thiomorpholine 1,1-dioxide. To a solution of 4-(6-vinylquinazolin-2-yl)thiomorpholine 1,1-dioxide (140. mg, 0.48 mmol), potassium osmate (16.8 mg, 0.045 mmol) and 4-methylmorpholine N-oxide (113 mg, 0.97 mmol) in 1-butanol (5 mL) and water (5 mL) was added citric acid (172 mg, 0.97 mmol) at room temperature and the resulting mixture was stirred at room temperature for 4 h under nitrogen. Then sodium periodate (310 mg, 1.45 mmol) was added in several portions to the above mixture at 0° C. and the resulting mixture was stirred at room temperature for 1 h. The mixture was added saturated sodium bicarbonate solution to pH~7 and extracted with ethyl acetate. The extracts were washed with brine, dried over sodium sulfate, filtered and concentrated to afford the title compound (50 mg, 0.17 mmol, 35% yield) as a yellow solid. MS (ESI) m/z 292.1 $[M+1]^+$.

3-(5-(((S)-1-((2-(1,1-Dioxidothiomorpholino)quinazolin-6-yl)methyl)pyrrolidin-3-yl)oxy)-1-oxoisoindolin-2-yl)piperidine-2,6-dione. To a stirred mixture of 2-(1,1-dioxidothiomorpholino)quinazoline-6-carbaldehyde (40. mg, 0.14 mmol), 3-[1-oxo-5-[(3S)-pyrrolidin-3-yl]oxy-isoindolin-2-yl]piperidine-2,6-dione; 2,2,2-trifluoroacetic acid (60 mg, 0.14 mmol) and triethylamine (27 mg, 0.27 mmol) in dichloromethane (5 mL) was added sodium triacetoxyborohydride (116 mg, 0.55 mmol) in several portions and was stirred at room temperature for 2 h under nitrogen. The mixture was concentrated and the residue was purified by silica gel chromatography (0-10% methanol in dichloromethane) firstly and further by preparative Chiral HPLC with the following conditions: Sunfire prep C18 column, 30*150 mm, 5 μm; Mobile phase A: water (0.1% formic acid), Mobile phase B: acetonitrile; Flow rate: 60 mL/min; Gradient: 2% B to 25% B in 7 min, 25% B; Wave Length: 254/220 nm; $RT_1$ (min): 6.3. The fractions containing desired product were collected and evaporated under reduced pressure to afford the title compound (18.2 mg, 0.03 mmol, 21% yield) as a white solid. $^1H$ NMR (400 MHz, methanol-$d_4$) δ 9.18 (s, 1H), 7.91 (m, 1H), 7.86 (m, 1H), 7.73 (d, J=8.5 Hz, 1H), 7.67 (d, J=8.7 Hz, 1H), 7.14-7.10 (m, 1H), 7.07 (m, 1H), 5.22-5.09 (m, 2H), 4.51-4.43 (m, 6H), 4.26-4.13 (m, 2H), 3.41-3.34 (m, 1H), 3.28 (m, 2H), 3.18-3.14 (m, 4H), 3.08 (m, 1H), 2.92 (m, 1H), 2.79 (m, 1H), 2.55-2.40 (m, 2H), 2.28-2.16 (m, 2H); MS (ESI) m/z 605.1 $[M+1]^+$.

Example S105. 3-(5-(((S)-1-((2-(7-Oxa-1-azaspiro[3.5]nonan-1-yl)quinolin-6-yl)methyl)pyrrolidin-3-yl)oxy)-1-oxoisoindolin-2-yl)piperidine-2,6-dione

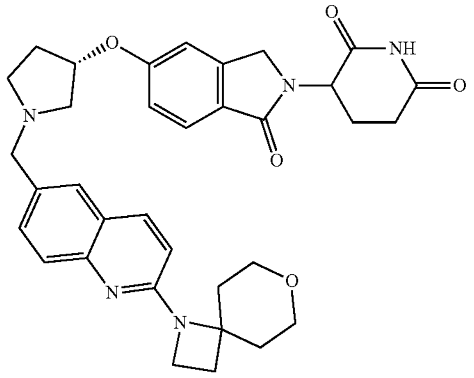 [SMILES: O=C1CCC(N2Cc3cc(O[C@H]4CCN(Cc5ccc6nc(N7CCC78CCOCC8)ccc6c5)C4)ccc3C2=O)C(=O)N1]

Methyl 2-(7-oxa-1-azaspiro[3.5]nonan-1-yl)quinoline-6-carboxylate. To a stirred solution of methyl 2-chloroquinoline-6-carboxylate (200 mg, 0.90 mmol) and 7-oxa-1-azaspiro[3.5]nonane (172 mg, 1.35 mmol) in 1,4-dioxane (5 mL) were added [4-(N,N-dimethylamino)phenyl]di-t-butylphosphine (64 mg, 0.24 mmol), methanesulfonato([4-N,N-dimethylamino]phenyl)dlt-butylphosphino)(2'-amino-1,1'-biphenyl-2-yl)palladium(II) (103 mg, 0.16 mmol) and cesium carbonate (879 mg, 2.71 mmol). The above mixture was stirred at 100° C. for 16 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (80 mg, 0.26 mmol, 28% yield) as a light-yellow oil. MS (ESI) m/z 313.0 $[M+1]^+$.

(2-(7-Oxa-1-azaspiro[3.5]nonan-1-yl)quinolin-6-yl) methanol. To a stirred solution of methyl 2-(7-oxa-1-azaspiro[3.5]nonan-1-yl)quinoline-6-carboxylate (80 mg, 0.26 mmol) in THF (5 mL) was added lithium aluminum hydride (2.5 M in THF, 0.02 mL, 0.50 mmol) at 0° C. and the mixture was warmed to room temperature and stirred for 12 h under nitrogen. The mixture was diluted with THF, added sodium sulfate decahydrate, filtered and concentrated. The residue was purified by silica gel chromatography (0 to 40% ethyl acetate in petroleum ether) to afford the title compound (60 mg, 0.21 mmol, 82% yield) as a light-yellow solid. MS (ESI) m/z 285.2 $[M+1]^+$.

2-(7-Oxa-1-azaspiro[3.5]nonan-1-yl)quinoline-6-carbaldehyde. To a stirred solution of (2-(7-oxa-1-azaspiro[3.5]nonan-1-yl)quinolin-6-yl)methanol (60 mg, 0.21 mmol) in dichloromethane (6 mL) was added manganese dioxide (367 mg, 4.22 mmol) and the mixture was stirred for 12 h at room temperature under nitrogen. The resulting mixture was added dichloromethane, filtered and concentrated. The residue was purified by silica gel chromatography (0 to 40% ethyl acetate in petroleum ether) to afford the title compound (50 mg, 0.18 mmol, 84% yield) as a light-yellow solid. MS (ESI) m/z 283.0 $[M+1]^+$.

3-(5-(((S)-1-((2-(7-Oxa-1-azaspiro[3.5]nonan-1-yl)quinolin-6-yl)methyl)pyrolidin-3-yl)oxy)-1-oxoisoindolin-2-yl)piperidine-2,6-dione. To a solution of 2-(7-oxa-1-azaspiro[3.5]nonan-1-yl)quinoline-6-carbaldehyde (60 mg, 0.21 mmol), 3-(1-oxo-5-(((S)-pyrrolidin-3-yl)oxy)isoindolin-2-yl)piperidine-2,6-dione; 2,2,2-trifluoroacetic acid (78 mg, 0.18 mmol) and triethylamine (42 mg, 0.42 mmol) in dichloromethane (5 mL) was added sodium triacetoxyborohydride (176 mg, 0.83 mmol). The mixture was stirred for 12 h at room temperature under nitrogen. The resulting mixture was concentrated and the residue was purified by silica gel chromatography (0 to 10% methanol in dichloromethane) and preparative-HPLC further with the following conditions: Column: Sunfire prep Cis column, 30*150 mm, 5 μm; Mobile Phase A: water (0.05% TFA), Mobile Phase B: acetonitrile; Flow rate: 60 mL/min; Gradient: 5% B to 17% B in 7 min, 17% B; Wave Length: 254/220 nm; $RT_1$ (min): 6.78. The fractions containing desired product were collected and evaporated under reduced pressure to afford the title compound (34.1 mg, 0.057 mmol, 27% yield) as a white solid. $^1H$ NMR (400 MHz, Methanol-$d_4$) δ 8.25 (m, 1H), 8.04 (m, 1H), 7.92 (m, 2H), 7.74-7.72 (m, 1H), 7.32 (m, 1H), 7.18 (d, J=6.1 Hz, 1H), 7.09 (m, 1H), 5.35 (m, 1H), 5.15-5.12 (m, 1H), 4.69-4.61 (m, 2H), 4.54-4.39 (m, 4H), 4.05-4.01 (m, 2H), 3.83-3.49 (m, 6H), 2.96-2.77 (m, 2H), 2.67-2.35 (m, 7H), 2.23-2.08 (m, 3H); MS (ESI) m/z 596.2 $[M+1]^+$.

Example S106. 3-(5-(((S)-1-((2-((R)-7-Oxa-1-azaspiro[4.4]nonan-1-yl)quinolin-6-yl)methyl)pyrrolidin-3-yl)oxy)-1-oxoisoindolin-2-yl)piperidine-2,6-dione

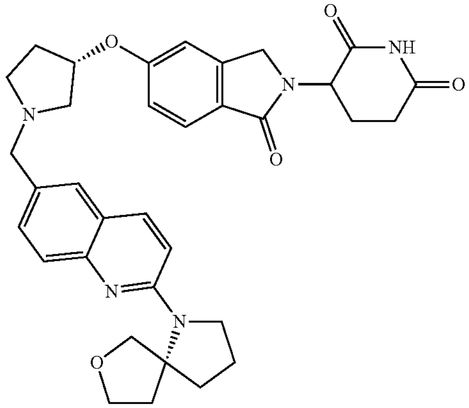 [SMILES: O=C1CCC(N2Cc3cc(O[C@H]4CCN(Cc5ccc6nc(N7CCC[C@]78CCOC8)ccc6c5)C4)ccc3C2=O)C(=O)N1]

Methyl 2-(7-oxa-1-azaspiro[4.4]nonan-1-yl)quinoline-6-carboxylate. To a stirred solution of methyl 2-chloroquinoline-6-carboxylate (500 mg, 2.26 mmol) in toluene (5 mL) was added 7-oxa-1-azaspiro[4.4]nonane; hydrochloride (557 mg, 3.40 mmol), methanesulfonato{[4-(N,N-dimethylamino)phenyl]di-t-butylphosphino}(2'-amino-1,1'-biphenyl-2-yl)palladium(II) (215 mg, 0.34 mmol), bis(di-tert-butyl)-4-dimethylaminophenylphosphine (91 mg, 0.34 mmol), cesium carbonate (2.2 g, 6.8 mmol) at room temperature. Then the reaction mixture was stirred for 12 h at 100° C. under nitrogen. The resulting mixture was filtered and the filtrate was concentrated. The residue was purified by reverse phase flash (30-80% acetonitrile+0.05% ammonium bicarbonate in water, over 20 min) to give the title compound (270 mg, 0.86 mmol, 38% yield) as a yellow solid. MS (ESI) m/z 313.1 $[M+1]^+$.

(2-(7-Oxa-1-azaspiro[4.4]nonan-1-yl)quinolin-6-yl) methanol. To a stirred solution of methyl 2-(7-oxa-1-azaspiro[4.4]nonan-1-yl)quinoline-6-carboxylate (260 mg, 0.83 mmol) in THF (10 mL) was added lithium aluminum hydride (2.5 M in THF, 0.4 mL, 1 mmol) dropwise at 0° C. Then the reaction mixture was warmed and stirred for 2 h at room temperature under nitrogen. The resulting mixture was quenched with sodium hydroxide (2 M in water, 1 mL, 2 mmol) at 0° C., then stirred for 10 min at this temperature and filtered. The filter cake was washed with 20 mL THF and 10 mL methanol. The residue was purified by reverse phase flash (30-70% acetonitrile+0.05% ammonium bicarbonate in water, over 20 min) to give the title compound (214 mg, 0.75 mmol, 90% yield) as a yellow solid. MS (ESI) m/z 285.1 $[M+1]^+$.

(R)-(2-(7-Oxa-1-azaspiro[4.4]nonan-1-yl)quinolin-6-yl) methanol. The (2-(7-oxa-1-azaspiro[4.4]nonan-1-yl) quinolin-6-yl)methanol (200 mg, 0.70 mmol) was purified by preparative chiral HPLC with the following conditions: column: chiralpak ig, 2*25 cm, 5 μm; mobile phase A: hexane (0.5% 2M triethylamine-methanol)-HPLC, mobile phase B: ethanol—HPLC; flow rate: 20 mL/min; gradient: 40% B to 40% B in 17 min; wave length: 220/254 nm; RT1 (min): 10.34; RT2 (min): 13.18; sample solvent: ethanol-HPLC; Injection volume: 0.6 mL; number of runs: 10. The fractions containing desired product were collected and evaporated under reduced pressure to afford the title compound (88 mg, 0.30 mmol, 43% yield) as a light-yellow solid. MS (ESI) m/z 285.1 $[M+1]^+$.

(R)-2-(7-Oxa-1-azaspiro[4.4]nonan-1-yl)quinoline-6-carbaldehyde. To a stirred solution of (R)-(2-(7-oxa-1-azaspiro[4.4]nonan-1-yl)quinolin-6-yl)methanol (40 mg, 0.14 mmol) in dichloromethane (5 mL) was added manganese dioxide (245 mg, 2.82 mmol) at room temperature. Then the reaction mixture was stirred for 12 h at room temperature under nitrogen. The resulting mixture was filtered and the filtrate was concentrated to afford the title compound (38 mg, 0.13 mmol, 93% yield) as a yellow solid. MS (ESI) m/z 283.2 $[M+1]^+$.

3-(5-(((S)-1-((2-((R)-7-Oxa-1-azaspiro[4.4]nonan-1-yl) quinolin-6-yl)methyl) pyrrolidin-3-yl)oxy)-1-oxoisoindolin-2-yl)piperidine-2,6-dione. To a stirred solution of (R)-2-(7-oxa-1-azaspiro[4.4]nonan-1-yl)quinoline-6-carbaldehyde (38 mg, 0.13 mmol), 3-[1-oxo-5-[(3S)-pyrrolidin-3-yl]oxy-isoindolin-2-yl]piperidine-2,6-dione; 2,2,2-trifluoroacetic acid (76 mg, 0.17 mmol), triethylamine (29 mg, 0.29 mmol) in dichloromethane (5 mL) pre-stirred for 15 min was added sodium triacetoxyborohydride (119 mg, 0.56 mmol) at 0° C. and the solution was stirred at room temperature for 12 h under nitrogen. The resulting solution was purified by silica gel chromatography (0 to 10% methanol in dichloromethane). The pure fractions were evaporated and purified further by preparative HPLC with the following conditions: Column: Sunfire prep C18 OBD column, 19×150 mm 5 μm 10 nm; mobile phase A: water (0.1% formic acid), mobile phase B: acetonitrile; flow rate: 60 mL/min; gradient: 10 B to 30 B in 10 min; 254/210 nm; $RT_1$: 9.67. The fractions containing desired product were collected and evaporated under reduced pressure to afford the title compound (21.2 mg, 0.035 mmol, 27% yield) as a white solid. $^1H$ NMR (300 MHz, DMSO-$d_6$) δ 10.97 (s, 1H), 7.99 (d, J=9.1 Hz, 1H), 7.64-7.56 (m, 2H), 7.50 (d, J=2.1 Hz, 2H), 7.11 (s, 1H), 7.06-6.90 (m, 2H), 5.14-4.92 (m, 2H), 4.47-4.32 (m, 2H), 4.31-4.16 (m, 2H), 3.91 (m, 1H), 3.74 (m, 2H), 3.64-3.51 (m, 2H), 3.40 (d, J=8.2 Hz, 1H), 2.93 (m, 2H), 2.88-2.80 (m, 1H), 2.77-2.56 (m, 3H), 2.47 (d, J=7.2 Hz, 1H), 2.35 (m, 2H), 2.18-2.03 (m, 2H), 1.95 (m, 3H), 1.86-1.76 (m, 1H), 1.70 (m, 1H); MS (ESI) m/z 596.2 $[M+1]^+$.

Example S107. 3-(5-(((S)-1-((2-((S)-7-Oxa-1-azaspiro[4.4]nonan-1-yl)quinolin-6-yl)methyl)pyrrolidin-3-yl)oxy)-1-oxoisoindolin-2-yl)piperidine-2,6-dione

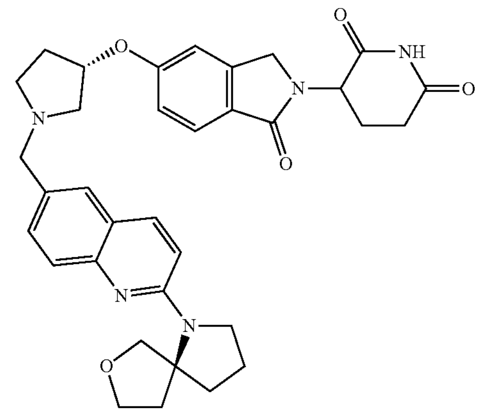 [SMILES: O=C1CCC(N2Cc3cc(O[C@H]4CCN(Cc5ccc6nc(N7CCC[C@@]78CCOC8)ccc6c5)C4)ccc3C2=O)C(=O)N1]

(S)-(2-(7-Oxa-1-azaspiro[4.4]nonan-1-yl)quinolin-6-yl) methanol. The (2-(7-oxa-1-azaspiro[4.4]nonan-1-yl)quinolin-6-yl)methanol (200 mg, 0.70 mmol) was purified by preparative chiral HPLC with the following conditions: Column: chiralpak ig, 2*25 cm, 5 μm; mobile phase A: hexane (0.5% 2M triethylamine-methanol)-HPLC, mobile phase B: ethanol-HPLC; flow rate: 20 m/min; gradient: 40% B to 40% B in 17 min; wave length: 220/254 nm; RT1 (min): 10.34; RT2 (min): 13.18; sample solvent: ethanol-HPLC; Injection volume: 0.6 mL; number of runs: 10. The fractions containing desired product were collected and evaporated under reduced pressure to afford the title compound (87 mg, 0.31 mmol, 44% yield). MS (ESI) m/z 285.1 $[M+1]^+$.

(S)-2-(7-oxa-1-azaspiro[4.4]nonan-1-yl)quinoline-6-carbaldehyde. To a stirred solution of (S)-(2-(7-oxa-1-azaspiro[4.4]nonan-1-yl)quinolin-6-yl)methanol (40 mg, 0.14 mmol) in dichloromethane (5 mL) was added manganese dioxide (245 mg, 2.82 mmol) at room temperature. Then the reaction mixture was stirred for 12 h at room temperature under nitrogen. The resulting mixture was filtered and concentrated to afford the title compound (39 mg, 0.14 mmol, 98% yield) as a yellow solid. MS (ESI) m/z 283.2 $[M+1]^+$.

3-(5-(((S)-1-((2-((S)-7-Oxa-1-azaspiro[4.4]nonan-1-yl) quinolin-6-yl)methyl) pyrrolidin-3-yl)oxy)-1-oxoisoindolin-2-yl)piperidine-2,6-dione. To a stirred solution of (S)-2-(7-oxa-1-azaspiro[4.4]nonan-1-yl)quinoline-6-carbaldehyde (39 mg, 0.14 mmol), 3-[1-oxo-5-[(3S)-pyrrolidin-3-yl]oxy-isoindolin-2-yl]piperidine-2,6-dione; 2,2,2-trifluoroacetic acid (76 mg, 0.17 mmol), triethylamine (29 mg, 0.29 mmol) in dichloromethane (5 mL) pre-stirred for 15 min was added sodium triacetoxyborohydride (120 mg, 0.56 mmol) at 0° C. and the solution was stirred at room temperature for 12 h under nitrogen. The resulting solution was purified by silica gel chromatography (0 to 10% methanol in dichloromethane). The pure fractions were evaporated and purified further by preparative HPLC with the following conditions: column: sunfire prep C18 OBD column, 19×150 mm 5 um 10 nm; mobile phase A: water (0.1% formic acid), mobile phase B: acetonitrile; flow rate: 60 mL/min; gradient: 10 B to 30 B in 10 min; 254/210 nm; $RT_1$: 9.67. The fractions containing desired product were collected and evaporated under reduced pressure to afford the title compound (29.5 mg, 0.05 mmol, 35% yield) as a yellow solid. $^1$H NMR (300 MHz, DMSO-$d_6$) δ 10.97 (s, 1H), 7.99 (d, J=9.1 Hz, 1H), 7.60 (d, J=8.8 Hz, 2H), 7.50 (d, J=2.0 Hz, 2H), 7.11 (d, J=2.3 Hz, 1H), 7.04-6.91 (m, 2H), 5.13-4.94 (m, 2H), 4.49-4.32 (m, 2H), 4.32-4.17 (m, 2H), 3.91 (m, 1H), 3.75 (s, 2H), 3.64-3.57 (m, 1H), 3.54 (m, 1H), 3.40 (d, J=8.2 Hz, 1H), 3.00-2.80 (m, 3H), 2.79-2.56 (m, 3H), 2.42-2.27 (m, 1H), 2.08 (m, 2H), 2.03-1.89 (m, 3H), 1.85 (m, 1H), 1.70 (m, 1H); MS (ESI) m/z 596.2 $[M+1]^+$.

Example S108. 3-(5-(((S)-1-((2-(6-Oxa-1-azaspiro [3.3] heptan-1-yl) quinazolin-6-yl) methyl)pyrrolidin-3-yl)oxy)-1-oxoisoindolin-2-yl) piperidine-2,6-dione

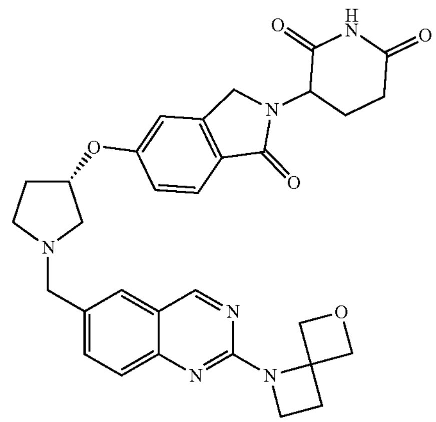 [SMILES: O=C1CCC(N2Cc3cc(O[C@H]4CCN(Cc5ccc6nc(N7CCC78COC8)ncc6c5)C4)ccc3C2=O)C(=O)N1]

1-(6-Bromoquinazolin-2-yl)-6-oxa-1-azaspiro[3.3]heptane. To a stirred solution of 6-bromo-2-chloroquinazoline (200 mg, 0.82 mmol), N,N-diisopropylethylamine (0.71 mL, 4.08 mmol) in ethanol (10 mL) was added 6-oxa-1-azaspiro [3.3]heptane (203 mg, 2.05 mmol) and the mixture stirred at 80° C. for 3 h under nitrogen. The resulting solution was concentrated to afford the title compound (221 mg, 0.72 mmol, 88% yield) as a yellow solid. MS (ESI) m/z 306.1 $[M+1]^+$.

1-(6-Vinylquinazolin-2-yl)-6-oxa-1-azaspiro[3.3]heptane. To a solution of 1-(6-bromoquinazolin-2-yl)-6-oxa-1-azaspiro[3.3]heptane (200 mg, 0.65 mmol) and potassium trifluoro(vinyl)borate (150 mg, 1.12 mmol) in 1,4-dioxane (10 mL) and water (2 mL) were added [1,1'-bis(diphenylphosphino)ferrocene]dichloropalladium(II) (120 mg, 0.16 mmol) and sodium carbonate (207 mg, 1.96 mmol) at room temperature. The reaction mixture was heated to 90° C. for 3 h under nitrogen. The resulting mixture was diluted with water and extracted with ethyl acetate. The extracts were washed with brine, dried over anhydrous sodium sulfate, filtered and concentrated. The residue was purified by reverse phase flash (10-70% acetonitrile+0.05% ammonium bicarbonate in water, over 20 min) to give the title compound (160 mg, 0.63 mmol, 97% yield) as a yellow solid. MS (ESI) m/z 254.0 $[M+1]^+$.

2-(6-Oxa-1-azaspiro[3.3]heptan-1-yl)quinazoline-6-carbaldehyde. To a solution of 1-(6-vinylquinazolin-2-yl)-6-oxa-1-azaspiro[3.3]heptane (100 mg, 0.39 mmol), potassium osmate (16 mg, 0.04 mmol) and 4-methylmorpholine N-oxide (92 mg, 0.79 mmol) in 1-butanol (5 mL) and water (5 mL) was added citric acid (172 mg, 0.79 mmol) and the above mixture was stirred at room temperature for 3 h under nitrogen. Then sodium periodate (253 mg, 1.18 mmol) was added in several portions to the above mixture at 0° C. and the resulting mixture was stirred at room temperature for 1 h. The mixture was added saturated sodium bicarbonate solution to pH~7 and extracted with ethyl acetate. The extracts were washed with brine, dried over sodium sulfate, filtered and concentrated to afford the title compound (55 mg, 0.21 mmol, 54% yield) as a yellow solid. MS (ESI) m/z 256.0 $[M+1]^+$.

3-(5-(((S)-1-((2-(6-Oxa-1-azaspiro[3.3]heptan-1-yl)quinazolin-6-yl)methyl)pyrrolidin-3-yl)oxy)-1-oxoisoindolin-2-yl)piperidine-2,6-dione. To a stirred mixture of 2-(6-oxa-1-azaspiro[3.3]heptan-1-yl)quinazoline-6-carbaldehyde (50 mg, 0.20 mmol), 3-[1-oxo-5-[(3S)-pyrrolidin-3-yl]oxy-isoindolin-2-yl]piperidine-2,6-dione; 2,2,2-trifluoroacetic acid (85 mg, 0.19 mmol) and triethylamine (39 mg, 0.39 mmol) in dichloromethane (10 mL) was added sodium triacetoxyborohydride (165 mg, 0.78 mmol) in several portions and the resulting mixture was stirred at room temperature for 2 h under nitrogen. The mixture was concentrated and the residue was purified by silica gel chromatography (0-10% methanol in dichloromethane) firstly and further by preparative HPLC with the following conditions: Sunfire C18 OBD prep Column, 19*250 mm, 5 μm; Mobile phase A: water (0.1% formic acid), Mobile phase B: acetonitrile; Flow rate: 60 mL/min; Gradient: 2% B to 20% B in 7 min, 20% B; Wave Length: 254/220 nm; RT1 (min): 6.5. The fractions containing desired product were collected and evaporated under reduced pressure to afford the title compound (37 mg, 0.06 mmol, 33% yield) as a light-yellow solid. $^1$H NMR (300 MHz, Methanol-$d_4$) δ 9.18 (s, 1H), 7.91 (d, J=1.9 Hz, 1H), 7.85-7.83 (m, 1H), 7.70-7.62 (m, 2H), 7.16-7.03 (m, 2H), 5.61 (d, J=6.7 Hz, 2H), 5.20 (m, 1H), 5.13-5.10 (m, 1H), 4.75 (d, J=6.7 Hz, 2H), 4.45 (d, J=3.8 Hz, 2H), 4.25 (d, J=2.4 Hz, 2H), 4.07-4.03 (m, 2H), 3.51-3.28 (m, 3H), 3.23-3.12 (m, 1H), 2.92-2.90 (m, 1H), 2.84-2.73 (m, 1H), 2.73 (m, 2H), 2.59-2.40 (m, 2H), 2.30-2.11 (m, 2H); MS (ESI) m/z 569.3 $[M+1]^+$.

Example S109. 3-(5-(((S)-1-((2-((R)-7-Oxa-1-azaspiro[4.4]nonan-1-yl)quinazolin-6-yl)methyl) pyrrolidin-3-yl)oxy)-1-oxoisoindolin-2-yl)piperidine-2,6-dione

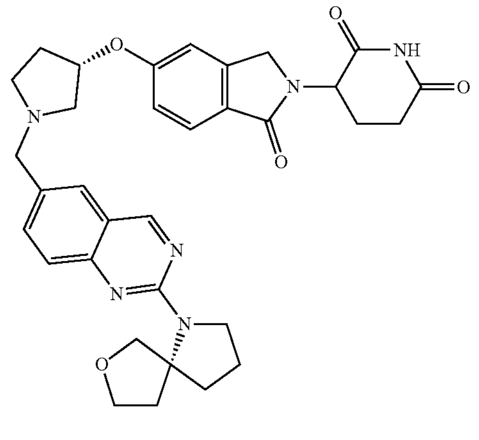 [SMILES: O=C1CCC(N2Cc3cc(O[C@H]4CCN(Cc5ccc6nc(N7CCC[C@]78CCOC8)ncc6c5)C4)ccc3C2=O)C(=O)N1]

1-(6-Bromoquinazolin-2-yl)-7-oxa-1-azaspiro[4.4] nonane. To a stirred solution of 6-bromo-2-chloro-quinazoline (600 mg, 2.46 mmol) in NMP (10 mL) were added 7-oxa-1-azaspiro[4.4]nonane; hydrochloride (1.0 g, 6.10 mmol) and N,N-diisopropylethylamine (1.10 mL, 6.31 mmol) at room temperature. Then the reaction mixture was stirred for 12 h at 120° C. under nitrogen. The resulting mixture was purified with reverse phase flash (30-80% acetonitrile+0.05% ammonium bicarbonate in water, over 20 min) to give the title compound (800 mg, 2.40 mmol, 97% yield) as a yellow solid. MS (ESI) m/z 334.1 $[M+1]^+$.

1-(6-Vinylquinazolin-2-yl)-7-oxa-1-azaspiro[4.4]nonane. To a stirred solution of 1-(6-bromoquinazolin-2-yl)-7-oxa-1-azaspiro[4.4]nonane (500 mg, 1.5 mmol) in 1,4-dioxane (20 mL) and water (2 mL) were added potassium vinyltrifluoroborate (400 mg, 3.0 mmol), dichlorobis (triphenylphosphine)palladium(II) dichloromethane adduct (245 mg, 0.31 mmol) and sodium carbonate (477 mg, 4.5 mmol) at room temperature. Then the reaction mixture was stirred for 12 h at 80° C. under nitrogen. The resulting mixture was filtered and the filtrate was concentrated. The residue was purified by reverse phase flash (30-80% acetonitrile+0.05% ammonium bicarbonate in water, over 20 min) to give the title compound (300 mg, 1.06 mmol, 71% yield) as a yellow solid. MS (ESI) m/z 282.2 $[M+1]^+$.

(R)-1-(6-Vinylquinazolin-2-yl)-7-oxa-1-azaspiro[4.4]nonane. The 1-(6-vinylquinazolin-2-yl)-7-oxa-1-azaspiro[4.4]nonane (300 mg, 1.06 mmol) was purified by preparative chiral HPLC with the following conditions: Column: Chiral art cellulose-sb, 3*25 cm, 5 μm; mobile phase A: carbon dioxide, mobile phase B: methanol (0.1% 2M ammonia-methanol); flow rate: 100 mL/min; gradient: isocratic 30% B; column temperature (° C.): 35; back pressure (bar): 100; wave length: 220 nm; $RT_1$ (min): 3.72; $RT_2$ (min): 4.32; sample solvent: methanol—preparative; injection volume: 4 mL; number of runs: 10. The fractions containing desired product were collected and evaporated under reduced pressure to afford the title compound (55 mg, 0.19 mmol, 18% yield). MS (ESI) m/z 282.2 $[M+1]^+$.

(R)-2-(7-Oxa-1-azaspiro[4.4]nonan-1-yl)quinazoline-6-carbaldehyde. To a stirred solution of (R)-1-(6-vinylquinazolin-2-yl)-7-oxa-1-azaspiro[4.4]nonane (55 mg, 0.19 mmol), 4-methylmorpholine N-oxide (47 mg, 0.40 mmol) and citric acid (77 mg, 0.40 mmol) in tert-butanol (5 mL) and water (5 mL) was added potassium osmate (8 mg, 0.02 mmol). The reaction mixture was stirred for 3 h at room temperature under nitrogen. Then the reaction mixture was added sodium periodate (129 mg, 0.60 mmol) and stirred for 1 h at room temperature. The mixture was added saturated sodium bicarbonate solution to pH~7 and extracted with ethyl acetate. The extracts were washed with brine, dried over anhydrous sodium sulfate, filtered and concentrated to afford the title compound (50 mg, 0.18 mmol, 92% yield) as a yellow oil. MS (ESI) m/z 284.2 $[M+1]^+$.

3-(5-(((S)-1-((2-((R)-7-Oxa-1-azaspiro[4.4]nonan-1-yl)quinazolin-6-yl)methyl) pyrrolidin-3-yl)oxy)-1-oxoisoindolin-2-yl)piperidine-2,6-dione. To a stirred solution of (R)-2-(7-oxa-1-azaspiro[4.4]nonan-1-yl)quinazoline-6-carbaldehyde (60 mg, 0.21 mmol), 3-[1-oxo-5-[(3S)-pyrrolidin-3-yl] oxy-isoindolin-2-yl]piperidine-2,6-dione; 2,2,2-trifluoroacetic acid (113 mg, 0.25 mmol), triethylamine (34 mg, 0.33 mmol) in dichloromethane (10 mL) pre-stirred for 15 min was added sodium triacetoxyborohydride (180 mg, 0.85 mmol) at 0° C. and the solution was stirred at room temperature for 12 h under nitrogen. The resulting solution was purified by silica gel chromatography (0 to 5% methanol in dichloromethane). The pure fractions were evaporated and purified further by preparative HPLC with the following conditions: column: sunfire prep C18 OBD column, 19×150 mm 5 um 10 nm; mobile phase A: water (0.1% formic acid), mobile phase B: acetonitrile; flow rate: 60 mL/min; gradient: 10 B to 30 B in 10 min; 254/210 nm; $RT_1$: 9.67. The fractions containing desired product were collected and evaporated under reduced pressure to afford the title compound (20.7 mg, 0.034 mmol, 16% yield) as a yellow solid. $^1H$ NMR (400 MHz, DMSO-$d_6$) δ 10.96 (s, 1H), 9.17 (s, 1H), 7.75-7.67 (m, 2H), 7.60 (d, J=8.4 Hz, 1H), 7.47 (d, J=8.6 Hz, 1H), 7.10 (t, J=2.2 Hz, 1H), 7.00 (m, 1H), 5.11-4.97 (m, 2H), 4.41-4.20 (m, 3H), 4.12 (d, J=7.8 Hz, 1H), 3.95 (m, 1H), 3.78 (m, 1H), 3.72-3.55 (m, 3H), 3.42 (d, J=7.7 Hz, 1H), 2.98-2.84 (m, 3H), 2.78-2.65 (m, 2H), 2.63-2.55 (m, 1H), 2.48 (m, 1H), 2.41-2.29 (m, 2H), 2.18-2.02 (m, 2H), 1.95 (m, 2H), 1.83 (m, 2H), 1.70 (m, 1H); MS (ESI) m/z 597.1 $[M+1]^+$.

Example S110. 3-(5-(((S)-1-((2-((S)-7-Oxa-1-azaspiro[4.4]nonan-1-yl)quinazolin-6-yl)methyl) pyrrolidin-3-yl)oxy)-1-oxoisoindolin-2-yl)piperidine-2,6-dione

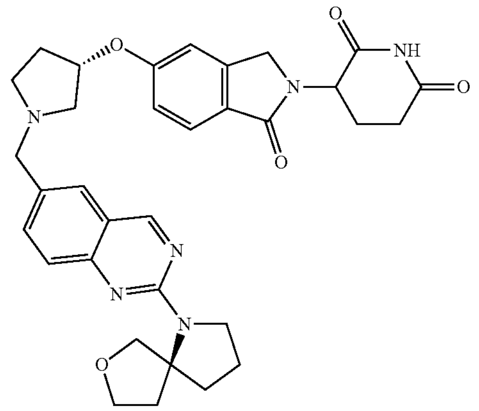 [SMILES: O=C1CCC(N2Cc3cc(O[C@H]4CCN(Cc5ccc6nc(N7CCC[C@@]78CCOC8)ncc6c5)C4)ccc3C2=O)C(=O)N1]

1-(6-Bromoquinazolin-2-yl)-7-oxa-1-azaspiro[4.4]nonane. To a stirred solution of 6-bromo-2-chloro-quinazoline (600 mg, 2.50 mmol) in NMP (10 mL) were added 7-oxa-1-azaspiro[4.4]nonane; hydrochloride (1.0 g, 6.11 mmol) and N,N-diisopropylethylamine (1.10 mL, 6.31 mmol) at room temperature. Then the reaction mixture was stirred for 12 h at 120° C. under nitrogen. The resulting mixture was purified with reverse phase flash (30-80% acetonitrile+0.05% ammonium bicarbonate in water, over 20 min) to give the title compound (800 mg, 2.39 mmol, 96% yield) as a yellow solid. MS (ESI) m/z 334.1 $[M+1]^+$.

1-(6-Vinylquinazolin-2-yl)-7-oxa-1-azaspiro[4.4]nonane. To a stirred solution of 1-(6-bromoquinazolin-2-yl)-7-oxa-1-azaspiro[4.4]nonane (500 mg, 1.50 mmol) in 1,4-dioxane (20 mL) and water (2 mL) were added potassium vinyltrifluoroborate (400 mg, 3.0 mmol), dichlorobis (triphenylphosphine)palladium(II) dichloromethane adduct (245 mg, 0.31 mmol) and sodium carbonate (477 mg, 4.5 mmol) at room temperature. Then the reaction mixture was stirred for 12 h at 80° C. under nitrogen. The resulting mixture was filtered and the filtrate was concentrated. The residue was purified by reverse phase flash (30-80% acetonitrile+0.05% ammonium bicarbonate in water, over 20 min) to give the title compound (300 mg, 1.10 mmol, 71% yield) as a yellow solid. MS (ESI) m/z 282.2 $[M+1]^+$.

(S)-1-(6-Vinylquinazolin-2-yl)-7-oxa-1-azaspiro[4.4]nonane. The 1-(6-vinylquinazolin-2-yl)-7-oxa-1-azaspiro[4.4]nonane (300 mg, 1.06 mmol) was purified by preparative chiral HPLC with the following conditions: Column: Chiral art cellulose-sb, 3*25 cm, 5 μm; mobile phase A: carbon dioxide, mobile phase B: methanol (0.1% 2 M ammonia-methanol); flow rate: 100 mL/min; gradient: isocratic 30% B; column temperature (° C.): 35; back pressure (bar): 100; wave length: 220 nm; $RT_1$ (min): 3.72; $RT_2$ (min): 4.32; sample solvent: methanol—preparative; injection volume: 4 mL; number of runs: 10. The fractions containing desired product were collected and evaporated under reduced pressure to afford the title compound (58 mg, 0.20 mmol, 19% yield). MS (ESI) m/z 282.2 $[M+1]^+$.

(S)-2-(7-Oxa-1-azaspiro[4.4]nonan-1-yl)quinazoline-6-carbaldehyde. To a stirred solution of (S)-1-(6-vinylquinazolin-2-yl)-7-oxa-1-azaspiro[4.4]nonane (58 mg, 0.20 mmol), 4-methylmorpholine N-oxide (47 mg, 0.40 mmol) and citric acid (77 mg, 0.40 mmol) in tert-butanol (5 mL) and water (5 mL) was added potassium osmate (8 mg, 0.02 mmol). The mixture was stirred for 3 h at room temperature under nitrogen. The resulting mixture was added sodium periodate (129 mg, 0.6 mmol) and stirred for 1 h at room temperature. The mixture was added saturated sodium bicarbonate solution to pH~7 and extracted with ethyl acetate. The extracts were washed with brine, dried over anhydrous sodium sulfate, filtered and concentrated to afford the title compound (50 mg, 0.18 mmol, 90% yield) as a yellow oil. MS (ESI) m/z 284.2 $[M+1]^+$.

3-(5-(((S)-1-((2-((S)-7-Oxa-1-azaspiro[4.4]nonan-1-yl)quinazolin-6-yl)methyl) pyrrolidin-3-yl)oxy)-1-oxoisoindolin-2-yl)piperidine-2,6-dione. To a stirred solution of (S)-2-(7-oxa-1-azaspiro[4.4]nonan-1-yl)quinazoline-6-carbaldehyde (50 mg, 0.18 mmol), 3-[1-oxo-5-[(3S)-pyrrolidin-3-yl] oxy-isoindolin-2-yl]piperidine-2,6-dione; 2,2,2-trifluoroacetic acid (113 mg, 0.25 mmol), triethylamine (33 mg, 0.33 mmol) in dichloromethane (10 mL) prestirred for 15 min was added sodium triacetoxyborohydride (180 mg, 0.85 mmol) at 0° C. and the solution was stirred at room temperature for 12 h under nitrogen. The resulting solution was purified by silica gel chromatography (0 to 5% methanol in dichloromethane). The pure fractions were evaporated and purified further by preparative HPLC with the following conditions: Column: Sunfire prep C18 OBD column, 19×150 mm, 5 um 10 nm; mobile phase A: water (0.1% formic acid), mobile phase B: acetonitrile; flow rate: 60 mL/min; gradient: 10 B to 30 B in 10 min; 254/210 nm; $RT_1$: 9.67; $RT_2$. The fractions containing desired product were collected and evaporated under reduced pressure to afford the title compound (32.5 mg, 0.054 mmol, 30% yield) as a yellow solid. $^1H$ NMR (400 MHz, DMSO-$d_6$) δ 10.96 (s, 1H), 9.17 (s, 1H), 7.75-7.66 (m, 2H), 7.60 (d, J=8.4 Hz, 1H), 7.47 (d, J=8.6 Hz, 1H), 7.10 (t, J=2.2 Hz, 1H), 7.00 (m, 1H), 5.12-4.94 (m, 2H), 4.37 (d, J=17.2 Hz, 1H), 4.24 (m, 2H), 4.12 (d, J=7.8 Hz, 1H), 3.95 (m, 1H), 3.77 (m, 1H), 3.70 (d, J=4.9 Hz, 2H), 3.60 (m, 1H), 3.42 (d, J=7.7 Hz, 1H), 2.99-2.84 (m, 3H), 2.80-2.65 (m, 2H), 2.64-2.56 (m, 1H), 2.47 (d, J=7.3 Hz, 1H), 2.43-2.30 (m, 2H), 2.14 (m, 1H), 2.09-1.79 (m, 5H), 1.70 (m, 1H); MS (ESI) m/z 597.1 $[M+1]^+$.

Example S111. 3-(5-(((S)-1-((2-((1R,2R)-2-(Methoxymethyl)cyclohexyl)quinolin-6-yl)methyl) pyrrolidin-3-yl)oxy)-1-oxoisoindolin-2-yl)piperidine-2,6-dione

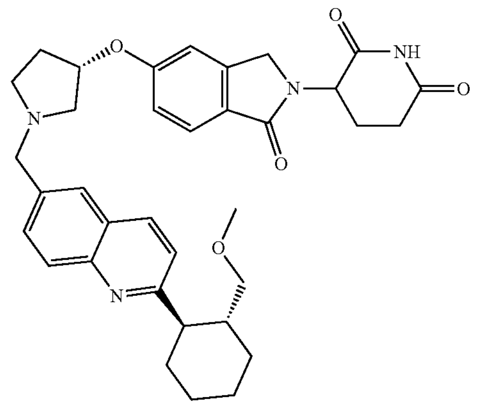 [SMILES: COC[C@@H]1CCCC[C@H]1c1ccc2cc(CN3CC[C@H](Oc4ccc5c(c4)CN(C4CCC(=O)NC4=O)C5=O)C3)ccc2n1]

Ethyl 2-(6-(((tert-butyldiphenylsilyl)oxy)methyl)quinolin-2-yl)cyclohex-1-ene-1-carboxylate. To a stirred solution of 6-(((tert-butyldiphenylsilyl)oxy) methyl)-2-chloroquinoline (3 g, 6.9 mmol) in 1,4-dioxane (20 mL) and water (4 mL) were added ethyl 2-(4,4,5,5-tetramethyl-1,3,2-dioxaborolan-2-yl)cyclohexene-1-carboxylate (2.2 g, 7.9 mmol), dichlorobis(triphenylphosphine)palladium(II) dichloromethane adduct (567 mg, 0.69 mmol) and sodium carbonate (2.2 g, 20.8 mmol) at room temperature. Then the reaction mixture was stirred for 12 h at 80° C. under nitrogen. The resulting mixture was filtered and the filtrate was concentrated. The residue was purified by reverse phase flash (40-90% acetonitrile+0.05% ammonium bicarbonate in water, over 20 min) to give the title compound (1.7 g, 3.10 mmol, 45% yield) as a yellow solid. MS (ESI) m/z 550.4 $[M+1]^+$.

(2-(6-(((Tert-butyldiphenylsilyl)oxy)methyl)quinolin-2-yl)cyclohex-1-en-1-yl) methanol. To a stirred solution of ethyl 2-(6-(((tert-butyldiphenylsilyl)oxy)methyl) quinolin-2-yl)cyclohex-1-ene-1-carboxylate (1.7 g, 3.10 mmol) in THF (50 mL) and ethanol (5 mL) was added sodium borohydride (1.2 g, 31.7 mmol) and anhydrous lithium chloride (1.34 g, 31.9 mmol) at room temperature. Then the reaction mixture was stirred for 48 h at 50° C. under nitrogen. The resulting mixture was quenched with ammonium chloride (3 M in water, 10 mL, 30 mmol) at 0° C. and extracted with ethyl acetate. The extracts were washed with brine, dried over sodium sulfate, filtered and concentrated to afford the title compound (1.5 g, 2.95 mmol, 95% yield) as a yellow oil. MS (ESI) m/z 508.3 $[M+1]^+$.

(2-(6-(((Tert-butyldiphenylsilyl)oxy)methyl)quinolin-2-yl)cyclohexyl)methanol. To a stirred solution of methyl (2-(6-(((tert-butyldiphenylsilyl)oxy) methyl)quinolin-2-yl) cyclohex-1-en-1-yl)methanol (1.5 g, 2.95 mmol) in methanol (50 mL) was added palladium 10% on carbon (450 mg, wetted with ca. 50% water) at room temperature under nitrogen. The reaction mixture was stirred at room temperature for 2 h under hydrogen (~2 bar). The resulting mixture was filtered and the filtrate was concentrated to give the title compound (1.3 g, 2.54 mmol, 86% yield) as a yellow oil which was used without further purification. MS (ESI) m/z 510.3 $[M+1]^+$.

6-(((Tert-butyldiphenylsilyl)oxy)methyl)-2-(2-(methoxymethyl)cyclohexyl) quinoline. To a stirred solution of (2-(6-(((tert-butyldiphenylsilyl)oxy)methyl) quinolin-2-yl)cyclohexyl)methanol (750 mg, 1.47 mmol) in dichloromethane (20 mL) were added trimethyloxonium tetrafluoroborate (409 mg, 2.76 mmol) and 2,6-di-tert-butylpyridine (844 mg, 4.41 mmol) at room temperature. Then the reaction mixture was stirred for 12 h at room temperature under nitrogen. The resulting solution was purified by silica gel chromatography (0 to 20% ethyl acetate in petroleum ether). The fractions containing desired product were collected and evaporated under reduced pressure to afford the title compound (700 mg, 1.33 mmol, 90% yield) as a yellow oil. MS (ESI) m/z 524.3 $[M+1]^+$.

(2-(2-(Methoxymethyl)cyclohexyl)quinolin-6-yl)methanol. To a stirred solution of 6-(((tert-butyldiphenylsilyl)oxy) methyl)-2-(2-(methoxymethyl)cyclohexyl) quinoline (500 mg, 0.95 mmol) in acetonitrile (3 mL) and water (3 mL) was added TFA (9.0 mL) at room temperature. Then the reaction mixture was stirred for 2 h at 60° C. under nitrogen. The resulting solution was concentrated. The crude product was purified by silica gel chromatography (20 to 70% ethyl acetate in petroleum ether). The fractions containing desired product were collected and evaporated under reduced pressure to afford the title compound (270 mg, 0.94 mmol, 99% yield) as a yellow oil. MS (ESI) m/z 286.2 $[M+1]^+$.

(2-((1R,2R)-2-(Methoxymethyl)cyclohexyl)quinolin-6-yl)methanol. The (2-(2-(methoxymethyl)cyclohexyl)quinolin-6-yl)methanol (600 mg, 2.1 mmol) was purified by preparative SFC with the following conditions: column: chiralpak IG, 3*25 cm, 5 μm; mobile phase A: carbon dioxide, mobile phase B: methanol (0.1% 2M ammonia-methanol); flow rate: 70 mL/min; gradient: isocratic 50% B; column temperature (° C.): 35; back pressure (bar): 100; wave length: 220 nm; $RT_1$ (min): 3.78; $RT_2$ (min): 6.57; sample solvent: methanol—preparative; injection volume: 4.8 mL; number of runs: 4. The fractions containing desired product were collected and evaporated under reduced pressure to afford the title compound (70 mg, 0.26 mmol, 12% yield). MS (ESI) m/z 272.2 $[M+1]^+$.

2-((1R,2R)-2-(Methoxymethyl)cyclohexyl)quinoline-6-carbaldehyde. To a stirred solution of (2-((1R,2R)-2-(methoxymethyl)cyclohexyl)quinolin-6-yl)methanol (70 mg, 0.26 mmol) in dichloromethane (5 mL) was added manganese dioxide (426 mg, 4.90 mmol) at room temperature. Then the reaction mixture was stirred for 12 h at room temperature under nitrogen. The resulting mixture was filtered and concentrated to afford the title compound (65 mg, 0.23 mmol, 88% yield) as a yellow oil. MS (ESI) m/z 286.1 $[M+1]^+$.

3-(5-(((S)-1-((2-((1R,2R)-2-(Methoxymethyl)cyclohexyl)quinolin-6-yl)methyl) pyrrolidin-3-yl)oxy)-1-oxoisoindolin-2-yl)piperidine-2,6-dione. To a stirred solution of 2-((1R,2R)-2-(methoxymethyl)cyclohexyl)quinoline-6-carbaldehyde (70 mg, 0.24 mmol), 3-(1-oxo-5-(((S)-pyrrolidin-3-yl)oxy)isoindolin-2-yl)piperidine-2,6-dione; 2,2,2-trifluoroacetic acid (110 mg, 0.25 mmol), triethylamine (50 mg, 0.5 mmol) in dichloromethane (5 mL) pre-stirred for 15 min was added sodium triacetoxyborohydride (212 mg, 1.00 mmol) at 0° C. and the solution was stirred at room temperature for 12 h under nitrogen. The resulting solution was purified by silica gel chromatography (0 to 15% methanol in dichloromethane). The pure fractions were evaporated and purified further by preparative HPLC with the following conditions: Column: Sunfire prep C18 OBD Column, 19×150 mm 5 um 10 nm; mobile phase A: water (0.1% formic acid), mobile phase B: acetonitrile; flow rate: 60 mL/min; gradient: 10 B to 30 B in 10 min; 254/210 nm; $RT_1$: 9.67. The fractions containing desired product were collected and evaporated under reduced pressure to afford the title compound (46.1 mg, 0.077 mmol, 32% yield) as a white solid. $^1H$ NMR (300 MHz, DMSO-$d_6$) δ 10.96 (s, 1H), 8.22 (d, J=8.5 Hz, 1H), 8.14 (s, 1H), 7.90 (d, J=8.6 Hz, 1H), 7.82 (s, 1H), 7.69 (dd, J=8.6, 1.8 Hz, 1H), 7.60 (d, J=8.4 Hz, 1H), 7.42 (d, J=8.5 Hz, 1H), 7.11 (s, 1H), 7.00 (m, 1H), 5.06 (m, 2H), 4.43-4.17 (m, 2H), 3.89-3.72 (m, 2H), 3.41-3.30 (m, 2H), 3.24-3.15 (m, 1H), 3.00-2.58 (m, 8H), 2.55 (m, 1H), 2.45-2.24 (m, 3H), 2.06-1.72 (m, 6H), 1.45 (m, 4H); MS (ESI) m/z 597.3 $[M+1]^+$.

Example S112. 3-(5-(((S)-1-((2-((1S,2S)-2-(Methoxymethyl)cyclohexyl)quinolin-6-yl)methyl) pyrrolidin-3-yl)oxy)-1-oxoisoindolin-2-yl)piperidine-2,6-dione

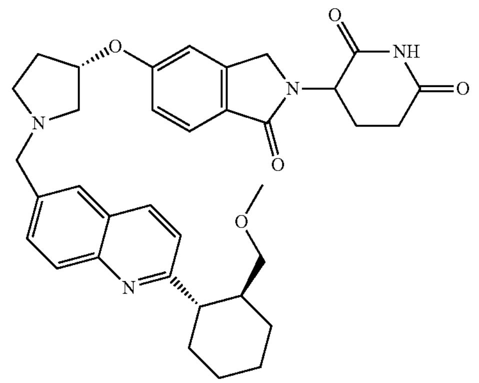 [SMILES: COC[C@H]1CCCC[C@@H]1c1ccc2cc(CN3CC[C@H](Oc4ccc5c(c4)CN(C4CCC(=O)NC4=O)C5=O)C3)ccc2n1]

(2-((1S,2S)-2-(Methoxymethyl)cyclohexyl)quinolin-6-yl)methanol. The (2-(2-(methoxymethyl)cyclohexyl)quinolin-6-yl)methanol (600 mg, 2.10 mmol) was purified by preparative SFC with the following conditions: column: chiralpak IG, 3*25 cm, 5 μm; mobile phase A: carbon dioxide, mobile phase B: methanol (0.1% 2M ammonia-methanol); flow rate: 70 mL/min; gradient: isocratic 50% B; column temperature (° C.): 35; back pressure (bar): 100; wave length: 220 nm; $RT_1$ (min): 3.78; $RT_2$ (min): 6.57; sample solvent: methanol—preparative; injection volume: 4.8 mL; number of runs: 4. The fractions containing desired product were collected and evaporated under reduced pressure to afford the title compound (70 mg, 0.24 mmol, 12% yield). MS (ESI) m/z 286.1 $[M+1]^+$.

2-((1S,2S)-2-(Methoxymethyl)cyclohexyl)quinoline-6-carbaldehyde. To a stirred solution of (2-((1S,2S)-2-(methoxymethyl)cyclohexyl)quinolin-6-yl)methanol (70 mg, 0.24 mmol) in dichloromethane (5 mL) was added manganese dioxide (426 mg, 4.90 mmol) at room temperature. Then the reaction mixture was stirred for 12 h at room temperature under nitrogen. The resulting mixture was filtered and concentrated to afford the title compound (13 mg, 0.046 mmol, 0.19% yield) as a yellow oil. MS (ESI) m/z 284.1 $[M+1]^+$.

3-(5-(((S)-1-((2-((1S,2S)-2-(Methoxymethyl)cyclohexyl) quinolin-6-yl)methyl) pyrrolidin-3-yl)oxy)-1-oxoisoindolin-2-yl)piperidine-2,6-dione. A solution of 2-[(1S,2S)-2-(methoxymethyl)cyclohexyl]quinoline-6-carbaldehyde (50 mg, 0.18 mmol), 3-(1-oxo-5-(((S)-pyrrolidin-3-yl)oxy) isoindolin-2-yl)piperidine-2,6-dione; 2,2-2-trifluoroacetic acid (94 mg, 0.21 mmol) and triethylamine (50 mg, 0.5 mmol) in dichloromethane (5 mL) was stirred for 10 min at room temperature under nitrogen atmosphere. Then to the above mixture was added sodium triacetoxyborohydride (150 mg, 0.71 mmol) and the reaction mixture was stirred for 1 h at room temperature. The reaction mixture was concentrated and the residue was purified by silica gel chromatography (0 to 15% methanol in dichloromethane) and further purified by preparative HPLC with the following conditions: SunFire Prep C18 OBD Column, 19×150 mm 5 um 10 nm; Mobile Phase A: water (0.1% formic acid), Mobile Phase B: acetonitrile; Flow rate: 60 mL/min; Gradient: 10 B to 30 B in 10 min; 254/210 nm; RT1:9.67; RT2. The fractions containing desired product were collected and evaporated under reduced pressure to afford the title compound (17.8 mg, 0.03 mmol, 18% yield) as a white solid. $^1$H NMR (300 MHz, DMSO-$d_6$) δ 10.96 (s, 1H), 8.22 (d, J=8.5 Hz, 1H), 7.90 (d, J=8.6 Hz, 1H), 7.82 (s, 1H), 7.69 (dd, J=8.6, 1.8 Hz, 1H), 7.60 (d, J=8.4 Hz, 1H), 7.42 (d, J=8.5 Hz, 1H), 7.11 (s, 1H), 7.00 (m, 1H), 5.06 (m, 2H), 4.43-4.17 (m, 2H), 3.89-3.72 (m, 2H), 3.41-3.20 (m, 1H), 3.24-3.15 (m, 1H), 3.00-2.58 (m, 8H), 2.55 (m, 1H), 2.43-2.24 (m, 3H), 2.06-1.72 (m, 6H), 1.49 (m, 4H); MS (ESI) m/z 597.3 [M+1]+.

Example S113. 3-(5-(((S)-1-((2-((1S,3R)-3-(Methoxymethyl)cyclopentyl)quinolin-6-yl)methyl)pyrrolidin-3-yl)oxy)-1-oxoisoindolin-2-yl)piperidine-2,6-dione

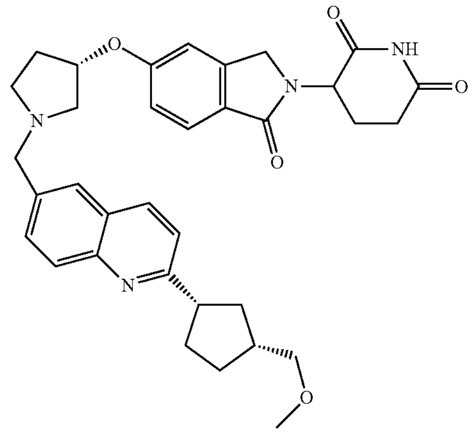 [SMILES: COC[C@@H]1CC[C@H](c2ccc3cc(CN4CC[C@H](Oc5ccc6c(c5)CN(C5CCC(=O)NC5=O)C6=O)C4)ccc3n2)C1]

Methyl 3-(((trifluoromethyl)sulfonyl)oxy)cyclopent-2-ene-1-carboxylate. To a solution of methyl 3-oxocyclopentane-1-carboxylate and N,N-diisopropylethylamine (28.7 mL, 80.9 mmol) in toluene (100 mL) were heated to 45° C. After reaching 45° C., trifluoromethanesulfonic anhydride (26.5 mL, 157.51 mmol) was added dropwise at room temperature. The reaction mixture was stirred at 45° C. for 30 min under nitrogen. The mixture was added water and extracted with ethyl acetate. The organic layers were concentrated and the residue was purified by a silica gel column chromatography (0 to 10% ethyl acetate in petroleum ether). The fractions containing desired product were collected and evaporated under reduced pressure to afford the title compound (17.5 g, 63.82 mmol, 78% yield) as a yellow oil.

Methyl 3-(4,4,5,5-tetramethyl-1,3,2-dioxaborolan-2-yl)cyclopent-2-ene-1-carboxylate. To a solution of methyl 3-(trifluoromethylsulfonyloxy)cyclopent-2-ene-1-carboxylate (10 g, 36.47 mmol) and bis(pinacolato)diboron (11.1 g, 43.71 mmol) in 1,4-dioxane (100 mL) was added potassium acetate (4.65 g, 36.47 mmol) and [1,1'-bis(diphenylphosphino)ferrocene]dichloropalladium(II) (3 g, 3.67 mmol) at room temperature. The reaction mixture was stirred at 90° C. for 16 h under nitrogen. The mixture was added water and extracted with ethyl acetate. The organic layers were concentrated and the residue was purified by a silica gel column chromatography (0 to 10% ethyl acetate in petroleum ether). The fractions containing desired product were collected and evaporated under reduced pressure to afford the title compound (8.6 g, 34.11 mmol, 93% yield) as a light yellow oil.

Methyl 3-[6-[[tert-butyl(diphenyl)silyl] oxymethyl]-2-quinolyl]cyclopent-2-ene-1-carboxylate. To a solution of methyl 3-(4,4,5,5-tetramethyl-1,3,2-dioxaborolan-2-yl)cyclopent-2-ene-1-carboxylate (6 g, 23.8 mmol), 6-(((tert-butyldiphenylsilyl)oxy)methyl)-2-chloroquinoline and cesium carbonate (10 g, 30.77 mmol) in 1,4-dioxane (100 mL) and water (10 mL) was added [1,1'-bis(diphenylphosphino)ferrocene]dichloropalladium(II) (1.3 g, 1.59 mmol) in several portions at room temperature. The resulting mixture was stirred at 80° C. for 2 h under nitrogen. The mixture was added water and extracted with ethyl acetate. The organic layers were concentrated and the residue was purified by reverse flash (30-80% acetonitrile+0.05% ammonium bicarbonate in water, over 20 min). The fractions containing desired product were collected and evaporated under reduced pressure to afford the title compound (1.46 g, 2.79 mmol, 11% yield) as a yellow oil. MS (ESI) m/z 522.3 $[M+1]^+$.

Methyl 3-(6-(((tert-butyldiphenylsilyl)oxy)methyl)quinolin-2-yl)cyclopentane-1-carboxylate. To a solution of methyl 3-[6-[[tert-butyl(diphenyl)silyl] oxymethyl]-2-quinolyl]cyclopent-2-ene-1-carboxylate (1.7 g, 3.26 mmol) in ethyl acetate (30 mL) was added 10% palladium on carbon, wetted with ca. 50% water (350 mg, 2.49 mmol) at room temperature under nitrogen. The resulting mixture was stirred at room temperature for 2 h under hydrogen. The mixture was added ethyl acetate and filtered. The fractions containing desired product were collected and evaporated under reduced pressure to afford the title compound (1.7 g, 3.24 mmol, 99% yield) as a yellow oil. MS (ESI) m/z 524.3 $[M+1]^+$.

(3-(6-(((Tert-butyldiphenylsilyl)oxy)methyl)quinolin-2-yl)cyclopentyl) methanol. To a solution of methyl 3-(6-(((tert-butyldiphenylsilyl)oxy)methyl)quinolin-2-yl)cyclopentane-1-carboxylate (1.7 g, 1.72 mmol) in THF (20 mL) was added lithium aluminum hydride (2.5 M in THF, 1.4 mL, 1.72 mmol) in several portions at 0° C. The resulting mixture was stirred at room temperature for 5 min under nitrogen. The mixture was quenched with little sodium sulfate decahydrate and filtered with THF. The fractions containing desired product were collected and evaporated under reduced pressure to afford the title compound (1.5 g, 1.75 mmol, 88% yield) as a yellow oil. MS (ESI) m/z 496.3 $[M+1]^+$.

6-(((Tert-butyldiphenylsilyl)oxy)methyl)-2-(3-(methoxymethyl)cyclopentyl) quinolone. To a solution of (3-(6-(((Tert-butyldiphenylsilyl)oxy)methyl)quinolin-2-yl) cyclopentyl) methanol (1.5 g, 1.0 mmol) and 2,6-di-tert-butylpyridine (1.8 g, 3.1 mmol) in dichloromethane (15 mL) was added trimethyloxonium tetrafluorborate (900 mg, 2.1 mmol) in several portions at 0° C. The resulting mixture was stirred at room temperature for 7 h under nitrogen. The mixture was added little water, extracted with dichloromethane and purified by a silica gel column chromatography (0 to 20% ethyl acetate in petroleum ether). The fractions containing desired product were collected and evaporated under reduced pressure to afford the title compound (480 mg, 0.45 mmol, 44% yield) as a yellow oil. MS (ESI) m/z 510.3 $[M+1]^+$.

(2-((1S,3R)-3-(methoxymethyl)cyclopentyl)quinolin-6-yl)methanol. To a solution of 6-(((Tert-butyldiphenylsilyl)oxy)methyl)-2-(3-(methoxymethyl)cyclopentyl)quinolone (470 mg, 0.49 mmol) in THF (10 mL) was added tetrabutylammonium fluoride (290 mg, 0.49 mmol) in several portions at room temperature. The resulting mixture was stirred at room temperature for 1 h under nitrogen. The mixture was purified by a silica gel column chromatography (0 to 50% ethyl acetate in petroleum ether) and further purified by preparative chiral HPLC with the following conditions: Column: chiralpak IH, 2*25 cm, 5 μm; mobile phase A: hexane (0.5% 2M ammonia-methanol)-HPLC, mobile phase B: ethanol-HPLC; flow rate: 20 mL/min; gradient: 30% B to 30% B in 25 min; wave length: 220/254 nm; $RT_1$ (min): 8.197; $RT_2$ (min): 15.177; sample solvent: ethanol—HPLC; injection volume: 0.75 mL; number of runs: 4. The fractions containing desired product were collected and evaporated under reduced pressure to afford the title compound (11 mg, 0.04 mmol, 5% yield) as a yellow oil. MS (ESI) m/z 272.0 $[M+1]^+$.

2-((1S,3R)-3-(Methoxymethyl)cyclopentyl)quinoline-6-carbaldehyde. To a solution of (2-((1S,3R)-3-(methoxymethyl)cyclopentyl)quinolin-6-yl)methanol (11 mg, 0.04 mmol) in dichloromethane (4 mL) was added manganese dioxide (36 mg, 0.41 mmol). The resulting mixture was stirred at 50° C. for 12 h under nitrogen. The mixture was filtered and concentrated. The fractions containing desired product were collected and evaporated under reduced pressure to afford the title compound (14 mg, 0.04 mmol, 93% yield) as a yellow oil. MS (ESI) m/z 270.2 $[M+1]^+$.

3-(5-(((S)-1-((2-((1S,3R)-3-(Methoxymethyl)cyclopentyl)quinolin-6-yl)methyl) pyrrolidin-3-yl)oxy)-1-oxoisoindolin-2-yl)piperidine-2,6-dione. To a solution of 2-((1S,3R)-3-(methoxymethyl)cyclopentyl)quinoline-6-carbaldehyde (14 mg, 0.05 mmol) and 3-(1-oxo-5-(((S)-pyrrolidin-3-yl)oxy)isoindolin-2-yl)piperidine-2,6-dione; 2,2,2-trifluoroacetic acid (40 mg, 0.09 mmol) in dichloromethane (5 mL) were added sodium triacetoxyborohydride (30 mg, 0.14 mmol) and triethylamine (0.04 mL, 0.23 mmol). The resulting mixture was stirred at room temperature for 12 h under nitrogen. The mixture was purified by silica gel chromatography (0-10% methanol in dichloromethane) and further purified by preparative HPLC with the following conditions: (column: xselect CSH C18 OBD column 30*150 mm 5 μm, n; mobile phase A: water (0.05% TFA), mobile phase B: acetonitrile; flow rate: 60 mL/min; gradient: 2% B to 23% B in 10 min, 23% B; wave length: 254 nm; $RT_1$ (min): 9.2. The fractions containing desired product were collected and evaporated under reduced pressure to afford the title compound (6.9 mg, 0.01 mmol, 22% yield) as a white solid. $^1H$ NMR (400 MHz, methanol-$d_4$) δ 8.81 (m, 1H), 8.33 (m, 1H), 8.23 (m, 1H), 8.13 (m, 1H), 7.96 (m, 1H), 7.71 (m, 1H), 7.15 (d, J=2.2 Hz, 1H), 7.07 (t, J=8.2 Hz, 1H), 5.35 (m, 1H), 5.16-5.07 (m, 1H), 4.76 (m, 2H), 4.48 (m, 1H), 3.90-3.50 (m, 5H), 3.48-3.30 (m, 5H), 2.90-2.87 (m, 1H), 2.77-2.74 (m, 1H), 2.65-2.57 (m, 2H), 2.55-2.30 (m, 3H), 2.21-2.09 (m, 4H), 2.05-1.94 (m, 1H), 1.58 (m, 1H); MS (ESI) m/z 583.2 $[M+1]^+$.

Example S114. 3-(5-(((S)-1-((2-((1r,4S)-4-(Methoxymethyl)cyclohexyl)quinolin-6-yl)methyl) pyrrolidin-3-yl) oxy)-1-oxoisoindolin-2-yl) piperidine-2,6-dione

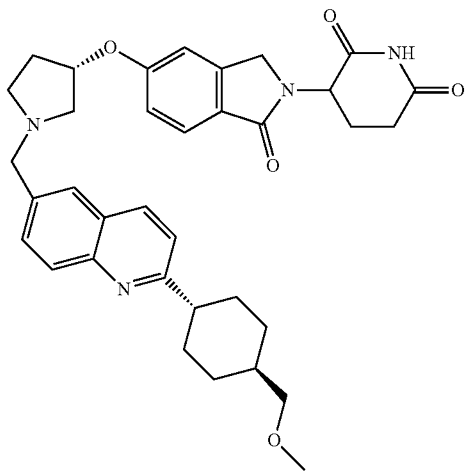 [SMILES: COC[C@H]1CC[C@H](c2ccc3cc(CN4CC[C@H](Oc5ccc6c(c5)CN(C5CCC(=O)NC5=O)C6=O)C4)ccc3n2)CC1]

(2-((1r,4r)-4-(Methoxymethyl)cyclohexyl)quinolin-6-yl) methanol. The (2-(4-(methoxymethyl)cyclohexyl)quinolin-6-yl)methanol (60 mg, 0.21 mmol) was purified by preparative Chiral HPLC (Column: CHIRALPAK IA-3, 4.6*50 mm 3 um; Mobile Phase A: hexane (0.1% diethylamine): ethanol=85:15; Flow rate: 1 mL/min) to afford the title compound (20 mg, 0.07 mmol, 33% yield) as a light-yellow oil. MS (ESI) m/z 286.1 $[M+1]^+$ 2-((1r,4r)-4-(Methoxymethyl)cyclohexyl)quinoline-6-carbaldehyde. To a stirred solution of (2-((1r,4r)-4-(methoxymethyl)cyclohexyl)quinolin-6-yl)methanol (20 mg, 0.07 mmol) in dichloromethane (5 mL) was added manganese dioxide (92 mg, 1.05 mmol). The resulting mixture was stirred at 50° C. for 12 h under nitrogen. The mixture was diluted, filtered and the filtrate was concentrated to afford the title compound (16 mg, 0.056 mmol, 80% yield) as a white solid. MS (ESI) m/z 284.2 $[M+1]^+$ 3-(5-(((S)-1-((2-((1r,4S)-4-(Methoxymethyl)cyclohexyl)quinolin-6-yl)methyl)-pyrrolidin-3-yl)oxy)-1-oxoisoindolin-2-yl)piperidine-2,6-dione. To a stirred mixture of 2-((1r, 4r)-4-(methoxymethyl)cyclohexyl)quinoline-6-carbaldehyde (16 mg, 0.056 mmol), 3-[1-oxo-5-[(3S)-pyrrolidin-3-yl]oxy-isoindolin-2-yl]piperidine-2,6-dione; 2,2,2-trifluoroacetic acid (25 mg, 0.056 mmol) and triethylamine (0.02 mL, 0.12 mmol) in dichloromethane (5 mL) was added sodium triacetoxyborohydride (50 mg, 0.24 mmol) in several portions and was stirred at room temperature for 2 h under nitrogen. The mixture was concentrated and the residue was purified by silica gel chromatography (0-10% methanol in dichloromethane) firstly and further by preparative chiral HPLC with the following conditions: Column: XBridge Prep Phenyl OBD Column, 19*250 mm, 5 μm; Mobile Phase A: water (0.1% formic acid), Mobile Phase B: acetonitrile; Flow rate: 60 mL/min; Gradient: 16% B to 41% B in 9 min, 41% B; Wave Length: 254/210 nm; RT1 (min): 7.13. The fractions containing desired product were collected and evaporated under reduced pressure to afford the title compound (7.5 mg, 0.012 mmol, 21% yield) as a white solid. $^1H$ NMR (400 MHz, Methanol-$d_4$) δ 8.30 (m, 1H), 8.24 (m, 1H), 8.12 (m, 1H), 7.95 (m, 1H), 7.80 (m, 1H), 7.71 (m, 1H), 7.50 (m, 1H), 7.15 (m, 2H), 5.20 (m, 2H), 4.50 (m, 2H), 4.20 (m, 2H), 3.50-3.20 (m, 8H), 3.10 (m, 1H), 2.92-2.83 (m, 2H), 2.82-2.73 (m, 1H), 2.63 (m, 2H), 2.30-2.10 (m, 2H), 2.00 (m, 1H), 1.88 (m, 3H), 1.20 (m, 2H); MS (ESI) m/z 597.3 $[M+1]^+$.

Example S115. 3-(5-(((S)-1-((2-((1S,3S)-3-(Methoxymethyl)cyclopentyl)quinolin-6-yl)methyl) pyrrolidin-3-yl)oxy)-1-oxoisoindolin-2-yl)piperidine-2,6-dione

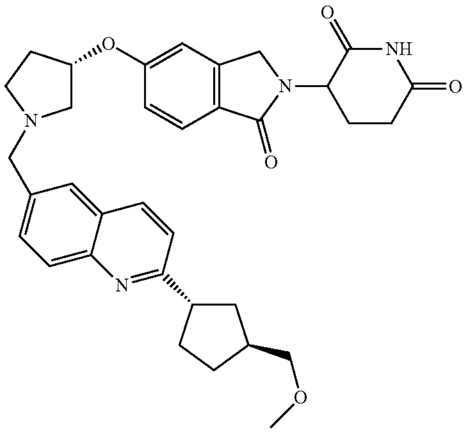 [SMILES: COC[C@H]1CC[C@H](c2ccc3cc(CN4CC[C@H](Oc5ccc6c(c5)CN(C5CCC(=O)NC5=O)C6=O)C4)ccc3n2)C1]

(2-((1S,3S)-3-(Methoxymethyl)cyclopentyl)quinolin-6-yl)methanol. To a solution of 6-(((Tert-butyldiphenylsilyl) oxy)methyl)-2-(3-(methoxymethyl)cyclopentyl) quinolone (470 mg, 0.92 mmol) in THF (10 mL) was added tetrabutylammonium fluoride (290 mg, 1.10 mmol) in several portions at room temperature. The resulting mixture was stirred at room temperature for 1 h under nitrogen. The mixture was purified by silica gel column chromatography (0 to 50% ethyl acetate in petroleum ether) and the pure fractions were evaporated. The crude product was purified further by preparative chiral HPLC with the following conditions: Column: chiralpak IH, 2*25 cm, 5 μm; mobile phase A: hexane (0.5% 2M ammonia-methanol)-HPLC, mobile phase B: ethanol-HPLC; flow rate: 20 mL/min; gradient: 30% B to 30% B in 25 min; wave length: 220/254 nm; $RT_1$ (min): 8.197; $RT_2$ (min): 15.177; sample solvent: ethanol—HPLC; injection volume: 0.75 mL; number of runs: 4. The fractions containing desired product were collected and evaporated under reduced pressure to afford the title compound (61 mg, 0.22 mmol, 24% yield) as a yellow oil. MS (ESI) m/z 272.0 $[M+1]^+$.

2-((1S,3S)-3-(Methoxymethyl)cyclopentyl)quinoline-6-carbaldehyde. To a solution of (2-((1S,3S)-3-(methoxymethyl)cyclopentyl)quinolin-6-yl)methanol (61. mg, 0.22 mmol) in dichloromethane (4 mL) was added manganese dioxide (36 mg, 0.41 mmol). The resulting mixture was stirred at 50° C. for 12 h under nitrogen. The mixture was filtered and the filtrate was concentrated to afford the title compound (55 mg, 0.20 mmol, 90% yield) as a yellow oil. MS (ESI) m/z 270.2 $[M+1]^+$.

3-(5-(((S)-1-((2-((1S,3S)-3-(Methoxymethyl)cyclopentyl)quinolin-6-yl)methyl) pyrrolidin-3-yl)oxy)-1-oxoisoindolin-2-yl)piperidine-2,6-dione. To a solution of 2-((1S,3S)-3-(methoxymethyl)cyclopentyl)quinoline-6-carbaldehyde (55 mg, 0.05 mmol) and 3-(1-oxo-5-(((S)-pyrrolidin-3-yl) oxy)isoindolin-2-yl)piperidine-2,6-dione; 2,2,2-trifluoroacetic acid (110 mg, 0.09 mmol) in dichloromethane (5 mL) were added sodium triacetoxyborohydride (110 mg, 0.14 mmol) and triethylamine (0.02 mL, 0.23 mmol). The resulting mixture was stirred at room temperature for 12 h under nitrogen. The mixture was purified by silica gel chromatography (0-10% methanol in dichloromethane) and further purified by preparative HPLC with the following conditions: Column: x select CSH C18 OBD column 30*150 mm 5 μm, n; mobile phase A: water (0.1% formic acid), mobile phase B: acetonitrile; flow rate: 60 mL/min; gradient: 2% B to 20% B in 10 min, 20% B; wave length: 254 nm; $RT_1$ (min): 9.8. The fractions containing desired product were collected and evaporated under reduced pressure to afford the title compound (43.6 mg, 0.0718 mmol, 30% yield as a white solid. $^1$H NMR (300 MHz, Methanol-$d_4$) δ 8.24 (d, J=8.6 Hz, 1H), 8.02 (d, J=8.7 Hz, 1H), 7.93 (s, 1H), 7.80-7.77 (m, 1H), 7.70 (d, J=8.4 Hz, 1H), 7.52 (d, J=8.6 Hz, 1H), 7.12-6.99 (m, 2H), 5.15-5.09 (m, 2H), 4.42 (m, 2H), 4.24 (m, 2H), 3.42 (m, 7H), 3.08 (m, 1H), 2.98-2.81 (m, 2H), 2.57-2.37 (m, 3H), 2.29 (m, 1H), 2.16 (m, 3H), 1.95 (m, 2H), 1.74-1.54 (m, 2H); MS (ESI) m/z 583.2 $[M+1]^+$.

Example S116. 3-(5-(((S)-1-((2-((1R,3R)-3-(Methoxymethyl)cyclopentyl)quinolin-6-yl)methyl) pyrrolidin-3-yl)oxy)-1-oxoisoindolin-2-yl)piperidine-2,6-dione

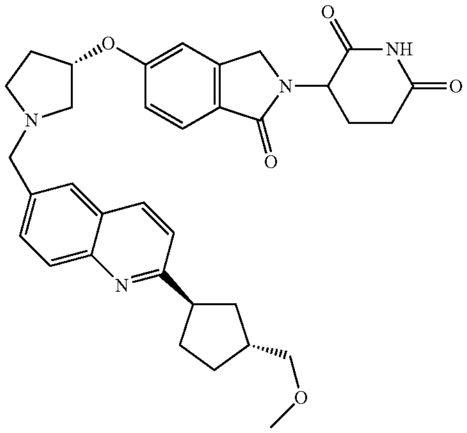 [SMILES: COC[C@@H]1CC[C@@H](c2ccc3cc(CN4CC[C@H](Oc5ccc6c(c5)CN(C5CCC(=O)NC5=O)C6=O)C4)ccc3n2)C1]

(2-((1R,3R)-3-(Methoxymethyl)cyclopentyl)quinolin-6-yl)methanol. To a solution of 6-(((Tert-butyldiphenylsilyl) oxy)methyl)-2-(3-(methoxymethyl)cyclopentyl) quinolone (470 mg, 0.92 mmol) in THF (10 mL) was added tetrabutylammonium fluoride (290 mg, 1.10 mmol) in several portions at room temperature. The resulting mixture was stirred at room temperature for 1 h under nitrogen. The mixture was purified by silica gel column chromatography (0 to 50% ethyl acetate in petroleum ether) and the pure fractions were evaporated. The crude product was purified further by preparative chiral HPLC with the following conditions: Column: chiralpak IH, 2*25 cm, 5 μm; mobile phase A: hexane (0.5% 2M ammonia-methanol)-HPLC, mobile phase B: ethanol-HPLC; flow rate: 20 mL/min; gradient: 30% B to 30% B in 25 min; wave length: 220/254 nm; $RT_1$ (min): 8.197; $RT_2$ (min): 15.177; sample solvent: ethanol—HPLC; injection volume: 0.75 mL; number of runs: 4. The fractions containing desired product were collected and evaporated under reduced pressure to afford the title compound (55 mg, 0.20 mmol, 21% yield) as a yellow oil. MS (ESI) m/z 272.0 $[M+1]^+$.

2-((1R,3R)-3-(Methoxymethyl)cyclopentyl)quinoline-6-carbaldehyde. To a solution of (2-((1R,3R)-3-(methoxymethyl)cyclopentyl)quinolin-6-yl)methanol (55 mg, 0.20 mmol) in dichloromethane (4 mL) was added manganese dioxide (36 mg, 0.41 mmol). The resulting mixture was stirred at 50° C. for 12 h under nitrogen. The mixture was filtered and the residue was concentrated to afford the title compound (52 mg, 0.19 mmol, 95% yield) as a yellow oil. MS (ESI) m/z 270.2 $[M+1]^+$.

3-(5-(((S)-1-((2-((1R,3R)-3-(Methoxymethyl)cyclopentyl)quinolin-6-yl)meth yl)pyrrolidin-3-yl)oxy)-1-oxoisoindolin-2-yl)piperidine-2,6-dione. To a solution of 2-((1R,3R)-3-(methoxymethyl)cyclopentyl)quinoline-6-carbaldehyde (52 mg, 0.19 mmol) and 3-(1-oxo-5-(((S)-pyrrolidin-3-yl)oxy)isoindolin-2-yl)piperidine-2,6-dione; 2,2,2-trifluoroacetic acid (90 mg, 0.09 mmol) in dichloromethane (5 mL) were added sodium triacetoxyborohydride (90 mg, 0.14 mmol) and triethylamine (0.02 mL, 0.23 mmol). The resulting mixture was stirred at room temperature for 12 h under nitrogen. The mixture was purified by silica gel chromatography (0-10% methanol in dichloromethane) and further purified by preparative HPLC with the following conditions: Column: xselect CSH $C^{18}$ OBD column 30*150 mm, 5 μm; mobile phase A: water (0.05% TFA), mobile phase B: acetonitrile; flow rate: 60 mL/min; gradient: 2% B to 20% B in 10 min, 20% B; wave length: 254 nm; $RT_1$ (min): 10.8. The fractions containing desired product were collected and evaporated under reduced pressure to afford the title compound (36.4 mg, 0.062 mmol, 33% yield) as a white solid. $^1H$ NMR (400 MHz, Methanol-$d_4$) δ 8.77 (d, J=8.8 Hz, 1H), 8.31 (s, 1H), 8.23 (d, J=8.8 Hz, 1H), 8.11 (d, J=8.7 Hz, 1H), 7.95 (d, J=8.7 Hz, 1H), 7.72-7.70 (m, 1H), 7.16 (d, J=2.6 Hz, 1H), 7.08-7.06 (m, 1H), 5.35 (m, 1H), 5.12-5.10 (m, 1H), 4.75 (s, 2H), 4.52-4.37 (m, 2H), 3.74 (m, 3H), 3.61 (m, 2H), 3.50-3.37 (m, 2H), 3.38 (s, 3H), 2.90-2.87 (m, 1H), 2.82-2.72 (m, 1H), 2.61-2.59 (m, 1H), 2.53-2.46 (m, 1H), 2.42-2.20 (m, 5H), 2.15-1.95 (m, 3H), 1.80-1.66 (m, 2H); MS (ESI) m/z 583.3 $[M+1]^+$.

Example S117. 3-(5-(((S)-1-((2-((1R,3S)-3-(Methoxymethyl)cyclopentyl)quinolin-6-yl)methyl) pyrrolidin-3-yl)oxy)-1-oxoisoindolin-2-yl)piperidine-2,6-dione

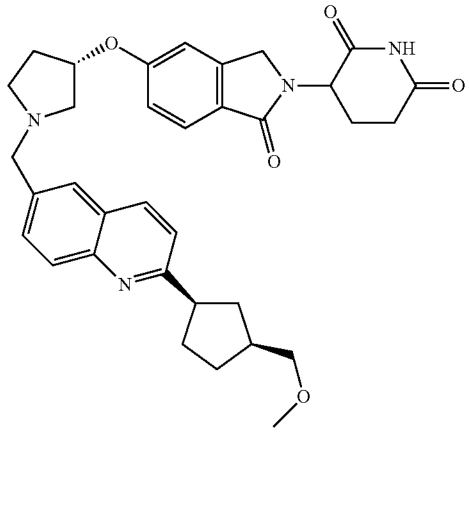 [SMILES: COC[C@H]1CC[C@@H](c2ccc3cc(CN4CC[C@H](Oc5ccc6c(c5)CN(C5CCC(=O)NC5=O)C6=O)C4)ccc3n2)C1]

(2-((1R,3S)-3-(Methoxymethyl)cyclopentyl)quinolin-6-yl)methanol. To a solution of 6-(((Tert-butyldiphenylsilyl)oxy)methyl)-2-(3-(methoxymethyl)cyclopentyl) quinolone (470 mg, 0.92 mmol) in THF (10 mL) was added tetrabutylammonium fluoride (290 mg, 1.10 mmol) in several portions at room temperature. The resulting mixture was stirred at room temperature for 1 h under nitrogen. The mixture was purified by silica gel column chromatography (0 to 50% ethyl acetate in petroleum ether) and the pure fractions were evaporated. The crude product was purified further by preparative chiral HPLC with the following conditions: Column: chiralpak IH, 2*25 cm, 5 μm; mobile phase A: hexane (0.5% 2M ammonia-methanol)-HPLC, mobile phase B: ethanol-HPLC; flow rate: 20 mL/min; gradient: 30% B to 30% B in 25 min; wave length: 220/254 nm; $RT_1$ (min): 8.197; $RT_2$ (min): 15.177; sample solvent: ethanol—HPLC; injection volume: 0.75 mL; number of runs: 4. The fractions containing desired product were collected and evaporated under reduced pressure to afford the title compound (11 mg, 0.04 mmol, 4% yield) as a yellow oil. MS (ESI) m/z 272.0 $[M+1]^+$.

2-((1R,3S)-3-(Methoxymethyl)cyclopentyl)quinoline-6-carbaldehyde. To a solution of (2-((1R,3S)-3-(methoxymethyl)cyclopentyl)quinolin-6-yl)methanol (13 mg, 0.04 mmol) in dichloromethane (4 mL) was added manganese dioxide (34 mg, 0.39 mmol). The resulting mixture was stirred at 50° C. for 12 h under nitrogen. The mixture was filtered and the filtrate was concentrated to afford the title compound (10 mg, 0.037 mmol, 92% yield) as a yellow oil. MS (ESI) m/z 270.2 $[M+1]^+$.

3-(5-(((S)-1-((2-((1R,3S)-3-(Methoxymethyl)cyclopentyl)quinolin-6-yl)methyl) pyrrolidin-3-yl)oxy)-1-oxoisoindolin-2-yl)piperidine-2,6-dione. To a solution of 2-((1R,3S)-3-(methoxymethyl)cyclopentyl)quinoline-6-carbaldehyde (10 mg, 0.037 mmol) and 3-(1-oxo-5-(((S)-pyrrolidin-3-yl)oxy)isoindolin-2-yl)piperidine-2,6-dione; 2,2,2-trifluoroacetic acid (40 mg, 0.09 mmol) in dichloromethane (5 mL) were added sodium triacetoxyborohydride (40 mg, 0.14 mmol) and triethylamine (0.01 mL, 0.23 mmol). The resulting mixture was stirred at room temperature for 12 h under nitrogen. The mixture was purified by silica gel chromatography (0-10% methanol in dichloromethane) and further purified by preparative HPLC with the following conditions: Column: xselect CSH C18 OBD column 30*150 mm, 5 μm; mobile phase A: water (0.05% TFA), mobile phase B: acetonitrile; flow rate: 60 mL/min; gradient: 2% B to 20% B in 10 min, 20% B; wave length: 254 nm; $RT_1$ (min): 6.5. The fractions containing desired product were collected and evaporated under reduced pressure to afford the title compound (6.9 mg, 0.012 mmol, 32% yield) as a white solid. $^1H$ NMR (400 MHz, Methanol-$d_4$) δ 8.64 (d, J=6.9 Hz, 1H), 8.25 (s, 1H), 8.23-8.16 (m, 1H), 8.05 (m, 1H), 7.84 (m, 1H), 7.72 (m, 1H), 7.15 (s, 1H), 7.09 (m, 1H), 5.34 (m, 1H), 5.16-5.07 (m, 1H), 4.84 (s, 7H), 4.52-4.37 (m, 2H), 3.82-3.61 (m, 5H), 3.52-3.33 (m, 4H), 2.97-2.83 (m, 1H), 2.82-2.73 (m, 1H), 2.60-2.20 (m, 6H), 2.13-2.10 (m, 4H), 1.75-1.65 (m, 2H); MS (ESI) m/z 583.2 $[M+1]^+$.

Example S118. 3-(5-(((S)-1-((2-((1S,3R)-3-(Methoxymethyl)cyclohexyl)quinolin-6-yl)methyl) pyrrolidin-3-yl)oxy)-1-oxoisoindolin-2-yl)piperidine-2,6-dione

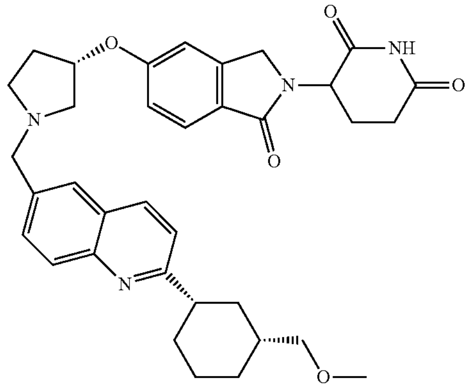 [SMILES: COC[C@@H]1CCC[C@H](c2ccc3cc(CN4CC[C@H](Oc5ccc6c(c5)CN(C5CCC(=O)NC5=O)C6=O)C4)ccc3n2)C1]

Methyl 2-(3-oxocyclohex-1-en-1-yl)quinoline-6-carboxylate. To a stirred solution of methyl 2-chloroquinoline-6-carboxylate (1.9 g, 8.57 mmol) and 3-(4,4,5,5-tetramethyl-1,3,2-dioxaborolan-2-yl)cyclohex-2-en-1-one (1.9 g, 8.56 mmol) in 1,4-dioxane (20 mL) and water (2 mL) was added [1,1'-bis(diphenylphosphino)ferrocene]dichloropalladium(II) (700 mg, 0.91 mmol) and sodium carbonate (2 g, 18.87 mmol). The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (2.20 g, 7.82 mmol, 91% yield) as a yellow oil. MS (ESI) m/z 282.0 $[M+1]^+$.

Methyl 2-(3-oxocyclohexyl)quinoline-6-carboxylate. To a stirred solution of methyl 2-(3-oxocyclohex-1-en-1-yl) quinoline-6-carboxylate (2.2 g, 7.82 mmol) in acetonitrile (30 mL) and methanol (15 mL) was added palladium 10% on carbon (660 mg, wetted with ca. 55% water) at room temperature for 3 h under hydrogen (~2 bar). The mixture was filtered and the filtrate was concentrated to afford title compound (2 g, 7.06 mmol, 90% yield) as a light-yellow solid. MS (ESI) m/z 284.2 $[M+1]^+$.

Methyl 2-(3-methylenecyclohexyl)quinoline-6-carboxylate. To a solution of methyltriphenylphosphonium bromide (4.92 g, 13.77 mmol) in THF (30 mL) was added potassium tert-butoxide (0.5 M in THF, 12.7 mL, 6.35 mmol) dropwise at 0° C. The reaction mixture was stirred for 30 min at room temperature. Then a solution of methyl 2-(3-oxocyclohexyl) quinoline-6-carboxylate (1.8 g, 6.35 mmol) in THF (30 mL) was added dropwise into the above mixture at this temperature. The reaction mixture was stirred at room temperature for 12 h under nitrogen. The reaction mixture was concentrated. The residue was added water and extracted with ethyl acetate. The extracts were washed with brine, dried over anhydrous sodium sulfate, filtered and concentrated. The residue was purified by silica gel chromatography (0 to 20% ethyl acetate in petroleum ether) to afford the title compound (600 mg, 2.13 mmol, 34% yield) as a light-yellow oil. MS (ESI) m/z 282.0 $[M+1]^+$.

Methyl 2-(3-(hydroxymethyl)cyclohexyl)quinoline-6-carboxylate. A solution of methyl 2-(3-methylenecyclohexyl)quinoline-6-carboxylate (600 mg, 2.13 mmol) in 9-borabicyclo[3.3.1]nonane (0.5 M in THF, 40 mL) was stirred for 12 h at room temperature. Then to the above mixture was added sodium hydroxide solution (3 mol/L, 4.5 mL, 13.5 mmol) at 0° C. and hydrogen peroxide (30% in water, 4.5 mL) at 0° C. The reaction mixture was stirred for 3 h at room temperature under nitrogen. The resulting mixture was added water and extracted with ethyl acetate. The extracts were washed with brine, dried over anhydrous sodium sulfate, filtered and concentrated to afford the title compound (500 mg, 1.67 mmol, 78% yield) as a light-yellow oil. MS (ESI) m/z 300.2 $[M+1]^+$.

Methyl 2-(3-(methoxymethyl)cyclohexyl)quinoline-6-carboxylate. To a stirred solution of methyl 2-[3-(hydroxymethyl)cyclohexyl]quinoline-6-carboxylate (500 mg, 1.67 mmol) in dichloromethane (5 mL) was added 2,6-di-tert-butylpyridine (770 mg, 4.03 mmol) and trimethyloxonium tetrafluoroborate (440 mg, 2.97 mmol) at 0° C. The mixture was stirred at room temperature for 5 h. The resulting mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (450 mg, 1.43 mmol, 86% yield) as a light-yellow oil. MS (ESI) m/z 314.3 $[M+1]^+$.

((2-(3-(Hydroxymethyl)cyclohexyl)quinolin-6-yl)methanol. To a stirred solution of methyl 2-(3-(methoxymethyl) cyclohexyl)quinoline-6-carboxylate (400 mg, 1.28 mmol) in THF (5 mL) and ethanol (5 mL) were added sodium borohydride (221 mg, 5.84 mmol) and anhydrous calcium chloride (350 mg, 3.15 mmol). The mixture was stirred at room temperature for 4 h under nitrogen. Then the mixture was concentrated and the residue was purified by reverse phase flash (10-40% acetonitrile+0.05% ammonium bicarbonate in water, over 25 min) to afford the title compound (280 mg, 0.98 mmol, 77% yield) as a light-yellow oil. MS (ESI) m/z 286.2 $[M+1]^+$.

(2-((1S,3R)-3-(Methoxymethyl)cyclohexyl)quinolin-6-yl)methanol. The product (110 mg) was purified by chiral preparative HPLC with the following conditions: Column: CHIRALPAK IH, 2*25 cm, 5 μm; Mobile Phase A: hexane (0.5% 2M ammonia in methanol)-HPLC, Mobile Phase B: isopropanol-HPLC; Flow rate: 20 mL/min; Gradient: 20% B to 20% B in 25 min; Wave Length: 220/254 nm; $RT_1$ (min): 10.688; $RT_2$ (min): 16.376; Sample Solvent: ethanol—HPLC; Injection Volume: 1.5 mL; Number Of Runs: 2. The fractions containing desired product were collected and evaporated under reduced pressure to afford the title compound (45 mg, 0.16 mmol, 41% yield) as a light-yellow oil. MS (ESI) m/z 286.2 $[M+1]^+$.

2-((1S,3R)-3-(Methoxymethyl)cyclohexyl)quinoline-6-carbaldehyde. To a stirred solution of (2-((1S,3R)-3-(methoxymethyl)cyclohexyl)quinolin-6-yl)methanol (45 mg, 0.16 mmol) in dichloromethane (6 mL) was added manganese dioxide (274 mg, 3.15 mmol) and stirred at room temperature for 12 h under nitrogen. The mixture was filtered and the filtrate was concentrated. The residue was purified by silica gel chromatography (0 to 40% ethyl acetate in petroleum ether) to afford the title compound (40 mg, 0.14 mmol, 89% yield) as a light-yellow solid. MS (ESI) m/z 284.3 $[M+1]^+$.

3-(5-(((S)-1-((2-((1S,3R)-3-(Methoxymethyl)cyclohexyl) quinolin-6-yl)methyl)pyrrolidin-3-yl)oxy)-1-oxoisoindolin-2-yl)piperidine-2,6-dione. To a solution of 2-((1S,3R)-3-(methoxymethyl)cyclohexyl)quinoline-6-carbaldehyde (40 mg, 0.14 mmol), 3-(1-oxo-5-(((S)-pyrrolidin-3-yl)oxy) isoindolin-2-yl)piperidine-2,6-dione; 2,2,2-trifluoroacetic acid (100 mg, 0.23 mmol) and triethylamine (39 mg, 0.39 mmol) in dichloromethane (5 mL) was added sodium triacetoxyborohydride (150 mg, 0.71 mmol). The mixture was stirred for 12 h at room temperature under nitrogen. The resulting mixture was concentrated. The residue was purified by silica gel chromatography (0 to 10% methanol in dichloromethane) and preparative HPLC further with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 3% B to 24% B in 9 min, 24% B; Wave Length: 254/220 nm; $RT_1$ (min): 8.72. The fractions containing desired product were collected and evaporated under reduced pressure to afford the title compound to afford the title compound (36.6 mg, 0.06 mmol, 42% yield) as a white solid. $^1$H NMR (400 MHz, DMSO-$d_6$) δ 8.24-8.22 (m, 1H), 7.90 (d, J=8.6 Hz, 1H), 7.84 (t, J=1.8 Hz, 1H), 7.70-7.68 (m, 1H), 7.61 (d, J=8.4 Hz, 1H), 7.44 (d, J=8.5 Hz, 1H), 7.11 (t, J=2.3 Hz, 1H), 7.01-6.99 (m, 1H), 5.06-5.02 (m, 2H), 4.43-4.22 (m, 2H), 3.92-3.81 (m, 2H), 3.28-3.17 (m, 5H), 3.03 (m, 1H), 2.96-2.74 (m, 4H), 2.65-2.55 (m, 2H), 2.38-2.33 (m, 2H), 2.05-1.84 (m, 5H), 1.75 (m, 2H), 1.59-1.28 (m, 3H), 1.00 (m, 1H); MS (ESI) m/z 597.2 $[M+1]^+$.

Example S119. 3-(5-(((S)-1-((2-((1S,3S)-3-(Methoxymethyl)cyclohexyl)quinolin-6-yl)methyl)pyrrolidin-3-yl)oxy)-1-oxoisoindolin-2-yl)piperidine-2,6-dione

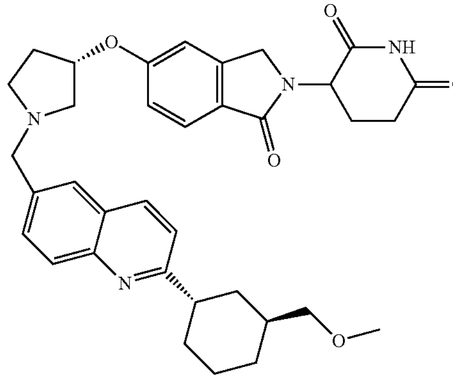

(2-((1S,3S)-3-(Methoxymethyl)cyclohexyl)quinolin-6-yl)methanol. The racemate (110 mg) was purified by preparative Chiral HPLC with the following conditions: Column: CHIRALPAK IH, 2*25 cm, 5 μm; Mobile Phase A: hexane (0.5% 2M ammonia in methanol)-HPLC, Mobile Phase B: isopropanol-HPLC; Flow rate: 20 mL/min; Gradient: 20% B to 20% B in 25 min; Wave Length: 220/254 nm; $RT_1$ (min): 10.688; $RT_2$ (min): 16.376; Sample Solvent: ethanol—HPLC; Injection Volume: 1.5 mL; Number of Runs: 2. The fractions containing desired product were collected and evaporated under reduced pressure to afford the title compound (50 mg, 0.17 mmol, 45% yield) as a light-yellow oil. MS (ESI) m/z 286.2 $[M+1]^+$.

2-((1S,3S)-3-(Methoxymethyl)cyclohexyl)quinoline-6-carbaldehyde. To a stirred solution of (2-((1S,3S)-3-(methoxymethyl)cyclohexyl)quinolin-6-yl)methanol (50 mg, 0.18 mmol) in dichloromethane (6 mL) was added manganese dioxide (305 mg, 3.5 mmol) at room temperature under nitrogen. The reaction mixture was stirred at room temperature for 12 h under nitrogen. The resulting mixture was filtered and the filtrate was concentrated. The residue was purified by silica gel chromatography (0 to 40% ethyl acetate in petroleum ether) to afford the title compound (40 mg, 0.14 mmol, 78% yield) as a light-yellow solid. MS (ESI) m/z 284.2 $[M+1]^+$.

3-(5-(((S)-1-((2-((1S,3S)-3-(Methoxymethyl)cyclohexyl)quinolin-6-yl)methyl)pyrrolidin-3-yl)oxy)-1-oxoisoindolin-2-yl)piperidine-2,6-dione. To a solution of 2-((1S,3S)-3-(methoxymethyl)cyclohexyl)quinoline-6-carbaldehyde (40 mg, 0.14 mmol), 3-(1-oxo-5-(((S)-pyrrolidin-3-yl)oxy)isoindolin-2-yl)piperidine-2,6-dione; 2,2,2-trifluoroacetic acid (100 mg, 0.23 mmol) and triethylamine (39 mg, 0.39 mmol) in dichloromethane (5 mL) was added sodium triacetoxyborohydride (150 mg, 0.71 mmol). The mixture was stirred for 12 h at room temperature under nitrogen. The resulting mixture was concentrated. The residue was purified by silica gel chromatography (0 to 10% methanol in dichloromethane) and preparative HPLC with the following conditions: Column: Sunfire Prep C18 OBD Column, 19*250 mm, 10 μm; Mobile Phase A: water (0.1% formic acid), Mobile Phase B: acetonitrile; Flow rate: 25 mL/min; Gradient: 17% B to 35% B in 9 min, 35% B; Wave Length: 254/220 nm; $RT_1$ (min): 8.05. The fractions containing desired product were collected and evaporated under reduced pressure to afford the title compound (38 mg, 0.06 mmol, 44% yield) as a white solid. $^1$H NMR (300 MHz, Methanol-$d_4$) δ 8.37-8.23 (m, 2H), 8.03 (d, J=8.7 Hz, 1H), 7.94 (s, 1H), 7.81-7.79 (m, 1H), 7.70-7.68 (m, 1H), 7.51 (d, J=8.6 Hz, 1H), 7.10-7.02 (m, 2H), 5.21-5.07 (m, 2H), 4.49-4.35 (m, 2H), 4.26 (s, 2H), 3.37 (d, J=4.5 Hz, 1H), 3.28 (m, 7H), 3.15-2.75 (m, 4H), 2.57-2.41 (m, 2H), 2.20-1.80 (m, 7H), 1.67-1.34 (m, 3H), 1.12-1.10 (m, 1H); MS (ESI) m/z 597.2 $[M+1]^+$.

Example S120. 3-(5-(((S)-1-((2-((1R,3R)-3-(Methoxymethyl)cyclohexyl)quinolin-6-yl)methyl)pyrrolidin-3-yl)oxy)-1-oxoisoindolin-2-yl)piperidine-2,6-dione

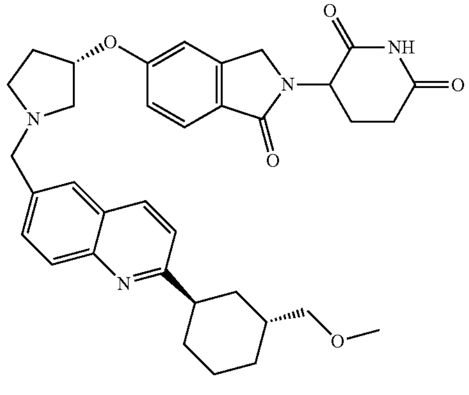 [SMILES: COC[C@@H]1CCC[C@@H](c2ccc3cc(CN4CC[C@H](Oc5ccc6c(c5)CN(C5CCC(=O)NC5=O)C6=O)C4)ccc3n2)C1]

(2-((1R,3R)-3-(Methoxymethyl)cyclohexyl)quinolin-6-yl)methanol. The racemates (75 mg) was purified by chiral preparative HPLC with the following conditions: Column: CHIRALPAK IH, 3*25 cm, 5 μm; Mobile Phase A: carbon dioxide, Mobile Phase B: isopropanol:dichloromethane=1:1 (0.1% 2M ammonia in methanol); Flow rate: 70 mL/min; Gradient: isocratic 50% B; Column Temperature (° C.): 35; Back Pressure (bar): 100; Wave Length: 254 nm; $RT_1$ (min): 2.46; $RT_2$ (min): 5.94; Sample Solvent: Dichloromethane-HPLC; Injection Volume: 4.8 mL; Number of Runs: 4. Pure fractions were evaporated to afford the title compound (30 mg, 0.11 mmol, 40% yield) as a light-yellow oil. MS (ESI) m/z 286.2 $[M+1]^+$.

2-((1R,3R)-3-(Methoxymethyl)cyclohexyl)quinoline-6-carbaldehyde. To a stirred solution of (2-((1R,3R)-3-(methoxymethyl)cyclohexyl)quinolin-6-yl)methanol (35 mg, 0.12 mmol) in dichloromethane (5 mL) was added manganese dioxide (213 mg, 2.45 mmol) at room temperature and the mixture was stirred for 12 h under nitrogen. The mixture was filtered and the filtrate was concentrated. The residue was purified by silica gel chromatography (0 to 40% ethyl acetate in petroleum ether) to afford the title compound (30 mg, 0.11 mmol, 86% yield) as a light-yellow solid. MS (ESI) m/z 284.1 $[M+1]^+$.

3-(5-(((S)-1-((2-((1R,3R)-3-(Methoxymethyl)cyclohexyl)quinolin-6-yl)methyl)pyrrolidin-3-yl)oxy)-1-oxoisoindolin-2-yl)piperidine-2,6-dione. To a solution of 2-((1R,3R)-3-(methoxymethyl)cyclohexyl)quinoline-6-carbaldehyde (30 mg, 0.11 mmol), 3-(1-oxo-5-(((S)-pyrrolidin-3-yl)oxy)isoindolin-2-yl)piperidine-2,6-dione; 2,2,2-trifluoroacetic acid (75 mg, 0.17 mmol) and triethylamine (31 mg, 0.31 mmol) in dichloromethane (5 mL) was added sodium triacetoxyborohydride (110 mg, 0.52 mmol). The mixture was stirred for 12 h at room temperature under nitrogen. The resulting mixture was concentrated. The residue was purified by silica gel chromatography (0 to 10% methanol in dichloromethane) and preparative-HPLC further with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 3% B to 25% B in 9 min, 25% B; Wave Length: 254/220 nm; $RT_1$ (min): 8.9. The fractions containing desired product were collected and evaporated under reduced pressure to afford the title compound (23.1 mg, 0.039 mmol, 36% yield) as a white solid. $^1H$ NMR (400 MHz, DMSO-$d_6$) δ 8.26-8.16 (m, 1H), 7.89 (d, J=8.6 Hz, 1H), 7.81 (s, 1H), 7.69-7.67 (m, 1H), 7.61 (d, J=8.4 Hz, 1H), 7.45 (d, J=8.6 Hz, 1H), 7.10 (t, J=2.3 Hz, 1H), 7.01-6.99 (m, 1H), 5.11-4.96 (m, 2H), 4.37 (d, J=17.2 Hz, 1H), 4.24-4.22 (m, 1H), 3.87-3.74 (m, 2H), 3.51 (m, 1H), 3.40 (d, J=7.3 Hz, 2H), 3.27 (s, 3H), 3.17-3.04 (m, 1H), 2.99-2.85 (m, 2H), 2.80-2.66 (m, 2H), 2.59 (m, 1H), 2.36-2.32 (m, 2H), 2.14-1.92 (m, 3H), 1.89-1.68 (m, 4H), 1.54 (d, J=12.7 Hz, 4H); MS (ESI) m/z 597.2 $[M+1]^+$.

Example S121. 3-(5-(((S)-1-((2-((1R,3S)-3-(Methoxymethyl)cyclohexyl)quinolin-6-yl)methyl)pyrrolidin-3-yl)oxy)-1-oxoisoindolin-2-yl)piperidine-2,6-dione

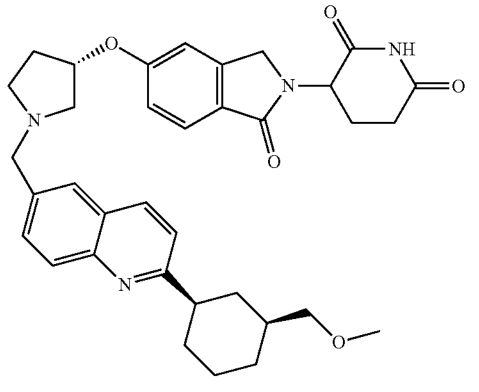 [SMILES: COC[C@H]1CCC[C@@H](c2ccc3cc(CN4CC[C@H](Oc5ccc6c(c5)CN(C5CCC(=O)NC5=O)C6=O)C4)ccc3n2)C1]

(2-((1R,3S)-3-(Methoxymethyl)cyclohexyl)quinolin-6-yl)methanol. The racemates (75 mg) was purified by Chiral preparative HPLC with the following conditions: Column: CHIRALPAK IH, 3*25 cm, 5 μm; Mobile Phase A: carbon dioxide, Mobile Phase B: Isopropanol:dichloromethane=1:1(0.1% 2M ammonia in methanol); Flow rate: 70 mL/min; Gradient: isocratic 50% B; Column Temperature (° C.): 35; Back Pressure (bar): 100; Wave Length: 254 nm; $RT_1$ (min): 2.46; $RT_2$ (min): 5.94; Sample Solvent: dichloromethane-HPLC; Injection Volume: 4.8 mL; Number Of Runs: 4. Pure fractions were evaporated to afford the title compound (30 mg, 0.10 mmol, 40% yield) as a light-yellow oil. MS (ESI) m/z 286.2 $[M+1]^+$.

2-((1R,3S)-3-(Methoxymethyl)cyclohexyl)quinoline-6-carbaldehyde. To a solution of (2-((1R,3S)-3-(methoxymethyl)cyclohexyl)quinolin-6-yl)methanol (35 mg, 0.12 mmol) in dichloromethane (5 mL) was added manganese dioxide (213 mg, 2.45 mmol) at room temperature and stirred for 12 h under nitrogen. The mixture was filtered and the filtrate was concentrated. The residue was purified by silica gel chromatography to afford the title compound (30 mg, 0.11 mmol, 86% yield) as a light-yellow solid. MS (ESI) m/z 284.1 $[M+1]^+$.

3-(5-(((S)-1-((2-((1R,3S)-3-(Methoxymethyl)cyclohexyl)quinolin-6-yl)methy-1)pyrrolidin-3-yl)oxy)-1-oxoisoindolin-2-yl)piperidine-2,6-dione. To a solution of 2-((1R,3S)-3-(methoxymethyl)cyclohexyl)quinoline-6-carbaldehyde (30 mg, 0.11 mmol), 3-[1-oxo-5-[(3S)-pyrrolidin-3-yl]oxy-isoindolin-2-yl]piperidine-2,6-dione; 2,2,2-trifluoroacetic acid (75 mg, 0.17 mmol) and triethylamine (31 mg, 0.31 mmol) in dichloromethane (5 mL) was added sodium triacetoxyborohydride (110 mg, 0.52 mmol). The mixture was stirred for 12 h at room temperature under nitrogen. The resulting mixture was concentrated. The residue was purified by silica gel chromatography (0 to 10% methanol in dichloromethane) and preparative-HPLC further with the following conditions: Column: Sunfire prep Cis column, 30*150 mm, 5 μm; Mobile Phase A: water (0.1% formic acid), Mobile Phase B: acetonitrile; Flow rate: 60 mL/min; Gradient: 5% B to 35% B in 7 min, 35% B; Wave Length: 254/220 nm; $RT_1$ (min): 6.3. The fractions containing desired product were collected and evaporated under reduced pressure to afford the title compound (22.1 mg, 0.037 mmol, 34% yield) as a white solid. $^1H$ NMR (400 MHz, DMSO-$d_6$) δ 8.34-8.17 (m, 2H), 7.89 (d, J=8.6 Hz, 1H), 7.81 (s, 1H), 7.69-7.67 (m, 1H), 7.61 (d, J=8.4 Hz, 1H), 7.45 (d, J=8.5 Hz, 1H), 7.10 (t, J=2.2 Hz, 1H), 7.01-6.99 (m, 1H), 5.11-4.96 (m, 2H), 4.37 (d, J=17.2 Hz, 1H), 4.24-4.22 (m, 1H), 3.86-3.75 (m, 2H), 3.40 (d, J=7.3 Hz, 2H), 3.27 (s, 3H), 3.10 (m, 1H), 3.01-2.85 (m, 2H), 2.81-2.67 (m, 2H), 2.64-2.56 (m, 1H), 2.44-2.30 (m, 2H), 2.07 (m, 1H), 2.02-1.93 (m, 2H), 1.89-1.79 (m, 3H), 1.74-1.72 (m, 1H), 1.55 (m, 4H); MS (ESI) m/z 597.3 $[M+1]^+$.

Example S122. 3-(1-Oxo-5-(((S)-1-((2-((3aR,6aS)-tetrahydro-1H-furo[3,4-c]pyrrol-5(3H)-yl)quinolin-6-yl)methyl)pyrrolidin-3-yl)oxy)isoindolin-2-yl)piperidine-2,6-dione

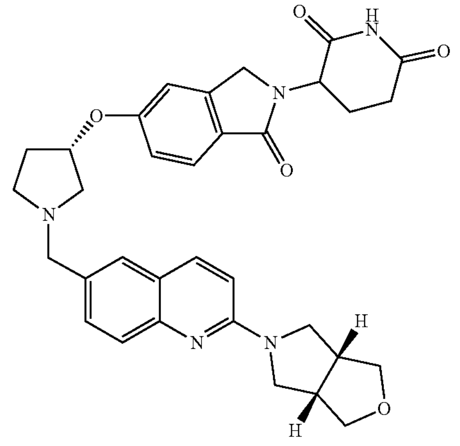 [SMILES: O=C1CCC(N2Cc3cc(O[C@H]4CCN(Cc5ccc6nc(N7C[C@H]8COC[C@H]8C7)ccc6c5)C4)ccc3C2=O)C(=O)N1]

Methyl 2-((3aR,6aS)-tetrahydro-1H-furo[3,4-c]pyrrol-5(3H)-yl)quinoline-6-carboxylate. To a stirred solution of methyl 2-chloroquinoline-6-carboxylate (300 mg, 1.35 mmol) and (3aR,6aS)-hexahydro-1H-furo[3,4-c]pyrrole (229 mg, 2.03 mmol) in 1,4-dioxane (5 mL) and water (0.5 mL) were added bis(di-tert-butyl)-4-dimethylaminophenylphosphine (96 mg, 0.36 mmol), methanesulfonato{[4-(N,N-dimethylamino)phenyl]di-t-butylphosphino}(2'-amino-1,1'-biphenyl-2-yl)palladium(II) (155 mg, 0.24 mmol) and cesium carbonate (1319 mg, 4.06 mmol). The above mixture was stirred at 100° C. for 16 h under nitrogen. The resulting mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (250 mg, 0.83 mmol, 62% yield) as a light-yellow oil. MS (ESI) m/z 299.0 $[M+1]^+$.

(2-((3aR,6aS)-Tetrahydro-1H-furo[3,4-c]pyrrol-5(3H)-yl)quinolin-6-yl)methanol. To a stirred solution of methyl 2-((3aR,6aS)-tetrahydro-1H-furo[3,4-c]pyrrol-5(3H)-yl)quinoline-6-carboxylate (250 mg, 0.83 mmol) in THF (6 mL) was added lithium aluminium hydride (2.5 M in THF, 0.4 mL, 1.0 mmol) at 0° C. and was stirred at room temperature for 12 h under nitrogen. The mixture was diluted with THF, added sodium sulfate decahydrate, filtered and concentrated. The residue was purified by silica gel chromatography (0 to 40% ethyl acetate in petroleum ether) to afford the title compound (200 mg, 0.74 mmol, 88% yield) as a light-yellow solid. MS (ESI) m/z 271.0 $[M+1]^+$.

2-((3aR,6aS)-Tetrahydro-1H-furo[3,4-c]pyrrol-5(3H)-yl)quinoline-6-carbaldehyde. To a stirred solution of (2-((3aR,6aS)-tetrahydro-1H-furo[3,4-c]pyrrol-5 (3H)-yl)quinolin-6-yl)methanol (250 mg, 0.84 mmol) in dichloromethane (6 mL) was added manganese dioxide (1.60 g, 18.40 mmol) at room temperature for 12 h under nitrogen. The mixture was diluted with dichloromethane and filtered. The filtrate was concentrated and the residue was purified by silica gel chromatography (0 to 40% ethyl acetate in petroleum ether) to afford the title compound (200 mg, 0.74 mmol, 88% yield) as a light-yellow solid. MS (ESI) m/z 269.0 $[M+1]^+$.

3-(1-Oxo-5-(((S)-1-((2-((3aR,6aS)-tetrahydro-1H-furo[3,4-c]pyrrol-5(3H)-yl)quinolin-6-yl)methyl)pyrrolidin-3-yl)oxy)isoindolin-2-yl)piperidine-2,6-dione. To a solution of 2-((3aR,6aS)-tetrahydro-1H-furo[3,4-c]pyrrol-5(3H)-yl)quinoline-6-carbaldehyde (90 mg, 0.34 mmol), 3-(1-oxo-5-(((S)-pyrrolidin-3-yl)oxy)isoindolin-2-yl)piperidine-2,6-dion; 2,2,2-trifluoroacetic acid (128 mg, 0.29 mmol) and triethylamine (67 mg, 0.67 mmol) in dichloromethane (5 mL) was added sodium triacetoxyborohydride (278 mg, 1.31 mmol). The mixture was stirred for 12 h at room temperature under nitrogen. The resulting mixture was concentrated and the residue was purified by silica gel chromatography (0 to 10% methanol in dichloromethane) and preparative-HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 22% B in 7 min, 22% B; Wave Length: 254/220 nm; $RT_1$ (min): 6.1. The fractions containing desired product were collected and evaporated under reduced pressure to afford the title compound (32.2 mg, 0.055 mmol, 16% yield) as a light-yellow solid. $^1H$ NMR (300 MHz, Methanol-$d_4$) δ 8.01 (d, J=9.2 Hz, 1H), 7.74-7.68 (m, 3H), 7.68-7.59 (m, 1H), 7.10-6.96 (m, 3H), 5.12-5.08 (m, 2H), 4.43 (d, J=4.0 Hz, 2H), 4.18 (d, J=4.8 Hz, 2H), 4.00-3.97 (m, 2H), 3.87-3.83 (m, 2H), 3.79-3.74 (m, 2H), 3.64-3.61 (m, 2H), 3.42-3.36 (m, 1H), 3.28 (m, 2H), 3.18 (m, 2H), 3.08 (m, 1H), 2.98-2.86 (m, 1H), 2.82-2.72 (m, 1H), 2.49 (m, 2H), 2.18 (m, 2H); MS (ESI) m/z 582.2 $[M+1]^+$.

Example S123. 3-(5-(((3S)-1-((2-((3aR,7aS)—Octahydro-2H-4,7-epoxyisoindol-2-yl)quinazolin-6-yl)methyl)pyrrolidin-3-yl)oxy)-1-oxoisoindolin-2-yl)piperidine-2,6-dione

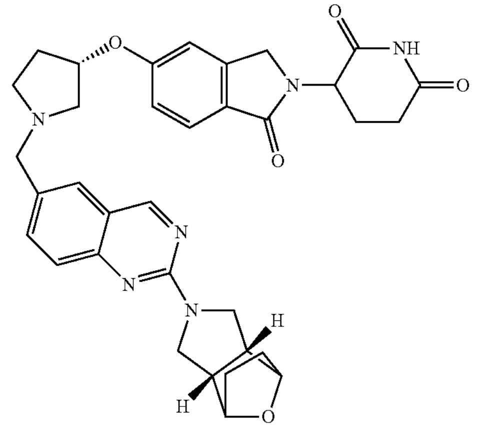 [SMILES: O=C1CCC(N2Cc3cc(O[C@H]4CCN(Cc5ccc6nc(N7C[C@@H]8C9CCC(O9)[C@@H]8C7)ncc6c5)C4)ccc3C2=O)C(=O)N1]

(3aR,7aS)-2-(6-Bromoquinazolin-2-yl)octahydro-1H-4,7-epoxyisoindole. To a stirred solution of 6-bromo-2-chloroquinazoline (200 mg, 0.82 mmol) in NMP (6 mL) were added (3aR,7aS)-octahydro-1H-4,7-epoxyisoindole (228 mg, 1.64 mmol) and N,N-diisopropylethylamine (0.72 mL, 4.13 mmol). The above mixture was stirred at 100° C. for 12 h under nitrogen. The solution was purified by reverse phase flash (40-100% acetonitrile+0.05% ammonium bicarbonate in water, over 25 min) to afford the title compound (200 mg, 0.58 mmol, 70% yield) as a light-yellow solid. MS (ESI) m/z 346.0 $[M+1]^+$.

(3aR,7aS)-2-(6-Vinylquinazolin-2-yl)octahydro-1H-4,7-epoxyisoindole. To a stirred solution of (3aR,7aS)-2-(6-bromoquinazolin-2-yl)octahydro-1H-4,7-epoxyisoindole (200 mg, 0.58 mmol) and potassium trifluoro(vinyl)borate (92 mg, 0.69 mmol) in 1,4-dioxane (5 mL) and water (0.5 mL) were added tetrakis(triphenylphosphine)palladium (48 mg, 0.042 mmol) and cesium carbonate (375 mg, 1.15 mmol). The above mixture was stirred at 80° C. for 3 h under nitrogen. Then the mixture was added water and extracted with ethyl acetate. The extracts were washed with brine, dried over anhydrous sodium sulfate, filtered and concentrated. The residue was purified by silica gel chromatography (0 to 60% ethyl acetate in petroleum ether) to afford the title compound (120 mg, 0.41 mmol, 71% yield) as a light-yellow oil. MS (ESI) m/z 293.4 $[M+1]^+$.

2-((3aR,7aS)—Octahydro-2H-4,7-epoxyisoindol-2-yl) quinazoline-6-carbaldehyde. To a stirred solution of (3aR, 7aS)-2-(6-vinylquinazolin-2-yl)octahydro-1H-4,7-epoxyisoindole (100 mg, 0.34 mmol) in tert-butanol (3 mL) and water (3 mL) were added 4-methyl-morpholin4-oxide (91 mg, 0.78 mmol), potassium osmate (14 mg, 0.04 mmol) and citric acid (150 mg, 0.78 mmol). The above mixture was stirred at room temperature for 3 h under nitrogen. Then the mixture was added sodium periodate (252 mg, 1.17 mmol) and stirred for 1 h at room temperature. The reaction mixture was concentrated. The reaction mixture was diluted with water and extracted with ethyl acetate. The extracts were dried over sodium sulfate, filtered and concentrated. The residue was purified by silica gel chromatography (0 to 40% ethyl acetate in petroleum ether) to afford the title compound (50 mg, 0.17 mmol, 50% yield) as a light-yellow oil. MS (ESI) m/z 296.1 $[M+1]^+$.

3-(5-(((3S)-1-((2-((3aR,7aS)—Octahydro-2H-4,7-epoxyisoindol-2-yl)quinazolin-6-yl)methyl)pyrrolidin-3-yl)oxy)-1-oxoisoindolin-2-yl)piperidine-2,6-dione. To a solution of 2-((3aR,7aS)-octahydro-2H-4,7-epoxyisoindol-2-yl) quinazoline-6-carbaldehyde (80 mg, 0.27 mmol), 3-(1-oxo-5-(((S)-pyrrolidin-3-yl)oxy)isoindolin-2-yl)piperidine-2,6-dione; 2,2,2-trifluoroacetic acid (100 mg, 0.23 mmol) and triethylamine (53 mg, 0.53 mmol) in dichloromethane (5 mL) was added sodium triacetoxyborohydride (224 mg, 1.06 mmol). The mixture was stirred for 12 h at room temperature under nitrogen. The resulting mixture was concentrated. The residue was purified by silica gel chromatography (0 to 10% methanol in dichloromethane) and preparative-HPLC further with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 20% B in 10 min, 20% B; Wave Length: 254/220 nm; $RT_1$ (min): 10.88. The fractions containing desired product were collected and evaporated under reduced pressure to afford the title compound (24.6 mg, 0.04 mmol, 14% yield) as a light-yellow solid. $^1H$ NMR (300 MHz, $CF_3COOD$) δ 9.49 (m, 1H), 8.30-8.26 (m, 2H), 8.02 (m, 2H), 7.19 (m, 2H), 5.54 (m, 2H), 4.92 (m, 4H), 4.70 (m, 2H), 4.49-3.73 (m, 8H), 3.15 (m, 5H), 2.65 (m, 3H), 2.06 (m, 2H), 1.86 (m, 2H); MS (ESI) m/z 609.2 $[M+1]^+$.

Example S124. 3-(1-Oxo-5-(((S)-1-((2-((3aR,6aS)-tetrahydro-1H-furo[3,4-c]pyrrol-5(3H)-yl)quinazolin-6-yl)methyl)pyrrolidin-3-yl)oxy)isoindolin-2-yl) piperidine-2,6-dione

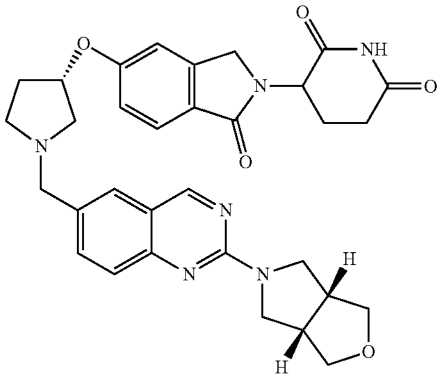 [SMILES: O=C1CCC(N2Cc3cc(O[C@H]4CCN(Cc5ccc6nc(N7C[C@H]8COC[C@H]8C7)ncc6c5)C4)ccc3C2=O)C(=O)N1]

(3aR,6aS)-5-(6-Bromoquinazolin-2-yl)hexahydro-1H-furo[3,4-c]pyrrole. To a stirred solution of 6-bromo-2-chloroquinazoline (200 mg, 0.82 mmol) in NMP (6 mL) were added (3aR,6aS)-hexahydro-1H-furo[3,4-c]pyrrole (185 mg, 1.64 mmol) and N,N-diisopropylethylamine (0.72 mL, 4.13 mmol). The above mixture was stirred at 100° C. for 12 h under nitrogen. The solution was purified by reverse phase flash (30-100% acetonitrile+0.05% ammonium bicarbonate in water, over 25 min) to afford the title compound (200 mg, 0.62 mmol, 76% yield) as a light-yellow solid. MS (ESI) m/z 319.9 $[M+1]^+$.

(3aR,6aS)-5-(6-Vinylquinazolin-2-yl)hexahydro-1H-furo [3,4-c]pyrrole. To a stirred solution of (3aR,6aS)-5-(6-bromoquinazolin-2-yl)hexahydro-1H-furo[3,4-c] pyrrole (200 mg, 0.62 mmol) and potassium trifluoro(vinyl)borate (100 mg, 0.75 mmol) in 1,4-doxane (5 mL) and water (0.5 mL) were added tetrakis (triphenylphosphine)palladium (52 mg, 0.045 mmol) and cesium carbonate (406 mg, 1.25 mmol). The above mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 60% ethyl acetate in petroleum ether) to afford the title compound (100 mg, 0.37 mmol, 60% yield) as a light-yellow oil. MS (ESI) m/z 268.0 $[M+1]^+$.

2-((3aR,6aS)-Tetrahydro-1H-furo[3,4-c]pyrrol-5(3H)-yl) quinazoline-6-carbaldehyde. To a stirred solution of (3aR, 6aS)-5-(6-vinylquinazolin-2-yl)hexahydro-1H-furo[3,4-c] pyrrole (100 mg, 0.37 mmol) in tert-butanol (3 mL) and water (3 mL) were added 4-methyl-morpholin4-oxide (91 mg, 0.78 mmol), potassium osmate (14 mg, 0.04 mmol) and citric acid (150 mg, 0.78 mmol). The above mixture was stirred at room temperature for 3 h under nitrogen. Then the mixture was added sodium periodate (253 mg, 1.17 mmol) and stirred for another 1 h. The resulting solution was concentrated. The reaction mixture was diluted with ethyl acetate and washed with water. The organic layer was dried over sodium sulfate, filtered and concentrated. The obtained orange sticky solid was purified by silica gel chromatography (0 to 40% ethyl acetate in petroleum ether) to afford the title compound (50 mg, 0.19 mmol, 50% yield) as a light-yellow oil. MS (ESI) m/z 270.0 $[M+1]^+$.

3-(1-Oxo-5-(((S)-1-((2-((3aR,6aS)-tetrahydro-1H-furo[3,4-c]pyrrol-5(3H)-yl)quinazolin-6-yl)methyl)pyrrolidin-3-yl)oxy)isoindolin-2-yl)piperidine-2,6-dione. To a solution of 2-((3aR,6aS)-tetrahydro-1H-furo[3,4-c]pyrrol-5(3H)-yl) quinazoline-6-carbaldehyde (50 mg, 0.19 mmol), 3-(1-oxo-5-(((S)-pyrrolidin-3-yl)oxy)isoindolin-2-yl)piperidine-2,6-dione; 2,2,2-trifluoroacetic acid (71 mg, 0.16 mmol) and triethylamine (39 mg, 0.39 mmol) in dichloromethane (5 mL) was added sodium triacetoxyborohydride (154 mg, 0.73 mmol). The mixture was stirred for 12 h at room temperature under nitrogen. The resulting mixture was concentrated. The residue was purified by silica gel chromatography (0 to 10% methanol in dichloromethane) and preparative-HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 25% B in 7 min, 25% B; Wave Length: 254/220 nm; $RT_1$ (min): 5.8; Number of Runs: 0 to afford the title compound (34.4 mg, 0.059 mmol, 30% yield) as a light-yellow solid. $^1$H NMR (300 MHz, Methanol-$d_4$) δ 9.10 (s, 1H), 7.91-7.60 (m, 4H), 7.16-7.01 (m, 2H), 5.22-5.08 (m, 2H), 4.44 (d, J=4.0 Hz, 2H), 4.19 (d, J=2.9 Hz, 2H), 4.05-3.87 (m, 4H), 3.73-3.63 (m, 4H), 3.39-3.37 (m, 1H), 3.28 (m, 2H), 3.18-3.04 (m, 3H), 2.98-2.75 (m, 2H), 2.62-2.42 (m, 2H), 2.27-2.11 (m, 2H); MS (ESI) m/z 583.3 $[M+1]^+$.

Example S125. 3-(5-(((S)-1-((2-((1S,2R)-2-Methoxycyclopentyl)quinolin-6-yl)methyl)pyrrolidin-3-yl)oxy)-1-oxoisoindolin-2-yl)piperidine-2,6-dione

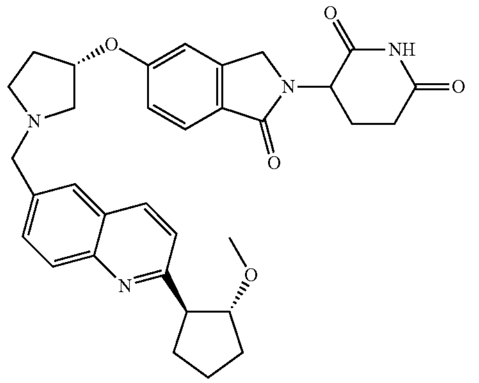 [SMILES: CO[C@@H]1CCC[C@H]1c1ccc2cc(CN3CC[C@H](Oc4ccc5c(c4)CN(C4CCC(=O)NC4=O)C5=O)C3)ccc2n1]

6-Bromoquinoline-1-oxide. To a solution of 6-bromoquinoline (5 g, 24.03 mmol) in dichloromethane (100 mL) was added meta-chloroperoxybenzoic acid (8.3 g, 48.1 mmol) in several portions at 0° C. The resulting mixture was stirred at room temperature for 12 h under nitrogen. The mixture was added little saturated sodium bicarbonate and extracted with ethyl acetate. The extracts were washed with brine, dried over anhydrous sodium sulfate, filtered and concentrated to afford the title compound (5.3 g, 23.65 mmol, 98% yield) as a brown solid. MS (ESI) m/z 224.0 $[M+1]^+$.

2-(6-Bromoquinolin-2-yl)cyclopentan-1-one. To a solution of 6-bromo quinoline-1-oxide (2000 mg, 8.93 mmol) and 4-(cyclohex-1-en-1-yl)morpholine (4 g, 26.11 mmol) in dichloromethane (15 mL) was added benzoyl chloride (1250 mg, 8.93 mmol) in several portions at 0° C. The resulting mixture was stirred at room temperature for 12 h under nitrogen. The mixture was added water and extracted with dichloromethane. The extracts were washed with brine, dried over anhydrous sodium sulfate, filtered and concentrated. The residue was purified by reverse flash (40-100% acetonitrile+0.05% ammonium bicarbonate in water, over 30 min). Pure fractions were evaporated to afford the title compound (900 mg, 3.1 mmol, 79% yield) as yellow solid. MS (ESI) m/z 290.1 $[M+1]^+$.

2-(6-Bromoquinolin-2-yl)cyclopentan-1-ol. To a solution of 2-(6-bromoquinolin-2-yl)cyclopentan-1-one (880 mg, 3.03 mmol) in methanol (20 mL) and was added sodium borohydride (232 mg, 6.13 mmol) in several portions at 0° C. The resulting mixture was stirred at room temperature for 2 h under nitrogen. The mixture was diluted with water and extracted with ethyl acetate. The extracts were washed with brine, dried over anhydrous sodium sulfate, filtered and concentrated and the residue was purified by reverse phase flash (40-100% acetonitrile+0.05% ammonium bicarbonate in water, over 30 min). Pure fractions were evaporated to afford the title compound (700 mg, 2.15 mmol, 71% yield) as a yellow solid. MS (ESI) m/z 292.1 $[M+1]^+$.

6-Bromo-2-(2-methoxycyclopentyl)quinoline. To a solution of 2-(6-bromoquinolin-2-yl)cyclopentan-1-ol (600 mg, 2.05 mmol) in DMF (10 mL) was added sodium hydride (60% dispersion in mineral oil, 0.14 mL, 8.58 mmol) at 0° C. in several portions and the resulting suspension was stirred at room temperature for 30 min and iodomethane (606 mg, 4.27 mmol) was added into the above suspension. The mixture was stirred at room temperature for 1 h under nitrogen. The extracts were washed with brine, dried over anhydrous sodium sulfate, filtered and concentrated and the residue was purified by reverse flash (30-100% acetonitrile+0.05% ammonium bicarbonate in water, over 30 min). Pure fractions were evaporated to afford the title compound (490 mg, 1.6 mmol, 77% yield) as a yellow oil. MS (ESI) m/z 306.0 $[M+1]^+$.

2-((1S,2R)-2-Methoxycyclopentyl)-6-vinylquinoline. To a solution of 6-bromo-2-(2-methoxycyclopentyl)quinoline (480 mg, 1.57 mmol) in 1,4-dioxane (10 mL) and water (2 mL) was added potassium hydride; trifluoro(vinyl)boron (421 mg, 3.12 mmol), sodium carbonate (499 mg, 4.71 mmol) and [1,1'-bis(diphenylphosphino)ferrocene]dichloropalladium(II) (120 mg, 0.16 mmol). The mixture was stirred at 80° C. for 2 h under nitrogen. The resulting mixture was diluted with water and extracted with ethyl acetate. The extracts were washed with brine, dried over anhydrous sodium sulfate, filtered and concentrated and the residue was purified by silica gel chromatography (0 to 50% ethyl acetate in petroleum ether) and further by preparative chiral HPLC with the following conditions: column: chiralpak IG, 2*25 cm, 5 μm; mobile phase A: hexane (0.5% 2M ammonia-methanol)-HPLC, mobile phase B: isopropyl alcohol-HPLC; flow rate: 20 mL/min; gradient: 2% B to 2% B in 16 min; wave length: 220/254 nm; $RT_1$ (min): 9.174; $RT_2$ (min): 12.125; sample solvent: ethanol-HPLC; injection volume: 0.29 mL; number of runs: 14. The fractions containing desired product were collected and evaporated under reduced pressure to afford the title compound ($RT_1$ (min): 12.125, 70 mg, 0.27 mmol, 17% yield) as a yellow oil. MS (ESI) m/z 254.0 $[M+1]^+$.

2-((1S,2R)-2-Methoxycyclopentyl)quinoline-6-carbaldehyde. To a solution of 2-((1S,2R)-2-methoxycyclopentyl)-6-vinylquinoline (30 mg, 0.04 mmol) in tert-butanol (3 mL) and water (3 mL) were added potassium osmate (5 mg, 0.01 mmol), 4-methylmorpholine N-oxide (28 mg, 0.24 mmol), citric acid (50 mg, 0.24 mmol). The resulting mixture was stirred at room temperature for 4 h under nitrogen. Then sodium periodate (0.03 mL, 0.24 mmol) was added above mixture and stirred at room temperature for 1 h under nitrogen. The mixture was added saturated sodium bicarbonate to pH-7 and extracted with ethyl acetate. The extracts were washed with brine, dried over anhydrous sodium sulfate, filtered and concentrated. The residue was purified by silica gel chromatography (0 to 20% ethyl acetate in petroleum ether) to afford the title compound (16 mg, 0.06 mmol, 52% yield) as a yellow oil. MS (ESI) m/z 256.0 $[M+1]^+$.

3-(5-(((S)-1-((2-((1S,2R)-2-Methoxycyclopentyl)quinolin-6-yl)methyl)pyrrolidin-3-yl)oxy)-1-oxoisoindolin-2-yl)piperidine-2,6-dione. To a solution of 2-((1S,2R)-2-methoxycyclopentyl)quinoline-6-carbaldehyde (16 mg, 0.06 mmol) and 3-(1-oxo-5-(((S)-pyrrolidin-3-yl)oxy)isoindolin-2-yl)piperidine-2,6-dione; 2,2,2-trifluoroacetic acid (50 mg, 0.15 mmol) in dichloromethane (6 mL) was added sodium triacetoxyborohydride (50 mg, 0.24 mmol) and triethylamine (0.1 mL, 0.57 mmol). The resulting mixture was stirred at 20° C. for 12 h under nitrogen. The mixture was concentrated. The residue was purified by silica gel chromatography (0-10% methanol in dichloromethane) and further purified by preparative-achiral-HPLC with the following conditions: column: Daicel DCpak P4VP, 2*25 cm, 5 μm; mobile phase B: ethanol; flow rate: 50 mL/min; gradient: isocratic 35% B; column temperature (° C.): 35; back pressure (bar): 100; wave length: 254 nm; $RT_1$ (min): 4.08; sample solvent: methanol—HPLC; injection volume: 1 mL; number of runs: 4. The fractions containing desired product were collected and evaporated under reduced pressure to afford the title compound (14.6 mg, 0.02 mmol, 40% yield) as a white solid. $^1H$ NMR (400 MHz, DMSO-$d_6$) δ 10.95 (s, 1H), 8.24-8.20 (m, 1H), 7.89 (d, J=8.6 Hz, 1H), 7.82 (s, 1H), 7.69-7.67 (m, 1H), 7.60 (d, J=8.5 Hz, 1H), 7.46 (d, J=8.5 Hz, 1H), 7.10 (t, J=2.3 Hz, 1H), 7.00-6.98 (m, 1H), 5.05-5.03 (m, 1H), 5.00-4.98 (m, 1H), 4.36 (d, J=17.2 Hz, 1H), 4.24-4.22 (m, 1H), 4.09 (m, 1H), 3.85-3.73 (m, 2H), 3.14 (s, 3H), 2.95-2.82 (m, 2H), 2.72-2.65 (m, 2H), 2.60-2.53 (m, 2H), 2.42-2.28 (m, 2H), 2.18-1.64 (m, 9H); MS (ESI) m/z 569.2 $[M+1]^+$.

Example S126. 3-(5-(((S)-1-((2-((1R,2S)-2-Methoxycyclopentyl)quinolin-6-yl)methyl)pyrrolidin-3-yl)oxy)-1-oxoisoindolin-2-yl)piperidine-2,6-dione

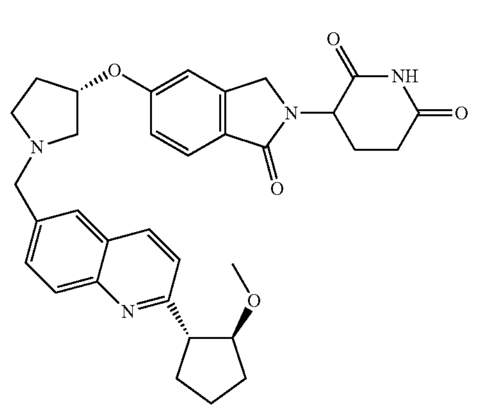 [SMILES: CO[C@H]1CCC[C@@H]1c1ccc2cc(CN3CC[C@H](Oc4ccc5c(c4)CN(C4CCC(=O)NC4=O)C5=O)C3)ccc2n1]

2-((1R,2S)-2-Methoxycyclopentyl)-6-vinylquinoline. To a solution of 6-bromo-2-(2-methoxycyclopentyl)quinoline (480 mg, 1.57 mmol) in 1,4-dioxane (10 mL) and water (2 mL) were added potassium hydride; trifluoro(vinyl)boron (421 mg, 3.12 mmol), sodium carbonate (499 mg, 4.71 mmol) and [1,1'-bis(diphenylphosphino)ferrocene]dichloropalladium(II) (120 mg, 0.16 mmol). The mixture was stirred at 80° C. for 2 h under nitrogen. The resulting mixture was diluted with water and extracted with ethyl acetate. The extracts were washed with brine, dried over anhydrous sodium sulfate, filtered and concentrated and the residue was purified by silica gel chromatography (0 to 50% ethyl acetate in petroleum ether) and further by preparative chiral HPLC with the following conditions: column: chiralpak IG, 2*25 cm, 5 μm; mobile phase A: hexane (0.5% 2M ammonia-methanol)-HPLC, mobile phase B: isopropyl alcohol-HPLC; flow rate: 20 mL/min; gradient: 2% B to 2% B in 16 min; wave length: 220/254 nm; $RT_1$ (min): 9.174; $RT_2$ (min): 12.125; sample solvent: ethanol—HPLC; injection volume: 0.29 mL; number of runs: 14. The fractions containing desired product were collected and evaporated under reduced pressure to afford the title compound ($RT_1$ (min): 9.174, 70 mg, 0.27 mmol, 17% yield) as a yellow oil. MS (ESI) m/z 254.0 $[M+1]^+$.

2-((1R,2S)-2-methoxycyclopentyl)quinoline-6-carbaldehyde. To a solution of 2-((1R,2S)-2-methoxycyclopentyl)-6-vinylquinoline (50 mg, 0.20 mmol) in tert-butanol (3 mL) and water (3 mL) were added potassium osmate (7.5 mg, 0.02 mmol), 4-methylmorpholine N-oxide (47 mg, 0.40 mmol), citric acid (83 mg, 0.39 mmol). The mixture was stirred at room temperature for 4 h under nitrogen. Then sodium periodate (0.06 mL, 0.39 mmol) was added above mixture and stirred at room temperature for 1 h under nitrogen. The mixture was added saturated sodium bicarbonate to pH-7 and extracted with ethyl acetate. The extracts were washed with brine, dried over anhydrous sodium sulfate, filtered and concentrated and the residue was purified by silica gel chromatography (0-20% ethyl acetate in petroleum ether) to afford the title compound (23 mg, 0.09 mmol, 45% yield) as a yellow oil. MS (ESI) m/z 256.0 $[M+1]^+$.

3-(5-(((S)-1-((2-((1R,2S)-2-Methoxycyclopentyl)quinolin-6-yl)methyl)pyrrolidin-3-yl)oxy)-1-oxoisoindolin-2-yl)piperidine-2,6-dione. To a solution of 2-((1R,2S)-2-methoxycyclopentyl)quinoline-6-carbaldehyde (23 mg, 0.09 mmol) and 3-(1-oxo-5-(((S)-pyrrolidin-3-yl)oxy)isoindolin-2-yl)piperidine-2,6-dione; 2,2,2-trifluoroacetic acid (100 mg, 0.3 mmol) in dichloromethane (5 mL) were added sodium triacetoxyborohydride (100 mg, 0.47 mmol) and triethylamine (0.11 mL, 0.66 mmol). The mixture was stirred at 20° C. for 12 h under nitrogen. The mixture was purified by silica gel chromatography (0-10% methanol in dichloromethane) and further purified by preparative SFC with the follow condition: Column (torus 2-PIC OBD, 186008592; mobile phase A: carbon dioxide, mobile phase B: ethanol; flow rate: 60 m/min; gradient: isocratic 32% B; column temperature (° C.): 35; back pressure (bar): 100; wave length: 254 nm; $RT_1$ (min): 5.11; sample solvent: ethanol; injection volume: 2 mL; number of runs: 5. The fractions containing desired product were collected and evaporated under reduced pressure to afford the title compound (13.9 mg, 0.02 mmol, 25% yield) as a white solid. $^1H$ NMR (400 MHz, Methanol-$d_4$) δ 8.22-8.20 (m, 1H), 7.97 (d, J=8.6 Hz, 1H), 7.83 (s, 1H), 7.77-7.75 (m, 1H), 7.68 (d, J=8.4 Hz, 1H), 7.47-7.45 (m, 1H), 7.08-6.98 (m, 2H), 5.09-5.07 (m, 1H), 5.01 (m, 1H), 4.48-4.33 (m, 2H), 4.22-4.13 (m, 1H), 3.90 (d, J=12.9 Hz, 1H), 3.85 (d, J=12.9 Hz, 1H), 3.40-3.32 (m, 1H), 3.22 (d, J=1.2 Hz, 3H), 3.01-2.99 (m, 1H), 2.88 (m, 3H), 2.76-2.74 (m, 1H), 2.69-2.59 (m, 1H), 2.53-2.35 (m, 2H), 2.24-1.74 (m, 8H); MS (ESI) m/z 569.4 $[M+1]^+$.

Example S127. 3-(5-(((3S,4R)-4-Methyl-1-((2-(tetrahydro-2H-pyran-4-yl)quinolin-6-yl)methyl)-pyrrolidin-3-yl)oxy)-1-oxoisoindolin-2-yl)piperidine-2,6-dione

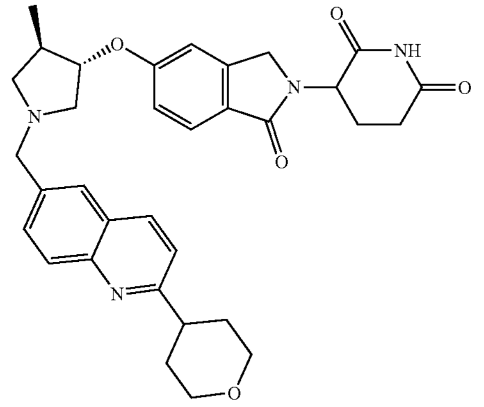 [SMILES: C[C@@H]1CN(Cc2ccc3nc(C4CCOCC4)ccc3c2)C[C@H]1Oc1ccc2c(c1)CN(C1CCC(=O)NC1=O)C2=O]

3-(5-(((3S,4R)-4-Methyl-1-((2-(tetrahydro-2H-pyran-4-yl)quinolin-6-yl)methyl) pyrrolidin-3-yl)oxy)-1-oxoisoindolin-2-yl)piperidine-2,6-dione. To a stirred mixture of 3-(5-(((3S,4R)-4-methylpyrrolidin-3-yl)oxy)-1-oxoisoindolin-2-yl)piperid-ine-2,6-dione; 2,2,2-trifluoroacetic acid (67 mg, 0.15 mmol), 2-(tetrahydro-2H-pyran-4-yl)quinoline-6-carbaldehyde (40 mg, 0.17 mmol) and triethylamine (0.08 mL, 0.59 mmol) in dichloromethane (5 mL) was added sodium triacetoxyborohydride (120 mg, 0.57 mmol) in several portions. The reaction mixture was stirred at room temperature for 2 h under nitrogen. The resulting mixture was concentrated and the residue was purified by silica gel chromatography (0-10% methanol in dichloromethane) and further purified by preparative HPLC with the following condition: Column: Sunfire prep C18 column, 30*150 mm, 5 μm; Mobile Phase A: water (0.1% formic acid), Mobile Phase B: acetonitrile; Flow rate: 60 m/min; Gradient: 4% B to 30% B in 8 min, 30% B; Wave Length: 254/220 nm; $RT_1$ (min): 6.83. The fractions containing desired product were collected and evaporated under reduced pressure to afford the title compound (28.1 mg, 0.049 mmol, 29% yield) as a white solid. $^1H$ NMR (400 MHz, Methanol-$d_4$) δ 8.27 (dd, J=8.6, 2.4 Hz, 1H), 8.01 (d, J=8.6 Hz, 1H), 7.88 (s, 1H), 7.80 (dd, J=8.8, 1.8 Hz, 1H), 7.71 (d, J=8.4 Hz, 1H), 7.52 (d, J=8.5 Hz, 1H), 7.10-7.00 (m, 2H), 5.12 (dd, J=13.3, 5.2 Hz, 1H), 4.67 (m, 1H), 4.51-4.36 (m, 2H), 4.16-3.95 (m, 4H), 3.64 (m, 2H), 3.29-3.11 (m, 4H), 2.91 (m, 1H), 2.84-2.74 (m, 1H), 2.56 (m, 1H), 2.54-2.41 (m, 2H), 2.16 (m, 1H), 2.04 (m, 2H), 1.91 (m, 2H), 1.24 (d, J=7.0 Hz, 3H); MS (ESI) m/z 569.2 $[M+1]^+$.

Example S128. 3-(1-Oxo-5-((1-((2-(tetrahydro-2H-pyran-4-yl)quinolin-6-yl)methyl)-4-(trifluoromethyl) pyrrolidin-3-yl)oxy)isoindolin-2-yl)piperidine-2,6-dione

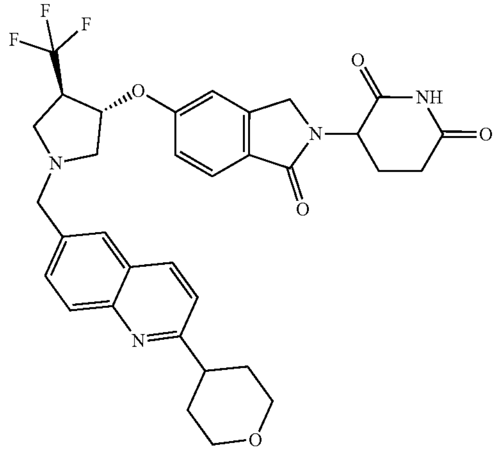 [SMILES: O=C1CCC(N2Cc3cc(O[C@@H]4CN(Cc5ccc6nc(C7CCOCC7)ccc6c5)C[C@H]4C(F)(F)F)ccc3C2=O)C(=O)N1]

(E)-(((3,3,3-Trifluoroprop-1-en-1-yl)oxy)methyl)benzene. To a stirred solution of (E)-1-chloro-3,3,3-trifluoroprop-1-ene (10 g, 76.6 mmol) in DMF (20 mL) were added phenylmethanol (5.0 g, 45.4 mmol) and potassium hydroxide (3.1 g, 55.4 mmol) at room temperature. Then the reaction mixture was stirred for 12 h at 80° C. under nitrogen. The reaction mixture was added water and extracted with dichloromethane. The extracts were dried over anhydrous sodium sulfate, filtered and concentrated to give the title compound (2.2 g, 10.88 mmol, 14% yield) as a yellow solid. MS (ESI) m/z 202.2 $[M+1]^+$.

1-Benzyl-3-(benzyloxy)-4-(trifluoromethyl)pyrrolidine. To a stirred solution of (E)-(((3,3,3-trifluoroprop-1-en-1-yl)oxy)methyl)benzene (2.5 g, 12.4 mmol) in N-benzyl-1-methoxy-N-((trimethylsilyl)methyl)methanamine (9 g, 37.9 mmol) was added TFA (0.1 mL) at 150° C. Then the reaction mixture was stirred for 3 h at 150° C. under nitrogen. The reaction mixture was added water and extracted with dichloromethane. The extracts were dried over anhydrous sodium sulfate, filtered and concentrated. The crude product was purified by silica gel chromatography (10 to 30% ethyl acetate in petroleum ether). The pure fractions were evaporated to give the title compound (2.2 g, 6.54 mmol, 53% yield) as a red oil. MS (ESI) m/z 336.2 $[M+1]^+$.

Tert-butyl 3-hydroxy-4-(trifluoromethyl)pyrrolidine-1-carboxylate. To a stirred solution of 1-benzyl-3-(benzyloxy)-4-(trifluoromethyl)pyrrolidine (500 mg, 1.5 mmol) in methanol (20 mL) were added di-tert-butyl dicarbonate (344 mg, 1.58 mmol), palladium hydroxide on carbon, 20% dihydroxypalladium (500 mg, wetted with ca. 50% water) at room temperature. Then the reaction mixture was stirred for 2 h at room temperature under hydrogen. The resulting mixture was filtered and concentrated to afford the title compound (380 mg, 1.5 mmol, 99% yield) as a yellow oil. MS (ESI) m/z 254.1 $[M-1]^-$.

Tert-butyl 3-((2-(1-(4-methoxybenzyl)-2,6-dioxopiperidin-3-yl)-1-oxoisoindo lin-5-yl)oxy)-4-(trifluoromethyl) pyrrolidine-1-carboxylate. The reaction was performed in a 10 mL round-bottomed flask and irradiated with dish blue-LED (450 nm) equipped photoreactor with fan cooling (to maintain <30 deg celsius temp.). To a stirred solution of 2,2,6,6-tetramethylpiperidine (62 mg, 0.44 mmol), (4,4'-Di-tert-butyl-2,2'-bipyridine)bis[2-(2',4'-difluorophenyl)-5-methylpyridine]iridium(III) Hexafluorophosphate (8 mg, 0.0079 mmol) in acetonitrile (2 mL) were added tert-butyl 3-hydroxy-4-(trifluoromethyl)pyrrolidine-1-carboxylate (100 mg, 0.39 mmol), 3-(5-bromo-1-oxoisoindolin-2-yl)-1-(4-methoxybenzyl)piperidine-2,6-dione (266 mg, 0.6 mmol), 4,4'-di-tert-butyl-2,2'-bipyridine (6 mg, 0.022 mmol), nickel(II) chloride ethylene glycol dimethyl ether complex (6 mg, 0.03 mmol) under nitrogen. Then the reaction mixture was stirred at room temperature for 18 h under nitrogen. The resulting mixture was filtered and concentrated. The residue was purified by silica gel chromatography (50 to 100% ethyl acetate in petroleum ether) to give the title compound (120 mg, 0.19 mmol, 50% yield) as a yellow solid. MS (ESI) m/z 618.3 $[M+1]^+$.

3-(1-Oxo-5-((4-(trifluoromethyl)pyrrolidin-3-yl)oxy)isoindolin-2-yl)piperidine-2,6-dione. To a solution of tert-butyl 3-((2-(1-(4-methoxybenzyl)-2,6-dioxopiperidin-3-yl)-1-oxoisoindolin-5-yl)oxy)-4-(trifluoromethyl)pyrrolidine-1-carboxylate (100 mg, 0.16 mmol) in TFA (5 mL, 65.3 mmol) was added trifluoromethanesulfonic acid (0.5 mL) under nitrogen. Then the reaction mixture was stirred for 2 h at 60° C. under nitrogen. The resulting mixture was added saturated sodium bicarbonate and extracted with dichloromethane. The extracts were washed with brine, dried over anhydrous sodium sulfate, filtered and concentrated. The crude product was purified by reverse phase flash (5-50% acetonitrile+0.05% ammonium bicarbonate in water, over 15 min) to give the title compound (60 mg, 0.15 mmol, 93% yield) as a yellow solid. MS (ESI) m/z 398.2 $[M+1]^+$.

3-(1-Oxo-5-((1-((2-(tetrahydro-2H-pyran-4-yl)quinolin-6-yl)methyl)-4-(trifluoromethyl)pyrrolidin-3-yl)oxy)isoindolin-2-yl)piperidine-2,6-dione. To a stirred solution of 2-(tetrahydro-2H-pyran-4-yl)quinoline-6-carbaldehyde (40 mg, 0.10 mmol), 3-(1-oxo-5-((4-(trifluoromethyl)pyrrolidin-3-yl)oxy)isoindolin-2-yl) piperidine-2,6-dione; 2,2,2-trifluoroacetic acid (65 mg, 0.15 mmol), triethylamine (33 mg, 0.33 mmol) in dichloromethane (10 mL) pre-stirred for 15 min was added sodium triacetoxyborohydride (140 mg, 0.66 mmol) at 0° C. and the solution was stirred at room temperature for 12 h under nitrogen. The resulting solution was purified by silica gel chromatography (0 to 10% methanol in dichloromethane). The pure fractions were evaporated and purified further by preparative HPLC with the following conditions: column: xselect CSH C18 OBD column 30*150 mm 5 μm; mobile phase A: water (0.05% TFA), mobile phase B: acetonitrile; flow rate: 60 mL/min; gradient: 8% B to 32% B in 7 min, 32% B; wave length: 254/220 nm; $RT_1$ (min): 5.82. The fractions containing desired product were collected and evaporated under reduced pressure to afford the title compound (16.1 mg, 0.026 mmol, 26% yield) as a white solid. $^1H$ NMR (300 MHz, DMSO-$d_6$) δ 8.56 (dd, J=8.6, 1.9 Hz, 1H), 8.18-8.06 (m, 2H), 7.98-7.89 (m, 1H), 7.72 (dd, J=13.4, 8.5 Hz, 2H), 7.26 (t, J=2.8 Hz, 1H), 7.14 (dd, J=8.6, 2.2 Hz, 1H), 5.40 (s, 1H), 5.06 (m, 1H), 4.59-4.36 (m, 3H), 4.29 (d, J=17.5 Hz, 1H), 4.07-3.96 (m, 2H), 3.82-3.65 (m, 3H), 3.51 (m, 3H), 3.41-3.19 (m, 2H), 2.90 (m, 1H), 2.67-2.58 (m, 1H), 2.36 (m, 1H), 2.04-1.82 (m, 5H); MS (ESI) m/z 623.3 $[M+1]^+$.

Example S129. (S)-3-(1-Oxo-5-(((S)-1-((2-((S)-tetrahydrofuran-3-yl)quinazolin-6-yl)methyl)pyrrolidin-3-yl)oxy)isoindolin-2-yl)piperidine-2,6-dione

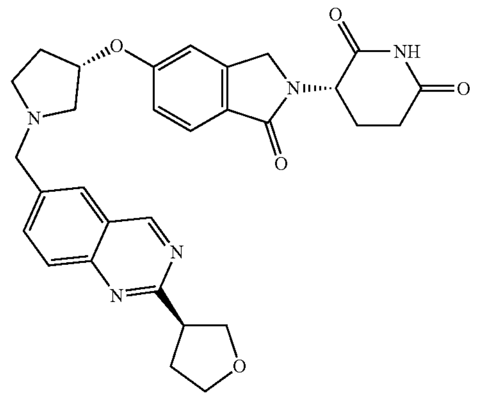 [SMILES: O=C1CC[C@H](N2Cc3cc(O[C@H]4CCN(Cc5ccc6nc([C@@H]7CCOC7)ncc6c5)C4)ccc3C2=O)C(=O)N1]

(S)-3-(1-Oxo-5-(((S)-1-((2-((S)-tetrahydrofuran-3-yl)quinazolin-6-yl)methyl)-pyrrolidin-3-yl)oxy)isoindolin-2-yl)piperidine-2,6-dione. To a solution of 3-[1-oxo-5-[(3S)-pyrrolidin-3-yl]oxy-isoindolin-2-yl]piperidine-2,6-dione; acetic acid (650 mg, 1.67 mmol), 2-[(3S)-tetrahydrofuran-3-yl]quinazoline-6-carbaldehyde (381 mg, 1.67 mmol) in dichloromethane (10 mL) were added triethylamine (0.34 mL, 2.48 mmol) and sodium triacetoxyborohydride (1.10 g, 5.01 mmol) at room temperature. The resulting mixture was stirred for 2 h at room temperature. The solution was concentrated and the residue was purified by preparative HPLC with the following conditions: Xselect CSH OBD Column 30*150 mm 5 μm; Mobile Phase A: water (0.05% TFA), Mobile Phase B: acetonitrile; Flow rate: 60 mL/min; Gradient: 5% B to 35% B in 7 min, 35% B; Wave Length: 254/220 nm; $RT_1$ (min): 6.55; and preparative chiral SFC with the following conditions: CHIRALPAK IH, 2*25 cm, 5 μm; Mobile Phase A: tert-butyl methyl ether-HPLC, Mobile Phase B: ethanol:dichloromethane=1:1-HPLC; Flow rate: 20 mL/min; Gradient: 70% B to 70% B in 11 min; Wave Length: 220/254 nm; $RT_1$ (min): 4.32; $RT_2$ (min): 7.59; Sample Solvent: ethanol:dichloromethane=1:1; Injection Volume: 0.5 mL; Number of Runs: 10. The fractions containing desired product were collected and evaporated under reduced pressure to afford the title compound (98.2 mg, 0.18 mmol, 11% yield) as an off-white solid. $^1H$ NMR (400 MHz, DMSO-$d_6$) δ 10.97 (s, 1H), 9.56 (s, 1H), 8.04-7.90 (m, 3H), 7.61 (d, J=8.4 Hz, 1H), 7.12 (s, 1H), 7.01 (m, 1H), 5.07 (m, 2H), 4.38 (d, J=17.2 Hz, 1H), 4.25 (d, J=17.2 Hz, 1H), 4.18 (m, 1H), 3.95 (m, 2H), 3.88-3.82 (m, 4H), 2.97-2.91 (m, 2H), 2.80-2.69 (m, 2H), 2.61-2.57 (m, 2H), 2.45-2.28 (m, 4H), 2.01-1.93 (m, 1H), 1.85 (m, 1H); MS (ESI) m/z 542.3 $[M+1]^+$.

Example S130. (S)-3-(5-(((S)-1-((5-Fluoro-2-(tetrahydro-2H-pyran-4-yl)quinolin-6-yl)methyl)pyrrolidin-3-yl)oxy)-1-oxoisoindolin-2-yl)piperidine-2,6-dione

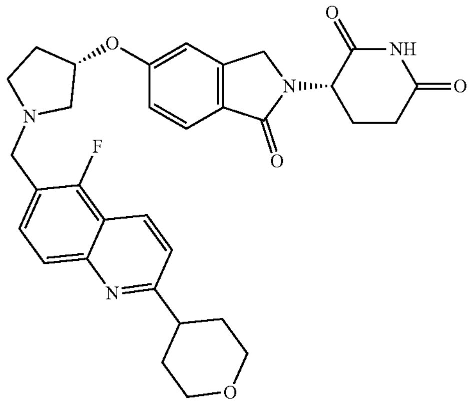 [SMILES: O=C1CC[C@H](N2Cc3cc(O[C@H]4CCN(Cc5ccc6nc(C7CCOCC7)ccc6c5F)C4)ccc3C2=O)C(=O)N1]

Tert-butyl (S)-5-amino-4-(5-(((S)-1-((5-fluoro-2-(tetrahydro-2H-pyran-4-yl)quinolin-6-yl)methyl)pyrrolidin-3-yl)oxy)-1-oxoisoindolin-2-yl)-5-oxopentanoate. To a stirred solution of 5-fluoro-2-(tetrahydro-2H-pyran-4-yl)quinoline-6-carbaldehyde (150 mg, 0.58 mmol), acetic acid (0.03 mL) and tert-butyl (S)-5-amino-5-oxo-4-(1-oxo-5-(((S)-pyrrolidin-3-yl)oxy)isoindolin-2-yl)pentanoate (acetic acid salt, 268 mg, 0.58 mmol) in THF (5 mL) was added sodium triacetoxyborohydride (306 mg, 1.45 mmol) at 0° C. and the solution was stirred at room temperature for 12 h under nitrogen. The resulting solution was added little DMSO and purified directly by reverse phase flash (10-40% acetonitrile+0.05% TFA in water, over 20 min) to afford the title compound (250 mg, 0.39 mmol, 67% yield) as a white oil. MS (ESI) m/z 647.2 $[M+1]^+$.

(S)-3-(5-(((S)-1-((5-Fluoro-2-(tetrahydro-2H-pyran-4-yl) quinolin-6-yl)meth yl)pyrrolidin-3-yl)oxy)-1-oxoisoindolin-2-yl)piperidine-2,6-dione. To a stirred solution of tert-butyl (S)-5-amino-4-(5-(((S)-1-((5-fluoro-2-(tetrahydro-2H-pyran-4-yl) quinolin-6-yl)methyl)pyrrolidin-3-yl)oxy)-1-oxoisoindolin-2-yl)-5-oxopentanoate (250 mg, 0.39 mmol) and benzenesulfonic acid (130 mg, 0.82 mmol) in acetonitrile (15 mL) was stirred at 60° C. for 12 h under nitrogen. The resulting mixture was cooled to room temperature and slowly neutralized with a buffer solution (0.05% potassium dihydrogen phosphate and 0.05% potassium phosphate dibasic in water) to pH~7 and extracted with dichloromethane. The extracts were washed with extra buffer solution (0.05% potassium dihydrogen phosphate and 0.05% potassium phosphate dibasic in water, 120 mL), dried over anhydrous sodium sulfate, filtered and concentrated. The residue was purified by preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 25% B in 7 min, 25% B; Wave Length: 254/220 nm; $RT_1$ (min): 6.8. The fractions were concentrated to afford the title compound (61.7 mg, 0.11 mmol, 28% yield) as a white solid. $^1H$ NMR (400 MHz, Methanol-$d_4$) δ 8.47 (d, J=8.7 Hz, 1H), 7.93-7.75 (m, 2H), 7.63 (dd, J=37.4, 8.6 Hz, 2H), 7.13-6.92 (m, 2H), 5.10 (m, 2H), 4.50-4.31 (m, 2H), 4.18-4.01 (m, 4H), 3.63 (m, 2H), 3.30-3.10 (m, 4H), 2.97-2.70 (m, 3H), 2.45 (m, 2H), 2.20-1.78 (m, 6H); MS (ESI) m/z 573.2 $[M+1]^+$.

Example S131. (S)-3-(5-(((S)-1-((8-Fluoro-2-(tetrahydro-2H-pyran-4-yl)quinolin-6-yl)methyl)pyrrolidin-3-yl)oxy)-1-oxoisoindolin-2-yl)piperidine-2,6-dione

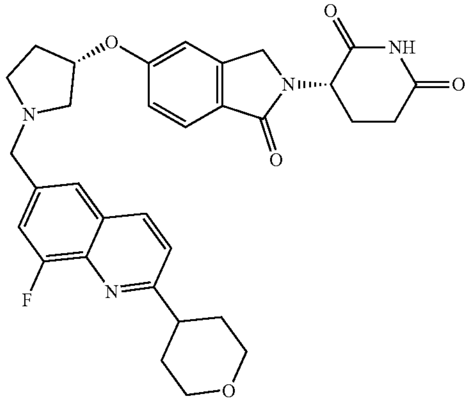 [SMILES: O=C1CC[C@H](N2Cc3cc(O[C@H]4CCN(Cc5cc(F)c6nc(C7CCOCC7)ccc6c5)C4)ccc3C2=O)C(=O)N1]

(2-Amino-5-bromo-3-fluorophenyl)methanol. To a stirred solution of 2-amino-5-bromo-3-fluorobenzoic acid (900 mg, 3.85 mmol) in THF (20 mL) was added lithium aluminum hydride (2.5 M in THF, 3 mL, 7.50 mmol) dropwise at 0° C. under nitrogen. Then the reaction mixture was warmed and stirred for 2 h at room temperature. The resulting mixture was quenched with sodium hydroxide (2 M in water, 5 mL, 10 mmol) at 0° C., then stirred for 30 min at this temperature and filtered. The filter cake was washed with 20 mL THF and 10 mL methanol. The filtrate combined were concentrated to afford the title compound (780 mg, 3.54 mmol, 92% yield) as a yellow solid. MS (ESI) m/z 220.0 $[M+1]^+$.

6-Bromo-8-fluoro-2-(tetrahydro-2H-pyran-4-yl)quinoline. To a stirred solution of (2-amino-5-bromo-3-fluorophenyl)methanol (760 mg, 3.45 mmol) and 1-(tetrahydro-2H-pyran-4-yl)ethan-1-one (885 mg, 6.91 mmol) in toluene (15 mL) was added lithium tert-butoxide (552 mg, 6.91 mmol) at room temperature. Then the reaction mixture was stirred at 110° C. for 12 h under nitrogen. The mixture was filtered and the filtrate was concentrated. The crude product was purified by reverse phase flash (10-40% acetonitrile+0.05% ammonium bicarbonate in water, over 25 min) to give the title compound (310 mg, 1.00 mmol, 29% yield) as a yellow solid. MS (ESI) m/z 310.0 $[M+1]^+$.

8-Fluoro-2-(tetrahydro-2H-pyran-4-yl)-6-vinylquinoline. To a solution of 6-bromo-8-fluoro-2-(tetrahydro-2H-pyran-4-yl)quinoline (300 mg, 0.97 mmol) in 1,4-dioxane (10 mL) and water (2 mL) were added potassium trifluoro(vinyl) borate (194 mg, 1.45 mmol), dichlorobis(triphenylphosphine)palladium(II) dichloromethane adduct (79 mg, 0.10 mmol) and sodium carbonate (307 mg, 2.90 mmol) at room temperature. Then the reaction mixture was stirred at 80° C. for 2 h under nitrogen. The resulting mixture was diluted with water and extracted with ethyl acetate. The extracts were washed with brine, dried over anhydrous sodium sulfate, filtered and concentrated. The residue was purified by silica gel chromatography (0 to 30% ethyl acetate in petroleum ether) to give the title compound (170 mg, 0.66 mmol, 68% yield) as a light-yellow oil. MS (ESI) m/z 258.1 $[M+1]^+$.

8-Fluoro-2-(tetrahydro-2H-pyran-4-yl)quinoline-6-carbaldehyde. To a stirred solution of 8-fluoro-2-(tetrahydro-2H-pyran-4-yl)-6-vinylquinoline (160 mg, 0.62 mmol), 4-methylmorpholine N-oxide (146 mg, 1.24 mmol) and citric acid (261 mg, 1.24 mmol) in tert-butanol (5 mL) and water (5 mL) was added potassium osmate (23 mg, 0.06 mmol). The reaction mixture was stirred for 3 h at room temperature under nitrogen. Then the reaction mixture was added sodium periodate (332 mg, 1.55 mmol) and stirred for 1 h at room temperature. The mixture was added saturated sodium bicarbonate solution to pH~7 and extracted with ethyl acetate. The extracts were washed with brine, dried over sodium sulfate, filtered and concentrated to afford the title compound (130 mg, 0.50 mmol, 81% yield) as an off-white solid. MS (ESI) m/z 260.0 $[M+1]^+$.

Tert-butyl (S)-5-amino-4-(5-(((S)-1-((8-fluoro-2-(tetrahydro-2H-pyran-4-yl)quinolin-6-yl)methyl)pyrrolidin-3-yl)oxy)-1-oxoisoindolin-2-yl)-5-oxopentanoate; 2,2,2-trifluoroacetic acid. To a stirred solution of 8-fluoro-2-(tetrahydro-2H-pyran-4-yl)quinoline-6-carbaldehyde (88 mg, 0.34 mmol), acetic acid (0.03 mL) and tert-butyl (S)-5-amino-5-oxo-4-(1-oxo-5-(((S)-pyrrolidin-3-yl)oxy)isoindolin-2-yl)pentanoate (acetic acid salt, 160 mg, 0.35 mmol) in THF (10 mL) pre-stirred for 15 min was added sodium triacetoxyborohydride (180 mg, 0.85 mmol) at 0° C. and the solution was stirred at room temperature for 12 h under nitrogen. The resulting solution was added little DMSO and purified directly by reverse phase flash (10-40% acetonitrile+0.05% TFA in water, over 20 min) to afford the title compound (120 mg, 0.16 mmol, 47% yield) as a light-yellow semi-solid. MS (ESI) m/z 647.2 $[M+1]^+$.

(S)-3-(5-(((S)-1-((8-Fluoro-2-(tetrahydro-2H-pyran-4-yl)quinolin-6-yl)methyl)pyrrolidin-3-yl)oxy)-1-oxoisoindolin-2-yl)piperidine-2,6-dione. A stirred solution of tert-butyl (S)-5-amino-4-(5-(((S)-1-((8-fluoro-2-(tetrahydro-2H-pyran-4-yl)quinolin-6-yl)methyl)pyrrolidin-3-yl)oxy)-1-oxoisoindolin-2-yl)-5-oxopentanoate; 2,2,2-trifluoroacetic acid (120 mg, 0.16 mmol) and benzenesulfonic acid (75 mg, 0.47 mmol) in acetonitrile (15 mL) was stirred at 60° C. for 12 h under nitrogen. The resulting mixture was cooled to room temperature and slowly neutralized with a buffer solution (0.05% potassium dihydrogen phosphate and 0.05% potassium phosphate dibasic in water) to pH~7 and filtered. The filtrate was purified directly by reverse-phased semi-preparative HPLC (10-30% acetonitrile+0.05% TFA in water, over 20 min) to afford the title compound (34.9 mg, 0.059 mmol, 38% yield) as a light-yellow solid. $^1H$ NMR (300 MHz, Methanol-$d_4$) δ 8.33 (d, J=8.6 Hz, 1H), 7.89 (s, 1H), 7.72 (d, J=8.4 Hz, 1H), 7.69-7.60 (m, 2H), 7.15 (s, 1H), 7.09 (d, J=8.5 Hz, 1H), 5.34 (s, 1H), 5.12 (dd, J=13.3, 5.2 Hz, 1H), 4.67 (s, 2H), 4.50-4.40 (m, 2H), 4.10 (m, 2H), 3.77-3.61 (m, 6H), 3.29-3.19 (m, 1H), 2.90-2.75 (m, 2H), 2.70-2.30 (m, 3H), 2.20-1.90 (m, 5H); MS (ESI) m/z 573.2 $[M+1]^+$.

Example S132. 3-(5-(((3S)-1-((2-((2R,6S)-2,6-Dimethyltetrahydro-2H-pyran-4-yl)quinolin-6-yl)methyl)pyrrolidin-3-yl)oxy)-1-oxoisoindolin-2-yl)piperidine-2,6-dione

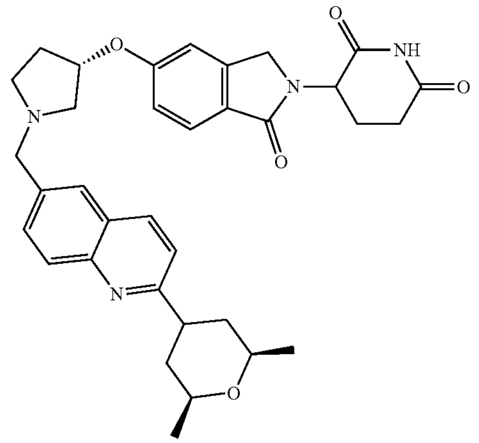 [SMILES: C[C@@H]1CC(c2ccc3cc(CN4CC[C@H](Oc5ccc6c(c5)CN(C5CCC(=O)NC5=O)C6=O)C4)ccc3n2)C[C@H](C)O1]

Methyl 2-(2,6-dimethyl-3,6-dihydro-2H-pyran-4-yl)quinoline-6-carboxylate. To a stirred solution of methyl 2-chloroquinoline-6-carboxylate (1.0 g, 4.5 mmol) in 1,4-dioxane (20 mL) and water (4 mL) were added 2-(2,6-dimethyl-3,6-dihydro-2H-pyran-4-yl)-4,4,5,5-tetramethyl-1,3,2-dioxaborolane (1.12 g, 4.70 mmol), dichlorobis (triphenylphosphine)palladium(II) dichloromethane adduct (320 mg, 0.42 mmol) and sodium carbonate (1.34 g, 12.6 mmol) at room temperature. Then the reaction mixture was stirred for 12 h at 80° C. under nitrogen. The resulting mixture was filtered and the filtrate was concentrated. The residue was purified with reverse phase flash (40-80% acetonitrile+0.05% ammonium bicarbonate in water, over 20 min) to give the title compound (1.24 g, 4.2 mmol, 92% yield) as a yellow solid. MS (ESI) m/z 298.2 $[M+1]^+$.

Methyl 2-(2,6-dimethyltetrahydro-2H-pyran-4-yl)quinoline-6-carboxylate. To a stirred solution of methyl 2-(2,6-dimethyl-3,6-dihydro-2H-pyran-4-yl) quinoline-6-carboxylate (600 mg, 2.01 mmol) in methanol (20 mL) was added palladium 10% on carbon (200 mg, wetted with ca. 50% water) at room temperature. The reaction mixture was stirred at room temperature for 2 h under hydrogen (~2 bar). The resulting mixture was filtered and the filtrate was concentrated to give the title compound (500 mg, 1.67 mmol, 83% yield) as a yellow oil. MS (ESI) m/z 300.2 $[M+1]^+$.

(2-(2,6-Dimethyltetrahydro-2H-pyran-4-yl)quinolin-6-yl)methanol. To a stirred solution of methyl 2-(2,6-dimethyltetrahydro-2H-pyran-4-yl)quinolone-6-carboxylate (500 mg, 1.67 mmol) in THF (10 mL) was added lithium aluminum hydride (2.5 M in THF, 1 mL, 2.5 mmol) dropwise at 0° C. under nitrogen. Then the reaction mixture was warmed and stirred for 2 h at room temperature. The resulting mixture was quenched with sodium hydroxide (2 M in water, 5 mL, 10 mmol) at 0° C., then stirred for 30 min at this temperature and filtered. The filter cake was washed with 20 mL THF and 10 mL methanol. The filtrate combined were concentrated to afford the title compound (300 mg, 1.10 mmol, 66% yield) as a yellow oil. MS (ESI) m/z 272.2 $[M+1]^+$.

(2-((2R,6S)-2,6-Dimethyltetrahydro-2H-pyran-4-yl)quinolin-6-yl)methanol. The (2-(2,6-dimethyltetrahydro-2H-pyran-4-yl)quinolin-6-yl)methanol (300 mg, 1.10 mmol) was purified by preparative SFC with the following conditions: column: YMC-actus triart diol-hilic, 2*25 cm, 5 μm; mobile phase A: carbon dioxide, mobile phase B: acetonitrile:methanol=4:1 (0.1% 2M ammonia-methanol); flow rate: 50 mL/min; gradient: isocratic 15% B; column temperature (° C.): 35; back pressure(bar): 100; wave length: 254 nm; $RT_1$ (min): 6.23; $RT_2$ (min): 8.23; sample solvent: methanol—HPLC; injection volume: 1.5 mL; number of runs: 10. The fractions containing desired product were collected and evaporated under reduced pressure to afford the title compound (170 mg, 0.63 mmol, 57% yield). MS (ESI) m/z 272.2 $[M+1]^+$.

2-((2R,6S)-2,6-dimethyltetrahydro-2H-pyran-4-yl)quinoline-6-carbaldehyde. To a stirred solution of (2-((2R,6S)-2,6-dimethyltetrahydro-2H-pyran-4-yl) quinolin-6-yl)methanol (50 mg, 0.18 mmol) in dichloromethane (10 mL) was added manganese dioxide (321 mg, 3.7 mmol) at room temperature. Then the reaction mixture was stirred for 12 h at room temperature under nitrogen. The resulting mixture was filtered and concentrated to afford the title compound (45 mg, 0.17 mmol, 91% yield) as a yellow solid. MS (ESI) m/z 270.0 $[M+1]^+$.

3-(5-(((3S)-1-((2-((2R,6S)-2,6-Dimethyltetrahydro-2H-pyran-4-yl)quinolin-6-yl)methyl)pyrrolidin-3-yl)oxy)-1-oxoisoindolin-2-yl)piperidine-2,6-dione. To a stirred solution of 2-((2R,6S)-2,6-dimethyltetrahydro-2H-pyran-4-yl) quinoline-6-carbaldehyde (45 mg, 0.17 mmol), 3-[1-oxo-5-[(3S)-pyrrolidin-3-yl]oxy-isoindolin-2-yl] piperidine-2,6-dione; 2,2,2-trifluoroacetic acid (96 mg, 0.22 mmol), triethylamine (28 mg, 0.28 mmol) in dichloromethane (10 mL) pre-stirred for 15 min was added sodium triacetoxyborohydride (153 mg, 0.72 mmol) at 0° C. and the solution was stirred at room temperature for 12 h under nitrogen. The resulting solution was purified by silica gel chromatography (0 to 10% methanol in dichloromethane). The pure fractions were evaporated and purified further by preparative HPLC with the following conditions: column: sunfire prep C18 OBD column, 19×150 mm 5 μm 10 nm; mobile phase A: water (0.1% formic acid), mobile phase B: acetonitrile; flow rate: 60 mL/min; gradient: 10 B to 30 B in 10 min; 254/210 nm; $RT_1$: 9.67; $RT_2$. The fractions containing desired product were collected and evaporated under reduced pressure to afford the title compound (36.9 mg, 0.063 mmol, 37% yield) as a yellow solid. $^1H$ NMR (300 MHz, DMSO-$d_6$) δ 10.95 (s, 1H), 8.25 (d, J=8.5 Hz, 1H), 7.90 (d, J=8.6 Hz, 1H), 7.83 (s, 1H), 7.69 (dd, J=8.7, 1.8 Hz, 1H), 7.60 (d, J=8.4 Hz, 1H), 7.45 (d, J=8.5 Hz, 1H), 7.10 (s, 1H), 7.00 (dd, J=8.4, 2.1 Hz, 1H), 5.11-4.94 (m, 2H), 4.37 (d, J=17.2 Hz, 1H), 4.30-4.17 (m, 1H), 3.87-3.73 (m, 2H), 3.61 (m, 2H), 3.20-3.10 (m, 1H), 2.91 (m, 2H), 2.81-2.67 (m, 2H), 2.58 (m, 2H), 2.35 (m, 2H), 2.03-1.73 (m, 4H), 1.44 (m, 2H), 1.16 (d, J=6.1 Hz, 6H); MS (ESI) m/z 583.3 $[M+1]^+$.

Example S133. 3-(5-(((3R,4R)-4-Fluoro-1-((2-(tetrahydro-2H-pyran-4-yl) quinolin-6-yl) methyl) pyrrolidin-3-yl) oxy)-1-oxoisoindolin-2-yl)piperidine-2,6-dione

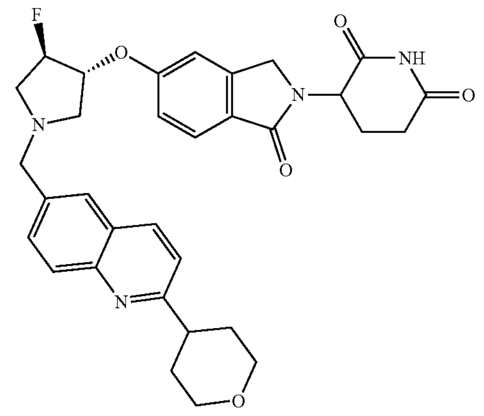 [SMILES: O=C1CCC(N2Cc3cc(O[C@@H]4CN(Cc5ccc6nc(C7CCOCC7)ccc6c5)C[C@H]4F)ccc3C2=O)C(=O)N1]

Tert-butyl (3R,4R)-3-fluoro-4-((2-(1-(4-methoxybenzyl)-2,6-dioxopiperidin-3-yl)-1-oxoisoindolin-5-yl)oxy)pyrrolidine-1-carboxylate. To a mixture of 4,4'-di-tert-butyl-2,2'-bipyridine (35 mg, 0.13 mmol), nickel(II) chloride ethylene glycol dimethyl ether complex (28 mg, 0.13 mmol), tert-butyl (3R,4R)-3-fluoro-4-hydroxypyrrolidine-1-carboxylate (813 mg, 3.96 mmol), 3-(5-bromo-1-oxoisoindolin-2-yl)-1-(4-methoxybenzyl)piperidine-2,6-dione (1 g, 2.25 mmol), (4,4'-di-t-butyl-2,2'-bipyridine)bis[3,5-difluoro-2-[5-trifluoromethyl-2-pyridinyl-kN)phenyl-kC]iridium(III) hexafluorophosphate (53 mg, 0.05 mmol) in acetonitrile (20 mL) was added 2,2,6,6-tetramethylpiperidine (425 mg, 2.89 mmol). The mixture was stirred at room temperature for 18 h under nitrogen with 80 W blue LED irradiation. The resulting mixture was filtered and concentrated. The residue was purified by silica gel chromatography (50 to 100% ethyl acetate in petroleum ether) to afford the title compound (700 mg, 1.23 mmol, 31% yield). MS (ESI) m/z 590.3 $[M+23]^+$.

3-(5-(((3R,4R)-4-Fluoropyrrolidin-3-yl)oxy)-1-oxoisoindolin-2-yl)piperidine-2,6-dione; 2,2,2-trifluoroacetic acid. To a solution of tert-butyl (3R,4R)-3-fluoro-4-((2-(1-(4-methoxybenzyl)-2,6-dioxopiperidin-3-yl)-1-oxoisoindolin-5-yl)oxy)pyrrolidine-1-carboxylate (700 mg, 1.23 mmol) in TFA (10 mL) was added trifluoromethanesulfonic acid (1 mL). The mixture was stirred at 60° C. for 12 h under nitrogen. The brown solution was concentrated under reduced pressure. The residue was diluted with water, then adjusted to pH 6-7 carefully with saturated sodium carbonate and filtered. The aqueous phase was purified by reverse flash chromatography (10-30% acetonitrile+0.05% TFA in water, over 20 min) to give the title compound (540 mg, 1.17 mmol, 95% yield) as a white solid. MS (ESI) m/z 348.1 $[M+1]^+$.

3-(5-(((3R,4R)-4-Fluoro-1-((2-(tetrahydro-2H-pyran-4-yl)quinolin-6-yl) methyl)pyrrolidin-3-yl)oxy)-1-oxoisoindolin-2-yl)piperidine-2,6-dione. To a stirred mixture of 3-(5-(((3R,4R)-4-fluoropyrrolidin-3-yl)oxy)-1-oxoisoindolin-2-yl)piperidine-2,6-dione; 2,2,2-trifluoroacetic acid (100 mg, 0.22 mmol), 2-(tetrahydro-2H-pyran-4-yl)quinoline-6-carbaldehyde (50 mg, 0.21 mmol) and triethylamine (40 mg, 0.40 mmol) in dichloromethane (10 mL) was added sodium triacetoxyborohydride (160 mg, 0.75 mmol) in several portions and the mixture was stirred at room temperature for 2 h under nitrogen. The resulting mixture was concentrated and the residue was purified by silica gel chromatography (0-10% methanol in dichloromethane) and purified further by preparative HPLC with the following conditions: Column: Sunfire prep C18 column, 30*150 mm, 5 μm; Mobile phase A: water (0.05% TFA), Mobile phase B: acetonitrile; Flow rate: 60 mL/min; Gradient: 2% B to 28% B in 7 min, 28% B; Wave Length: 254/220 nm; $RT_1$ (min): 6.3. The fractions containing desired product were collected and evaporated under reduced pressure to afford the title compound (35.9 mg, 0.063 mmol, 30% yield) as a white solid. $^1H$ NMR (300 MHz, DMSO-$d_6$) δ 10.96 (s, 1H), 8.29 (d, J=8.5 Hz, 1H), 7.94 (d, J=8.7 Hz, 1H), 7.86 (m, 1H), 7.72 (m, 1H), 7.65 (d, J=8.4 Hz, 1H), 7.51 (d, J=8.5 Hz, 1H), 7.19 (s, 1H), 7.12-7.03 (m, 1H), 5.30-5.05 (m, 3H), 4.39 (d, J=17.3 Hz, 1H), 4.32-4.19 (m, 1H), 3.99 (d, J=11.4 Hz, 2H), 3.85 (m, 2H), 3.50-3.45 (m, 3H), 3.30-2.80 (m, 4H), 2.59-2.55 (m, 2H), 2.35-2.33 (m, 1H), 1.96-1.82 (m, 5H); MS (ESI) m/z 573.2 $[M+1]^+$.

Example S134. 3-(5-(((3S)-1-((2-((2R,6S)-2,6-Dimethyltetrahydro-2H-pyran-4-yl)quinolin-6-yl)methyl)pyrrolidin-3-yl)oxy)-1-oxoisoindolin-2-yl)piperidine-2,6-dione

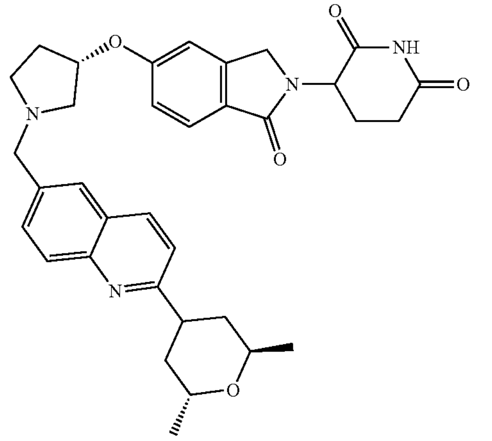 [SMILES: C[C@@H]1CC(c2ccc3cc(CN4CC[C@H](Oc5ccc6c(c5)CN(C5CCC(=O)NC5=O)C6=O)C4)ccc3n2)C[C@@H](C)O1]

(2-((2R,6R)-2,6-Dimethyltetrahydro-2H-pyran-4-yl)quinolin-6-yl)methanol. The (2-(2,6-dimethyltetrahydro-2H-pyran-4-yl)quinolin-6-yl)methanol (300 mg, 1.1 mmol) was purified by preparative SFC with the following conditions: Column: YMC-actus triart diol-hilic, 2*25 cm, 5 μm; mobile phase A: $CO_2$, mobile phase B: acetonitrile:methanol=4:1 (0.1% 2M ammonia-methanol); flow rate: 50 mL/min; gradient: isocratic 15% B; column temperature (° C.): 35; back pressure (bar): 100; wave length: 254 nm; $RT_1$ (min): 6.23; $RT_2$ (min): 8.23; sample solvent: methanol—HPLC; injection volume: 1.5 mL; number of runs: 10. The fractions containing desired product were collected and evaporated under reduced pressure to afford the title compound (40 mg, 0.15 mmol, 14% yield). MS (ESI) m/z 272.2 $[M+1]^+$.

2-((2R,6R)-2,6-Dimethyltetrahydro-2H-pyran-4-yl)quinoline-6-carbaldehyde. To a stirred solution of (2-((2R,6R)-2,6-dimethyltetrahydro-2H-pyran-4-yl)quinolin-6-yl) methanol (40 mg, 0.15 mmol) in dichloromethane (10 mL) was added manganese dioxide (257 mg, 2.96 mmol) at room temperature. Then the reaction mixture was stirred for 12 h at room temperature under nitrogen. The resulting mixture was filtered and concentrated to afford the title compound (35 mg, 0.13 mmol, 88% yield) as a yellow solid. MS (ESI) m/z 270.0 $[M+1]^+$.

3-(5-(((S)-1-((2-((2R,6R)-2,6-Dimethyltetrahydro-2H-pyran-4-yl)quinolin-6-yl)methyl)pyrrolidin-3-yl)oxy)-1-oxoisoindolin-2-yl)piperidine-2,6-dione. To a stirred solution of 2-[(2R,6R)-2,6-dimethyltetrahydropyran-4-yl] quinoline-6-carbaldehyde (40 mg, 0.15 mmol), 3-[1-oxo-5-[(3S)-pyrrolidin-3-yl]oxy-isoindolin-2-yl] piperidine-2,6-dione; 2,2,2-trifluoroacetic acid (91 mg, 0.21 mmol), triethylamine (40 mg, 0.40 mmol) in dichloromethane (10 mL) pre-stirred for 15 min was added sodium triacetoxyborohydride (144 mg, 0.68 mmol) at 0° C. and the solution was stirred at room temperature for 12 h under nitrogen. The resulting solution was purified by silica gel chromatography (0 to 10% methanol in dichloromethane). The pure fractions were evaporated and purified further by preparative HPLC with the following conditions: column: sunfire prep C18 OBD column, 19×150 mm 5 um 10 nm; mobile phase A: water (0.1% formic acid), mobile phase B: acetonitrile; flow rate: 60 mL/min; gradient: 10 B to 30 B in 10 min; 254/210 nm; $RT_1$: 9.67; $RT_2$. The fractions containing desired product were collected and evaporated under reduced pressure to afford the title compound (21.1 mg, 0.035 mmol, 24% yield) as a white solid. $^1H$ NMR (300 MHz, DMSO-$d_6$) δ 10.95 (s, 1H), 8.24 (d, J=8.6 Hz, 1H), 8.14 (s, 1H), 7.94-7.79 (m, 2H), 7.75-7.48 (m, 3H), 7.10 (s, 1H), 7.00 (dd, J=8.4, 2.1 Hz, 1H), 5.04 (m, 2H), 4.37 (d, J=17.2 Hz, 1H), 4.24 (d, J=17.2 Hz, 1H), 3.78 (m, 4H), 3.47 (m, 1H), 3.00-2.69 (m, 4H), 2.64-2.52 (m, 2H), 2.43-2.18 (m, 4H), 2.02-1.79 (m, 2H), 1.61 (m, 2H), 1.07 (d, J=6.1 Hz, 6H); MS (ESI) m/z 583.3 $[M+1]^+$.

Example S135. 3-(5-(((3S)-1-((2-((2R)-2-Methyltetrahydro-2H-pyran-4-yl)quinolin-6-yl)methyl)-pyrrolidin-3-yl)oxy)-1-oxoisoindolin-2-yl)piperidine-2,6-dione

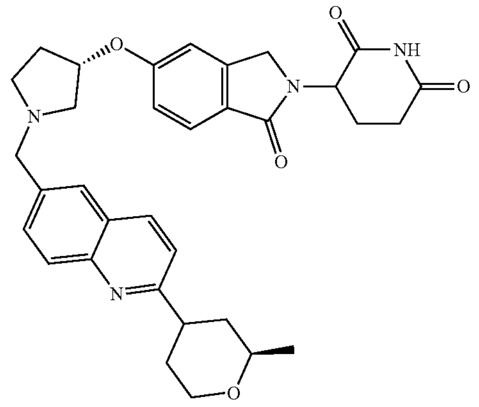 [SMILES: C[C@@H]1CC(c2ccc3cc(CN4CC[C@H](Oc5ccc6c(c5)CN(C5CCC(=O)NC5=O)C6=O)C4)ccc3n2)CCO1]

6-Bromo-2-(2-methyltetrahydro-2H-pyran-4-yl)quinoline. To a stirred solution of (2-amino-5-bromophenyl) methanol (500 mg, 2.47 mmol) and 1-(2-methyltetrahydro-2H-pyran-4-yl)ethan-1-one (852 mg, 5.99 mmol) in toluene (6 mL) was added lithium tert-butoxide (591 mg, 7.38 mmol) in one portion. The reaction mixture was stirred at 110° C. for 16 h under nitrogen. The resulting mixture was concentrated and the residue was purified via reverse phase flash (10-100% acetonitrile+0.05% ammonium bicarbonate in water, over 25 min) to afford the title compound (500 mg, 1.63 mmol, 66% yield) as a yellow oil. MS (ESI) m/z 306.0 $[M+1]^+$.

2-((2R)-2-Methyltetrahydro-2H-pyran-4-yl)-6-vinylquinoline. To a stirred solution of 6-bromo-2-(2-methyltetrahydro-2H-pyran-4-yl)quinoline (500 mg, 1.63 mmol) and potassium trifluoro(vinyl)borate (262 mg, 1.96 mmol) in 1,4-dioxane (3 mL) and water (0.3 mL) were added tetrakis (triphenylphosphine)palladium (188 mg, 0.16 mmol) and cesium carbonate (1061 mg, 3.27 mmol). The above mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 30% ethyl acetate in petroleum ether) to afford the crude product (380 mg) which was purified by chiral preparative HPLC with the following conditions: Column: CHIRALPAK IH-3, 4.6*50 mm, 3 μm; Mobile Phase A: hexane (0.1% diethyl amine): ethanol=90:10; Flow rate: 1 mL/min; Gradient: 0% B to 0% B; Injection Volume: 5 mL. Pure fractions were evaporated to afford the title compound (120 mg, 0.47 mmol, 29% yield) as a light-yellow oil. MS (ESI) m/z 254.0 $[M+1]^+$.

2-((2R)-2-Methyltetrahydro-2H-pyran-4-yl)quinoline-6-carbaldehyde. To a stirred solution of 2-((2R)-2-methyltetrahydro-2H-pyran-4-yl)-6-vinylquinoline (120 mg, 0.47 mmol) in tert-butanol (8 mL) and water (8 mL) were added 4-methyl-morpholin4-oxide (55 mg, 0.47 mmol), potassium osmate (174 mg, 0.47 mmol) and citric acid (90 mg, 0.47 mmol). The above mixture was stirred at room temperature for 3 h under nitrogen. Then the mixture was added sodium periodate (101 mg, 0.47 mmol) and stirred for another 1 h. The reaction mixture was added saturated sodium bicarbonate to pH~7 and extracted with ethyl acetate. The extracts were washed with brine, dried over sodium sulfate, filtered and concentrated. The residue was purified by silica gel chromatography (0 to 40% ethyl acetate in petroleum ether) to afford the title compound (60 mg, 0.24 mmol, 50% yield) as a light-yellow oil. MS (ESI) m/z 256.0 $[M+1]^+$.

3-(5-(((3S)-1-((2-((2R)-2-Methyltetrahydro-2H-pyran-4-yl)quinolin-6-yl)methyl)pyrrolidin-3-yl)oxy)-1-oxoisoindolin-2-yl)piperidine-2,6-dione. To a solution of 2-((2R)-2-methyltetrahydro-2H-pyran-4-yl)quinoline-6-carbaldehyde (60 mg, 0.24 mmol), 3-(1-oxo-5-(((S)-pyrrolidin-3-yl)oxy) isoindolin-2-yl)piperidine-2,6-dione; 2,2,2-trifluoroacetic acid (100 mg, 0.23 mmol) and triethylamine (46 mg, 0.46 mmol) in dichloromethane (5 mL) was added sodium triacetoxyborohydride (150 mg, 0.71 mmol). The mixture was stirred for 12 h at room temperature under nitrogen. The resulting mixture was concentrated. The residue was purified by silica gel chromatography (0 to 10% methanol in dichloromethane) and preparative-HPLC further with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 30% B in 7 min, 30% B; Wave Length: 254/220 nm; $RT_1$ (min): 6.3. The fractions containing desired product were collected and evaporated under reduced pressure to afford the title compound (56.1 mg, 0.099 mmol, 42% yield) as a white solid. $^1H$ NMR (400 MHz, Methanol-$d_4$) δ 8.25 (m, 1H), 8.02 (d, J=8.6 Hz, 1H), 7.91 (d, J=2.0 Hz, 1H), 7.80-7.78 (m, 1H), 7.69-7.66 (m, 1H), 7.50 (d, J=8.6 Hz, 1H), 7.11-6.96 (m, 2H), 5.15-5.03 (m, 2H), 4.49-4.33 (m, 2H), 4.11-4.05 (m, 3H), 3.75-3.60 (m, 2H), 3.27-3.09 (m, 4H), 3.00-2.72 (m, 3H), 2.47-2.42 (m, 2H), 2.22-2.06 (m, 2H), 1.92-1.86 (m, 3H), 1.72-1.54 (m, 1H), 1.24 (d, J=6.2 Hz, 3H); MS (ESI) m/z 569.2 $[M+1]^+$.

Example S136. 3-(5-(((3S)-1-((2-((2S)-2-Methyltetrahydro-2H-pyran-4-yl)quinolin-6-yl)methyl)-pyrrolidin-3-yl)oxy)-1-oxoisoindolin-2-yl)piperidine-2,6-dione

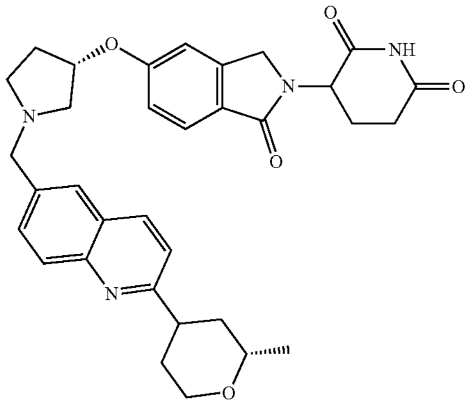 [SMILES: C[C@H]1CC(c2ccc3cc(CN4CC[C@H](Oc5ccc6c(c5)CN(C5CCC(=O)NC5=O)C6=O)C4)ccc3n2)CCO1]

2-((2S)-2-Methyltetrahydro-2H-pyran-4-yl)-6-vinylquinoline. The racemates (380 mg) was purified by Chiral preparative HPLC with the following conditions: Column: CHIRALPAK IH-3, 4.6*50 mm, 3 μm; Mobile Phase A: hexane (0.1% diethyl amine):ethanol=90:10; Flow rate: 1 mL/min; Gradient: 0% B to 0% B; Injection Volume: 5 mL. Pure fractions were evaporated to afford the title compound (120 mg, 0.47 mmol, 31% yield) as a light-yellow oil. MS (ESI) m/z 254.0 $[M+1]^+$.

2-((2S)-2-Methyltetrahydro-2H-pyran-4-yl)quinoline-6-carbaldehyde. To a stirred solution of 2-((2S)-2-methyltetrahydro-2H-pyran-4-yl)-6-vinylquinoline (120 mg, 0.47 mmol) in tert-butanol (8 mL) and water (8 mL) was added 4-methyl-morpholin4-oxide (110 mg, 0.95 mmol), potassium osmate (17 mg, 0.04 mmol) and citric acid (181 mg, 0.95 mmol). The above mixture was stirred at room temperature for 3 h under nitrogen. Then the mixture was added sodium periodate (304 mg, 1.42 mmol) and stirred for another 1 h. The reaction mixture was added saturated sodium bicarbonate to pH~7 and extracted with ethyl acetate. The extracts were washed with brine, dried over sodium sulfate, filtered and concentrated. The residue was purified by silica gel chromatography (0 to 40% ethyl acetate in petroleum ether) to afford the title compound (50 mg, 0.20 mmol, 41% yield) as a light-yellow oil. MS (ESI) m/z 256.2 $[M+1]^+$.

3-(5-(((3S)-1-((2-((2S)-2-Methyltetrahydro-2H-pyran-4-yl)quinolin-6-yl)methyl)pyrrolidin-3-yl)oxy)-1-oxoisoindolin-2-yl)piperidine-2,6-dione. To a solution of 2-((2S)-2-methyltetrahydro-2H-pyran-4-yl)quinoline-6-carbaldehyde (50 mg, 0.20 mmol), 3-(1-oxo-5-(((S)-pyrrolidin-3-yl)oxy) isoindolin-2-yl)piperidine-2,6-dione; 2,2,2-trifluoroacetic acid (69 mg, 0.16 mmol) and triethylamine (40 mg, 0.40 mmol) in dichloromethane (5 mL) was added sodium triacetoxyborohydride (125 mg, 0.59 mmol). The mixture was stirred for 12 h at room temperature under nitrogen. The resulting mixture was concentrated. The residue was purified by silica gel chromatography (0 to 10% methanol in dichloromethane) and preparative-HPLC further with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 3% B to 24% B in 7 min, 24% B; Wave Length: 254/220 nm; $RT_1$ (min): 6.5. The fractions containing desired product were collected and evaporated under reduced pressure to afford the title compound to afford the title compound (58.8 mg, 0.10 mmol, 52% yield) as a white solid. $^1$H NMR (400 MHz, Methanol-$d_4$) δ 8.22 (m, 1H), 8.02 (d, J=8.7 Hz, 1H), 7.90 (s, 1H), 7.80 (d, J=8.8 Hz, 1H), 7.74-7.64 (m, 1H), 7.50 (d, J=8.6 Hz, 1H), 7.11-6.97 (m, 2H), 5.17-5.05 (m, 2H), 4.49-4.33 (m, 2H), 4.22-4.00 (m, 3H), 3.67 (m, 2H), 3.21-3.12 (m, 4H), 2.99-2.70 (m, 3H), 2.54-2.40 (m, 2H), 2.13-2.09 (m, 2H), 1.92-1.85 (m, 3H), 1.64 (q, J=12.3 Hz, 1H), 1.24 (d, J=6.2 Hz, 3H); MS (ESI) m/z 569.3 $[M+1]^+$.

Example S137. 3-(5-(((3R,4R)-4-Methoxy-1-((2-(tetrahydro-2H-pyran-4-yl)quinolin-6-yl)meth-yl) pyrrolidin-3-yl)oxy)-1-oxoisoindolin-2-yl)piperidine-2,6-dione

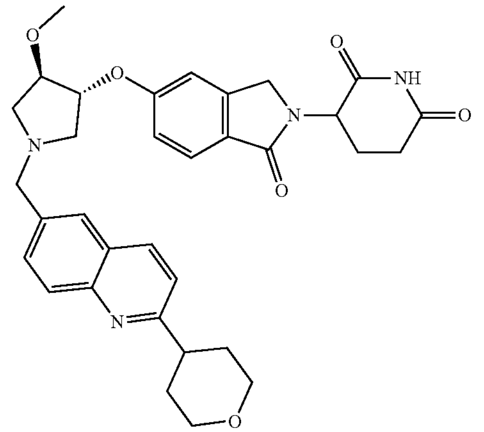 [SMILES: CO[C@@H]1CN(Cc2ccc3nc(C4CCOCC4)ccc3c2)C[C@H]1Oc1ccc2c(c1)CN(C1CCC(=O)NC1=O)C2=O]

3-(5-(((3R,4R)-4-Methoxy-1-((2-(tetrahydro-2H-pyran-4-yl)quinolin-6-yl) methyl)pyrrolidin-3-yl)oxy)-1-oxoisoindolin-2-yl)piperidine-2,6-dione. To a solution of 2-(tetrahydro-2H-pyran-4-yl)quinoline-6-carbaldehyde (90 mg, 0.37 mmol), 3-(5-(((3R,4R)-4-methoxypyrrolidin-3-yl) oxy)-1-oxoisoindolin-2-yl)piperidin e-2,6-dione; 2,2,2-trifluoroacetic acid (160 mg, 0.34 mmol) and triethylamine (0.15 mL, 1.08 mmol) in dichloromethane (6 mL) was added sodium triacetoxyborohydride (201 mg, 0.95 mmol) in several portions at room temperature. The resulting mixture was stirred at room temperature for 1 h under nitrogen. The mixture was added little methanol and purified by silica gel chromatography (0-10% methanol in dichloromethane) and further purified by preparative HPLC with the following conditions: Column: sunfire prep C18 column, 30*150 mm, 5 μm; mobile phase A: water (0.1% formic acid), mobile phase B: acetonitrile; flow rate: 60 mL/min; gradient: 2% B to 30% B in 7 min, 30% B; wave length: 254/220 nm; $RT_1$ (min): 6.8. The fractions containing desired product were collected and evaporated under reduced pressure to afford the title compound (46.4 mg, 0.079 mmol, 22% yield) as an off-white solid. $^1$H NMR (400 MHz, Methanol-$d_4$) δ 8.25 (d, J=8.5 Hz, 1H), 7.99 (d, J=8.7 Hz, 1H), 7.85 (d, J=1.8 Hz, 1H), 7.81-7.74 (m, 1H), 7.70-7.68 (m, 1H), 7.50 (d, J=8.5 Hz, 1H), 7.16-7.04 (m, 2H), 5.10-5.08 (m, 1H), 4.50-4.35 (m, 2H), 4.10-4.08 (m, 2H), 4.06-3.90 (m, 5H), 3.63 (m, 2H), 3.36 (m, 3H), 3.25-3.12 (m, 4H), 2.88 (m, 2H), 2.81-2.73 (m, 2H), 2.45 (m, 1H), 2.02 (m, 2H), 1.89 (m, 2H), 1.85 (m, 2H); MS (ESI) m/z 585.2 $[M+1]^+$.

Example S138. 3-(5-(((3S,4R)-4-Methyl-1-((2-((R)-tetrahydrofuran-3-yl)quinolin-6-yl)methyl)pyrrolidin-3-yl)oxy)-1-oxoisoindolin-2-yl)piperidine-2,6-dione

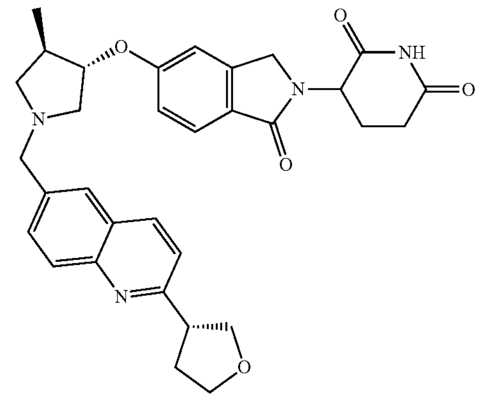 [SMILES: C[C@@H]1CN(Cc2ccc3nc([C@H]4CCOC4)ccc3c2)C[C@H]1Oc1ccc2c(c1)CN(C1CCC(=O)NC1=O)C2=O]

3-(5-(((3S,4R)-4-Methylpyrrolidin-3-yl)oxy)-1-oxoisoindolin-2-yl)piperidine-2,6-dione; 2,2,2-trifluoroacetic acid. To a solution of tert-butyl (3S,4R)-3-((2-(1-(4-methoxybenzyl)-2,6-dioxopiperidin-3-yl)-1-oxoisoindolin-5-yl)oxy)-4-methylpyrrolidine-1-carboxylate (734 mg, 1.30 mmol) in TFA (5 mL) was slowly added trifluoromethanesulfonic acid (1 mL) at 0° C. The brown solution was stirred for 1 h at 60° C. under nitrogen. The mixture was added saturated sodium bicarbonate to pH~7, filtered and the filtrate was purified by reverse flash (10-70% acetonitrile+0.05% TFA in water, over 20 min). The fractions containing desired product were collected and evaporated under reduced pressure to afford the title compound (545 mg, 1.19 mmol, 90% yield) as a yellow oil. MS (ESI) m/z 344.1 $[M+1]^+$.

3-(5-(((3S,4R)-4-Methyl-1-((2-((R)-tetrahydrofuran-3-yl)quinolin-6-yl)methyl)pyrrolidin-3-yl)oxy)-1-oxoisoindolin-2-yl)piperidine-2,6-dione. To a solution of 3-(5-(((3S, 4R)-4-methylpyrrolidin-3-yl)oxy)-1-oxoisoindolin-2-yl) piperidine-2,6-dione; 2,2,2-trifluoroacetic acid (90 mg, 0.20 mmol), (R)-2-(tetrahydrofuran-3-yl) quinoline-6-carbaldehyde (40 mg, 0.18 mmol) and triethylamine (0.08 mL, 0.58 mmol) in dichloromethane (6 mL) was added sodium triacetoxyborohydride (150 mg, 0.71 mmol) in several portions at room temperature. The resulting mixture was stirred at room temperature for 1 h under nitrogen. The mixture was concentrated. The residue was purified by silica gel chromatography (0-10% methanol in dichloromethane) and further purified by preparative HPLC with the following conditions: column: sunfire prep C18 column, 30*150 mm, 5 μm; mobile phase A: water (0.1% formic acid), mobile phase B: acetonitrile; flow rate: 60 mL/min; gradient: 5% B to 30% B in 7 min, 30% B; wave length: 254/220 nm; $RT_1$ (min): 5.5. The fractions containing desired product were collected and evaporated under reduced pressure to afford the title compound (30.8 mg, 0.055 mmol, 31% yield) as a white solid. $^1$H NMR (400 MHz, Methanol-$d_4$) δ 8.30-8.22 (m, 1H), 8.02 (d, J=8.7 Hz, 1H), 7.92 (t, J=1.6 Hz, 1H), 7.80-7.78 (m, 1H), 7.70-7.68 (m, 1H), 7.52 (d, J=8.6 Hz, 1H), 7.09-6.99 (m, 2H), 5.10-5.08 (m, 1H), 4.74 (m, 1H), 4.49-4.40 (m, 2H), 4.27-4.15 (m, 3H), 4.12 (m, 1H), 4.02-4.00 (m, 1H), 3.94 (m, 1H), 3.80 (m, 1H), 3.46-3.44 (m, 1H), 3.38 (m, 1H), 3.31-3.21 (m, 1H), 2.96-2.82 (m, 1H), 2.82-2.71 (m, 1H), 2.75-2.63 (m, 2H), 2.54-2.37 (m, 2H), 2.35-2.22 (m, 1H), 2.14 (m, 1H), 1.24 (d, J=6.8 Hz, 3H); MS (ESI) m/z 555.2 $[M+1]^+$.

Example S139. 3-(1-Oxo-5-((1-((2-((R)-tetrahydrofuran-3-yl)quinolin-6-yl)methyl)-4-(trifluoromethyl) pyrrolidin-3-yl)oxy)isoindolin-2-yl)piperidine-2,6-dione

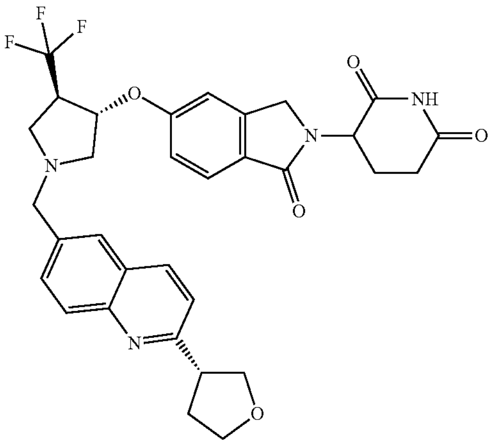 [SMILES: O=C1CCC(N2Cc3cc(O[C@@H]4CN(Cc5ccc6nc([C@H]7CCOC7)ccc6c5)C[C@H]4C(F)(F)F)ccc3C2=O)C(=O)N1]

3-(1-Oxo-5-((1-((2-((R)-tetrahydrofuran-3-yl)quinolin-6-yl)methyl)-4-(trifluoromethyl)pyrrolidin-3-yl)oxy)isoindolin-2-yl)piperidine-2,6-dione. To a stirred solution of (R)-2-(tetrahydrofuran-3-yl)quinoline-6-carbaldehyde (65 mg, 0.29 mmol), 3-(1-oxo-5-((4-(trifluoromethyl)pyrrolidin-3-yl)oxy)isoindolin-2-yl) piperidine-2,6-dione; 2,2,2-trifluoroacetic acid (137 mg, 0.31 mmol), acetic acid (0.03 mL) in THF (10 mL) pre-stirred for 15 min was added sodium triacetoxyborohydride (60 mg, 0.28 mmol) at 0° C. and the solution was stirred at room temperature for 12 h under nitrogen. The resulting solution was purified by silica gel chromatography (0 to 5% methanol in dichloromethane) and purified further by preparative HPLC with the following conditions: column sunfire prep C18 OBD column, 19×150 mm 5 um 10 nm; mobile phase A: water (0.1% formic acid), mobile phase B: acetonitrile; flow rate: 60 mL/min; gradient: 10 B to 30 B in 10 min; 254/210 nm; $RT_1$: 9.67; $RT_2$. The fractions containing desired product were collected and evaporated under reduced pressure to afford the title compound (47.5 mg, 0.076 mmol, 27% yield) as an off-white solid. $^1H$ NMR (300 MHz, DMSO-$d_6$) δ 8.29-8.19 (m, 2H), 7.91 (d, J=8.6 Hz, 1H), 7.83 (s, 1H), 7.73-7.61 (m, 2H), 7.48 (d, J=8.5 Hz, 1H), 7.23 (d, J=2.3 Hz, 1H), 7.10 (dd, J=8.4, 2.2 Hz, 1H), 5.17-4.97 (m, 2H), 4.39 (d, J=17.4 Hz, 1H), 4.26 (dd, J=17.4, 5.5 Hz, 1H), 4.13 (t, J=7.9 Hz, 1H), 3.98 (m, 1H), 3.90-3.79 (m, 4H), 3.77-3.67 (m, 1H), 3.39 (m, 1H), 3.18 (m, 1H), 3.03-2.77 (m, 3H), 2.67-2.54 (m, 2H), 2.43-2.15 (m, 3H), 1.99 (m, 1H); MS (ESI) m/z 609.2 $[M+1]^+$.

Example S140. 3-(5-(((R)-4,4-Difluoro-1-((2-((R)-tetrahydrofuran-3-yl)quinolin-6-yl)methyl)pyrrolidin-3-yl)oxy)-1-oxoisoindolin-2-yl)piperidine-2,6-dione

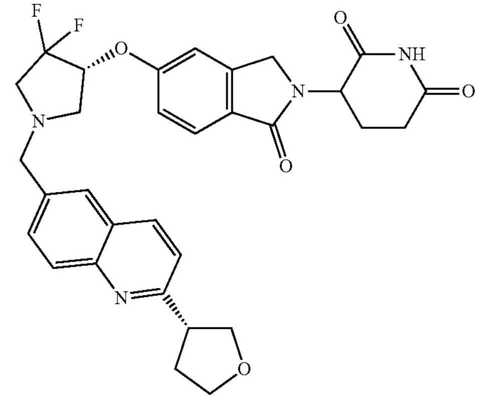 [SMILES: O=C1CCC(N2Cc3cc(O[C@@H]4CN(Cc5ccc6nc([C@H]7CCOC7)ccc6c5)CC4(F)F)ccc3C2=O)C(=O)N1]

3-(5-(((R)-4,4-Difluoro-1-((2-((R)-tetrahydrofuran-3-yl)quinolin-6-yl)methyl) pyrrolidin-3-yl)oxy)-1-oxoisoindolin-2-yl)piperidine-2,6-dione. To a solution of 3-(5-(((R)-4,4-difluoropyrrolidin-3-yl)oxy)-1-oxoisoindolin-2-yl) piperidine-2,6-dione; 2,2,2-trifluoroacetic acid (90 mg, 0.19 mmol), (R)-2-(tetrahydrofuran-3-yl)quinoline-6-carbaldehyde (40 mg, 0.18 mmol) and triethylamine (0.1 mL, 0.57 mmol) in dichloromethane (6 mL) was added sodium triacetoxyborohydride (150 mg, 0.71 mmol) in several portions at room temperature. The resulting mixture was stirred at room temperature for 1 h under nitrogen. The mixture was added little methanol and purified by silica gel chromatography (0-10% methanol in dichloromethane) and further purified by preparative-HPLC with the following conditions: column: xselect CSH $C^{18}$ OBD column 30*150 mm, 5 μm; mobile phase A: water (0.1% formic acid), mobile phase B: acetonitrile; flow rate: 60 mL/min; gradient: 10% B to 40% B in 10 min, 40% B; wave length: 254/220 nm; $RT_1$ (min): 9.55. The fractions containing desired product were collected and evaporated under reduced pressure to afford the title compound (38.8 mg, 0.06 mmol, 35% yield) as an off-white solid. $^1H$ NMR (400 MHz, Methanol-$d_4$) δ 8.26 (d, J=8.6 Hz, 1H), 7.99 (d, J=8.7 Hz, 1H), 7.85 (d, J=1.9 Hz, 1H), 7.78-7.76 (m, 1H), 7.72 (d, J=8.4 Hz, 1H), 7.50 (d, J=8.5 Hz, 1H), 7.20-7.08 (m, 2H), 5.11-5.09 (m, 1H), 5.02-5.00 (m, 1H), 4.51-4.36 (m, 2H), 4.21 (m, 1H), 4.13 (m, 1H), 4.02-4.00 (m, 1H), 3.95-3.80 (m, 3H), 3.70 (m, 1H), 3.48-3.39 (m, 1H), 3.21-3.15 (m, 1H), 3.06-2.91 (m, 1H), 2.95-2.71 (m, 3H), 2.55-2.38 (m, 2H), 2.29 (m, 1H), 2.14 (m, 1H); MS (ESI) m/z 577.2 $[M+1]^+$ Example S141. 3-(5-(((3R,4R)-4-Fluoro-1-((2-((R)-tetrahydrofuran-3-yl) quinolin-6-yl)methyl)pyrrolidin-3-yl)oxy)-1-oxoisoindolin-2-yl)piperidine-2,6-dione

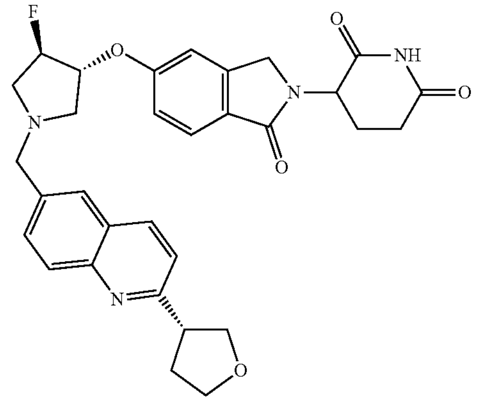 [SMILES: O=C1CCC(N2Cc3cc(O[C@@H]4CN(Cc5ccc6nc([C@H]7CCOC7)ccc6c5)C[C@H]4F)ccc3C2=O)C(=O)N1]

3-(5-(((3R,4R)-4-Fluoro-1-((2-((R)-tetrahydrofuran-3-yl) quinolin-6-yl)methyl)pyrrolidin-3-yl)oxy)-1-oxoisoindolin-2-yl)piperidine-2,6-dione. To a stirred mixture of 3-[5-[(3R, 4R)-4-fluoropyrrolidin-3-yl]oxy-1-oxo-isoindolin-2-yl] piperidine-2,6-dione; 2,2,2-trifluoroacetic acid (120 mg, 0.26 mmol), (R)-2-(tetrahydrofuran-3-yl)quinoline-6-carbaldehyde (58 mg, 0.26 mmol) and triethylamine (51 mg, 0.51 mmol) in dichloromethane (10 mL) was added sodium triacetoxyborohydride (220 mg, 1.04 mmol) in several portions and the mixture was stirred at room temperature for 2 h under nitrogen. The mixture was concentrated and the residue was purified by silica gel chromatography (0-10% methanol in dichloromethane) and the filtrate was purified further by preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 30% B in 7 min, 30% B; Wave Length: 254/220 nm; $RT_1$ (min): 6.63. The fractions containing desired product were collected and evaporated under reduced pressure to give the title compound (19.1 mg, 0.03 mmol, 13% yield) as a white solid. $^1H$ NMR (400 MHz, DMSO-$d_6$) δ 10.96 (s, 1H), 8.28 (d, J=8.5 Hz, 1H), 7.92 (d, J=8.6 Hz, 1H), 7.84 (s, 1H), 7.70-7.67 (m, 1H), 7.64 (d, J=8.4 Hz, 1H), 7.48 (d, J=8.5 Hz, 1H), 7.17 (d, J=2.5 Hz, 1H), 7.07-7.05 (m, 1H), 5.30-5.02 (m, 3H), 4.39 (d, J=17.3 Hz, 1H), 4.26-4.24 (m, 1H), 4.13 (t, J=8.0 Hz, 1H), 3.98 (m, 1H), 3.92-3.79 (m, 4H), 3.74 (m, 1H), 3.41-3.33 (m, 1H), 2.96-2.83 (m, 3H), 2.63-2.51 (m, 2H), 2.44-2.18 (m, 3H), 1.97-1.95 (m, 1H); MS (ESI) m/z 559.2 $[M+1]^+$.

Example S142. 3-(5-(((3R,4S)-4-Fluoro-1-((2-((R)-tetrahydrofuran-3-yl)quinolin-6-yl)methyl)pyrrolidin-3-yl)oxy)-1-oxoisoindolin-2-yl)piperidine-2,6-dione

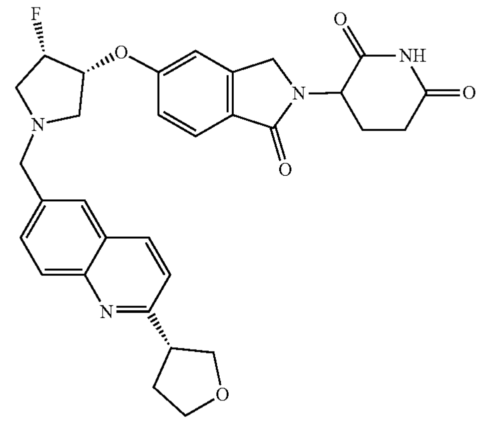 [SMILES: O=C1CCC(N2Cc3cc(O[C@@H]4CN(Cc5ccc6nc([C@H]7CCOC7)ccc6c5)C[C@@H]4F)ccc3C2=O)C(=O)N1]

3-(5-(((3R,4S)-4-Fluoro-1-((2-((R)-tetrahydrofuran-3-yl) quinolin-6-yl)methyl)pyrrolidin-3-yl)oxy)-1-oxoisoindolin-2-yl)piperidine-2,6-dione. To a solution of (R)-2-(tetrahydrofuran-3-yl)quinoline-6-carbaldehyde (25 mg, 0.11 mmol), 3-(5-(((3R,4S)-4-fluoropyrrolidin-3-yl)oxy)-1-oxoisoindolin-2-yl)piperidine-2,6-dione (80 mg, 0.17 mmol) and triethylamine (31 mg, 0.31 mmol) in dichloromethane (5 mL) was added sodium triacetoxyborohydride (100 mg, 0.47 mmol). The mixture was stirred for 12 h at room temperature under nitrogen. The resulting mixture was concentrated. The residue was purified by silica gel chromatography (0 to 10% methanol in dichloromethane) and preparative-HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 5% B to 25% B in 7 min, 25% B; Wave Length: 254/220 nm; $RT_1$ (min): 6.05. The fractions containing desired product were collected and evaporated under reduced pressure to afford the title compound (11.7 mg, 0.02 mmol, 19% yield) as a white solid. $^1H$ NMR (400 MHz, DMSO-$d_6$) δ 10.97 (s, 1H), 8.30 (d, J=8.5 Hz, 1H), 8.02-7.83 (m, 2H), 7.73 (m, 1H), 7.63 (d, J=8.4 Hz, 1H), 7.50 (d, J=8.5 Hz, 1H), 7.26 (d, J=2.3 Hz, 1H), 7.13-7.11 (m, 1H), 5.43 (m, 1H), 5.07-5.04 (m, 2H), 4.39-4.36 (m, 1H), 4.26 (d, J=17.2 Hz, 1H), 4.14 (m, 1H), 4.03-3.66 (m, 6H), 3.20-3.00 (m, 1H), 2.90-2.86 (m, 2H), 2.64-2.55 (m, 1H), 2.43-2.19 (m, 3H), 2.03-1.92 (m, 1H); MS (ESI) m/z 559.2 $[M+1]^+$.

Example S143. 3-(5-(((3S,4R)-1-((8-Fluoro-2-((R)-tetrahydrofuran-3-yl)quinolin-6-yl)methyl)-4-methylpyrrolidin-3-yl)oxy)-1-oxoisoindolin-2-yl)piperidine-2,6-dione

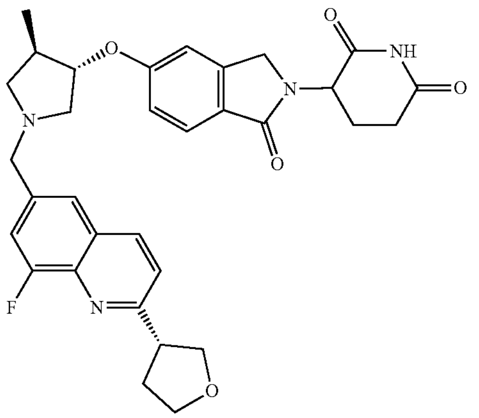 [SMILES: C[C@@H]1CN(Cc2cc(F)c3nc([C@H]4CCOC4)ccc3c2)C[C@H]1Oc1ccc2c(c1)CN(C1CCC(=O)NC1=O)C2=O]

6-Bromo-8-fluoro-2-(tetrahydrofuran-3-yl)quinoline. To a solution of (2-amino-5-bromo-3-fluorophenyl)methanol (800 mg, 3.64 mmol) and 1-(tetrahydrofuran-3-yl)ethan-1-one (1 g, 8.76 mmol) in toluene (10 mL) was added lithium tert-butoxide (580 mg, 7.24 mmol). The resulting mixture was stirred at 110° C. for 12 h under nitrogen. The mixture was filtered and the filtrate was concentrated. The residue was purified by reverse flash (20-100% acetonitrile+0.05% ammonium bicarbonate in water, over 30 min) to afford the title compound (400 mg, 1.35 mmol, 37% yield) as a yellow solid. MS (ESI) m/z 296.1 $[M+1]^+$.

(R)-8-Fluoro-2-(tetrahydrofuran-3-yl)-6-vinylquinoline. To a solution of 6-bromo-8-fluoro-2-(tetrahydrofuran-3-yl)quinoline (400 mg, 1.35 mmol) in 1,4-dioxane (5 mL) and water (1 mL) were added sodium carbonate (275 mg, 2.59 mmol), potassium vinyltrifluoroborate (350 mg, 2.61 mmol) and [1,1'-bis(diphenylphosphino)ferrocene]dichloropalladium(II) (80 mg, 0.11 mmol). The mixture was stirred at 80° C. for 2 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) and further purified by preparative chiral HPLC with the follow condition: Column: chiralpak IH-3, 4.6*50 mm, 3 μm; mobile phase A: hexane (0.1% diethylamine):isopropyl alcohol=85:15; flow rate: 1 mL/min; gradient: 0% B to 0% B. The fractions containing desired product were collected and evaporated under reduced pressure to afford the title compound (60 mg, 0.24 mmol, 18% yield) as a yellow oil. MS (ESI) m/z 244.2 $[M+1]^+$.

(R)-8-Fluoro-2-(tetrahydrofuran-3-yl)quinoline-6-carbaldehyde. To a solution of (R)-8-fluoro-2-(tetrahydrofuran-3-yl)-6-vinylquinoline (60 mg, 0.24 mmol) in tert-butanol (3 mL) and water (3 mL) were added potassium osmate (10 mg, 0.027 mmol), 4-methylmorpholine N-oxide (58 mg, 0.50 mmol), citric acid (104 mg, 0.54 mmol). The resulting mixture was stirred at room temperature for 4 h under nitrogen. Then sodium periodate (108 mg, 0.50 mmol) was added above mixture and stirred at room temperature for 1 h under nitrogen. The mixture was added saturated sodium bicarbonate to pH-7 and extracted with ethyl acetate. The extracts were washed with brine, dried over anhydrous sodium sulfate, filtered and concentrated. The residue was purified by silica gel column chromatography (0 to 50% ethyl acetate in petroleum ether) to afford the title compound (45 mg, 0.18 mmol, 75% yield) as a yellow solid. MS (ESI) m/z 246.2 $[M+1]^+$.

3-(5-(((3S,4R)-1-((8-Fluoro-2-((R)-tetrahydrofuran-3-yl)quinolin-6-yl)methyl)-4-methylpyrrolidin-3-yl)oxy)-1-oxoisoindolin-2-yl)piperidine-2,6-dione. To a solution of 3-(5-(((3S,4R)-4-methylpyrrolidin-3-yl)oxy)-1-oxoisoindolin-2-yl)piperidine-2,6-dione; 2,2,2-trifluoroacetic acid (80 mg, 0.17 mmol), (R)-8-fluoro-2-(tetrahydrofuran-3-yl)quinoline-6-carbaldehyde (46 mg, 0.19 mmol) and triethylamine (0.08 mL, 0.57 mmol) in dichloromethane (6 mL) was added sodium triacetoxyborohydride (150 mg, 0.71 mmol). The mixture was stirred at room temperature for 1 h under nitrogen. The resulting mixture was added little methanol and purified by silica gel chromatography (0-10% methanol in dichloromethane) and further by preparative-HPLC with the follow condition: Column: Sunfire prep C18 column, 30*150 mm, 5 μm; mobile phase A: water (0.1% formic acid), mobile phase B: acetonitrile; flow rate: 60 m/min; gradient: 2% B to 30% B in 7 min, 30% B; wave length: 254/220 nm; $RT_1$ (min): 5.8. The fractions containing desired product were collected and evaporated under reduced pressure to afford the title compound (25.7 mg, 0.045 mmol, 26% yield) as an off-white solid. $^1H$ NMR (400 MHz, methanol-$d_4$) δ 8.26 (m, 1H), 7.72-7.63 (m, 2H), 7.59-7.49 (m, 2H), 7.07-6.98 (m, 2H), 5.10-5.08 (m 1H), 4.61 (m, 1H), 4.49-4.33 (m, 2H), 4.20 (m, 1H), 4.13 (m, 1H), 4.02-4.00 (m, 1H), 3.98-3.77 (m, 4H), 3.20 (m, 1H), 3.10-2.82 (m, 3H), 2.76 (m, 1H), 2.57-2.37 (m, 3H), 2.37-2.23 (m, 2H), 2.19-2.09 (m, 1H), 1.22 (d, J=7.1 Hz, 3H); MS (ESI) m/z 573.2 $[M+1]^+$.

Example S144. 6-(((4R)-4-((2-(2,6-Dioxopiperidin-3-yl)-1-oxoisoindolin-5-yl)oxy)-3,3-difluoropyrrolidin-1-yl)methyl)quinoline-2-carbonitrile

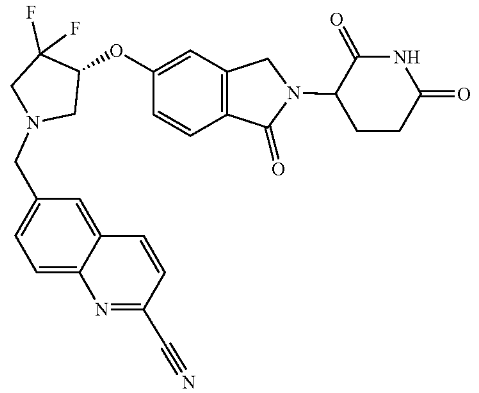 [SMILES: N#Cc1ccc2cc(CN3C[C@@H](Oc4ccc5c(c4)CN(C4CCC(=O)NC4=O)C5=O)C(F)(F)C3)ccc2n1]

6-(((4R)-4-((2-(2,6-Dioxopiperidin-3-yl)-1-oxoisoindolin-5-yl)oxy)-3,3-difluoropyrrolidin-1-yl)methyl)quinoline-2-carbonitrile. To a solution of 3-(5-(((R)-4,4-difluoropyrrolidin-3-yl)oxy)-1-oxoisoindolin-2-yl)piperidine-2,6-dione; 2,2,2-trifluoroacetic acid (120 mg, 0.25 mmol), 6-formylquinoline-2-carbonitrile (80 mg, 0.44 mmol) and triethylamine (0.15 mL, 1.08 mmol) in dichloromethane (6 mL) was added sodium triacetoxyborohydride (160 mg, 0.75 mmol). The resulting mixture was stirred at room temperature for 1 h under nitrogen. The mixture was added little methanol and purified by silica gel chromatography (0-10% methanol in dichloromethane) and further by preparative HPLC with the follow condition: Column: Sunfire prep C18 column, 30*150 mm, 5 μm; mobile phase A: water (0.1% formic acid), mobile phase B: acetonitrile; flow rate: 60 m/min; gradient: 28% B to 50% B in 9 min, 50% B; wave length: 254/220 nm; $RT_1$ (min): 9.3. The fractions containing desired product were collected and evaporated under reduced pressure to afford the title compound (30.4 mg, 0.057 mmol, 22% yield) as an off-white solid. $^1$H NMR (400 MHz, Methanol-$d_4$) δ 8.51 (d, J=8.4 Hz, 1H), 8.11 (d, J=8.7 Hz, 1H), 8.01 (d, J=1.9 Hz, 1H), 7.95-7.93 (m, 1H), 7.86 (d, J=8.4 Hz, 1H), 7.72 (d, J=8.4 Hz, 1H), 7.17 (d, J=2.1 Hz, 1H), 7.13 (m, 1H), 5.16-4.98 (m, 2H), 4.51-4.36 (m, 2H), 3.96 (s, 2H), 3.45-3.43 (m, 1H), 3.23-3.21 (m, 1H), 3.02-3.00 (m, 1H), 2.95-2.85 (m, 1H), 2.85-2.83 (m, 1H), 2.77-2.75 (m, 1H), 2.46 (m, 1H), 2.15 (m, 1H); MS (ESI) m/z 532.1 $[M+1]^+$.

Example S145. 6-(((3R,4R)-3-((2-(2,6-Dioxopiperidin-3-yl)-1-oxoisoindolin-5-yl)oxy)-4-fluoropyrrolidin-1-yl)methyl)quinoline-2-carbonitrile

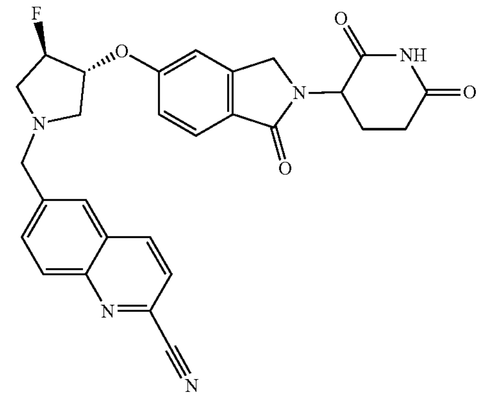 [SMILES: N#Cc1ccc2cc(CN3C[C@@H](F)[C@H](Oc4ccc5c(c4)CN(C4CCC(=O)NC4=O)C5=O)C3)ccc2n1]

6-(((3R,4R)-3-((2-(2,6-Dioxopiperidin-3-yl)-1-oxoisoindolin-5-yl)oxy)-4 fluoropyrrolidin-1-yl)methyl)quinoline-2-carbonitrile. To a stirred mixture of 3-[5-[(3R,4R)-4-fluoro-pyrrolidin-3-yl]oxy-1-oxo-isoindolin-2-yl]piperidine-2,6-dione; 2,2,2-trifluoroacetic acid (90 mg, 0.20 mmol), 6-formylquinoline-2-carbonitrile (36 mg, 0.20 mmol) and triethylamine (39 mg, 0.39 mmol) in dichloromethane (10 mL) was added sodium triacetoxyborohydride (160 mg, 0.75 mmol) in several portions and was stirred at room temperature for 2 h under nitrogen. The crude product was purified by silica gel chromatography (0-10% methanol in dichloromethane) firstly and further by preparative HPLC with the following conditions: Column: Sunfire prep C18 column, 30*150 mm, 5 μm; Mobile phase A: water (0.1% formic acid), Mobile phase B: acetonitrile; Flow rate: 60 mL/min; Gradient: 5% B to 35% B in 7 min, 35% B; Wave Length: 254/220 nm; $RT_1$ (min): 6.7. The fractions containing desired product were collected and evaporated under reduced pressure to afford the title compound (35 mg, 0.069 mmol, 35% yield) as a white solid. $^1$H NMR (400 MHz, Methanol-$d_4$) δ 8.54-8.46 (m, 1H), 8.09 (d, J=8.7 Hz, 1H), 8.00 (d, J=1.8 Hz, 1H), 7.95-7.93 (m, 1H), 7.85 (d, J=8.4 Hz, 1H), 7.72 (d, J=8.4 Hz, 1H), 7.15 (d, J=2.2 Hz, 1H), 7.09-7.07 (m, 1H), 5.23 (d, J=3.5 Hz, 1H), 5.15-4.99 (m, 2H), 4.51-4.36 (m, 2H), 3.99 (d, J=13.5 Hz, 1H), 3.94 (d, J=13.5 Hz, 1H), 3.43-3.41 (m, 1H), 3.11-3.04 (m, 1H), 3.02 (m, 1H), 2.89-2.69 (m, 3H), 2.54-2.38 (m, 1H), 2.14-2.08 (m, 1H); MS (ESI) m/z 514.2 $[M+1]^+$.

Example S146. 6-(((3R,4S)-3-((2-(2,6-Dioxopiperidin-3-yl)-1-oxoisoindolin-5-yl)oxy)-4-fluoropyrrolidin-1-yl)methyl)quinoline-2-carbonitrile

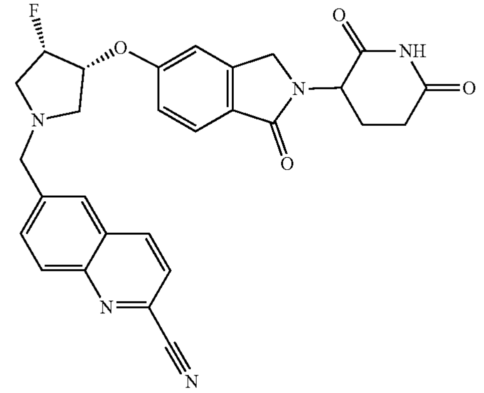 [SMILES: N#Cc1ccc2cc(CN3C[C@H](F)[C@H](Oc4ccc5c(c4)CN(C4CCC(=O)NC4=O)C5=O)C3)ccc2n1]

6-(((3R,4S)-3-((2-(2,6-Dioxopiperidin-3-yl)-1-oxoisoindolin-5-yl)oxy)-4-fluoropyrrolidin-1-yl)methyl)quinoline-2-carbonitrile. To the stirred solution of 3-(5-(((3R,4S)-4-fluoropyrrolidin-3-yl)oxy)-1-oxoisoindolin-2-yl)piperidine-2,6-dione; 2,2,2-trifluoroacetic acid (150 mg, 0.33 mmol), 6-formylquinoline-2-carbonitrile (60 mg, 0.33 mmol) and triethylamine (0.14 mL, 0.99 mmol) in dichloromethane (3 mL) was added sodium triacetoxyborohydride (200 mg, 0.94 mmol) under nitrogen. The resulting mixture was stirred for 12 h at room temperature. The mixture was purified by silica gel chromatography (0 to 10% methanol in dichloromethane) and further purified by preparative HPLC with following conditions: Column: XBridge Prep Phenyl OBD Column, 19*250 mm, 5 μm; Mobile Phase A: water (0.1% formic acid), Mobile Phase B: acetonitrile; Flow rate: 25 mL/min; Gradient: 20% B to 35% B in 10 min, 35% B; Wave Length: 254/220 nm; RT1 (min): 9.18. The pure fractions were collected and concentrated to afford the title compound (12.6 mg, 0.024 mmol, 7% yield) as a white solid. $^1$H NMR (400 MHz, DMSO-$d_6$) δ 10.95 (s, 1H), 8.65 (d, J=8.4 Hz, 1H), 8.12-8.02 (m, 3H), 7.93-7.90 (m, 1H), 7.62 (d, J=8.4 Hz, 1H), 7.25 (s, 1H), 7.13-7.11 (m, 1H), 5.49-5.33 (m, 1H), 5.09-5.01 (m, 2H), 4.40-4.23 (m, 2H), 3.98-3.90 (m, 2H), 3.15-2.86 (m, 5H), 2.67-2.56 (m, 1H), 2.43-2.32 (m, 1H), 2.07-1.95 (m, 1H); MS (ESI) m/z 514.1 $[M+1]^+$.

Example S147. 3-(5-(((3S,4R)-1-((8-Fluoro-2-(tetrahydro-2H-pyran-4-yl)quinolin-6-yl)methyl)-4-methylpyrrolidin-3-yl)oxy)-1-oxoisoindolin-2-yl)piperidine-2,6-dione

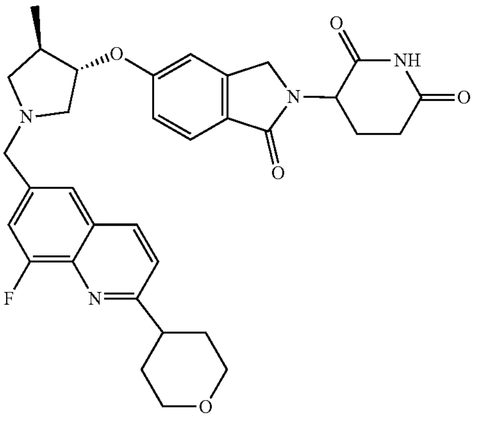 [SMILES: C[C@@H]1CN(Cc2cc(F)c3nc(C4CCOCC4)ccc3c2)C[C@H]1Oc1ccc2c(c1)CN(C1CCC(=O)NC1=O)C2=O]

3-(5-(((3S,4R)-1-((8-Fluoro-2-(tetrahydro-2H-pyran-4-yl)quinolin-6-yl)methyl)-4-methylpyrrolidin-3-yl)oxy)-1-oxoisoindolin-2-yl)piperidine-2,6-dione. To a solution of 3-(5-(((3S,4R)-4-methylpyrrolidin-3-yl)oxy)-1-oxoisoindolin-2-yl)piperidine-2,6-dione; 2,2,2-trifluoroacetic acid (100 mg, 0.22 mmol), 8-fluoro-2-(tetrahydro-2H-pyran-4-yl)quinoline-6-carbaldehyde (50 mg, 0.19 mmol) and triethylamine (0.16 mL, 1.15 mmol) in dichloromethane (6 mL) was added sodium triacetoxyborohydride (150 mg, 0.71 mmol). The resulting mixture was stirred at room temperature for 1 h under nitrogen. The mixture was added little methanol and purified by silica gel chromatography (0-10% methanol in dichloromethane) and further by preparative HPLC with the follow condition: Column: Sunfire prep C18 column, 30*150 mm, 5 μm; mobile phase A: water (0.1% formic acid), mobile phase B: acetonitrile; flow rate: 60 mL/min; gradient: 5% B to 27% B in 7 min, 27% B; wave length: 254/220 nm; $RT_1$ (min): 6.13. The fractions containing desired product were collected and evaporated under reduced pressure to afford the title compound (36.8 mg, 0.063 mmol, 29% yield) as an off-white solid. $^1H$ NMR (400 MHz, methanol-$d_4$) δ 8.25 (m, 1H), 7.72-7.62 (m, 2H), 7.53 (m, 2H), 7.07-6.98 (m, 2H), 5.09-5.07 (m, 1H), 4.61 (m, 1H), 4.48-4.34 (m, 2H), 4.13-4.04 (m, 2H), 3.94-3.81 (m, 2H), 3.62 (m, 2H), 3.21 (m, 2H), 3.03 (m, 1H), 2.99-2.92 (m, 1H), 2.89-2.86 (m, 1H), 2.82-2.71 (m, 1H), 2.56-2.36 (m, 2H), 2.34-2.25 (m, 1H), 2.18-2.10 (m, 1H), 2.01 (m, 2H), 1.89 (m, 2H), 1.22 (d, J=7.1 Hz, 3H); MS (ESI) m/z 587.2 $[M+1]^+$.

Example S148. 3-(5-(((3R,4S)-4-Fluoro-1-((2-((S)-tetrahydrofuran-3-yl)quinolin-6-yl)methyl)pyrrolidin-3-yl)oxy)-1-oxoisoindolin-2-yl)piperidine-2,6-dione

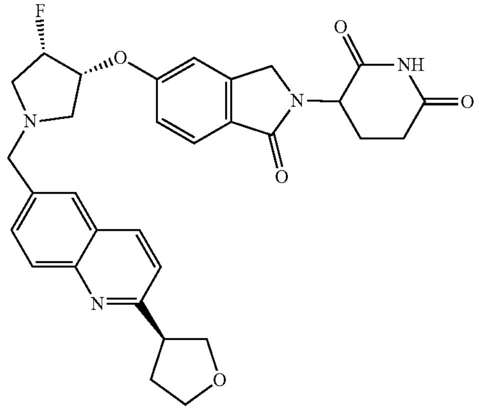 [SMILES: O=C1CCC(N2Cc3cc(O[C@@H]4CN(Cc5ccc6nc([C@@H]7CCOC7)ccc6c5)C[C@@H]4F)ccc3C2=O)C(=O)N1]

3-(5-(((3R,4S)-4-Fluoro-1-((2-((S)-tetrahydrofuran-3-yl)quinolin-6-yl)methyl)pyrrolidin-3-yl)oxy)-1-oxoisoindolin-2-yl)piperidine-2,6-dione. To a solution of (S)-2-(tetrahydrofuran-3-yl)quinoline-6-carbaldehyde (30 mg, 0.13 mmol), 3-(5-(((3R,4S)-4-fluoropyrrolidin-3-yl)oxy)-1-oxoisoindolin-2-yl)piperidine-2,6-dione (90 mg, 0.26 mmol) and triethylamine (31 mg, 0.31 mmol) in dichloromethane (5 mL) was added sodium triacetoxyborohydride (100 mg, 0.47 mmol) at room temperature. The mixture was stirred for 12 h at room temperature under nitrogen. The resulting mixture was concentrated. The residue was purified by silica gel chromatography (0 to 10% methanol in dichloromethane) and preparative-HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 2% B to 30% B in 7 min, 30% B; Wave Length: 254/220 nm; $RT_1$ (min): 6.5. The fractions containing desired product were collected and evaporated under reduced pressure to afford the title compound (20.9 mg, 0.037 mmol, 28% yield) as a white solid. $^1H$ NMR (400 MHz, DMSO-$d_6$) δ 10.96 (s, 1H), 8.29 (d, J=8.5 Hz, 1H), 7.96-7.83 (m, 2H), 7.72-7.70 (m, 1H), 7.62 (d, J=8.4 Hz, 1H), 7.49 (d, J=8.5 Hz, 1H), 7.26 (d, J=2.4 Hz, 1H), 7.12-7.10 (m, 1H), 5.42 (m, 1H), 5.07-5.03 (m, 2H), 4.39-4.37 (m, 1H), 4.26 (d, J=17.2 Hz, 1H), 4.14 (t, J=8.0 Hz, 1H), 4.01-3.69 (m, 6H), 3.20-2.82 (m, 5H), 2.59-2.57 (m, 1H), 2.36-2.31 (m, 2H), 2.30-2.21 (m, 1H), 2.02-1.94 (m, 1H); MS (ESI) m/z 559.2 $[M+1]^+$.

Example S149. 3-(5-(((3R,4R)-4-fluoro-1-((2-((S)-tetrahydrofuran-3-yl)quinolin-6-yl)methyl)pyrrolidin-3-yl)oxy)-1-oxoisoindolin-2-yl)piperidine-2,6-dione

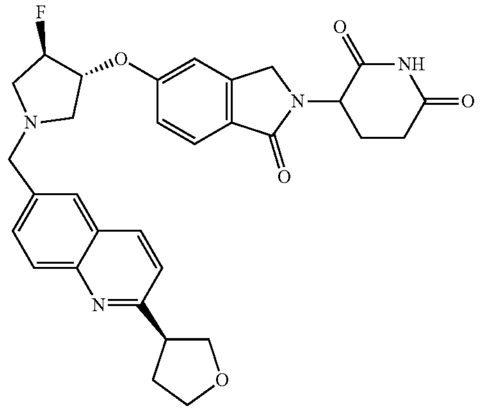 [SMILES: O=C1CCC(N2Cc3cc(O[C@@H]4CN(Cc5ccc6nc([C@@H]7CCOC7)ccc6c5)C[C@H]4F)ccc3C2=O)C(=O)N1]

3-(5-(((3R,4R)-4-Fluoro-1-((2-((S)-tetrahydrofuran-3-yl) quinolin-6-yl)methyl)pyrrolidin-3-yl)oxy)-1-oxoisoindolin-2-yl)piperidine-2,6-dione. To a stirred mixture of 3-[5-[(3R, 4R)-4-fluoropyrrolidin-3-yl] oxy-1-oxo-isoindolin-2-yl] piperidine-2,6-dione; 2,2,2-trifluoroacetic acid (90 mg, 0.20 mmol), 2-[(3S)-tetrahydrofuran-3-yl]quinoline-6-carbaldehyde (45 mg, 0.20 mmol) and triethylamine (39 mg, 0.39 mmol) in dichloromethane (10 mL) was added sodium triacetoxyborohydride (160 mg, 0.75 mmol) in several portions and the mixture was stirred at room temperature for 2 h under nitrogen. The mixture was concentrated and the residue was purified by silica gel chromatography (0-10% methanol in dichloromethane) and purified further by preparative HPLC with the following conditions: Column: Sunfire prep C18 column, 30*150 mm, 5 μm; Mobile Phase A: water (0.1% formic acid), Mobile Phase B: acetonitrile; Flow rate: 60 mL/min; Gradient: 5% B to 35% B in 7 min, 35% B; Wave Length: 254/220 nm. The fractions containing desired product were collected and evaporated under reduced pressure to afford the title compound (26.3 mg, 0.047 mmol, 24% yield) as a white solid. $^1H$ NMR (300 MHz, DMSO-$d_6$) δ 10.95 (s, 1H), 8.28 (d, J=8.5 Hz, 1H), 7.92 (d, J=8.6 Hz, 1H), 7.84 (s, 1H), 7.74-7.60 (m, 2H), 7.48 (d, J=8.4 Hz, 1H), 7.18 (s, 1H), 7.07-7.05 (m, 1H), 5.30-5.03 (m, 3H), 4.39 (d, J=17.4 Hz, 1H), 4.25-4.23 (m, 1H), 4.13 (m, 1H), 4.04-3.66 (m, 6H), 3.32-3.30 (m, 1H), 2.98-2.84 (m, 3H), 2.64-2.52 (m, 2H), 2.42-2.16 (m, 2H), 2.02-1.92 (m, 2H); MS (ESI) m/z 559.2 $[M+1]^+$.

Example S150. 3-(1-oxo-5-(((S)-2-oxo-1-((2-(tetrahydro-2H-pyran-4-yl)quinolin-6-yl)methylpyrrolidin-3-yl) oxy) isoindolin-2-yl)piperidine-2,6-dione

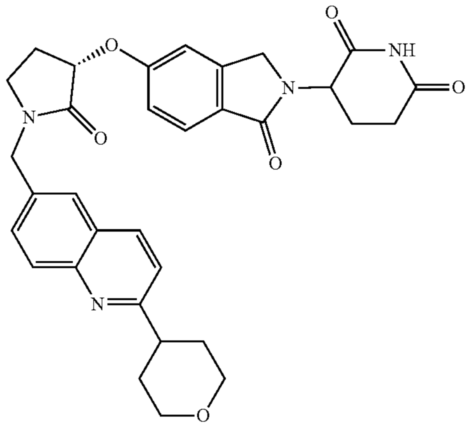 [SMILES: O=C1CCC(N2Cc3cc(O[C@H]4CCN(Cc5ccc6nc(C7CCOCC7)ccc6c5)C4=O)ccc3C2=O)C(=O)N1]

(R)-3-((Tert-butyldiphenylsilyl)oxy)-1-((2-(tetrahydro-2H-pyran-4-yl)quinolin-6-yl)methyl)pyrrolidin-2-one. To a stirred mixture of (R)-3-((tert-butyldiphenylsilyl)oxy)pyrrolidin-2-one (778 mg, 2.29 mmol) and 6-(chloromethyl)-2-(tetrahydro-2H-pyran-4-yl)quinolone (200 mg, 0.76 mmol) in DMF (20 mL) was added sodium hydride (60% dispersion in mineral oil, 55 mg, 1.37 mmol) and the mixture was stirred at 0° C. for 3 h under nitrogen. The resulting mixture was diluted with water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (147 mg, 0.26 mmol, 34% yield) as a white solid. MS (ESI) m/z 565.4 $[M+1]^+$.

(R)-3-hydroxy-1-((2-(tetrahydro-2H-pyran-4-yl) quinolin-6-yl)methyl)pyrrolidin-2-one. To a stirred mixture of (R)-3-((tert-butyldiphenylsilyl)oxy)-1-((2-(tetrahydro-2H-pyran-4-yl)quinolin-6-yl)methyl)pyrrolidin-2-one (147 mg, 0.26 mmol) in THF (10 mL) was added tetrabutylammonium fluoride (68 mg, 0.26 mmol) and the solution was stirred at 0° C. for 3 h under nitrogen. The solution was concentrated and the residue was purified by silica gel chromatography (0 to 30% ethyl acetate in petroleum ether) to afford the title compound (66 mg, 0.20 mmol, 78% yield) as a white solid. MS (ESI) m/z 327.2 $[M+1]^+$.

1-(4-Methoxybenzyl)-3-(1-oxo-5-(((S)-2-oxo-1-((2-(tetrahydro-2H-pyran-4-yl)quinolin-6-yl)methyl)pyrrolidin-3-yl)oxy)isoindolin-2-yl)piperidine-2,6-dione. To a stirred solution of (R)-3-hydroxy-1-((2-(tetrahydro-2H-pyran-4-yl) quinolin-6-yl)methyl)pyrrolidin-2-one (66 mg, 0.20 mmol) and 3-(5-hydroxy-1-oxo-isoindolin-2-yl)-1-[(4-methoxyphenyl)methyl]piperidine-2,6-dione (77 mg, 0.20 mmol) and triphenylphosphine (212 mg, 0.81 mmol) in dichloromethane (6 mL) was added a solution of di-tert-butyl (E)-diazene-1,2-dicarboxylate (234 mg, 0.81 mmol) in dichloromethane (6 mL) dropwise. Then the reaction mixture was stirred at 40° C. for 3 h under nitrogen. The resulting mixture was diluted with water and extracted with ethyl acetate. The extracts were washed with brine, dried over anhydrous sodium sulfate, filtered and concentrated. The residue was purified by silica gel chromatography (0 to 20% ethyl acetate in petroleum ether) to give the title compound (50 mg, 0.07 mmol, 36% yield) as a light-yellow solid. MS (ESI) m/z 689.2 $[M+1]^+$.

3-(1-Oxo-5-(((S)-2-oxo-1-((2-(tetrahydro-2H-pyran-4-yl) quinolin-6-yl)methyl)pyrrolidin-3-yl)oxy)isoindolin-2-yl) piperidine-2,6-dione. To a solution of 1-(4-methoxybenzyl)-3-(1-oxo-5-(((S)-2-oxo-1-((2-(tetrahydro-2H-pyran-4-yl) quinolin-6-yl)methyl)pyrrolidin-3-yl)oxy)isoindolin-2-yl) piperidine-2,6-dione (40 mg, 0.06 mmol) in TFA (4 mL) was added trifluoromethanesulfonic acid (0.5 mL, 5.66 mmol). The mixture was stirred at 60° C. for 12 h under nitrogen. The brown solution was concentrated under reduced pressure. The residue was diluted with water, then adjusted to pH 6-7 carefully with saturated sodium carbonate and filtered. The aqueous phase was purified by preparative HPLC with the following conditions: Column: Xselect CSH C18 OBD Column 30*150 mm 5 μm; Mobile Phase A: water (0.05% TFA), Mobile Phase B: ACETONITRILE; Flow rate: 60 mL/min; Gradient: 5% B to 25% B in 10 min, 25% B; Wave Length: 254/220 nm; $RT_1$ (min): 8. The fractions containing desired product were collected and evaporated under reduced pressure to afford the title compound (5.5 mg, 0.01 mmol, 17% yield) as a white solid. $^1H$ NMR (300 MHz, Methanol-$d_4$) δ 8.95 (m, 1H), 8.21-8.10 (m, 2H), 8.05-7.90 (m, 2H), 7.74 (d, J=8.4 Hz, 1H), 7.30 (s, 1H), 7.21 (d, J=8.7 Hz, 1H), 5.29 (m, 1H), 5.12-5.10 (m, 1H), 4.75 (m, 2H), 4.46 (d, J=4.3 Hz, 2H), 4.14-4.10 (m, 2H), 3.71-3.57 (m, 2H), 3.50 (m, 3H), 3.00-2.72 (m, 3H), 2.57-2.42 (m, 1H), 2.23-1.90 (m, 6H); MS (ESI) m/z 569.2 $[M+1]^+$.

Example S151. (S)-3-(5-(((S)-1-((8-Fluoro-2-(tetrahydro-2H-pyran-4-yl)quinazolin-6-yl)methyl)-pyrrolidin-3-yl)oxy)-1-oxoisoindolin-2-yl)piperidine-2,6-dione

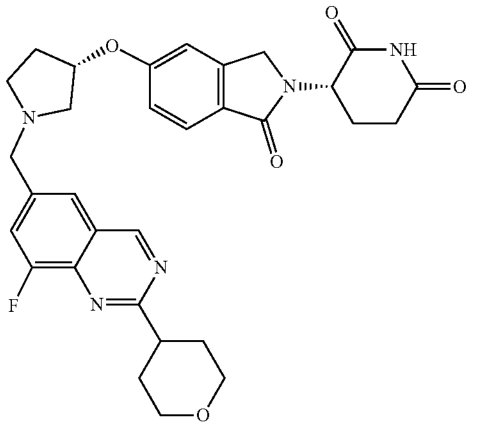 [SMILES: O=C1CC[C@H](N2Cc3cc(O[C@H]4CCN(Cc5cc(F)c6nc(C7CCOCC7)ncc6c5)C4)ccc3C2=O)C(=O)N1]

2-Chloro-8-fluoro-6-vinylquinazoline. The mixture of 6-bromo-2-chloro-8-fluoroquinazoline (6 g, 22.94 mmol), tributyl(vinyl)stannane (7.2 g, 22.71 mmol) and cesium fluoride (6 g, 39.47 mmol) in toluene (60 mL) was added tetrakis(triphenylphosphine)palladium (1.2 g, 1.04 mmol) under nitrogen. The resulting solution was stirred for 40 min at 100° C. under nitrogen. Most solution was removed and the residue was purified by silica gel column chromatography (0 to 10% ethyl acetate in petroleum ether) to afford title compound (2.6 g, 12.46 mmol, 54% yield) as an off-white solid. MS (ESI) m/z 209.1 $[M+1]^+$.

2-Chloro-8-fluoroquinazoline-6-carbaldehyde. To a stirred solution of 2-chloro-8-fluoro-6-vinylquinazoline (2.6 g, 12.46 mmol), 4-methylmorpholine N-oxide (2.92 g, 24.93 mmol) and critic acid (4.79 g, 24.93 mmol) in tert-butanol (30 mL) and water (30 mL) was added potassium osmate (830 mg, 2.49 mmol) at room temperature. The reaction was stirred for 4 h at room temperature. Then sodium periodate (8 g, 37.39 mmol) was added into the above mixture at 0° C. The mixture was stirred for 1 h at room temperature under nitrogen. The resulting mixture was added saturated sodium bicarbonate to pH~7 and extracted with ethyl acetate. The extracts were dried over anhydrous sodium sulfate, filtered and concentrated. The residue was purified by silica gel chromatography (0 to 50% ethyl acetate in petroleum ether) to afford title compound (1.2 g, 5.57 mmol, 45% yield) as an off-white solid. MS (ESI) m/z 211.1 $[M+1]^+$.

2-(3,6-Dihydro-2H-pyran-4-yl)-8-fluoroquinazoline-6-carbaldehyde. To a stirred solution of 2-chloro-8-fluoroquinazoline-6-carbaldehyde (600 mg, 2.85 mmol), 2-(3,6-dihydro-2H-pyran-4-yl)-4,4,5,5-tetramethyl-1,3,2-dioxaborolane (1.2 g, 5.71 mmol) and sodium carbonate (906 mg, 8.55 mmol) in 1,4-dioxane (15 mL) and water (1.5 mL) was added dichlorobis(triphenylphosphine)palladium (II) dichloromethane adduct (232 mg, 0.28 mmol) under nitrogen. The reaction was stirred for 2 h at 80° C. under nitrogen. Most solution was removed and the residue was purified by reverse phase flash (10-60% acetonitrile+0.05% ammonium bicarbonate in water, over 25 min) to give title compound (400 mg, 1.54 mmol, 54% yield) as an off-white solid. MS (ESI) m/z 259.1 $[M+1]^+$.

(8-Fluoro-2-(tetrahydro-2H-pyran-4-yl)quinazolin-6-yl) methanol and (8-fluoro-2-(tetrahydro-2H-pyran-4-yl)-1,2-dihydroquinazolin-6-yl)methanol. The solution of 2-(3,6-dihydro-2H-pyran-4-yl)-8-fluoroquinazoline-6-carbaldehyde (400 mg, 1.55 mmol) in ethanol (10 mL) was added palladium 10% on carbon (50 mg, wetted with ca. 55% water) under nitrogen. The reaction was stirred for 4 h at room temperature under hydrogen (~2 bar). The resulting mixture was filtered and the filtrate was concentrated to afford the mixture of title compound (290 mg, 1.10 mmol, 71% yield) as a yellow solid. MS (ESI) m/z 263.1 $[M+1]^+$.

8-Fluoro-2-(tetrahydro-2H-pyran-4-yl)quinazoline-6-carbaldehyde. A mixture of (8-fluoro-2-(tetrahydro-2H-pyran-4-yl)quinazolin-6-yl)methanol and (8-fluoro-2-(tetrahydro-2H-pyran-4-yl)-1,2-dihydroquinazolin-6-yl)methanol (290 mg, 1.10 mmol) in dichloromethane (5 mL) was added manganese dioxide (961 mg, 11.06 mmol) at room temperature. The reaction was stirred for 12 h at 50° C. under nitrogen. The resulting mixture was filtered and the filter cake was washed with dichloromethane. The filtrate was concentrated and the residue was purified by silica gel chromatography (30% to 100% ethyl acetate in petroleum ether) to afford title compound (160 mg, 0.61 mmol, 55% yield) as a yellow oil. MS (ESI) m/z 261.2 $[M+1]^+$.

(3S)-3-(5-(((3S)-1-((8-fluoro-2-(tetrahydro-2H-pyran-4-yl)-1,2-dihydroquinazolin-6-yl)methyl)pyrrolidin-3-yl) oxy)-1-oxoisoindolin-2-yl)piperidine-2,6-dione The mixture of 8-fluoro-2-(tetrahydro-2H-pyran-4-yl)quinazoline-6-carbaldehyde (120 mg, 0.46 mmol), (S)-3-(1-oxo-5-(((S)-pyrrolidin-3-yl)oxy)isoindolin-2-yl) piperidine-2,6-dione; 2,2,2-trifluoroacetic acid (480 mg, 1.23 mmol) and triethylamine; (92 mg, 0.92 mmol) and zinc chloride (0.7 M in THF, 0.1 mL, 0.7 mmol) in ethanol (3 mL) was added sodium cyanoborohydride (104 mg, 1.65 mmol) at room temperature. The reaction was stirred for 1 h at 80° C. under nitrogen. The resulting mixture was basified to pH~7 with saturated sodium bicarbonate and extracted with dichloromethane. The combined organic layers were washed with brine, dried over anhydrous sodium sulfate and concentrated to afford crude title compound (160 mg, 0.28 mmol, 60% yield) as a yellow solid. MS (ESI) m/z 576.3 $[M+1]^+$.

(3S)-3-(5-(((3S)-1-((8-Fluoro-2-(tetrahydro-2H-pyran-4-yl)-1,2-dihydroquinazolin-6-yl)methyl)pyrrolidin-3-yl)oxy)-1-oxoisoindolin-2-yl)piperidine-2,6-dione. To a solution of (3S)-3-(5-(((3S)-1-((8-fluoro-2-(tetrahydro-2H-pyran-4-yl)-1,2-dihydroquinazolin-6-yl)methyl)pyrrolidin-3-yl)oxy)-1-oxoisoindolin-2-yl)piperidine-2,6-dione (140 mg, 0.24 mmol) in dichloromethane (5 mL) was added manganese dioxide (200 mg, 2.30 mmol) and the reaction was stirred for 12 h at room temperature. The resulting mixture was filtered and the filter cake was washed with dichloromethane. The filtrate was concentrated under vacuum. The residue was purified by silica gel chromatography (0 to 10% methanol in dichloromethane) and further purified by preparative chiral HPLC with following condition: Column: CHIRALPAK IF, 2*25 cm, 5 μm; Mobile Phase A: tert-butyl methyl ether—HPLC, Mobile Phase B: ethanol:dichloromethane=1:1-HPLC; Flow rate: 20 mL/min; Gradient: 40% B to 40% B in 12.5 min; Wave Length: 220/254 nm; $RT_1$ (min): 9.016; $RT_2$ (min): 11.704; Sample Solvent: ethanol:dichloromethane=1:1; Injection Volume: 1 mL. The pure fractions were concentrated and further purified by preparative HPLC with next condition: Column: Xselect CSH C18 OBD Column 30*150 mm 5 μm; Mobile Phase A: water (0.1% formic acid), Mobile Phase B: acetonitrile; Flow rate: 60 mL/min; Gradient: 2% B to 20% B in 10 min, 20% B; Wave Length: 254 nm; $RT_1$ (min): 9.5. The fractions containing desired product were collected and evaporated under reduced pressure to afford the title compound (7.8 mg, 0.014 mmol, 6% yield) as a white solid. $^1H$ NMR (400 MHz, DMSO-$d_6$) δ 10.94 (s, 1H), 9.62 (d, J=1.5 Hz, 1H), 7.89 (s, 1H), 7.80 (dd, J=11.5, 1.6 Hz, 1H), 7.60 (d, J=8.4 Hz, 1H), 7.11 (d, J=2.1 Hz, 1H), 7.01 (dd, J=8.4, 2.2 Hz, 1H), 5.04 (m, 2H), 4.37 (d, J=17.2 Hz, 1H), 4.24 (d, J=17.2 Hz, 1H), 4.02-3.93 (m, 2H), 3.87-3.80 (m, 2H), 3.51 (m, 2H), 3.34-3.23 (m, 2H), 2.99 (dd, J=10.6, 6.1 Hz, 1H), 2.90 (m, 1H), 2.83-2.68 (m, 2H), 2.63-2.51 (m, 2H), 2.40-2.35 (m, 2H), 2.02-1.86 (m, 5H); MS (ESI) m/z 574.3 $[M+1]^+$.

Example S152. (S)-3-(5-(((S)-1-((5-Fluoro-2-(tetrahydro-2H-pyran-4-yl)quinazolin-6-yl)methyl)-pyrrolidin-3-yl)oxy)-1-oxoisoindolin-2-yl)piperidine-2,6-dione

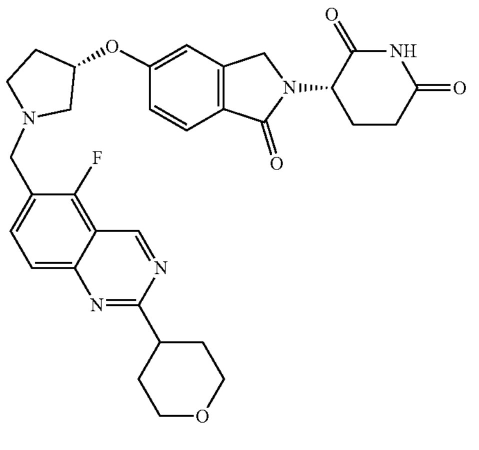 [SMILES: O=C1CC[C@H](N2Cc3cc(O[C@H]4CCN(Cc5ccc6nc(C7CCOCC7)ncc6c5F)C4)ccc3C2=O)C(=O)N1]

N-(6-amino-3-bromo-2-fluorobenzyl)tetrahydro-2H-pyran-4-carboxamide. A solution of tetrahydro-2H-pyran-4-carboxylic acid (2 g, 15.37 mmol) in thionyl chloride (10 mL) was stirred at 80° C. for 2 h under nitrogen. The solution was concentrated to afford the crude tetrahydro-2H-pyran-4-carbonyl chloride, which was used for the next step directly. To a stirred solution of tetrahydro-2H-pyran-4-carbonyl chloride (5.2 g, 34.99 mmol) and triethylamine (16.7 g, 167.01 mmol) in dichloromethane (50 mL) was added 2-(aminomethyl)-4-bromo-3-fluoroaniline (2 g, 9.13 mmol) at 0° C. and the mixture was stirred at this temperature for 30 min. The above mixture was stirred at room temperature for 3 h under nitrogen. The reaction mixture was concentrated to afford the crude title compound. MS (ESI) m/z 331.1 $[M+1]^+$.

6-Bromo-5-fluoro-2-(tetrahydro-2H-pyran-4-yl)-1,4-dihydroquinazoline. A solution of N-(6-amino-3-bromo-2-fluorobenzyl)tetrahydro-2H-pyran-4-carboxamide (1.5 g, 4.53 mmol) in phosphorus oxychloride (10 mL) was stirred at 80° C. for 2 h under nitrogen. The reaction mixture was concentrated. The residue was acidified to pH~8 with saturated sodium bicarbonate and extracted with ethyl acetate. The extracts were washed with brine, dried over anhydrous sodium sulfate, filtered and concentrated to afford the crude title compound (1.2 g, 3.83 mmol, 84% yield). MS (ESI) m/z 313.1 $[M+1]^+$.

6-Bromo-5-fluoro-2-(tetrahydro-2H-pyran-4-yl)quinazoline. To a stirred solution of 6-bromo-5-fluoro-2-(tetrahydro-2H-pyran-4-yl)-1,4-dihydroquinazoline (1.2 g, 3.83 mmol) in dichloromethane (20 mL) was added manganese dioxide (6.67 g, 76.64 mmol). The mixture stirred at room temperature for 12 h under nitrogen. The resulting mixture was filtered and the filtrate was concentrated to afford the title compound (1 g, 3.21 mmol, 84% yield) as a light-yellow solid. MS (ESI) m/z 311.1 $[M+1]^+$.

5-Fluoro-2-(tetrahydro-2H-pyran-4-yl)-6-vinylquinazoline. To a stirred solution of 6-bromo-5-fluoro-2-(tetrahydro-2H-pyran-4-yl)quinazoline (900 mg, 2.89 mmol) and potassium vinyltrifluoroborate (465 mg, 3.47 mmol) in 1,4-dioxane (10 mL) and water (1 mL) were added tetrakis (triphenylphosphine)palladium (334 mg, 0.29 mmol) and cesium carbonate (1880 mg, 5.78 mmol). The above mixture was stirred at 80° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound. (600 mg, 2.32 mmol, 80% yield) as a light-yellow solid. MS (ESI) m/z 259.0 $[M+1]^+$.

5-Fluoro-2-(tetrahydro-2H-pyran-4-yl)quinazoline-6-carbaldehyde. To a stirred solution of 5-fluoro-2-(tetrahydro-2H-pyran-4-yl)-6-vinylquinazoline (300 mg, 1.16 mmol) in tert-butanol (8 mL) and water (8 mL) were added 4-methylmorpholin4-oxide (135 mg, 1.16 mmol), potassium osmate (42 mg, 0.11 mmol) and citric acid (223 mg, 1.16 mmol). The above mixture was stirred at room temperature for 3 h under nitrogen. Then the mixture was added sodium periodate (248 mg, 1.16 mmol) and stirred for another 1 h. The resulting mixture was added saturated sodium bicarbonate to pH~7 and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (230 mg, 0.88 mmol, 76% yield) as a light-yellow oil. MS (ESI) m/z 261.1 $[M+1]^+$.

(S)-3-(5-(((S)-1-((5-Fluoro-2-(tetrahydro-2H-pyran-4-yl) quinazolin-6-yl)methyl)pyrrolidin-3-yl)oxy)-1-oxoisoindolin-2-yl)piperidine-2,6-dione. To a solution of 5-fluoro-2-(tetrahydro-2H-pyran-4-yl)quinazoline-6-carbaldehyde (100 mg, 0.38 mmol) and (S)-3-(5-(((S)-112-pyrrolidin-3-yl)oxy)-1-oxoisoindolin-2-yl)piperidine-2,6-dione; 2,2,2-trifluoroacetic acid (204 mg, 0.46 mmol) in dichloromethane (1 mL) were added sodium triacetoxyborohydride (325 mg, 1.53 mmol) and triethylamine (144 mg, 1.43 mmol). The mixture was stirred for 16 h at room temperature under nitrogen. The resulting mixture was concentrated. The residue was purified by silica gel chromatography (0 to 10% methanol in dichloromethane) and preparative chiral HPLC further with the following conditions: Column: CHIRALPAK IF-3, 4.6*50 mm; 3 um; Mobile Phase A: tert-butyl methyl ether: (ethanol:dichloromethane=1:1)=20:80; Flow rate: 1 mL/min; Gradient: 0% B to 0% B; Injection Volume: 5 ul. The fractions containing desired product were collected and evaporated under reduced pressure to afford the title compound (38.1 mg, 0.07 mmol, 17% yield) as a brown solid. $^1$H NMR (300 MHz, Methanol-$d_4$) δ 9.72 (s, 1H), 8.10 (t, J=8.3 Hz, 1H), 7.90 (d, J=8.8 Hz, 1H), 7.71 (d, J=8.4 Hz, 1H), 7.28-7.01 (m, 2H), 5.27 (m, 1H), 5.11-5.09 (m, 1H), 4.57 (s, 2H), 4.44 (d, J=4.6 Hz, 2H), 4.15-4.01 (m, 2H), 3.76-3.49 (m, 5H), 3.44-3.32 (m, 2H), 2.97-2.72 (m, 2H), 2.57-2.40 (m, 2H), 2.34-2.22 (m, 1H), 2.20-2.00 (m, 5H); MS (ESI) m/z 574.2 [M+1]$^+$.

Example S153. (S)-3-(5-(((S)-1-((8-Chloro-2-morpholinoquinazolin-6-yl)methyl)pyrrolidin-3-yl)oxy)-1-oxoisoindolin-2-yl)piperidine-2,6-dione

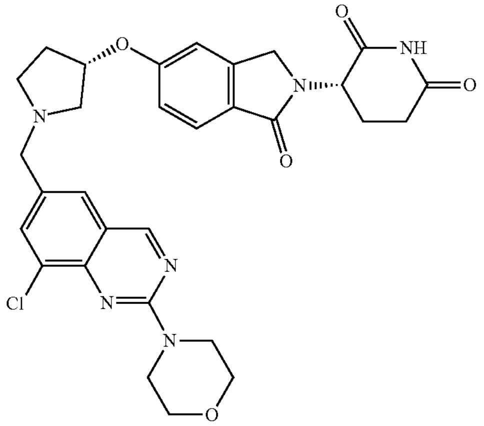 [SMILES: O=C1CC[C@H](N2Cc3cc(O[C@H]4CCN(Cc5cc(Cl)c6nc(N7CCOCC7)ncc6c5)C4)ccc3C2=O)C(=O)N1]

6-Bromo-8-chloroquinazolin-2(1H)-one. To a solution of 2-amino-5-bromo-3-chlorobenzaldehyde (500 mg, 2.13 mmol) and urea (5 g, 83.25 mmol) in NMP (20 mL) was stirred at 160° C. for 1 h under nitrogen. The mixture was added water and filtered. The filter cake was the title compound (330 mg, 1.27 mmol, 60% yield) as yellow solid. MS (ESI) m/z 258.9 [M+1]$^+$.

6-Bromo-2,8-dichloroquinazoline. To a solution of 6-bromo-8-chloroquinazolin-2(1H)-one (320 mg, 1.23 mmol) in phosphorus oxychloride (10 mL) was stirred at 120° C. for 30 min under nitrogen. The mixture was concentrated. The residue was added saturated sodium bicarbonate to PH~7 and extracted with dichloromethane. The extracts were washed with brine, dried over anhydrous sodium sulfate, filtered and concentrated to afford the title compound (210 mg, 0.75 mmol, 61% yield) as a yellow solid. MS (ESI) m/z 278.9 [M+3]$^+$.

4-(6-Bromo-8-chloroquinazolin-2-yl)morpholine. To a solution of 6-bromo-2,8-dichloro-quinazoline (190 mg, 0.68 mmol), morpholine (120 mg, 1.38 mmol) and potassium carbonate (285 mg, 2.07 mmol) in acetonitrile (10 mL) was stirred at 70° C. for 2 h under nitrogen. The mixture was filtered and the filtrate was concentrated. The crude product was purified by reverse phase flash (10-40% acetonitrile+0.05% ammonium bicarbonate in water, over 25 min) to give the title compound (180 mg, 0.55 mmol, 80% yield) as a yellow solid. MS (ESI) m/z 328.10 [M+1]$^+$.

4-(8-Chloro-6-vinylquinazolin-2-yl)morpholine. To a solution of 4-(6-bromo-8-chloro-quinazolin-2-yl)morpholine (160 mg, 0.49 mmol), potassium vinyltrifluoroborate (131 mg, 0.97 mmol) and sodium carbonate (104 mg, 0.98 mmol) in 1,4-dioxane (5 mL) and water (1 mL) was added [1,1'-bis(diphenylphosphino)ferrocene]dichloropalladium (II) (40 mg, 0.05 mmol). The resulting mixture was stirred at 80° C. for 2 h under nitrogen. The mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (130 mg, 0.47 mmol, 97% yield) as yellow solid. MS (ESI) m/z 276.2 [M+1]$^+$.

8-Chloro-2-morpholinoquinazoline-6-carbaldehyde. To a solution of 4-(8-chloro-6-vinylquinazolin-2-yl)morpholine (115 mg, 0.42 mmol) in tert-butanol (3 mL) and water (3 mL) were added potassium osmate (15 mg, 0.04 mmol), 4-methylmorpholine N-oxide (98 mg, 0.84 mmol) and citric acid (176 mg, 0.84 mmol). The resulting mixture was stirred at room temperature for 4 h under nitrogen. Then sodium periodate (270 mg, 1.25 mmol) was added to the above mixture and stirred at room temperature for 1 h under nitrogen. The mixture was added saturated sodium bicarbonate to PH~7 and extracted with ethyl acetate. The extracts were washed with brine, dried over anhydrous sodium sulfate, filtered and concentrated. The residue was concentrated and the residue was purified by silica gel chromatography (0 to 30% ethyl acetate in petroleum ether) to afford the title compound (78 mg, 0.28 mmol, 67% yield) as a yellow solid. MS (ESI) m/z 278.2 [M+1]$^+$.

Tert-butyl (S)-5-amino-4-(5-(((S)-1-((8-chloro-2-morpholinoquinazolin-6-yl)methyl)pyrrolidin-3-yl)oxy)-1-oxoisoindolin-2-yl)-5-oxopentanoate. A solution of 8-chloro-2-morpholinoquinazoline-6-carbaldehyde (66 mg, 0.24 mmol), tert-butyl (S)-5-amino-5-oxo-4-(1-oxo-5-(((S)-pyrrolidin-3-yl)oxy)isoindolin-2-yl)pentanoate (acetic acid salt, 115 mg, 0.25 mmol) and acetic acid (0.1 mL) in THF (15 mL) was stirred for 1 h at room temperature. The above mixture was added sodium triacetoxyborohydride (150 mg, 0.71 mmol) in several portions at 0° C. The mixture was stirred for 16 h at room temperature under nitrogen and concentrated. The residue was purified by reverse phase flash (10-40% acetonitrile+0.05% TFA in water, over 25 min) to afford the title compound (160 mg, 0.24 mmol, 101% yield) as a light-yellow solid. MS (ESI) m/z 665.2 [M+1]$^+$.

(S)-3-(5-(((S)-1-((8-Chloro-2-morpholinoquinazolin-6-yl)methyl)pyrrolidin-3-yl)oxy)-1-oxoisoindolin-2-yl)piperidine-2,6-dione. A solution of tert-butyl (S)-5-amino-4-(5-(((S)-1-((8-chloro-2-morpholinoquinazolin-6-yl)methyl) pyrrolidin-3-yl)oxy)-1-oxoisoindolin-2-yl)-5-oxopentanoate; 2,2,2-trifluoroacetic acid (160 mg, 0.21 mmol) and benzenesulfonic acid (100 mg, 0.63 mmol) in acetonitrile (15 mL) was stirred at 60° C. for 16 h under nitrogen. The resulting solution was added saturated sodium bicarbonate to pH~7 and extracted with chloroform. The extracts were washed with saturated sodium bicarbonate, brine, dried over anhydrous sodium sulfate, filtered and concentrated. The residue was purified by silica gel chromatography (0-10% methanol in dichloromethane) and further purified by preparative Chiral HPLC with the following conditions: Column: CHIRALPAK IF, 2*25 cm, 5 μm; Mobile Phase A: tert-butyl methyl ether-HPLC, Mobile Phase B: ethanol:dichloromethane=1:1; Flow rate: 20 mL/min; Gradient: 50% B to 50% B in 17 min; Wave Length: 254/220 nm; $RT_1$ (min): 11.434; $RT_2$ (min): 14.685; Sample Solvent: ethanol:dichloromethane=1:1; Injection Volume: 1.4 mL; Number of Runs: 4. The fractions containing desired product were collected and evaporated under reduced pressure to afford the title compound (29.8 mg, 0.05 mmol, 24% yield) as a light-yellow solid. $^1H$ NMR (400 MHz, DMSO-$d_6$) δ 10.96 (s, 1H), 9.26 (s, 1H), 7.88 (d, J=1.8 Hz, 1H), 7.76 (d, J=1.8 Hz, 1H), 7.60 (d, J=8.4 Hz, 1H), 7.11 (d, J=2.2 Hz, 1H), 7.00 (dd, J=8.4, 2.2 Hz, 1H), 5.03 (m, 2H), 4.37 (d, J=17.2 Hz, 1H), 4.24 (d, J=17.2 Hz, 1H), 3.88 (m, 4H), 3.74-3.63 (m, 6H), 2.99-2.83 (m, 2H), 2.80-2.66 (m, 3H), 2.63-2.54 (m, 1H), 2.44-2.29 (m, 2H), 1.97 (m, 1H), 1.89-1.75 (m, 1H). MS (ESI) m/z 591.1 $[M+1]^+$.

Example S154. 3-(5-(((3S,4R)-4-Methyl-1-((2-((S)-tetrahydrofuran-3-yl)quinolin-6-yl)methyl)pyrrolidin-3-yl)oxy)-1-oxoisoindolin-2-yl)piperidine-2,6-dione

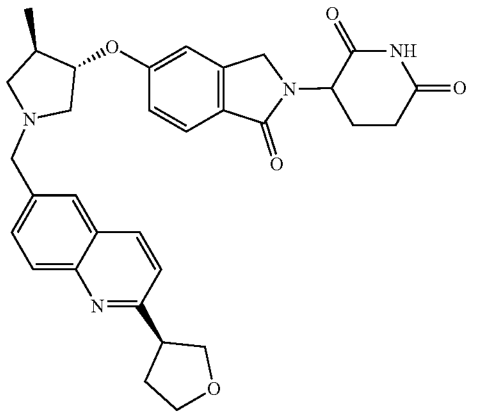 [SMILES: C[C@@H]1CN(Cc2ccc3nc([C@@H]4CCOC4)ccc3c2)C[C@H]1Oc1ccc2c(c1)CN(C1CCC(=O)NC1=O)C2=O]

3-(5-(((3S,4R)-4-Methyl-1-((2-((S)-tetrahydrofuran-3-yl) quinolin-6-yl)methyl)pyrrolidin-3-yl)oxy)-1-oxoisoindolin-2-yl)piperidine-2,6-dione. To a solution of 3-(5-(((3S,4R)-4-methylpyrrolidin-3-yl)oxy)-1-oxoisoindolin-2-yl)piperidine-2,6-dione; 2,2,2-trifluoroacetic acid (90 mg, 0.20 mmol), (S)-2-(tetrahydrofuran-3-yl)quinoline-6-carbaldehyde (40 mg, 0.18 mmol) and triethylamine (0.08 mL, 0.57 mmol) in dichloromethane (6 mL) was added sodium triacetoxyborohydride (150 mg, 0.71 mmol). The resulting mixture was stirred at room temperature for 1 h under nitrogen. The mixture was added little methanol and purified by silica gel chromatography (0-10% methanol in dichloromethane) and further by preparative-HPLC with the following conditions: Column: sunfire prep C18 column, 30*150 mm, 5 μm; mobile phase A: water (0.1% formic acid), mobile phase B: acetonitrile; flow rate: 60 mL/min; gradient: 5% B to 30% B in 7 min, 30% B; wave length: 254/220 nm; $RT_1$ (min): 5.5. The fractions containing desired product were collected and evaporated under reduced pressure to afford the title compound (36.8 mg, 0.066 mmol, 33% yield) as an off-white solid. $^1H$ NMR (400 MHz, Methanol-$d_4$) δ 8.30-8.22 (m, 1H), 8.02 (d, J=8.7 Hz, 1H), 7.92 (t, J=1.6 Hz, 1H), 7.80-7.78 (m, 1H), 7.70-7.68 (m, 1H), 7.52 (d, J=8.6 Hz, 1H), 7.09-6.99 (m, 2H), 5.10-5.08 (m, 1H), 4.74 (m, 1H), 4.49-4.40 (m, 2H), 4.27-4.15 (m, 3H), 4.12 (m, 1H), 4.02-4.00 (m, 1H), 3.94 (m, 1H), 3.80 (m, 1H), 3.46-3.44 (m, 1H), 3.38 (m, 1H), 3.31-3.21 (m, 1H), 2.96-2.82 (m, 1H), 2.82-2.71 (m, 1H), 2.65 (m, 2H), 2.54-2.37 (m, 2H), 2.35-2.22 (m, 1H), 2.14 (m, 1H), 1.24 (d, J=6.8 Hz, 3H); MS (ESI) m/z 555.2 $[M+1]^+$.

Example S155. 3-(5-(((R)-4,4-Difluoro-1-((2-((S)-tetrahydrofuran-3-yl)quinolin-6-yl)methyl)pyrrolidin-3-yl)oxy)-1-oxoisoindolin-2-yl)piperidine-2,6-dione

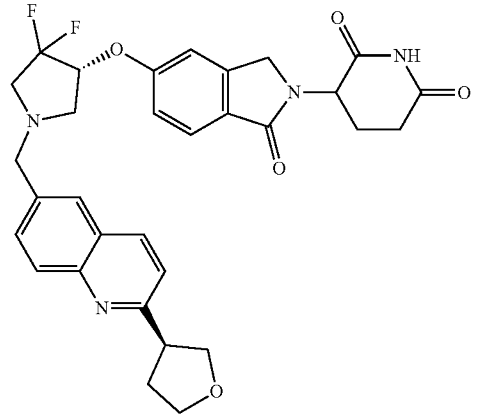 [SMILES: O=C1CCC(N2Cc3cc(O[C@@H]4CN(Cc5ccc6nc([C@@H]7CCOC7)ccc6c5)CC4(F)F)ccc3C2=O)C(=O)N1]

3-(5-(((R)-4,4-Difluoro-1-((2-((S)-tetrahydrofuran-3-yl) quinolin-6-yl)methyl)pyrrolidin-3-yl)oxy)-1-oxoisoindolin-2-yl)piperidine-2,6-dione. To a solution of 3-(5-(((R)-4,4-difluoropyrrolidin-3-yl)oxy)-1-oxoisoindolin-2-yl) piperidine-2,6-dione; 2,2,2-trifluoroacetic acid (90 mg, 0.19 mmol), (S)-2-(tetrahydrofuran-3-yl)quinoline-6-carbaldehyde (40 mg, 0.18 mmol) and triethylamine (0.08 mL, 0.57 mmol) in dichloromethane (5 mL) was added sodium triacetoxyborohydride (150 mg, 0.71 mmol). The resulting mixture was stirred at room temperature for 1 h under nitrogen. The mixture was added little methanol and purified by silica gel chromatography (0-10% methanol in dichloromethane) and further by preparative-HPLC with the with the following conditions: Column: sunfire prep C18 column, 30*150 mm, 5 μm; mobile phase A: water (0.1% formic acid), mobile phase B: acetonitrile; flow rate: 60 mL/min; gradient: 15% B to 45% B in 7 min, 45% B; wave length: 254/220 nm; $RT_1$ (min): 7.1. The fractions containing desired product were collected and evaporated under reduced pressure to afford the title compound (11.7 mg, 0.02 mmol, 11% yield) as an off-white solid. $^1H$ NMR (400 MHz, Methanol-$d_4$) δ 8.27 (d, J=8.5 Hz, 1H), 7.99 (d, J=8.7 Hz, 1H), 7.85 (d, J=1.9 Hz, 1H), 7.78-7.76 (m, 1H), 7.72 (d, J=8.4 Hz, 1H), 7.50 (d, J=8.6 Hz, 1H), 7.17 (t, J=2.4 Hz, 1H), 7.12 (m, 1H), 5.11-5.09 (m, 1H), 5.06-4.97 (m, 1H), 4.45 (m, 1H), 4.21 (m, 1H), 4.13 (m, 1H), 4.02-4.00 (m, 1H), 3.99-3.88 (m, 3H), 3.88-3.73 (m, 1H), 3.48-3.39 (m, 1H), 3.21-3.19 (m, 1H), 3.06-2.90 (m, 1H), 2.88-2.74 (m, 3H), 2.55-2.38 (m, 2H), 2.29 (m, 1H), 2.15 (m, 1H); MS (ESI) m/z 577.2 $[M+1]^+$.

Example S156. (R)-3-(5-(((S)-1-((2-Morpholinoquinazolin-6-yl)methyl)pyrrolidin-3-yl)oxy)-1-oxoisoindolin-2-yl)piperidine-2,6-dione

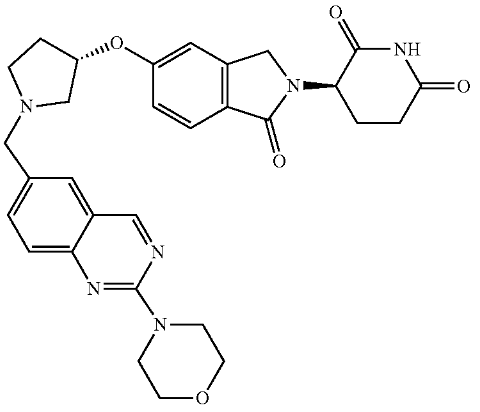 [SMILES: O=C1CC[C@@H](N2Cc3cc(O[C@H]4CCN(Cc5ccc6nc(N7CCOCC7)ncc6c5)C4)ccc3C2=O)C(=O)N1]

(R)-3-(5-(((S)-1-((2-Morpholinoquinazolin-6-yl)methyl)pyrrolidin-3-yl)oxy)-1-oxoisoindolin-2-yl)piperidine-2,6-dione. To a stirred solution of 2-morpholino quinazoline-6-carbaldehyde (100 mg, 0.41 mmol), 3-(1-oxo-5-(((S)-pyrrolidin-3-yl) oxy)isoindolin-2-yl)piperidine-2,6-dione; 2,2,2-trifluoroacetic acid (220 mg, 0.5 mmol), triethylamine (1.1 mL, 0.82 mmol) in dichloromethane (10 mL) pre-stirred for 15 min was added sodium triacetoxyborohydride (348 mg, 1.64 mmol) at 0° C. and the solution was stirred at room temperature for 12 h under nitrogen. The resulting solution was purified by silica gel chromatography (0 to 5% methanol in dichloromethane) and further by preparative chiral HPLC with the following conditions: Column: Chiralpak IF-3, 4.6*50 mm; 3 µm; mobile phase A: tert-butyl methyl ether: (ethanol:dichloromethane=1:1)=20:80; flow rate: 1 mL/min; gradient: 0% B to 0% B; injection volume: 5 mL. The fractions containing desired product were collected and evaporated under reduced pressure to afford the title compound (28.1 mg, 0.05 mmol, 12% yield) as a yellow solid. $^{1}$H NMR (300 MHz, DMSO-$d_6$) δ 9.20 (s, 1H), 7.83-7.70 (m, 2H), 7.62 (d, J=8.4 Hz, 1H), 7.50 (d, J=8.6 Hz, 1H), 7.11 (d, J=2.2 Hz, 1H), 7.01 (dd, J=8.4, 2.2 Hz, 1H), 5.04 (m, 2H), 4.45-4.17 (m, 2H), 3.88-3.62 (m, 10H), 3.05-2.61 (m, 5H), 2.57 (m, 1H), 2.37 (m, 2H), 2.05-1.77 (m, 2H); MS (ESI) m/z 557.2 $[M+1]^+$.

Example S157. (S)-3-(5-(((S)-1-((7-Fluoro-2-morpholinoquinazolin-6-yl)methyl)pyrrolidin-3-yl)oxy)-1-oxoisoindolin-2-yl)piperidine-2,6-dione

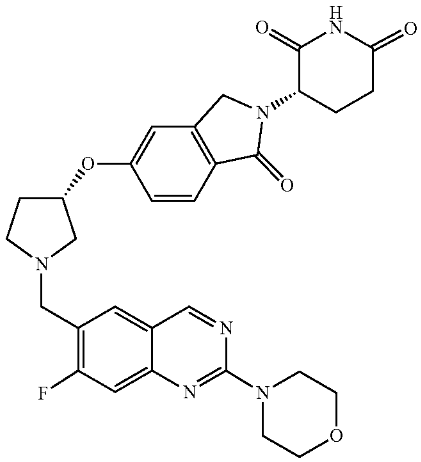 [SMILES: O=C1CC[C@H](N2Cc3cc(O[C@H]4CCN(Cc5cc6cnc(N7CCOCC7)nc6cc5F)C4)ccc3C2=O)C(=O)N1]

Tert-butyl (2-amino-5-bromo-4-fluorobenzyl)carbamate. To a stirred solution of 2-amino-5-bromo-4-fluorobenzonitrile (3 g, 13.95 mmol) in methanol (15 mL) were added di-tert-butyl dicarbonate (6.12 g, 28.04 mmol) and nickel chloride hexahydrate (3.32 g, 13.95 mmol) at 0° C. Then sodium borohydride (3.7 g, 98.85 mmol) was added in small portions over 30 min at 0° C. The resulting reaction mixture was allowed to warm to room temperature and was stirred for 1 h. The resulting mixture was added saturated sodium bicarbonate and extracted with ethyl acetate. The extracts were washed with brine, dried over anhydrous sodium sulfate, filtered and concentrated to afford title compound (2 g, 6.26 mmol, 45% yield) as a yellow solid. MS (ESI) m/z 319.0 $[M+1]^+$.

2-(Aminomethyl)-4-bromo-5-fluoroaniline. The solution of tert-butyl (2-amino-5-bromo-4-fluorobenzyl)carbamate (2 g, 6.26 mmol) in 1,4-dioxane (15 mL) was added hydrogen chloride (4M in 1.4-dioxane, 30 mL) at 0° C. The reaction was stirred for 12 h at room temperature. The resulting mixture was concentrated to afford title compound (1.10 g, 5.02 mmol, 80% yield) as a yellow solid. MS (ESI) m/z 217.0 $[M+1]^+$.

6-Bromo-7-fluoro-2-morpholino-1,2,3,4-tetrahydroquinazolin-2-ol. To a solution of 2-(aminomethyl)-4-bromo-5-fluoroaniline; dihydrochloride (800 mg, 2.74 mmol) in dichloromethane (10 mL) was added a solution of morpholine-4-carbonyl chloride (409 mg, 2.74 mmol) and triethylamine (1.67 mL, 12.01 mmol) in dichloromethane dropwise at 0° C. The reaction was stirred for 1 h at room temperature. The resulting mixture was diluted with saturated sodium bicarbonate and extracted with ethyl acetate. The combined organic layers were washed with brine, dried over anhydrous sodium sulfate and concentrated under vacuum. The residue was purified by silica gel chromatography (30% to 100% ethyl acetate in petroleum ether) to afford title compound (560 mg, 1.69 mmol, 62% yield) as a yellow solid. MS (ESI) m/z 331.9 $[M+1]^+$.

4-(6-Bromo-7-fluoro-1,4-dihydroquinazolin-2-yl)morpholine. The solution of 6-bromo-7-fluoro-2-morpholino-1,2,3,4-tetrahydroquinazolin-2-ol (550 mg, 1.66 mmol) in phosphorus oxychloride (5 mL) was stirred for 30 min at 80° C. The resulting mixture was concentrated. The residue was basified to pH~8 with saturated sodium carbonate and extracted with ethyl acetate. The combined organic layers were washed with brine, dried over anhydrous sodium sulfate and concentrated to afford title compound (380 mg, 1.21 mmol, 73% yield) as a yellow solid. MS (ESI) m/z 313.9 $[M+1]^+$.

4-(6-Bromo-7-fluoroquinazolin-2-yl)morpholine. A solution of 4-(6-bromo-7-fluoro-1,4-dihydroquinazolin-2-yl) morpholine (380 mg, 1.21 mmol) in dichloromethane (5 mL) was added manganese dioxide (1052 mg, 12.10 mmol) at room temperature. The reaction was stirred for 12 h at 50° C. under nitrogen. The resulting mixture was filtered and the filter cake was washed with dichloromethane. The filtrate was concentrated to afford title compound (300 mg, 0.96 mmol, 79% yield) as a yellow solid. MS (ESI) m/z 311.9 $[M+1]^+$.

4-(7-Fluoro-6-vinylquinazolin-2-yl)morpholine. The mixture of 4-(6-bromo-7-fluoroquinazolin-2-yl)morpholine (300 mg, 0.96 mmol), potassium vinyltrifluoroborate (259 mg, 1.92 mmol) and sodium carbonate (305 mg, 2.88 mmol) in 1,4-dioxane (6 mL) and water (0.6 mL) was added dichlorobis(triphenylphosphine)palladium(II) dichloromethane adduct (78 mg, 0.10 mmol) under nitrogen. The reaction was stirred for 4 h at 80° C. under nitrogen. The resulting mixture was diluted with water and extracted with ethyl acetate. The combined organic layers were washed with brine, dried over anhydrous sodium sulfate and concentrated under vacuum. The residue was purified by silica gel chromatography (30% to 100% ethyl acetate in petroleum ether) to afford title compound (140 mg, 0.54 mmol, 56% yield) as a yellow solid. MS (ESI) m/z 260.1 $[M+1]^+$.

7-Fluoro-2-morpholinoquinazoline-6-carbaldehyde. The mixture of 4-(7-fluoro-6-vinylquinazolin-2-yl)morpholine (140 mg, 0.54 mmol), 4-methylmorpholine N-oxide (126 mg, 1.08 mmol) and critic acid (207 mg, 1.08 mmol) in tert-butanol (5 mL) and water (5 mL) was added potassium osmate (17 mg, 0.04 mmol) at room temperature. The reaction was stirred for 12 h at room temperature under nitrogen. To the above mixture was added sodium periodate (346 mg, 1.62 mmol) at 0° C. The resulting mixture was basified to pH~8 with saturated sodium bicarbonate and extracted with ethyl acetate. The combined organic layers were washed with brine, dried over anhydrous sodium sulfate and concentrated under vacuum. The residue was purified by silica gel chromatography (30% to 100% ethyl acetate in petroleum ether) to afford title compound (75 mg, 0.28 mmol, 52% yield) as a yellow solid. MS (ESI) m/z 262.1 $[M+1]^+$.

Tert-butyl (S)-5-amino-4-(5-(((S)-1-((7-fluoro-2-morpholinoquinazolin-6-yl)methyl)pyrrolidin-3-yl)oxy)-1-oxoisoindolin-2-yl)-5-oxopentanoate. The mixture of 7-fluoro-2-morpholinoquinazoline-6-carbaldehyde (75 mg, 0.28 mmol) and tert-butyl (S)-5-amino-5-oxo-4-(1-oxo-5-(((S)-pyrrolidin-3-yl)oxy)isoindolin-2-yl)pentanoate (acetic acid salt, 133 mg, 0.29 mmol) in THF (3 mL) was added acetic acid (0.02 mL) at room temperature under nitrogen. The reaction was stirred for 30 min at room temperature. To the above mixture was added sodium triacetoxyborohydride (152 mg, 0.72 mmol) under nitrogen. The reaction was stirred for 12 h at room temperature under nitrogen. The resulting mixture was purified by silica gel chromatography (0 to 10% methanol in dichloromethane) to afford title compound (70 mg, 0.11 mmol, 39% yield) as a yellow oil. MS (ESI) m/z 649.2 $[M+1]^+$.

(S)-3-(5-(((S)-1-((7-Fluoro-2-morpholinoquinazolin-6-yl)methyl)pyrrolidin-3-yl)oxy)-1-oxoisoindolin-2-yl)piperidine-2,6-dione. A solution of tert-butyl (S)-5-amino-4-(5-(((S)-1-((7-fluoro-2-morpholinoquinazolin-6-yl)methyl) pyrrolidin-3-yl)oxy)-1-oxoisoindolin-2-yl)-5-oxopentanoate (65 mg, 0.10 mmol) in acetonitrile (3 mL) was added benzenesulfonic acid (50 mg, 0.32 mmol) at room temperature. The reaction was stirred for 12 h at 60° C. under nitrogen. The resulting mixture was basified to pH~7 with saturated sodium bicarbonate and extracted with dichloromethane. The extracts were washed with saturated sodium bicarbonate, brine, dried over anhydrous sodium sulfate, filtered and concentrated under vacuum. The residue was purified by silica gel chromatography (0 to 10% methanol in dichloromethane) and further purified by preparative chiral HPLC with following condition: Column: CHIRALPAK IF, 2*25 cm, 5 μm; Mobile Phase A: tert-butyl methyl ether-HPLC, Mobile Phase B: ethanol:dichloromethane=1:1; Flow rate: 17 mL/min; Gradient: 80% B to 80% B in 9 min; Wave Length: 220/254 nm; $RT_1$ (min): 7.11; $RT_2$ (min): 8.16; Sample Solvent: ethanol—HPLC; Injection Volume: 0.5 mL. The fractions containing desired product were collected and evaporated under reduced pressure to afford the title compound (13.9 mg, 0.024 mmol, 24% yield) as a yellow solid. $^1$H NMR (400 MHz, DMSO-$d_6$) δ 10.98 (s, 1H), 9.22 (s, 1H), 7.93 (d, J=8.1 Hz, 1H), 7.61 (d, J=8.4 Hz, 1H), 7.23 (d, J=11.7 Hz, 1H), 7.12 (s, 1H), 7.01 (d, J=8.4 Hz, 1H), 5.09-5.01 (m, 2H), 4.38 (d, J=17.3 Hz, 1H), 4.24 (d, J=17.2 Hz, 1H), 3.83 (m, 4H), 3.78-3.65 (m, 6H), 2.99 (m, 1H), 2.96-2.84 (m, 1H), 2.75 (m, 2H), 2.58 (m, 1H), 2.41-2.33 (m, 1H), 2.01-1.93 (m, 1H), 1.83 (m, 1H); MS (ESI) m/z 575.2 $[M+1]^+$.

Example S158. (S)-3-(5-(((S)-1-((8-Cyclopropyl-2-morpholinoquinazolin-6-yl)methyl)pyrrolidin-3-yl)oxy)-1-oxoisoindolin-2-yl)piperidine-2,6-dione

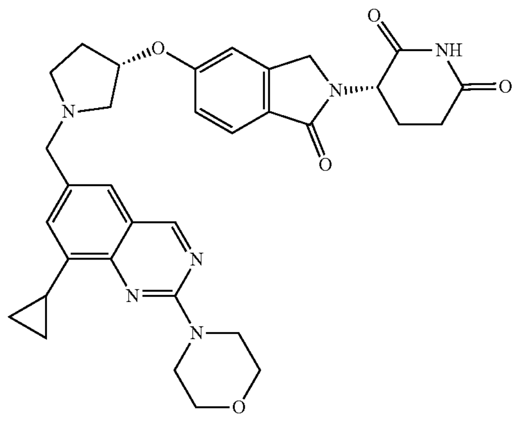 [SMILES: O=C1CC[C@H](N2Cc3cc(O[C@H]4CCN(Cc5cc(C6CC6)c6nc(N7CCOCC7)ncc6c5)C4)ccc3C2=O)C(=O)N1]

6-Bromo-8-chloroquinazolin-2-amine. A solution of 2-amino-5-bromo-3-chlorobenzaldehyde (1 g, 4.26 mmol) and guanidine (504 mg, 8.53 mmol) in N,N-dimethylacetamide (6 mL) was stirred at 140° C. for 4 h under nitrogen. The reaction mixture was diluted with water (20 mL) and the solids were collected which was suspended in refluxing methanol (6 mL) for 16 h. The resulting mixture was allowed to cool and was suction-filtered, washed with methanol, and dried in air to afford the title compound (800 mg, 3.09 mmol, 73% yield) as a yellow solid. MS (ESI) m/z 258.5 $[M+1]^+$.

4-(6-Bromo-8-chloroquinazolin-2-yl)morpholine. To a stirred solution of 6-bromo-8-chloroquinazolin-2-amine (500 mg, 1.93 mmol) in DMF (4 mL) was added sodium hydride (60% dispersion in mineral oil, 75 mg, 1.88 mmol) at 0° C. and the mixture was stirred for 30 min. Then to the above mixture was added a solution of 1-bromo-2-(2-bromoethoxy)ethane (269 mg, 1.16 mmol) in DMF (2.0 mL) and the mixture was stirred at room temperature for 12 h under nitrogen. The resulting mixture was purified by reverse phase flash (30-80% acetonitrile+0.05% ammonium bicarbonate in water, over 25 min) to afford the title compound (600 mg, 1.83 mmol, 95% yield) as a light-yellow solid. MS (ESI) m/z 328.6 $[M+1]^+$.

4-(8-Chloro-6-vinylquinazolin-2-yl)morpholine. To a stirred solution of 4-(6-Bromo-8-chloroquinazolin-2-yl)morpholine (600 mg, 1.83 mmol) and potassium trifluoro(vinyl)boranuide (294 mg, 2.19 mmol) in 1,4-dioxane (8 mL) and water (0.8 mL) were added tetrakis(triphenylphosphine)palladium (210 mg, 0.18 mmol) and cesium carbonate (1186 mg, 3.65 mmol). The above mixture was stirred at 80° C. for 3 h under nitrogen. Then the mixture extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (400 mg, 1.45 mmol, 79% yield) as a light-yellow solid. MS (ESI) m/z 275.7 $[M+1]^+$.

4-(8-Cyclopropyl-6-vinylquinazolin-2-yl)morpholine. To a stirred solution of 4-(8-chloro-6-vinyl-quinazolin-2-yl)morpholine (400 mg, 1.45 mmol) and cyclopropylboronic acid (249 mg, 2.90 mmol) in 1,4-dioxane (5 mL) and water (0.5 mL) were added bis(di-tert-butyl(4-dimethylaminophenyl)phosphine)dichloropalladium(II) (102 mg, 0.15 mmol) and potassium carbonate (600 mg, 4.34 mmol). The above mixture was stirred at 80° C. for 3 h under nitrogen. Then the mixture was added water and extracted with ethyl acetate. The extracts were washed with brine, dried over anhydrous sodium sulfate, filtered and concentrated. The residue was purified by silica gel chromatography (0 to 20% ethyl acetate in petroleum ether) to afford the title compound (120 mg, 0.43 mmol, 29% yield) as a yellow oil. MS (ESI) m/z 281.4 $[M+1]^+$.

8-Cyclopropyl-2-morpholinoquinazoline-6-carbaldehyde. To a stirred solution of 4-(8-cyclopropyl-6-vinylquinazolin-2-yl)morpholine. (120 mg, 0.43 mmol) in tert-butanol (4 mL, 0.3 mmol) and water (4 mL, 0.3 mmol) were added 4-methyl-morpholin4-oxide (50 mg, 0.43 mmol), potassium osmate (15.6 mg, 0.04 mmol) and citric acid (82 mg, 0.43 mmol). The above mixture was stirred at room temperature for 3 h under nitrogen. Then the mixture was added sodium periodate (91 mg, 0.43 mmol) and the mixture was stirred for another 1 h. The mixture was added saturated sodium bicarbonate solution to pH~7 and extracted with ethyl acetate. The extracts were washed with brine, dried over sodium sulfate, filtered and concentrated. The residue was purified by silica gel chromatography (0 to 40% ethyl acetate in petroleum ether) to afford the title compound (80 mg, 0.28 mmol, 66% yield) as a light-yellow oil. MS (ESI) m/z 283.3 $[M+1]^+$.

Tert-butyl (S)-5-amino-4-(5-(((S)-1-((8-cyclopropyl-2-morpholinoquinazolin-6-yl)methyl)pyrrolidin-3-yl)oxy)-1-oxoisoindolin-2-yl)-5-oxopentanoate. To a solution of 8-cyclopropyl-2-morpholino-quinazoline-6-carbaldehyde (60 mg, 0.21 mmol), tert-butyl(4S)-5-amino-5-oxo-4-[1-oxo-5-[(3S)-pyrrolidin-3-yl]oxy-isoindo lin-2-yl]pentanoate (102 mg, 0.25 mmol) and acetic acid (0.01 mL) in THF (3 mL) was added sodium triacetoxyborohydride (112 mg, 0.53 mmol). The mixture was stirred for 12 h at room temperature under nitrogen. The resulting mixture was concentrated. The residue was purified by reverse phase flash (10-40% acetonitrile+0.05% trifluoroacetic acid in water, over 25 min) to afford the title compound (60 mg, 0.088 mmol, 41% yield) as a light-yellow oil. MS (ESI) m/z 670.8 $[M+1]^+$.

(S)-3-(5-(((S)-1-((8-Cyclopropyl-2-morpholinoquinazolin-6-yl)methyl)pyrrolidin-3-yl)oxy)-1-oxoisoindolin-2-yl)piperidine-2,6-dione. To a solution of tert-butyl (S)-5-amino-4-(5-(((S)-1-((8-cyclopropyl-2-morpholinoquinazolin-6-yl)methyl)pyrrolidin-3-yl)oxy)-1-oxoisoindolin-2-yl)-5-oxopentanoate (60 mg, 0.088 mmol) in acetonitrile (3 mL) was added benzenesulfonic acid (35 mg, 0.22 mmol) in and the mixture was stirred for 12 h at 60° C. under nitrogen. The reaction was quenched with water, acidified to pH~7 with saturated sodium bicarbonate and extracted with dichloromethane. The extracts were washed with brine, dried over anhydrous sodium sulfate, filtered and concentrated. The residue was purified by silica gel chromatography (0 to 40% ethyl acetate in petroleum ether) and preparative chiral HPLC with the follow conditions: Column: CHIRALPAK IF-3, 4.6*50 mm; 3 um; Mobile Phase A: tert-butyl methyl ether: (ethanol:dichloromethane=1:1) =70:30; Flow rate: 1 mL/min; Gradient: 0% B to 0% B; Injection Volume: 5 mL and preparative HPLC with the follow conditions: Column: Xselect CSH Cis OBD Column 30*150 mm 5 μm, n; Mobile Phase A: Water (0.05% TFA), Mobile Phase B: acetonitrile; Flow rate: 60 mL/min; Gradient: 10% B to 35% B in 7 min, 35% B; Wave Length: 254/220 nm; $RT_1$ (min): 6.3. The fractions containing desired product were collected and evaporated under reduced pressure to afford the title compound (11.5 mg, 0.017 mmol, 21% yield) as a yellow solid. $^1H$ NMR (400 MHz, DMSO-$d_6$) δ 9.22 (s, 1H), 7.78 (d, J=2.0 Hz, 1H), 7.69 (d, J=8.4 Hz, 1H), 7.35 (s, 1H), 7.19 (d, J=2.2 Hz, 1H), 7.10 (s, 1H), 5.27 (d, J=22.6 Hz, 1H), 5.06 (d, J=11.2 Hz, 1H), 4.55-4.39 (m, 3H), 4.29 (d, J=17.4 Hz, 1H), 3.89 (t, J=4.7 Hz, 4H), 3.72 (t, J=4.8 Hz, 4H), 3.39 (d, J=36.1 Hz, 3H), 2.96-2.81 (m, 2H), 2.73-2.59 (m, 2H), 2.47-2.28 (m, 2H), 2.19-1.96 (m, 2H), 1.09 (s, 2H), 0.86 (s, 2H); MS (ESI) m/z 670.8 $[M+1]^+$.

Example S159. (S)-3-(5-(((S)-1-((8-cyclopropyl-2-(tetrahydro-2H-pyran-4-yl)quinolin-6-yl)-methyl)pyrrolidin-3-yl)oxy)-1-oxoisoindolin-2-yl)piperidine-2,6-dione

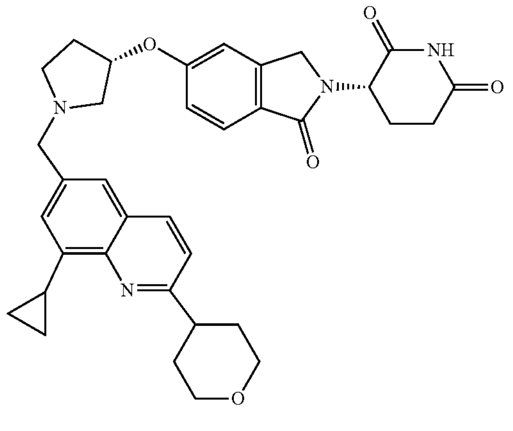 [SMILES: O=C1CC[C@H](N2Cc3cc(O[C@H]4CCN(Cc5cc(C6CC6)c6nc(C7CCOCC7)ccc6c5)C4)ccc3C2=O)C(=O)N1]

6-Bromo-8-chloro-2-tetrahydro-2H-pyran-4-yl-quinoline. To a mixture of 2-amino-5-bromo-3-chloro-benzaldehyde (3.50 g, 14.9 mmol) and 1-tetrahydro-2H-pyran-4-ylethan-1-one (1913 mg, 14.9 mmol) in ethanol (100 mL)

was added potassium hydroxide (835 mg, 14.9 mmol). Then the reaction mixture was stirred for 2 h at 80° C. under nitrogen. The resulting mixture was diluted with water and extracted with ethyl acetate. The extracts were washed with brine, dried over sodium sulfate, filtered and concentrated to give the title compound (3.2 g, 9.8 mmol, 66% yield) as a white solid. MS (ESI) m/z 326.0 $[M+1]^+$.

8-Chloro-2-(tetrahydro-2H-pyran-4-yl)-6-vinylquinoline. To a solution of 6-bromo-8-chloro-2-tetrahydropyran-4-yl-quinoline (640 mg, 1.96 mmol) and potassium vinyltrifluoroborate (528 mg, 3.92 mmol) in 1,4-dioxane (50 mL) and water (10 mL) were added [1,1'-bis(diphenylphosphino) ferrocene]dichloropalladium(II) (226 mg, 0.31 mmol) and sodium carbonate (623 mg, 5.88 mmol) at room temperature under nitrogen. The reaction was heated to 90° C. and stirred for 3 h under nitrogen. The resulting mixture was added DMF, filtered and the filtrate was purified by reverse phase flash (10-60% acetonitrile+0.05% ammonium bicarbonate in water, over 20 min) to give the title compound (400 mg, 1.46 mmol, 75% yield) as a white solid. MS (ESI) m/z 274.2 $[M+1]^+$.

8-Cyclopropyl-2-(tetrahydro-2H-pyran-4-yl)-6-vinylquinoline. To a solution of 8-chloro-2-tetrahydropyran-4-yl-6-vinyl-quinoline (280 mg, 1.02 mmol) and cyclopropylboronic acid (439 mg, 5.11 mmol) in 1,4-dioxane (10 mL) and water (0.5 mL) were added bis(di-tert-butyl(4-dimethylaminophenyl)phosphine) dichloropalladium(II) (144 mg, 0.20 mmol) and cesium carbonate (1662 mg, 5.11 mmol) at room temperature under nitrogen. The reaction was heated to 120° C. and stirred for 3 h under nitrogen. The resulting mixture was added little DMF, filtered and the filtrate was purified directly by reverse phase flash (10-60% acetonitrile+0.05% TFA in water, over 20 min) to give the title compound (190 mg, 0.68 mmol, 67% yield) as a white solid. MS (ESI) m/z 280.1 $[M+1]^+$.

(8-Cyclopropyl-2-(tetrahydro-2H-pyran-4-yl)quinolin-6-yl)methanol. To a solution of 8-Cyclopropyl-2-(tetrahydro-2H-pyran-4-yl)-6-vinylquinoline (180 mg, 0.64 mmol), potassium osmate (16.8 mg, 0.045 mmol) and 4-methylmorpholine n-oxide (150 mg, 1.29 mmol) in 1-butanol (10 mL) and water (10 mL) was added citric acid (172 mg, 1.29 mmol) at room temperature and the resulting mixture was stirred at room temperature for 4 h. Then sodium periodate (413 mg, 1.93 mmol) was added to the above mixture at 0° C. and the resulting mixture was stirred at room temperature for 1 h. The mixture was added saturated sodium bicarbonate solution to pH~7 and extracted with ethyl acetate. The extracts were washed with brine, dried over sodium sulfate, filtered and concentrated to afford the title compound (120 mg, 0.42 mmol, 66% yield) as a yellow solid. MS (ESI) m/z 282.2 $[M+1]^+$.

Tert-butyl (S)-5-amino-4-(5-(((S)-1-((8-cyclopropyl-2-(tetrahydro-2H-pyran-4-yl)quinolin-6-yl)methyl)pyrrolidin-3-yl)oxy)-1-oxoisoindolin-2-yl)-5-oxopentanoate. To a stirred solution of (8-cyclopropyl-2-(tetrahydro-2H-pyran-4-yl)quinolin-6-yl)methanol (120 mg, 0.42 mmol) and tert-butyl (S)-5-amino-5-oxo-4-(1-oxo-5-(((S)-pyrrolidin-3-yl) oxy)isoindolin-2-yl)pentanoate (255 mg, 0.55 mmol) in THF (10 mL) was added sodium triacetoxyborohydride (269 mg, 1.27 mmol). The reaction mixture was stirred for 12 h at room temperature under nitrogen. The resulting mixture was concentrated and the residue was purified by silica gel chromatography (0-10% methanol in dichloromethane) to give the title compound (100 mg, 0.15 mmol, 35% yield) as a white solid. MS (ESI) m/z 669.3 $[M+1]^+$.

(S)-3-(5-(((S)-1-((S-cyclopropyl-2-(tetrahydro-2H-pyran-4-yl)quinolin-6-yl)-methyl)pyrrolidin-3-yl)oxy)-1-oxoisoindolin-2-yl)piperidine-2,6-dione. To a solution of tert-butyl (S)-5-amino-4-(5-(((S)-1-((8-cyclopropyl-2-(tetrahydro-2H-pyr-an-4-yl)quinolin-6-yl)methyl)pyrrolidin-3-yl)oxy)-1-oxoisoindolin-2-yl)-5-oxopentanoate (100 mg, 0.15 mmol) and benzenesulfonic acid (70 mg, 0.44 mmol) in acetonitrile (10 mL) was stirred at 60° C. for 12 h under nitrogen. The reaction mixture was cooled to room temperature and slowly neutralized with saturated sodium bicarbonate carefully to pH~7. Then the above mixture was extracted with dichloromethane. The extracts were washed with brine, dried over sodium sulfate, filtered and concentrated. The crude product was purified by silica gel chromatography (0-10% methanol in dichloromethane) and preparative Chiral SFC with the following conditions: Column: CHIRALPAK IH, 2*25 cm, 5 μm; mobile phase A: tert-butyl methyl ether HPLC, mobile phase B: ethanol:dichloromethane=1:1-HPLC; Flow rate: 20 mL/min; Gradient: 30% B to 30% B in 11 min; Wave Length: 220/254 nm; $RT_1$ (min): 8.84; Sample Solvent: ethanol HPLC; Injection Volume: 0.5 mL; Number of Runs: 4. The fractions containing desired product were collected and evaporated under reduced pressure to afford the title compound (16 mg, 0.027 mmol, 18% yield) as a white solid. $^1H$ NMR (300 MHz, DMSO-$d_6$) δ 10.94 (s, 1H), 8.22 (d, J=8.5 Hz, 1H), 8.14 (s, 1H), 7.64-7.55 (m, 2H), 7.47 (d, J=8.5 Hz, 1H), 7.12-7.08 (m, 2H), 7.00-6.98 (m, 1H), 5.05-5.03 (m, 2H), 4.37 (d, J=17.2 Hz, 1H), 4.24 (d, J=17.2 Hz, 1H), 4.00-3.96 (m, 2H), 3.74 (s, 2H), 3.58-3.43 (m, 2H), 3.27-3.05 (m, 2H), 2.99-2.52 (m, 7H), 2.46-2.26 (m, 2H), 2.04-1.78 (m, 6H), 1.19-1.01 (m, 2H), 0.87-0.83 (m, 2H); MS (ESI) m/z 595.3 $[M+1]^+$.

Example S160. 3-(1-oxo-5-((1-((2-((S)-Tetrahydrofuran-3-yl)quinolin-6-yl)methyl)-4-(trifluoromethyl) pyrrolidin-3-yl)oxy)isoindolin-2-yl)piperidine-2,6-dione

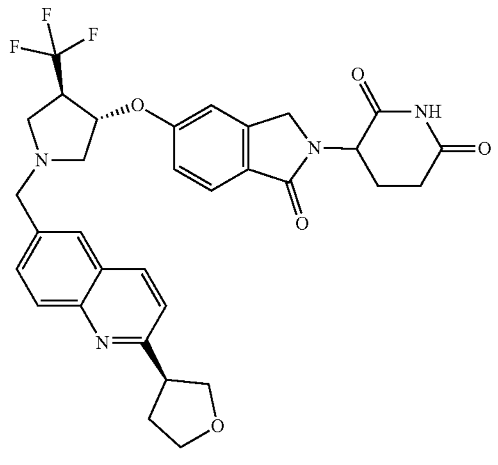 [SMILES: O=C1CCC(N2Cc3cc(O[C@@H]4CN(Cc5ccc6nc([C@@H]7CCOC7)ccc6c5)C[C@H]4C(F)(F)F)ccc3C2=O)C(=O)N1]

3-(1-oxo-5-((1-((2-((S)-Tetrahydrofuran-3-yl)quinolin-6-yl)methyl)-4-(trifluoromethyl)pyrrolidin-3-yl)oxy)isoindolin-2-yl)piperidine-2,6-dione. To a stirred solution of (S)-2-(tetrahydrofuran-3-yl)quinoline-6-carbaldehyde (50 mg, 0.22 mmol), 3-(1-oxo-5-((4-(trifluoromethyl)pyrrolidin-3-yl)oxy)isoindolin-2-yl)piperidine-2,6-dione; 2,2,2-trifluoroacetic acid (105 mg, 0.24 mmol), acetic acid (0.01 mL) in THF (10 mL) pre-stirred for 15 min was added sodium triacetoxyborohydride (117 mg, 0.55 mmol) at 0° C. and the solution was stirred at room temperature for 12 h under nitrogen. The resulting solution was purified by silica gel chromatography (0 to 5% methanol in dichloromethane) and purified further by preparative HPLC with the following conditions: column: sunfire preparative C18 OBD column, 19×150 mm 5 um 10 nm; mobile phase A: water (0.1% formic acid), mobile phase B: acetonitrile; flow rate: 60 mL/min; gradient: 10 B to 30 B in 10 min; 254/210 nm; $RT_1$: 9.67. The fractions containing desired product were collected and evaporated under reduced pressure to afford the title compound (37.5 mg, 0.06 mmol, 28% yield) as a white solid. $^1$H NMR (400 MHz, DMSO-$d_6$) δ 8.30-8.22 (m, 1H), 7.91 (d, J=8.6 Hz, 1H), 7.83 (d, J=1.9 Hz, 1H), 7.70 (dd, J=8.8, 1.9 Hz, 1H), 7.64 (d, J=8.4 Hz, 1H), 7.48 (d, J=8.5 Hz, 1H), 7.23 (t, J=2.7 Hz, 1H), 7.10 (dd, J=8.5, 2.2 Hz, 1H), 5.16-4.97 (m, 2H), 4.38 (dd, J=17.6, 2.4 Hz, 1H), 4.26 (dd, J=17.4, 7.6 Hz, 1H), 4.12 (t, J=8.0 Hz, 1H), 3.98 (m, 1H), 3.93-3.67 (m, 5H), 3.39 (d, J=7.7 Hz, 1H), 3.24-3.13 (m, 1H), 3.02-2.76 (m, 3H), 2.65-2.53 (m, 2H), 2.44-2.15 (m, 3H), 2.07-1.91 (m, 1H); MS (ESI) m/z 609.3 $[M+1]^+$.

Example S161. (R)-3-(5-(((S)-1-((8-Fluoro-2-(tetrahydro-2H-pyran-4-yl)quinolin-6-yl)methyl)pyrrolidin-3-yl)oxy)-1-oxoisoindolin-2-yl)piperidine-2,6-dione

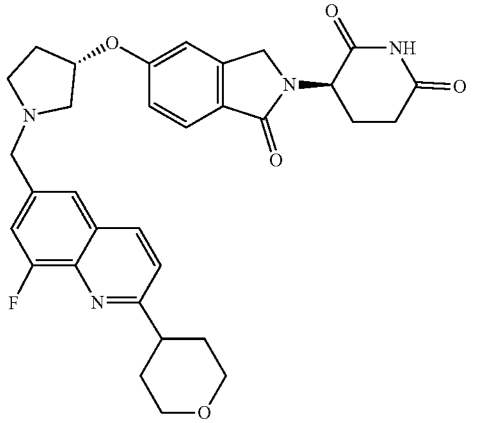 [SMILES: O=C1CC[C@@H](N2Cc3cc(O[C@H]4CCN(Cc5cc(F)c6nc(C7CCOCC7)ccc6c5)C4)ccc3C2=O)C(=O)N1]

(R)-3-(5-(((S)-1-((8-Fluoro-2-(tetrahydro-2H-pyran-4-yl)quinolin-6-yl)methyl)pyrrolidin-3-yl)oxy)-1-oxoisoindolin-2-yl)piperidine-2,6-dione. To a solution of 8-fluoro-2-(tetrahydro-2H-pyran-4-yl)quinoline-6-carbaldehyde (500 mg, 1.92 mmol), 3-(1-oxo-5-(((S)-pyrrolidin-3-yl)oxy)isoindolin-2-yl)piperidine-2,6-dione; 2,2,2-trifluoroacetic acid (1 g, 2.26 mmol) and triethylamine (0.8 mL, 5.74 mmol) in dichloromethane (20 mL) was added sodium triacetoxyborohydride (1 g, 4.72 mmol). The resulting mixture was stirred at room temperature for 12 h under nitrogen. The mixture was added little methanol, removed dichloromethane with nitrogen and purified by a silica gel chromatography (0-10% methanol in dichloromethane). Pure fractions were evaporated and the residue was further purified by preparative chiral HPLC with the follow condition: Column: Chiralpak IF, 2*25 cm, 5 μm; mobile phase A: tert-Butyl methyl ether—HPLC, mobile phase B: ethanol:dichloromethane=1:1-HPLC; flow rate: 20 mL/min; gradient: 60% B to 60% B in 13.5 min; wave length: 220/254 nm; $RT_1$ (min): 9.146; $RT_2$ (min): 11.518; sample solvent: ethanol—HPLC; injection volume: 1.75 mL; number of runs: 4 and preparative HPLC with the follow condition: column: sunfire prep C18 column, 30*150 mm, 5 μm; mobile phase A: water (0.1% formic acid), mobile phase B: acetonitrile; flow rate: 60 mL/min; gradient: 2% B to 30% B in 7 min, 30% B; wave length: 254/220 nm; $RT_1$ (min): 6.07. The fractions containing desired product were collected and evaporated under reduced pressure to afford the title compound (136.3 mg, 0.24 mmol, 12% yield) as a white solid. $^1$H NMR (300 MHz, DMSO-$d_6$) δ 10.96 (s, 1H), 8.34-8.31 (m, 1H), 7.69 (d, J=1.5 Hz, 1H), 7.59-7.57 (m, 2H), 7.51-7.49 (m, 1H), 7.11 (d, J=2.1 Hz, 1H), 7.00-6.98 (m, 1H), 5.06-5.04 (m, 1H), 4.37 (d, J=17.3 Hz, 1H), 4.23 (d, J=17.2 Hz, 1H), 4.04-3.94 (m, 2H), 3.87-3.70 (m, 2H), 3.49 (m, 2H), 3.15 (m, 1H), 3.02-2.76 (m, 2H), 2.79-2.64 (m, 4H), 2.40-2.30 (m, 2H), 2.01-1.80 (m, 6H); MS (ESI) m/z 573.2 $[M+1]^+$.

Example S162. (S)-3-(5-(((S)-1-((8-(Azetidin-1-yl)-2-(tetrahydro-2H-pyran-4-yl)quinolin-6-yl)methyl)pyrrolidin-3-yl)oxy)-1-oxoisoindolin-2-yl)piperidine-2,6-dione

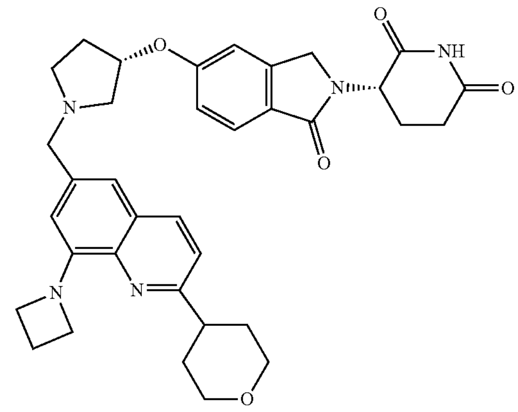 [SMILES: O=C1CC[C@H](N2Cc3cc(O[C@H]4CCN(Cc5cc(N6CCC6)c6nc(C7CCOCC7)ccc6c5)C4)ccc3C2=O)C(=O)N1]

8-(Azetidin-1-yl)-6-bromo-2-(tetrahydro-2H-pyran-4-yl)quinoline. To a stirred solution of 6-bromo-8-iodo-2-(tetrahydro-2H-pyran-4-yl)quinoline (500 mg, 1.2 mmol), sodium tert-butoxide (345 mg, 3.59 mmol), 4,5-bis(diphenylphosphino)-9,9-dimethylxanthene (140 mg, 0.24 mmol), tris(dibenzylideneacetone)dipalladium (110 mg, 0.12 mmol) and azetidine (75 mg, 1.31 mmol) in toluene (10 mL) was stirred at 60° C. for 3 h under nitrogen. The resulting mixture was added water and extracted with ethyl acetate. The extracts were dried over anhydrous sodium sulfate, filtered and concentrated. The residue was purified by silica gel chromatography (0 to 50% ethyl acetate in petroleum ether) to afford the title compound (200 mg, 0.58 mmol, 48% yield) as a yellow solid. MS (ESI) m/z 347.2 $[M+1]^+$.

8-(Azetidin-1-yl)-2-(tetrahydro-2H-pyran-4-yl)quinoline-6-carbaldehyde. A mixture of 8-(azetidin-1-yl)-6-bromo-2-(tetrahydro-2H-pyran-4-yl)quinoline (250 mg, 0.72 mmol), palladium acetate (50 mg, 0.22 mmol), N,N,N,N'-tetramethylethylenediamine (250 mg, 2.16 mmol), and butyldi-1-adamantylphosphine (83 mg, 0.23 mmol) in toluene (20 mL) was stirred at 100° C. for 60 h under 50 bar carbon monoxide/hydrogen (1:1). The brown solution was added saturated sodium bicarbonate to pH~7 and extracted with ethyl acetate. The extracts were washed with brine, dried over anhydrous sodium sulfate, filtered and concentrated. The residue was purified by silica gel chromatography (0-10% methanol in dichloromethane) to give the title compound (60 mg, 0.20 mmol, 28% yield) as a light-yellow solid. MS (ESI) m/z 297.2 $[M+1]^+$.

(S)-3-(5-(((S)-1-((8-(Azetidin-1-yl)-2-(tetrahydro-2H-pyran-4-yl)quinolin-6-yl)methyl)pyrrolidin-3-yl)oxy)-1-oxoisoindolin-2-yl)piperidine-2,6-dione. A solution of 8-(azetidin-1-yl)-2-(tetrahydro-2H-pyran-4-yl)quinoline-6-carbaldehyde (40 mg, 0.13 mmol), (S)-3-(1-oxo-5-(((S)-pyrrolidin-3-yl)oxy)isoindolin-2-yl)piperid-ine-2,6-dione; 2,2,2-trifluoroacetic acid (60 mg, 0.14 mmol), zinc chloride (0.7 M in THF, 0.4 mL, 0.28 mmol) and sodium cyanoborohydride (19 mg, 0.31 mmol) in ethanol (3 mL) was stirred at room temperature for 12 h under nitrogen. The resulting mixture was added saturated sodium bicarbonate to pH~7 and extracted with ethyl acetate. The extracts were washed with brine, dried over anhydrous sodium sulfate, filtered and concentrated. The residue was purified by silica gel chromatography (0-10% methanol in dichloromethane) and further purified by preparative Chiral HPLC with the following conditions: CHIRALPAK IF, 2*25 cm, 5 μm; Mobile Phase A: tert-Butyl methyl ether—HPLC, Mobile Phase B: ethanol—HPLC; Flow rate: 20 mL/min; Gradient: 50% B to 50% B in 33 min; Wave Length: 220/254 nm; $RT_1$ (min): 22.98; $RT_2$ (min): 30.41; Sample Solvent: ethanol—HPLC; Injection Volume: 1.6 mL; Number of Runs: 2. The fractions containing desired product were collected and evaporated under reduced pressure to afford the title compound (4.2 mg, 0.0066 mmol, 5% yield) as an off-white solid. $^1$H NMR (400 MHz, Methanol-$d_4$) δ 8.03 (d, J=8.6 Hz, 1H), 7.70 (d, J=8.4 Hz, 1H), 7.35 (d, J=8.5 Hz, 1H), 7.16 (d, J=1.8 Hz, 1H), 7.10-7.00 (m, 2H), 6.61 (d, J=1.8 Hz, 1H), 5.11 (m, 2H), 4.50-4.32 (m, 6H), 4.11-3.99 (m, 4H), 3.61 (m, 2H), 3.28-3.16 (m, 3H), 3.13-3.04 (m, 1H), 2.90 (m, 1H), 2.81-2.72 (m, 1H), 2.54-2.35 (m, 2H), 2.20-1.87 (m, 7H); MS (ESI) m/z 610.2 $[M+1]^+$.

Example S163. 3-(5-(((S)-1-((2-(4-(Methylamino)piperidin-1-yl)quinolin-6-yl)methyl)pyrrolidin-3-yl)oxy)-1-oxoisoindolin-2-yl)piperidine-2,6-dione

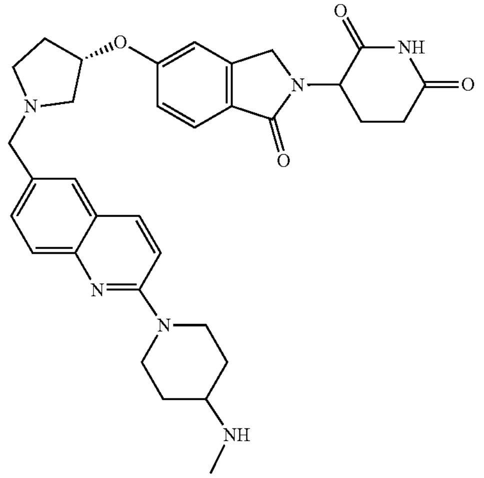 [SMILES: CNC1CCN(c2ccc3cc(CN4CC[C@H](Oc5ccc6c(c5)CN(C5CCC(=O)NC5=O)C6=O)C4)ccc3n2)CC1]

Methyl 2-(4-((tert-butoxycarbonyl)(methyl)amino)piperidin-1-yl)quinoline-6-carboxylate. A mixture of the compound of methyl 2-chloroquinoline-6-carboxylate (200 mg, 0.90 mmol) and tert-butyl methyl(piperidin-4-yl)carbamate (966 mg, 4.51 mmol) in ethanol (10 mL) was stirred at 80° C. for 12 h under nitrogen. The reaction mixture is concentrated to afford the title compound (300 mg, 0.75 mmol, 83% yield) as a yellow solid. MS (ESI) m/z 400.1 $[M+1]^+$.

Tert-butyl (1-(6-(hydroxymethyl)quinolin-2-yl)piperidin-4-yl)(methyl)carbamate. To a solution of methyl 2-(4-((tert-butoxycarbonyl)(methyl)amino)piperidin-1-yl)quinoline-6-carboxylate (280 mg, 0.70 mmol) in THF (15 mL) at 0° C. was added lithium aluminum hydride (2.5 M in THF, 0.60 mL, 1.50 mmol) dropwise at 0° C. After stirred at 0° C. for 2 h, the reaction mixture was quenched with water and purified by reverse phase flash (10-60% acetonitrile+0.05% ammonium bicarbonate in water, over 25 min) afford the title compound (250 mg, 0.67 mmol, 95% yield) as a white solid. MS (ESI) m/z 372.1 $[M+1]^+$.

Tert-butyl (1-(6-formylquinolin-2-yl)piperidin-4-yl)(methyl)carbamate. To a stirred solution of tert-butyl (1-(6-(hydroxymethyl)quinolin-2-yl)piperidin-4-yl)-(methyl)carbamate (270 mg, 0.73 mmol) in dichloromethane (6 mL) was added manganese dioxide (1264 mg, 14.54 mmol) and the mixture was stirred at room temperature for 16 h. The mixture was diluted with dichloromethane, filtered and the filtrate was concentrated to afford the title compound (200 mg, 0.54 mmol, 74% yield) as a light-yellow oil. MS (ESI) m/z 370.1 $[M+1]^+$.

Tert-butyl (1-(6-(((3S)-3-((2-(2,6-dioxopiperidin-3-yl)-1-oxoisoindolin-5-yl)oxy)pyrrolidin-1-yl)methyl)quinolin-2-yl)piperidin-4-yl)(methyl)carbamate. To a solution of tert-butyl (1-(6-formylquinolin-2-yl)piperidin-4-yl)(methyl)carbamate (100 mg, 0.27 mmol), 3-[1-oxo-5-[(3S)-pyrrolidin-3-yl]oxy-isoindolin-2-yl]piperidine-2,6-dione; 2,2,2-trifluoroacetic acid (92 mg, 0.21 mmol) and triethylamine (0.07 mL, 0.53 mmol) in dichloromethane (5 mL) was added sodium triacetoxyborohydride (168 mg, 0.79 mmol). The mixture was stirred for 12 h at room temperature under nitrogen. The reaction mixture was concentrated. The residue was purified by silica gel chromatography (0 to 10% methanol in dichloromethane) and reverse phase flash (10-40% acetonitrile+0.05% ammonium bicarbonate in water, over 25 min) to afford the title compound (50 mg, 0.07 mmol, 27% yield) as a white solid. MS (ESI) m/z 683.5 $[M+1]^+$.

3-(5-(((S)-1-((2-(4-(Methylamino)piperidin-1-yl)quinolin-6-yl)methyl)pyrrolidin-3-yl)oxy)-1-oxoisoindolin-2-yl)piperidine-2,6-dione. To a stirred solution of tert-butyl (1-(6-(((3S)-3-((2-(2,6-dioxopiperidin-3-yl)-1-oxoisoindolin-5-yl)oxy)pyro lidin-1-yl)methyl)quinolin-2-yl)piperidin-4-yl)(methyl)carbamate (50 mg, 0.07 mmol) in dichloromethane (6 mL) was added TFA (2 mL, 26.12 mmol) at room temperature and the resulting solution was stirred for 2 h. The reaction mixture was concentrated. The residue was purified by preparative HPLC with the following conditions: Column: Xselect CSH C18 OBD Column 30*150 mm 5 μm; Mobile Phase A: water (0.05% TFA), Mobile Phase B: acetonitrile; Flow rate: 60 mL/min; Gradient: 4% B to 17% B in 10 min, 17% B; Wave Length: 254/220 nm; $RT_1$ (min): 9.6. The fractions containing desired product were collected and evaporated under reduced pressure to afford the title compound (12.9 mg, 0.02 mmol, 31% yield) as an off-white solid. $^1$H NMR (400 MHz, Methanol-$d_4$) δ 8.10-7.91 (m, 3H), 7.73-7.54 (m, 2H), 7.18-6.99 (m, 2H), 5.31 (s, 1H), 5.11-5.09 (m, 1H), 4.66 (d, J=9.6 Hz, 4H), 4.45 (m, 2H), 3.67 (m, 4H), 3.51-3.44 (m, 4H), 2.90 (m, 1H), 2.79 (m, 4H), 2.63-2.33 (m, 5H), 2.16 (m, 1H), 1.85 (m, 2H); MS (ESI) m/z 583.3 $[M+1]^+$.

Example S164. 3-(5-(((S)-1-((2-(4-(Dimethylamino)piperidin-1-yl)quinolin-6-yl)methyl)pyrrolidin-3-yl)oxy)-1-oxoisoindolin-2-yl)piperidine-2,6-dione

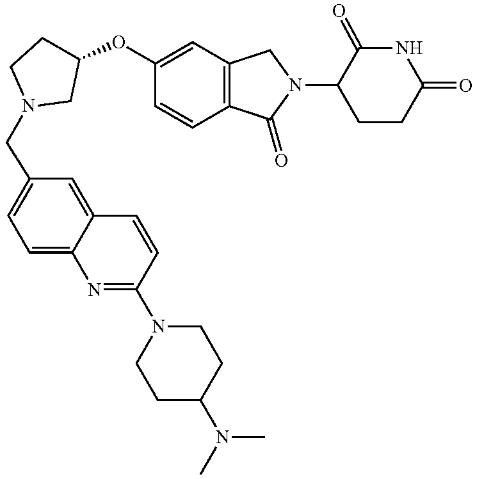 [SMILES: CN(C)C1CCN(c2ccc3cc(CN4CC[C@H](Oc5ccc6c(c5)CN(C5CCC(=O)NC5=O)C6=O)C4)ccc3n2)CC1]

Methyl 2-(4-(dimethylamino)piperidin-1-yl)quinoline-6-carboxylate. A mixture of methyl 2-chloroquinoline-6-carboxylate (300 mg, 1.35 mmol) and N, N-dimethylpiperidin-4-amine (867 mg, 6.77 mmol) in ethanol (10 mL) was stirred at 80° C. for 12 h under nitrogen. The solution was concentrated to afford the title compound (300 mg, 0.96 mmol, 71% yield) as yellow solid. MS (ESI) m/z 314.1 $[M+1]^+$.

(2-(4-(Dimethylamino)piperidin-1-yl)quinolin-6-yl)methanol. To a solution of methyl 2-(4-(dimethylamino)piperidin-1-yl)quinoline-6-carboxylate (280 mg, 0.89 mmol) in THF (15 mL) at 0° C. was added lithium aluminum hydride (2.5 M in THF, 0.5 mL, 1.25 mmol). After stirred at 0° C. for 2 h, the reaction mixture was quenched with water and stirred for 5 min. The mixture was filtered and the reaction mixture was concentrated. The residue was purified by reverse phase flash (100-40% acetonitrile+0.05% ammonium bicarbonate in water, over 20 min) to afford the title compound (170 mg, 0.60 mmol, 67% yield) as a white solid. MS (ESI) m/z 286.1 $[M+1]^+$.

2-(4-(Dimethylamino)piperidin-1-yl)quinoline-6-carbaldehyde. To a stirred solution of (2-(4-(dimethylamino)piperidin-1-yl)quinolin-6-yl)methanol (170 mg, 0.6 mmol) in dichloromethane (6 mL) was added manganese dioxide (1036 mg, 11.91 mmol) at room temperature for 12 h. The mixture was filtered and the filtrate was concentrated and to afford the title compound (150 mg, 0.53 mmol, 89% yield) as a light-yellow oil. MS (ESI) m/z 284.3 $[M+1]^+$.

3-(5-(((S)-1-((2-(4-(Dimethylamino)piperidin-1-yl)quinolin-6-yl)methyl)pyr-rolidin-3-yl)oxy)-1-oxoisoindolin-2-yl)piperidine-2,6-dione. To a solution of 2-(4-(dimethylamino)piperidin-1-yl)quinoline-6-carbaldehyde (100 mg, 0.35 mmol), 3-(1-oxo-5-(((S)-pyrrolidin-3-yl)oxy)isoindolin-2-yl)piperidine-2,6-dione; 2,2-2-trifluoroacetic acid (120 mg, 0.27 mmol) and triethylamine (0.10 mL, 0.70 mmol) in dichloromethane (5 mL) was added triacetoxyborohydride (220 mg, 1.04 mmol). The mixture was stirred for 12 h at room temperature under nitrogen atmosphere and concentrated. The residue was purified by silica gel chromatography (0 to 10% methanol in dichloromethane) and preparative HPLC with the following conditions: Column: Xselect CSH C18 OBD Column 30*150 mm 5 μm; Mobile Phase A: water (0.05% TFA), Mobile Phase B: acetonitrile; Flow rate: 60 mL/min; Gradient: 2% B to 15% B in 7 min, 15% B; Wave Length: 254/220 nm; $RT_1$ (min): 6.4. The fractions containing desired product were collected and evaporated under reduced pressure to afford the title compound (46.1 mg, 0.077 mmol, 22% yield) as a white solid. $^1H$ NMR (400 MHz, Methanol-$d_4$) δ 8.34 (m, 1H), 8.09-7.90 (m, 3H), 7.74-7.53 (m, 2H), 7.17-7.09 (m, 1H), 7.02 (m, 1H), 5.31 (m, 1H), 5.10-5.05 (m, 1H), 4.71 (m, 2H), 4.64 (m, 2H), 4.51-4.38 (m, 2H), 3.86-3.58 (m, 5H), 3.46 (t, J=13.1 Hz, 2H), 3.00-2.90 (m, 7H), 2.83-2.74 (m, 1H), 2.60 (m, 1H), 2.50-2.31 (m, 4H), 2.24-2.12 (m, 1H), 2.06-1.93 (m, 2H); MS (ESI) m/z 597.2 $[M+1]^+$.

Example S165. (S)-3-(5-(((S)-1-((2-(4-Methylpiperazin-1-yl)quinazolin-6-yl)methyl)pyrrolidin-3-yl)oxy)-1-oxoisoindolin-2-yl)piperidine-2,6-dione

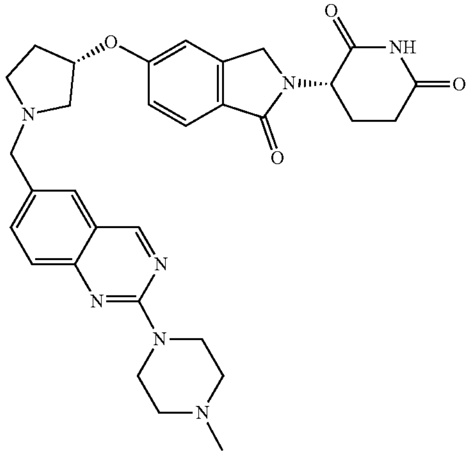 [SMILES: CN1CCN(c2ncc3cc(CN4CC[C@H](Oc5ccc6c(c5)CN([C@H]5CCC(=O)NC5=O)C6=O)C4)ccc3n2)CC1]

6-Bromo-2-(4-methylpiperazin-1-yl)quinazoline. To a solution of 6-bromo-2-chloroquinazoline (1 g, 4.11 mmol) in NMP (10 mL) was added 1-methylpiperazine (2.05 g, 20.47 mmol) at room temperature and the solution was stirred at 150° C. for 1 h under nitrogen. The resulting solution was purified by reverse phase flash (30-100% acetonitrile+0.05% ammonium bicarbonate in water, over 30 min) to afford the title compound (1.20 g, 3.90 mmol, 95% yield) as a yellow solid. MS (ESI) m/z 307.1 $[M+1]^+$.

2-(4-Methylpiperazin-1-yl)-6-vinylquinazoline. To a solution of 6-bromo-2-(4-methylpiperazin-1-yl)quinazoline (700 mg, 2.28 mmol) in 1,4-dioxane (20 mL) and water (4 mL) were added potassium vinyltrifluoroborate (611 mg, 4.53 mmol), sodium carbonate (483 mg, 4.56 mmol), [1,1'-Bis(diphenylphosphino)ferrocene]dichloropalladium(II) (186 mg, 0.26 mmol) and the mixture was stirred at 80° C. for 2 h under nitrogen. The mixture was added water and extracted with ethyl acetate. The extracts were washed with brine, dried over anhydrous sodium sulfate, filtered and concentrated. The residue was purified by reverse phase flash (30-100% acetonitrile+0.05% ammonium bicarbonate in water, over 30 min) to afford the title compound (300 mg, 1.17 mmol, 51% yield). MS (ESI) m/z 255.2 $[M+1]^+$.

2-(4-Methylpiperazin-1-yl)quinazoline-6-carbaldehyde. To a solution of 2-(4-methylpiperazin-1-yl)-6-vinylquinazoline (300 mg, 1.17 mmol) in tert-butanol (7 mL) and water (7 mL) were added potassium osmate (44 mg, 0.12 mmol), 4-methylmorpholine N-oxide (277 mg, 2.36 mmol), citric acid (496 mg, 2.58 mmol) at room temperature. The mixture was stirred at room temperature for 4 h under nitrogen. Then sodium periodate (507 mg, 2.35 mmol) was added above mixture and the mixture was stirred at room temperature for 1 h under nitrogen. The mixture was added saturated sodium bicarbonate to pH~7 and extracted with ethyl acetate. The extracts were washed with brine, dried over anhydrous sodium sulfate, filtered and concentrated. The residue was purified by silica gel chromatography (0-10% methanol in dichloromethane) to afford the title compound (180 mg, 0.70 mmol, 60% yield) as a brown solid. MS (ESI) m/z 257.2 [M+1]$^+$.

Tert-butyl(S)-5-amino-4-(5-(((S)-1-((2-(4-methylpiperazin-1-yl)quinazolin-6-yl)methyl)pyrrolidin-3-yl)oxy)-1-oxoisoindolin-2-yl)-5-oxopentanoate. To a solution of 2-(4-methylpiperazin-1-yl)quinazoline-6-carbaldehyde (180 mg, 0.70 mmol) and tert-butyl (S)-5-amino-5-oxo-4-(1-oxo-5-(((S)-pyrrolidin-3-yl)oxy) isoindolin-2-yl)pentanoate (250 mg, 0.62 mmol) in THF (7 mL) was added acetic acid (0.1 mL) and the mixture was stirred at room temperature for 30 min under nitrogen. Then sodium triacetoxyborohydride (200 mg, 0.94 mmol) was added into the above mixture and stirred at room temperature for 5 h under nitrogen. The mixture was added saturated sodium bicarbonate to pH~7 and extracted with ethyl acetate. The extracts were washed with brine, dried over anhydrous sodium sulfate, filtered and concentrated. The residue was purified by silica gel chromatography (0-10% methanol in dichloromethane) to afford the title compound (230 mg, 0.36 mmol, 51% yield) as a yellow solid. MS (ESI) m/z 644.2 [M+1]$^+$.

(S)-3-(5-(((S)-1-((2-(4-Methylpiperazin-1-yl)quinazolin-6-yl)methyl)pyrrolidin-3-yl)oxy)-1-oxoisoindolin-2-yl)piperidine-2,6-dione. To a solution of tert-butyl (S)-5-amino-4-(5-(((S)-1-((2-(4-methylpiperazin-1-yl)quinazolin-6-yl) methyl)pyrrolidin-3-yl)oxy)-1-oxoisoindolin-2-yl)-5-oxopentanoate (230 mg, 0.36 mmol) in acetonitrile (7 mL) was added benzenesulfonic acid (170 mg, 1.08 mmol) and the mixture was stirred at 60° C. for 12 h under nitrogen. The resulting mixture was added little saturated sodium bicarbonate to pH~7 and extracted with dichloromethane. The extracts were washed with saturated sodium bicarbonate, dried over anhydrous sodium sulfate, filtered and concentrated. The residue was purified by silica gel chromatography (0-10% methanol in dichloromethane) and further purified by preparative chiral HPLC with the following conditions: Column: Chiralpak IF-3, 4.6*50 mm; 3 um; mobile phase A: tert-Butyl methyl ether: (ethanol:dichloromethane=1:1)=30:70; flow rate: 1 mL/min; gradient: 0% B to 0% B). Pure fractions were evaporated and the residue was dissolved in 0.5% formic acid, lyophilized to afford the title compound (40.5 mg, 0.071 mmol, 20% yield) as a yellow solid. $^1$H NMR (400 MHz, DMSO-$d_6$) δ 10.95 (s, 1H), 9.22 (s, 1H), 7.78 (d, J=2.0 Hz, 1H), 7.73-7.70 (m, 1H), 7.60 (d, J=8.4 Hz, 1H), 7.50 (d, J=8.7 Hz, 1H), 7.11 (d, J=2.2 Hz, 1H), 7.00-6.97 (m, 1H), 5.10-4.98 (m, 2H), 4.37 (d, J=17.2 Hz, 1H), 4.24 (d, J=17.2 Hz, 1H), 3.93 (m, 3H), 3.76 (m, 2H), 2.97 (m, 2H), 2.90-2.87 (m, 1H), 2.73 (m, 5H), 2.63-2.54 (m, 2H), 2.45 (m, 3H), 2.41-2.33 (m, 3H), 2.01-1.93 (m, 1H), 1.89-1.81 (m, 1H); MS (ESI) m/z 570.3 [M+1]$^+$.

Example S166. (S)-3-(5-(((S)-1-((2-(Azetidin-1-yl) quinazolin-6-yl)methyl)pyrrolidin-3-yl)oxy)-1-oxoisoindolin-2-yl)piperidine-2,6-dione

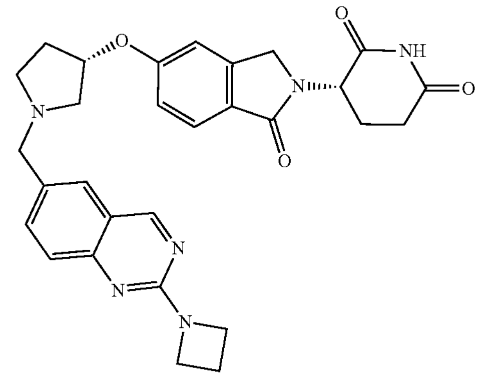 [SMILES: O=C1CC[C@H](N2Cc3cc(O[C@H]4CCN(Cc5ccc6nc(N7CCC7)ncc6c5)C4)ccc3C2=O)C(=O)N1]

2-(Azetidin-1-yl)-6-bromo-quinazoline. To a mixture of 6-bromo-2-chloro-quinazoline (800 mg, 3.29 mmol) and azetidine (187 mg, 3.29 mmol) in DMF (20 mL) was added triethylamine (1.34 mL, 9.86 mmol). The resulting solution was stirred for 2 h at 100° C. under nitrogen. The solution was diluted with water and extracted with ethyl acetate. The extracts were washed with brine, dried over sodium sulfate, filtered and concentrated to afford the title compound (850 mg, 3.22 mmol, 98% yield) as a white solid. MS (ESI) m/z 266.1 [M+1]$^+$.

2-(Azetidin-1-yl)-6-vinyl-quinazoline. To a solution of 2-(azetidin-1-yl)-6-bromo-quinazoline (500 mg, 1.89 mmol) and potassium vinyltrifluoroborate (255 mg, 1.89 mmol) in 1,4-dioxane (20 mL) and water (4 mL) were added [1,1'-bis(diphenylphosphino)ferrocene]dichloropalladium(II) (308 mg, 0.38 mmol) and sodium carbonate (602 mg, 5.68 mmol) at room temperature. The reaction was heated to 90° C. and stirred for 5 h under nitrogen. The reaction mixture was concentrated and the residue was purified by reverse-phase flash (10-60% acetonitrile+0.05% ammonium bicarbonate in water, over 20 min) to give the title compound (300 mg, 1.42 mmol, 75% yield) as a white solid. MS (ESI) m/z 212.2 [M+1]$^+$.

2-(Azetidin-1-yl)quinazoline-6-carbaldehyde. To a solution of 2-(azetidin-1-yl)-6-vinyl-quinazoline (300 mg, 1.42 mmol), potassium osmate (52 mg, 0.14 mmol) and 4-methylmorpholine n-oxide (332 mg, 2.84 mmol) in 1-butanol (10 mL) and water (10 mL) was added citric acid (545 mg, 2.84 mmol) at room temperature and the reaction mixture was stirred at room temperature for 4 h under nitrogen. Then sodium periodate (911 mg, 4.26 mmol) was added in several portions to the above mixture at 0° C. and the resulting mixture was stirred at room temperature for 1 h. The mixture was added saturated sodium bicarbonate solution to pH~7 and extracted with ethyl acetate. The extracts were washed with brine, dried over sodium sulfate, filtered and concentrated to afford the title compound (200 mg, 0.94 mmol, 66% yield) as a yellow solid. MS (ESI) m/z 214.0 [M+1]$^+$.

Tert-butyl (S)-5-amino-4-(5-(((S)-1-((2-(azetidin-1-yl) quinazolin-6-yl)methyl)pyrrolidin-3-yl)oxy)-1-oxoisoindolin-2-yl)-5-oxopentanoate. To a stirred solution of 2-(azetidin-1-yl)quinazoline-6-carbaldehyde (150 mg, 0.70 mmol) and tert-butyl (S)-5-amino-5-oxo-4-(1-oxo-5-(((S)-pyrrolidin-3-yl)oxy)isoindolin-2-yl)pentanoate (851 mg, 2.11 mmol) in THF (10 mL) was added sodium triacetoxyborohydride (298 mg, 1.41 mmol). The reaction solution was stirred for 12 h at room temperature under nitrogen. The solution was evaporated and the residue was purified by silica gel chromatography (0-10% methanol in dichloromethane) to give the title compound (100 mg, 0.17 mmol, 24% yield) as a white solid. MS (ESI) m/z 601.4 $[M+1]^+$.

(S)-3-(5-(((S)-1-((2-(azetidin-1-yl)quinazolin-6-yl)methyl)pyrrolidin-3-yl)oxy)-1-oxoisoindolin-2-yl)piperidine-2,6-dione. To a solution of tert-butyl (S)-5-amino-4-(5-(((S)-1-((2-(azetidin-1-yl)quinazolin-6-yl)methyl)pyrrolidin-3-yl)oxy)-1-oxoisoindolin-2-yl)-5-oxopentanoate (180 mg, 0.29 mmol) and benzenesulfonic acid (120 mg, 0.76 mmol) in acetonitrile (20 mL) was stirred at 60° C. for 12 h under nitrogen. The reaction mixture was cooled to room temperature and slowly neutralized with sodium bicarbonate carefully to pH~7. Then the above mixture was extracted with dichloromethane. The combined organic layers were washed with brine, dried over sodium sulfate, filtered and concentrated. The crude product was purified by silica gel chromatography (0-10% methanol in dichloromethane) and preparative Chiral SFC with the following conditions: Column: CHIRALPAK IF, 2*25 cm, 5 μm; Mobile phase A: tert-butyl methyl ether HPLC, Mobile phase B: ethanol:dichloromethane=1:1; Flow rate: 20 mL/min; Gradient: 70% B to 70% B in 24 min; Wave Length: 220/254 nm; $RT_1$ (min): 11.20; $RT_2$ (min): 19.86; Sample Solvent: ethanol HPLC; Injection Volume: 2 mL; Number of Runs: 3. The fractions containing desired product were collected and evaporated under reduced pressure to afford the title compound (59 mg, 0.11 mmol, 38% yield) as yellow solid. $^1H$ NMR (400 MHz, DMSO-$d_6$) δ 10.96 (s, 1H), 9.15 (s, 1H), 8.15 (s, 1H), 7.85-7.70 (m, 2H), 7.60 (d, J=8.4 Hz, 1H), 7.48 (d, J=8.6 Hz, 1H), 7.10 (d, J=2.2 Hz, 1H), 7.00-6.98 (m, 1H), 5.06-5.03 (m, 1H), 4.99-4.97 (m, 1H), 4.37 (d, J=17.2 Hz, 1H), 4.24 (d, J=17.2 Hz, 1H), 4.12 (m, 4H), 3.73-3.68 (m, 2H), 2.99-2.83 (m, 2H), 2.79-2.66 (m, 2H), 2.60-2.54 (m, 2H), 2.44-2.30 (m, 4H), 1.97-1.95 (m, 1H), 1.88-1.78 (m, 1H); MS (ESI) m/z 527.2 $[M+1]^+$.

Example S167. (S)-3-(1-Oxo-5-(((S)-1-((2-(pyrrolidin-1-yl)quinazolin-6-yl)methyl)pyrrolidin-3-yl)oxy)isoindolin-2-yl)piperidine-2,6-dione

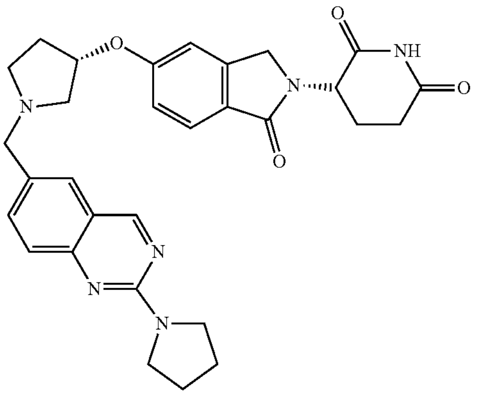

6-Bromo-2-(pyrrolidin-1-yl)quinazoline. A mixture of the compound of 6-bromo-2-chloroquinazoline (300 mg, 1.23 mmol) and pyrrolidine (438 mg, 6.16 mmol) in ethanol (6 mL) was stirred at 80° C. for 12 h under nitrogen. The reaction solution was concentrated to afford the title compound (260 mg, 0.93 mmol, 76% yield) as yellow solid. MS (ESI) m/z 277.9 $[M+1]^+$.

2-(Pyrrolidin-1-yl)-6-vinylquinazoline. To a stirred solution of 6-bromo-2-(pyrrolidin-1-yl)quinazoline (260 mg, 0.93 mmol) and potassium trifluoro(vinyl)boranuide (150 mg, 1.12 mmol) in 1,4-dioxane (5 mL) and water (0.5 mL) were added tetrakis(triphenylphosphine)palladium (108 mg, 0.09 mmol) and cesium carbonate (607 mg, 1.87 mmol). The above mixture was stirred at 80° C. for 3 h under nitrogen. Then the reaction mixture was added water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (160 mg, 0.71 mmol, 76% yield) as a light-yellow solid. MS (ESI) m/z 226.1 $[M+1]^+$.

2-(Pyrrolidin-1-yl)quinazoline-6-carbaldehyde. To a stirred solution of 2-(pyrrolidin-1-yl)-6-vinylquinazoline (160 mg, 0.71 mmol) in tert-butanol (3 mL) and water (3 mL) were added 4-methyl-morpholin4-oxide (83 mg, 0.71 mmol), potassium osmate (26 mg, 0.07 mmol) and citric acid (136 mg, 0.71 mmol). The above mixture was stirred at room temperature for 3 h under nitrogen. Then the mixture was added sodium periodate (152 mg, 0.71 mmol) and stirred for another 1 h. The reaction mixture was diluted with water and extracted with ethyl acetate. The extracts were washed with brine, dried over sodium sulfate, filtered and concentrated. The residue was purified by silica gel chromatography (0 to 40% ethyl acetate in petroleum ether) to afford the title compound (100 mg, 0.44 mmol, 62% yield) as a light-yellow oil. MS (ESI) m/z 228.1 $[M+1]^+$.

Tert-butyl(S)-5-amino-5-oxo-4-(1-oxo-5-(((S)-1-((2-(pyrrolidin-1-yl)quinazolin-6-yl)methyl)pyrrolidin-3-yl)oxy)isoindolin-2-yl)pentanoate. To a solution of 2-(pyrrolidin-1-yl)quinazoline-6-carbaldehyde (100 mg, 0.44 mmol), tert-butyl tert-butyl(S)-5-amino-5-oxo-4-(1-oxo-5-(((S)-pyrrolidin-3-yl)oxy)isoindolin-2-yl)pentanoate (266 mg, 0.58 mmol) and acetic acid (0.02 mL, 0.44 mmol) in THF (10 mL) was added sodium triacetoxyborohydride (233 mg, 1.1 mmol). The mixture was stirred for 12 h at room temperature under nitrogen. The resulting mixture was concentrated and the residue was purified by reverse phase flash (10-40% acetonitrile+0.05% ammonium bicarbonate in water, over 25 min) to afford the title compound (150 mg, 0.24 mmol, 55% yield) as a light-yellow oil. MS (ESI) m/z 615.2 $[M+1]^+$.

(S)-3-(1-Oxo-5-(((S)-1-((2-(pyrrolidin-1-yl)quinazolin-6-yl)methyl)pyrrolidin-3-yl)oxy)isoindolin-2-yl)piperidine-2,6-dione. A solution of tert-butyl (S)-5-amino-5-oxo-4-(1-oxo-5-(((S)-1-((2-(pyrrolidin-1-yl)quinazolin-6-yl)methyl)pyrrolidin-3-yl)oxy)isoindolin-2-yl)pentanoate (150 mg, 0.24 mmol) and benzenesulfonic acid (120 mg, 0.76 mmol) in acetonitrile (10 mL) was stirred for 12 h at 60° C. under nitrogen. The reaction mixture was quenched with water, acidified to pH~7 with saturated sodium bicarbonate and extracted with chloroform. The extracts were washed with brine, dried over anhydrous sodium sulfate, filtered and concentrated. The crude product was purified further by silica gel chromatography (0 to 30% ethyl acetate in petroleum ether) and preparative Chiral HPLC with the following conditions: Column: CHIRALPAK IF-3, 4.6*50 mm, 3 μm; Mobile Phase A: tert-butyl methyl ether: (ethanol:dichloromethane=1:1)=30:70; Flow rate: 1 mL/min; Gradient: 0% B to 0% B; Injection Volume: 5 mL. Pure fractions were evaporated, dissolved into 0.1% formic acid and lyophilized to afford the title compound (12.8 mg, 0.023 mmol, 10% yield) as a yellow solid. $^1$H NMR (400 MHz, DMSO-$d_6$) δ 10.94 (s, 1H), 9.14 (s, 1H), 7.76-7.57 (m, 3H), 7.46 (d, J=8.6 Hz, 1H), 7.10 (d, J=2.2 Hz, 1H), 7.00-6.98 (m, 1H), 5.10-4.96 (m, 2H), 4.37 (d, J=17.3 Hz, 1H), 4.24 (d, J=17.2 Hz, 1H), 3.73-3.64 (m, 2H), 3.59 (m, 4H), 2.91-2.87 (m, 2H), 2.78-2.66 (m, 2H), 2.64-2.55 (m, 1H), 2.48-2.41 (m, 1H), 2.35-2.31 (m, 2H), 1.96 (m, 5H), 1.87-1.76 (m, 1H); MS (ESI) m/z 541.2 [M+1]$^+$.

Example S168. (S)-3-(5-(((S)-1-((2-(4-Acetylpiperazin-1-yl)quinolin-6-yl)methyl)pyrrolidin-3-yl)oxy)-1-oxoisoindolin-2-yl)piperidine-2,6-dione

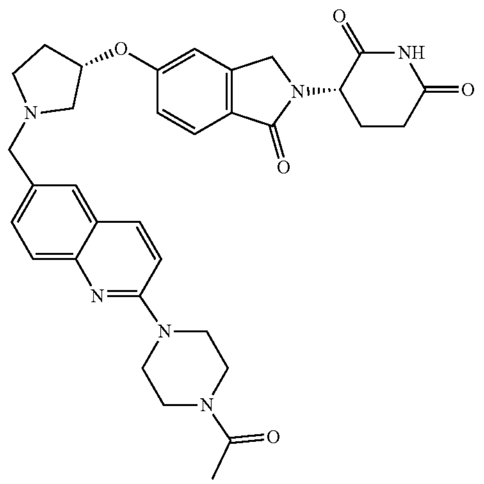 [SMILES: CC(=O)N1CCN(c2ccc3cc(CN4CC[C@H](Oc5ccc6c(c5)CN([C@H]5CCC(=O)NC5=O)C6=O)C4)ccc3n2)CC1]

1-(4-(6-Bromoquinolin-2-yl)piperazin-1-yl)ethan-1-one. To a stirred solution of 6-bromo-2-chloroquinoline (1.0 g, 4.12 mmol) and 1-(piperazin-1-yl)ethan-1-one (1.59 g, 12.37 mmol) in NMP (10 mL) was added N,N-diisopropylethylamine (2.74 mL, 16.49 mmol) at 0° C. The reaction was stirred for 12 h at 150° C. under nitrogen. The resulting mixture was purified directly by reverse phase flash (10-60% acetonitrile+0.05% ammonium bicarbonate in water, over 25 min) afford title compound (1.2 g, 3.54 mmol, 86% yield) as a yellow solid. MS (ESI) m/z 334.0 [M+1]$^+$.

1-(4-(6-Vinylquinolin-2-yl)piperazin-1-yl)ethan-1-one. To a mixture of 1-(4-(6-bromoquinolin-2-yl)piperazin-1-yl)ethan-1-one (600 mg, 1.80 mmol), potassium trifluoro(vinyl)borate (484 mg, 3.59 mmol) and sodium carbonate (570 mg, 5.39 mmol) in 1,4-dioxane (5 mL) and water (0.50 mL) was added dichlorobis(triphenylphosphine)palladium(II) dichloromethane adduct (146 mg, 0.19 mmol) and the reaction was stirred for 2 h at 80° C. under nitrogen. The resulting mixture was concentrated and the residue was purified by silica gel chromatography (0 to 50% ethyl acetate in petroleum ether) to afford title compound (350 mg, 1.24 mmol, 68% yield) as a yellow solid. MS (ESI) m/z 282.0 [M+1]$^+$.

2-(4-Acetylpiperazin-1-yl)quinoline-6-carbaldehyde. To a stirred mixture of 1-(4-(6-vinylquinolin-2-yl)piperazin-1-yl)ethan-1-one (350 mg, 1.24 mmol), 4-methylmorpholine N-oxide (291 mg, 2.49 mmol) and critic acid (477 mg, 2.49 mmol) in tert-butanol (5 mL) and water (5 mL) was added potassium osmate (41 mg, 0.12 mmol) at room temperature. The reaction was stirred for 12 h at room temperature. To the above mixture was added sodium periodate (805 mg, 3.73 mmol) at 0° C. The mixture was added saturated sodium bicarbonate to pH~7 and extracted with ethyl acetate. The extracts were dried over anhydrous sodium sulfate, filtered and concentrated. The residue was purified by silica gel chromatography (0 to 40% methanol in dichloromethane) to afford title compound (240 mg, 0.84 mmol, 67% yield) as a yellow oil. MS (ESI) m/z 284.2 [M+1]$^+$.

Tert-butyl (S)-4-(5-(((S)-1-((2-(4-acetylpiperazin-1-yl)quinolin-6-yl)methyl)pyrrolidin-3-yl)oxy)-1-oxoisoindolin-2-yl)-5-amino-5-oxopentanoate. To a stirred solution of 2-(4-acetylpiperazin-1-yl)quinoline-6-carbaldehyde (120 mg, 0.42 mmol), acetic acid (0.01 mL) and tert-butyl (S)-5-amino-5-oxo-4-(1-oxo-5-(((S)-pyrrolidin-3-yl)oxy)isoindolin-2-yl)pentanoate (acetic acid salt, 196 mg, 0.42 mmol) in THF (5 mL) pre-stirred for 15 min was added sodium triacetoxyborohydride (224 mg, 1.06 mmol) at 0° C. and the solution was stirred at room temperature for 12 h under nitrogen. Most solution was removed and the residue was purified by silica gel chromatography (0 to 10% methanol in dichloromethane) to afford title compound (90 mg, 0.12 mmol, 29% yield) as a yellow oil. MS (ESI) m/z 671.4 [M+1]$^+$.

(S)-3-(5-(((S)-1-((2-(4-Acetylpiperazin-1-yl)quinolin-6-yl)methyl)pyrrolidin-3-yl)oxy)-1-oxoisoindolin-2-yl)piperidine-2,6-dione. To a stirred solution of tert-butyl (S)-4-(5-(((S)-1-((2-(4-acetylpiperazin-1-yl)quinolin-6-yl)methyl)pyrolidin-3-yl)oxy)-1-oxoisoindolin-2-yl)-5-amino-5-oxopentanoate (90 mg, 0.12 mmol) and benzenesulfonic acid (64 mg, 0.41 mmol) in acetonitrile (5 mL) was stirred at 60° C. for 12 h under nitrogen. The resulting mixture was cooled to room temperature and slowly neutralized with a buffer solution (0.05% potassium dihydrogen phosphate and 0.05% potassium phosphate dibasic in water) to pH~7 and extracted with dichloromethane. The extracts were dried over anhydrous sodium sulfate, filtered and concentrated. The residue was purified by silica gel chromatography (0-7% methanol in dichloromethane) and further purified by preparative chiral HPLC with following conditions: Column: CHIRALPAK IF, 2*25 cm, 5 μm; Mobile Phase A: tert-butyl methyl ether—HPLC, Mobile Phase B: ethanol: dichloromethane=1:1; Flow rate: 17 mL/min; Gradient: 70% B to 70% B in 14 min; Wave Length: 220/254 nm; $RT_1$ (min): 9.71; $RT_2$ (min): 13.18; Sample Solvent: ethanol—HPLC; Injection Volume: 2.4 mL. Pure fractions were evaporated, dissolved in 0.1% formic acid and lyophilized to afford title compound (28.2 mg, 0.047 mmol, 39% yield) as a yellow solid. $^1$H NMR (400 MHz, DMSO-$d_6$) δ 10.94 (s, 1H), 8.05 (d, J=9.2 Hz, 1H), 7.64-7.59 (m, 2H), 7.56-7.51 (m, 2H), 7.24 (d, J=9.2 Hz, 1H), 7.13-7.09 (m, 1H), 7.00 (dd, J=8.4, 2.0 Hz, 1H), 5.08-5.01 (m, 2H), 4.37 (d, J=17.2 Hz, 1H), 4.24 (d, J=17.2 Hz, 1H), 3.76-3.72 (m, 4H), 3.67-3.64 (m, 2H), 3.58-3.56 (m, 4H), 3.00-2.93 (m, 1H), 2.91-2.85 (m, 1H), 2.80-2.73 (m, 2H), 2.67-2.56 (m, 2H), 2.38-2.31 (m, 2H), 2.06 (s, 3H), 1.98-1.95 (m, 1H), 1.86-1.80 (m, 1H); MS (ESI) m/z 597.2 [M+1]$^+$.

Example S169. (S)-3-(5-(((S)-1-((2-(1-Acetylpiperidin-4-yl)quinazolin-6-yl)methyl)pyrrolidin-3-yl)oxy)-1-oxoisoindolin-2-yl)piperidine-2,6-dione

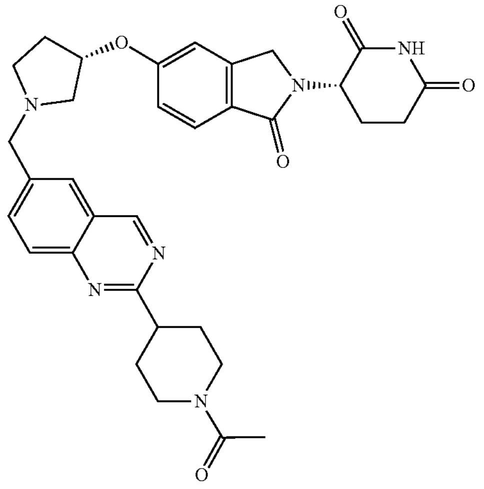 [SMILES: CC(=O)N1CCC(c2ncc3cc(CN4CC[C@H](Oc5ccc6c(c5)CN([C@H]5CCC(=O)NC5=O)C6=O)C4)ccc3n2)CC1]

1-Acetyl-N-(2-amino-5-bromobenzyl)piperidine-4-carboxamide. To a stirred solution of 1-acetylpiperidine-4-carbonyl chloride (1.8 g, 9.50 mmol) and triethylamine (7.30 mL, 52.4 mmol) in dichloromethane (30 mL) was added 2-(aminomethyl)-4-bromoaniline (850 mg, 4.23 mmol) at 0° C. for 10 min. The above mixture was stirred at room temperature for 2 h. The resulting mixture was diluted with water and extracted with dichloromethane. The extracts were washed with brine, dried over anhydrous sodium sulfate, filtered and concentrated to afford the title compound (1.6 g, 4.52 mmol, 48% yield) as a light-yellow oil. MS (ESI) m/z 354.0 $[M+1]^+$.

1-(4-(6-Bromo-1,4-dihydroquinazolin-2-yl)piperidin-1-yl)ethan-1-one. A stirred solution of 1-acetyl-N-(2-amino-5-bromobenzyl)piperidine-4-carboxamide (1.10 g, 3.11 mmol) in acetic acid (10 mL) was stirred at 100° C. for 12 h. The resulting mixture was concentrated to afford the title compound as an orange oil. MS (ESI) m/z 336.0 $[M+1]^+$.

1-(4-(6-Bromoquinazolin-2-yl)piperidin-1-yl)ethan-1-one. To a stirred solution of 1-(4-(6-bromo-1,4-dihydroquinazolin-2-yl)piperidin-1-yl)ethan-1-one (1.00 g, 2.97 mmol) in dichloromethane (30 mL) was added manganese dioxide (5.18 g, 59.48 mmol) at room temperature. The reaction mixture was stirred at room temperature for 12 h. The mixture was filtered and the filtrate was concentrated to afford the title compound (800 mg, 2.39 mmol, 81% yield) as a yellow oil. MS (ESI) m/z 334 $[M+1]^+$.

1-(4-(6-Vinylquinazolin-2-yl)piperidin-1-yl)ethan-1-one. To a stirred solution of 1-(4-(6-bromoquinazolin-2-yl)piperidin-1-yl)ethan-1-one (400 mg, 1.2 mmol) and potassium trifluoro(vinyl)boranuide (192 mg, 1.44 mmol) in 1,4-dioxane (5 mL) and water (0.5 mL) were added tetrakis (triphenylphosphine)palladium (138 mg, 0.12 mmol) and cesium carbonate (778 mg, 2.39 mmol). The above mixture was stirred at 80° C. for 3 h under nitrogen. Then the mixture extracted with water and ethyl acetate. The extracts were washed with brine, dried over anhydrous sodium sulfate, filtered and concentrated. The residue was purified by silica gel chromatography (0 to 40% ethyl acetate in petroleum ether) to afford the title compound (250 mg, 0.89 mmol, 74% yield) as a light-yellow solid. MS (ESI) m/z 281 $[M+1]^+$.

2-(1-Acetylpiperidin-4-yl)quinazoline-6-carbaldehyde. To a stirred solution of 1-(4-(6-vinylquinazolin-2-yl)piperidin-1-yl)ethan-1-one (170 mg, 0.60 mmol) in tert-butanol (4 mL, 0.3 mmol) and water (4 mL, 0.3 mmol) were added 4-methyl-morpholin4-oxide (141 mg, 1.21 mmol), potassium osmate (22 mg, 0.06 mmol) and citric acid (232 mg, 1.21 mmol). The above mixture was stirred at room temperature for 3 h. Then the mixture was added sodium periodate (387 mg, 1.81 mmol) and stirred for another 1 h. The resulting mixture was added saturated sodium bicarbonate to pH~7 and extracted with ethyl acetate. The extracts were washed with brine, dried over sodium sulfate, filtered and concentrated. The residue was purified by silica gel chromatography (0 to 30% ethyl acetate in petroleum ether) to afford the title compound (100 mg, 0.35 mmol, 58% yield) as a light-yellow oil. MS (ESI) m/z 283 $[M+1]^+$.

(S)-3-(5-(((S)-1-((2-(1-Acetylpiperidin-4-yl)quinazolin-6-yl)methyl)pyrrolidin-3-yl)oxy)-1-oxoisoindolin-2-yl)piperidine-2,6-dione. To a solution of 2-(1-acetylpiperidin-4-yl)quinazoline-6-carbaldehyde (80 mg, 0.28 mmol), (3S)-3-[1-oxo-5-[(3S)-pyrrolidin-3-yl]oxy-isoindolin-2-yl] piperidine-2,6-dione; 2,2,2-trifluoroacetic acid (96 mg, 0.22 mmol) and triethylamine (56 mg, 0.56 mmol) in dichloromethane (5 mL) was added sodium triacetoxyborohydride (176 mg, 0.83 mmol). The mixture was stirred for 12 h at room temperature under nitrogen. The resulting mixture was concentrated. The residue was purified by silica gel chromatography (0 to 10% methanol in dichloromethane) and preparative chiral-HPLC with the following conditions: Column: CHIRALPAK IF, 2*25 cm, 5 μm; Mobile Phase A: tert-butyl methyl ether—HPLC, Mobile Phase B: ethanol: dichloromethane=1:1-HPLC; Flow rate: 18 mL/min; Gradient: 80% B to 50% B in 13 min; Wave Length: 220/254 nm; $RT_1$ (min): 8.52; $RT_2$ (min): 10.69; Sample Solvent: ethanol-HPLC; Injection Volume: 0.8 mL; Number Of Runs: 5 and preparative HPLC with the follow conditions: Column: Xselect CSH C18 OBD Column 30*150 mm, 5 μm; Mobile Phase A: water (0.1% formic acid), Mobile Phase B: acetonitrile; Flow rate: 60 mL/min; Gradient: 2% B to 20% B in 10 min, 20% B; Wave Length: 254 nm; $RT_1$ (min): 8.5. The fractions containing desired product were collected and evaporated under reduced pressure to afford the title compound (36.1 mg, 0.06 mmol, 21% yield) as an off-white solid. $^1H$ NMR (300 MHz, DMSO-$d_6$) δ 9.53 (s, 1H), 8.28-7.84 (m, 4H), 7.62 (d, J=8.4 Hz, 1H), 7.11 (d, J=2.1 Hz, 1H), 7.01-6.99 (m, 1H), 5.05-5.01 (m, 2H), 4.47 (d, J=13.0 Hz, 1H), 4.41-4.21 (m, 2H), 3.99-3.77 (m, 3H), 3.23-3.19 (m, 2H), 3.01-2.70 (m, 5H), 2.67-2.54 (m, 2H), 2.38-2.34 (m, 2H), 2.05 (s, 6H), 1.92-1.63 (m, 3H); MS (ESI) m/z 597.3 $[M+1]^+$.

Example S170. (S)-3-(5-(((S)-1-((2-(1-Acetylpiperidin-4-yl)quinolin-6-yl)methyl)pyrrolidin-3-yl)oxy)-1-oxoisoindolin-2-yl)piperidine-2,6-dione

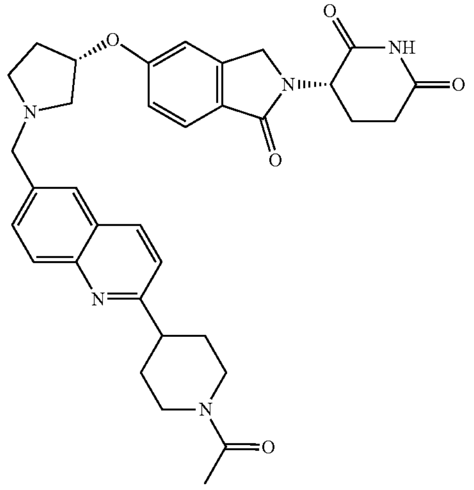 [SMILES: CC(=O)N1CCC(c2ccc3cc(CN4CC[C@H](Oc5ccc6c(c5)CN([C@H]5CCC(=O)NC5=O)C6=O)C4)ccc3n2)CC1]

Tert-butyl 4-(6-bromoquinolin-2-yl)piperidine-1-carboxylate. To a stirred solution of (2-amino-5-bromo-phenyl) methanol (1.5 g, 7.42 mmol) and tert-butyl 4-acetylpiperidine-1-carboxylate (1.69 g, 7.42 mmol) in toluene (20 mL) was added lithium tert-butoxide (890 mg, 11.14 mmol). The resulting mixture was stirred at 110° C. for 3 h under nitrogen. The resulting mixture was diluted with water and extracted with ethyl acetate. The extracts were washed with brine, dried over anhydrous sodium sulfate, filtered and concentrated. The residue was purified by reverse phase flash (10-70% acetonitrile+0.05% ammonium bicarbonate in water, over 20 min) to give the title compound (1.5 g, 3.83 mmol, 52% yield) as a light yellow oil. MS (ESI) m/z 393.1 $[M+1]^+$.

6-Bromo-2-(piperidin-4-yl)quinoline. To a mixture of tert-butyl 4-(6-bromoquinolin-2-yl)piperidine-1-carboxylate (1.5 g, 3.83 mmol) in dichloromethane (5 mL) were added hydrochloric acid (2 M in dioxane, 8 mL) and 1,4-dioxane (8 mL). The reaction mixture was stirred at room temperature for 3 h. The resulting mixture was concentrated and the residue was purified by reverse phase flash (10-70% acetonitrile+0.05% TFA, over 20 min) to give the title compound (1.2 g, 4.12 mmol, 61% yield) as a white solid. MS (ESI) m/z 292.9 $[M+1]^+$.

1-(4-(6-Bromoquinolin-2-yl)piperidin-1-yl)ethan-1-one. To a mixture of 6-bromo-2-(piperidin-4-yl)quinoline (1.2 g, 4.12 mmol) and N,N-diisopropylethylamine (0.69 mL, 4.12 mmol) in dichloromethane (20 mL) was added acetyl chloride (485 mg, 6.18 mmol) at 0° C. under nitrogen. The reaction mixture was stirred at room temperature for 3 h. The resulting mixture was added water and extracted with ethyl acetate. The extracts were washed with brine, dried over anhydrous sodium sulfate, filtered and concentrated. The residue was purified by reverse phase flash (10-70% acetonitrile+0.05% ammonium bicarbonate in water, over 20 min) to give the title compound (1 g, 3.00 mmol, 73% yield) as a white solid. MS (ESI) m/z 333.1 $[M+1]^+$.

1-(4-(6-Vinylquinolin-2-yl)piperidin-1-yl)ethan-1-one. To a solution of 1-(4-(6-bromoquinolin-2-yl)piperidin-1-yl) ethan-1-one (1000 mg, 3 mmol) and potassium vinyltrifluoroborate (405 mg, 3 mmol) in 1,4-dioxane (20 mL) and water (4 mL) were added [1,1'-bis(diphenylphosphino)ferrocene]dichloropalladium(II) (489 mg, 0.60 mmol) and sodium carbonate (954 mg, 9 mmol) at room temperature. The reaction was heated to 90° C. and stirred for 5 h under nitrogen. The reaction mixture was concentrated and the residue was purified by reverse-phase flash (10-70% acetonitrile+0.05% ammonium bicarbonate in water, over 20 min) to give the title compound (520 mg, 1.86 mmol, 62% yield) as a white solid. MS (ESI) m/z 281.2 $[M+1]^+$.

2-(1-Acetylpiperidin-4-yl)quinoline-6-carbaldehyde. To a solution of 1-(4-(6-vinylquinolin-2-yl)piperidin-1-yl)ethan-1-one (520 mg, 1.85 mmol), potassium osmate (68 mg, 0.19 mmol) and 4-methylmorpholine N-oxide (434 mg, 3.71 mmol) in 1-butanol (20 mL) and water (20 mL) was added citric acid (712 mg, 3.71 mmol) at room temperature and the resulting mixture was stirred at room temperature for 4 h. Then sodium periodate (1190 mg, 5.56 mmol) was added in several portions to the above mixture at 0° C. and the resulting mixture was stirred at room temperature for 2 h under nitrogen. The mixture was added saturated sodium bicarbonate solution to pH~7 and extracted with ethyl acetate. The extracts were washed with brine, dried over sodium sulfate, filtered and concentrated to afford the title compound (350 mg, 1.24 mmol, 67% yield) as a yellow solid. MS (ESI) m/z 283.2 $[M+1]^+$.

Tert-butyl(4S)-4-[5-[(3S)-1-[[2-(1-acetyl-4-piperidyl)-6-quinolyl] methyl]pyrrolidin-3-yl]oxy-1-oxo-isoindolin-2-yl]-5-amino-5-oxo-pentanoate. To a stirred solution of 2-(1-acetyl-4-piperidyl)quinoline-6-carbaldehyde (150 mg, 0.53 mmol) and tert-butyl (4S)-5-amino-5-oxo-4-[1-oxo-5-[(3S)-pyrrolidin-3-yl]oxy-isoindolin-2-yl]pentanoate (300 mg, 0.74 mmol) in THF (10 mL) was added sodium triacetoxyborohydride (225 mg, 1.06 mmol). The resulting mixture was stirred for 12 h at room temperature. The mixture was concentrated and the residue was purified by silica gel chromatography (0-10% methanol in dichloromethane) to afford the title compound (120 mg, 0.18 mmol, 34% yield) as a white solid. MS (ESI) m/z 670.4 $[M+1]^+$.

(S)-3-(5-(((S)-1-((2-(1-acetylpiperidin-4-yl)quinolin-6-yl)methyl)pyrrolidin-3-yl)oxy)-1-oxoisoindolin-2-yl)piperidine-2,6-dione. To a solution of tert-butyl (S)-4-(5-(((S)-1-((2-(1-acetylpiperidin-4-yl)quinolin-6-yl)methyl)pyrrolidin-3-yl)oxy)-1-oxoisoindolin-2-yl)-5-amino-5-oxopentanoate (260 mg, 0.39 mmol) and benzenesulfonic acid (185. mg, 1.17 mmol) in acetonitrile (10 mL) was stirred at 60° C. for 12 h under nitrogen. The reaction mixture was cooled to room temperature and slowly neutralized with a buffer solution sodium bicarbonate carefully to pH~7. Then the above mixture was extracted with dichloromethane. The combined organic layers were washed with brine, dried over sodium sulfate, filtered and concentrated. The crude product was purified by silica gel chromatography (0-10% methanol in dichloromethane) and preparative Chiral SFC with the following conditions: Column: CHIRALPAK IF-3, 4.6*50 mm, 3 μm; Mobile phase A: tert-butyl methyl ether: (ethanol:dichloromethane=1:1)=40:60; Flow rate: 1 mL/min; Gradient: 0% B to 0% B). The fractions containing desired product were collected and evaporated under reduced pressure to afford the title compound (92 mg, 0.15 mmol, 39% yield) as yellow semi-solid. $^1H$ NMR (300 MHz, DMSO-$d_6$) δ 10.96 (s, 1H), 8.26 (d, J=8.5 Hz, 1H), 8.14 (s, 1H), 7.89 (d, J=8.6 Hz, 1H), 7.84 (d, J=1.9 Hz, 1H), 7.70-7.68 (m, 1H), 7.60 (d, J=8.4 Hz, 1H), 7.47 (d, J=8.5 Hz, 1H), 7.10 (d, J=2.2 Hz, 1H), 7.00-6.98 (m, 1H), 5.04-5.02 (m, 2H), 4.53 (m, 1H), 4.37 (d, J=17.2 Hz, 1H), 4.24 (d, J=17.2 Hz, 1H), 3.95 (m, 1H), 3.88-3.72 (m, 2H), 3.27-3.04 (m, 3H), 3.02-2.82

(m, 2H), 2.82-2.50 (m, 4H), 2.35 (m, 2H), 2.01-1.80 (m, 8H), 1.64-1.62 (m, 1H); MS (ESI) m/z 596.2 [M+1]+.

Example S171. (S)-3-(5-(((S)-1-((8-Fluoro-2-morpholinoquinolin-6-yl)methyl)pyrrolidin-3-yl)oxy)-1-oxoisoindolin-2-yl)piperidine-2,6-dione

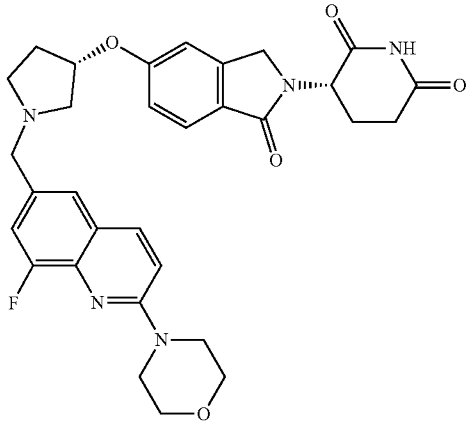 [SMILES: O=C1CC[C@H](N2Cc3cc(O[C@H]4CCN(Cc5cc(F)c6nc(N7CCOCC7)ccc6c5)C4)ccc3C2=O)C(=O)N1]

4-(6-Bromo-8-fluoroquinolin-2-yl)morpholine. To a solution of 6-bromo-2-chloro-8-fluoroquinoline (400 mg, 1.54 mmol) in NMP (10 mL) was added morpholine (672 mg, 7.71 mmol). The resulting mixture was stirred at 150° C. for 1 h under nitrogen. The mixture was purified by reverse phase flash (30-100% acetonitrile+0.05% ammonium bicarbonate in water, over 30 min) to afford the title compound (650 mg, 2.0 mmol, 93% yield) as a yellow solid. MS (ESI) m/z 311.1 $[M+1]^+$.

4-(8-Fluoro-6-vinylquinolin-2-yl)morpholine. To a solution of 4-(6-bromo-8-fluoroquinolin-2-yl)morpholine (650 mg, 2.1 mmol), sodium carbonate (420 mg, 4.0 mmol) and potassium hydride trifluoro(vinyl)boron (545 mg, 4.0 mmol) in 1,4-dioxane (10 mL) and water (2 mL) was added [1,1'-bis(diphenylphosphino)ferrocene]dichloropalladium (II) (150 mg, 0.18 mmol). The mixture was stirred at 80° C. for 2 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (350 mg, 1.29 mmol, 62% yield) as a yellow solid. MS (ESI) m/z 259.2 $[M+1]^+$.

8-Fluoro-2-morpholinoquinoline-6-carbaldehyde. To a solution of 4-(8-fluoro-6-vinylquinolin-2-yl)morpholine (350 mg, 1.36 mmol) in tert-butanol (5 mL) and water (5 mL) were added potassium osmate (50 mg, 1.36 mmol), 4-methylmorpholine N-oxide (317 mg, 2.7 mmol) and citric acid (570 mg, 1.36 mmol). The mixture was stirred at room temperature for 4 h under nitrogen. Then sodium periodate (0.39 mL, 2.7 mmol) was added into the above mixture and stirred at room temperature for 1 h under nitrogen. The mixture was added saturated sodium bicarbonate to pH-7 and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (260 mg, 0.99 mmol, 73% yield) as a yellow solid. MS (ESI) m/z 261.2 $[M+1]^+$.

Tert-butyl (S)-5-amino-4-(5-(((S)-1-((8-fluoro-2-morpholinoquinolin-6-yl) methyl)pyrrolidin-3-yl)oxy)-1-oxoisoindolin-2-yl)-5-oxopentanoate. To a solution of 8-fluoro-2-morpholinoquinoline-6-carbaldehyde (130 mg, 0.50 mmol) in THF (6 mL) were added tert-butyl (S)-5-amino-5-oxo-4-(1-oxo-5-(((S)-pyrrolidin-3-yl) oxy)isoindolin-2-yl)pentanoate (232 mg, 0.58 mmol), acetic acid (0.05 mL, 0.7 mmol). After 30 min stirring, sodium triacetoxyborohydride (212 mg, 1 mmol) was added into the above mixture. The resulting mixture was stirred at room temperature for 12 h under nitrogen. The mixture was purified by reverse phase flash (5-70% acetonitrile+0.05% TFA in water, over 20 min) to afford the title compound (160 mg, 0.24 mmol, 49% yield) as a yellow oil. MS (ESI) m/z 648.2 $[M+1]^+$.

(S)-3-(5-(((S)-1-((8-Fluoro-2-morpholinoquinolin-6-yl) methyl)pyrrolidin-3-yl) oxy)-1-oxoisoindolin-2-yl)piperidine-2,6-dione. To a solution of tert-butyl (S)-5-amino-4-(5-(((S)-1-((8-fluoro-2-morpholinoquinolin-6-yl)methyl) pyrrolidin-3-yl)oxy)-1-oxoisoindolin-2-yl)-5-oxopentanoate; 2,2,2-trifluoroacetic acid (188.1 mg, 0.25 mmol) in acetonitrile (7 mL) was added benzenesulfonic acid (117 mg, 0.74 mmol). The resulting mixture was stirred at 60° C. for 12 h under nitrogen. The mixture was added little saturated sodium bicarbonate to pH-7 and extracted with dichloromethane. The organic layers were washed with saturated sodium bicarbonate, dried over anhydrous sodium sulfate, filtered and concentrated. The residue was purified by silica gel chromatography (0-10% methanol in dichloromethane) and further purified by preparative chiral HPLC with the follow condition: column: chiralpak IF, 2*25 cm, 5 μm; mobile phase A: tert-butyl methyl ether-HPLC, mobile phase B: ethanol:dichloromethane=1:1-HPLC; flow rate: 15 mL/min; gradient: 40% B to 40% B in 30 min; wave length: 220/254 nm; $RT_1$ (min): 19.808; $RT_2$ (min): 27.988; sample solvent: ethanol-HPLC; injection volume: 1 mL; number of runs: 3. Pure fractions were evaporated and the residue was dissolved in 0.5% formic acid/water and lyophilized to afford the title compound (37 mg, 0.06 mmol, 25% yield) as a white solid. $^1H$ NMR (400 MHz, DMSO-$d_6$) δ 10.96 (s, 1H), 8.17-8.06 (m, 1H), 7.60 (d, J=8.5 Hz, 1H), 7.48 (d, J=1.8 Hz, 1H), 7.37-7.26 (m, 2H), 7.11 (d, J=2.2 Hz, 1H), 7.00-6.98 (m, 1H), 5.06-5.04 (m, 1H), 4.99 (m, 1H), 4.37 (d, J=17.2 Hz, 1H), 4.24 (d, J=17.2 Hz, 1H), 3.76-3.63 (m, 10H), 2.99-2.85 (m, 2H), 2.84-2.65 (m, 2H), 2.58 (m, 2H), 2.36 (m, 2H), 1.97 (m, 1H), 1.88-1.76 (m, 1H); MS (ESI) m/z 574.2 $[M+1]^+$.

Example S172. (S)-3-(5-(((S)-1-((8-fluoro-2-((R)-tetrahydrofuran-3-yl)quinolin-6-yl)methyl)pyrrolidin-3-yl)oxy)-1-oxoisoindolin-2-yl)piperidine-2,6-dione

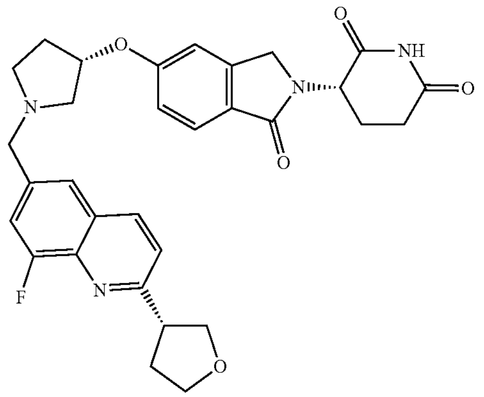 [SMILES: O=C1CC[C@H](N2Cc3cc(O[C@H]4CCN(Cc5cc(F)c6nc([C@H]7CCOC7)ccc6c5)C4)ccc3C2=O)C(=O)N1]

6-Bromo-8-fluoro-2-tetrahydrofuran-3-yl-quinoline. To a stirred solution of 1-tetrahydrofuran-3-ylethanone (1.40 g, 12.27 mmol) and (2-amino-5-bromo-3-fluoro-phenyl) methanol (4.05 g, 18.40 mmol) in toluene (50 mL) was added lithium tert-butoxide (1471 mg, 18.40 mmol) in one portion. The resulting mixture was stirred at 110° C. for 3 h under nitrogen. The resulting mixture was diluted with water and extracted with ethyl acetate. The extracts were washed with brine, dried over anhydrous sodium sulfate, filtered and concentrated. The residue was purified by reverse phase flash (10-70% acetonitrile+0.05% ammonium bicarbonate in water, over 20 min) to give the title compound (700 mg, 2.36 mmol, 19% yield) as a light yellow oil. MS (ESI) m/z 297.9 $[M+1]^+$.

8-Fluoro-2-tetrahydrofuran-3-yl-6-vinyl-quinoline. To a solution of 6-bromo-8-fluoro-2-tetrahydrofuran-3-yl-quinoline (700 mg, 2.36 mmol) and potassium vinyltrifluoroborate (638 mg, 4.73 mmol) in 1,4-dioxane (50 mL) and water (10 mL) were added [1,1'-bis(diphenylphosphino)ferrocene] dichloropalladium-(II) (273 mg, 0.37 mmol) and sodium carbonate (752 mg, 7.09 mmol) at room temperature. The reaction was heated to 90° C. and stirred for 5 h under nitrogen. The reaction mixture was concentrated and the residue was purified by reverse-phase flash (10-70% acetonitrile+0.05% ammonium bicarbonate in water, over 20 min) to give the title compound (380 mg, 1.56 mmol, 66% yield) as a white solid. MS (ESI) m/z 244.2 $[M+1]^+$ 8-Fluoro-2-tetrahydrofuran-3-yl-quinoline-6-carbaldehyde. To a solution of 8-fluoro-2-tetrahydrofuran-3-yl-6-vinyl-quinoline (380 mg, 1.56 mmol), potassium osmate (57 mg, 0.16 mmol) and 4-methylmorpholine n-oxide (365 mg, 3.12 mmol) in 1-butanol (20 mL) and water (20 mL) was added citric acid (599 mg, 3.12 mmol) at room temperature and the resulting mixture was stirred at room temperature for 4 h. Then sodium periodate (1002 mg, 4.69 mmol) was added in several portions to the above mixture at 0° C. and the resulting mixture was stirred at room temperature for 2 h. The mixture was added saturated sodium bicarbonate solution to pH~7 and extracted with ethyl acetate. The extracts were washed with brine, dried over sodium sulfate, filtered and concentrated to afford the title compound (260 mg, 1.06 mmol, 68% yield) as a yellow solid. MS (ESI) m/z 246.2 $[M+1]^+$.

Tert-butyl (4S)-5-amino-4-[5-[(3S)-1-[(8-fluoro-2-tetrahydrofuran-3-yl-6-quinolyl)methyl]pyrrolidin-3-yl]oxy-1-oxo-isoindolin-2-yl]-5-oxo-pentanoate. To a stirred mixture 8-fluoro-2-tetrahydrofuran-3-yl-quinoline-6-carbaldehyde (200 mg, 0.82 mmol), tert-butyl (4S)-5-amino-5-oxo-4-[1-oxo-5-[(3S)-pyrrolidin-3-yl]oxy-isoindolin-2-yl]pentanoate (329 mg, 0.82 mmol) and zinc chloride (0.7 M in THF, 2 mL, 1.40 mmol) in ethanol (5 mL) was added sodium cyanoborohydride (150 mg, 2.38 mmol) in several portions and was stirred at 80° C. for 1 h under nitrogen. The reaction mixture was added DMSO, filtered and the filtrate was purified by reverse phase flash (10-70% acetonitrile+0.05% TFA in water, over 20 min) to give the title compound (180 mg, 0.28 mmol, 34% yield) as a white solid. MS (ESI) m/z 633.4 $[M+1]^+$.

(3S)-3-(5-(((3S)-1-((8-fluoro-2-(tetrahydrofuran-3-yl) quinolin-6-yl)methyl)p-yrrolidin-3-yl)oxy)-1-oxoisoindolin-2-yl)piperidine-2,6-dione. To a solution of tert-butyl (4S)-5-amino-4-[5-[(3S)-1-[(8-fluoro-2-tetrahydrofuran-3-yl-6-quinolyl)methyl]pyrrolidin-3-yl]oxy-1-oxo-isoindolin-2-yl]-5-oxo-pentanoate (240 mg, 0.38 mmol) and benzenesulfonic acid (179 mg, 1.14 mmol) in acetonitrile (10 mL) was stirred at 60° C. for 12 h under nitrogen. The reaction mixture was cooled to room temperature, slowly neutralized with a buffer solution sodium bicarbonate carefully to pH~7 and extracted with dichloromethane. The combined organic layers were washed with brine, dried over sodium sulfate, filtered and concentrated. The crude product was purified by silica gel chromatography (0-10% methanol in dichloromethane) and preparative Chiral SFC with the following conditions: Column: CHIRALPAK IH-3, 4.6*50 mm, 3 μm; Mobile phase A: tert-Butyl methyl ether: (ethanol:dichloromethane=1:1)=60:40; Flow rate: 1 mL/min; Gradient: 0% B to 0% B; Injection Volume: 5 mL. The fractions containing desired product were collected and evaporated under reduced pressure to afford the title compound (66 mg, 0.12 mmol, 31% yield) as white solid. MS (ESI) m/z 581.2 $[M+23]^+$.

(S)-3-(5-(((S)-1-((8-fluoro-2-((R)-tetrahydrofuran-3-yl) quinolin-6-yl)methyl)-pyrrolidin-3-yl)oxy)-1-oxoisoindolin-2-yl)piperidine-2,6-dione. The (3S)-3-(5-(((3S)-1-((8-fluoro-2-(tetrahydrofuran-3-yl)quinolin-6-yl)methyl) pyrrolidin-3-yl)oxy)-1-oxoisoindolin-2-yl)piperidine-2,6-dione (60 mg, 0.10 mmol) was Purified by preparative Chiral HPLC with the following conditions: Column: Chiral pak IH-3, 4.6*50 mm, 3 μm; Mobile Phase A: tert-Butyl methyl ether: (ethanol:dichloromethane=1:1)=60:40; Flow rate: 1 mL/min; Injection Volume: 5 mL). The pure fractions of the first peak assigned arbitrarily of R isomer on the chiral HPLC was evaporated to afford the title compound (9.1 mg, 0.02 mmol, 14% yield) as a white solid. $^1$H NMR (300 MHz, DMSO-$d_6$) δ 10.96 (s, 1H), 8.35-8.33 (m, 1H), 7.70 (d, J=1.7 Hz, 1H), 7.59 (t, J=8.2 Hz, 2H), 7.52-7.48 (m, 1H), 7.11 (d, J=2.1 Hz, 1H), 7.01-6.98 (m, 1H), 5.04-4.98 (m, 2H), 4.37 (d, J=17.2 Hz, 1H), 4.24 (d, J=17.2 Hz, 1H), 4.13 (t, J=7.9 Hz, 1H), 3.99-3.97 (m, 1H), 3.93-3.69 (m, 5H), 3.03-2.82 (m, 2H), 2.82-2.65 (m, 2H), 2.64-2.51 (m, 2H), 2.47-2.15 (m, 4H), 1.90-1.70 (m, 2H); MS (ESI) m/z 559.2 $[M+1]^+$.

Example S173. (S)-3-(5-(((S)-1-((8-fluoro-2-((S)-tetrahydrofuran-3-yl) quinolin-6-yl) methyl) pyrrolidin-3-yl) oxy)-1-oxoisoindolin-2-yl)piperidine-2,6-dione

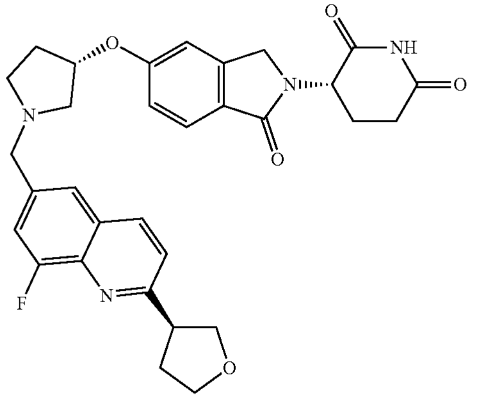 [SMILES: O=C1CC[C@H](N2Cc3cc(O[C@H]4CCN(Cc5cc(F)c6nc([C@@H]7CCOC7)ccc6c5)C4)ccc3C2=O)C(=O)N1]

(S)-3-(5-(((S)-1-((8-fluoro-2-((S)-tetrahydrofuran-3-yl) quinolin-6-yl)methyl)-pyrrolidin-3-yl)oxy)-1-oxoisoindolin-2-yl)piperidine-2,6-dione. The (3S)-3-(5-(((3S)-1-((8-fluoro-2-(tetrahydrofuran-3-yl)quinolin-6-yl)methyl) pyrrolidin-3-yl)oxy)-1-oxoisoindolin-2-yl)piperidine-2,6-dione (60 mg, 0.11 mmol) was purified by preparative Chiral HPLC with the following conditions: Column: CHIRALPAK IH-3, 4.6*50 mm, 3 μm; Mobile Phase A: tert-Butyl methyl ether: (ethanol:dichloromethane=1:1)=60:40; Flow rate: 1 mL/min; Gradient: 0% B to 0% B. The fractions containing desired product were collected and evaporated under reduced pressure to afford the title compound (5.6 mg, 0.0096 mmol, 9% yield) as a white solid. $^1$H NMR (300 MHz, DMSO-$d_6$) δ 10.96 (s, 1H), 8.35-8.33 (m, 1H), 7.70 (d, J=1.7 Hz, 1H), 7.59 (t, J=8.2 Hz, 2H), 7.52-7.48 (m, 1H), 7.11 (d, J=2.1 Hz, 1H), 7.01-6.98 (m, 1H), 5.04-5.98 (m, 2H), 4.37 (d, J=17.2 Hz, 1H), 4.24 (d, J=17.2 Hz, 1H), 4.13 (t, J=7.9 Hz, 1H), 3.99-3.97 (m, 1H), 3.93-3.69 (m, 5H), 3.03-2.82 (m, 2H), 2.82-2.65 (m, 2H), 2.64-2.51 (m, 2H), 2.47-2.15 (m, 3H), 1.90-1.70 (m, 2H); MS (ESI) m/z 581.2 $[M+1]^+$.

Example S174. (S)-3-(5-(((R)-4,4-Difluoro-1-((2-((S)-tetrahydrofuran-3-yl)quinolin-6-yl)methyl) pyrrolidin-3-yl)oxy)-1-oxoisoindolin-2-yl)piperidine-2,6-dione

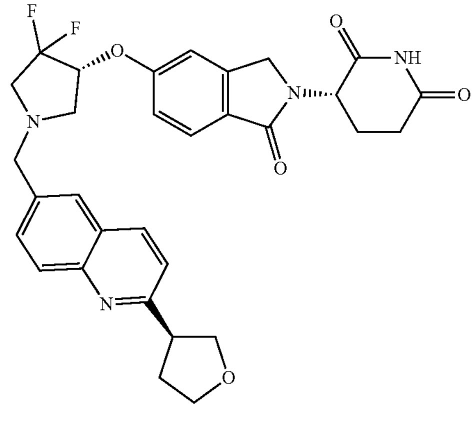 [SMILES: O=C1CC[C@H](N2Cc3cc(O[C@@H]4CN(Cc5ccc6nc([C@@H]7CCOC7)ccc6c5)CC4(F)F)ccc3C2=O)C(=O)N1]

(S)-3-(5-(((R)-4,4-Difluoro-1-((2-((S)-tetrahydrofuran-3-yl)quinolin-6-yl)me-thyl)pyrrolidin-3-yl)oxy)-1-oxoisoindolin-2-yl)piperidine-2,6-dione. To a stirred mixture of (S)-2-(tetrahydrofuran-3-yl)quinoline-6-carbaldehyde (80 mg, 0.35 mmol), (S)-3-(5-(((R)-4,4-difluoropyrrolidin-3-yl) oxy)-1-oxoisoindolin-2-yl)piperidine-2,6-dione; 2,2,2-trifluoroacetic acid (180 mg, 0.38 mmol) and triethylamine (82 mg, 0.82 mmol) in dichloromethane (10 mL) was added sodium triacetoxyborohydride (158 mg, 0.75 mmol) in several portions and the reaction mixture was stirred at room temperature for 3 h under nitrogen. The mixture was concentrated and the residue was purified by silica gel chromatography (0-10% methanol in dichloromethane) and purified further by preparative HPLC with the following conditions: Column: CHIRALPAK IH, 2*25 cm, 5 μm; Mobile Phase A: tert-butyl methyl ether—HPLC, Mobile Phase B: ethanol—HPLC; Flow rate: 20 mL/min; Gradient: 30% B to 30% B in 12 min; Wave Length: 220/254 nm; RT1 (min): 8.95; RT2 (min): 9.87; Sample Solvent: ethanol-HPLC; Injection Volume: 0.4 mL; Number of Runs: 6. The fractions containing desired product were collected and evaporated under reduced pressure to afford the title compound (35 mg, 0.060 mmol, 17% yield) as a white solid. $^1$H NMR (400 MHz, Methanol-$d_4$) δ 8.25 (m, 1H), 7.99 (d, J=8.7 Hz, 1H), 7.85 (d, J=2.0 Hz, 1H), 7.81-7.69 (m, 2H), 7.50-7.48 (m, 1H), 7.18 (d, J=2.2 Hz, 1H), 7.13-7.11 (m, 1H), 5.11-5.09 (m, 1H), 5.00 (m, 1H), 4.52-4.37 (m, 2H), 4.25-4.09 (m, 2H), 4.02-3.88 (m, 3H), 3.80-3.78 (m, 1H), 3.47-3.40 (m, 1H), 3.19 (m, 1H), 3.06-2.72 (m, 4H), 2.55-2.39 (m, 2H), 2.29-2.27 (m, 1H), 2.15-2.13 (m, 1H); MS (ESI) m/z 577.2 $[M+1]^+$.

Example S175. (S)-3-(5-(((R)-4,4-Difluoro-1-((2-((R)-tetrahydrofuran-3-yl)quinolin-6-yl)methyl)-pyrrolidin-3-yl)oxy)-1-oxoisoindolin-2-yl)piperidine-2,6-dione

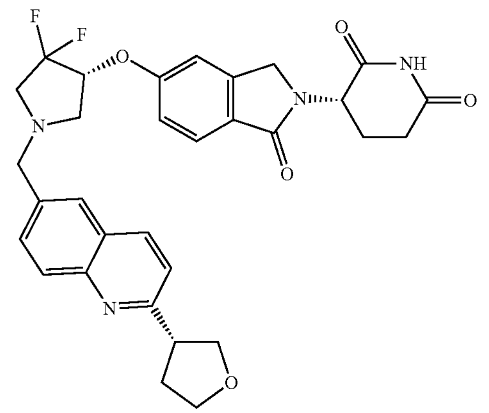 [SMILES: O=C1CC[C@H](N2Cc3cc(O[C@@H]4CN(Cc5ccc6nc([C@H]7CCOC7)ccc6c5)CC4(F)F)ccc3C2=O)C(=O)N1]

(S)-3-(5-(((R)-4,4-Difluoro-1-((2-((R)-tetrahydrofuran-3-yl)quinolin-6-yl) methyl)pyrrolidin-3-yl)oxy)-1-oxoisoindolin-2-yl)piperidine-2,6-dione. To a solution of 2-[(3R)-tetrahydrofuran-3-yl]quinoline-6-carbaldehyde (75 mg, 0.33 mmol) and (S)-3-(5-(((R)-4,4-difluoropyrrolidin-3-yl)oxy)-1-oxoisoindolin-2-yl)piperidine-2,6-dione; 2,2,2-trifluoroacetic acid (157 mg, 0.33 mmol) in dichloromethane (6 mL) were added sodium triacetoxyborohydride (279 mg, 1.32 mmol) and triethylamine (0.16 mL, 1.15 mmol). The resulting mixture was stirred at room temperature for 12 h under nitrogen. The mixture was added little methanol and purified by silica gel chromatography (0-10% methanol in dichloromethane) and further purified by preparative HPLC with the following conditions: Column: chiralpak IH, 2*25 cm, 5 μm; mobile phase A: tert-butyl methyl ether-HPLC, mobile phase B: ethanol—HPLC; flow rate: 20 mL/min; gradient: 30% B to 30% B in 12 min; wave length: 220/254 nm; $RT_1$ (min): 8.62; $RT_2$ (min): 10.46; sample solvent: ethanol-HPLC; injection volume: 0.3 mL; number of runs: 5. Pure fractions were evaporated and the residue was purified again by preparative HPLC with the following conditions: Column: Select CSH C18 OBD column 30*150 mm 5 μm; mobile phase A: water (0.1% formic acid), mobile phase B: acetonitrile; flow rate: 60 mL/min; gradient: 15% B to 45% B in 10 min, 45% B; wave length: 254 nm; $RT_1$ (min): 7.87. The fractions containing desired product were collected and evaporated under reduced pressure to afford the title compound (20.9 mg, 0.036 mmol, 11% yield) as a white solid. $^1H$ NMR (400 MHz, Methanol-$d_4$) δ 8.26 (d, J=8.6 Hz, 1H), 7.99 (d, J=8.6 Hz, 1H), 7.85 (d, J=1.9 Hz, 1H), 7.78-7.76 (m, 1H), 7.72 (d, J=8.5 Hz, 1H), 7.50 (d, J=8.5 Hz, 1H), 7.17 (d, J=2.2 Hz, 1H), 7.12-7.10 (m, 1H), 5.11-5.09 (m, 1H), 5.02-5.00 (m, 1H), 4.47 (d, J=17.1 Hz, 1H), 4.41 (d, J=17.1 Hz, 1H), 4.21 (t, J=8.1 Hz, 1H), 4.13 (m, 1H), 4.02-4.00 (m, 1H), 3.99-3.91 (m, 1H), 3.94-3.85 (m, 2H), 3.79 (m, 1H), 3.44-3.42 (m, 1H), 3.21-3.19 (m, 1H), 3.06-2.83 (m, 2H), 2.83-2.81 (m, 1H), 2.77-2.75 (m, 1H), 2.55-2.38 (m, 2H), 2.29 (m, 1H), 2.15 (m, 1H); MS (ESI) m/z 577.1 $[M+1]^+$.

Example S176. (S)-3-(5-(((S)-1-((2-((S)-2,2-Dimethyltetrahydro-2H-pyran-4-yl)quinolin-6-yl)methyl) pyrrolidin-3-yl)oxy)-1-oxoisoindolin-2-yl)piperidine-2,6-dione

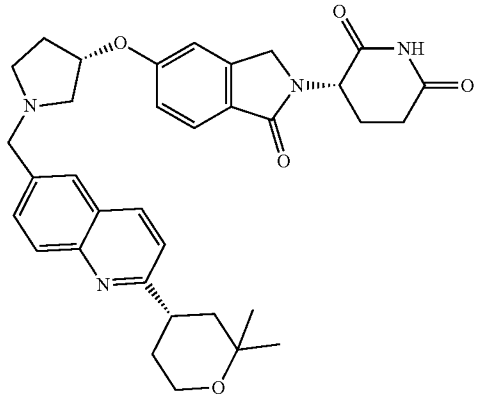 [SMILES: CC1(C)C[C@@H](c2ccc3cc(CN4CC[C@H](Oc5ccc6c(c5)CN([C@H]5CCC(=O)NC5=O)C6=O)C4)ccc3n2)CCO1]

N-methoxy-N,2,2-trimethyltetrahydro-2H-pyran-4-carboxamide. To a solution of 2,2-dimethyltetrahydro-2H-pyran-4-carboxylic acid (3 g, 18.96 mmol) in dichloromethane (30 mL) was added CDI (3.3 g, 20.35 mmol) in several portions at 0° C. The reaction mixture was stirred for 30 min at 0° C. Then a solution of N,O-dimethylhydroxylamine (2.1 g, 21.53 mmol) in dichloromethane (20 mL) was added into the above mixture dropwise at this temperature. The reaction mixture was warmed and stirred for 12 h at room temperature. Then the mixture was added water and extracted with dichloromethane. The extracts were washed with brine, dried over saturated sodium bicarbonate solution, filtered and concentrated to afford the title compound (2.1 g, 10.43 mmol, 55% yield) as a light-yellow oil. MS (ESI) m/z 202.1 $[M+1]^+$.

1-(2,2-Dimethyltetrahydropyran-4-yl)ethanone. To a solution of N-methoxy-N,2,2-trimethyltetrahydro-2H-pyran-4-carboxamide (2.1 g, 10.43 mmol) in THF (30 mL) was added methyl magnesium bromide (1 M in THF, 31 mL, 31 mmol) dropwise at 0° C. The reaction mixture was stirred for 12 h at room temperature. The resulting mixture was added water and extracted with ethyl acetate. The extracts were washed with saturated sodium bicarbonate, brine, dried over anhydrous sodium sulfate, filtered and concentrated to afford the title compound (1.6 g, 10.24 mmol, 98% yield) as a yellow oil. MS (ESI) m/z 157.0 $[M+1]^+$.

6-Bromo-2-(2,2-dimethyltetrahydro-2H-pyran-4-yl)quinoline. To a stirred solution of 2-amino-5-bromobenzaldehyde (2.1 g, 10.5 mmol) and 1-(2,2-dimethyltetrahydropyran-4-yl)ethanone (1.64 g, 10.5 mmol) in ethanol (20 mL) was added potassium hydroxide (294 mg, 5.25 mmol) in one portion. The resulting mixture was stirred at 50° C. for 12 h under nitrogen. Then the mixture was added water and extracted with ethyl acetate. The extracts were washed with brine, dried over anhydrous sodium sulfate, filtered and concentrated to afford the title compound (3.20 g, 10.00 mmol, 95% yield) as a light-yellow sloid. MS (ESI) m/z 320.0 $[M+1]^+$.

2-(2,2-Dimethyltetrahydro-2H-pyran-4-yl)-6-vinylquinoline. To a stirred solution of 6-bromo-2-(2,2-dimethyltetrahydro-2H-pyran-4-yl)quinoline (3.2 g, 10.00 mmol) and potassium trifluoro(vinyl)boranuide (1.61 g, 11.99 mmol) in 1,4-dioxane (30 mL) and water (3 mL) were added tetrakis (triphenylphosphine)palladium (1.15 g, 1 mmol) and cesium carbonate (6.5 g, 19.99 mmol). The above mixture was stirred at 80° C. for 3 h under nitrogen. Then the mixture was added water and extracted with ethyl acetate. The extracts were washed with brine, dried over anhydrous sodium sulfate, filtered and concentrated. The residue was purified by reverse phase flash (40-90% acetonitrile+0.05% ammonium bicarbonate in water, over 25 min) to afford product 1.2 g crude product which was purified by preparative chiral HPLC with the follow condition: Column: CHIRALPAK IG, 3*25 cm, 5 μm; Mobile Phase A: carbon dioxide, Mobile Phase B: methanol (0.1% 2M ammonia in methanol); Flow rate: 60 mL/min; Gradient: isocratic 30% B; Column Temperature(° C.): 35; Back Pressure(bar): 100; Wave Length: 220 nm; $RT_1$ (min): 9.65; $RT_2$ (min): 11.36; Sample Solvent: methanol—Preparative; Injection Volume: 0.6 mL; Number of Runs: 100 to afford the title compound (800 mg, 2.99 mmol, 30% yield) as a light-yellow oil. MS (ESI) m/z 268.0 $[M+1]^+$.

(S)-2-(2,2-Dimethyltetrahydro-2H-pyran-4-yl)quinoline-6-carbaldehyde. To a stirred solution of 2-(2,2-dimethyltetrahydro-2H-pyran-4-yl)-6-vinylquinoline (800 mg, 2.99 mmol) in tert-butanol (8 mL) and water (8 mL) were added 4-methyl-morpholin4-oxide (350 mg, 2.99 mmol), potassium osmate (11 mg, 0.29 mmol) and citric acid (574 mg, 2.99 mmol). The above mixture was stirred at room temperature for 3 h. Then the mixture was added sodium periodate (640 mg, 2.99 mmol) and stirred for another 1 h. The reaction mixture was diluted with water, pH to ~7 with saturated sodium carbonate and extracted with ethyl acetate. The extracts were washed with brine, dried over sodium sulfate, filtered and concentrated. The residue was purified by silica gel chromatography (0 to 40% ethyl acetate in petroleum ether) to afford the title compound (650 mg, 2.41 mmol, 81% yield) as a light-yellow oil. MS (ESI) m/z 270.1 [M+1]+.

((S)-3-(5-(((S)-1-((2-((S)-2,2-dimethyltetrahydro-2H-pyran-4-yl)quinolin-6-yl) methyl)pyrrolidin-3-yl)oxy)-1-oxoisoindolin-2-yl)piperidine-2,6-dione. To a solution of (S)-2-(2,2-dimethyltetrahydro-2H-pyran-4-yl)quinoline-6-carbaldehyde (60 mg, 0.22 mmol), (S)-3-(1-oxo-5-(((S)-pyrrolidin-3-yl)oxy)isoindolin-2-yl)piperi-dine-2,6-dione; 2,2,2-trifluoroacetic acid (120 mg, 0.27 mmol) and triethylamine (0.06 mL, 0.46 mmol) in dichloromethane (5 mL) was added sodium triacetoxyborohydride (180 mg, 0.85 mmol). The mixture was stirred for 12 h at room temperature under nitrogen atmosphere. The resulting mixture was concentrated. The residue was purified by silica gel chromatography (0 to 10% methanol in dichloromethane) and preparative Chiral HPLC further with the following conditions: Column: CHIRALPAK IF, 2*25 cm, 5 μm; Mobile Phase A: tert-butyl methyl ether—HPLC, Mobile Phase B: ethanol: dichloromethane=1:1-HPLC; Flow rate: 15 mL/min; Gradient: 50% B to 50% B in 47 min; Wave Length: 220/254 nm; $RT_1$ (min): 15.664; $RT_2$ (min): 38.189; Sample Solvent: ethanol—HPLC; Injection Volume: 1 mL; Number of Runs: 2. The fractions containing desired product were collected and evaporated under reduced pressure to afford the title compound (30.8 mg, 0.052 mmol, 23% yield) as a white solid. $^1H$ NMR (300 MHz, DMSO-$d_6$) δ 10.96 (s, 1H), 8.26 (d, J=8.7 Hz, 2H), 7.96-7.80 (m, 2H), 7.64-7.61 (m, 2H), 7.47 (d, J=8.5 Hz, 1H), 7.10 (s, 1H), 7.05-6.96 (m, 1H), 5.14-4.92 (m, 2H), 4.45-4.18 (m, 2H), 3.87-3.65 (m, 4H), 3.29 (m, 2H), 3.05-2.85 (m, 2H), 2.73-2.70 (m, 2H), 2.58 (m, 1H), 2.37 (m, 2H), 1.96 (m, 1H), 1.87-1.64 (m, 5H), 1.29 (s, 3H), 1.20 (s, 3H); MS (ESI) m/z 583.5 $[M+1]^+$.

Example S177. (R)-3-(5-(((S)-1-((2-((R)-2,2-Dimethyltetrahydro-2H-pyran-4-yl)quinolin-6-yl)methyl) pyrrolidin-3-yl)oxy)-1-oxoisoindolin-2-yl)piperidine-2,6-dione

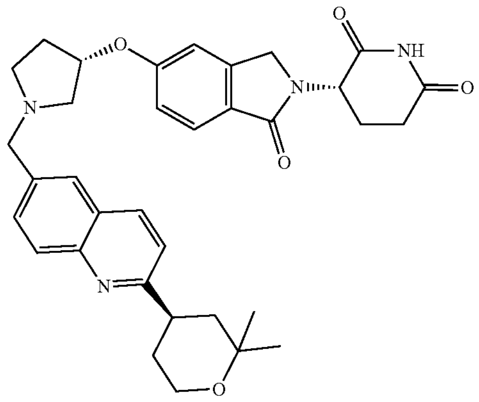 [SMILES: CC1(C)C[C@H](c2ccc3cc(CN4CC[C@H](Oc5ccc6c(c5)CN([C@H]5CCC(=O)NC5=O)C6=O)C4)ccc3n2)CCO1]

(R)-2-(2,2-Dimethyltetrahydro-2H-pyran-4-yl)-6-vinylquinoline. To a stirred solution of 2-(2,2-dimethyltetrahydro-2H-pyran-4-yl)-6-vinylquinoline (3.2 g, 11.96 mmol) and potassium trifluoro(vinyl)boranuide (1.61 g, 11.99 mmol) in 1,4-dioxane (30 mL) and water (3 mL) were added tetrakis(triphenylphosphine)palladium (1.15 g, 1.00 mmol) and cesium carbonate (6.5 g, 19.99 mmol). The above mixture was stirred at 80° C. for 3 h under nitrogen. Then the mixture was added water and extracted with ethyl acetate. The extracts were washed with brine, dried over anhydrous sodium sulfate, filtered and concentrated. The residue was purified by reverse phase flash (40-90% acetonitrile+0.05% ammonium bicarbonate in water, over 25 min) to afford 1.2 g crude product which was purified further by preparative chiral HPLC with the following conditions: Column: CHIRALPAK IG, 3*25 cm, 5 μm; Mobile Phase A: carbon dioxide, Mobile Phase B: methanol (0.1% 2M ammonia in methanol); Flow rate: 60 mL/min; Gradient: isocratic 30% B; Column Temperature (° C.): 35; Back Pressure (bar): 100; Wave Length: 220 nm; $RT_1$ (min): 9.65; $RT_2$ (min): 11.36; Sample Solvent: methanol—Preparative; Injection Volume: 0.6 mL; Number of Runs: 100. The fractions containing desired product were collected and evaporated under reduced pressure to afford the title compound to afford the title compound (750 mg, 2.81 mmol, 23% yield) as a light-yellow oil. MS (ESI) m/z 268.2 $[M+1]^+$.

(R)-2-(2,2-Dimethyltetrahydro-2H-pyran-4-yl)quinoline-6-carbaldehyde. To a stirred solution of (R)-2-(2,2-dimethyltetrahydro-2H-pyran-4-yl)-6-vinyl quinoline (750 mg, 2.81 mmol) in tert-butanol (8 mL) and water (8 mL) were added 4-methyl-morpholin4-oxide (328 mg, 2.81 mmol), potassium osmate (10 mg, 0.28 mmol) and citric acid (538 mg, 2.81 mmol). The above mixture was stirred at room temperature for 3 h under nitrogen. Then the mixture was added sodium periodate (600 mg, 2.81 mmol) and the resulting mixture was stirred for another 1 h. The reaction mixture was concentrated. The reaction mixture was diluted with water and extracted with ethyl acetate. The extracts were washed with brine, dried over anhydrous sodium sulfate, filtered and concentrated. The residue was purified by silica gel chromatography (0 to 40% ethyl acetate in petroleum ether) to afford the title compound (600 mg, 2.23 mmol, 79% yield) as a light-yellow oil. MS (ESI) m/z 270 $[M+1]^+$.

(R)-3-(5-(((S)-1-((2-((R)-2,2-Dimethyltetrahydro-2H-pyran-4-yl)quinolin-6-yl)methyl)pyrrolidin-3-yl)oxy)-1-oxoisoindolin-2-yl)piperidine-2,6-dione. To a solution of 2(R)-2-(2,2-dimethyltetrahydro-2H-pyran-4-yl)quinoline-6-carbaldehyde (60 mg, 0.22 mmol), (S)-3-(1-oxo-5-(((S)-pyrrolidin-3-yl)oxy)isoindolin-2-yl) piperidine-2,6-dione; 2,2,2-trifluoroacetic acid (120 mg, 0.27 mmol) and triethylamine (0.06 mL, 0.46 mmol) in dichloromethane (5 mL) was added sodium triacetoxyborohydride (180 mg, 0.85 mmol). The mixture was stirred for 12 h at room temperature under nitrogen. The resulting mixture was concentrated. The residue was purified by silica gel chromatography (0 to 10% methanol in dichloromethane) and preparative chiral HPLC with the following conditions: Column: CHIRALPAK IF, 2*25 cm, 5 μm; Mobile Phase A: tert-butyl methyl ether—HPLC, Mobile Phase B: ethanol:dichloromethane=1:1-HPLC; Flow rate: 15 mL/min; Gradient: 50% B to 50% B in 28 min; Wave Length: 220/254 nm; $RT_1$ (min): 14.986; $RT_2$ (min): 24.536; Sample Solvent: Ethanol-HPLC; Injection Volume: 0.8 mL; Number of Runs: 2. The fractions containing desired product were collected and evaporated under reduced pressure to afford the title compound to afford the title compound (37.2 mg, 0.062 mmol, 28% yield) as a white solid. $^1H$ NMR (300 MHz, DMSO-$d_6$) δ 8.26 (d, J=8.6 Hz, 1H), 8.16 (s, 1H), 7.92 (d, J=8.6 Hz, 1H), 7.83 (d, J=1.8 Hz, 1H), 7.70-7.68 (m, 1H), 7.62 (d, J=8.4 Hz, 1H), 7.48 (d, J=8.5 Hz, 1H), 7.11 (d, J=2.2 Hz, 1H), 7.01-6.99 (m, 1H), 5.04-5.01 (m, 2H), 4.43-4.19 (m, 2H), 3.86-3.67 (m, 4H), 3.30 (s, 1H), 3.03-2.55 (m, 6H), 2.44-2.26 (m, 2H), 2.05-1.93 (m, 1H), 1.88-1.63 (m, 5H), 1.29 (s, 3H), 1.20 (s, 3H); MS (ESI) m/z 584 $[M+1]^+$.

Example S178. (S)-3-(5-(((3S,4S)-1-((2-((S)-2,2-Dimethyltetrahydro-2H-pyran-4-yl)quinolin-6-yl)methyl)-4-(methoxymethyl)pyrrolidin-3-yl)oxy)-1-oxoisoindolin-2-yl)piperidine-2,6-dione

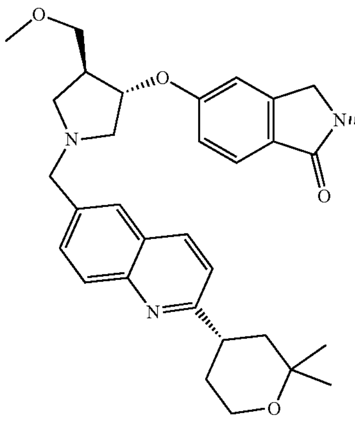

(S)-3-(5-(((3S,4S)-1-((2-((S)-2,2-Dimethyltetrahydro-2H-pyran-4-yl)quinolin-6-yl)methyl)-4-(methoxymethyl)pyrrolidin-3-yl)oxy)-1-oxoisoindolin-2-yl)piperidine-2,6-dione. To a stirred solution of (S)-2-(2,2-Dimethyltetrahydro-2H-pyran-4-yl)quinoline-6-carbaldehyde (100 mg, 0.37 mmol), (S)-3-(5-(((3S,4S)-4-(methoxymethyl)pyrrolidin-3-yl)oxy)-1-oxoisoindolin-2-yl)piperidine-2,6-dione; 2,2,2-trifluoroacetic acid (150 mg, 0.31 mmol), triethylamine (65 mg, 0.64 mmol) in dichloromethane (10 mL) pre-stirred for 15 min was added sodium triacetoxyborohydride (272 mg, 1.28 mmol) at 0° C. and the solution was stirred at room temperature for 48 h under nitrogen. The resulting solution was purified by silica gel chromatography (0 to 10% methanol in dichloromethane) and further by preparative chiral HPLC with the following conditions: Column: Chiralpak IG, 2*25 cm, 5 μm; mobile phase A: hexane:dichloromethane=1:1-HPLC, mobile phase B: ethanol—HPLC; flow rate: 16 mL/min; gradient: 50% B to 50% B in 30 min; wave length: 220/254 nm; $RT_1$ (min): 16.289; $RT_2$ (min): 18.323; sample solvent: ethanol-HPLC; injection volume: 2 mL; number of runs: 4. The fractions containing desired product were collected and evaporated under reduced pressure to afford the title compound (17.6 mg, 0.028 mmol, 8% yield) as a white solid. $^1H$ NMR (300 MHz, DMSO-$d_6$) δ 8.36-8.23 (m, 1H), 8.00 (d, J=8.7 Hz, 1H), 7.86 (m, 1H), 7.79 (dd, J=8.8, 1.9 Hz, 1H), 7.74-7.66 (m, 1H), 7.50 (dd, J=8.6, 1.4 Hz, 1H), 7.27-7.02 (m, 2H), 5.11 (dd, J=13.4, 5.1 Hz, 1H), 4.91 (m, 1H) 4.42 (d, J=4.1 Hz, 2H), 4.03-3.84 (m, 4H), 3.53 (d, J=6.5 Hz, 2H), 3.38 (m, J=3.8 Hz, 4H), 3.20 (t, J=8.7 Hz, 1H), 3.05 (d, J=4.2 Hz, 2H), 2.97-2.80 (m, 3H), 2.47 (m, 2H), 2.15 (m, 1H), 1.99-1.75 (m, 4H), 1.40 (s, 3H), 1.29 (s, 3H); MS (ESI) m/z 627.3 $[M+1]^+$.

Example S179. (S)-3-(5-(((3S,4S)-1-((2-((R)-2,2-Dimethyltetrahydro-2H-pyran-4-yl)quinolin-6-yl)methyl)-4-(methoxymethyl)pyrrolidin-3-yl)oxy)-1-oxoisoindolin-2-yl)piperidine-2,6-dione

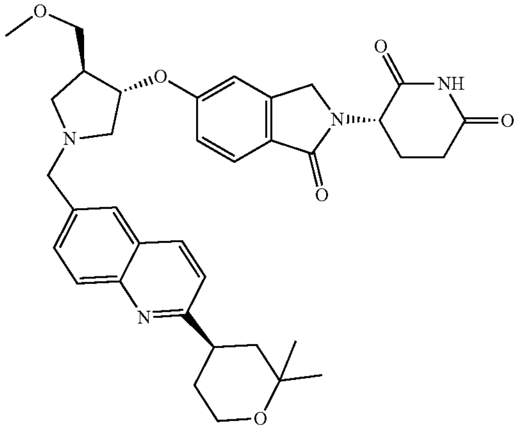 [SMILES: COC[C@@H]1CN(Cc2ccc3nc([C@@H]4CCOC(C)(C)C4)ccc3c2)C[C@H]1Oc1ccc2c(c1)CN([C@H]1CCC(=O)NC1=O)C2=O]

(S)-3-(5-(((3S,4S)-1-((2-((R)-2,2-Dimethyltetrahydro-2H-pyran-4-yl)quinolin-6-yl)methyl)-4-(methoxymethyl)pyrrolidin-3-yl)oxy)-1-oxoisoindolin-2-yl)piperidine-2,6-dione. To a stirred solution of (R)-2-(2,2-dimethyltetrahydro-2H-pyran-4-yl)quinolone-6-carbaldehyde (70 mg, 0.26 mmol), (S)-3-(5-(((3S,4S)-4-(methoxy methyl)pyrrolidin-3-yl)oxy)-1-oxoisoindolin-2-yl)piperidine-2,6-dione; 2,2,2-trifluoroacetic acid (150 mg, 0.31 mmol) and triethylamine (0.11 mL, 0.77 mmol) in dichloromethane (4 mL) was added sodium triacetoxyborohydride (130 mg, 0.61 mmol) at room temperature. The reaction was stirred for 2 h at room temperature. Most solution was removed and the residue was purified by silica gel chromatography (eluted with 5% methanol in dichloromethane) and further purified by preparative chiral HPLC with following conditions: Column: CHIRALPAK IG, 2*25 cm, 5 μm; Mobile Phase A: hexane:dichloromethane=1:1-HPLC, Mobile Phase B: ethanol—HPLC; Flow rate: 20 mL/min; Gradient: 50% B to 50% B in 25 min; Wave Length: 220/254 nm; $RT_1$ (min): 17.629; $RT_2$ (min): 21.076; Sample Solvent: ethanol—HPLC; Injection Volume: 0.5 mL. Pure fractions were evaporated, dissolved in 0.1% formic acid and lyophilized to obtain title compound (11.5 mg, 0.018 mmol, 7% yield) as an off-white solid. $^1$H NMR (400 MHz, Methanol-$d_4$) δ 8.29-8.22 (m, 2H), 7.89 (d, J=2.0 Hz, 1H), 7.79 (dd, J=8.7, 1.9 Hz, 1H), 7.69 (d, J=8.4 Hz, 1H), 7.51 (d, J=8.6 Hz, 1H), 7.13 (d, J=2.2 Hz, 1H), 7.07 (dd, J=8.5, 2.3 Hz, 1H), 5.10 (dd, J=13.3, 5.2 Hz, 1H), 4.93-4.91 (m, 1H), 4.44-4.38 (m, 2H), 4.15-4.03 (m, 2H), 3.97-3.80 (m, 2H), 3.57-3.51 (m, 2H), 3.43-3.33 (m, 5H), 3.24-3.14 (m, 2H), 2.94-2.84 (m, 1H), 2.79-2.67 (m, 3H), 2.51-2.40 (m, 1H), 2.17-2.12 (m, 1H), 1.96-1.76 (m, 4H), 1.39 (s, 3H), 1.28 (s, 3H); MS (ESI) m/z 627.2 $[M+1]^+$.

Example S180. (S)-3-(5-(((R)-4,4-Difluoro-1-((7-(tetrahydro-2H-pyran-4-yl)isoquinolin-3-yl)methyl)pyrrolidin-3-yl)oxy)-1-oxoisoindolin-2-yl)piperidine-2,6-dione

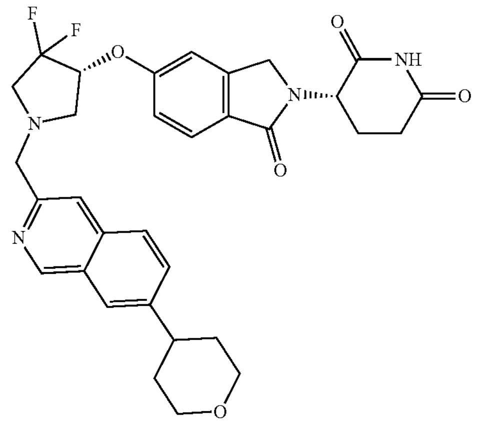 [SMILES: O=C1CC[C@H](N2Cc3cc(O[C@@H]4CN(Cc5cc6ccc(C7CCOCC7)cc6cn5)CC4(F)F)ccc3C2=O)C(=O)N1]

(S)-3-(5-(((R)-4,4-Difluoro-1-((7-(tetrahydro-2H-pyran-4-yl)isoquinolin-3-yl) methyl)pyrrolidin-3-yl)oxy)-1-oxoisoindolin-2-yl)piperidine-2,6-dione. To a solution of 7-(tetrahydro-2H-pyran-4-yl)isoquinoline-3-carbaldehyde (50 mg, 0.21 mmol), (S)-3-(5-(((3S,4S)-4-(methoxymethyl)pyrrolidin-3-yl)oxy)-1-oxoisoindolin-2-yl)piperidine-2,6-dione; 2,2,2-trifluoroacetic acid (124 mg, 0.25 mmol) and triethylamine (0.06 mL, 0.41 mmol) in dichloromethane (5 mL) was added sodium triacetoxyborohydride (185 mg, 0.87 mmol). The mixture was stirred for 12 h at room temperature under nitrogen. The resulting mixture was concentrated. The residue was purified by silica gel chromatography (0 to 10% methanol in dichloromethane) and preparative Chiral HPLC with the following conditions: Column: CHIRALPAK IH, 2*25 cm, 5 μm; Mobile Phase A: tert-butyl methyl ether—HPLC, Mobile Phase B: ethanol—HPLC; Flow rate: 20 mL/min; Gradient: 50% B to 50% B in 19 min; Wave Length: 220/254 nm; $RT_1$ (min): 4.939; $RT_2$ (min): 7.322; Sample Solvent: ethanol—HPLC; Injection Volume: 1 mL; Number of Runs: 4. The fractions containing desired product were collected and evaporated under reduced pressure to afford the title compound to afford the title compound (37.4 mg, 0.063 mmol, 30% yield) as a white solid. $^1$H NMR (400 MHz, Methanol-$d_4$) δ 9.19 (s, 1H), 7.94 (s, 1H), 7.89 (d, J=8.6 Hz, 1H), 7.83 (s, 1H), 7.78-7.70 (m, 2H), 7.18 (d, J=2.2 Hz, 1H), 7.12-7.10 (m, 1H), 5.11-5.09 (m, 1H), 5.06-4.97 (m, 1H), 4.49-4.39 (m, 2H), 4.09-4.06 (m, 2H), 4.03-3.94 (m, 2H), 3.70-3.60 (m, 2H), 3.50 (m, 1H), 3.29-3.22 (m, 1H), 3.10-2.99 (m, 2H), 2.90-2.86 (m, 2H), 2.81-2.73 (m, 2H), 2.51-2.40 (m, 1H), 2.15-2.12 (m, 1H), 1.97-1.85 (m, 4H); MS (ESI) m/z 591.3 $[M+1]^+$.

Example S181. (S)-3-(5-(((3S,4S)-4-(Methoxymethyl)-1-((2-morpholinoquinazolin-6-yl)methyl)pyrrolidin-3-yl)oxy)-1-oxoisoindolin-2-yl)piperidine-2,6-dione

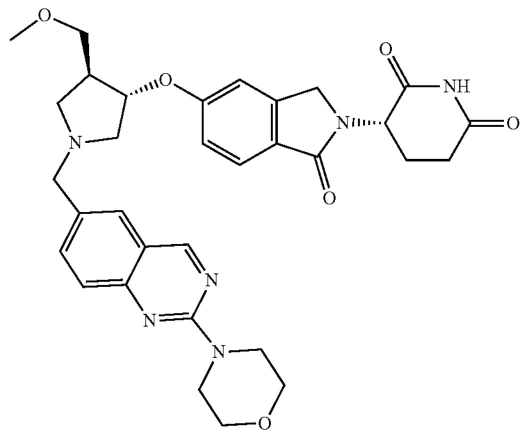 [SMILES: COC[C@@H]1CN(Cc2ccc3nc(N4CCOCC4)ncc3c2)C[C@H]1Oc1ccc2c(c1)CN([C@H]1CCC(=O)NC1=O)C2=O]

(S)-3-(5-(((3S,4S)-4-(Methoxymethyl)-1-((2-morpholinoquinazolin-6-yl)methyl)pyrrolidin-3-yl)oxy)-1-oxoisoindolin-2-yl)piperidine-2,6-dione. To a solution of 2-morpholinoquinazoline-6-carbaldehyde (60 mg, 0.25 mmol), (S)-3-(5-(((3S,4S)-4-(methoxymethyl)pyrrolidin-3-yl)oxy)-1-oxoisoindolin-2-yl)piperidine-2,6-dione; 2,2,2-trifluoroacetic acid (150 mg, 0.31 mmol) and triethylamine (0.06 mL, 0.46 mmol) in dichloromethane (5 mL) was added sodium triacetoxyborohydride (220 mg, 1.04 mmol). The mixture was stirred for 12 h at room temperature under nitrogen. The resulting mixture was concentrated. The residue was purified by silica gel chromatography (0 to 10% methanol in dichloromethane), further purified by preparative chiral HPLC with the following conditions: Column: Xselect CSH C18 OBD Column 30*150 mm 5 μm; Mobile Phase A: water (0.05% TFA), Mobile Phase B: acetonitrile; Flow rate: 60 m/min; Gradient: 2% B to 15% B in 7 min, 15% B; Wave Length: 254/220 nm; $RT_1$ (min): 6.4 to obtain 50 mg crude and preparative HPLC with the following conditions: Column: Xselect CSH C18 OBD Column 30*150 mm, 5 μm; Mobile Phase A: water (0.1% formic acid), Mobile Phase B: acetonitrile; Flow rate: 60 m/min; Gradient: 2% B to 32% B in 10 min, 32% B; Wave Length: 254 nm; $RT_1$ (min): 7.83. The fractions containing desired product were collected and evaporated under reduced pressure to afford the title compound (21.3 mg, 0.035 mmol, 14% yield) as a light yellow solid. $^1$H NMR (400 MHz, DMSO-$d_6$) δ 9.19 (s, 1H), 7.80-7.67 (m, 2H), 7.61 (d, J=8.4 Hz, 1H), 7.49 (d, J=8.6 Hz, 1H), 7.14 (d, J=2.2 Hz, 1H), 7.03-7.01 (m, 1H), 5.04-5.02 (m, 1H), 4.78-4.70 (m, 1H), 4.37 (d, J=17.3 Hz, 1H), 4.25 (d, J=17.3 Hz, 1H), 3.87-3.78 (m, 4H), 3.74-3.64 (m, 6H), 3.60-3.50 (m, 4H), 3.46-3.40 (m, 2H), 2.96-2.85 (m, 3H), 2.74 (m, 1H), 2.62 (m, 1H), 2.36-2.34 (m, 1H), 2.21-2.19 (m, 1H), 1.98 (m, 1H); MS (ESI) m/z 601.3 $[M+1]^+$.

Example S182. (S)-3-(5-(((3S,4S)-4-(Methoxymethyl)-1-((2-(tetrahydro-2H-pyran-4-yl)quinazolin-6-yl)methyl)pyrrolidin-3-yl)oxy)-1-oxoisoindolin-2-yl)piperidine-2,6-dione

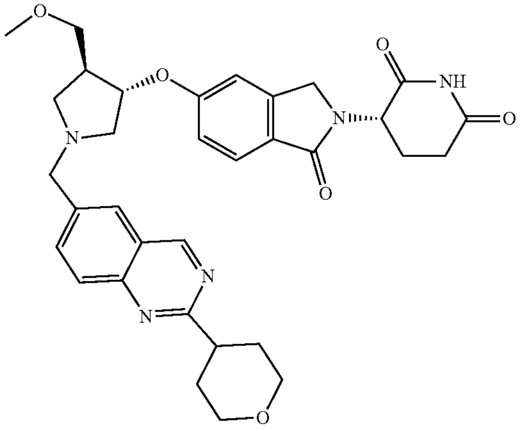 [SMILES: COC[C@@H]1CN(Cc2ccc3nc(C4CCOCC4)ncc3c2)C[C@H]1Oc1ccc2c(c1)CN([C@H]1CCC(=O)NC1=O)C2=O]

(S)-3-(5-(((3S,4S)-4-(Methoxymethyl)-1-((2-(tetrahydro-2H-pyran-4-yl)quinazolin-6-yl)methyl)pyrrolidin-3-yl)oxy)-1-oxoisoindolin-2-yl)piperidine-2,6-dione. To a stirred solution of 2-(tetrahydro-2H-pyran-4-yl)quinazoline-6-carbaldehyde (70 mg, 0.29 mmol), (S)-3-(5-(((3S,4S)-4-(methoxymethyl)pyrrolidin-3-yl)oxy)-1-oxoisoindolin-2-yl)piperidine-2,6-dione; 2,2,2-trifluoroacetic acid (150 mg, 0.31 mmol) and triethylamine (0.12 mL, 0.85 mmol) in dichloromethane (4 mL) was added sodium triacetoxyborohydride (160 mg, 0.75 mmol) at room temperature. The reaction was stirred for 2 h at room temperature. Most solution was removed and the residue was purified by silica gel chromatography (0-5% methanol in dichloromethane) and further purified by preparative chiral HPLC with following conditions: Column: CHIRALPAK IF, 2*25 cm, 5 μm; Mobile Phase A: tert-butyl methyl ether—HPLC, Mobile Phase B: ethanol:dichloromethane=1:1-HPLC; Flow rate: 18 mL/min; Gradient: 30% B to 30% B in 42 min; Wave Length: 220/254 nm; $RT_1$ (min): 24.169; $RT_2$ (min): 30.572; Sample Solvent: ethanol—HPLC; Injection Volume: 1.25 mL. Pure fractions were evaporated, dissolved in 0.1% formic acid and lyophilized to afford title compound (27 mg, 0.045 mmol, 15% yield) as a yellow solid. $^1$H NMR (400 MHz, Methanol-$d_4$) δ 9.45 (s, 1H), 8.04 (d, J=8.3 Hz, 2H), 7.97 (d, J=8.7 Hz, 1H), 7.69 (d, J=8.4 Hz, 1H), 7.13 (d, J=2.1 Hz, 1H), 7.07 (dd, J=8.5, 2.2 Hz, 1H), 5.10 (dd, J=13.3, 5.1 Hz, 1H), 4.93-4.87 (m, 1H), 4.49-4.34 (m, 2H), 4.13-3.99 (m, 4H), 3.63 (m, 2H), 3.53 (d, J=6.2 Hz, 2H), 3.37 (s, 3H), 3.31-3.17 (m, 2H), 3.17-3.04 (m, 2H), 2.89 (m, 1H), 2.82-2.73 (m, 1H), 2.77-2.69 (m, 1H), 2.59 (m, 1H), 2.45 (m, 1H), 2.13-1.97 (m, 3H), 2.01-1.94 (m, 2H); MS (ESI) m/z 600.3 $[M+1]^+$.

Example S183. (S)-3-(5-(((R)-4,4-Difluoro-1-((2-morpholinoquinazolin-6-yl)methyl)pyrrolidin-3-yl)oxy)-1-oxoisoindolin-2-yl)piperidine-2,6-dione

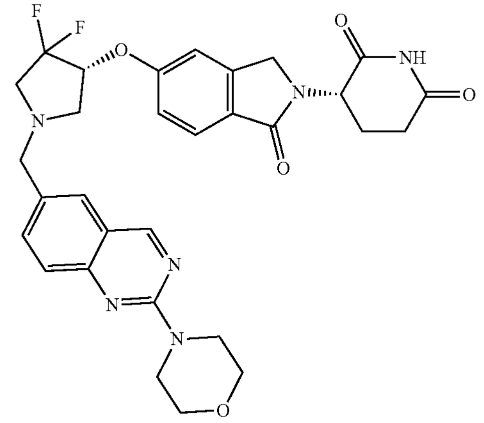 [SMILES: O=C1CC[C@H](N2Cc3cc(O[C@@H]4CN(Cc5ccc6nc(N7CCOCC7)ncc6c5)CC4(F)F)ccc3C2=O)C(=O)N1]

(S)-3-(5-(((R)-4,4-Difluoro-1-((2-morpholinoquinazolin-6-yl)methyl)pyrrolidin-3-yl)oxy)-1-oxoisoindolin-2-yl)piperidine-2,6-dione. To a stirred solution of 2-morpholinoquinazoline-6-carbaldehyde (100 mg, 0.38 mmol), (S)-3-(5-(((R)-4,4-difluoropyrrolidin-3-yl)oxy)-1-oxoisoindolin-2-yl)piperidine-2,6-dione; 2,2,2-trifluoroacetic acid (150 mg, 0.31 mmol), triethylamine (82 mg, 0.82 mmol) in dichloromethane (5 mL) and acetonitrile (5 mL) pre-stirred for 15 min was added sodium triacetoxyborohydride (348 mg, 1.64 mmol) at 0° C. and the solution was stirred at room temperature for 48 h under nitrogen. The resulting solution was purified by silica gel chromatography (0 to 20% methanol in dichloromethane) and further by preparative chiral HPLC with the following conditions: Column: Chiralpak IH, 2*25 cm, 5 μm; mobile phase A: tert-butyl methyl ether-HPLC, mobile phase B: ethanol:dichloromethane=1:1-HPLC; flow rate: 20 mL/min; gradient: 30% B to 30% B in 13 min; wave length: 220/254 nm; $RT_1$ (min): 7.773; $RT_2$ (min): 9.822; sample solvent: ethanol—HPLC; injection volume: 0.917 mL; number of runs: 4. The fractions containing desired product were collected and evaporated under reduced pressure to afford the title compound (39.2 mg, 0.066 mmol, 16% yield) as a yellow solid. $^1$H NMR (400 MHz, DMSO-$d_6$) δ 10.98 (s, 1H), 9.23 (d, J=0.7 Hz, 1H), 7.78 (d, J=2.0 Hz, 1H), 7.71 (dd, J=8.7, 2.0 Hz, 1H), 7.65 (d, J=8.4 Hz, 1H), 7.52 (d, J=8.6 Hz, 1H), 7.21 (d, J=2.2 Hz, 1H), 7.11 (dd, J=8.4, 2.2 Hz, 1H), 5.19-5.04 (m, 2H), 4.41 (d, J=17.4 Hz, 1H), 4.26 (d, J=17.4 Hz, 1H), 3.83 (m, 4H), 3.79 (m, 2H), 3.70 (dd, J=5.6, 4.0 Hz, 4H), 3.44-3.40 (m, 1H), 3.19 (m, 1H), 2.92 (m, 2H), 2.72 (m, 1H), 2.60 (m, 1H), 2.42-2.33 (m, 1H), 1.98 (m, 1H); MS (ESI) m/z 593.2 $[M+1]^+$.

Example S184. (S)-3-(5-(((R)-4,4-difluoro-1-((2-(tetrahydro-2H-pyran-4-yl)quinazolin-6-yl)methyl) pyrrolidin-3-yl)oxy)-1-oxoisoindolin-2-yl)piperidine-2,6-dione

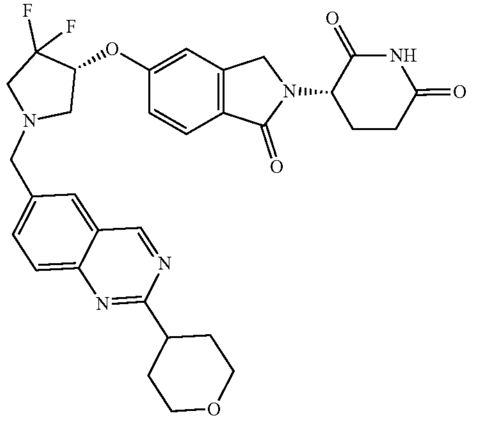 [SMILES: O=C1CC[C@H](N2Cc3cc(O[C@@H]4CN(Cc5ccc6nc(C7CCOCC7)ncc6c5)CC4(F)F)ccc3C2=O)C(=O)N1]

Tert-butyl (R)-4-((2-((S)-1-amino-5-(tert-butoxy)-1,5-dioxopentan-2-yl)-1-oxoisoindolin-5-yl)oxy)-3,3-difluoropyrrolidine-1-carboxylate. A mixture of 4,4'-di-tert-butyl-2,2'-bipyridine (16 mg, 0.06 mmol), nickel(II) chloride ethylene glycol dimethyl ether complex (13 mg, 0.06 mmol), tert-butyl (R)-3,3-difluoro-4-hydroxypyrrolidine-1-carboxylate (504 mg, 2.26 mmol), tert-butyl (S)-5-amino-4-(5-bromo-1-oxoisoindolin-2-yl)-5-oxopentanoate (500 mg, 1.26 mmol), (4,4'-Di-tert-butyl-2,2'-bipyridine)bis[2-(2',4'-difluorophenyl)-5-methylpyridine]iridium(III) hexafluorophosphate (25 mg, 0.025 mmol) and 2,2,6,6-tetramethylpiperidine (220 mg, 1.56 mmol) in acetonitrile (10 mL) was stirred at room temperature for 18 h under nitrogen with 100 W blue LED irradiation. The resulting mixture was filtered and concentrated. The residue was purified by silica gel chromatography (50 to 100% ethyl acetate in petroleum ether) to give the title compound (300 mg, 0.56 mmol, 44% yield) as a yellow solid. MS (ESI) m/z 540.3 $[M+1]^+$.

(S)-3-(5-(((R)-4,4-difluoropyrrolidin-3-yl)oxy)-1-oxoisoindolin-2-yl)piperidine-2,6-dione; 2,2,2-trifluoroacetic acid. To a solution of tert-butyl (R)-4-((2-((S)-1-amino-5-(tert-butoxy)-1,5-dioxopentan-2-yl)-1-oxoisoindolin-5-yl) oxy)-3,3-difluoropyrrolidine-1-carboxylate (300 mg, 0.56 mmol) and benzenesulfonic acid (270 mg, 1.71 mmol) in acetonitrile (10 mL) was stirred at 60° C. for 6 h under nitrogen. The reaction mixture was cooled to room temperature and slowly neutralized with saturated sodium bicarbonate carefully to pH~7 and extracted with dichloromethane. The combined organic layers were washed with brine, dried over sodium sulfate, filtered and concentrated. The resulting mixture was concentrated and the residue was purified by silica gel chromatography (0-10% methanol in dichloromethane) to afford the title compound (240 mg, 0.49 mmol, 88% yield) as white solid. MS (ESI) m/z 366.2 $[M+1]^+$.

(S)-3-(5-(((R)-4,4-difluoro-1-((2-(tetrahydro-2H-pyran-4-yl)quinazolin-6-yl)methyl)pyrrolidin-3-yl)oxy)-1-oxoisoindolin-2-yl)piperidine-2,6-dione. To a stirred mixture of 2-tetrahydropyran-4-ylquinazoline-6-carbaldehyde (66 mg, 0.27 mmol), (3S)-3-[5-[(3R)-4,4-difluoropyrrolidin-3-yl] oxy-1-oxo-isoindolin-2-yl]piperidine-2,6-dione; 2,2,2-trifluoroacetic acid (100 mg, 0.21 mmol) and triethylamine (0.08 mL, 0.54 mmol) in dichloromethane (10 mL) was added sodium triacetoxyborohydride (232 mg, 1.09 mmol) in several portions and the mixture was stirred at room temperature for 2 h under nitrogen. The resulting mixture was concentrated and the residue was purified by silica gel chromatography (0-10% methanol in dichloromethane) and purified further by preparative HPLC with the following conditions: Column: CHIRAL ART Cellulose-SB, 2*25 cm, 5 μm; mobile phase A: tert-butyl methyl ether HPLC, Mobile phase B: IPA—HPLC; Flow rate: 20 mL/min; Gradient: 30% B to 30% B in 20 min; Wave Length: 220/254 nm; $RT_1$ (min): 13.12; $RT_2$ (min): 15.56; Sample Solvent: ethanol HPLC; Injection Volume: 0.5 mL; Number of Runs: 8. The fractions containing desired product were collected and evaporated under reduced pressure to afford the title compound (22 mg, 0.037 mmol, 13% yield) as a white solid. $^1H$ NMR (400 MHz, Methanol-$d_4$) δ 9.46 (s, 1H), 8.08-8.01 (m, 2H), 7.98 (d, J=9.3 Hz, 1H), 7.72 (d, J=8.5 Hz, 1H), 7.18 (d, J=2.2 Hz, 1H), 7.13-7.11 (m, 1H), 5.12-5.10 (m, 1H), 5.03-5.01 (m, 1H), 4.48 (d, J=17.1 Hz, 1H), 4.41 (d, J=17.1 Hz, 1H), 4.09-4.05 (m, 2H), 3.94 (s, 2H), 3.63-3.59 (m, 2H), 3.45-3.43 (m, 1H), 3.31-3.16 (m, 2H), 3.01-2.75 (m, 4H), 2.46-2.44 (m, 1H), 2.20-1.94 (m, 5H); MS (ESI) m/z 592.2 $[M+1]^+$.

Example S185. (S)-3-(5-(((3S,4S)-1-((2-((S)-2,2-Dimethyltetrahydro-2H-pyran-4-yl)-8-fluoroquinolin-6-yl)methyl)-4-(methoxymethyl)pyrrolidin-3-yl) oxy)-1-oxoisoindolin-2-yl)piperidine-2,6-dione

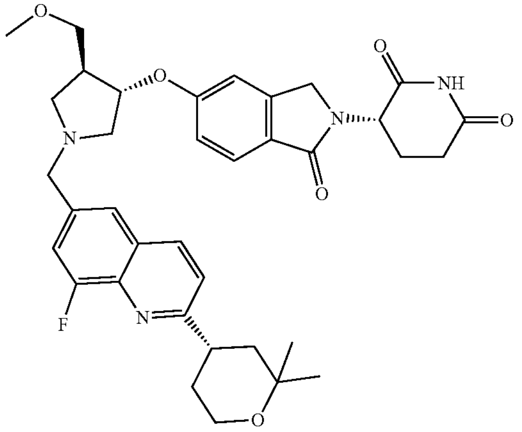 [SMILES: COC[C@@H]1CN(Cc2cc(F)c3nc([C@H]4CCOC(C)(C)C4)ccc3c2)C[C@H]1Oc1ccc2c(c1)CN([C@H]1CCC(=O)NC1=O)C2=O]

(S)-3-(5-(((3S,4S)-1-((2-((S)-2,2-Dimethyltetrahydro-2H-pyran-4-yl)-8-fluoroquinolin-6-yl)methyl)-4-(methoxymethyl)pyrrolidin-3-yl)oxy)-1-oxoisoindolin-2-yl) piperidine-2,6-dione. To a stirred solution of (S)-2-(2,2-dimethyl-tetrahydro-2H-pyran-4-yl)-8-fluoroquinoline-6-carbaldehyde (60 mg, 0.21 mmol), (S)-3-(5-(((3S,4S)-4-(methoxymethyl)pyrrolidin-3-yl)oxy)-1-oxoisoindolin-2-yl) piperidine-2,6-dione; 2,2,2-trifluoroacetic acid (100 mg, 0.21 mmol) and triethylamine (0.08 mL, 0.59 mmol) in dichloromethane (3 mL) was added sodium triacetoxyborohydride (110 mg, 0.52 mmol) at room temperature. The reaction was stirred for 2 h at room temperature. Most solution was removed and the residue was purified by silica gel chromatography (0 to 5% methanol in dichloromethane) and further purified by preparative chiral HPLC with following conditions: Column: CHIRAL ART Amylose-SA, 2*25 cm, 5 μm; Mobile Phase A: tert-butyl methyl ether—

HPLC, Mobile Phase B: ethanol:dichloromethane=1:1-HPLC; Flow rate: 20 mL/min; Gradient: 60% B to 60% B in 8 min; Wave Length: 220/254 nm; $RT_1$ (min): 6.026; $RT_2$ (min): 7.219; Sample Solvent: ethanol—HPLC; Injection Volume: 0.5 mL. Pure fractions were evaporated, dissolved in 0.1% formic acid and lyophilized to afford title compound (36.3 mg, 0.055 mmol, 26% yield) as an off-white solid. $^1H$ NMR (400 MHz, Methanol-$d_4$) δ 8.26 (dd, J=8.7, 1.5 Hz, 1H), 7.72-7.64 (m, 2H), 7.59-7.49 (m, 2H), 7.13 (d, J=2.1 Hz, 1H), 7.07 (dd, J=8.4, 2.2 Hz, 1H), 5.10 (dd, J=13.3, 5.1 Hz, 1H), 4.92-4.91 (m, 1H), 4.49-4.34 (m, 2H), 3.98-3.80 (m, 4H), 3.52 (d, J=6.4 Hz, 2H), 3.46-3.37 (m, 4H), 3.19-3.15 (m, 1H), 3.07-2.99 (m, 2H), 2.94-2.71 (m, 3H), 2.52-2.40 (m, 2H), 2.16-2.12 (m, 1H), 1.96-1.76 (m, 4H), 1.39 (s, 3H), 1.28 (s, 3H); MS (ESI) m/z 645.2 $[M+1]^+$.

Example S186. (S)-3-(5-(((3S,4S)-1-((2-(4-Acetylpiperazin-1-yl)quinolin-6-yl)methyl)-4-(methoxymethyl)pyrrolidin-3-yl)oxy)-1-oxoisoindolin-2-yl)piperidine-2,6-dione

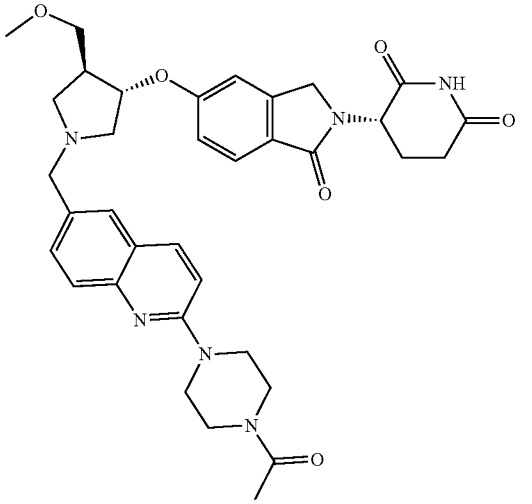 [SMILES: COC[C@@H]1CN(Cc2ccc3nc(N4CCN(C(C)=O)CC4)ccc3c2)C[C@H]1Oc1ccc2c(c1)CN([C@H]1CCC(=O)NC1=O)C2=O]

(S)-3-(5-(((3S,4S)-1-((2-(4-Acetylpiperazin-1-yl)quinolin-6-yl)methyl)-4-(methoxymethyl)pyrrolidin-3-yl)oxy)-1-oxoisoindolin-2-yl)piperidine-2,6-dione. To a stirred solution of 2-(4-acetylpiperazin-1-yl)quinoline-6-carbaldehyde (65 mg, 0.23 mmol), (S)-3-(5-(((3S,4S)-4-(methoxymethyl)pyrrolidin-3-yl)oxy)-1-oxoisoindolin-2-yl)piperidine-2,6-dione; 2,2,2-trifluoroacetic acid (140 mg, 0.29 mmol) and triethylamine (0.10 mL, 0.70 mmol) in dichloromethane (4 mL) was added sodium triacetoxyborohydride (120 mg, 0.57 mmol) at room temperature. The reaction was stirred for 2 h at room temperature. Most solution was removed and the residue was purified by silica gel chromatography (0 to 5% methanol in dichloromethane) and further purified by preparative chiral HPLC with following conditions: Column: CHIRALPAK IF, 2*25 cm, 5 μm; Mobile Phase A: tert-butyl methyl ether—HPLC, Mobile Phase B: ethanol—HPLC; Flow rate: 19 mL/min; Gradient: 35% B to 35% B in 43 min; Wave Length: 220/254 nm; $RT_1$ (min): 35.331; $RT_2$ (min): 41.356; Sample Solvent: ethanol—HPLC; Injection Volume: 2.2 mL. Pure fractions were evaporated, dissolved in 0.1% formic acid and lyophilized to obtain title compound (30 mg, 0.047 mmol, 20% yield) as a white solid. $^1H$ NMR (400 MHz, Methanol-$d_4$) δ 7.99 (d, J=9.2 Hz, 1H), 7.72-7.62 (m, 3H), 7.59 (dd, J=8.7, 2.0 Hz, 1H), 7.19 (dd, J=9.3, 1.9 Hz, 1H), 7.11 (s, 1H), 7.06 (dd, J=8.5, 2.3 Hz, 1H), 5.10 (dd, J=13.3, 5.0 Hz, 1H), 4.93 (s, 1H), 4.48-4.33 (m, 2H), 4.13-4.00 (m, 2H), 3.86-3.79 (m, 2H), 3.71 (m, 6H), 3.59-3.49 (m, 2H), 3.37 (m, 4H), 3.20 (m, 2H), 2.93-2.84 (m, 1H), 2.78-2.74 (m, 3H), 2.50-2.39 (m, 1H), 2.16-2.12 (m, 4H); MS (ESI) m/z 641.2 $[M+1]^+$.

Example S187. 3-(1-Oxo-5-(((S)-1-((7-((R)-tetrahydrofuran-3-yl)isoquinolin-3-yl)methyl)pyrrolidin-3-yl)oxy)isoindolin-2-yl)piperidine-2,6-dione

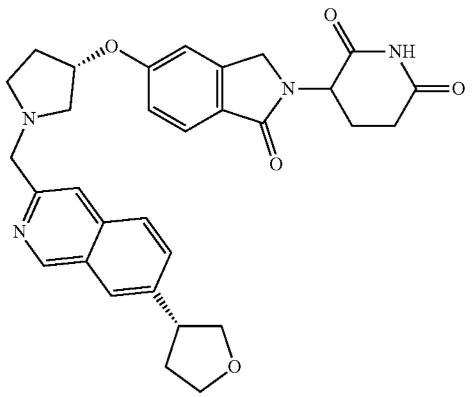 [SMILES: O=C1CCC(N2Cc3cc(O[C@H]4CCN(Cc5cc6ccc([C@H]7CCOC7)cc6cn5)C4)ccc3C2=O)C(=O)N1]

(7-Bromoisoquinolin-3-yl)methanol. To a stirred solution of methyl 7-bromoisoquinoline-3-carboxylate (500 mg, 1.9 mmol) in THF (10 mL) and ethanol (1 mL) was added lithium chloride (160 mg, 3.8 mmol), sodium borohydride (286 mg, 7.6 mmol) at 0° C. The reaction mixture was stirred at room temperature for 12 h under nitrogen. The resulting mixture was quenched with sodium hydroxide (2 M in water, 5 mL, 10 mmol) at 0° C., then stirred for 30 min at this temperature and filtered. The filter cake was washed with 20 mL THF and 10 mL methanol. The filtrate combined were concentrated to afford the title compound (400 mg, 1.67 mmol, 88% yield) as a yellow oil. MS (ESI) m/z 239.9 $[M+1]^+$.

(7-(2,5-Dihydrofuran-3-yl)isoquinolin-3-yl)methanol. To a stirred solution of (7-bromoisoquinolin-3-yl)methanol (500 mg, 2.08 mmol) in 1,4-dioxane (10 mL) were added 2-(3,6-dihydro-2H-pyran-4-yl)-4,4,5,5-tetramethyl-1,3,2-dioxaborolane (708 mg, 3.37 mmol), dichlorobis(triphenylphosphine)palladium(II) dichloromethane adduct (329 mg, 0.45 mmol) and cesium carbonate (2.19 g, 6.74 mmol) at room temperature. The reaction mixture was stirred at 100° C. for 12 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to give the title compound (400 mg, 1.75 mmol, 84% yield) as a brown solid. MS (ESI) m/z 228.2 $[M+1]^+$.

(7-(Tetrahydrofuran-3-yl)isoquinolin-3-yl)methanol. To a stirred solution of (7-(2,5-dihydrofuran-3-yl)isoquinolin-3-yl)methanol (270 mg, 1.2 mmol) in methanol (20 mL) was added palladium 10% on carbon (270 mg, wetted with ca. 50% water) at room temperature. The reaction mixture was stirred at room temperature for 6 h under hydrogen (~2 bar). The resulting mixture was filtered and the filtrate was concentrated to give the title compound (200 mg, 0.87 mmol, 73% yield) as a yellow solid. MS (ESI) m/z 230.1 $[M+1]^+$.

(R)-(7-(Tetrahydrofuran-3-yl)isoquinolin-3-yl)methanol. The (7-(tetrahydrofuran-3-yl)isoquinolin-3-yl)methanol (200 mg, 0.87 mmol) was purified via preparative SFC with the following conditions: Column: CHIRALPAK AD-H, 2*25 cm, 5 μm; Mobile Phase A: Carbon dioxide, Mobile Phase B: methanol (0.1% 2M ammonia-methanol); Flow rate: 50 mL/min; Gradient: 40% B; Column Temperature: 35° C.; Back Pressure: 100 bar; 220 nm; RT1:4.93; $RT_2$: 7.72; Injection Volume: 4.8 ml; Number of Runs: 4. The fractions containing desired product were collected and evaporated under reduced pressure to afford the title compound (70 mg, 0.30 mmol, 34% yield). MS (ESI) m/z 230.1 $[M+1]^+$.

2-(Tetrahydro-2H-pyran-4-yl)quinazoline-6-carbaldehyde. To a stirred solution of (R)-(7-(tetrahydrofuran-3-yl) isoquinolin-3-yl)methanol (70 mg, 0.30 mmol) in dichloromethane (5 mL) was added Dess-Martin periodinane (168 mg, 0.4 mmol) at 0° C. Then the reaction mixture was stirred for 2 h at room temperature under nitrogen. The resulting mixture was purified by silica gel chromatography (0 to 30% ethyl acetate in petroleum ether). The pure fractions were evaporated to afford the title compound (45 mg, 0.20 mmol, 67% yield) as a yellow oil. MS (ESI) m/z 228.2 $[M+1]^+$.

3-(1-Oxo-5-(((S)-1-((2-(tetrahydro-2H-pyran-4-yl)quinazolin-6-yl)methyl)pyrolidin-3-yl)oxy)isoindolin-2-yl)piperidine-2,6-dione. To a stirred solution of 2-tetrahydropyran-4-ylquinazoline-6-carbaldehyde (40 mg, 0.17 mmol), 3-[1-oxo-5-[(3S)-pyrrolidin-3-yl]oxy-isoindolin-2-yl]piperidine-2,6-dione (54 mg, 0.16 mmol), triethylamine (0.05 mL, 0.33 mmol) in dichloromethane (5 mL) pre-stirred for 15 min was added sodium triacetoxyborohydride (140 mg, 0.66 mmol) at 0° C. and the solution was stirred at room temperature for 12 h under nitrogen. The resulting solution was purified silica gel chromatography (0 to 15% methanol in dichloromethane). The pure fractions were evaporated and purified further by preparative HPLC with the following conditions: Column: X select CSH OBD Column 30*150 mm, 5 um; Mobile Phase A: water (0.05% TFA), Mobile Phase B: acetonitrile; Flow rate: 60 mL/min; Gradient: 3 B to 23 B in 7 min. The fractions containing desired product were collected and evaporated under reduced pressure to afford the title compound (13.9 mg, 0.025 mmol, 15% yield) as a white solid. $^1H$ NMR (300 MHz, DMSO-$d_6$) δ 10.97 (s, 1H), 9.21 (s, 1H), 8.16 (s, 1H), 8.00-7.88 (m, 2H), 7.80 (s, 1H), 7.71 (dd, J=8.6, 1.8 Hz, 1H), 7.62 (d, J=8.4 Hz, 1H), 7.13 (s, 1H), 7.02 (dd, J=8.4, 2.2 Hz, 1H), 5.07 (dd, J=13.4, 5.1 Hz, 2H), 4.39 (d, J=17.2 Hz, 1H), 4.30-4.21 (m, 1H), 4.12 (t, J=7.4 Hz, 1H), 4.02 (m, 1H), 3.96-3.80 (m, 3H), 3.64 (m, 2H), 3.05 (m, 1H), 2.99-2.78 (m, 3H), 2.62 (m, 2H), 2.41 (m, 3H), 2.13-1.79 (m, 3H); MS (ESI) m/z 541.2 $[M+1]^+$.

Example S188. 3-(5-(((S)-1-((4-Methyl-3-oxo-3,4-dihydro-2H-benzo[b][1,4]oxazin-6-yl)methyl) pyrrolidin-3-yl)oxy)-1-oxoisoindolin-2-yl)piperidine-2,6-dione

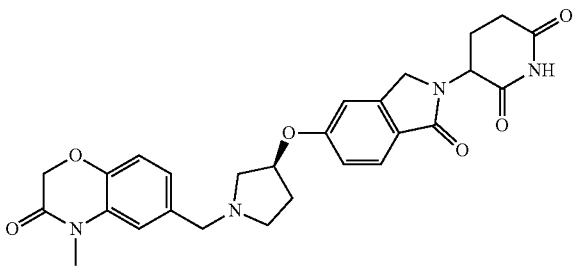 [SMILES: CN1C(=O)COc2ccc(CN3CC[C@H](Oc4ccc5c(c4)CN(C4CCC(=O)NC4=O)C5=O)C3)cc21]

4-Methyl-3-oxo-3,4-dihydro-2H-benzo[b][1,4]oxazine-6-carbaldehyde. The mixture of 3-oxo-3,4-dihydro-2H-benzo[b][1,4]oxazine-6-carbaldehyde (250 mg, 1.41 mmol), iodomethane (400 mg, 2.82 mmol) and cesium carbonate (1.4 g, 4.24 mmol) in acetonitrile (6 mL) was stirred at 80° C. for 2 h under nitrogen. The resulting mixture was filtered and the filtrate was purified by reverse phase flash (10-90% acetonitrile+0.05% TFA, over 20 min) to give the title compound (77 mg, 0.40 mmol, 29% yield) as an off-white solid. MS (ESI) m/z 192.0 $[M+1]^+$.

3-(5-(((S)-1-((4-methyl-3-oxo-3,4-dihydro-2H-benzo[b][1,4] oxazin-6-yl) methyl)pyrrolidin-3-yl)oxy)-1-oxoisoindolin-2-yl)piperidine-2,6-dione. To a solution of 4-methyl-3-oxo-3,4-dihydro-2H-benzo[b][1,4]oxazine-6-carbaldehyde (70 mg, 0.40 mmol), 3-[1-oxo-5-[(3S)-pyrrolidin-3-yl]oxy-isoindolin-2-yl]piperidine-2,6-dione (90 mg, 0.27 mmol) and triethylamine (49 mg, 0.49 mmol) in dichloromethane (10 mL) was added sodium triacetoxyborohydride (20 mg, 0.94 mmol) at 0° C. and the resulting mixture was stirred at room temperature for 12 h under nitrogen. The mixture was concentrated and the residue was purified by silica gel chromatography (0-10% methanol in dichloromethane) firstly and further by preparative HPLC with the following conditions: Column: Sunfire prep C18 obd Column, 19*150 mm, 5 μm; Mobile phase A: water (0.05% formic acid), Mobile phase B: acetonitrile; Flow rate: 60 mL/min; Gradient: 2% B to 20% B in 10 min, 20% B; Wave Length: 254/210 nm; $RT_1$ (min): 8.85; The fractions containing desired product were collected and evaporated under reduced pressure to afford the title compound (20 mg, 0.04 mmol, 15% yield) as a white solid. $^1H$ NMR (400 MHz, Methanol-$d_4$) δ 7.74 (d, J=8.4 Hz, 1H), 7.23 (d, J=1.9 Hz, 1H), 7.08-7.06 (m, 3H), 7.00 (d, J=8.2 Hz, 1H), 5.14-5.12 (m, 2H), 4.63 (s, 2H), 4.53-4.38 (m, 2H), 3.95 (d, J=13.0 Hz, 1H), 3.89 (d, J=12.6 Hz, 1H), 3.38 (s, 3H), 3.13 (m, 3H), 2.92-2.75 (m, 3H), 2.57-2.44 (m, 2H), 2.15-2.13 (m, 2H); MS (ESI) m/z 505.1 $[M+1]^+$.

Example S189. 3-(5-(((S)-1-((2-(Methoxymethyl)quinolin-6-yl)methyl)pyrrolidin-3-yl)oxy)-1-oxoisoindolin-2-yl)piperidine-2,6-dione

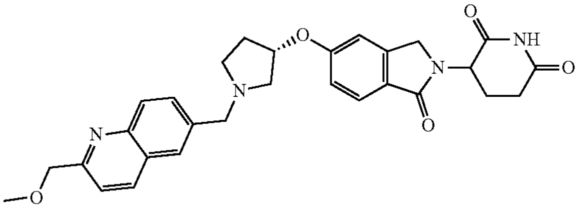 [SMILES: COCc1ccc2cc(CN3CC[C@H](Oc4ccc5c(c4)CN(C4CCC(=O)NC4=O)C5=O)C3)ccc2n1]

6-Bromo-2-(methoxymethyl)quinoline. To a solution of (6-bromoquinolin-2-yl)methanol (300 mg, 1.26 mmol) in THF (5 mL) was added sodium hydride (60% dispersion in mineral oil, 90 mg, 2.25 mmol) in several portions at 0° C. and the mixture was stirred for 5 min at room temperature. Then to the above mixture was added a solution of iodomethane (268 mg, 1.89 mmol) in THF (0.50 mL) and the mixture was stirred at room temperature for 2 h under nitrogen. The mixture was added water and extracted with ethyl acetate. The extracts were dried over anhydrous sodium sulfate, filtered and concentrated. The residue was purified by reverse phase flash (10-40% acetonitrile+0.05% TFA in water, over 25 min) to afford the title compound (150 mg, 0.59 mmol, 47% yield) as a white solid. MS (ESI) m/z 251.9 $[M+1]^+$.

2-(Methoxymethyl)quinoline-6-carbaldehyde. A stirred mixture of 6-bromo-2-(methoxymethyl)quinoline (150 mg, 0.59 mmol), palladium (II) acetate (30 mg, 0.13 mmol), 1,2-bis(diphenylphosphino)ethane (40 mg, 0.10 mmol) and sodium formate (150 mg, 2.20 mmol) in DMSO (10 mL) was added tert-butyl isocyanide (49 mg, 0.59 mmol) and the solution was stirred at 120° C. for 2 h under nitrogen. The resulting solution was added water and extracted with ethyl acetate. The extracts were dried over anhydrous sodium sulfate, filtered and concentrated. The residue was purified by silica gel chromatography (0 to 50% ethyl acetate in petroleum ether) to afford the title compound (85 mg, 0.42 mmol, 71.0% yield) as a yellow semi-solid. MS (ESI) m/z 202.0 $[M+1]^+$.

3-(5-(((S)-1-((2-(Methoxymethyl)quinolin-6-yl)methyl)pyrrolidin-3-yl)oxy)-oxoisoindolin-2-yl)piperidine-2,6-dione. To a stirred solution of 2-(methoxymethyl)quinoline-6-carbaldehyde (180 mg, 0.89 mmol) in dichloromethane (10 mL) were added 3-(1-oxo-5-(((S)-pyrrolidin-3-yl)oxy)isoindolin-2-yl)piperidine-2,6-dione; 2,2,2-trifluoroacetic acid (396 mg, 0.89 mmol), triethylamine (180 mg, 1.79 mmol) and sodium triacetoxyborohydride (758 mg, 3.58 mmol). The mixture was stirred at room temperature for 4 h under nitrogen. The resulting mixture was concentrated and the residue was purified firstly by silica gel chromatography (0 to 10% methanol in dichloromethane) and further purified by preparative HPLC with following condition: Column: Sunfire prep C18 column, 30*150 mm, 5 um; Mobile Phase A: water (0.1% formic acid), Mobile Phase B: acetonitrile; Flow rate: 60 mL/min; 254/220 nm; RT1:9.62. The fractions containing desired product were collected and evaporated under reduced pressure to afford the title compound (172.1 mg, 0.33 mmol, 37% yield) as a light-yellow solid. $^1H$ NMR (400 MHz, Methanol-$d_4$) δ 8.38 (d, J=8.5 Hz, 1H), 8.11-8.01 (m, 2H), 7.88 (dd, J=8.7, 1.9 Hz, 1H), 7.76-7.67 (m, 2H), 7.11-7.07 (m, 2H), 5.21 (m, 1H), 5.12 (dd, J=13.3, 5.2 Hz, 1H), 4.75 (s, 2H), 4.50-4.30 (m, 4H), 3.52-3.47 (m, 4H), 3.41-3.34 (m, 2H), 3.21 (m, 1H), 2.91 (m, 1H), 2.78 (m, 1H), 2.62-2.40 (m, 2H), 2.27-2.11 (m, 2H); MS (ESI) m/z 515.1 $[M+1]^+$.

Example S190. 3-(1-Oxo-5-(((R)-1-(pyrazin-2-yl)pyrrolidin-3-yl)oxy)isoindolin-2-yl)piperidine-2,6-dione

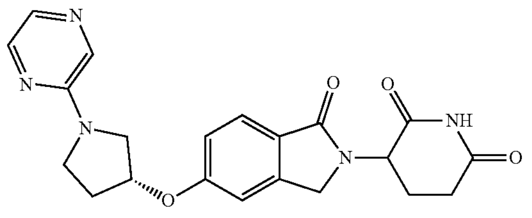 [SMILES: O=C1CCC(N2Cc3cc(O[C@@H]4CCN(c5cnccn5)C4)ccc3C2=O)C(=O)N1]

3-(5-Hydroxy-1-oxoisoindolin-2-yl)-1-(4-methoxybenzyl)piperidine-2,6-dione. To a solution of 3-(5-bromo-1-oxoisoindolin-2-yl)-1-(4-methoxybenzyl) piperidine-2,6-dione (120 mg, 0.27 mmol) in DMF (3 mL) were added RockPhos Pd G3 (7 mg, 0.0081 mmol), (E)-benzaldehyde oxime (39 mg, 0.32 mmol) and cesium carbonate (176 mg, 0.54 mmol) at room temperature. Then the reaction mixture was stirred for 12 h at 80° C. under nitrogen. The resulting mixture was filtered and the filtrate was purified by reverse phase flash (0-80% acetonitrile+0.05% TFA in water, over 20 min) to afford the title compound (75 mg, 0.19 mmol, 70% yield) as a light-yellow solid. MS (ESI) m/z 403.1 $[M+23]^+$.

(S)-1-(Pyrazin-2-yl)pyrrolidin-3-ol. To a stirred 2-bromopyrazine (390 mg, 2.47 mmol) and (S)-pyrrolidin-3-ol (235 mg, 2.70 mmol) in THF (5 mL) were added lithium hexamethyldisilazide (1 M in THF, 7.4 mL, 7.40 mmol) and methanesulfonato(2-dicyclohexylphosphino-2,6-dimethoxy-1,1-biphenyl)(2-amino-1,1-biphenyl-2-yl)palladium (II) (191 mg, 0.22 mmol) at 0° C. and the reaction mixture was stirred at 60° C. for 2 h under nitrogen. The resulting mixture was concentrated and the residue was purified by silica gel chromatography (0 to 50% ethyl acetate in petroleum ether) to afford the title compound (220 mg, 1.33 mmol, 54% yield) as a yellow oil. MS (ESI) m/z 166.2 $[M+1]^+$.

1-(4-Methoxybenzyl)-3-(1-oxo-5-(((R)-1-(pyrazin-2-yl)pyrrolidin-3-yl)oxy)isoindolin-2-yl)piperidine-2,6-dione. To a stirred solution of (S)-1-(pyrazin-2-yl)pyrrolidin-3-ol (120 mg, 0.73 mmol) and 3-(5-hydroxy-1-oxoisoindolin-2-yl)-1-(4-meth-oxybenzyl)piperidine-2,6-dione (304 mg, 0.80 mmol) in toluene (5 mL) were added triphenylphosphine (285 mg, 1.09 mmol) and di-tert-butyl azodicarboxylate (250 mg, 1.09 mmol) at 0° C. and the reaction mixture was stirred at 80° C. for 2 h under nitrogen. The resulting mixture was concentrated and the residue was purified by silica gel chromatography (0 to 50% ethyl acetate in petroleum ether) to afford the title compound (130 mg, 0.24 mmol, 34% yield) as a colorless oil. MS (ESI) m/z 528.2 $[M+1]^+$.

3-(1-Oxo-5-(((R)-1-(pyrazin-2-yl)pyrrolidin-3-yl)oxy)isoindolin-2-yl)piperidine-2,6-dione. To a stirred solution of 1-(4-methoxybenzyl)-3-(1-oxo-5-(((R)-1-(pyrazin-2-yl)pyrrolidin-3-yl)oxy)isoindolin-2-yl)piperidine-2,6-dione (120 mg, 0.23 mmol) in TFA (6 mL) was added trifluoromethanesulfonic acid (6 mL). The mixture was stirred at 60° C. for 8 h under nitrogen. The reaction mixture was concentrated. The residue was firstly purified by preparative HPLC with following conditions: Column: SunFire Prep C18 OBD Column, 19×150 mm 5 um 10 nm; Mobile Phase A: water (0.1% formic acid), Mobile Phase B: acetonitrile; Flow rate: 60 mL/min; Gradient: 11 B to 41 B in 7 min; 254/210 nm; $RT_1$ (min): 6.32. The fractions containing desired product were collected and evaporated under reduced pressure to afford the title compound (14.7 mg, 0.036 mmol, 16% yield) as a white solid. $^1$H NMR (400 MHz, DMSO-$d_6$) δ 10.97 (s, 1H), 8.05-7.99 (m, 2H), 7.79 (d, J=2.7 Hz, 1H), 7.64 (d, J=8.4 Hz, 1H), 7.23 (d, J=2.2 Hz, 1H), 7.13-7.05 (m, 1H), 5.31-5.26 (m, 1H), 5.08 (dd, J=13.3, 5.1 Hz, 1H), 4.44-4.23 (m, 2H), 3.85-3.80 (m, 1H), 3.75-3.65 (m, 2H), 3.59-3.48 (m, 1H), 2.98-2.84 (m, 1H), 2.64-2.55 (m, 1H), 2.43-2.26 (m, 3H), 2.03-1.93 (m, 1H); MS (ESI) m/z 408.0 $[M+1]^+$.

Example S191. 2-(2,6-dioxopiperidin-3-yl)-5-(((R)-1-(quinolin-5-ylmethyl)pyrrolidin-3-yl)oxy)isoindoline-1,3-dione

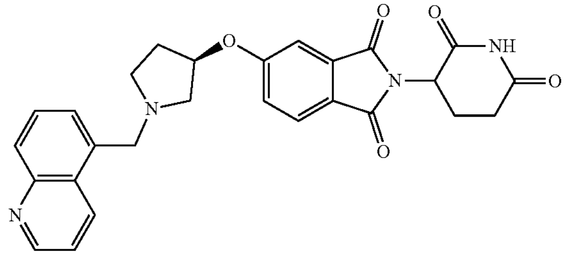 [SMILES: O=C1CCC(N2C(=O)c3ccc(O[C@@H]4CCN(Cc5cccc6ncccc56)C4)cc3C2=O)C(=O)N1]

The above-identified compound can be prepared following the methods disclosed in Examples S3 and/or S4 using quinoline-5-carbaldehyde as a starting material. $^1$H NMR (400 MHz, Methanol-$d_4$) δ 8.91-8.84 (m, 2H), 8.02 (d, J=8.5 Hz, 1H), 7.83-7.71 (m, 2H), 7.69-7.63 (m, 1H), 7.60-7.56 (m, 1H), 7.34 (d, J=2.3 Hz, 1H), 7.27 (dd, J=8.3, 2.3 Hz, 1H), 5.16-5.07 (m, 2H), 4.27 (s, 2H), 3.15 (dd, J=11.1, 6.0 Hz, 1H), 3.04-2.94 (m, 2H), 2.88-2.84 (m, 1H), 2.81-2.65 (m, 3H), 2.45-2.41 (m, 1H), 2.18-2.08 (m, 1H), 2.08-1.99 (m, 1H); MS (ESI) m/z 485.1 $[M+1]^+$.

Example S192. 2-(2,6-dioxopiperidin-3-yl)-5-(((R)-1-(quinolin-4-ylmethyl)pyrrolidin-3-yl)oxy)isoindoline-1,3-dione

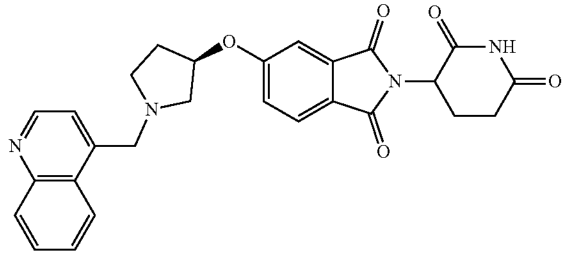 [SMILES: O=C1CCC(N2C(=O)c3ccc(O[C@@H]4CCN(Cc5ccnc6ccccc56)C4)cc3C2=O)C(=O)N1]

The above-identified compound can be prepared following the methods disclosed in Examples S3 and/or S4 using quinoline-4-carbaldehyde as a starting material. $^1$H NMR (400 MHz, Methanol-$d_4$) δ 8.82 (d, J=4.5 Hz, 1H), 8.37 (d, J=8.4 Hz, 1H), 8.22 (s, 1H), 8.07 (d, J=8.5 Hz, 1H), 7.85-7.74 (m, 2H), 7.70-7.60 (m, 2H), 7.36 (d, J=2.3 Hz, 1H), 7.28 (dd, J=8.3, 2.3 Hz, 1H), 5.19-5.07 (m, 2H), 4.28 (s, 2H), 3.17 (dd, J=10.9, 5.9 Hz, 1H), 3.01 (m, 2H), 2.95-2.84 (m, 1H), 2.75-2.69 (m, 3H), 2.48-2.46 (m, 1H), 2.15-2.00 (m, 2H); MS (ESI) m/z 485.0 $[M+1]^+$.

Example S193. 3-(5-(((R)-1-((1H-pyrrolo[2,3-b]pyridin-3-yl)methyl)pyrrolidin-3-yl)oxy)-1-oxoisoindolin-2-yl)piperidine-2,6-dione

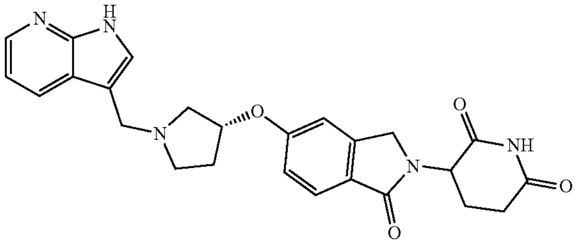 [SMILES: O=C1CCC(N2Cc3cc(O[C@@H]4CCN(Cc5c[nH]c6ncccc56)C4)ccc3C2=O)C(=O)N1]

The above-identified compound can be prepared following the methods in General Scheme 1 and/or 2.

Example S194. 3-(1-oxo-5-(((R)-1-(quinolin-6-ylmethyl)pyrrolidin-3-yl)oxy)isoindolin-2-yl)piperidine-2,6-dione

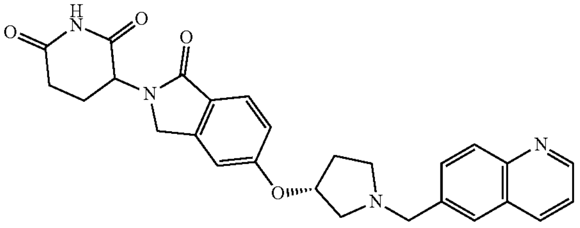 [SMILES: O=C1CCC(N2Cc3cc(O[C@@H]4CCN(Cc5ccc6ncccc6c5)C4)ccc3C2=O)C(=O)N1]

The above-identified compound can be prepared following the methods in General Scheme 1 and/or 2.

Example S195. 3-(1-oxo-5-(((R)-1-(quinolin-4-ylmethyl)pyrrolidin-3-yl)oxy)isoindolin-2-yl)piperidine-2,6-dione

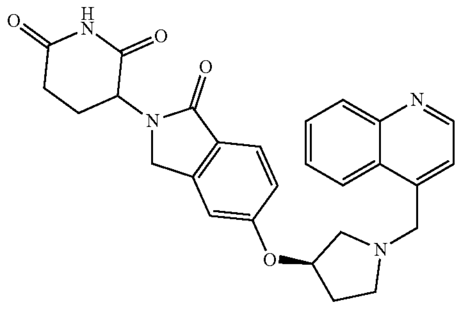 [SMILES: O=C1CCC(N2Cc3cc(O[C@@H]4CCN(Cc5ccnc6ccccc56)C4)ccc3C2=O)C(=O)N1]

The above-identified compound can be prepared following the methods in General Scheme 1 and/or 2.

Example S196. 3-(1-oxo-5-(((R)-1-(quinolin-3-ylmethyl)pyrrolidin-3-yl)oxy)isoindolin-2-yl)piperidine-2,6-dione

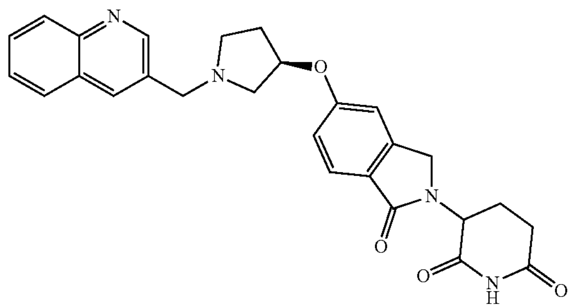 [SMILES: O=C1CCC(N2Cc3cc(O[C@@H]4CCN(Cc5cnc6ccccc6c5)C4)ccc3C2=O)C(=O)N1]

The above-identified compound can be prepared following the methods in General Scheme 1 and/or 2.

Example S197. 3-(1-oxo-5-(((R)-1-(quinolin-5-ylmethyl)pyrrolidin-3-yl)oxy)isoindolin-2-yl)piperidine-2,6-dione

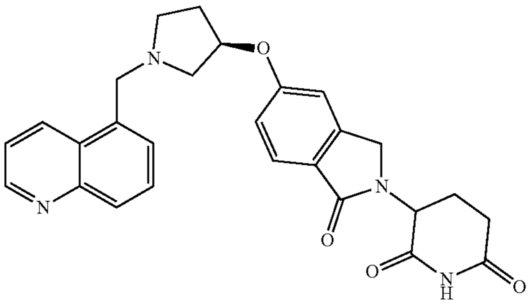 [SMILES: O=C1CCC(N2Cc3cc(O[C@@H]4CCN(Cc5cccc6ncccc56)C4)ccc3C2=O)C(=O)N1]

The above-identified compound can be prepared following the methods in General Scheme 1 and/or 2.

Example S198. 3-(5-(((R)-1-((1H-pyrrolo[2,3-c]pyridin-3-yl)methyl)pyrrolidin-3-yl)oxy)-1-oxoisoindolin-2-yl)piperidine-2,6-dione

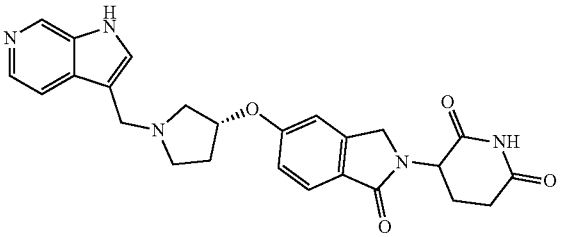 [SMILES: O=C1CCC(N2Cc3cc(O[C@@H]4CCN(Cc5c[nH]c6cnccc56)C4)ccc3C2=O)C(=O)N1]

The above-identified compound can be prepared following the methods in General Scheme 1 and/or 2.

Example S199. 3-(5-(((R)-1-((2,4-dimethylthiazol-5-yl)methyl)pyrrolidin-3-yl)oxy)-1-oxoisoindolin-2-yl)piperidine-2,6-dione

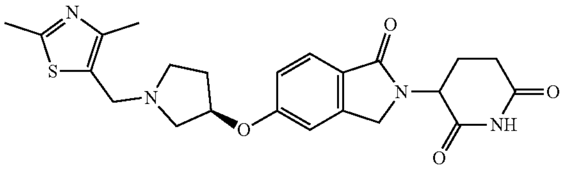 [SMILES: Cc1nc(C)c(CN2CC[C@@H](Oc3ccc4c(c3)CN(C3CCC(=O)NC3=O)C4=O)C2)s1]

The above-identified compound can be prepared following the methods in General Scheme 1 and/or 2.

Example S200. (R)-3-(1-oxo-5-(((S)-1-(quinolin-6-ylmethyl)pyrrolidin-3-yl)oxy)isoindolin-2-yl)piperidine-2,6-dione

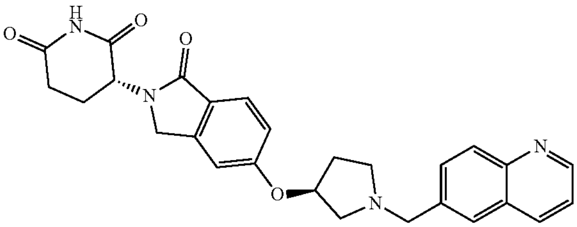 [SMILES: O=C1CC[C@@H](N2Cc3cc(O[C@H]4CCN(Cc5ccc6ncccc6c5)C4)ccc3C2=O)C(=O)N1]

The above-identified compound can be prepared following the methods in General Scheme 1. It can be obtained, for example, from the chiral separation of the mixture of stereoisomers obtained in Example S36 $^1$H NMR (400 MHz, Chloroform-d) δ 8.93 (dd, J=8.0 Hz, J=4.0 Hz, 1H), 8.26 (s, 1H), 8.20-8.08 (m, 2H), 7.84-7.74 (m, 3H), 7.42 (dd, J=8.0 Hz, J=4.0 Hz, 1H), 6.97 (dd, J=12.0 Hz, J=4.0 Hz, 1H), 6.88 (d, J=4 Hz, 1H), 5.21 (dd, J=12.0 Hz, J=4.0 Hz, 1H), 4.94 (m, 1H), 4.44 (d, J=16 Hz, 1H), 4.29 (d, J=16 Hz, 1H), 3.94 (m, 2H), 3.13 (m, 1H), 2.99-2.66 (m, 5H), 2.47-2.27 (m, 2H), 2.27-2.16 (m, 1H), 2.15-2.03 (m, 1H); MS (ESI) m/z 471.2 [M+1]+.

Example S201. (S)-3-(1-oxo-5-(((S)-1-(quinolin-6-ylmethyl)pyrrolidin-3-yl)oxy)isoindolin-2-yl)piperidine-2,6-dione

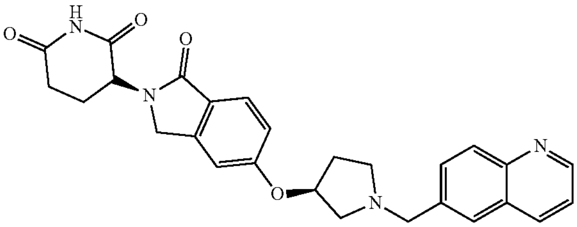

The above-identified compound can be prepared following the methods in General Scheme 1. It can be obtained, for example, from the chiral separation of the mixture of stereoisomers obtained in Example S36. s$^1$H NMR (400 MHz, Methanol-$d_4$) δ 8.86 (dd, J=8.0 Hz, J=4.0 Hz, 1H), 8.37 (d, J=4 Hz, 1H), 8.20-8.10 (m, 2H), 7.80 (m, 3H), 7.57 (dd, J=8.0 Hz, J=4.0 Hz, 1H), 7.11-7.02 (m, 2H), 5.15 (m, 2H), 4.90 (m, 1H), 4.50-4.36 (m, 2H), 4.12-4.00 (m, 2H), 3.21-3.13 (m, 1H), 3.13-3.00 (m, 2H), 2.98-2.73 (m, 3H), 2.55-2.39 (m, 2H), 2.21-2.04 (m, 2H); MS (ESI) m/z 471.2 $[M+1]^+$.

Example S202. (R)-3-(5-(((S)-1-((2-morpholinoquinazolin-6-yl)methyl)pyrrolidin-3-yl)oxy)-1-oxoisoindolin-2-yl)piperidine-2,6-dione

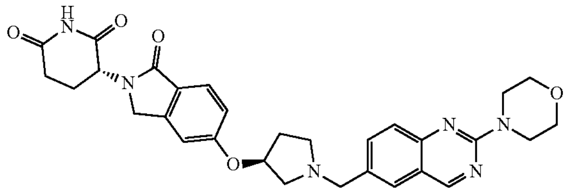 [SMILES: O=C1CC[C@@H](N2Cc3cc(O[C@H]4CCN(Cc5ccc6nc(N7CCOCC7)ncc6c5)C4)ccc3C2=O)C(=O)N1]

The above-identified compound can be prepared following the methods in General Scheme 1 and/or 2. It can be obtained, for example, from the chiral separation of that mixture of stereoisomers obtained in Example S205. $^1$H NMR (300 MHz, DMSO-$d_6$) δ 9.20 (s, 1H), 7.83-7.70 (m, 2H), 7.62 (d, J=8.4 Hz, 1H), 7.50 (d, J=8.6 Hz, 1H), 7.11 (d, J=2.2 Hz, 1H), 7.01 (dd, J=8.4, 2.2 Hz, 1H), 5.04 (m, 2H), 4.45-4.17 (m, 2H), 3.88-3.62 (m, 10H), 3.05-2.61 (m, 5H), 2.57 (m, 1H), 2.37 (m, 2H), 2.05-1.77 (m, 2H); MS (ESI) m/z 557.2 $[M+1]^+$.

Example S203. (R)-3-(1-oxo-5-(((S)-1-((2-(tetrahydro-2H-pyran-4-yl)quinolin-6-yl)methyl)pyrrolidin-3-yl)oxy)isoindolin-2-yl)piperidine-2,6-dione

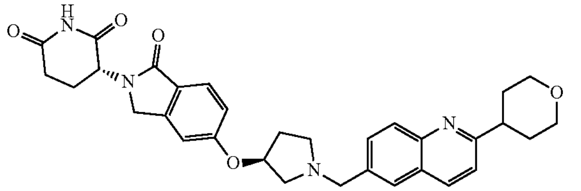 [SMILES: O=C1CC[C@@H](N2Cc3cc(O[C@H]4CCN(Cc5ccc6nc(C7CCOCC7)ccc6c5)C4)ccc3C2=O)C(=O)N1]

The above-identified compound can be prepared following the methods in General Scheme 1 and/or 2. It can be obtained, for example, from the chiral separation of that mixture of stereoisomers obtained in Example S204. $^1$H N MR (400 MHz, Methanol-$d_4$) δ 8.34 (d, J=8.6 Hz, 1H), 8.16-8.09 (m, 2H), 7.90 (dd, J=8.7, 2.1 Hz, 1H), 7.74 (d, J=8.5 Hz, 1H), 7.60 (d, J=8.6 Hz, 1H), 7.17 (d, J=2.2 Hz, 1H), 7.10 (dd, J=8.5, 2.2 Hz, 1H), 5.34 (m, 1H), 5.13 (dd, J=13.3, 5.2 Hz, 1H), 4.67 (s, 2H), 4.49-4.43 (m, 2H), 4.16-4.08 (m, 2H), 3.81 (m, 1H), 3.75-3.56 (m, 5H), 3.23-3.17 (m, 1H), 3.01-2.85 (m, 1H), 2.80-2.79 (m, 1H), 2.65 (m, 1H), 2.48-2.33 (m, 2H), 2.19-2.15 (m, 1H), 2.10-1.99 (m, 2H), 1.92-1.88 (m, 2H); MS (ESI) m/z 555.2 [M+1].

Example S204. 3-(1-Oxo-5-(((S)-1-((2-(tetrahydro-2H-pyran-4-yl)quinolin-6-yl)methyl)pyrrolidin-3-yl)oxy)isoindolin-2-yl)piperidine-2,6-dione

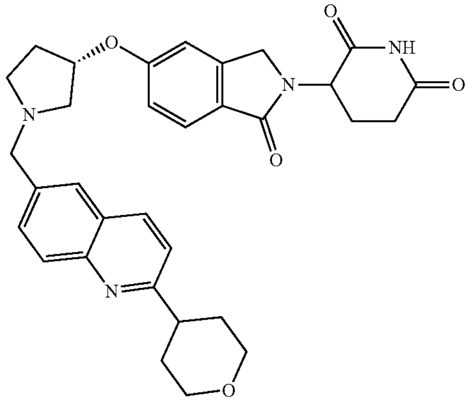 [SMILES: O=C1CCC(N2Cc3cc(O[C@H]4CCN(Cc5ccc6nc(C7CCOCC7)ccc6c5)C4)ccc3C2=O)C(=O)N1]

6-Bromo-2-(tetrahydro-2H-pyran-4-yl)quinoline. To a stirred solution of (2-amino-5-bromophenyl)methanol (440 mg, 2.18 mmol) in toluene (5 mL) were added 1-(tetrahydro-2H-pyran-4-yl)ethan-1-one (560 mg, 4.37 mmol) and lithium t-butoxide (348 mg, 4.35 mmol). The mixture was stirred at 110° C. for 2 days under nitrogen. The resulting mixture was added water and extracted with ethyl acetate. The extracts were washed with brine, dried over anhydrous sodium sulfate, filtered and concentrated. The residue was purified by silica gel chromatography (0-10% methanol in dichloromethane) to afford the title compound (200 mg, 0.68 mmol, 31% yield) as a light-yellow oil. MS (ESI) m/z 292.0 $[M+1]^+$.

2-(Tetrahydro-2H-pyran-4-yl)quinoline-6-carbaldehyde. To a stirred solution of 6-bromo-2-(tetrahydro-2H-pyran-4-yl)quinoline (200 mg, 0.68 mmol) in DMSO (1 mL) were added sodium formate (140 mg, 2.05 mmol), palladium (II) acetate (30 mg, 0.14 mmol), 1,2-bis(diphenylphosphino)ethane (109 mg, 0.27 mmol) and tert-butyl isocyanide (56 mg, 0.68 mmol). The mixture was stirred at 110° C. for 2 h under nitrogen. The resulting mixture was added water and extracted with ethyl acetate. The extracts were washed with brine, dried over anhydrous sodium sulfate, filtered and concentrated. The residue was purified by silica gel chromatography (0-10% methanol in dichloromethane) to afford the title compound (50 mg, 0.21 mmol, 31% yield) as a light-yellow solid. MS (ESI) m/z 242.1 $[M+1]^+$.

3-(1-Oxo-5-(((S)-1-((2-(tetrahydro-2H-pyran-4-yl)quinolin-6-yl)methyl)-pyrrolidin-3-yl)oxy)isoindolin-2-yl)piperidine-2,6-dione. To a solution of 3-[1-oxo-5-[(3S)-pyrrolidin-3-yl]oxy-isoindolin-2-yl]piperidine-2,6-dione hydrochloride (50 mg, 0.14 mmol), 2-(tetrahydro-2H-pyran-4-yl)quinoline-6-carbaldehyde (32 mg, 0.13 mmol) and triethylamine (0.03 mL, 0.21 mmol) in dichloromethane (10 mL) was added sodium triacetoxyborohydride (87 mg, 0.41 mmol). The mixture was stirred for 12 h under nitrogen. The resulting mixture was concentrated and the residue was purified by preparative HPLC with the following conditions: Column: Sunfire prep C18 Column, 30*150 mm, 5 um; Mobile Phase A: water (0.1% formic acid), Mobile Phase B: acetonitrile; Flow rate: 60 mL/min; Gradient: 2 B to 20 B in 7 min; 254/210 nm; $RT_1$ (min): 6.3. The fractions containing desired product were collected and evaporated under reduced pressure to afford the title compound (11.6 mg, 0.021 mmol, 15% yield) as an off-white solid. $^1$H NMR (300 MHz, Methanol-$d_4$) δ 8.30 (d, J=9.0 Hz, 2H), 8.05 (d, J=9.0 Hz 1H), 7.95 (s, 1H), 7.83 (dd, J=9.0 Hz, J=3.0 Hz, 1H), 7.72 (d, J=6.0 Hz, 1H), 7.55 (d, J=9.0 Hz, 1H), 7.14-7.02 (m, 2H), 5.21-5.06 (m, 2H), 4.54-4.35 (m, 2H), 4.28-4.06 (m, 4H), 3.65 (m, 2H), 3.33-3.28 (m, 1H), 3.27-3.14 (m, 3H), 3.09-2.72 (m, 3H), 2.60-2.37 (m, 2H), 2.22-2.12 (m, 2H), 2.11-1.85 (m, 4H); MS (ESI) m/z 555.3 [M+1]$^+$.

Example S205. 3-(5-(((S)-1-((2-Morpholinoquinazolin-6-yl)methyl)pyrrolidin-3-yl)oxy)-1-oxoisoindolin-2-yl)piperidine-2,6-dione

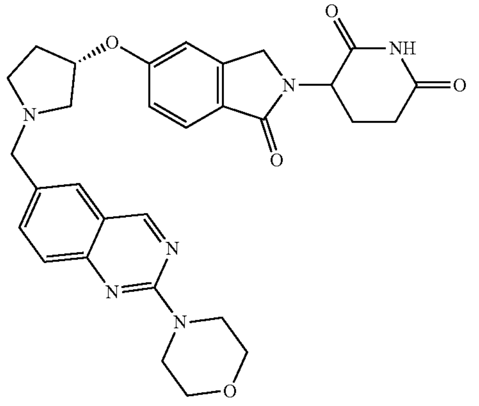 [SMILES: O=C1CCC(N2Cc3cc(O[C@H]4CCN(Cc5ccc6nc(N7CCOCC7)ncc6c5)C4)ccc3C2=O)C(=O)N1]

4-(6-Bromoquinazolin-2-yl)morpholine. To a solution of 6-bromo-2-chloroquinazoline (500 mg, 2.05 mmol) and morpholine (358 mg, 4.11 mmol) in acetonitrile (4 mL) was added potassium carbonate (850 mg, 6.16 mmol) at room temperature. The mixture was stirred at 70° C. for 16 h under nitrogen. The resulting mixture is filtered and the filtrate cake was washed with ethyl acetate. The filtrate was concentrated and the residue was purified by silica gel chromatography (0 to 20% ethyl acetate in petroleum ether) to afford the title compound (405 mg, 1.38 mmol, 67% yield) as a yellow solid. MS (ESI) m/z 294.0 [M+1]$^+$.

4-(6-Vinylquinazolin-2-yl)morpholine. To a solution of 4-(6-bromoquinazolin-2-yl)morpholine (200 mg, 0.68 mmol) and tributyl(vinyl)stannane (259 mg, 0.82 mmol.) in 1,4-dioxane (5 mL) were added trans-dichlorobis(triphenylphosphine)palladium (157 mg, 0.22 mmol) and cesium fluoride (207 mg, 1.36 mmol) at room temperature. The mixture was stirred at 100° C. for 3 h under nitrogen. The resulting mixture was filtered and the filter cake was washed with ethyl acetate. The filtrate was concentrated and the residue was purified by silica gel chromatography (0 to 25% ethyl acetate in petroleum ether) to afford the title compound (95 mg, 0.39 mmol, 57% yield) as a black liquid. MS (ESI) m/z 242.1 [M+1]$^+$.

2-Morpholinoquinazoline-6-carbaldehyde. To a stirred solution of 4-(6-vinylquinazolin-2-yl)morpholine (114 mg, 0.47 mmol) in tert-butanol (2 mL) and water (2 mL) were added potassium osmate (17 mg, 0.046 mmol), citric acid (181 mg, 0.94 mmol) and 4-methyl-morpholin4-oxide (111 mg, 0.94 mmol) and the mixture was stirred for 3 h at room temperature under nitrogen. Then sodium periodate (303 mg, 1.40 mmol) was added and the mixture was stirred for another 1 h under nitrogen. The mixture was added saturated sodium bicarbonate to PH~7 and extracted with ethyl acetate. The extracts were washed with brine, dried over anhydrous sodium sulfate, filtered and concentrated at room temperature to afford the title compound (98 mg, 0.40 mmol, 85% yield) as a yellow solid. MS (ESI) m/z 244.2 [M+1]$^+$.

3-(5-(((S)-1-((2-Morpholinoquinazolin-6-yl)methyl)pyrrolidin-3-yl)oxy)-1-oxoisoindolin-2-yl)piperidine-2,6-dione. To a solution of 2-morpholinoquinazol-ine-6-carbaldehyde (47 mg, 0.19 mmol), 3-[1-oxo-5-[(3S)-pyrrolidin-3-yl]oxy-isoindolin-2-yl]piperidine-2,6-dione; 2,2,2-trifluoroacetic acid (86 mg, 0.19 mmol) and triethylamine (0.06 mL, 0.46 mmol) in dichloromethane (3 mL) was added sodium triacetoxyborohydride (127 mg, 0.60 mmol) and the mixture was stirred at room temperature for 2 h under nitrogen. The resulting mixture is filtered and the filter cake was washed with 5 mL dichloromethane. The filtrate was concentrated. The residue was purified by silica gel chromatography (0 to 5% methanol in dichloromethane) and purified further by preparative HPLC with the following conditions: Column: SunFire Prep C18 OBD Column, 19×150 mm 5 um 10 nm; Mobile Phase A: water (0.1% formic acid), Mobile Phase B: acetonitrile; Flow rate: 60 mL/min; Gradient: 5 B to 25 B in 7 min; 254/210 nm; $RT_1$ (min): 6.32. The fractions containing desired product were collected and evaporated under reduced pressure to afford the title compound (19 mg, 0.034 mmol, 17% yield) as a white solid. $^1$H NMR (300 MHz, Methanol-$d_4$) δ 9.12 (s, 1H), 8.33 (s, 1H), 7.93-7.77 (m, 2H), 7.73-7.70 (m, 1H), 7.61-7.57 (m, 1H), 7.17-7.01 (m, 2H), 5.26-5.06 (m, 2H), 4.45-4.39 (m, 2H), 4.25 (m, 2H), 3.95-3.85 (m, 4H), 3.80-3.70 (m, 4H), 3.43 (m, 2H), 3.15 (m, 2H), 2.96-2.70 (m, 2H), 2.51-2.30 (m, 2H), 2.15 (m, 2H); MS (ESI) m/z 557.2 [M+1]$^+$.

Example S206. 3-(5-(((S)-1-((2-Morpholinoquinolin-6-yl)methyl)pyrrolidin-3-yl)oxy)-1-oxoisoindolin-2-yl)piperidine-2,6-dione

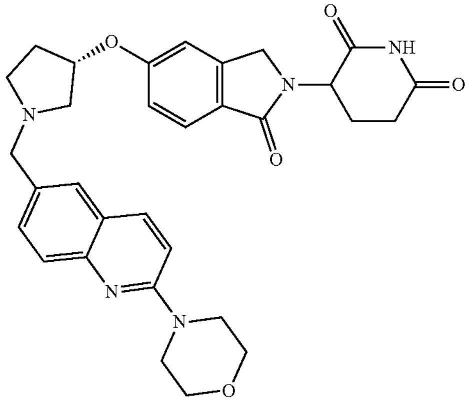 [SMILES: O=C1CCC(N2Cc3cc(O[C@H]4CCN(Cc5ccc6nc(N7CCOCC7)ccc6c5)C4)ccc3C2=O)C(=O)N1]

(2-Morpholinoquinolin-6-yl)methanol. A mixture of methyl 2-chloroquinoline-6-carboxylate (300 mg, 1.35 mmol) and morpholine (589 mg, 6.77 mmol) in ethanol (10 mL) was stirred at 80° C. for 12 h under nitrogen. The solution was concentrated to afford methyl 2-morpholinoquinoline-6-carboxylate (300 mg, 1.10 mmol, 81% yield) as a yellow solid. To a solution of methyl 2-morpholinoquinoline-6-carboxylate (200 mg, 0.73 mmol) in THF (4 mL) was added lithium aluminium hydride (2.5 M in THF, 0.46 mL, 1.15 mmol) dropwise at 0° C. and the mixture was stirred at this temperature for 20 min under nitrogen. The reaction mixture was quenched with little ethanol and stirred for another 5 min. The resulting mixture was added saturated sodium carbonate to pH~7 and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (160 mg, 0.65 mmol, 89% yield) as a light-yellow solid. MS (ESI) m/z 245.2 $[M+1]^+$.

2-Morpholinoquinoline-6-carbaldehyde. To a stirred solution of (2-morpholinoquinolin-6-yl)methanol (75 mg, 0.31 mmol) in dichloromethane (6 mL) was added Dess-Martin periodinane (169 mg, 0.40 mmol) at 0° C. and the mixture was stirred at room temperature for 12 h under nitrogen. The resulting mixture was diluted with dichloromethane, filtered and the filtrate was concentrated. The residue was purified by silica gel chromatography (0 to 50% ethyl acetate in petroleum ether) to afford the title compound (60 mg, 0.25 mmol, 81% yield) as a light-yellow oil. MS (ESI) m/z 243.2 $[M+1]^+$.

3-(5-(((S)-1-((2-Morpholinoquinolin-6-yl)methyl)pyrrolidin-3-yl)oxy)-1-oxoisoindolin-2-yl)piperidine-2,6-dione. To a stirred solution of 3-(1-oxo-5-(((S)-pyrrolidin-3-yl)oxy)isoindolin-2-yl)piperidine-2,6-dione; 2,2,2-trifluoroacetic acid (82 mg, 0.18 mmol), 2-morpholinoquinoline-6-carbaldehyde (60 mg, 0.25 mmol) and triethylamine (50 mg, 0.5 mmol) in dichloromethane (3 mL) was added sodium triacetoxyborohydride (210 mg, 0.99 mmol). The mixture was stirred for 2 h at room temperature under nitrogen. The resulting mixture was concentrated under reduced pressure. The residue was purified firstly by silica gel chromatography (0 to 5% methanol in dichloromethane) and further purified by preparative HPLC with the following conditions: Column: Sunfire prep C18 Column, 30*150 mm, 5 um; Mobile Phase A: water (0.1% formic acid), Mobile Phase B: acetonitrile; Flow rate: 60 mL/min; Gradient: 3 B to 18 B in 7 min. The fractions containing desired product were collected and evaporated under reduced pressure to afford the title compound (15.8 mg, 0.028 mmol, 16% yield) as an off-white solid. $^1$H NMR (300 MHz, Methanol-$d_4$) δ 8.00 (d, J=8.8 Hz, 1H), 7.72-7.55 (m, 4H), 7.16 (d, J=9.2 Hz, 1H), 7.10-7.00 (m, 2H), 5.10-5.06 (m, 2H), 4.43 (d, J=3.8 Hz, 2H), 3.97-3.78 (m, 6H), 3.70-3.62 (m, 4H), 2.97 (m, 4H), 2.82-2.73 (m, 2H), 2.52-2.42 (m, 2H), 2.06 (m, 2H); MS (ESI) m/z 556.2 $[M+1]^+$.

Example S207. 3-(1-Oxo-5-(((S)-1-((2-(tetrahydro-2H-pyran-4-yl)quinazolin-6-yl)methyl)pyrrolidin-3-yl)oxy)isoindolin-2-yl)piperidine-2,6-dione

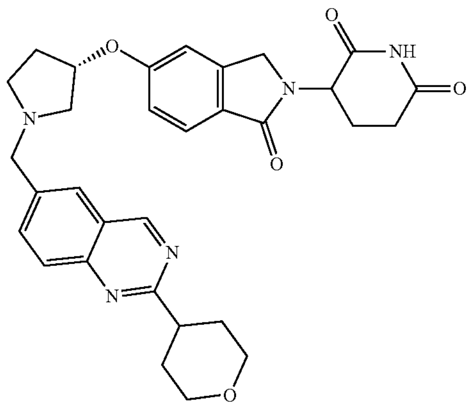 [SMILES: O=C1CCC(N2Cc3cc(O[C@H]4CCN(Cc5ccc6nc(C7CCOCC7)ncc6c5)C4)ccc3C2=O)C(=O)N1]

3-(1-Oxo-5-(((S)-1-((2-(tetrahydro-2H-pyran-4-yl)quinazolin-6-yl)methyl)-pyrrolidin-3-yl)oxy)isoindolin-2-yl) piperidine-2,6-dione. To a stirred solution of 2-(tetrahydro-2H-pyran-4-yl)quinazoline-6-carbaldehyde (40 mg, 0.17 mmol) in dichloromethane (5 mL) were added 3-[1-oxo-5-[(3S)-pyrrolidin-3-yl]oxy-isoindoli-2-yl]piperidine-2,6-dione (54 mg, 0.16 mmol), triethylamine (0.05 mL, 0.33 mmol) and sodium triacetoxyborohydride (140 mg, 0.66 mmol). The mixture was stirred at room temperature for 1 h under nitrogen. The resulting mixture was concentrated. The residue was purified firstly by silica gel chromatography (0 to 10% methanol in dichloromethane) and further purified by preparative HPLC with the following conditions: Xselect CSH OBD Column 30*150 mm 5 um; Mobile Phase A: water (0.05% TFA), Mobile Phase B: acetonitrile; Flow rate: 60 mL/min; Gradient: 3 B to 23 B in 7 min. The fractions containing desired product were collected and evaporated under reduced pressure to afford the title compound (13.9 mg, 0.024 mmol, 15% yield) as an off-white solid. $^1$H NMR (400 MHz, DMSO-$d_6$) δ 9.61 (s, 1H), 8.28 (d, J=2.1 Hz, 1H), 8.11-8.09 (m, 1H), 8.05 (d, J=8.7 Hz, 1H), 7.67 (d, J=8.2 Hz, 1H), 7.19 (m, 1H), 7.08 (m, 1H), 5.29 (m, 1H), 5.09-5.01 (m, 1H), 4.67 (m, 2H), 4.40 (m, 1H), 4.27 (m, 1H), 4.02-3.94 (m, 2H), 3.70-3.60 (m, 4H), 3.50-3.40 (m, 1H), 3.31-3.21 (m, 1H), 2.88 (m, 1H), 2.63 (m, 1H), 2.50-2.10 (m, 4H), 2.00-1.85 (m, 5H); MS (ESI) m/z 541.2 $[M+1]^+$.

Example S208. 3-(1-Oxo-5-(((S)-1-((7-(tetrahydro-2H-pyran-4-yl)isoquinolin-3-yl)methyl)pyrrolidin-3-yl)oxy)isoindolin-2-piperidine-2,6-dione

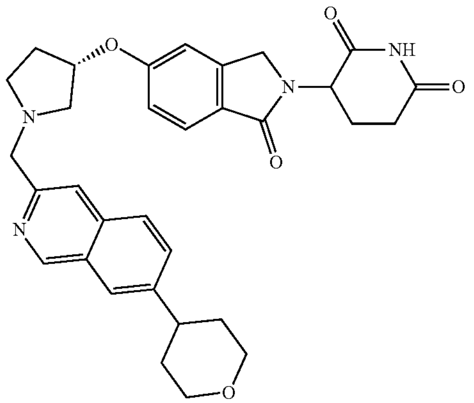 [SMILES: O=C1CCC(N2Cc3cc(O[C@H]4CCN(Cc5cc6ccc(C7CCOCC7)cc6cn5)C4)ccc3C2=O)C(=O)N1]

3-(1-Oxo-5-(((S)-1-((7-(tetrahydro-2H-pyran-4-yl)isoquinolin-3-yl)methyl)-pyrrolidin-3-yl)oxy)isoindolin-2-yl) piperidine-2,6-dione. To a stirred solution of 7-(tetrahydro-2H-pyran-4-yl)isoquinoline-3-carbaldehyde (40 mg, 0.17 mmol) in dichloromethane (5 mL) were added 3-(1-oxo-5-(((S)-pyrrolidin-3-yl)oxy)isoindolin-2-yl)piperidine-2,6-dione (55 mg, 0.17 mmol), triethylamine (0.05 mL, 0.34 mmol) and sodium triacetoxyborohydride (140 mg, 0.66 mmol). The mixture was stirred at room temperature for 1 h under nitrogen. The resulting mixture was concentrated. The residue was purified firstly by silica gel chromatography (0 to 10% methanol in dichloromethane) and further purified by preparative HPLC with the following conditions: Column: Sunfire prep C18 Column, 30*150 mm, 5 um; Mobile Phase A: water (0.1% formic acid), Mobile Phase B: acetonitrile; Flow rate: 60 mL/min; Gradient: 3 B to 30 B in 8 min; $RT_1$ (min): 7.6. The fractions containing desired product were collected and evaporated under reduced pressure to afford the title compound (10.8 mg, 0.02 mmol, 11% yield) as an off-white solid. $^1$H NMR (400 MHz, Methanol-$d_4$) δ 9.24 (s, 1H), 7.97-7.85 (m, 3H), 7.81-7.69 (m, 2H), 7.13-7.03 (m, 2H), 5.17-5.08 (m, 2H), 4.44 (m, 2H), 4.25 (m, 2H), 4.11 (d, J=12.0 Hz, 2H), 3.64 (m, 2H), 3.30-3.25 (m, 1H), 3.20-3.10 (m, 2H), 3.06 (m, 2H), 2.91-2.65 (m, 2H), 2.49 (m, 2H), 2.10 (m, 2H), 1.91 (m, 4H); MS (ESI) m/z 555.2 $[M+1]^+$.

Example S209. 3-(5-(((S)-1-((2-(2-Hydroxypropan-2-yl)quinolin-6-yl)methyl)pyrrolidin-3-yl)oxy-1-oxoisoindolin-2-yl)piperidine-2,6-dione

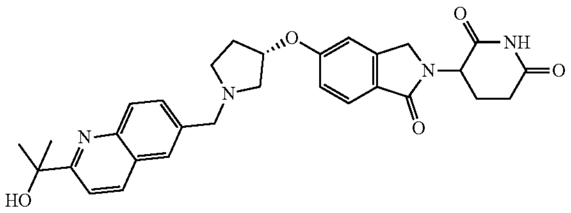 [SMILES: CC(C)(O)c1ccc2cc(CN3CC[C@H](Oc4ccc5c(c4)CN(C4CCC(=O)NC4=O)C5=O)C3)ccc2n1]

3-(5-(((S)-1-((2-(2-Hydroxypropan-2-yl)quinolin-6-yl)methyl)pyrrolidin-3-yl)oxy)-1-oxoisoindolin-2-yl)piperidine-2,6-dione. To a stirred solution of 2-(2-hydroxypropan-2-yl)quinoline-6-carbaldehyde (72 mg, 0.33 mmol), 3-(1-oxo-5-(((S)-pyrrolidin-3-yl)oxy)isoindolin-2-yl)piperidine-2,6-dione hydrochloride (100 mg, 0.27 mmol) and triethylamine (60 mg, 0.60 mmol) in dichloromethane (6 mL) was added sodium triacetoxyborohydride (191 mg, 0.90 mmol). The mixture was stirred at room temperature for 2 h under nitrogen. The resulting mixture was concentrated at room temperature. The residue was purified by silica gel column chromatography (0-10% methanol in dichloromethane) and further purified by preparative HPLC with the following conditions: Column: SunFire Prep C18 OBD Column, 19*150 mm, 5 μm; Mobile Phase A: water (0.1% formic acid), Mobile Phase B: acetonitrile; Flow rate: 60 mL/min; Gradient: 5% B to 20% B in 7 min, 20% B; Wave Length: 210/254 nm; RT1 (min): 5.73. The fractions containing desired product were collected and evaporated under reduced pressure to afford the title compound (30.1 mg, 0.057 mmol, 21% yield) as a light-yellow solid. $^1$H NMR (400 MHz, Methanol-$d_4$) δ 8.30 (m, 2H), 8.10 (m, 1H), 8.00 (m, 1H), 7.84 (d, J=2.0 Hz, 2H), 7.77-7.70 (m, 2H), 7.11-7.02 (m, 2H), 5.15-5.05 (m, 2H), 4.46-4.40 (m, 2H), 4.30-4.23 (m, 2H), 3.50-3.40 (m, 1H), 3.30 (m, 2H), 3.15-3.10 (m, 1H), 3.00-2.75 (m, 2H), 2.49 (m, 2H), 2.20-2.15 (m, 2H), 1.65 (s, 6H); MS (ESI) m/z 529.2 $[M+1]^+$.

Example S210. 3-(1-Oxo-5-(((S)-1-((2-((R)-tetrahydrofuran-3-yl)quinazolin-6-yl)methyl)pyrrolidin-3-yl)oxy)isoindolin-2-yl)piperidine-2,6-dione

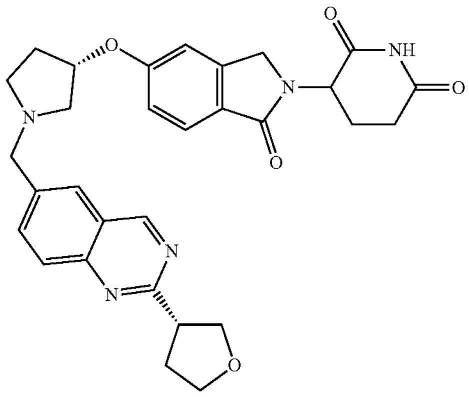 [SMILES: O=C1CCC(N2Cc3cc(O[C@H]4CCN(Cc5ccc6nc([C@H]7CCOC7)ncc6c5)C4)ccc3C2=O)C(=O)N1]

3-(1-Oxo-5-(((S)-1-((2-((R)-tetrahydrofuran-3-yl)quinazolin-6-yl)methyl)pyrrolidin-3-yl)oxy)isoindolin-2-yl)piperidine-2,6-dione. To a solution of (R)-2-(tetrahydrofuran-3-yl)quinazoline-6-carbaldehyde (55 mg, 0.24 mmol) and 3-[1-oxo-5-[(3S)-pyrrolidin-3-yl]oxy-isoindolin-2-yl]piperidine-2,6-dione (80 mg, 0.24 mmol) in dichloromethane (3 mL) and acetonitrile (2 mL) were added triethylamine (74 mg, 0.73 mmol) and sodium triacetoxyborohydride (103 mg, 0.49 mmol). The mixture was stirred for another 3 h under nitrogen. The resulting mixture was filtered and the filtrate was concentrated. The residue was purified firstly by silica gel chromatography (0 to 20% methanol in dichloromethane) and further purified by preparative HPLC with the following conditions: Column: Xselect CSH C18 OBD Column 30*150 mm 5 μm; Mobile Phase A: water (0.05% TFA), Mobile Phase B: acetonitrile; Flow rate: 60 mL/min; Gradient: 3% B to 23% B in 7 min, 23% B; Wave Length: 254/210 nm; $RT_1$ (min): 5.85. The fractions containing desired product were collected and evaporated under reduced pressure to afford the title compound (16.9 mg, 0.030 mmol, 12% yield) as a white solid. $^1$H NMR (400 MHz, DMSO-$d_6$) δ 9.63 (s, 1H), 8.30 (s, 1H), 8.13 (dd, J=8.6, 2.0 Hz, 1H), 8.06 (d, J=8.7 Hz, 1H), 7.67 (d, J=8.3 Hz, 2H), 7.20 (m, 1H), 7.08 (m, 1H), 5.36-5.20 (m, 1H), 5.07 (dd, J=13.3, 5.0 Hz, 1H), 4.71 (m, 2H), 4.40 (m, 1H), 4.28 (m, 1H), 4.19 (t, J=8.1 Hz, 1H), 4.05-3.91 (m, 2H), 3.90-3.81 (m, 2H), 2.96-2.84 (m, 2H), 2.70-2.60 (m, 3H), 2.42-2.32 (m, 5H), 2.17-1.94 (m, 2H); MS (ESI) m/z 542.3 $[M+1]^+$.

Example S211. 3-(1-Oxo-5-(((S)-1-((2-((R)-tetrahydrofuran-3-yl)quinolin-6-yl)methyl)pyrrolidi-n-3-yl)oxy)isoindolin-2-yl)piperidine-2,6-dione

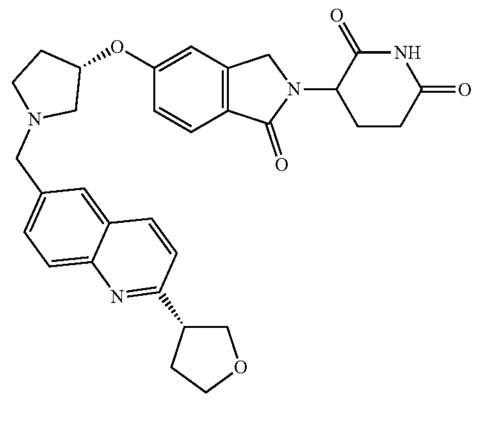 [SMILES: O=C1CCC(N2Cc3cc(O[C@H]4CCN(Cc5ccc6nc([C@H]7CCOC7)ccc6c5)C4)ccc3C2=O)C(=O)N1]

(R)-N-methoxy-N-methyltetrahydrofuran-3-carboxamide. To a solution of (R)-tetrahydrofuran-3-carboxylic acid (1.0 g, 8.61 mmol) in dichloromethane (20 mL) was added CDI (1.5 g, 9.47 mmol) in several portions at 0° C. and the reaction mixture was stirred at this temperature for 30 min under nitrogen. Then a solution of N,O-dimethylhydroxylamine hydrochloride (1.0 g, 10.33 mmol) in 5 mL dichloromethane was added into the above mixture dropwise at this temperature. The reaction mixture was warmed to room temperature and stirred for 12 h under nitrogen. The resulting mixture was purified directly by reverse phase flash (10-100% acetonitrile+0.05% TFA in water, over 20 min) to afford the title compound (1.2 g, 7.50 mmol, 87% yield) as a light-yellow oil. MS (ESI) m/z 160.1 $[M+1]^+$.

(R)-1-(Tetrahydrofuran-3-yl)ethan-1-one. To a solution of (R)-N-methoxy-N-methyltetrahydrofuran-3-carboxamide (600 mg, 3.77 mmol) in THF (10 mL) was added methyl magnesium bromide (2 M in THF, 3 mL, 6 mmol) dropwise at 0° C. and the mixture was stirred for 3 h at room temperature under nitrogen. The resulting mixture was added water and extracted with ethyl acetate. The extracts were washed with brine, dried over anhydrous sodium sulfate, filtered and concentrated to afford the title compound which was used in the next step directly without further purification. MS (ESI) m/z 115.1 $[M+1]^+$.

(R)-6-Bromo-2-(tetrahydrofuran-3-yl)quinoline. To a solution of (2-amino-5-bromophenyl)methanol (343 mg, 1.70 mmol) and (R)-1-(tetrahydrofuran-3-yl)ethan-1-one (387 mg, 3.40 mmol) in toluene (10 mL) was added lithium t-butoxide (271 mg, 3.40 mmol). The mixture was stirred for 3 h at 110° C. under nitrogen. The resulting mixture was added water and extracted with ethyl acetate. The extracts were washed with brine, dried over anhydrous sodium sulfate, filtered and concentrated. The residue was purified by silica gel chromatography (20 to 50% ethyl acetate in petroleum ether) to afford the title compound (200 mg, 0.72 mmol, 42% yield) as a light yellow oil. MS (ESI) m/z 278.0 $[M+1]^+$.

(R)-2-(Tetrahydrofuran-3-yl)-6-vinylquinoline. To a solution of (R)-6-bromo-2-(tetrahydrofuran-3-yl)quinoline (200 mg, 0.72 mmol), tributyl(vinyl)stannane (273 mg, 0.86 mmol) in 1,4-dioxane (10 mL) were added bis(triphenylphosphine)palladium(II) chloride (100 mg, 0.14 mmol) and cesium fluoride (327 mg, 2.16 mmol). The mixture was stirred at 100° C. for 3 h under nitrogen. The resulting mixture was added water and extracted with ethyl acetate. The extracts were washed with brine, dried over anhydrous sodium sulfate, filtered and concentrated. The residue was purified by silica gel chromatography (0 to 50% ethyl acetate in petroleum ether) to afford the title compound (90 mg, 0.40 mmol, 55% yield) as a yellow oil. MS (ESI) m/z 226.1 $[M+1]^+$.

(R)-2-(Tetrahydrofuran-3-yl)quinoline-6-carbaldehyde. To a solution of 2-(R)-2-(Tetrahydrofuran-3-yl)-6-vinylquinoline (90 mg, 0.40 mmol), 4-methylmorpholine N-oxide (90 mg, 0.77 mmol) and citric acid (155 mg, 0.81 mmol) in tert-butanol (1 mL) and water (1 mL) was added potassium osmate (20 mg, 0.054 mmol) under nitrogen. The mixture was stirred for 5 h at room temperature. Then the mixture was added sodium periodate (115 mg, 0.54 mmol) and the mixture was stirred for 1 h at room temperature. The resulting mixture was added water and extracted with ethyl acetate. The extracts were washed with brine, dried over anhydrous sodium sulfate, filtered and concentrated. The residue was purified by silica gel chromatography (0 to 20% ethyl acetate in petroleum ether) to afford the title compound (50 mg, 0.22 mmol, 55% yield) as a black solid. MS (ESI) m/z 228.1 $[M+1]^+$.

3-(1-Oxo-5-(((S)-1-((2-((R)-tetrahydrofuran-3-yl)quinolin-6-yl)methyl)-pyrrolidin-3-yl)oxy)isoindolin-2-yl)piperidine-2,6-dione. To a solution of 3-[1-oxo-5-[(3S)-pyrrolidin-3-yl]oxy-isoindolin-2-yl]piperidine-2,6-dionehydrochloride (85 mg, 0.23 mmol), (R)-2-(tetrahydrofuran-3-yl)quinoline-6-carbaldehyde (53 mg, 0.23 mmol) and triethylamine (47 mg, 0.47 mmol) in dichloromethane (10 mL) was added sodium triacetoxyborohydride (197 mg, 0.93 mmol) in several portions at 0° C. The mixture was stirred for 12 h at room temperature under nitrogen. The resulting mixture was purified by preparative HPLC with the following conditions: Column: Xselect CSH OBD Column 30*150 mm 5 um; Mobile Phase A: water (0.1% formic acid), Mobile Phase B: acetonitrile; Flow rate: 60 mL/min; Gradient: 3 B to 27 B in 7 min; 254/210 nm; $RT_1$ (min): 5.9. The fractions containing desired product were collected and evaporated under reduced pressure to afford the title compound (35.7 mg, 0.066 mmol, 29% yield) as an off-white solid. $^1H$ NMR (400 MHz, Methanol-$d_4$) δ 8.25 (d, J=8.0 Hz, 1H), 8.00 (d, J=8.0 Hz, 1H), 7.89 (s, 1H), 7.80 (d, J=12.0 Hz, 1H), 7.69 (d, J=12.0 Hz, 1H), 7.51 (d, J=8.0 Hz, 1H), 7.09-6.98 (m, 2H), 5.14-5.05 (m, 2H), 4.48-4.35 (m, 2H), 4.24-4.17 (m, 1H), 4.16-3.88 (m, 5H), 3.85-3.73 (m, 1H), 3.25-3.16 (m, 1H), 3.15-3.03 (m, 2H), 2.95-2.82 (m, 2H), 2.81-2.71 (m, 1H), 2.54-2.37 (m, 3H), 2.35-2.22 (m, 1H), 2.18-2.08 (m, 2H); MS (ESI) m/z 541.2 $[M+1]^+$.

Example S212. 3-(1-Oxo-5-(((S)-1-((2-(2-oxopyrrolidin-1-yl)quinolin-6-yl)methyl)pyrrolidin-3-yl)oxy)isoindolin-2-yl)piperidine-2,6-dione

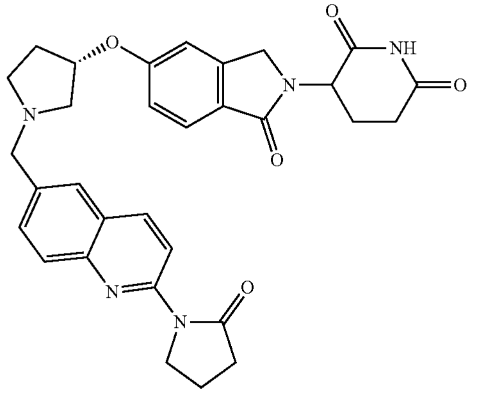 [SMILES: O=C1CCC(N2Cc3cc(O[C@H]4CCN(Cc5ccc6nc(N7CCCC7=O)ccc6c5)C4)ccc3C2=O)C(=O)N1]

2-(2-Oxopyrrolidin-1-yl)quinoline-6-carbaldehyde. A vial containing 2-pyrrolidone (0.06 mL, 0.7800 mmol), 2-chloroquinoline-6-carbaldehyde (100. mg, 0.5200 mmol), cesium carbonate (510.13 mg, 1.57 mmol), and [(4,5-bis(diphenylphosphino)-9,9-dimethylxanthene)-2-(2'-amino-1,1'-biphenyl)]palladium(II) methanesulfonate (49.49 mg, 0.0500 mmol) was placed under argon. 1,4-dioxane (2.5 mL) was added, and the mixture was stirred and purged with argon for 5 min. The mixture was then heated at 100° C. overnight. The mixture was cooled to room temperature, diluted with dichloromethane, and filtered through celite. The mixture was then concentrated under reduced pressure. The crude product was purified by column chromatography (silica, 5% to 100% ethyl acetate in hexanes), and fractions containing the desired product were combined and concentrated to afford 2-(2-oxopyrrolidin-1-yl)quinoline-6-carbaldehyde (23 mg, 0.0957 mmol, 18.3% yield). MS (ESI) m/z 241.000 [M+1]+.

3-(1-oxo-5-(((S)-1-((2-(2-oxopyrrolidin-1-yl)quinolin-6-yl)methyl)pyrrolidin-3-yl)oxy)isoindolin-2-yl)piperidine-2,6-dione. A vial containing 2-(2-oxopyrrolidin-1-yl)quinoline-6-carbaldehyde (22.3 mg, 0.100 mmol) and 3-(1-oxo-5-(((S)-pyrrolidin-3-yl)oxy)isoindolin-2-yl)piperidine-2,6-dione (30 mg, 0.0900 mmol) was charged with dichloromethane (1 mL). The mixture was stirred at room temperature for 5 min, and sodium triacetoxyborohydride (77.2 mg, 0.360 mmol) was added in a single portion. Stirring was continued overnight. The reaction mixture was diluted with methanol and directly concentrated. The residue was redissolved in methanol and purified by reverse-phase HPLC (5% to 95% acetonitrile in water, 10 mM ammonium acetate modifier). Fractions containing the desired product were concentrated under reduced pressure. The material was then redissolved in 1:1 water/acetonitrile, frozen, and lyophilized to afford 3-(1-oxo-5-(((S)-1-((2-(2-oxopyrrolidin-1-yl)quinolin-6-yl)methyl)pyrrolidin-3-yl)oxy)isoindolin-2-yl)piperidine-2,6-dione, acetic acid salt (10 mg, 0.0163 mmol, 17.9% yield). $^1$H NMR (400 MHz, DMSO-$d_6$) S=10.95 (br d, J=3.8 Hz, 1H), 8.50 (d, J=9.0 Hz, 1H), 8.32 (d, J=9.2 Hz, 1H), 7.81 (d, J=9.4 Hz, 2H), 7.69 (dd, J=1.6, 8.6 Hz, 1H), 7.60 (d, J=8.3 Hz, 1H), 7.11 (s, 1H), 7.01 (dd, J=2.1, 8.3 Hz, 1H), 5.09-4.98 (m, 2H), 4.41-4.34 (m, 1H), 4.27-4.21 (m, 1H), 4.14 (t, J=7.1 Hz, 2H), 3.84-3.75 (m, 2H), 3.01-2.81 (m, 4H), 2.42-2.30 (m, 3H), 2.14-2.06 (m, 2H), 2.02-1.92 (m, 1H), 1.88-1.79 (m, 1H); MS (ESI) m/z 554.200 [M+1]+.

Example S213. (S)-3-(1-Oxo-5-(((S)-1-((2-(tetrahydro-2H-pyran-4-yl)quinolin-6-yl)methyl)pyrrolidin-3-yl)oxy)isoindolin-2-yl)piperidine-2,6-dione

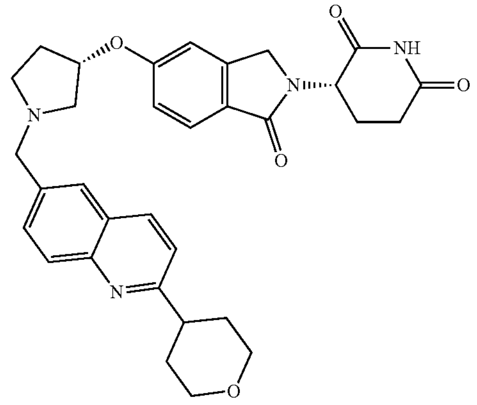 [SMILES: O=C1CC[C@H](N2Cc3cc(O[C@H]4CCN(Cc5ccc6nc(C7CCOCC7)ccc6c5)C4)ccc3C2=O)C(=O)N1]

Tert-butyl(S)-5-amino-4-(5-bromo-1-oxoisoindolin-2-yl)-5-oxopentanoate. To a stirred solution of methyl 4-bromo-2-(bromomethyl)benzoate (500 mg, 1.62 mmol) in acetonitrile (10 mL) were added N,N-diisopropylethylamine (0.42 mL, 4.86 mmol) and tert-butyl (S)-4,5-diamino-5-oxopentanoate (328 mg, 1.62 mmol). The resulting mixture was stirred at 50° C. for 18 h under nitrogen. The reaction mixture was concentrated. The residue was stirred with methyl tert-butyl ether (10 ml) at 25° C. for 1 h and filtered. The obtained solid was then stirred with water (10 ml) at 25° C. for another 1 h, filtered and dried to afford the title compound (470 mg, 1.18 mmol, 72% yield) as an off-white solid. MS (ESI) m/z 397.0 $[M+1]^+$.

Benzyl (S)-3-((2-((S)-1-amino-5-(tert-butoxy)-1,5-dioxopentan-2-yl)-1-oxoisoindolin-5-yl)oxy)pyrrolidine-1-carboxylate. To a solution of tert-butyl (S)-5-amino-4-(5-bromo-1-oxoisoindolin-2-yl)-5-oxopentanoate (800 mg, 2 mmol), benzyl(S)-3-hydroxypyrrolidine-1-carboxylate (670 mg, 3 mmol), $[Ir(dF(CH_3)ppy)_2(dtbpy)][PF_6]$ (41 mg, 2 mmol), 2,2,6,6-tetramethylpiperidine (320 mg, 2.17 mmol) in dry acetonitrile (4 mL) were added a solution of nickel(II) chloride, dimethoxyethane adduct (22 mg, 0.1 mmol) and 4,4'-di-tert-butyl-2,2'-bipyridine (27 mg, 0.1 mmol) in dry acetonitrile (2 mL). The reaction mixture was stirred for 12 h at room temperature under nitrogen with 100 W blue LED (450 nm). The resulting mixture was filtered and the filtrate was concentrated under reduced pressure. The residue was purified by silica gel chromatography (0 to 80% ethyl acetate in petroleum ether) to afford the title compound (500 mg, 0.93 mmol, 46% yield) as a yellow solid. MS (ESI) m/z 538.4 $[M+1]^+$.

Benzyl (S)-3-((2-((S)-2,6-dioxopiperidin-3-yl)-1-oxoisoindolin-5-yl)oxy)pyrrolidine-1-carboxylate. To a stirred solution of benzyl (S)-3-((2-((S)-1-amino-5-(tert-butoxy)-1,5-dioxopentan-2-yl)-1-oxoisoindolin-5-yl)oxy)pyrrolidine-1-carboxylate (310 mg, 0.57 mmol) in acetonitrile (8 mL) was added benzenesulfonic acid (273 mg, 1.72 mmol). The reaction mixture was stirred for 12 h at 60° C. under nitrogen. The resulting mixture was diluted with water, adjusted pH value to 7 with saturated sodium bicarbonate, and extracted with ethyl acetate. The extracts were washed with brine, dried over sodium sulfate, filtered and concentrated under reduced pressure. The crude product was purified by silica gel chromatography (0-5% methanol in dichloromethane) to afford the title compound (270 mg, 0.58 mmol, 101% yield) as a light-yellow solid. MS (ESI) m/z 464.1 $[M+1]^+$.

(S)-3-(1-Oxo-5-(((S)-pyrrolidin-3-yl)oxy)isoindolin-2-yl)piperidine-2,6-dione. To a solution of benzyl (S)-3-((2-((S)-2,6-dioxopiperidin-3-yl)-1-oxoisoindolin-5-yl)oxy)pyrrolidine-1-carboxylate (270 mg, 0.58 mmol) in ethanol (2 mL) and dichloromethane (6 mL) were added 10% Pd/C (130 mg) and acetic acid (0.03 mL, 0.58 mmol) under nitrogen. Then the reaction mixture was stirred for 3 h at room temperature under hydrogen. The resulting reaction mixture was filtered and concentrated to afford the title compound (210 mg, 0.54 mmol, 92% yield) as a light-yellow solid which was used in the next step directly without further purification. MS (ESI) m/z 330.1 $[M+1]^+$.

(S)-3-(1-Oxo-5-(((S)-1-((2-(tetrahydro-2H-pyran-4-yl)quinolin-6-yl)methyl)pyrrolidin-3-yl)oxy)isoindolin-2-yl)piperidine-2,6-dione. To a stirred solution of (S)-3-(1-oxo-5-(((S)-pyrrolidin-3-yl)oxy)isoindolin-2-yl)piperidine-2,6-dione (acetic acid salt, 200 mg, 0.51 mmol), 2-(tetrahydro-2H-pyran-4-yl)quinoline-6-carbaldehyde (124 mg, 0.51 mmol) and triethylamine (0.14 mL, 1.02 mmol) in dichloromethane (5 mL) was added sodium triacetoxyborohydride (435 mg, 2.05 mmol) at 0° C. under nitrogen. The reaction mixture was stirred at room temperature for 2 h under nitrogen. The resulting solution was concentrated at 25° C. under reduced pressure. The crude was purified by silica gel column chromatography (0-10% methanol in dichloromethane) and further purified by preparative chiral HPLC with the following conditions: Column: CHIRALPAK IF, 5*25 cm, 5 μm; Mobile Phase A: HEX-AR, Mobile Phase B: isopropyl alcohol:dichloromethane=1:1; Flow rate: 1 mL/min; Gradient: 60% B to 60% B in 15 min; Wave Length: 220 nm; RT1 (min): 16; RT2 (min): 24; Injection Volume: 1.5 mL. The fractions containing desired product were collected and evaporated under reduced pressure to afford the title compound (145 mg, 0.26 mmol, 50% yield) as a light-yellow solid. $^1H$ NMR (400 MHz, Methanol-$d_4$) δ 8.45 (s, 1H), 8.24-8.11 (m, 2H), 7.95 (dd, J=8.7, 2.1 Hz, 1H), 7.74-7.65 (m, 2H), 7.21 (d, J=2.2 Hz, 1H), 7.10 (dd, J=8.4, 2.3 Hz, 1H), 5.35 (s, 1H), 5.14 (dd, J=13.3, 5.2 Hz, 1H), 4.70 (s, 2H), 4.50-4.44 (m, 2H), 4.17-4.08 (m, 2H), 3.98-3.50 (m, 6H), 3.24-3.18 (m, 1H), 2.92-2.86 (m, 1H), 2.84-2.30 (m, 4H), 2.23-2.13 (m, 1H), 2.05-2.00 (m, 2H), 1.98-1.89 (m, 2H). MS (ESI) m/z 555.2 $[M+1]^+$.

Example S214. (S)-3-(5-(((S)-1-((2-Morpholinoquinolin-6-yl)methyl)pyrrolidin-3-yl)oxy)-1-oxo-isoindolin-2-yl)piperidine-2,6-dione

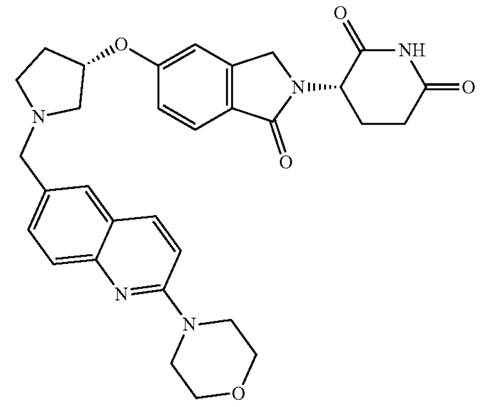

Tert-butyl (S)-5-amino-4-(5-(((S)-1-((2-morpholinoquinolin-6-yl)methyl)pyrrolidin-3-yl)oxy)-1-oxoisoindolin-2-yl)-5-oxopentanoate 2,2,2-trifluoroacetic acid. To a solution of 2-morpholinoquinoline-6-carbaldehyde (300 mg, 1.24 mmol), tert-butyl (S)-5-amino-5-oxo-4-(1-oxo-5-(((S)-pyrrolidin-3-yl)oxy)isoindolin-2-yl)pentanoate acetic acid (442 mg, 0.95 mmol) and acetic acid (107 mg, 1.78 mmol) in THF (8 mL) was stirred for 1 h at room temperature. The above mixture was added sodium triacetoxyborohydride (690 mg, 3.25 mmol) at 0° C. The mixture was stirred for 4 h at room temperature under nitrogen. The resulting mixture was concentrated. The residue was purified by reverse phase flash (10-100% acetonitrile+0.05% TFA in water, over 25 min) to afford the title compound (500 mg, 0.69 mmol, 63% yield) as a light-yellow solid. MS (ESI) m/z 630.4 $[M+1]^+$.

(S)-3-(5-(((S)-1-((2-Morpholinoquinolin-6-yl)methyl)pyrrolidin-3-yl)oxy)-1-oxoisoindolin-2-yl)piperidine-2,6-dione. To a solution of tert-butyl (S)-5-amino-4-(5-(((S)-1-((2-morpholinoquinolin-6-yl)methyl)pyrrolidin-3-yl)oxy)-1-oxoisoindolin-2-yl)-5-oxopentanoate; 2,2,2-trifluoroacetic acid (1200 mg, 1.61 mmol) and benzenesulfonic acid (765 mg, 4.84 mmol) in acetonitrile (20 mL) was stirred at 60° C. for 12 h under nitrogen. The resulting solution was diluted with water, added buffer solution (potassium phosphate dibasic and potassium phosphate monobasic solution) to pH~6 at 0° C. carefully. The resulting solution was filtered and the filtrate was purified firstly by reverse phase flash (10-100% acetonitrile+0.1% formic acid in water, over 25 min) and purified further by preparative HPLC with the following conditions: Column: Sunfire prep C18 Column, 30*150 mm, 5 μm; Mobile Phase A: water (0.1% formic acid), Mobile Phase B: acetonitrile; Flow rate: 60 mL/min; Gradient: 2% B to 22% B in 7 min, 22% B; Wave Length: 254/220 nm; RT1 (min): 6.75. The pure fractions were evaporated to afford the title compound (168.4 mg, 0.30 mmol, 19% yield) as a light-yellow solid. $^1H$ NMR (400 MHz, DMSO-$d_6$) δ 10.96 (s, 1H), 8.20 (s, 1H), 8.05 (d, J=9.2 Hz, 1H), 7.66-7.57 (m, 2H), 7.57-7.48 (m, 2H), 7.22 (d, J=9.2 Hz, 1H), 7.11 (d, J=2.2 Hz, 1H), 7.00-6.96 (m, 1H), 5.05-5.01 (m, 1H), 5.00 (m, 1H), 4.37 (d, J=17.2 Hz, 1H), 4.24 (d, J=17.2 Hz, 1H), 3.72-3.64 (m, 6H), 3.63-3.56 (m, 4H), 2.91-2.86 (m, 3H), 2.72-2.68 (m, 3H), 2.40 (m, 2H), 2.02-1.93 (m, 1H), 1.82 (m, 1H); MS (ESI) m/z 556.3 $[M+1]^+$.

Example S215. 3-(5-(((S)-1-((2-(4-hydroxytetrahydro-2H-pyran-4-yl)quinolin-6-yl)methyl)pyrrolidin-3-yl)oxy)-1-oxoisoindolin-2-yl)piperidine-2,6-dione

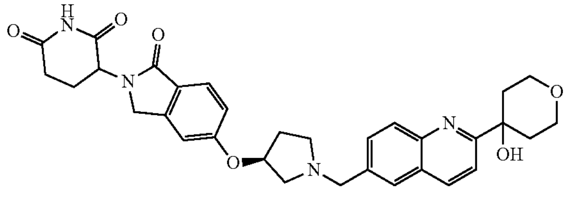 [SMILES: O=C1CCC(N2Cc3cc(O[C@H]4CCN(Cc5ccc6nc(C7(O)CCOCC7)ccc6c5)C4)ccc3C2=O)C(=O)N1]

2-(3,6-dihydro-2H-pyran-4-yl)quinoline-6-carbaldehyde. A vial containing 2-chloroquinoline-6-carbaldehyde (250 mg, 1.305 mmol), $Pd(dppf)Cl_2{\cdot}DCM$ (53.3 mg, 0.065 mmol), 2-(3,6-dihydro-2H-pyran-4-yl)-4,4,5,5-tetramethyl-1,3,2-dioxaborolane (548 mg, 2.61 mmol), and cesium carbonate (1275 mg, 3.91 mmol) was charged with 1,4-dioxane (4 mL) under argon. Degassed water (1 mL) was added, and the mixture was heated to 80° C. After 4 hours the mixture was cooled to room temperature and diluted with water and ethyl acetate. The layers were separated, and the aqueous layer was extracted with additional ethyl acetate. The combined organic layers were dried over magnesium sulfate and concentrated. The crude product was purified by column chromatography (silica, 5% to 100% ethyl acetate in hexanes). Fractions containing the desired product were concentrated under reduced pressure to afford 2-(3,6-dihydro-2H-pyran-4-yl)quinoline-6-carbaldehyde (241.2 mg, 1.008 mmol, 77% yield). MS (ESI) m/z 240.000 $[M+1]^+$.

2-(4-hydroxytetrahydro-2H-pyran-4-yl)quinoline-6-carbaldehyde. A vial containing 2-(3,6-dihydro-2H-pyran-4-yl)quinoline-6-carbaldehyde (241.2 mg, 1.008 mmol) and Mn(dpm)3 (61.0 mg, 0.101 mmol) was charged with dichloromethane (2 mL) and 2-propanol (8 mL). The mixture was stirred and cooled in an ice/water bath to 0° C. under air. Phenylsilane (0.199 mL, 1.613 mmol) was then added dropwise. After 1 hr, additional Mn(dpm)3 (61.0 mg, 0.101 mmol) and phenylsilane (0.199 mL, 1.613 mmol) were added. After 3 hours, additional Mn(dpm)3 (61.0 mg, 0.101 mmol) and phenylsilane (0.199 mL, 1.613 mmol) were added. After 4 hours, the reaction mixture was directly loaded onto silica gel and purified (0% to 10% MeOH in dichloromethane). Fractions containing the desired product were concentrated under reduced pressure. The material was repurified by column chromatography (silica, 5% to 100% ethyl acetate in hexanes). Fractions containing the desired product were concentrated under reduced pressure to afford 2-(4-hydroxytetrahydro-2H-pyran-4-yl)quinoline-6-carbaldehyde (66 mg, 0.257 mmol, 25.4% yield). The material was used without further purification. MS (ESI) m/z 258.200 $[M+1]^+$.

3-(5-(((S)-1-((2-(4-hydroxytetrahydro-2H-pyran-4-yl)quinolin-6-yl)methyl)pyrrolidin-3-yl)oxy)-1-oxoisoindolin-2-yl)piperidine-2,6-dione. A vial containing 2-(4-hydroxytetrahydro-2H-pyran-4-yl)quinoline-6-carbaldehyde (63.3 mg, 0.246 mmol) and 3-(1-oxo-5-(((S)-pyrrolidin-3-yl)oxy)isoindolin-2-yl)piperidine-2,6-dione, HCl (50 mg, 0.137 mmol) was charged with N,N-diisopropylethylamine (0.048 mL, 0.273 mmol), acetic acid (0.039 mL, 0.683 mmol), and acetonitrile (2 mL). The mixture was stirred at room temperature for 15 min, and sodium triacetoxyborohydride (57.9 mg, 0.273 mmol) was then added. After stirring overnight, the reaction mixture was diluted with water/MeOH, filtered, and purified by reverse-phase HPLC (5% to 95% acetonitrile in water, 10 mM ammonium acetate modifier). Fractions containing the desired product were concentrated under reduced pressure then frozen and lyophilized. The obtained material was then redissolved in 1:1 water/MeCN, frozen, and lyophilized to afford 3-(5-(((S)-1-((2-(4-hydroxytetrahydro-2H-pyran-4-yl)quinolin-6-yl)methyl)pyrrolidin-3-yl)oxy)-1-oxoisoindolin-2-yl)piperidine-2,6-dione, acetic acid salt (11.4 mg, 0.019 mmol, 14.11% yield). 1H NMR (400 MHz, DMSO-$d_6$) S=10.95 (s, 1H), 8.33 (d, J=8.7 Hz, 1H), 7.93 (d, J=8.6 Hz, 1H), 7.86-7.82 (m, 2H), 7.72 (dd, J=1.7, 8.6 Hz, 1H), 7.59 (d, J=8.4 Hz, 1H), 7.10 (s, 1H), 7.00 (dd, J=2.1, 8.5 Hz, 1H), 5.47 (s, 1H), 5.08-4.97 (m, 2H), 4.40-4.32 (m, 1H), 4.27-4.19 (m, 1H), 3.85-3.74 (m, 7H), 2.99-2.85 (m, 2H), 2.80-2.74 (m, 1H), 2.72-2.66 (m, 1H), 2.63-2.53 (m, 1H), 2.37-2.23 (m, 4H), 2.01-1.92 (m, 1H), 1.88-1.79 (m, 1H), 1.58 (br d, J=12.6 Hz, 2H); MS (ESI) m/z 571.200 $[M+1]^+$.

Example S216. 3-(1-oxo-5-(((S)-1-((2-((tetrahydro-2H-pyran-4-yl)oxy)quinolin-6-yl)methyl)pyrrolidin-3-yl)oxy)isoindolin-2-yl)piperidine-2,6-dione

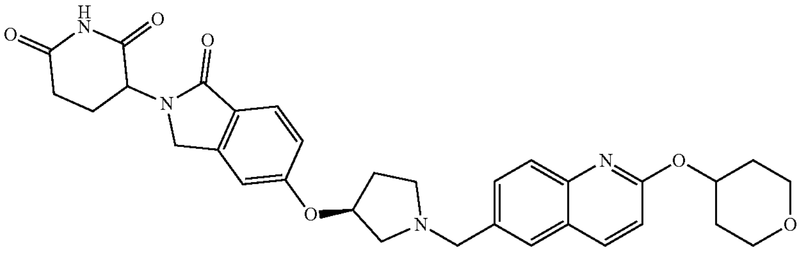 [SMILES: O=C1CCC(N2Cc3cc(O[C@H]4CCN(Cc5ccc6nc(OC7CCOCC7)ccc6c5)C4)ccc3C2=O)C(=O)N1]

Methyl 2-((tetrahydro-2H-pyran-4-yl)oxy)quinoline-6-carboxylate. A vial containing methyl 2-chloroquinoline-6-carboxylate (150 mg, 0.677 mmol), tetrahydro-2H-pyran-4-ol (0.077 mL, 0.812 mmol), cesium carbonate (441 mg, 1.354 mmol), and Josiphos SL-J009-1 Pd G3 (31.8 mg, 0.034 mmol) was purged with argon. Toluene (3 mL) was added, and the mixture was heated to 90° C. overnight. The mixture was cooled to room temperature and diluted with ethyl acetate. The mixture was then filtered through Celite and concentrated under reduced pressure. The crude product was purified by column chromatography (5% to 100% ethyl acetate in hexanes). Fractions containing the desired product were concentrated under reduced pressure to afford methyl 2-((tetrahydro-2H-pyran-4-yl)oxy)quinoline-6-carboxylate (139.5 mg, 0.486 mmol, 71.7% yield). MS (ESI) m/z 288.200 $[M+1]^+$.

(2-((Tetrahydro-2H-pyran-4-yl)oxy)quinolin-6-yl)methanol. A vial containing methyl 2-((tetrahydro-2H-pyran-4-yl)oxy)quinoline-6-carboxylate (139.5 mg, 0.486 mmol) was charged with tetrahydrofuran (3 mL) and lithium borohydride (21.15 mg, 0.971 mmol). The mixture was stirred at room temperature overnight. Some starting material remained, so additional lithium borohydride (21.15 mg, 0.971 mmol) was added, and the mixture was stirred. Upon completion, the mixture was quenched with saturated aqueous ammonium chloride and extracted 3× with dichloromethane. The combined organic layers were dried over magnesium sulfate and concentrated to afford (2-((tetrahydro-2H-pyran-4-yl)oxy)quinoline-6-yl)methanol (111.6 mg, 0.430 mmol, 89% yield). MS (ESI) m/z 260.200 $[M+1]^+$.

2-((Tetrahydro-2H-pyran-4-yl)oxy)quinoline-6-carbaldehyde. A vial containing (2-((tetrahydro-2H-pyran-4-yl)oxy)quinolin-6-yl)methanol (111.6 mg, 0.430 mmol) and dichloromethane (5 mL) was charged with Dess-Martin periodinane (365 mg, 0.861 mmol), and the mixture was stirred at room temperature overnight. The mixture was quenched with 10% aqueous potassium carbonate and saturated aqueous sodium thiosulfate and stirred for 30 min. The mixture was then diluted with ethyl acetate. The layers were separated, and the organic layer was dried over magnesium sulfate and concentrated to afford 2-((tetrahydro-2H-pyran-4-yl)oxy)quinoline-6-carbaldehyde in quantitative yield. The material was used without further purification. MS (ESI) m/z 258.200 $[M+1]^+$.

3-(1-Oxo-5-(((S)-1-((2-((tetrahydro-2H-pyran-4-yl)oxy)quinolin-6-yl)methyl)pyrrolidin-3-yl)oxy)isoindolin-2-yl)piperidine-2,6-dione. A vial containing 2-((tetrahydro-2H-pyran-4-yl)oxy)quinoline-6-carbaldehyde (114 mg, 0.444 mmol) and 3-(1-oxo-5-(((S)-pyrrolidin-3-yl)oxy)isoindolin-2-yl)piperidine-2,6-dione, HCl (65 mg, 0.178 mmol) was charged with acetic acid (0.05 mL) and dimethyl sulfoxide (1 mL). The mixture was stirred at room temperature, and a solution of decaborane (10.86 mg, 0.089 mmol) in dimethyl sulfoxide (1 mL) was added. The mixture was stirred at room temperature overnight. The mixture was diluted with MeOH, filtered, and purified by HPLC (5% to 95% acetonitrile in water, 10 mM ammonium acetate modifier). Fractions containing the desired product were concentrated by Genevac. The obtained material was redissolved in 1:1 water/acetonitrile, frozen, and lyophilized. The material was redissolved in 1:1 water/acetonitrile, frozen, and lyophilized to afford 3-(1-oxo-5-(((S)-1-((2-((tetrahydro-2H-pyran-4-yl)oxy)quinolin-6-yl)methyl)pyrrolidin-3-yl)oxy)isoindolin-2-yl)piperidine-2,6-dione (35.5 mg, 0.062 mmol, 35% yield). $^1H$ NMR (400 MHz, DMSO-$d_6$) δ=10.95 (s, 1H), 8.20 (dd, J=1.5, 8.9 Hz, 1H), 7.78 (s, 1H), 7.71-7.68 (m, 1H), 7.64-7.55 (m, 2H), 7.10 (s, 1H), 7.02-6.95 (m, 2H), 5.44-5.35 (m, 1H), 5.05 (dd, J=5.0, 13.3 Hz, 1H), 5.02-4.95 (m, 1H), 4.41-4.32 (m, 1H), 4.27-4.20 (m, 1H), 3.89 (td, J=4.3, 11.7 Hz, 2H), 3.80-3.69 (m, 2H), 3.58-3.51 (m, 2H), 2.97-2.84 (m, 2H), 2.79-2.65 (m, 2H), 2.58 (br d, J=16.6 Hz, 1H), 2.38-2.31 (m, 2H), 2.12-2.04 (m, 2H), 1.96 (tdd, J=2.6, 5.0, 9.8 Hz, 1H), 1.90-1.80 (m, 1H), 1.73-1.62 (m, 2H). MS (ESI) m/z 571.200 $[M+1]^+$.

BIOLOGICAL EXAMPLES

Example B1. WEE1-ePL Degradation Assay

To generate LentiX-WEE1-ePL-GSPT1-ND cells for the WEE1 degradation assay, LentiX-HEK293T (Invitrogen) were transduced by lentivirus with a C-terminal ePL-tagged (DiscoverX, Fremont, CA) full-length WEE1 expression construct. A separate lentiviral construct was introduced to over-express a mutated form of GSPT1, termed GSPT1-GN, which contains a G576N mutation and is truncated in the first 158 amino acids which does not bind Cereblon. Cells were selected and maintained in complete DMEM media (DMEM, 10% Heat Inactivated FBS, 400 μg/mL Geneticin, and 1 μg/mL puromycin at 37 C and 5% $CO_2$). Cells were passaged every 3-4 days by reseeding $1\times10^6$ cells in a T150 flask.

Cells were dispensed into 384-well white plates (Corning #3570, NY) that were pre-spotted with compounds using an acoustic dispenser (Echo acoustic transfer system, Beckman Coulter Life Sciences, Carlsbad, CA) as a 10-point dose-response curve with a 3-fold dilution starting at either 1 uM or 10 uM and including a DMSO control. Twenty-five microliters of media containing 2500 cells for LentiX-oeWEE1-ePL was dispensed per well. Assay plates were incubated at 37° C. with 5% $CO_2$ for four hours (WEE1) After incubation, 25 μL of the InCELL Hunter™ Detection Reagent Working Solution (DiscoverX, Fremont, CA) was added to each well and incubated at room temperature for 30 minutes protected from light. After 30 minutes, luminescence was read on a PHERAstar luminometer (Cary, NC).

To determine the half-maximal effective concentration (EC50) values for WEE1-ePL degradation, a four parameter logistic model was used: (Sigmoidal Dose-Response Model) (FIT=(A+((B−A)/1+((C/x)^D)))) where C is the inflection point (EC50), D is the Hill slope, and A and B are the low and high limits of the fit respectively). The lower limit of the fit (value A) is referred to as Ymin. The Ymin was constrained by using a luciferase inhibitor at a concentration of 20 μM to fully inhibit the luciferase signal and was used as the Ymin=0 constraint value within each assay. The maximum limit constraint, Ymax, is similarly derived using DMSO control. The curves were processed and evaluated using Activity Base (IDBS, Alameda, CA). The results are shown in Table 2 below.

Example B2. MKN45 Cell Proliferation Assay

MKN45 cells were obtained from Celgene internal cell banks and cultured in RPMI complete media (RPMI-1640, 1× Penicillin/Streptomycin, 1× glutamine, 1× Sodium Pyruvate, Non-essential Amino Acids, 10% Fetal Bovine serum, all component from Thermo-Fisher). Compounds were dispensed into 384-well plates using an HP DE300 compound printer in triplicate with 8 compounds on each plate. For each compound, a 10-point dose response was printed at half-log dilutions starting at either 1 uM or 10 uM. The DMSO concentration was kept constant for a final assay concentration of 0.1% per well assuming 50 ul final media volume. Compound plates were sealed and frozen at −20 C until use.

For each assay batch, compound plates were thawed and allowed to reach room temperature, and cells were seeded at 400 cells per well in 50 ul complete RPMI media. After 120 hours of incubation at 37 C and 5% CO2, cells were lysed by addition of 25 μL of Cell-Titer-Glo Reagent (Promega Corporation, Madison, WI), as per manufacturer's instructions, protected from light, shaken for 45 minutes, and total luminescence read by a Perkin Elmer Envision plate reader. Total luminescence signal is linearly correlated with cell number remaining in the well.

Luminescence data was processed per plate by subtracting reagent-only "blank" well luminescence from all measured values and calculating a percent of DMSO control value for each treatment well. Then, to determine the half-maximal effective concentration (EC50) values for cell growth inhibition, a four parameter logistic model was fit to the data for each DMSO-normalized compound: Sigmoidal Dose-Response Model: (FIT=(A+((B−A)/1+((C/x)^D)))) where C is the inflection point (EC50), D is the Hill slope, and A and B are the low and high limits of the fit respectively. The lower limit of the fit (value A) is referred to as Ymin-calculated. The minimal percent of DMSO control that is observed in the concentrations tested for each compound is labeled as "Ymin-obs", and was recorded and reported in the tables. Sigmoidal fit curves were processed and evaluated using Activity Base (IDBS, Alameda, CA). The results are shown in Table 2 below.

TABLE 2

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 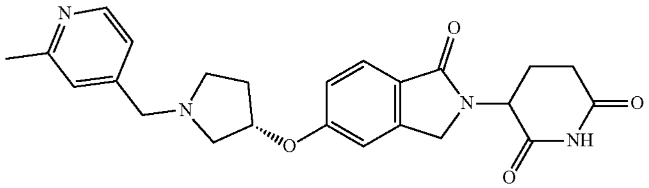 [SMILES: Cc1cc(CN2CC[C@H](Oc3ccc4c(c3)CN(C3CCC(=O)NC3=O)C4=O)C2)ccn1] 3-(5-{[(3S)-1-[(2-methylpyridin-4-yl)methyl]pyrrolidin-3-yl]oxy}-1-oxo-2,3-dihydro-1H-isoindol-2-yl)piperidine-2,6-dione | 0.6633755 | 37.845 | 0.039503 | 39.18 |
| 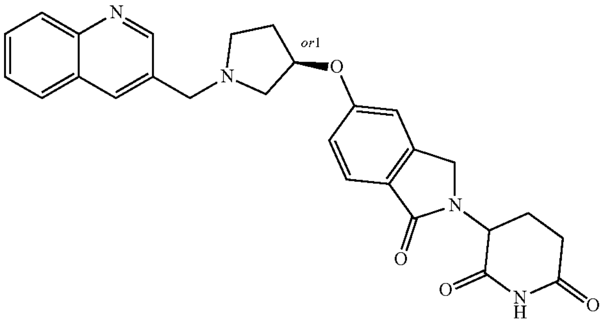 [SMILES: O=C1CCC(N2Cc3cc(O[C@@H]4CCN(Cc5cnc6ccccc6c5)C4)ccc3C2=O)C(=O)N1] rel-3-(1-oxo-5-{[(3R)-1-[(quinolin-3-yl)methyl]pyrrolidin-3-yl]oxy}-2,3-dihydro-1H-isoindol-2-yl)piperidine-2,6-dione | 0.057046645 | 11.38741935 | 0.006569615 | 26.81820513 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 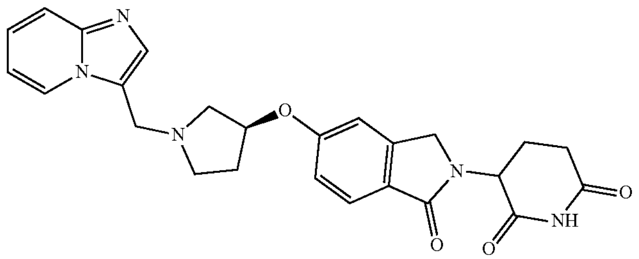 [SMILES: O=C1CCC(N2Cc3cc(O[C@H]4CCN(Cc5cnc6ccccn56)C4)ccc3C2=O)C(=O)N1] 3-(5-{[(3S)-1-({imidazo[1,2-a]pyridin-3-yl}methyl)pyrrolidin-3-yl]oxy}-1-oxo-2,3-dihydro-1H-isoindol-2-yl)piperidine-2,6-dione | 0.933063 | 21.75 | 0.149572 | 33.52 |
| 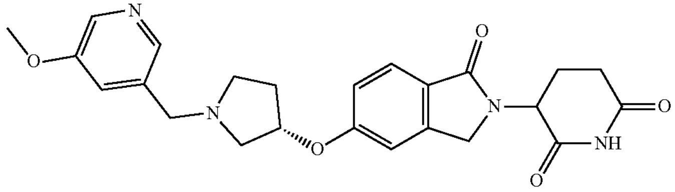 [SMILES: COc1cncc(CN2CC[C@H](Oc3ccc4c(c3)CN(C3CCC(=O)NC3=O)C4=O)C2)c1] 3-(5-{[(3S)-1-[(5-methoxypyridin-3-yl)methyl]pyrrolidin-3-yl]oxy}-1-oxo-2,3-dihydro-1H-isoindol-2-yl)piperidine-2,6-dione | 3.320361 | 48.12 | 0.061426 | 37.55 |
| 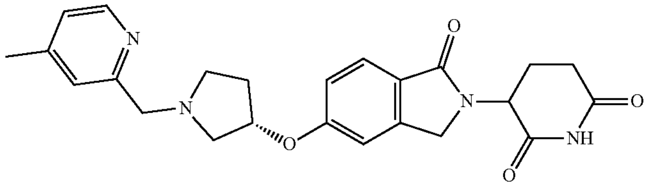 [SMILES: Cc1ccnc(CN2CC[C@H](Oc3ccc4c(c3)CN(C3CCC(=O)NC3=O)C4=O)C2)c1] 3-(5-{[(3S)-1-[(4-methylpyridin-2-yl)methyl]pyrrolidin-3-yl]oxy}-1-oxo-2,3-dihydro-1H-isoindol-2-yl)piperidine-2,6-dione | 1.327792 | 42.67 | 0.065356 | 38.55 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 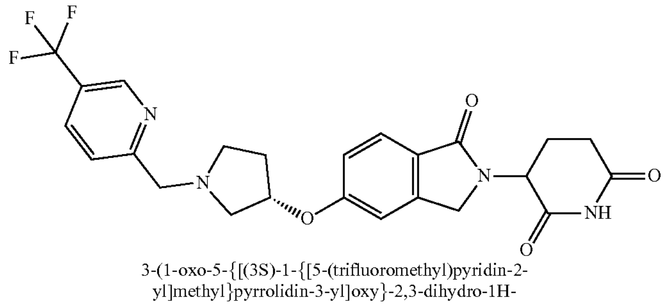 3-(1-oxo-5-{[(3S)-1-{[5-(trifluoromethyl)pyridin-2-yl]methyl}pyrrolidin-3-yl]oxy}-2,3-dihydro-1H-isoindol-2-yl)piperidine-2,6-dione | 0.363226 | 65.6 | 0.0526 | 53.66 |
| 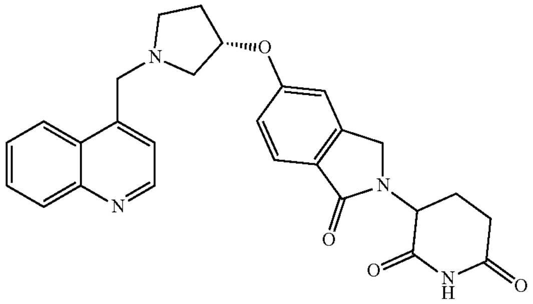 [SMILES: O=C1CCC(N2Cc3cc(O[C@H]4CCN(Cc5ccnc6ccccc56)C4)ccc3C2=O)C(=O)N1] 3-(1-oxo-5-{[(3S)-1-[(quinolin-4-yl)methyl]pyrrolidin-3-yl]oxy}-2,3-dihydro-1H-isoindol-2-yl)piperidine-2,6-dione | 0.056826 | 13.21 | 0.023417 | 33.025 |
| 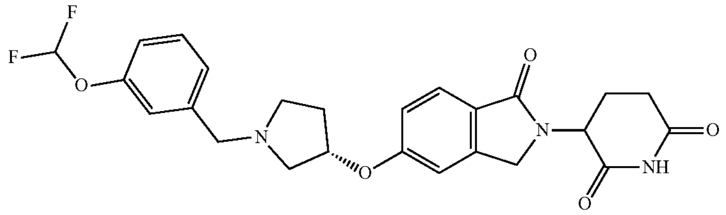 [SMILES: O=C1CCC(N2Cc3cc(O[C@H]4CCN(Cc5cccc(OC(F)F)c5)C4)ccc3C2=O)C(=O)N1] 3-(5-{[(3S)-1-{[3- | | | 0.196412 | 75.96 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| (difluoromethoxy)phenyl]methyl}pyrrolidin-3-yl]oxy}-1-oxo-2,3-dihydro-1H-isoindol-2-yl)piperidine-2,6-dione | | | | |
| 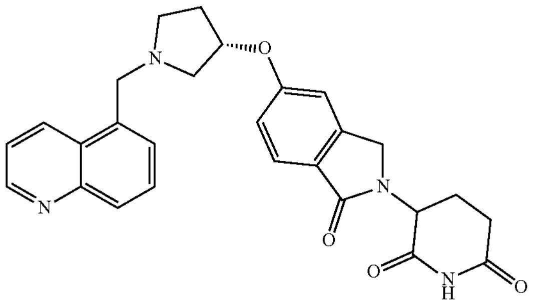 [SMILES: O=C1CCC(N2Cc3cc(O[C@H]4CCN(Cc5cccc6ncccc56)C4)ccc3C2=O)C(=O)N1] 3-(1-oxo-5-{[(3S)-1-[(quinolin-5-yl)methyl]pyrrolidin-3-yl]oxy}-2,3-dihydro-1H-isoindol-2-yl)piperidine-2,6-dione | 0.104477 | 19 | 0.014628 | 32.69 |
| 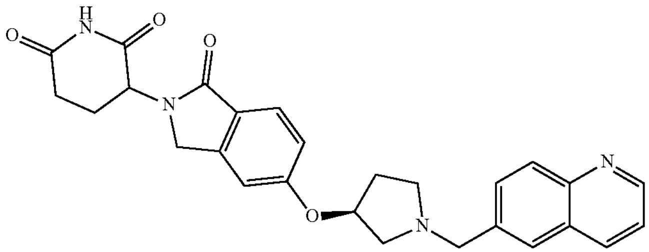 [SMILES: O=C1CCC(N2Cc3cc(O[C@H]4CCN(Cc5ccc6ncccc6c5)C4)ccc3C2=O)C(=O)N1] 3-(1-oxo-5-{[(3S)-1-[(quinolin-6-yl)methyl]pyrrolidin-3-yl]oxy}-2,3-dihydro-1H-isoindol-2-yl)piperidine-2,6-dione | 0.030351345 | 14.86640181 | 0.003450571 | 28.66489529 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 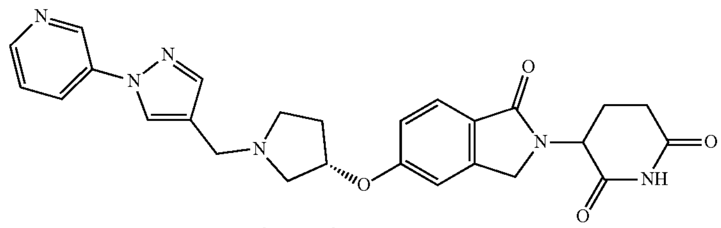 [SMILES: O=C1CCC(N2Cc3cc(O[C@H]4CCN(Cc5cnn(-c6cccnc6)c5)C4)ccc3C2=O)C(=O)N1] 3-(1-oxo-5-{[(3S)-1-{[1-(pyridin-3-yl)-1H-pyrazol-4-yl]methyl}pyrrolidin-3-yl]oxy}-2,3-dihydro-1H-isoindol-2-yl)piperidine-2,6-dione | 0.269396 | 11.53 | 0.0598245 | 31.735 |
| 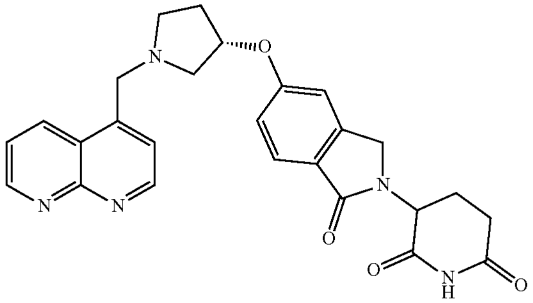 [SMILES: O=C1CCC(N2Cc3cc(O[C@H]4CCN(Cc5ccnc6ncccc56)C4)ccc3C2=O)C(=O)N1] 3-(5-{[(3S)-1-[(1,8-naphthyridin-4-yl)methyl]pyrrolidin-3-yl]oxy}-1-oxo-2,3-dihydro-1H-isoindol-2-yl)piperidine-2,6-dione | | | 10 | 96.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| --- | --- | --- | --- | --- |
| 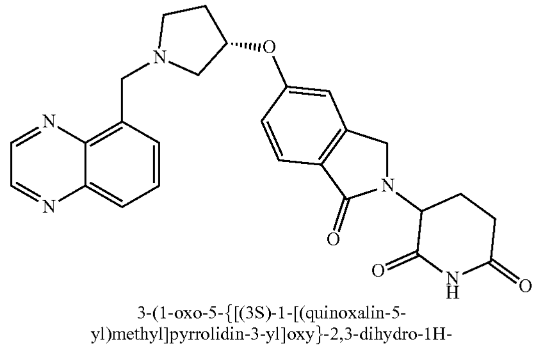 3-(1-oxo-5-{[(3S)-1-[(quinoxalin-5-yl)methyl]pyrrolidin-3-yl]oxy}-2,3-dihydro-1H-isoindol-2-yl)piperidine-2,6-dione | | | 0.173918 | 53.34 |
| 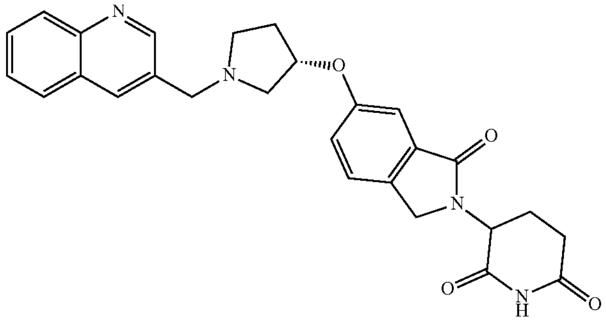 [SMILES: O=C1CCC(N2Cc3ccc(O[C@H]4CCN(Cc5cnc6ccccc6c5)C4)cc3C2=O)C(=O)N1] 3-(1-oxo-6-{[(3S)-1-[(quinolin-3-yl)methyl]pyrrolidin-3-yl]oxy}-2,3-dihydro-1H-isoindol-2-yl)piperidine-2,6-dione | 0.04238 | 12.43 | 0.008740333 | 27.97666667 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 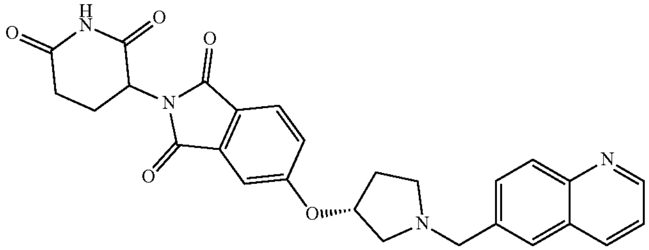 [SMILES: O=C1CCC(N2C(=O)c3ccc(O[C@@H]4CCN(Cc5ccc6ncccc6c5)C4)cc3C2=O)C(=O)N1] 2-(2,6-dioxopiperidin-3-yl)-5-{[(3R)-1-[(quinolin-6-yl)methyl]pyrrolidin-3-yl]oxy}-2,3-dihydro-1H-isoindole-1,3-dione | | | 10 | 83.71 |
| 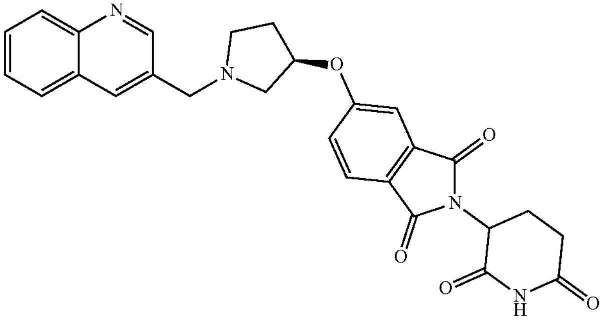 [SMILES: O=C1CCC(N2C(=O)c3ccc(O[C@@H]4CCN(Cc5cnc6ccccc6c5)C4)cc3C2=O)C(=O)N1] 2-(2,6-dioxopiperidin-3-yl)-5-{[(3R)-1-[(quinolin-3-yl)methyl]pyrrolidin-3-yl]oxy}-2,3-dihydro-1H-isoindole-1,3-dione | | | 10 | 86.31 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 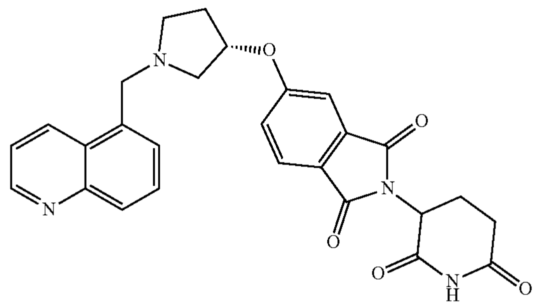 [SMILES: O=C1CCC(N2C(=O)c3ccc(O[C@H]4CCN(Cc5cccc6ncccc56)C4)cc3C2=O)C(=O)N1] 2-(2,6-dioxopiperidin-3-yl)-5-{[(3S)-1-[(quinolin-5-yl)methyl]pyrrolidin-3-yl]oxy}-2,3-dihydro-1H-isoindole-1,3-dione | 2.230758 | 44.93 | 0.079238 | 30.52 |
| 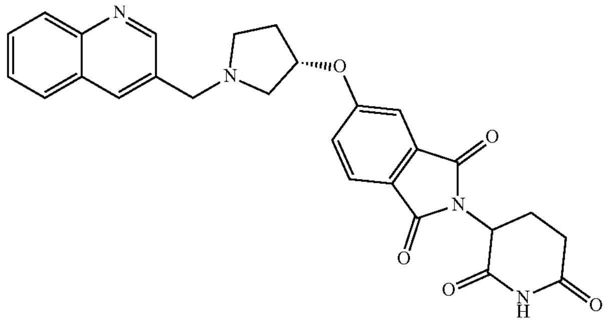 [SMILES: O=C1CCC(N2C(=O)c3ccc(O[C@H]4CCN(Cc5cnc6ccccc6c5)C4)cc3C2=O)C(=O)N1] 2-(2,6-dioxopiperidin-3-yl)-5-{[(3S)-1-[(quinolin-3-yl)methyl]pyrrolidin-3-yl]oxy}-2,3-dihydro-1H-isoindole-1,3-dione | 0.62083 | 15.39 | 0.032925 | 30.205 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 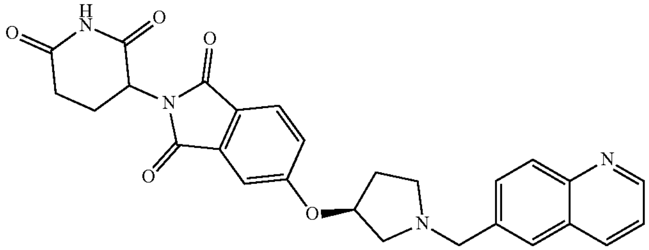 [SMILES: O=C1CCC(N2C(=O)c3ccc(O[C@H]4CCN(Cc5ccc6ncccc6c5)C4)cc3C2=O)C(=O)N1] 2-(2,6-dioxopiperidin-3-yl)-5-{[(3S)-1-[(quinolin-6-yl)methyl]pyrrolidin-3-yl]oxy}-2,3-dihydro-1H-isoindole-1,3-dione | 1.026554 | 21.24 | 0.0434075 | 29.65 |
| 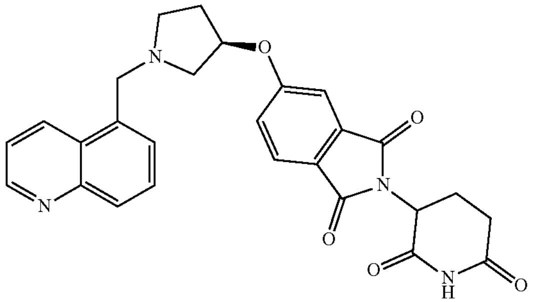 [SMILES: O=C1CCC(N2C(=O)c3ccc(O[C@@H]4CCN(Cc5cccc6ncccc56)C4)cc3C2=O)C(=O)N1] 2-(2,6-dioxopiperidin-3-yl)-5-{[(3R)-1-[(quinolin-5-yl)methyl]pyrrolidin-3-yl]oxy}-2,3-dihydro-1H-isoindole-1,3-dione | | | 10 | 89.045 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 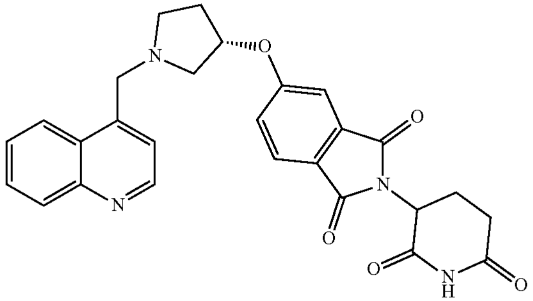 [SMILES: O=C1CCC(N2C(=O)c3ccc(O[C@H]4CCN(Cc5ccnc6ccccc56)C4)cc3C2=O)C(=O)N1] 2-(2,6-dioxopiperidin-3-yl)-5-{[(3S)-1-[(quinolin-4-yl)methyl]pyrrolidin-3-yl]oxy}-2,3-dihydro-1H-isoindole-1,3-dione | 2.506428 | 48.18 | 1.2262045 | 38.05 |
| 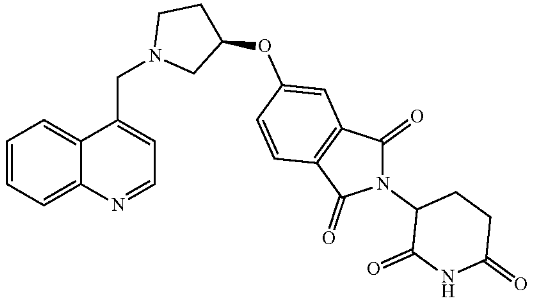 [SMILES: O=C1CCC(N2C(=O)c3ccc(O[C@@H]4CCN(Cc5ccnc6ccccc56)C4)cc3C2=O)C(=O)N1] 2-(2,6-dioxopiperidin-3-yl)-5-{[(3R)-1-[(quinolin-4-yl)methyl]pyrrolidin-3-yl]oxy}-2,3-dihydro-1H-isoindole-1,3-dione | | | 10 | 90.1 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 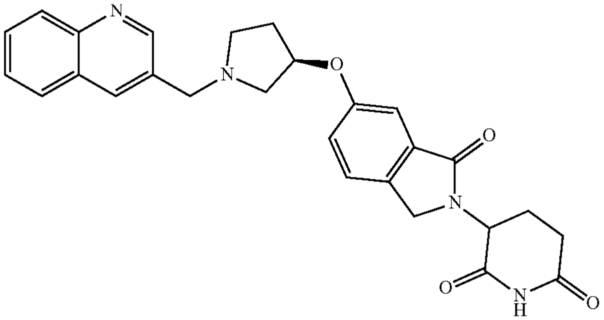 [SMILES: O=C1CCC(N2Cc3ccc(O[C@@H]4CCN(Cc5cnc6ccccc6c5)C4)cc3C2=O)C(=O)N1] 3-(1-oxo-6-{[(3R)-1-[(quinolin-3-yl)methyl]pyrrolidin-3-yl]oxy}-2,3-dihydro-1H-isoindol-2-yl)piperidine-2,6-dione | | | 10 | 89.42 |
| 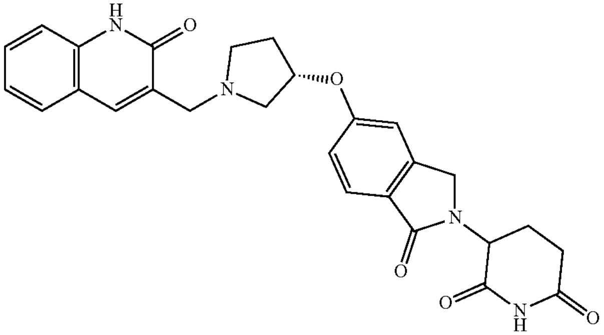 [SMILES: O=C1CCC(N2Cc3cc(O[C@H]4CCN(Cc5cc6ccccc6[nH]c5=O)C4)ccc3C2=O)C(=O)N1] 3-(1-oxo-5-{[(3S)-1-[(2-oxo-1,2-dihydroquinolin-3-yl)methyl]pyrrolidin-3-yl]oxy}-2,3-dihydro-1H-isoindol-2-yl)piperidine-2,6-dione | 1.71259525 | 30.3825 | 0.112153 | 37.28 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 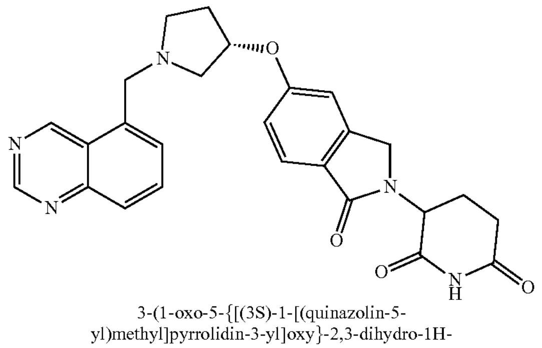 3-(1-oxo-5-{[(3S)-1-[(quinazolin-5-yl)methyl]pyrrolidin-3-yl]oxy}-2,3-dihydro-1H-isoindol-2-yl)piperidine-2,6-dione | | | 0.407676 | 58.74 |
| 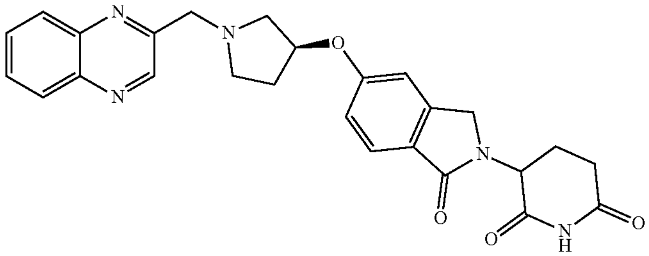 [SMILES: O=C1CCC(N2Cc3cc(O[C@H]4CCN(Cc5cnc6ccccc6n5)C4)ccc3C2=O)C(=O)N1] 3-(1-oxo-5-{[(3S)-1-[(quinoxalin-2-yl)methyl]pyrrolidin-3-yl]oxy}-2,3-dihydro-1H-isoindol-2-yl)piperidine-2,6-dione | 10 | 64.16 | 0.046914 | 43.82 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 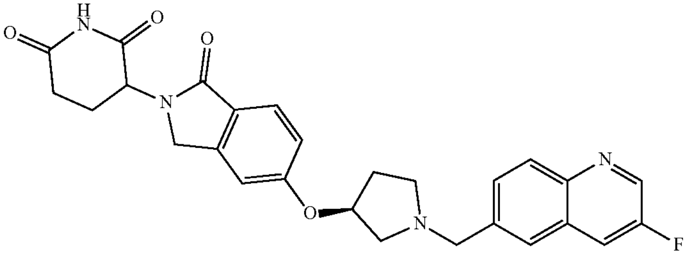 [SMILES: O=C1CCC(N2Cc3cc(O[C@H]4CCN(Cc5ccc6ncc(F)cc6c5)C4)ccc3C2=O)C(=O)N1] 3-(5-{[(3S)-1-[(3-fluoroquinolin-6-yl)methyl]pyrrolidin-3-yl]oxy}-1-oxo-2,3-dihydro-1H-isoindol-2-yl)piperidine-2,6-dione | 0.07574625 | 19.555 | 0.0087155 | 34.66 |
| 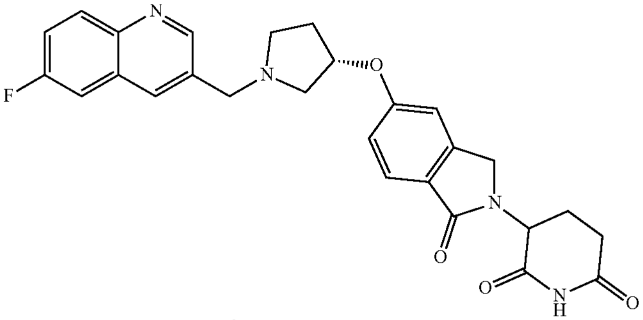 [SMILES: O=C1CCC(N2Cc3cc(O[C@H]4CCN(Cc5cnc6ccc(F)cc6c5)C4)ccc3C2=O)C(=O)N1] 3-(5-{[(3S)-1-[(6-fluoroquinolin-3-yl)methyl]pyrrolidin-3-yl]oxy}-1-oxo-2,3-dihydro-1H-isoindol-2-yl)piperidine-2,6-dione | 0.064515 | 16.03 | 0.0091915 | 30.015 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| --- | --- | --- | --- | --- |
| 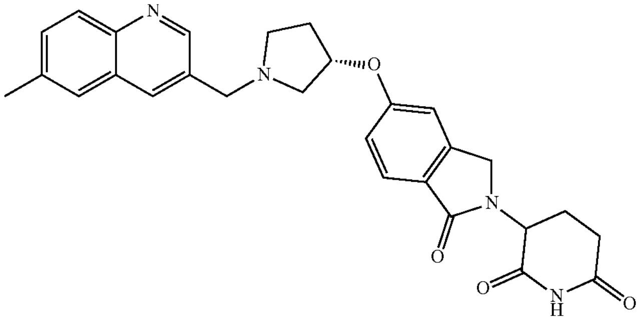 [SMILES: Cc1ccc2ncc(CN3CC[C@H](Oc4ccc5c(c4)CN(C4CCC(=O)NC4=O)C5=O)C3)cc2c1] 3-(5-{[(3S)-1-[(6-methylquinolin-3-yl)methyl]pyrrolidin-3-yl]oxy}-1-oxo-2,3-dihydro-1H-isoindol-2-yl)piperidine-2,6-dione | 0.033637 | 13.08 | 0.0093805 | 29.6 |
| 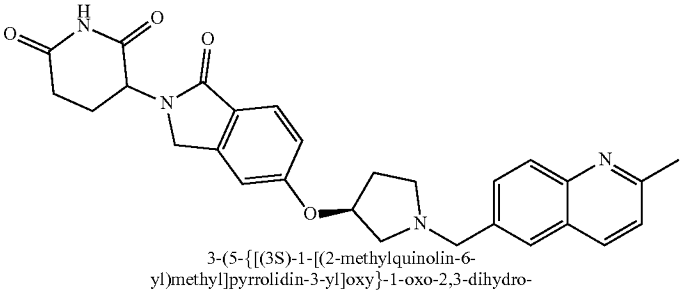 3-(5-{[(3S)-1-[(2-methylquinolin-6-yl)methyl]pyrrolidin-3-yl]oxy}-1-oxo-2,3-dihydro-1H-isoindol-2-yl)piperidine-2,6-dione | 0.022320042 | 13.84899541 | 0.003809 | 30.29857143 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 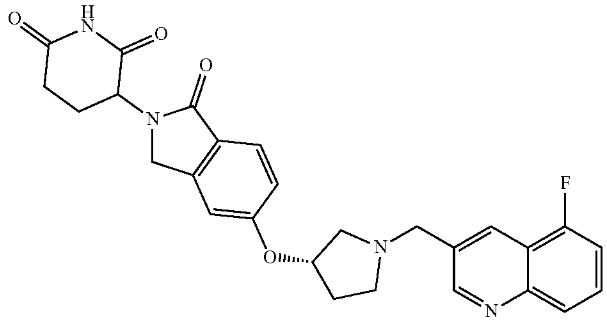 [SMILES: O=C1CCC(N2Cc3cc(O[C@H]4CCN(Cc5cnc6cccc(F)c6c5)C4)ccc3C2=O)C(=O)N1] 3-(5-{[(3S)-1-[(5-fluoroquinolin-3-yl)methyl]pyrrolidin-3-yl]oxy}-1-oxo-2,3-dihydro-1H-isoindol-2-yl)piperidine-2,6-dione | 0.30914 | 35.14 | 0.012014 | 31.52 |
| 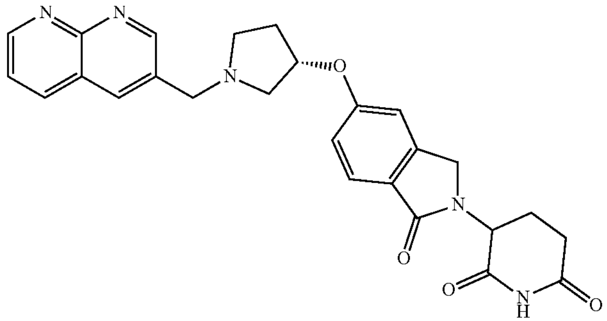 [SMILES: O=C1CCC(N2Cc3cc(O[C@H]4CCN(Cc5cnc6ncccc6c5)C4)ccc3C2=O)C(=O)N1] 3-(5-{[(3S)-1-[(1,8-naphthyridin-3-yl)methyl]pyrrolidin-3-yl]oxy}-1-oxo-2,3-dihydro-1H-isoindol-2-yl)piperidine-2,6-dione | 0.547009 | 12.27 | 0.070645 | 27.365 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 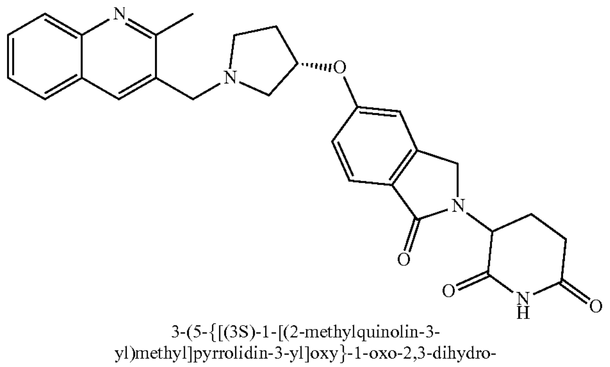 3-(5-{[(3S)-1-[(2-methylquinolin-3-yl)methyl]pyrrolidin-3-yl]oxy}-1-oxo-2,3-dihydro-1H-isoindol-2-yl)piperidine-2,6-dione | 0.034762 | 11.29 | 0.00804 | 34.08 |
| 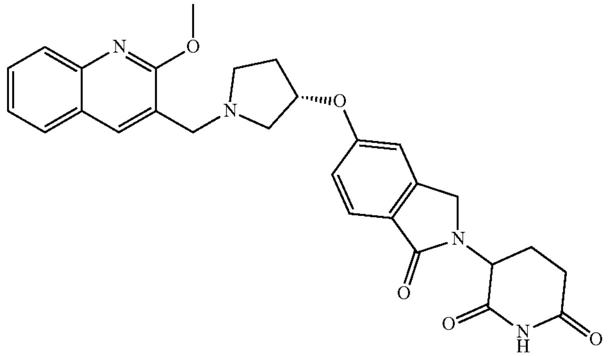 [SMILES: COc1nc2ccccc2cc1CN1CC[C@H](Oc2ccc3c(c2)CN(C2CCC(=O)NC2=O)C3=O)C1] 3-(5-{[(3S)-1-[(2-methoxyquinolin-3-yl)methyl]pyrrolidin-3-yl]oxy}-1-oxo-2,3-dihydro-1H-isoindol-2-yl)piperidine-2,6-dione | | | 0.018316 | 45.09 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 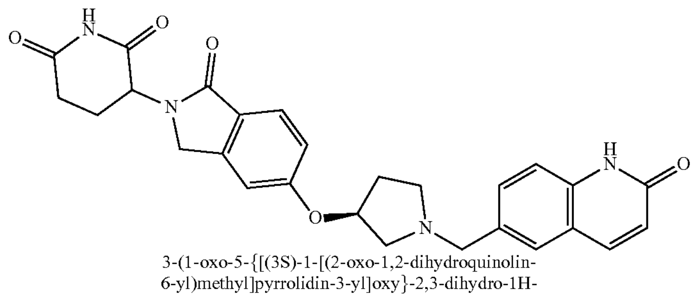 3-(1-oxo-5-{[(3S)-1-[(2-oxo-1,2-dihydroquinolin-6-yl)methyl]pyrrolidin-3-yl]oxy}-2,3-dihydro-1H-isoindol-2-yl)piperidine-2,6-dione | 0.609514 | 17.75 | 0.074688 | 40.56 |
| 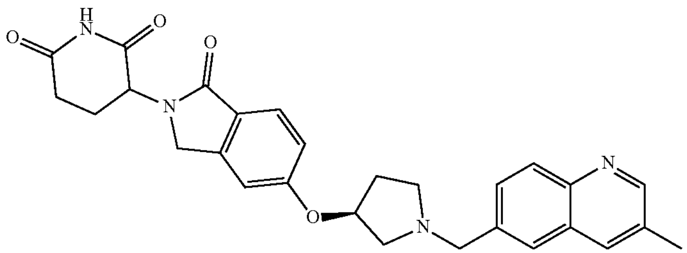 [SMILES: Cc1cnc2ccc(CN3CC[C@H](Oc4ccc5c(c4)CN(C4CCC(=O)NC4=O)C5=O)C3)cc2c1] 3-(5-{[(3S)-1-[(3-methylquinolin-6-yl)methyl]pyrrolidin-3-yl]oxy}-1-oxo-2,3-dihydro-1H-isoindol-2-yl)piperidine-2,6-dione | 0.063518 | 21.51 | 0.004468 | 38.21 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 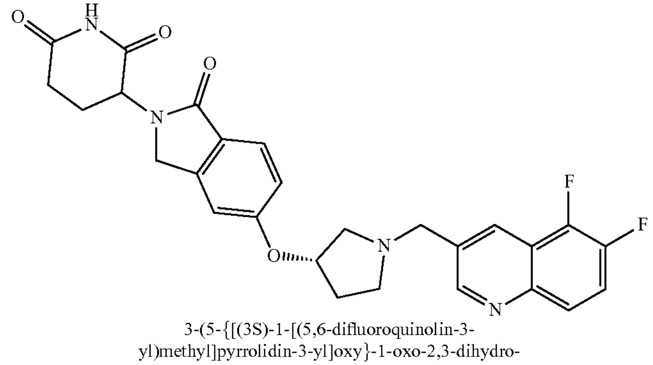 3-(5-{[(3S)-1-[(5,6-difluoroquinolin-3-yl)methyl]pyrrolidin-3-yl]oxy}-1-oxo-2,3-dihydro-1H-isoindol-2-yl)piperidine-2,6-dione | 0.165523 | 44.73 | 0.0133 | 43.98 |
| 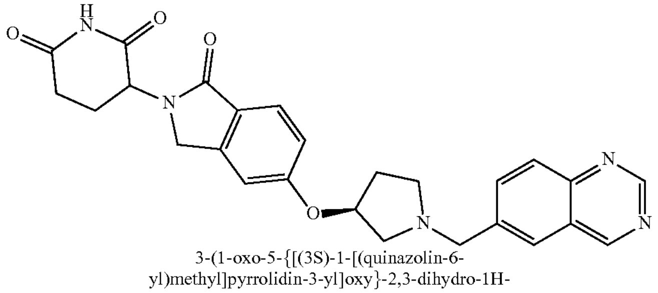 3-(1-oxo-5-{[(3S)-1-[(quinazolin-6-yl)methyl]pyrrolidin-3-yl]oxy}-2,3-dihydro-1H-isoindol-2-yl)piperidine-2,6-dione | 0.283614 | 20.44 | 0.056952 | 36.57 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 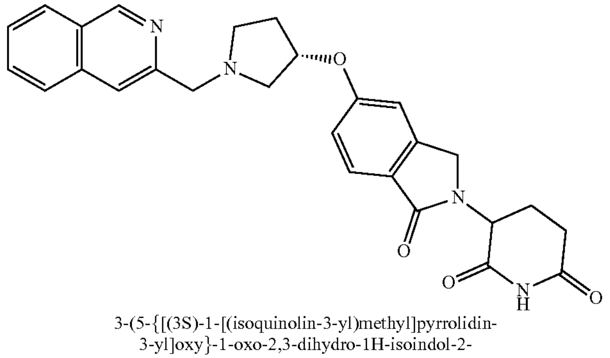 3-(5-{[(3S)-1-[(isoquinolin-3-yl)methyl]pyrrolidin-3-yl]oxy}-1-oxo-2,3-dihydro-1H-isoindol-2-yl)piperidine-2,6-dione | 0.0441085 | 13.47 | 0.0040475 | 30.345 |
| 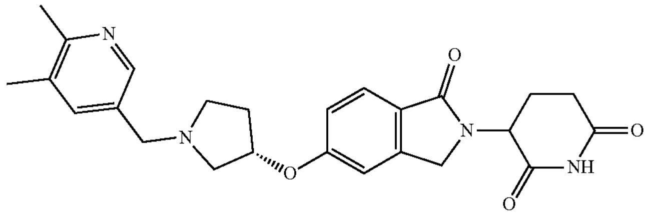 [SMILES: Cc1cc(CN2CC[C@H](Oc3ccc4c(c3)CN(C3CCC(=O)NC3=O)C4=O)C2)cnc1C] 3-(5-{[(3S)-1-[(5,6-dimethylpyridin-3-yl)methyl]pyrrolidin-3-yl]oxy}-1-oxo-2,3-dihydro-1H-isoindol-2-yl)piperidine-2,6-dione | 0.955095 | 43.03 | 0.025945 | 35.675 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 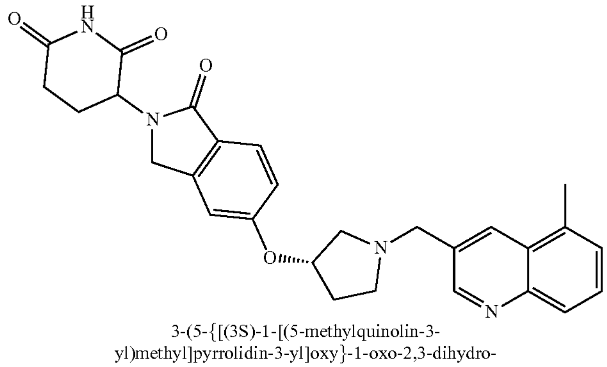 3-(5-{[(3S)-1-[(5-methylquinolin-3-yl)methyl]pyrrolidin-3-yl]oxy}-1-oxo-2,3-dihydro-1H-isoindol-2-yl)piperidine-2,6-dione | 0.036988 | 12.09 | 0.0053135 | 26.805 |
| 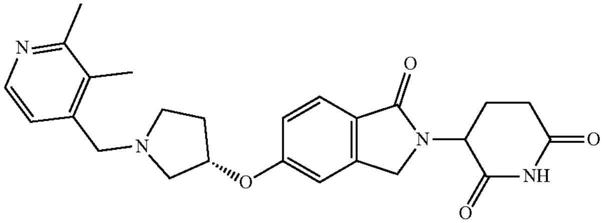 [SMILES: Cc1nccc(CN2CC[C@H](Oc3ccc4c(c3)CN(C3CCC(=O)NC3=O)C4=O)C2)c1C] 3-(5-{[(3S)-1-[(2,3-dimethylpyridin-4-yl)methyl]pyrrolidin-3-yl]oxy}-1-oxo-2,3-dihydro-1H-isoindol-2-yl)piperidine-2,6-dione | | | 0.054474 | 43.42 |
| 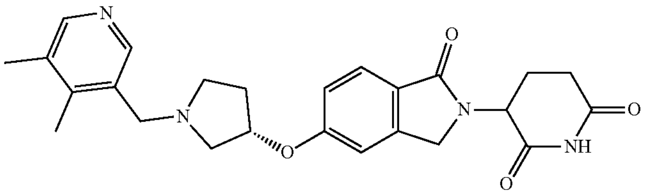 [SMILES: Cc1cncc(CN2CC[C@H](Oc3ccc4c(c3)CN(C3CCC(=O)NC3=O)C4=O)C2)c1C] 3-(5-{[(3S)-1-[(4,5-dimethylpyridin-3-yl)methyl]pyrrolidin-3-yl]oxy}-1-oxo-2,3-dihydro-1H-isoindol-2-yl)piperidine-2,6-dione | 0.407493 | 62.92 | 0.04072 | 37.63 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 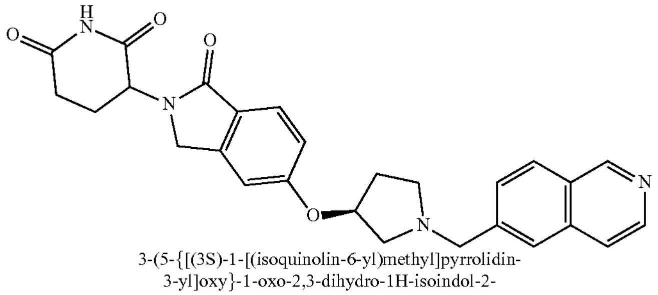 3-(5-{[(3S)-1-[(isoquinolin-6-yl)methyl]pyrrolidin-3-yl]oxy}-1-oxo-2,3-dihydro-1H-isoindol-2-yl)piperidine-2,6-dione | 0.052749 | 15.77 | 0.017021 | 25.71 |
| 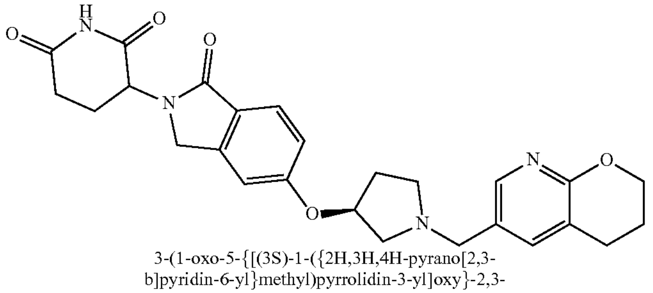 3-(1-oxo-5-{[(3S)-1-({2H,3H,4H-pyrano[2,3-b]pyridin-6-yl}methyl)pyrrolidin-3-yl]oxy}-2,3-dihydro-1H-isoindol-2-yl)piperidine-2,6-dione | 1.120987 | 23.52 | 0.03539 | 33.245 |
| 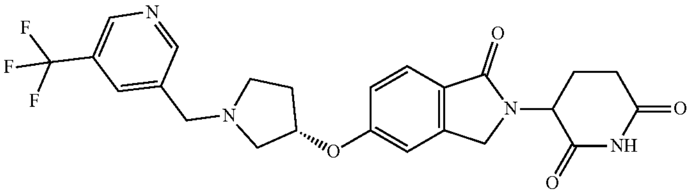 [SMILES: O=C1CCC(N2Cc3cc(O[C@H]4CCN(Cc5cncc(C(F)(F)F)c5)C4)ccc3C2=O)C(=O)N1] 3-(1-oxo-5-{[(3S)-1-{[5-(trifluoromethyl)pyridin-3-yl]methyl}pyrrolidin-3-yl]oxy}-2,3-dihydro-1H-isoindol-2-yl)piperidine-2,6-dione | 0.8415 | 54.82 | 0.036882 | 33.76 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 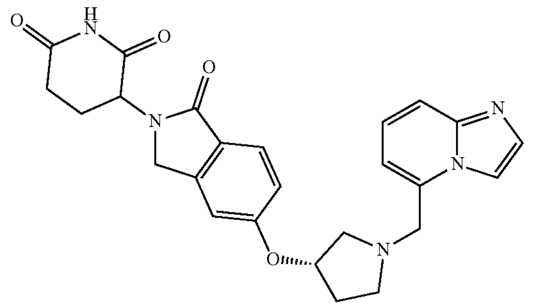 [SMILES: O=C1CCC(N2Cc3cc(O[C@H]4CCN(Cc5cccc6nccn56)C4)ccc3C2=O)C(=O)N1] 3-(5-{[(3S)-1-({imidazo[1,2-a]pyridin-5-yl}methyl)pyrrolidin-3-yl]oxy}-1-oxo-2,3-dihydro-1H-isoindol-2-yl)piperidine-2,6-dione | | | 0.182977 | 57.26 |
| 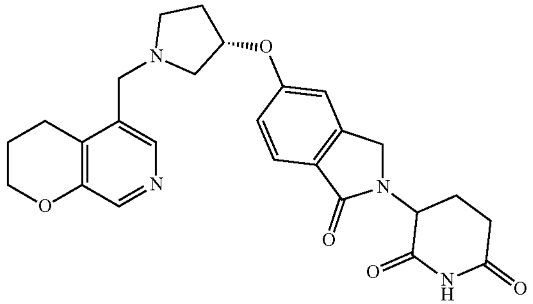 [SMILES: O=C1CCC(N2Cc3cc(O[C@H]4CCN(Cc5cncc6c5CCCO6)C4)ccc3C2=O)C(=O)N1] 3-(1-oxo-5-{[(3S)-1-({2H,3H,4H-pyrano[2,3-c]pyridin-5-yl}methyl)pyrrolidin-3-yl]oxy}-2,3-dihydro-1H-isoindol-2-yl)piperidine-2,6-dione | 0.0699245 | 11.03 | 0.0246025 | 29.38 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 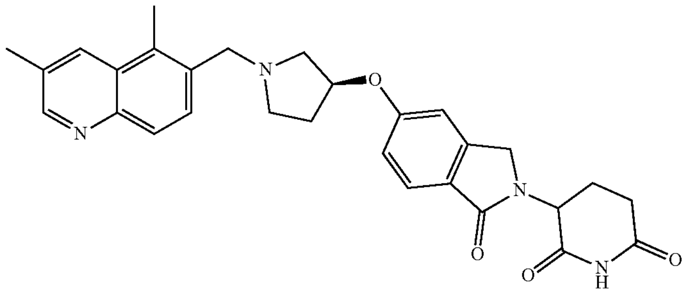 [SMILES: Cc1cnc2ccc(CN3CC[C@H](Oc4ccc5c(c4)CN(C4CCC(=O)NC4=O)C5=O)C3)c(C)c2c1] 3-(5-{[(3S)-1-[(3,5-dimethylquinolin-6-yl)methyl]pyrrolidin-3-yl]oxy}-1-oxo-2,3-dihydro-1H-isoindol-2-yl)piperidine-2,6-dione | 0.093771 | 53.11 | 0.007921 | 39.05 |
| 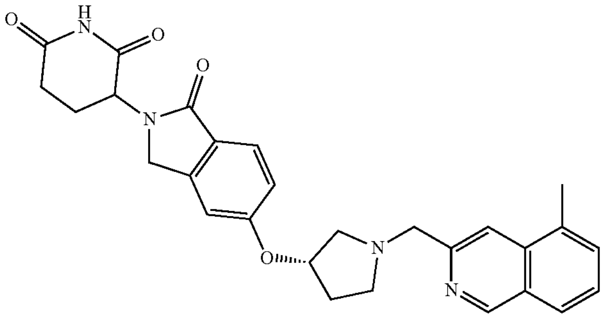 [SMILES: Cc1cccc2cnc(CN3CC[C@H](Oc4ccc5c(c4)CN(C4CCC(=O)NC4=O)C5=O)C3)cc12] 3-(5-{[(3S)-1-[(5-methylisoquinolin-3-yl)methyl]pyrrolidin-3-yl]oxy}-1-oxo-2,3-dihydro-1H-isoindol-2-yl)piperidine-2,6-dione | 0.086097 | 19.01 | 0.004625 | 31.91 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 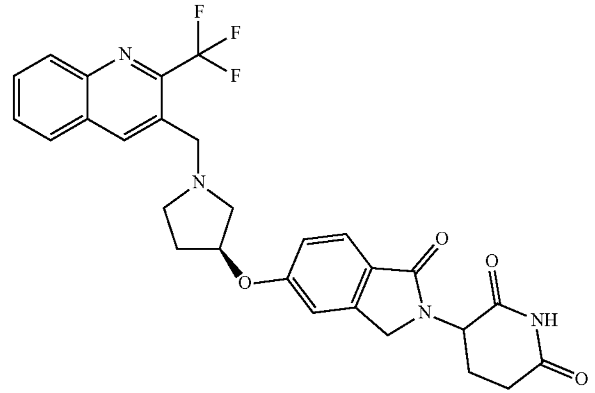 [SMILES: O=C1CCC(N2Cc3cc(O[C@H]4CCN(Cc5cc6ccccc6nc5C(F)(F)F)C4)ccc3C2=O)C(=O)N1] 3-(1-oxo-5-{[(3S)-1-{[2-(trifluoromethyl)quinolin-3-yl]methyl}pyrrolidin-3-yl]oxy}-2,3-dihydro-1H-isoindol-2-yl)piperidine-2,6-dione | 0.257403 | 73.03 | 0.029281 | 39.87 |
| 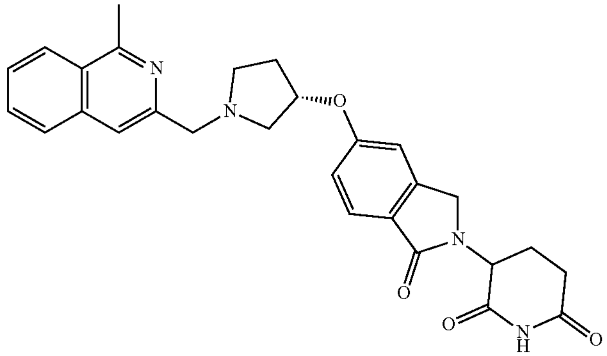 [SMILES: Cc1nc(CN2CC[C@H](Oc3ccc4c(c3)CN(C3CCC(=O)NC3=O)C4=O)C2)cc2ccccc12] 3-(5-{[(3S)-1-[(1-methylisoquinolin-3-yl)methyl]pyrrolidin-3-yl]oxy}-1-oxo-2,3-dihydro-1H-isoindol-2-yl)piperidine-2,6-dione | 5.040958 | 50.77 | 0.031013 | 47.56 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 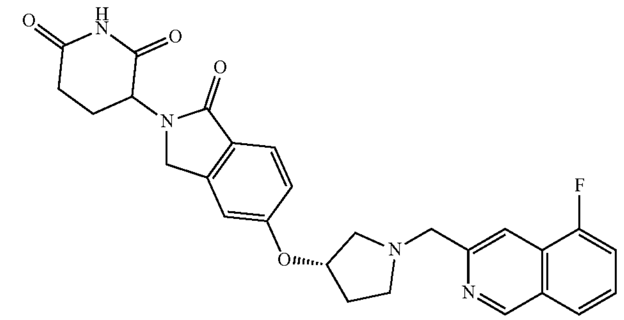 [SMILES: O=C1CCC(N2Cc3cc(O[C@H]4CCN(Cc5cc6c(F)cccc6cn5)C4)ccc3C2=O)C(=O)N1] 3-(5-{[(3S)-1-[(5-fluoroisoquinolin-3-yl)methyl]pyrrolidin-3-yl]oxy}-1-oxo-2,3-dihydro-1H-isoindol-2-yl)piperidine-2,6-dione | 0.185365 | 53.33 | 0.013307 | 43.45 |
| 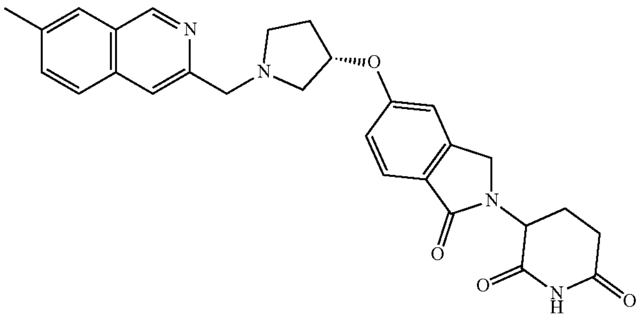 [SMILES: Cc1ccc2cc(CN3CC[C@H](Oc4ccc5c(c4)CN(C4CCC(=O)NC4=O)C5=O)C3)ncc2c1] 3-(5-{[(3S)-1-[(7-methylisoquinolin-3-yl)methyl]pyrrolidin-3-yl]oxy}-1-oxo-2,3-dihydro-1H-isoindol-2-yl)piperidine-2,6-dione | 0.070726 | 15.68 | 0.0122215 | 32.315 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 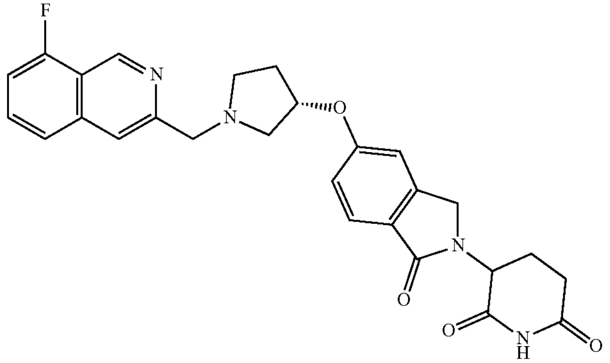 [SMILES: O=C1CCC(N2Cc3cc(O[C@H]4CCN(Cc5cc6cccc(F)c6cn5)C4)ccc3C2=O)C(=O)N1] 3-(5-{[(3S)-1-[(8-fluoroisoquinolin-3-yl)methyl]pyrrolidin-3-yl]oxy}-1-oxo-2,3-dihydro-1H-isoindol-2-yl)piperidine-2,6-dione | 0.024387 | 10.49 | 0.005324 | 30.295 |
| 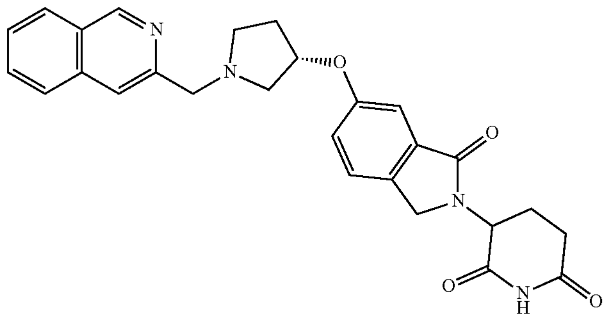 [SMILES: O=C1CCC(N2Cc3ccc(O[C@H]4CCN(Cc5cc6ccccc6cn5)C4)cc3C2=O)C(=O)N1] 3-(6-{[(3S)-1-[(isoquinolin-3-yl)methyl]pyrrolidin-3-yl]oxy}-1-oxo-2,3-dihydro-1H-isoindol-2-yl)piperidine-2,6-dione | 0.000399 | 82.45 | 10 | 93.8 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 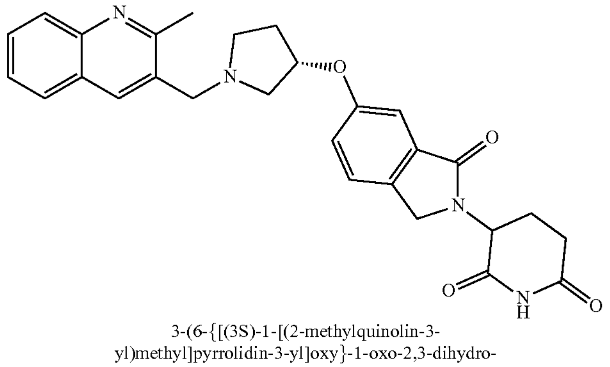 3-(6-{[(3S)-1-[(2-methylquinolin-3-yl)methyl]pyrrolidin-3-yl]oxy}-1-oxo-2,3-dihydro-1H-isoindol-2-yl)piperidine-2,6-dione | | 79.9 | 10 | 87.055 |
| 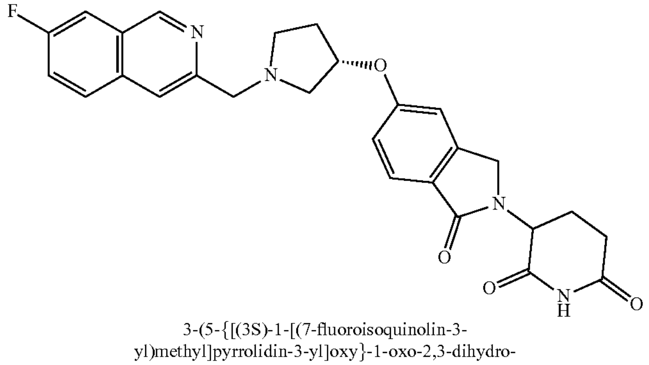 3-(5-{[(3S)-1-[(7-fluoroisoquinolin-3-yl)methyl]pyrrolidin-3-yl]oxy}-1-oxo-2,3-dihydro-1H-isoindol-2-yl)piperidine-2,6-dione | 0.02482 | 10.88 | 0.004934 | 28.82 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 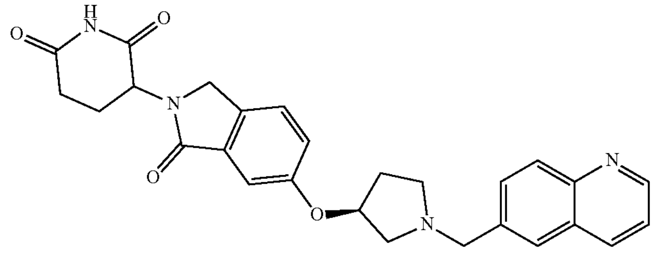 [SMILES: O=C1CCC(N2Cc3ccc(O[C@H]4CCN(Cc5ccc6ncccc6c5)C4)cc3C2=O)C(=O)N1] 3-(1-oxo-6-{[(3S)-1-[(quinolin-6-yl)methyl]pyrrolidin-3-yl]oxy}-2,3-dihydro-1H-isoindol-2-yl)piperidine-2,6-dione | 0.014554 | 82.37 | 10 | 88.79 |
| 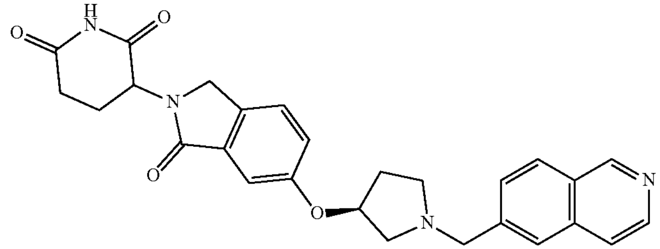 [SMILES: O=C1CCC(N2Cc3ccc(O[C@H]4CCN(Cc5ccc6cnccc6c5)C4)cc3C2=O)C(=O)N1] 3-(6-{[(3S)-1-[(isoquinolin-6-yl)methyl]pyrrolidin-3-yl]oxy}-1-oxo-2,3-dihydro-1H-isoindol-2-yl)piperidine-2,6-dione | | | 10 | 80.095 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 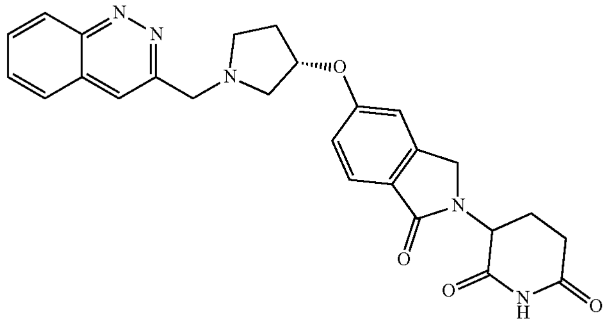 [SMILES: O=C1CCC(N2Cc3cc(O[C@H]4CCN(Cc5cc6ccccc6nn5)C4)ccc3C2=O)C(=O)N1] 3-(5-{[(3S)-1-[(cinnolin-3-yl)methyl]pyrrolidin-3-yl]oxy}-1-oxo-2,3-dihydro-1H-isoindol-2-yl)piperidine-2,6-dione | 0.066291 | 8.97 | 0.012468 | 26.03333333 |
| 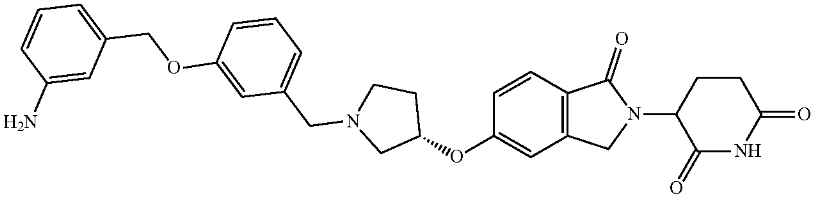 [SMILES: Nc1cccc(COc2cccc(CN3CC[C@H](Oc4ccc5c(c4)CN(C4CCC(=O)NC4=O)C5=O)C3)c2)c1] 3-(5-{[(3S)-1-({3-[(3-aminophenyl)methoxy]phenyl}methyl)pyrrolidin-3-yl]oxy}-1-oxo-2,3-dihydro-1H-isoindol-2-yl)piperidine-2,6-dione | | | 0.817948 | 78.15 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 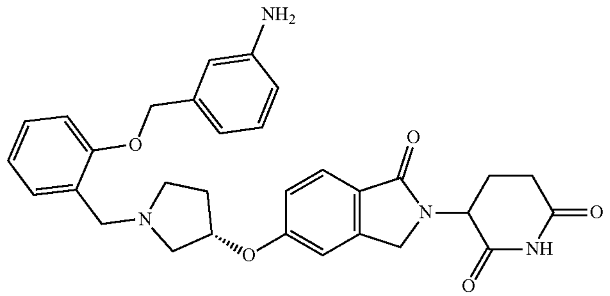 [SMILES: Nc1cccc(COc2ccccc2CN2CC[C@H](Oc3ccc4c(c3)CN(C3CCC(=O)NC3=O)C4=O)C2)c1] 3-(5-{[(3S)-1-({2-[(3-aminophenyl)methoxy]phenyl}methyl)pyrrolidin-3-yl]oxy}-1-oxo-2,3-dihydro-1H-isoindol-2-yl)piperidine-2,6-dione | | | 10 | 92.17 |
| 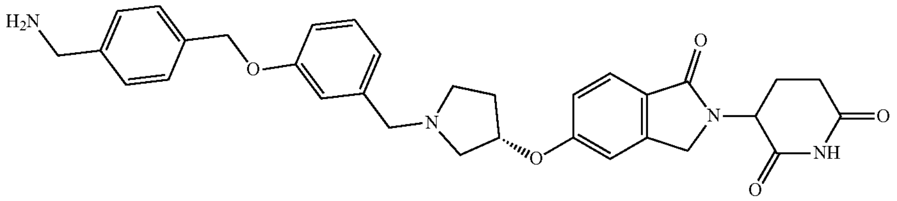 [SMILES: NCc1ccc(COc2cccc(CN3CC[C@H](Oc4ccc5c(c4)CN(C4CCC(=O)NC4=O)C5=O)C3)c2)cc1] 3-(5-{[(3S)-1-[(3-{[4-(aminomethyl)phenyl]methoxy}phenyl)methyl]pyrrolidin-3-yl]oxy}-1-oxo-2,3-dihydro-1H-isoindol-2-yl)piperidine-2,6-dione | | | 10 | 87 |
| 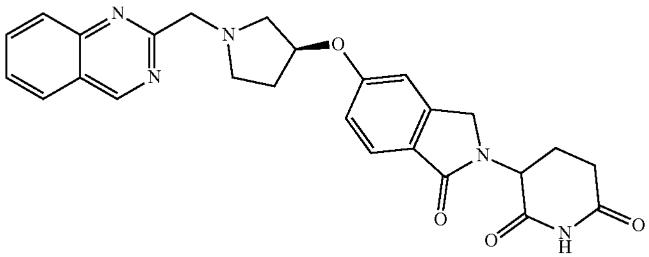 [SMILES: O=C1CCC(N2Cc3cc(O[C@H]4CCN(Cc5ncc6ccccc6n5)C4)ccc3C2=O)C(=O)N1] | 4.772416 | 74.28 | 0.051934 | 48.23 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(1-oxo-5-{[(3S)-1-[(quinazolin-2-yl)methyl]pyrrolidin-3-yl]oxy}-2,3-dihydro-1H-isoindol-2-yl)piperidine-2,6-dione | | | | |
| 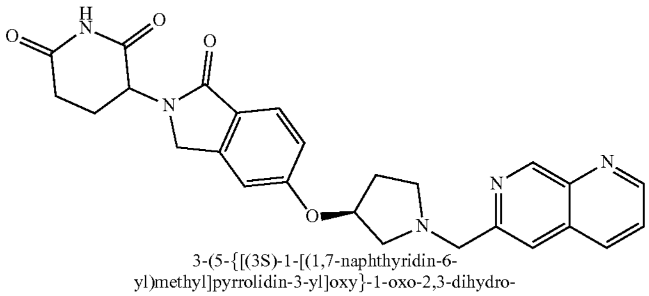 3-(5-{[(3S)-1-[(1,7-naphthyridin-6-yl)methyl]pyrrolidin-3-yl]oxy}-1-oxo-2,3-dihydro-1H-isoindol-2-yl)piperidine-2,6-dione | 0.101741 | 9.59 | 0.014721 | 26.505 |
| 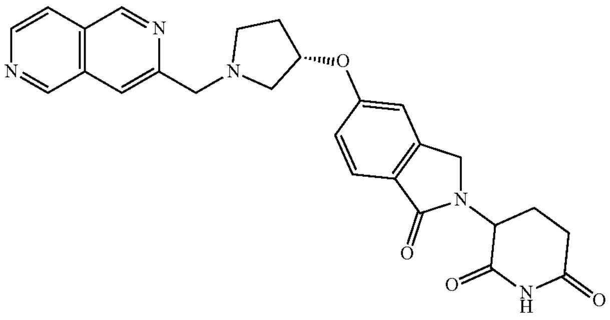 [SMILES: O=C1CCC(N2Cc3cc(O[C@H]4CCN(Cc5cc6cnccc6cn5)C4)ccc3C2=O)C(=O)N1] 3-(5-{[(3S)-1-[(2,6-naphthyridin-3-yl)methyl]pyrrolidin-3-yl]oxy}-1-oxo-2,3-dihydro-1H-isoindol-2-yl)piperidine-2,6-dione | 0.543563 | 24.28 | 0.039919 | 34.11 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 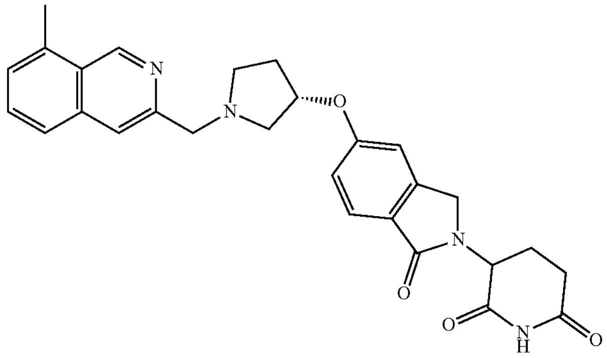 [SMILES: Cc1cccc2cc(CN3CC[C@H](Oc4ccc5c(c4)CN(C4CCC(=O)NC4=O)C5=O)C3)ncc12] 3-(5-{[(3S)-1-[(8-methylisoquinolin-3-yl)methyl]pyrrolidin-3-yl]oxy}-1-oxo-2,3-dihydro-1H-isoindol-2-yl)piperidine-2,6-dione | 0.117738 | 19.68 | 0.006413 | 32.22 |
| 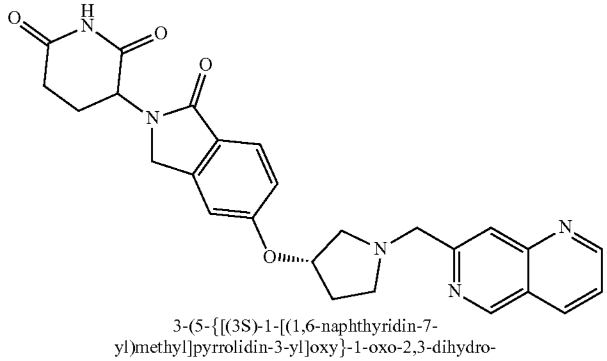 3-(5-{[(3S)-1-[(1,6-naphthyridin-7-yl)methyl]pyrrolidin-3-yl]oxy}-1-oxo-2,3-dihydro-1H-isoindol-2-yl)piperidine-2,6-dione | 0.960129 | 84.48 | 0.122291 | 67.53 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 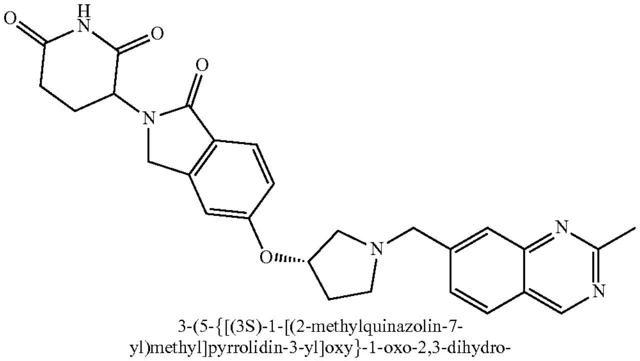 3-(5-{[(3S)-1-[(2-methylquinazolin-7-yl)methyl]pyrrolidin-3-yl]oxy}-1-oxo-2,3-dihydro-1H-isoindol-2-yl)piperidine-2,6-dione | 0.364974 | 32.41 | 0.065544 | 35.02 |
| 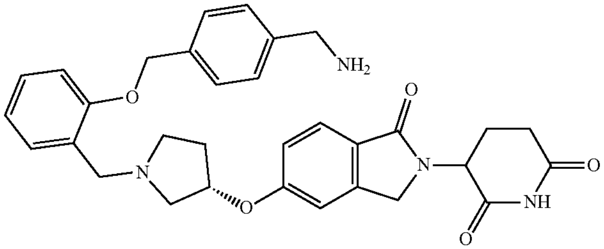 [SMILES: NCc1ccc(COc2ccccc2CN2CC[C@H](Oc3ccc4c(c3)CN(C3CCC(=O)NC3=O)C4=O)C2)cc1] 3-(5-{[(3S)-1-[(2-{[4-(aminomethyl)phenyl]methoxy}phenyl)methyl]pyrrolidin-3-yl]oxy}-1-oxo-2,3-dihydro-1H-isoindol-2-yl)piperidine-2,6-dione | | | 10 | 88.71 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 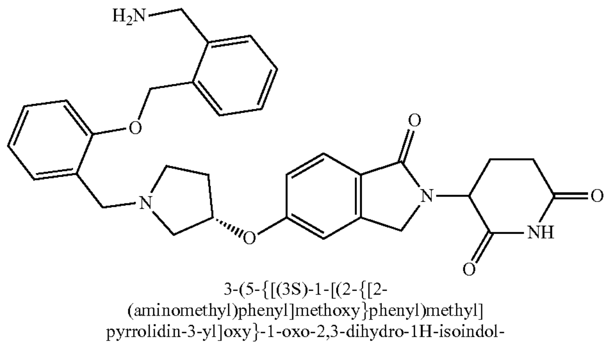 3-(5-{[(3S)-1-[(2-{[2-(aminomethyl)phenyl]methoxy}phenyl)methyl]pyrrolidin-3-yl]oxy}-1-oxo-2,3-dihydro-1H-isoindol-2-yl)piperidine-2,6-dione | | | 10 | 89.91 |
| 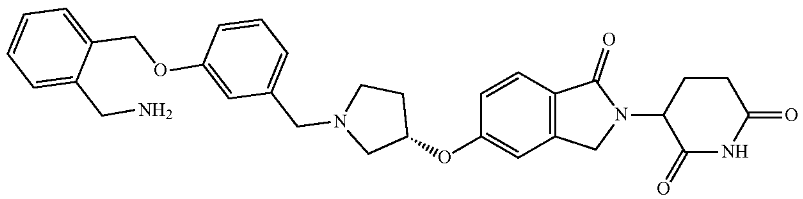 [SMILES: NCc1ccccc1COc1cccc(CN2CC[C@H](Oc3ccc4c(c3)CN(C3CCC(=O)NC3=O)C4=O)C2)c1] 3-(5-{[(3S)-1-[(3-{[2-(aminomethyl)phenyl]methoxy}phenyl)methyl]pyrrolidin-3-yl]oxy}-1-oxo-2,3-dihydro-1H-isoindol-2-yl)piperidine-2,6-dione | | | 10 | 74.31 |
| 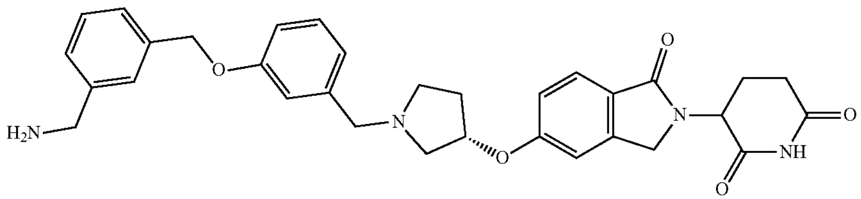 [SMILES: NCc1cccc(COc2cccc(CN3CC[C@H](Oc4ccc5c(c4)CN(C4CCC(=O)NC4=O)C5=O)C3)c2)c1] 3-(5-{[(3S)-1-[(3-{[3-(aminomethyl)phenyl]methoxy}phenyl)methyl]pyrrolidin-3-yl]oxy}-1-oxo-2,3-dihydro-1H-isoindol-2-yl)piperidine-2,6-dione | | | 10 | 81.05 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 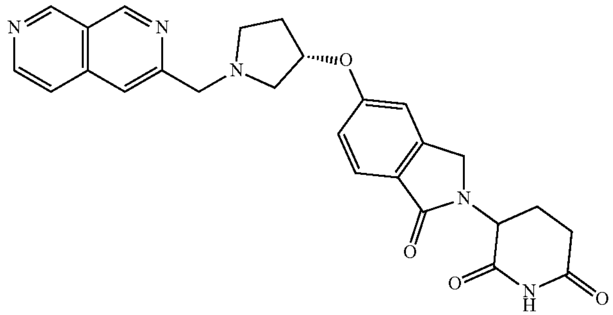 3-(5-{[(3S)-1-[(2,7-naphthyridin-3-yl)methyl]pyrrolidin-3-yl]oxy}-1-oxo-2,3-dihydro-1H-isoindol-2-yl)piperidine-2,6-dione | 0.098842 | 6.92 | 0.0193435 | 28.095 |
| 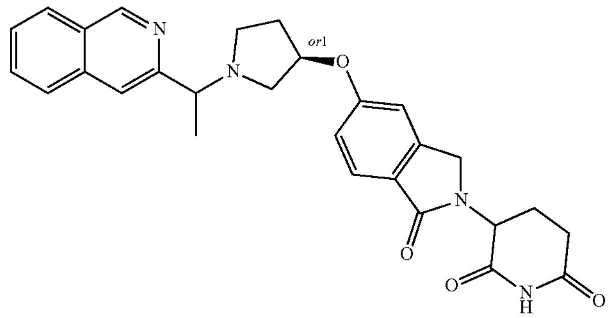 [SMILES: CC(c1cc2ccccc2cn1)N1CC[C@@H](Oc2ccc3c(c2)CN(C2CCC(=O)NC2=O)C3=O)C1] rel-3-(1-oxo-5-{[(3R)-1-[1-(quinolin-3-yl)ethyl]pyrrolidin-3-yl]oxy}-2,3-dihydro-1H-isoindol-2-yl)piperidine-2,6-dione | 10 | 84.97 | 0.041372 | 58.885 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 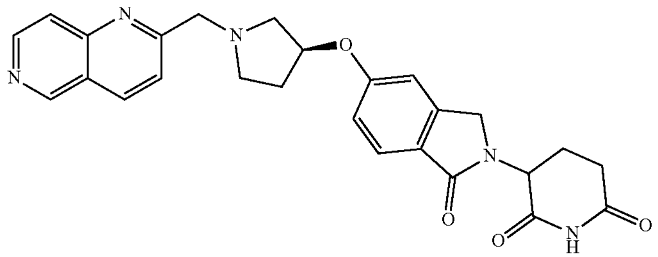 [SMILES: O=C1CCC(N2Cc3cc(O[C@H]4CCN(Cc5ccc6cnccc6n5)C4)ccc3C2=O)C(=O)N1] 3-(5-{[(3S)-1-[(1,6-naphthyridin-2-yl)methyl]pyrrolidin-3-yl]oxy}-1-oxo-2,3-dihydro-1H-isoindol-2-yl)piperidine-2,6-dione | | | 0.108575 | 42.7 |
| 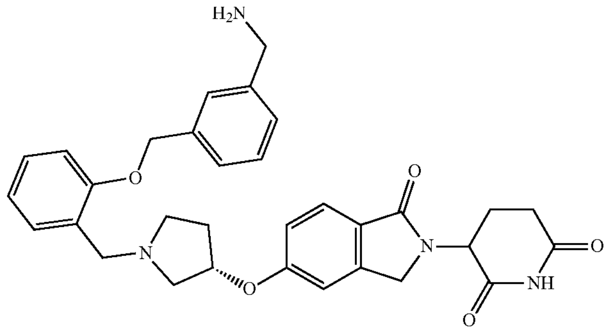 [SMILES: NCc1cccc(COc2ccccc2CN2CC[C@H](Oc3ccc4c(c3)CN(C3CCC(=O)NC3=O)C4=O)C2)c1] 3-(5-{[(3S)-1-[(2-{[3-(aminomethyl)phenyl]methoxy}phenyl)methyl]pyrrolidin-3-yl]oxy}-1-oxo-2,3-dihydro-1H-isoindol-2-yl)piperidine-2,6-dione | | | 10 | 87.63 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 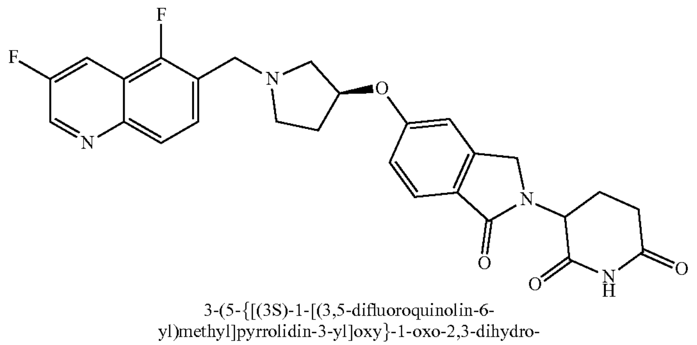 3-(5-{[(3S)-1-[(3,5-difluoroquinolin-6-yl)methyl]pyrrolidin-3-yl]oxy}-1-oxo-2,3-dihydro-1H-isoindol-2-yl)piperidine-2,6-dione | 0.038347 | 12.86 | 0.008713 | 28.96 |
| 3-(1-oxo-5-{[(3S)-1-{[(2-$^{2}$H)quinolin-3-yl]methyl}pyrrolidin-3-yl]oxy}-2,3-dihydro-1H-isoindol-2-yl)piperidine-2,6-dione | 0.028459 | 9.675 | 0.0084115 | 25.75 |
| 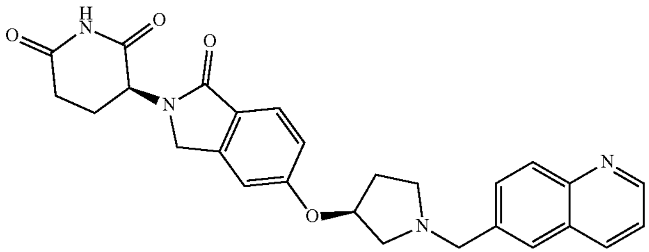 [SMILES: O=C1CC[C@H](N2Cc3cc(O[C@H]4CCN(Cc5ccc6ncccc6c5)C4)ccc3C2=O)C(=O)N1] (3S)-3-(1-oxo-5-{[(3S)-1-[(quinolin-6-yl)methyl]pyrrolidin-3-yl]oxy}-2,3-dihydro-1H-isoindol-2-yl)piperidine-2,6-dione | 0.0314325 | 12.265 | 0.007421 | 26.52 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 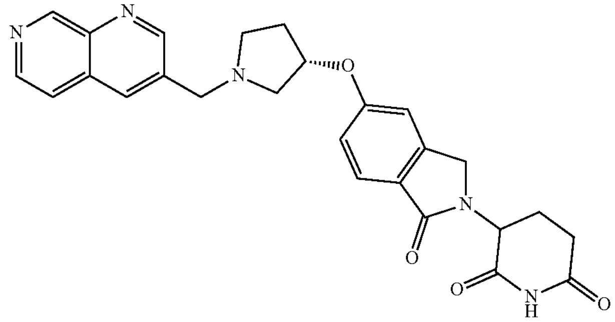 [SMILES: O=C1CCC(N2Cc3cc(O[C@H]4CCN(Cc5cnc6cnccc6c5)C4)ccc3C2=O)C(=O)N1] 3-(5-{[(3S)-1-[(1,7-naphthyridin-3-yl)methyl]pyrrolidin-3-yl]oxy}-1-oxo-2,3-dihydro-1H-isoindol-2-yl)piperidine-2,6-dione | 0.092305 | 9.14 | 0.020827 | 26.94 |
| 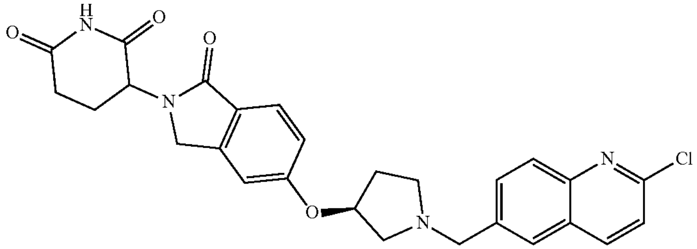 [SMILES: O=C1CCC(N2Cc3cc(O[C@H]4CCN(Cc5ccc6nc(Cl)ccc6c5)C4)ccc3C2=O)C(=O)N1] 3-(5-{[(3S)-1-[(2-chloroquinolin-6-yl)methyl]pyrrolidin-3-yl]oxy}-1-oxo-2,3-dihydro-1H-isoindol-2-yl)piperidine-2,6-dione | 0.00958 | 12.57 | 0.0028185 | 29.2 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 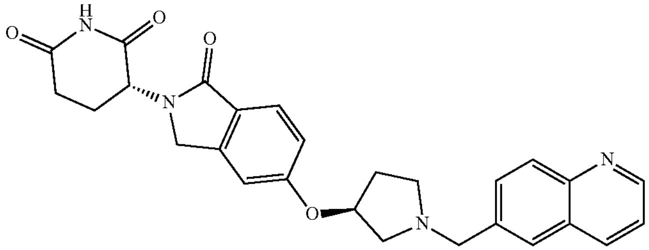 (3R)-3-(1-oxo-5-{[(3S)-1-[(quinolin-6-yl)methyl]pyrrolidin-3-yl]oxy}-2,3-dihydro-1H-isoindol-2-yl)piperidine-2,6-dione | 0.026473 | 12.45 | 0.003552 | 26.94 |
| 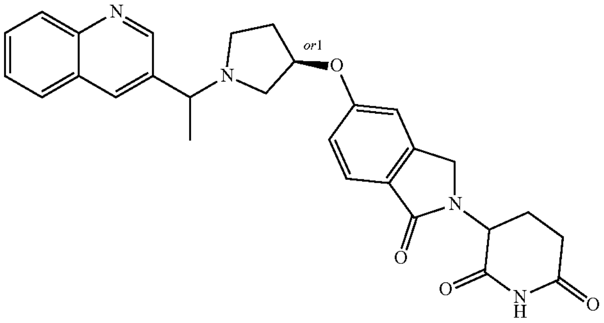 rel-3-(1-oxo-5-{[(3R)-1-[1-(quinolin-3-yl)ethyl]pyrrolidin-3-yl]oxy}-2,3-dihydro-1H-isoindol-2-yl)piperidine-2,6-dione | 10 | 76.71 | 0.083399 | 50.89 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 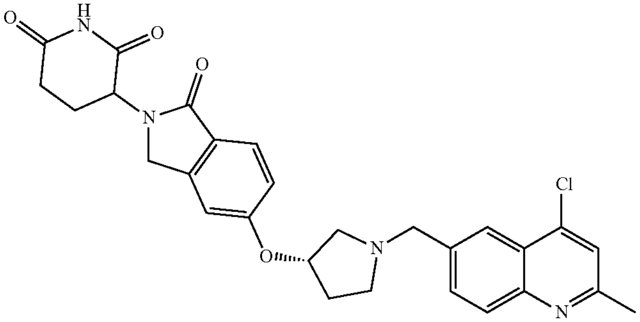 3-(5-{[(3S)-1-[(4-chloro-2-methylquinolin-6-yl)methyl]pyrrolidin-3-yl]oxy}-1-oxo-2,3-dihydro-1H-isoindol-2-yl)piperidine-2,6-dione | 0.391693 | 44.06 | 0.004288 | 32.06 |
| 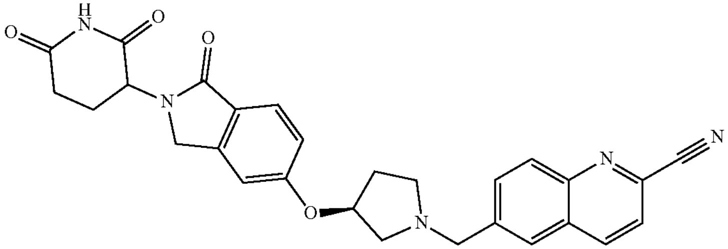 [SMILES: N#Cc1ccc2cc(CN3CC[C@H](Oc4ccc5c(c4)CN(C4CCC(=O)NC4=O)C5=O)C3)ccc2n1] 6-{[(3S)-3-{[2-(2,6-dioxopiperidin-3-yl)-1-oxo-2,3-dihydro-1H-isoindol-5-yl]oxy}pyrrolidin-1-yl]methyl}quinoline-2-carbonitrile | 0.007922893 | 9.503565765 | 0.003054302 | 27.48620544 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 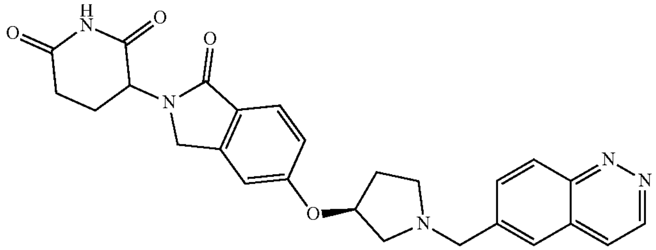 3-(5-{[(3S)-1-[(cinnolin-6-yl)methyl]pyrrolidin-3-yl]oxy}-1-oxo-2,3-dihydro-1H-isoindol-2-yl)piperidine-2,6-dione | 0.032832 | 8.19 | 0.0125155 | 26.65 |
| 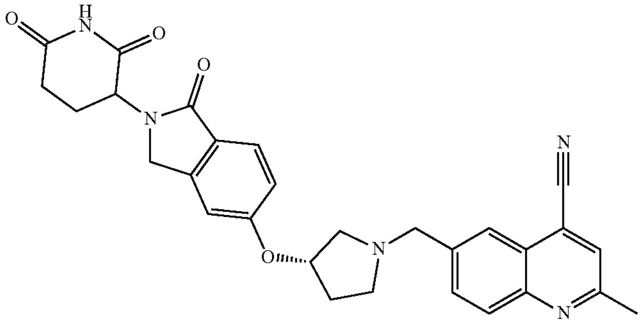 [SMILES: Cc1cc(C#N)c2cc(CN3CC[C@H](Oc4ccc5c(c4)CN(C4CCC(=O)NC4=O)C5=O)C3)ccc2n1] 6-{[(3S)-3-{[2-(2,6-dioxopiperidin-3-yl)-1-oxo-2,3-dihydro-1H-isoindol-5-yl]oxy}pyrrolidin-1-yl]methyl}-2-methylquinoline-4-carbonitrile | 10 | 86.89 | 0.0207185 | 66.8 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 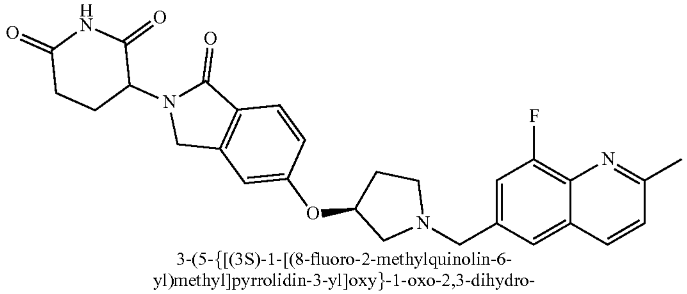 3-(5-{[(3S)-1-[(8-fluoro-2-methylquinolin-6-yl)methyl]pyrrolidin-3-yl]oxy}-1-oxo-2,3-dihydro-1H-isoindol-2-yl)piperidine-2,6-dione | 0.0031975 | 7.555 | 0.001039667 | 25.34666667 |
| 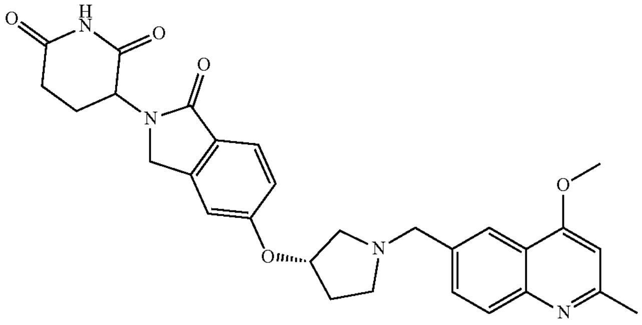 [SMILES: COc1cc(C)nc2ccc(CN3CC[C@H](Oc4ccc5c(c4)CN(C4CCC(=O)NC4=O)C5=O)C3)cc12] 3-(5-{[(3S)-1-[(4-methoxy-2-methylquinolin-6-yl)methyl]pyrrolidin-3-yl]oxy}-1-oxo-2,3-dihydro-1H-isoindol-2-yl)piperidine-2,6-dione | 1.498301 | 47.92 | 0.0268145 | 44.38 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 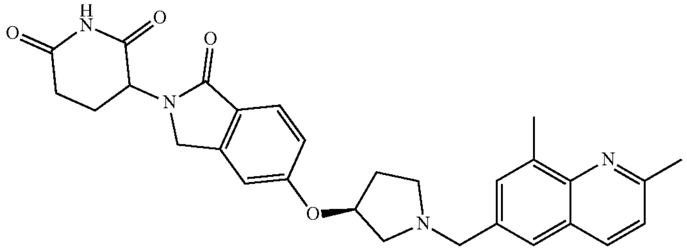 3-(5-{[(3S)-1-[(2,8-dimethylquinolin-6-yl)methyl]pyrrolidin-3-yl]oxy}-1-oxo-2,3-dihydro-1H-isoindol-2-yl)piperidine-2,6-dione | 0.055523 | 13.61 | 0.006436 | 29.33 |
| 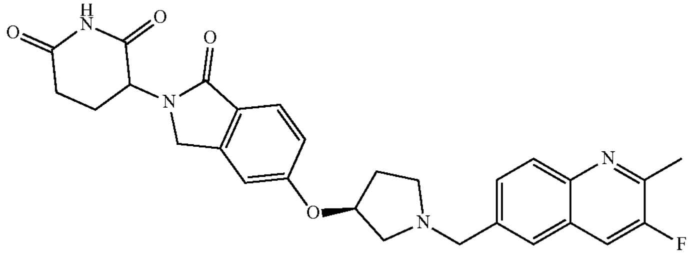 [SMILES: Cc1nc2ccc(CN3CC[C@H](Oc4ccc5c(c4)CN(C4CCC(=O)NC4=O)C5=O)C3)cc2cc1F] 3-(5-{[(3S)-1-[(3-fluoro-2-methylquinolin-6-yl)methyl]pyrrolidin-3-yl]oxy}-1-oxo-2,3-dihydro-1H-isoindol-2-yl)piperidine-2,6-dione | 0.053616 | 18.86 | 0.0069525 | 33.29 |
| 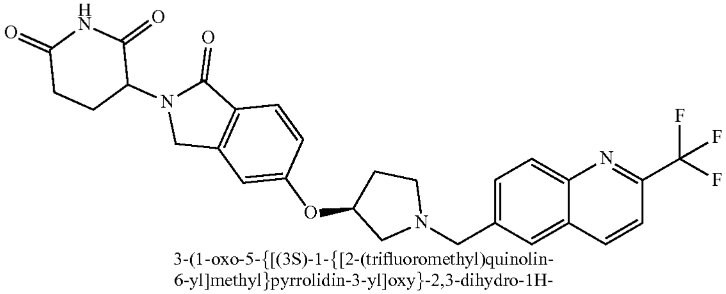 3-(1-oxo-5-{[(3S)-1-{[2-(trifluoromethyl)quinolin-6-yl]methyl}pyrrolidin-3-yl]oxy}-2,3-dihydro-1H- | 0.00729 | 8.76 | 0.005423667 | 24.71666667 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| isoindol-2-yl)piperidine-2,6-dione | | | | |
| 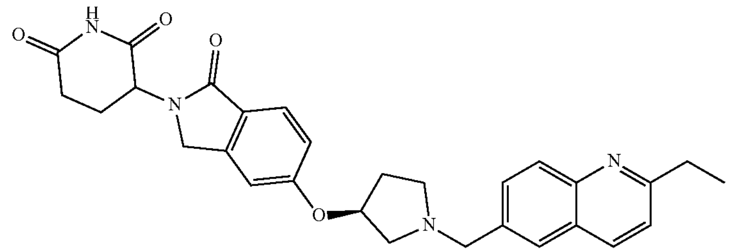 [SMILES: CCc1ccc2cc(CN3CC[C@H](Oc4ccc5c(c4)CN(C4CCC(=O)NC4=O)C5=O)C3)ccc2n1] 3-(5-{[(3S)-1-[(2-ethylquinolin-6-yl)methyl]pyrrolidin-3-yl]oxy}-1-oxo-2,3-dihydro-1H-isoindol-2-yl)piperidine-2,6-dione | 0.025189 | 12.49 | 0.003018 | 27 |
| 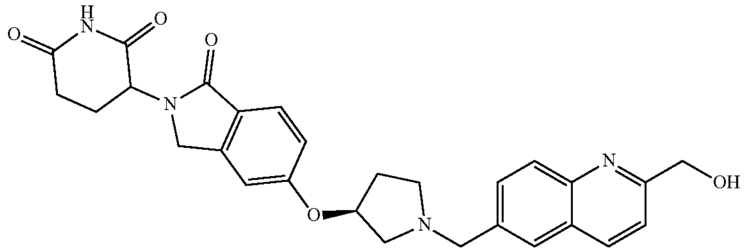 [SMILES: O=C1CCC(N2Cc3cc(O[C@H]4CCN(Cc5ccc6nc(CO)ccc6c5)C4)ccc3C2=O)C(=O)N1] 3-(5-{[(3S)-1-{[2-(hydroxymethyl)quinolin-6-yl]methyl}pyrrolidin-3-yl]oxy}-1-oxo-2,3-dihydro-1H-isoindol-2-yl)piperidine-2,6-dione | 0.054389 | 11.84 | 0.0093905 | 31.475 |
| 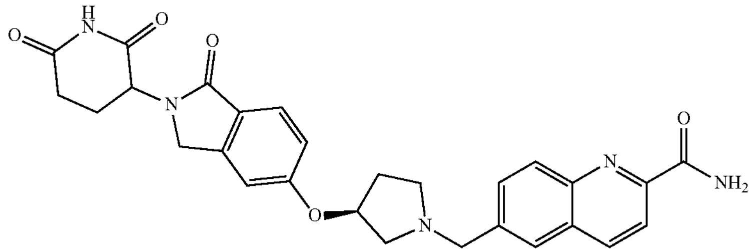 [SMILES: NC(=O)c1ccc2cc(CN3CC[C@H](Oc4ccc5c(c4)CN(C4CCC(=O)NC4=O)C5=O)C3)ccc2n1] | 0.017143 | 10.71 | 0.0035315 | 26.545 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 6-{[(3S)-3-{[2-(2,6-dioxopiperidin-3-yl)-1-oxo-2,3-dihydro-1H-isoindol-5-yl]oxy}pyrrolidin-1-yl]methyl}quinoline-2-carboxamide | | | | |
| 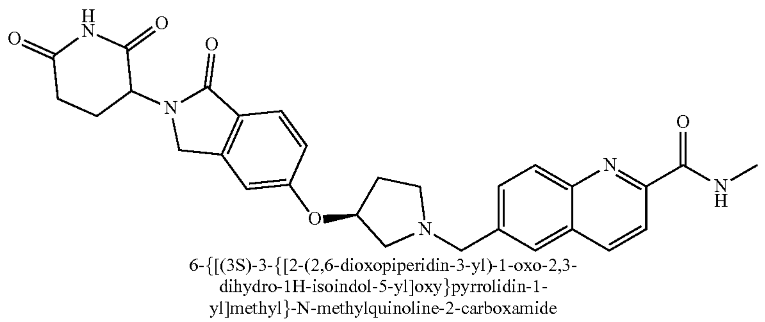 6-{[(3S)-3-{[2-(2,6-dioxopiperidin-3-yl)-1-oxo-2,3-dihydro-1H-isoindol-5-yl]oxy}pyrrolidin-1-yl]methyl}-N-methylquinoline-2-carboxamide | 0.011734 | 9.36 | 0.004274 | 26.91 |
| 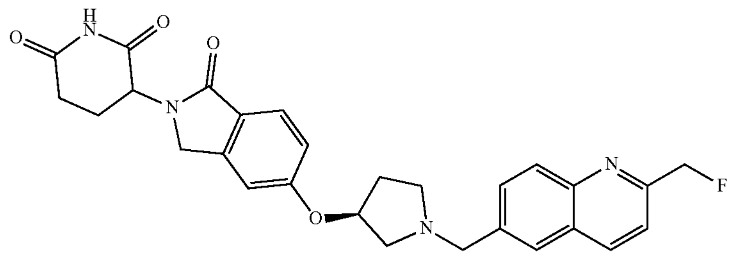 [SMILES: O=C1CCC(N2Cc3cc(O[C@H]4CCN(Cc5ccc6nc(CF)ccc6c5)C4)ccc3C2=O)C(=O)N1] 3-(5-{[(3S)-1-{[2-(fluoromethyl)quinolin-6-yl]methyl}pyrrolidin-3-yl]oxy}-1-oxo-2,3-dihydro-1H-isoindol-2-yl)piperidine-2,6-dione | 0.0118435 | 10.025 | 0.0016175 | 26.21 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 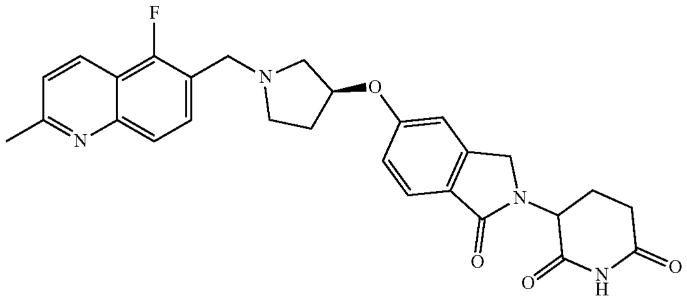 [SMILES: Cc1ccc2c(F)c(CN3CC[C@H](Oc4ccc5c(c4)CN(C4CCC(=O)NC4=O)C5=O)C3)ccc2n1] 3-(5-{[(3S)-1-[(5-fluoro-2-methylquinolin-6-yl)methyl]pyrrolidin-3-yl]oxy}-1-oxo-2,3-dihydro-1H-isoindol-2-yl)piperidine-2,6-dione | 0.008082 | 9.22 | 0.0015105 | 28.365 |
| 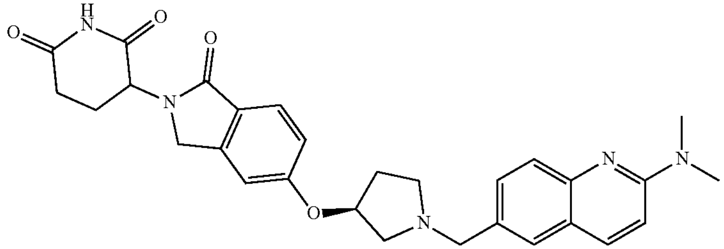 [SMILES: CN(C)c1ccc2cc(CN3CC[C@H](Oc4ccc5c(c4)CN(C4CCC(=O)NC4=O)C5=O)C3)ccc2n1] 3-(5-{[(3S)-1-{[2-(dimethylamino)quinolin-6-yl]methyl}pyrrolidin-3-yl]oxy}-1-oxo-2,3-dihydro-1H-isoindol-2-yl)piperidine-2,6-dione | 0.020002 | 12.34 | 0.002715 | 26.59 |
| 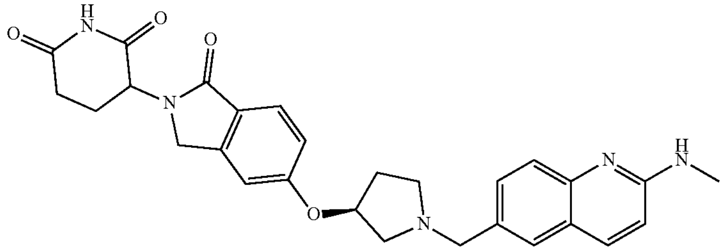 [SMILES: CNc1ccc2cc(CN3CC[C@H](Oc4ccc5c(c4)CN(C4CCC(=O)NC4=O)C5=O)C3)ccc2n1] | 0.021773 | 9.31 | 0.007212 | 31.06 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| --- | --- | --- | --- | --- |
| 3-(5-{[(3S)-1-{[2-(methylamino)quinolin-6-yl]methyl}pyrrolidin-3-yl]oxy}-1-oxo-2,3-dihydro-1H-isoindol-2-yl)piperidine-2,6-dione | | | | |
| 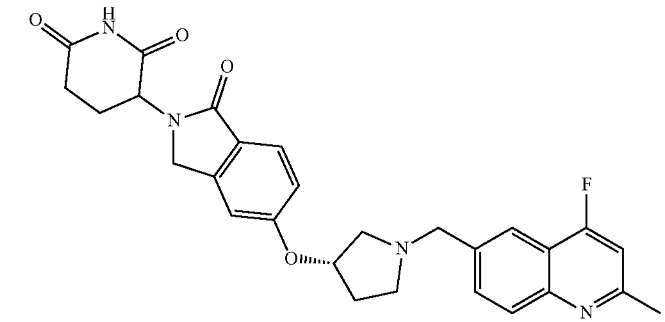 [SMILES: Cc1cc(F)c2cc(CN3CC[C@H](Oc4ccc5c(c4)CN(C4CCC(=O)NC4=O)C5=O)C3)ccc2n1] 3-(5-{[(3S)-1-[(4-fluoro-2-methylquinolin-6-yl)methyl]pyrrolidin-3-yl]oxy}-1-oxo-2,3-dihydro-1H-isoindol-2-yl)piperidine-2,6-dione | 10 | 24.82 | 0.022689 | 69.445 |
| 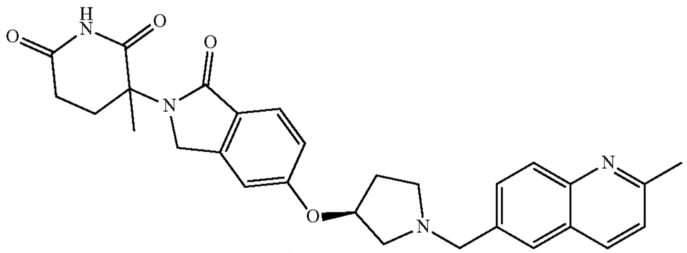 [SMILES: Cc1ccc2cc(CN3CC[C@H](Oc4ccc5c(c4)CN(C4(C)CCC(=O)NC4=O)C5=O)C3)ccc2n1] 3-methyl-3-(5-{[(3S)-1-[(2-methylquinolin-6-yl)methyl]pyrrolidin-3-yl]oxy}-1-oxo-2,3-dihydro-1H-isoindol-2-yl)piperidine-2,6-dione | 10 | 83.56 | 5.074278 | 69.05 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 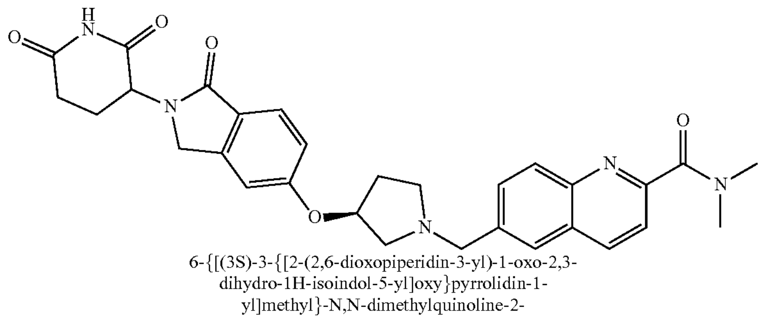 6-{[(3S)-3-{[2-(2,6-dioxopiperidin-3-yl)-1-oxo-2,3-dihydro-1H-isoindol-5-yl]oxy}pyrrolidin-1-yl]methyl}-N,N-dimethylquinoline-2-carboxamide | 0.017542 | 8.56 | 0.009052333 | 29.42 |
| 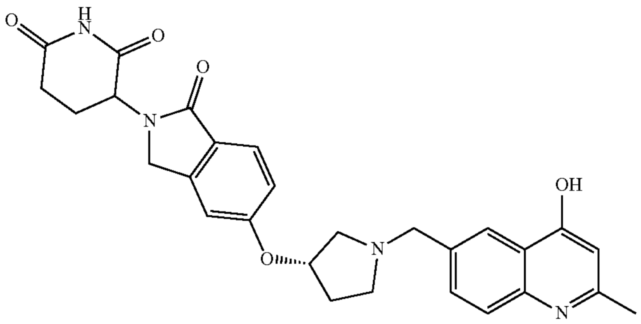 [SMILES: Cc1cc(O)c2cc(CN3CC[C@H](Oc4ccc5c(c4)CN(C4CCC(=O)NC4=O)C5=O)C3)ccc2n1] 3-(5-{[(3S)-1-[(4-hydroxy-2-methylquinolin-6-yl)methyl]pyrrolidin-3-yl]oxy}-1-oxo-2,3-dihydro-1H-isoindol-2-yl)piperidine-2,6-dione | 10 | 87.83 | 0.527523 | 73 |
| 3-(1-oxo-5-{[(3S)-1-{[(2-$^{2}$H)quinolin-6-yl]methyl}pyrrolidin-3-yl]oxy}-2,3-dihydro-1H-isoindol-2-yl)piperidine-2,6-dione | 0.026885 | 9.14 | 0.004093 | 29.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 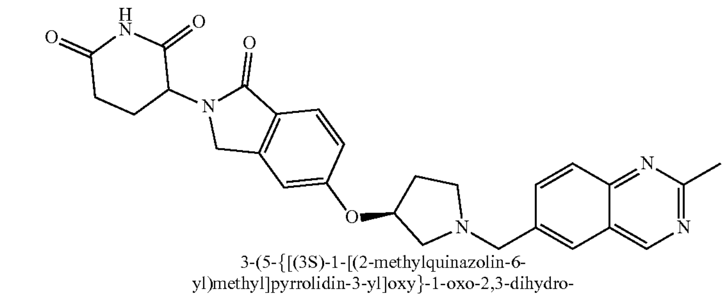 3-(5-{[(3S)-1-[(2-methylquinazolin-6-yl)methyl]pyrrolidin-3-yl]oxy}-1-oxo-2,3-dihydro-1H-isoindol-2-yl)piperidine-2,6-dione | 0.027056 | 7.995 | 0.0296425 | 34.5 |
| 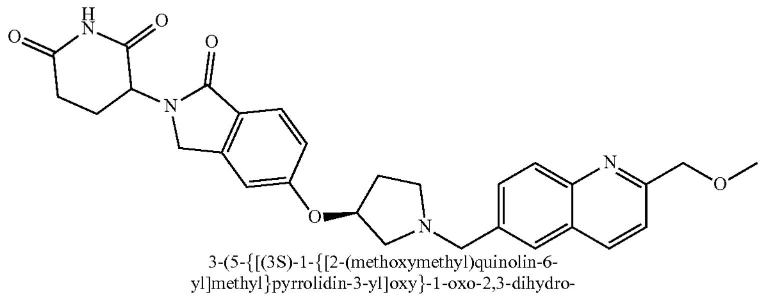 3-(5-{[(3S)-1-{[2-(methoxymethyl)quinolin-6-yl]methyl}pyrrolidin-3-yl]oxy}-1-oxo-2,3-dihydro-1H-isoindol-2-yl)piperidine-2,6-dione | 0.0205315 | 8.38 | 0.00555025 | 30.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 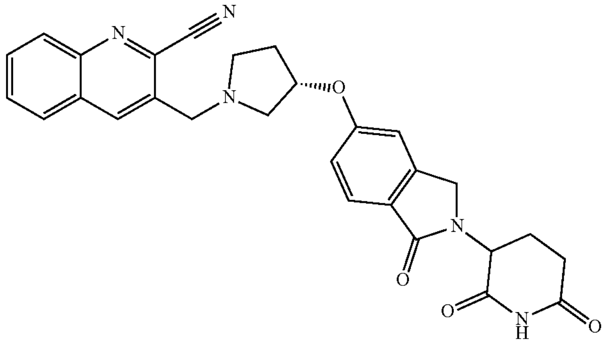 [SMILES: N#Cc1nc2ccccc2cc1CN1CC[C@H](Oc2ccc3c(c2)CN(C2CCC(=O)NC2=O)C3=O)C1] 3-{[(3S)-3-{[2-(2,6-dioxopiperidin-3-yl)-1-oxo-2,3-dihydro-1H-isoindol-5-yl]oxy}pyrrolidin-1-yl]methyl}quinoline-2-carbonitrile | 0.0058335 | 6.985 | 0.0012 | 29 |
| 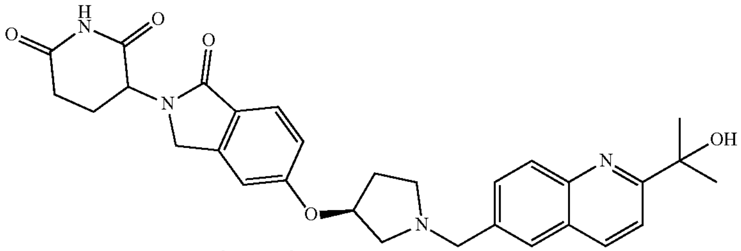 [SMILES: CC(C)(O)c1ccc2cc(CN3CC[C@H](Oc4ccc5c(c4)CN(C4CCC(=O)NC4=O)C5=O)C3)ccc2n1] 3-(5-{[(3S)-1-{[2-(2-hydroxypropan-2-yl)quinolin-6-yl]methyl}pyrrolidin-3-yl]oxy}-1-oxo-2,3-dihydro-1H-isoindol-2-yl)piperidine-2,6-dione | 0.01406375 | 11.2475 | 0.00409375 | 32.75 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 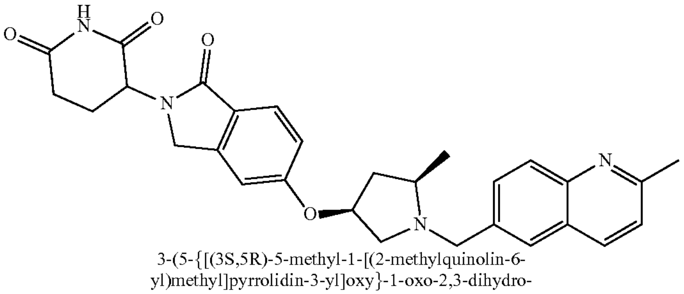 3-(5-{[(3S,5R)-5-methyl-1-[(2-methylquinolin-6-yl)methyl]pyrrolidin-3-yl]oxy}-1-oxo-2,3-dihydro-1H-isoindol-2-yl)piperidine-2,6-dione | 10 | 80.29 | 10 | 88.5 |
| 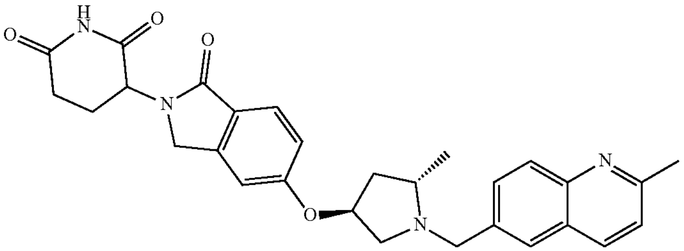 [SMILES: Cc1ccc2cc(CN3C[C@@H](Oc4ccc5c(c4)CN(C4CCC(=O)NC4=O)C5=O)C[C@@H]3C)ccc2n1] 3-(5-{[(3S,5S)-5-methyl-1-[(2-methylquinolin-6-yl)methyl]pyrrolidin-3-yl]oxy}-1-oxo-2,3-dihydro-1H-isoindol-2-yl)piperidine-2,6-dione | 10 | 82.25 | 0.0838905 | 64.5 |
| 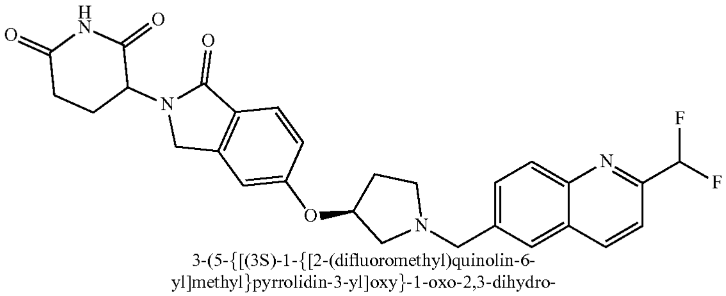 3-(5-{[(3S)-1-{[2-(difluoromethyl)quinolin-6-yl]methyl}pyrrolidin-3-yl]oxy}-1-oxo-2,3-dihydro- | 0.007169 | 9.875 | 0.002963749 | 29.41699982 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 1H-isoindol-2-yl)piperidine-2,6-dione | | | | |
| 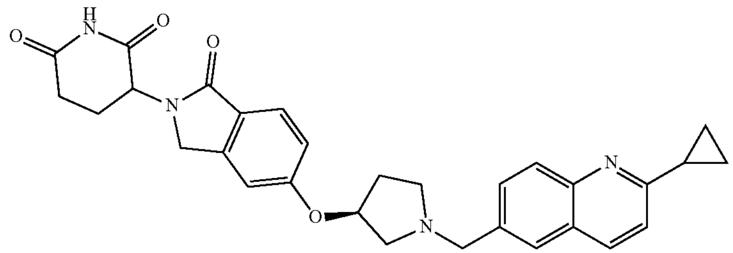 [SMILES: O=C1CCC(N2Cc3cc(O[C@H]4CCN(Cc5ccc6nc(C7CC7)ccc6c5)C4)ccc3C2=O)C(=O)N1]<br>3-(5-{[(3S)-1-[(2-cyclopropylquinolin-6-yl)methyl]pyrrolidin-3-yl]oxy}-1-oxo-2,3-dihydro-1H-isoindol-2-yl)piperidine-2,6-dione | 0.006025 | 12.12 | 0.002209667 | 34.33333333 |
| 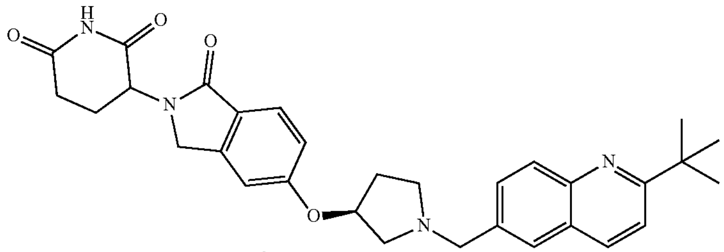 [SMILES: CC(C)(C)c1ccc2cc(CN3CC[C@H](Oc4ccc5c(c4)CN(C4CCC(=O)NC4=O)C5=O)C3)ccc2n1]<br>3-(5-{[(3S)-1-[(2-tert-butylquinolin-6-yl)methyl]pyrrolidin-3-yl]oxy}-1-oxo-2,3-dihydro-1H-isoindol-2-yl)piperidine-2,6-dione | 0.0092005 | 11.88 | 0.002796333 | 29 |
| 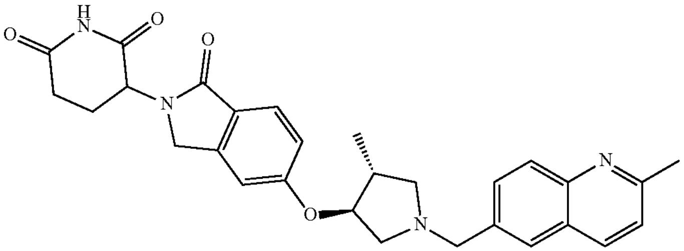 [SMILES: Cc1ccc2cc(CN3C[C@@H](C)[C@H](Oc4ccc5c(c4)CN(C4CCC(=O)NC4=O)C5=O)C3)ccc2n1] | 0.017482667 | 12.51 | 0.003101333 | 33 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(5-{[(3S,4R)-4-methyl-1-[(2-methylquinolin-6-yl)methyl]pyrrolidin-3-yl]oxy}-1-oxo-2,3-dihydro-1H-isoindol-2-yl)piperidine-2,6-dione | | | | |
| 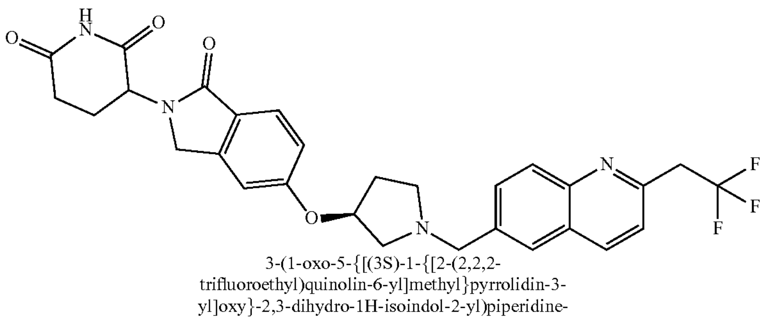 | 0.020820889 | 13.32366237 | 0.005403333 | 33.66666667 |
| 3-(1-oxo-5-{[(3S)-1-{[2-(2,2,2-trifluoroethyl)quinolin-6-yl]methyl}pyrrolidin-3-yl]oxy}-2,3-dihydro-1H-isoindol-2-yl)piperidine-2,6-dione | | | | |
| 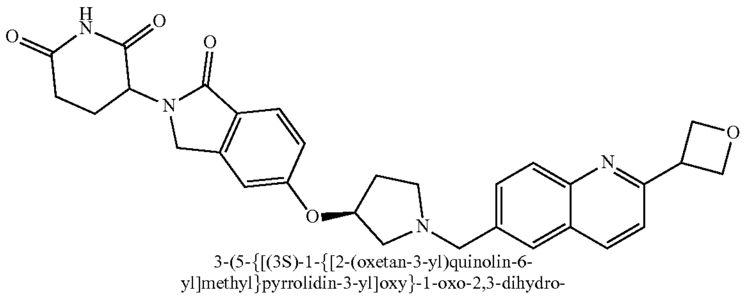 | 0.011189 | 10.08 | 0.003786333 | 33 |
| 3-(5-{[(3S)-1-{[2-(oxetan-3-yl)quinolin-6-yl]methyl}pyrrolidin-3-yl]oxy}-1-oxo-2,3-dihydro-1H-isoindol-2-yl)piperidine-2,6-dione | | | | |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 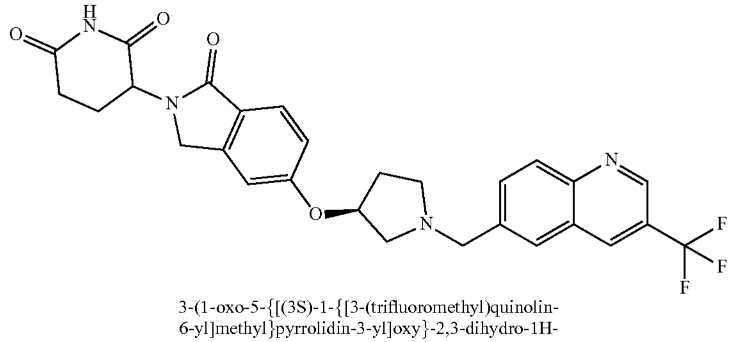 3-(1-oxo-5-{[(3S)-1-{[3-(trifluoromethyl)quinolin-6-yl]methyl}pyrrolidin-3-yl]oxy}-2,3-dihydro-1H-isoindol-2-yl)piperidine-2,6-dione | 0.015949 | 11.23 | 0.0028535 | 32 |
| 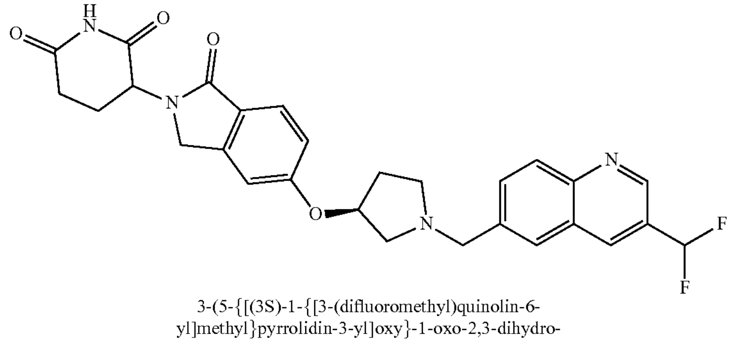 3-(5-{[(3S)-1-{[3-(difluoromethyl)quinolin-6-yl]methyl}pyrrolidin-3-yl]oxy}-1-oxo-2,3-dihydro-1H-isoindol-2-yl)piperidine-2,6-dione | 0.014376199 | 11.03622603 | 0.0033845 | 33 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 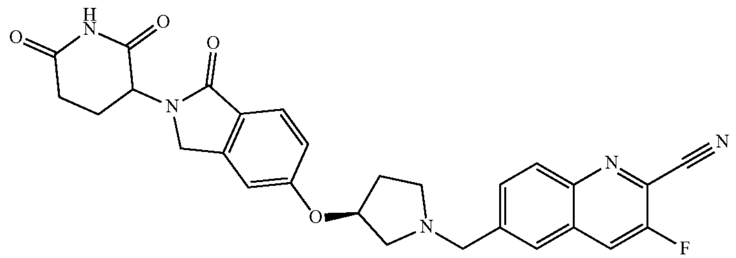 [SMILES: N#Cc1nc2ccc(CN3CC[C@H](Oc4ccc5c(c4)CN(C4CCC(=O)NC4=O)C5=O)C3)cc2cc1F] 6-{[(3S)-3-{[2-(2,6-dioxopiperidin-3-yl)-1-oxo-2,3-dihydro-1H-isoindol-5-yl]oxy}pyrrolidin-1-yl]methyl}-3-fluoroquinoline-2-carbonitrile | 0.0328415 | 12.265 | 0.007788 | 35 |
| 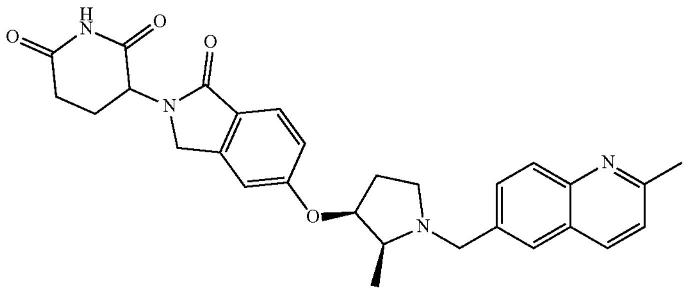 [SMILES: Cc1ccc2cc(CN3CC[C@H](Oc4ccc5c(c4)CN(C4CCC(=O)NC4=O)C5=O)[C@@H]3C)ccc2n1] 3-(5-{[(2S,3S)-2-methyl-1-[(2-methylquinolin-6-yl)methyl]pyrrolidin-3-yl]oxy}-1-oxo-2,3-dihydro-1H-isoindol-2-yl)piperidine-2,6-dione | 10 | 87.455 | 10 | 99.5 |
| 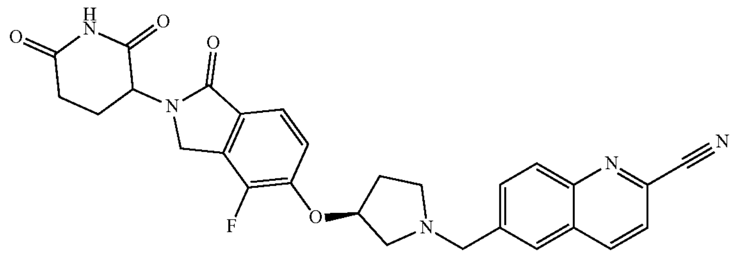 [SMILES: N#Cc1ccc2cc(CN3CC[C@H](Oc4ccc5c(c4F)CN(C4CCC(=O)NC4=O)C5=O)C3)ccc2n1] | 1.430267 | 62.465 | 0.061494 | 47 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 6-{[(3S)-3-{[2-(2,6-dioxopiperidin-3-yl)-4-fluoro-1-oxo-2,3-dihydro-1H-isoindol-5-yl]oxy}pyrrolidin-1-yl]methyl}quinoline-2-carbonitrile | | | | |
| 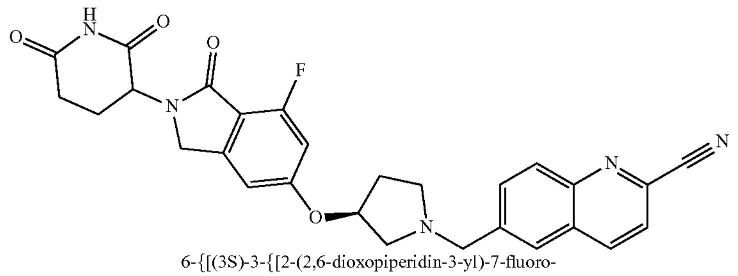 6-{[(3S)-3-{[2-(2,6-dioxopiperidin-3-yl)-7-fluoro-1-oxo-2,3-dihydro-1H-isoindol-5-yl]oxy}pyrrolidin-1-yl]methyl}quinoline-2-carbonitrile | 10 | 84.865 | 10 | 100.5 |
| 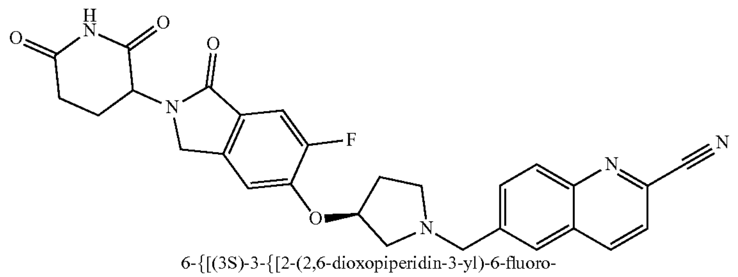 6-{[(3S)-3-{[2-(2,6-dioxopiperidin-3-yl)-6-fluoro-1-oxo-2,3-dihydro-1H-isoindol-5-yl]oxy}pyrrolidin-1-yl]methyl}quinoline-2-carbonitrile | 0.023819 | 8.55 | 0.0052795 | 30.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 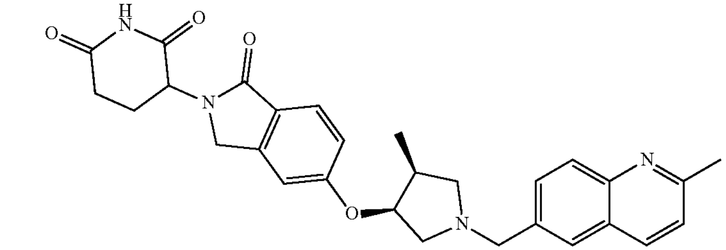 [SMILES: Cc1ccc2cc(CN3C[C@H](C)[C@H](Oc4ccc5c(c4)CN(C4CCC(=O)NC4=O)C5=O)C3)ccc2n1] 3-(5-{[(3S,4S)-4-methyl-1-[(2-methylquinolin-6-yl)methyl]pyrrolidin-3-yl]oxy}-1-oxo-2,3-dihydro-1H-isoindol-2-yl)piperidine-2,6-dione | 10 | 85.96 | 10 | 88.5 |
| 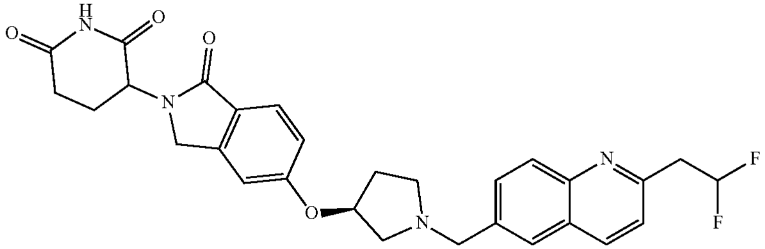 [SMILES: O=C1CCC(N2Cc3cc(O[C@H]4CCN(Cc5ccc6nc(CC(F)F)ccc6c5)C4)ccc3C2=O)C(=O)N1] 3-(5-{[(3S)-1-{[2-(2,2-difluoroethyl)quinolin-6-yl]methyl}pyrrolidin-3-yl]oxy}-1-oxo-2,3-dihydro-1H-isoindol-2-yl)piperidine-2,6-dione | 0.350048333 | 21.74333333 | 0.0334365 | 43.5 |
| 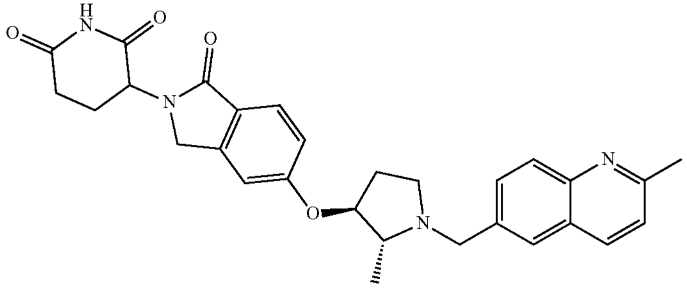 [SMILES: Cc1ccc2cc(CN3CC[C@H](Oc4ccc5c(c4)CN(C4CCC(=O)NC4=O)C5=O)[C@H]3C)ccc2n1] | 0.338928 | 28.935 | 0.016668 | 34 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(5-{[(2R,3S)-2-methyl-1-[(2-methylquinolin-6-yl)methyl]pyrrolidin-3-yl]oxy}-1-oxo-2,3-dihydro-1H-isoindol-2-yl)piperidine-2,6-dione | | | | |
| 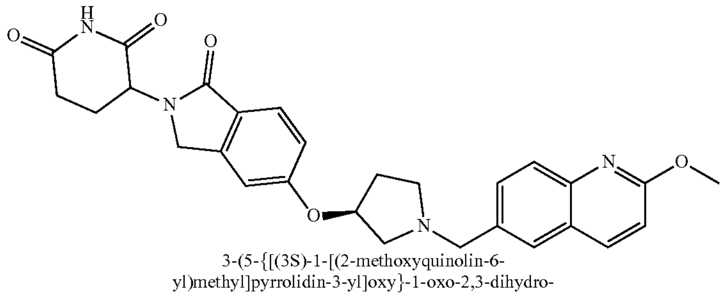 3-(5-{[(3S)-1-[(2-methoxyquinolin-6-yl)methyl]pyrrolidin-3-yl]oxy}-1-oxo-2,3-dihydro-1H-isoindol-2-yl)piperidine-2,6-dione | 0.045233 | 19.71 | 0.006238 | 36 |
| 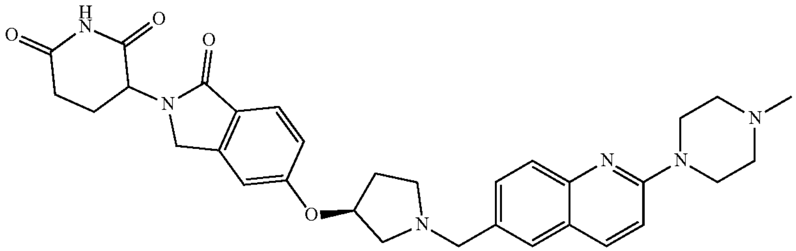 [SMILES: CN1CCN(c2ccc3cc(CN4CC[C@H](Oc5ccc6c(c5)CN(C5CCC(=O)NC5=O)C6=O)C4)ccc3n2)CC1] 3-(5-{[(3S)-1-{[2-(4-methylpiperazin-1-yl)quinolin-6-yl]methyl}pyrrolidin-3-yl]oxy}-1-oxo-2,3-dihydro-1H-isoindol-2-yl)piperidine-2,6-dione | 0.019985 | 13.365 | 0.006775 | 33.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 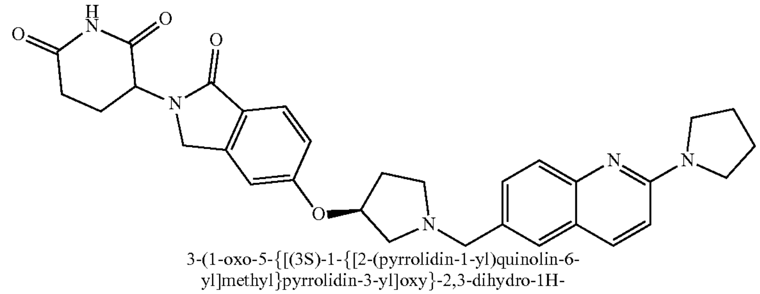 3-(1-oxo-5-{[(3S)-1-{[2-(pyrrolidin-1-yl)quinolin-6-yl]methyl}pyrrolidin-3-yl]oxy}-2,3-dihydro-1H-isoindol-2-yl)piperidine-2,6-dione | 0.0060175 | 11.865 | 0.003971 | 34 |
| 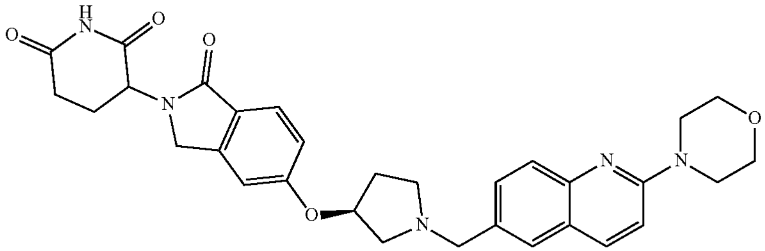 3-(5-{[(3S)-1-{[2-(morpholin-4-yl)quinolin-6-yl]methyl}pyrrolidin-3-yl]oxy}-1-oxo-2,3-dihydro-1H-isoindol-2-yl)piperidine-2,6-dione | 0.011928 | 12.168 | 0.0026926 | 35 |
| 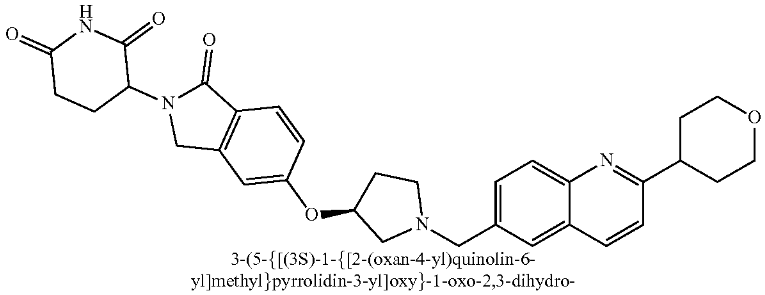 3-(5-{[(3S)-1-{[2-(oxan-4-yl)quinolin-6-yl]methyl}pyrrolidin-3-yl]oxy}-1-oxo-2,3-dihydro- | 0.004904576 | 12.83315243 | 0.0028338 | 32.6 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 1H-isoindol-2-yl)piperidine-2,6-dione | | | | |
| 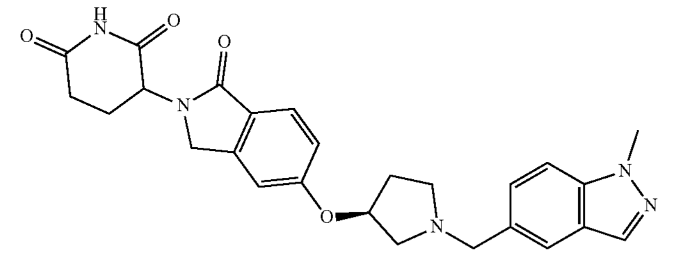 [SMILES: Cn1ncc2cc(CN3CC[C@H](Oc4ccc5c(c4)CN(C4CCC(=O)NC4=O)C5=O)C3)ccc21] 3-(5-{[(3S)-1-[(1-methyl-1H-indazol-5-yl)methyl]pyrrolidin-3-yl]oxy}-1-oxo-2,3-dihydro-1H-isoindol-2-yl)piperidine-2,6-dione | 10 | 86.69 | 0.068849 | 61 |
| 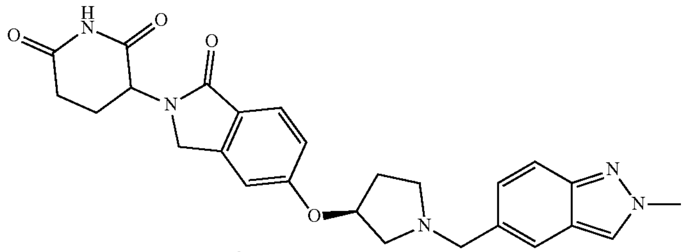 [SMILES: Cn1cc2cc(CN3CC[C@H](Oc4ccc5c(c4)CN(C4CCC(=O)NC4=O)C5=O)C3)ccc2n1] 3-(5-{[(3S)-1-[(2-methyl-2H-indazol-5-yl)methyl]pyrrolidin-3-yl]oxy}-1-oxo-2,3-dihydro-1H-isoindol-2-yl)piperidine-2,6-dione | 10 | 81.985 | 0.040491 | 52 |
| 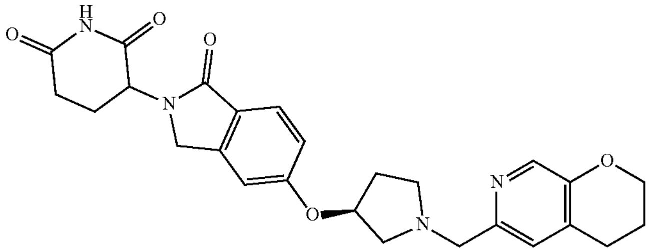 [SMILES: O=C1CCC(N2Cc3cc(O[C@H]4CCN(Cc5cc6c(cn5)OCCC6)C4)ccc3C2=O)C(=O)N1] | 0.1533802 | 12.988 | 0.012255 | 33 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(1-oxo-5-{[(3S)-1-({2H,3H,4H-pyrano[2,3-c]pyridin-6-yl}methyl)pyrrolidin-3-yl]oxy}-2,3-dihydro-1H-isoindol-2-yl)piperidine-2,6-dione | | | | |
| 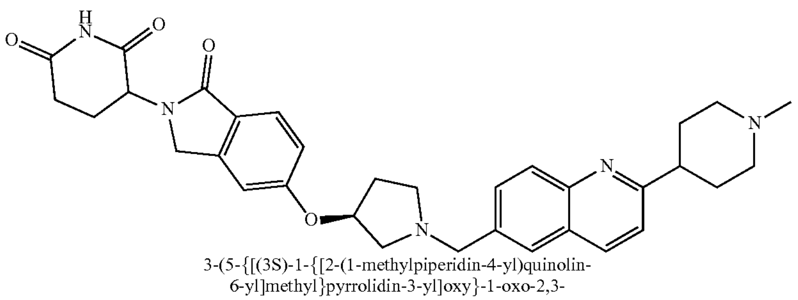<br>3-(5-{[(3S)-1-{[2-(1-methylpiperidin-4-yl)quinolin-6-yl]methyl}pyrrolidin-3-yl]oxy}-1-oxo-2,3-dihydro-1H-isoindol-2-yl)piperidine-2,6-dione | 0.021691 | 7.273333333 | 0.028597 | 30 |
| 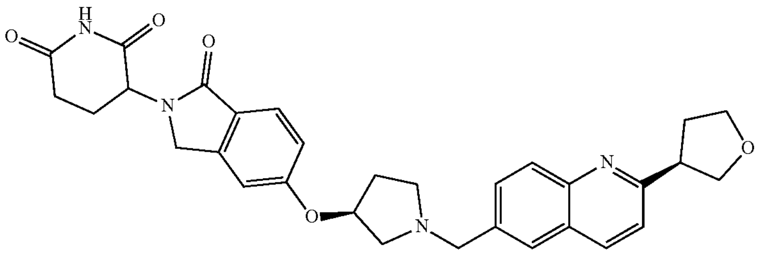 [SMILES: O=C1CCC(N2Cc3cc(O[C@H]4CCN(Cc5ccc6nc([C@H]7CCOC7)ccc6c5)C4)ccc3C2=O)C(=O)N1]<br>3-(1-oxo-5-{[(3S)-1-({2-[(3R)-oxolan-3-yl]quinolin-6-yl}methyl)pyrrolidin-3-yl]oxy}-2,3-dihydro-1H-isoindol-2-yl)piperidine-2,6-dione | 0.006073778 | 8.454073752 | 0.00271 | 29 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 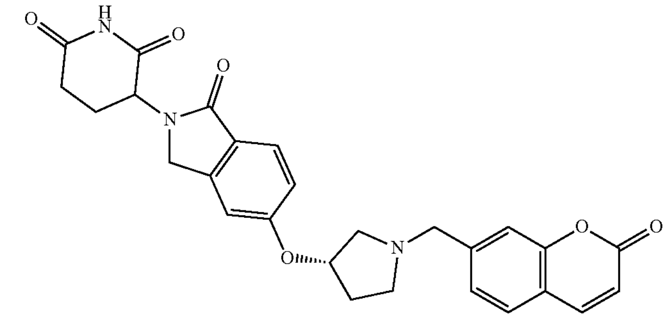 [SMILES: O=C1CCC(N2Cc3cc(O[C@H]4CCN(Cc5ccc6ccc(=O)oc6c5)C4)ccc3C2=O)C(=O)N1] 3-(1-oxo-5-{[(3S)-1-[(2-oxo-2H-chromen-7-yl)methyl]pyrrolidin-3-yl]oxy}-2,3-dihydro-1H-isoindol-2-yl)piperidine-2,6-dione | 10 | 85.765 | 0.028782 | 55 |
| 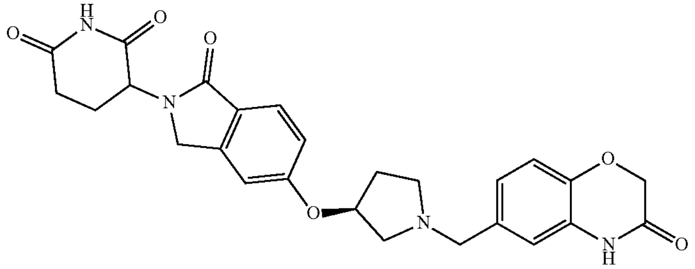 [SMILES: O=C1CCC(N2Cc3cc(O[C@H]4CCN(Cc5ccc6c(c5)NC(=O)CO6)C4)ccc3C2=O)C(=O)N1] 3-(1-oxo-5-{[(3S)-1-[(3-oxo-3,4-dihydro-2H-1,4-benzoxazin-6-yl)methyl]pyrrolidin-3-yl]oxy}-2,3-dihydro-1H-isoindol-2-yl)piperidine-2,6-dione | 10 | 88.425 | 0.557928 | 70 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 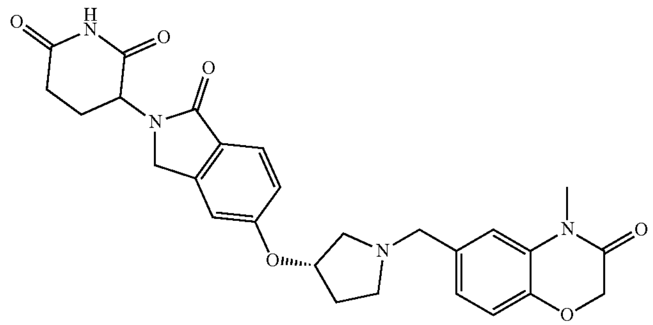 [SMILES: CN1C(=O)COc2ccc(CN3CC[C@H](Oc4ccc5c(c4)CN(C4CCC(=O)NC4=O)C5=O)C3)cc21] 3-(5-{[(3S)-1-[(4-methyl-3-oxo-3,4-dihydro-2H-1,4-benzoxazin-6-yl)methyl]pyrrolidin-3-yl]oxy}-1-oxo-2,3-dihydro-1H-isoindol-2-yl)piperidine-2,6-dione | 10 | 84.725 | 0.047916 | 56 |
| 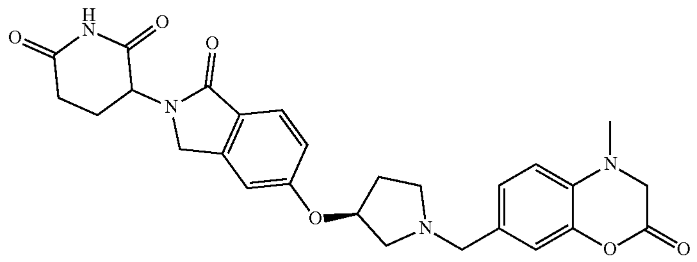 [SMILES: CN1CC(=O)Oc2cc(CN3CC[C@H](Oc4ccc5c(c4)CN(C4CCC(=O)NC4=O)C5=O)C3)ccc21] 3-(5-{[(3S)-1-[(4-methyl-2-oxo-3,4-dihydro-2H-1,4-benzoxazin-7-yl)methyl]pyrrolidin-3-yl]oxy}-1-oxo-2,3-dihydro-1H-isoindol-2-yl)piperidine-2,6-dione | 10 | 91.915 | 0.024151 | 52 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 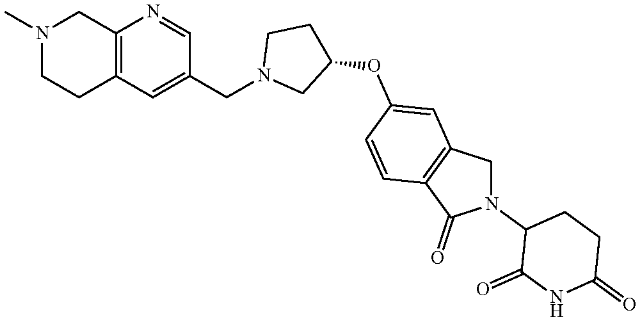 [SMILES: CN1CCc2cc(CN3CC[C@H](Oc4ccc5c(c4)CN(C4CCC(=O)NC4=O)C5=O)C3)cnc2C1] 3-(5-{[(3S)-1-[(7-methyl-5,6,7,8-tetrahydro-1,7-naphthyridin-3-yl)methyl]pyrrolidin-3-yl]oxy}-1-oxo-2,3-dihydro-1H-isoindol-2-yl)piperidine-2,6-dione | 0.425376 | 11.9 | 0.0651 | 34 |
| 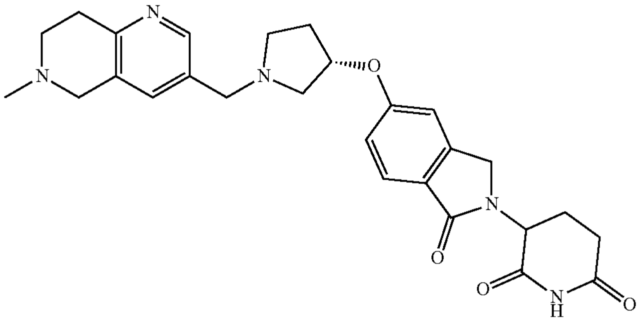 [SMILES: CN1CCc2ncc(CN3CC[C@H](Oc4ccc5c(c4)CN(C4CCC(=O)NC4=O)C5=O)C3)cc2C1] 3-(5-{[(3S)-1-[(6-methyl-5,6,7,8-tetrahydro-1,6-naphthyridin-3-yl)methyl]pyrrolidin-3-yl]oxy}-1-oxo-2,3-dihydro-1H-isoindol-2-yl)piperidine-2,6-dione | 5.0452695 | 33.405 | 0.216096 | 34 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 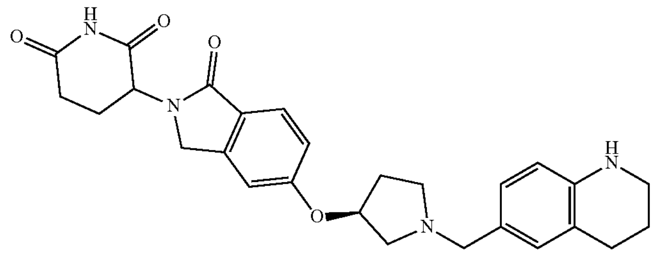 [SMILES: O=C1CCC(N2Cc3cc(O[C@H]4CCN(Cc5ccc6c(c5)CCCN6)C4)ccc3C2=O)C(=O)N1] 3-(1-oxo-5-{[(3S)-1-[(1,2,3,4-tetrahydroquinolin-6-yl)methyl]pyrrolidin-3-yl]oxy}-2,3-dihydro-1H-isoindol-2-yl)piperidine-2,6-dione | 10 | 93.175 | 3.333333 | 79 |
| 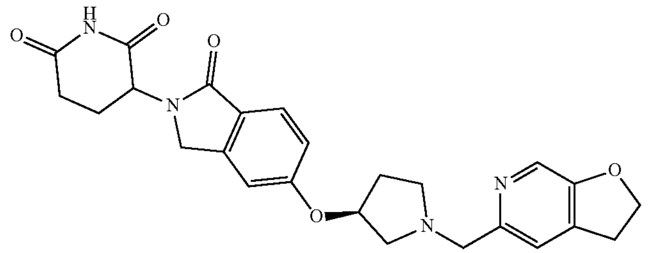 [SMILES: O=C1CCC(N2Cc3cc(O[C@H]4CCN(Cc5cc6c(cn5)OCC6)C4)ccc3C2=O)C(=O)N1] 3-(5-{[(3S)-1-({2H,3H-furo[2,3-c]pyridin-5-yl}methyl)pyrrolidin-3-yl]oxy}-1-oxo-2,3-dihydro-1H-isoindol-2-yl)piperidine-2,6-dione | 0.751104 | 25.455 | 0.020799 | 34 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 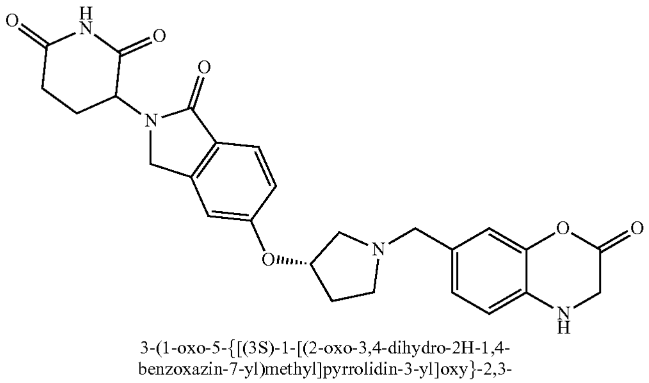 3-(1-oxo-5-{[(3S)-1-[(2-oxo-3,4-dihydro-2H-1,4-benzoxazin-7-yl)methyl]pyrrolidin-3-yl]oxy}-2,3-dihydro-1H-isoindol-2-yl)piperidine-2,6-dione | 10 | 90.28 | 10 | 80 |
| 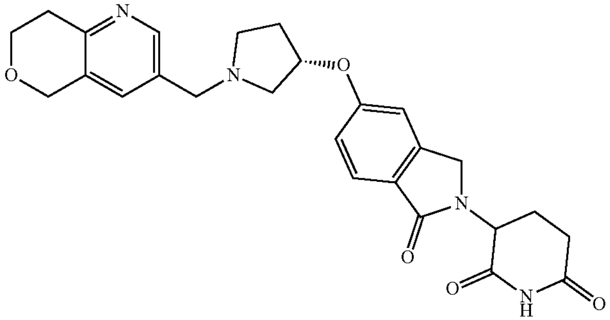 3-(1-oxo-5-{[(3S)-1-({5H,7H,8H-pyrano[4,3-b]pyridin-3-yl}methyl)pyrrolidin-3-yl]oxy}-2,3-dihydro-1H-isoindol-2-yl)piperidine-2,6-dione | 0.45619 | 11.67 | 0.039855 | 35 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 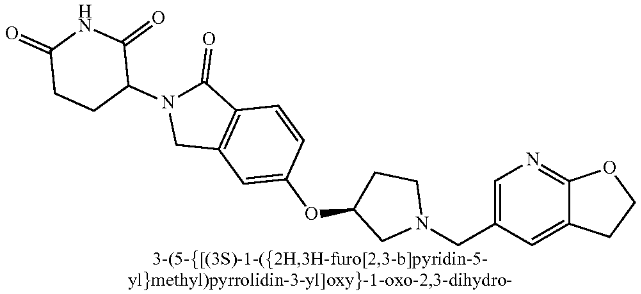 3-(5-{[(3S)-1-({2H,3H-furo[2,3-b]pyridin-5-yl}methyl)pyrrolidin-3-yl]oxy}-1-oxo-2,3-dihydro-1H-isoindol-2-yl)piperidine-2,6-dione | 2.037107 | 40.58 | 0.060113 | 42 |
| 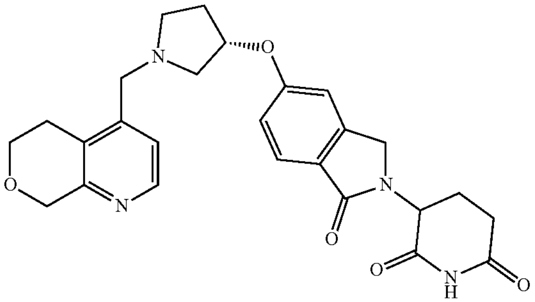 [SMILES: O=C1CCC(N2Cc3cc(O[C@H]4CCN(Cc5ccnc6c5CCOC6)C4)ccc3C2=O)C(=O)N1] 3-(1-oxo-5-{[(3S)-1-({5H,6H,8H-pyrano[3,4-b]pyridin-4-yl}methyl)pyrrolidin-3-yl]oxy}-2,3-dihydro-1H-isoindol-2-yl)piperidine-2,6-dione | 1.281827 | 56.39 | 0.062727 | 51 |
| 3-(5-{[(3S)-1-{[3-fluoro(2-$^2$H)quinolin-6-yl]methyl}pyrrolidin-3-yl]oxy}-1-oxo-2,3-dihydro-1H-isoindol-2-yl)piperidine-2,6-dione | 0.094935 | 21.68 | 0.003573 | 35 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 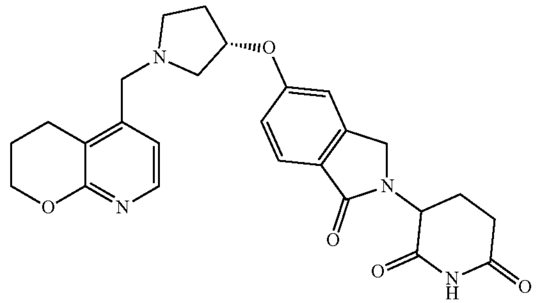 [SMILES: O=C1CCC(N2Cc3cc(O[C@H]4CCN(Cc5ccnc6c5CCCO6)C4)ccc3C2=O)C(=O)N1] 3-(1-oxo-5-{[(3S)-1-({2H,3H,4H-pyrano[2,3-b]pyridin-5-yl}methyl)pyrrolidin-3-yl]oxy}-2,3-dihydro-1H-isoindol-2-yl)piperidine-2,6-dione | 0.489245 | 27.04 | 0.038911 | 44 |
| 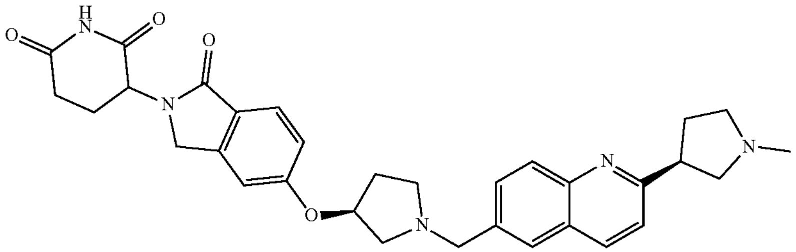 [SMILES: CN1CC[C@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(3S)-1-methylpyrrolidin-3-yl]quinolin-6-yl}methyl)pyrrolidin-3-yl]oxy}-1-oxo-2,3-dihydro-1H-isoindol-2-yl)piperidine-2,6-dione | 0.059719 | 12.73 | 0.067535 | 37 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 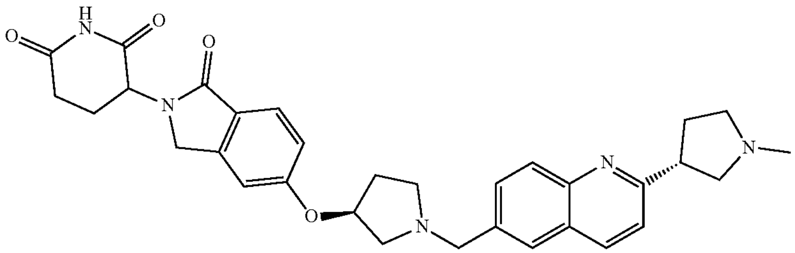 [SMILES: CN1CC[C@@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(3R)-1-methylpyrrolidin-3-yl]quinolin-6-yl}methyl)pyrrolidin-3-yl]oxy}-1-oxo-2,3-dihydro-1H-isoindol-2-yl)piperidine-2,6-dione | 0.090523 | 11.69 | 0.067423 | 37 |
| 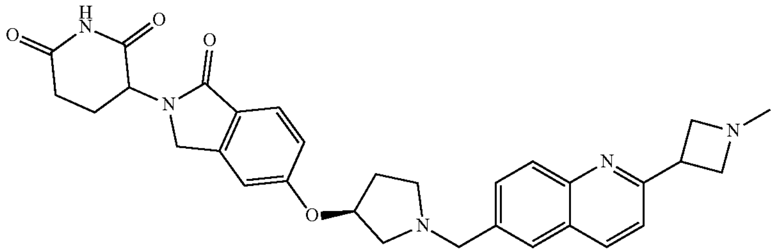 [SMILES: CN1CC(c2ccc3cc(CN4CC[C@H](Oc5ccc6c(c5)CN(C5CCC(=O)NC5=O)C6=O)C4)ccc3n2)C1] 3-(5-{[(3S)-1-{[2-(1-methylazetidin-3-yl)quinolin-6-yl]methyl}pyrrolidin-3-yl]oxy}-1-oxo-2,3-dihydro-1H-isoindol-2-yl)piperidine-2,6-dione | 0.093382 | 11.97 | 0.100257 | 32 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 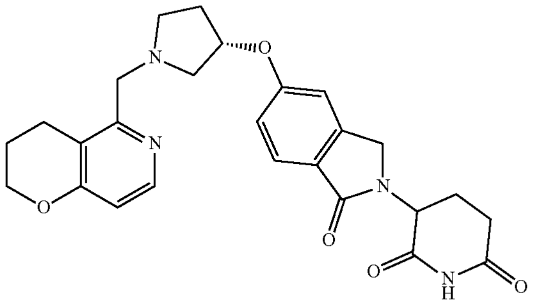 [SMILES: O=C1CCC(N2Cc3cc(O[C@H]4CCN(Cc5nccc6c5CCCO6)C4)ccc3C2=O)C(=O)N1] 3-(1-oxo-5-{[(3S)-1-({2H,3H,4H-pyrano[3,2-c]pyridin-5-yl}methyl)pyrrolidin-3-yl]oxy}-2,3-dihydro-1H-isoindol-2-yl)piperidine-2,6-dione | 0.122294 | 16.99 | 0.016149 | 36 |
| 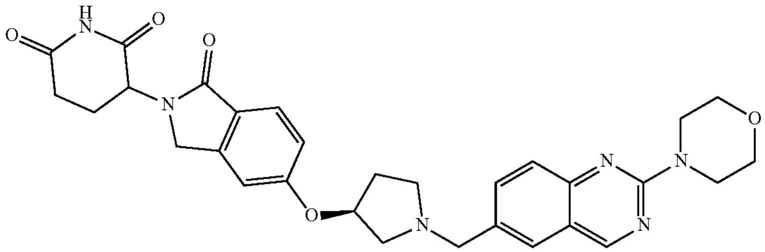 3-(5-{[(3S)-1-{[2-(morpholin-4-yl)quinazolin-6-yl]methyl}pyrrolidin-3-yl]oxy}-1-oxo-2,3-dihydro-1H-isoindol-2-yl)piperidine-2,6-dione | 0.016093333 | 9.636666667 | 0.007198667 | 31.33333333 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 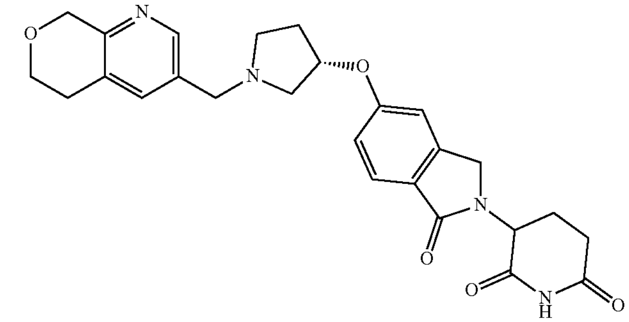 [SMILES: O=C1CCC(N2Cc3cc(O[C@H]4CCN(Cc5cnc6c(c5)CCOC6)C4)ccc3C2=O)C(=O)N1] 3-(1-oxo-5-{[(3S)-1-({5H,6H,8H-pyrano[3,4-b]pyridin-3-yl}methyl)pyrrolidin-3-yl]oxy}-2,3-dihydro-1H-isoindol-2-yl)piperidine-2,6-dione | 0.25197 | 8.89 | 0.027288 | 30 |
| 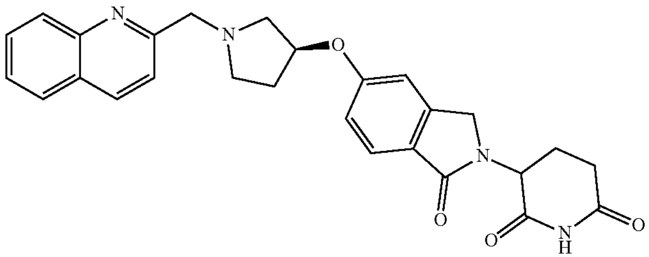 [SMILES: O=C1CCC(N2Cc3cc(O[C@H]4CCN(Cc5ccc6ccccc6n5)C4)ccc3C2=O)C(=O)N1] 3-(1-oxo-5-{[(3S)-1-[(quinolin-2-yl)methyl]pyrrolidin-3-yl]oxy}-2,3-dihydro-1H-isoindol-2-yl)piperidine-2,6-dione | 10 | 81.45 | 0.025584 | 58 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 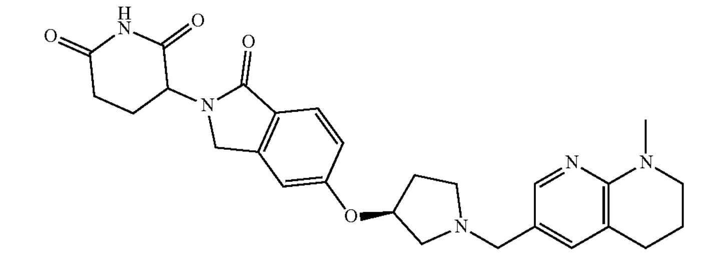 [SMILES: CN1CCCc2cc(CN3CC[C@H](Oc4ccc5c(c4)CN(C4CCC(=O)NC4=O)C5=O)C3)cnc21] 3-(5-{[(3S)-1-[(8-methyl-5,6,7,8-tetrahydro-1,8-naphthyridin-3-yl)methyl]pyrrolidin-3-yl]oxy}-1-oxo-2,3-dihydro-1H-isoindol-2-yl)piperidine-2,6-dione | 10 | 79.28 | 0.019112 | 58 |
| 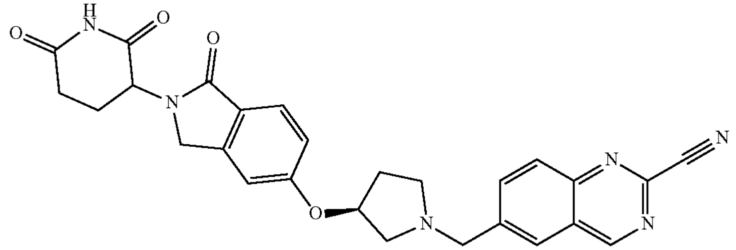 [SMILES: N#Cc1ncc2cc(CN3CC[C@H](Oc4ccc5c(c4)CN(C4CCC(=O)NC4=O)C5=O)C3)ccc2n1] 6-{[(3S)-3-{[2-(2,6-dioxopiperidin-3-yl)-1-oxo-2,3-dihydro-1H-isoindol-5-yl]oxy}pyrrolidin-1-yl]methyl}quinazoline-2-carbonitrile | 0.072981 | 17.27 | 0.012084 | 35 |
| 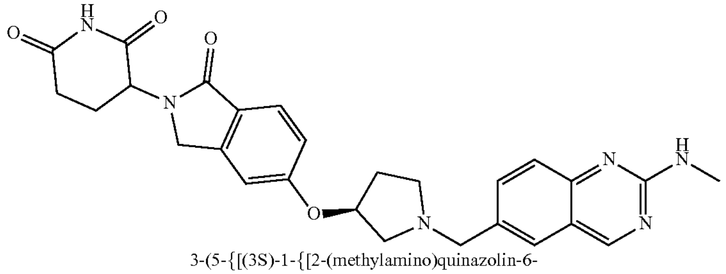 3-(5-{[(3S)-1-{[2-(methylamino)quinazolin-6- | 0.23363 | 22.48 | 0.044777 | 41 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| yl]methyl}pyrrolidin-3-yl]oxy}-1-oxo-2,3-dihydro-1H-isoindol-2-yl)piperidine-2,6-dione | | | | |
| 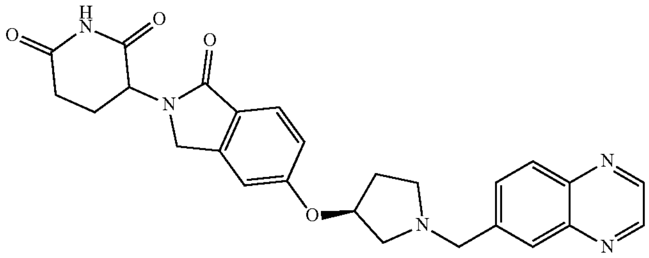 [SMILES: O=C1CCC(N2Cc3cc(O[C@H]4CCN(Cc5ccc6nccnc6c5)C4)ccc3C2=O)C(=O)N1] 3-(1-oxo-5-{[(3S)-1-[(quinoxalin-6-yl)methyl]pyrrolidin-3-yl]oxy}-2,3-dihydro-1H-isoindol-2-yl)piperidine-2,6-dione | 0.878894 | 70.03 | 0.014242 | 43 |
| 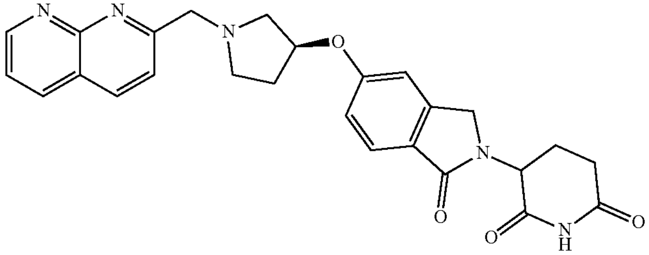 [SMILES: O=C1CCC(N2Cc3cc(O[C@H]4CCN(Cc5ccc6cccnc6n5)C4)ccc3C2=O)C(=O)N1] 3-(5-{[(3S)-1-[(1,8-naphthyridin-2-yl)methyl]pyrrolidin-3-yl]oxy}-1-oxo-2,3-dihydro-1H-isoindol-2-yl)piperidine-2,6-dione | 1.024062 | 65.94 | 0.291757 | 75 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 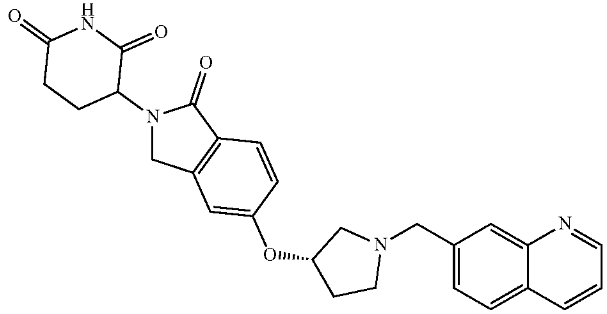 [SMILES: O=C1CCC(N2Cc3cc(O[C@H]4CCN(Cc5ccc6cccnc6c5)C4)ccc3C2=O)C(=O)N1] 3-(1-oxo-5-{[(3S)-1-[(quinolin-7-yl)methyl]pyrrolidin-3-yl]oxy}-2,3-dihydro-1H-isoindol-2-yl)piperidine-2,6-dione | 10 | 76.22 | 0.030123 | 57 |
| 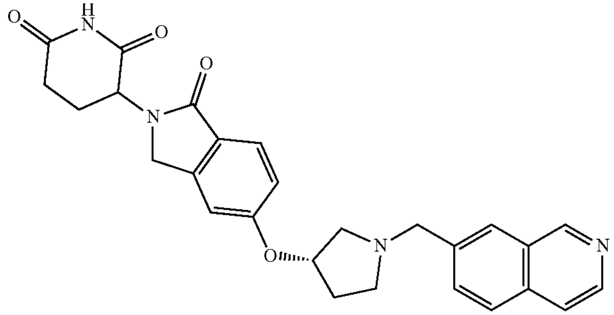 [SMILES: O=C1CCC(N2Cc3cc(O[C@H]4CCN(Cc5ccc6ccncc6c5)C4)ccc3C2=O)C(=O)N1] 3-(5-{[(3S)-1-[(isoquinolin-7-yl)methyl]pyrrolidin-3-yl]oxy}-1-oxo-2,3-dihydro-1H-isoindol-2-yl)piperidine-2,6-dione | 0.290157 | 54.45 | 0.020955 | 46 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 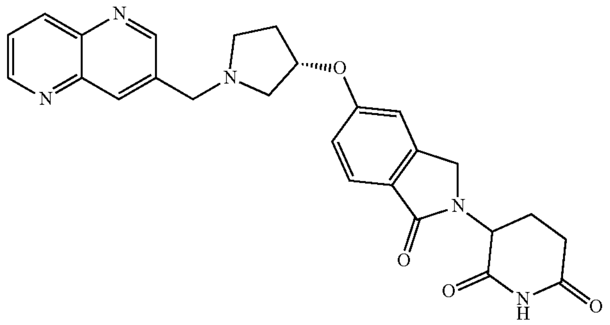 3-(5-{[(3S)-1-[(1,5-naphthyridin-3-yl)methyl]pyrrolidin-3-yl]oxy}-1-oxo-2,3-dihydro-1H-isoindol-2-yl)piperidine-2,6-dione | 0.560501 | 73.34 | 0.075391 | 66 |
| 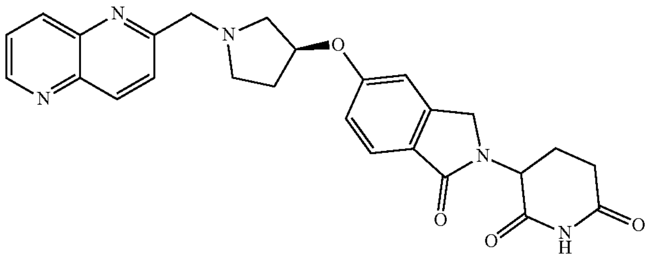 [SMILES: O=C1CCC(N2Cc3cc(O[C@H]4CCN(Cc5ccc6ncccc6n5)C4)ccc3C2=O)C(=O)N1] 3-(5-{[(3S)-1-[(1,5-naphthyridin-2-yl)methyl]pyrrolidin-3-yl]oxy}-1-oxo-2,3-dihydro-1H-isoindol-2-yl)piperidine-2,6-dione | 2.523437 | 54.03 | 0.027916 | 37 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 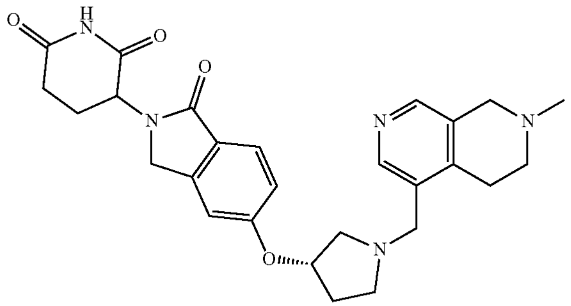 [SMILES: CN1CCc2c(cncc2CN2CC[C@H](Oc3ccc4c(c3)CN(C3CCC(=O)NC3=O)C4=O)C2)C1] 3-(5-{[(3S)-1-[(7-methyl-5,6,7,8-tetrahydro-2,7-naphthyridin-4-yl)methyl]pyrrolidin-3-yl]oxy}-1-oxo-2,3-dihydro-1H-isoindol-2-yl)piperidine-2,6-dione | 10 | 84.06 | 0.558139 | 68 |
| 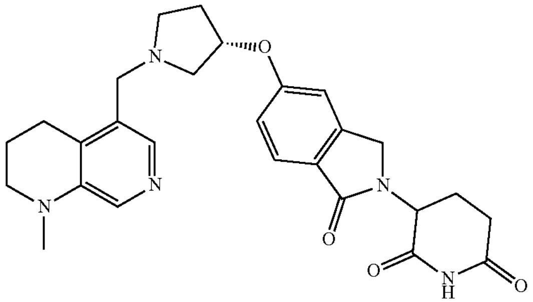 [SMILES: CN1CCCc2c(CN3CC[C@H](Oc4ccc5c(c4)CN(C4CCC(=O)NC4=O)C5=O)C3)cncc21] 3-(5-{[(3S)-1-[(1-methyl-1,2,3,4-tetrahydro-1,7-naphthyridin-5-yl)methyl]pyrrolidin-3-yl]oxy}-1-oxo-2,3-dihydro-1H-isoindol-2-yl)piperidine-2,6-dione | 0.312721 | 43.26 | 0.019621 | 40 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 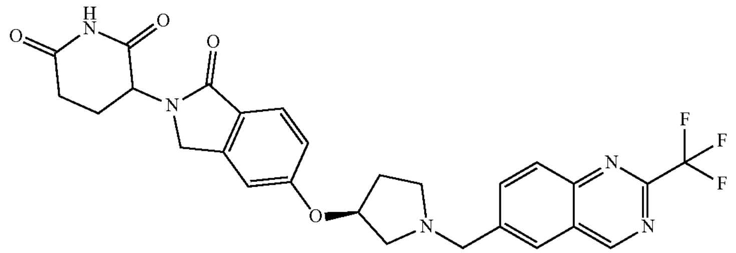 [SMILES: O=C1CCC(N2Cc3cc(O[C@H]4CCN(Cc5ccc6nc(C(F)(F)F)ncc6c5)C4)ccc3C2=O)C(=O)N1] 3-(1-oxo-5-{[(3S)-1-{[2-(trifluoromethyl)quinazolin-6-yl]methyl}pyrrolidin-3-yl]oxy}-2,3-dihydro-1H-isoindol-2-yl)piperidine-2,6-dione | 0.033225997 | 14.73823163 | 0.008108667 | 29.66666667 |
| 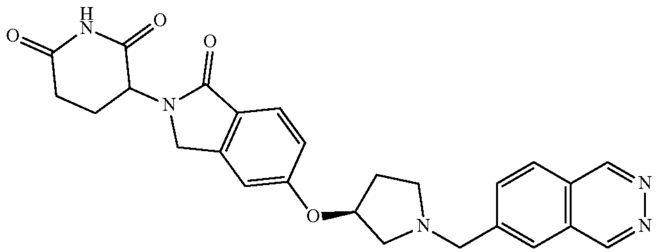 [SMILES: O=C1CCC(N2Cc3cc(O[C@H]4CCN(Cc5ccc6cnncc6c5)C4)ccc3C2=O)C(=O)N1] 3-(1-oxo-5-{[(3S)-1-[(phthalazin-6-yl)methyl]pyrrolidin-3-yl]oxy}-2,3-dihydro-1H-isoindol-2-yl)piperidine-2,6-dione | 0.88301 | 16.7 | 0.148388 | 38 |
| 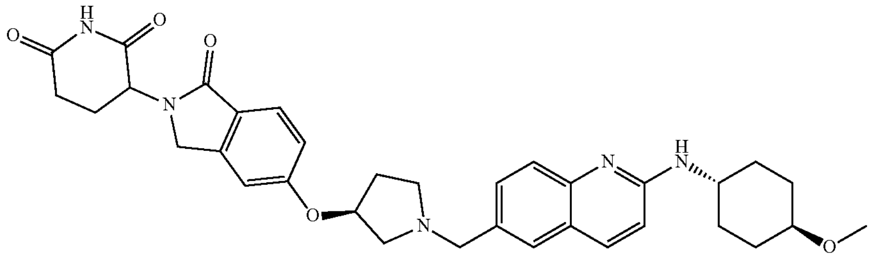 [SMILES: CO[C@H]1CC[C@H](Nc2ccc3cc(CN4CC[C@H](Oc5ccc6c(c5)CN(C5CCC(=O)NC5=O)C6=O)C4)ccc3n2)CC1] 3-(1-oxo-5-{[(3S)-1-[(2-{[(1r,4r)-4- | 0.005046 | 8.26 | 0.006284 | 32.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| methoxycyclohexyl]amino}quinolin-6-yl)methyl]pyrrolidin-3-yl]oxy}-2,3-dihydro-1H-isoindol-2-yl)piperidine-2,6-dione | | | | |
| 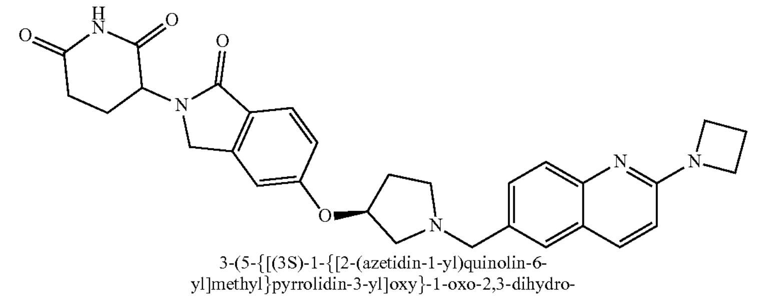 | 0.006712 | 10.91 | 0.0030055 | 37 |
| 3-(5-{[(3S)-1-{[2-(azetidin-1-yl)quinolin-6-yl]methyl}pyrrolidin-3-yl]oxy}-1-oxo-2,3-dihydro-1H-isoindol-2-yl)piperidine-2,6-dione | | | | |
| 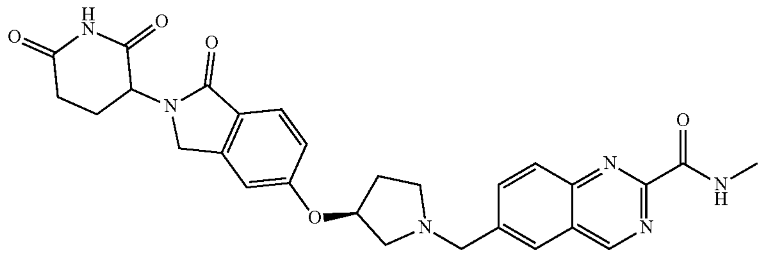 [SMILES: CNC(=O)c1ncc2cc(CN3CC[C@H](Oc4ccc5c(c4)CN(C4CCC(=O)NC4=O)C5=O)C3)ccc2n1] | 0.33716 | 8.51 | 0.174845 | 38 |
| 6-{[(3S)-3-{[2-(2,6-dioxopiperidin-3-yl)-1-oxo-2,3-dihydro-1H-isoindol-5-yl]oxy}pyrrolidin-1-yl]methyl}-N-methylquinazoline-2-carboxamide | | | | |
| 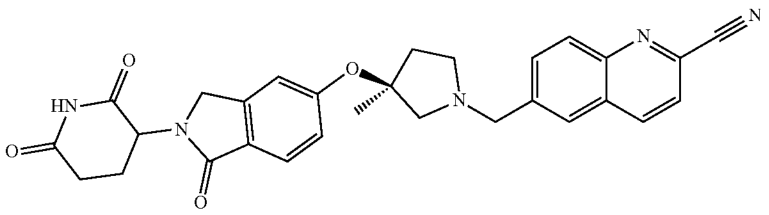 [SMILES: C[C@]1(Oc2ccc3c(c2)CN(C2CCC(=O)NC2=O)C3=O)CCN(Cc2ccc3nc(C#N)ccc3c2)C1] | 10 | 80.88 | 10 | 94 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 6-{[(3S)-3-{[2-(2,6-dioxopiperidin-3-yl)-1-oxo-2,3-dihydro-1H-isoindol-5-yl]oxy}-3-methylpyrrolidin-1-yl]methyl}quinoline-2-carbonitrile 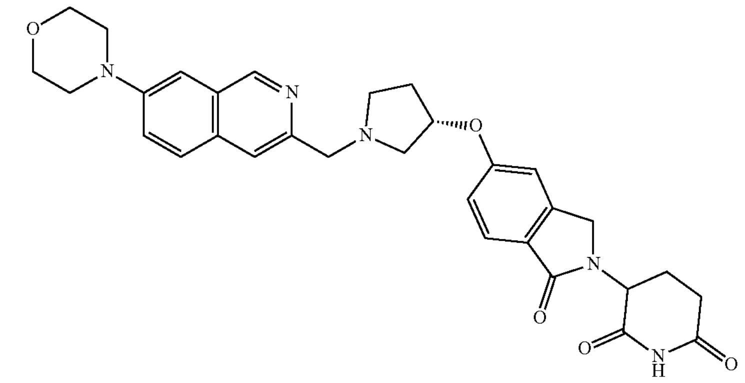 [SMILES: O=C1CCC(N2Cc3cc(O[C@H]4CCN(Cc5cc6ccc(N7CCOCC7)cc6cn5)C4)ccc3C2=O)C(=O)N1] | 0.003174 | 6.72 | 0.003821 | 36 |
| 3-(5-{[(3S)-1-{[7-(morpholin-4-yl)isoquinolin-3-yl]methyl}pyrrolidin-3-yl]oxy}-1-oxo-2,3-dihydro-1H-isoindol-2-yl)piperidine-2,6-dione 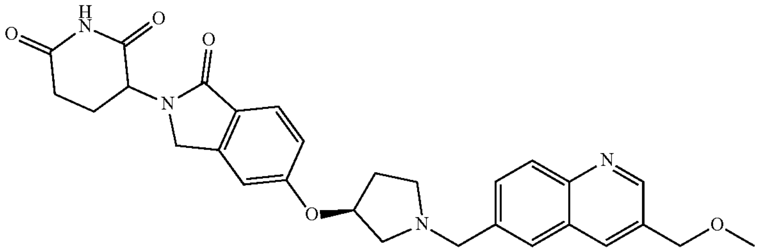 [SMILES: COCc1cnc2ccc(CN3CC[C@H](Oc4ccc5c(c4)CN(C4CCC(=O)NC4=O)C5=O)C3)cc2c1] 3-(5-{[(3S)-1-{[3-(methoxymethyl)quinolin-6-yl]methyl}pyrrolidin-3-yl]oxy}-1-oxo-2,3-dihydro-1H-isoindol-2-yl)piperidine-2,6-dione | 0.011074 | 7.64 | 0.004282 | 33 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 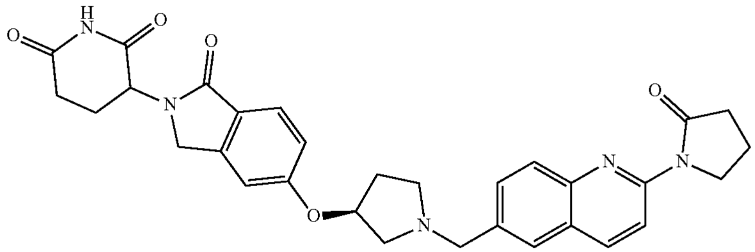 [SMILES: O=C1CCC(N2Cc3cc(O[C@H]4CCN(Cc5ccc6nc(N7CCCC7=O)ccc6c5)C4)ccc3C2=O)C(=O)N1] 3-(1-oxo-5-{[(3S)-1-{[2-(2-oxopyrrolidin-1-yl)quinolin-6-yl]methyl}pyrrolidin-3-yl]oxy}-2,3-dihydro-1H-isoindol-2-yl)piperidine-2,6-dione | 0.007185 | 10.36 | 0.0018285 | 31 |
| 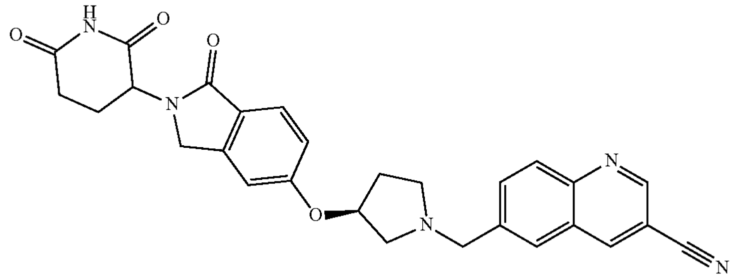 [SMILES: N#Cc1cnc2ccc(CN3CC[C@H](Oc4ccc5c(c4)CN(C4CCC(=O)NC4=O)C5=O)C3)cc2c1] 6-{[(3S)-3-{[2-(2,6-dioxopiperidin-3-yl)-1-oxo-2,3-dihydro-1H-isoindol-5-yl]oxy}pyrrolidin-1-yl]methyl}quinoline-3-carbonitrile | 0.044026 | 12.18 | 0.004183 | 33 |
| 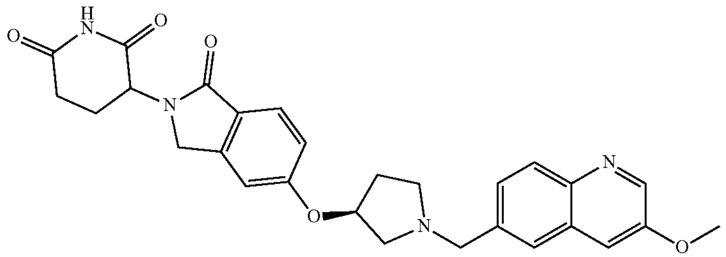 [SMILES: COc1cnc2ccc(CN3CC[C@H](Oc4ccc5c(c4)CN(C4CCC(=O)NC4=O)C5=O)C3)cc2c1] 3-(5-{[(3S)-1-[(3-methoxyquinolin-6- | 0.019087 | 12.81 | 0.003255 | 34 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| yl)methyl]pyrrolidin-3-yl]oxy}-1-oxo-2,3-dihydro-1H-isoindol-2-yl)piperidine-2,6-dione | | | | |
| 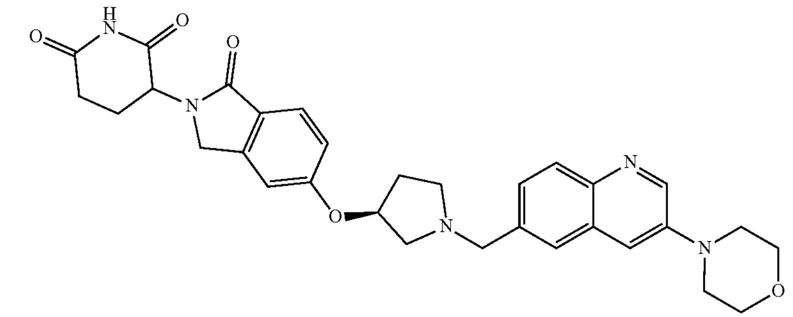 [SMILES: O=C1CCC(N2Cc3cc(O[C@H]4CCN(Cc5ccc6ncc(N7CCOCC7)cc6c5)C4)ccc3C2=O)C(=O)N1] 3-(5-{[(3S)-1-{[3-(morpholin-4-yl)quinolin-6-yl]methyl}pyrrolidin-3-yl]oxy}-1-oxo-2,3-dihydro-1H-isoindol-2-yl)piperidine-2,6-dione | 0.002963 | 7.83 | 0.0031885 | 27 |
| 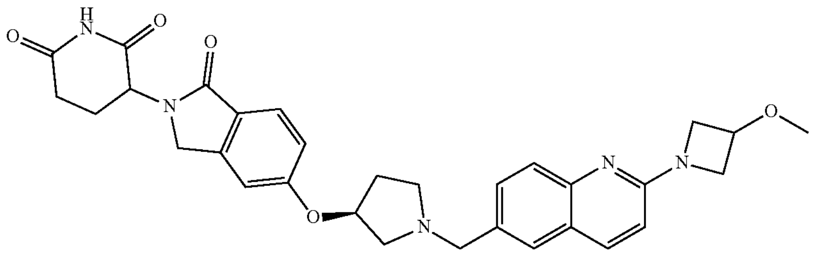 [SMILES: COC1CN(c2ccc3cc(CN4CC[C@H](Oc5ccc6c(c5)CN(C5CCC(=O)NC5=O)C6=O)C4)ccc3n2)C1] 3-(5-{[(3S)-1-{[2-(3-methoxyazetidin-1-yl)quinolin-6-yl]methyl}pyrrolidin-3-yl]oxy}-1-oxo-2,3-dihydro-1H-isoindol-2-yl)piperidine-2,6-dione | 0.006816 | 11.6 | 0.002301 | 36 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 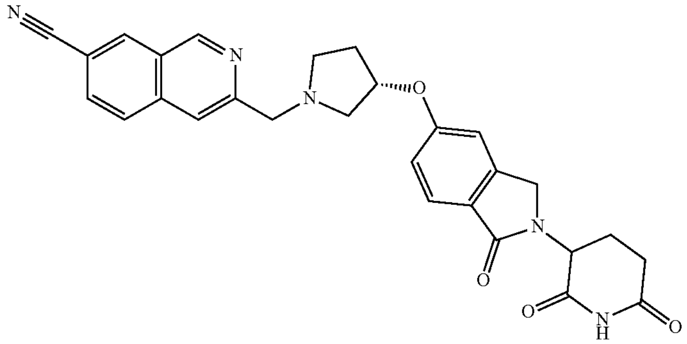 [SMILES: N#Cc1ccc2cc(CN3CC[C@H](Oc4ccc5c(c4)CN(C4CCC(=O)NC4=O)C5=O)C3)ncc2c1] 3-{[(3S)-3-{[2-(2,6-dioxopiperidin-3-yl)-1-oxo-2,3-dihydro-1H-isoindol-5-yl]oxy}pyrrolidin-1-yl]methyl}isoquinoline-7-carbonitrile | 0.010040237 | 8.661117213 | 0.001871 | 29 |
| 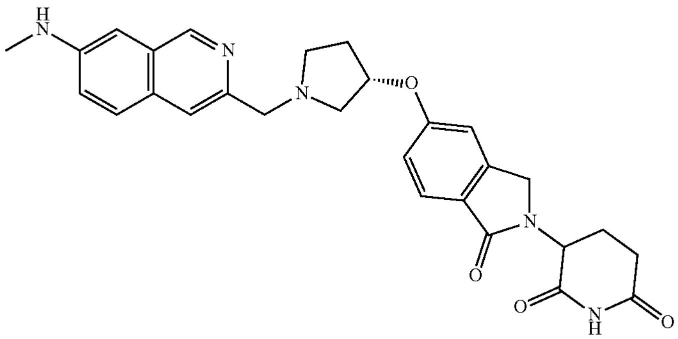 [SMILES: CNc1ccc2cc(CN3CC[C@H](Oc4ccc5c(c4)CN(C4CCC(=O)NC4=O)C5=O)C3)ncc2c1] 3-(5-{[(3S)-1-{[7-(methylamino)isoquinolin-3-yl]methyl}pyrrolidin-3-yl]oxy}-1-oxo-2,3-dihydro-1H-isoindol-2-yl)piperidine-2,6-dione | 0.042138 | 12.46 | 0.009012 | 32 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 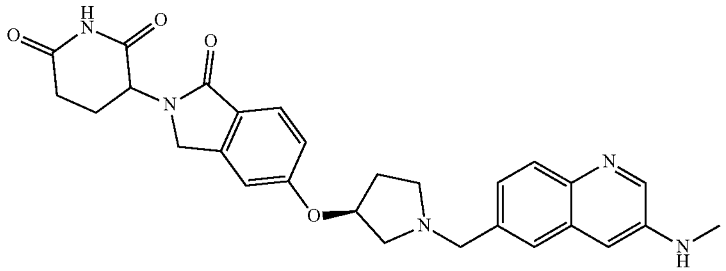 [SMILES: CNc1cnc2ccc(CN3CC[C@H](Oc4ccc5c(c4)CN(C4CCC(=O)NC4=O)C5=O)C3)cc2c1] 3-(5-{[(3S)-1-{[3-(methylamino)quinolin-6-yl]methyl}pyrrolidin-3-yl]oxy}-1-oxo-2,3-dihydro-1H-isoindol-2-yl)piperidine-2,6-dione | 0.204197 | 16.86 | 0.018128 | 34 |
| 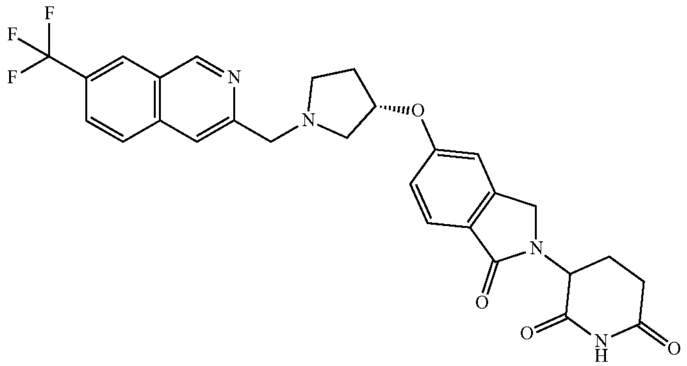 [SMILES: O=C1CCC(N2Cc3cc(O[C@H]4CCN(Cc5cc6ccc(C(F)(F)F)cc6cn5)C4)ccc3C2=O)C(=O)N1] 3-(1-oxo-5-{[(3S)-1-{[7-(trifluoromethyl)isoquinolin-3-yl]methyl}pyrrolidin-3-yl]oxy}-2,3-dihydro-1H-isoindol-2-yl)piperidine-2,6-dione | 0.001138 | 6.875 | 0.001473 | 31 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 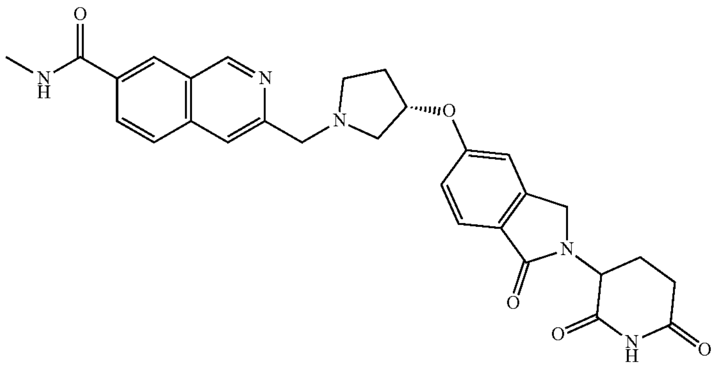 [SMILES: CNC(=O)c1ccc2cc(CN3CC[C@H](Oc4ccc5c(c4)CN(C4CCC(=O)NC4=O)C5=O)C3)ncc2c1] 3-{[(3S)-3-{[2-(2,6-dioxopiperidin-3-yl)-1-oxo-2,3-dihydro-1H-isoindol-5-yl]oxy}pyrrolidin-1-yl]methyl}-N-methylisoquinoline-7-carboxamide | 0.066839 | 7.51 | 0.0297975 | 28 |
| 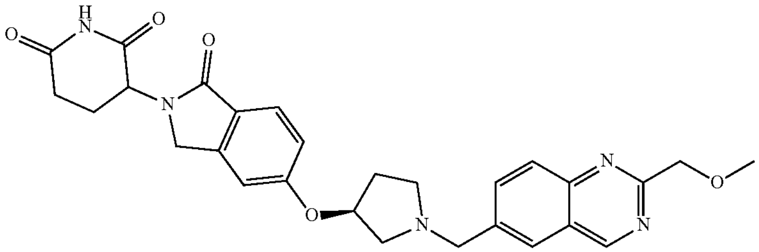 [SMILES: COCc1ncc2cc(CN3CC[C@H](Oc4ccc5c(c4)CN(C4CCC(=O)NC4=O)C5=O)C3)ccc2n1] 3-(5-{[(3S)-1-{[2-(methoxymethyl)quinazolin-6-yl]methyl}pyrrolidin-3-yl]oxy}-1-oxo-2,3-dihydro-1H-isoindol-2-yl)piperidine-2,6-dione | 0.078519 | 9.73 | 0.047498 | 32 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 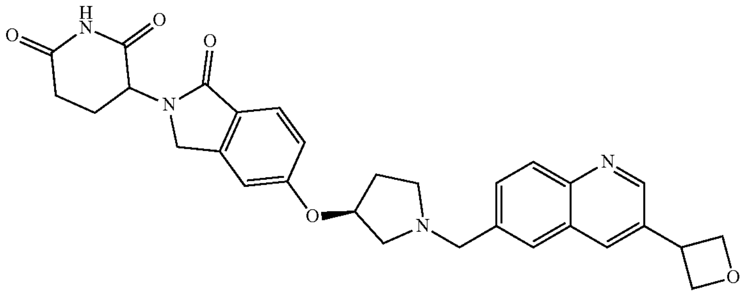 [SMILES: O=C1CCC(N2Cc3cc(O[C@H]4CCN(Cc5ccc6ncc(C7COC7)cc6c5)C4)ccc3C2=O)C(=O)N1] 3-(5-{[(3S)-1-{[3-(oxetan-3-yl)quinolin-6-yl]methyl}pyrrolidin-3-yl]oxy}-1-oxo-2,3-dihydro-1H-isoindol-2-yl)piperidine-2,6-dione | 0.005036 | 8.08 | 0.0046725 | 30 |
| 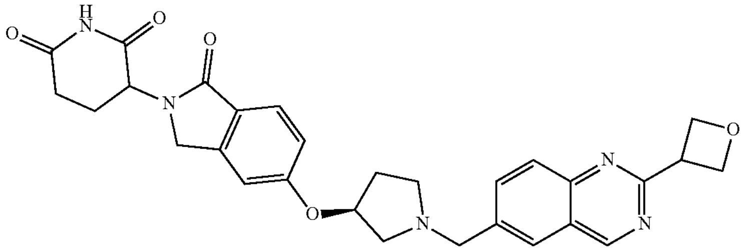 [SMILES: O=C1CCC(N2Cc3cc(O[C@H]4CCN(Cc5ccc6nc(C7COC7)ncc6c5)C4)ccc3C2=O)C(=O)N1] 3-(5-{[(3S)-1-{[2-(oxetan-3-yl)quinazolin-6-yl]methyl}pyrrolidin-3-yl]oxy}-1-oxo-2,3-dihydro-1H-isoindol-2-yl)piperidine-2,6-dione | 0.016665 | 7.8 | 0.016819 | 30 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 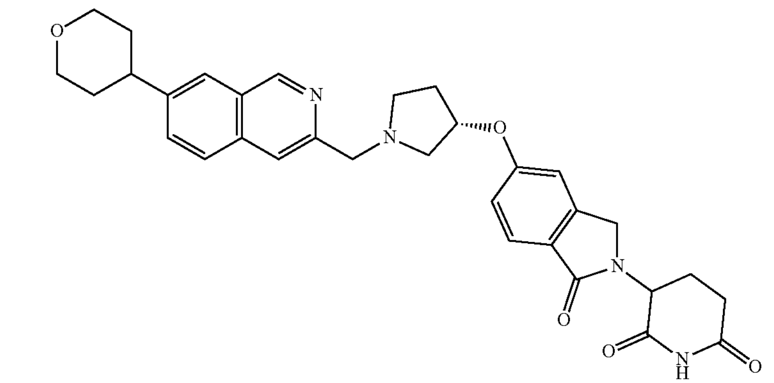 3-(5-{[(3S)-1-{[7-(oxan-4-yl)isoquinolin-3-yl]methyl}pyrrolidin-3-yl]oxy}-1-oxo-2,3-dihydro-1H-isoindol-2-yl)piperidine-2,6-dione | 0.0020869 | 8.822234489 | 0.00145675 | 29.75 |
| 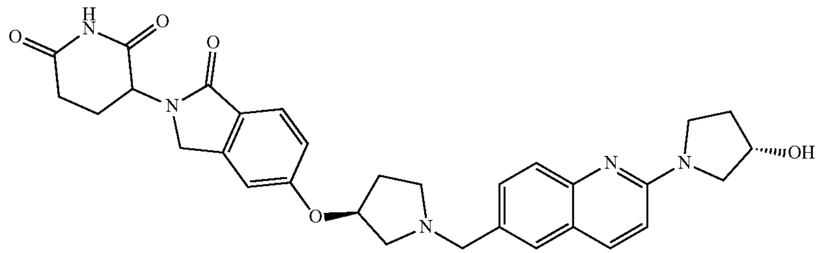 [SMILES: O=C1CCC(N2Cc3cc(O[C@H]4CCN(Cc5ccc6nc(N7CC[C@H](O)C7)ccc6c5)C4)ccc3C2=O)C(=O)N1] 3-(5-{[(3S)-1-({2-[(3S)-3-hydroxypyrrolidin-1-yl]quinolin-6-yl}methyl)pyrrolidin-3-yl]oxy}-1-oxo-2,3-dihydro-1H-isoindol-2-yl)piperidine-2,6-dione | 0.011445 | 7.1 | 0.0103925 | 36.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 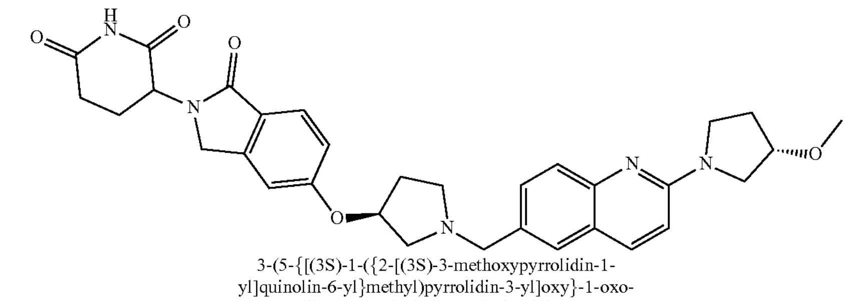 3-(5-{[(3S)-1-({2-[(3S)-3-methoxypyrrolidin-1-yl]quinolin-6-yl}methyl)pyrrolidin-3-yl]oxy}-1-oxo-2,3-dihydro-1H-isoindol-2-yl)piperidine-2,6-dione | 0.001578 | 9.12 | 0.003576 | 34 |
| 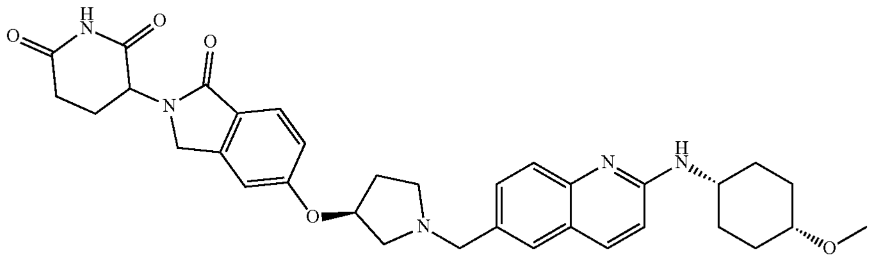 [SMILES: CO[C@H]1CC[C@@H](Nc2ccc3cc(CN4CC[C@H](Oc5ccc6c(c5)CN(C5CCC(=O)NC5=O)C6=O)C4)ccc3n2)CC1] 3-(1-oxo-5-{[(3S)-1-[(2-{[(1s,4s)-4-methoxycyclohexyl]amino}quinolin-6-yl)methyl]pyrrolidin-3-yl]oxy}-2,3-dihydro-1H-isoindol-2-yl)piperidine-2,6-dione | 0.001044 | 6.285 | 0.006384 | 29.5 |
| 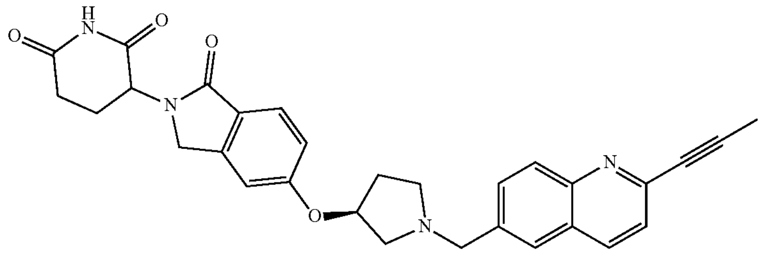 [SMILES: CC#Cc1ccc2cc(CN3CC[C@H](Oc4ccc5c(c4)CN(C4CCC(=O)NC4=O)C5=O)C3)ccc2n1] | 0.002024 | 8.03 | 0.003183333 | 29.33333333 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(1-oxo-5-{[(3S)-1-{[2-(prop-1-yn-1-yl)quinolin-6-yl]methyl}pyrrolidin-3-yl]oxy}-2,3-dihydro-1H-isoindol-2-yl)piperidine-2,6-dione | | | | |
| 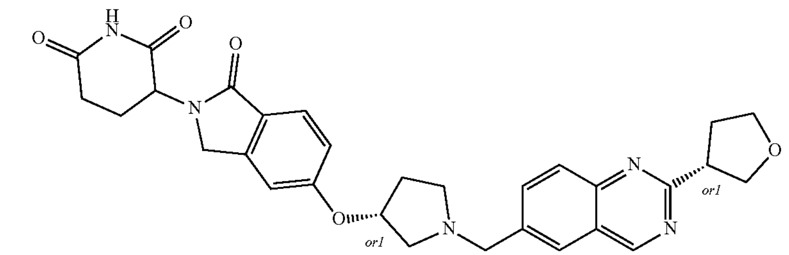 [SMILES: O=C1CCC(N2Cc3cc(O[C@@H]4CCN(Cc5ccc6nc([C@@H]7CCOC7)ncc6c5)C4)ccc3C2=O)C(=O)N1] rel-3-(1-oxo-5-{[(3R)-1-({2-[(3S)-oxolan-3-yl]quinazolin-6-yl}methyl)pyrrolidin-3-yl]oxy}-2,3-dihydro-1H-isoindol-2-yl)piperidine-2,6-dione | 0.0185105 | 7.06 | 0.021814 | 34 |
| 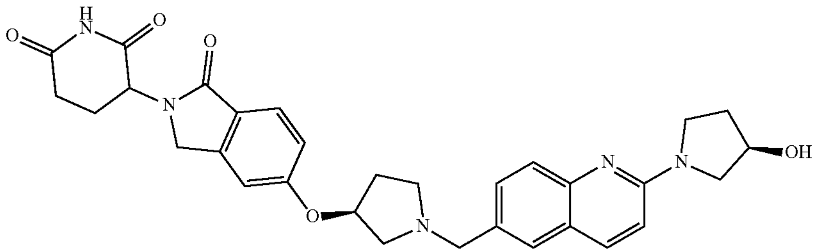 [SMILES: O=C1CCC(N2Cc3cc(O[C@H]4CCN(Cc5ccc6nc(N7CC[C@@H](O)C7)ccc6c5)C4)ccc3C2=O)C(=O)N1] 3-(5-{[(3S)-1-({2-[(3R)-3-hydroxypyrrolidin-1-yl]quinolin-6-yl}methyl)pyrrolidin-3-yl]oxy}-1-oxo-2,3-dihydro-1H-isoindol-2-yl)piperidine-2,6-dione | 0.020868 | 11.85 | 0.017461 | 36 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 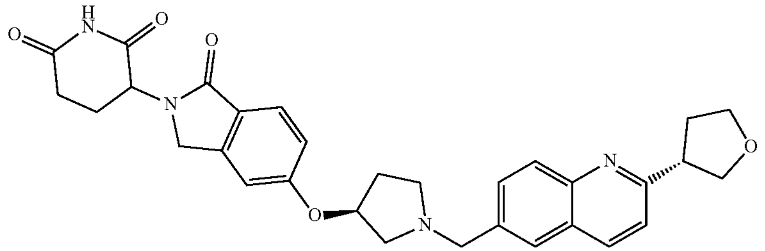 [SMILES: O=C1CCC(N2Cc3cc(O[C@H]4CCN(Cc5ccc6nc([C@@H]7CCOC7)ccc6c5)C4)ccc3C2=O)C(=O)N1] 3-(1-oxo-5-{[(3S)-1-({2-[(3S)-oxolan-3-yl]quinolin-6-yl}methyl)pyrrolidin-3-yl]oxy}-2,3-dihydro-1H-isoindol-2-yl)piperidine-2,6-dione | 0.0024465 | 8.77 | 0.002408 | 30 |
| 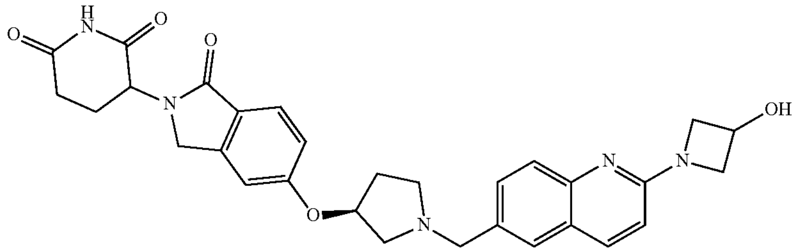 [SMILES: O=C1CCC(N2Cc3cc(O[C@H]4CCN(Cc5ccc6nc(N7CC(O)C7)ccc6c5)C4)ccc3C2=O)C(=O)N1] 3-(5-{[(3S)-1-{[2-(3-hydroxyazetidin-1-yl)quinolin-6-yl]methyl}pyrrolidin-3-yl]oxy}-1-oxo-2,3-dihydro-1H-isoindol-2-yl)piperidine-2,6-dione | 0.026834 | 13.6 | 0.014137 | 34 |
| 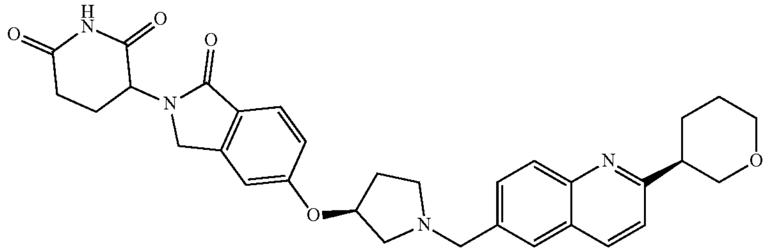 [SMILES: O=C1CCC(N2Cc3cc(O[C@H]4CCN(Cc5ccc6nc([C@H]7CCCOC7)ccc6c5)C4)ccc3C2=O)C(=O)N1] 3-(5-{[(3S)-1-({2-[(3R)-oxan-3-yl]quinolin-6-yl}methyl)pyrrolidin-3-yl]oxy}-1-oxo-2,3-dihydro- | 0.005280638 | 12.50241832 | 0.003325333 | 32.33333333 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 1H-isoindol-2-yl)piperidine-2,6-dione | | | | |
| 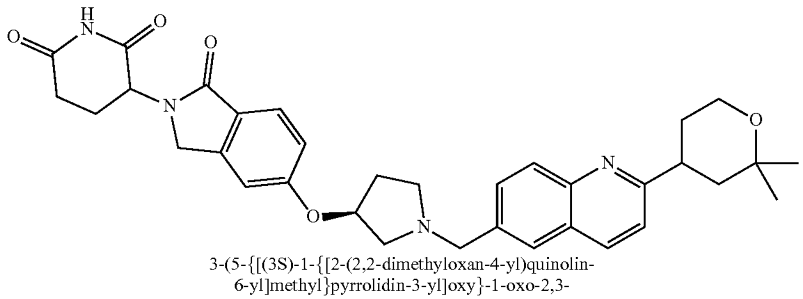 3-(5-{[(3S)-1-{[2-(2,2-dimethyloxan-4-yl)quinolin-6-yl]methyl}pyrrolidin-3-yl]oxy}-1-oxo-2,3-dihydro-1H-isoindol-2-yl)piperidine-2,6-dione | 0.002141386 | 7.959308922 | 0.00256 | 29 |
| 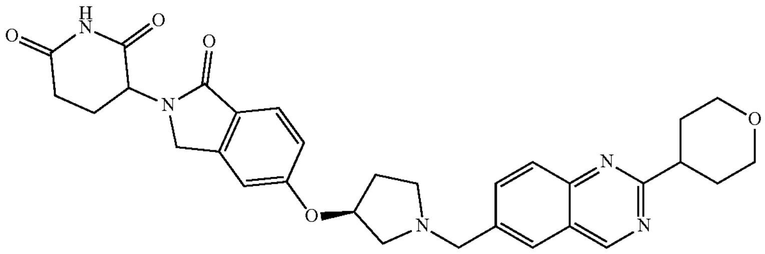 [SMILES: O=C1CCC(N2Cc3cc(O[C@H]4CCN(Cc5ccc6nc(C7CCOCC7)ncc6c5)C4)ccc3C2=O)C(=O)N1] 3-(5-{[(3S)-1-{[2-(oxan-4-yl)quinazolin-6-yl]methyl}pyrrolidin-3-yl]oxy}-1-oxo-2,3-dihydro-1H-isoindol-2-yl)piperidine-2,6-dione | 0.0213845 | 6.11 | 0.032648 | 30.5 |
| 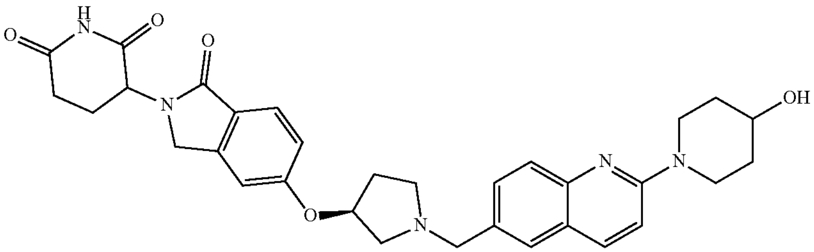 [SMILES: O=C1CCC(N2Cc3cc(O[C@H]4CCN(Cc5ccc6nc(N7CCC(O)CC7)ccc6c5)C4)ccc3C2=O)C(=O)N1] | 0.006588 | 9.69 | 0.00286 | 34.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(5-{[(3S)-1-{[2-(4-hydroxypiperidin-1-yl)quinolin-6-yl]methyl}pyrrolidin-3-yl]oxy}-1-oxo-2,3-dihydro-1H-isoindol-2-yl)piperidine-2,6-dione | | | | |
| 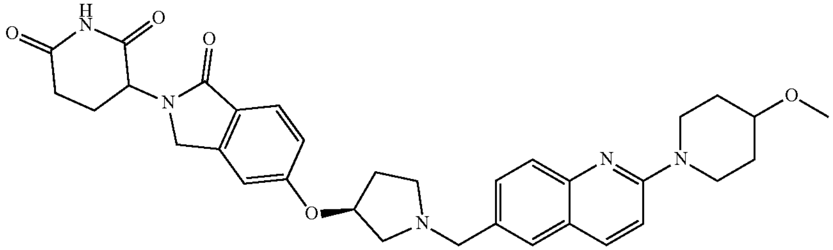 3-(5-{[(3S)-1-{[2-(4-methoxypiperidin-1-yl)quinolin-6-yl]methyl}pyrrolidin-3-yl]oxy}-1-oxo-2,3-dihydro-1H-isoindol-2-yl)piperidine-2,6-dione | 0.003755 | 9.39 | 0.0024855 | 30.5 |
| 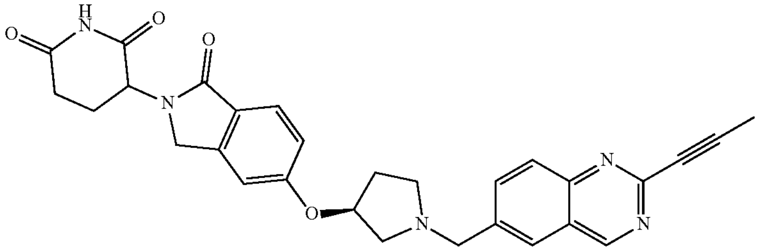 [SMILES: CC#Cc1ncc2cc(CN3CC[C@H](Oc4ccc5c(c4)CN(C4CCC(=O)NC4=O)C5=O)C3)ccc2n1] 3-(1-oxo-5-{[(3S)-1-{[2-(prop-1-yn-1-yl)quinazolin-6-yl]methyl}pyrrolidin-3-yl]oxy}-2,3-dihydro-1H-isoindol-2-yl)piperidine-2,6-dione | 0.051561 | 8.56 | 0.038894 | 29 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 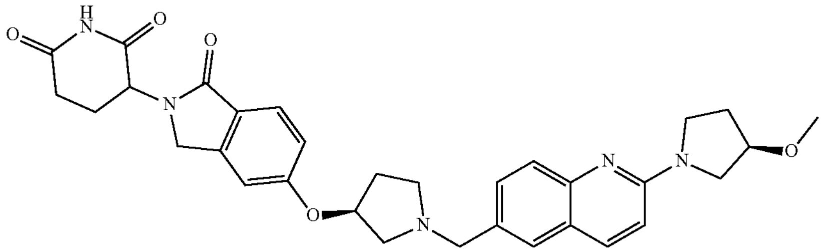 [SMILES: CO[C@@H]1CCN(c2ccc3cc(CN4CC[C@H](Oc5ccc6c(c5)CN(C5CCC(=O)NC5=O)C6=O)C4)ccc3n2)C1] 3-(5-{[(3S)-1-({2-[(3R)-3-methoxypyrrolidin-1-yl]quinolin-6-yl}methyl)pyrrolidin-3-yl]oxy}-1-oxo-2,3-dihydro-1H-isoindol-2-yl)piperidine-2,6-dione | 0.003668 | 8.99 | 0.002459 | 37 |
| 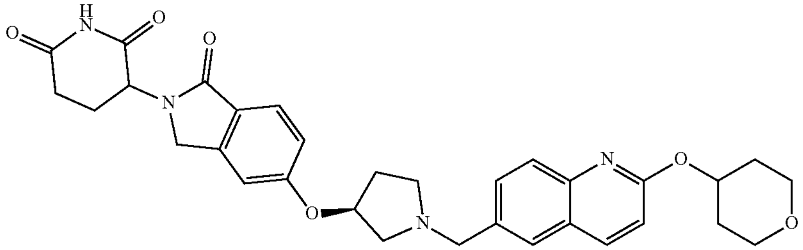 [SMILES: O=C1CCC(N2Cc3cc(O[C@H]4CCN(Cc5ccc6nc(OC7CCOCC7)ccc6c5)C4)ccc3C2=O)C(=O)N1] 3-(5-{[(3S)-1-{[2-(oxan-4-yloxy)quinolin-6-yl]methyl}pyrrolidin-3-yl]oxy}-1-oxo-2,3-dihydro-1H-isoindol-2-yl)piperidine-2,6-dione | 0.009832055 | 13.54266423 | 0.004522 | 33 |
| 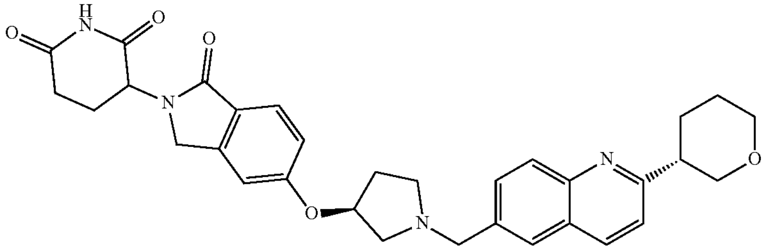 [SMILES: O=C1CCC(N2Cc3cc(O[C@H]4CCN(Cc5ccc6nc([C@@H]7CCCOC7)ccc6c5)C4)ccc3C2=O)C(=O)N1] 3-(5-{[(3S)-1-({2-[(3S)-oxan-3-yl]quinolin-6- | 0.003592875 | 10.59630324 | 0.002149 | 32 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| yl}methyl)pyrrolidin-3-yl]oxy}-1-oxo-2,3-dihydro-1H-isoindol-2-yl)piperidine-2,6-dione | | | | |
| 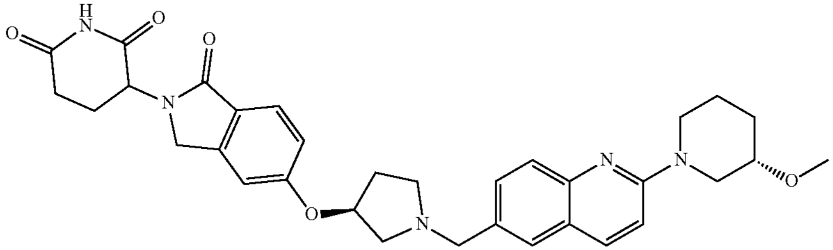 [SMILES: CO[C@H]1CCCN(c2ccc3cc(CN4CC[C@H](Oc5ccc6c(c5)CN(C5CCC(=O)NC5=O)C6=O)C4)ccc3n2)C1] 3-(5-{[(3S)-1-({2-[(3S)-3-methoxypiperidin-1-yl]quinolin-6-yl}methyl)pyrrolidin-3-yl]oxy}-1-oxo-2,3-dihydro-1H-isoindol-2-yl)piperidine-2,6-dione | 0.005286 | 10.12 | 0.005831 | 34 |
| 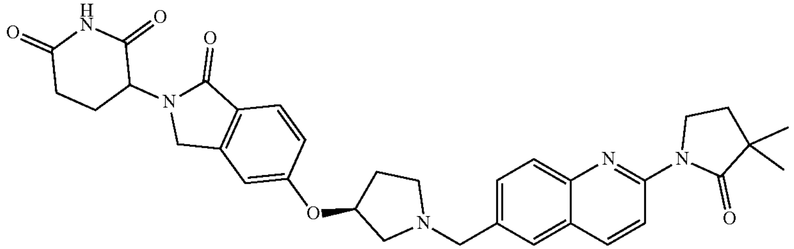 [SMILES: CC1(C)CCN(c2ccc3cc(CN4CC[C@H](Oc5ccc6c(c5)CN(C5CCC(=O)NC5=O)C6=O)C4)ccc3n2)C1=O] 3-(5-{[(3S)-1-{[2-(3,3-dimethyl-2-oxopyrrolidin-1-yl)quinolin-6-yl]methyl}pyrrolidin-3-yl]oxy}-1-oxo-2,3-dihydro-1H-isoindol-2-yl)piperidine-2,6-dione | 0.003882 | 7.37 | 0.007364 | 29.66666667 |
| 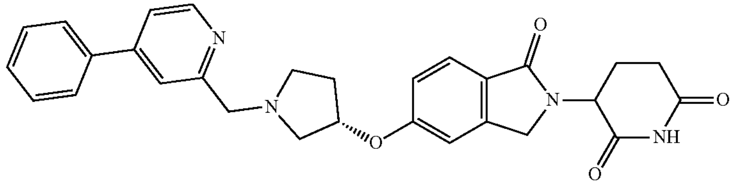 [SMILES: O=C1CCC(N2Cc3cc(O[C@H]4CCN(Cc5cc(-c6ccccc6)ccn5)C4)ccc3C2=O)C(=O)N1] | 0.016672 | 8.59 | 0.005296 | 34.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(1-oxo-5-{[(3S)-1-[(4-phenylpyridin-2-yl)methyl]pyrrolidin-3-yl]oxy}-2,3-dihydro-1H-isoindol-2-yl)piperidine-2,6-dione | | | | |
| 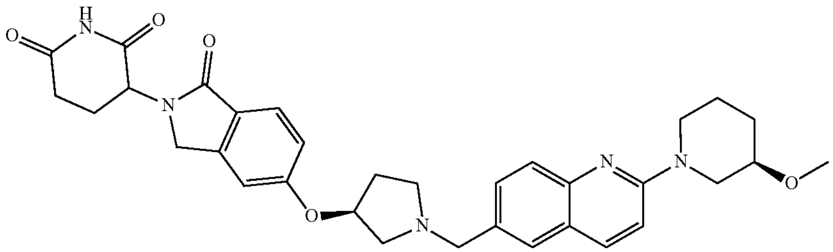 3-(5-{[(3S)-1-({2-[(3R)-3-methoxypiperidin-1-yl]quinolin-6-yl}methyl)pyrrolidin-3-yl]oxy}-1-oxo-2,3-dihydro-1H-isoindol-2-yl)piperidine-2,6-dione | 0.003914 | 6.79 | 0.004315 | 34 |
| 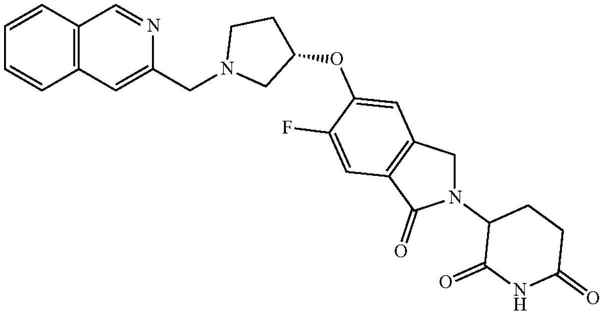 [SMILES: O=C1CCC(N2Cc3cc(O[C@H]4CCN(Cc5cc6ccccc6cn5)C4)c(F)cc3C2=O)C(=O)N1] 3-(6-fluoro-5-{[(3S)-1-[(isoquinolin-3-yl)methyl]pyrrolidin-3-yl]oxy}-1-oxo-2,3-dihydro-1H-isoindol-2-yl)piperidine-2,6-dione | 0.053743 | 7.57 | 0.010632 | 34 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 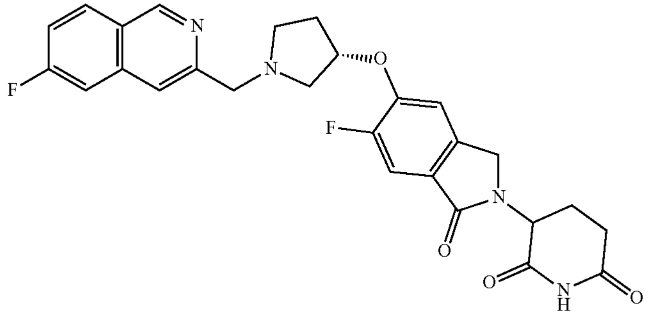 [SMILES: O=C1CCC(N2Cc3cc(O[C@H]4CCN(Cc5cc6cc(F)ccc6cn5)C4)c(F)cc3C2=O)C(=O)N1] 3-(6-fluoro-5-{[(3S)-1-[(6-fluoroisoquinolin-3-yl)methyl]pyrrolidin-3-yl]oxy}-1-oxo-2,3-dihydro-1H-isoindol-2-yl)piperidine-2,6-dione | 0.104072 | 11.55 | 0.014333 | 36 |
| 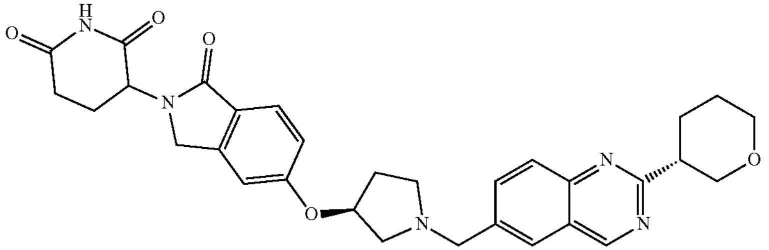 [SMILES: O=C1CCC(N2Cc3cc(O[C@H]4CCN(Cc5ccc6nc([C@@H]7CCCOC7)ncc6c5)C4)ccc3C2=O)C(=O)N1] 3-(5-{[(3S)-1-({2-[(3S)-oxan-3-yl]quinazolin-6-yl}methyl)pyrrolidin-3-yl]oxy}-1-oxo-2,3-dihydro-1H-isoindol-2-yl)piperidine-2,6-dione | 0.019426 | 5.31 | 0.0338035 | 31 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 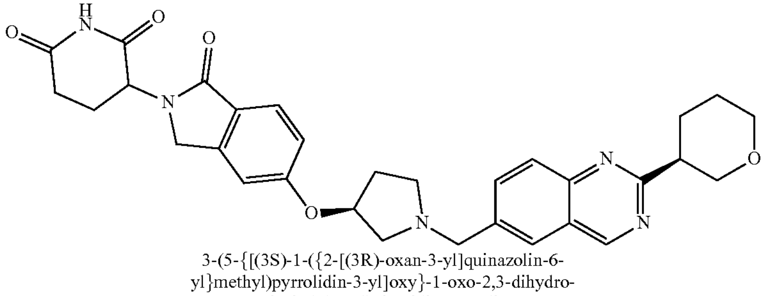 3-(5-{[(3S)-1-({2-[(3R)-oxan-3-yl]quinazolin-6-yl}methyl)pyrrolidin-3-yl]oxy}-1-oxo-2,3-dihydro-1H-isoindol-2-yl)piperidine-2,6-dione | 0.008799 | 6.66 | 0.016016 | 28.5 |
| 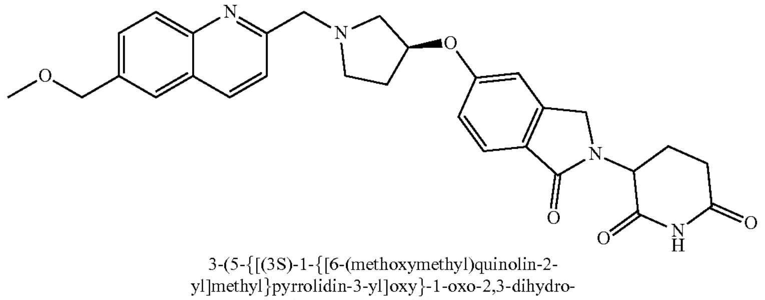 3-(5-{[(3S)-1-{[6-(methoxymethyl)quinolin-2-yl]methyl}pyrrolidin-3-yl]oxy}-1-oxo-2,3-dihydro-1H-isoindol-2-yl)piperidine-2,6-dione | 0.089585 | 26.02 | 0.011713 | 46 |
| 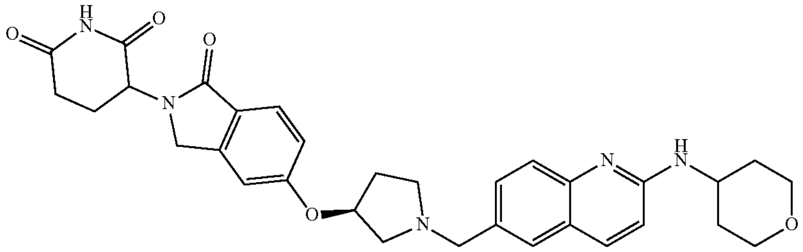 [SMILES: O=C1CCC(N2Cc3cc(O[C@H]4CCN(Cc5ccc6nc(NC7CCOCC7)ccc6c5)C4)ccc3C2=O)C(=O)N1] 3-(5-{[(3S)-1-({2-[(oxan-4-yl)amino]quinolin-6-yl}methyl)pyrrolidin-3-yl]oxy}-1-oxo-2,3-dihydro- | 0.00427 | 7.78 | 0.01059 | 37 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 1H-isoindol-2-yl)piperidine-2,6-dione | | | | |
| 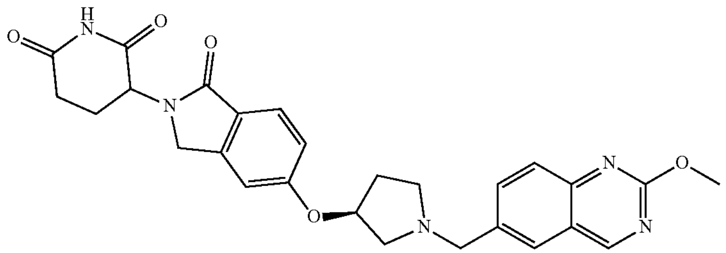 [SMILES: COc1ncc2cc(CN3CC[C@H](Oc4ccc5c(c4)CN(C4CCC(=O)NC4=O)C5=O)C3)ccc2n1] 3-(5-{[(3S)-1-[(2-methoxyquinazolin-6-yl)methyl]pyrrolidin-3-yl]oxy}-1-oxo-2,3-dihydro-1H-isoindol-2-yl)piperidine-2,6-dione | 0.022292 | 8.47 | 0.008055 | 37 |
| 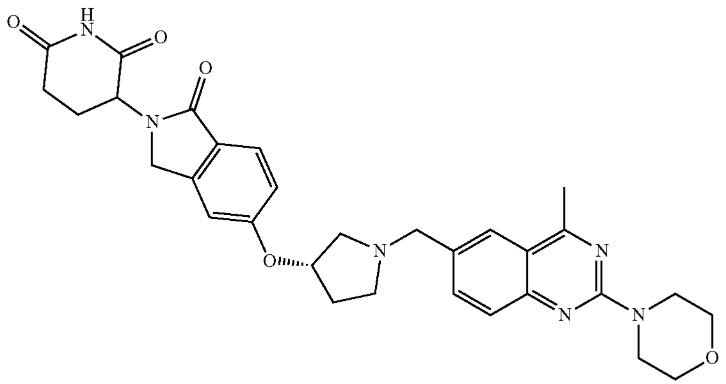 [SMILES: Cc1nc(N2CCOCC2)nc2ccc(CN3CC[C@H](Oc4ccc5c(c4)CN(C4CCC(=O)NC4=O)C5=O)C3)cc12] 3-(5-{[(3S)-1-{[4-methyl-2-(morpholin-4-yl)quinazolin-6-yl]methyl}pyrrolidin-3-yl]oxy}-1-oxo-2,3-dihydro-1H-isoindol-2-yl)piperidine-2,6-dione | 0.009282 | 7.12 | 0.005366 | 36 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 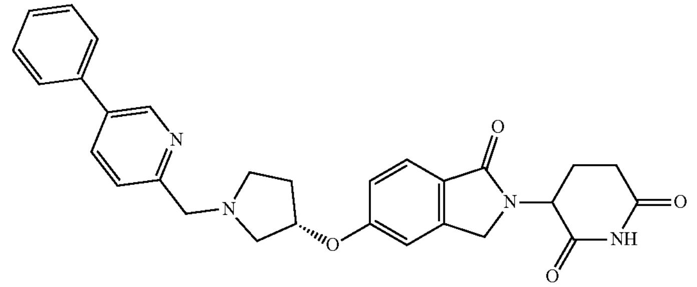 [SMILES: O=C1CCC(N2Cc3cc(O[C@H]4CCN(Cc5ccc(-c6ccccc6)cn5)C4)ccc3C2=O)C(=O)N1] 3-(1-oxo-5-{[(3S)-1-[(5-phenylpyridin-2-yl)methyl]pyrrolidin-3-yl]oxy}-2,3-dihydro-1H-isoindol-2-yl)piperidine-2,6-dione | 0.131026 | 31.28 | 0.007588 | 46 |
| 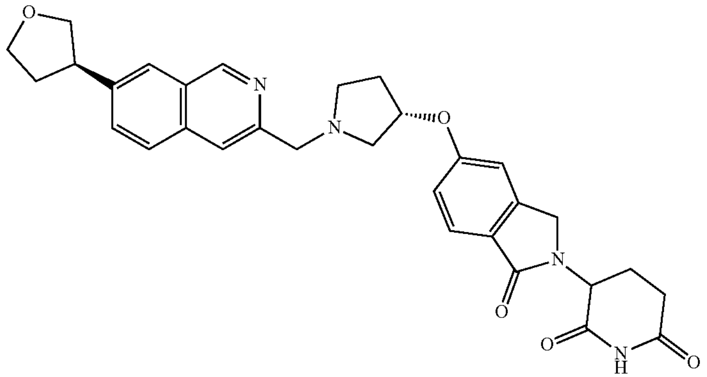 [SMILES: O=C1CCC(N2Cc3cc(O[C@H]4CCN(Cc5cc6ccc([C@H]7CCOC7)cc6cn5)C4)ccc3C2=O)C(=O)N1] 3-(1-oxo-5-{[(3S)-1-({7-[(3R)-oxolan-3-yl]isoquinolin-3-yl}methyl)pyrrolidin-3-yl]oxy}-2,3-dihydro-1H-isoindol-2-yl)piperidine-2,6-dione | 0.002964 | 8.5 | 0.001412 | 28 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 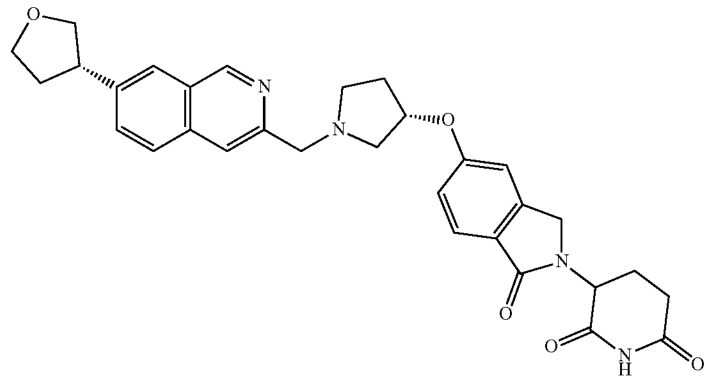 [SMILES: O=C1CCC(N2Cc3cc(O[C@H]4CCN(Cc5cc6ccc([C@@H]7CCOC7)cc6cn5)C4)ccc3C2=O)C(=O)N1] 3-(1-oxo-5-{[(3S)-1-({7-[(3S)-oxolan-3-yl]isoquinolin-3-yl}methyl)pyrrolidin-3-yl]oxy}-2,3-dihydro-1H-isoindol-2-yl)piperidine-2,6-dione | 0.001845 | 7.635 | 0.001662 | 30 |
| 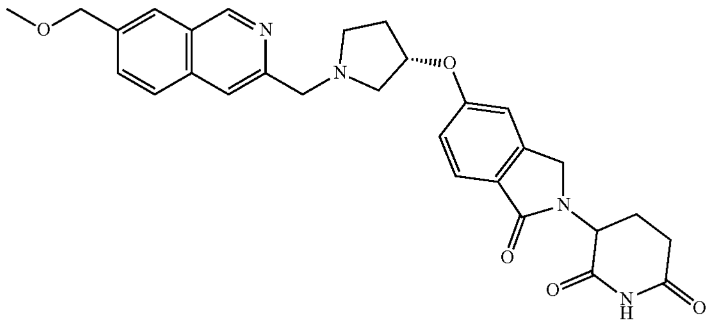 [SMILES: COCc1ccc2cc(CN3CC[C@H](Oc4ccc5c(c4)CN(C4CCC(=O)NC4=O)C5=O)C3)ncc2c1] 3-(5-{[(3S)-1-{[7-(methoxymethyl)isoquinolin-3-yl]methyl}pyrrolidin-3-yl]oxy}-1-oxo-2,3-dihydro-1H-isoindol-2-yl)piperidine-2,6-dione | 0.002854 | 8.95 | 0.001418 | 30 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 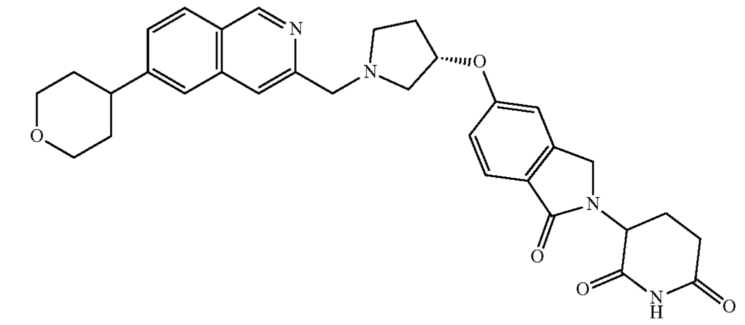 [SMILES: O=C1CCC(N2Cc3cc(O[C@H]4CCN(Cc5cc6cc(C7CCOCC7)ccc6cn5)C4)ccc3C2=O)C(=O)N1] 3-(5-{[(3S)-1-{[6-(oxan-4-yl)isoquinolin-3-yl]methyl}pyrrolidin-3-yl]oxy}-1-oxo-2,3-dihydro-1H-isoindol-2-yl)piperidine-2,6-dione | 0.01226784 | 13.119518 | 0.0055505 | 33.5 |
| 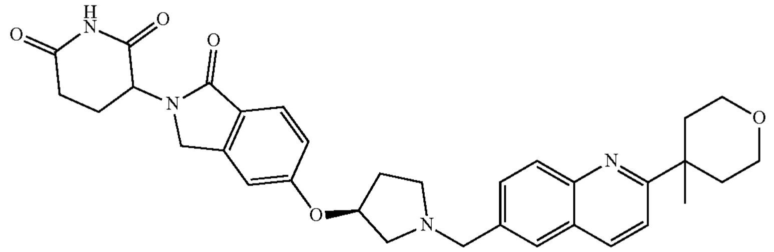 [SMILES: CC1(c2ccc3cc(CN4CC[C@H](Oc5ccc6c(c5)CN(C5CCC(=O)NC5=O)C6=O)C4)ccc3n2)CCOCC1] 3-(5-{[(3S)-1-{[2-(4-methyloxan-4-yl)quinolin-6-yl]methyl}pyrrolidin-3-yl]oxy}-1-oxo-2,3-dihydro-1H-isoindol-2-yl)piperidine-2,6-dione | 0.004029 | 10.29 | 0.0019875 | 32 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 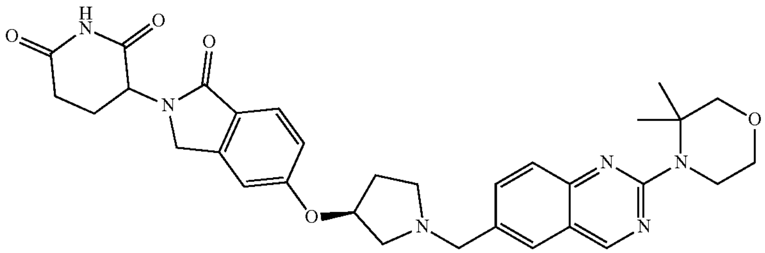 [SMILES: CC1(C)COCCN1c1ncc2cc(CN3CC[C@H](Oc4ccc5c(c4)CN(C4CCC(=O)NC4=O)C5=O)C3)ccc2n1] 3-(5-{[(3S)-1-{[2-(3,3-dimethylmorpholin-4-yl)quinazolin-6-yl]methyl}pyrrolidin-3-yl]oxy}-1-oxo-2,3-dihydro-1H-isoindol-2-yl)piperidine-2,6-dione | 0.017623928 | 17.2963623 | 0.0048155 | 31.5 |
| 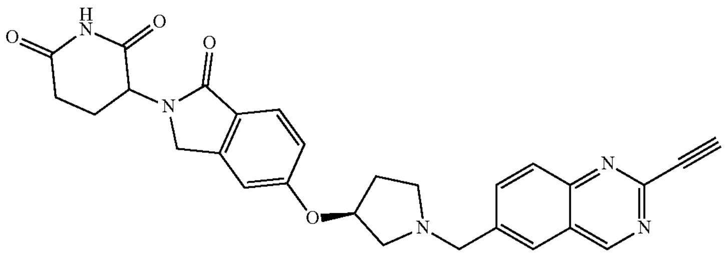 [SMILES: C#Cc1ncc2cc(CN3CC[C@H](Oc4ccc5c(c4)CN(C4CCC(=O)NC4=O)C5=O)C3)ccc2n1] 3-(5-{[(3S)-1-[(2-ethynylquinazolin-6-yl)methyl]pyrrolidin-3-yl]oxy}-1-oxo-2,3-dihydro-1H-isoindol-2-yl)piperidine-2,6-dione | 0.0702214 | 28.856 | 0.016544 | 45 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 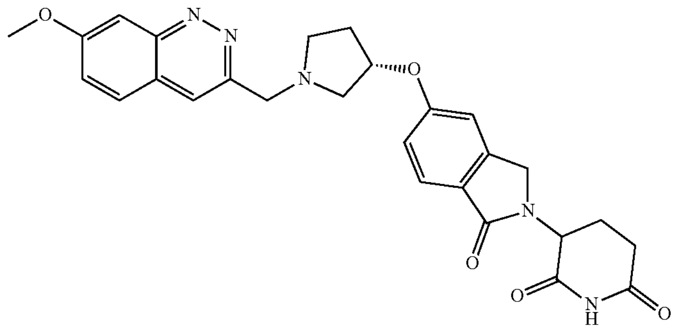 [SMILES: COc1ccc2cc(CN3CC[C@H](Oc4ccc5c(c4)CN(C4CCC(=O)NC4=O)C5=O)C3)nnc2c1] 3-(5-{[(3S)-1-[(7-methoxycinnolin-3-yl)methyl]pyrrolidin-3-yl]oxy}-1-oxo-2,3-dihydro-1H-isoindol-2-yl)piperidine-2,6-dione | 0.012413 | 7.52 | 0.005483 | 28 |
| 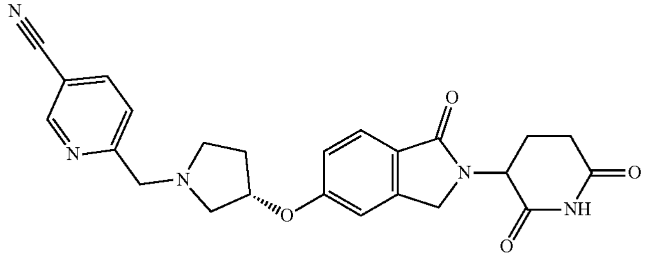 [SMILES: N#Cc1ccc(CN2CC[C@H](Oc3ccc4c(c3)CN(C3CCC(=O)NC3=O)C4=O)C2)nc1] 6-{[(3S)-3-{[2-(2,6-dioxopiperidin-3-yl)-1-oxo-2,3-dihydro-1H-isoindol-5-yl]oxy}pyrrolidin-1-yl]methyl}pyridine-3-carbonitrile | 10 | 69.48 | 0.060965 | 64 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 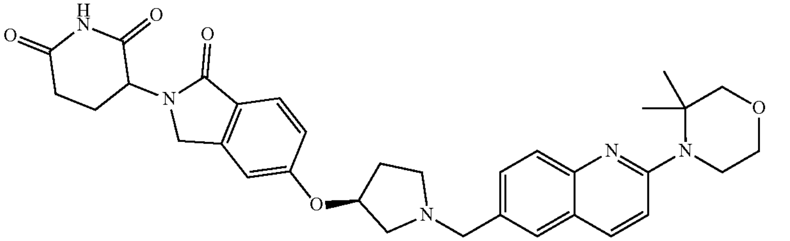 [SMILES: CC1(C)COCCN1c1ccc2cc(CN3CC[C@H](Oc4ccc5c(c4)CN(C4CCC(=O)NC4=O)C5=O)C3)ccc2n1] 3-(5-{[(3S)-1-{[2-(3,3-dimethylmorpholin-4-yl)quinolin-6-yl]methyl}pyrrolidin-3-yl]oxy}-1-oxo-2,3-dihydro-1H-isoindol-2-yl)piperidine-2,6-dione | 0.0020805 | 9.02 | 0.0028415 | 34 |
| 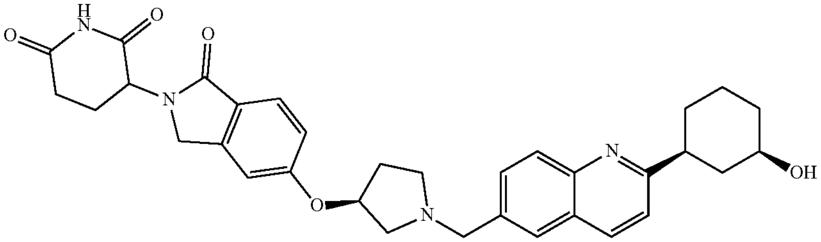 [SMILES: O=C1CCC(N2Cc3cc(O[C@H]4CCN(Cc5ccc6nc([C@H]7CCC[C@@H](O)C7)ccc6c5)C4)ccc3C2=O)C(=O)N1] 3-(5-{[(3S)-1-({2-[(1S,3R)-3-hydroxycyclohexyl]quinolin-6-yl}methyl)pyrrolidin-3-yl]oxy}-1-oxo-2,3-dihydro-1H-isoindol-2-yl)piperidine-2,6-dione | 0.011071 | 7.93 | 0.009665 | 32 |
| 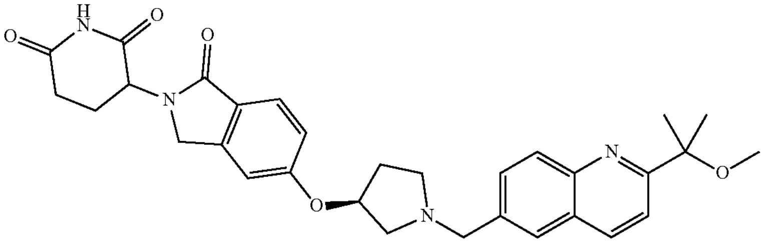 [SMILES: COC(C)(C)c1ccc2cc(CN3CC[C@H](Oc4ccc5c(c4)CN(C4CCC(=O)NC4=O)C5=O)C3)ccc2n1] 3-(5-{[(3S)-1-{[2-(2-methoxypropan-2-yl)quinolin- | 0.002976 | 6.21 | 0.002603 | 32.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 6-yl]methyl}pyrrolidin-3-yl]oxy}-1-oxo-2,3-dihydro-1H-isoindol-2-yl)piperidine-2,6-dione | | | | |
| 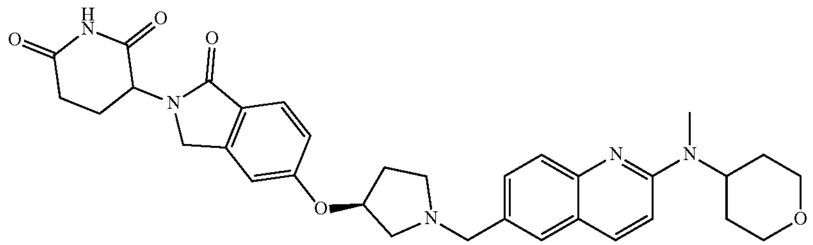 [SMILES: CN(c1ccc2cc(CN3CC[C@H](Oc4ccc5c(c4)CN(C4CCC(=O)NC4=O)C5=O)C3)ccc2n1)C1CCOCC1] 3-(5-{[(3S)-1-({2-[methyl(oxan-4-yl)amino]quinolin-6-yl}methyl)pyrrolidin-3-yl]oxy}1-oxo-2,3-dihydro-1H-isoindol-2-yl)piperidine-2,6-dione | 0.003499 | 8.45 | 0.0018245 | 32 |
| 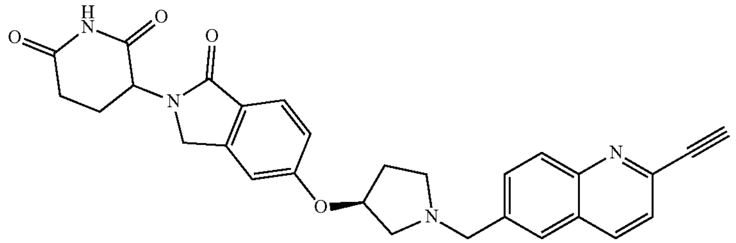 [SMILES: C#Cc1ccc2cc(CN3CC[C@H](Oc4ccc5c(c4)CN(C4CCC(=O)NC4=O)C5=O)C3)ccc2n1] 3-(5-{[(3S)-1-[(2-ethynylquinolin-6-yl)methyl]pyrrolidin-3-yl]oxy}-1-oxo-2,3-dihydro-1H-isoindol-2-yl)piperidine-2,6-dione | 0.259571667 | 6.523333333 | 0.003138 | 32 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 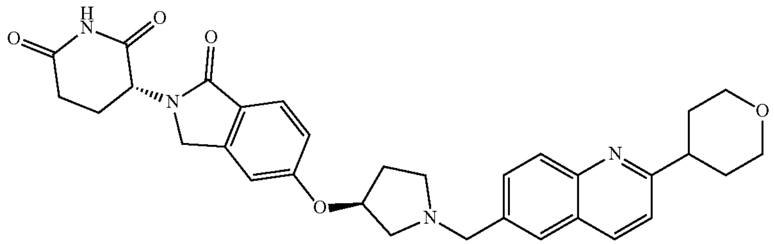 [SMILES: O=C1CC[C@@H](N2Cc3cc(O[C@H]4CCN(Cc5ccc6nc(C7CCOCC7)ccc6c5)C4)ccc3C2=O)C(=O)N1] (3R)-3-(5-{[(3S)-1-{[2-(oxan-4-yl)quinolin-6-yl]methyl}pyrrolidin-3-yl]oxy}-1-oxo-2,3-dihydro-1H-isoindol-2-yl)piperidine-2,6-dione | 0.006120951 | 9.677358883 | 0.00675 | 33 |
| 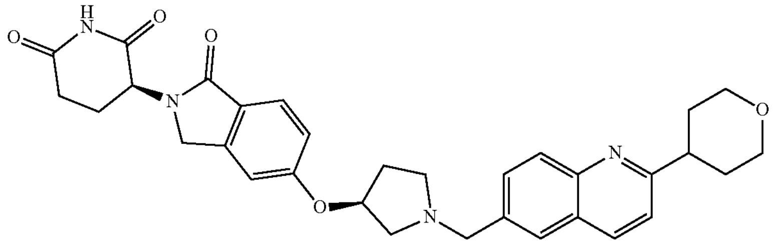 [SMILES: O=C1CC[C@H](N2Cc3cc(O[C@H]4CCN(Cc5ccc6nc(C7CCOCC7)ccc6c5)C4)ccc3C2=O)C(=O)N1] (3S)-3-(5-{[(3S)-1-{[2-(oxan-4-yl)quinolin-6-yl]methyl}pyrrolidin-3-yl]oxy}-1-oxo-2,3-dihydro-1H-isoindol-2-yl)piperidine-2,6-dione | 0.003118796 | 10.42904036 | 0.001617818 | 31.89795685 |
| 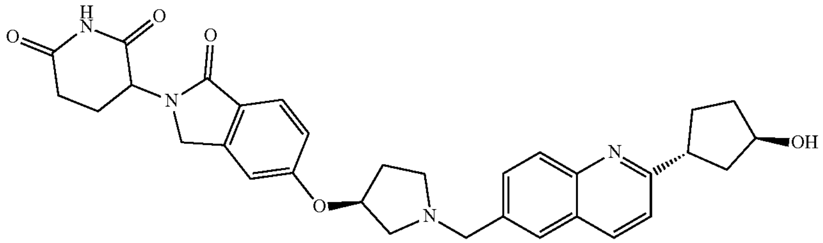 [SMILES: O=C1CCC(N2Cc3cc(O[C@H]4CCN(Cc5ccc6nc([C@@H]7CC[C@@H](O)C7)ccc6c5)C4)ccc3C2=O)C(=O)N1] 3-(5-{[(3S)-1-({2-[(1R,3R)-3-hydroxycyclopentyl]quinolin-6-yl}methyl)pyrrolidin-3-yl]oxy}-1-oxo-2,3-dihydro- | 0.00137825 | 8.2675 | 0.002601 | 31.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 1H-isoindol-2-yl)piperidine-2,6-dione | | | | |
| 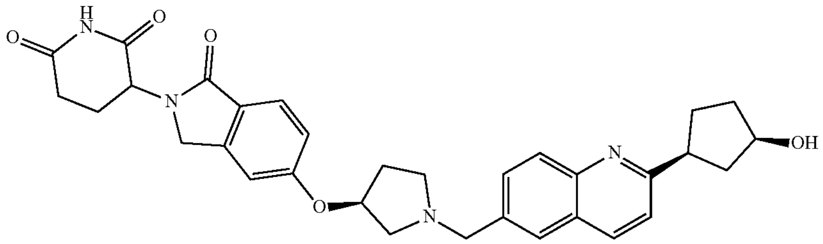 [SMILES: O=C1CCC(N2Cc3cc(O[C@H]4CCN(Cc5ccc6nc([C@H]7CC[C@@H](O)C7)ccc6c5)C4)ccc3C2=O)C(=O)N1] 3-(5-{[(3S)-1-({2-[(1S,3R)-3-hydroxycyclopentyl]quinolin-6-yl}methyl)pyrrolidin-3-yl]oxy}-1-oxo-2,3-dihydro-1H-isoindol-2-yl)piperidine-2,6-dione | 0.0026645 | 7.68 | 0.002993 | 31 |
| 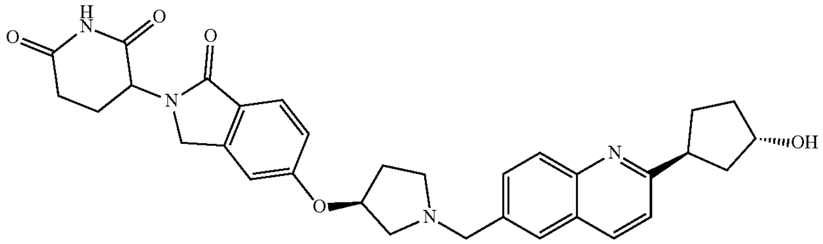 [SMILES: O=C1CCC(N2Cc3cc(O[C@H]4CCN(Cc5ccc6nc([C@H]7CC[C@H](O)C7)ccc6c5)C4)ccc3C2=O)C(=O)N1] 3-(5-{[(3S)-1-({2-[(1S,3S)-3-hydroxycyclopentyl]quinolin-6-yl}methyl)pyrrolidin-3-yl]oxy}-1-oxo-2,3-dihydro-1H-isoindol-2-yl)piperidine-2,6-dione | 0.00324125 | 8.695 | 0.002665 | 27.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 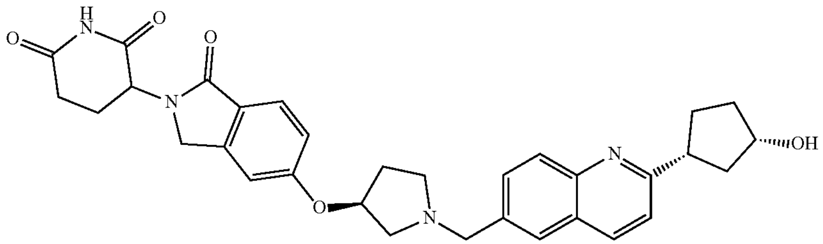 [SMILES: O=C1CCC(N2Cc3cc(O[C@H]4CCN(Cc5ccc6nc([C@@H]7CC[C@H](O)C7)ccc6c5)C4)ccc3C2=O)C(=O)N1] 3-(5-{[(3S)-1-({2-[(1R,3S)-3-hydroxycyclopentyl]quinolin-6-yl}methyl)pyrrolidin-3-yl]oxy}-1-oxo-2,3-dihydro-1H-isoindol-2-yl)piperidine-2,6-dione | 0.000655 | 7.585 | 0.003331 | 32 |
| 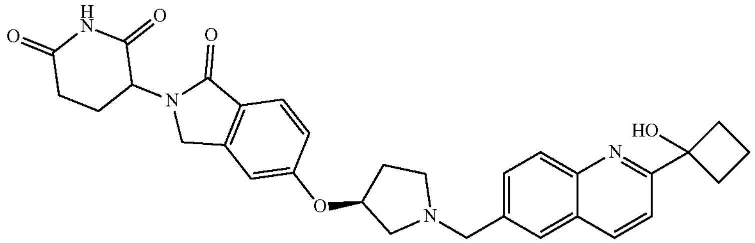 [SMILES: O=C1CCC(N2Cc3cc(O[C@H]4CCN(Cc5ccc6nc(C7(O)CCC7)ccc6c5)C4)ccc3C2=O)C(=O)N1] 3-(5-{[(3S)-1-{[2-(1-hydroxycyclobutyl)quinolin-6-yl]methyl}pyrrolidin-3-yl]oxy}-1-oxo-2,3-dihydro-1H-isoindol-2-yl)piperidine-2,6-dione | 0.0024 | 7.94 | 0.002577 | 29.5 |
| 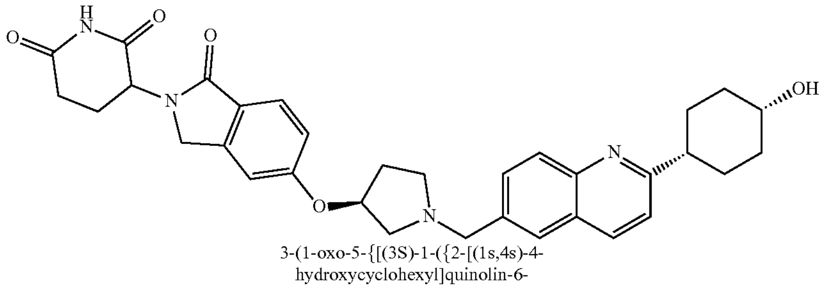 3-(1-oxo-5-{[(3S)-1-({2-[(1s,4s)-4-hydroxycyclohexyl]quinolin-6- | 0.0003288 | 7.956 | 0.00103 | 33 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| yl}methyl)pyrrolidin-3-yl]oxy}-2,3-dihydro-1H-isoindol-2-yl)piperidine-2,6-dione | | | | |
| 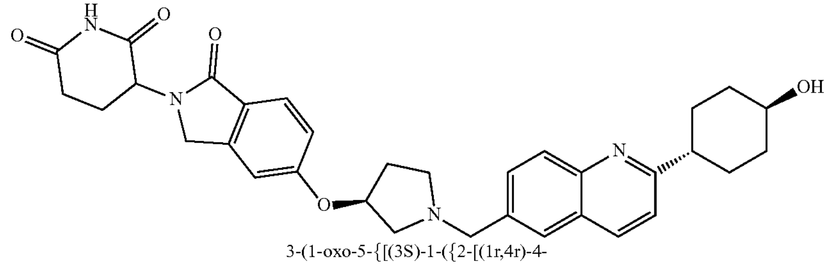 3-(1-oxo-5-{[(3S)-1-({2-[(1r,4r)-4-hydroxycyclohexyl]quinolin-6-yl}methyl)pyrrolidin-3-yl]oxy}-2,3-dihydro-1H-isoindol-2-yl)piperidine-2,6-dione | 0.0027885 | 7.3325 | 0.00467 | 30 |
| 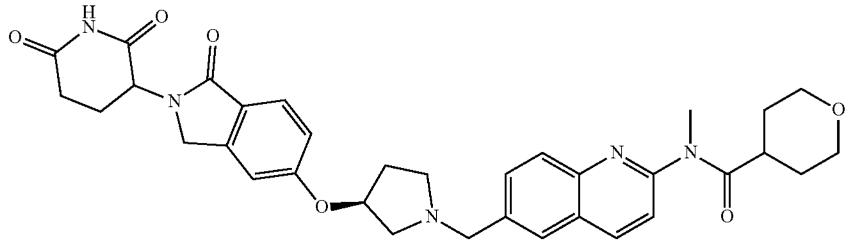 [SMILES: CN(C(=O)C1CCOCC1)c1ccc2cc(CN3CC[C@H](Oc4ccc5c(c4)CN(C4CCC(=O)NC4=O)C5=O)C3)ccc2n1] N-(6-{[(3S)-3-{[2-(2,6-dioxopiperidin-3-yl)-1-oxo-2,3-dihydro-1H-isoindol-5-yl]oxy}pyrrolidin-1-yl]methyl}quinolin-2-yl)-N-methyloxane-4-carboxamide | 0.003346 | 6.6 | 0.005038 | 32.5 |
| 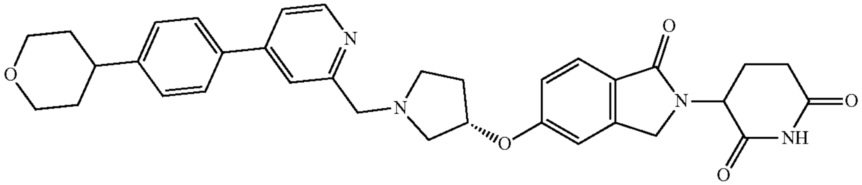 [SMILES: O=C1CCC(N2Cc3cc(O[C@H]4CCN(Cc5cc(-c6ccc(C7CCOCC7)cc6)ccn5)C4)ccc3C2=O)C(=O)N1] 3-(5-{[(3S)-1-({4-[4-(oxan-4-yl)phenyl]pyridin-2- | 0.000192 | 6.39 | 0.001327 | 31 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| yl}methyl)pyrrolidin-3-yl]oxy}-1-oxo-2,3-dihydro-1H-isoindol-2-yl)piperidine-2,6-dione | | | | |
| 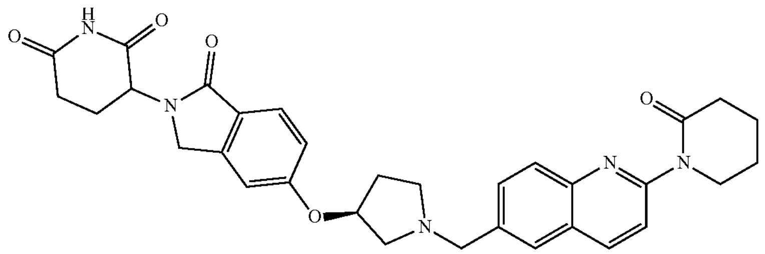 [SMILES: O=C1CCC(N2Cc3cc(O[C@H]4CCN(Cc5ccc6nc(N7CCCCC7=O)ccc6c5)C4)ccc3C2=O)C(=O)N1] 3-(1-oxo-5-{[(3S)-1-{[2-(2-oxopiperidin-1-yl)quinolin-6-yl]methyl}pyrrolidin-3-yl]oxy}-2,3-dihydro-1H-isoindol-2-yl)piperidine-2,6-dione | 0.000959 | 7.56 | 0.001731 | 31.5 |
| 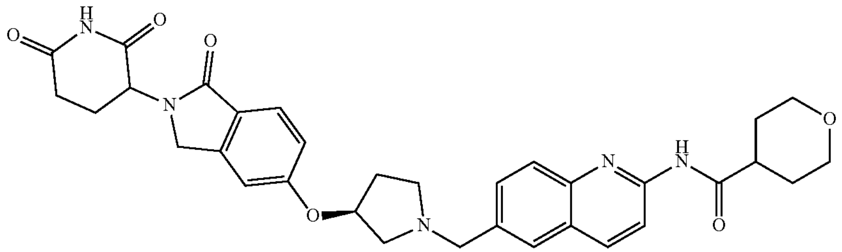 [SMILES: O=C1CCC(N2Cc3cc(O[C@H]4CCN(Cc5ccc6nc(NC(=O)C7CCOCC7)ccc6c5)C4)ccc3C2=O)C(=O)N1] N-(6-{[(3S)-3-{[2-(2,6-dioxopiperidin-3-yl)-1-oxo-2,3-dihydro-1H-isoindol-5-yl]oxy}pyrrolidin-1-yl]methyl}quinolin-2-yl)oxane-4-carboxamide | 0.002033 | 5.73 | 0.001776 | 29 |
| 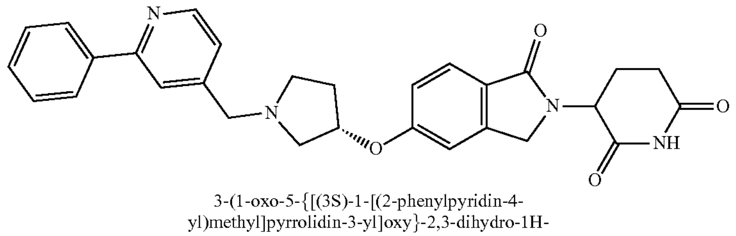 3-(1-oxo-5-{[(3S)-1-[(2-phenylpyridin-4-yl)methyl]pyrrolidin-3-yl]oxy}-2,3-dihydro-1H- | 0.023018 | 9.19 | 0.006943 | 38 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| isoindol-2-yl)piperidine-2,6-dione | | | | |
| 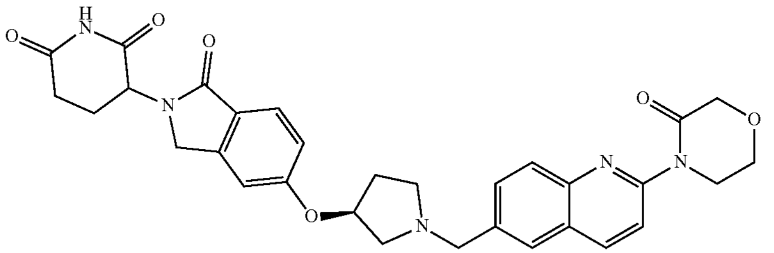 [SMILES: O=C1CCC(N2Cc3cc(O[C@H]4CCN(Cc5ccc6nc(N7CCOCC7=O)ccc6c5)C4)ccc3C2=O)C(=O)N1] 3-(1-oxo-5-{[(3S)-1-{[2-(3-oxomorpholin-4-yl)quinolin-6-yl]methyl}pyrrolidin-3-yl]oxy}-2,3-dihydro-1H-isoindol-2-yl)piperidine-2,6-dione | 0.002911 | 6.88 | 0.002434 | 32 |
| 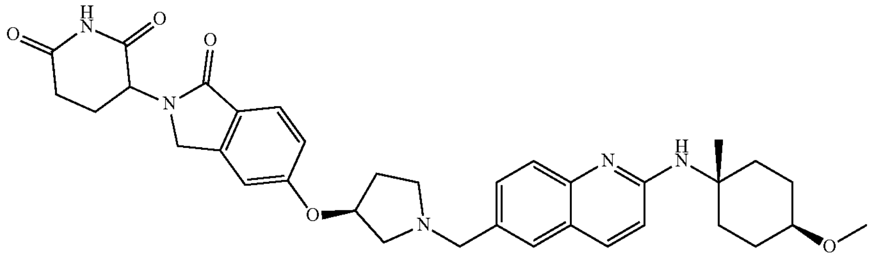 [SMILES: CO[C@H]1CC[C@](C)(Nc2ccc3cc(CN4CC[C@H](Oc5ccc6c(c5)CN(C5CCC(=O)NC5=O)C6=O)C4)ccc3n2)CC1] 3-(1-oxo-5-{[(3S)-1-[(2-{[(1r,4r)-4-methoxy-1-methylcyclohexyl]amino}quinolin-6-yl)methyl]pyrrolidin-3-yl]oxy}-2,3-dihydro-1H-isoindol-2-yl)piperidine-2,6-dione | 0.004203 | 8.155 | 0.005361 | 30 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 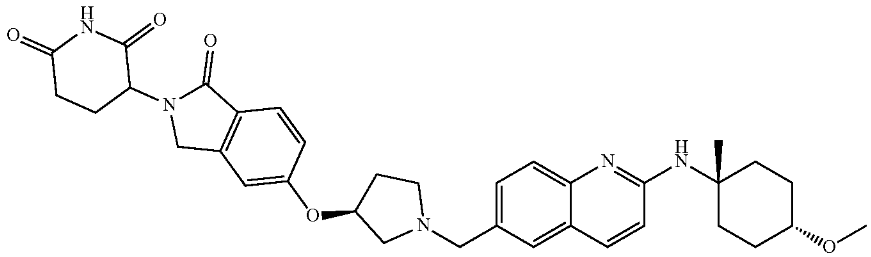 [SMILES: CO[C@H]1CC[C@@](C)(Nc2ccc3cc(CN4CC[C@H](Oc5ccc6c(c5)CN(C5CCC(=O)NC5=O)C6=O)C4)ccc3n2)CC1] 3-(1-oxo-5-{[(3S)-1-[(2-{[(1s,4s)-4-methoxy-1-methylcyclohexyl]amino}quinolin-6-yl)methyl]pyrrolidin-3-yl]oxy}-2,3-dihydro-1H-isoindol-2-yl)piperidine-2,6-dione | 0.000882333 | 8.44 | 0.003414 | 26 |
| 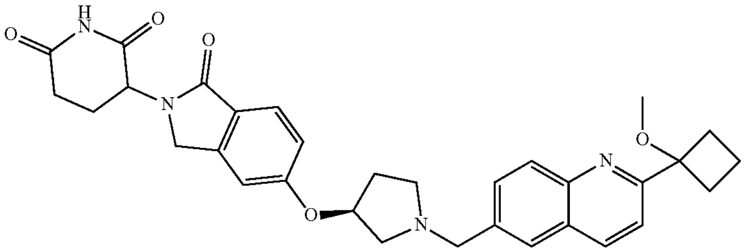 [SMILES: COC1(c2ccc3cc(CN4CC[C@H](Oc5ccc6c(c5)CN(C5CCC(=O)NC5=O)C6=O)C4)ccc3n2)CCC1] 3-(5-{[(3S)-1-{[2-(1-methoxycyclobutyl)quinolin-6-yl]methyl}pyrrolidin-3-yl]oxy}-1-oxo-2,3-dihydro-1H-isoindol-2-yl)piperidine-2,6-dione | 0.003319 | 7.4 | 0.0026925 | 31 |
| 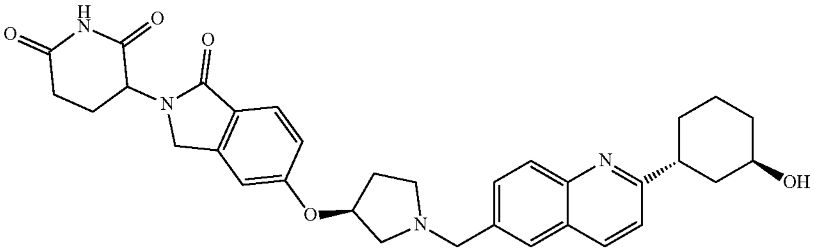 [SMILES: O=C1CCC(N2Cc3cc(O[C@H]4CCN(Cc5ccc6nc([C@@H]7CCC[C@@H](O)C7)ccc6c5)C4)ccc3C2=O)C(=O)N1] 3-(5-{[(3S)-1-({2-[(1R,3R)-3- | 0.001181 | 8.405 | 0.003182 | 31 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| hydroxycyclohexyl]quinolin-6-yl}methyl)pyrrolidin-3-yl]oxy}-1-oxo-2,3-dihydro-1H-isoindol-2-yl)piperidine-2,6-dione | | | | |
| 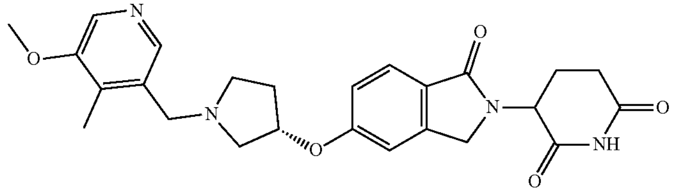 [SMILES: COc1cncc(CN2CC[C@H](Oc3ccc4c(c3)CN(C3CCC(=O)NC3=O)C4=O)C2)c1C] 3-(5-{[(3S)-1-[(5-methoxy-4-methylpyridin-3-yl)methyl]pyrrolidin-3-yl]oxy}-1-oxo-2,3-dihydro-1H-isoindol-2-yl)piperidine-2,6-dione | 0.832623 | 59.99 | 0.028518 | 61 |
| 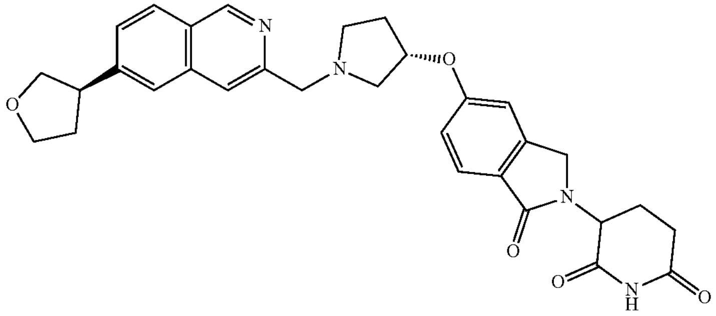 [SMILES: O=C1CCC(N2Cc3cc(O[C@H]4CCN(Cc5cc6cc([C@H]7CCOC7)ccc6cn5)C4)ccc3C2=O)C(=O)N1] 3-(1-oxo-5-{[(3S)-1-({6-[(3R)-oxolan-3-yl]isoquinolin-3-yl}methyl)pyrrolidin-3-yl]oxy}-2,3-dihydro-1H-isoindol-2-yl)piperidine-2,6-dione | 0.003394 | 6.69 | 0.001988 | 28 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 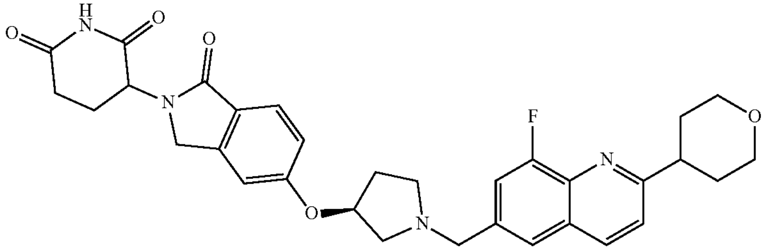 [SMILES: O=C1CCC(N2Cc3cc(O[C@H]4CCN(Cc5cc(F)c6nc(C7CCOCC7)ccc6c5)C4)ccc3C2=O)C(=O)N1] 3-(5-{[(3S)-1-{[8-fluoro-2-(oxan-4-yl)quinolin-6-yl]methyl}pyrrolidin-3-yl]oxy}-1-oxo-2,3-dihydro-1H-isoindol-2-yl)piperidine-2,6-dione | 0.001090306 | 7.098126396 | 0.001238 | 28 |
| 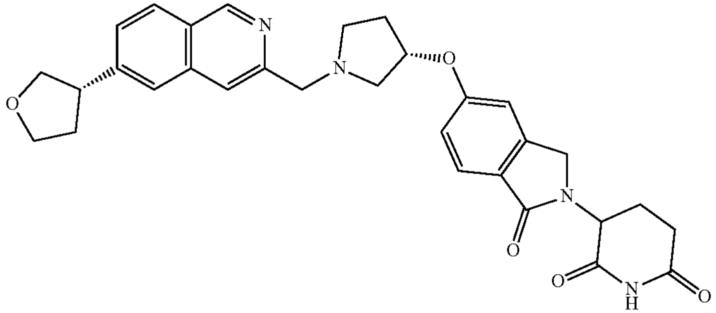 [SMILES: O=C1CCC(N2Cc3cc(O[C@H]4CCN(Cc5cc6cc([C@@H]7CCOC7)ccc6cn5)C4)ccc3C2=O)C(=O)N1] 3-(1-oxo-5-{[(3S)-1-({6-[(3S)-oxolan-3-yl]isoquinolin-3-yl}methyl)pyrrolidin-3-yl]oxy}-2,3-dihydro-1H-isoindol-2-yl)piperidine-2,6-dione | 0.012915 | 5.87 | 0.005385 | 28 |
| 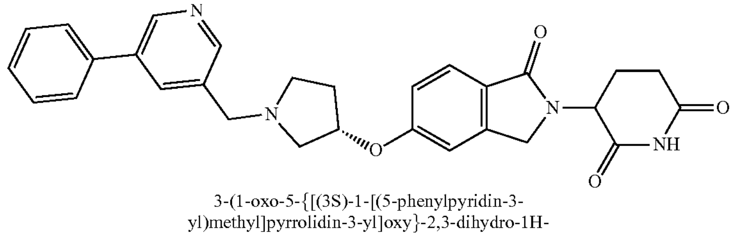 3-(1-oxo-5-{[(3S)-1-[(5-phenylpyridin-3-yl)methyl]pyrrolidin-3-yl]oxy}-2,3-dihydro-1H- | 0.008397 | 7.52 | 0.002166 | 33 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| isoindol-2-yl)piperidine-2,6-dione | | | | |
| 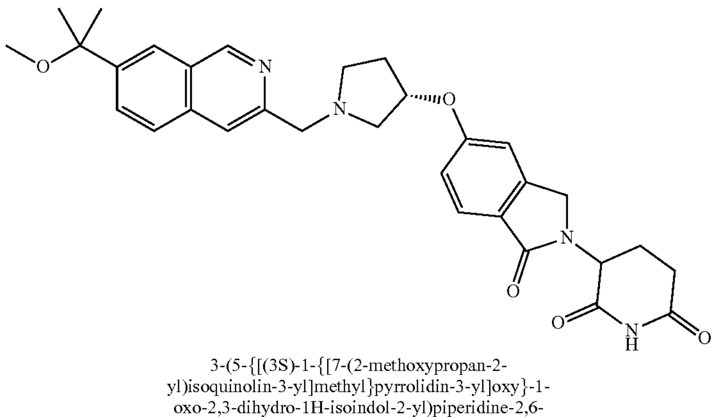 3-(5-{[(3S)-1-{[7-(2-methoxypropan-2-yl)isoquinolin-3-yl]methyl}pyrrolidin-3-yl]oxy}-1-oxo-2,3-dihydro-1H-isoindol-2-yl)piperidine-2,6-dione | 0.00604 | 11.51 | 0.001207 | 32 |
| 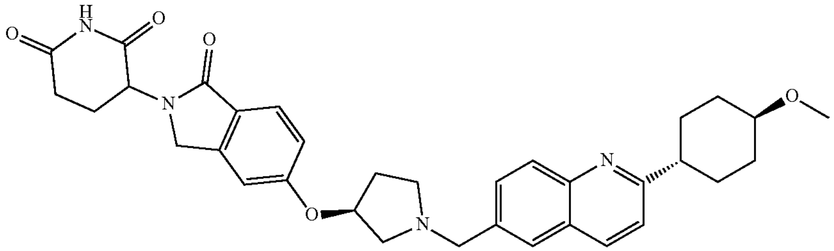 [SMILES: CO[C@H]1CC[C@H](c2ccc3cc(CN4CC[C@H](Oc5ccc6c(c5)CN(C5CCC(=O)NC5=O)C6=O)C4)ccc3n2)CC1] 3-(1-oxo-5-{[(3S)-1-({2-[(1r,4r)-4-methoxycyclohexyl]quinolin-6-yl}methyl)pyrrolidin-3-yl]oxy}-2,3-dihydro-1H-isoindol-2-yl)piperidine-2,6-dione | 0.001289 | 11.035 | 0.00188 | 26 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 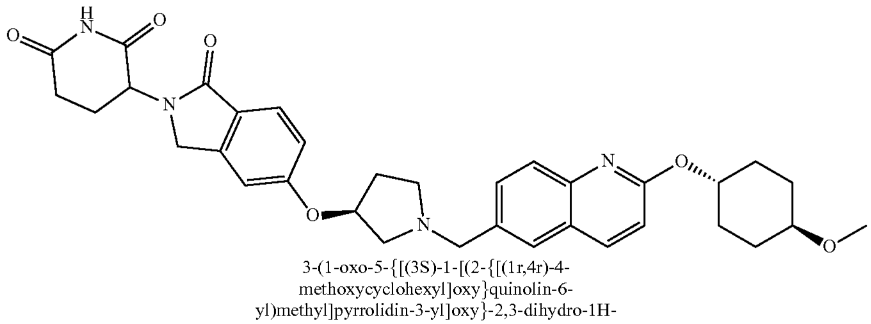 3-(1-oxo-5-{[(3S)-1-[(2-{[(1r,4r)-4-methoxycyclohexyl]oxy}quinolin-6-yl)methyl]pyrrolidin-3-yl]oxy}-2,3-dihydro-1H-isoindol-2-yl)piperidine-2,6-dione | 0.009047 | 8.57 | 0.011534333 | 30.66666667 |
| 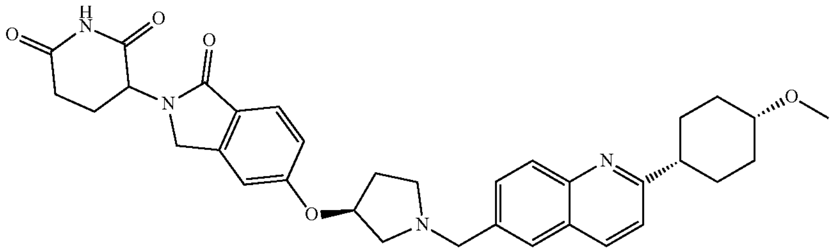 [SMILES: CO[C@H]1CC[C@@H](c2ccc3cc(CN4CC[C@H](Oc5ccc6c(c5)CN(C5CCC(=O)NC5=O)C6=O)C4)ccc3n2)CC1] 3-(1-oxo-5-{[(3S)-1-({2-[(1s,4s)-4-methoxycyclohexyl]quinolin-6-yl}methyl)pyrrolidin-3-yl]oxy}-2,3-dihydro-1H-isoindol-2-yl)piperidine-2,6-dione | 0.001143661 | 9.583262732 | 0.001115 | 30 |
| 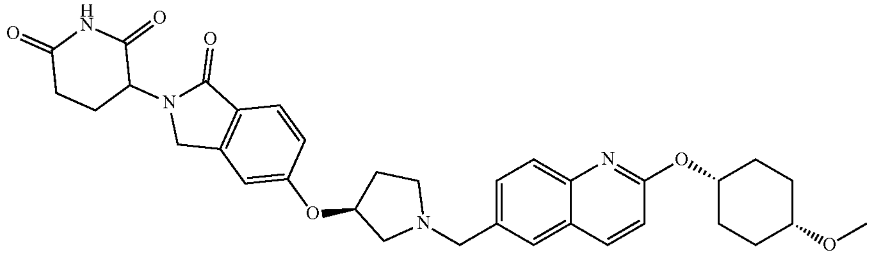 [SMILES: CO[C@H]1CC[C@@H](Oc2ccc3cc(CN4CC[C@H](Oc5ccc6c(c5)CN(C5CCC(=O)NC5=O)C6=O)C4)ccc3n2)CC1] | 0.0053535 | 8.79 | 0.004617667 | 31.33333333 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| --- | --- | --- | --- | --- |
| 3-(1-oxo-5-{[(3S)-1-[(2-{[(1s,4s)-4-methoxycyclohexyl]oxy}quinolin-6-yl)methyl]pyrrolidin-3-yl]oxy}-2,3-dihydro-1H-isoindol-2-yl)piperidine-2,6-dione | | | | |
| 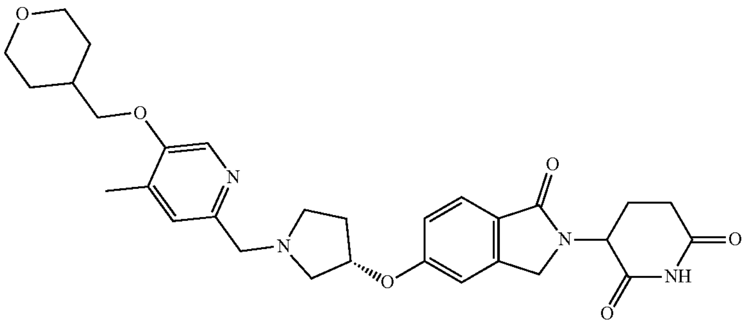 [SMILES: Cc1cc(CN2CC[C@H](Oc3ccc4c(c3)CN(C3CCC(=O)NC3=O)C4=O)C2)ncc1OCC1CCOCC1] 3-(5-{[(3S)-1-({4-methyl-5-[(oxan-4-yl)methoxy]pyridin-2-yl}methyl)pyrrolidin-3-yl]oxy}-1-oxo-2,3-dihydro-1H-isoindol-2-yl)piperidine-2,6-dione | 0.044916 | 16.9 | 0.009709 | 42 |
| 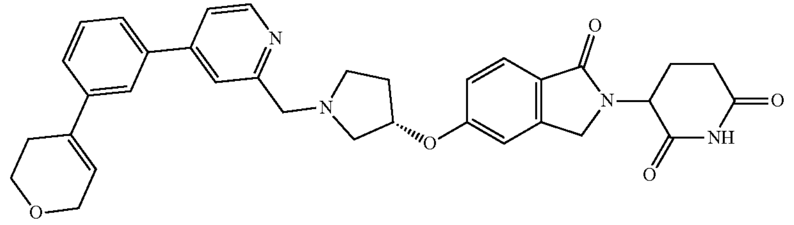 3-(5-{[(3S)-1-({4-[3-(3,6-dihydro-2H-pyran-4-yl)phenyl]pyridin-2-yl}methyl)pyrrolidin-3-yl]oxy}-1-oxo-2,3-dihydro-1H-isoindol-2-yl)piperidine-2,6-dione | 0.000738 | 7.53 | 0.002005 | 28 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 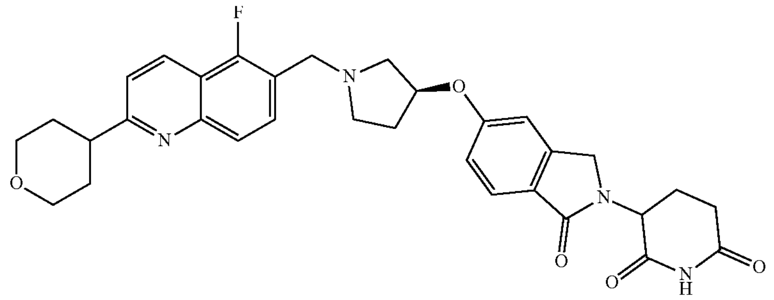 [SMILES: O=C1CCC(N2Cc3cc(O[C@H]4CCN(Cc5ccc6nc(C7CCOCC7)ccc6c5F)C4)ccc3C2=O)C(=O)N1] 3-(5-{[(3S)-1-{[5-fluoro-2-(oxan-4-yl)quinolin-6-yl]methyl}pyrrolidin-3-yl]oxy}-1-oxo-2,3-dihydro-1H-isoindol-2-yl)piperidine-2,6-dione | 0.001285412 | 10.02081059 | 0.001334 | 32 |
| 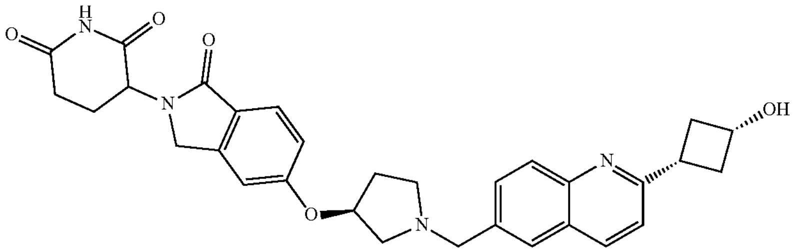 [SMILES: O=C1CCC(N2Cc3cc(O[C@H]4CCN(Cc5ccc6nc([C@H]7C[C@@H](O)C7)ccc6c5)C4)ccc3C2=O)C(=O)N1] 3-(1-oxo-5-{[(3S)-1-({2-[(1s,3s)-3-hydroxycyclobutyl]quinolin-6-yl}methyl)pyrrolidin-3-yl]oxy}-2,3-dihydro-1H-isoindol-2-yl)piperidine-2,6-dione | 0.005214 | 6.89 | 0.002091 | 31 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 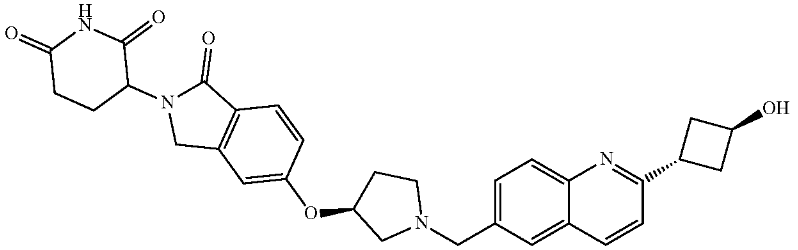 [SMILES: O=C1CCC(N2Cc3cc(O[C@H]4CCN(Cc5ccc6nc([C@H]7C[C@H](O)C7)ccc6c5)C4)ccc3C2=O)C(=O)N1] 3-(1-oxo-5-{[(3S)-1-({2-[(1r,3r)-3-hydroxycyclobutyl]quinolin-6-yl}methyl)pyrrolidin-3-yl]oxy}-2,3-dihydro-1H-isoindol-2-yl)piperidine-2,6-dione | 0.005024 | 7.85 | 0.003799 | 32 |
| 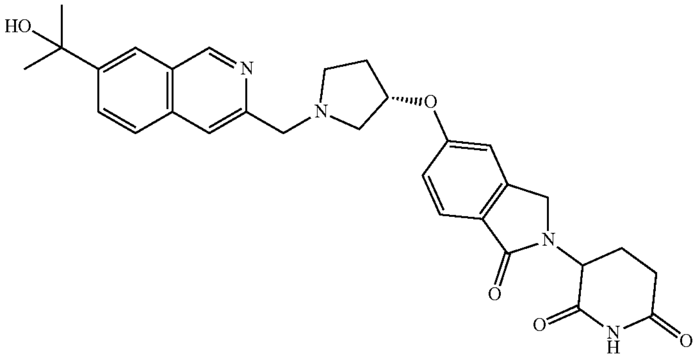 [SMILES: CC(C)(O)c1ccc2cc(CN3CC[C@H](Oc4ccc5c(c4)CN(C4CCC(=O)NC4=O)C5=O)C3)ncc2c1] 3-(5-{[(3S)-1-{[7-(2-hydroxypropan-2-yl)isoquinolin-3-yl]methyl}pyrrolidin-3-yl]oxy}-1-oxo-2,3-dihydro-1H-isoindol-2-yl)piperidine-2,6-dione | 0.016189 | 7.18 | 0.005408 | 31 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 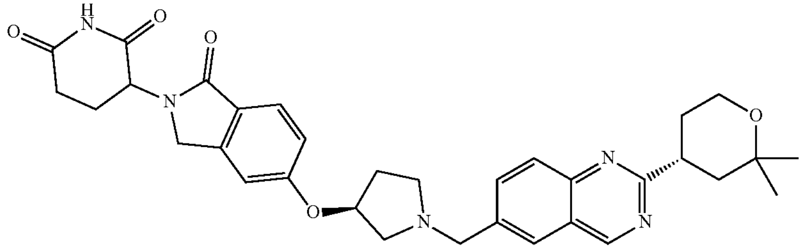 [SMILES: CC1(C)C[C@H](c2ncc3cc(CN4CC[C@H](Oc5ccc6c(c5)CN(C5CCC(=O)NC5=O)C6=O)C4)ccc3n2)CCO1] 3-(5-{[(3S)-1-({2-[(4R)-2,2-dimethyloxan-4-yl]quinazolin-6-yl}methyl)pyrrolidin-3-yl]oxy}-1-oxo-2,3-dihydro-1H-isoindol-2-yl)piperidine-2,6-dione | 0.019685962 | 9.865939224 | 0.064999 | 27 |
| 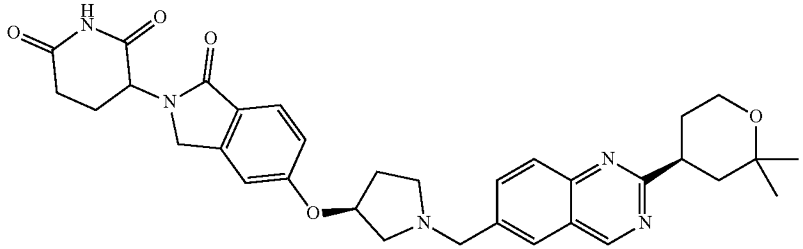 [SMILES: CC1(C)C[C@@H](c2ncc3cc(CN4CC[C@H](Oc5ccc6c(c5)CN(C5CCC(=O)NC5=O)C6=O)C4)ccc3n2)CCO1] 3-(5-{[(3S)-1-({2-[(4S)-2,2-dimethyloxan-4-yl]quinazolin-6-yl}methyl)pyrrolidin-3-yl]oxy}-1-oxo-2,3-dihydro-1H-isoindol-2-yl)piperidine-2,6-dione | 0.009523697 | 8.353940441 | 0.043384 | 31 |
| 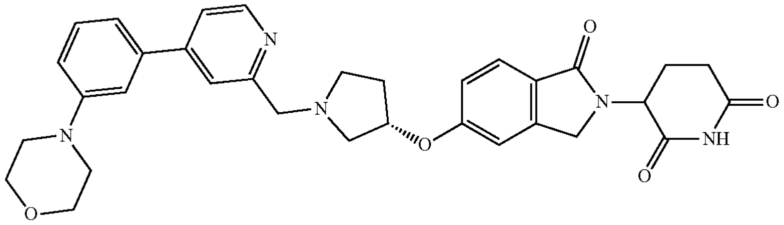 [SMILES: O=C1CCC(N2Cc3cc(O[C@H]4CCN(Cc5cc(-c6cccc(N7CCOCC7)c6)ccn5)C4)ccc3C2=O)C(=O)N1] 3-(5-{[(3S)-1-({4-[3-(morpholin-4- | 0.007331 | 4.54 | 0.002321 | 28 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| yl)phenyl]pyridin-2-yl}methyl)pyrrolidin-3-yl]oxy}-1-oxo-2,3-dihydro-1H-isoindol-2-yl)piperidine-2,6-dione | | | | |
| 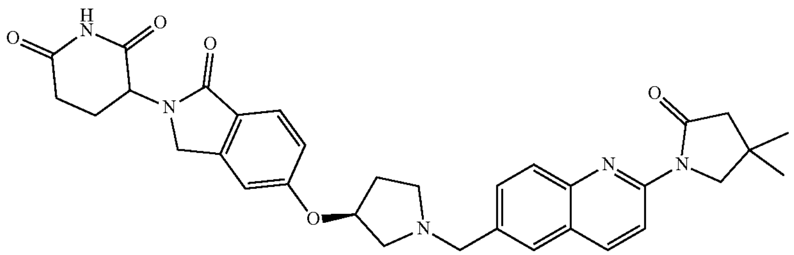 [SMILES: CC1(C)CC(=O)N(c2ccc3cc(CN4CC[C@H](Oc5ccc6c(c5)CN(C5CCC(=O)NC5=O)C6=O)C4)ccc3n2)C1] 3-(5-{[(3S)-1-{[2-(4,4-dimethyl-2-oxopyrrolidin-1-yl)quinolin-6-yl]methyl}pyrrolidin-3-yl]oxy}-1-oxo-2,3-dihydro-1H-isoindol-2-yl)piperidine-2,6-dione | 0.0027725 | 8.145 | 0.001581 | 31 |
| 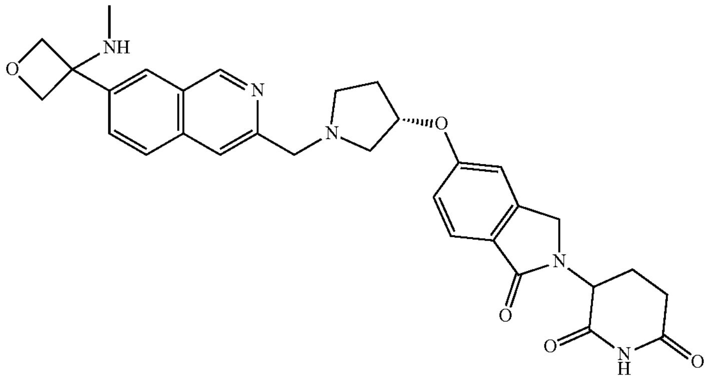 [SMILES: CNC1(c2ccc3cc(CN4CC[C@H](Oc5ccc6c(c5)CN(C5CCC(=O)NC5=O)C6=O)C4)ncc3c2)COC1] 3-(5-{[(3S)-1-({7-[3-(methylamino)oxetan-3-yl]isoquinolin-3-yl}methyl)pyrrolidin-3-yl]oxy}-1-oxo-2,3-dihydro-1H-isoindol-2-yl)piperidine-2,6-dione | 0.056356 | 7.77 | 0.096725 | 33 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 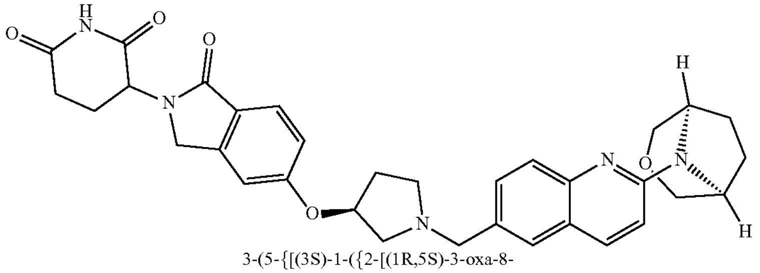 3-(5-{[(3S)-1-({2-[(1R,5S)-3-oxa-8-azabicyclo[3.2.1]octan-8-yl]quinolin-6-yl}methyl)pyrrolidin-3-yl]oxy}-1-oxo-2,3-dihydro-1H-isoindol-2-yl)piperidine-2,6-dione | 0.009725 | 11.965 | 0.004467 | 28 |
| 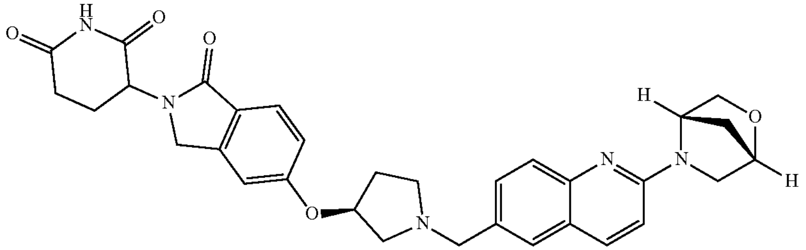 [SMILES: O=C1CCC(N2Cc3cc(O[C@H]4CCN(Cc5ccc6nc(N7C[C@@H]8C[C@H]7CO8)ccc6c5)C4)ccc3C2=O)C(=O)N1] 3-(5-{[(3S)-1-({2-[(1S,4S)-2-oxa-5-azabicyclo[2.2.1]heptan-5-yl]quinolin-6-yl}methyl)pyrrolidin-3-yl]oxy}-1-oxo-2,3-dihydro-1H-isoindol-2-yl)piperidine-2,6-dione | 0.005544 | 8.09 | 0.002981 | 34 |
| 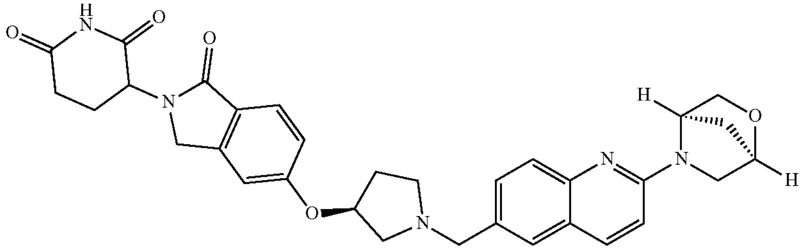 [SMILES: O=C1CCC(N2Cc3cc(O[C@H]4CCN(Cc5ccc6nc(N7C[C@H]8C[C@@H]7CO8)ccc6c5)C4)ccc3C2=O)C(=O)N1] | 0.0061895 | 9.745 | 0.005669 | 33 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(5-{[(3S)-1-({2-[(1R,4R)-2-oxa-5-azabicyclo[2.2.1]heptan-5-yl]quinolin-6-yl}methyl)pyrrolidin-3-yl]oxy}-1-oxo-2,3-dihydro-1H-isoindol-2-yl)piperidine-2,6-dione | | | | |
| 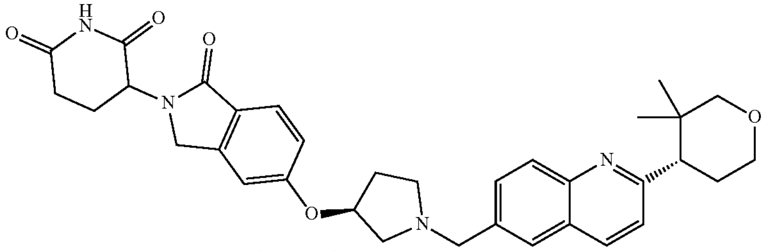 [SMILES: CC1(C)COCC[C@@H]1c1ccc2cc(CN3CC[C@H](Oc4ccc5c(c4)CN(C4CCC(=O)NC4=O)C5=O)C3)ccc2n1] 3-(5-{[(3S)-1-({2-[(4S)-3,3-dimethyloxan-4-yl]quinolin-6-yl}methyl)pyrrolidin-3-yl]oxy}-1-oxo-2,3-dihydro-1H-isoindol-2-yl)piperidine-2,6-dione | 0.001698 | 6.945 | 0.001776 | 34 |
| 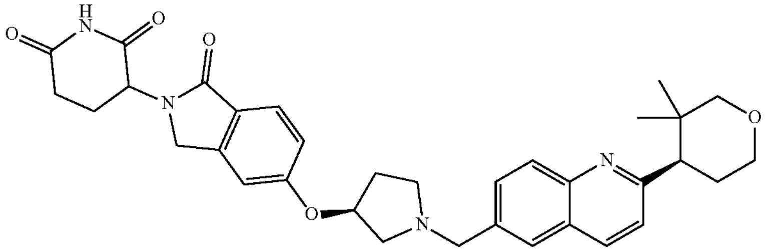 [SMILES: CC1(C)COCC[C@H]1c1ccc2cc(CN3CC[C@H](Oc4ccc5c(c4)CN(C4CCC(=O)NC4=O)C5=O)C3)ccc2n1] 3-(5-{[(3S)-1-({2-[(4R)-3,3-dimethyloxan-4-yl]quinolin-6-yl}methyl)pyrrolidin-3-yl]oxy}-1-oxo-2,3-dihydro-1H-isoindol-2-yl)piperidine-2,6-dione | 0.008034 | 11.03 | 0.003315 | 41 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 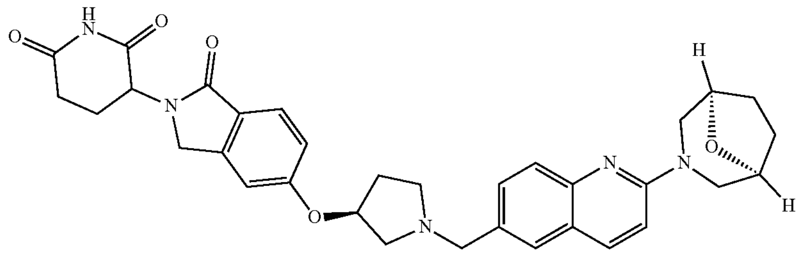 [SMILES: O=C1CCC(N2Cc3cc(O[C@H]4CCN(Cc5ccc6nc(N7C[C@H]8CC[C@@H](C7)O8)ccc6c5)C4)ccc3C2=O)C(=O)N1] 3-(5-{[(3S)-1-({2-[(1R,5S)-8-oxa-3-azabicyclo[3.2.1]octan-3-yl]quinolin-6-yl}methyl)pyrrolidin-3-yl]oxy}-1-oxo-2,3-dihydro-1H-isoindol-2-yl)piperidine-2,6-dione | 0.00642 | 11.085 | 0.0064965 | 37 |
| 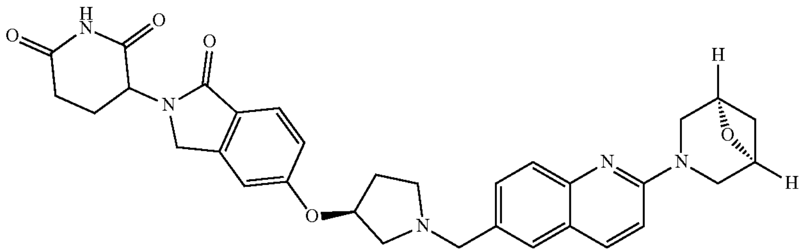 [SMILES: O=C1CCC(N2Cc3cc(O[C@H]4CCN(Cc5ccc6nc(N7C[C@H]8C[C@@H](C7)O8)ccc6c5)C4)ccc3C2=O)C(=O)N1] 3-(5-{[(3S)-1-({2-[(1R,5S)-6-oxa-3-azabicyclo[3.1.1]heptan-3-yl]quinolin-6-yl}methyl)pyrrolidin-3-yl]oxy}-1-oxo-2,3-dihydro-1H-isoindol-2-yl)piperidine-2,6-dione | 0.0031875 | 9.79 | 0.001982 | 38 |
| 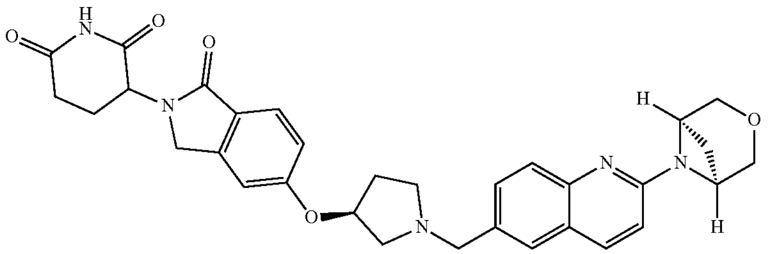 [SMILES: O=C1CCC(N2Cc3cc(O[C@H]4CCN(Cc5ccc6nc(N7[C@@H]8COC[C@H]7C8)ccc6c5)C4)ccc3C2=O)C(=O)N1] | 0.011178 | 9.645 | 0.008623 | 37 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(5-{[(3S)-1-({2-[(1R,5S)-3-oxa-6-azabicyclo[3.1.1]heptan-6-yl]quinolin-6-yl}methyl)pyrrolidin-3-yl]oxy}-1-oxo-2,3-dihydro-1H-isoindol-2-yl)piperidine-2,6-dione<br>4-(6-{[(3S)-3-{[2-(2,6-dioxopiperidin-3-yl)-1-oxo-2,3-dihydro-1H-isoindol-5-yl]oxy}pyrrolidin-1-yl]methyl}quinolin-2-yl)-1λ$^6$-thiomorpholine-1,1-dione | 0.029435 | 10.02 | 0.019096 | 40 |
| 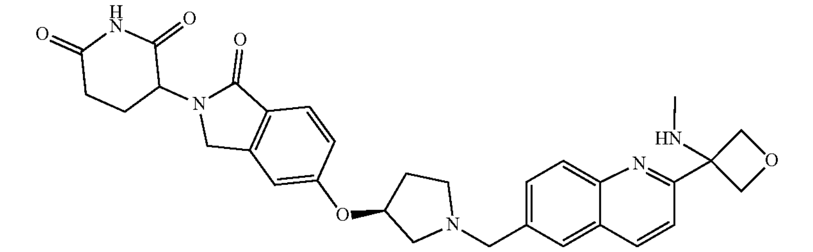 [SMILES: CNC1(c2ccc3cc(CN4CC[C@H](Oc5ccc6c(c5)CN(C5CCC(=O)NC5=O)C6=O)C4)ccc3n2)COC1]<br>3-(5-{[(3S)-1-({2-[3-(methylamino)oxetan-3-yl]quinolin-6-yl}methyl)pyrrolidin-3-yl]oxy}-1-oxo-2,3-dihydro-1H-isoindol-2-yl)piperidine-2,6-dione | 0.019941 | 9.16 | 0.037568 | 36 |
| 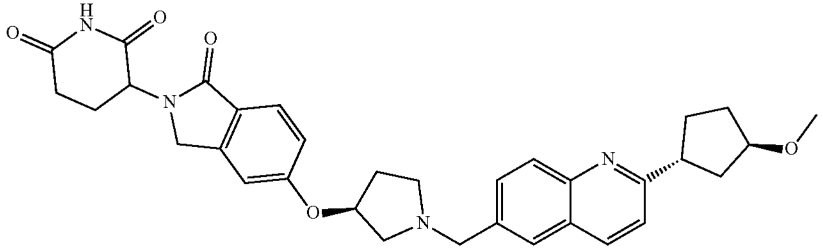<br>3-(5-{[(3S)-1-({2-[(1R,3R)-3-methoxycyclopentyl]quinolin-6-yl}methyl)pyrrolidin-3-yl]oxy}-1-oxo-2,3-dihydro-1H-isoindol-2-yl)piperidine-2,6-dione | 0.001949667 | 7.45 | 0.0047445 | 30 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 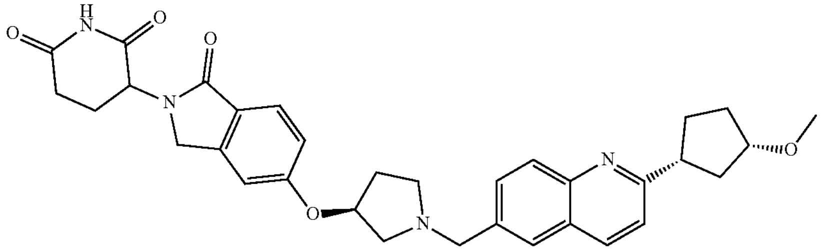 [SMILES: CO[C@H]1CC[C@@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1R,3S)-3-methoxycyclopentyl]quinolin-6-yl}methyl)pyrrolidin-3-yl]oxy}-1-oxo-2,3-dihydro-1H-isoindol-2-yl)piperidine-2,6-dione | 0.000741333 | 7.233333333 | 0.003199667 | 28.33333333 |
| 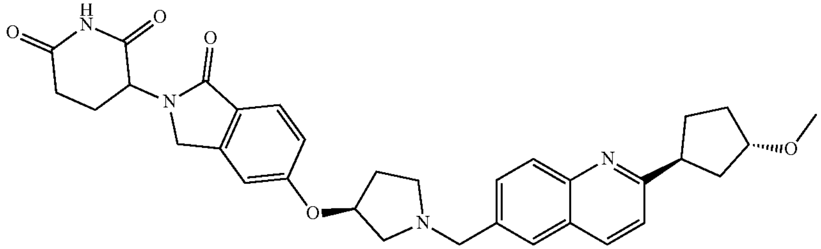 [SMILES: CO[C@H]1CC[C@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1S,3S)-3-methoxycyclopentyl]quinolin-6-yl}methyl)pyrrolidin-3-yl]oxy}-1-oxo-2,3-dihydro-1H-isoindol-2-yl)piperidine-2,6-dione | 0.004798667 | 8.926666667 | 0.0061865 | 32.5 |
| 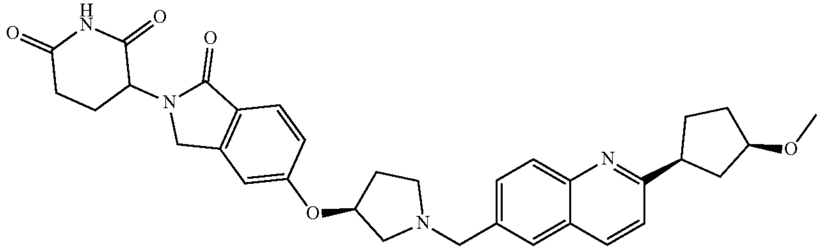 [SMILES: CO[C@@H]1CC[C@H](c2ccc3cc(CN4CC[C@H](Oc5ccc6c(c5)CN(C5CCC(=O)NC5=O)C6=O)C4)ccc3n2)C1] | 0.001609494 | 8.775572428 | 0.002074333 | 29.66666667 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(5-{[(3S)-1-({2-[(1S,3R)-3-methoxycyclopentyl]quinolin-6-yl}methyl)pyrrolidin-3-yl]oxy}-1-oxo-2,3-dihydro-1H-isoindol-2-yl)piperidine-2,6-dione | | | | |
| 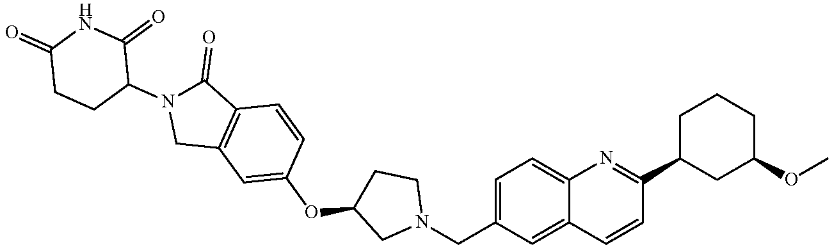 [SMILES: CO[C@@H]1CCC[C@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1S,3R)-3-methoxycyclohexyl]quinolin-6-yl}methyl)pyrrolidin-3-yl]oxy}-1-oxo-2,3-dihydro-1H-isoindol-2-yl)piperidine-2,6-dione | 0.016485 | 9.143333333 | 0.028746 | 32 |
| 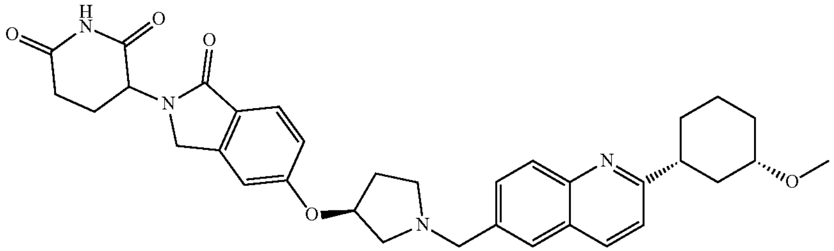 [SMILES: CO[C@H]1CCC[C@@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1R,3S)-3-methoxycyclohexyl]quinolin-6-yl}methyl)pyrrolidin-3-yl]oxy}-1-oxo-2,3-dihydro-1H-isoindol-2-yl)piperidine-2,6-dione | 0.001958333 | 7.623333333 | 0.003488 | 27.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 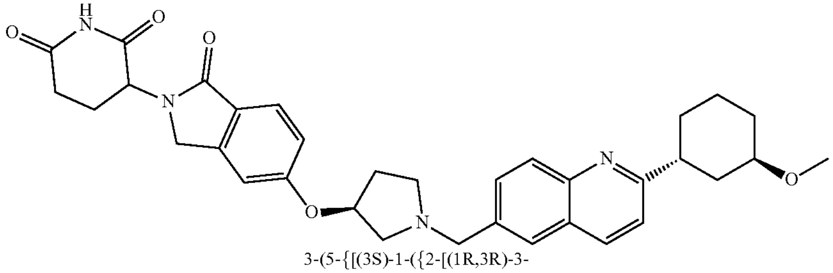 3-(5-{[(3S)-1-({2-[(1R,3R)-3-methoxycyclohexyl]quinolin-6-yl}methyl)pyrrolidin-3-yl]oxy}-1-oxo-2,3-dihydro-1H-isoindol-2-yl)piperidine-2,6-dione | 0.000930333 | 7.97 | 0.002835 | 29 |
| 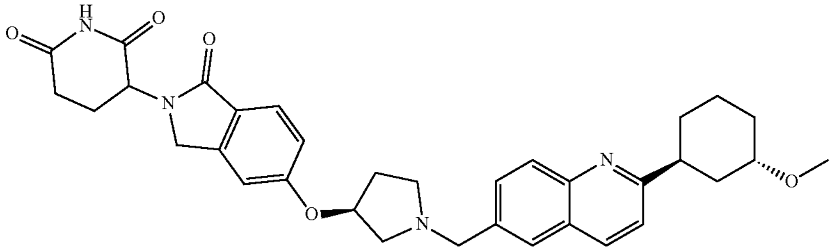 [SMILES: CO[C@H]1CCC[C@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1S,3S)-3-methoxycyclohexyl]quinolin-6-yl}methyl)pyrrolidin-3-yl]oxy}-1-oxo-2,3-dihydro-1H-isoindol-2-yl)piperidine-2,6-dione | 0.0020115 | 9.255 | 0.0035815 | 30.5 |
| 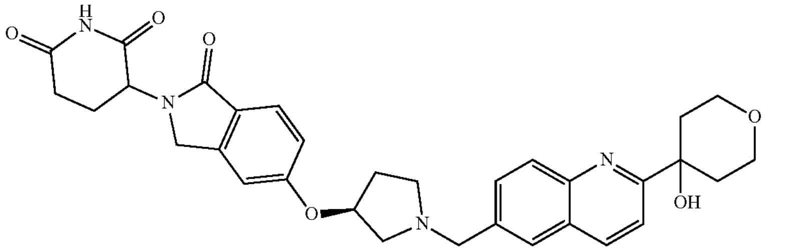 [SMILES: O=C1CCC(N2Cc3cc(O[C@H]4CCN(Cc5ccc6nc(C7(O)CCOCC7)ccc6c5)C4)ccc3C2=O)C(=O)N1] | 0.007408 | 6.55 | 0.008836 | 31.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(5-{[(3S)-1-{[2-(4-hydroxyoxan-4-yl)quinolin-6-yl]methyl}pyrrolidin-3-yl]oxy}-1-oxo-2,3-dihydro-1H-isoindol-2-yl)piperidine-2,6-dione 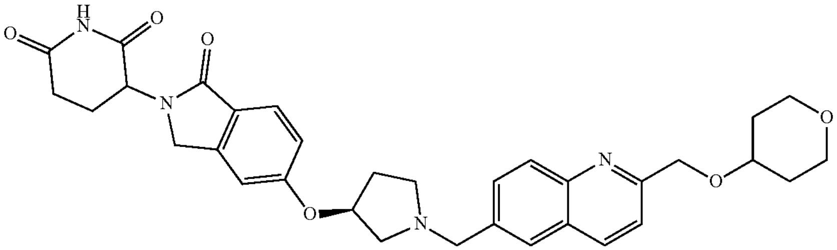 [SMILES: O=C1CCC(N2Cc3cc(O[C@H]4CCN(Cc5ccc6nc(COC7CCOCC7)ccc6c5)C4)ccc3C2=O)C(=O)N1] 3-(5-{[(3S)-1-({2-[(oxan-4-yloxy)methyl]quinolin-6-yl}methyl)pyrrolidin-3-yl]oxy}-1-oxo-2,3-dihydro-1H-isoindol-2-yl)piperidine-2,6-dione | 0.002194902 | 7.294539461 | 0.004727 | 33 |
| 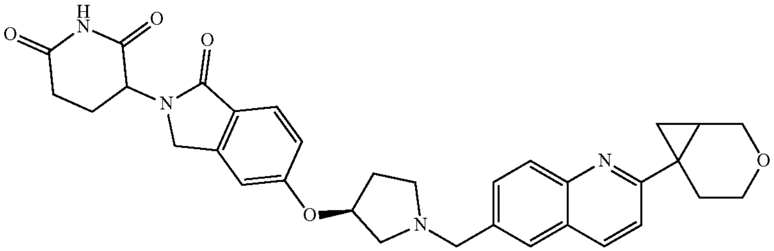 [SMILES: O=C1CCC(N2Cc3cc(O[C@H]4CCN(Cc5ccc6nc(C78CCOCC7C8)ccc6c5)C4)ccc3C2=O)C(=O)N1] 3-(5-{[(3S)-1-[(2-{3-oxabicyclo[4.1.0]heptan-6-yl}quinolin-6-yl)methyl]pyrrolidin-3-yl]oxy}-1-oxo-2,3-dihydro-1H-isoindol-2-yl)piperidine-2,6-dione | 0.002163382 | 9.735276584 | 0.003104667 | 33.33333333 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 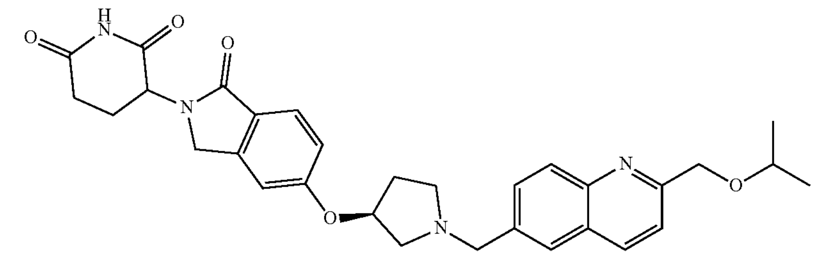 [SMILES: CC(C)OCc1ccc2cc(CN3CC[C@H](Oc4ccc5c(c4)CN(C4CCC(=O)NC4=O)C5=O)C3)ccc2n1] 3-(1-oxo-5-{[(3S)-1-({2-[(propan-2-yloxy)methyl]quinolin-6-yl}methyl)pyrrolidin-3-yl]oxy}-2,3-dihydro-1H-isoindol-2-yl)piperidine-2,6-dione | 0.003402573 | 8.146907101 | 0.006512 | 36 |
| 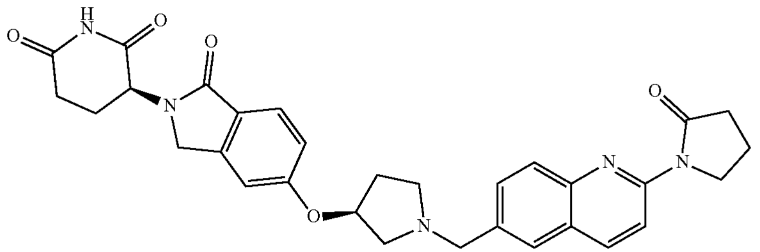 [SMILES: O=C1CC[C@H](N2Cc3cc(O[C@H]4CCN(Cc5ccc6nc(N7CCCC7=O)ccc6c5)C4)ccc3C2=O)C(=O)N1] (3S)-3-(1-oxo-5-{[(3S)-1-{[2-(2-oxopyrrolidin-1-yl)quinolin-6-yl]methyl}pyrrolidin-3-yl]oxy}-2,3-dihydro-1H-isoindol-2-yl)piperidine-2,6-dione | 0.002821333 | 8.56 | 0.001511 | 40 |
| 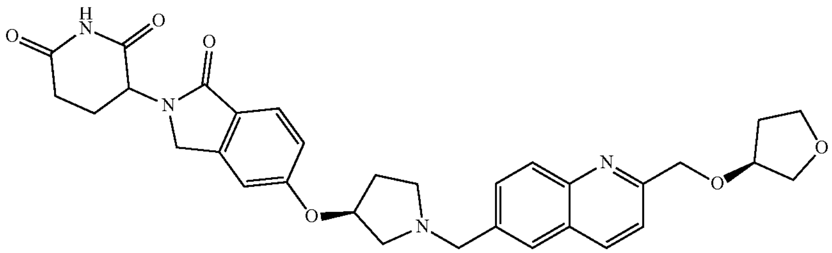 [SMILES: O=C1CCC(N2Cc3cc(O[C@H]4CCN(Cc5ccc6nc(CO[C@H]7CCOC7)ccc6c5)C4)ccc3C2=O)C(=O)N1] 3-(1-oxo-5-{[(3S)-1-[(2-{[(3S)-oxolan-3- | 0.003119 | 7.75 | 0.007036 | 33 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| yloxy]methyl}quinolin-6-yl)methyl]pyrrolidin-3-yl]oxy}-2,3-dihydro-1H-isoindol-2-yl)piperidine-2,6-dione | | | | |
| 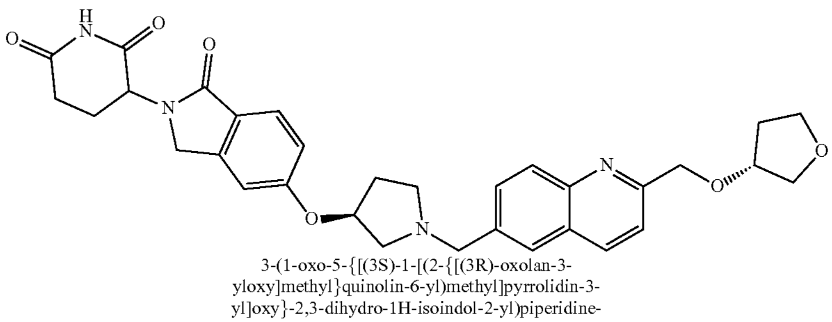 3-(1-oxo-5-{[(3S)-1-[(2-{[(3R)-oxolan-3-yloxy]methyl}quinolin-6-yl)methyl]pyrrolidin-3-yl]oxy}-2,3-dihydro-1H-isoindol-2-yl)piperidine-2,6-dione | 0.002625 | 6.56 | 0.004507 | 30 |
| 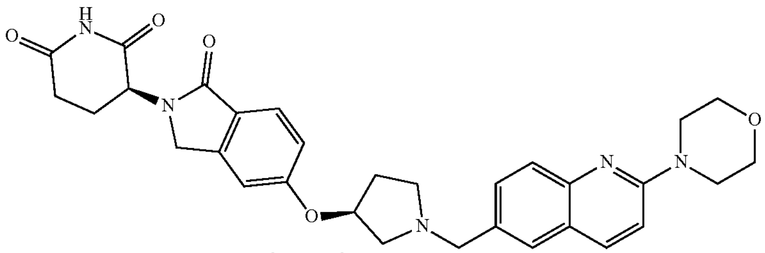 [SMILES: O=C1CC[C@H](N2Cc3cc(O[C@H]4CCN(Cc5ccc6nc(N7CCOCC7)ccc6c5)C4)ccc3C2=O)C(=O)N1] (3S)-3-(5-{[(3S)-1-{[2-(morpholin-4-yl)quinolin-6-yl]methyl}pyrrolidin-3-yl]oxy}-1-oxo-2,3-dihydro-1H-isoindol-2-yl)piperidine-2,6-dione | 0.009714541 | 14.56095405 | 0.001829168 | 34.59000015 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 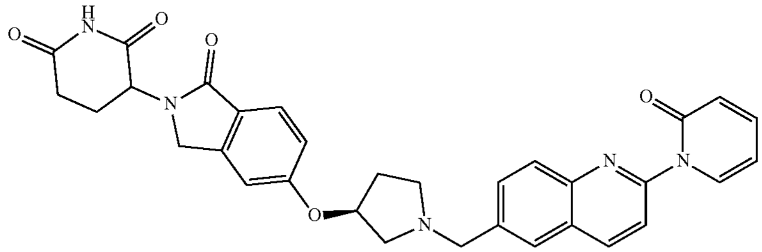 [SMILES: O=C1CCC(N2Cc3cc(O[C@H]4CCN(Cc5ccc6nc(-n7ccccc7=O)ccc6c5)C4)ccc3C2=O)C(=O)N1] 3-(1-oxo-5-{[(3S)-1-{[2-(2-oxo-1,2-dihydropyridin-1-yl)quinolin-6-yl]methyl}pyrrolidin-3-yl]oxy}-2,3-dihydro-1H-isoindol-2-yl)piperidine-2,6-dione | 0.0019315 | 8.805 | 0.0022695 | 35 |
| 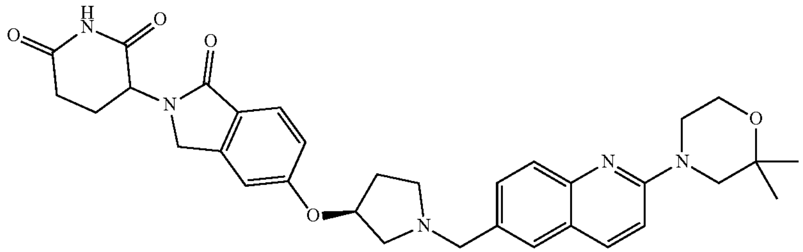 [SMILES: CC1(C)CN(c2ccc3cc(CN4CC[C@H](Oc5ccc6c(c5)CN(C5CCC(=O)NC5=O)C6=O)C4)ccc3n2)CCO1] 3-(5-{[(3S)-1-{[2-(2,2-dimethylmorpholin-4-yl)quinolin-6-yl]methyl}pyrrolidin-3-yl]oxy}-1-oxo-2,3-dihydro-1H-isoindol-2-yl)piperidine-2,6-dione | 0.002614154 | 10.47609367 | 0.002407 | 32 |
| 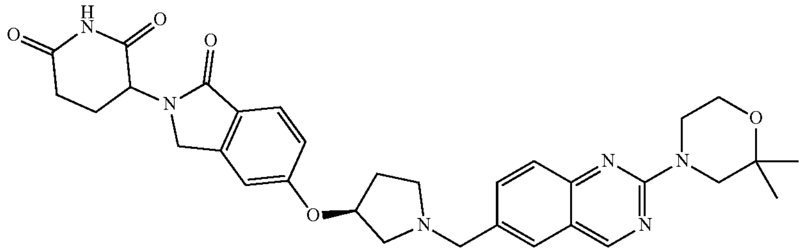 [SMILES: CC1(C)CN(c2ncc3cc(CN4CC[C@H](Oc5ccc6c(c5)CN(C5CCC(=O)NC5=O)C6=O)C4)ccc3n2)CCO1] | 0.007668547 | 9.381135283 | 0.0116225 | 31 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(5-{[(3S)-1-{[2-(2,2-dimethylmorpholin-4-yl)quinazolin-6-yl]methyl}pyrrolidin-3-yl]oxy}-1-oxo-2,3-dihydro-1H-isoindol-2-yl)piperidine-2,6-dione | | | | |
| 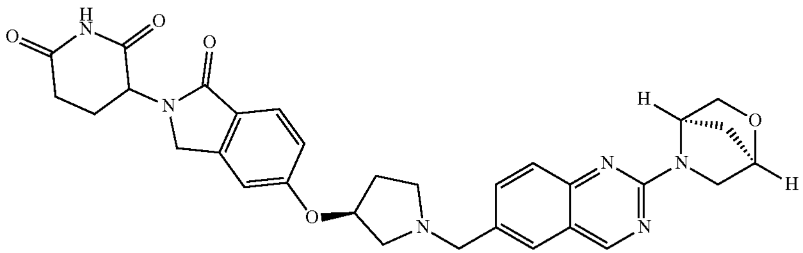 [SMILES: O=C1CCC(N2Cc3cc(O[C@H]4CCN(Cc5ccc6nc(N7C[C@H]8C[C@@H]7CO8)ncc6c5)C4)ccc3C2=O)C(=O)N1] 3-(5-{[(3S)-1-({2-[(1R,4R)-2-oxa-5-azabicyclo[2.2.1]heptan-5-yl]quinazolin-6-yl}methyl)pyrrolidin-3-yl]oxy}-1-oxo-2,3-dihydro-1H-isoindol-2-yl)piperidine-2,6-dione | 0.076619 | 16.57 | 0.080115 | 39 |
| 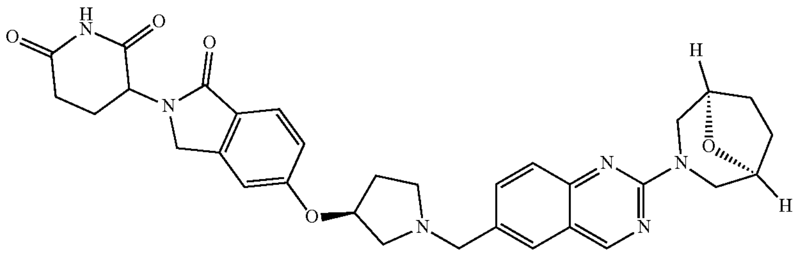 [SMILES: O=C1CCC(N2Cc3cc(O[C@H]4CCN(Cc5ccc6nc(N7C[C@H]8CC[C@@H](C7)O8)ncc6c5)C4)ccc3C2=O)C(=O)N1] 3-(5-{[(3S)-1-({2-[(1R,5S)-8-oxa-3-azabicyclo[3.2.1]octan-3-yl]quinazolin-6-yl}methyl)pyrrolidin-3-yl]oxy}-1-oxo-2,3-dihydro-1H-isoindol-2-yl)piperidine-2,6-dione | 0.015604 | 11.04 | 0.045854 | 35 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 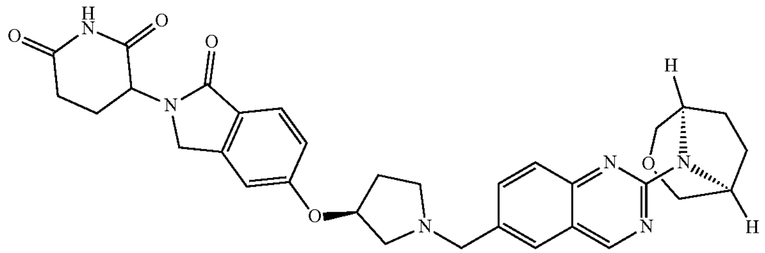 [SMILES: O=C1CCC(N2Cc3cc(O[C@H]4CCN(Cc5ccc6nc(N7[C@@H]8CC[C@H]7COC8)ncc6c5)C4)ccc3C2=O)C(=O)N1] 3-(5-{[(3S)-1-({2-[(1R,5S)-3-oxa-8-azabicyclo[3.2.1]octan-8-yl]quinazolin-6-yl}methyl)pyrrolidin-3-yl]oxy}-1-oxo-2,3-dihydro-1H-isoindol-2-yl)piperidine-2,6-dione | 0.024854 | 8.88 | 0.100692 | 33 |
| 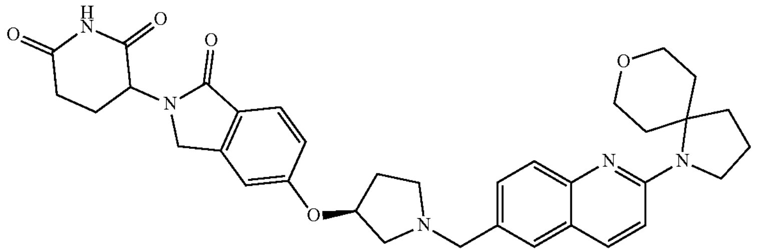 [SMILES: O=C1CCC(N2Cc3cc(O[C@H]4CCN(Cc5ccc6nc(N7CCCC78CCOCC8)ccc6c5)C4)ccc3C2=O)C(=O)N1] 3-(5-{[(3S)-1-[(2-{8-oxa-1-azaspiro[4.5]decan-1-yl}quinolin-6-yl)methyl]pyrrolidin-3-yl]oxy}-1-oxo-2,3-dihydro-1H-isoindol-2-yl)piperidine-2,6-dione | 0.015475 | 20.2 | 0.011275 | 47 |
| 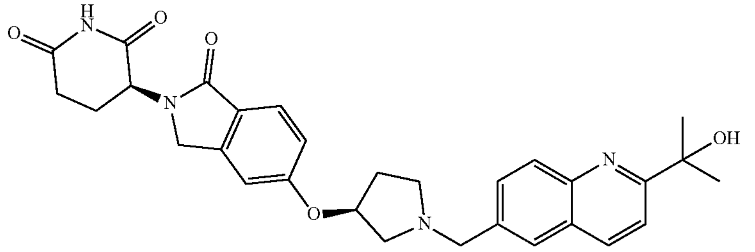 [SMILES: CC(C)(O)c1ccc2cc(CN3CC[C@H](Oc4ccc5c(c4)CN([C@H]4CCC(=O)NC4=O)C5=O)C3)ccc2n1] | 0.010088768 | 12.89005417 | 0.001687122 | 33.91906071 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| (3S)-3-(5-{[(3S)-1-{[2-(2-hydroxypropan-2-yl)quinolin-6-yl]methyl}pyrrolidin-3-yl]oxy}-1-oxo-2,3-dihydro-1H-isoindol-2-yl)piperidine-2,6-dione | | | | |
| 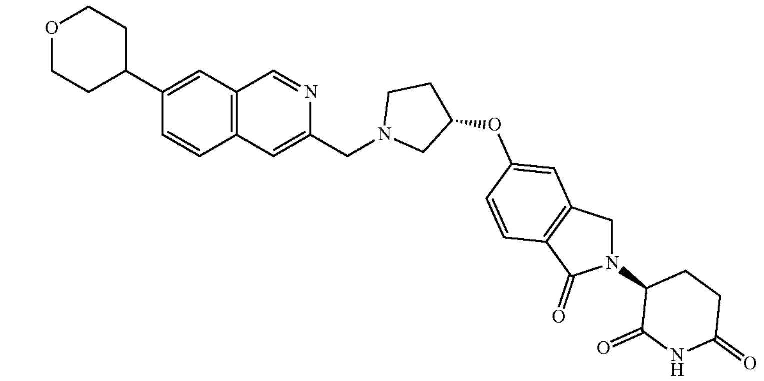 [SMILES: O=C1CC[C@H](N2Cc3cc(O[C@H]4CCN(Cc5cc6ccc(C7CCOCC7)cc6cn5)C4)ccc3C2=O)C(=O)N1] (3S)-3-(5-{[(3S)-1-{[7-(oxan-4-yl)isoquinolin-3-yl]methyl}pyrrolidin-3-yl]oxy}-1-oxo-2,3-dihydro-1H-isoindol-2-yl)piperidine-2,6-dione | 0.001821229 | 8.913043903 | 0.00084434 | 33.41593075 |
| 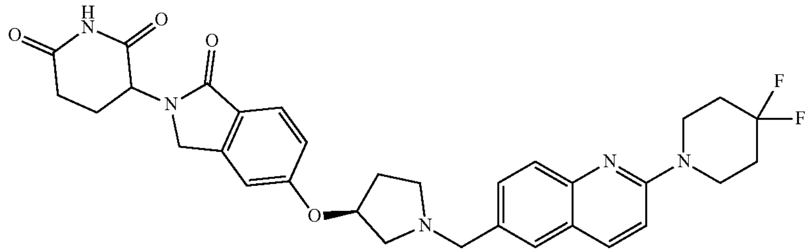 [SMILES: O=C1CCC(N2Cc3cc(O[C@H]4CCN(Cc5ccc6nc(N7CCC(F)(F)CC7)ccc6c5)C4)ccc3C2=O)C(=O)N1] 3-(5-{[(3S)-1-{[2-(4,4-difluoropiperidin-1-yl)quinolin-6-yl]methyl}pyrrolidin-3-yl]oxy}-1-oxo-2,3-dihydro-1H-isoindol-2-yl)piperidine-2,6-dione | 0.017852 | 17.9 | 0.038423506 | 21.62199974 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 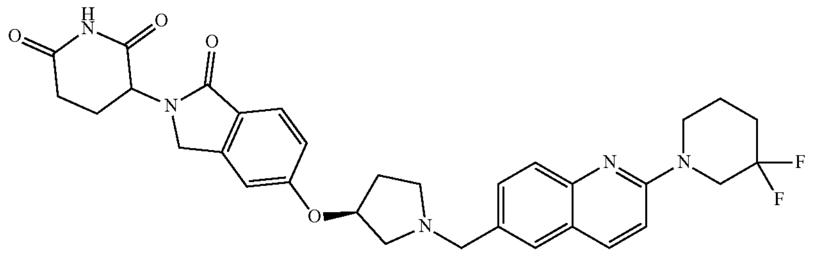 [SMILES: O=C1CCC(N2Cc3cc(O[C@H]4CCN(Cc5ccc6nc(N7CCCC(F)(F)C7)ccc6c5)C4)ccc3C2=O)C(=O)N1] 3-(5-{[(3S)-1-{[2-(3,3-difluoropiperidin-1-yl)quinolin-6-yl]methyl}pyrrolidin-3-yl]oxy}-1-oxo-2,3-dihydro-1H-isoindol-2-yl)piperidine-2,6-dione | 0.011229 | 12.35 | 0.018533198 | 25.84199905 |
| 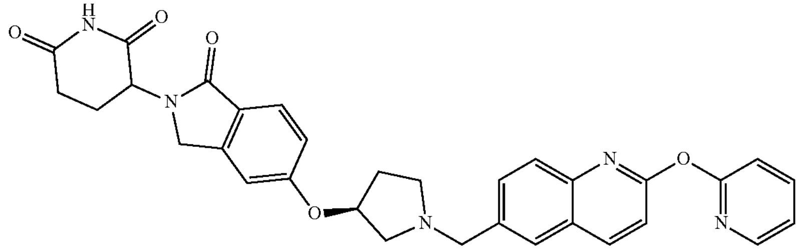 [SMILES: O=C1CCC(N2Cc3cc(O[C@H]4CCN(Cc5ccc6nc(Oc7ccccn7)ccc6c5)C4)ccc3C2=O)C(=O)N1] 3-(1-oxo-5-{[(3S)-1-{[2-(pyridin-2-yloxy)quinolin-6-yl]methyl}pyrrolidin-3-yl]oxy}-2,3-dihydro-1H-isoindol-2-yl)piperidine-2,6-dione | 0.002875 | 7.62 | 0.006393 | 35 |
| 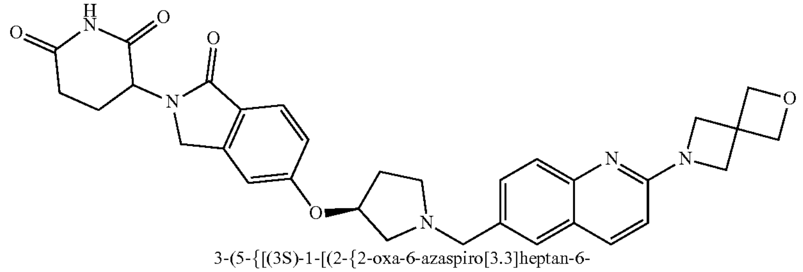 3-(5-{[(3S)-1-[(2-{2-oxa-6-azaspiro[3.3]heptan-6- | 0.010661532 | 14.91290038 | 0.007757 | 41.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| yl}quinolin-6-yl)methyl]pyrrolidin-3-yl]oxy}-1-oxo-2,3-dihydro-1H-isoindol-2-yl)piperidine-2,6-dione | | | | |
| 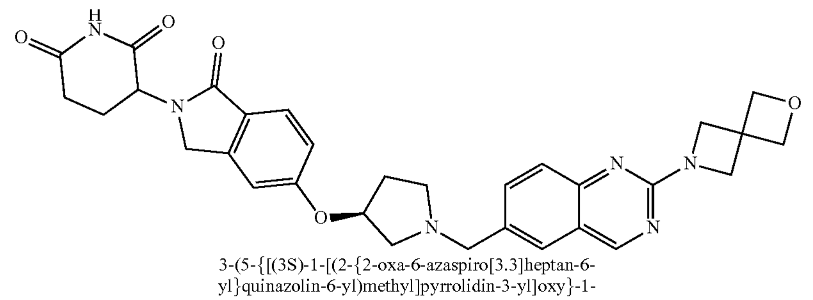 3-(5-{[(3S)-1-[(2-{2-oxa-6-azaspiro[3.3]heptan-6-yl}quinazolin-6-yl)methyl]pyrrolidin-3-yl]oxy}-1-oxo-2,3-dihydro-1H-isoindol-2-yl)piperidine-2,6-dione | 0.021766535 | 15.5042561 | 0.0354915 | 37 |
| 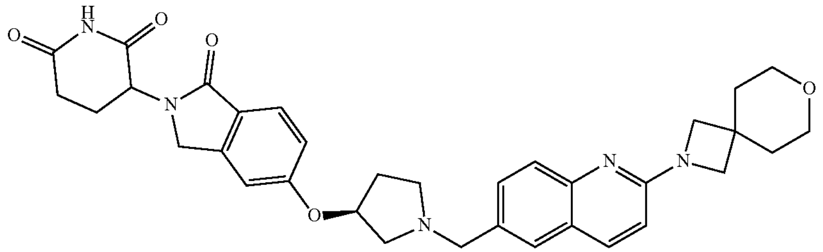 [SMILES: O=C1CCC(N2Cc3cc(O[C@H]4CCN(Cc5ccc6nc(N7CC8(CCOCC8)C7)ccc6c5)C4)ccc3C2=O)C(=O)N1] 3-(5-{[(3S)-1-[(2-{7-oxa-2-azaspiro[3.5]nonan-2-yl}quinolin-6-yl)methyl]pyrrolidin-3-yl]oxy}-1-oxo-2,3-dihydro-1H-isoindol-2-yl)piperidine-2,6-dione | 0.002836162 | 10.12529081 | 0.0019395 | 36 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 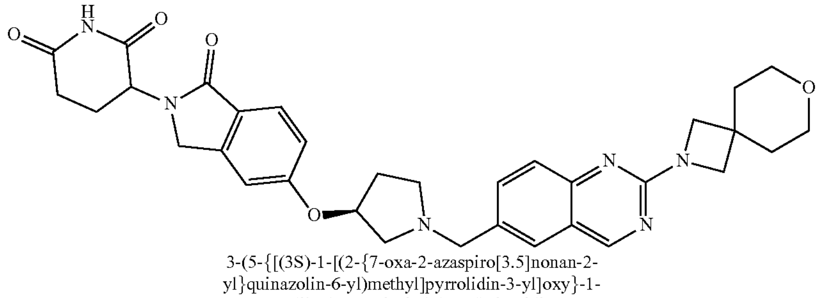 3-(5-{[(3S)-1-[(2-{7-oxa-2-azaspiro[3.5]nonan-2-yl}quinazolin-6-yl)methyl]pyrrolidin-3-yl]oxy}-1-oxo-2,3-dihydro-1H-isoindol-2-yl)piperidine-2,6-dione | 0.010241881 | 9.958359566 | 0.016598 | 35 |
| 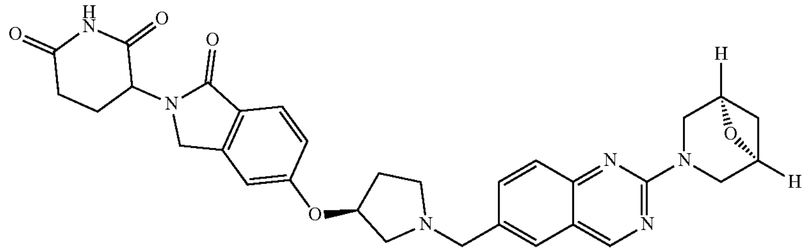 [SMILES: O=C1CCC(N2Cc3cc(O[C@H]4CCN(Cc5ccc6nc(N7C[C@H]8C[C@@H](C7)O8)ncc6c5)C4)ccc3C2=O)C(=O)N1] 3-(5-{[(3S)-1-({2-[(1R,5S)-6-oxa-3-azabicyclo[3.1.1]heptan-3-yl]quinazolin-6-yl}methyl)pyrrolidin-3-yl]oxy}-1-oxo-2,3-dihydro-1H-isoindol-2-yl)piperidine-2,6-dione | 0.016416526 | 13.42419036 | 0.020233 | 39 |
| 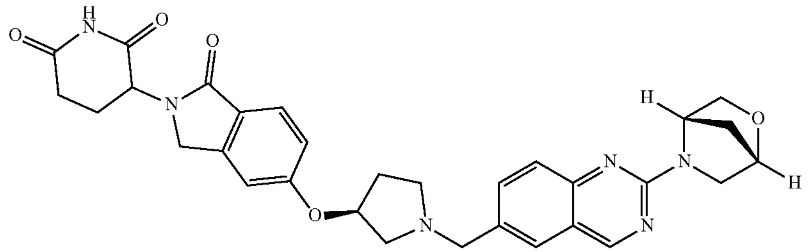 [SMILES: O=C1CCC(N2Cc3cc(O[C@H]4CCN(Cc5ccc6nc(N7C[C@@H]8C[C@H]7CO8)ncc6c5)C4)ccc3C2=O)C(=O)N1] | 0.009862503 | 9.575561022 | 0.0122515 | 34.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(5-{[(3S)-1-({2-[(1S,4S)-2-oxa-5-azabicyclo[2.2.1]heptan-5-yl]quinazolin-6-yl}methyl)pyrrolidin-3-yl]oxy}-1-oxo-2,3-dihydro-1H-isoindol-2-yl)piperidine-2,6-dione | | | | |
| 4-(6-{[(3S)-3-{[2-(2,6-dioxopiperidin-3-yl)-1-oxo-2,3-dihydro-1H-isoindol-5-yl]oxy}pyrrolidin-1-yl]methyl}quinazolin-2-yl)-1$\lambda^6$-thiomorpholine-1,1-dione | 0.051025084 | 17.08950503 | 0.023571 | 42 |
| 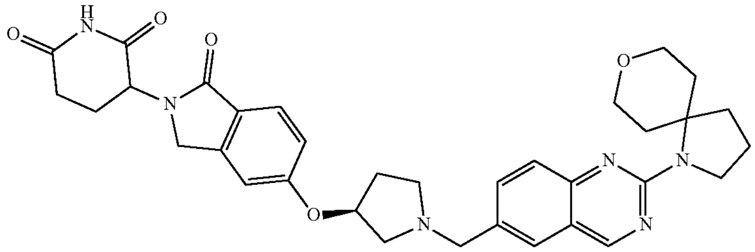 [SMILES: O=C1CCC(N2Cc3cc(O[C@H]4CCN(Cc5ccc6nc(N7CCCC78CCOCC8)ncc6c5)C4)ccc3C2=O)C(=O)N1] 3-(5-{[(3S)-1-[(2-{8-oxa-1-azaspiro[4.5]decan-1-yl}quinazolin-6-yl)methyl]pyrrolidin-3-yl]oxy}-1-oxo-2,3-dihydro-1H-isoindol-2-yl)piperidine-2,6-dione | 0.014121 | 20.87 | 0.018086 | 47 |
| 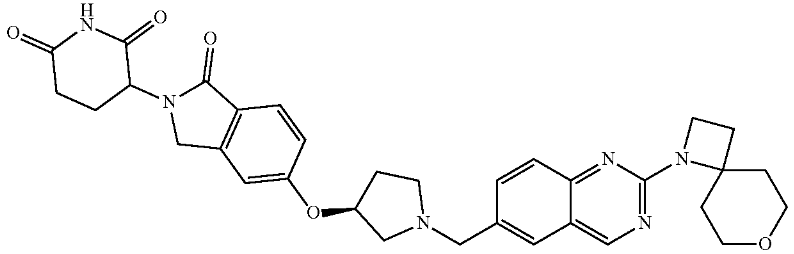 [SMILES: O=C1CCC(N2Cc3cc(O[C@H]4CCN(Cc5ccc6nc(N7CCC78CCOCC8)ncc6c5)C4)ccc3C2=O)C(=O)N1] 3-(5-{[(3S)-1-[(2-{7-oxa-1-azaspiro[3.5]nonan-1-yl}quinazolin-6-yl)methyl]pyrrolidin-3-yl]oxy}-1-oxo-2,3-dihydro-1H-isoindol-2-yl)piperidine-2,6-dione | 0.012621414 | 13.58939464 | 0.011355 | 37 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 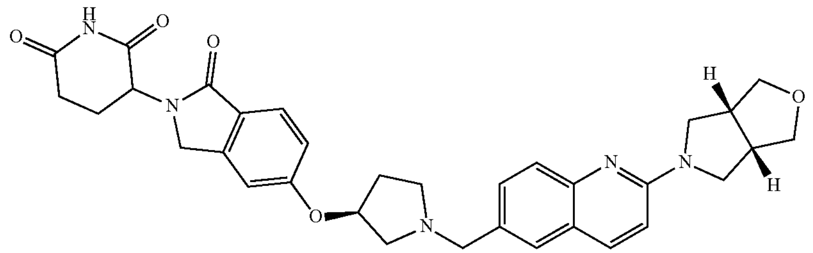 [SMILES: O=C1CCC(N2Cc3cc(O[C@H]4CCN(Cc5ccc6nc(N7C[C@H]8COC[C@H]8C7)ccc6c5)C4)ccc3C2=O)C(=O)N1] 3-(5-{[(3S)-1-({2-[(3aR,6aS)-hexahydro-1H-furo[3,4-c]pyrrol-5-yl]quinolin-6-yl}methyl)pyrrolidin-3-yl]oxy}-1-oxo-2,3-dihydro-1H-isoindol-2-yl)piperidine-2,6-dione | 0.006402683 | 14.72973956 | 0.00361 | 39 |
| 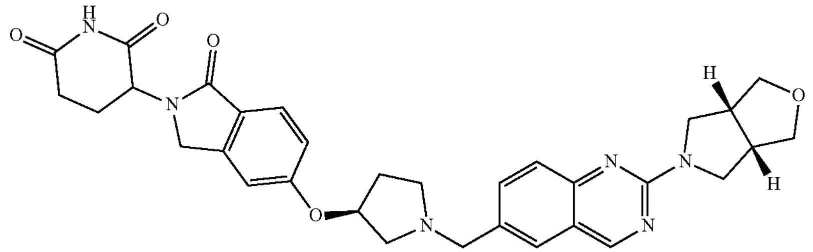 [SMILES: O=C1CCC(N2Cc3cc(O[C@H]4CCN(Cc5ccc6nc(N7C[C@H]8COC[C@H]8C7)ncc6c5)C4)ccc3C2=O)C(=O)N1] 3-(5-{[(3S)-1-({2-[(3aR,6aS)-hexahydro-1H-furo[3,4-c]pyrrol-5-yl]quinazolin-6-yl}methyl)pyrrolidin-3-yl]oxy}-1-oxo-2,3-dihydro-1H-isoindol-2-yl)piperidine-2,6-dione | 0.01296031 | 12.42971036 | 0.013981 | 38 |
| 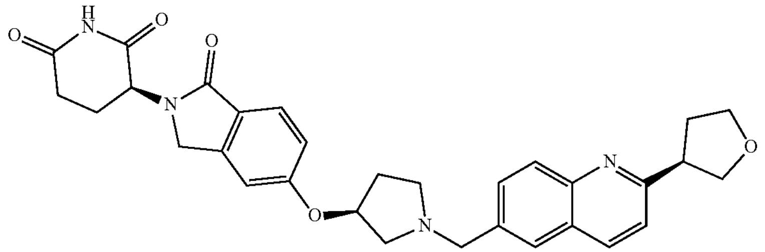 [SMILES: O=C1CC[C@H](N2Cc3cc(O[C@H]4CCN(Cc5ccc6nc([C@H]7CCOC7)ccc6c5)C4)ccc3C2=O)C(=O)N1] | 0.002683396 | 8.547140908 | 0.0025895 | 35.5 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| (3S)-3-(1-oxo-5-{[(3S)-1-({2-[(3R)-oxolan-3-yl]quinolin-6-yl}methyl)pyrrolidin-3-yl]oxy}-2,3-dihydro-1H-isoindol-2-yl)piperidine-2,6-dione | | | | |
| 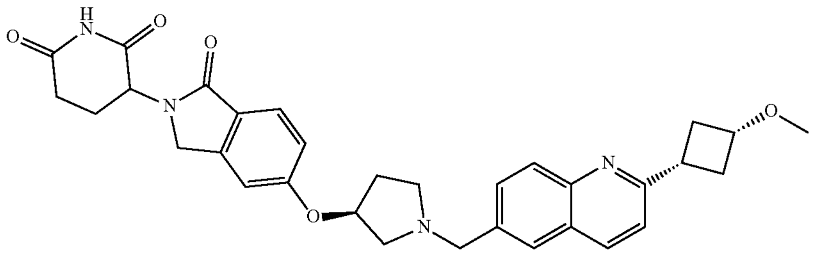 3-(1-oxo-5-{[(3S)-1-({2-[(1s,3s)-3-methoxycyclobutyl]quinolin-6-yl}methyl)pyrrolidin-3-yl]oxy}-2,3-dihydro-1H-isoindol-2-yl)piperidine-2,6-dione | 0.002665125 | 7.759870695 | 0.00209083 | 28.27479172 |
| 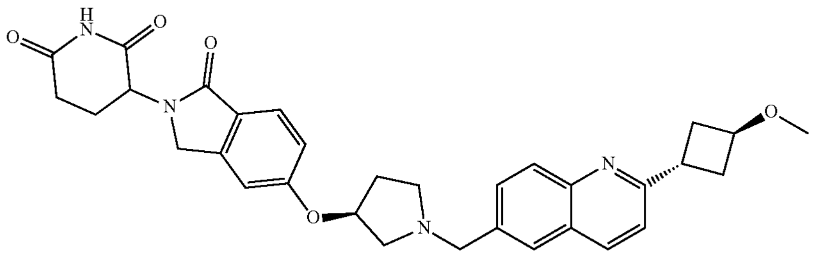 [SMILES: CO[C@H]1C[C@H](c2ccc3cc(CN4CC[C@H](Oc5ccc6c(c5)CN(C5CCC(=O)NC5=O)C6=O)C4)ccc3n2)C1] 3-(1-oxo-5-{[(3S)-1-({2-[(1r,3r)-3-methoxycyclobutyl]quinolin-6-yl}methyl)pyrrolidin-3-yl]oxy}-2,3-dihydro-1H-isoindol-2-yl)piperidine-2,6-dione | 0.003303437 | 7.412305846 | 0.003605777 | 27.12400055 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 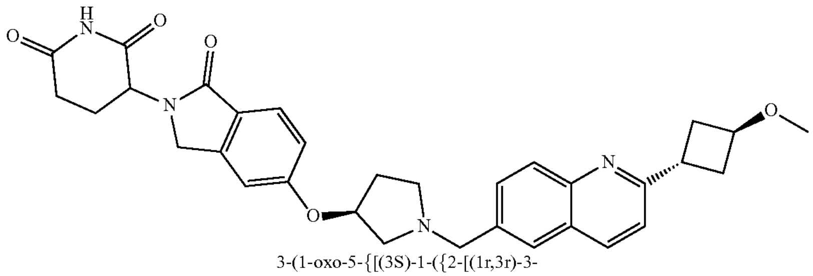 3-(1-oxo-5-{[(3S)-1-({2-[(1r,3r)-3-methoxycyclobutyl]quinolin-6-yl}methyl)pyrrolidin-3-yl]oxy}-2,3-dihydro-1H-isoindol-2-yl)piperidine-2,6-dione | 0.004886091 | 8.615041159 | 0.012776415 | 21.76499939 |
| 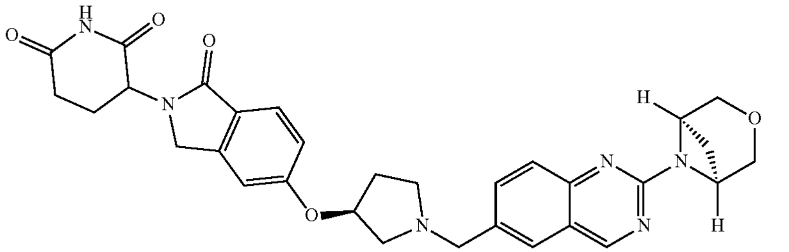 [SMILES: O=C1CCC(N2Cc3cc(O[C@H]4CCN(Cc5ccc6nc(N7[C@@H]8COC[C@H]7C8)ncc6c5)C4)ccc3C2=O)C(=O)N1] 3-(5-{[(3S)-1-({2-[(1R,5S)-3-oxa-6-azabicyclo[3.1.1]heptan-6-yl]quinazolin-6-yl}methyl)pyrrolidin-3-yl]oxy}-1-oxo-2,3-dihydro-1H-isoindol-2-yl)piperidine-2,6-dione | 0.017008 | 10.76 | 0.117429 | 38 |
| 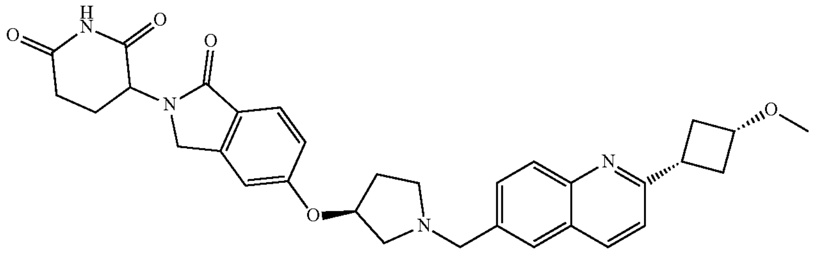 [SMILES: CO[C@H]1C[C@@H](c2ccc3cc(CN4CC[C@H](Oc5ccc6c(c5)CN(C5CCC(=O)NC5=O)C6=O)C4)ccc3n2)C1] | 0.00241114 | 7.750143119 | 0.005353699 | 23.80083656 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(1-oxo-5-{[(3S)-1-({2-[(1s,3s)-3-methoxycyclobutyl]quinolin-6-yl}methyl)pyrrolidin-3-yl]oxy}-2,3-dihydro-1H-isoindol-2-yl)piperidine-2,6-dione | | | | |
| 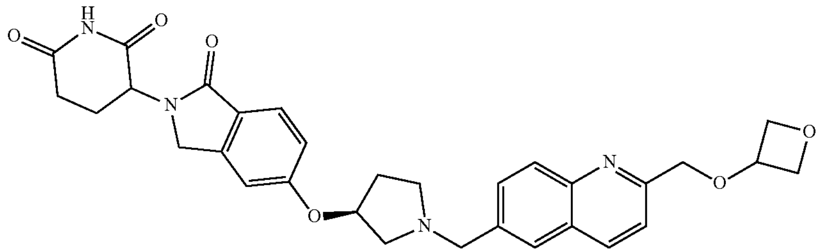 [SMILES: O=C1CCC(N2Cc3cc(O[C@H]4CCN(Cc5ccc6nc(COC7COC7)ccc6c5)C4)ccc3C2=O)C(=O)N1] 3-(5-{[(3S)-1-({2-[(oxetan-3-yloxy)methyl]quinolin-6-yl}methyl)pyrrolidin-3-yl]oxy}-1-oxo-2,3-dihydro-1H-isoindol-2-yl)piperidine-2,6-dione | 0.005370854 | 9.251722918 | 0.122322842 | 23.83514977 |
| 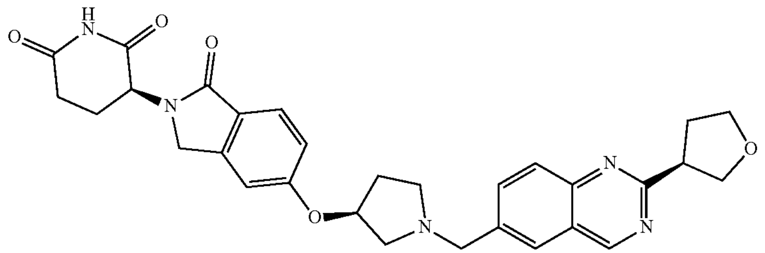 [SMILES: O=C1CC[C@H](N2Cc3cc(O[C@H]4CCN(Cc5ccc6nc([C@H]7CCOC7)ncc6c5)C4)ccc3C2=O)C(=O)N1] (3S)-3-(1-oxo-5-{[(3S)-1-({2-[(3R)-oxolan-3-yl]quinazolin-6-yl}methyl)pyrrolidin-3-yl]oxy}-2,3-dihydro-1H-isoindol-2-yl)piperidine-2,6-dione | 0.014648539 | 8.265992609 | 0.017767 | 31 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 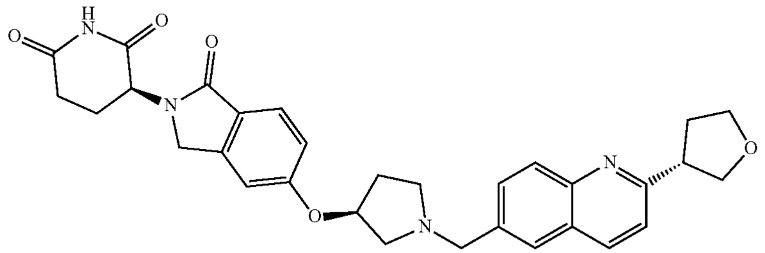 [SMILES: O=C1CC[C@H](N2Cc3cc(O[C@H]4CCN(Cc5ccc6nc([C@@H]7CCOC7)ccc6c5)C4)ccc3C2=O)C(=O)N1] (3S)-3-(1-oxo-5-{[(3S)-1-({2-[(3S)-oxolan-3-yl]quinolin-6-yl}methyl)pyrrolidin-3-yl]oxy}-2,3-dihydro-1H-isoindol-2-yl)piperidine-2,6-dione | 0.004091169 | 9.488633621 | 0.002134 | 30 |
| 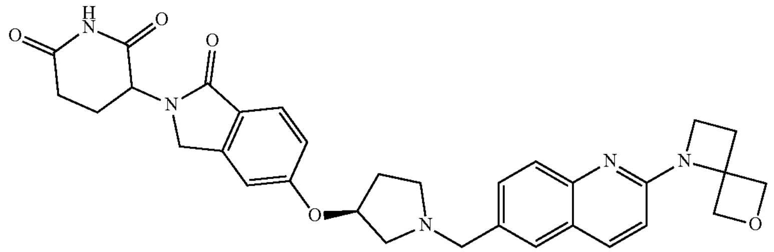 [SMILES: O=C1CCC(N2Cc3cc(O[C@H]4CCN(Cc5ccc6nc(N7CCC78COC8)ccc6c5)C4)ccc3C2=O)C(=O)N1] 3-(5-{[(3S)-1-[(2-{6-oxa-1-azaspiro[3.3]heptan-1-yl}quinolin-6-yl)methyl]pyrrolidin-3-yl]oxy}-1-oxo-2,3-dihydro-1H-isoindol-2-yl)piperidine-2,6-dione | 0.003825 | 8.91 | 0.006167 | 35 |
| 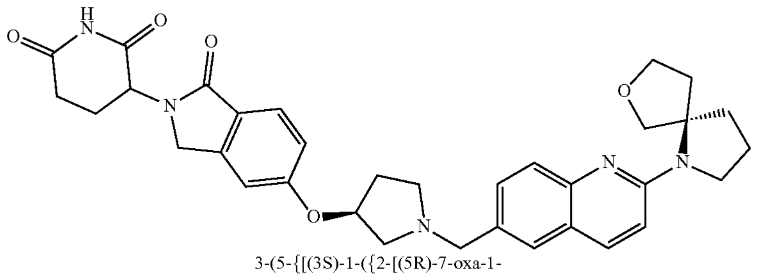 3-(5-{[(3S)-1-({2-[(5R)-7-oxa-1- | 0.010892 | 17.85 | 0.006805 | 46 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| azaspiro[4.4]nonan-1-yl]quinolin-6-yl}methyl)pyrrolidin-3-yl]oxy}-1-oxo-2,3-dihydro-1H-isoindol-2-yl)piperidine-2,6-dione | | | | |
| 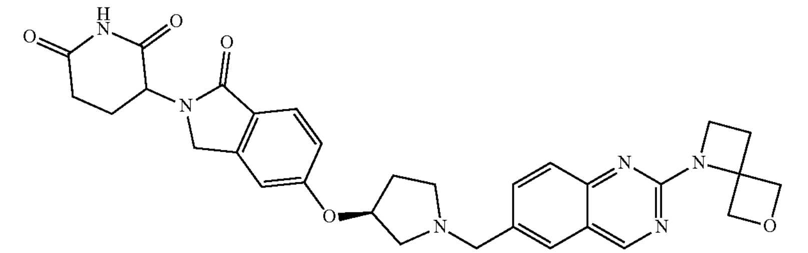 [SMILES: O=C1CCC(N2Cc3cc(O[C@H]4CCN(Cc5ccc6nc(N7CCC78COC8)ncc6c5)C4)ccc3C2=O)C(=O)N1] 3-(5-{[(3S)-1-[(2-{6-oxa-1-azaspiro[3.3]heptan-1-yl}quinazolin-6-yl)methyl]pyrrolidin-3-yl]oxy}-1-oxo-2,3-dihydro-1H-isoindol-2-yl)piperidine-2,6-dione | 0.014239583 | 14.04998087 | 0.008503 | 37 |
| 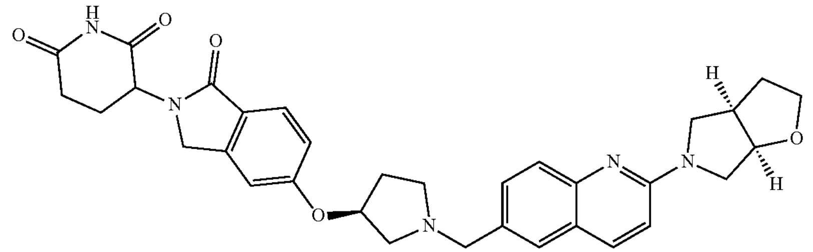 [SMILES: O=C1CCC(N2Cc3cc(O[C@H]4CCN(Cc5ccc6nc(N7C[C@H]8CCO[C@H]8C7)ccc6c5)C4)ccc3C2=O)C(=O)N1] 3-(5-{[(3S)-1-({2-[(3aR,6aR)-hexahydro-2H-furo[2,3-c]pyrrol-5-yl]quinolin-6-yl}methyl)pyrrolidin-3-yl]oxy}-1-oxo-2,3-dihydro-1H-isoindol-2-yl)piperidine-2,6-dione | 0.006090338 | 14.13089199 | 0.003201 | 37 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 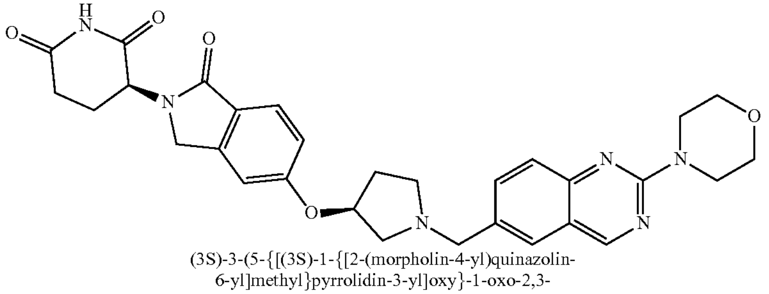 (3S)-3-(5-{[(3S)-1-{[2-(morpholin-4-yl)quinazolin-6-yl]methyl}pyrrolidin-3-yl]oxy}-1-oxo-2,3-dihydro-1H-isoindol-2-yl)piperidine-2,6-dione | 0.011688984 | 11.85503781 | 0.007357 | 34 |
| 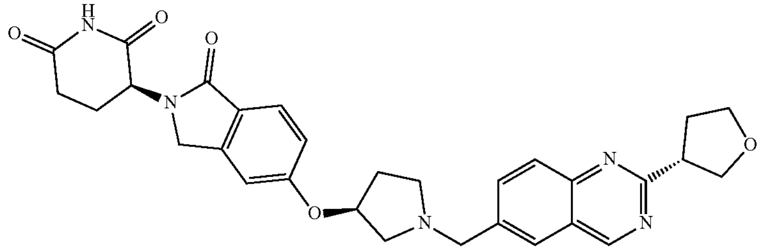 [SMILES: O=C1CC[C@H](N2Cc3cc(O[C@H]4CCN(Cc5ccc6nc([C@@H]7CCOC7)ncc6c5)C4)ccc3C2=O)C(=O)N1] (3S)-3-(1-oxo-5-{[(3S)-1-({2-[(3S)-oxolan-3-yl]quinazolin-6-yl}methyl)pyrrolidin-3-yl]oxy}-2,3-dihydro-1H-isoindol-2-yl)piperidine-2,6-dione | 0.012952738 | 9.409151118 | 0.017967 | 33 |
| 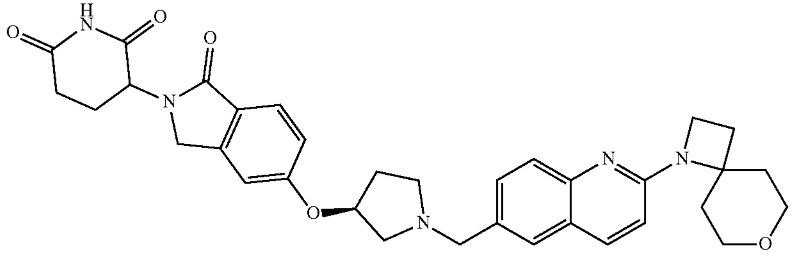 [SMILES: O=C1CCC(N2Cc3cc(O[C@H]4CCN(Cc5ccc6nc(N7CCC78CCOCC8)ccc6c5)C4)ccc3C2=O)C(=O)N1] 3-(5-{[(3S)-1-[(2-{7-oxa-1-azaspiro[3.5]nonan-1-yl}quinolin-6-yl)methyl]pyrrolidin-3-yl]oxy}-1-oxo- | 0.0037005 | 7.36 | 0.006054 | 33 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 2,3-dihydro-1H-isoindol-2-yl)piperidine-2,6-dione | | | | |
| 3-(5-{[(3S)-1-({2-[(2R,6S)-10-oxa-4-azatricyclo[5.2.1.0$^{2,6}$]decan-4-yl]quinolin-6-yl}methyl)pyrrolidin-3-yl]oxy}-1-oxo-2,3-dihydro-1H-isoindol-2-yl)piperidine-2,6-dione | 0.003834103 | 10.93097753 | 0.003193 | 38 |
| 3-(5-{[(3S)-1-({2-[(2R,6S)-10-oxa-4-azatricyclo[5.2.1.0$^{2,6}$]decan-4-yl]quinazolin-6-yl}methyl)pyrrolidin-3-yl]oxy}-1-oxo-2,3-dihydro-1H-isoindol-2-yl)piperidine-2,6-dione | 0.010543355 | 12.8246041 | 0.00925 | 35 |
| 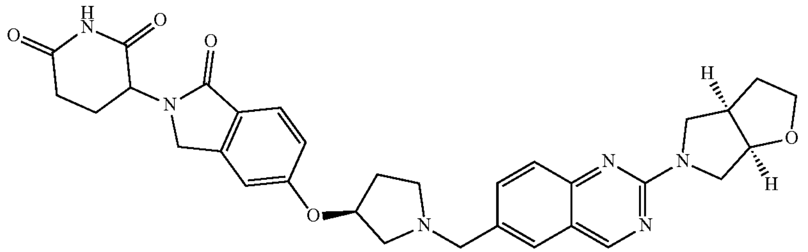 [SMILES: O=C1CCC(N2Cc3cc(O[C@H]4CCN(Cc5ccc6nc(N7C[C@H]8CCO[C@H]8C7)ncc6c5)C4)ccc3C2=O)C(=O)N1] 3-(5-{[(3S)-1-({2-[(3aR,6aR)-hexahydro-2H-furo[2,3-c]pyrrol-5-yl]quinazolin-6-yl}methyl)pyrrolidin-3-yl]oxy}-1-oxo-2,3-dihydro-1H-isoindol-2-yl)piperidine-2,6-dione | 0.013385044 | 13.09308748 | 0.012604 | 35 |
| 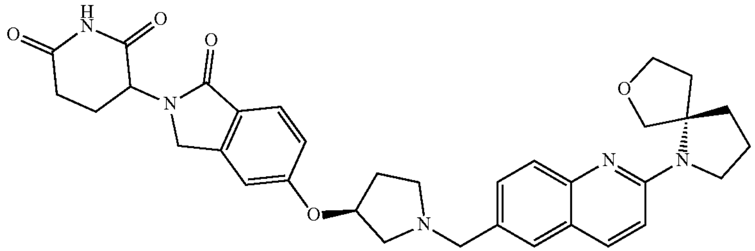 [SMILES: O=C1CCC(N2Cc3cc(O[C@H]4CCN(Cc5ccc6nc(N7CCC[C@@]78CCOC8)ccc6c5)C4)ccc3C2=O)C(=O)N1] 3-(5-{[(3S)-1-({2-[(5S)-7-oxa-1-azaspiro[4.4]nonan-1-yl]quinolin-6-yl}methyl)pyrrolidin-3-yl]oxy}-1-oxo-2,3-dihydro-1H-isoindol-2-yl)piperidine-2,6-dione | 0.010068 | 26.44 | 0.003657 | 47 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 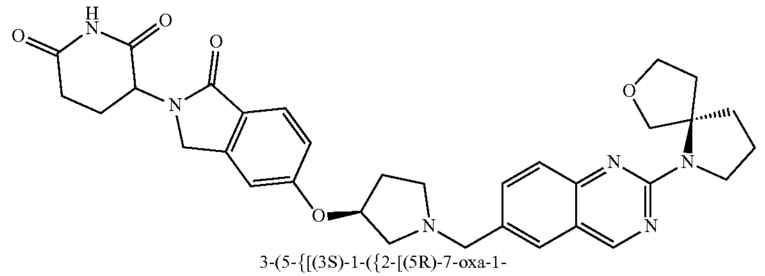 3-(5-{[(3S)-1-({2-[(5R)-7-oxa-1-azaspiro[4.4]nonan-1-yl]quinazolin-6-yl}methyl)pyrrolidin-3-yl]oxy}-1-oxo-2,3-dihydro-1H-isoindol-2-yl)piperidine-2,6-dione | 0.006608 | 6.57 | 0.012262922 | 32.50301743 |
| 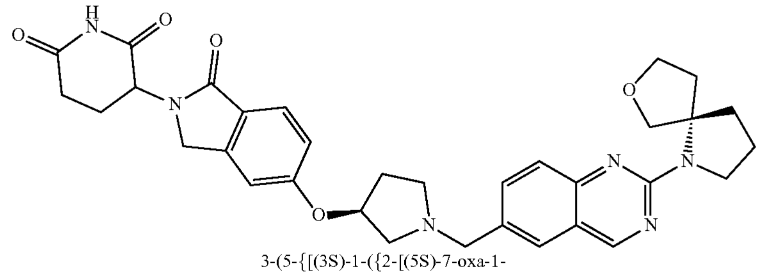 3-(5-{[(3S)-1-({2-[(5S)-7-oxa-1-azaspiro[4.4]nonan-1-yl]quinazolin-6-yl}methyl)pyrrolidin-3-yl]oxy}-1-oxo-2,3-dihydro-1H-isoindol-2-yl)piperidine-2,6-dione | 0.009375 | 9.64 | 0.012603832 | 34.0799675 |
| 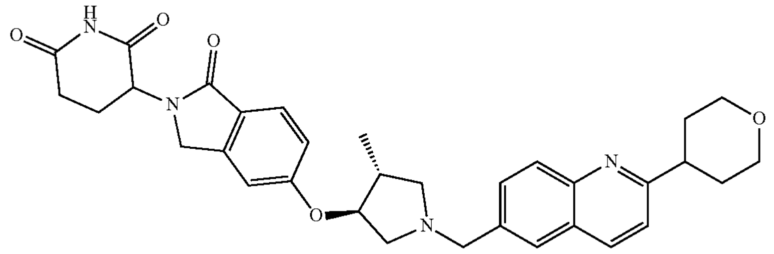 [SMILES: C[C@@H]1CN(Cc2ccc3nc(C4CCOCC4)ccc3c2)C[C@H]1Oc1ccc2c(c1)CN(C1CCC(=O)NC1=O)C2=O] | 0.003516274 | 9.682657012 | 0.00270796 | 27.68199921 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(5-{[(3S,4R)-4-methyl-1-{[2-(oxan-4-yl)quinolin-6-yl]methyl}pyrrolidin-3-yl]oxy}-1-oxo-2,3-dihydro-1H-isoindol-2-yl)piperidine-2,6-dione | | | | |
| 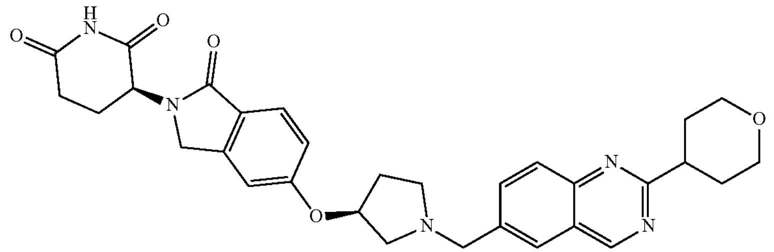 [SMILES: O=C1CC[C@H](N2Cc3cc(O[C@H]4CCN(Cc5ccc6nc(C7CCOCC7)ncc6c5)C4)ccc3C2=O)C(=O)N1] (3S)-3-(5-{[(3S)-1-{[2-(oxan-4-yl)quinazolin-6-yl]methyl}pyrrolidin-3-yl]oxy}-1-oxo-2,3-dihydro-1H-isoindol-2-yl)piperidine-2,6-dione | 0.029322949 | 9.326929573 | 0.074956258 | 32.12380409 |
| 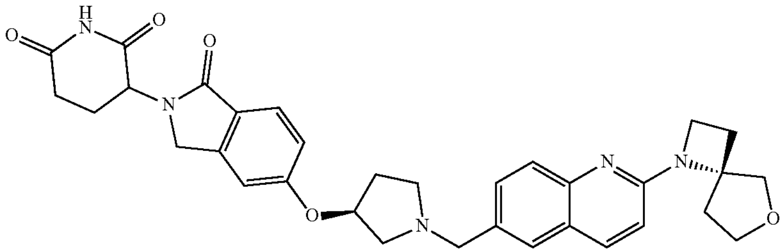 [SMILES: O=C1CCC(N2Cc3cc(O[C@H]4CCN(Cc5ccc6nc(N7CC[C@@]78CCOC8)ccc6c5)C4)ccc3C2=O)C(=O)N1] 3-(5-{[(3S)-1-({2-[(4S)-6-oxa-1-azaspiro[3.4]octan-1-yl]quinolin-6-yl}methyl)pyrrolidin-3-yl]oxy}-1-oxo-2,3-dihydro-1H-isoindol-2-yl)piperidine-2,6-dione | 0.006529 | 7.225 | 0.006071 | 40 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 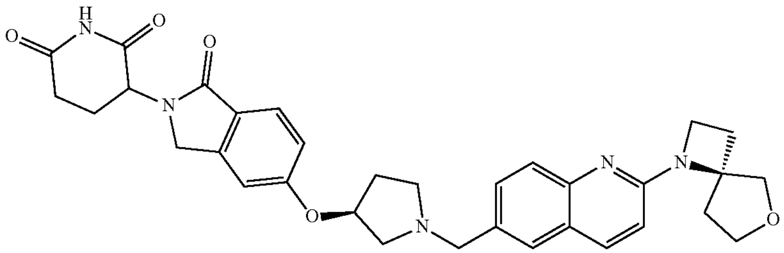 [SMILES: O=C1CCC(N2Cc3cc(O[C@H]4CCN(Cc5ccc6nc(N7CC[C@]78CCOC8)ccc6c5)C4)ccc3C2=O)C(=O)N1] 3-(5-{[(3S)-1-({2-[(4R)-6-oxa-1-azaspiro[3.4]octan-1-yl]quinolin-6-yl}methyl)pyrrolidin-3-yl]oxy}-1-oxo-2,3-dihydro-1H-isoindol-2-yl)piperidine-2,6-dione | 0.0054045 | 7.715 | 0.005382 | 42 |
| 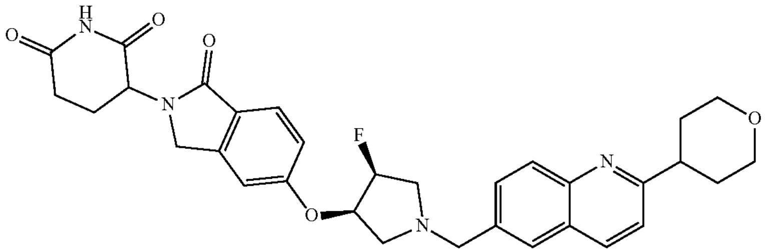 [SMILES: O=C1CCC(N2Cc3cc(O[C@@H]4CN(Cc5ccc6nc(C7CCOCC7)ccc6c5)C[C@@H]4F)ccc3C2=O)C(=O)N1] 3-(5-{[(3R,4S)-4-fluoro-1-{[2-(oxan-4-yl)quinolin-6-yl]methyl}pyrrolidin-3-yl]oxy}-1-oxo-2,3-dihydro-1H-isoindol-2-yl)piperidine-2,6-dione | 0.007129717 | 8.922906985 | 0.013194 | 36 |
| 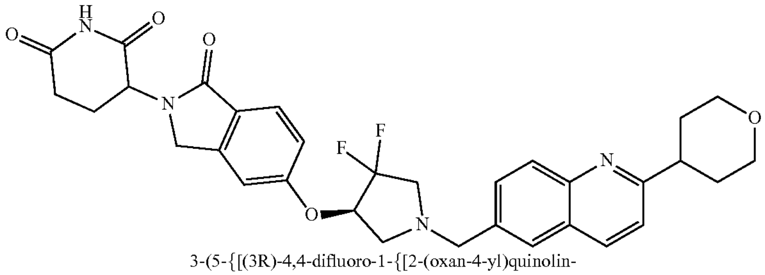 3-(5-{[(3R)-4,4-difluoro-1-{[2-(oxan-4-yl)quinolin- | 0.021320635 | 10.77994999 | 0.039111309 | 27.9040184 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 6-yl]methyl}pyrrolidin-3-yl]oxy}-1-oxo-2,3-dihydro-1H-isoindol-2-yl)piperidine-2,6-dione | | | | |
| 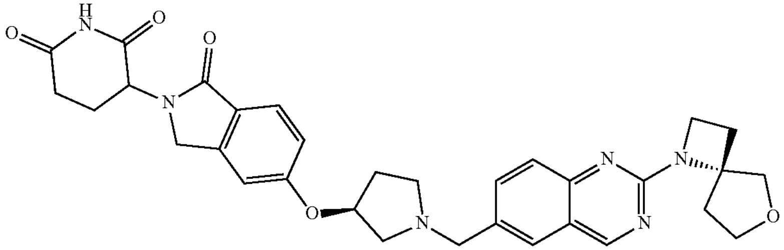 [SMILES: O=C1CCC(N2Cc3cc(O[C@H]4CCN(Cc5ccc6nc(N7CC[C@@]78CCOC8)ncc6c5)C4)ccc3C2=O)C(=O)N1] 3-(5-{[(3S)-1-({2-[(4S)-6-oxa-1-azaspiro[3.4]octan-1-yl]quinazolin-6-yl}methyl)pyrrolidin-3-yl]oxy}-1-oxo-2,3-dihydro-1H-isoindol-2-yl)piperidine-2,6-dione | 0.013328428 | 12.15687521 | 0.01464999 | 34.38689804 |
| 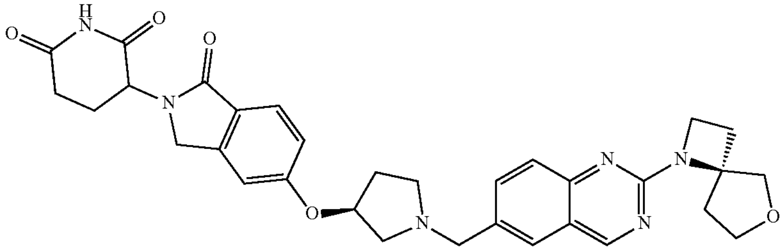 [SMILES: O=C1CCC(N2Cc3cc(O[C@H]4CCN(Cc5ccc6nc(N7CC[C@]78CCOC8)ncc6c5)C4)ccc3C2=O)C(=O)N1] 3-(5-{[(3S)-1-({2-[(4R)-6-oxa-1-azaspiro[3.4]octan-1-yl]quinazolin-6-yl}methyl)pyrrolidin-3-yl]oxy}-1-oxo-2,3-dihydro-1H-isoindol-2-yl)piperidine-2,6-dione | 0.016662301 | 13.42410015 | 0.01950017 | 35.43169403 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 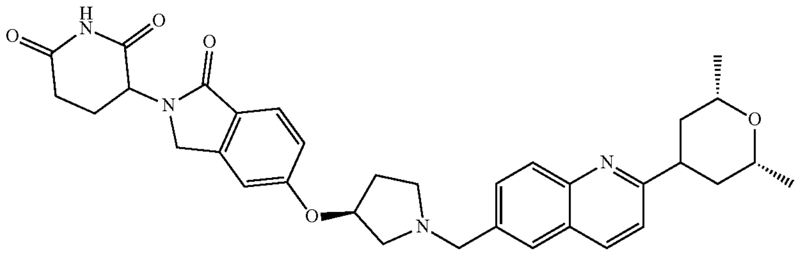 [SMILES: C[C@@H]1CC(c2ccc3cc(CN4CC[C@H](Oc5ccc6c(c5)CN(C5CCC(=O)NC5=O)C6=O)C4)ccc3n2)C[C@H](C)O1] 3-(5-{[(3S)-1-({2-[(2R,6S)-2,6-dimethyloxan-4-yl]quinolin-6-yl}methyl)pyrrolidin-3-yl]oxy}-1-oxo-2,3-dihydro-1H-isoindol-2-yl)piperidine-2,6-dione | 0.010356581 | 14.47592397 | 0.011715501 | 30.42110443 |
| 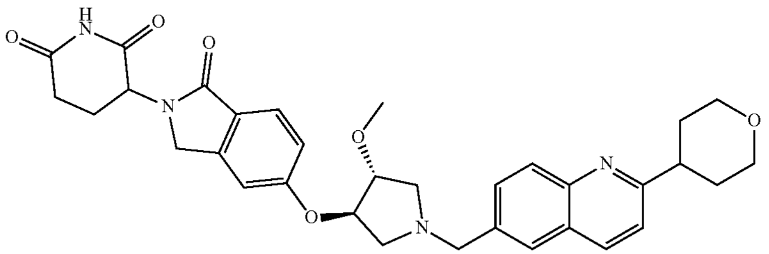 [SMILES: CO[C@@H]1CN(Cc2ccc3nc(C4CCOCC4)ccc3c2)C[C@H]1Oc1ccc2c(c1)CN(C1CCC(=O)NC1=O)C2=O] 3-(5-{[(3R,4R)-4-methoxy-1-{[2-(oxan-4-yl)quinolin-6-yl]methyl}pyrrolidin-3-yl]oxy}-1-oxo-2,3-dihydro-1H-isoindol-2-yl)piperidine-2,6-dione | 0.016931716 | 22.77684966 | 0.011710622 | 37.6661644 |
| 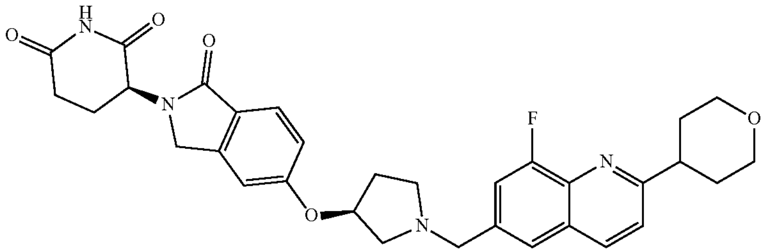 | 0.002289526 | 8.429883256 | 0.001445794 | 29.02333164 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| (3S)-3-(5-{[(3S)-1-{[8-fluoro-2-(oxan-4-yl)quinolin-6-yl]methyl}pyrrolidin-3-yl]oxy}-1-oxo-2,3-dihydro-1H-isoindol-2-yl)piperidine-2,6-dione<br>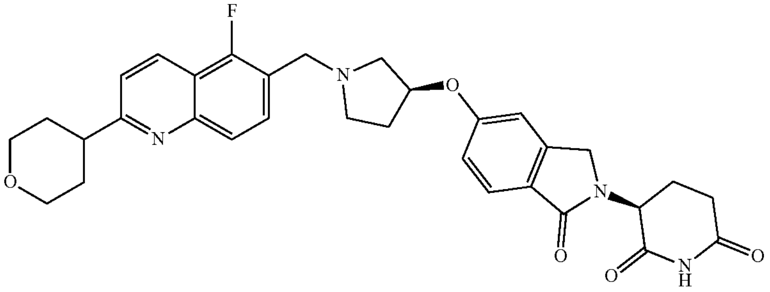 [SMILES: O=C1CC[C@H](N2Cc3cc(O[C@H]4CCN(Cc5ccc6nc(C7CCOCC7)ccc6c5F)C4)ccc3C2=O)C(=O)N1]<br>(3S)-3-(5-{[(3S)-1-{[5-fluoro-2-(oxan-4-yl)quinolin-6-yl]methyl}pyrrolidin-3-yl]oxy}-1-oxo-2,3-dihydro-1H-isoindol-2-yl)piperidine-2,6-dione | 0.002098706 | 12.14249279 | 0.000305541 | 34.42116165 |
| 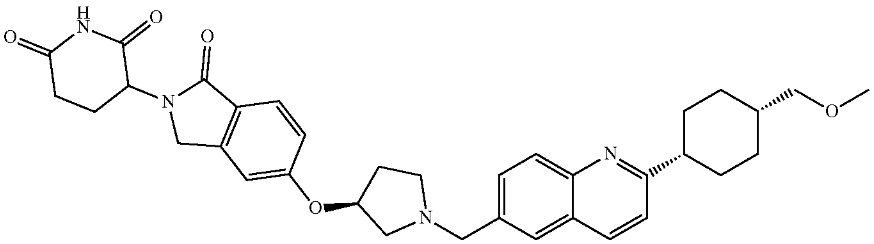 [SMILES: COC[C@H]1CC[C@@H](c2ccc3cc(CN4CC[C@H](Oc5ccc6c(c5)CN(C5CCC(=O)NC5=O)C6=O)C4)ccc3n2)CC1]<br>3-(1-oxo-5-{[(3S)-1-({2-[(1s,4s)-4-(methoxymethyl)cyclohexyl]quinolin-6-yl}methyl)pyrrolidin-3-yl]oxy}-2,3-dihydro-1H-isoindol-2-yl)piperidine-2,6-dione | 0.002657368 | 12.53072815 | 0.001220225 | 28.90361404 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 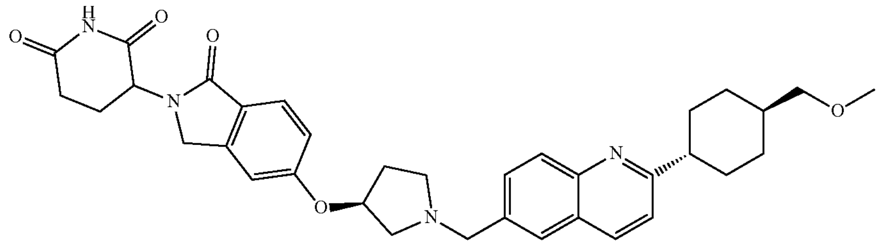 [SMILES: COC[C@H]1CC[C@H](c2ccc3cc(CN4CC[C@H](Oc5ccc6c(c5)CN(C5CCC(=O)NC5=O)C6=O)C4)ccc3n2)CC1] 3-(1-oxo-5-{[(3S)-1-({2-[(1r,4r)-4-(methoxymethyl)cyclohexyl]quinolin-6-yl}methyl)pyrrolidin-3-yl]oxy}-2,3-dihydro-1H-isoindol-2-yl)piperidine-2,6-dione | 0.002561008 | 14.12718876 | 0.001565463 | 33.24285507 |
| 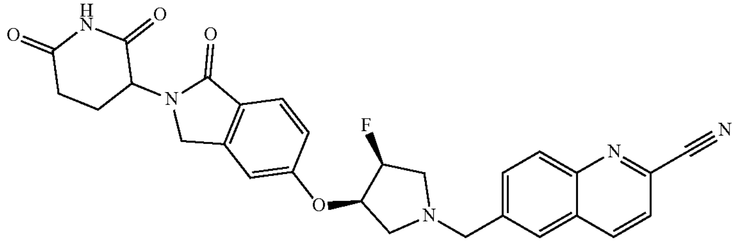 [SMILES: N#Cc1ccc2cc(CN3C[C@H](F)[C@H](Oc4ccc5c(c4)CN(C4CCC(=O)NC4=O)C5=O)C3)ccc2n1] 6-{[(3R,4S)-3-{[2-(2,6-dioxopiperidin-3-yl)-1-oxo-2,3-dihydro-1H-isoindol-5-yl]oxy}-4-fluoropyrrolidin-1-yl]methyl}quinoline-2-carbonitrile | 0.022697587 | 24.13230595 | 0.013077475 | 33.70503235 |
| 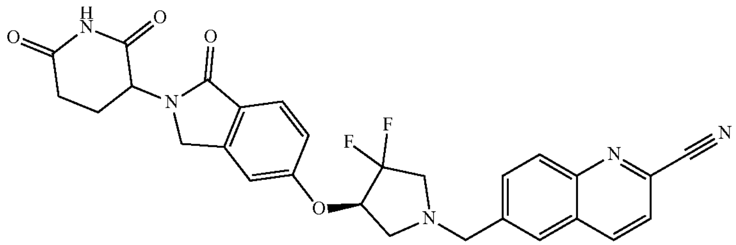 [SMILES: N#Cc1ccc2cc(CN3C[C@@H](Oc4ccc5c(c4)CN(C4CCC(=O)NC4=O)C5=O)C(F)(F)C3)ccc2n1] 6-{[(4R)-4-{[2-(2,6-dioxopiperidin-3-yl)-1-oxo- | 0.022850934 | 22.80463864 | 0.020245783 | 30.83238792 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 2,3-dihydro-1H-isoindol-5-yl]oxy}-3,3-difluoropyrrolidin-1-yl]methyl}quinoline-2-carbonitrile | | | | |
| 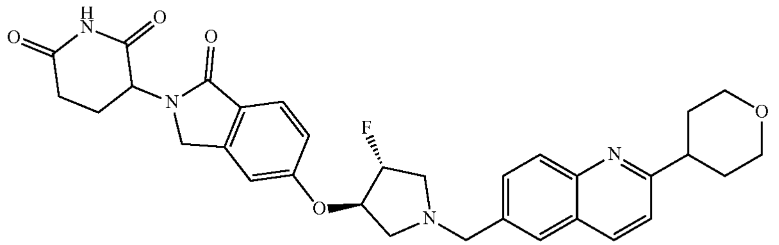 [SMILES: O=C1CCC(N2Cc3cc(O[C@@H]4CN(Cc5ccc6nc(C7CCOCC7)ccc6c5)C[C@H]4F)ccc3C2=O)C(=O)N1] 3-(5-{[(3R,4R)-4-fluoro-1-{[2-(oxan-4-yl)quinolin-6-yl]methyl}pyrrolidin-3-yl]oxy}-1-oxo-2,3-dihydro-1H-isoindol-2-yl)piperidine-2,6-dione | 0.028557641 | 30.8939935 | 0.014605277 | 36.81307602 |
| 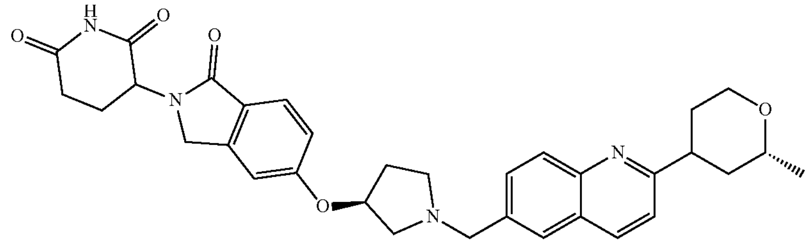 [SMILES: C[C@@H]1CC(c2ccc3cc(CN4CC[C@H](Oc5ccc6c(c5)CN(C5CCC(=O)NC5=O)C6=O)C4)ccc3n2)CCO1] 3-(5-{[(3S)-1-({2-[(2R)-2-methyloxan-4-yl]quinolin-6-yl}methyl)pyrrolidin-3-yl]oxy}-1-oxo-2,3-dihydro-1H-isoindol-2-yl)piperidine-2,6-dione | 0.01085043 | 14.50057161 | 0.010452431 | 29.53748703 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 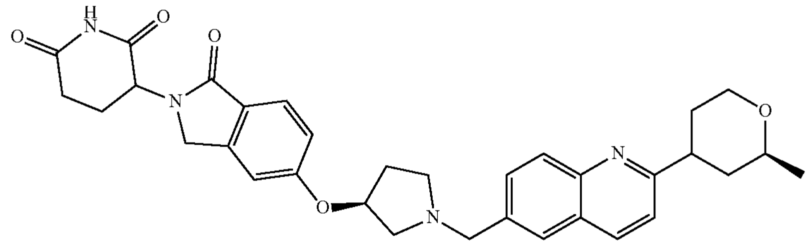 [SMILES: C[C@H]1CC(c2ccc3cc(CN4CC[C@H](Oc5ccc6c(c5)CN(C5CCC(=O)NC5=O)C6=O)C4)ccc3n2)CCO1] 3-(5-{[(3S)-1-({2-[(2S)-2-methyloxan-4-yl]quinolin-6-yl}methyl)pyrrolidin-3-yl]oxy}-1-oxo-2,3-dihydro-1H-isoindol-2-yl)piperidine-2,6-dione | 0.004393849 | 10.88238142 | 0.002968731 | 28.55217934 |
| 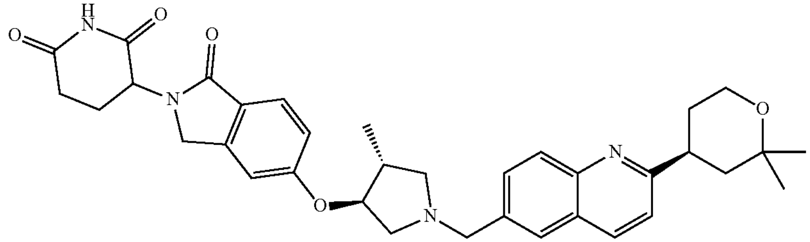 [SMILES: C[C@@H]1CN(Cc2ccc3nc([C@H]4CCOC(C)(C)C4)ccc3c2)C[C@H]1Oc1ccc2c(c1)CN(C1CCC(=O)NC1=O)C2=O] 3-(5-{[(3S,4R)-1-({2-[(4S)-2,2-dimethyloxan-4-yl]quinolin-6-yl}methyl)-4-methylpyrrolidin-3-yl]oxy}-1-oxo-2,3-dihydro-1H-isoindol-2-yl)piperidine-2,6-dione | 0.000917718 | 8.183127473 | 0.001936662 | 24.36599922 |
| 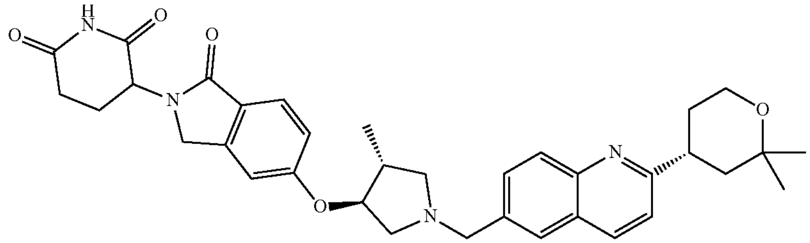 [SMILES: C[C@@H]1CN(Cc2ccc3nc([C@@H]4CCOC(C)(C)C4)ccc3c2)C[C@H]1Oc1ccc2c(c1)CN(C1CCC(=O)NC1=O)C2=O] 3-(5-{[(3S,4R)-1-({2-[(4R)-2,2-dimethyloxan-4- | 0.004654322 | 9.178284994 | 0.004248274 | 27.42649841 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| --- | --- | --- | --- | --- |
| yl]quinolin-6-yl}methyl)-4-methylpyrrolidin-3-yl]oxy}-1-oxo-2,3-dihydro-1H-isoindol-2-yl) piperidine-2,6-dione | | | | |
| 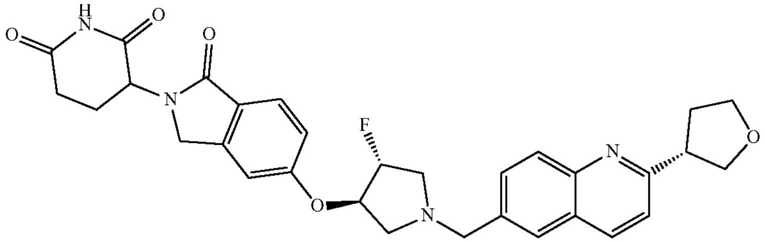 [SMILES: O=C1CCC(N2Cc3cc(O[C@@H]4CN(Cc5ccc6nc([C@@H]7CCOC7)ccc6c5)C[C@H]4F)ccc3C2=O)C(=O)N1] 3-(5-{[(3R,4R)-4-fluoro-1-({2-[(3S)-oxolan-3-yl]quinolin-6-yl}methyl)pyrrolidin-3-yl]oxy}-1-oxo-2,3-dihydro-1H-isoindol-2-yl)piperidine-2,6-dione | 0.029100743 | 20.10035562 | 0.009694377 | 29.32499123 |
| 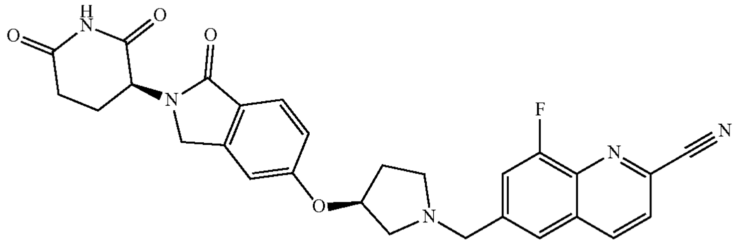 [SMILES: N#Cc1ccc2cc(CN3CC[C@H](Oc4ccc5c(c4)CN([C@H]4CCC(=O)NC4=O)C5=O)C3)cc(F)c2n1] 6-{[(3S)-3-({2-[(3S)-2,6-dioxopiperidin-3-yl]-1-oxo-2,3-dihydro-1H-isoindol-5-yl}oxy)pyrrolidin-1-yl]methyl}-8-fluoroquinoline-2-carbonitrile | 0.002721911 | 8.5787705 | 0.001713914 | 27.19400024 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 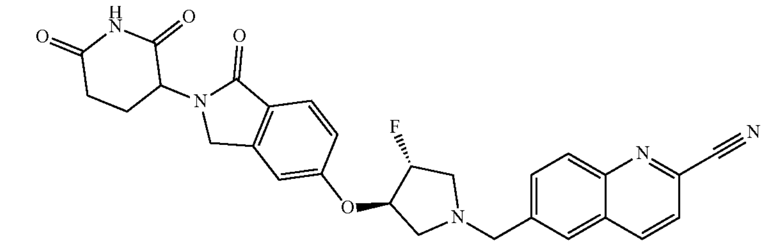 [SMILES: N#Cc1ccc2cc(CN3C[C@@H](F)[C@H](Oc4ccc5c(c4)CN(C4CCC(=O)NC4=O)C5=O)C3)ccc2n1] 6-{[(3R,4R)-3-{[2-(2,6-dioxopiperidin-3-yl)-1-oxo-2,3-dihydro-1H-isoindol-5-yl]oxy}-4-fluoropyrrolidin-1-yl]methyl}quinoline-2-carbonitrile | 0.091567801 | 37.36302352 | 0.022298686 | 32.69850159 |
| 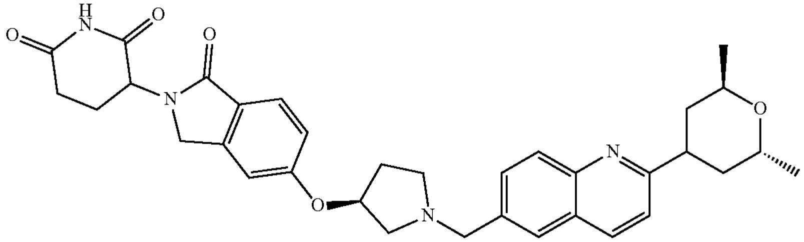 [SMILES: C[C@@H]1CC(c2ccc3cc(CN4CC[C@H](Oc5ccc6c(c5)CN(C5CCC(=O)NC5=O)C6=O)C4)ccc3n2)C[C@@H](C)O1] 3-(5-{[(3S)-1-({2-[(2R,6R)-2,6-dimethyloxan-4-yl]quinolin-6-yl}methyl)pyrrolidin-3-yl]oxy}-1-oxo-2,3-dihydro-1H-isoindol-2-yl)piperidine-2,6-dione | 0.005091277 | 10.08703573 | 0.005195352 | 25.33004761 |
| 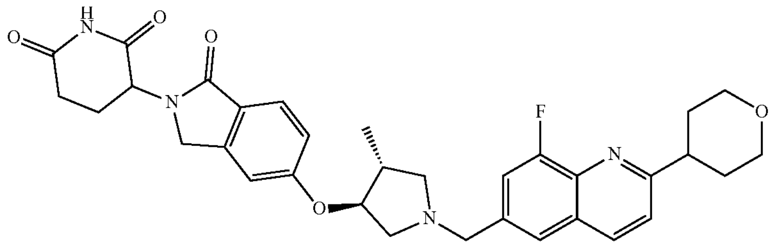 [SMILES: C[C@@H]1CN(Cc2cc(F)c3nc(C4CCOCC4)ccc3c2)C[C@H]1Oc1ccc2c(c1)CN(C1CCC(=O)NC1=O)C2=O] 3-(5-{[(3S,4R)-1-{[8-fluoro-2-(oxan-4-yl)quinolin- | 0.0014857 | 7.781496851 | 0.001134092 | 27.42000008 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 6-yl]methyl}-4-methylpyrrolidin-3-yl]oxy}-1-oxo-2,3-dihydro-1H-isoindol-2-yl)piperidine-2,6-dione | | | | |
| 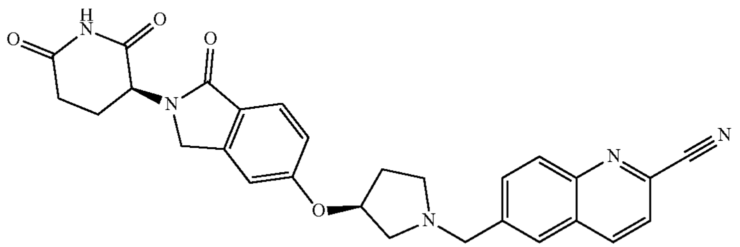 [SMILES: N#Cc1ccc2cc(CN3CC[C@H](Oc4ccc5c(c4)CN([C@H]4CCC(=O)NC4=O)C5=O)C3)ccc2n1] 6-{[(3S)-3-({2-[(3S)-2,6-dioxopiperidin-3-yl]-1-oxo-2,3-dihydro-1H-isoindol-5-yl}oxy)pyrrolidin-1-yl]methyl}quinoline-2-carbonitrile | 0.006009308 | 14.77777524 | 0.0024641 | 28.06276131 |
| 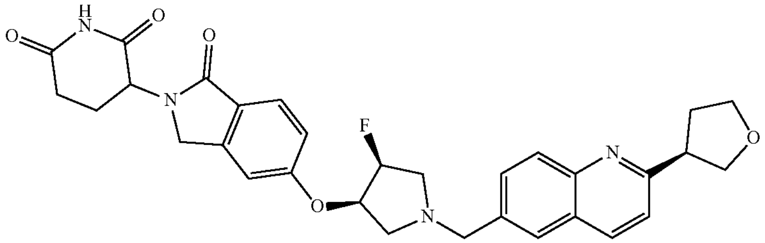 [SMILES: O=C1CCC(N2Cc3cc(O[C@@H]4CN(Cc5ccc6nc([C@H]7CCOC7)ccc6c5)C[C@@H]4F)ccc3C2=O)C(=O)N1] 3-(5-{[(3R,4S)-4-fluoro-1-({2-[(3R)-oxolan-3-yl]quinolin-6-yl}methyl)pyrrolidin-3-yl]oxy}-1-oxo-2,3-dihydro-1H-isoindol-2-yl)piperidine-2,6-dione | 0.004958052 | 13.19723484 | 0.003835982 | 30.72099876 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 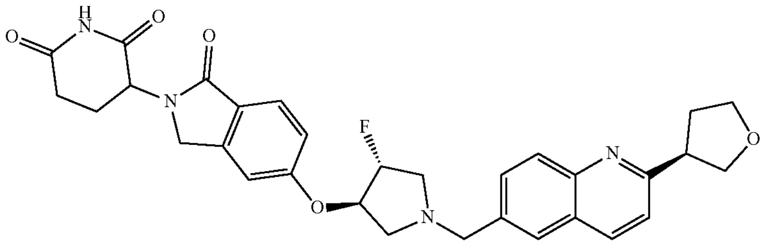 [SMILES: O=C1CCC(N2Cc3cc(O[C@@H]4CN(Cc5ccc6nc([C@H]7CCOC7)ccc6c5)C[C@H]4F)ccc3C2=O)C(=O)N1] 3-(5-{[(3R,4R)-4-fluoro-1-({2-[(3R)-oxolan-3-yl]quinolin-6-yl}methyl)pyrrolidin-3-yl]oxy}-1-oxo-2,3-dihydro-1H-isoindol-2-yl)piperidine-2,6-dione | 0.018665598 | 20.39463839 | 0.00843122 | 34.70584869 |
| 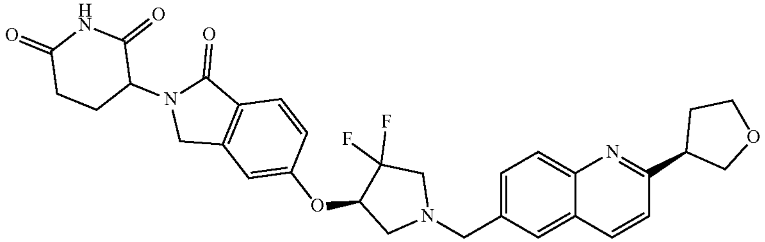 [SMILES: O=C1CCC(N2Cc3cc(O[C@@H]4CN(Cc5ccc6nc([C@H]7CCOC7)ccc6c5)CC4(F)F)ccc3C2=O)C(=O)N1] 3-(5-{[(3R)-4,4-difluoro-1-({2-[(3R)-oxolan-3-yl]quinolin-6-yl}methyl)pyrrolidin-3-yl]oxy}-1-oxo-2,3-dihydro-1H-isoindol-2-yl)piperidine-2,6-dione | 0.008422224 | 8.764418788 | 0.008494974 | 30.80900574 |
| 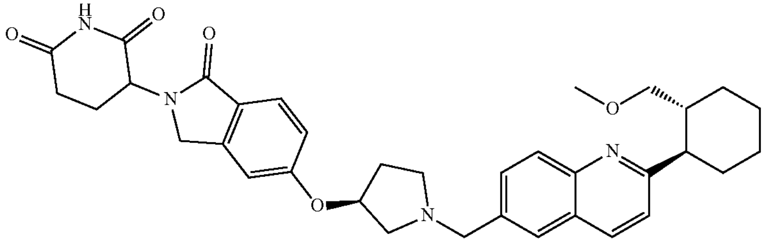 [SMILES: COC[C@@H]1CCCC[C@H]1c1ccc2cc(CN3CC[C@H](Oc4ccc5c(c4)CN(C4CCC(=O)NC4=O)C5=O)C3)ccc2n1] 3-(5-{[(3S)-1-({2-[(1R,2R)-2- | 0.002533598 | 12.90728429 | 0.003653584 | 20.91799927 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| --- | --- | --- | --- | --- |
| (methoxymethyl)cyclohexyl]quinolin-6-yl}methyl)pyrrolidin-3-yl]oxy}-1-oxo-2,3-dihydro-1H-isoindol-2-yl)piperidine-2,6-dione | | | | |
| 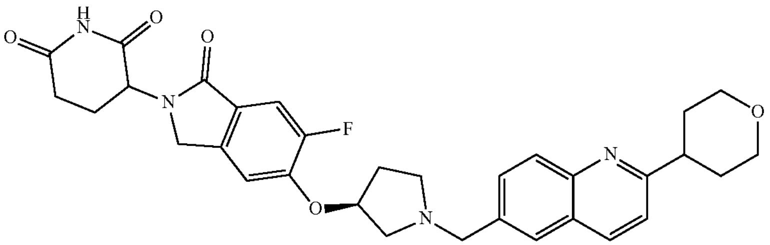 [SMILES: O=C1CCC(N2Cc3cc(O[C@H]4CCN(Cc5ccc6nc(C7CCOCC7)ccc6c5)C4)c(F)cc3C2=O)C(=O)N1] 3-(6-fluoro-5-{[(3S)-1-{[2-(oxan-4-yl)quinolin-6-yl]methyl}pyrrolidin-3-yl]oxy}-1-oxo-2,3-dihydro-1H-isoindol-2-yl)piperidine-2,6-dione | 0.007686773 | 15.43527003 | 0.002995706 | 30.27099991 |
| 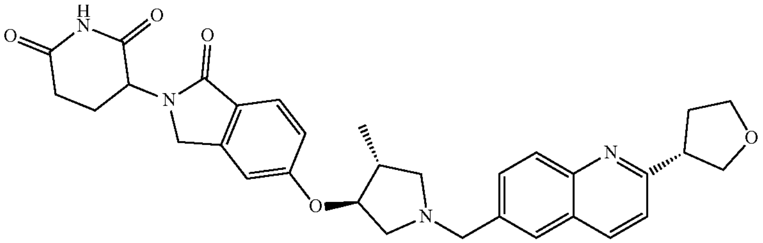 [SMILES: C[C@@H]1CN(Cc2ccc3nc([C@@H]4CCOC4)ccc3c2)C[C@H]1Oc1ccc2c(c1)CN(C1CCC(=O)NC1=O)C2=O] 3-(5-{[(3S,4R)-4-methyl-1-({2-[(3S)-oxolan-3-yl]quinolin-6-yl}methyl)pyrrolidin-3-yl]oxy}-1-oxo-2,3-dihydro-1H-isoindol-2-yl)piperidine-2,6-dione | 0.003672411 | 10.01464665 | 0.00194828 | 33.95500183 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| --- | --- | --- | --- | --- |
| 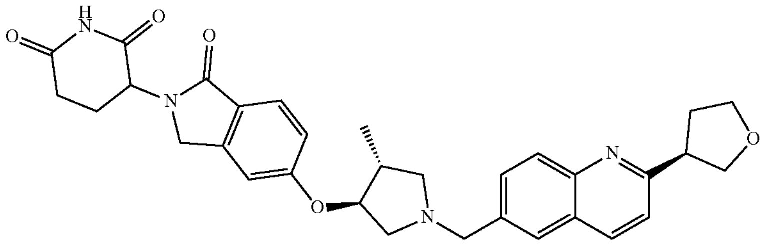 [SMILES: C[C@@H]1CN(Cc2ccc3nc([C@H]4CCOC4)ccc3c2)C[C@H]1Oc1ccc2c(c1)CN(C1CCC(=O)NC1=O)C2=O] 3-(5-{[(3S,4R)-4-methyl-1-({2-[(3R)-oxolan-3-yl]quinolin-6-yl}methyl)pyrrolidin-3-yl]oxy}-1-oxo-2,3-dihydro-1H-isoindol-2-yl)piperidine-2,6-dione | 0.002324771 | 10.25833075 | 0.001411636 | 33.40999985 |
| 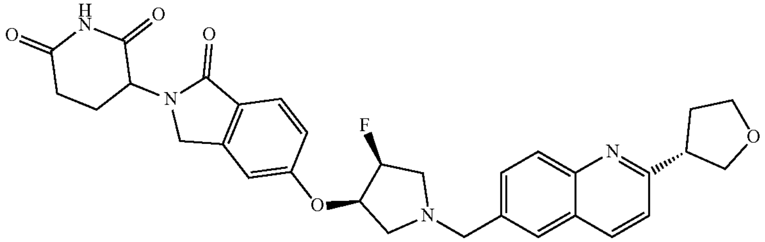 [SMILES: O=C1CCC(N2Cc3cc(O[C@@H]4CN(Cc5ccc6nc([C@@H]7CCOC7)ccc6c5)C[C@@H]4F)ccc3C2=O)C(=O)N1] 3-(5-{[(3R,4S)-4-fluoro-1-({2-[(3S)-oxolan-3-yl]quinolin-6-yl}methyl)pyrrolidin-3-yl]oxy}-1-oxo-2,3-dihydro-1H-isoindol-2-yl)piperidine-2,6-dione | 0.00942301 | 10.87972223 | 0.005687602 | 33.59773254 |
| 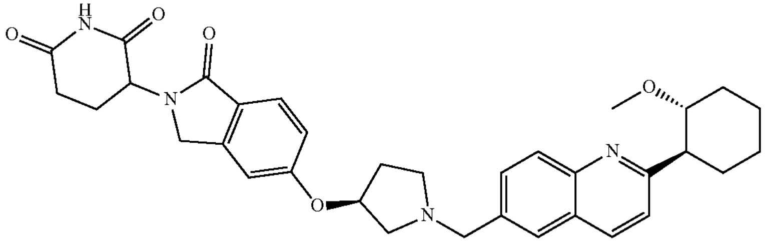 [SMILES: CO[C@@H]1CCCC[C@H]1c1ccc2cc(CN3CC[C@H](Oc4ccc5c(c4)CN(C4CCC(=O)NC4=O)C5=O)C3)ccc2n1] 3-(5-{[(3S)-1-({2-[(1S,2R)-2- | 0.4280491 | 51.57954158 | 0.021453977 | 32.43199921 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| methoxycyclohexyl]quinolin-6-yl}methyl)pyrrolidin-3-yl]oxy}-1-oxo-2,3-dihydro-1H-isoindol-2-yl)piperidine-2,6-dione | | | | |
| 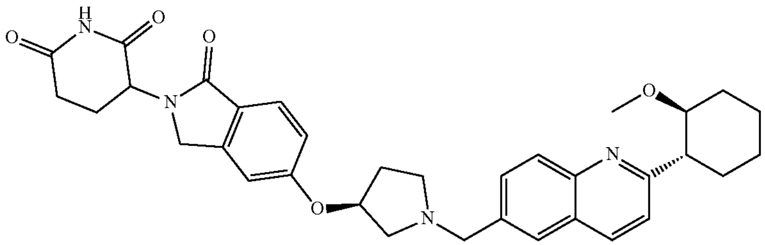 [SMILES: CO[C@H]1CCCC[C@@H]1c1ccc2cc(CN3CC[C@H](Oc4ccc5c(c4)CN(C4CCC(=O)NC4=O)C5=O)C3)ccc2n1] 3-(5-{[(3S)-1-({2-[(1R,2S)-2-methoxycyclohexyl]quinolin-6-yl}methyl)pyrrolidin-3-yl]oxy}-1-oxo-2,3-dihydro-1H-isoindol-2-yl)piperidine-2,6-dione | 0.007631044 | 23.81610782 | 0.004520618 | 25.39100075 |
| 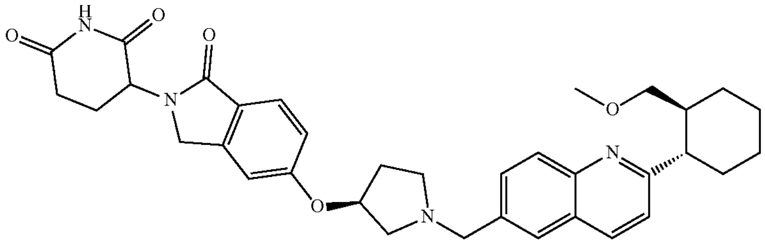 [SMILES: COC[C@H]1CCCC[C@@H]1c1ccc2cc(CN3CC[C@H](Oc4ccc5c(c4)CN(C4CCC(=O)NC4=O)C5=O)C3)ccc2n1] 3-(5-{[(3S)-1-({2-[(1S,2S)-2-(methoxymethyl)cyclohexyl]quinolin-6-yl}methyl)pyrrolidin-3-yl]oxy}-1-oxo-2,3-dihydro-1H-isoindol-2-yl)piperidine-2,6-dione | 0.0014257 | 11.37465151 | 0.003033174 | 21.70199966 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 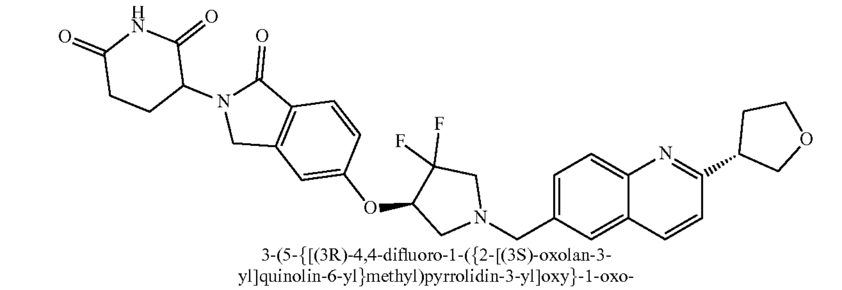 3-(5-{[(3R)-4,4-difluoro-1-({2-[(3S)-oxolan-3-yl]quinolin-6-yl}methyl)pyrrolidin-3-yl]oxy}-1-oxo-2,3-dihydro-1H-isoindol-2-yl)piperidine-2,6-dione | 0.009928483 | 9.158949494 | 0.008393945 | 30.60877609 |
| 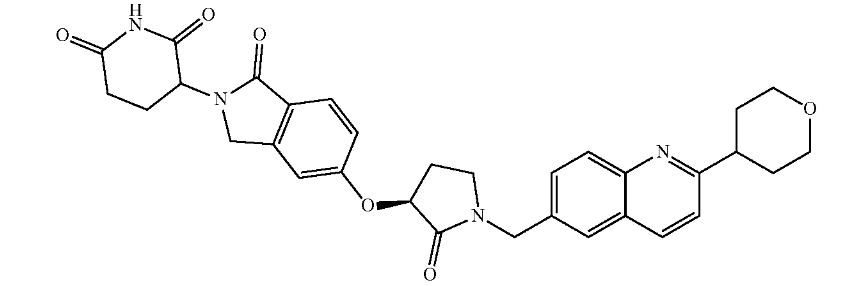 [SMILES: O=C1CCC(N2Cc3cc(O[C@H]4CCN(Cc5ccc6nc(C7CCOCC7)ccc6c5)C4=O)ccc3C2=O)C(=O)N1] 3-(5-{[(3S)-1-{[2-(oxan-4-yl)quinolin-6-yl]methyl}-2-oxopyrrolidin-3-yl]oxy}-1-oxo-2,3-dihydro-1H-isoindol-2-yl)piperidine-2,6-dione | | | 10 | 80.98058319 |
| 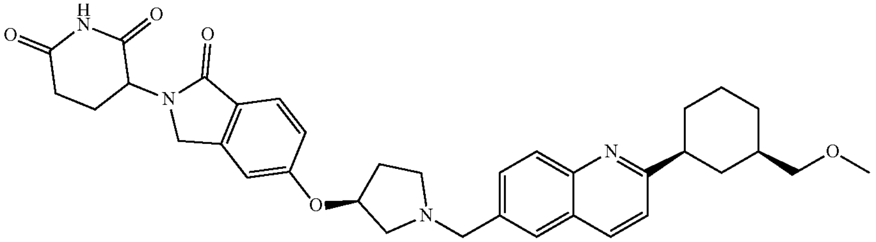 [SMILES: COC[C@@H]1CCC[C@H](c2ccc3cc(CN4CC[C@H](Oc5ccc6c(c5)CN(C5CCC(=O)NC5=O)C6=O)C4)ccc3n2)C1] | 0.001731894 | 10.2347253 | 0.001627384 | 27.1248064 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 3-(5-{[(3S)-1-({2-[(1S,3R)-3-(methoxymethyl)cyclohexyl]quinolin-6-yl}methyl)pyrrolidin-3-yl]oxy}-1-oxo-2,3-dihydro-1H-isoindol-2-yl)piperidine-2,6-dione | | | | |
| 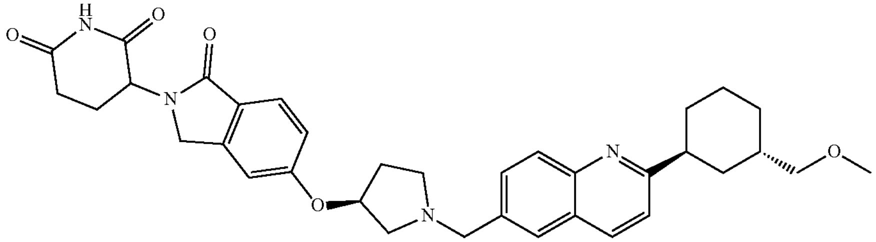 [SMILES: COC[C@H]1CCC[C@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1S,3S)-3-(methoxymethyl)cyclohexyl]quinolin-6-yl}methyl)pyrrolidin-3-yl]oxy}-1-oxo-2,3-dihydro-1H-isoindol-2-yl)piperidine-2,6-dione | 0.005707754 | 11.34109049 | 0.007614213 | 32.49178314 |
| 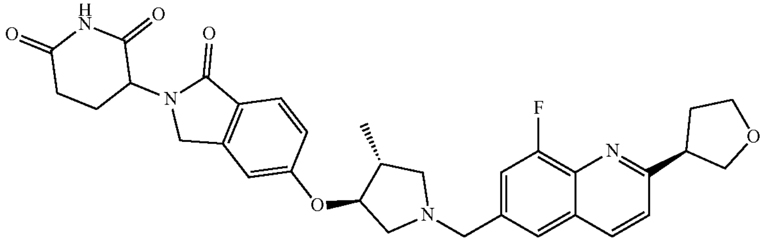 [SMILES: C[C@@H]1CN(Cc2cc(F)c3nc([C@H]4CCOC4)ccc3c2)C[C@H]1Oc1ccc2c(c1)CN(C1CCC(=O)NC1=O)C2=O] 3-(5-{[(3S,4R)-1-({8-fluoro-2-[(3R)-oxolan-3-yl]quinolin-6-yl}methyl)-4-methylpyrrolidin-3-yl]oxy}-1-oxo-2,3-dihydro-1H-isoindol-2-yl)piperidine-2,6-dione | 0.001296054 | 8.037876362 | 0.001562748 | 30.52757835 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 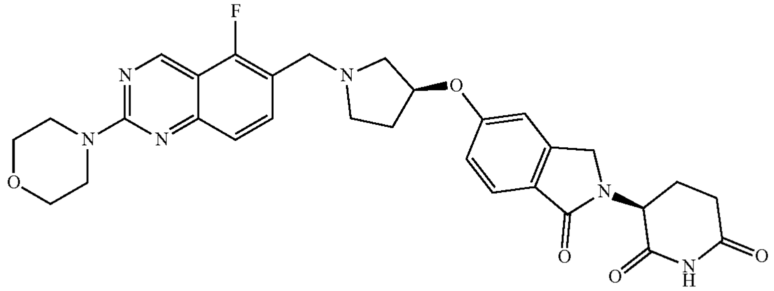 [SMILES: O=C1CC[C@H](N2Cc3cc(O[C@H]4CCN(Cc5ccc6nc(N7CCOCC7)ncc6c5F)C4)ccc3C2=O)C(=O)N1] (3S)-3-(5-{[(3S)-1-{[5-fluoro-2-(morpholin-4-yl)quinazolin-6-yl]methyl}pyrrolidin-3-yl]oxy}-1-oxo-2,3-dihydro-1H-isoindol-2-yl)piperidine-2,6-dione | | | 0.003269162 | 32.24064509 |
| 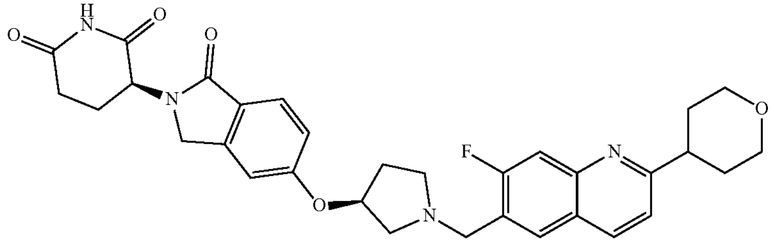 [SMILES: O=C1CC[C@H](N2Cc3cc(O[C@H]4CCN(Cc5cc6ccc(C7CCOCC7)nc6cc5F)C4)ccc3C2=O)C(=O)N1] (3S)-3-(5-{[(3S)-1-{[7-fluoro-2-(oxan-4-yl)quinolin-6-yl]methyl}pyrrolidin-3-yl]oxy}-1-oxo-2,3-dihydro-1H-isoindol-2-yl)piperidine-2,6-dione | | | 0.005819352 | 29.76880646 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 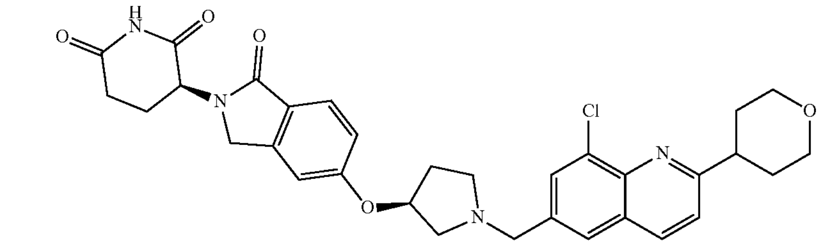 [SMILES: O=C1CC[C@H](N2Cc3cc(O[C@H]4CCN(Cc5cc(Cl)c6nc(C7CCOCC7)ccc6c5)C4)ccc3C2=O)C(=O)N1] (3S)-3-(5-{[(3S)-1-{[8-chloro-2-(oxan-4-yl)quinolin-6-yl]methyl}pyrrolidin-3-yl]oxy}-1-oxo-2,3-dihydro-1H-isoindol-2-yl)piperidine-2,6-dione | 0.004440033 | 10.21616284 | 0.001095352 | 29.99000072 |
| 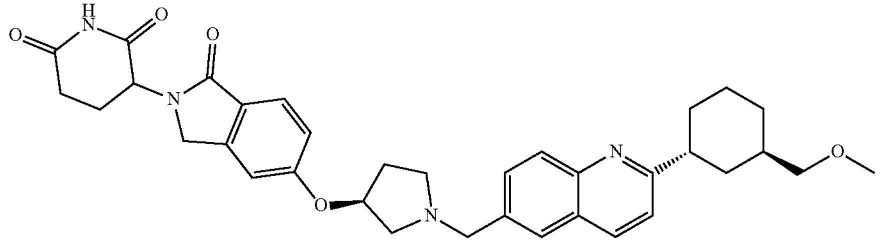 [SMILES: COC[C@@H]1CCC[C@@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1R,3R)-3-(methoxymethyl)cyclohexyl]quinolin-6-yl}methyl)pyrrolidin-3-yl]oxy}-1-oxo-2,3-dihydro-1H-isoindol-2-yl)piperidine-2,6-dione | | | 0.002170664 | 26.53988743 |
| 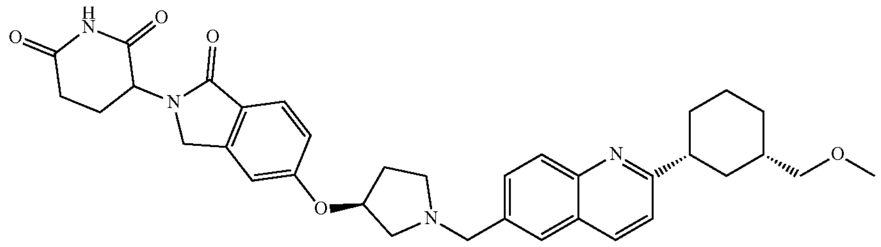 [SMILES: COC[C@H]1CCC[C@@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1R,3S)-3- | | | 0.001822579 | 26.3239994 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| (methoxymethyl)cyclohexyl]quinolin-6-yl}methyl)pyrrolidin-3-yl]oxy}-1-oxo-2,3-dihydro-1H-isoindol-2-yl)piperidine-2,6-dione | | | | |
| 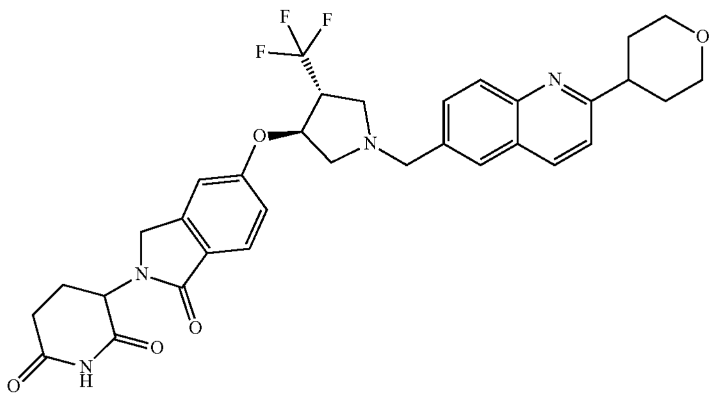 [SMILES: O=C1CCC(N2Cc3cc(O[C@@H]4CN(Cc5ccc6nc(C7CCOCC7)ccc6c5)C[C@H]4C(F)(F)F)ccc3C2=O)C(=O)N1] 3-(5-{[(3S,4R)-1-{[2-(oxan-4-yl)quinolin-6-yl]methyl}-4-(trifluoromethyl)pyrrolidin-3-yl]oxy}-1-oxo-2,3-dihydro-1H-isoindol-2-yl)piperidine-2,6-dione | 0.026843654 | 28.54950965 | 0.013141309 | 35.15149307 |
| 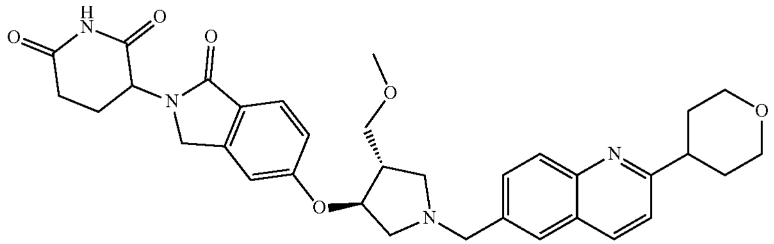 [SMILES: COC[C@@H]1CN(Cc2ccc3nc(C4CCOCC4)ccc3c2)C[C@H]1Oc1ccc2c(c1)CN(C1CCC(=O)NC1=O)C2=O] 3-(5-{[(3S,4S)-4-(methoxymethyl)-1-{[2-(oxan-4-yl)quinolin-6-yl]methyl}pyrrolidin-3-yl]oxy}-1-oxo-2,3-dihydro-1H-isoindol-2-yl)piperidine-2,6-dione | 0.001888999 | 9.503955485 | 0.003079352 | 29.16170502 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 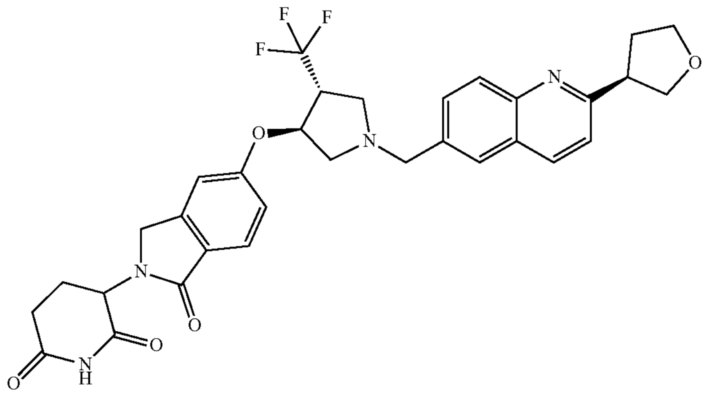 [SMILES: O=C1CCC(N2Cc3cc(O[C@@H]4CN(Cc5ccc6nc([C@H]7CCOC7)ccc6c5)C[C@H]4C(F)(F)F)ccc3C2=O)C(=O)N1] 3-(1-oxo-5-{[(3S,4R)-1-({2-[(3R)-oxolan-3-yl]quinolin-6-yl}methyl)-4-(trifluoromethyl)pyrrolidin-3-yl]oxy}-2,3-dihydro-1H-isoindol-2-yl)piperidine-2,6-dione | 0.022647665 | 24.25701373 | 0.003643857 | 27.13931751 |
| 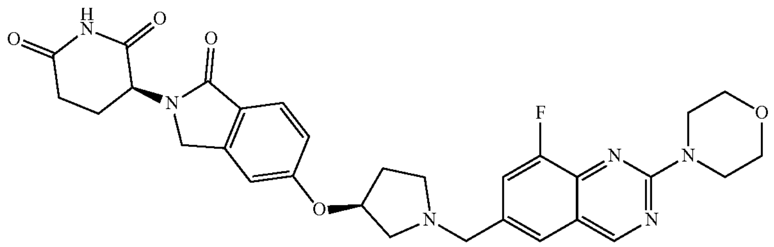 [SMILES: O=C1CC[C@H](N2Cc3cc(O[C@H]4CCN(Cc5cc(F)c6nc(N7CCOCC7)ncc6c5)C4)ccc3C2=O)C(=O)N1] (3S)-3-(5-{[(3S)-1-{[8-fluoro-2-(morpholin-4-yl)quinazolin-6-yl]methyl}pyrrolidin-3-yl]oxy}-1-oxo-2,3-dihydro-1H-isoindol-2-yl)piperidine-2,6-dione | 0.007585446 | 10.24838672 | 0.00313475 | 32.62580109 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 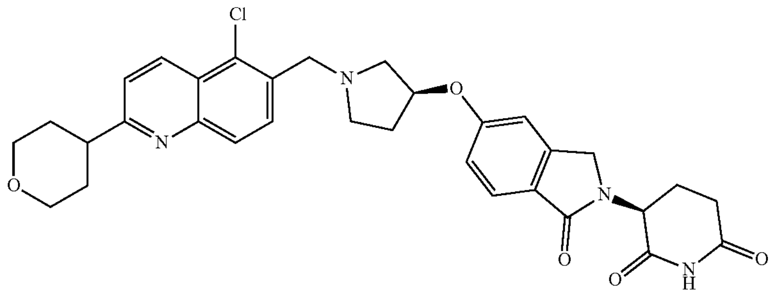 [SMILES: O=C1CC[C@H](N2Cc3cc(O[C@H]4CCN(Cc5ccc6nc(C7CCOCC7)ccc6c5Cl)C4)ccc3C2=O)C(=O)N1] (3S)-3-(5-{[(3S)-1-{[5-chloro-2-(oxan-4-yl)quinolin-6-yl]methyl}pyrrolidin-3-yl]oxy}-1-oxo-2,3-dihydro-1H-isoindol-2-yl)piperidine-2,6-dione | | | 0.002797974 | 28.8210001 |
| 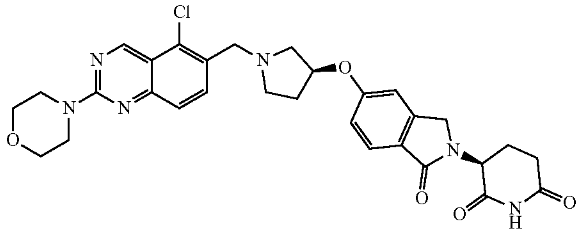 [SMILES: O=C1CC[C@H](N2Cc3cc(O[C@H]4CCN(Cc5ccc6nc(N7CCOCC7)ncc6c5Cl)C4)ccc3C2=O)C(=O)N1] (3S)-3-(5-{[(3S)-1-{[5-chloro-2-(morpholin-4-yl)quinazolin-6-yl]methyl}pyrrolidin-3-yl]oxy}-1-oxo-2,3-dihydro-1H-isoindol-2-yl)piperidine-2,6-dione | 0.018294577 | 17.48841306 | 0.003576719 | 28.45624924 |
| 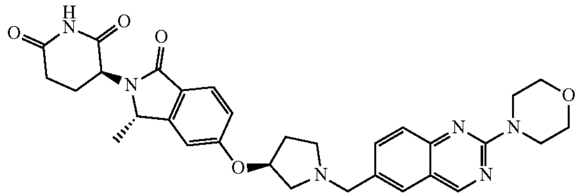 [SMILES: C[C@H]1c2cc(O[C@H]3CCN(Cc4ccc5nc(N6CCOCC6)ncc5c4)C3)ccc2C(=O)N1[C@H]1CCC(=O)NC1=O] (3S)-3-[(3S)-3-methyl-5-{[(3S)-1-{[2-(morpholin-4-yl)quinazolin-6-yl]methyl}pyrrolidin-3-yl]oxy}-1- | | | 1.177727938 | 37.95499992 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| oxo-2,3-dihydro-1H-isoindol-2-yl]piperidine-2,6-dione | | | | |
| 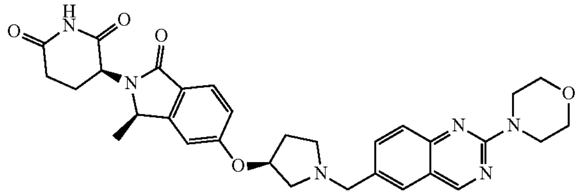 [SMILES: C[C@@H]1c2cc(O[C@H]3CCN(Cc4ccc5nc(N6CCOCC6)ncc5c4)C3)ccc2C(=O)N1[C@H]1CCC(=O)NC1=O] (3S)-3-[(3R)-3-methyl-5-{[(3S)-1-{[2-(morpholin-4-yl)quinazolin-6-yl]methyl}pyrrolidin-3-yl]oxy}-1-oxo-2,3-dihydro-1H-isoindol-2-yl]piperidine-2,6-dione | 0.030830269 | 36.11461535 | 0.00483835 | 40.42961502 |
| 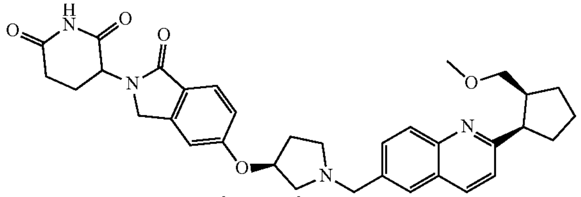 3-(5-{[(3S)-1-({2-[(1R,2S)-2-(methoxymethyl)cyclopentyl]quinolin-6-yl}methyl)pyrrolidin-3-yl]oxy}-1-oxo-2,3-dihydro-1H-isoindol-2-yl)piperidine-2,6-dione | 0.012298936 | 15.32598591 | | |
| 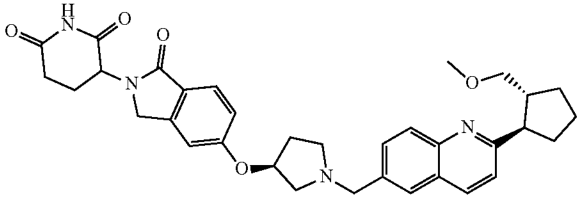 [SMILES: COC[C@@H]1CCC[C@H]1c1ccc2cc(CN3CC[C@H](Oc4ccc5c(c4)CN(C4CCC(=O)NC4=O)C5=O)C3)ccc2n1] 3-(5-{[(3S)-1-({2-[(1R,2R)-2-(methoxymethyl)cyclopentyl]quinolin-6-yl}methyl)pyrrolidin-3-yl]oxy}-1-oxo-2,3-dihydro-1H-isoindol-2-yl)piperidine-2,6-dione | 0.016605341 | 12.32705408 | | |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 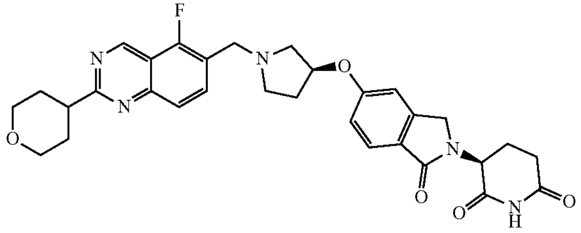 (3S)-3-(5-{[(3S)-1-{[5-fluoro-2-(oxan-4-yl)quinazolin-6-yl]methyl}pyrrolidin-3-yl]oxy}-1-oxo-2,3-dihydro-1H-isoindol-2-yl)piperidine-2,6-dione | 0.017054556 | 9.880240925 | | |
| 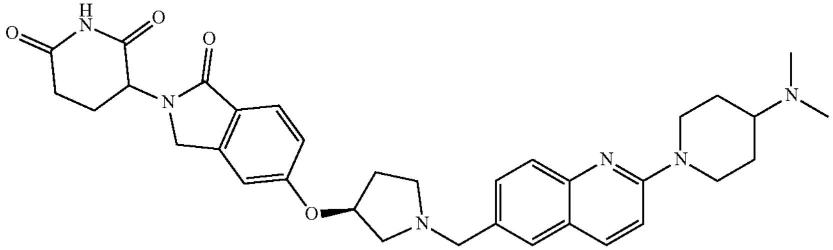 [SMILES: CN(C)C1CCN(c2ccc3cc(CN4CC[C@H](Oc5ccc6c(c5)CN(C5CCC(=O)NC5=O)C6=O)C4)ccc3n2)CC1] 3-(5-{[(3S)-1-({2-[4-(dimethylamino)piperidin-1-yl]quinolin-6-yl}methyl)pyrrolidin-3-yl]oxy}-1-oxo-2,3-dihydro-1H-isoindol-2-yl)piperidine-2,6-dione | 0.01968461 | 15.13811983 | 0.026179839 | 32.07406616 |
| 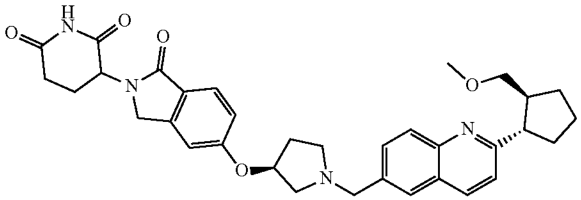 [SMILES: COC[C@H]1CCC[C@@H]1c1ccc2cc(CN3CC[C@H](Oc4ccc5c(c4)CN(C4CCC(=O)NC4=O)C5=O)C3)ccc2n1] 3-(5-{[(3S)-1-({2-[(1S,2S)-2-(methoxymethyl)cyclopentyl]quinolin-6-yl}methyl)pyrrolidin-3-yl]oxy}-1-oxo-2,3-dihydro- | 0.011941744 | 11.36633328 | 0.00537906 | 27.67920685 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 1H-isoindol-2-yl)piperidine-2,6-dione | | | | |
| 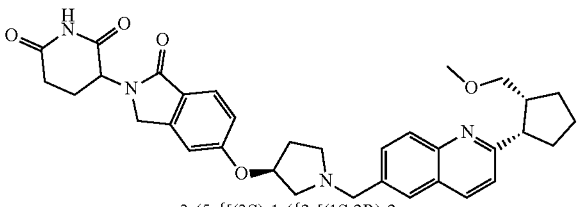 3-(5-{[(3S)-1-({2-[(1S,2R)-2-(methoxymethyl)cyclopentyl]quinolin-6-yl}methyl)pyrrolidin-3-yl]oxy}-1-oxo-2,3-dihydro-1H-isoindol-2-yl)piperidine-2,6-dione | 0.005757372 | 11.33897748 | 0.000334152 | 26.3595314 |
| 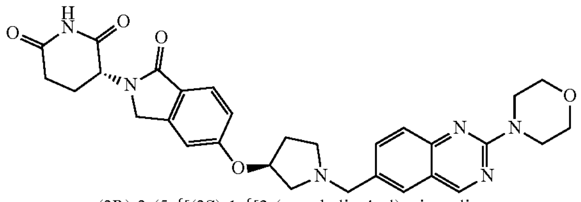 (3R)-3-(5-{[(3S)-1-{[2-(morpholin-4-yl)quinazolin-6-yl]methyl}pyrrolidin-3-yl]oxy}-1-oxo-2,3-dihydro-1H-isoindol-2-yl)piperidine-2,6-dione | 0.023788849 | 17.4336544 | 0.046277575 | 31.07138252 |
| 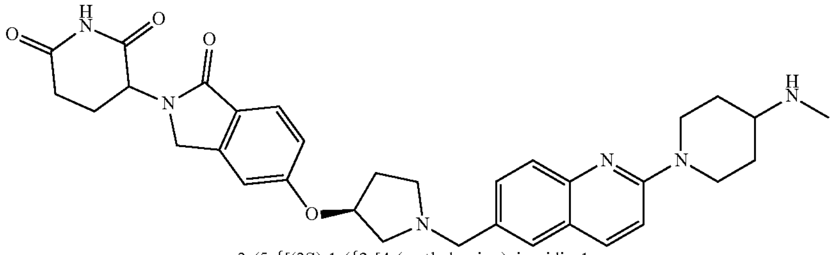 3-(5-{[(3S)-1-({2-[4-(methylamino)piperidin-1-yl]quinolin-6-yl}methyl)pyrrolidin-3-yl]oxy}-1-oxo-2,3-dihydro-1H-isoindol-2-yl)piperidine-2,6-dione | 0.084883263 | 25.09304233 | 0.064439468 | 38.12295914 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 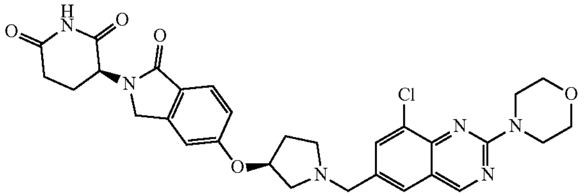 (3S)-3-(5-{[(3S)-1-{[8-chloro-2-(morpholin-4-yl)quinazolin-6-yl]methyl}pyrrolidin-3-yl]oxy}-1-oxo-2,3-dihydro-1H-isoindol-2-yl)piperidine-2,6-dione | 0.010846436 | 12.54022211 | 0.002883872 | 38.33839417 |
| 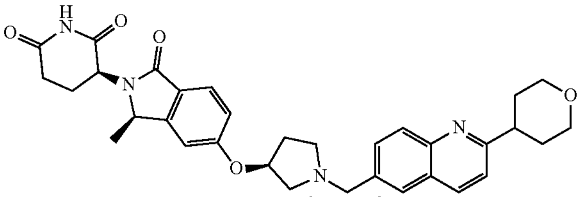 (3S)-3-[(3R)-3-methyl-5-{[(3S)-1-{[2-(oxan-4-yl)quinolin-6-yl]methyl}pyrrolidin-3-yl]oxy}-1-oxo-2,3-dihydro-1H-isoindol-2-yl]piperidine-2,6-dione | 0.017848399 | 20.63252247 | 0.002671007 | 42.3203125 |
| 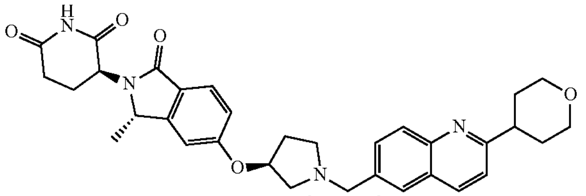 [SMILES: C[C@H]1c2cc(O[C@H]3CCN(Cc4ccc5nc(C6CCOCC6)ccc5c4)C3)ccc2C(=O)N1[C@H]1CCC(=O)NC1=O] (3S)-3-[(3S)-3-methyl-5-{[(3S)-1-{[2-(oxan-4-yl)quinolin-6-yl]methyl}pyrrolidin-3-yl]oxy}-1-oxo-2,3-dihydro-1H-isoindol-2-yl]piperidine-2,6-dione | 0.374420912 | 86.82198261 | 0.211558908 | 49.25304413 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 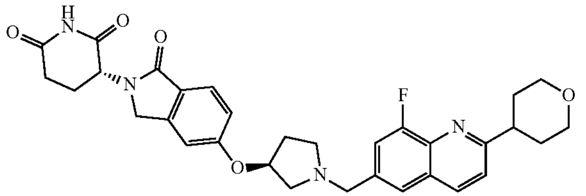 (3R)-3-(5-{[(3S)-1-{[8-fluoro-2-(oxan-4-yl)quinolin-6-yl]methyl}pyrrolidin-3-yl]oxy}-1-oxo-2,3-dihydro-1H-isoindol-2-yl)piperidine-2,6-dione | 0.002185069 | 9.199862323 | 0.009490123 | 32.16553879 |
| 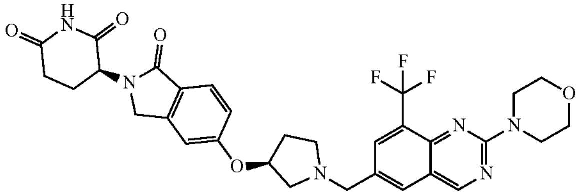 [SMILES: O=C1CC[C@H](N2Cc3cc(O[C@H]4CCN(Cc5cc(C(F)(F)F)c6nc(N7CCOCC7)ncc6c5)C4)ccc3C2=O)C(=O)N1] (3S)-3-(5-{[(3S)-1-{[2-(morpholin-4-yl)-8-(trifluoromethyl)quinazolin-6-yl]methyl}pyrrolidin-3-yl]oxy}-1-oxo-2,3-dihydro-1H-isoindol-2-yl)piperidine-2,6-dione | 0.008913815 | 3.502321167 | 0.00180286 | 33.05699921 |
| 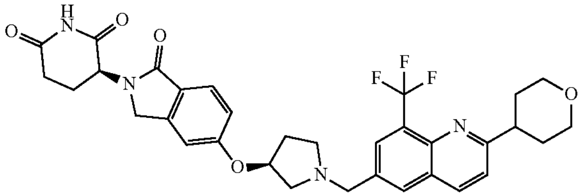 [SMILES: O=C1CC[C@H](N2Cc3cc(O[C@H]4CCN(Cc5cc(C(F)(F)F)c6nc(C7CCOCC7)ccc6c5)C4)ccc3C2=O)C(=O)N1] (3S)-3-(5-{[(3S)-1-{[2-(oxan-4-yl)-8-(trifluoromethyl)quinolin-6-yl]methyl}pyrrolidin-3-yl]oxy}-1-oxo-2,3-dihydro-1H-isoindol-2-yl)piperidine-2,6-dione | 0.002987438 | 2.250057193 | 0.002476335 | 42.83058929 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 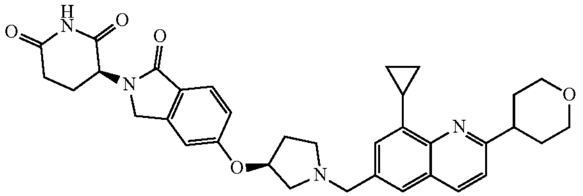 [SMILES: O=C1CC[C@H](N2Cc3cc(O[C@H]4CCN(Cc5cc(C6CC6)c6nc(C7CCOCC7)ccc6c5)C4)ccc3C2=O)C(=O)N1] (3S)-3-(5-{[(3S)-1-{[8-cyclopropyl-2-(oxan-4-yl)quinolin-6-yl]methyl}pyrrolidin-3-yl]oxy}-1-oxo-2,3-dihydro-1H-isoindol-2-yl)piperidine-2,6-dione | 0.000159914 | 3.046952449 | 0.002577859 | 54.54346466 |
| 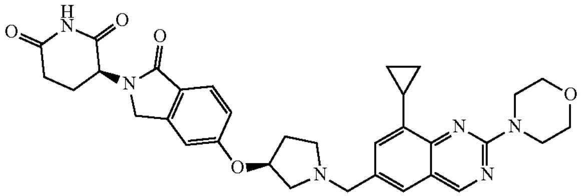 [SMILES: O=C1CC[C@H](N2Cc3cc(O[C@H]4CCN(Cc5cc(C6CC6)c6nc(N7CCOCC7)ncc6c5)C4)ccc3C2=O)C(=O)N1] (3S)-3-(5-{[(3S)-1-{[8-cyclopropyl-2-(morpholin-4-yl)quinazolin-6-yl]methyl}pyrrolidin-3-yl]oxy}-1-oxo-2,3-dihydro-1H-isoindol-2-yl)piperidine-2,6-dione | 0.002279439 | 2.135760442 | 0.002501285 | 42.10200119 |
| 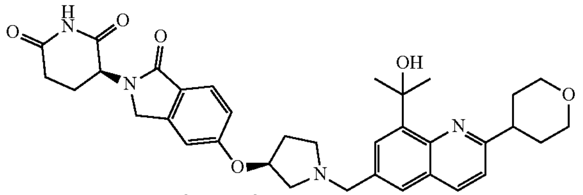 (3S)-3-(5-{[(3S)-1-{[8-(2-hydroxypropan-2-yl)-2-(oxan-4-yl)quinolin-6-yl]methyl}pyrrolidin-3-yl]oxy}-1-oxo-2,3-dihydro-1H-isoindol-2-yl)piperidine-2,6-dione | 0.166358202 | 75.97213165 | 0.006715128 | 53.75143814 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 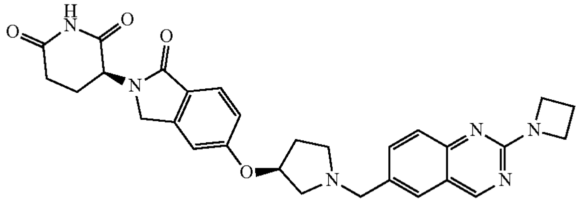 [SMILES: O=C1CC[C@H](N2Cc3cc(O[C@H]4CCN(Cc5ccc6nc(N7CCC7)ncc6c5)C4)ccc3C2=O)C(=O)N1] (3S)-3-(5-{[(3S)-1-{[2-(azetidin-1-yl)quinazolin-6-yl]methyl}pyrrolidin-3-yl]oxy}-1-oxo-2,3-dihydro-1H-isoindol-2-yl)piperidine-2,6-dione | 0.033761548 | 31.75302094 | 0.012069213 | 45.20487213 |
| 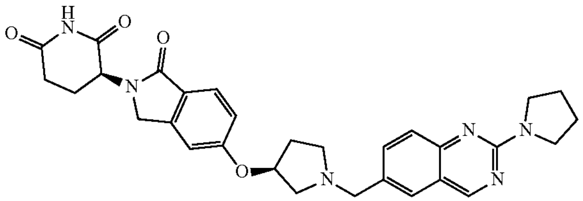 [SMILES: O=C1CC[C@H](N2Cc3cc(O[C@H]4CCN(Cc5ccc6nc(N7CCCC7)ncc6c5)C4)ccc3C2=O)C(=O)N1] (3S)-3-(1-oxo-5-{[(3S)-1-{[2-(pyrrolidin-1-yl)quinazolin-6-yl]methyl}pyrrolidin-3-yl]oxy}-2,3-dihydro-1H-isoindol-2-yl)piperidine-2,6-dione | 0.026850716 | 21.91746395 | 0.006036787 | 43.18066788 |
| 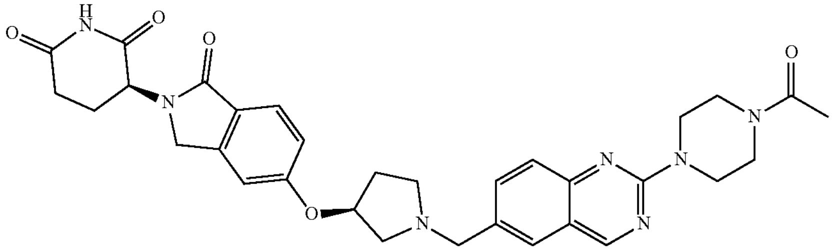 (3S)-3-(5-{[(3S)-1-{[2-(4-acetylpiperazin-1-yl)quinazolin-6-yl]methyl}pyrrolidin-3-yl]oxy}-1-oxo-2,3-dihydro-1H-isoindol-2-yl)piperidine-2,6-dione | 0.008627392 | 9.800997756 | 0.009265739 | 39.39255142 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 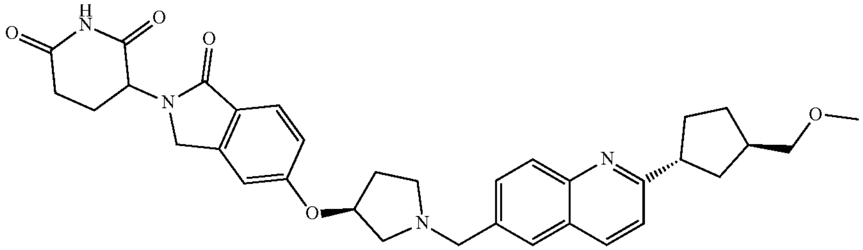 [SMILES: COC[C@@H]1CC[C@@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1R,3R)-3-(methoxymethyl)cyclopentyl]quinolin-6-yl}methyl)pyrrolidin-3-yl]oxy}-1-oxo-2,3-dihydro-1H-isoindol-2-yl)piperidine-2,6-dione | 0.003047003 | 8.78985983 | 0.003005121 | 34.19909286 |
| 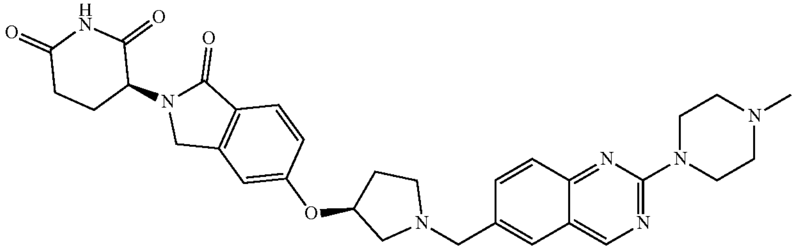 [SMILES: CN1CCN(c2ncc3cc(CN4CC[C@H](Oc5ccc6c(c5)CN([C@H]5CCC(=O)NC5=O)C6=O)C4)ccc3n2)CC1] (3S)-3-(5-{[(3S)-1-{[2-(4-methylpiperazin-1-yl)quinazolin-6-yl]methyl}pyrrolidin-3-yl]oxy}-1-oxo-2,3-dihydro-1H-isoindol-2-yl)piperidine-2,6-dione | 0.015213413 | 12.23375573 | 0.011060205 | 37.97434998 |
| 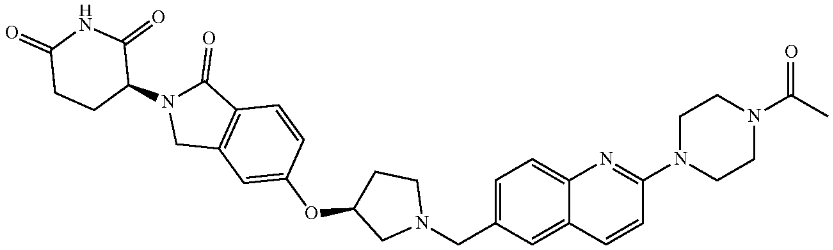 [SMILES: CC(=O)N1CCN(c2ccc3cc(CN4CC[C@H](Oc5ccc6c(c5)CN([C@H]5CCC(=O)NC5=O)C6=O)C4)ccc3n2)CC1] | 0.009935824 | 17.95495516 | 0.001687755 | 40.43999863 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| --- | --- | --- | --- | --- |
| (3S)-3-(5-{[(3S)-1-{[2-(4-acetylpiperazin-1-yl)quinolin-6-yl]methyl}pyrrolidin-3-yl]oxy}-1-oxo-2,3-dihydro-1H-isoindol-2-yl)piperidine-2,6-dione | | | | |
| 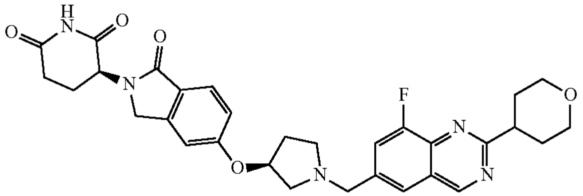 [SMILES: O=C1CC[C@H](N2Cc3cc(O[C@H]4CCN(Cc5cc(F)c6nc(C7CCOCC7)ncc6c5)C4)ccc3C2=O)C(=O)N1] (3S)-3-(5-{[(3S)-1-{[8-fluoro-2-(oxan-4-yl)quinazolin-6-yl]methyl}pyrrolidin-3-yl]oxy}-1-oxo-2,3-dihydro-1H-isoindol-2-yl)piperidine-2,6-dione | 0.013444674 | 9.240970437 | 0.027551053 | 33.60453796 |
| 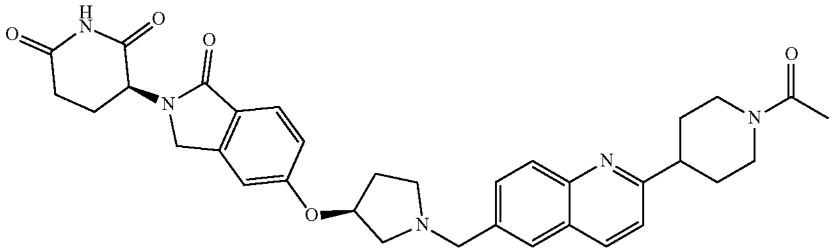 (3S)-3-(5-{[(3S)-1-{[2-(1-acetylpiperidin-4-yl)quinolin-6-yl]methyl}pyrrolidin-3-yl]oxy}-1-oxo-2,3-dihydro-1H-isoindol-2-yl)piperidine-2,6-dione | 0.011812484 | 10.38464725 | 0.010148603 | 36.61550522 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 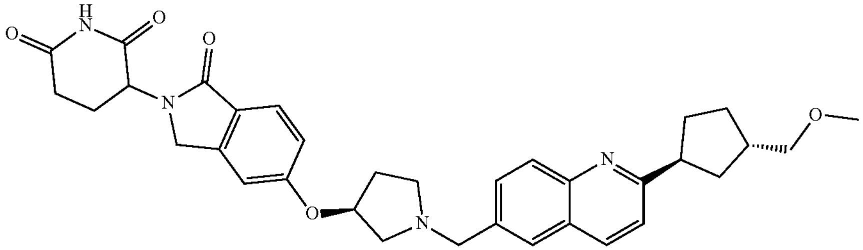 [SMILES: COC[C@H]1CC[C@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1S,3S)-3-(methoxymethyl)cyclopentyl]quinolin-6-yl}methyl)pyrrolidin-3-yl]oxy}-1-oxo-2,3-dihydro-1H-isoindol-2-yl)piperidine-2,6-dione | 0.002523603 | 8.033355501 | 0.006804882 | 33.90356064 |
| 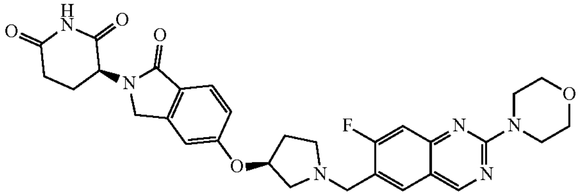 [SMILES: O=C1CC[C@H](N2Cc3cc(O[C@H]4CCN(Cc5cc6cnc(N7CCOCC7)nc6cc5F)C4)ccc3C2=O)C(=O)N1] (3S)-3-(5-{[(3S)-1-{[7-fluoro-2-(morpholin-4-yl)quinazolin-6-yl]methyl}pyrrolidin-3-yl]oxy}-1-oxo-2,3-dihydro-1H-isoindol-2-yl)piperidine-2,6-dione | 0.015210947 | 10.84341749 | 0.014739759 | 36.0160408 |
| 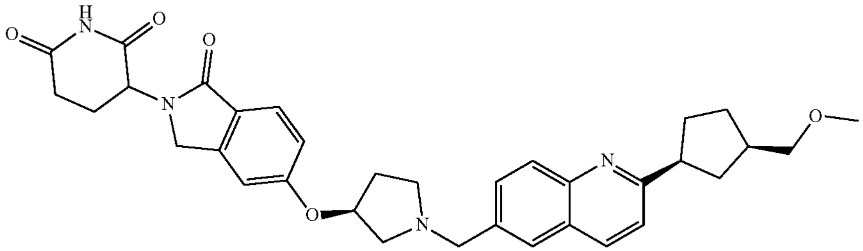 [SMILES: COC[C@@H]1CC[C@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1S,3R)-3-(methoxymethyl)cyclopentyl]quinolin-6-yl}methyl)pyrrolidin-3-yl]oxy}-1-oxo-2,3-dihydro- | 0.002555648 | 8.786448578 | 0.00590246 | 32.36553955 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 1H-isoindol-2-yl)piperidine-2,6-dione | | | | |
| 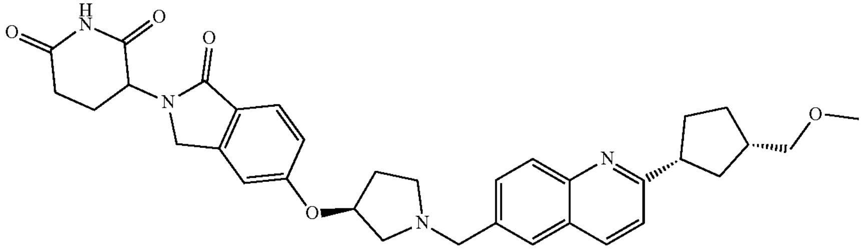 [SMILES: COC[C@H]1CC[C@@H](c2ccc3cc(CN4CC[C@H](Oc5ccc6c(c5)CN(C5CCC(=O)NC5=O)C6=O)C4)ccc3n2)C1] 3-(5-{[(3S)-1-({2-[(1R,3S)-3-(methoxymethyl)cyclopentyl]quinolin-6-yl}methyl)pyrrolidin-3-yl]oxy}-1-oxo-2,3-dihydro-1H-isoindol-2-yl)piperidine-2,6-dione | 0.003087491 | 8.887746091 | 0.003121665 | 34.11127853 |
| 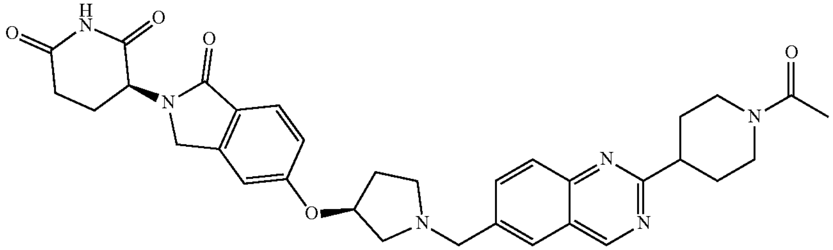 [SMILES: CC(=O)N1CCC(c2ncc3cc(CN4CC[C@H](Oc5ccc6c(c5)CN([C@H]5CCC(=O)NC5=O)C6=O)C4)ccc3n2)CC1] (3S)-3-(5-{[(3S)-1-{[2-(1-acetylpiperidin-4-yl)quinazolin-6-yl]methyl}pyrrolidin-3-yl]oxy}-1-oxo-2,3-dihydro-1H-isoindol-2-yl)piperidine-2,6-dione | 0.013813886 | 9.034650985 | 0.035757113 | 36.08767319 |
| 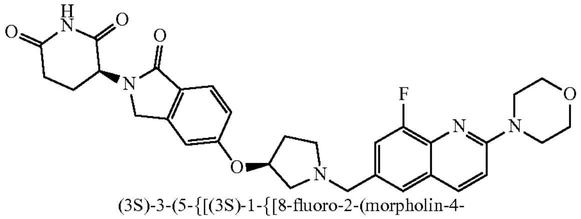 (3S)-3-(5-{[(3S)-1-{[8-fluoro-2-(morpholin-4- | 0.007188397 | 12.70478101 | | |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| yl)quinolin-6-yl]methyl}pyrrolidin-3-yl]oxy}-1-oxo-2,3-dihydro-1H-isoindol-2-yl)piperidine-2,6-dione | | | | |
| 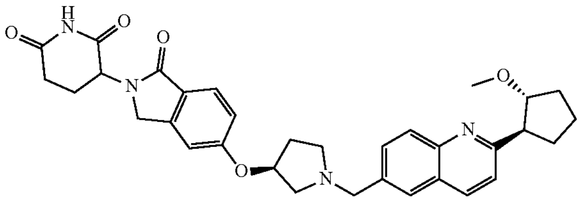 [SMILES: CO[C@@H]1CCC[C@H]1c1ccc2cc(CN3CC[C@H](Oc4ccc5c(c4)CN(C4CCC(=O)NC4=O)C5=O)C3)ccc2n1]<br>3-(5-{[(3S)-1-({2-[(1S,2R)-2-methoxycyclopentyl]quinolin-6-yl}methyl)pyrrolidin-3-yl]oxy}-1-oxo-2,3-dihydro-1H-isoindol-2-yl)piperidine-2,6-dione | 0.01202283 | 13.62680271 | 0.003005554 | 37.17211533 |
| 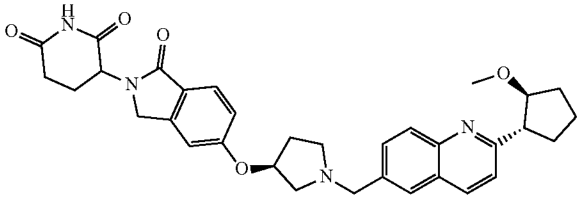 [SMILES: CO[C@H]1CCC[C@@H]1c1ccc2cc(CN3CC[C@H](Oc4ccc5c(c4)CN(C4CCC(=O)NC4=O)C5=O)C3)ccc2n1]<br>3-(5-{[(3S)-1-({2-[(1R,2S)-2-methoxycyclopentyl]quinolin-6-yl}methyl)pyrrolidin-3-yl]oxy}-1-oxo-2,3-dihydro-1H-isoindol-2-yl)piperidine-2,6-dione | 0.005540494 | 8.858177944 | 0.004344447 | 30.79247856 |
| 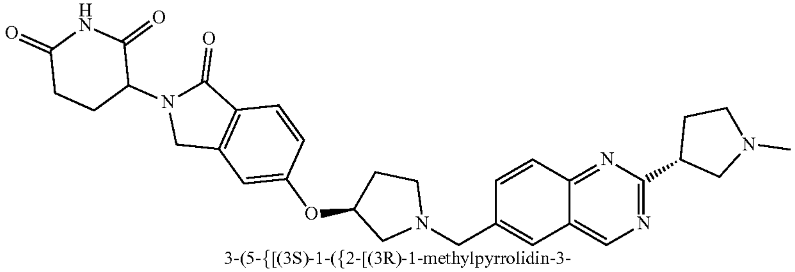<br>3-(5-{[(3S)-1-({2-[(3R)-1-methylpyrrolidin-3- | 0.048367117 | 13.18706156 | 0.225112125 | 37.05465317 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| yl]quinazolin-6-yl}methyl)pyrrolidin-3-yl]oxy}-1-oxo-2,3-dihydro-1H-isoindol-2-yl)piperidine-2,6-dione | | | | |
| 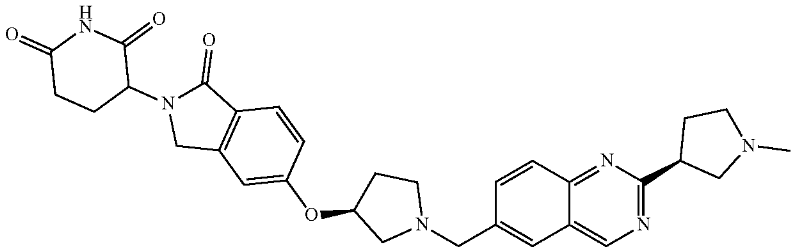 [SMILES: CN1CC[C@H](c2ncc3cc(CN4CC[C@H](Oc5ccc6c(c5)CN(C5CCC(=O)NC5=O)C6=O)C4)ccc3n2)C1] 3-(5-{[(3S)-1-({2-[(3S)-1-methylpyrrolidin-3-yl]quinazolin-6-yl}methyl)pyrrolidin-3-yl]oxy}-1-oxo-2,3-dihydro-1H-isoindol-2-yl)piperidine-2,6-dione | 0.084109598 | 17.35139679 | 0.248011827 | 36.51951599 |
| 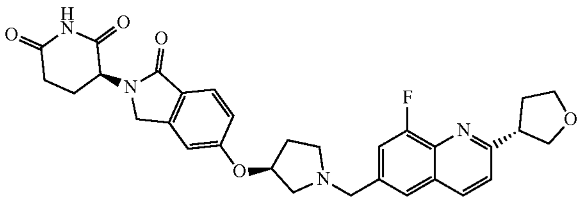 (3S)-3-(5-{[(3S)-1-({8-fluoro-2-[(3S)-oxolan-3-yl]quinolin-6-yl}methyl)pyrrolidin-3-yl]oxy}-1-oxo-2,3-dihydro-1H-isoindol-2-yl)piperidine-2,6-dione | 0.001450507 | 9.273469093 | 0.001732123 | 34.19458771 |
| 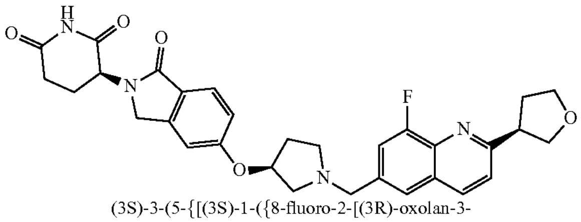 (3S)-3-(5-{[(3S)-1-({8-fluoro-2-[(3R)-oxolan-3- | 0.001021019 | 9.52822733 | 0.001338313 | 34.38580704 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| yl]quinolin-6-yl}methyl)pyrrolidin-3-yl]oxy}-1-oxo-2,3-dihydro-1H-isoindol-2-yl)piperidine-2,6-dione | | | | |
| 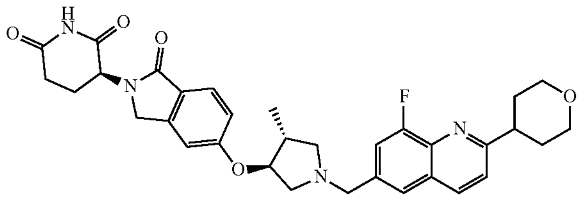 [SMILES: C[C@@H]1CN(Cc2cc(F)c3nc(C4CCOCC4)ccc3c2)C[C@H]1Oc1ccc2c(c1)CN([C@H]1CCC(=O)NC1=O)C2=O] (3S)-3-(5-{[(3S,4R)-1-{[8-fluoro-2-(oxan-4-yl)quinolin-6-yl]methyl}-4-methylpyrrolidin-3-yl]oxy}-1-oxo-2,3-dihydro-1H-isoindol-2-yl)piperidine-2,6-dione | 0.001415751 | 9.049897945 | 0.001052665 | 33.51815796 |
| 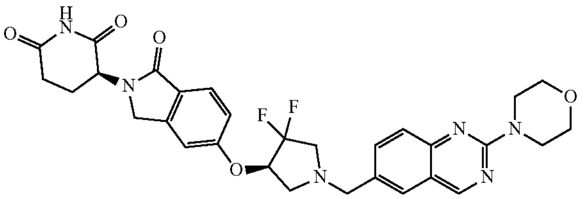 [SMILES: O=C1CC[C@H](N2Cc3cc(O[C@@H]4CN(Cc5ccc6nc(N7CCOCC7)ncc6c5)CC4(F)F)ccc3C2=O)C(=O)N1] (3S)-3-(5-{[(3R)-4,4-difluoro-1-{[2-(morpholin-4-yl)quinazolin-6-yl]methyl}pyrrolidin-3-yl]oxy}-1-oxo-2,3-dihydro-1H-isoindol-2-yl)piperidine-2,6-dione | 0.017813954 | 10.02986714 | | |
| 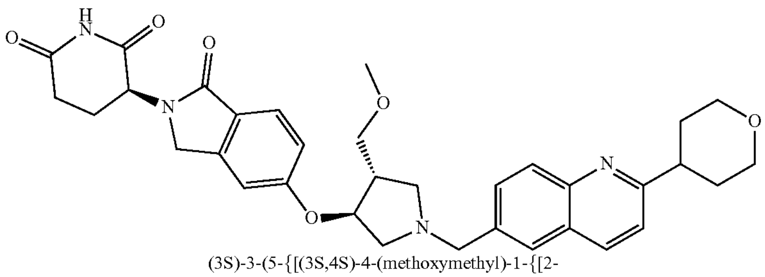 (3S)-3-(5-{[(3S,4S)-4-(methoxymethyl)-1-{[2- | 0.000727532 | 9.194366315 | | |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| (oxan-4-yl)quinolin-6-yl]methyl}pyrrolidin-3-yl]oxy}-1-oxo-2,3-dihydro-1H-isoindol-2-yl)piperidine-2,6-dione | | | | |
| 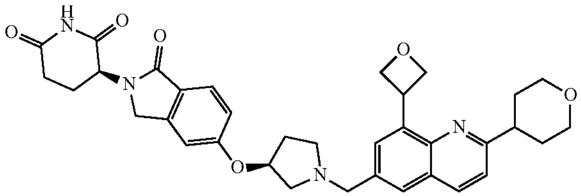 [SMILES: O=C1CC[C@H](N2Cc3cc(O[C@H]4CCN(Cc5cc(C6COC6)c6nc(C7CCOCC7)ccc6c5)C4)ccc3C2=O)C(=O)N1] (3S)-3-(5-{[(3S)-1-{[2-(oxan-4-yl)-8-(oxetan-3-yl)quinolin-6-yl]methyl}pyrrolidin-3-yl]oxy}-1-oxo-2,3-dihydro-1H-isoindol-2-yl)piperidine-2,6-dione | 0.002936948 | 96.91038515 | 10 | 88.4276886 |
| 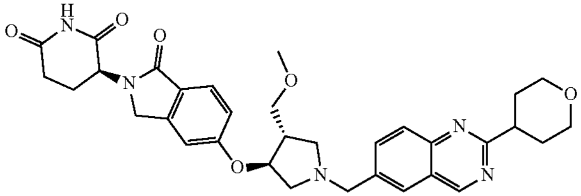 [SMILES: COC[C@@H]1CN(Cc2ccc3nc(C4CCOCC4)ncc3c2)C[C@H]1Oc1ccc2c(c1)CN([C@H]1CCC(=O)NC1=O)C2=O] (3S)-3-(5-{[(3S,4S)-4-(methoxymethyl)-1-{[2-(oxan-4-yl)quinazolin-6-yl]methyl}pyrrolidin-3-yl]oxy}-1-oxo-2,3-dihydro-1H-isoindol-2-yl)piperidine-2,6-dione | 0.004895082 | 8.81309556 | 0.017573541 | 23.10810852 |
| 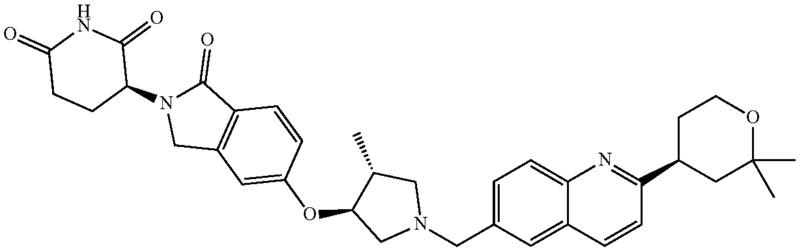 [SMILES: C[C@@H]1CN(Cc2ccc3nc([C@H]4CCOC(C)(C)C4)ccc3c2)C[C@H]1Oc1ccc2c(c1)CN([C@H]1CCC(=O)NC1=O)C2=O] (3S)-3-(5-{[(3S,4R)-1-({2-[(4S)-2,2- | 0.001436807 | 9.434296524 | 0.003511775 | 24.62528038 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| dimethyloxan-4-yl]quinolin-6-yl}methyl)-4-methylpyrrolidin-3-yl]oxy}-1-oxo-2,3-dihydro-1H-isoindol-2-yl)piperidine-2,6-dione | | | | |
| 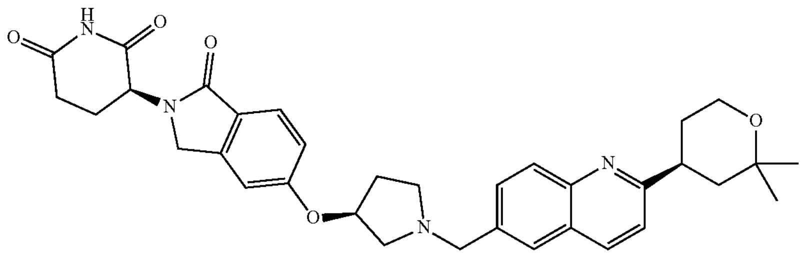 [SMILES: CC1(C)C[C@@H](c2ccc3cc(CN4CC[C@H](Oc5ccc6c(c5)CN([C@H]5CCC(=O)NC5=O)C6=O)C4)ccc3n2)CCO1] (3S)-3-(5-{[(3S)-1-({2-[(4S)-2,2-dimethyloxan-4-yl]quinolin-6-yl}methyl)pyrrolidin-3-yl]oxy}-1-oxo-2,3-dihydro-1H-isoindol-2-yl)piperidine-2,6-dione | 0.001344658 | 9.025420111 | 0.001771018 | 24.69387817 |
| 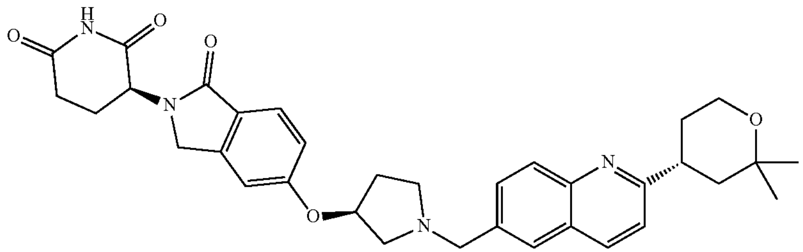 [SMILES: CC1(C)C[C@H](c2ccc3cc(CN4CC[C@H](Oc5ccc6c(c5)CN([C@H]5CCC(=O)NC5=O)C6=O)C4)ccc3n2)CCO1] (3S)-3-(5-{[(3S)-1-({2-[(4R)-2,2-dimethyloxan-4-yl]quinolin-6-yl}methyl)pyrrolidin-3-yl]oxy}-1-oxo-2,3-dihydro-1H-isoindol-2-yl)piperidine-2,6-dione | 0.001826877 | 11.18929106 | 0.001850614 | 26.67243767 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 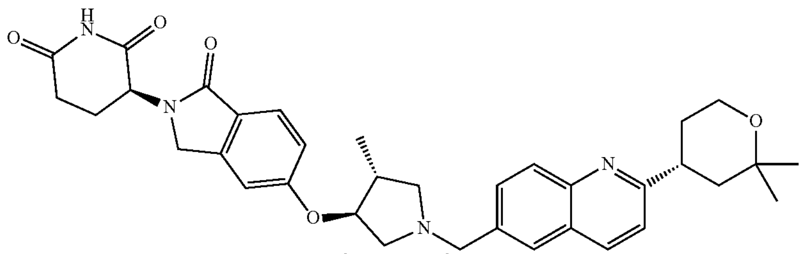 (3S)-3-(5-{[(3S,4R)-1-({2-[(4R)-2,2-dimethyloxan-4-yl]quinolin-6-yl}methyl)-4-methylpyrrolidin-3-yl]oxy}-1-oxo-2,3-dihydro-1H-isoindol-2-yl)piperidine-2,6-dione | 0.000423942 | 8.112950591 | 0.001149334 | 24.64075089 |
| 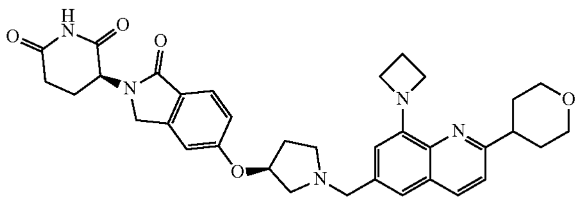 [SMILES: O=C1CC[C@H](N2Cc3cc(O[C@H]4CCN(Cc5cc(N6CCC6)c6nc(C7CCOCC7)ccc6c5)C4)ccc3C2=O)C(=O)N1] (3S)-3-(5-{[(3S)-1-{[8-(azetidin-1-yl)-2-(oxan-4-yl)quinolin-6-yl]methyl}pyrrolidin-3-yl]oxy}-1-oxo-2,3-dihydro-1H-isoindol-2-yl)piperidine-2,6-dione | 0.010781158 | 3.15488925 | 0.025985572 | 33.36193466 |
| 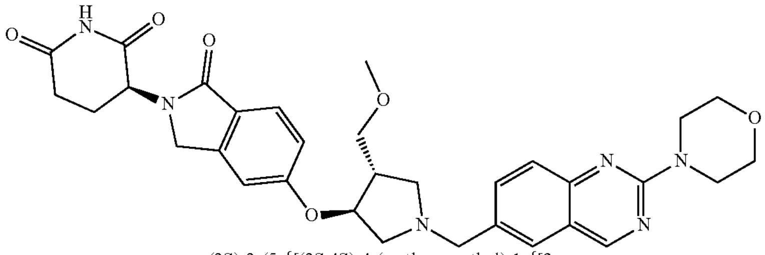 (3S)-3-(5-{[(3S,4S)-4-(methoxymethyl)-1-{[2-(morpholin-4-yl)quinazolin-6-yl]methyl}pyrrolidin-3-yl]oxy}-1-oxo-2,3-dihydro-1H-isoindol-2- | 0.001642544 | 8.574151925 | 0.005401397 | 25.61192894 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| yl)piperidine-2,6-dione | | | | |
| 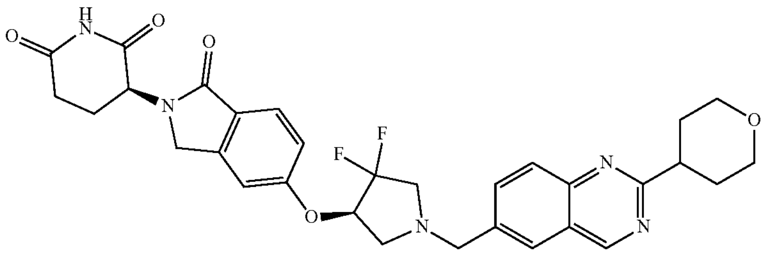 [SMILES: O=C1CC[C@H](N2Cc3cc(O[C@@H]4CN(Cc5ccc6nc(C7CCOCC7)ncc6c5)CC4(F)F)ccc3C2=O)C(=O)N1] (3S)-3-(5-{[(3R)-4,4-difluoro-1-{[2-(oxan-4-yl)quinazolin-6-yl]methyl}pyrrolidin-3-yl]oxy}-1-oxo-2,3-dihydro-1H-isoindol-2-yl)piperidine-2,6-dione | 0.045812193 | 10.36734584 | 0.104858041 | 22.61218452 |
| 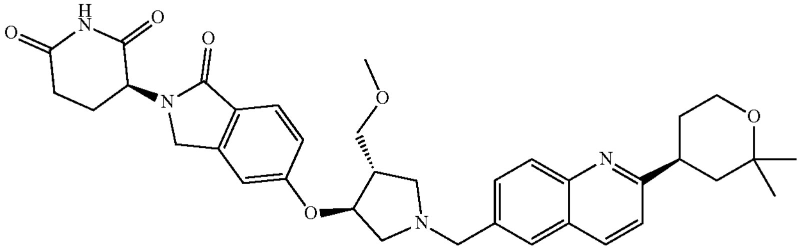 [SMILES: COC[C@@H]1CN(Cc2ccc3nc([C@H]4CCOC(C)(C)C4)ccc3c2)C[C@H]1Oc1ccc2c(c1)CN([C@H]1CCC(=O)NC1=O)C2=O] (3S)-3-(5-{[(3S,4S)-1-({2-[(4S)-2,2-dimethyloxan-4-yl]quinolin-6-yl}methyl)-4-(methoxymethyl)pyrrolidin-3-yl]oxy}-1-oxo-2,3-dihydro-1H-isoindol-2-yl)piperidine-2,6-dione | 0.000558201 | 8.284719238 | 0.001247579 | 25.45120716 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 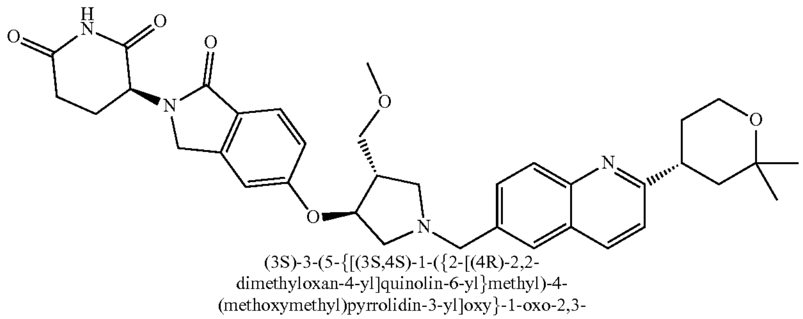 (3S)-3-(5-{[(3S,4S)-1-({2-[(4R)-2,2-dimethyloxan-4-yl]quinolin-6-yl}methyl)-4-(methoxymethyl)pyrrolidin-3-yl]oxy}-1-oxo-2,3-dihydro-1H-isoindol-2-yl)piperidine-2,6-dione | 0.000246657 | 7.691883685 | 0.000726013 | 25.48431778 |
| 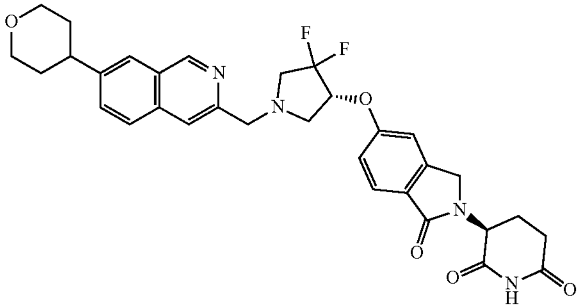 [SMILES: O=C1CC[C@H](N2Cc3cc(O[C@@H]4CN(Cc5cc6ccc(C7CCOCC7)cc6cn5)CC4(F)F)ccc3C2=O)C(=O)N1] (3S)-3-(5-{[(3R)-4,4-difluoro-1-{[7-(oxan-4-yl)isoquinolin-3-yl]methyl}pyrrolidin-3-yl]oxy}-1-oxo-2,3-dihydro-1H-isoindol-2-yl)piperidine-2,6-dione | 0.002168314 | 9.546008469 | 0.002757439 | 26.77254295 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 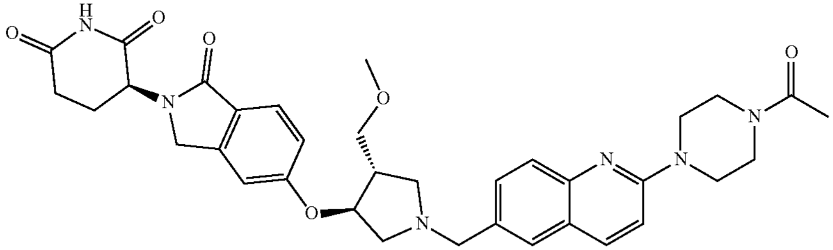 [SMILES: COC[C@@H]1CN(Cc2ccc3nc(N4CCN(C(C)=O)CC4)ccc3c2)C[C@H]1Oc1ccc2c(c1)CN([C@H]1CCC(=O)NC1=O)C2=O] (3S)-3-(5-{[(3S,4S)-1-{[2-(4-acetylpiperazin-1-yl)quinolin-6-yl]methyl}-4-(methoxymethyl)pyrrolidin-3-yl]oxy}-1-oxo-2,3-dihydro-1H-isoindol-2-yl)piperidine-2,6-dione | 0.001115159 | 8.784670371 | 0.001412528 | 27.26815224 |
| 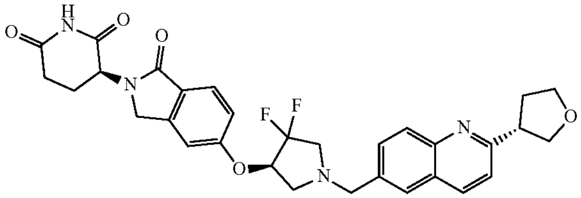 [SMILES: O=C1CC[C@H](N2Cc3cc(O[C@@H]4CN(Cc5ccc6nc([C@@H]7CCOC7)ccc6c5)CC4(F)F)ccc3C2=O)C(=O)N1] (3S)-3-(5-{[(3R)-4,4-difluoro-1-({2-[(3S)-oxolan-3-yl]quinolin-6-yl}methyl)pyrrolidin-3-yl]oxy}-1-oxo-2,3-dihydro-1H-isoindol-2-yl)piperidine-2,6-dione | 0.006362082 | 8.016677675 | 0.008724238 | 30.03457069 |
| 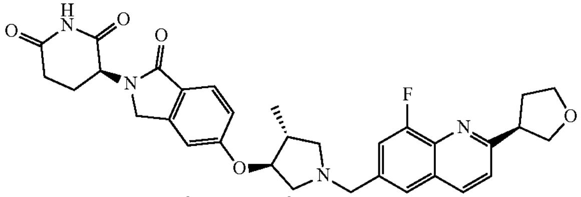 (3S)-3-(5-{[(3S,4R)-1-({8-fluoro-2-[(3R)-oxolan-3-yl]quinolin-6-yl}methyl)-4-methylpyrrolidin-3-yl]oxy}-1-oxo-2,3-dihydro-1H-isoindol-2-yl)piperidine-2,6-dione | 0.000955326 | 7.865448515 | 0.000984508 | 26.61438751 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 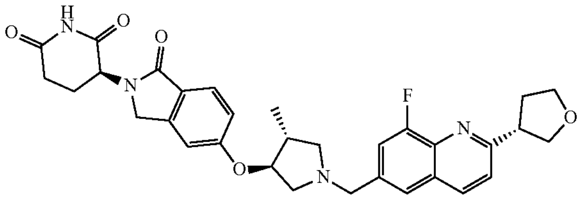 [SMILES: C[C@@H]1CN(Cc2cc(F)c3nc([C@@H]4CCOC4)ccc3c2)C[C@H]1Oc1ccc2c(c1)CN([C@H]1CCC(=O)NC1=O)C2=O] (3S)-3-(5-{[(3S,4R)-1-({8-fluoro-2-[(3S)-oxolan-3-yl]quinolin-6-yl}methyl)-4-methylpyrrolidin-3-yl]oxy}-1-oxo-2,3-dihydro-1H-isoindol-2-yl)piperidine-2,6-dione | 0.001130059 | 7.978783508 | 0.001410143 | 26.16897774 |
| 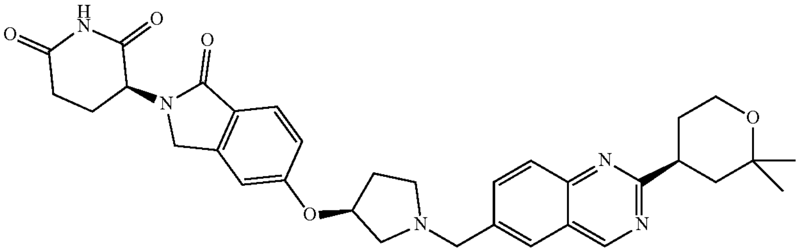 [SMILES: CC1(C)C[C@@H](c2ncc3cc(CN4CC[C@H](Oc5ccc6c(c5)CN([C@H]5CCC(=O)NC5=O)C6=O)C4)ccc3n2)CCO1] (3S)-3-(5-{[(3S)-1-({2-[(4S)-2,2-dimethyloxan-4-yl]quinazolin-6-yl}methyl)pyrrolidin-3-yl]oxy}-1-oxo-2,3-dihydro-1H-isoindol-2-yl)piperidine-2,6-dione | 0.0077728 | 8.717712958 | 0.024865473 | 26.32917786 |
| 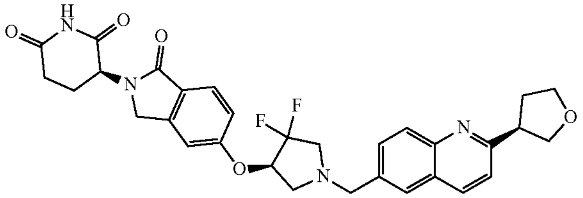 [SMILES: O=C1CC[C@H](N2Cc3cc(O[C@@H]4CN(Cc5ccc6nc([C@H]7CCOC7)ccc6c5)CC4(F)F)ccc3C2=O)C(=O)N1] (3S)-3-(5-{[(3R)-4,4-difluoro-1-({2-[(3R)-oxolan-3-yl]quinolin-6-yl}methyl)pyrrolidin-3-yl]oxy}-1-oxo-2,3-dihydro-1H-isoindol-2-yl)piperidine-2,6-dione | 0.007632826 | 8.318788487 | 0.011676797 | 28.36779976 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 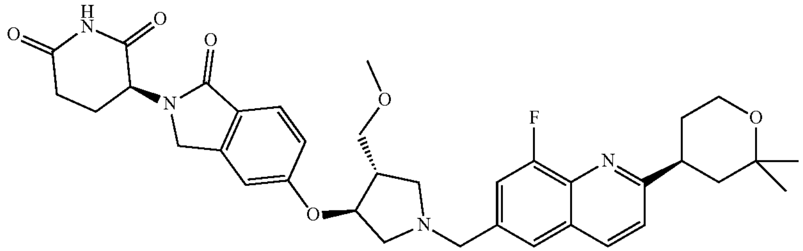 [SMILES: COC[C@@H]1CN(Cc2cc(F)c3nc([C@H]4CCOC(C)(C)C4)ccc3c2)C[C@H]1Oc1ccc2c(c1)CN([C@H]1CCC(=O)NC1=O)C2=O] (3S)-3-(5-{[(3S,4S)-1-({2-[(4S)-2,2-dimethyloxan-4-yl]-8-fluoroquinolin-6-yl}methyl)-4-(methoxymethyl)pyrrolidin-3-yl]oxy}-1-oxo-2,3-dihydro-1H-isoindol-2-yl)piperidine-2,6-dione | 0.000637644 | 8.946846663 | 0.001195038 | 25.18751717 |
| 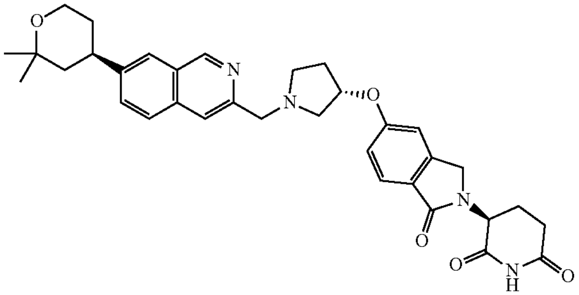 [SMILES: CC1(C)C[C@H](c2ccc3cc(CN4CC[C@H](Oc5ccc6c(c5)CN([C@H]5CCC(=O)NC5=O)C6=O)C4)ncc3c2)CCO1] (3S)-3-(5-{[(3S)-1-({7-[(4R)-2,2-dimethyloxan-4-yl]isoquinolin-3-yl}methyl)pyrrolidin-3-yl]oxy}-1-oxo-2,3-dihydro-1H-isoindol-2-yl)piperidine-2,6-dione | 0.000592575 | 9.481652534 | 0.001088075 | 24.44191742 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 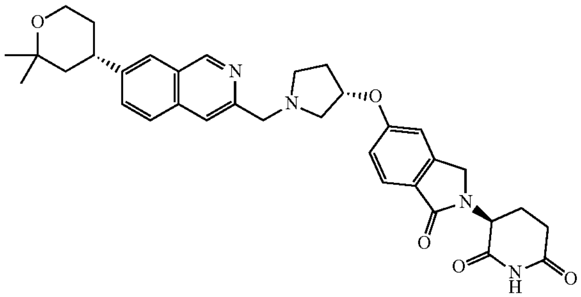 [SMILES: CC1(C)C[C@@H](c2ccc3cc(CN4CC[C@H](Oc5ccc6c(c5)CN([C@H]5CCC(=O)NC5=O)C6=O)C4)ncc3c2)CCO1] (3S)-3-(5-{[(3S)-1-({7-[(4S)-2,2-dimethyloxan-4-yl]isoquinolin-3-yl}methyl)pyrrolidin-3-yl]oxy}-1-oxo-2,3-dihydro-1H-isoindol-2-yl)piperidine-2,6-dione | 0.001114637 | 9.866378746 | 0.001187786 | 26.79358673 |
| 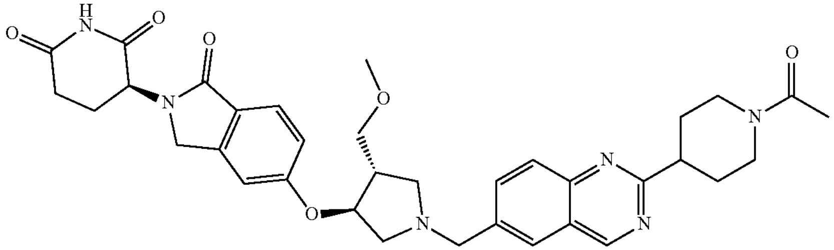 [SMILES: COC[C@@H]1CN(Cc2ccc3nc(C4CCN(C(C)=O)CC4)ncc3c2)C[C@H]1Oc1ccc2c(c1)CN([C@H]1CCC(=O)NC1=O)C2=O] (3S)-3-(5-{[(3S,4S)-1-{[2-(1-acetylpiperidin-4-yl)quinazolin-6-yl]methyl}-4-(methoxymethyl)pyrrolidin-3-yl]oxy}-1-oxo-2,3-dihydro-1H-isoindol-2-yl)piperidine-2,6-dione | 0.003540477 | 9.280308755 | 0.011888552 | 26.93017769 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 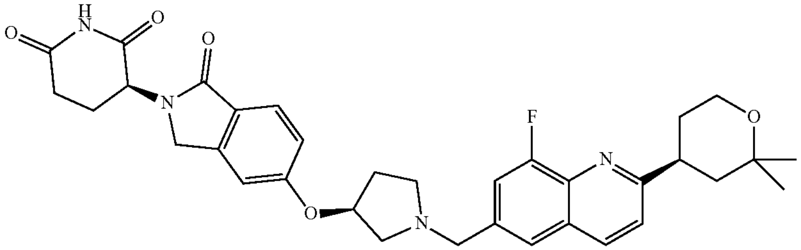 [SMILES: CC1(C)C[C@@H](c2ccc3cc(CN4CC[C@H](Oc5ccc6c(c5)CN([C@H]5CCC(=O)NC5=O)C6=O)C4)cc(F)c3n2)CCO1] (3S)-3-(5-{[(3S)-1-({2-[(4S)-2,2-dimethyloxan-4-yl]-8-fluoroquinolin-6-yl}methyl)pyrrolidin-3-yl]oxy}-1-oxo-2,3-dihydro-1H-isoindol-2-yl)piperidine-2,6-dione | 0.001642189 | 9.620776661 | 0.003804854 | 28.17049789 |
| 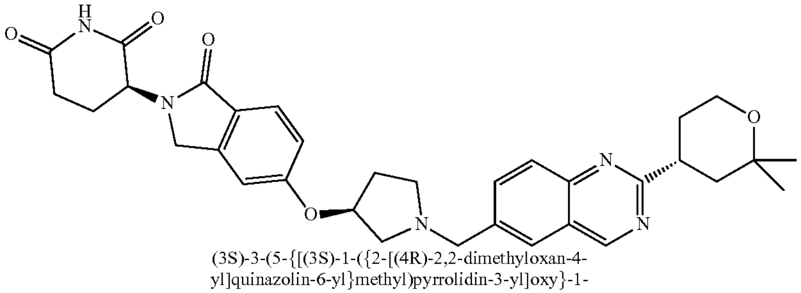 (3S)-3-(5-{[(3S)-1-({2-[(4R)-2,2-dimethyloxan-4-yl]quinazolin-6-yl}methyl)pyrrolidin-3-yl]oxy}-1-oxo-2,3-dihydro-1H-isoindol-2-yl)piperidine-2,6-dione | 0.015540133 | 11.78685594 | 0.032314334 | 29.31269455 |
| 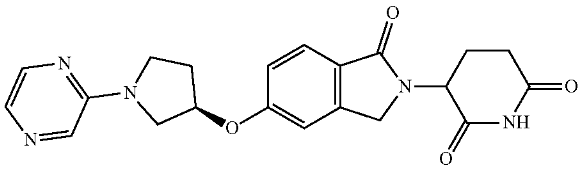 [SMILES: O=C1CCC(N2Cc3cc(O[C@@H]4CCN(c5cnccn5)C4)ccc3C2=O)C(=O)N1] 3-(1-oxo-5-{[(3R)-1-(pyrazin-2-yl)pyrrolidin-3-yl]oxy}-2,3-dihydro-1H-isoindol-2-yl)piperidine-2,6-dione | | | 10 | 110 |

TABLE 2-continued

| MKN45 cell proliferation and WEE1-ePL degradation. | | | | |
|---|---|---|---|---|
| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
| 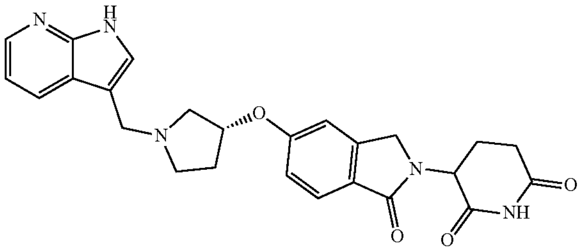 [SMILES: O=C1CCC(N2Cc3cc(O[C@@H]4CCN(Cc5c[nH]c6ncccc56)C4)ccc3C2=O)C(=O)N1] 3-(1-oxo-5-{[(3R)-1-({1H-pyrrolo[2,3-b]pyridin-3-yl}methyl)pyrrolidin-3-yl]oxy}-2,3-dihydro-1H-isoindol-2-yl)piperidine-2,6-dione | | | 10 | 87.61 |
| 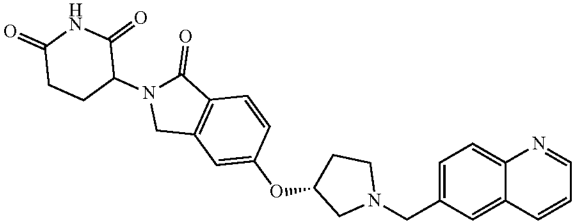 [SMILES: O=C1CCC(N2Cc3cc(O[C@@H]4CCN(Cc5ccc6ncccc6c5)C4)ccc3C2=O)C(=O)N1] 3-(1-oxo-5-{[(3R)-1-[(quinolin-6-yl)methyl]pyrrolidin-3-yl]oxy}-2,3-dihydro-1H-isoindol-2-yl)piperidine-2,6-dione | | | 10 | 90.24 |
| 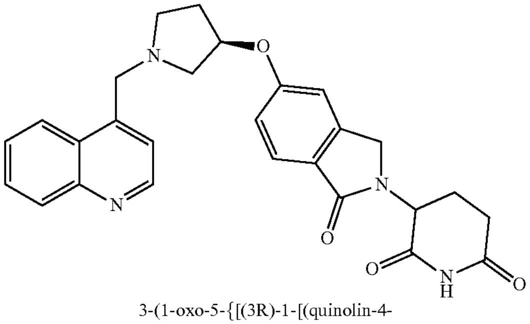 3-(1-oxo-5-{[(3R)-1-[(quinolin-4- | | | 10 | 87.11 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| yl)methyl]pyrrolidin-3-yl]oxy}-2,3-dihydro-1H-isoindol-2-yl)piperidine-2,6-dione | | | | |
| 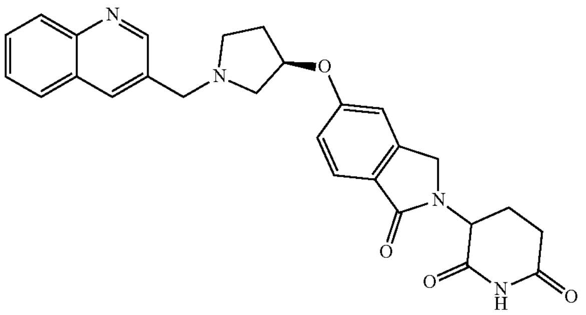 [SMILES: O=C1CCC(N2Cc3cc(O[C@@H]4CCN(Cc5cnc6ccccc6c5)C4)ccc3C2=O)C(=O)N1] 3-(1-oxo-5-{[(3R)-1-[(quinolin-3-yl)methyl]pyrrolidin-3-yl]oxy}-2,3-dihydro-1H-isoindol-2-yl)piperidine-2,6-dione | | | 10 | 83.91 |
| 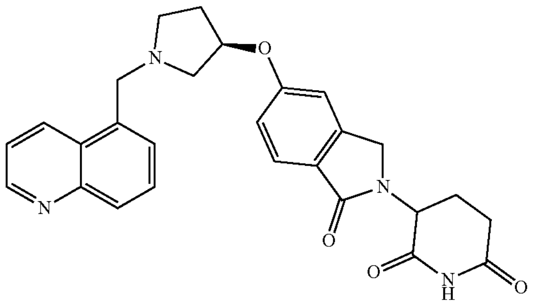 [SMILES: O=C1CCC(N2Cc3cc(O[C@@H]4CCN(Cc5cccc6ncccc56)C4)ccc3C2=O)C(=O)N1] 3-(1-oxo-5-{[(3R)-1-[(quinolin-5-yl)methyl]pyrrolidin-3-yl]oxy}-2,3-dihydro-1H-isoindol-2-yl)piperidine-2,6-dione | | | 10 | 91.51 |

TABLE 2-continued

MKN45 cell proliferation and WEE1-ePL degradation.

| Structure and IUPAC Name | MKN45 Cell Prolif. 120 hr (EC50, uM) | MKN45 Cell Prolif. 120 hr (Ymin-Obs) | 293T-LentiX WEE1-ePL Degradation 4 hr (EC50, uM) | 293T-LentiX WEE1-ePL Degradation 4 hr (Ymin) |
|---|---|---|---|---|
| 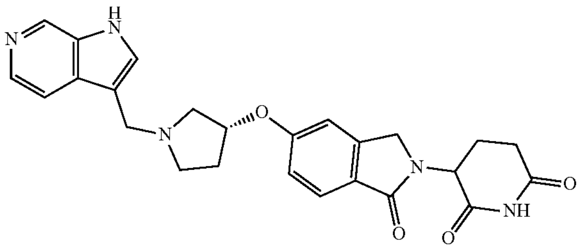 [SMILES: O=C1CCC(N2Cc3cc(O[C@@H]4CCN(Cc5c[nH]c6cnccc56)C4)ccc3C2=O)C(=O)N1] 3-(1-oxo-5-{[(3R)-1-({1H-pyrrolo[2,3-c]pyridin-3-yl}methyl)pyrrolidin-3-yl]oxy}-2,3-dihydro-1H-isoindol-2-yl)piperidine-2,6-dione | | | 10 | 93.39 |
| 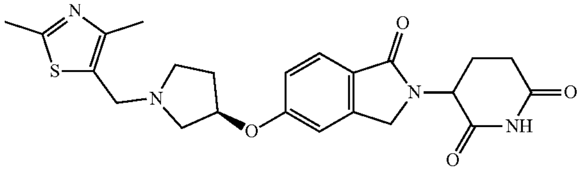 [SMILES: Cc1nc(C)c(CN2CC[C@@H](Oc3ccc4c(c3)CN(C3CCC(=O)NC3=O)C4=O)C2)s1] 3-(5-{[(3R)-1-[(2,4-dimethyl-1,3-thiazol-5-yl)methyl]pyrrolidin-3-yl]oxy}-1-oxo-2,3-dihydro-1H-isoindol-2-yl)piperidine-2,6-dione | | | 10 | 94.2 |

Although the present invention has been described in some detail by way of illustration and example for purposes of clarity of understanding, the descriptions and examples should not be construed as limiting the scope of the invention. The disclosures of all patent and scientific literature cited herein are expressly incorporated herein in their entirety by reference.

The invention claimed is:

1. A compound of the following formula:

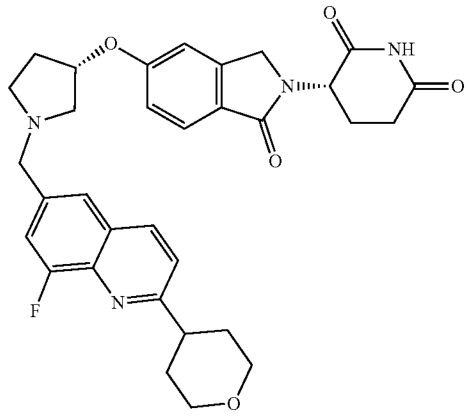 [SMILES: O=C1CC[C@H](N2Cc3cc(O[C@H]4CCN(Cc5cc(F)c6nc(C7CCOCC7)ccc6c5)C4)ccc3C2=O)C(=O)N1]

or a pharmaceutically acceptable salt, tautomer, isotopologue, or stereoisomer thereof.

2. A compound of the following formula:

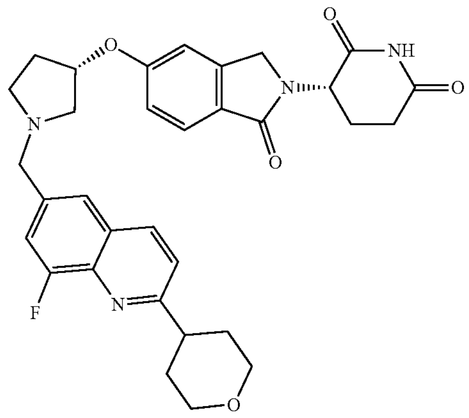 [SMILES: O=C1CC[C@H](N2Cc3cc(O[C@H]4CCN(Cc5cc(F)c6nc(C7CCOCC7)ccc6c5)C4)ccc3C2=O)C(=O)N1]

or a pharmaceutically acceptable salt thereof.

3. A compound of the following formula:

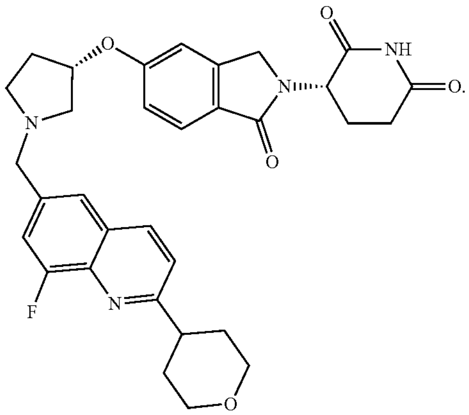 [SMILES: O=C1CC[C@H](N2Cc3cc(O[C@H]4CCN(Cc5cc(F)c6nc(C7CCOCC7)ccc6c5)C4)ccc3C2=O)C(=O)N1]

4. A pharmaceutical composition comprising the compound of claim 1 or a pharmaceutically acceptable salt, tautomer, isotopologue, or stereoisomer thereof, and a pharmaceutically acceptable carrier or vehicle, wherein the pharmaceutically acceptable carrier or vehicle can comprise an excipient, diluent, or a mixture thereof.

5. A pharmaceutical composition comprising the compound of claim 2 or a pharmaceutically acceptable salt thereof, and a pharmaceutically acceptable carrier or vehicle, wherein the pharmaceutically acceptable carrier or vehicle can comprise an excipient, diluent, or a mixture thereof.

6. A pharmaceutical composition comprising the compound of claim 3 and a pharmaceutically acceptable carrier or vehicle, wherein the pharmaceutically acceptable carrier or vehicle can comprise an excipient, diluent, or a mixture thereof.

* * * * *